United States Patent
Busch et al.

(10) Patent No.: US 8,703,805 B2
(45) Date of Patent: Apr. 22, 2014

(54) MODULATORS OF LXR

(75) Inventors: Brett B. Busch, San Diego, CA (US); Brenton T. Flatt, San Diego, CA (US); Xiao Hui Gu, San Diego, CA (US); Shao Po Lu, San Diego, CA (US); Richard Martin, San Diego, CA (US); Raju Mohan, Encinitas, CA (US); Michael Charles Nyman, San Diego, CA (US); Edwin Schweiger, San Diego, CA (US); William C. Stevens, Jr., San Diego, CA (US); Tie Lin Wang, San Diego, CA (US); Yinong Xie, San Diego, CA (US)

(73) Assignee: Exelixis Patent Company LLC, South San Francisco, CA (US)

( * ) Notice: Subject to any disclaimer, the term of this patent is extended or adjusted under 35 U.S.C. 154(b) by 364 days.

(21) Appl. No.: 11/993,806

(22) PCT Filed: Jun. 26, 2006

(86) PCT No.: PCT/US2006/024749
§ 371 (c)(1),
(2), (4) Date: Feb. 3, 2010

(87) PCT Pub. No.: WO2007/002559
PCT Pub. Date: Jan. 4, 2007

(65) Prior Publication Data
US 2010/0331295 A1 Dec. 30, 2010

Related U.S. Application Data

(60) Provisional application No. 60/694,372, filed on Jun. 27, 2005, provisional application No. 60/736,120, filed on Nov. 10, 2005.

(51) Int. Cl.
*A61K 31/4155* (2006.01)
*C07D 231/12* (2006.01)

(52) U.S. Cl.
USPC ........................................ 514/406; 548/365.7

(58) Field of Classification Search
USPC ...................................................... 548/365.7
See application file for complete search history.

(56) References Cited

U.S. PATENT DOCUMENTS

| | | | |
|---|---|---|---|
| 5,466,823 A | 11/1995 | Talley et al. | |
| 5,504,215 A | 4/1996 | Talley et al. | |
| 5,760,068 A | 6/1998 | Talley et al. | |
| 6,071,955 A | 6/2000 | Elias et al. | |
| 6,184,215 B1 | 2/2001 | Elias et al. | |
| 6,294,558 B1 | 9/2001 | Ando et al. | |
| 6,358,634 B1 | 3/2002 | Igarashi et al. | |
| RE37,936 E | 12/2002 | Huang et al. | |
| 6,492,411 B1 | 12/2002 | Talley et al. | |
| 6,635,655 B1 | 10/2003 | Jayyosi et al. | |
| 7,566,709 B2 | 7/2009 | Schiemann et al. | |
| 2002/0035156 A1 | 3/2002 | Roniker et al. | |

(Continued)

FOREIGN PATENT DOCUMENTS

AU 2005268023 A1 2/2006
DE 103 15 569 A1 10/2004

(Continued)

OTHER PUBLICATIONS

Vippagunta, et al. Advanced Drug Delivery Reviews 48 (2001) 3-26.*
Concise Encyclopedia Chemistry (1993) Walter de Gruyter Berlin New York.*
Yanborisov, et al. Document No. 130:153601 (1998) retrieved from CAPLUS.*
Hopper, et al. Document No. 141:379922, retrieved from CAPLUS; Nov. 4, 2004.*
Finn, J. et al., "Discovery of a Potent and Selective Series of Pyrazole Bacterial Methionyl-Trna Sythetase Inhibitors", Bioorganic & Medicinal Chemistry Letters, 2003, 13(13), 2231-2234.

(Continued)

*Primary Examiner* — Shawquia Young
(74) *Attorney, Agent, or Firm* — Fox Rothschild LLP; Gerard P. Norton; Wansheng Jerry Liu

(57) ABSTRACT

Compounds of the invention, such as compounds of Formulae Ia, Ib, Ic, or Id and pharmaceutically acceptable salts, isomers, and prodrugs thereof, which are useful as modulators of the activity of liver X receptors, where R1, R2, R21, R3, and G are defined herein. Pharmaceutical compositions containing the compounds and methods of using the compounds are also disclosed.

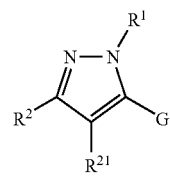

Ia

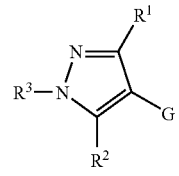

Ib

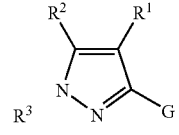

Ic

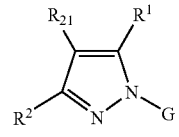

Id

41 Claims, No Drawings

(56) References Cited

U.S. PATENT DOCUMENTS

| | | |
|---|---|---|
| 2004/0152739 A1 | 8/2004 | Hanau et al. |
| 2004/0157883 A1 | 8/2004 | Chen et al. |
| 2004/0248956 A1 | 12/2004 | Hagmann et al. |
| 2005/0004115 A1 | 1/2005 | Sharma et al. |
| 2006/0241157 A1 | 10/2006 | Conner et al. |
| 2006/0276650 A1 | 12/2006 | Schadt et al. |
| 2007/0010531 A1 | 1/2007 | Schadt et al. |
| 2008/0090834 A1 | 4/2008 | Hoover et al. |

FOREIGN PATENT DOCUMENTS

| | | |
|---|---|---|
| DE | 103 15 571 A1 | 10/2004 |
| DE | 103 15 573 A1 | 10/2004 |
| DE | 103 15 573 Al | 10/2004 |
| EP | 0418845 A1 | 3/1991 |
| EP | 0 839 810 A1 | 5/1998 |
| EP | 0 839 810 Al | 5/1998 |
| EP | 0839810 | 5/1998 |
| EP | 1 285 908 A1 | 2/2003 |
| EP | 1 398 029 A | 3/2004 |
| EP | 1 884 513 A | 2/2008 |
| GB | 1510107 A | 5/1978 |
| JP | 03-141261 | 6/1991 |
| JP | 2004-146368 A | 5/2004 |
| JP | 2005-504093 A | 2/2005 |
| WO | 03/086287 A2 | 10/2003 |
| WO | WO 03/086287 A2 | 10/2003 |
| WO | 2004/011446 A | 2/2004 |
| WO | 2004/033432 A | 4/2004 |
| WO | WO 2004/033432 A | 4/2004 |
| WO | 2004/056740 A1 | 7/2004 |
| WO | 2004/069158 A | 8/2004 |
| WO | 2004/071447 A2 | 8/2004 |
| WO | 2004/080972 A | 9/2004 |
| WO | 2004076418 A1 | 9/2004 |
| WO | WO 2004/080972 A | 9/2004 |
| WO | 2004/089303 A2 | 10/2004 |
| WO | 2004/089888 A1 | 10/2004 |
| WO | 2004/089932 A1 | 10/2004 |
| WO | WO 2004/089303 A2 | 10/2004 |
| WO | 2004/094411 A1 | 11/2004 |
| WO | 2004/106307 A2 | 12/2004 |
| WO | 2005/009435 A | 2/2005 |
| WO | 2005/012263 A | 2/2005 |
| WO | WO 2005/009435 A | 2/2005 |
| WO | 2005/037199 A2 | 4/2005 |
| WO | 2005/037271 A1 | 4/2005 |
| WO | 2005/037763 A1 | 4/2005 |
| WO | WO 2005/037199 A2 | 4/2005 |
| WO | 2005/044130 A1 | 5/2005 |
| WO | 2005/047266 A | 5/2005 |
| WO | 2005/049578 A | 6/2005 |
| WO | 2005/054176 A1 | 6/2005 |
| WO | WO 2005/049578 A | 6/2005 |
| WO | 2005/066137 A | 7/2005 |
| WO | 2006/014005 A1 | 2/2006 |
| WO | 2006/044528 A | 4/2006 |
| WO | WO 2006/044528 A | 4/2006 |
| WO | 2006/076202 A | 7/2006 |
| WO | 2007/002559 A | 1/2007 |
| WO | 2007/002563 A1 | 1/2007 |
| WO | 2008/073825 A1 | 6/2008 |

OTHER PUBLICATIONS

Bennett et al., "Liver X receptor agonist as a treatment for atherosclerosis", Expert Opinion on Therapeutic Patents, 2004, 14(7), 967-982.

Tischenko et al., "Some derivatives of 1,2,5-triphenylimidazole", Deposited Doc. (1980) SPSTL 358Khp-D80, Caplus Accession No. 1982:423694, 8pp.

Tischenko et al., "Synthesis and luminescence of 1,2,5-triphenylimidazoles", Sisintill Org Lyuminofory, 1972, 93-9.

Lettau et al., "Imidazol-N-oxide 1); Eline einfache Synthese substituierter Imidazole", Zeischrift fuer Chemie, 1971, 11(1), 10-11.

Schubert et al., "Diimidazoles. II. Synthesis of aliphatically and aromatically bridged N,N'-diimidazoles", Journal fuer Praktische Chemie (Leipzig), 1963, 22(3-4), 130-9.

Yanborisov et al., "Synthesis and pharmaceutical activity of heteroylpyruvic acids and their derivatives", Khimiko-Farmatsevticheskii Zhurnal [Pharmaceutical Chemistry Journal], 1998, 32(9), 480-2.

Kalaany et al., "LXRs regulate the balance between fat storage and oxidation", Cell Metabolism, 2005, vol. 1, 231-244 and Supplemental Data (4 sheets).

Giorelli et al., "Immunomodulatory properties of increased levels of liver X receptor β in peripheral blood mononuclear cells from multiple sclerosis patients", Experimental Neurology, 2007, vol. 204, 759-766.

Zanlungo et al., "The Molecular and Metabolic Basis of Biliary Cholesterol Secretion and Gallstone Disease", Frontiers in Bioscience, 2003, vol. 8, 1166-1174.

Zelcer et al., "Liver X receptors as integrators of metabolic and inflammatory signaling", The Journal of Clinical Investigation, 2006, 116(3), 607-614.

Joseph et al., "Synthetic LXR ligand inhibits the development of atherosclerosis in mice", PNAS, 2002, 99(11), 7604-7609.

Tontonoz et al., "Liver X Receptor Signaling Pathways in Cardiovascular Disease", Molecular Endocrinology, 2003, 17(6), 985-993.

Goralski et al., "Chipping away at gallstones", Nature Medicine, 2004, 10(12), 1301-1302.

Bennett et al: "Liver X receptor agonist as a treatment for atherosclerosis" Expert Opinion of Therapeutic Patents International, Ashley Publications, GB, 2204, vol. 14(7), 967-982.

* cited by examiner

MODULATORS OF LXR

CROSS-REFERENCE TO RELATED APPLICATIONS

This application is a US national phase of international application PCT/US2006/024749 filed on Jun. 26, 2006, which claims priority to U.S. Provisional Application No. 60/694,372, filed Jun. 27, 2005, and U.S. Provisional Application No. 60/736,120, filed Nov. 10, 2005, both of which are hereby incorporated by reference in their entirety.

FIELD OF THE INVENTION

This invention relates to compounds that modulate the activity of liver X receptors (LXRs). The invention also provides pharmaceutical compositions comprising the compounds of the invention and methods of utilizing those compositions for modulating the activity of liver X receptor. In particular, pyrazole isomers and derivatives are provided for modulating the activity of LXRs.

BACKGROUND OF THE INVENTION

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression.

There are three RXR genes (see, e.g., Mangelsdorf et al. (1992) *Genes Dev.* 6:329-344), coding for RXRα, β, and γ, all of which are able to heterodimerize with any of the class II receptors, although there appear to be preferences for distinct RXR subtypes by partner receptors in vivo (see, e.g., Chiba et al. (1997) *Mol. Cell. Biol.* 7:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for the franesoid X receptor (FXR).

Because it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

LXRα and LXRβ

LXRα is found predominantly in the liver, with lower levels found in kidney, intestine, spleen and adrenal tissue (see, e.g., Willy, et al. (1995) *Gene Dev.* 9(9):1033-1045) LXRβ is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137-3140). LXRα is activated by oxycholesterol and promotes cholesterol metabolism (Peet et al. (1998) *Cell* 93:693-704). Thus, LXRs appear to play a role in, e.g., cholesterol metabolism (see, e.g., Janowski, et al. (1996) *Nature* 383:728-731).

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see e.g., International Patent Application Publication No. WO 00/17334). Activity of nuclear receptors, including LXRs, FXRs and PPARs, and orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) *J. Biol. Chem.* 275:10918-10924), HDL metabolism (see, e.g., Urizar et al. (2000) *J. Biol. Chem.* 275:39313-39317 and International Patent Application Publication No. WO 01/03705), and increased cholesterol efflux and increased expression of ATP binding cassette transporter protein ($ABC_1$) (see, e.g., International Patent Application Publication No. WO 00/78972).

Thus, there is a need for compounds, compositions and methods of modulating the activity of nuclear receptors, including LXRs, FXRs, PPARs and orphan nuclear receptors. Such compounds are useful in the treatment, prevention, inhibition or amelioration of one or more symptoms of diseases or disorders in which nuclear receptor activity is implicated.

SUMMARY OF THE INVENTION

In one aspect, the present invention provides a compound according the following formulas Ia-d,

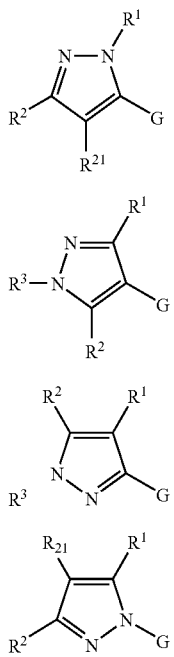

or a pharmaceutically acceptable salt, isomer, or prodrug thereof, which are useful as modulators of the activity of liver X receptors (LXR), where $R^1$, $R^2$, $R^{21}$, $R^3$, and G are defined herein.

Compounds for use in compositions and methods for modulating the activity of nuclear receptors are provided. In particular, compounds of the invention which are useful for modulating liver X receptors, LXRα and LXRβ, FXR, PPAR and/or orphan nuclear receptors are provided.

In one embodiment, the compounds provided herein are agonists of LXR. In another embodiment, the compounds provided herein are antagonists of LXR. Agonists that exhibit low efficacy are, in certain embodiments, antagonists.

Another aspect of this invention is directed to methods of treating, preventing, or ameliorating the symptoms of a disease or disorder that is modulated or otherwise affected by nuclear receptor activity or in which nuclear receptor activity is implicated, comprising administering to a subject in need thereof a therapeutically effective amount of a compound of formulae Ia, Ib, Ic, or Id, or a pharmaceutically acceptable derivative thereof.

Another aspect of this invention is directed to methods of reducing cholesterol levels in a subject in need thereof, comprising administering an effective cholesterol level-reducing amount of a compound of formulae Ia, Ib, Ic or Id, or a pharmaceutically acceptable derivative thereof.

Another aspect of this invention is directed to methods of treating, preventing, inhibiting, or ameliorating one or more symptoms of a disease or disorder which is affected by cholesterol, triglyceride, or bile acid levels, comprising administering to a subject in need thereof a therapeutically effective amount of a compound of formulae Ia, Ib, Ic, or Id, or a pharmaceutically acceptable derivative thereof.

Another aspect of this invention is directed to methods of modulating nuclear receptor activity, comprising contacting the nuclear receptor with a compound of formulae Ia, Ib, Ic or Id, or a pharmaceutically acceptable derivative thereof.

Another aspect of this invention is directed to methods of modulating cholesterol metabolism, comprising administering an effective cholesterol metabolism-modulating amount of a compound of formulae Ia, Ib, Ic or Id, or a pharmaceutically acceptable derivative thereof.

Another aspect of this invention is directed to methods of treating, preventing, inhibiting or ameliorating one or more symptoms of hypocholesterolemia in a subject in need thereof, comprising administering a therapeutically effective amount of a compound of formulae Ia, Ib, Ic or Id, or a pharmaceutically acceptable derivative thereof.

Another aspect of this invention is directed to methods of increasing cholesterol efflux from cells of a subject, comprising administering an effective cholesterol efflux-increasing amount of a compound of formulae Ia, Ib, Ic or Id, or a pharmaceutically acceptable derivative thereof.

Another aspect of this invention is directed to methods of increasing the expression of ATP-Binding Cassette ($ABC_1$) in the cells of a subject, comprising administering an effective $ABC_1$ expression-increasing mount of a compound of formulae Ia, Ib, Ic, or Id, or a pharmaceutically acceptable derivative thereof.

Another aspect of this invention is directed to in vitro methods for altering nuclear receptor activity, comprising contacting the nuclear receptor with a compound of formulae Ia, Ib, Ic or Id, or a pharmaceutically acceptable derivative thereof.

Another aspect of this invention is directed to methods of reducing cholesterol levels in a subject in need thereof, comprising administering an effective cholesterol level-reducing amount of a compound of formulae Ia, Ib, Ic or Id, or a pharmaceutically acceptable derivative thereof.

Another aspect of this invention is directed to pharmaceutical compositions comprising a pharmaceutically acceptable carrier, excipient and/or diluent and a compound of formulae Ia, Ib, Ic or Id.

Another aspect of this invention is directed to regulation of cholesterol transport and inflammatory signaling pathways that are implicated in human disease pathology including atherosclerosis and associated diseases such as myocardial infarction and ischemic stroke in a subject in need thereof, comprising administering an effective cholesterol transport and inflammatory signaling pathways regulating amount of a compound of formulae Ia, Ib, Ic or Id, or a pharmaceutically acceptable derivative thereof.

Another aspect of this invention is directed to treatment of the metabolic syndrome which comprises a constellation of disorders of the body's metabolism including obesity, hypertension and insulin resistance and diabetes including treatment of diseases resulting from compromised metabolism and immunity including atherosclerosis and diabetes as well as autoimmune disorders and diseases in a subject in need thereof, comprising administering a therapeutically effective amount of a compound of formulae Ia, Ib, Ic or Id, or a pharmaceutically acceptable derivative thereof.

DETAILED DESCRIPTION OF THE INVENTION

In a first embodiment, the present invention provides a compound according to one of the following formulas,

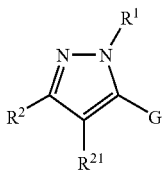

Ia

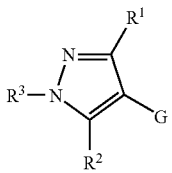

Ib

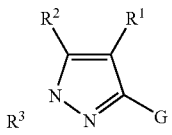

Ic

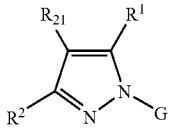

Id or a pharmaceutically acceptable salt, isomer, or prodrug thereof, wherein, (A) $R^1$ is -$L^1$-$R^5$, wherein $L^1$ is a bond, $L^5$, $L^6$, -$L^5$-$L^6$-$L^5$-, or -$L^6$-$L^5$-$L^6$-, wherein
  each $L^5$ is independently —$[C(R^{15})_2]_m$—, wherein
    each $R^{15}$ is independently hydrogen, halogen, ($C_1$-$C_6$)alkyl, ($C_3$-$C_8$)cycloalkyl, or ($C_1$-$C_6$)haloalkyl;
  each $L^6$ is independently —$C(R^{11})_2$—, —$C(R^{11})C(R^{11})_2$—, —$C(R^{11})$=$C(R^{11})$—, —$C(R^{11})_2O$—, —$C(R^{11})_2NR^{11}$—, —C≡C—, —O—, —S—, —$NR^{11}$—, —$N(R^{10})CO$—, —$N(R^{10})CO_2$—, —$CON(R^{10})$—, —CO—, —CS—, —$CO_2$—, —OC(=O)—, —OC(=O)$N(R^{10})$—, —$CONR^{11}N(R^{11})_2$—, —$CONR^{11}$—, —$OCONR^{11}$—, —$SO_2$—, —$N(R^{10})SO_2$—, —$SO_2N(R^{10})$—, —$NR^{10}CONR^{10}$—, —$NR^{10}CSNR^{10}$—, —C(=$NR^{11}$)—, —C(=$NOR^{11}$)—, —C(=NN$(R^{11})_2$)—, aryl, $C_3$-$C_8$ cycloalkyl, cyclo$C_3$ haloalkyl, heteroaryl, heterocyclyl, wherein the aryl, cycloalkyl, cyclo$C_{3-8}$haloalkyl, heteroaryl, or heterocyclyl are optionally substituted with one or more radicals of $R^4$;
  or $L^1$ is a $C_{2-6}$ alidiyl chain, wherein the alidiyl chain is optionally interrupted by —$C(R^{11})_2$—, —$C(R^{11})_2C(R^{11})_2$—, —$C(R^{11})$=$C(R^{11})$—, —$C(R^{11})_2O$—, —$C(R^{11})_2NR^{11}$—, —C≡C—, —O—, —S—, —$N(R^{10})CO$—, —$N(R^{10})CO_2$—, —$CON(R^{10})$—, —CO—, —$CO_2$—, —OC(=O)—, —OC(=O)$N(R^{10})$—, —$SO_2$—, —$N(R^{10})SO_2$—, or —$SO_2N(R^{10})$—, and $R^5$ is aryl, heterocyclyl, heteroaryl, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl, $C_3$-$C_8$ cycloalkyl, —C, —B—C, -A-B—C, wherein
  A is —O—;
  B is —$[C(R^{15})_2]_m$— or $C_3$-$C_8$ cycloalkyl;
  C is $C_1$-$C_6$ alkyl, $C_1$-$C_6$ haloalkyl, $SO_2R^{11}$, $SR^{11}$, $SO_2N(R^{11})_2$, $SO_2NR^{11}COR^{11}$, C≡N, C(O)$OR^{11}$, CON$(R^{11})_2$, or N$(R^{11})_2$;

wherein $R^5$ is optionally substituted with one or more $R^{5a}$,
  wherein each $R^{5a}$ is independently $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$cycloalkenyl)-$C_1$-$C_6$ alkyl-, ($C_3$-$C_8$ cycloalkyl)-$C_2$-$C_6$ alkenyl, halogen, nitro, heterocyclyloxy, aryl, aryloxy, arylalkyl, aryloxyaryl, aryl $C_1$-$C_6$ alkoxy, —C', —B'—C', or -A'-B'—C' wherein
  A' is —O—;
  B' is —$[C(R^{15})_2]_m$— or —$C_3$-$C_8$ cycloalkyl-;
  C' is —H, halogen, —$SO_2R^{11}$, —$OR^{11}$, —$SR^{11}$, —$N_3$, —$COR^{11}$, —$SO_2N(R^{11})_2$, —$SO_2NR^{11}COR^{11}$, —C≡N, —C(O)$OR^{11}$, —OC(=O)$R^{11}$, —CON$(R^{11})_2$, —CON$(R^{11})OR^{11}$, —OCON$(R^{11})_2$, —$NR^{11}COR^{11}$, —$NR^{11}CON(R^{11})_2$, —$NR^{11}COOR^{11}$, —N$(R^{11})_2$, aryl, heteroaryl, or heterocyclyl;

wherein each $R^{5a}$ is optionally substituted one or more groups which are independently $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, $C_0$-$C_6$ alkoxyaryl, $C_1$-$C_6$ alkyl, $C_3$-$C_8$ cycloalkyl, aryl, aryl-$C_1$-$C_6$ alkyl-, heteroaryl, halogen, —$NO_2$, —C≡N, —$COR^{11}$, —$COOR^{11}$, —CON$(R^{11})_2$, —$SO_2R^{11}$, —$OR^{11}$, —$SR^{11}$, —$SO_2R^{11}$, —$SO_2N(R^{11})_2$, —$SO_2NR^{11}COR^{11}$, —OCON$(R^{11})_2$, —$NR^{11}COR^{11}$, —$NR^{11}CON(R)_2$, —$NR^{11}COOR^{11}$, or —N$(R)_2$;

$R^2$ and $R^{21}$ are -$L^3$-$R^7$, wherein
  each $L^3$ is independently a bond —$V^1$—(CH$_2$)$_n$—$V^1$—, or —(CH$_2$)$_m$—$V^1$—(CH$_2$)$_n$— wherein
    n is 0-6; and
    each $V^1$ is independently —$C(R^{11})_2$—, —$C(R^{11})_2C(R^{11})_2$—, —$C(R^{11})$=$C(R^{11})$—, —$C(R^{11})_2O$—, —$C(R^{11})_2NR^{11}$—, —C≡C—, —O—, —S—, —$NR^7$—, —$N(R^{10})CO$—, —$N(R^{10})CO_2$—, —OCO—, —CO—, —CS—, —$CONR^{10}$—, —C(=N)(R^{11})—, —C(=N—$OR^{11}$)—, —C[=N—N$(R^{11})_2$], —$CO_2$—, —OC(=O)—, —OC(=O)N$(R^{10})$—, —$SO_2$—, —$N(R^{10})SO_2$—, —$SO_2N(R^{10})$—, —$NR^{10}CONR^{10}$, —$NR^{10}CSNR^{10}$—, $C_3$-$C_8$ cycloalkyl, or $C_3$-$C_8$ cyclohaloalkyl;
  or each $L^3$ is independently a $C_{2-6}$ alidiyl chain, wherein the alidiyl chain is optionally interrupted by —$C(R^{11})_2$—, —$C(R^{11})_2C(R^{11})_2$—, —$C(R^{11})$=$C(R^{11})$—, —$C(R^{11})_2O$—, —$C(R^{11})_2NR^{11}$—, —C≡C—, —O—, —S—, —$N(R^{10})CO$—, —$N(R^{10})CO_2$—, —$CON(R^{10})$—, —CO—, —$CO_2$—, —OC(=O)—, —OC(=O)N$(R^{10})$—, —$SO_2$—, —$N(R^{10})SO_2$—, or —$SO_2N(R^{10})$; and
  each $R^7$ is independently hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, —Z, —Y—Z, or —X—Y—Z, wherein
    X is —O—;
    Y is —$[C(R^{15})_2]_m$—, —$C_2$-$C_6$ alkenyl, or $C_3$-$C_8$ cycloalkyl;
    Z is —H, —CN, halogen, —$OR^{11}$, —C(=O)$R^{11}$, —C(=O)$OR^{11}$, —C(=O)N$(R^{11})_2$, —N$(R^{11})_2$, —CN, —$N_3$, —$SO_2R^{11}$, —S(=O)$_2N(R^{11})_2$, —C(=O)N$(R^{11})N(R^{11})_2$, —C(=O)N$(R^{11})(OR^{11})$, —OC(=O)—$R^{11}$, —OC(=O)—N$(R^{11})_2$, or —N$(R^{11})COOR^{11}$;

wherein R$^7$ is optionally substituted with one or more R$^{7a}$, wherein

R$^{7a}$ is halogen, C$_2$-C$_6$ alkenyl, —C$_1$-C$_6$ alkyl-heterocyclyl, —C$_1$-C$_6$ alkyl-heteroaryl, —C$_1$-C$_6$ alkyl-aryl, C$_0$-C$_6$ alkoxyheteroaryl, C$_0$-C$_6$alkoxyheterocyclyl, haloaryl, aryloxy, aralkyloxy, aryloxyalkyl, C$_1$-C$_6$ alkoxyaryl, aryl C$_0$-C$_6$ alkylcarboxy, C(R$^{11}$)=C(R$^{11}$)—COOR$^{11}$, C$_0$-C$_6$alkoxyheteroaryl, C$_0$-C$_6$ alkoxyheterocyclyl, aryl, heteroaryl, heterocyclyl, C$_3$-C$_8$ cycloalkyl, heteroaryloxy, —Z', —Y'—Z', or —X'—Y'—Z', wherein X' is —O—;
Y' is —[C(R$^{15}$)$_2$]$_m$— or C$_3$-C$_8$ cycloalkyl;
Z' is —C$_1$-C$_6$ alkyl, —C$_1$-C$_6$ haloalkyl, —OR$^{11}$, —SR$^{11}$, —S(=O)$_2$R$^{11}$, —C(O)R$^{11}$, —C(=O)OR$^{11}$, —C(=O)N(R$^{11}$)$_2$, —N(R$^{11}$)$_2$, —N(R$^{11}$)C(O)R$^{11}$, —S(=O)$_2$N(R$^{11}$)C(=O)R$^{11}$, —CN, —S(=O)N(R$^{11}$)$_2$, —C(=O)N(R$^{11}$)N(R$^{11}$)$_2$, —C(=O)N(R$^{11}$)(OR$^{11}$), —OC(=O)—R$^{11}$, —OC(=O)—OR$^{11}$, —N(R$^{11}$)C(=O)O—R$^{11}$, or —N(R$^{11}$)S(=O)$_2$R$^{11}$;

wherein each R$^{7a}$ is optionally substituted with one or more R$^8$, wherein each R$^8$ is independently halogen, nitro, cyano, heteroaryl, C$_1$-C$_6$ alkyl, C$_1$-C$_6$ alkoxy, C$_1$-C$_6$ haloalkyl, C$_1$-C$_6$ haloalkyl(OR$^{11}$), C$_0$-C$_6$ alkylOR$^{11}$, C$_0$-C$_6$ alkylCON(R$^{11}$)$_2$, C$_0$-C$_6$ alkylCOR$^{11}$, C$_0$-C$_6$ alkylCOOR$^{11}$, or C$_0$-C$_6$ alkylSO$_2$R$^{11}$; and wherein if two R$^{7a}$ are present on the same carbon, then they may be taken together to form a cycloalkyl or heterocyclyl group; provided that R$^2$ and R$^{21}$ are not simultaneously —H;

R$^3$ is -L-R$^6$, wherein

L is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$— wherein n is 0-6; each w is independently 0-5; and each X$^3$ is independently a bond, —C(R$^{11}$)$_2$—, —C(R$^{11}$)$_2$C(R$^{11}$)$_2$—, —C(R$^{11}$)=C(R$^{11}$)—, —C≡C—, —CO—, —CS—, —CONR$^{10}$—, —C(=N)(R$^{11}$)—, —C(=N—OR$^{11}$)—, —C[=N—N(R$^{11}$)$_2$], —CO$_2$—, —SO$_2$—, or —SO$_2$N(R$^{10}$)—; and Y$^3$ is —O—, —S—, —NR$^7$—, —N(R$^{10}$)CO—, —N(R$^{10}$)CO$_2$—, —OCO—, —OC(=O)N(R$^{10}$)—, —NR$^{10}$CONR$^{10}$—, —N(R$^{10}$)SO$_2$—, or —NR$^{10}$CSNR$^{10}$—;

or L is a C$_{2-6}$ alidiyl chain, wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$); and R$^6$ is C$_1$-C$_6$ alkyl, C$_1$-C$_6$ haloalkyl, aryl, C$_3$-C$_8$ cycloalkyl, heteroaryl, heterocyclyl, —CN, —C(=O)R$^{11}$, —C(=O)OR$^{11}$, —C(=O)N(R$^{11}$)$_2$, —N(R$^{11}$)$_2$, —SO$_2$R$^{11}$, —S(=O)$_2$N(R$^{11}$)$_2$, —C(=O)N(R$^{11}$)N(R$^{11}$)$_2$, or —C(O)N(R$^{11}$)(OR$^{11}$), wherein the aryl, heteroaryl, cycloalkyl, or heterocyclyl is optionally substituted with one or more R$^{6a}$, wherein each R$^{6a}$ is independently —Z", —Y"—Z", or —X"—Y"—Z", wherein X" is —O—;
Y" is —[C(R$^{15}$)$_2$]$_m$—, —C$_2$-C$_6$ alkenyl, C$_3$-C$_8$ cycloalkyl, heterocyclyl, aryl, or heteroaryl, wherein the aryl, heteroaryl, cycloalkyl, or heterocyclyl is optionally substituted with at least one group which is each independently Z";

Z" is —H, —CN, halogen, —OR$^{11}$, —C(=O)R$^{11}$, —C(O)R$^{11}$, —C(=O)N(R$^{11}$)$_2$, —N(R$^{11}$)$_2$, —N$_3$, —SO$_2$R$^{11}$, —S(=O)$_2$N(R$^{11}$)$_2$, —C(=O)N(R$^{11}$)N(R$^{11}$)$_2$, —N(R$^{11}$)C(=O)N(R$^{11}$)$_2$, —OC(=O)—OR$^{11}$, —C(=O)N(R$^{11}$)(OR$^{11}$), —OC(O)—R$^{11}$, —OC(O)N(R$^{11}$)$_2$, or —N(R$^{11}$)COOR$^{11}$;

each R$^{10}$ is independently —R$^{11}$, —C(O)R$^{11}$, —CO$_2$R$^{11}$, or —SO$_2$R$^{11}$;

each R$^{11}$ is independently -hydrogen, C$_2$-C$_6$ alkenyl, C$_2$-C$_6$ alkynyl, (C$_3$-C$_8$ cycloalkenyl)-C$_1$-C$_6$ alkyl-, (C$_3$-C$_8$ cycloalkyl)-C$_2$-C$_6$ alkenyl-, —N(R$^{12}$)$_2$, —C$_1$-C$_6$ alkyl, —C$_1$-C$_6$ haloalkyl, —C$_3$-C$_8$ cycloalkyl, —C$_1$-C$_6$) alkyl-(C$_3$-C$_8$)cycloalkyl, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl, wherein any of R$^{11}$ is optionally substituted with one or more radicals of R$^{12}$;

each R$^{12}$ is independently hydrogen, halogen, C$_1$-C$_6$haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkyl-COR$^{13}$, C$_0$-C$_6$ alkylSO$_2$R$^{13}$, C$_0$-C$_6$ alkylCN, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_0$-C$_6$alkoxyaryl, aryl C$_0$-C$_6$ alkylcarboxy, C$_0$-C$_6$ alkylNR$^{13}$SO$_2$R$^{13}$, —C$_0$-C$_6$alkylN(R$^{13}$)$_2$, or OC$_0$-C$_6$ alkylCOOR$^{13}$;

each R$^{13}$ is independently hydrogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$ alkylCONR$^{11}$OR$^{11}$, C$_0$-C$_6$ alkylOR$^{11}$, or C$_0$-C$_6$alkylCOOR$^{11}$;

G is a group of the formula,

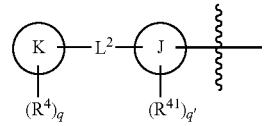

wherein

J is aryl, heteroaryl, or absent;
K is aryl, heteroaryl, or absent;
each R$^4$ is independently halogen, nitro, C$_2$-C$_6$ alkenyl, C$_3$-C$_8$ cycloalkyl, —C$_1$-C$_6$ alkyl-heterocyclyl, —C$_1$-C$_6$ alkyl-heteroaryl, —C$_1$-C$_6$ alkyl-aryl, -heterocyclyl-aryl, -heterocyclyl-heteroaryl, CR$^{11}$=CR$^{11}$COOR$^{11}$, aryloxy, —S-aryl, aralkyloxy, aryloxyalkyl, C$_1$-C$_6$ alkoxyaryl, aryl C$_0$-C$_6$ alkylcarboxy, C$_0$-C$_6$ alkoxyheteroaryl, C$_0$-C$_6$ alkoxyheterocyclyl, aryl, heteroaryl, heterocyclyl, -M, -E-M, or -D-E-M, wherein D is —O—;
E is —[C(R$^{15}$)$_2$]$_m$— or C$_3$-C$_8$ cycloalkyl;
M is C$_1$-C$_6$alkyl, C$_1$-C$_6$haloalkyl, —COR$^{11}$, —COOR$^{11}$, —OC(O)R$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, N(R$^{11}$)$_2$, —NR$^{11}$COOR$^{11}$, —SO$_2$R$^{11}$, —SO$_2$NR$^{11}$COR$^{11}$, —SOR$^{11}$, —SO$_2$N(R$^{11}$)$_2$, or —SR$^{11}$, wherein each $R^4$ is optionally substituted with one or more $R^{4a}$,
  wherein each $R^{4a}$ is independently halogen, aryloxy, aralkyloxy, aryloxyalkyl, $C_1$-$C_6$ alkoxyaryl, aryl —$C_1$-$C_6$ alkyl-aryl, $C_0$-$C_6$ alkylcarboxy, -M', -E'-M', or -D'-E'-M'
    D' is —O—;
    E' is —[C($R^{15}$)$_2$]$_m$— or $C_3$-$C_8$ cycloalkyl;
    M' is —$C_1$-$C_6$alkyl, —$C_1$-$C_6$haloalkyl, COR$^{11}$, —CON(R$^{11}$)$_2$, —N(R$^{11}$)COOR$^{11}$, —N(R$^{11}$)$_2$, COOR$^{11}$, C≡N, OR$^{11}$, —NR$^{11}$COR$^{11}$, NR$^{11}$SO$_2$R$^{11}$, SO$_2$R$^{11}$, SO$_2$N(R$^{11}$)$_2$, or SR$^{11}$;
  each $R^{41}$ is independently halogen, nitro, $C_1$-$C_6$ alkyl-heterocyclyl, —$C_1$-$C_6$ alkyl-heteroaryl, —$C_1$-$C_6$ alkyl-aryl, -M", -E"-M", or -D"-E"-M", wherein
    D" is —O—;
    E" is —[C($R^{15}$)$_2$]$_m$— or $C_3$-$C_8$ cycloalkyl;
    M" is —$C_1$-$C_6$alkyl, —$C_1$-$C_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$,
  wherein each $R^{41}$ is optionally substituted with one or more $R^{4a}$;
$L^2$ is a bond, —CH═CHCOO—, —OC$_0$-C$_6$alkylCOO—, —[C(R$^{15}$)$_2$]$_m$—V$^2$—[C(R$^{15}$)$_2$]$_n$—, or —V$^2$—[C(R$^{15}$)$_2$]$_m$—V$^2$—, wherein
  n is 0-6; and
  each V$^2$ is independently —C(R$^{11}$)$_2$—, —C(R$^{11}$)$_2$—C(R$^{11}$)$_2$—, —C(R$^{11}$)═C(R$^{11}$)—, —C(R$^{11}$)$_2$NR$^{11}$—, —C(R$^{11}$)$_2$O—, —C≡C—, —O—, —S—, —N(R$^{10}$)CO—, —N(R$^{10}$)CO$_2$—, —CON(R$^{10}$)—, —CON(R$^{11}$)—, —CON(R$^{11}$)O—, —CO—, —CS—, —CO$_2$—, —OR$^{11}$N—, —OR$^{11}$COO—, —OC(═O)—, —OC(═O)N(R$^{10}$)—, —SO$_2$—, —N(R$^{10}$)SO$_2$—, —SO$_2$N(R$^{10}$)—, —NR$^{10}$CONR$^{10}$—, $C_3$-$C_8$ cycloalkyl, —C(═NR$^{11}$)—, —C(═NOR$^{11}$)—, —C(═NN(R$^{11}$)$_2$)—, —NR$^{10}$CSNR$^{10}$—, —C(O)-heterocyclyl, or cycloC$_{3-8}$haloalkyl, wherein the heterocyclyl is optionally substituted with one or more groups independently selected from —OR$^{11}$, —COOR$^{11}$, and —CON(R$^{11}$)$_2$;
or $L^2$ is a $C_{2-6}$ alidiyl chain, wherein alidiyl chain is optionally interrupted by —C(R$^{11}$)$_2$—, —C(R$^{11}$)$_2$C(R$^{11}$)$_2$—, —C(R$^{11}$)═C(R$^{11}$)—, —C(R$^{11}$)$_2$O—, —C(R$^{11}$)$_2$NR$^{11}$—, —C(R$^{11}$)$_2$NR$^{11}$—, C≡C—, —O—, —S—, —N(R$^{10}$)CO—, —N(R$^{10}$)CO$_2$—, —CON(R$^{10}$)—, —CON(R$^{11}$)—, —CON(R$^{11}$)O—, —CO—, —CO$_2$—, —OC(═O)—, —OC(═O)N(R$^{10}$)—, —SO$_2$—, —N(R$^{10}$)SO$_2$—, —SO$_2$N(R$^{10}$)—; aryl, $C_3$-$C_8$ cycloalkyl, heteroaryl, or heterocyclyl
  wherein the aryl, cycloalkyl, heteroaryl, or heterocyclyl is optionally substituted with one or more $R^9$, wherein each $R^9$ is independently halogen, $C_1$-$C_6$ haloalkyl, $C_1$-$C_6$ alkyl, $C_1$-$C_6$ alkyloxy, $C_0$-$C_6$ alkyl or $C_1$-$C_6$ alkylCOOR$^{11}$;
each m is independently 0, 1, 2, 3, 4, 5 or 6;
q is 0, 1, 2, 3, 4 or 5;
q' is 0, 1, 2, 3, or 4, and
(B) provided that,
  (i) q may be 0 only if $L^2$ is not a bond or if K is not phenyl;
  (ii) the compound is not 2-methyl-5-(1-m-tolyl-3-(trifluoromethyl)-1H-pyrazol-5-yl)benzenesulfonamide;
  (iii) if $L^2$ is a bond, then both J and K are not absent;
  (iv) if K is absent, then q is 1 and $R^4$ is bonded directly to $L^2$;
  (v) if $L^2$ is SO$_2$ or SO$_2$N(R$^{10}$), then $R^5$ is substituted with at least one $R^{5a}$;
  (vi) if the compound is defined by formula Ia, then
    (a) $R^1$ is not 4-(NH$_2$SO$_2$)phenyl, 4-(CH$_3$SO$_2$)phenyl, or 4-(CH$_2$FSO$_2$)phenyl;
    (b) if $R^1$ is 4-fluorophenyl, then G is not 4-[(H$_2$NS(═O)$_2$—]phenyl-; and
    (c) $R^2$ and $R^{21}$ are not 4-hydroxyphenyl;
  (vii) if the compound is defined by formula Ib, then
    (a) $R^2$ and $R^3$ are not 4-(NH$_2$SO$_2$)phenyl, 4-(CH$_3$SO$_2$)phenyl, or 4-(CH$_2$FSO$_2$)phenyl; and
    (b) $R^1$ is not 4-hydroxyphenyl;
  (viii) if the compound is defined by formula Ic, then
    (a) $R^2$ and $R^3$ are not 4-(NH$_2$SO$_2$)phenyl, 4-(CH$_3$SO$_2$)phenyl, or 4-(CH$_2$FSO$_2$)phenyl;
    (b) J is not pyridyl; and
    (c) G is not 3- or 4-methoxyphenyl; and
  (ix) if the compound is defined by formula Id, then
    (a) if $L^1$ is a bond, then $R^1$ is not thienyl or 5-methylthienyl;
    (b) G is not 4-(NH$_2$SO$_2$)phenyl, 4-(CH$_3$SO$_2$)phenyl, or 4-(CH$_2$FSO$_2$)phenyl;
    (c) if G is 4-fluorophenyl, then $R^1$ is not 4-[(H$_2$NS(═O)$_2$—]phenyl-;
    (d) if J═Ph, $L^2$ is a bond, and q is 1, than K and $R^4$ together are not 4-fluorophenyl, 3-fluorophenyl, 4-methoxyphenyl, or 5-chlorothienyl;
    (e) if J═pyridyl, $L^2$ is a bond, and q is 1, then K and $R^4$ together are not 4-fluorophenyl;
    (f) if J═Ph, $L^2$ is a bond, and q is 2, then K and both $R^4$ together are not 3-fluoro-4-methoxyphenyl; and
    (g) $R^1$ is not 4-Me-phenyl.
In one embodiment, the invention provides the compound according to formula Ia, Ib, Ic, or Id, wherein:
$R^1$ is -$L^1$-$R^5$, wherein
  $L^1$ is a bond, $L^5$, $L^6$, -$L^5$-$L^6$-$L^5$-, or -$L^6$-$L^5$-$L^6$-, wherein
    each $L^5$ is independently —[C(R$^{15}$)$_2$]$_m$—, wherein
      m is 0, 1, 2, 3, or 4; and
    each $R^{15}$ is independently hydrogen, halogen, ($C_1$-$C_6$) alkyl, or ($C_1$-$C_6$)haloalkyl; and
    $L^6$ is —CO—, —SO$_2$—, —O—, —CON(R$^{11}$)—, —$C_3$-$C_6$cycloalkyl-, or -heterocyclyl-,
      wherein the cycloalkyl, or heterocyclyl is optionally substituted with one or more $R^{14}$; and
  $R^5$ is aryl, heterocyclyl, heteroaryl, —C, or —B—C, wherein
    B is —[C(R$^{15}$)$_2$]$_m$— or —$C_3$-$C_6$cycloalkyl-; and
    C is halogen, —$C_1$-$C_6$alkyl, or —$C_1$-$C_6$haloalkyl;
wherein $R^5$ is optionally substituted with one or more $R^{5a}$, wherein
  each $R^{5a}$ is independently halogen, nitro, heteroaryl, heterocyclyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-; aryl, aralkyl, aryloxy, aryloxyaryl, arylC$_{1-6}$ alkoxy, $C_1$-$C_6$ alkyl, $C_1$-$C_6$ haloalkyl, $C_3$-$C_6$cycloalkyl, SO$_2$R$^{11}$, OR$^{11}$, SR$^{11}$, N$_3$, SO$_2$R$^{11}$, COR$^{11}$, SO$_2$N(R$^{11}$)$_2$, SO$_2$NR$^{11}$COR$^{11}$, C≡N, C(O)OR$^{11}$, CON(R$^{11}$)$_2$, CON(R$^{11}$)OR$^{11}$OCON(R$^{11}$)$_2$, NR$^{11}$COR$^{11}$, NR$^{11}$CON(R$^{11}$)$_2$, NR$^{11}$COOR$^{11}$, or N(R$^{11}$)$_2$, wherein
    each $R^{5a}$ is optionally substituted with one or more groups which independently are -halogen, —$C_1$-$C_6$ alkyl, aryloxy $C_{0-6}$ alkylSO$_2$R$^{11}$, $C_{0-6}$ alkylCOOR$^{11}$, $C_{0-6}$ alkoxyaryl, —$C_1$-$C_6$ haloalkyl, —SO$_2$R$^{11}$, —OR$^{11}$, —SR$^{11}$, —N$_3$, —SO$_2$R$^{11}$, —COR$^{11}$, —SO$_2$N(R$^{11}$)$_2$, —SO$_2$NR$^{11}$COR$^{11}$, —C(O)OR$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;

R$^2$ is -L$^3$-R$^7$, wherein
  L$^3$ is a bond; and
  R$^7$ is, halogen, aryl, heteroaryl, heterocyclyl, —Z, or —Y—Z, wherein
    Y is —[C(R$^{15}$)$_2$]$_m$— or —C$_3$-C$_6$cycloalkyl; and
    Z is —H, halogen, —OR$^{11}$, —C(=O)R$^{11}$, —C(=O)OR$^{11}$, —C(O)N(R$^{11}$)$_2$, —N(R$^{11}$)$_2$, —C(=N—OH)R$^{11}$, —C(=S)N(R$^{11}$)$_2$, —CN, —S(O)$_2$N(R$^{11}$)$_2$, —C(=O)N(R$^{11}$)N(R$^{11}$)$_2$, or —C(=O)N(R$^{11}$)(OR$^{11}$);
  wherein R$^7$ is optionally substituted with one or more R$^{7a}$, wherein
    R$^{7a}$ is halogen —Z', —Y'—Z', or —X'—Y'—Z', wherein
      X' is —O—;
      Y' is —[C(R$^{15}$)$_2$]$_m$— or —C$_3$-C$_6$cycloalkyl; and
      Z' is —H, halogen, —OR$^{11}$, —SR$^{11}$, —S(=O)$_2$R$^{11}$, —C(=O)R$^{11}$, —C(=O)OR$^{11}$, —C(=O)N(R$^{11}$)$_2$, —N(R$^{11}$)$_2$, —N(R$^{11}$)C(=O)R$^{11}$, —CN, —S(=O)$_2$N(R$^{11}$), —C(=O)N(R$^{11}$)(OR$^{11}$), or —N(R$^{11}$)S(O)$_2$R$^{11}$;

R$^{21}$ and R$^3$ are each independently hydrogen, halogen, C$_1$-C$_6$alkyl, or C$_1$-C$_6$haloalkyl; and G is a group of the formula,

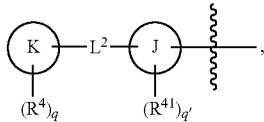

wherein
  J is aryl or heteroaryl;
  K is aryl or heteroaryl;
  each R$^4$ and R$^{41}$ are independently halogen, aryloxy, aralkyloxy, aryloxyalkyl, arylC$_0$-C$_6$ alkylcarboxy, aryl, heteroaryl, heterocyclyl, heteroaryloxy, heterocyclyloxy, -M, -E-M, or -D-E-M, wherein
    D is —O—;
    E is —[C(R$^{15}$)$_2$]$_m$— or —C$_3$-C$_6$cycloalkyl; and
    M is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$,
  L$^2$ is a bond;
  q is 1, 2, or 3; and
  q' is 0, 1, 2, or 3;

each R$^{10}$ is independently —R$^{11}$, —C(=O)R$^{11}$, —CO$_2$R$^{11}$, or —SO$_2$R$^{11}$;

each R$^{11}$ is independently -hydrogen, —C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-; C$_1$-C$^6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_3$-C$_8$ cycloalkyl, —C$_1$-C$_6$ haloalkyl, —N(R$^{12}$)$_2$, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl,
  wherein any of R$^{11}$ is optionally substituted with one or more radicals of R$^{12}$;
    each R$^{12}$ is independently halogen, C$_0$-C$_6$alkylN(R$^{13}$)$_2$, C$_1$-C$_6$haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_0$-C$_6$alkoxyaryl, arylC$_0$-C$_6$ alkylcarboxy, C$_0$-C$_6$ alkyl, —NR$^{13}$SO$_2$R$^{13}$, or —OC$_{0-6}$ alkylCOOR$^{13}$;

each R$^{13}$ is independently hydrogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-; and each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$alkylCONR$^{11}$OR$^{11}$, C$_0$-C$_6$alkylOR$^{11}$, or C$_0$-C$_6$ alkylCOOR$^{11}$.

In one embodiment, the invention provides the compound according to formula Ia, Ib, Ic, or Id, wherein:

R$^1$ is -L$^1$-R$^5$, wherein
  L$^1$ is a bond, —C$_3$-C$_8$ cycloalkyl- or L$^5$, wherein
    each L$^5$ is independently —[C(R$^{15}$)$_2$]$_m$—, wherein
      m is 0, 1, 2, or 3; and
    each R$^{15}$ is independently hydrogen, halogen, (C$_1$-C$_6$) alkyl, or (C$_1$-C$_6$)haloalkyl; and
  R$^5$ is aryl, heterocyclyl, heteroaryl, —C, or —B—C, wherein
    B is —[C(R$^{15}$)$_2$]$_m$—, —C$_3$-C$_6$cycloalkyl-; and
    C is —C$_1$-C$_6$alkyl or —C$_1$-C$_6$haloalkyl;
  wherein R$^5$ is optionally substituted with one or more R$^{5a}$, wherein
    each R$^{5a}$ is independently halogen, nitro, heteroaryl, heterocyclyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, aryl, aralkyl, aryloxy, aryloxyaryl, arylC$_{1-6}$ alkoxy, C$_1$-C$_6$ alkyl, C$_1$-C$_6$ haloalkyl, C$_3$-C$_6$cycloalkyl, SO$_2$R$^{11}$, OR$^{11}$, SR$^{11}$, N$_3$, SO$_2$R$^{11}$, COR$^{11}$, SO$_2$N(R$^{11}$)$_2$, SO$_2$NR$^{11}$COR$^{11}$, C≡N, C(O)OR$^{11}$, CON(R$^{11}$)$_2$, CON(R$^{11}$)OR$^{11}$OCON(R$^{11}$)$_2$, NR$^{11}$COR$^{11}$, NR$^{11}$CON(R$^{11}$)$_2$, NR$^{11}$COOR$^{11}$, or N(R$^{11}$)$_2$, wherein
      each R$^{5a}$ is optionally substituted with one or more groups which independently are -halogen, —C$_1$-C$_6$ alkyl, aryloxy, C$_{0-6}$ alkylSO$_2$R$^{11}$, C$_{0-6}$ alkylCOOR$^{11}$, C$_{0-6}$ alkoxyaryl, —C$_1$-C$_6$ haloalkyl, —SO$_2$R$^{11}$, —OR$^{11}$, —SR$^{11}$, —N$_3$, —SO$_2$R$^{11}$, —COR$^{11}$, —SO$_2$N(R$^{11}$)$_2$, —SO$_2$NR$^{11}$COR$^{11}$, —C≡N, —C(O)OR$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;

R$^2$ is -L$^3$-R$^7$, wherein
  L$^3$ is a bond; and
  R$^7$ is —Z or —Y—Z, wherein
    Y is —[C(R$^{15}$)$_2$]$_m$—, or —C$_3$-C$_6$cycloalkyl; and
    Z is —H, halogen, —OR$^{11}$, —C(O)R$^{11}$, —C(=O)OR$^{11}$, —C(=O)N(R$^{11}$)$_2$, —N(R$^{11}$)$_2$, —C(N—OH)R$^{11}$, —C(=S)N(R$^{11}$)$_2$, —CN, —S(=O)$_2$N(R$^{11}$)$_2$, —OC(=O)—R$^{11}$, or —OC(=O)—N(R$^{11}$)$_2$;

R$^{21}$ and R$^3$ are each independently hydrogen, halogen, C$_1$-C$_6$ alkyl, or C$_1$-C$_6$haloalkyl; and G is a group of the formula,

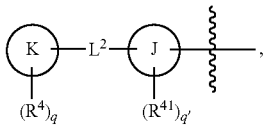

wherein
J is aryl or heteroaryl;
K is aryl or heteroaryl;
each $R^4$ and $R^{41}$ are independently halogen, heteroaryl, heterocyclyl, -M, -E-M, or -D-E-M, wherein
D is —O—;
E is —$[C(R^{15})_2]_m$— or —$C_3$-$C_6$cycloalkyl; and
M is —$C_1$-$C_6$alkyl, —$C_1$-$C_6$haloalkyl, —$COR^{11}$, —$COOR^{11}$, —$CON(R^{11})_2$, —C≡N, —$OR^{11}$, —$SOR^{11}$, —$SO_2R^{11}$, —$SO_2N(R^{11})_2$, or —$SR^{11}$,
$L^2$ is a bond;
q is 1, 2, or 3, and
q' is 0, 1, 2 or 3,
each $R^{10}$ is independently —$R^{11}$, —$C(=O)R^{11}$, —$CO_2R^{11}$, or —$SO_2R^{11}$;
each $R^{11}$ is independently -hydrogen, —$C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$cycloalkenyl)-$C_1$-$C_6$ alkyl-, ($C_3$-$C_8$ cycloalkyl)-$C_2$-$C_6$ alkenyl-, —$C_3$-$C_8$ cycloalkyl, —($C_1$-$C_6$)alkyl-($C_3$-$C_8$)cycloalkyl, —$C_1$-$C_6$ haloalkyl, —$N(R^{12})_2$, aryl, —($C_1$-$C_6$) alkyl-aryl, heteroaryl, —($C_1$-$C_6$)alkyl-heteroaryl, heterocyclyl, or —($C_1$-$C_6$)alkyl-heterocyclyl,
wherein any of $R^{11}$ is optionally substituted with one or more radicals of $R^{12}$;
each $R^{12}$ is independently halogen, $OR^{13}$, $N(R^{13})_2$, $C_1$-$C_6$haloalkyl, $C_1$-$C_6$ alkyl, $C_1$-$C_6$ alkoxy, ($C_0$-$C_6$ alkyl)C=O($OR^{13}$); $C_0$-$C_6$ alkyl$OR^{13}$, $C_0$-$C_6$ alkyl-$COR^{13}$, $C_0$-$C_6$ alkyl$SO_2R^{13}$, $C_0$-$C_6$ alkyl$CON(R^{13})_2$, $C_0$-$C_6$ alkyl$CONR^{13}OR^{13}$, $C_0$-$C_6$ alkyl$SO_2N(R^{13})_2$, $C_0$-$C_6$ alkyl$SR^{13}$, $C_0$-$C_6$ haloalkyl$OR^{13}$, aryloxy, aralkyloxy, aryloxyalkyl, $C_{0-6}$alkoxyaryl, aryl$C_{0-6}$ alkylcarboxy, $C_0$-$C_6$ alkyl, —$NR^{13}SO_2R^{13}$, or —$OC_{0-6}$ alkyl$COOR^{13}$;
each $R^{13}$ is independently hydrogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;
each $R^{14}$ is independently $C_1$-$C_6$ alkyl, $C_1$-$C_6$ alkoxy, halogen, $C_1$-$C_6$ haloalkyl, $C_0$-$C_6$ alkyl$CON(R^{11})_2$, $C_0$-$C_6$ alkyl$CONR^{11}OR^{11}$, $C_0$-$C_6$ alkyl$OR^{11}$, or $C_0$-$C_6$alkyl$COOR^{11}$.

In one embodiment, the invention provides the compound according to formula Ia or Id, wherein:
$R^1$ is -$L^1$-$R^5$, wherein
$L^1$ is a bond, $L^5$, $L^6$, -$L^5$-$L^6$-$L^5$-, or -$L^6$-$L^5$-$L^6$-, wherein
each $L^5$ is independently —$[C(R^{15})_2]_m$—, wherein
m is 0, 1, 2, 3, or 4; and
each $R^{15}$ is independently hydrogen, halogen, ($C_1$-$C_6$) alkyl, or ($C_1$-$C_6$)haloalkyl; and
$L^6$ is —CO—, —$SO_2$—, —O—, —$CON(R^{11})$—, —$C_3$-$C_6$cycloalkyl-, or -heterocyclyl-,
wherein the cycloalkyl, or heterocyclyl is optionally substituted with one or more $R^{14}$; and
$R^5$ is aryl, heterocyclyl, heteroaryl, —C, or —B—C, wherein B is —$[C(R^{15})_2]_m$— or —$C_3$-$C_6$cycloalkyl-; and
C is halogen, —$C_1$-$C_6$alkyl, or —$C_1$-$C_6$haloalkyl;
wherein $R^5$ is optionally substituted with one or more $R^{5a}$, wherein
each $R^{5a}$ is independently halogen, nitro, heteroaryl, heterocyclyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, aryl, aralkyl, aryloxy, aryloxyaryl, aryl$C_{1-6}$ alkoxy, $C_1$-$C_6$ alkyl, $C_1$-$C_6$ haloalkyl, $C_3$-$C_6$cycloalkyl, $SO_2R^{11}$, $OR^{11}$, $SR^{11}$, $N_3$, $SO_2R^{11}$, $COR^{11}$, $SO_2N(R^{11})_2$, $SO_2NR^{11}COR^{11}$, C≡N, C(O)$OR^{11}$, $CON(R^{11})_2$, $CON(R^{11})OR^{11}OCON(R^{11})_2$, $NR^{11}COR^{11}$, $NR^{11}CON(R^{11})_2$, $NR^{11}COOR^{11}$, or $N(R^{11})_2$, wherein
each $R^{5a}$ is optionally substituted with one or more groups which independently are -halogen, —$C_1$-$C_6$ alkyl, aryloxy $C_{0-6}$ alkyl$SO_2R^{11}$, $C_{0-6}$ alkyl$COOR^{11}$, $C_{0-6}$ alkoxyaryl, —$C_1$-$C_6$ haloalkyl, —$SO_2R^{11}$, —$OR^{11}$, —$SR^{11}$, —$N_3$, —$SO_2R^{11}$, —$COR^{11}$, —$SO_2N(R^{11})_2$, —$SO_2NR^{11}COR^{11}$, —C≡N, —C(O)$OR^{11}$, —$CON(R^{11})_2$, —$CON(R^{11})OR^{11}$, —$OCON(R^{11})_2$, —$NR^{11}COR^{11}$, —$NR^{11}CON(R^{11})_2$, —$NR^{11}COOR^{11}$, or —$N(R^{11})_2$;
$R^2$ is -$L^3$-$R^7$, wherein $L^3$ is a bond; and
$R^7$ is, halogen, aryl, heteroaryl, heterocyclyl, —Z, or —Y—Z, wherein
Y is —$[C(R^{15})_2]_m$— or —$C_3$-$C_6$cycloalkyl; and
Z is —H, halogen, $OR^{11}$, —$C(=O)R^{11}$, —C(=O)$OR^{11}$, —$C(=O)N(R^{11})_2$, —$N(R^{11})_2$, —C(=N—OH)$R^{11}$, —$C(=S)N(R^{11})_2$, —CN, —$S(=O)_2N(R^{11})_2$, —$C(=O)N(R^{11})N(R^{11})_2$, or —C(O)N($R^{11}$)($OR^{11}$);
wherein $R^7$ is optionally substituted with one or more $R^{7a}$, wherein
$R^{7a}$ is halogen, —Z', —Y'—Z', or —X'—Y'—Z', wherein
X' is —O—;
Y' is —$[C(R^{15})_2]_m$— or —$C_3$-$C_6$cycloalkyl; and
Z' is —H, halogen, —$OR^{11}$, —$SR^{11}$, —$S(=O)_2R^{11}$, —$C(=O)R^{11}$, —$C(=O)OR^{11}$, —$C(=O)N(R^{11})_2$, —$N(R^{11})_2$, —$N(R^{11})C(=O)R^{11}$, —CN, —$S(=O)_2N(R^{11})_2$, —$C(=O)N(R^{11})(OR^{11})$, or —$N(R^{11})S(O=)_2R^{11}$;
$R^{21}$ is hydrogen, halogen, $C_1$-$C_6$alkyl, or $C_1$-$C_6$haloalkyl; and
G is a group of the formula,

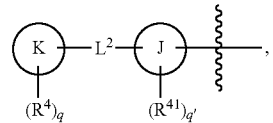

wherein
J is aryl or heteroaryl;
K is aryl or heteroaryl;
each $R^4$ and $R^{41}$ are independently halogen, aryloxy, aralkyloxy, aryloxyalkyl, aryl$C_0$-$C_6$ alkylcarboxy, aryl, heteroaryl, heterocyclyl, heteroaryloxy, heterocyclyloxy, -M, -E-M, or -D-E-M, wherein
D is —O—;
E is —$[C(R^{15})_2]_m$— or —$C_3$-$C_6$cycloalkyl; and
M is —$C_1$-$C_6$alkyl, —$COR^{11}$, —$COOR^{11}$, —$CON(R^{11})_2$, —C≡N, —$OR^{11}$, —$OCON(R^{11})_2$, —$NR^{11}COR^{11}$, —$NR^{11}SO_2R^{11}$, —$N(R^{11})_2$, —$NR^{11}COOR^{11}$, —$SOR^{11}$, —$SO_2R^{11}$, —$SO_2NR^{11}COR^{11}$, —$SO_2N(R^{11})_2$, or —$SR^{11}$, $L^2$ is a bond;
q is 1, 2, or 3; and
q' is 0, 1, 2, or 3;
each $R^{10}$ is independently —$R^{11}$, —C(=O)$R^{11}$, —CO$_2R^{11}$, or —SO$_2R^{11}$;
each $R^{11}$ is independently -hydrogen, —$C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, —$C_3$-$C_8$ cycloalkyl, —$C_1$-$C_6$ haloalkyl, —N($R^{12}$)$_2$, aryl, ($C_1$-$C_6$)alkyl-aryl, heteroaryl, —($C_1$-$C_6$)alkyl-heteroaryl, heterocyclyl, or —($C_1$-$C_6$)alkyl-heterocyclyl,
wherein any of $R^{11}$ is optionally substituted with one or more radicals of $R^{12}$;
each $R^{12}$ is independently halogen, $C_0$-$C_6$alkylN($R^{13}$)$_2$, $C_1$-$C_6$haloalkyl, $C_1$-$C_6$ alkyl, $C_1$-$C_6$ alkoxy, ($C_0$-$C_6$ alkyl)C=O(O$R^{13}$); $C_0$-$C_6$ alkylO$R^{13}$, $C_0$-$C_6$ alkylCO$R^{13}$, $C_0$-$C_6$ alkylSO$_2R^{13}$, $C_0$-$C_6$ alkylCON($R^{13}$)$_2$, $C_0$-$C_6$ alkylCON$R^{13}$O$R^{13}$, $C_0$-$C_6$ alkylSO$_2$N($R^{13}$)$_2$, $C_0$-$C_6$ alkylS$R^{13}$, $C_0$-$C_6$ haloalkylO$R^{13}$, aryloxy, aralkyloxy, aryloxyalkyl, $C_{0-6}$alkoxyaryl, aryl$C_{0-6}$alkylcarboxy, $C_0$-$C_6$ alkyl, —N$R^{13}$SO$_2R^{13}$, or —O$C_{0-6}$ alkylCOO$R^{13}$;
each $R^{13}$ is independently hydrogen $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-; and
each $R^{14}$ is independently $C_1$-$C_6$ alkyl, $C_1$-$C_6$ alkoxy, halogen, $C_1$-$C_6$ haloalkyl, $C_0$-$C_6$ alkylCON($R^{11}$)$_2$, $C_0$-$C_6$ alkylCON$R^{11}$O$R^{11}$, $C_0$-$C_6$ alkylO$R^{11}$, or $C_0$-$C_6$ alkylCOO$R^{11}$.

In one embodiment, the invention provides the compound according to formula Ia or Id, wherein:
$R^1$ is -$L^1$-$R^5$, wherein
$L^1$ is a bond, —$C_3$-$C_8$ cycloalkyl-, or $L^5$, wherein
each $L^5$ is independently —[C($R^{15}$)$_2$]$_m$—, wherein
m is 0, 1, 2, or 3; and
each $R^{15}$ is independently hydrogen, halogen, ($C_1$-$C_6$) alkyl, or ($C_1$-$C_6$)haloalkyl; and
$R^5$ is aryl, heterocyclyl, heteroaryl, —C, or —B—C, wherein
B is —[C($R^{15}$)$_2$]$_m$— or —$C_3$-$C_6$cycloalkyl-; and
C is —$C_1$-$C_6$alkyl or —$C_1$-$C_6$haloalkyl;
wherein $R^5$ is optionally substituted with one or more $R^{5a}$, wherein
each $R^{5a}$ is independently halogen, nitro, heteroaryl, heterocyclyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl, aryl, arylalkyl, aryloxy, aryloxyaryl, aryl$C_{1-6}$ alkoxy, $C_1$-$C_6$ alkyl, $C_1$-$C_6$ haloalkyl, $C_3$-$C_6$cycloalkyl, SO$_2R^{11}$, O$R^{11}$, S$R^{11}$, N$_3$, SO$_2R^{11}$, CO$R^{11}$, SO$_2$N($R^{11}$)$_2$, SO$_2$N$R^{11}$CO$R^{11}$, C=N, C(O)O$R^{11}$, CON($R^{11}$)$_2$, CON($R^{11}$)O$R^{11}$OCON($R^{11}$)$_2$, N$R^{11}$CO$R^{11}$, N$R^{11}$CON($R^{11}$)$_2$, N$R^{11}$COO$R^{11}$, or N($R^{11}$)$_2$, wherein
each $R^{5a}$ is optionally substituted with one or more groups which independently are -halogen, —$C_1$-$C_6$ alkyl, aryloxy, $C_{0-6}$ alkylSO$_2R^{11}$, $C_{0-6}$ alkylCOO$R^{11}$, $C_{0-6}$ alkoxyaryl, —$C_1$-$C_6$ haloalkyl, —SO$_2R^{11}$, —O$R^{11}$, —S$R^{11}$, —N$_3$, —SO$_2R^{11}$, —CO$R^{11}$, —SO$_2$N($R^{11}$)$_2$, —SO$_2$N$R^{11}$CO$R^{11}$, —C=N, —C(O)O$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, or —N($R^{11}$)$_2$;
$R^2$ is -$L^3$-$R^7$, wherein
$L^3$ is a bond; and
$R^7$ is —Z or —Y—Z, wherein
Y is —[C($R^{15}$)$_2$]$_m$— or —$C_3$-$C_6$cycloalkyl; and Z is —H, halogen, —O$R^{11}$, —C(=O)$R^{11}$, —C(=O)O$R^{11}$, —C(=O)N($R^{11}$)$_2$, —N($R^{11}$)$_2$, —C(=N—OH)$R^{11}$, —C(=S)N($R^{11}$)$_2$, —CN, —S(O)$_2$N($R^{11}$)$_2$, —OC(=O)—$R^{11}$, or —OC(=O)—N($R^{11}$)$_2$;
$R^{21}$ is hydrogen, halogen, $C_1$-$C_6$ alkyl, or $C_1$-$C_6$ haloalkyl; and
G is a group of the formula,

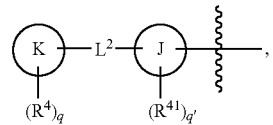

wherein
J is aryl or heteroaryl;
K is aryl or heteroaryl;
each $R^4$ and $R^{41}$ are independently halogen, heteroaryl, heterocyclyl, -M, -E-M, or D-E-M, wherein
D is —O—;
E is —[C($R^{15}$)$_2$]$_m$— or —$C_3$-$C_6$cycloalkyl; and
M is —$C_1$-$C_6$alkyl, —$C_1$-$C_6$haloalkyl, —CO$R^{11}$, —COO$R^{11}$, —CON($R^{11}$)$_2$, —C=N, —O$R^{11}$, —SO$R^{11}$, —SO$_2R^{11}$, —SO$_2$N($R^{11}$)$_2$, or —S$R^{11}$;
$L^2$ is a bond;
q is 1, 2, or 3, and
q' is 0, 1, 2 or 3,
each $R^{10}$ is independently —$R^{11}$, —C(=O)$R^{11}$, —CO$_2R^{11}$, or —SO$_2R^{11}$;
each $R^{11}$ is independently -hydrogen, —$C_1$-$C_6$ alkyl, $C_2$-$C_6$ alkenyl, $C_2$-$C_6$alkynyl, ($C_3$-$C_8$ cycloalkyl)-$C_1$-$C_6$ alkyl-, ($C_3$-$C_8$ cycloalkenyl)-$C_1$-$C_6$alkyl-, ($C_3$-$C_8$ cycloalkyl)-$C_2$-$C_6$ alkenyl-$C_3$-$C_8$ cycloalkyl, —$C_1$-$C_6$ haloalkyl, —N($R^{12}$)$_2$, aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl,
wherein any of $R^{11}$ is optionally substituted with one or more radicals of $R^{12}$;
each $R^{12}$ is independently halogen, O$R^{13}$, N($R^{13}$)$_2$, $C_1$-$C_6$haloalkyl, $C_1$-$C_6$ alkyl, $C_1$-$C_6$ alkoxy, ($C_0$-$C_6$ alkyl)C=O(O$R^{13}$); $C_0$-$C_6$ alkylO$R^{13}$, $C_0$-$C_6$ alkylCO$R^{13}$, $C_0$-$C_6$ alkylSO$_2R^{13}$, $C_0$-$C_6$ alkylCON($R^{13}$)$_2$, $C_0$-$C_6$ alkylCON$R^{13}$O$R^{13}$, $C_0$-$C_6$ alkylSO$_2$N($R^{13}$)$_2$, $C_0$-$C_6$ alkylS$R^{13}$, $C_0$-$C_6$ haloalkylO$R^{13}$, aryloxy, aralkyloxy, aryloxyalkyl, $C_{0-6}$alkoxyaryl, aryl$C_{0-6}$ alkylcarboxy, $C_0$-$C_6$ alkyl, —N$R^{13}$SO$_2R^{13}$, or —O$C_{0-6}$ alkylCOO$R^{13}$;
each $R^{13}$ is independently hydrogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;
each $R^{14}$ is independently $C_1$-$C_6$ alkyl, $C_1$-$C_6$ alkoxy, halogen, $C_1$-$C_6$ haloalkyl, $C_0$-$C_6$ alkylCON($R^{11}$)$_2$, $C_0$-$C_6$ alkylCON$R^{11}$O$R^{11}$, $C_0$-$C_6$ alkylO$R^{11}$, or $C_0$-$C_6$alkylCOO$R^{11}$.

In another embodiment, the invention provides the compound according to formulas Ia-d, wherein
$R^1$ is -$L^5$-$R^5$ or -$L^6$-$R^5$ wherein
$L^5$ is —[C($R^{15}$)$_2$]$_m$—;
$L^6$ is $C_3$-$C_8$ cycloalkyl, cyclo$C_{3-8}$ haloalkyl, or heterocyclyl, wherein the cycloalkyl, cyclo$C_{3-8}$haloalkyl 1, or heterocyclyl are optionally substituted with one or more radicals of $R^{14}$;
$R^5$ is aryl, heterocyclyl, or heteroaryl, wherein $R^5$ is optionally substituted with one or more $R^{5a}$, wherein each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C', or -A'-B'—C' wherein A' is —O—;

B' is —[C($R^{15}$)$_2$]$_m$— or —$C_3$-$C_8$ cycloalkyl-;

C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl.

In another embodiment, the invention provides the compound according to formulas Ia-d, wherein $R^1$ is -$L^5$-$R^5$ or -$L^6$-$R^5$ wherein $L^5$ is —[C($R^{15}$)$_2$]$_m$—;

$L^6$ is $C_3$-$C_8$ cycloalkyl, cyclo$C_{3-8}$haloalkyl, or heterocyclyl, wherein the cycloalkyl, cyclo$C_{3-8}$haloalkyl, or heterocyclyl are optionally substituted with one or more radicals of $R^{14}$;

$R^5$ is aryl, heterocyclyl, or heteroaryl, wherein $R^5$ is optionally substituted with one or more $R^{5a}$, wherein each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C', or -A'-B'—C' wherein A' is —O—;

B' is —[C($R^{15}$)$_2$]$_m$— or —$C_3$-$C_8$ cycloalkyl-;

C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl; and J is aryl or heteroaryl; and K is aryl or heteroaryl.

In another embodiment, the invention provides the compound according to formulas Ia-d, wherein $R^1$ is -$L^5$-$R^5$ or -$L^6$-$R^5$ wherein $L^5$ is —[C($R^{15}$)$_2$]$_m$—;

$L^6$ is $C_3$-$C_8$ cycloalkyl, cyclo$C_{3-8}$haloalkyl, or heterocyclyl, wherein the cycloalkyl, cyclo$C_{3-8}$haloalkyl, or heterocyclyl are optionally substituted with one or more radicals of $R^{14}$;

$R^5$ is aryl, heterocyclyl, or heteroaryl, wherein $R^5$ is optionally substituted with one or more $R^{5a}$, wherein each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C, or -A'-B'—C wherein A' is —O—;

B' is —[C($R^{15}$)$_2$]$_m$- or —$C_3$-$C_8$cycloalkyl-;

C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl;

J is aryl or heteroaryl;

K is aryl or heteroaryl;

$R^2$ is -$L^3$-$R^7$, wherein $L^3$ is a bond; and $R^7$ is hydrogen, —Z, or —Y—Z, wherein Y is —[C($R^{15}$)$_2$]$_m$— or —$C_2$-$C_6$ alkenyl;

Z is —H, halogen, —O$R^{11}$, —C(=O)O$R^{11}$, —C(=O)N($R^{11}$)$_2$, —N($R^{11}$)$_2$, —CN, —SO$_2$$R^{11}$, or —S(=O)$_2$N($R^{11}$)$_2$; and $R^{21}$ is hydrogen, halogen, $C_1$-$C_6$ alkyl, or $C_1$-$C_6$ haloalkyl.

In another embodiment, the invention provides the compound according to formulas Ia and Id.

In another embodiment, the invention provides the compound according to formulas Ia and Id, wherein $R^1$ is -$L^5$-$R^5$ or -$L^6$-$R^5$ wherein $L^5$ is —[C($R^{15}$)$_2$]$_m$—;

$L^6$ is $C_3$-$C_8$ cycloalkyl, cyclo$C_{3-8}$haloalkyl, or heterocyclyl, wherein the cycloalkyl, cyclo$C_{3-8}$haloalkyl, or heterocyclyl are optionally substituted with one or more radicals of $R^{14}$;

$R^5$ is aryl, heterocyclyl, or heteroaryl, wherein $R^5$ is optionally substituted with one or more $R^{5a}$, wherein each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C', or -A'-B'—C' wherein A' is —O—;

B' is —[C($R^{15}$)$_2$]$_m$— or —$C_3$-$C_8$ cycloalkyl-;

C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl.

In another embodiment, the invention provides the compound according to formulas Ia and Id, wherein $R^1$ is -$L^5$-$R^5$ or -$L^6$-$R^5$ wherein $L^5$ is —[C($R^{15}$)$_2$]$_m$—;

$L^6$ is $C_3$-$C_8$ cycloalkyl, cyclo$C_{3-8}$haloalkyl, or heterocyclyl, wherein the cycloalkyl, cyclo$C_{3-8}$haloalkyl, or heterocyclyl are optionally substituted with one or more radicals of $R^{14}$;

$R^5$ is aryl, heterocyclyl, or heteroaryl, wherein $R^5$ is optionally substituted with one or more $R^{5a}$, wherein each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C', or -A-B'—C' wherein A' is —O—;

B' is —[C($R^{15}$)$_2$]$_m$— or —$C_3$-$C_8$ cycloalkyl-;

C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl; and J is aryl or heteroaryl; and K is aryl or heteroaryl.

In another embodiment, the invention provides the compound according to formulas Ia and Id, wherein
$R^1$ is -$L^5$-$R^5$ or -$L^6$-$R^5$ wherein
  $L^5$ is —[C($R^{15}$)$_2$]$_m$—;
  $L^6$ is $C_3$-$C_8$ cycloalkyl, cyclo$C_{3-8}$haloalkyl, or heterocyclyl, wherein the cycloalkyl, cyclo$C_{3-8}$haloalkyl, or heterocyclyl are optionally substituted with one or more radicals of $R^{14}$;
  $R^5$ is aryl, heterocyclyl, or heteroaryl, wherein $R^5$ is optionally substituted with one or more $R^{5a}$, wherein each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$alkoxy, —C', —B'—C', or -A'-B'—C' wherein
    A' is —O—;
    B' is —[C($R^{15}$)$_2$]$_m$— or —$C_3$-$C_8$ cycloalkyl-;
    C' is —H, halogen, —SO$_2R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, N($R^{11}$)$_2$, aryl, heteroaryl, or heterocyclyl;
  J is aryl or heteroaryl;
  K is aryl or heteroaryl;
  $R^2$ is -$L^3$-$R^7$, wherein
    $L^3$ is a bond; and
    $R^7$ is hydrogen, —Z, or —Y—Z, wherein
    Y is —[C($R^{15}$)$_2$]$_m$— or —$C_2$-$C_6$ alkenyl;
    Z is —H, halogen, —O$R^{11}$, —C(O)O$R^{11}$, —C(=O)N($R^{11}$)$_2$, —N($R^{11}$)$_2$, —CN, —SO$_2R^{11}$, or —S(=O)$_2$N($R^{11}$)$_2$; and
  $R^{21}$ is hydrogen, halogen, $C_1$-$C_6$ alkyl, or $C_1$-$C_6$ haloalkyl; such compounds are referred to hereafter and compounds of formula XL.

In another embodiment, the invention provides the compound according to formula XL, wherein J and K are both phenyl.

In another embodiment, the invention provides the compound according to formula XL, wherein J and K are both phenyl; and
  $R^5$ is aryl or heteroaryl, wherein $R^5$ is optionally substituted with one or more $R^{5a}$.

In another embodiment, the invention provides the compound according to formula XL, wherein J and K are both phenyl; and
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or In another embodiment, the invention provides the compound according to formula XL, wherein J and K are both phenyl;
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$; and
each $R^4$ is independently halogen, aryl, heteroaryl, heterocyclyl, -M, or -E-M, wherein
  E is —[C($R^{15'}$)$_2$]$_m$—, wherein
    each $R^{15'}$ is independently hydrogen or halogen; and M is —$C_1$-$C_6$alkyl, —$C_1$-$C_6$haloalkyl, halogen, —O$R^{11}$, or —SO$_2R^{11}$.

In another embodiment, the invention provides the compound according to formula XL, wherein J and K are both phenyl; and
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$ In another embodiment, the invention provides the compound according to formula XL, wherein J and K are both phenyl;
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$;
  and
  each $R^{41}$ is independently halogen, -M", or -E"-M", wherein
    E" is —[C($R^{15'}$)$_2$]$_{m'}$—,
      wherein each $R^{15'}$ is independently hydrogen or halogen; and
    M" is —$C_1$-$C_6$alkyl, —$C_1$-$C_6$haloalkyl, or halogen.

In another embodiment, the invention provides the compound according to formula XL, wherein J and K are both phenyl; and
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$.

In another embodiment, the invention provides the compound according to formula XL, wherein J and K are both phenyl;
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$;
  and
$R^7$ is hydrogen, —Z, or —Y—Z, wherein
  Y is —[C($R^{15}$)$_2$]$_{m'}$— or —$C_2$-$C_6$ alkenyl, wherein
    m' is 0, 1, or 2; and
  Z is —H, halogen, —O$R^{11}$, —C(=O)$R^{11}$, —C(=O)N($R^{11}$)$_2$, —N($R^{11}$)$_2$, —CN, —SO$_2R^{11}$, or —S(=O)$_2$N($R^{11}$)$_2$;
  and $R^{21}$ is hydrogen.

In another embodiment, the invention provides the compound according to formula XL, wherein J is heteroaryl and K is phenyl.

In another embodiment, the invention provides the compound according to formula XL, wherein J is pyrroyl, thienyl, furyl, thiazoyl, oxazoyl, or pyrazoyl, and K is phenyl.

In another embodiment, the invention provides the compound according to formula XL, wherein J is pyrroyl, thienyl, furyl, thiazoyl, oxazoyl, or pyrazoyl, and K is phenyl; and
  $R^5$ is aryl or heteroaryl,
    wherein $R^5$ is optionally substituted with one or more R.

In another embodiment, the invention provides the compound according to formula XL, wherein J is pyrroyl, thienyl, furyl, thiazoyl, oxazoyl, or pyrazoyl, and K is phenyl; and
  $R^5$ is phenyl optionally substituted with one or more $R^{5a}$, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$.

In another embodiment, the invention provides the compound according to formula XL, wherein J is pyrroyl, thienyl, furyl, thiazoyl, oxazoyl, or pyrazoyl, and K is phenyl; and R⁵ is phenyl optionally substituted with one or more R⁵ᵃ, wherein each R⁵ᵃ is independently -halogen, —C₁-C₆alkyl, —C₁-C₆haloalkyl, —OR¹¹, —COR¹¹, —C≡N, —C(O)OR¹¹, —CON(R¹¹)₂, or —N(R¹¹)₂; and each R⁴ is independently halogen, aryl, heteroaryl, heterocyclyl, -M, or -E-M, wherein
E is —[C(R¹⁵')₂]ₘ—, wherein
each R¹⁵' is independently hydrogen or halogen; and
M is —C₁-C₆alkyl, —C₁-C₆haloalkyl, halogen, —OR¹¹, or —SO₂R¹¹.

In another embodiment, the invention provides the compound according to formula XL, wherein J is pyrroyl, thienyl, furyl, thiazoyl, oxazoyl, or pyrazoyl, and K is phenyl; and
R⁵ is phenyl optionally substituted with one or more R⁵ᵃ, wherein each R⁵ᵃ is independently -halogen, —C₁-C₆alkyl, —OR¹¹, —COR¹¹, —C≡N, —C(O)OR¹¹, —CON(R¹¹)₂, or —N(R¹¹)₂; and
each R⁴¹ is independently halogen, -M", or -E"-M", wherein
E" is —[C(R¹⁵')₂]ₘ"—,
wherein each R¹⁵' is independently hydrogen or halogen; and
M" is —C₁-C₆alkyl, —C₁-C₆haloalkyl, or halogen.

In another embodiment, the invention provides the compound according to formula XL, wherein J is pyrroyl, thienyl, furyl, thiazoyl, oxazoyl, or pyrazoyl, and K is phenyl; and
R⁵ is phenyl optionally substituted with one or more R⁵ᵃ, wherein each R⁵ᵃ is independently -halogen, —C₁-C₆alkyl, —C₁-C₆haloalkyl, —OR¹¹, —COR¹¹, —C≡N, —C(O)OR¹¹, —CON(R¹¹)₂, or —N(R¹¹)₂; and
R⁷ is hydrogen, —Z, or —Y—Z, wherein
Y is —[C(R¹⁵')₂]ₘ'— or —C₂-C₆ alkenyl, wherein m' is 0, 1, or 2; and
Z is —H, halogen, —OR¹¹, —C(=O)R¹¹, —C(=O)OR¹¹, —C(=O)N(R¹¹)₂, —N(R¹¹)₂, —CN, —SO₂R¹¹, or —S(D)₂N(R¹¹)₂;
and R²¹ is hydrogen.

In an embodiment of the fast aspect, the invention provides the compound according to formulas Ia-d, wherein J is phenyl.

In other embodiments, the invention provides a compound according to formula Ia, Ib, Ic, or Id.

In another embodiment, the invention provides the compound according to any one of formulas Ia-d, wherein K is phenyl or pyridyl.

In another embodiment, the invention provides the compound according to any one of formulas Ia-d, wherein J and K are phenyl.

In another embodiment, the invention provides the compound according to formula II,

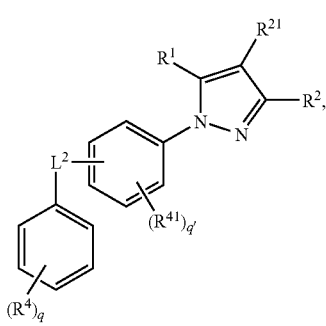

(II)

or a pharmaceutically acceptable salt, isomer, or prodrug thereof, wherein R¹, R², R²¹, R⁴, R⁴¹, L², q, and q' are as defined in formulas Ia-d.

In another embodiment, the invention provides the compound according to formula III

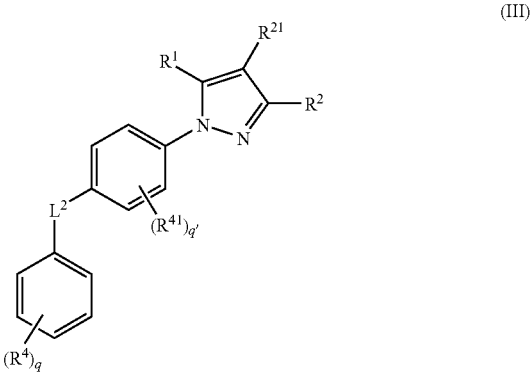

(III)

or a pharmaceutically acceptable salt, isomer, or prodrug thereof, wherein R¹, R², R²¹, R⁴, R⁴¹, L², q, and q' are as defined in formulas Ia-d.

In another embodiment, the invention provides the compound according to formula III wherein L² is a bond; such compounds are referred to hereafter as compounds of formula IV.

In another embodiment, the invention provides the compound according to formula IV, wherein R⁵ is pyridyl optionally substituted with one or more R.

In another embodiment, the invention provides the compound according to formula IV, wherein R⁵ is pyridyl optionally substituted with one or more R⁵ᵃ; and each R⁵ᵃ is independently -halogen, —C₁-C₆alkyl, —C₁-C₆haloalkyl, —OR¹¹, —COR¹¹, —C≡N, —C(O)OR¹¹, —CON(R¹¹)₂, or —N(R¹¹)₂.

In another embodiment, the invention provides the compound according to formula IV, wherein R⁵ is pyridyl optionally substituted with one or more R⁵ᵃ; and each R⁴¹ is independently hydrogen, halogen, —C₁-C₆alkyl, or —C₁-C₆haloalkyl.

In another embodiment, the invention provides the compound according to formula IV, wherein R⁵ is pyridyl optionally substituted with one or more R⁵ᵃ; and R² is -L³-R⁷, wherein
L³ is a bond or —C(R¹¹")₂; and
R⁷ is hydrogen, halogen, —C₁-C₆alkyl, —C₁-C₆haloalkyl, —OR¹¹", —C(=O)R¹¹", —C(=O)OR¹¹", —C(=O)N(R¹¹")₂, —N(R¹¹")₂, —CN, SO₂R¹¹", or —S(=O)₂N(R¹¹")₂,
wherein each R¹¹" is independently —H or —C₁-C₆alkyl.

In another embodiment, the invention provides the compound according to formula IV, wherein R⁵ is pyridyl optionally substituted with one or more R⁵ᵃ; and each R⁴ is independently halogen —C₁-C₆alkyl, —C₁-C₆haloalkyl, —COR¹¹', —COOR¹¹', —CON(R¹¹')₂, —C≡N, —OR¹¹', —N(R¹¹')₂, —SO₂R¹¹', or —SO₂N(R¹¹')₂, wherein each R¹¹' is independently -hydrogen, —C₁-C₆ alkyl, or —C₁-C₆ haloalkyl.

In another embodiment, the invention provides the compound according to formula III wherein L¹ is a bond and R⁵ is phenyl optionally substituted with one or more R⁵ᵃ

In another embodiment, the invention provides the compound according to formula IV, wherein L¹ is a bond and R⁵ is phenyl optionally substituted with one or more $R^{5a}$; such compounds are referred to hereafter as compounds of formula V.

In another embodiment, the invention provides the compound according to formula V, wherein each $R^{5a}$ is independently halogen —C', or —B'—C', wherein
B' is —[C($R^{15'}$)$_2$]$_m$—, wherein
each $R^{15'}$ is independently —H or -halogen; and
C' is —H, -halogen, —SO$_2$R$^{11}$, —OR$^{11}$, —COR$^{11}$, —SO$_2$N(R$^{11}$)$_2$, —C≡N, —C(O)OR$^{11}$, —CON(R$^{11}$)$_2$, or —N(R$^{11}$)$_2$.

In another embodiment, the invention provides the compound according to formula V, wherein each $R^{5a}$ is independently -halogen, —C$_1$-C$_6$alkyl, —C$_1$-C$_6$haloalkyl, —OR$^{11}$, —COR$^{11}$, —C≡N, —C(O)OR$^{11}$, —CON(R$^{11}$)$_2$, or —N(R$^{11}$)$_2$; such compounds are referred to hereafter as compounds of formula Va.

In another embodiment, the invention provides the compound according to formula V, wherein each $R^{41}$ is independently hydrogen, halogen, —C$_1$-C$_6$alkyl, —C$_1$-C$_6$haloalkyl, —COR$^{16}$, —COOR$^{16}$, —CON(R$^{16}$)$_2$, —C≡N, —OR$^{16}$, —N(R$^{16}$)$_2$, wherein each $R^{16}$ is independently hydrogen, —C$_1$-C$_6$ alkyl, or —C$_1$-C$_6$ haloalkyl.

In another embodiment, the invention provides the compound according to formula V, wherein each $R^{41}$ is independently hydrogen, halogen, —C$_1$-C$_6$alkyl, or —C$_1$-C$_6$haloalkyl; such compounds are referred to hereafter as compounds of formula Vb.

In another embodiment, the invention provides the compound according to formula V, wherein each $R^4$ is independently halogen, nitro, C$_1$-C$_6$alkyl, C$_1$-C$_6$haloalkyl, —COOR$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SO$_2$R$^{11}$, —SO$_2$NR$^{11}$COR$^{11}$, —SO$_2$N(R$^{11}$)$_2$, or —SR$^{11}$.

In another embodiment, the invention provides the compound according to formula V, wherein each $R^4$ is independently halogen, nitro, C$_1$-C$_6$alkyl, C$_1$-C$_6$haloalkyl, —COR$^{11}$, —COOR$^{11}$, —CON(R$^{11}$)$_2$, —C≡N, —OR$^{11}$, —N(R$^{11}$)$_2$, SO$_2$R$^{11}$, or —SO$_2$N(R$^{11}$)$_2$; such compounds are referred to hereafter as compounds of formula Vc.

In another embodiment, the invention provides the compound according to formula V, wherein $R^2$ is -L$^3$-R$^7$, wherein
L$^3$ is a bond; and R$^7$ is hydrogen, halogen, nitro, cyano, —Z, or —Y—Z, wherein
Y is —[C(R$^{15}$)$_2$]$_m$—;
Z is —H, halogen, —OR$^{11}$, —C(=O)R$^{11}$, —C(=O)OR$^{11}$, —C(=O)N(R$^{11}$)$_2$, —N(R$^{11}$)$_2$, —CN, —SO$_2$R$^{11}$, —S(=O)$_2$N(R$^{11}$)$_2$, —C(=O)N(R$^{11}$)$_2$, —C(=O)N(R$^{11}$)(OR$^{11}$), —OC(=O)—R$^{11}$, or —OC(=O)N(R$^{11}$)$^2$.

In another embodiment, the invention provides the compound according to formula V, wherein $R^2$ is -L$^3$-R$^7$, wherein
L$^3$ is a bond; and R$^7$ is hydrogen, halogen, —Z, or —Y—Z, wherein
Y is —[C(R$^{15}$)$_2$]$_m$—, wherein
Z is —H, halogen, —OR$^{11}$, —C(=O)R$^{11}$, —C(=O)OR$^{11}$, —C(=O)N(R$^{11}$)$_2$, —CN, —SO$_2$R$^{11}$, or —S(=O)$_2$N(R$^{11}$)$_2$;
such compounds are referred to hereafter as compounds of formula Vd.

In another embodiment, the invention provides the compound according to formula Va, wherein each $R^{41}$ is independently hydrogen, halogen, —C$_1$-C$_6$alkyl, or —C$_1$-C$_6$haloalkyl; such compounds are referred to hereafter as compounds of formula Ve.

In another embodiment, the invention provides the compound according to formula Vb, wherein each $R^4$ is independently halogen, nitro, C$_1$-C$_6$alkyl, C$_1$-C$_6$haloalkyl, —COR$^{11}$, —COOR$^{11}$, —CON(R$^{11}$)$_2$, —C≡N, —OR$^{11}$, —N(R$^{11}$)$_2$, —SO$_2$R$^{11}$, or —SO$_2$N(R$^{11}$)$_2$; such compounds are referred to hereafter as compounds of formula Vf.

In another embodiment, the invention provides the compound according to formula Vc, wherein $R^2$ is -L$^3$-R$^7$, wherein
L$^3$ is a bond; and R$^7$ is hydrogen, halogen, —Z, or —Y—Z, wherein
Y is —[C(R$^{15}$)$_2$]$_m$—, wherein
Z is —H, halogen, —OR$^{11}$, —C(=O)R$^{11}$, —C(=O)OR$^{11}$, —C(=O)N(R$^{11}$)$_2$, —N(R$^{11}$)$_2$, —CN, —SO$_2$R$^{11}$, or —S(=O)$_2$N(R$^{11}$)$_2$;
such compounds are referred to hereafter as compounds of formula Vg.

In another embodiment, the invention provides the compound according to formula Vd, wherein each $R^{5a}$ is independently -halogen, —C$_1$-C$_6$alkyl, —C$_1$-C$_6$haloalkyl, —OR$^{11}$, —COR$^{11}$, —C≡N, —C(O)OR$^{11}$, —CON(R$^{11}$)$_2$, or —N(R$^{11}$)$_2$; such compounds are referred to hereafter as compounds of formula Vh.

In another embodiment, the invention provides the compound according to formula Ve, wherein each $R^4$ is independently halogen, nitro, C$_1$-C$_6$alkyl, C$_1$-C$_6$haloalkyl, —COR$^{11}$, —COOR$^{11}$, —CON(R$^{11}$)$_2$, —C≡N, —OR$^{11}$, —N(R$^{11}$)$_2$, —SO$_2$R$^{11}$, or —SO$_2$N(R$^{11}$)$_2$; such compounds are referred to hereafter as compounds of formula Vi.

In another embodiment, the invention provides the compound according to formula Vf, wherein $R^2$ is -L$^3$-R$^7$, wherein
L$^3$ is a bond; and R$^7$ is hydrogen, halogen, —Z, or —Y—Z, wherein
Y is —[C(R$^{15}$)$_2$]$_m$—, wherein
Z is —H, halogen, —OR$^{11}$, —C(=O)R$^{11}$, —C(=O)OR$^{11}$, —C(=O)N(R$^{11}$)$_2$, —N(R$^{11}$)$_2$, —CN, —SO$_2$R$^{11}$, or —S(=O)$_2$N(R$^{11}$)$_2$.

In another embodiment, the invention provides the compound according to formula Vg, wherein each $R^{5a}$ is independently -halogen, —C$_1$-C$_6$alkyl, —C$_1$-C$_6$haloalkyl, —OR$^{11}$, —COR$^{11}$, —C≡N, —C(O)OR$^{11}$, —CON(R$^{11}$)$_2$, or —N(R$^{11}$)$_2$.

In another embodiment, the invention provides the compound according to formula Vh, wherein each $R^{41}$ is independently hydrogen, halogen, —C$_1$-C$_6$alkyl, or —C$_1$-C$_6$haloalkyl.

In another embodiment, the invention provides the compound according to formula Vi, wherein $R^2$ is -L$^3$-R$^7$, wherein
L$^3$ is a bond; and R$^7$ is hydrogen, halogen, —Z, or —Y—Z, wherein
Y is —[C(R$^{15}$)$_2$]$_m$—, wherein
Z is —H, halogen, —OR$^{11}$, —C(=O)$^{11}$, —C(O)OR$^{11}$, —C(=O)N(R$^{11}$)$_2$, —N(R$^{11}$)$_2$, —CN, —SO$_2$R$^{11}$, or —S(D)$_2$N(R$^{11}$)$_2$.

In another embodiment, the invention provides the compound according to formula V, wherein $R^{21}$ is hydrogen, halogen, nitro, cyano, aryl, heteroaryl, heterocyclyl, —C$_1$-C$_6$ alkyl-heterocyclyl, —C$_1$-C$_6$ alkyl-heteroaryl, —C$_1$-C$_6$—Z, —Y—Z, or —X—Y—Z, wherein
X is —O—;
Y is —[C(R$^{15}$)$_2$]$_m$— —C$_2$-C$_6$ alkenyl, or C$_3$-C$_8$ cycloalkyl;
Z is —H, —CN, halogen, —OR$^{11}$, —C(=O)R$^{11}$, —C(=O)OR$^{11}$, —C(=O)N(R$^{11}$)$_2$, —N(R$^{11}$)$_2$, —CN, —N$_3$, —SO$_2$R$^{11}$, —S(=O)$_2$N(R$^{11}$)$_2$, —C(=C)N(R$^{11}$)

$N(R^{11})_2$, $-C(=)N(R^{11})(OR^{11})$, $-OC(=O)-R^{11}$, $-OC(O)-N(R^{11})_2$, or $-N(R^{11})COOR^{11}$.

In another embodiment, the invention provides the compound according to formula V, wherein $R^{21}$ is hydrogen, halogen, nitro, cyano, $C_1$-$C_6$alkyl, or $C_1$-$C_6$haloalkyl.

In another embodiment, the invention provides the compound according to any of formulas Va-Vi, wherein $R^{21}$ is hydrogen, halogen, nitro, cyano, $C_1$-$C_6$alkyl, or $C_1$-$C_6$haloalkyl.

In another embodiment, the invention provides the compound according to formula VI

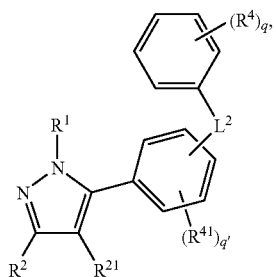
(VI)

or a pharmaceutically acceptable salt, isomer, or prodrug thereof, wherein $R^1$, $R^2$, $R^{21}$, $R^4$, $R^{41}$, $L^2$, q, and q' are as defined in formulas Ia-d.

In another embodiment, the invention provides the compound according to formula VII

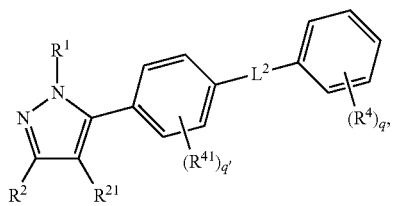
(VII)

wherein $R^1$, $R^2$, $R^{21}$, $R^4$, $R^{41}$, $L^2$, q, and q' are as defined in formulas Ia-d.

In another embodiment, the invention provides the compound according to formula VII, wherein $L^2$ is a bond or $-[C(R^{15})_2]_{m''}-V^2-[C(R^{15})_2]_n-$, wherein m" is 0; n is 0-3; and $V^2$ is $-O-$, $-S-$, $-OC(=O)O-$, $-OC(=O)O-$, or $-OC(=O)N(R^{10})-$; such compounds are referred to hereafter as compounds of formula VIII.

In another embodiment, the invention provides the compound according to formula VIII wherein $L^2$ is a bond; such compounds are referred to hereafter as compounds of formula IX.

In another embodiment, the invention provides the compound according to formula IX, wherein $L^1$ is a bond; and $R^5$ is aryl or heteroaryl optionally substituted with one or more $R^{5a}$.

In another embodiment, the invention provides the compound according to formula X

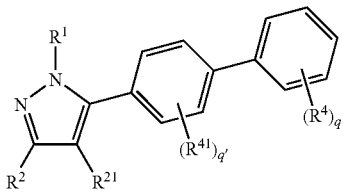
(X)

wherein $R^1$, $R^2$, $R^{21}$, $R^4$, $R^{41}$, $L^2$ and q' are as defined in formulas Ia-d.

In another embodiment, the invention provides the compound according to formula X, wherein $R^5$ is phenyl optionally substituted with one or more $R^{5a}$; such compounds are referred to hereafter as compounds of formula XI.

In another embodiment, the invention provides the compound according to formula XI wherein each $R^{5a}$ is independently halogen, $-C'$, or $-B'-C'$, wherein
  $B'$ is $-[C(R^{15'})_2]_m-$, wherein
    each $R^{15'}$ is independently $-H$ or -halogen; and
  $C'$ is $-H$, -halogen, $-SO_2R^{11}$, $-OR^{11}$, $-COR^{11}$, $-SO_2N(R^{11})_2$, $-C\equiv N$, $-C(O)OR^{11}$, $-CON(R^{11})_2$, or $-N(R^{11})_2$.

In another embodiment, the invention provides the compound according to formula XI, wherein each $R^{5a}$ is independently -halogen, $-C_1$-$C_6$alkyl, $-C_1$-$C_6$haloalkyl, $-OR^{11}$, $-COR^{11}$, $-C\equiv N$, $-C(O)OR^{11}$, $-CON(R^{11})_2$, or $-N(R^{11})_2$; such compounds are referred to hereafter as compounds of formula XIa.

In another embodiment, the invention provides the compound according to formula XI wherein each $R^{41}$ is independently hydrogen, halogen, $-C_1$-$C_6$alkyl, $-C_1$-$C_6$haloalkyl, $-COR^{16}$, $-COOR^{16}$, $-CON(R^{16})_2$, $-C\equiv N$, $-OR^{16}$, $-N(R^{16})_2$, wherein each $R^{16}$ is independently hydrogen, $-C_1$-$C_6$ alkyl, or $-C_1$-$C_6$ haloalkyl.

In another embodiment, the invention provides the compound according to formula XI wherein each $R^{41}$ is independently hydrogen, halogen, $-C_1$-$C_6$alkyl, or $-C_1$-$C_6$haloalkyl; such compounds are referred to hereafter as compounds of formula XIb.

In another embodiment, the invention provides the compound according to formula XI wherein each $R^4$ is independently halogen, -M, or -E-M, wherein
  E is $-[C(R^{15})_2]_m-$;
  M is $C_1$-$C_6$alkyl, $C_1$-$C_6$haloalkyl, $-COR^{11}$, $COOR^{11}$, $-CON(R^{11})_2$, $-C\equiv N$, $-OR^{11}$, $-OCON(R^{11})_2$, $-OCO_2-R^{11}$, $-N_3$, $-NR^{11}COR^{11}$, $-NR^{11}SO_2R^{11}$, $-N(R^{11})_2$, $-NR^{11}COOR^{11}$, $-SO_2R^{11}$, $-SO_2NR^{11}COR^{11}$, $-SO_2N(R^{11})_2$, or $-SR^{11}$.

In another embodiment, the invention provides the compound according to formula XI wherein each $R^4$ is independently halogen, -M, or -E-M, wherein
  E is $-[C(R^{15'})_2]_m-$, wherein
    each $R^{15'}$ is independently $-H$ or -halogen; and
  M is $-C_1$-$C_6$alkyl, $-C_1$-$C_6$haloalkyl, $-COR^{11'}$, $-COOR^{11'}$, $-CON(R^{11'})_2$, $-C\equiv N$, $-OR^{11'}$, $-N(R^{11'})_2$, $-SO_2R^{11'}$, or $-SO_2N(R^{11'})_2$, wherein
    each $R^{11'}$ is independently -hydrogen, $-C_1$-$C_6$ alkyl, or $-C_fC_6$haloalkyl,
      wherein each $R^{11'}$ is optionally substituted with $-OR^{13}$, $-COOR^{13}$, $-COR^{13}$, $-SO_2R^{13}$, $-CON(R^{13})_2$, $-SO_2N(R^{13})_2$, or $-N(R^{13})_2$;
such compounds are referred to hereafter as compounds of formula XIc.

In another embodiment, the invention provides the compound according to formula XI wherein $R^2$ is -$L^3$-$R^7$, wherein
$L^3$ is a bond, —C($R^{11}$)$_2$—, —O—, —S—, —N$R^7$—, —N($R^{10}$)CO—, —CO—, —CS—, —CON$R^{11}$—, —CO$_2$—, —OC(=O)—, or —SO$_2$—; and
$R^7$ is hydrogen, halogen, heterocyclyl, —Z, or —Y—Z, wherein
Y is —[C($R^{15}$)$_2$]$_m$—;
Z is —H, halogen, —O$R^{11}$, —C(=O)$R^{11}$, —C(O)O$R^{11}$, —C(=O)N($R^{11}$)$_2$, —N($R^{11}$)$_2$, —CN, —SO$_2R^{11}$, —S(O)$_2$N($R^{11}$)$_2$, —C(=O)N($R^{11}$)N($R^{11}$)$_2$, —C(=O)N($R^{11}$)(O$R^{11}$), —OC(=O)—$R^{11}$, or —OC(=O)—N($R^{11}$)$_2$.

In another embodiment, the invention provides the compound according to formula XI, wherein $R^2$ is -$L^3$-$R^7$, wherein
$L^3$ is a bond, —C($R^{11"}$)$_2$—, —CO—, or —SO$_2$—; and
$R^7$ is hydrogen, halogen, heterocyclyl, —$C_1$-$C_6$haloalkyl, —O$R^{11"}$, —C(=O)$^{11"}$, —C(=O)O$R^{11"}$, —C(=O)N($R^{11"}$)$_2$, —N($R^{11"}$)$_2$, —CN, —SO$_2R^{11"}$, or —S(=O)$_2$N($R^{11"}$)$_2$,
wherein each $R^{11"}$ is independently —H or —$C_1$-$C_6$alkyl;
such compounds are referred to hereafter as compounds of formula XId.

In another embodiment, the invention provides the compound according to formula XIa, wherein each $R^{41}$ is independently hydrogen, halogen, —$C_1$-$C_6$alkyl, or —$C_1$-$C_6$haloalkyl; such compounds are referred to hereafter as compounds of formula XIe.

In another embodiment, the invention provides the compound according to formula XIb, wherein each $R^4$ is independently halogen, -M, or -E-M, wherein
E is —[C($R^{15'}$)$_2$]$_m$—, wherein
each $R^{15'}$ is independently —H or -halogen; and
M is —$C_1$-$C_6$alkyl, —$C_1$-$C_6$haloalkyl, —CO$R^{11'}$, —COO$R^{11'}$, —CON($R^{11'}$))$_2$, —C≡N, —O$R^{11'}$, —N($R^{11'}$)$_2$, —SO$_2R^{11'}$, or —SO$_2$N($R^{11'}$)$_2$, wherein
each $R^{11'}$ is independently -hydrogen, —$C_1$-$C_6$ alkyl, —$C_1$-$C_6$ haloalkyl,
wherein each $R^{11'}$ is optionally substituted with —O$R^{13}$, —COO$R^{13}$, —CO$R^{13}$, —SO$_2R^{13}$, —CON($R^{13}$)$_2$, —SO$_2$N($R^{13}$)$_2$, or —N($R^{13}$)$_2$;
such compounds are referred to hereafter as compounds of formula XIf.

In another embodiment, the invention provides the compound according to formula XIc, wherein $R^2$ is -$L^3$-$R^7$, wherein $L^3$ is a bond, —C($R^{11"}$)$_2$—, —CO—, or —SO$_2$—; and
$R^7$ is hydrogen, halogen, heterocyclyl, —$C_1$-$C_6$alkyl, —$C_1$-$C_6$haloalkyl, —O$R^{1"}$, —C(=O)$R^{11"}$, —C(=O)O$R^{11"}$, —C(=O)N($R^{11"}$)$_2$, —N($R^{11"}$)$_2$, —CN, —SO$_2R^{11"}$, or —S(=O)$_2$N($R^{11"}$)$_2$,
wherein each $R^{11"}$ is independently —H or —$C_1$-$C_6$alkyl;
such compounds are referred to hereafter as compounds of formula XIg.

In another embodiment, the invention provides the compound according to formula XId, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$; such compounds are referred to hereafter as compounds of formula XIh.

In another embodiment, the invention provides the compound according to formula XIe, wherein each $R^4$ is independently halogen, -M, or -E-M, wherein
E is —[C($R^{15'}$)$_2$]$_m$—, wherein
each $R^{15'}$ is independently —H or -halogen; and
M is —$C_1$-$C_6$alkyl, —$C_1$-$C_6$haloalkyl, —CO$R^{11'}$, —COO$R^{11'}$, —CON($R^{11'}$)$_2$, —C≡N, —O$R^{11'}$, —N($R^{11'}$)$_2$, —SO$_2R^{11'}$, or —SO$_2$N($R^{11'}$)$_2$, wherein
each $R^{11'}$ is independently -hydrogen, —$C_1$-$C_6$ alkyl, —$C_1$-$C_6$haloalkyl,
wherein each $R^{11'}$ is optionally substituted with —O$R^{13}$, —COO$R^{13}$, —CO$R^{13}$, —SO$_2R^{13}$, —CON($R^{13}$)$_2$, —SO$_2$N($R^{13}$)$_2$, or —N($R^{13}$)$_2$;
such compounds are referred to hereafter as compounds of formula XIi.

In another embodiment, the invention provides the compound according to formula XIf, wherein $R^2$ is -$L^3$-$R^7$, wherein $L^3$ is a bond, —C($R^{11"}$)$_2$—, —CO—, or —SO$_2$—; and
$R^7$ is hydrogen, halogen, heterocyclyl, —$C_1$-$C_6$alkyl, —$C_1$-$C_6$haloalkyl, —O$R^{11"}$, —C(=O)$R^{11"}$, —C(=O)O$R^{11"}$, —C(=O)N($R^{11"}$)$_2$, —CN, —SO$_2R^{11"}$, or —S(=O)$_2$N($R^{11"}$)$_2$,
wherein each $R^{11"}$ is independently —H or —$C_1$-$C_6$alkyl.

In another embodiment, the invention provides the compound according to formula XIg, wherein each $R^{5a}$ is independently -halogen, —$C_1$-$C_6$alkyl, —$C_1$-$C_6$haloalkyl, —O$R^{11}$, —CO$R^{11}$, —C(O)O$R^{11}$, —CON($R^{11}$)$_2$, or —N($R^{11}$)$_2$.

In another embodiment, the invention provides the compound according to formula XIh, wherein each $R^{41}$ is independently hydrogen, halogen, —$C_1$-$C_6$alkyl, or —$C_1$-$C_6$haloalkyl.

In another embodiment, the invention provides the compound according to formula wherein $R^2$ is -$L^3$-$R^7$, wherein $L^3$ is a bond, —C($R^{11"}$)$_2$—, —CO—, or —SO$_2$—; and
$R^7$ is hydrogen, halogen, heterocyclyl, —$C_1$-$C_6$alkyl, —$C_1$-$C_6$haloalkyl, —O$R^{11"}$, —C(=O)$R^{11"}$, —C(=O)O$R^{11"}$, —C(=O)N($R^{11"}$)$_2$, —N($R^{11"}$)$_2$, —CN, —SO$_2R^{11"}$, or —S(=O)$_2$N($R^{11"}$)$_2$,
wherein each $R^{11"}$ is independently —H or —$C_1$-$C_6$alkyl.

In another embodiment, the invention provides the compound according to formula XI, wherein $R^{21}$ is hydrogen, halogen, nitro, cyano, aryl, heteroaryl, heterocyclyl, —$C_1$-$C_6$ alkyl-heterocyclyl, $C_1$-$C_6$-alkyl-heteroaryl, —$C_1$-$C_6$—Z, —Y—Z, or —X—Y—Z, wherein
X is —O—;
Y is —[C($R^{15}$)$_2$]$_m$—, —$C_2$-$C_6$ alkenyl, or $C_3$-$C_8$cycloalkyl;
Z is —H, —CN, halogen, —O$R^{11}$, —C(=O)$R^{11}$, —C(=O)O$R^{11}$, —C(=O)N($R^{11}$)$_2$, N($R^{11}$)$_2$, —CN, —N$_3$, —SO$_2R^{11}$, —S(=O)N($R^{11}$)$_2$, —C(=O)N($R^{11}$)N($R^{11}$)$_2$, —C(=O)N($R^{11}$)(O$R^{11}$), —OC(=O)—$R^{11}$, —OC(=O)—N($R^{11}$)$_2$, or —N($R^{11}$)COO$R^{11}$.

In another embodiment, the invention provides the compound according to formula XI, wherein $R^{21}$ is hydrogen, halogen, nitro, cyano, $C_1$-$C_6$alkyl, or $C_1$-$C_6$haloalkyl.

In another embodiment, the invention provides the compound according to any of formulas XIa-XIi, wherein $R^{21}$ is hydrogen, halogen, nitro, cyano, $C_1$-$C_6$alkyl, or $C_1$-$C_6$haloalkyl.

In another embodiment, the invention provides the compound according to formula IX, wherein $L^1$ is a bond; and $R^5$ is pyridyl optionally substituted with one or more $R^{5a}$, such compounds are referred to hereafter as compounds of formula XII.

In another embodiment, the invention provides the compound according to formula XII, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$.

In another embodiment, the invention provides the compound according to formula XII, wherein each $R^{41}$ is independently hydrogen, halogen, —$C_1$-$C_6$alkyl, or —$C_1$-$C_6$haloalkyl.

In another embodiment, the invention provides the compound according to formula XII, wherein $R^2$ is -$L^3$-$R^7$, wherein $L^3$ is a bond or —$C(R^{11'''})_2$—; and
  $R^7$ is hydrogen, halogen, —$C_1$-$C_6$alkyl, —$C_1$-$C_6$haloalkyl, —$OR^{11'''}$, —$C(=O)R^{11'''}$, —$C(=O)OR^{11'''}$, —$C(=O)N(R^{11'''})_2$, —$N(R^{11'''})_2$, —CN, —$SO_2R^{11'''}$ or —$S(=O)_2N(R^{11'''})_2$,
wherein each $R^{11'''}$ is independently —H or —$C_1$-$C_6$alkyl.

In another embodiment, the invention provides the compound according to formula XII, wherein each $R^4$ is independently halogen —$C_1$-$C_6$alkyl, —$C_1$-$C_6$haloalkyl, —$COR^{11'}$, —$COOR^{11'}$, —$CON(R^{11'})_2$, —C≡N, —$OR^{11'}$, —$N(R^{11'})_2$, —$SO_2R^{11'}$, or —$SO_2N(R^{11'})_2$, wherein
  each $R^{11'}$ is independently -hydrogen, —$C_1$-$C_6$ alkyl, or —$C_1$-$C_6$ haloalkyl.

In another embodiment, the invention provides the compound according to formula XII, wherein $R^{21}$ is hydrogen, halogen, nitro, cyano, $C_1$-$C_6$alkyl, or $C_1$-$C_6$haloalkyl.

In another embodiment, the invention provides the compound according to formula VIII, wherein
  $L^2$ is —$V^2$—$[C(R^{15})_2]_{n''}$—, wherein
  n'' is 0-3; and $V^2$ is —O—, —S—, —OC(=O)—, —OC(O)O—, or —OC(=O)N($R^{10}$)—,
such compounds are referred to hereafter as compounds of formula XIII.

In another embodiment, the invention provides the compound according to formula XIII, wherein each $R^{5a}$ is independently -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XIII, wherein each $R^{41}$ is independently hydrogen, halogen, —$C_1$-$C_6$alkyl, or —$C_1$-$C_6$haloalkyl.

In another embodiment, the invention provides the compound according to formula XIII, wherein $R^2$ is -$L^3$-$R^7$, wherein $L^3$ is a bond or —$C(R^{11'''})_2$—; and
  $R^7$ is hydrogen, halogen, —$C_1$-$C_6$alkyl, —$OR^{11'''}$, —$C(=O)R^{11'''}$, —$C(=O)OR^{11'''}$, —$C(=O)N(R^{11'''})_2$, —$N(R^{11'''})_2$, —CN, —$SO_2R^{11'''}$, or —$S(=O)_2N(R^{11'''})_2$,
wherein each $R^{11'''}$ is independently —H or —$C_1$-$C_6$alkyl.

In another embodiment, the invention provides the compound according to formula XIII, wherein each $R^4$ is independently halogen —$C_1$-$C_6$alkyl, —$C_1$-$C_6$haloalkyl, —$COR^{11'}$, —$COOR^{11'}$, —$CON(R^{11'})_2$, —C≡N, —$OR^{11'}$, —$N(R^{11'})_2$, —$SO_2R^{11'}$, or —$SO_2N(R^{11'})_2$, wherein
  each $R^{11'}$ is independently -hydrogen, —$C_1$-$C_6$ alkyl, or —$C_1$-$C_6$haloalkyl.

In another embodiment, the invention provides the compound according to formula XIII, wherein $R^{21}$ is hydrogen, halogen, nitro, cyano, $C_1$-$C_6$alkyl, or $C_1$-$C_6$haloalkyl.

In another embodiment, the invention provides the compound according to formulas Ia-d, wherein K is absent q is 1; and $L^2$ is —$V^2$—$[C(R^{15})_2]_n$—, wherein
  n is 0-6; and $V^2$ is —O—, —S—, —$SO_2$—, —CON($R^{10}$)—, —CON($R^{11}$)—, —CO—, —$CO_2$—, —OC(=O)—, —OC(=O)O—, or —OC(=O)N($R^{10}$)—;
such compounds are referred to hereafter as compounds of formula XIV.

In another embodiment, the invention provides the compound according to formula XIV, wherein $L^2$ is —CO—; and $R^4$ is heterocyclyl optionally substituted with one or more groups which independently are -M wherein M is —H, halogen, $COR^{11}$, $COOR^{11}$, C≡N, $OR^{11}$, —$NR^{11}COR^{11}$, $NR^{11}SO_2R^{11}$, $SO_2R^{11}$, $SO_2N(R^{11})_2$, or $SR^{11}$;
such compounds are referred to hereafter as compounds of formula XV.

In another embodiment, the invention provides the compound according to formula XV, wherein each $R^{5a}$ is independently -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XV, wherein $R^2$ is -$L^3$-$R^7$, wherein $L^3$ is a bond or —$C(R^{11'''})_2$—; and
  $R^7$ is hydrogen, halogen, —$C_1$-$C_6$alkyl, —$C_1$-$C_6$haloalkyl, —$OR^{11'''}$, —$C(=O)OR^{11'''}$, —$C(=O)OR^{11'''}$, —$C(=O)N(R^{11'''})_2$, —$N(R^{11'''})_2$, —CN, —$SO_2R^{11'''}$, or —$S(=O)_2N(R^{11'''})_2$,
  wherein each $R^{11'''}$ is independently —H or —$C_1$-$C_6$alkyl.

In another embodiment, the invention provides the compound according to formula XV, wherein each $R^{41}$ is independently hydrogen, halogen, —$C_1$-$C_6$alkyl, or —$C_1$-$C_6$haloalkyl.

In another embodiment, the invention provides the compound according to formula XV, wherein $R^{21}$ is hydrogen, halogen, nitro, cyano, $C_1$-$C_6$alkyl, or $C_1$-$C_6$haloalkyl.

In another embodiment, the invention provides the compound according to formula XIV, wherein $L^2$ is —O—; and $R^4$ is -E-M, wherein
  E is —$[C(R^{15})_2]_m$—; and
  M is —H, halogen, —$COR^{11}$, —$COOR^{11}$, —$CON(R^{11})_2$, —C≡N, —$OR^{11}$, —$OCON(R^{11})_2$, —$OCO_2$—$R^{11}$, —$N(R^{11})_2$;
such compounds are referred to hereafter as compounds of formula XVI.

In another embodiment, the invention provides the compound according to formula XVI, wherein each $R^{41}$ is independently hydrogen, halogen, —$C_1$-$C_6$alkyl, or —$C_1$-$C_6$haloalkyl.

In another embodiment, the invention provides the compound according to formula XVI, wherein each $R^{5a}$ is independently -halogen, $C_1$-$C_6$alkyl, $C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XVI, wherein $R^2$ is -$L^3$-$R^7$, wherein $L^3$ is a bond or —$C(R^{11'''})_2$—; and
  $R^7$ is hydrogen, halogen, —$C_1$-$C_6$alkyl, —$C_1$-$C_6$haloalkyl, —$OR^{11'''}$, —$C(=O)OR^{11'''}$, —$C(=O)OR^{11'''}$, —$C(=O)N(R^{11'''})_2$, —$N(R^{11'''})_2$, —CN, —$SO_2R^{11'''}$, or —$S(=O)_2N(R^{11'''})_2$,
wherein each $R^{11'''}$ is independently —H or —$C_1$-$C_6$alkyl.

In another embodiment, the invention provides the compound according to formula XVI, wherein $R^{21}$ is hydrogen, halogen, nitro, cyano, or $C_1$-$C_6$haloalkyl.

In another embodiment, the invention provides the compound according to formula XIV, wherein
  $L^2$ is —$V^2$—$[C(R^{15})_2]_n$—, wherein
  n is 0-6; and $V^2$ is —$CON(R^{11})$— or —$CO_2$—; and
  $R^4$ is heterocyclyl, or -E-M, wherein
  E is —$[C(R^{15})_2]_m$—; and
  M is —H, halogen, —$COR^{11}$, —$COOR^{11}$, —$CON(R^{11})_2$, —C≡N, —$OR^{11}$, —$OCON(R^{11})_2$, —$OCO_2$—$R^{11}$, —$N_3$, —$NR^{11}COR^{11}$, —$NR^{11}SO_2R^{11}$, —$N(R^{11})_2$, —$NR^{11}COOR^{11}$, —$SO_2R^{11}$, —$SO_2NR^{11}COR^{11}$, —$SO_2N(R^{11})_2$, or —$SR^{11}$;

such compounds are referred to hereafter as compounds of formula XVII.

In another embodiment, the invention provides the compound according to formula XVII, wherein each $R^{41}$ is independently hydrogen, halogen, —$C_1$-$C_6$alkyl, or —$C_1$-$C_6$haloalkyl.

In another embodiment, the invention provides the compound according to formula XVII, wherein each $R^{5a}$ is independently -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XVII, wherein $R^2$ is -$L^3$-$R^7$, wherein $L^3$ is a bond or —$C(R^{11''})_2$—; and
$R^7$ is hydrogen, halogen, —$C_1$-$C_6$alkyl, —$C_1$-$C_6$haloalkyl, —$OR^{11''}$, —C(=O)$R^{11''}$, —C(=O)$OR^{11''}$, —C(=O)N$(R^{11''})_2$, —N$(R^{11''})_2$, —CN, —$SO_2R^{11''}$, or —S(=O)$_2$N$(R^{11''})_2$,
wherein each $R^{11''}$ is independently —H or —$C_1$-$C_6$alkyl.

In another embodiment, the invention provides the compound according to formula XVII, wherein $R^{21}$ is hydrogen, halogen, nitro, cyano, $C_1$-$C_6$alkyl, or $C_1$-$C_6$haloalkyl.

In another embodiment, the invention provides the compound according to formulas Ia-d, wherein J is heteroaryl.

In another embodiment, the invention provides the compound according to formulas Ia-d, wherein J is thienyl, furyl, pyrrolyl, thiazoyl, oxazoyl, isothiazoyl, isoxazoyl, pyridyl, pyrimidinyl, or pyrazinyl.

In another embodiment, the invention provides the compound according to formulas Ia-d, wherein J is thienyl, furyl, pyrrolyl, thiazoyl, oxazoyl, isothiazoyl, isoxazoyl, pyridyl, pyrimidinyl, or pyrazinyl; and K is phenyl.

In another embodiment, the invention provides the compound according to formulas Ia-d, wherein J is pyridyl.

In another embodiment, the invention provides the compound according to formulas Ia-d, wherein J is pyridyl; $L^1$ is a bond; and $R^5$ is phenyl optionally substituted with one or more $R^{5a}$.

In another embodiment, the invention provides the compound according to formulas Ia-d, wherein J is pyridyl; $L^1$ is a bond; $R^5$ is phenyl optionally substituted with one or more $R^{5a}$; and K is phenyl; such compounds are referred to hereafter as compounds of formula XVIII.

In another embodiment, the invention provides the compound according to formula XVIII, wherein each $R^{41}$ is independently hydrogen, halogen, —$C_1$-$C_6$alkyl, or —$C_1$-$C_6$haloalkyl.

In another embodiment, the invention provides the compound according to formula XVIII, wherein $R^2$ is -$L^3$-$R^7$, wherein $L^3$ is a bond or —$C(R^{11''}_{-2}$; and
$R^7$ is hydrogen, halogen, —$C_1$-$C_6$alkyl, —$C_1$-$C_6$haloalkyl, —$OR^{11''}$, —C(=O)$R^{11''}$, —C(=O)$OR^{11''}$, —C(=O)N$(R^{11''})_2$, —N$(R^{11''})_2$, —CN, —$SO_2R^{11''}$, or —S(=O)$_2$N$(R^{11''})_2$,
wherein each $R^{11''}$ is independently —H or —$C_1$-$C_6$alkyl.

In another embodiment, the invention provides the compound according to formula XVIII, wherein each $R^4$ is independently halogen —$C_1$-$C_6$alkyl, —$C_1$-$C_6$haloalkyl, —$COR^{11'}$, —$COOR^{11'}$, —$CON(R^{11'})_2$, —C≡N, —$OR^{11'}$, —$N(R^{11'})_2$, —$SO_2R^{11'}$, or —$SO_2N(R^{11'})_2$, wherein
each $R^{11'}$ is independently -hydrogen, —$C_1$-$C_6$ alkyl, or —$C_1$-$C_6$ haloalkyl.

In another embodiment, the invention provides the compound according to formula XVIII, wherein each $R^{5a}$ is independently -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XVIII, wherein $R^{21}$ is hydrogen, halogen, nitro, cyano, $C_1$-$C_6$alkyl, or $C_1$-$C_6$haloalkyl.

In another embodiment, the invention provides the compound according to formulas Ia-d, wherein J is thienyl, furyl, or pyrroyl.

In another embodiment, the invention provides the compound according to formulas Ia-d, wherein J is thienyl.

In another embodiment, the invention provides the compound according to formulas Ia-d, wherein J is thienyl; K is phenyl; and $L^2$ is a bond.

In another embodiment, the invention provides the compound according to formula XIX,

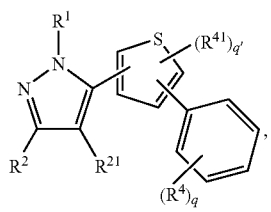

(XIX)

or a pharmaceutically acceptable salt, isomer, or prodrug thereof, wherein $R^1$, $R^2$, $R^{21}$, $R^4$, $R^{41}$, $L^2$, q, and q' are as defined in formulas Ia-d.

In another embodiment, the invention provides the compound according to formula XIX, wherein K is absent and $L^2$ is —$SO_2$— or —CO—.

In another embodiment, the invention provides the compound according to formula XIX, wherein K is absent $L^2$ is —$SO_2$— or —CO—; and $R^4$ is heterocyclyl, $OR^{11}$, or —$N(R^{11})_2$,
wherein the heterocyclyl is optionally substituted with one or more -E'-M', wherein E' is —[C(R^{15})_2]_m— or $C_3$-$C_8$ cycloalkyl;
M' is —H, halogen, $COR^{11}$, $COOR^{11}$, C≡N, $OR^{11}$, —$NR^{11}COR^{11}$, $NR^{11}SO_2R^{11}$, $SO_2R^{11}$, $SO_2N(R^{11})_2$, or $SR^{11}$.

In another embodiment, the invention provides the compound according to formula XX,

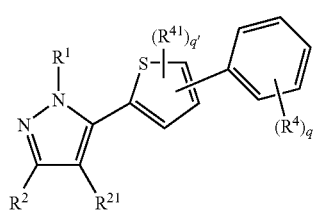

(XX)

or a pharmaceutically acceptable salt, isomer, or prodrug thereof, wherein $R^1$, $R^2$, $R^{21}$, $R^4$, $R^{41}$, $L^2$, q, and q' are as defined in formulas Ia-d.

In another embodiment, the invention provides the compound according to formula XXI,

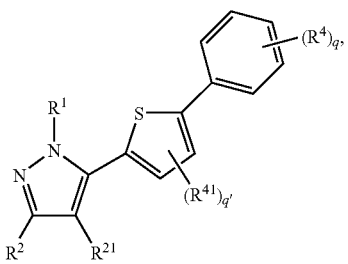

(XXI)

or a pharmaceutical acceptable salt, isomer, or prodrug thereof, wherein $R^1$, $R^2$, $R^{21}$, $R^4$, $R^{41}$, q, and q' are as defined in formulas Ia-d.

In another embodiment, the invention provides the compound according to formula XXI, wherein $L^1$ is a bond; and $R^5$ is phenyl optionally substituted with one or more $R^{5a}$; such compounds are referred to hereafter as compounds of formula XXII.

In another embodiment, the invention provides the compound according to formula XXII, wherein each $R^{5a}$ is independently halogen, nitro, heterocyclyloxy, aryloxy, —C', —B'—C' or -A'—B'—C' wherein
A' is —O—;
B' is —[C(R$^{15}$)$_2$]$_m$—;
C' is —H, halogen, —SO$_2$R$^{11}$, —OR$^{11}$, —SR$^{11}$, —COR$^{11}$, —SO$_2$N(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, —N(R$^{11}$)$_2$, aryl, heteroaryl, or heterocyclyl;
wherein each $R^{5a}$ is optionally substituted one or more groups which are independently C$_1$-C$_6$ alkyl, C$_3$-C$_8$ cycloalkyl, halogen, —C≡N, —COR$^{11}$, —COOR$^{11}$, —CON(R$^{11}$)$_2$, —SO$_2$R$^{11}$, —OR$^{11}$, —SR$^{11}$, —SO$_2$R$^{11}$, —SO$_2$N(R$^{11}$)$_2$, —SO$_2$NR$^{11}$COR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$.

In another embodiment, the invention provides the compound according to formula XXII, wherein each $R^{5a}$ is independently halogen, nitro, heterocyclyloxy, phenoxy, —C', —B'—C', or -A'-B'—C' wherein
A' is —O—;
B' is —[C(R$^{15}$)$_2$]$_m$—;
C' is —H, halogen, —OR$^{18}$, —COR$^{18}$, C≡N, —C(O)OR$^{18}$, —OC(=O)R$^{18}$, —CON(R$^{18}$)$_2$, —OCON(R$^{18}$)$_2$, —N(R$^{18}$COR$^{18}$, —NR$^{18}$CON(R$^{18}$)$_2$, —NR$^{18}$COOR$^{18}$, —N(R$^{18}$)$_2$, or heterocyclyl;
wherein each $R^{18}$ is independently —H, —C$_1$-C$_6$ alkyl, —C$_1$-C$_6$ haloalkyl, —C$_3$-C$_8$ cycloalkyl, aryl, heteroaryl, or heterocyclyl; and
wherein each $R^{5a}$ is optionally substituted one or more groups which are independently C$_1$-C$_6$ alkyl, halogen, —COR$^{19}$, —COOR$^{19}$, —CON(R$^{19}$)$_2$, —OR$^{19}$, or —N(R$^{19}$)$_2$,
wherein each $R^{19}$ is independently —H or —C$_1$-C$_6$alkyl;
such compounds are referred to hereafter as compounds of formula XXIIa.

In another embodiment, the invention provides the compound according to formula XXII, wherein each $R^{41}$ is independently hydrogen, halogen, —C$_1$-C$_6$alkyl, —C$_1$-C$_6$haloalkyl, —COR$^{16}$, —COOR$^{16}$, —CON(R$^{16}$)$_2$, —C≡N, —OR$^{16}$, or —N(R$^{16}$)$_2$, wherein each $R^{16}$ is independently hydrogen, —C$_1$-C$_6$ alkyl, or —C$_1$-C$_6$ haloalkyl.

In another embodiment, the invention provides the compound according to formula XXII, wherein each $R^{41}$ is independently hydrogen, halogen, —C$_1$-C$_6$alkyl, or —C$_1$-C$_6$haloalkyl; such compounds are referred to hereafter as compounds of formula XXIIb.

In another embodiment, the invention provides the compound according to formula XXII, wherein each $R^4$ is independently halogen, nitro, CR$^{11}$=CR$^{11}$COOR$^{11}$, -M, or -E-M, wherein
E is —[C(R$^{15}$)$_2$]$_m$— or C$_3$-C$_8$ cycloalkyl;
M is C$_1$-C$_6$alkyl, C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —NR$^{11}$COR$^{11}$, —NR$^{11}$SO$_2$R$^{11}$, —N(R$^{11}$)$_2$, —NR$^{11}$COOR$^{11}$, —SO$_2$R$^{11}$, —SO$_2$NR$^{11}$COR$^{11}$, —SO$_2$N(R$^{11}$)$_2$, or —SR$^{11}$.

In another embodiment, the invention provides the compound according to formula XXII, wherein each $R^4$ is independently halogen, CR$^{11'}$=CR$^{11'}$COOR$^{11'}$, -M, or -E-M, wherein
E is —[C(R$^{15}$)$_2$]$_m$— or C$_3$-C$_8$ cycloalkyl;
M is C$_1$-C$_6$alkyl, C$_1$-C$_6$haloalkyl, —COR$^{11'}$, —COOR$^{11'}$, —CON(R$^{11'}$)$_2$, —C≡N, —OR$^{11'}$, —NR$^{11'}$O$_2$R$^{11'}$, —N(R$^{11'}$)$_2$, SO$_2$R$^{11'}$, —SO$_2$NR$^{11'}$COR$^{11'}$, or —SO$_2$N(R$^{11'}$)$_2$,
wherein each $R^{11'}$ is independently -hydrogen, —C$_1$-C$_6$ alkyl, or —C$_1$-C$_6$ haloalkyl,
wherein any of $R^{11'}$ is optionally substituted with one or more radicals of $R^{12'}$;
each $R^{12'}$ is independently halogen, C$_1$-C$_6$haloalkyl, C$_1$-C$_6$ alkyl, C$_1$-C$_6$ alkoxy, C=O(OR$^{13}$), COR$^{13}$, SO$_2$R$^{13}$, CON(R$^{13}$)$_2$, SO$_2$N(R$^{13}$)$_2$, or —N(R$^{13}$)$_2$;
such compounds are referred to hereafter as compounds of formula XXIIc.

In another embodiment, the invention provides the compound according to formula XXII, wherein $R^2$ is -L$^3$-R$^7$, wherein
L$^3$ is a bond or —(CH$_2$)$_{m''}$—V$^1$—(CH$_2$)$_n$— wherein m" is 0-3; n is 0-3; and V$^1$ is —C(R$^{11}$)$_2$, —O—, —S—, —NR$^7$—, —CO—, —CO$_2$—, —OC(=O)—, or —SO$_2$—; and
$R^7$ is hydrogen, halogen, nitro, aryl, heteroaryl, heterocyclyl, —C$_1$-C$_6$haloalkyl, —C$_2$-C$_6$ alkenyl, C$_3$-C$_8$ cycloalkyl, or —(C(R$^{15}$)$_2$)$_m$—Z, wherein
Z is —OR$^{11}$, —C(=O)R$^{11}$, —C(=O)OR$^{11}$, —C(=O)N(R$^{11}$)$_2$, —N(R$^{11}$)$_2$, —CN, —SO$_2$R$^{11}$, —S(=O)$_2$N(R$^{11}$)$_2$, —C(=O)(R$^{11}$)N(R$^{11}$)$_2$, —C(=O)N(R$^{11}$)(OR$^{11}$), —OC(=O)—R$^{11}$, or —OC(=O)—N(R$^{11}$)$_2$,
wherein $R^7$ is optionally substituted with one or more $R^{7a}$, wherein
$R^{7a}$ is halogen, C$_1$-C$_6$alkyl, C$_1$-C$_6$haloalkyl, —OR$^{20}$, —C(=O)R$^{20}$, —C(=O)OR$^{20}$, —C(=O)N(R$^{20}$)$_2$, —N(R$^{20}$)$_2$, —N(R$^{20}$)C(=O)R$^{20}$, or —CN, wherein each $R^{20}$ is independently —H or C$_1$-C$_6$alkyl.

In another embodiment, the invention provides the compound according to formula XXII, wherein $R^2$ is -L$^3$-R$^7$, wherein
L$^3$ is a bond or —(CH$_2$)$_{m''}$—V$^1$—(CH$_2$)$_n$— wherein m" is 0-1; n is 0-2; and V$^1$ is —CH$_2$—, —O—, —S—, or —NR$^7$—; and
$R^7$ is hydrogen, halogen, phenyl, heteroaryl, heterocyclyl, —C$_2$-C$_6$ alkenyl, C$_3$-C$_8$ cycloalkyl, or —(C(R$^{15}$)$_2$)$_m$—Z, wherein
Z is —OR$^{11''}$, —C(=O)R$^{11''}$, —C(=O)OR$^{11''}$, —C(=O)N(R$^{11''}$)$_2$, —N(R$^{11''}$)$_2$, —CN, or —SO$_2$R$^{11''}$, wherein $R^7$ is optionally substituted with one or more $R^{7a}$, wherein
$R^{7a}$ is halogen, $C_1$-$C_6$alkyl, $C_1$-$C_6$haloalkyl, —$OR^{11'}$, —$N(R^{11''})_2$, —$COOR^{11''}$, wherein each $R^{11''}$ is independently —H, —$C_1$-$C_6$alkyl, —$C_1$-$C_6$haloalkyl, heterocyclyl, or heteroaryl;
such compounds are referred to hereafter as compounds of formula XXIId.

In another embodiment, the invention provides the compound according to formula XXII, wherein $R^2$ is -$L^3$-$R^7$, wherein $L^3$ is a bond; and
$R^7$ is hydrogen, halogen, —$C_1$-$C_3$alkyl, —$C_1$-$C_3$haloalkyl, or —$(C(R^{15})_2)$—Z, wherein
Z is —$OR^{11''}$ or —$SO_2R^{11''}$, wherein $R^{11''}$ is —H or $C_1$-$C_6$alkyl.

In another embodiment, the invention provides the compound according to formula XXIIa, wherein each $R^{41}$ is independently hydrogen, halogen, —$C_1$-$C_6$alkyl, or —$C_1$-$C_6$haloalkyl; such compounds are referred to hereafter as compounds of formula XXIIe.

In another embodiment, the invention provides the compound according to formula XXIIb, wherein each $R^4$ is independently halogen, $CR^{11'}$=$CR^{11'}COOR^{11'}$, -M, or -E-M, wherein
E is —$[C(R^{15})_2]_m$— or $C_3$-$C_8$ cycloalkyl;
M is $C_1$-$C_6$alkyl, $C_1$-$C_6$haloalkyl, —$COR^{11'}$, —$COOR^{11'}$, —$CON(R^{11'})_2$, —C≡N, —$OR^{11'}$, —$NR^{11'}SO_2R^{11'}$, —$N(R^{11'})_2$, —$SO_2R^{11'}$, —$SO_2NR^{11'}COR^{11'}$, or —$SO_2N(R^{11'})_2$,
wherein each $R^{11'}$ is independently -hydrogen, —$C_1$-$C_6$ alkyl, or —$C_1$-$C_6$haloalkyl,
wherein each $R^{11'}$ is optionally substituted with one or more radicals of $R^{12'}$;
each $R^{11'}$ is independently halogen, $C_1$-$C_6$ haloalkyl, $C_1$-$C_6$ alkoxy, C=$O(OR^{13})$, $COR^{13}$, $SO_2R^{13}$, $CON(R^{13})_2$, or —$N(R^{13})_2$;
such compounds are referred to hereafter as compounds of formula XXIIf.

In another embodiment, the invention provides the compound according to formula XXIIc, wherein $R^2$ is -$L^3$-$R^7$, wherein
$L^3$ is a bond or —$(CH_2)_{m''}$—$V^1$—$(CH_2)_n$— wherein m" is 0-1; n is 0-2; and $V^1$ is —$CH_2$—, —O—, —S—, or —$NR^7$—; and
$R^7$ is hydrogen, halogen, phenyl, heteroaryl, heterocyclyl, —$C_1$-$C_6$alkyl, —$C_1$-$C_6$haloalkyl, —$C_2$-$C_6$ alkenyl, $C_3$-$C_8$ cycloalkyl, or —$(C(R^{15})_2)_m$—Z, wherein
Z is —$OR^{11''}$, —C(=O)$R^{11''}$, —C(=O)$OR^{11''}$, —C(=O)N($R^{11''}$)$_2$, —N($R^{11''}$)$_2$, —CN, or —$SO_2R^{11''}$,
wherein $R^7$ is optionally substituted with one or more $R^{7a}$, wherein
$R^{7a}$ is halogen, $C_1$-$C_6$alkyl, $C_1$-$C_6$haloalkyl, —$OR^{11''}$, —$N(R^{11''})_2$, —$COOR^{11''}$,
wherein $R^{11''}$ is —H, heterocyclyl, or heteroaryl;
such compounds are referred to hereafter as compounds of formula XXIIg.

In another embodiment, the invention provides the compound according to formula XXIId, wherein each $R^{5a}$ is independently halogen, nitro, heterocyclyloxy, phenoxy, —C', —B'—C', or -A'-B'—C' wherein
A' is —O—;
B' is —$[C(R^{15})_2]_m$—;
C' is —H, halogen, —$OR^{18}$, —$COR^{18}$, —C≡N, —C(O)$OR^{18}$, —OC(=O)$R^{18}$, —CON($R^{18}$)$_2$, —OCON($R^{18}$)$_2$, —$NR^{18}COR^{18}$, —$NR^{18}CON(R^{18})_2$, —$NR^{18}COOR^{18}$, —N($R^{18}$)$_2$, or heterocyclyl;
wherein each $R^{18}$ is independently —H, —$C_1$-$C_6$ alkyl, —$C_1$-$C_6$ haloalkyl, —$C_3$-$C_8$ cycloalkyl, aryl, heteroaryl, or heterocyclyl; and
wherein each $R^{5a}$ is optionally substituted one or more groups which are independently $C_1$-$C_6$ alkyl, halogen, —$COR^{19}$, —$COOR^{19}$, —$CON(R^{19})_2$, —$OR^{19}$, or —$N(R^{19})_2$,
wherein $R^{19}$ is —H or —$C_1$-$C_6$alkyl;
such compounds are referred to hereafter as compounds of formula XXIIh.

In another embodiment, the invention provides the compound according to formula XXIIe, wherein each $R^4$ is independently halogen, $CR^{11'}$=$CR^{11'}COOR^{11'}$, -M, or -E-M, wherein
E is —$[C(R^{15})_2]_m$— or $C_3$-$C_8$cycloalkyl;
M is $C_1$-$C_6$alkyl, $C_1$-$C_6$haloalkyl, —$COR^{11'}$, —$COOR^{11'}$, —$CON(R^{11'})_2$, —C≡N, —$OR^{11'}$, —$NR^{11'}O_2R^{11'}$, —$N(R^{11'})_2$, —$SO_2R^{11'}$, —$SO_2NR^{11'}COR^{11'}$, or —$SO_2N(R^{11'})_2$,
wherein each $R^{11'}$ is independently -hydrogen, —$C_1$-$C_6$ alkyl, or —$C_1$-$C_6$haloalkyl,
wherein any of $R^{11'}$ is optionally substituted with one or more radicals of $R^{12'}$;
each $R^{12'}$ is independently halogen, $C_1$-$C_6$haloalkyl, $C_1$-$C_6$ alkyl, $C_1$-$C_6$ alkoxy, C=$O(OR^{13})$, $COR^{13}$, $SO_2R^{13}$, $CON(R^{13})_2$, $SO_2N(R^{13})_2$, or —$N(R^{13})_2$;
such compounds are referred to hereafter as compounds of formula XXIIi.

In another embodiment, the invention provides the compound according to formula XXIIf, wherein $R^2$ is -$L^3$-$R^7$, wherein $L^3$ is a bond or —$(CH_2)_{m''}$—$V^1$—$(CH_2)_n$— wherein m" is 0-1; n is 0-2; and $V^1$ is —$CH_2$—, —O—, —S—, or —$NR^7$—; and
$R^7$ is hydrogen, halogen, phenyl, heteroaryl, heterocyclyl, —$C_1$-$C_6$alkyl, —$C_1$-$C_6$haloalkyl, —$C_2$-$C_6$ alkenyl, $C_3$-$C_8$cycloalkyl, or —$(C(R^{15})_2)_m$—Z, wherein
Z is —$OR^{11''}$, —C(=O)$R^{11''}$, —C(=O)$OR^{11''}$, —C(=O)N($R^{11''}$)$_2$, —N($R^{11''}$)$_2$, —CN, or —$SO_2R^{11''}$,
wherein $R^7$ is optionally substituted with one or more $R^{7a}$, wherein
$R^{7a}$ is halogen, $C_1$-$C_6$alkyl, $C_1$-$C_6$haloalkyl, —$OR^{11''}$, —$N(R^{11''})_2$, —$COOR^{11''}$,
wherein $R^{11''}$ is —H, —$C_1$-$C_6$alkyl, heterocyclyl, or heteroaryl.

In another embodiment, the invention provides the compound according to formula XXIIg, wherein each $R^{5a}$ is independently halogen, nitro, heterocyclyloxy, phenoxy, —C', —B'—C', or -A'-B'—C' wherein
A' is —O—;
B' is —$[C(R^{15})_2]_m$—;
C' is —H, halogen, —$OR^{18}$, —$COR^{18}$, —C≡N, —C(O)$OR^{18}$, —OC(=O)$R^{18}$, —CON($R^{18}$)$_2$, —OCON($R^{18}$)$_2$, —$NR^{18}COR^{18}$, —$NR^{18}CON(R^{18})_2$, —$NR^{18}COOR^{18}$, —N($R^{18}$)$_2$, or heterocyclyl;
wherein each $R^{18}$ is independently —H, —$C_1$-$C_6$ alkyl, —$C_1$-$C_6$ haloalkyl, —$C_3$-$C_8$ cycloalkyl, aryl, heteroaryl, or heterocyclyl; and
wherein each $R^{5a}$ is optionally substituted one or more groups which are independently $C_1$-$C_6$ alkyl, halogen, —$COR^{19}$, —$COOR^{19}$, —$CON(R^{19})_2$, —$OR^{19}$, or —$N(R^{19})_2$, wherein $R^{19}$ is —H or —$C_1$-$C_6$alkyl.

In another embodiment, the invention provides the compound according to formula XXIIh, wherein each $R^{41}$ is independently hydrogen, halogen, —$C_1$-$C_6$alkyl, or —$C_1$-$C_6$haloalkyl.

In another embodiment, the invention provides the compound according to formula XXIIi, wherein $R^2$ is -$L^3$-$R^7$, wherein $L^3$ is a bond or —$(CH_2)_{m''}$—$V^1$—$(CH_2)_n$— wherein m" is 0-1; n is 0-2; and $V^1$ is —$CH_2$—, —O—, —S—, or —$NR^7$—; and $R^7$ is hydrogen, halogen, phenyl, heteroaryl, heterocyclyl, —$C_1$-$C_6$haloalkyl, —$C_2$-$C_6$ alkenyl, $C_3$-$C_8$ cycloalkyl, or —$(C(R^{15})_2)_m$—Z, wherein Z is —$OR^{11'''}$, —$C(=O)R^{11'''}$, —$C(=O)N(R^{11'''})_2$, —CN, or —$SO_2R^{11'''}$, wherein $R^7$ is optionally substituted with one or more $R^{7a}$, wherein $R^{7a}$ is halogen, $C_1$-$C_6$alkyl, $C_1$-$C_6$haloalkyl, —$OR^{11'''}$, —$N(R^{11'''})_2$, —$COOR^{11'''}$, wherein $R^{11'''}$ is —H, —$C_1$-$C_6$haloalkyl, heterocyclyl, or heteroaryl.

In another embodiment, the invention provides the compound according to formula XXII, wherein $R^{21}$ is hydrogen, halogen, nitro, cyano, aryl, heteroaryl, heterocyclyl, alkylheterocyclyl, alkyl-heteroaryl, —$C_1$-$C_6$ alkyl-aryl, —Z, —Y—Z, or —X—Y—Z, wherein X is —O—;

Y is —$[C(R^{15})_2]_m$—, —$C_2$-$C_6$ alkenyl, or $C_3$-$C_8$ cycloalkyl;

Z is —H, —CN, halogen, —$OR^{11}$, —$C(=O)R^{11}$, —$C(=O)OR^{11}$, —$C(=O)N(R^{11})_2$, —$N(R^{11})_2$, —CN, —$N_3$, —$SO_2R^{11}$, —$S(=O)_2N(R^{11})_2$, —$C(=O)N(R^{11})N(R^{11})_2$, —$C(=O)N(R^{11})(OR^{11})$, —$OC(=O)$—$R^{11}$, —$OC(=O)$—$N(R^{11})_2$, or —$N(R^{11})COOR^{11}$;

In another embodiment, the invention provides the compound according to formula XXII, wherein $R^{21}$ is hydrogen, halogen, nitro, cyano, $C_1$-$C_6$alkyl, or $C_1$-$C_6$haloalkyl.

In another embodiment, the invention provides the compound according to any of formulas XXIIa-XXIIi, wherein $R^{21}$ is hydrogen, halogen, nitro, cyano, $C_1$-$C_6$alkyl, or $C_1$-$C_6$haloalkyl.

In another embodiment, the invention provides the compound according to formula XXI, wherein $R^1$ is -$L^1$-$R^5$, wherein $L^1$ is -$L^5$- or -$L^6$-, wherein each $L^5$ is —$C(R^{15})_2$—, wherein each $R^{15}$ is independently hydrogen, halogen, ($C_1$-$C_6$) alkyl, or ($C_1$-$C_6$)haloalkyl; and $L^6$ is —CS—, —CO—, or —$SO_2$—; and $R^5$ is aryl or heteroaryl optionally substituted with one or more $R^{5a}$.

In another embodiment, the invention provides the compound according to formula XXI, wherein $R^1$ is -$L^1$-$R^5$, wherein $L^1$ is -$L^5$- or -$L^6$-, wherein each $L^5$ is —$C(R^{15})_2$—, wherein each $R^{15}$ is independently hydrogen, halogen, ($C_1$-$C_6$) alkyl, or ($C_1$-$C_6$)haloalkyl; and $L^6$ is —CS—, —CO—, or —$SO_2$—; and $R^5$ is phenyl, thienyl, furyl, pyrrolyl, thiazoyl, oxazoyl, isothiazoyl, isoxazoyl, pyridyl, pyrimidinyl, or pyrazinyl optionally substituted with one or more $R^{5a}$; such compounds are referred to hereafter as compounds of formula XXIII.

In another embodiment, the invention provides the compound according to formula XXIII, wherein $R^2$ is -$L^3$-$R^7$, wherein $L^3$ is a bond or —$C(R^{11'''})_2$—; and $R^7$ is hydrogen, halogen, —$C_1$-$C_6$alkyl, —$C_1$-$C_6$haloalkyl, —$OR^{11'''}$, —$C(=O)R^{11'''}$, —$C(=O)OR^{11'''}$, —$C(=O)N(R^{11'''})_2$, —$N(R^{11'''})_2$, —CN, —$SO_2R^{11'''}$, or —$S(=O)_2N(R^{11'''})_2$, wherein each $R^{11'''}$ is independently —H or —$C_1$-$C_6$alkyl.

In another embodiment, the invention provides the compound according to formula XXIII, wherein each $R^{5a}$ is independently -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XXIII, wherein each $R^{41}$ is independently hydrogen, halogen, —$C_1$-$C_6$alkyl, or —$C_1$-$C_6$haloalkyl.

In another embodiment, the invention provides the compound according to formula XXIII, wherein each $R^4$ is independently halogen, —$C_1$-$C_6$alkyl, —$C_1$-$C_6$haloalkyl, —$COR^{11'}$, —$COOR^{11'}$, —$CON(R^{11'})_2$, —C≡N, —$OR^{11'}$, —$N(R^{11'})_2$, —$SO_2R^{11'}$, or —$SO_2N(R^{11'})_2$, wherein each $R^{11'}$ is independently -hydrogen, —$C_1$-$C_6$ alkyl, or —$C_1$-$C_6$haloalkyl.

In another embodiment, the invention provides the compound according to formula XXIII, wherein $R^{21}$ is hydrogen, halogen, nitro, cyano, $C_1$-$C_6$alkyl, or $C_1$-$C_6$haloalkyl.

In another embodiment, the invention provides the compound according to formula XXI, wherein $L^1$ is a bond; and $R^5$ is heteroaryl optionally substituted with one or more $R^{5a}$.

In another embodiment, the invention provides the compound according to formula XXI, wherein $L^1$ is a bond; and $R^5$ is thienyl, furyl, pyrrolyl, thiazoyl, oxazoyl, isothiazoyl, isoxazoyl, pyridyl, pyrimidinyl, or pyrazinyl optionally substituted with one or more $R^{5a}$.

In another embodiment, the invention provides the compound according to formula XXI, wherein $L^1$ is a bond; and $R^5$ is thienyl, furyl, pyrrolyl, thiazoyl, oxazoyl, isothiazoyl, or isoxazoyl optionally substituted with one or more $R^{5a}$; such compounds are referred to hereafter as compounds of formula XXIV.

In another embodiment, the invention provides the compound according to formula XXIV, wherein each $R^{5a}$ is independently -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XXIV, wherein each $R^4$ is independently halogen, —$C_1$-$C_6$alkyl, —$C_1$-$C_6$haloalkyl, —$COR^{11'}$, —$COOR^{11'}$, —$CON(R^{11'})_2$, —C≡N, $OR^{11'}$, —$N(R^{11'})_2$, —$SO_2R^{11'}$, or —$SO_2N(R^{11'})_2$, wherein each $R^{11'}$ is independently -hydrogen, —$C_1$-$C_6$ alkyl, or —$C_1$-$C_6$haloalkyl.

In another embodiment, the invention provides the compound according to formula XXIV, wherein $R^2$ is -$L^3$-$R^7$, wherein $L^3$ is a bond or —$C(R^{11'''})_2$—; and $R^7$ is hydrogen, halogen, —$C_1$-$C_6$alkyl, —$C_1$-$C_6$haloalkyl, —$OR^{11'''}$, —$C(=O)R^{11'''}$, —$C(=O)OR^{11'''}$, —$C(=O)N(R^{11'''})_2$, —$N(R^{11'''})_2$, —CN, —$SO_2R^{11'''}$, or —$S(O)_2N(R^{11'''})_2$, wherein each $R^{11'''}$ is independently —H or —$C_1$-$C_6$alkyl.

In another embodiment, the invention provides the compound according to formula XXIV, wherein each $R^{41}$ is independently hydrogen, halogen, —$C_1$-$C_6$alkyl, or —$C_1$-$C_6$haloalkyl.

In another embodiment, the invention provides the compound according to formula XXIV, wherein $R^{21}$ is hydrogen, halogen, nitro, cyano, $C_1$-$C_6$alkyl, or $C_1$-$C_6$haloalkyl.

In another embodiment, the invention provides the compound according to formula XXI, wherein $L^1$ is a bond; and $R^5$ is pyridyl, pyrimidinyl, or pyrazinyl optionally substituted with one or more $R^{5a}$ such compounds are referred to hereafter as compounds of formula XXV.

In another embodiment, the invention provides the compound according to formula XXV, wherein each $R^{5a}$ is -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XXV, wherein each $R^4$ is independently halogen —$C_1$-$C_6$alkyl, —$COR^{11'}$, —$COOR^{11'}$, —$CON(R^{11'})_2$, —C≡N, —$OR^{11'}$, —$N(R^{11'})_2$, —$SO_2R^{11'}$, or —$SO_2N(R^{11'})_2$, wherein each $R^{11'}$ is independently -hydrogen, —$C_1$-$C_6$ alkyl, or —$C_1$-$C_6$ haloalkyl.

In another embodiment, the invention provides the compound according to formula XXV, wherein $R^2$ is -$L^3$-$R^7$, wherein $L^3$ is a bond; and $R^7$ is hydrogen, halogen, —$C_1$-$C_6$alkyl, —$C_1$-$C_6$haloalkyl, alkenyl, $C_3$-$C_8$ cycloalkyl, or —$(C(R^{15})_2)_{m'}$—Z, wherein m' is 0-1; and Z is —$OR^{11}$, —$C(=O)R^{11}$, —$C(=O)OR^{11}$, —$C(=O)N(R^{11})_2$, —$N(R^{11})_2$, —CN, or —$SO_2R^{11}$, wherein $R^{11}$ is —H or $C_1$-$C_6$alkyl.

In another embodiment, the invention provides the compound according to formula XXV, wherein each $R^{41}$ is independently hydrogen, halogen, —$C_1$-$C_6$alkyl, or —$C_1$-$C_6$haloalkyl.

In another embodiment, the invention provides the compound according to formula XXV, wherein $R^{21}$ is hydrogen, halogen, nitro, cyano, $C_1$-$C_6$alkyl, or $C_1$-$C_6$haloalkyl.

In another embodiment, the invention provides the compound according to formula XIX, wherein K is heteroaryl; and $L^2$ is a bond.

In another embodiment, the invention provides the compound according to formula XIX, wherein K is thienyl, furyl, pyrrolyl, thiazoyl, oxazoyl, isothiazoyl, isoxazoyl, pyridyl, pyrimidinyl, or pyrazinyl; and $L^2$ is a bond.

In another embodiment, the invention provides the compound according to formula XIX, wherein K is pyridyl; and $L^2$ is a bond.

In another embodiment, the invention provides the compound according to formula XIX, wherein K is pyridyl; $L^2$ is a bond; $L^1$ is a bond; and $R^5$ is phenyl optionally substituted with one or more $R^{5a}$.

In another embodiment, the invention provides the compound according to formula XXVI,

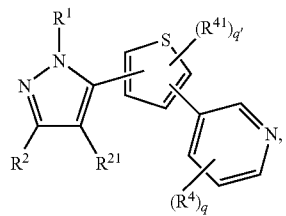

(XXVI)

or a pharmaceutically acceptable salt, isomer, or prodrug thereof, wherein $R^1$, $R^2$, $R^{21}$, $R^4$, $R^{41}$, $L^2$, q, and q' are as defined in formulas Ia-d.

In another embodiment, the invention provides the compound according to formula XXVII,

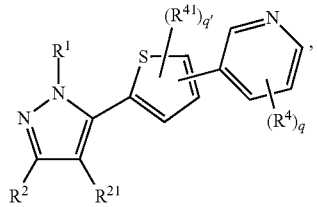

(XXVII)

or a pharmaceutically acceptable salt, isomer, or prodrug thereof, wherein $R^1$, $R^2$, $R^{21}$, $R^4$, $R^{41}$, $L^2$, q, and q' are as defined in formulas Ia-d.

In another embodiment, the invention provides the compound according to formula XXVIII,

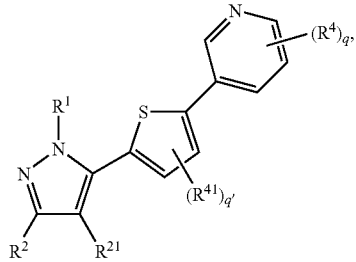

(XXVIII)

or a pharmaceutically acceptable salt, isomer, or prodrug thereof, wherein $R^1$, $R^2$, $R^{21}$, $R^4$, $R^{41}$, $L^2$, q, and q' are as defined in formulas Ia-d.

In another embodiment, the invention provides the compound according to formula XXVIII, wherein each $R^{5a}$ is -halogen, —$C_1$-$C_6$alkyl, —$C_1$-$C_6$haloalkyl, —$OR^{11}$, —$COR^{11}$, —C≡N, —$C(O)OR^{11}$, —$CON(R^{11})_2$, or —$N(R^{11})_2$.

In another embodiment, the invention provides the compound according to formula XXVIII, wherein each $R^{41}$ is independently hydrogen, halogen, —$C_1$-$C_6$alkyl, or —$C_1$-$C_6$haloalkyl.

In another embodiment, the invention provides the compound according to formula XXVIII, wherein each $R^4$ is independently halogen —$C_1$-$C_6$alkyl, —$C_1$-$C_6$haloalkyl, —$COR^{11'}$, —$COOR^{11'}$, —$CON(R^{11'})_2$, —C≡N, —$OR^{11'}$, —$N(R^{11'})_2$, —$SO_2R^{11'}$, or —$SO_2N(R^{11'})_2$, wherein each $R^{11'}$ is independently -hydrogen, —$C_1$-$C_6$ alkyl, or —$C_1$-$C_6$ haloalkyl.

In another embodiment, the invention provides the compound according to formula XXVIII, wherein $R^2$ is -$L^3$-$R^7$, wherein $L^3$ is a bond or —$C(R^{11''})_2$—; and $R^7$ is hydrogen, halogen, —$C_1$-$C_6$alkyl, —$C_1$-$C_6$haloalkyl, —$OR^{11'''}$, —$C(=O)R^{11'''}$, —$C(=O)OR^{11'''}$, —$C(=O)N(R^{11'''})_2$, —$N(R^{11'''})_2$, —CN, —$SO_2R^{11'''}$, or —$S(=O)_2N(R^{11'''})_2$, wherein each $R^{11'''}$ is independently —H or —$C_1$-$C_6$alkyl.

In another embodiment, the invention provides the compound according to formula XXVIII, wherein $R^{21}$ is hydrogen, halogen, nitro, cyano, $C_1$-$C_6$alkyl, or $C_1$-$C_6$haloalkyl.

In another embodiment, the invention provides the compound according to formula Ia-d, wherein J is aryl or heteroaryl.

In another embodiment, the invention provides the compound according to formula Ia-d, wherein J is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl.

In another embodiment, the invention provides the compound according to formula Ia-d, wherein J is phenyl, pyridyl, thienyl, pyrrolyl, or furanyl.

In another embodiment, the invention provides the compound according to formula Ia-d, wherein J is phenyl, pyridyl, or thienyl.

In another embodiment, the invention provides the compound according to formula Ia-d, wherein J is phenyl.

In another embodiment, the invention provides the compound according to formula Ia-d, wherein J is pyridyl.

In another embodiment, the invention provides the compound according to formula Ia-d, wherein J is thienyl.

In another embodiment, the invention provides the compound according to formula Ia-d, wherein K is aryl or heteroaryl.

In another embodiment, the invention provides the compound according to formula Ia-d, wherein K is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl.

In another embodiment, the invention provides the compound according to formula Ia-d, wherein K is phenyl, pyridyl, thienyl, pyrrolyl, or furanyl.

In another embodiment, the invention provides the compound according to formula wherein K is phenyl or pyridyl.

In another embodiment, the invention provides the compound according to formula Ia-d, wherein K is pyridyl.

In another embodiment, the invention provides the compound according to formula Ia-d, wherein K is phenyl.

In another embodiment, the invention provides the compound according to formula Ia-d, wherein $L^2$ is a bond.

In another embodiment, the invention provides the compound according to formula Ia-d, wherein J is aryl or heteroaryl; and K is aryl or heteroaryl.

In another embodiment, the invention provides the compound according to formula Ia-d, wherein J is aryl or heteroaryl; K is aryl or heteroaryl; and $L^2$ is a bond.

In another embodiment, the invention provides the compound according to formula Ia-d, wherein
J is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl;
K is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl; and
$L^2$ is a bond.

In another embodiment, the invention provides the compound according to formula Ia-d, wherein J is phenyl, pyridyl, thienyl, pyrrolyl, or furanyl; K is phenyl, pyridyl, thienyl, pyrrolyl, or furanyl; and $L^2$ is a bond.

In another embodiment, the invention provides the compound according to formula Ia-d, wherein J is phenyl, pyridyl, or thienyl; K is phenyl or pyridyl; and $L^2$ is a bond.

In another embodiment, the invention provides the compound according to formula Ia-d, wherein J is phenyl; K is phenyl; and $L^2$ is a bond.

In another embodiment, the invention provides the compound according to formula Ia-d, wherein J is pyridyl; K is phenyl; and $L^2$ is a bond.

In another embodiment, the invention provides the compound according to formula Ia-d, wherein J is thienyl; K is phenyl; and $L^2$ is a bond.

In another embodiment, the invention provides the compound according to formula Ia-d, wherein J is phenyl; K is pyridyl; and $L^2$ is a bond.

In another embodiment, the invention provides the compound according to formula Ia-d, wherein J is pyridyl; K is pyridyl; and $L^2$ is a bond.

In another embodiment, the invention provides the compound according to formula Ia-d, wherein J is thienyl; K is pyridyl; and $L^2$ is a bond.

In another embodiment, the invention provides the compound according to formula Ia-d, wherein $R^5$ is aryl, heterocyclyl, or heteroaryl, wherein $R^5$ is optionally substituted with one or more $R^{5a}$.

In another embodiment, the invention provides the compound according to formula Ia-d, wherein $R^5$ is aryl or heteroaryl, wherein $R^5$ is optionally substituted with one or more $R^{5a}$.

In another embodiment, the invention provides the compound according to formula Ia-d, wherein $R^5$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl wherein $R^5$ is optionally substituted with one or more $R^{5a}$.

In another embodiment, the invention provides the compound according to formula Ia-d, wherein $L^1$ is a bond; and $R^5$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl, wherein $R^5$ is optionally substituted with one or more $R^{5a}$.

In another embodiment, the invention provides the compound according to formula Ia-d, wherein $L^1$ is a bond; and $R^5$ is phenyl, pyridyl, thienyl, pyrrolyl, or furanyl, wherein $R^5$ is optionally substituted with one or more $R^{5a}$.

In another embodiment, the invention provides the compound according to formula Ia-d, wherein $L^1$ is a bond; and $R^5$ is phenyl optionally substituted with one or more $R^{5a}$.

In another embodiment, the invention provides the compound according to formula Ia-d, wherein $L^1$ is a bond; and $R^5$ is pyridyl optionally substituted with one or more $R^{5a}$.

In another embodiment, the invention provides the compound according to formula Ia-d, wherein $L^1$ is a bond; and $R^5$ is thienyl optionally substituted with one or more $R^{5a}$.

In another embodiment, the invention provides the compound according to formula Ia-d wherein $R^{21}$ is hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, —Z, —Y—Z, or —X—Y—Z, wherein
X is —O—;
Y is —[C($R^{15}$)$_2$]$_m$—, —$C_2$-$C_6$ alkenyl, or $C_3$-$C_8$ cycloalkyl;
Z is —H, —CN, halogen, —O$R^{11}$, —C(=O)$R^{11}$, —C(=O)O$R^{11}$, —C(=O)N($R^{11}$)$_2$, —N($R^{11}$)$_2$, —CN, —$N_3$, —SO$_2$$R^{11}$, —S(=O)$_2$N($R^{11}$)$_2$, —C(=O)($R^{11}$)N($R^{11}$)$_2$, —C(=O)N($R^{11}$)(O$R^{11}$), —OC(=O)—$R^{11}$, —OC(=O)—N($R^{11}$)$_2$, or —N($R^{11}$)COO$R^{11}$.

In another embodiment, the invention provides the compound according to formula Ia-d wherein $R^{21}$ is hydrogen, halogen, nitro, cyano, $C_1$-$C_6$alkyl, or $C_1$-$C_6$haloalkyl.

In another embodiment, the invention provides the compound according to formula XXIXa-d wherein $R^3$ is hydrogen, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, —Z, or —Y—Z wherein
Y is —[C($R^{15}$)$_2$]$_m$—, —$C_2$-$C_6$ alkenyl, or $C_3$-$C_8$ cycloalkyl;
Z is —H, —CN, halogen, —O$R^{11}$, —C(=O)$R^{11}$, —C(=O)O$R^{11}$, C(=O)N($R^{11}$)$_2$, —N($R^{11}$)$_2$, —CN, —N$_3$, —SO$_2$R$^{11}$, —S(=O)$_2$N(R$^{11}$)$_2$, —C(=O)N(R$^{11}$) N(R$^{11}$)$_2$, —C(=O)N(R$^{11}$)(OR$^{11}$), —OC(O)—R$^{11}$, —OC(=O)—N(R$^{11}$)$_2$, or —N(R$^{11}$)COOR$^{11}$.

In another embodiment, the invention provides the compound according to formula Ia-d wherein R$^3$ is hydrogen, C$_1$-C$_6$alkyl, or C$_1$-C$_6$haloalkyl.

In another embodiment, the invention provides the compound according to any of the formulas Ia-d, II-XXVIII, wherein R$^2$ is -L$^3$-R$^7$, wherein L$^3$ is a bond; and
R$^7$ is hydrogen, halogen, —Z, or —Y—Z, wherein
Y is —[C(R$^{15'}$)$_2$]$_m$— or C$_2$-C$_6$alkenyl, .
wherein each R$^{15'}$ is independently H, halogen, or (C$_1$-C$_6$)alkyl; and
Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$.

In another embodiment, the invention provides the compound according to any of the formulas Ia-d, II-XXVIII, wherein R$^2$ is -L$^3$-R$^7$, wherein L$^3$ is a bond; and
R$^7$ is hydrogen, halogen, or —[C(R$^{15'}$)$_2$]—Z, wherein
each R$^{15'}$ is independently H, halogen, or (C$_1$-C$_2$)alkyl; and
Z is —H, halogen, —OR$^{11'''}$, —C(=O)R$^{11'''}$, —C(=O)OR$^{11'''}$, —C(=O)N(R$^{11'''}$)$_2$, —C(=N—OH)R$^{11'''}$, or —C(=S)N(R$^{11'''}$)$_2$,
wherein R$^{11'''}$ is —H or —(C$_1$-C$_6$ alkyl).

In another embodiment, the invention provides the compound according to any of the formulas Ia-d, II-XXVIII, wherein R$^2$ is -halogen, —CF$_3$, —CH$_2$OH, —CH$_2$SO$_2$Me, —C(CH$_3$)$_2$OH, or —C(CH$_3$)$_2$SO$_2$Me.

In another embodiment, the invention provides the compound according to any of the formulas Ia-d, II-XXVIII, wherein R$^2$ is -halogen, —CF$_3$, —CH$_2$OH, or —C(CH$_3$)$_2$OH.

In another embodiment, the invention provides the compound according to any of the formulas Ia-d, II-XXVIII, wherein R$^2$ is —CF$_3$ or —C(CH$_3$)$_2$OH.

In another embodiment, the invention provides the compound according to any of the formulas Ia-d, wherein
each R$^4$ is independently halogen, aryl, heteroaryl, heterocyclyl, -M, or -E-M, wherein
E is —[C(R$^{15'}$)$_2$]$_m$—, wherein
each R$^{15'}$ is independently hydrogen or halogen; and
M is —C$_1$-C$_6$alkyl, —C$_1$-C$_6$haloalkyl, halogen, —OR$^{11}$, or —SO$_2$R$^{11}$.

In another embodiment, the invention provides the compound according to any of the formulas Ia-d, II-XXVIII, wherein each R$^4$ is independently halogen, —CH$_2$-M, —C(H)(F)-M, —CF$_2$-M, wherein
M is —C$_1$-C$_6$alkyl, —C$_1$-C$_6$haloalkyl, —F, —OR$^{11'}$, or —SO$_2$R$^{11'}$
wherein R$^{11'}$ is —H or —C$_1$-C$_6$alkyl.

In another embodiment, the invention provides the compound according to any of the formulas Ia-d, II-XXVIII, wherein each R$^4$ is independently —CH$_3$, —CF$_3$, —CF$_2$H, —CH$_2$F, —OH, —OMe, —CH$_2$OH, or —SO$_2$(C$_1$-C$_3$alkyl).

In one embodiment, the invention provides the compound according to any of the formulas Ia-d, II-XXVIII, wherein each R$^{41}$ is independently halogen, -M'', or -E''-M'', wherein
E'' is —[C(R$^{15'}$)$_2$]$_m$—,
wherein each R$^{15'}$ is independently hydrogen or halogen; and
M'' is —C$_1$-C$_6$alkyl, —C$_1$-C$_6$haloalkyl, or halogen.

In another embodiment, the invention provides the compound according to formulas Ia-d, II-XXVIII, wherein each R$^{41}$ is independently halogen, methyl or trifluoromethyl.

In another embodiment, the invention provides the compound according to formulas Ia-d, II-IV, VI-IX, XIII, XIV-XVII, and XIX-XXI wherein
R$^1$ is -L$^5$-R$^5$ or -L$^6$-R$^5$ wherein
L$^5$ is —[C(R$^{15}$)$_2$]$_m$—;
L$^6$ is C$_3$-C$_8$ cycloalkyl, cycloC$_{3-8}$haloalkyl, or heterocyclyl, wherein the cycloalkyl, cycloC$_{3-8}$haloalkyl 1, or heterocyclyl are optionally substituted with one or more radicals of R$^{14}$;
R$^5$ is aryl, heterocyclyl, or heteroaryl, wherein R$^5$ is optionally substituted with one or more R$^{5a}$, wherein each R$^{5a}$ is independently halogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, nitro, heterocyclyloxy, aryl, aryloxy, arylalkyl, aryloxyaryl, aryl C$_1$-C$_6$ alkoxy, —C', —B'—C', or -A'-B'—C' wherein
A' is —O—;
B' is —[C(R$^{15}$)$_2$]$_m$— or —C$_3$-C$_8$ cycloalkyl-;
C' is —H, halogen, —SO$_2$R$^{11}$, —OR$^{11}$, —SR$^{11}$, —N$_3$, —COR$^{11}$, —SO$_2$N(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, —N(R$^{11}$)$_2$, aryl, heteroaryl, or heterocyclyl.

In another embodiment, the invention provides the compound according to formulas Ia-d, II-XXVIII, wherein R$^{21}$ is hydrogen, halogen, nitro, cyano, aryl, heteroaryl, heterocyclyl, —C$_1$-C$_6$ alkyl-heterocyclyl, —C$_1$-C$_6$ alkyl-heteroaryl, —C$_1$-C$_6$ alkyl-aryl, —Z, —Y—Z, or —X—Y—Z, wherein
X is —O—;
Y is —[C(R$^{15}$)$_2$]$_m$—, —C$_2$-C$_6$ alkenyl, or C$_3$-C$_8$ cycloalkyl;
Z is —H, —CN, halogen, —OR$^{11}$, —C(=O)R$^{11}$, —C(=O)OR$^{11}$, —C(=O)N(R$^{11}$)$_2$, —N(R$^{11}$)$_2$, —CN, —N$_3$, —SO$_2$R$^{11}$, —S(=O)$_2$N(R$^{11}$)$_2$, —C(=O)N(R$^{11}$) N(R$^{11}$)$_2$, —C(=O)N(R$^{11}$)(OR$^{11}$), —OC(=O)—R$^{11}$, —OC(=O)N(R$^{11}$)$_2$, or —N(R$^{11}$)COOR$^{11}$.

In another embodiment, the invention provides the compound according to formulas Ia-d, II-XXVIII, wherein R$^{21}$ is hydrogen, halogen, nitro, cyano, C$_1$-C$_6$alkyl, or C$_1$-C$_6$haloalkyl.

In another embodiment, the invention provides the compound according to formulas Ia-d, and XL wherein R$^{21}$ is hydrogen.

In a second aspect, the invention provides intermediate compounds according to one of the formulas XXIXa-d,

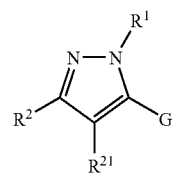

XXIXa

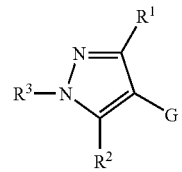

XXIXb

-continued

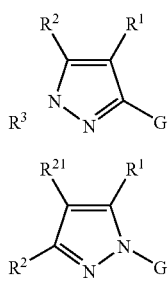

XXIXc

XXIXd wherein,
(A) R$^1$ is -L$^1$-R$^5$, wherein
L$^1$ is a bond, L$^5$, L$^6$, -L$^5$-L$^6$-L$^5$-, or -L$^6$-L$^5$-L$^6$-, wherein
each L$^5$ is independently —[C(R$^{15}$)$_2$]$_m$—, wherein
each m is independently 0, 1, 2, 3, 4, 5 or 6; and
each R$^{15}$ is independently hydrogen, halogen, (C$_1$-C$_6$)alkyl, or (C$_1$-C$_6$)haloalkyl;
each L$^6$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —N(R$^{10}$)CO—, —N(R$^{10}$)CO$_2$—, —CON(R$^{10}$)—, —CO—, —CS—, —CO$_2$—, —OC(=O)—, —OC(=O)N(R$^{10}$)—, —CONR$^{11}$N(R$^{11}$)$_2$—, —CONR$^{11}$—, —OCONR$^{11}$—, —SO$_2$—, —N(R$^{10}$)SO$_2$—, —SO$_2$N(R$^{10}$)—, —NR$^{10}$CONR$^{10}$—, —NR$^{10}$CSNR$^{10}$—, —C(=NR$^{11}$)—, —C(=NOR$^{11}$)—, —C(=NN(R$^{11}$)$_2$)—; aryl, C$_3$-C$_8$ cycloalkyl, cycloC$_{3-8}$haloalkyl, heteroaryl, or heterocyclyl, wherein the aryl, cycloalkyl, cyclohaloalkyl heteroaryl, or heterocyclyl are optionally substituted with one or more radicals of R$^{14}$;
or L$^1$ is a C$_{2-6}$ alidiyl chain wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡N, —O—, —S—, —N(R$^{10}$)CO—, —N(R$^{10}$)CO$_2$—, —CON(R$^{10}$)—, —CO—, —CO$_2$—, —OC(O)—, —OC(O)N(R$^{10}$)—, —SO$_2$—, —N(R$^{10}$)SO$_2$—, or —SO$_2$N(R$^{10}$)—, and
R$^5$ is aryl, heterocyclyl, heteroaryl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, C$_3$-C$_8$ cycloalkyl, —C, —B—C, or -A-B—C, wherein
A is —O—;
B is —[C(R$^{15}$)$_2$]$_m$— or C$_3$-C$_8$ cycloalkyl;
C is C$_1$-C$_6$alkyl, C$_1$-C$_6$haloalkyl, SO$_2$R$^{11}$, SR$^{11}$, SO$_2$N(R$^{11}$)$_2$, SO$_2$NR$^{11}$COR$^{11}$, —C≡N, C(O)OR$^{11}$, CON(R$^{11}$)$_2$, or N(R$^{11}$)$_2$;
wherein R$^5$ is optionally substituted with one or more R$^{5a}$,
wherein each R$^{5a}$ is independently C$_1$-C$_6$ alkyl, C$_2$-C$_6$ alkenyl, C$_2$-C$_6$ alkenyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, halogen, nitro, heterocyclyloxy, aryl, aryloxy, arylalkyl, aryloxyaryl, aryl C$_1$-C$_6$ alkoxy, —C', —B'—C', or -A'-B'—C' wherein
A' is —O—;
B' is —[C(R$^{15}$)$_2$]$_m$— or —C$_3$-C$_8$ cycloalkyl-;
C' is —H, halogen, —SO$_2$R$^{11}$, —OR$^{11}$, —SR$^{11}$, —N$_3$, —COR$^{11}$, —SO$_2$N(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, —N(R$^{11}$)$_2$, aryl, heteroaryl, or heterocyclyl;
wherein each R$^{5a}$ is optionally substituted one or more groups which are independently C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, C$_0$-C$_6$ alkoxyaryl, C$_1$-C$_6$ alkyl, C$_3$-C$_8$ cycloalkyl, aryl, aryl-C$_1$-C$_6$ alkyl-, heteroaryl, halogen, —NO$_2$, —C≡N, —COR$^{11}$, —COOR$^{11}$, —CON(R$^{11}$)$_2$, —SO$_2$R$^{11}$, —OR$^{11}$, —SR$^{11}$, —SO$_2$R$^{11}$, —SO$_2$N(R$^{11}$)$_2$, —SO$_2$NR$^{11}$COR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;
R$^2$ and R$^{21}$ are -L$^3$-R$^7$, wherein
each L$^3$ is independently a bond —V$^1$—(CH$_2$)$_n$—V$^1$—, or —(CH$_2$)$_m$—V$^1$—(CH$_2$)$_n$— wherein
n is 0-6; and
each V$^1$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^7$—, —N(R$^{10}$)CO—, —N(R$^{10}$)CO$_2$—, —OCO—, —CO—, —CS—, —CONR$^{10}$—, —C(=N)(R$^{11}$)—, —C(=N—OR$^{11}$)—, —C[=N—N(R$^{11}$)$_2$], —CO$_2$—, —OC(=O)—, —OC(=O)N(R$^{10}$)—, —SO$_2$—, —N(R$^{10}$)SO$_2$—, —SO$_2$N(R$^{10}$)—, —NR$^{10}$CONR$^{10}$—, —NR$^{10}$CSNR$^{10}$—, C$_3$-C$_8$ cycloalkyl, or C$_3$-C$_8$ cyclohaloalkyl;
or each L$^3$ is independently a C$_{2-6}$ alidiyl chain, wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$); and
each R$^7$ is independently hydrogen, halogen, nitro, cyano, aryl, heteroaryl, heterocyclyl, —C$_1$-C$_6$ alkyl-heterocyclyl, —C$_1$-C$_6$ alkyl-heteroaryl, —C$_1$-C$_6$alkyl-aryl, —Z, —Y—Z, or —X—Y—Z, wherein
X is —O—;
Y is —[C(R$^{15}$)$_2$]$_m$— —C$_2$-C$_6$ alkenyl, or C$_3$-C$_8$ cycloalkyl;
Z is —H, —CN, halogen, —OR$^{11}$, —C(=O)R$^{11}$, —C(=O)OR$^{11}$, —C(=O)N(R$^{11}$)$_2$, —N(R$^{11}$)$_2$, —CN, —N$_3$, —SO$_2$R$^{11}$, —S(=O)$_2$N(R$^{11}$)$_2$, —C(=O)N(R$^{11}$)N(R$^{11}$)$_2$, —C(=O)N(R$^{11}$)(OR$^{11}$), —OC(=O)—R$^{11}$, —OC(=O)—N(R$^{11}$)$_2$, or —N(R$^{11}$)COOR$^{11}$;
wherein R$^7$ is optionally substituted with one or more R$^{7a}$, wherein
R$^{7a}$ is halogen, C$_2$-C$_6$ alkenyl, —C$_1$-C$_6$ alkyl-heterocyclyl, —C$_1$-C$_6$ alkyl-heteroaryl, —C$_1$-C$_6$ alkyl-aryl, C$_0$-C$_6$ alkoxyheteroaryl, C$_0$-C$_6$alkoxyheterocyclyl, haloaryl, aryloxy, aralkyloxy, aryloxyalkyl, C$_1$-C$_6$alkoxyaryl, aryl C$_0$-C$_6$ alkylcarboxy, C(R$^{11}$)=C(R$^{11}$)—COOR$^{11}$, C$_0$-C$_6$alkoxyheteroaryl, C$_0$-C$_6$alkoxyheterocyclyl, aryl, heteroaryl, heterocyclyl, C$_3$-C$_8$ cycloalkyl, heteroaryloxy, —Z', —Y'—Z', or —X'—Y'—Z', wherein
X' is —O—;
Y' is —[C(R$^{15}$)$_2$]$_m$— or C$_3$-C$_8$ cycloalkyl;
Z' is —C$_1$-C$_6$alkyl, —C$_1$-C$_6$haloalkyl, —OR$^{11}$, —SR$^{11}$, —S(=O)$_2$R$^{11}$, —C(=O)R$^{11}$, —C(=O)OR$^{11}$, —C(=O)N(R$^{11}$)$_2$, —N(R$^{11}$)$_2$, —N(R$^{11}$)C(=O)R$^{11}$, —S(=O)$_2$N(R$^{11}$)C(=O)$^{11}$, —CN, —S(=O)$_2$N(R$^{11}$)$_2$, —C(=O)N(R$^{11}$)N(R$^{11}$)$_2$, —C(=O)N(R$^{11}$)(OR$^{11}$), —OC(=O)—R$^{11}$, —OC(=O)—OR$^{11}$, —N(R$^{11}$)C(=O)O—R$^{11}$, or —N(R$^{11}$)S(=O)$_2$R$^{11}$;

wherein each R$^{7a}$ is optionally substituted with one or more R$^8$, wherein each R$^8$ is independently halogen, nitro, cyano, heteroaryl, C$_1$-C$_6$ alkyl, C$_1$-C$_6$ alkoxy, C$_1$-C$_6$ haloalkyl, C$_1$-C$_6$ haloalkyl(OR$^{11}$), C$_0$-C$_6$ alkylCON(R$^{11}$)$_2$, C$_0$-C$_6$ alkylCOR$^{11}$, C$_0$-C$_6$ alkylCOOR$^{11}$, or C$_0$-C$_6$ alkylSO$_2$R$^{11}$; and wherein if two R$^{7a}$ are present on the same carbon, then they may be taken together to form a cycloalkyl or heterocyclyl group; provided that R$^2$ and R$^{21}$ are not simultaneously —H;

R$^3$ is -L-R$^6$, wherein

L is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$— wherein n is 0-6; each w is independently 0-5; and each X$^3$ is independently a bond, —C(R$^{11}$)$_2$—, —C(R$^{11}$)$_2$C(R$^{11}$)$_2$—, —C(R$^{11}$)=C(R$^{11}$)—, —C≡C—, —CO—, —CS—, —CONR$^{10}$—, —C(=N)(R$^{11}$)—, —C(=N—OR$^{11}$)—, —C[=N—N(R$^{11}$)$_2$], —CO$_2$—, —SO$_2$—, or —SO$_2$N(R$^{10}$)—; and Y$^3$ is —O—, —S—, —NR$^7$—, —N(R$^{10}$)CO—, —N(R$^{10}$)CO$_2$—, —OCO—, —OC(=O)N(R$^{10}$)—, —NR$^{10}$CONR$^{10}$—, —N(R$^{10}$)SO$_2$—, or —NR$^{10}$CSNR$^{10}$—;

or L is a C$_{2-6}$ alidiyl chain, wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$); and R$^6$ is C$_1$-C$_6$ alkyl, C$_1$-C$_6$ haloalkyl, aryl, C$_3$-C$_8$ cycloalkyl, heteroaryl, heterocyclyl, —CN, —C(=O)R$^{11}$, —C(=O)OR$^{11}$, —C(=O)N(R$^{11}$)$_2$, —N(R$^{11}$)$_2$, —SO$_2$R$^{11}$, —S(=)$_2$N(R$^{11}$)$_2$, —C(=O)N(R$^{11}$)N(R$^{11}$)$_2$, or —C(=O)N(R$^{11}$)(OR$^{11}$), wherein the aryl, heteroaryl, cycloalkyl, or heterocyclyl is optionally substituted with one or more R$^{6a}$, wherein each R$^{6a}$ is independently —Z", —Y"—Z", or —X"—Y"—Z", wherein X" is —O—;

Y" is —[C(R$^{15}$)$_2$]$_m$—, —C$_2$-C$_6$ alkenyl, C$_3$-C$_8$ cycloalkyl, heterocyclyl, aryl, or heteroaryl, wherein the aryl, heteroaryl, cycloalkyl, or heterocyclyl is optionally substituted with at least one group which is each independently Z";

Z" is —H, —CN, halogen, —OR$^{11}$, —C(=O)R$^{11}$, —C(=O)OR$^{11}$, —C(=O)N(R$^{11}$)$_2$, —N(R$^{11}$)$_2$, —N$_3$, —SO$_2$R$^{11}$, —S(=O)$_2$N(R$^{11}$)$_2$, —C(=O)N(R$^{11}$)N(R$^{11}$)$_2$, —N(R$^{11}$)C(=O)N(R$^{11}$)$_2$, —OC(=O)OR$^{11}$, —C(=O)N(R$^{11}$)(OR$^{11}$), —OC(=O)—R$^{11}$, —OC(=O)—N(R$^{11}$)$_2$, or —N(R$^{11}$)COOR$^{11}$;

each R$^{10}$ is independently —R$^{11}$, —C(O)R$^{11}$, —CO$_2$R$^{11}$, or —SO$_2$R$^{11}$;

each R$^{11}$ is independently -hydrogen, C$_2$-C$_6$ alkenyl, C$_2$-C$_6$ alkynyl, (C$_3$-C$_8$ cycloalkenyl)-C$_1$-C$_6$ alkyl-, (C$_3$-C$_8$ cycloalkyl)-C$_2$-C$_6$ alkenyl-, —N(R$^{12}$)$_2$, —C$_1$-C$_6$ alkyl, —C$_1$-C$_6$ haloalkyl, —C$_3$-C$_8$ cycloalkyl, —(C$_1$-C$_6$)alkyl-(C$_3$-C$_8$) cycloalkyl, aryl, —(C$_1$-C$_6$)alkyl-aryl, heteroaryl, —(C$_1$-C$_6$) alkyl-heteroaryl, heterocyclyl, or —(C$_1$-C$_6$)alkyl-heterocyclyl, wherein any of R$^{11}$ is optionally substituted with one or more radicals of R$^{12}$;

each R$^{12}$ is independently hydrogen, halogen, C$_1$-C$_6$ haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkyl-COR$^{13}$, C$_0$-C$_6$ alkylSO$_2$R$^{13}$, C$_0$-C$_6$ alkylCN, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_0$-C$_6$alkoxyaryl, aryl C$_0$-C$_6$ alkylcarboxy, C$_0$-C$_6$ alkylNR$^{13}$SO$_2$R$^{13}$, —C$_0$-C$_6$alkylN(R$^{13}$)$_2$, or OC$_0$-C$_6$ alkylCOOR$^{13}$;

each R$^{13}$ is independently hydrogen, C1-C6 alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$alkylCONR$^{11}$OR$^{11}$, C$_0$-C$_6$ alkylOR$^{11}$, or C$_0$-C$_6$ alkyl-COOR$^{11}$;

G is a group of the formula,

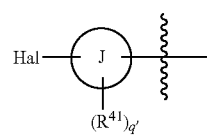

wherein

J is aryl, heteroaryl, or absent;

Hal is halogen;

each R$^{41}$ is independently halogen, nitro, C$_1$-C$_6$ alkyl-heterocyclyl, —C$_1$-C$_6$ alkyl-heteroaryl, —C$_1$-C$_6$ alkyl-aryl, -M", -E"-M", or -D"-E"-M", wherein D" is —O—;

E" is —[C(R$^{15}$)$_2$]$_m$— or C$_3$-C$_8$cycloalkyl;

M" is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SO$_2$R$^{11}$, —SO$_2$NR$^{11}$COR$^{11}$, —SO$_2$N(R$^{11}$)$_2$, or —SR$^{11}$, wherein each R$^{41}$ is optionally substituted with one or more R$^{4a}$, wherein each R$^{4a}$ is independently halogen, aryloxy, aralkyloxy, aryloxyalkyl, —C$_1$-C$_6$ alkyl-aryl, C$_1$-C$_6$ alkoxyaryl, aryl C$_0$-C$_6$ alkylcarboxy, -M', -E'-M', or -D'-E'-M'

D' is —O—;

E' is —[C(R$^{15}$)$_2$]$_m$— or C$_3$-C$_8$cycloalkyl;

M' is —C$_1$-C$_6$alkyl, —C$_1$-C$_6$haloalkyl, COR$^{11}$, —CON(R$^{11}$)$_2$, —N(R$^{11}$)COOR$^{11}$, —N(R$^{11}$)$_2$, COOR$^{11}$, C≡N, OR$^{11}$, —NR$^{11}$COR$^{11}$, NR$^{11}$SO$_2$R$^{11}$, SO$_2$R$^{11}$, SO$_2$N(R$^{11}$)$_2$, or SR$^{11}$; and q' is 0, 1, 2, 3, or 4, and provided that, (i) if the compound is defined by formula XXIXa, then
(a) R$^1$ is not 4-(NH$_2$SO$_2$)phenyl, 4-(CH$_3$SO$_2$)phenyl, or 4-(CH$_2$FSO$_2$)phenyl;
(b) if R$^1$ is 4-fluorophenyl, then G is not 4-[(H$_2$NS(=O)-]phenyl-
(c) R$^2$ is not 4-hydroxyphenyl;

(ii) if the compound is defined by formula XXIXb, then
(a) R$^2$ is not 4-(NH$_2$SO$_2$)phenyl, 4-(CH$_3$SO$_2$)phenyl, or 4-(CH$_2$FSO$_2$)phenyl (b) J is not pyridyl;
(c) $R^1$ is not 4-hydroxyphenyl;
(iii) if the compound is defined by formula XXIXc, then
(a) $R^2$ is not 4-$(NH_2SO_2)$phenyl, 4-$(CH_3SO_2)$phenyl, or 4-$(CH_2FSO_2)$phenyl
(b) J is not pyridyl;
(iv) if the compound is defined by formula XXIXd, then
(a) if $L^1$ is a bond, then $R^1$ is not thienyl or 5-methylthienyl;
(b) if G is 4-fluorophenyl, then $R^1$ is not 4-[$(H_2NS(=O)_2$-]phenyl-
(c) $R^1$ is not 4-Me-phenyl In another embodiment, the invention provides the compound according to formula XXIXa-d, wherein Hal is —Cl, —Br, or —I.

In another embodiment, the invention provides the compound according to formula XXIXa-d wherein $R^{21}$ is hydrogen, halogen, nitro, cyano, aryl, heteroaryl, heterocyclyl, alkyl-heterocyclyl, —$C_1$-$C_6$ alkyl-heteroaryl, —$C_1$-$C_6$ alkyl-aryl, —Z, —Y—Z, or —X—Y—Z, wherein
X is —O—;
Y is —[C($R^{15}$)$_2$]$_m$—, —$C_2$-$C_6$ alkenyl, or $C_3$-$C_8$ cycloalkyl; and
Z is —H, —CN, halogen, —$OR^{11}$, —C(=O)$R^{11}$, —C(=O)$OR^{11}$, —C(=O)N($R^{11}$)$_2$, —N($R^{11}$)$_2$, —CN, —$N_3$, —$SO_2R^{11}$, —S(=O)$_2$N($R^{11}$)$_2$, —C(=O)N($R^{11}$)N($R^{11}$)$_2$, —C(=O)N($R^{11}$)($OR^{11}$), —OC(=O)—$R^{11}$, —OC(=O)—N($R^{11}$)$_2$, or —N($R^{11}$)COO$R^{11}$;

In another embodiment, the invention provides the compound according to formula XXIXa-d wherein $R^{21}$ is hydrogen, halogen, nitro, cyano, $C_1$-$C_6$alkyl, or $C_1$-$C_6$haloalkyl.

In another embodiment, the invention provides the compound according to formula XXIXa-d wherein $R^3$ is hydrogen, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, —Z, or —Y—Z wherein
Y is —[C($R^{15}$)$_2$]$_m$— —$C_2$-$C_6$ alkenyl, or $C_3$-$C_8$ cycloalkyl;
Z is —H, —CN, halogen, —$OR^{11}$, —C(=O)$R^{11}$, —C(=O)$OR^{11}$, —C(=O)N($R^{11}$)$_2$, —N($R^{11}$)$_2$, —CN, —$N_3$, —$SO_2R^{11}$, —S(=O)$_2$N($R^{11}$)$_2$, —C(=O)N($R^{11}$)N($R^{11}$)$_2$, —C(=O)N($R^{11}$)($OR^{11}$), —OC(=O)—$R^{11}$, —OC(=O)—N($R^{11}$)$_2$, or —N($R^{11}$)COO$R^{11}$;

In another embodiment, the invention provides the compound according to formula XXIXa-d wherein $R^3$ is hydrogen, $C_1$-$C_6$alkyl, or $C_1$-$C_6$haloalkyl.

In another embodiment, the invention provides the compound according to formula XXIXa-d, wherein J is aryl or heteroaryl.

In another embodiment, the invention provides the compound according to formula XXIXa-d, wherein J is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl.

In another embodiment, the invention provides the compound according to formula XXIXa-d, wherein J is phenyl, pyridyl, thienyl, pyrrolyl, or furanyl.

In another embodiment, the invention provides the compound according to formula XXIXa-d, wherein J is phenyl, pyridyl, or thienyl.

In another embodiment, the invention provides the compound according to formula XXIXa-d, wherein J is phenyl.

In another embodiment, the invention provides the compound according to formula XXIXa-d, wherein J is pyridyl.

In another embodiment, the invention provides the compound according to formula XXIXa-d, wherein J is thienyl.

In another embodiment, the invention provides the compound according to formula XXIXa-d, wherein $R^5$ is aryl, heterocyclyl, or heteroaryl, wherein $R^5$ is optionally substituted with one or more $R^{5a}$.

In another embodiment, the invention provides the compound according to formula XXIXa-d, wherein $R^5$ is aryl or heteroaryl, wherein $R^5$ is optionally substituted with one or more $R^{5a}$.

In another embodiment, the invention provides the compound according to formula XXIXa-d, wherein $R^5$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl wherein $R^5$ is optionally substituted with one or more $R^{5a}$.

In another embodiment, the invention provides the compound according to formula XXIXa-d, wherein $L^1$ is a bond.

In another embodiment, the invention provides the compound according to formula XXIXa-d, wherein $L^1$ is a bond; and $R^5$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl, wherein $R^5$ is optionally substituted with one or more $R^{5a}$.

In another embodiment, the invention provides the compound according to formula XXIXa-d, wherein $L^1$ is a bond; and $R^5$ is phenyl, pyridyl, thienyl, pyrrolyl, or furanyl, wherein $R^5$ is optionally substituted with one or more $R^{5a}$.

In another embodiment, the invention provides the compound according to formula XXIXa-d, wherein $L^1$ is a bond; and $R^5$ is phenyl optionally substituted with one or more $R^{58}$.

In another embodiment, the invention provides the compound according to formula XXIXa-d, wherein $L^1$ is a bond; and $R^5$ is pyridyl optionally substituted with one or more $R^{5a}$.

In another embodiment, the invention provides the compound according to formula XXIXa-d, wherein $L^1$ is a bond; and $R^5$ is thienyl optionally substituted with one or more $R^5$.

In another embodiment, the invention provides the compound according to formulas XXIXa-d, wherein
$R^2$ is -$L^3$-$R^7$, wherein $L^3$ is a bond; and
$R^7$ is hydrogen, halogen, —Z, or —Y—Z, wherein
Y is —[C($R^{15'}$)$_2$]$_m$— or $C_2$-$C_6$alkenyl,
wherein each $R^{15'}$ is independently H, halogen, or ($C_1$-$C_6$)alkyl; and
Z is —H, halogen, —$OR^{11}$, —C(=O)$OR^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formulas XXIXa-d, wherein
$R^2$ is -$L^3$-$R^7$, wherein $L^3$ is a bond; and
$R^7$ is hydrogen, halogen, or —[C($R^{15'}$)$_2$]—Z, wherein
each $R^{15'}$ is independently H, halogen, or ($C_1$-$C_2$)alkyl; and
Z is —H, halogen, —$OR^{11'''}$, —C(=O)$R^{11'''}$, —C(=O)$OR^{11'''}$, —C(=O)N($R^{11'''}$)—, —C(=N—OH)$R^{11}$, or —C(=S)N($R^{11'''}$)$_2$,
wherein $R^{11'''}$ is —H or —($C_1$-$C_6$ alkyl).

In another embodiment, the invention provides the compound according to formulas XXIXa-d, wherein $R^2$ is -halogen, —$CF_3$, —$CH_2OH$, —$CH_2SO_2Me$, —$C(CH_3)_2OH$, or —$C(CH_3)_2SO_2Me$.

In another embodiment, the invention provides the compound according to formulas XXIXa-d, wherein $R^2$ is -halogen, —$CF_3$, —$CH_2OH$, or —$C(CH_3)_2OH$.

In another embodiment, the invention provides the compound according to formulas XXIXa-d, wherein $R^2$ is —$CF_3$ or —$C(CH_3)_2OH$.

In one embodiment, the invention provides the compound according to formulas XXIXa-d, wherein each $R^{41}$ is independently halogen, -M", or -E"-M", wherein E" is $—[C(R^{15'})_2]_m—$,
wherein each $R^{15'}$ is independently hydrogen or halogen; and M" is $-C_1-C_6$alkyl, $—C_1-C_6$haloalkyl, or halogen.

In another embodiment, the invention provides the compound according to formula XXIXa-d, wherein $R^1$ is $L^1-R^5$, wherein $L^1$ is a bond; and $R^5$ is phenyl or pyridyl, each optionally substituted with one or two $R^{5a}$, wherein
each $R^{5a}$ is independently -halogen, $—CH_3$, or $—CF_3$;
$R^2$ is $—H$, $—C(R^{20})_2OH$, $—CH_3$, $—CF_3$, or halogen, wherein
each $R^{20}$ is independently $—H$, $—F$, $—CH_3$, or $—CF_3$;
J is phenyl, pyridyl, or thienyl; and
each $R^{41}$ is -halogen, $—CH_3$, $—CH_2CH_3$, $—CF_3$, $—CF_2CF_3$, or $—CH_2CF_3$.

In another embodiment, the invention provides the compound according to formula XXIXa-d, wherein q' is 0 or 1; $R^1$ is $L^1-R^5$, wherein $L^1$ is a bond;

$R^5$ is phenyl optionally substituted with one or two $R^{5a}$, wherein
each $R^{5a}$ is independently -halogen, $—CH_3$, or $—CF_3$;
each $R^2$ is $—H$, $—C(R^{20})_2OH$, $—CH_3$, $—CF_3$, or halogen, wherein
each $R^{20}$ is independently $—H$, $—F$, $—C_{1-13}$, or $—CF_3$; and
$R^{41}$ is -halogen, $—CH_3$, $—CH_2CH_3$, $—CF_3$, $—CF_2CF_3$, or $—CH_2CF_3$.

In another embodiment, the invention provides the compound according to formulas XXIXa-d, wherein each $R^{41}$ is independently halogen, methyl or trifluoromethyl.

In another embodiment, the invention provides the compound according any of the previous embodiments wherein $R^{21}$ is hydrogen. In the following embodiments of the first aspect, it is understood that the following provisos apply:

(i) q may be 0 only if $L^2$ is not a bond or if K is not phenyl;
(ii) the compound is not 2-methyl-5-(1-m-tolyl-3-(trifluoromethyl)-1H-pyrazol-5-yl)benzenesulfonamide;
(iii) if $L^2$ is a bond, then both J and K are not absent;
(iv) if K is absent, then q is 1 and $R^4$ is bonded directly to $L^2$;
(v) if $L^2$ is $SO_2$ or $SO_2N(R^{10})$, then $R^5$ is substituted with at least one $R^{5a}$;
(vi) if the compound is defined by formula Ia, then
  a) $R^1$ is not 4-$(NH_2SO_2)$phenyl, 4-$(CH_3SO_2)$Phenyl, or 4-$(CH_2FSO_2)$phenyl;
  b) if $R^1$ is 4-fluorophenyl, then G is not 4-[$(H_2NS(=O)_2)$-]phenyl-;
  c) $R^2$ is not 4-hydroxyphenyl;
(vii) if the compound is defined by formula Ib, then
  a) $R^2$ is not 4-$(NH_2SO_2)$phenyl, 4-$(CH_3SO_2)$phenyl, or 4-$(CH_2FSO_2)$phenyl;
  b) $R^1$ is not 4-hydroxyphenyl;
(viii) if the compound is defined by formula Ic, then
  a) $R^2$ is not 4-$(NH_2SO_2)$phenyl, 4-$(CH_3SO_2)$phenyl, or 4-$(CH_2FSO_2)$phenyl;
  b) J is not pyridyl;
  c) G is not 3- or 4-methoxyphenyl
(ix) if the compound is defined by formula Id, then
  a) if $L^1$ is a bond, then $R^1$ is not thienyl or 5-methylthienyl;
  b) G is not 4-$(NH_2SO_2)$phenyl, 4-$(CH_3SO_2)$phenyl, or 4-$(CH_2FSO_2)$phenyl;

c) if G is 4-fluorophenyl, then $R^1$ is not 4-[$(H_2NS(=O)_2$-]phenyl-;
  d) if J=Ph, $L^2$ is a bond, and q is 1, then K and $R^4$ together are not 4-fluorophenyl, 3-fluorophenyl, 4-methoxyphenyl, or 5-chlorothienyl;
  e) if J=pyridyl, $L^2$ is a bond, and q is 1, then K and $R^4$ together are not 4-fluorophenyl;
  f) if J=Ph, $L^2$ is a bond, and q is 2, then K and both $R^4$ together are not 3-fluoro-4-methoxyphenyl;
  g) $R^1$ is not 4-Me-phenyl.

One embodiment of the invention relates to compounds represented by formulae Iaa, Ibb, Icc or Idd:

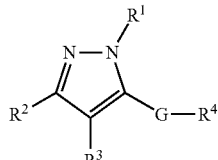

Iaa

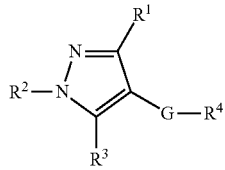

Ibb

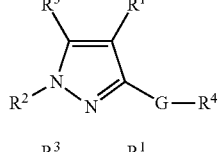

Icc

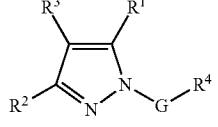

Idd as an isomer, a mixture of stereoisomers, a racemic mixture thereof of stereoisomers, or as a tautomer, or as a pharmaceutically acceptable salt, prodrug, solvate or polymorph thereof, wherein each $R^1$ substitutent is independently selected from the group consisting of $R^5$ and -$L_1$-$R^5$.

Another embodiment is that $R^1$ substitutent is $R^5$; Preferred $R^5$ for this embodiment is selected from the group consisting of 5-12 membered aromatic or non-aromatic ring, 5-12 membered heterocyclyl or heteroaryl having one or more heteroatoms N, O or S; $R^5$ is optionally substituted at a substitutable position with one or more radicals of $R^{5a}$. $R^5$ is preferably thienyl, furanyl, piperidinyl, pyrrolidinyl, piperazinyl, morpholinyl, thiazolyl, indolyl, oxazolyl, isoxazolyl, pyridinyl, pyrimidinyl, imidazolyl and phenyl.

Examples of $R^{5a}$ groups include halogen, $C_{1-6}$ haloalkyl, nitro, $C_{1-6}$ aliphatic group, $C_{1-6}$ alkoxy, $C_{0-6}$alkylOR$^{11}$, NR$^{11}$COR$^{11}$, NR$^{11}$CON(R$^{11}$)$_2$, $C_{0-6}$ alkylSO$_2$R$^{11}$, $C_{0-6}$ alkylSR$^{11}$, $C_{0-6}$ alkylSO$_2$N(R$^{11}$)$_2$—, arylalkyl, aryloxyaryl, arylC$_{1-6}$ alkoxy, OC$_{1-6}$ alkylCOR$^{11}$, OC$_{1-6}$ alkylN(R$^{11}$)$_2$, $C_{0-6}$ alkylN(R$^{11}$)$_2$, $C_{0-6}$ alkylCOOR$^{11}$, $C_{0-6}$ alkylCOON(R$^{11}$)$_2$, $C_{0-6}$ alkylCON(R$^{11}$)$_2$; $C_{0-6}$ alkylC≡N, OC$_{0-6}$ alkylCOOR$^{11}$, OC$_{1-6}$ alkylCON(R$^{11}$)$_2$, or $C_{1-6}$ alkylOC$_{1-6}$ alkyl. $R^{5a}$ is optionally substituted at substitutable position with $C_{0-6}$ alkylSO$_2$R$^{11}$, $C_{0-6}$ alkoxyaryl, 5-12 membered aromatic or non-aromatic ring, or 5-12 membered heterocyclyl or heteroaryl having one or more heteroatoms N, O or S. Preferably, $R^{5a}$ is Cl, Br, F, $C_{1-6}$ alkyl, $C_{1-6}$ haloalkyl, $C_{1-6}$ alkoxy, $OC_{0-6}$ alkylCOOR$^{11}$, OCON(R$^{11}$)$_2$, NHCOR$^{11}$, CON(R$^{11}$)$_2$, NO$_2$, OCON(R$^{11}$)$_2$, and OC$_{1-6}$ alkylCON(R$^{11}$)$_2$. Examples of $R^{5a}$ include OCH$_2$C(CH$_3$)$_3$, Cl, F, Br, OCH$_2$CH(CH$_3$)$_2$, OCH$_2$CH$_3$, CF$_3$, COOH, OCH$_3$, OH, NO$_2$, OCOCH(CH$_3$)$_2$, OCOC(CH$_3$)$_3$, NHCOCH$_3$, OCON(CH$_3$)$_2$, OCONHCH$_3$, OCON(CH$_2$)$_2$CH$_3$, OCONHCH(CH$_3$)$_2$, O(CH$_2$)$_2$, CONH$_2$, O(CH)(CH$_3$)$_2$, $C_{1-6}$ alkyl, OCH$_2$COOH, OCH$_2$COOC(CH$_3$)$_3$, O(CH$_2$)$_2$N(CH$_2$CH$_3$)$_2$, OC(CH$_3$)$_2$COOC(CH$_3$)$_3$, and OCH$_2$CH$_2$OH.

Another embodiment is that $R^1$ substitutent is -L$_1$-R$^5$. Preferred $R^5$ for this embodiment is selected from the group consisting of 5-12 membered aromatic or non-aromatic ring, 5-12 membered heterocyclyl or heteroaryl having one or more heteroatoms N, O or S; $R^5$ is optionally substituted at a substitutable position with one or more radicals of $R^{5a}$. Examples of preferred $R^5$ include phenyl, pyridinyl, oxazolyl, thienyl, thiazolyl, morpholinyl, furanyl, imidazolyl, piperazinyl, pyrimidinyl, isoxazolyl or piperidinyl. More preferably, oxazolyl, pyridinyl, phenyl, furanyl, thienyl or thiazolyl. Most preferred $R^5$ includes pyridinyl or pyridinyl.

Embodiments for $L_1$ include a direct bond, —CS—, —$C_{1-6}$ alkoxy-, -carbonyl-, —SO$_2$—, —CON(R$^{11}$)—, —CONR$^{11}$OR$^{11}$—, —CONR$^{11}$N(R$^{11}$)—, —C(=NR$^{11}$)—, —C(=NOR$^{11}$)—, —C(=NN(R$^{11}$)$_2$)—, 5-12 membered aromatic or non-aromatic ring, 5-12 membered heteroaryl or heterocyclyl having one or more heteroatoms N, O, or S which is optionally substituted at a substitutable position with one or more radicals of $R^{14}$. Another embodiment for $L_1$ is —(CH$_2$)$_m$—V—(CH$_2$)$_n$— or —V—(CH$_2$)$_n$—V; m is 0-6; n is 0-6; V is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, C≡C—, —O—, —S—, —NR$^{11}$—, —N(R$^{10}$)CO—, —N(R$^{10}$)CO$_2$—, —CON(R$^{10}$)—, —CO—, —CO$_2$—, —OC(=C))—, —OC(=O)N(R$^{10}$)—, —CONR$^{11}$NR$^{11}$—, —CONR$^{11}$—, —OCONR$^{11}$—, —SO$_2$—, —N(R$^{10}$)SO$_2$—, —SO$_2$N(R$^{10}$)—, —NR$^{10}$CONR$^{10}$—, —NR$^{10}$CSNR$^{10}$—, cycloC$_{3-8}$haloalkyl or cycloC$_{3-6}$ alkyl. A preferred $L_1$ is selected from the group consisting of —CS—, —CONH—, —$C_{1-6}$ alidiyl-, —CO—, —SO$_2$—, —CH$_2$—, —CH$_2$O—, —CH$_2$CH$_2$—, —C=O—, —CONH—, —CONHC(CH$_3$)$_2$—, —CONH(CH$_2$)$_3$OCH$_2$—, —OCH$_2$CH$_2$—, —OCH$_2$CO—, —OCH$_2$CH$_2$N(CH$_3$)$_2$—, and —CONHCH$_2$CH$_2$N(CH$_3$)$_2$—. More preferred $L_1$ is selected from the group consisting of —CH$_2$—, —CH$_2$O—, —CH$_2$CH$_2$—, —C=O—, —SO$_2$—, —CONH—, —CONHC(CH$_3$)$_2$—, —CONH(CH$_2$)$_3$OCH$_2$—, —CONHCH$_2$CH$_2$N(CH$_3$)$_2$—, —OCH$_2$— and —OCH$_2$CH$_2$—. Examples of preferred $R^5$ are selected from the group consisting of phenyl, pyridinyl, oxazolyl, thienyl, thiazolyl, morpholinyl, imidazolyl, piperazinyl, pyrimidinyl, isoxazolyl and piperidinyl.

Examples of preferred $R^{5a}$ include halogen, haloalkyl, OCH$_2$CON(CH$_3$)$_2$, OCH$_2$COOC(CH$_3$)$_3$, OCH$_2$CH$_2$N(CH$_2$CH$_3$)$_2$, OCH$_2$COOH, OC(CH$_3$)$_2$COOC(CH$_3$)$_2$, OCON(CH$_3$)$_2$, OCONHCH$_3$, OCH$_2$CH$_2$OH, OCONHCH$_2$CHCH$_3$, or NHCOCH$_3$.

$R^5$ is optionally substituted at a substitutable position with one or more radicals of $R^{5a}$.

$L_1$ is —(CH$_2$)$_m$—V—(CH$_2$)$_n$—; or —V—(CH$_2$)$_n$—V; m is 0-6; n is 0-6; V is independently —C(=NR$^{11}$)—, —C(=NOR$^{11}$)—, —C(=NN(R$^{11}$)$_2$)—; —C(R$^{11}$)$_2$—, —C(R$^{11}$)$_2$C(R$^{11}$)$_2$—, —C(R$^{11}$)=C(R$^{11}$)—, C(R$^{11}$)$_2$NR$^{11}$—, —C≡C—, —O—, —S—, —NR$^{11}$—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —CONR$^{11}$NR$^{11}$—, —CONR$^{11}$—, —SO$_2$—, —N(R$^{10}$)SO$_2$—, —SO$_2$N(R$^{10}$)— or —NR$^{10}$CONR$^{10}$—, —NR$^{10}$CSNR$^{10}$—, cycloC$_{3-6}$ haloalkyl or cycloC$_{3-6}$ alkyl. Examples of preferred $L_1$ are selected from the group consisting of —CONH—, —$C_{1-6}$ alkyl-, —$C_{1-6}$ alkoxy-, —CO—, —SO$_2$—, —CH$_2$—, —CH$_2$O—, —CH$_2$CH$_2$—, —C=O—, —CONH—, —CONHC(CH$_3$)$_2$—, —CONH(CH$_2$)$_3$OCH$_2$—, —OCH$_2$CH$_2$—, —OCH$_2$CO—, —OCH$_2$CH$_2$N(CH$_3$)$_2$— and —CONHCH$_2$CH$_2$N(CH$_3$)$_2$—. More preferred $L_1$ is selected from the group consisting of —CH$_2$—, —CH$_2$O—, —CH$_2$CH$_2$—, —C=O—, —SO$_2$—, —CONH—, —CONHC(CH$_3$)$_2$—, —CONH(CH$_2$)$_3$OCH$_2$—, —CONHCH$_2$CH$_2$N(CH$_3$)$_2$—, and —OCH$_2$CH$_2$—.

Another embodiment is that $R^2$ is independently selected from the group consisting of $R^7$ and L$_3$-R$^7$; each $R^7$ for this embodiment is independently selected from hydrogen, $C_{1-6}$ alkyl, halogen, $C_{1-6}$ haloalkyl, $C_{1-6}$ alkoxy, $C_{1-6}$ haloalkyl (OR$^{11}$), $C_{0-6}$ alkylCOOR$^{11}$, $C_{0-6}$ alkylCON(R$^{11}$)$_2$, $C_{0-6}$alkylN(R$^{11}$)$_2$, $C_{1-6}$ alkylOR$^{11}$, $C_{0-6}$ alkylSO$_2$N(R$^{11}$)$_2$, $C_{0-6}$ alkylC≡N, cycloC$_{3-6}$ alkylC≡N, $C_{0-6}$ alkylCONR$^{11}$N(R$^{11}$)$_2$, $C_{0-6}$ alkylCONR$^{11}$OR$^{11}$, $C_{0-6}$ alkylOCOR$^{11}$, cycloC$_{3-6}$ alkyl, cycloC$_{3-6}$ alkylOR$^{11}$; 5-12 membered aromatic or non-aromatic ring; or 5-12 membered heteroaryl and heterocyclyl having one or more heteroatoms N, O or S; $R^7$ is optionally substituted at a substitutable position with one or more radicals of $R^{7a}$;

Another embodiment is that $R^2$ is $R^7$, each $R^7$ for this embodiment is selected from the group consisting of 5-12 membered aromatic or non-aromatic ring, 5-12 membered heteroaryl and heterocyclyl having one or more heteroatoms N, O or S. $R^7$ is optionally substituted at a substitutable position with one or more radicals of $R^{7a}$;

Preferred $R^7$ is phenyl, pyridinyl, thienyl, furanyl, piperidinyl, pyrrolidinyl, piperazinyl, morpholinyl, thiazolyl, indolyl, oxazolyl, pyridinyl, isoxazolyl, pyrimidinyl, naphthyl, hydrogen, CF$_3$, $C_{0-6}$ alkylC≡N, CH$_2$OH, COOCH$_3$, COON(R$^{11}$)$_2$ or COOR$^{11}$. Other examples of $R^7$ include trifluoromethyl, CH$_2$C≡N, C(CH$_3$)$_2$C≡N, COOCH$_3$, CH$_2$OH, CONHCH$_2$CH$_3$, CONHOCH$_2$CH(OH) CH$_2$OH, CONHCH$_2$CH$_2$N(CH$_3$)$_2$, CONHCH$_2$CH$_2$OCH$_3$, CONHCH$_2$CH$_2$OCH$_3$, CH$_2$COOCH$_3$, CON(CH$_3$)$_2$, COOCH(CH$_3$)$_2$, CONHCH$_2$CH$_2$CH$_2$OCH$_3$, OCOCH(CH$_3$)$_2$, OCH$_2$CON(CH$_3$)$_2$, CH$_2$CONHCH$_2$(CH$_3$), C(CH$_3$)$_2$OH, COOH, nitro, cycloC$_{3-6}$ alkyl, cycloC$_{3-6}$ alkylOR$^{11}$, cycloC$_{3-6}$ alkylamine, or COOCH(CH$_3$)$_2$. More preferably, $R^7$ is CF$_3$, COOCH$_3$, COOH, or CONHCH$_2$CH$_3$. When $R^7$ is phenyl or pyridinyl, preferred $R^{7a}$ is selected from the group consisting of halogen, $C_{1-6}$ alkyl, $C_{1-6}$ alkoxy, and $C_{1-6}$ haloalkyl. Examples of $R^{7a}$ is selected from the group consisting of halogen, trifluoromethyl, $C_{1-6}$alkyl, $C_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$OCOCH(CH$_3$)$_2$, OCONHCH$_3$, OCH$_2$CH$_3$, and OCH(CH$_3$)$_2$.

Another embodiment is that $R^2$ is L$_3$-R$^7$. Each $R^7$ for this embodiment is selected from the group consisting of 5-12 membered aromatic or non-aromatic ring; 5-12 membered heteroaryl and heterocyclyl having one or more heteroatoms N, O or S. $R^7$ is optionally substituted at a substitutable position with one or more radicals of $R^{7a}$;

A preferred $L_3$ for this embodiment is independently selected from a direct bond, —CS—, —CO—, —CONR$^{11}$—, —C(=NR$^{11}$)—, —C(=NOR$^{11}$)—, —C(=NN(R$^{11}$)$_2$)—; (CH$_2$)$_m$—V$_1$—(CH$_2$)$_n$—, or —V$_1$—(CH$_2$)$_n$—V$_1$—; m is 0-6; n is 0-6; V$_1$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C≡C—, —O—, —S—, —NR$^{11}$—, —C($R^{11}$)$_2$N$R^{11}$, —N($R^{10}$)CO, —N($R^{10}$)CO$_2$, —CON($R^{10}$)—, —OCO—, —CO—, —CO$_2$—, —OC(=O)—, —OC(=O)N($R^{10}$)—, —SO$_2$—, —N($R^{10}$)SO$_2$—, —N$R^{10}$CON$R^{10}$—, —N$R^{10}$CSN$R^{10}$—, cycloC$_{3-6}$ alkyl, cycloC$_{3-6}$ haloalkyl or —SO$_2$N($R^{10}$)—. More preferably, L$_3$ is —CH$_2$—, —CO—, —OCH$_2$—, —CH$_2$OCH$_2$—, —CONH—, —CH$_2$OCOH$_2$—, —CH$_2$NHCH$_2$—, —CH$_2$NC(CH$_3$)$_2$—, —CH$_2$N(CH$_3$)CH$_2$—, —CH$_2$COCH$_3$—, —CH$_2$N(CH$_3$)$_2$CH$_2$—, cyclohexamine or cyclopropanamine.

Each $R^{7a}$ is independently a halogen, $C_{1-6}$ alkyl, C$R^{11}$=C$R^{11}$COOH, C$_{1-6}$ alkoxy, C$_{0-6}$ alkylO$R^{11}$, C$_{0-6}$ alkyl OVCOO$R^{11}$, C$_{0-6}$ alkylN$R^{11}$CO$R^{11}$, C$_{0-6}$ alkyl SO$_2$N$R^{11}$CO$R^{11}$, C$_{0-6}$ alkylSO$_2$N($R^{11}$)$_2$; C$_{0-6}$ alkylS$R^{11}$, (C$_{0-6}$ alkyl)C=O(O$R^{11}$), OVO$R^{11}$, C$_{1-6}$ haloalkyl, OC$_{1-6}$ haloalkyl, haloaryl, aryloxy, aralkyloxy, aryloxyalkyl, C$_{1-6}$ alkoxyaryl, arylC$_{0-6}$ alkylcarboxy, N$R^{11}$SO$_2$$R^{11}$, OC$_{1-6}$ alkyl, OC$_{0-6}$ alkylCOO$R^{11}$, C$_{0-6}$ alkoxyheteroaryl, C$_{0-6}$alkoxyheterocyclyl, cycloC$_{3-6}$alkylCOO$R^{11}$, C$_{3-6}$cycloalkylamine; 5-12 membered aromatic or non-aromatic ring, or 5-12 membered heteroaryl or heterocyclyl having one or more heteroatoms N, O or S; Examples of $R^{7a}$ is selected from the group consisting of halogen, trifluoromethyl, C$_{1-6}$alkyl, C$_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$OCOCH(CH$_3$)$_2$, OCONHCH$_3$, OCH$_2$CH$_3$, and OCH(CH$_3$)$_2$.

Each $R^{7a}$ may be substituted at a substitutable position with one or more radicals of $R^8$; each $R^8$ is independently C$_{1-6}$ alkyl, C$_{1-6}$ alkoxy, C$_{1-6}$ haloalkyl, C$_{0-6}$ alkylO$R^{11}$, C$_{1-6}$ haloalkylO$R^{11}$, C$_{0-6}$ alkylCON($R^{11}$)$_2$, C$_{0-6}$alkylCO$R^{11}$, C$_{0-6}$ alkylCOO$R^{11}$, N$R^{11}$COO$R^{11}$, or C$_{0-6}$ alkylSO$_2$$R^{11}$.

Other examples of $R^7$ include trifluoromethyl, CH$_2$C≡N, C(CH$_3$)$_2$C≡N, COOCH$_3$, CH$_2$OH, CONHCH$_2$CH$_3$, CONHOCH$_2$CH(OH)CH$_2$OH, CONHCH$_2$CH$_2$N(CH$_3$)$_2$, CONHCH$_2$CH$_2$OCH$_3$, CONHCH$_2$CH$_2$OCH$_3$, CH$_2$COOCH$_3$, CON(CH$_3$)$_2$, COOCH(CH$_3$)$_2$, CONHCH$_2$CH$_2$CH$_2$OCH$_3$, OCOCH(CH$_3$)$_2$, OCH$_2$CON(CH$_3$)$_2$, CH$_2$CONHCH$_2$(CH$_3$), C(CH$_3$)$_2$OH, COOH, nitro, cycloC$_{3-6}$ alkyl, cycloC$_{3-6}$ alkylO$R^{11}$ or COOCH(CH$_3$)$_2$. More preferably, $R^7$ is CF$_3$, COOCH$_3$, COOH, or CONHCH$_2$CH$_3$. When $R^7$ is phenyl, pyridinyl, thienyl, furanyl, piperidinyl, pyrrolidinyl, piperazinyl, morpholinyl, thiazolyl, indolyl, oxazolyl, pyridinyl, isoxazolyl, pyrimidinyl, naphthyl. Examples of $R^{7a}$ is selected from the group consisting of halogen, trifluoromethyl, C$_{1-6}$alkyl, C$_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$OCOCH(CH$_3$)$_2$, OCONHCH$_3$, OCH$_2$CH$_3$, and OCH(CH$_3$)$_2$. Preferred $R^{7a}$ is selected from the group consisting of halogen, C$_{1-6}$ alkyl, C$_{1-6}$ alkoxy, and C$_{1-6}$ haloalkyl.

Each $R^3$ is independently selected from the group consisting of $R^6$ and -L-$R^6$; Another embodiment is that $R^3$ is $R^6$ where $R^6$ is independently hydrogen, halogen, C$_{1-6}$ alkyl, C$_{1-6}$ haloalkyl, C$_{1-6}$ haloalkylO$R^{11}$, C$_{0-6}$ alkylO$R^{11}$, C$_{0-6}$ alkylCON($R^{11}$)$_2$, C$_{0-6}$ alkylCO$R^{11}$, OCON($R^{11}$)$_2$, CON$R^{11}$O$R^{11}$, nitro, C$_{1-6}$ alkylCOO$R^{11}$; 5-12 membered aromatic or non-aromatic ring; 5-12 membered heteroaryl or heterocyclyl having one or more heteroatoms N, O or S; Preferred $R^6$ is hydrogen or optionally substituted phenyl. Each $R^6$ is optionally substituted at a substitutable position with one or more radicals of $R^{6a}$.

Each $R^{6a}$ is independently halogen, C$_{1-6}$ alkyl, C$_{1-6}$ alkoxy, C$_{1-6}$ haloalkyl, C$_{1-6}$ haloalkylO$R^{11}$, CON($R^{11}$)$_2$, CON$R^{11}$O$R^{11}$, C$_{0-6}$ alkylCOO$R^{11}$; C$R^{11}$=C$R^{11}$COOH, C$_{0-6}$ alkylO$R^{11}$, C$_{0-6}$ alkylCO$R^{11}$, C$_{0-6}$ alkylSO$_2$$R^{11}$, C$_{0-6}$ alkylOCO$R^{11}$, C$_{0-6}$ alkylN$R^{11}$CO$R^{11}$, C$_{0-6}$ alkyl SO$_2$N$R^{11}$CO$R^{11}$, C$_{0-6}$ alkyl SO$_2$N($R^{11}$)$_2$; C$_{0-6}$ alkylS$R^{11}$, (C$_{0-6}$ alkyl)C=O(O$R^{11}$), OVO$R^{11}$, OC$_{1-6}$ haloalkyl, aryloxy, aralkyloxy, aryloxyalkyl, C$_{1-6}$ alkoxyaryl, arylC$_{0-6}$ alkylcarboxy, N$R^{11}$SO$_2$$R^{11}$, OC$_{1-6}$ alkyl, OC$_{0-6}$ alkylCOO$R^{11}$, C$_{0-6}$ alkoxyheteroaryl, C$_{0-6}$alkoxyheterocyclyl, cycloalkyl-COO$R^{11}$.

Another embodiment is that $R^3$ is L-$R^6$, L is independently selected from direct bond, —CO—, —CON$R^{11}$—, —C(=N$R^{11}$)—, —C(=NO$R^{11}$)—, —C(=NN($R^{11}$)$_2$)—; C$_{2-6}$ alidiyl chain, wherein the alidiyl chain is optionally interrupted by —C($R^{11}$)$_2$—, —C($R^{11}$)$_2$C($R^{11}$)$_2$—, —C($R^{11}$)=C($R^{11}$)—, —C≡C—, —O—, —S—, N($R^{10}$)CO—, —N($R^{10}$)CO$_2$—, —N$R^{11}$—, —CON($R^{10}$)—, —CO—, —CO$_2$—, —OC(=O)—, —OC(=O)N($R^{10}$)—, —SO$_2$—, N($R^{10}$)SO$_2$—, or —SO$_2$N($R^{10}$)—; —(CH$_2$)$_m$—V$_0$—(CH$_2$)$_n$— or —V$_0$—(CH$_2$)$_n$—V$_0$—; m is 0-6; n is 0-6; V$_0$ is independently —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$N$R^{11}$—, —C≡C—, —O—, —S—, —O$R^{11}$N—, —O$R^{11}$CO—, —N$R^{11}$—, —N($R^{10}$)CO—, —N($R^{10}$)CO$_2$—, —CON($R^{10}$)—, —OCO—, —CO—, —CO$_2$—, —OC(=O)—, —OC(=O)N($R^{10}$)—, —SO$_2$—, —N($R^{10}$)SO$_2$—, —N$R^{10}$CON$R^{10}$—, —N$R^{10}$CSN$R^{10}$—, —SO$_2$N($R^{10}$)—, cycloC$_{3-6}$ haloalkyl or cycloC$_{3-6}$ alkyl; Examples of L include —O—, —CH$_2$—, —CH$_2$O—, —CH$_2$CH$_2$—, —SO$_2$—, —CONH—, —CONHC(CH$_3$)$_2$—, —CONH(CH$_2$)$_3$OCH$_2$—, —CONHCH$_2$CH$_2$N(CH$_3$)$_2$—, or —OCH$_2$CH$_2$—.

Each $R^4$ is independently selected from, C$_{1-6}$ alkyl, C$R^{11}$=C$R^{11}$COO$R^{11}$, C$_{0-6}$ alkylC≡N, C$_{1-6}$ alkoxy, C$_{0-6}$ alkylO$R^{11}$, C$_{0-6}$ alkylCO$R^{11}$, C$_{0-6}$ alkylSO$_2$$R^{11}$, C$_{0-6}$ alkylO-COO$R^{11}$, C$_{0-6}$ alkylN$R^{11}$CO$R^{11}$, C$_{0-6}$ alkylSO$_2$N$R^{11}$CO$R^{11}$, C$_{0-6}$ alkyl SO$_2$N($R^{11}$)$_2$, C$_{0-6}$ alkylS$R^{11}$, (C$_{0-6}$ alkyl)C=O(O$R^{11}$), OVO$R^{11}$, halogen, C$_{1-6}$haloalkyl, OC$_{1-6}$ haloalkyl, aryloxy, aralkyloxy, aryloxyalkyl, C$_{1-6}$ alkoxyaryl, arylC$_{0-6}$ alkylcarboxy, N$R^{11}$SO$_2$$R^{11}$, OC$_{1-6}$ alkyl, OC$_{0-6}$ alkylCOO$R^{11}$, C$_{0-6}$ alkoxyheteroaryl, C$_{0-6}$alkoxyheterocyclyl, cycloalkyl COO$R^{11}$, 5-12 membered aromatic ring or non-aromatic ring, or 5-12 membered heteroaryl or heterocyclyl having one or more heteroatoms N, O or S. Preferred $R^4$ is selected from the group consisting of OH, CN, C(CH$_3$)$_2$OH, SO$_2$CH$_3$, SO$_2$C(CH$_3$)$_3$, SO$_2$CH$_2$CH$_3$, SCH$_2$CH$_3$, SCH$_3$, OCH$_3$, C$_{1-6}$ alkyl, CH$_2$COOH, C(CH$_3$)$_2$COOH, NHSO$_2$CH$_3$, F, Cl, Br, cyclobutane-COOH, OC(CH$_3$)$_2$COOH, CF$_3$, C(CH$_3$)$_2$COOH, CH$_2$COOCH$_3$, CH$_2$COOH, OCH$_2$COOCH$_3$, and COCH$_3$. More preferably, $R^4$ is SO$_2$CH$_3$, SO$_2$CH$_2$CH$_3$, SCH$_2$CH$_3$, or SCH$_3$.

Each $R^4$ is optionally substituted at a substitutable position with one or more radicals of $R^{4a}$; Each $R^{4a}$ is independently selected from, C$_{1-6}$ alkyl, (C$_{1-6}$ alkyl)C=O(O$R^{11}$); C$_{1-6}$ alkoxy, C$_{0-6}$ alkylO$R^{11}$, C$_{0-6}$ alkylCO$R^{11}$, C$_{0-6}$ alkylSO$_2$$R^{11}$, C$_{0-6}$ alkylSO$_2$N($R^{11}$)$_2$, C$_{0-6}$ alkylS$R^{11}$, (C$_{0-6}$ alkyl)C=O (O$R^{11}$), halogen, C$_{1-6}$haloalkyl, aryloxy, aralkyloxy, aryloxyalkyl, C$_{1-6}$ alkoxyaryl, arylC$_{0-6}$ alkylcarboxy, N$R^{11}$SO$_2$$R^{11}$, OC$_{1-6}$ alkyl, C$_{0-6}$ alkylC≡N, or OC$_{0-6}$ alkylCOO$R^{11}$.

Each $R^{10}$ is independently selected from $R^{11}$, C(=O)$R^{11}$, CO$_2$$R^{11}$, SO$_2$$R^{11}$; each $R^{11}$ is independently selected from hydrogen or substituted or unsubstituted C$_{1-8}$ aliphatic group; C$_{1-6}$haloalkyl; N($R^{12}$)$_2$; 5-12 membered aromatic or non-aromatic ring, or 5-12 membered heteroaryl or heterocyclyl having one or more heteroatoms, N, S or O; which is optionally substituted at a substitutable position with one or more radicals of $R^{12}$.

Each $R^{12}$ is independently halogen, C$_{1-6}$haloalkyl, C$_{1-6}$ alkyl, C$_{1-6}$ alkoxy, (C$_{1-6}$ alkyl)C=O(O$R^{13}$); C$_{1-6}$ alkoxyalkyl, C$_{0-6}$ alkylCO$R^{13}$, C$_{0-6}$ alkylO$R^{13}$, C$_{0-6}$ alkylSO$_2$$R^{13}$, $C_{0-6}$ alkylCON($R^{13}$)$_2$, $C_{0-6}$ alkylCONR$^{13}$OR$^{13}$, $C_{0-6}$ alkylSO$_2$N($R^{13}$)$_2$, $C_{0-6}$ alkylSR$^{13}$, ($C_{0-6}$ alkyl)C=O(OR$^{13}$), $C_{0-6}$ haloalkylOR$^{13}$, aryloxy, aralkyloxy, aryloxyalkyl, $C_{0-6}$ alkoxyaryl, aryl$C_{0-6}$ alkylcarboxy, $C_{0-6}$ alkylNR$^{13}$SO$_2$R$^{13}$, OC$_{1-6}$ alkyl, or OC$_{0-6}$ alkylCOOR$^{13}$.

Each $R^{13}$ is independently hydrogen or substituted or unsubstituted $C_{1-8}$ aliphatic group.

Each $R^{14}$ is independently $C_{1-6}$ alkyl, $C_{1-6}$ alkoxy, halogen, $C_{1-6}$ haloalkyl, $C_{0-6}$ alkylCON($R^{11}$)$_2$, $C_{0-6}$ alkylCONR$^{11}$OR$^{11}$, $C_{0-6}$ alkylOR$^{11}$, or $C_{0-6}$ alkylCOOR$^{11}$.

Another embodiment of the invention is that G is independently G1, G2 or G3;

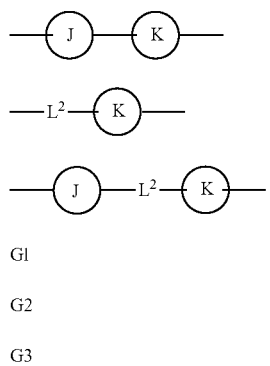

1. G1
2. G2
3. G3

Each Ring J or Ring K may be independently absent, same or different and is independently selected from a 5-12 membered aromatic or non-aromatic ring, or 5-12 membered heterocyclyl or heteroaryl having one or more hetero atoms, N, S or O.

Each Ring J or Ring K independently is optionally substituted at a substitutable position with one or more radicals of $R^4$. Ring J is preferably a phenyl ring or a 5-membered heteroaryl ring. Examples of Ring J include phenyl, pyridinyl, thienyl, furanyl, morpholinyl, thiazolyl, indolyl, oxazolyl, biphenyl, naphthyl, piperidinyl, piperazinyl, or imidazolyl. A preferred Ring J is thienyl or phenyl. Ring J is optionally substituted at a substitutable position with one or more radicals of $R^4$.

Suitable Ring J substituents designated as $R^4$ include, methylsulfonyl, or $C_{1-6}$ aliphatic or substituents selected from the group consisting of CR$^{11}$=CR$^{11}$COOR$^{11}$, $C_{1-6}$ alkyl, $C_{1-6}$ alkoxy, $C_{0-6}$ alkylOR$^{11}$, $C_{1-6}$ alkylCOR$^{11}$, $C_{0-6}$ alkylSO$_2$R$^{11}$, $C_{0-6}$ alkylOCOOR$^{11}$, $C_{0-6}$ alkylNR$^{11}$COR$^{11}$, $C_{0-6}$ alkylSO$_2$NR$^{11}$COR$^{11}$, $C_{0-6}$ alkyl SO$_2$N($R^{11}$)$_2$, $C_{0-6}$ alkylSR$^{11}$, ($C_{0-6}$ alkyl)C=O(OR$^{11}$), OVOR$^{11}$, halogen, $C_{1-6}$haloalkyl, OC$_{1-6}$ haloalkyl, aryloxy, aralkyloxy, aryloxyalkyl, $C_{1-6}$ alkoxyaryl, aryl$C_{0-6}$ alkylcarboxy, NR$^{11}$SO$_2$R$^{11}$, OC$_{1-6}$ alkyl, OC$_{0-6}$ alkylCOOR$^{11}$, $C_{1-6}$ alkoxyheteroaryl, $C_{0-6}$alkoxyheterocyclyl, $C_{0-6}$ alkylC≡N, cycloalkyl-COOR$^{11}$, 5-12 membered aromatic ring or non-aromatic ring, and 5-12 membered heteroaryl or heterocyclyl having one or more heteroatoms N, O or S. Examples of preferred $R^4$ include OH, CN, C(CH$_3$)$_2$OH, SO$_2$CH$_3$, SO$_2$NH$_2$, SO$_2$CH$_2$CH$_3$, SO$_2$C(CH$_3$)$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, C(CH$_2$CH$_3$)$_2$COOH, CH$_2$COOCH$_3$, C(CH$_3$)$_2$COOCH$_3$, CH$_2$CH$_2$COOH, CH=CHCOOH, OCH$_2$COOCH$_3$, COCH$_3$, OCH$_3$, COOC(CH$_3$)$_3$, cyclobutane-COOH, OC(CH$_3$)$_2$COOH, CH$_2$CH$_3$, CH$_3$, CH(CH$_3$)$_2$, CH$_2$COOCH$_3$, OCON(CH$_2$CH$_3$)$_2$, NHCOCH$_3$, or CF$_3$.

Examples of Ring K include phenyl, pyridinyl, thienyl, furanyl, morpholinyl, thiazolyl, indolyl, oxazolyl, biphenyl, naphthyl, piperidinyl, piperazinyl, isoxazolyl, pyrimidinyl, or imidazolyl. Ring K is optionally substituted at a substitutable position with one or more radicals of $R^4$. Suitable Ring K substituents designated as $R^4$ include, methylsulfonyl, or $C_{1-6}$ aliphatic or substituents selected from the group consisting of CR$^{11}$=CR$^{11}$COOR$^{11}$, $C_{1-6}$ alkyl, $C_{1-6}$ alkoxy, $C_{0-6}$ alkylOR$^{11}$, $C_{1-6}$ alkylCOR$^{11}$, $C_{0-6}$ alkylSO$_2$R$^{11}$, $C_{0-6}$ alkylOCOOR$^{11}$, $C_{0-6}$ alkylNR$^{11}$COR$^{11}$, $C_{0-6}$ alkyl SO$_2$NR$^{11}$COR$^{11}$, $C_{0-6}$ alkyl SO$_2$N($R^{11}$)$_2$, $C_{0-6}$ alkylSR$^{11}$, ($C_{0-6}$ alkyl)C=O(OR$^{11}$), OVOR$^{11}$, $C_{0-6}$ alkylC≡N, halogen, $C_{1-6}$haloalkyl, OC$_{1-6}$ haloalkyl, aryloxy, aralkyloxy, aryloxyalkyl, $C_{1-6}$ alkoxyaryl, aryl$C_{0-6}$ alkylcarboxy, NR$^{11}$SO$_2$R$^{11}$, OC$_{1-6}$ alkyl, OC$_{0-6}$ alkylCOOR$^{11}$, $C_{0-6}$ alkoxyheteroaryl, $C_{0-6}$alkoxyheterocyclyl, cycloalkyl COOR$^{11}$, 5-12 membered aromatic ring or non-aromatic ring, and 5-12 membered heteroaryl or heterocyclyl having one or more heteroatoms N, O or S. Preferably, Ring K is phenyl, pyridinyl, thienyl, furanyl, morpholinyl, thiazolyl, indolyl, oxazolyl, biphenyl, naphthyl, piperidinyl, piperazinyl, isoxazolyl, pyrimidinyl, or imidazolyl. When Ring K is a phenyl or pyridinyl, it is preferably substituted by methylsulfonyl. Examples of preferred $R^4$ groups include OH, CN, C(CH$_3$)$_2$OH, SO$_2$CH$_3$, SO$_2$NH$_2$, SO$_2$CH$_2$CH$_3$, SO$_2$C(CH$_3$)$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, C(CH$_2$CH$_3$)$_2$COOH, CH$_2$COOCH$_3$, C(CH$_3$)$_2$COOCH$_3$, CH$_2$CH$_2$COOH, CH=CHCOOH, OCH$_2$COOCH$_3$, COCH$_3$, OCH$_3$, COOC(CH$_3$)$_3$, cyclobutane-COOH, OC(CH$_3$)$_2$COOH, CH$_2$CH$_3$, CH$_3$, CH(CH$_3$)$_2$, CH$_2$COOCH$_3$, OCON(CH$_2$CH$_3$)$_2$, NHCOCH$_3$, or CF$_3$.

$L_2$ is —(CH$_2$)$_m$—V$^2$—(CH$_2$)$_n$— or —V$^2$—(CH$_2$)$_m$—V$^2$—; m is 0-6; n is 0-6; V$^2$ is independently —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$NR$^{11}$—, —C≡C—, —O—, —S—, —N($R^{10}$)CO—, —N($R^{10}$)CO$_2$—, —CON($R^{10}$)—, —CON($R^{11}$)—, —CON($R^{11}$)O—, —CO—, —CO$_2$, —OR$^{11}$N—, —OR$^{11}$COO—, —OC(=O)—, —OC(=O)N($R^{10}$)—, —SO$_2$—, —N($R^{10}$)SO$_2$—, —NR$^{10}$CONR$^{10}$—, —SO$_2$N($R^{10}$)—, —NR$^{10}$CSNR$^{10}$—, cycloC$_{3-8}$haloalkyl or cycloC$_{3-6}$ alkyl; $C_{2-6}$ alidiyl chain wherein alidiyl chain is optionally interrupted by —C($R^{11}$)$_2$—, C($R^{11}$)$_2$C($R^{11}$)$_2$, —C($R^{11}$)=C($R^{11}$)—, —C($R^{11}$)$_2$O—, —C≡C—, —O—, —S—, —N($R^{10}$)CO—, —N($R^{10}$)CO$_2$—, —CON($R^{10}$)—, —CON($R^{11}$)—, —CON($R^{11}$)O—, —CO—, —CO$_2$, —OC(=O)—, OC(=O)N($R^{10}$)—, —SO$_2$—, —N($R^{10}$)SO$_2$—, or —SO$_2$N($R^{10}$)—; 5-12 membered aromatic or non-aromatic ring, or 5-12 membered heteroaryl or heterocyclyl having one or more heteroatoms, N, S or O which is optionally substituted at a substitutable position with one or more radicals of $R^9$. Alternatively, $L_2$ is a direct bond, —C$_{1-6}$ alkyl-, —C$_{1-6}$ alkoxy-, —C$_{0-6}$ alkylCOOR$^{11}$—, —CH=CHCOO—, —C$_{0-6}$alkylCONR$^{11}$—, —OC$_{0-6}$alkyl-COOR$^{11}$—, —C$_{0-6}$alkylSO$_2$R$^{11}$—, —C$_{0-6}$alkylSO$_2$—, —C$_{0-6}$alkylN($R^{11}$)—, —C$_{0-6}$alkylO—, —OC$_{0-6}$ alkylN($R^{11}$)—, —C$_{0-6}$ alkylCO—, —C$_{1-6}$ carboxyl-, -cycloalkylamine-, —C(=NR$^{11}$)—, —C(=NOR$^{11}$)—, —C(=NN($R^{11}$)$_2$)—; 5-12 membered aromatic or non-aromatic ring, 5-12 membered heteroaryl or heterocyclyl having one or more heteroatoms, N, S or O which is optionally substituted at a substitutable position with one or more radicals of $R^9$. A preferred $L_2$ is selected from the group consisting of —CONH—, —CONHCH$_2$—, —CH$_2$O—, —OCH$_2$COOCH$_2$—, —CONHCH$_2$—, and —C≡C—.

Another embodiment is that G is G1, $R^1$ is $R^5$ and $R^2$ is $R^7$. When G of formulae Iaa, Ibb, Icc, or Idd is G1, a more preferred embodiment of this invention relates to a compound having one or more features selected from the group consisting of:
- $R^1$ is phenyl, pyridinyl, thienyl, furanyl, morpholinyl, thiazolyl, indolyl, oxazolyl, isoxazolyl, pyrimidinyl, or imidazolyl; $R^5$ is optionally substituted at a substitutable position with one or more radicals of $R^{5a}$;
- $R^{5a}$ is halogen, trifluoromethyl, $OCONHCH(CH_3)_2$, $NHCOCH_3$, $OH$, $OCH_3$, $COOH$, $COOCH_3$, $OCH_2C(CH_3)_3$, $OCH_2CH(CH_3)_2$, $OCH_2CH_2N(CH_3)_2$, $OCH(CH_3)_2OCOCH(CH_3)_2$, $OCONHCH_3$, $OCH_2CH_3$, or $OCH(CH_3)_2$;
- $R^2$ is trifluoromethyl, $COOCH_3$, $CH_2OH$, $CONHCH_2CH_3$, $CONHOCH_2CH(OH)CH_2OH$, $CONHCH_2CH_2N(CH_3)_2$, $CONHCH_2CH_2OCH_3$, $CONHCH_2CH_2OCH_3$, $CH_2COOCH_3$, $CON(CH_3)_2$, $COOCH(CH_3)_2$, $CONHCH_2CH_2OCH_3$, $OCOCH(CH_3)_2$, $OCH_2CON(CH_3)_2$, $CH_2CONHCH_2(CH_3)$, $C(CH_3)_2OH$, $COOH$, nitro or $COOCH(CH_3)_2$;
- $R^3$ is hydrogen or optionally substituted phenyl;
- Ring J is thienyl, thiazolyl, furanyl, pyridinyl or phenyl;
- Ring K is optionally substituted phenyl or pyridinyl; and
- $R^4$ is $SO_2CH_3$, $SO_2C(CH_3)_3$, $CH_3$, $SO_2NH_2$, $SO_2CH_2CH_3$, $SCH_2CH_3$, $SCH_3$, $OCH_3$, $CF_3$, $OCF_3$, $CH_2CF_3$, $C_{1-6}$ alkyl, halogen or $CH_2COOH$.

Another embodiment is that G is G1, $R^1$ is $R^5$ and $R^2$ is $R^7$. When G of formulae Iaa, Ibb, Icc, or Idd is G1, a more preferred embodiment of this invention relates to a compound having one or more features selected from the group consisting of:
- $R^1$ is thienyl, furanyl, morpholinyl, thiazolyl, indolyl, oxazolyl, pyridinyl, imidazolyl, isoxazolyl, pyrimidinyl or phenyl; $R^5$ is optionally substituted at a substitutable position with one or more radicals of $R^{5a}$;
- $R^{5a}$ is halogen, trifluoromethyl, $OCONH(CH_2)_2CH_3$, $OCONH(CH_2CH_3)_2$, $NHCOCH_3$, $OH$, $OCH_3$, $COOH$, $COOCH_3$, $OCH_2C(CH_3)_3$, $OCH_2CH(CH_3)_2$, $OCH(CH_3)_2OCOCH(CH_3)_2$, $OCONHCH_3$, $OCH_2CH_3$, or $OCH(CH_3)_2$;
- $R^2$ is $R^7$ selected from $CH_2C\!\!=\!\!N$, $C(CH_3)_2C\!\!=\!\!N$, cyclo$C_{3-6}$ alkyl$C\!\!=\!\!N$, thienyl, furanyl, morpholinyl, thiazolyl, indolyl, oxazolyl, pyridinyl, imidazolyl, isoxazolyl, pyrimidinyl or phenyl; $R^7$ is optionally substituted at a substitutable position with one or more radicals of $R^{7a}$;
- $R^{7a}$ is selected from the group consisting of halogen, trifluoromethyl, $C_{1-6}$alkyl, $C_{1-6}$alkoxy, $CH\!\!=\!\!CHCOOH$, $CH_2COOH$, $OCH_2COOH$, $OCONHCH(CH_3)_2$, $NHCOCH_3$, $OH$, $OCH_3$, $COOH$, $COOCH_3$, $OCH_2C(CH_3)_3$, $OCH_2CH(CH_3)_2$, $OCH(CH_3)_2OCOCH(CH_3)_2$, $OCONHCH_3$, $OCH_2CH_3$, or $OCH(CH_3)_2$;
- $R^3$ is hydrogen or optionally substituted phenyl;
- Ring J is thienyl, thiazolyl, furanyl, pyridinyl, or phenyl;
- Ring K is optionally substituted phenyl or pyridinyl; and
- $R^4$ is $CH\!\!=\!\!CHCOOH$, $SO_2CH_3$, $SO_2NH_2$, $SO_2CH_2CH_3$, $SCH_2CH_3$, $SO_2C(CH_3)_3$, $SCH_3$, $OCH_3$, $C_{1-6}$ alkyl, $CF_3$, F, Cl, or Br.

Another embodiment is that G is G1, $R^1$ is $L_1$-$R^5$ and $R^2$ is $R^7$. When G of formulae Iaa, Ibb, Icc, or Idd is G1, a more preferred embodiment of this invention relates to a compound having one or more features selected from the group consisting of
- $R^1$ is $L_1$-$R^5$; $R^5$ is phenyl, pyridinyl, morpholinyl, oxazolyl, furanyl, thiazolyl or thienyl; $R^5$ is optionally substituted with $R^{5a}$;
- $R^{5a}$ is halogen or trifluoromethyl;
- $L_1$ is —CS—, $CH_2$, $CH_2O$, $CH_2CH_2$, $C\!\!=\!\!O$, $SO_2$, $CONH$, $CONHC(CH_3)_2$, $CONH(CH_2)_3OCH_2$, $OCH_2$, $OCH_2CO$, or $OCH_2CH_2$;
- $R^2$ is trifluoromethyl, $CONHCH_2CH_2N(CH_3)_2$, $CONHCH_2CH_2CH_2N(CH_3)_2$, or $CONHCH_2CH_2CH_2OCH_3$.
- $R^3$ is hydrogen or phenyl optionally substituted with $R^{6a}$;
- Ring J is thienyl, pyridinyl, thiazolyl or phenyl; Ring K is substituted phenyl or pyridinyl; and
- $R^4$ is $SO_2CH_3$, $SO_2NH_2$, $SO_2CH_2CH_3$, $SCH_2CH_3$, $SCH_3$, $OCH_3$, $C_{1-6}$ alkyl, halogen or $CH_2COOH$.

Another embodiment is that G is G1, $R^1$ is $R^5$ and $R^2$ is $L_3R^7$. When G of formulae Iaa, Ibb, Icc, or Idd is G1, a more preferred embodiment of this invention relates to a compound having one or more features selected from the group consisting of:
- $R^1$ is $R^5$ selected from the group consisting of thienyl, furanyl, morpholinyl, thiazolyl, indolyl, oxazolyl, pyridinyl, imidazolyl, isoxazolyl, pyrimidinyl and phenyl; $R^5$ is optionally substituted at a substitutable position with one or more radicals of Rya;
- $R^{5a}$ is $OCH_2C(CH_3)_3$, Cl, F, Br, $OCH_2CH(CH_3)_2$, $OCH_2CH_3$, $CF_3$, $COOH$, $OCH_3$, $OH$, $NO_2$, $OCOCH(CH_3)_2$, $NHCOCH_3$, $OCONHCH(CH_3)_2$, $O(CH_2)_2CONH_2$, $O(CH)(CH_3)_2$, $C_{1-6}$ alkyl, $OCH_2COOH$, $OCH_2COOC(CH_3)_3$, $O(CH_2)_2N(CH_2CH_3)_2$, $OCOC(CH_3)_3$, $OC(CH_2)_2COOH$, $OCONH(CH_3)_2$, $OCONCH_3$, $OCONHCH_2CH_3$, $OC(CH_3)_2COOC(CH_3)_3$, or $O(CH_2)_2OH$;
- $R^2$ is $L_3$-$R^7$; $R^7$ is phenyl, pyridinyl, thienyl, furanyl, morpholinyl, thiazolyl, oxazolyl, piperidinyl, imidazolyl, piperazinyl, or pyridinyl;
- $L_3$ is —CS—, —CO—, —$C_{1-6}$ alidiyl-, —CONH—, —$CONR^{11}$—, —$CONR^{11}NR^{11}$—, —$CH_2OCH_2$—, —$CH_2OCH_2CH_2$—, —$OCH_2$—, —$CH_2N(CH_3)_2$—, —$CH_2NHCH_2$—, —$CONR^{11}O$—, —$CH_2OCOCH_2$—, —$CH_3N(CH_3)(CH_2)$—, —$CH_2N(cyclopropane)CH_2$—, —$CH_2NC(CH_3)_2CH_2$—, —$CH_2N(cyclohexane)CH_2$—, —$CH_2NCH(CH_3)_2CH_2$—, —$CH_2N(CF_3)(CH_2)_2$—, —$CH_2N(CH_3)(CH_2)CH_2OCOCH_2CH_2$—, —$CONHCH_2CH_2N(CH_3)_2$—, or —$CH_2N(CH_2C\!\!=\!\!N)CH_2$—;
- $R^{7a}$ is selected from the group consisting of halogen, $C_{1-6}$alkyl, $C_{1-6}$ alkoxy, $CF_3$, $OCH_2COOH$, $CH_2COOH$, $COOCH_3$, $CH_2OH$ and $OCH_3$;
- $R^3$ is hydrogen or phenyl optionally substituted with $R^{6a}$;
- Ring J is thienyl, pyridinyl, thiazolyl, furanyl or phenyl;
- Ring K is substituted phenyl or pyridinyl; and
- $R^4$ is $SO_2CH_3$, $SO_2CH_2CH_3$, $SCH_2CH_3$, $SCH_3$, $SO_2NH_2$, $OCH_3$, $C_{1-6}$ alkyl, $CH_2COOH$, $C(CH_3)_2COOH$, $NHSO_2CH_3$, F, Cl, Br, $CF_3$ or $COCH_3$;

Another embodiment is that G is G1, $R^1$ is $L_1$-$R^5$ and $R^2$ is $L_3$-$R^7$. When G of formulae Iaa, Ibb, Icc, or Idd is G1, a more preferred embodiment of this invention relates to a compound having one or more features selected from the group consisting of:
- $R^5$ is $L_1$-$R^5$; $R^5$ is selected from the group consisting of thienyl, furanyl, morpholinyl, thiazolyl, indolyl, imidazolyl, piperazinyl, piperidinyl, oxazolyl, pyridinyl, isoxazolyl, pyrimidinyl, imidazolyl and phenyl; $R^5$ is optionally substituted at a substitutable position with one or more radicals of $R^{5a}$;
- $R^{5a}$ is $C_{1-6}$ alkyl, $C_{1-6}$ alkoxy, $COOH$, halogen or trifluoromethyl;
- $L_1$ is —CS—, —$CH_2$—, —$CH_2O$—, —$CH_2CH_2$—, —$OCH_2CH_2$—, —$OCH_2CO$—, —$C\!\!=\!\!O$—, —$SO_2$—, —CONH—, —CONHC(CH$_3$)$_2$—, —CONH(CH$_2$)$_3$OCH$_2$—, or —CONHCH$_2$CH$_2$N(CH$_3$)$_2$—;

R$^2$ is L$_3$-R$^7$; R$^7$ is selected from the group consisting of phenyl, pyridinyl, thienyl, furanyl, morpholinyl, thiazolyl, oxazolyl, pyridinyl, isoxazolyl, pyrimidinyl, imidazolyl, CF$_3$, and COOCH$_3$; R$^7$ is optionally substituted at a substitutable position with one or more radicals of R$^{7a}$;

L$_3$ is CH$_2$, CH$_2$OCH$_2$, NC(CH$_3$)$_2$, CH$_2$NH(CH$_2$)$_2$, CONH, CO, CONR$^{11}$, OCH$_2$, CH$_2$N(CH$_3$)$_2$CH$_2$, CH$_2$OCOCH$_2$, CH$_2$CONHCH$_2$, CH$_2$CONHCH$_2$CH$_2$, cycloalkylamine, CH$_2$N(CH$_3$)CH$_2$, or CH$_2$NCH(CH$_3$)$_2$CH$_2$;

R$^{7a}$ is selected from the group consisting of halogen, trifluoromethyl, C$_{1-6}$alkyl, C$_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$OCOCH(CH$_3$)$_2$, OCONHCH$_3$, OCH$_2$CH$_3$, CH$_2$N(CH$_2$)CH$_2$CF$_3$, and OCH(CH$_3$)$_2$;

R$^3$ is hydrogen or phenyl optionally substituted with R$^{6a}$;

Ring J is thienyl, thiazolyl, furanyl, pyridinyl, or phenyl;

Ring K is optionally substituted phenyl or pyridinyl; and

R$^4$ is SO$_2$CH$_3$, SO$_2$CH$_2$CH$_3$, SCH$_2$CH$_3$, SCH$_3$, OCH$_3$, C$_{1-6}$alkyl, CH$_2$COOH, C(CH$_3$)$_2$COOH, NHSO$_2$CH$_3$, F, Cl, or Br.

Another embodiment is that G is G2 and R$^1$ is R$^5$ and R$^2$ is R$^7$. When G of formulae Iaa, Ibb, Icc, or Idd is G2, a more preferred embodiment of this invention relates to a compound having one or more features selected from the group consisting of:

R$^1$ is R$^5$ selected from the group consisting of thienyl, furanyl, morpholinyl, thiazolyl, indolyl, oxazolyl, pyridinyl, isoxazolyl, pyrimidinyl, imidazolyl and phenyl; R$^5$ is optionally substituted at a substitutable position with one or more radicals of R$^{5a}$;

R$^2$ is R$^7$ selected from the group consisting of phenyl, pyridinyl, thienyl, furanyl, morpholinyl, thiazolyl, oxazolyl, pyridinyl, isoxazolyl, pyrimidinyl, imidazolyl, CF$_3$, and COOCH$_3$; R$^7$ is optionally substituted at a substitutable position with one or more radicals of R$^{7a}$;

R$^3$ is hydrogen or optionally substituted phenyl;

L$_2$ is selected from the group consisting of —CONH—, —CONHCH$_2$—, —CH$_2$O—, —OCH$_2$COOCH$_2$—, —O—, —C≡C—, —OCH$_2$CH$_2$—, and —CONHOCH$_2$CH(OH)CH$_2$O—;

Ring J or K is substituted phenyl, biphenyl, pyridinyl, piperidinyl, piperazinyl, morpholinyl, thienyl, or naphthyl; and R$^4$ is selected from the group consisting of SO$_2$CH$_3$, SO$_2$CH$_2$CH$_3$, SO$_2$CH$_2$CH$_2$CH$_3$, SCH$_2$CH$_3$, SCH$_3$, OCH$_3$, C$_{1-6}$ alkyl, CH$_2$COOH, C(CH$_3$)$_2$COOH, NHSO$_2$CH$_3$, F, Cl, Br, C(CH$_3$)$_2$COOH, CH$_2$COOCH$_3$, C(CH$_3$)$_2$COOCH$_3$, CH$_2$CH$_2$COOH, OCH$_2$CON(R$^{11}$)$_2$, OCH$_2$CH$_2$N(CH$_3$)$_2$, OCH$_2$COOH, OCH$_2$COOCH$_3$, CH$_2$OH, COCH$_3$, COOC(CH$_3$)$_3$, cyclobutane-COOH, OC(CH$_3$)$_2$COOH and CF$_3$.

Another embodiment is that G is G2, R$^1$ is L$_1$-R$^5$ and R$^2$ is R$^7$. When G of formulae Iaa, Ibb, Icc, or Idd is G2, a more preferred embodiment of this invention relates to a compound having one or more features selected from the group consisting of:

R$^1$ is L$_1$-R$^5$; R$^5$ is substituted phenyl or pyridinyl;

R$^{5a}$ is halogen, trifluoromethyl, C$_{1-6}$ alkyl, C$_{1-6}$ haloalkyl, nitro, C$_{1-6}$ alkoxy, or OCON(C$_{1-6}$ alkyl)$_2$;

L$_1$ is —CS—, —CH$_2$—, —CH$_2$O—, —CH$_2$CH$_2$—, —C=O—, —SO$_2$—, —CONH—, —CONHC(CH$_3$)$_2$—, —CONH(CH$_2$)$_3$OCH$_2$—, —CONHCH$_2$CH$_2$N(CH$_3$)$_2$—, or —OCH$_2$CH$_2$—;

R$^2$ is R$^7$ is selected from the group consisting of phenyl, pyridinyl, thienyl, furanyl, morpholinyl, thiazolyl, oxazolyl, pyridinyl, CF$_3$, or COOCH$_3$;

R$^3$ is hydrogen or phenyl optionally substituted with R$^{6a}$;

Ring J or K is substituted phenyl, thienyl, furanyl, piperazinyl, piperidinyl or pyridinyl;

L$_2$ is —CONH—, —CONHCH$_2$—, —CH$_2$O—, —OCH$_2$COOCH$_2$—, —O—, —C≡C—, —OCH$_2$CH$_2$—, or —CONHOCH$_2$CH(OH)CH$_2$O—; and R$^4$ is selected from the group consisting of halogen, C$_{1-6}$ haloalkyl, C$_{1-6}$ alkylCOOR$^{11}$, and methyl sulfonyl.

Another embodiment is that G is G2, R$^1$ is R$^5$ and R$^2$ is L$_3$R$^7$. When G of formulae Iaa, Ibb, Icc, or Idd is G2, a more preferred embodiment of this invention relates to a compound having one or more features selected from the group consisting of:

R$^1$ is R$^5$ selected from the group consisting of thienyl, furanyl, morpholinyl, thiazolyl, indolyl, oxazolyl, pyridinyl, imidazolyl, isoxazolyl, pyrimidinyl and phenyl; R$^5$ is optionally substituted at a substitutable position with one or more radicals of R$^{5a}$;

R$^{5a}$ is halogen or trifluoromethyl;

R$^2$ is L$_3$-R$^7$; R$^7$ is selected from the group consisting of phenyl, pyridinyl, thienyl, furanyl, morpholinyl, thiazolyl, oxazolyl, pyridinyl, phenyl, imidazolyl, isoxazole, pyrimidinyl, CF$_3$, cycloC$_{3-6}$ alkylC≡N, C$_{0-6}$ alkylC≡N, and COOCH$_3$; R$^7$ is optionally substituted at a substitutable position with one or more radicals of R$^{7a}$;

L$_3$ is —CS—, CH$_2$, CH$_2$OCH$_2$, NCH$_2$(CH$_2$)$_2$, CH$_2$N(CH$_2$)$_2$, CH$_2$CN, CONH, CO, or CONHCH$_2$—;

R$^3$ is hydrogen or optionally substituted phenyl;

Ring J or K is substituted phenyl, pyridinyl, furanyl, biphenyl or naphthyl;

L$_2$ is —CS—, CONH, CONHCH$_2$, CH$_2$O, OCH$_2$COOCH$_2$, OCH$_2$CH$_2$, or or OCH$_2$—; and R$^4$ is SO$_2$CH$_3$, SO$_2$CH$_2$CH$_3$, SCH$_2$CH$_3$, CH$_2$COOH, C(CH$_3$)$_2$COOH, NHSO$_2$CH$_3$, F, Cl, Br, SCH$_3$, OCH$_3$, C$_{1-6}$ alkyl, COOCH$_2$CO, OCH$_3$, CH$_2$COOH, CH$_2$COOCH$_3$, CH(CH$_3$)$_2$COOH, OC(CH$_3$)$_2$COOH, COOC(CH$_3$)$_3$, cyclobutane-COOH, C(CH$_3$)$_2$COOH, OCH$_2$COOCH$_3$, and CF$_3$.

Another embodiment is that G is G3, R$^1$ is R$^5$ and R$^2$ is R$^7$. When G of formulae Iaa, Ibb, Icc, or Idd is G3, a more preferred embodiment of this invention relates to a compound having one or more features selected from the group consisting of:

R$^1$ is R$^5$ selected from the group consisting of thienyl, furanyl, morpholinyl, thiazolyl, indolyl, oxazolyl, pyridinyl, imidazolyl, isoxazole, pyrimidinyl and phenyl; R$^5$ is optionally substituted at a substitutable position with one or more radicals of R$^{5a}$;

R$^2$ is R$^7$ selected from the group consisting of phenyl, pyridinyl, thienyl, furanyl, morpholinyl, thiazolyl, oxazolyl, pyridinyl, imidazolyl, isoxazole, pyrimidinyl, CF$_3$, halogen, and COOCH$_3$; R$^7$ is optionally substituted at a substitutable position with one or more radicals of R$^{7a}$;

R$^3$ is hydrogen or optionally substituted phenyl;

L$^2$ is selected from the group consisting of —CS—, —CONH—, —CONHCH$_2$—, —CH$_2$O—, —OCH$_2$COOCH$_2$—, —COOCH$_2$—, —CO—, —OCH$_2$—, —OCO—, —NHCONH—, —O—, —OCH$_2$CH$_2$—, —OCONH—, and —SO$_2$—;

Ring J or K is substituted phenyl, biphenyl, pyridinyl, piperidinyl, piperazinyl, morpholinyl, thienyl, furanyl, pyrimidinyl or naphthyl;

$R^4$ is methylsulfonyl, halogen, haloalkyl, $CH_2COOH$, $OCH_2$-phenyl, $CH_2COO$-phenyl, $OCH_2COOH$, or $OCH_2CHN(CH_3)_2$; and $R^{5a}$ is $OCH_2C(CH_3)_3$, Cl, F, Br, $OCH_2CH(CH_3)_2$, $OCH_2CH_3$, $CF_3$, COOH, $OCH_3$, OH, $NO_2$, OCOCH$(CH_3)_2$, $NHCOCH_3$, $OCONHCH(CH_3)_2$, $O(CH_2)_2$, $CONH_2$, $O(CH)(CH_3)_2$, $C_{1-6}$ alkyl, $OCH_2COOH$, $OCH_2COOC(CH_3)_3$, $O(CH_2)_2N(CH_2CH_3)_2$, $OCOC(CH_3)_3$, $OC(CH_2)_2COOH$, $OCONH(CH_3)_2$, $OCONCH_3$, $OCONHCH_2CH_2CH_3$, $OC(CH_3)_2COOC(CH_3)_3$, and $O(CH_2)_2OH$.

Another embodiment is that G is G3, $R^1$ is $L_1$-$R^5$ and $R^2$ is $R^7$. When G of formulae Iaa, Ibb, Icc, or Idd is G3, a more preferred embodiment of this invention relates to a compound having one or more features selected from the group consisting of:

$R^1$ is $L_1$-$R^5$; $R^5$ is substituted phenyl or pyridinyl;
$R^{5a}$ is halogen or trifluoromethyl;
$L_1$ is $-CH_2-$, $-CH_2O-$, $-CH_2CH_2-$, $-C=O-$, $-SO_2-$, $-CS-$, $-CONH-$, $-CONHC(CH_3)_2-$, $-CONH(CH_2)_3OCH_2-$, $-CONHCH_2CH_2N(CH_3)_2-$, or $-OCH_2CH_2-$;
$R^2$ is halogen, $C_{1-6}$ alkyl, $C_{1-6}$ alkoxy, $C_{1-6}$ alkyl$COOR^{11}$, or $CF_3$;
$R^3$ is hydrogen or phenyl optionally substituted with $R^{6a}$;
Ring J or K is phenyl, pyridinyl, thienyl, furanyl, piperidinyl, pyrrolidinyl, piperazinyl, morpholinyl, thiazolyl, indolyl, oxazolyl, isoxazolyl, pyrimidinyl, imidazolyl, or biphenyl;
$L_2$ is $-CONH$, $-CONHCH_2-$, $-CH_2O-$, $-OCH_2COOCH_2-$, $-OCH_2-$, or $-OCH_2CH_2-$; and
$R^4$ is selected from the group consisting of halogen, $C_{1-6}$ haloalkyl, $C_{1-6}$ alkyl$COOR^{11}$, and methyl sulfonyl.

Another embodiment is that G is G3, $R^1$ is $R^5$ and $R^2$ is $L_3R^7$. When G of formulae Iaa, Ibb, Icc, or Idd is G3, a more preferred embodiment of this invention relates to a Compound having one or more features selected from the group consisting of $R^1$ is selected from the group consisting of thienyl, furanyl, morpholinyl, thiazolyl, indolyl, oxazolyl, pyridinyl, isoxazolyl, imidazolyl, pyrimidinyl and phenyl; $R^5$ is optionally substituted at a substitutable position with one or more radicals of $R^{5a}$;
$R^2$ is $L_3$-$R^7$; $R^7$ is phenyl, pyridinyl, thienyl, furanyl, morpholinyl, thiazolyl, oxazolyl, piperidinyl, imidazolyl, piperazinyl, pyridinyl, isoxazolyl, imidazolyl, pyrimidinyl, $CF_3$, and $COOCH_3$; $R^7$ is optionally substituted at a substitutable position with one or more radicals of $R^{7a}$;
$L_3$ is $-CS-$, $-CO-$, $-C_{1-6}$ alidiyl-, $-CONH-$, $-CONR^{11}-$, $-CONR^{11}NR^{11}-$, $-CH_2OCH_2-$, $-CH_2OCH_2CH_2-$, $-OCH_2-$, $-CH_2N(CH_3)_2$, $-CH_2NHCH_2-$, $-CONR^{11}O-$, $-CH_2OCOCH_2-$, $-CH_3N(CH_3)(CH_2)-$, $-CS-$, $-CH_2N(cyclopropane)CH_2-$, $-CH_2NC(CH_3)_2CH_2-$, $-CH_2N(cyclohexane)CH_2-$, $-CH_2NCH(CH_3)_2CH_2-$, $-CH_2N(CF_3)(CH_2)_2-$, $-CH_2N(CH_3)(CH_2)CH_2OCOCH_2CH_2-$, $-CONHCH_2CH_2N(CH_3)_2-$, or $-CH_2N(CH_2N)CH_2-$;
$R^3$ is hydrogen or optionally substituted phenyl;
Ring J or K is substituted phenyl, furanyl, thienyl, pyridinyl, biphenyl or naphthyl;
$L_2$ is $CONH-$, $-CONHCH_2-$, $-CH_2O$, $-OCH_2COOCH_2-$, or $-CONHCH_2-$; and $R^4$ is OH, CN, $C(CH_3)_2OH$, $SO_2CH_3$, $SO_2CH_2CH_3$, $SCH_2CH_3$, $SCH_3$, $SO_2NH_2$, $OCH_3$, $C_{1-6}$ alkyl, $CH_2COOH$, $C(CH_3)_2COOH$, $NHSO_2CH_3$, F, Cl, Br, $CF_3$ or $COCH_3$.

Another embodiment of this invention relates to compounds represented by formulae Iaa-1, Iaa-2, Iaa-3 or Iaa-4 (Embodiment Iaa):

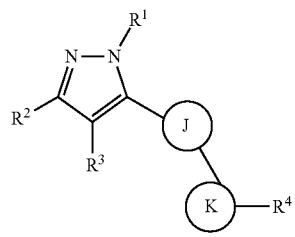

Iaa-1

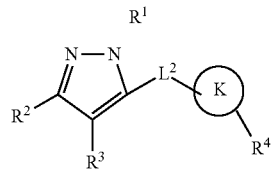

Iaa-2

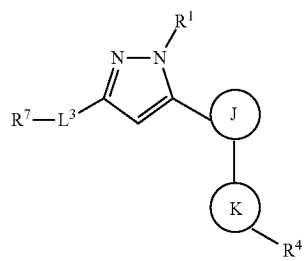

Iaa-3

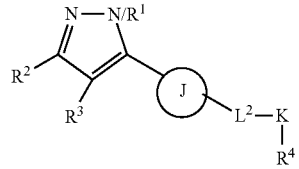

Iaa-4

Another embodiment of this invention relates to compounds represented by formulae Ibb-1, Ibb-2, Ibb-3, or Ibb-4 (Embodiment Ibb):

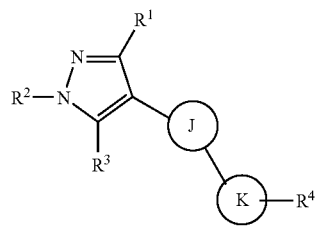

Ibb-1

Ibb-2

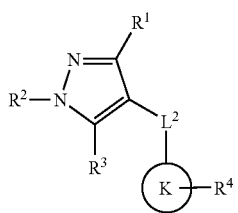

Ibb-3

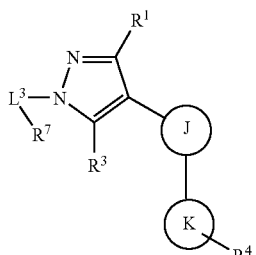

Ibb-4

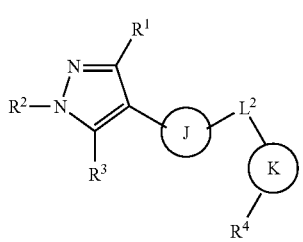

Another embodiment of this invention relates to compounds represented by formulae Icc-1, Icc-2, Icc-3, or Icc-4 (Embodiment Icc):

Icc-1

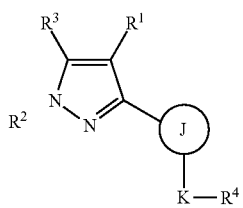

Icc-2

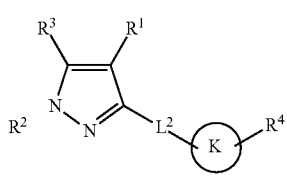

Icc-3

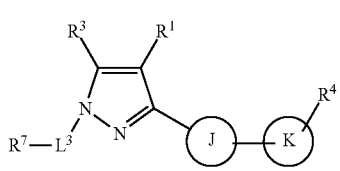

Icc-4

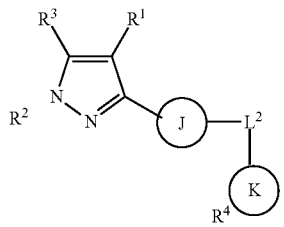

Another embodiment of this invention relates to compounds represented by formulae Idd-1, Idd-2, Idd-3, or Idd-4 (Embodiment Idd):

Idd-1

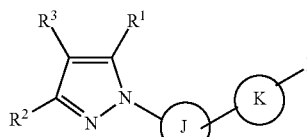

Idd-2

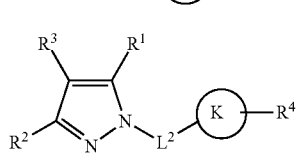

Idd-3

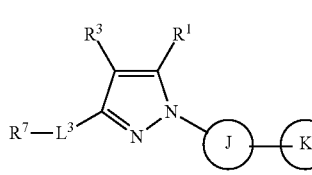

Idd-4

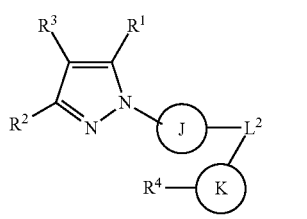

Of the above embodiments 1a-1d, $R^1$ is $R^5$ selected from the group consisting of thienyl, furanyl, morpholinyl, thiazolyl, indolyl, oxazolyl, pyridinyl, isoxazolyl, pyrimidinyl, imidazolyl, and phenyl; $R^5$ is optionally substituted at a substitutable position with one or more radicals of $R^{5a}$. Preferably, $R^5$ is phenyl or pyridinyl optionally substituted with $R^{5a}$.

$R^2$ is $R^7$ selected from the group consisting of trifluoromethyl, $COOCH_3$, $CH_2OH$, $CONHCH_2CH_3$, $CONHOCH_2CH(OH)CH_2OH$, $CONHCH_2CH_2N(CH_3)_2$, $CONHCH_2CH_2OCH_3$, $CONHCH_2CH_2OCH_3$, $CH_2COOCH_3$, $CON(CH_3)_2$, $COOCH(CH_3)_2$, $CONHCH_2CH_2CH_2OCH_3$, $OCOCH(CH_3)_2$, $OCH_2CON(CH_3)_2$, $CH_2CONHCH_2(CH_3)$, $C(CH_3)_2OH$, $COOH$, nitro or $COOCH(CH_3)_2$, $CH_2C\equiv N$, $C(CH_3)_2C\equiv N$, cyclo$C_{3-6}$ alkyl$C\equiv N$, thienyl, furanyl, morpholinyl, thiazolyl, indolyl, oxazolyl, pyridinyl, imidazolyl, isoxazolyl, pyrimidinyl and phenyl; $R^7$ is optionally substituted at a substitutable position with one or more radicals of $R^{7a}$.

$L_1$ is independently selected from direct bond, —CO—, —CONH—, —CONR$^{11}$—, —C($=$NR$^{11}$)—, —C($=$NOR$^{11}$)—, —C($=$NN(R$^{11}$)$_2$)—; $C_{2-6}$ alidiyl chain, wherein the alidiyl chain is optionally interrupted by —C(R¹¹)₂—, —C(R¹¹)₂C(R¹¹)₂—; —C(R¹¹)=C(R¹¹)—, —C≡C—, —O—, —S—, —N(R¹⁰)CO—, —N(R¹⁰)CO₂, —NR¹¹—, —OR¹¹—, —CON(R¹⁰)—, —CO—, —CO₂—, —OC(=O)—, —OC(=O)N(R¹⁰)—, —SO₂—, —N(R¹⁰)SO₂—, or —SO₂N(R¹⁰)—; —(CH₂)ₘ—V₀—(CH₂)ₙ— or —V₀—(CH₂)ₙ—V₀—; m is 0-6; n is 0-6; V₀ is independently —C(R¹¹)₂—, —C(R¹¹)₂C(R¹¹)₂—, —C(R¹¹)=C(R¹¹)—, —C(R¹¹)₂O—, —C(R¹¹)₂NR¹¹, —C≡C—, —O—, —S—, —NR¹¹—, —CR¹¹NR¹¹—, —N(R¹⁰)CO—, —N(R¹⁰)CO₂—, —CON(R¹⁰)—, —OCO—, —COR¹¹—, —COOR¹¹—, —CO—, —CO₂, —OC(=O), —OC(=O)N(R¹⁰)—, —SO₂—, —N(R¹⁰)SO₂—, —NR¹⁰COR¹⁰—, —NR¹⁰CSNR¹⁰—, cycloC₃₋₈haloalkyl or —SO₂N(R¹⁰)—. More specifically, L₁ is selected from the group consisting of —CONH—, —C₁₋₆ alkyl-, —C₁₋₆ alkoxy-, —CO—, —SO₂—, —CH₂—, —CH₂O—, —CH₂CH₂—, —C=O—, —CONH—, —CONHC(CH₃)₂—, —CONH(CH₂)₃OCH₂—, —OCH₂CH₂—, —OCH₂CH₂N(CH₃)₂—, and —CONHCH₂CH₂N(CH₃)₂—.

L₃ is independently selected from direct bond, —CO—, —CONH—, —CONR¹¹—, —C(=NR¹¹)—, —C(=NOR¹¹)—, —C(=NN(R¹¹)₂)—; C₂₋₆ alidiyl chain, wherein the alidiyl chain is optionally interrupted by —C(R¹¹)₂—, —C(R¹¹)₂C(R¹¹)₂—, —C(R¹¹)=C(R¹¹)—, —C≡C—, —O—, —S—, —N(R¹⁰)CO—, —N(R¹⁰)CO₂, —NR¹¹—, —OR¹¹—, —CON(R¹⁰)—, —CO—, —CO₂—, —OC(=O)—, —OC(=O)N(R¹⁰)—, —SO₂—, —N(R¹⁰)SO₂—, or —SO₂N(R¹⁰)—; —(CH₂)ₘ—V₀—(CH₂)ₙ— or —V₀—(CH₂)ₙ—V₀—; m is 0-6; n is 0-6; V₀ is independently —C(R¹¹)₂—, —C(R¹¹)₂C(R¹¹)₂—, —C(R¹¹)=C(R¹¹)—, —C(R¹¹)₂O—, —C(R¹¹)₂NR¹¹, —C≡C—, —O—, —S—, —NR¹¹—, —CR¹¹NR¹¹—, —N(R¹⁰)CO—, —N(R¹⁰)CO₂—, —CON(R¹⁰)—, —OCO—, —COR¹¹—, —COOR¹¹—, —CO—, —CO₂, —OC(=O), —OC(=O)N(R¹⁰)—, —SO₂—, —N(R¹⁰)SO₂—, —NR¹⁰COR¹⁰—, —NR¹⁰CSNR¹⁰—, cycloC₃₋₈haloalkyl or —SO₂N(R¹⁰)—. More specifically, L₃ is —CO—, —C₁₋₆ alkyl-, —CONH—, —CONR¹¹—, —CONR¹¹NR¹¹—, —CH₂OCH₂—, —CH₂OCH₂CH₂—, —OCH₂—, —CH₂N(CH₃)₂—, —CH₂NHCH₂—, —CONR¹¹O—, —CH₂OCOCH₂—, —CH₃N(CH₃)(CH₂)—, —CH₂N(cyclopropane)CH₂—, —CH₂NC(CH₃)₂CH₂—, —CH₂N(cyclohexane)CH₂—, —CH₂NCH(CH₃)₂CH₂—, —CH₂N(CF₃)(CH₂)₂—, —CH₂N(CH₃)(CH₂)CH₂OCOCH₂CH₂—, —CONHCH₂CH₂N(CH₃)₂—, or —CH₂N(CH₂C≡N)CH₂—.

R⁷ᵃ is selected from the group consisting of halogen, trifluoromethyl, C₁₋₆alkyl, C₁₋₆alkoxy, CH=CHCOOH, CH₂COOH, OCH₂COOH, OCONHCH(CH₃)₂, NHCOCH₃, OH, OCH₃, COOH, COOCH₃, OCH₂C(CH₃)₃, OCH₂CH(CH₃)₂, OCH(CH₃)₂OCOCH(CH₃)₂, OCONHCH₃, OCH₂CH₃, or OCH(CH₃)₂.

L₂ is independently selected from direct bond, —CO—, —CONH—, —C(=NR¹¹)—, —C(=NOR¹¹)—, —C(=NN(R¹¹)₂)—; C₂₋₆ alidiyl chain, wherein the alidiyl chain is optionally interrupted by —C(R¹¹)₂—, —C(R¹¹)₂C(R¹¹)₂—, —C(R¹¹)=C(R¹¹)—, —C≡C—, —O—, —S—, —N(R¹⁰)CO—, —N(R¹⁰)CO₂, —NR¹¹—, —OR¹¹—, —CON(R¹⁰)—, —CO—, —CO₂—, —OC(=O)—, —OC(=O)N(R¹⁰)—, —SO₂—, —N(R¹⁰)SO₂—, —SO₂N(R¹⁰)—; —(CH₂)ₘ—V₀—(CH₂)ₙ— or —V₀—(CH₂)ₙ—V₀—; m is 0-6; n is 0-6; V₀ is independently —C(R¹¹)₂—, —C(R¹¹)₂C(R¹¹)₂—, —C(R¹¹)=C(R¹¹)—, —C(R¹¹)₂O—, —C(R¹¹)₂NR¹¹—, —C≡C—, —O—, —S—, —NR¹¹—, —CR¹¹NR¹¹—, —N(R¹⁰)CO—, —N(R¹⁰)CO₂—, —CON(R¹⁰)—, —OCO—, —COR¹¹—, —COOR¹¹—, —CO—, —CO₂—, —OC(=O), —OC(=O)N(R¹⁰)—, —SO₂—, —N(R¹⁰)SO₂—, —NR¹⁰COR¹⁰—, —NR¹⁰CSNR¹⁰—, cycloC₃₋₈haloalkyl or —SO₂N(R¹⁰)—. More specifically, L₂ is selected from the group consisting of —CONH—, —CONHCH₂—, —CH₂O—, —OCH₂COOCH₂—, —O—, —C≡C—, —OCH₂CH₂— and —CONHOCH₂CH(OH)CH₂O—.

R⁵ᵃ is independently selected from the group consisting of OCH₂C(CH₃)₃, Cl, F, Br, OCH₂CH(CH₃)₂, OCH₂CH₃, CF₃, COOH, OCH₃, OH, NO₂, OCOCH(CH₃)₂, OCOC(CH₃)₃, NHCOCH₃, OCON(CH₃)₂, OCONHCH₃, OCON(CH₂)₂CH₃, OCONHCH(CH₃)₂, O(CH₂)₂CONH₂, O(CH)(CH₃)₂, C₁₋₆ alkyl, OCH₂COOH, OCH₂COOC(CH₃)₃, O(CH₂)₂N(CH₂CH₃)₂, OC(CH₃)₂COOC(CH₃)₃, and OCH₂CH₂OH. Preferred R⁵ᵃ is halogen or trifluoromethyl.

R⁴ is selected from the group consisting of OH, CN, C(CH₃)₂OH, SO₂CH₃, SO₂C(CH₃)₃, SO₂NH₂, SO₂CH₂CH₃, SCH₂CH₃, SCH₃, OCH₃, C₁₋₆ alkyl, CH₂COOH, C(CH₃)₂COOH, NHSO₂CH₃, F, Cl, Br, C(CH₃)₂ COOH, CH₂COOCH₃, C(CH₃)₂COOCH₃, CH₂CH₂COOH, OCH₂COOCH₃, COCH₃, COOC(CH₃)₃, cyclobutane-COOH, OC(CH₃)₂COOH, COOCH₂CH₃, OCF₃, and CF₃.

Another embodiment of this invention relates to compounds as described above wherein G is selected from the group consisting of:

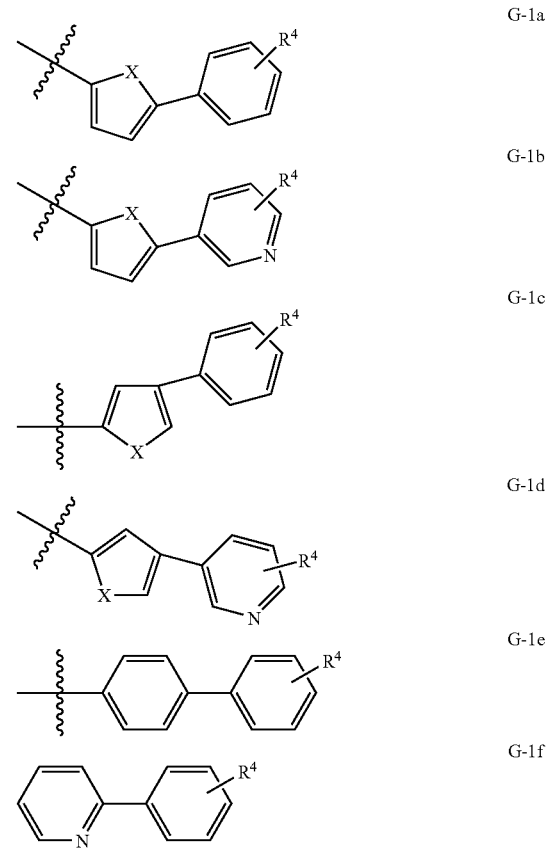

Of the above compounds, R is selected from the group consisting of C₀₋₆ alidiyl chain wherein the alidiyl chain is optionally interrupted by —C(R¹¹)₂—, —C(R¹¹)₂C(R¹¹)₂—, —C(R¹¹)=C(R¹¹)—, —C(R¹¹)₂O—, —C(R¹¹)₂NR¹¹—, —C≡C—, —O—, —S—, N(R¹⁰)CO—, —N($R^{10}$)$CO_2$—, —CON($R^{10}$)—, —CO—, —$CO_2$—, —OC(=O)—, —OC(=O)N($R^{10}$)—, —$SO_2$—, —N($R^{10}$)$SO_2$—, or —$SO_2$N($R^{10}$)—.

Each $R^4$ is independently selected from, $C_{1-6}$ alkyl, $CR^{11}$=$CR^{11}COOR^{11}$, $C_{1-6}$ alkoxy, $C_{0-6}$ alkyl$OR^{11}$, $C_{0-6}$ alkyl$COR^{11}$, $C_{0-6}$ alkyl$SO_2R^{11}$, $C_{0-6}$ alkyl$OCOOR^{11}$, $C_{0-6}$ alkyl$NR^{11}COR^{11}$, $C_{0-6}$ alkyl$SO_2NR^{11}COR^{11}$, $C_{0-6}$ alkyl$SO_2N(R^{11})_2$, $C_{0-6}$ alkyl$SR^{11}$, ($C_{0-6}$ alkyl)C=O($OR^{11}$), $OVOR^{11}$, halogen, $C_{1-6}$haloalkyl, $C_{1-6}$haloalkyl$OR^{11}$, $OC_{1-6}$haloalkyl, aryloxy, aralkyloxy, aryloxyalkyl, $C_{1-6}$ alkoxyaryl, aryl$C_{0-6}$ alkylcarboxy, $NR^{11}SO_2R^{11}$, $OC_{1-6}$ alkyl, $OC_{0-6}$ alkyl$COOR^{11}$, $C_{0-6}$ alkylC=N, $C_{0-6}$ alkoxyheteroaryl, $C_{0-6}$alkoxyheterocyclyl, cycloalkyl$COOR^{11}$, a 5-12 membered aromatic ring or non-aromatic ring, or 5-12 membered heteroaryl or heterocyclyl having one or more heteroatoms N, O or S. Preferred $R^4$ is selected from the group consisting of $SO_2CH_3$, $SO_2C(CH_3)_3$, $SO_2CH_2CH_3$, $SCH_2CH_3$, $SCH_3$, $OCH_3$, $C_{1-6}$ alkyl, $CH_2COOH$, $C(CH_3)_2COOH$, $NHSO_2CH_3$, F, Cl, Br, cyclobutane-COOH, $OC(CH_3)_2COOH$, $CF_3$, $C(CH_3)_2COOH$, $CH_2COOCH_3$, $CH_2CH_2COOH$, $OCH_2COOCH_3$, and $COCH_3$. More preferably, $R^4$ is $SO_2CH_3$, $SO_2CH_2CH_3$, $SCH_2CH_3$, or $SCH_3$.

X is selected from the group consisting of S, $NR^{11}$ and O.

Each $R^4$ is optionally substituted at a substitutable position with one or more radicals of $R^{4a}$; Each $R^{4a}$ is independently selected from hydrogen, $C_{1-6}$ alkyl, ($C_{1-6}$ alkyl)C=O($OR^{11}$); $C_{1-6}$ alkoxy, $C_{0-6}$ alkyl$OR^{11}$, $C_{0-6}$ alkyl$COR^{11}$, $C_{0-6}$ alkyl$SO_2R^{11}$, $C_{0-6}$ alkyl$SO_2N(R^{11})_2$; $C_{0-6}$ alkyl$SR^{11}$, ($C_{0-6}$ alkyl)OC=O($OR^{11}$), halogen, $C_{1-6}$ haloalkyl, aryloxy, aralkyloxy, aryloxyalkyl, $C_{1-6}$ alkoxyaryl, aryl$C_{0-6}$ alkylcarboxy, $NR^{11}SO_2R^{11}$, $OC_{1-6}$ alkyl, $C_{0-6}$ alkylC=N, or $OC_{0-6}$ alkyl$COOR^{11}$.

In a third aspect, the invention provides a pharmaceutical composition comprising a compound of any of formulas Ia-d, and XXIXa-d, or a pharmaceutically acceptable derivative thereof in a pharmaceutically acceptable carrier.

In another embodiment, the invention provides a pharmaceutical composition comprising a compound of formula XIX, or a pharmaceutically acceptable derivative thereof, in a pharmaceutically acceptable carrier.

In another embodiment, the invention provides a pharmaceutical composition comprising a compound of formula XXII, or a pharmaceutically acceptable derivative thereof, in a pharmaceutically acceptable carrier.

In another embodiment, the invention provides a pharmaceutical composition comprising a compound of formula XXV, or a pharmaceutically acceptable derivative thereof; in a pharmaceutically acceptable carrier In another embodiment, the invention provides a pharmaceutical composition comprising a compound of formula XXIIi, or a pharmaceutically acceptable derivative thereof, in a pharmaceutically acceptable carrier.

In another embodiment, the invention provides a pharmaceutical composition comprising a compound of formula Ia-d, or a pharmaceutically acceptable derivative thereof, in a pharmaceutically acceptable carrier.

In a fourth aspect, the invention provides a kit, comprising a packaging material and a compound of any of formula Ia-d, II-XXVIII, and XXIXa-d, or a pharmaceutically acceptable derivative thereof, which is effective for modulating the activity of a nuclear receptor or for treatment, prevention, inhibition, or amelioration of one or more symptoms of nuclear receptor mediated diseases or disorders.

In another embodiment, the invention provides a kit, comprising a packaging material, and a compound of formula Ia-d, or a pharmaceutically acceptable derivative thereof, which is effective for modulating the activity of a nuclear receptor or for treatment, prevention, inhibition, or amelioration of one or more symptoms of nuclear receptor mediated diseases or disorders.

In another embodiment, the invention provides a kit, comprising a packaging material, a compound of formula Ia-d, or a pharmaceutically acceptable derivative thereof, which is effective for modulating the activity of a nuclear receptor or for treatment, prevention, inhibition, or amelioration of one or more symptoms of nuclear receptor mediated diseases or disorders, further comprising a label that indicates that the compound of formula Ia-d, or pharmaceutically acceptable derivative thereof, is used for modulating the activity of a nuclear receptor or for treatment, prevention or amelioration of one or more symptoms of nuclear receptor mediated diseases or disorders, or diseases or disorders in which nuclear receptor activity is implicated.

In a sixth aspect, the invention provides a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound of any of formula Ia-d, II-XXVIII, and XXIXa-d, In a preferred embodiment of the sixth aspect, the invention provides a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound according to part (A) of formulas Ia-d.

When part (A) of formulas Ia-d is referenced herein with respect to methods of using compounds of the invention, such as for treatment, prevention, inhibition, or amelioration of disease, or for use in preparation of a medicament for the treatment, prevention, or amelioration of disease, it is meant that all compounds defined by part (A) are included and the provisos of part (B) of the same formulas are not to be considered when determining the scope of the compounds defined for the uses therein.

In a preferred embodiment of the sixth aspect, the invention provides the method wherein the disease or disorder is hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, or cardiovascular disorders.

In a seventh aspect, the invention provides a method of reducing cholesterol levels in a subject in need thereof, comprising administering an effective cholesterol level-reducing amount of a compound of any of formula Ia-d, XXVIII, and XXIXa-d.

In a preferred embodiment of the seventh aspect, the invention provides a method of reducing cholesterol levels in a subject in need thereof, comprising administering an effective cholesterol level-reducing amount of a compound according to part (A) of formulas Ia-d.

In an eighth aspect, the invention provides a method of treating, preventing, or ameliorating one or more symptoms of a disease or disorder which is affected by cholesterol, triglyceride, or bile acid levels, comprising administering to a subject in need thereof a therapeutically effective amount of a compound of any of formula Ia-d, II-XXVIII, and XXIXa-d.

In a preferred embodiment of the eighth aspect, the invention provides a method of treating, preventing, or ameliorating one or more symptoms of a disease or disorder which is affected by cholesterol, triglyceride, or bile acid levels, comprising administering to a subject in need thereof a therapeutically effective amount of a compound according to part (A) of formulas Ia-d.

In a ninth aspect, the invention provides a method of modulating nuclear receptor activity, comprising contacting the nuclear receptor with a compound of any of formula Ia-d, II-XVIII, and XXIXa-d.

In a preferred embodiment of the ninth aspect, the invention provides a method of modulating nuclear receptor activity, comprising contacting the nuclear receptor with a compound according to part (A) of formulas Ia-d.

In an embodiment of the ninth aspect, the invention provides the method wherein the nuclear receptor is an orphan nuclear receptor.

In an embodiment of the ninth aspect, the invention provides the method wherein the nuclear receptor is a liver X receptor.

In a preferred embodiment of the ninth aspect, the invention provides the method wherein the nuclear receptor is a liver X receptor, wherein the liver X receptor is LXRα or LXRβ.

In an eleventh aspect, the invention provides a method of modulating cholesterol metabolism, comprising administering an effective cholesterol metabolism-modulating amount of a compound of any of formula Ia-d, II-XXVIII, and XXIXa-d.

In a preferred embodiment of the eleventh aspect, the invention provides a method of modulating cholesterol metabolism, comprising administering an effective cholesterol metabolism-modulating amount of a compound according to part (A) of formulas Ia-d.

In a twelfth aspect, the invention provides a method of treating, preventing, inhibiting, or ameliorating one or more symptoms of hypocholesterolemia in a subject in need thereof, comprising administering a therapeutically effective amount of a compound of any of formula Ia-d, and XXIXa-d.

In a preferred embodiment of the twelfth aspect, the invention provides a method of treating, preventing, inhibiting, or ameliorating one or more symptoms of hypocholesterolemia in a subject in need thereof, comprising administering a therapeutically effective amount of a compound according to part (A) of formulas Ia-d.

In a thirteenth aspect, the invention provides a method of increasing cholesterol efflux from cells of a subject, comprising administering an effective cholesterol efflux-increasing amount of a compound of any of formula Ia-d, and II-XXVIII, and XXIXa-d.

In a preferred embodiment of the thirteenth aspect, the invention provides a method of increasing cholesterol efflux from cells of a subject, comprising administering an effective cholesterol efflux-increasing amount of a compound according to part (A) of formulas Ia-d.

In a fourteenth aspect, the invention provides a method of increasing the expression of ATP-Binding Cassette ($ABC_1$) in the cells of a subject, comprising administering an effective $ABC_1$ expression-increasing amount of a compound of any of formula Ia-d, II-XXVIII, and XXIXa-d.

DEFINITIONS

The following definitions apply to the terms used herein, unless expressly stated to the contrary. So, for example, "alkyl" is defined hereinbelow as containing from 1 to 12 carbon atoms, but a substituent defined as $C_{1-6}$alkyl is limited to an alkyl moiety of from 1 to 6 carbons. All selections of any variables in connection with any of the general structures or formulas herein are understood to be proper only when said selection yields a stable chemical structure as recognized by one skilled in the art.

When particular embodiments are referred to by structure only, all otherwise unnamed chemical groups making up that structure are as defined in each embodiment of that structure. So, for example, when it is stated, "In another embodiment, the invention provides the compound according to any one of formulas Ia-d, wherein K is phenyl or pyridyl," it is meant that another embodiment of the invention comprises each embodiment of any one of formulas Ia-d described in the specification in which K is phenyl or pyridyl and all other moieties are as defined in the respective embodiment.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0, the moiety is B—, and when a is 1 the moiety is A-B—. Similarly, $C_{0-6}$alkyl$OR^{11}$ includes both —$OR^{11}$ and $C_1$-$C_6$—$OR^{11}$, and —$[C(R^{15})_2]_m$— is a bond when m is 0. In the instances when a moiety is a divalent radical, there is no implied limitation on the location of the two bonds connecting the linking radical to its two supporting chemical units. For example, for a divalent cyclohexyl radical, the cyclohexyl can be connected either through two separate chemical bonds to two distinct carbons atoms within the ring; or the two bonds can be connected to the same carbon atom in the ring. In an illustrative example, if a divalent cyclopropyl radical connects connect two phenyl rings together, this definition encompasses both 1,2-diphenylcyclopropyl and 1,1-diphenylcyclopropyl units.

As used herein the singular forms "a", "an", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated.

The term "absent" as used herein means the group is replaced by a single bond. If replacing the group with a bond results in two connected moieties both defined as bonds, then -bond-bond- groups are understood to reduce to a single bond.

The term "interrupted by" as used herein means the group specified is inserted at any point within the specified chain, but not at the termini. For example, if a $C_3$-alkyl chain, as defined herein, is interrupted by —O—, then the following groups would be encompassed: —$CH_2$—O—$CH_2CH_2$—, —$CH_2$—$CH_2$—O—$CH_2$, —$CH(CH_3)$—O—$CH_2$—, and —$CH_2$—O—$CH(CH_3)$—.

The terms "alphatic" and "aliphatic group" as used herein means straight-chain, branched or cyclic $C_1$-$C_{12}$ (unless stated otherwise) hydrocarbon radicals which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms.

The terms "alkenyl" and "alkynyl" used alone or as part of a larger moiety include both straight and branched chains containing two to twelve carbon atoms.

The term "alkoxy" refers to an —O-alkyl radical, where alkyl is defined herein.

"Alkyl" refers to a straight or branched hydrocarbon chain radical consisting solely of carbon and hydrogen atoms, containing no unsaturation, having from one to twelve carbon atoms, preferably one to eight, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical is optionally substituted by one or more substituents selected from the group consisting of halo, cyano, nitro, —$OR^{11}$, —$N(R^{11})_2$, —$COR^{11}$, —$COOR^{11}$, —$CON(R^{11})_2$, —$N(R^{11})COOR^{10}$, —$N(R^{11})COR^{11}$, —$NSO_2R^{11}$, —$N(R^{11})SO_2R^{11}$, —$SO_2OR^{11}$, —$SO_2R^{11}$, and —$SO_2N(R^{11})_2$ where each $R^{10}$ and $R^{11}$ are as defined above in the first aspect of the invention. Unless stated otherwise specifically in the specification, it is understood that for radicals, as defined below, that contain a substituted alkyl group that the substitution can occur on any carbon of the alkyl group.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical is optionally substituted by one or more substituents selected from the group consisting of halo, cyano, nitro, —$OR^{11}$, —$N(R^{11})_2$, —$COR^{11}$, —$COOR^{11}$, —$CON(R^{11})_2$, —$N(R^{11})COOR^{10}$, —$N(R^{11})COR^{11}$, —$NSO_2R^{11}$, —$N(R^{11})SO_2R^{11}$, —$SO_2OR^{11}$, —$SO_2R^{11}$, and —$SO_2N(R^{11})_2$ where each $R^{10}$ and $R^{11}$ are as defined above in the first aspect of the invention. Unless stated otherwise specifically in the specification, it is understood that for radicals, as defined below, that contain a substituted alkenyl group that the substitution can occur on any carbon of the alkenyl group.

"Aryl" refers to aromatic monocyclic or multicyclic ring system containing from 6 to 19 carbon atoms, where the ring system is optionally partially or fully saturated. Aryl groups include, but are not limited to groups such as fluorenyl, phenyl and naphthyl. Unless stated otherwise specifically in the specification, the term "aryl" is meant to include aryl radicals optionally substituted by one or more substituents selected from the group consisting of alkyl, alkenyl, halogen, haloalkyl, haloalkenyl, cyano, nitro, aryl, aralkyl, cycloalkyl, cycloalkylalkyl, heteroaryl, heteroarylalkyl, heterocyclyl, heterocyclylalkyl, —$R^O$—$OR^{11}$, —$R^O$—$N(R^{11})_2$—, —$R^O$—$COR^{11}$, —$R^O$—$COOR^{11}$, —$R^O$—$CON(R^{11})_2$, —$R^O$—$N(R^{11})COOR^{10}$, —$R^O$—$N(R^{11})COR^{11}$, —$R^O$—$NSO_2R^{11}$, —$R^O$—$N(R^{11})SO_2R^{11}$, —$R^OSO_2OR^{11}$, —$R^O$—$SO_2R^{11}$, and —$R^O$—$SO_2N(R^{11})_2$ where each $R^O$ is independently selected from a substituted or an unsubstituted aliphatic group, an unsubstituted heteroaryl or heterocyclic ring, phenyl (Ph), substituted Ph, —OPh, substituted —OPh, or substituted —$CH_2Ph$. Examples of substituents on the aliphatic group or phenyl ring of $R^O$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy or haloalkyl.

An aliphatic group or non-aromatic heterocyclic ring may contain one or more substituents. Examples of suitable substituents on the saturated carbon of an aliphatic group or of non-aromatic heterocyclic ring include those listed above for unsaturated carbon of an aryl or heteroaryl group and including the following: =O, =S, =$NNHR^O$, =$NN(R^O)_2$, =N—, =$NNHC(O)R^O$, =$NNHCO_2$ (alkyl), =$NNHSO_2$(alkyl), or =$NR^O$, where $R^O$ is independently selected from hydrogen, unsubstituted or substituted aliphatic group, an unsubstituted heteroaryl or heterocyclic ring, phenyl (Ph), substituted Ph, —OPh, substituted —OPh, —$CH_2Ph$ or substituted —$CH_2Ph$. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy or haloalkyl.

Suitable substituents on the nitrogen of a non-aromatic heterocyclic ring include —$R^O$, —$N(R^O)_2$, —$C(O)R^O$, $CO_2R^O$, —$C(O)C(O)R^O$, —$SO_2R$, —$SO_2N(R^O)_2$, —C(=S) $N(R^O)_2$, —C(=NH)—$N(R^O)_2$, and $NR^ORSO_2R^O$ wherein each $R^O$ is independently selected from hydrogen, unsubstituted or substituted aliphatic group, an unsubstituted heteroaryl or heterocyclic ring, phenyl (Ph), substituted Ph, —OPh, substituted —OPh, or substituted —$CH_2Ph$. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy or haloalkyl.

The term "alkoxyaryl" as used herein means an aryl group, as defined herein, substituted with one or more alkoxy groups, as defined herein. Examples of alkoxyaryl groups include, but are not limited to, methoxyphenyl, butyloxyphenyl, and dimethoxynaphthyl.

"Aralkyl" or "arylalkyl" refers to a radical of the formula —RaRb where Ra is an alkyl radical as defined above and Rb is one or more aryl radicals as defined above, e.g., benzyl, diphenylmethyl and the like. The aryl radical(s) and the alkyl radical is optionally substituted as described above.

The term "aralkyloxy" or "arylalkoxy" as used herein, means an aralkyl group, as defined herein, appended to the parent molecule through a oxygen atom. Examples of aralkyloxy include, but are not limited to, benzyloxy, 2-phenylethoxy, 4-phenylbutoxy, 9-fluorenylmethoxy, and the like.

The term "arylalkylcarboxy" as used herein, means an arylalkyl group, as defined herein, appended to the parent molecule through a carboxy group, as defined herein. The carboxy group can be bonded in either sense; either with the carbonyl carbon bonded to the arylalkyl group and the oxygen bonded to the parent molecule; or the carbonyl bonded to the parent molecule and the oxygen bonded to the arylalkyl group. Examples of arylalkylcarboxy groups include, but are not limited to, benzylacetoxy, (benzyloxy)carbonyl, (2-phenylethoxy)carbonyl, phenyl-acetyloxy, and 1-oxo-5-phenylpentyloxy.

The term "aryloxy" as used herein, means an aryl group, as defined herein, appended to a parent molecule through an oxygen atom. Examples of "aryloxy" groups include, but are not limited to phenoxy, 1-naphthyloxy, and 2-naphthyloxy.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain. The alkylene chain is optionally substituted by one or more substituents selected from the group consisting of halo, cyano, nitro, $-OR^{11}$, $-N(R^{11})_2$, $-COR^{11}$, $-COOR^{11}$, $-CON(R^{11})_2$, $-N(R^{11})COOR^{10}$, $-N(R^{11})COR^{11}$, $-NSO_2R^{11}$, $-N(R^{11})SO_2R^{11}$, $-SO_2OR^{11}$, $-SO_2R^{11}$, and $-SO_2N(R^{11})_2$ where each $R^{10}$ and $R^{11}$ are as defined above in the first aspect of the invention. The alkylene chain may be attached to the rest of the molecule through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. The alkenylene chain is optionally substituted by one or more substituents selected from the group consisting of halo, cyano, nitro, $-OR^{11}$, $-N(R^{11})_2$, $-COR^{11}$, $-COOR^{11}$, $-CON(R^{11})_2$, $-N(R^{11})COOR^{10}$, $-N(R^{11})COR^{11}$, $-NSO_2R^{11}$, $-N(R^{11})SO_2R^{11}$, $-SO_2OR^{11}$, $-SO_2R^{11}$, and $-SO_2N(R^{11})_2$ where each $R^{10}$ and $R^{11}$ are as defined above in the first aspect of the invention.

The term "aryloxyalkyl" as used herein, means an alkyl group appended to the parent molecule, wherein the alkyl group is substituted with one aryloxy group, as defined herein. Examples of aryloxyalkyl groups include, but are not limited to phenoxymethyl, naphthyloxybutyl, and phenoxyhexyl.

The term "aryloxyaryl" as used herein, means an aryl group appended to the parent molecule, wherein the aryl group is substituted with one aryloxy group, as defined herein. Examples of aryloxyaryl groups include, but are not limited to phenoxyphenyl, naphthyloxyphenyl, and phenoxynaphthyl.

The term "carbonyl" as used herein, means a $-C(=O)-$ group.

The term "carboxy" as used herein, means a $-C(=O)O-$ group.

"Cycloalkyl" refers to a stable monovalent monocyclic or bicyclic hydrocarbon radical consisting solely of carbon and hydrogen atoms, having from three to ten carbon atoms (unless stated otherwise), and which is saturated or includes one more unsaturated units (but is not aromatic) and is attached to the rest of the molecule by a single bond, e.g., cyclopropyl, cyclobutyl, cyclopentyl, cylcopent-1-enyl, cyclohexyl, cyclohex-2,4-dienyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-OR^{11}$, $-N(R^{11})_2$, $-COR^{11}$, $-COOR^{11}$, $-CON(R^{11})_2$, $-N(R^{11})COOR^{10}$, $-N(R^{11})COR^{11}$, $-NSO_2R^{11}$, $-N(R^{11})SO_2R^{11}$, $-SO_2OR^{11}$, $-SO_2R^{11}$, and $-SO_2N(R^{11})_2$ where each $R^{10}$ and $R^{11}$ are as defined above in the first aspect of the invention.

"Cycloalkylalkyl" refers to a radical of the formula $-R_aR_d$ where $R_a$ is an alkyl radical as defined above and $R_d$ is a cycloalkyl radical as defined above. The alkyl radical and the cycloalkyl radical may be optionally substituted as defined above.

The term "cyclohaloalkyl" as used herein means a cycloalkyl group, as defined herein which is substituted by one or more halo groups, as defined herein. Examples of "cyclohaloalkyl" groups include, but are not limited to, bromocyclohexyl, trifluorocyclopentyl, dichlorocyclohexyl and the like.

"Halo" or "Halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethenyl, 3-bromoprop-1-enyl, and the like.

The term "haloaryl" as used herein, means an aryl group, as defined herein, substituted with one or more halo groups. Examples of haloaryl groups include, but are not limited to, bromophenyl, fluorophenyl, pentafluorophenyl, chloronaphthyl, chloro-iodophenyl, and the like.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, nitro, aryl, aralkyl, cycloalkyl, cycloalkylalkyl, heterocyclyl, heterocyclylalkyl, heteroaryl, heteroarylalkyl, $-OR^{11}$, $-N(R^{11})_2-$, $-COR^{11}$, $-COOR^{11}$, $-CON(R^{11})_2$, $-N(R^{11})COOR^{10}$, $-N(R^{11})COR^{11}$, $-NSO_2R^{11}$, —N(R$^{11}$)SO$_2$R$^{11}$, —SO$_2$OR$^{11}$, —SO$_2$R$^{11}$, and —SO$_2$N(R$^{11}$)$_2$ where each R$^{10}$ and R$^{11}$ are as defined above in the first aspect of the invention.

"Heterocyclylalkyl" refers to a radical of the formula —R$_a$R$_e$ where R$_a$ is an alkyl radical as defined above and R$_e$ is a heterocyclyl radical as defined above, and if the heterocyclyl is a nitrogen-containing heterocyclyl, the heterocyclyl may be attached to the alkyl radical at the nitrogen atom. The heterocyclyl radical and the alkyl radical is optionally substituted as defined above.

The term "heterocyclyloxy" as used herein, means a heterocyclyl group, as defined herein, appended to a parent molecule through an oxygen atom. Examples of "heterocyclyloxy" groups include, but are not limited to piperidinyloxy, tetrahydrofuranyloxy, tetrahydrotheinyloxy tetrahydropyranyloxy, dihydropyranyloxy, pyrrolidinyloxy, oxetanyloxy, and oxiranyloxy.

"Heteroaryl" refers to a 3- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical is optionally oxidized; the nitrogen atom is optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, phthalimidyl pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, nitro, aryl, aralkyl, cycloalkyl, cycloalkylalkyl, heterocyclyl, heterocyclylalkyl, heteroaryl, heteroarylalkyl, —OR$^{11}$, —N(R$^{11}$)$_2$, —COR$^{11}$, —COOR$^{11}$, —CON(R$^{11}$)$_2$, —N(R$^{11}$)COOR$^{10}$, —N(R$^{11}$)COR$^{11}$, —NSO$_2$R$^{11}$, —N(R$^{11}$)SO$_2$R$^{11}$, —SO$_2$OR$^{11}$, —SO$_2$R$^{11}$, and —SO$_2$N(R$^{11}$)$_2$ where each R$^{10}$ and R$^{11}$ are as defined above in the first aspect of the invention. For purposes of this invention, the term "N-heteroaryl" refers to heteroaryl radicals as defined above containing at least one nitrogen atom in ring.

The term "heteroaryloxy" as used herein, means a heteroaryl group, as defined herein, appended to a parent molecule through an oxygen atom. Examples of "heteroaryloxy" groups include, but are not limited to pyridyloxy, indolyloxy, and quinolyloxy.

"Heteroarylalkyl" refers to a radical of the formula —R$_a$R$_f$ where R$_a$ is an alkyl radical as defined above and R$_f$ is a heteroaryl radical as defined above, and if the heteroaryl is a nitrogen-containing heteroaryl, the heteroaryl may be attached to the alkyl radical at the nitrogen atom. The heteroaryl radical and the alkyl radical are optionally substituted as defined above.

The term "linker group" or "linker" means an organic moiety that connects two parts of a compound. Linkers are typically comprised of an atom such as oxygen or sulfur, a unit such as —NH—, —CH$_2$—, —CO—, —CONH—, or a chain of atoms, such as an alidiyl chain. The molecular mass of a linker is typically in the range of about 14 to 200, preferably in the range of 14 to 96 with a length of up to about six atoms. Examples of linkers include a saturated or unsaturated C$_1$-C$_6$ alidiyl chain which is optionally substituted, and wherein one or two saturated carbons of the chain are optionally replaced by —CO—, —COCO—, —CONH—, —CONHNH—, —CO$_2$—, —NHCO$_2$—, —O—, —NHCONH—, —OCONH—, —NHNH—, —NHCO—, —S—, —SO—, —SO$_2$—, —NH—, —SO$_2$NH—, or —NHSO$_2$—.

The term "alidiyl chain" refers to an optionally substituted, straight or branched carbon chain that may be fully saturated or have one or more units of unsaturation. The optional substituents are as described above for an aliphatic group. Alidiyl chain used herein may include alidiyl chains containing 0-4 fluorine substituents.

An "agonist for a nuclear receptor" is an agent that, when bound to the nuclear receptor, activates nuclear receptor activity to activate or repress gene function. In some cases, nuclear receptors can act through second messenger signaling pathways, and the invention would apply to these actions as well. The activation can be similar in degree to that provided by a natural hormone for the receptor, or can be stronger (optionally referred to as a "strong agonist"), or can be weaker (optionally referred to as a "weak agonist" or "partial agonist"). An example of a hormone for a nuclear receptor is thyroid hormone, which is a natural hormone for the thyroid receptor. A "putative agonist" is an agent to be tested for agonist activity.

Partial agonists or partial antagonists bind to receptors and yield a response less than that of a full agonist at saturating ligand concentrations. A partial agonist will block binding of a full agonist and suppress receptor activity to the level induced by the partial agonist alone. For example, partial agonists bind to receptors and induce only part of the changes in the receptors that are induced by agonists. The differences can be qualitative or quantitative. Thus, a partial agonist can induce some of the conformation changes induced by agonists, but not others, or it may only induce certain changes to a limited extent. Some of these compounds are naturally produced. For example, many plant estrogens (phytoestrogens), such as genistein, can behave as partial estrogen receptor agonists.

An "antagonist for a nuclear receptor" is an agent that reduces or blocks activity mediated by the receptor in response to an agonist of the receptor. The activity of the antagonist can be mediated, e.g., by blocking binding of the agonist to the receptor, or by altering receptor configuration and/or activity of the receptor. A "putative antagonist" is an agent to be tested for antagonist activity.

A "nuclear receptor" is a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound. Nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is LXR.

As used herein, an orphan nuclear receptor is a nuclear receptor for which the natural ligand is unknown.

As used herein, liver X receptor or LXR refers to a nuclear receptor implicated in cholesterol biosynthesis. As used herein, the term LXR refers to both LXRα and LXRβ, two forms of the protein found in mammals. Liver X receptor-α or LXRα refers to the receptor described in U.S. Pat. Nos. 5,571,696, 5,696,233 and 5,710,004, and Willy et al. (1995) Gene Dev. 9(9):1033-1045. Liver X receptor-β or LXRβ refers to the receptor described in Peet et al. (1998) Curr. Opin. Genet. Dev. 8(5):571-575; Song et al. (1995) Ann. N.Y. Acad. Sci. 761:38-49; Alberti et al. (2000) Gene 243(1-2):93-103; and references cited therein; and in U.S. Pat. Nos. 5,571,696, 5,696,233 and 5,710,004.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392). Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals as defined herein and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable derivative" refers to pharmaceutically acceptable salts as defined herein and also includes esters, prodrugs, solvates and polymorphs of the compounds of the invention.

"Therapeutically effective amount" refers to that amount of a compound of the invention which, when administered to a mammal, preferably a human, is sufficient to effect treatment, as defined below, for a disease-state associated with nuclear receptor activity. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Modulating" or "modulate" refers to the treating, prevention, suppression, enhancement or induction of a function or condition. For example, the compounds of the present invention can modulate hyperlipidemia by lowering cholesterol in a human, thereby suppressing hyperlipidemia.

"Treating" or "treatment" as used herein covers the treatment of a disease or condition associated with the nuclear receptor activity as disclosed herein, in a mammal, preferably a human, and includes:
  i. Preventing a disease or condition associated with the nuclear receptor activity from occurring in a mammal, in particular, when such mammal is predisposed to the disease or condition but has not yet been diagnosed as having it;
  ii. inhibiting a disease or condition associated with the nuclear receptor activity, i.e., arresting its development; or
  iii. relieving a disease or condition associated with the nuclear receptor activity, i.e., causing regression of the condition.

The compounds of formulae Ia, Ib, Ic or Id or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active ($^+$) and ($-$), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of this invention.

The chemical naming protocol and structure diagrams used herein employ and rely on the chemical naming features as utilized by the ChemDraw program (available from Cambridgesoft Corp., Cambridge, Mass.). In particular, the compound names were derived from the structures using the Autonom program as utilized by Chemdraw Ultra or ISIS base (MDL Corp.).

The term "atherosclerosis" refers to process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

As used herein, "$EC_{50}$" refers to a dosage, concentration or amount of a particular test compound that elicits a dose-dependent response at 50% of maximal expression of a particular response that is induced, provoked or potentiated by the particular test compound.

The term "cholesterol" refers to a steroid alcohol that is an essential component of cell membranes and myelin sheaths and, as used herein, incorporates its common usage Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

The term "hyperlipidemia" refers to the presence of an abnormally elevated level of lipids in the blood. Hyperlipidemia can appear in at least three forms: (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels; Familial Dysbetalipoproteinemia, also referred to as Type III Hyperlipoproteinemia, is an uncommon inherited disorder resulting in moderate to severe elevations of serum triglyceride (TG) and cholesterol levels with abnormal apolipoprotein E function. HDL levels are usually normal; and Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various beta blockers; (3) dietary risk factors include dietary fat intake per total calories greater than 40%; saturated fat intake per total calories greater than 10%; cholesterol intake greater than 300 mg per day; habitual and excessive alcohol use; and obesity; and (4) non-genetic dyslipidemias.

The methods of the present invention can be used effectively in combination with one or more additional active diabetes agents depending on the desired target therapy (see, e.g., Turner, N. et al. Prog. Drug Res. (1998) 51:33-94; Haffner, S. Diabetes Care (1998) 21: 160178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999) 84:1165-71; United Kingdom Prospective Diabetes Study Group: UKPDS 28, Diabetes Care (1998) 21:87-92; Bardin, C. W. (ed.), CURRENT THERAPY IN ENDOCRINOLOGY AND METABOLISM, 6th Edition (Mosby-Year Book, Inc., St. Louis, Mo. 1997); Chiasson, J. et al, Ann. Intern. Med. (1994) 121: 928-935; Coniff, R. et al., Clin. Ther. (1997) 19: 16-26; Coniff, R. et al., Am. J. Med. (1995) 98: 443-451; and Iwamoto, Y. et al, Diabet. Med. (1996) 13: 365-370; Kwiterovich, P. Am. J. Cardiol (1998) 82(12A):3U-17U). These studies indicate that diabetes and hyperlipidemia modulation can be further improved by the addition of a second agent to therapeutic regimen. As used herein, "$IC_{50}$" refers to an amount, concentration or dosage of a particular test compound that achieves a 50% inhibition of a maximal response, such as modulation of nuclear receptor, including the LXRα or LXRβ activity, in an assay that measures such response.

As used herein, "LXRα" (LXR alpha) refers to all mammalian forms of such receptor including, for example, alternative splice isoforms and naturally occurring isoforms. Representative LXRα species include, without limitation the rat (Genbank Accession NM_031627), mouse (Genbank Accession $BC_0$12646), and human (GenBank Accession No. U22662) forms of the receptor.

As used herein, "LXRβ" (LXR beta) refers to all mammalian forms of such receptor including, for example, alternative splice isoforms and naturally occurring isoforms. Representative LXRβ species include, without limitation the rat (GenBank Accession NM_031626), mouse (Genbank Accession NM_009473), and human (GenBank Accession No. U07132) forms of the receptor.

As used herein "LXR" or "LXRs" refers to both LXRα and LXRβ.

The terms "obese" and "obesity" refers to a Body Mass Index (BMI) greater than 27.8 kg/m$^2$ for men and 273 kg/m$^2$ for women (BMI equals weight (kg)/(height)$^2$(m$^2$).

Use of the Compounds of the Invention

The compounds of the invention exhibit valuable pharmacological properties in mammals, and are particularly useful as selective LXR agonists, antagonists, inverse agonists, partial agonists and antagonists, for the treatment, or prevention of diseases associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

These diseases include, for example, hyperlipidemia, dyslipidemia, hypercholesterolemia, atherosclerosis, atherosclerotic cardiovascular diseases, hyperlipoproteinemia, (see, e.g., Patent Application Publication Nos. WO 00/57915 and WO 00/37077), hyperglycemia, insulin resistance, diabetes, lipodystrophy, obesity, syndrome X (US Patent Application No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retintis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), Parkinson's disease or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem*. (1996), Vol. 33, No. 2, pp. 148-150), and autoimmune diseases (*J. Lipid Res*. (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a patient with atherosclerosis or atherosclerotic cardiovascular disease manifest by clinical signs of such disease, wherein the methods comprise administering to the patient a therapeutically effective amount of a compound or composition of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a patient at risk for such an event. The patient may already have atherosclerotic cardiovascular disease at the time of administration, or may be at risk for developing it. Risk factors for developing atherosclerotic cardiovascular disease events include increasing age (65 and over), male gender, a family history of atherosclerotic cardiovascular disease events, high blood cholesterol (especially LDL or "bad" cholesterol over 100 mg/dL), cigarette smoking and exposure to tobacco smoke, high blood pressure, diabetes, obesity and physical inactivity.

Also contemplated herein is the use of a compound of the invention, or a pharmaceutically acceptable derivative thereof, in combination with one or more of the following therapeutic agents in treating atherosclerosis: antihyperlipidemic agents, plasma HDL-raising agents, antihypercholesterolemic agents, cholesterol biosynthesis inhibitors (for example, HMG CoA reductase inhibitors, such as lovastatin, simvastatin, pravastatin, fluvastatin, atorvastatin, and rivastatin), acyl-coenzyme A:cholesterol acytransferase (ACAT) inhibitors, probucol, raloxifene, nicotinic acid, niacinamide, cholesterol absorption inhibitors, HMG-CoA reductase inhibitor-cholesterol absorption inhibitor combinations (e.g., Vytorin), bile acid sequestrants (such as anion exchange resins, or quaternary amines (e.g., cholestyramine or colestipol), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In one embodiment compounds of the invention are used in combination with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rosuvastatin (CRESTOR®). The structural formulas of these and additional HMG-CoA reductase inhibitors that can be used in combination with the compounds of the invention are described at page 87 of M. Yalpani, "Cholesterol Lowering Drugs," *Chemistry & Industry*, pp. 85-89 (5 Feb. 1996). In presently preferred embodiments, the HMG-CoA reductase inhibitor is selected from lovastatin and simvastatin.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a patient in need of such treatment. Additionally, the instant invention also provides a method for preventing or reducing the risk of developing hyperglycemia, insulin resistance, diabetes or syndrome X in a patient, comprising the administration of a prophylactically effective amount of a compound or composition of the present invention to a patient at risk for developing such a condition.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased risk and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chico. Med. (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., Diabetes (1974), Vol. 23, pp. 105-11 (1974); and Laakso, M. and Lehto, S., Diabetes Reviews (1997), Vol. 5, No. 4, pp. 294-315). Several lipoprotein abnormalities have been described among diabetic subjects (Howard B., et al., Arteriosclerosis (1978), Vol. 30, pp. 153-162).

The compounds of the invention can also be used effectively in combination with one or more additional active diabetes agents depending on the desired target therapy (see, e.g., Turner, N. et al., Prog. Drug Res. (1998), Vol. 51, pp. 33-94; Haffner, S., Diabetes Care (1998), Vol. 21, pp. 160-178; and DeFronzo, R. et al. (eds.), Diabetes Reviews (1997), Vol. 5, No. 4). A number of studies have investigated the benefits of combination therapies with oral agents (see, e.g., Mahler, R., J. Clin. Endocrinol. Metal). (1999), Vol. 84, pp. 1165-71; United Kingdom Prospective Diabetes Study Group: UKPDS 28, Diabetes Care (1998), Vol. 21, pp. 87-92; Bardin, C. W. (ed), CURRENT THERAPY IN ENDOCRINOLOGY AND METABOLISM, 6th Edition (Mosby-Year Book, Inc., St. Louis, Mo. 1997); Chiasson, J. et al., Ann. Intern. Med. (1994), Vol. 121, pp. 928-935; Coniff, R. et al., Clin. Ther. (1997), Vol. 19, pp. 16-26; Coniff, R. et al., Am. J. Med. (1995), Vol. 98, pp. 443-451; Iwamoto, Y. et al., Diabet. Med. (1996), Vol. 13, pp. 365-370; Kwiterovich, P., Am. J. Cardiol (1998), Vol 82 (12A), pp. 3U-17U). These studies indicate that diabetes and hyperlipidemia modulation can be further improved by the addition of a second agent to therapeutic regimen.

Accordingly, the compounds of the invention may be used in combination with one or more of the following therapeutic agents in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, and rosiglitazone), and related insulin sensitizers, such as selective and non-selective activators of PPARα, PPARβ/δ and PPARγ; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as therapeutic agents discussed above for treating atherosclerosis.

Further provided by this invention are methods of using the compounds of the invention to treat obesity, as well as the complications of obesity. Obesity is linked to a variety of medical conditions including diabetes and hyperlipidemia. Obesity is also a known risk factor for the development of type 2 diabetes (See, e.g., Barrett-Conner, E., Epidemol. Rev. (1989), Vol. 11, pp. 172-181; and Knowler, et al., Am. J. Clin. Nutr. (1991), Vol. 53, pp. 1543-1551).

In addition, the compounds of the invention can be used in combination with agents used in treated obesity or obesity-related disorders. Such agents, include, but are not limited to, phenylpropanolamine, phentermine, diethylpropion, mazindol, fenfluramine, dexfenfluramine, phentiramine, $\beta_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

Evaluation of the Use of the Compounds of the Invention

Standard physiological, pharmacological and biochemical procedures are available for testing the compounds to identify those that possess biological activities that modulate the activity or nuclear receptors, including the LXRs (LXRα and LXRβ). Such assays include, for example, biochemical assays such as binding assays, fluorescence polarization assays, FRET based coactivator recruitment assays (see, generally, Glickman et al, J. Biomolecular Screening (2002), Vol.

7, No. 1, pp. 3-10, as well as cell based assays including the co-transfection assay, the use of LBD-Gal 4 chimeras and protein-protein interaction assays, (see, Lehmann. et al., J. Biol. Chem. (1997), Vol. 272, No. 6, pp. 3137-3140.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., Biomol. Screen (2000 October), Vol. 5, No 5, pp. 297), scintillation proximity assays (SPA) (see, for example, Carpenter et al., Methods Mol. Biol. (2002), Vol 190, pp. 31-49) and fluorescence resonance energy transfer energy transfer (FRED or time resolved FRET based coactivator recruitment assays (Mukherjee et al., J. Steroid Biochem. Mol. Biol. (2002 July); Vol. 81, No. 3, pp. 217-25; (Zhou et al., Mol. Endocrinol. (1998 October), Vol. 12, No. 10, pp. 1594-604). Generally such assays can be preformed using either the full length receptor, or isolated ligand binding domain (LBD). In the case of LXRα, the LBD comprises amino acids 188-447, for LXRβ the LDB comprises amino acids 198-461, and for oat, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, [$^3$H] 24,25 Epoxycholesterol) generates an optical signal when it is brought into close proximity to a scintillant such as a YSI-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of LXR with RXRα can also be measured by fluorescence resonance energy transfer (FRET), or time resolved FRET, to monitor the ability of the compounds provided herein to bind to LXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor In addition, a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, Co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor (see, for example, U.S. Pat. Nos. 5,071, 773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

For those receptors that function as heterodimers with RXR, such as the LXRs, the co-transfection assay typically includes the use of expression plasmids for both the nuclear receptor of interest and RXR. Typical co-transfection assays require access to the full length nuclear receptor and suitable response elements that provide sufficient screening sensitivity and specificity to the nuclear receptor of interest.

Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or fragment thereof, ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development 9 1033-1045 (1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example, see U.S. Pat. Nos. 6,534,261 and 6,503,7171) or a strong promoter or enhancer sequence together with a targeting sequence to enable homologous or non-homologous recombination of the activating sequence upstream of the gene of interest.

Genes encoding the following full-length previously described proteins, which are suitable for use in the co-transfection studies and profiling the compounds described herein, include human LXRα (accession U22662), human LXRβ (accession U07132), rat FXR (accession U18374), human FXR (accession NM_005123), human RXRα (accession NM_002957), human RXRβ (accession XM_042579), human RXRγ (accession XM_053680), human PPARα (accession X57638) and human PPARδ (accession U10375). All accession numbers in this application refer to GenBank accession numbers.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) Mol. Cell. Biol. 7 725-735) down stream from the herpes virus thymidine kinase promoter (located at nucleotides residues-105 to $^{+}51$ of the thymidine kinase nucleotide sequence, obtained for example, from the plasmid pBLCAT2 (Luckow & Schutz (1987) Nucl. Acid. Res. 15 5490-5494)) which is linked in turn to the appropriate response element (RE).

The choice of hormone response element is dependent upon the type of assay to be used. In the case of the use of the full-length LXRα or LXRβ a reporter plasmid comprising a known LXR RE would typically be used, such as for example in a reporter plasmid such as LXREx1-tk-luciferase, (see U.S. Pat. No. 5,747,661, which is hereby incorporated by reference). In the case of a LXRα or LXRβ-LBD-Gal4 fusion, GAL4 Upstream Activating Sequences (UAS) would be used. Typically the GAL4. UAS would comprise the sequence 5'CGGRNNRCYNYNCNCCG-3', where Y=C or T, R=A or G, and N=A, C, T or G, and would be present as a tandem repeat of 4 copies.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase (see, Berger, J., et al., Gene (1988), Vol. 66, pp. 1-10; and Kain, S. R., Methods. Mol. Biol. (1997), Vol. 63, pp. 49-60), (3-galactosidase (See, U.S. Pat. No. 5,070,012, issued Dec. 3, 1991 to Nolan et al., and Bronstein, I., et al., J. Chemilum. Biolum. (1989), Vol. 4, pp. 99-111), chloramphenicol acetyltransferase (See, Gorman et al., Mol. Cell. Biol. (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., Annu. Rev. Biochem. (1998), Vol. 67, pp. 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used A third cell based assay of utility for screening compounds of the present invention is a mammalian two-hybrid assay that measures the ability of the nuclear hormone receptor to interact with a cofactor in the presence of a ligand (see, for example, U.S. Pat. Nos. 5,667,973, 5,283,173 and 5,468, 614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene which can be measured for various reporter genes as described above. Transcription of the reporter gene is thus driven by the interaction of the interacting protein and nuclear receptor of interest in a ligand dependent fashion.

Any compound which is a candidate for activation of LXRα or LXRβ may be tested by these methods. Generally, compounds are tested at several different concentrations to optimize the chances that activation of the receptor will be detected and recognized if present. Typically assays are performed in triplicate and vary within experimental error by less than 15%. each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by LXRα or LXRβ and other nuclear receptors in vivo, using Northern-blot RT PCR or oligonucleotide microarray analysis to analyze RNA levels. Western-blot analysis can be used to measure expression of proteins encoded by LXR target genes. Genes that are known to be regulated by the LXRs include the ATP binding cassette transporters ABCA1, ABCG1, ABCG5, ABCG8, the sterol response element binding protein 1c (SREBP1c) gene, stearoyl CoA desaturase 1 (SCD-1) and the apolipoprotein apoE gene (ApoE).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDLR$^{-/-}$) and atherosclerosis using both the Apo E($^{-/-}$) and LDLR($^{-/-}$) mice fed a western diet. (21% fat 0.05% cholesterol). Additionally LXR or FXR animal models (e.g., knockout mice) can be used to further evaluate the present compounds and compositions in vivo (see, for example, Peet, et al., Cell (1998), Vol. 93, pp. 693-704, and Sinal, et al., Cell (2000), Vol. 102, pp. 731-744).

Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof for treatment of a disease-state associated with the activity of a nuclear receptor in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of therapeutic agents described above in the Utility of the Compounds of the Invention. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the Physicians' Desk Reference (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for 1,2-dihydroxys include ketal- and acetal-forming groups. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, Protective Groups in Organic Synthesis (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of the invention, as described above in the Summary of the Invention and first aspect of the invention, may not possess pharmacological activity as such, they may be administered to a mammal having a disease associated with defects in cholesterol transport, glucose metabolism, fatty acid metabolism and cholesterol metabolism, and thereafter metabolized in the body to form compounds of the invention which are pharmacologically active. Such derivatives may therefore be described as "prodrugs". All prodrugs of compounds of the invention are included within the scope of the invention.

It is understood that one of ordinary skill in the art would be able to make the compounds of the invention not specifically prepared herein in light of the following disclosure, including the Preparations and Examples, and information known to those of ordinary skill in the chemical synthesis field.

Starting materials in the synthesis examples provided herein are either available from commercial sources or via literature procedures or by methods disclosed herein. All commercially available compounds were used without further purification unless otherwise indicated. Deuterated solvents such as DMSO or $CDCl_3$ (99.8% D, Cambridge Isotope Laboratories) were used in all experiments as indicated. $^1$H NMR spectra were recorded on a Bruker Avance 400 MHz NMR spectrometer. Significant peaks are tabulated and typically include: number of protons, multiplicity (s, singlet d, double; t, triplet; q, quartet m, multiplet; br s, broad singlet) and coupling constant(s) in Hertz. Chemical shifts are reported as parts per million ($\delta$) relative to tetramethylsilane. Mass spectra were recorded on a Perkin-Elmer SCIEX HPLC/MS instrument using reverse-phase conditions (acetonitrile/water, 0.05% trifluoroacetic acid) and electrospray (ES) ionization. Abbreviations used in the examples below have their accepted meanings in the chemical literature. For example, $CH_2Cl_2$ (dichloromethane), $C_6H_6$ (benzene), TFA (trifluoroacetic acid), EtOAc (Ethyl Acetate), $Et_2O$ (diethyl ether), DMAP (4-dimethylaminopyridine), DMF (N,N-dimethylformamide) and THF (tetrahydrofuran). Flash chromatography was performed using Merck Silica Gel 60 (230-400 mesh).

For purposes of illustration only, most of the formulae in the following Reaction Schemes are directed to specific embodiments of the compounds of invention. However, one of ordinary skill in the art, in view of the teachings of this specification would reasonably be expected to be able to prepare all the compounds of the invention in the Summary of the Invention and first aspect of the invention utilizing the appropriately-substituted starting materials and methods known to one skilled in the art.

In the general descriptions immediately following each Reaction Scheme, the phrase "standard isolation procedures" is meant to include one or more of the following techniques familiar to one schooled in the art of organic chemistry: organic extraction, washing of organic solutions with dilute aqueous acid or base, use of drying agents, filtration, concentration in vacuo, followed by purification using distillation, crystallization, or solid-liquid phase chromatography. The phrase "elevated temperature" refers to a temperature above ambient temperature and the phrase "reduced temperature" refers to a temperature below ambient temperature.

The following specific Preparations (for intermediates) and Examples (for compounds, pharmaceutical compositions and methods of use of the invention) are provided as a guide to assist in the practice of the invention, and are not intended as a limitation on the scope of the invention. Without further description, it is believed that one of ordinary skill in the art can, using the preceding description and the following illustrative examples, make and utilize the compounds of the present invention and practice the claimed methods. It should be understood that the foregoing discussion and examples merely present a detailed description of certain preferred embodiments. It will be apparent to one of ordinary skill in the art that various modifications and equivalents can be made without departing from the spirit and scope of the invention.

Synthesis
Pyrazole Ia

Scheme 1

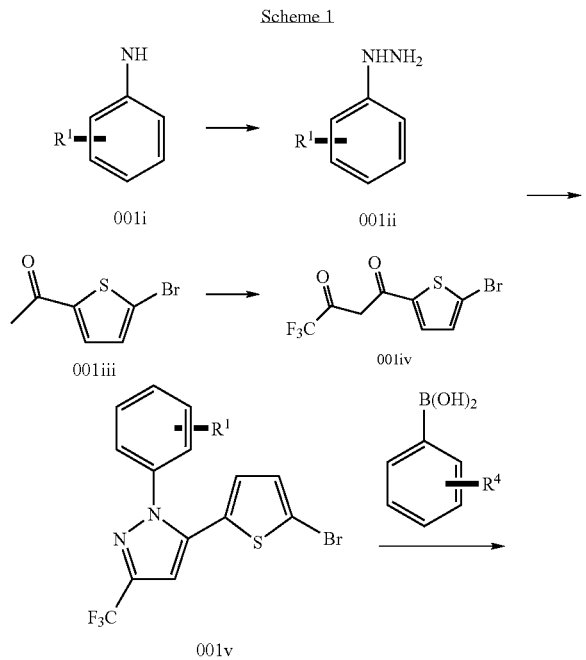

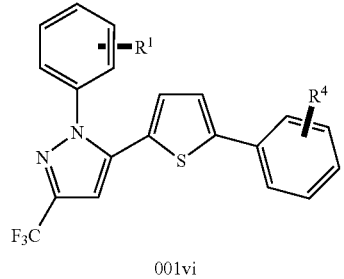

The method for preparing compounds of the invention is illustrated in Scheme 1. Amines (001i) can be converted to hydrazines (001ii) using standard techniques that are readily apparent to one skilled in the arts. Acetophenones (001iii) can be converted to diketones (001iv) via a Claisen condensation. Hydrazines (001ii) and diketones (001iv) can be condensed to form pyrazoles (001v) thermally or with the aid of catalysts such as acid. Aryl bromides such as (001v) can then be elaborated further by an arylation reaction such as a Suzuki reaction to form a tetra-aryl ring system (001vi).

An alternative means of preparing compounds of the present invention is shown in Scheme 2. Thiophene ketones (002iii) can be elaborated upon by addition of substituents such as aryl rings and these (002vii) elaborated ketones can then be converted to diketones (002viii). Diketones (002viii) and hydrazines (00211) can condense to form pyrazoles (002vi) either thermally or with the aid of catalyst

Scheme 2

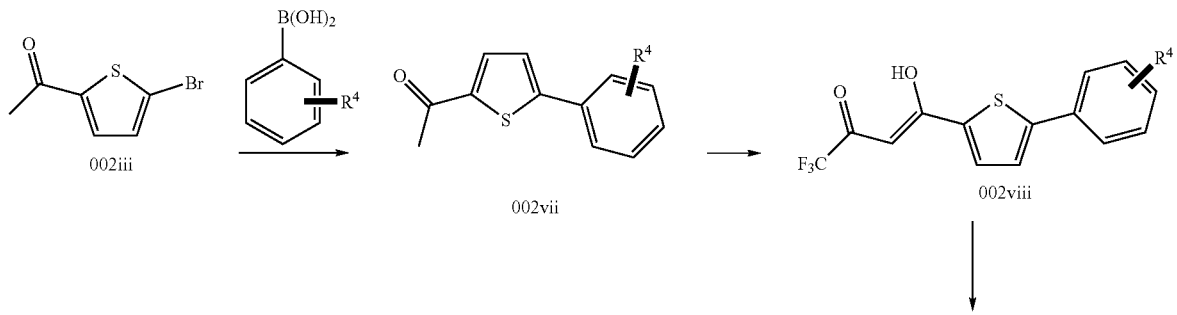

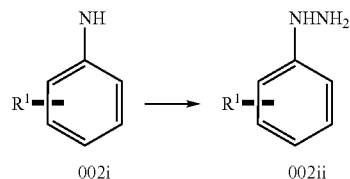

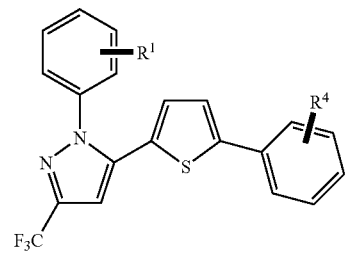

Example 1

3-{5-[2-(2,5-Dichloro-phenyl)-5-trifluoromethyl-2H-pyrazol-3-yl]-thiophen-2-yl}-benzenesulfonamide

Example 1a

Preparation of 1-(5-Bromo-thiophen-2-yl)-4,4,4-trifluoro-butane-1,3-dione

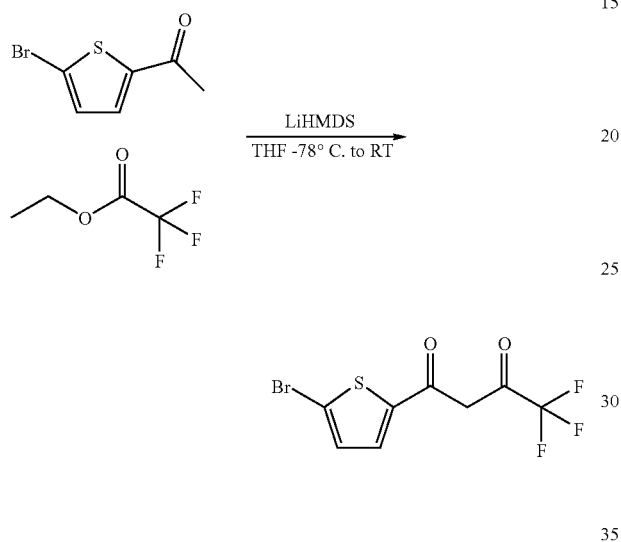

In a 2-L, three-necked round bottom flask fitted with a 250 mL pressure equalizing addition funnel, an overhead stirrer, and a thermocouple was placed lithium hexamethyldisilazide (500 mL of a 1.0 M solution in THF, 500 mmol) and THF (100 mL). A solution of 1-(5-bromo-thiophen-2-yl)-ethanone (75.5 g, 368 mmol) was prepared in THF (350 mL). This solution was added via cannula to the addition funnel in portions and added slowly from the addition funnel to the reaction flask at a rate such that the internal temperature was <−70° C. (~40 minutes). The ketone flask and addition funnel were then rinsed with additional THF (25 mL) to insure complete transfer. After stirring for 15 minutes at <−70° C., ethyl trifluoroacetate (66 mL 553 mmol) was added from the addition funnel as a solution in THF (100 mL) over ~45 minutes. The pale brown reaction was allowed to warm to ambient temperature overnight. After stirring for ~16 hours the reaction was cooled in an ice bath and carefully quenched by the addition of 3N aqueous HCl (150 mL). The quench was highly exothermic. After the completion of the HCl addition the basic aqueous layer was separated and the organic layer was concentrated under reduced pressure to remove most of the THF. The resulting brown biphasic mixture was combined with the aqueous layer and diluted with Et$_2$O (~700 mL). The mixture was acidified by the addition of 3N HCl to pH <3. The layers were separated and the acidic aqueous was extracted with Et$_2$O (3×150 mL). The combined organic layers were dried over Na$_2$SO$_4$, filtered, and concentrated under reduced pressure to afford a brown oil. This oil was taken up in benzene and concentrated under reduced pressure to remove any residual water present. The resulting oil was pumped down under high vacuum and seeded with authentic product to afford 1-(5-bromo-thiophen-2-yl)-4,4,4-trifluoro-butane-1,3-dione (111.7 g, 100.8% yield) as a pale brown solid. $^1$H-NMR (400 MHz, CDCl$_3$): δ 14.5 (broad s, 1H), 7.57 (d, J=4.0 Hz, 1H), 7.17 (d, J=4.0 Hz, 1H), 6.37 (s, 1H).

Example 1b

Preparation of 5-(5-Bromo-thiophen-2-yl)-1-(2,5-dichloro-phenyl)-3-trifluoromethyl-1H-pyrazole

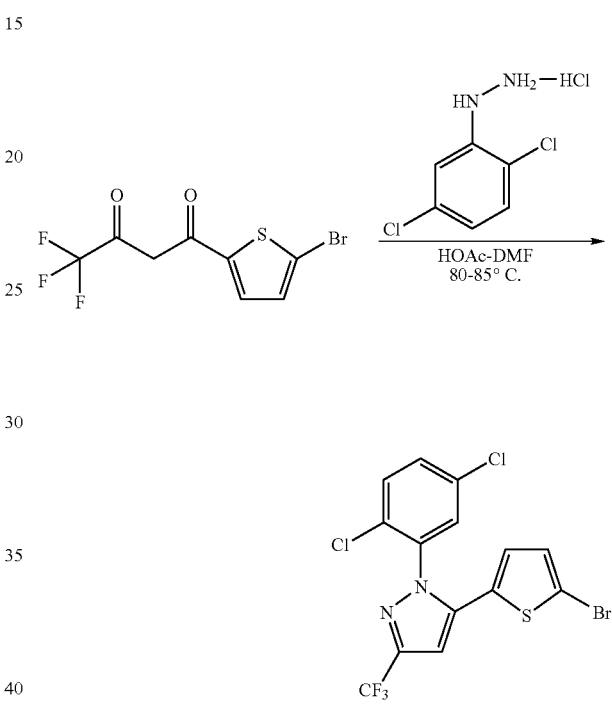

Into a 250 mL flask was weighted 2.01 g (9.41 mmol) of 2,5-dichlorophenylhydrazine hydrochloride (Aldrich), 1.79 g (5.95 mmol) of diketone, and 10 mL of glacial acetic acid. The suspension was stirred and heated at 80-85° C. and 5.0 mL of DMF was added to effect dissolution. The resulting solution was heated at 80-85° C. for 1 h then was cooled and washed into a separatory funnel with 150 mL of ethyl acetate and 250 mL of water. The ethyl acetate was separated, washed with 200 mL of 1 M NaOH, 50 mL of brine, then was dried (Na$_2$SO$_4$), and was concentrated in vacuo. The resulting yellow oil was treated with 200 mL of hexanes and a precipitate formed. The precipitate was removed by filtration and the filtrate was concentrated in vacuo affording the desired product as a faintly yellow solid (2.7 g) which was used in the next transformation without further purification. $^1$H NMR (400 MHz, CDCl$_3$): δ 7.55 (s, 1H), 7.49 (m, 2H), 6.94 (d, J=4 Hz, 1H), 6.81 (s, 1H), 6.69 (d, J=4 Hz, 1H).

The following compounds are prepared essentially according to the previous examples:

1-(2-chlorophenyl)-5-{3-[(phenylmethyl)oxy]phenyl}-3-(trifluoromethyl)-1H-pyrazole; MS(ES): =428.5 [M+H]$^+$;

1-(2-chlorophenyl)-5-{4-[(phenylmethyl)oxy]phenyl}-3-(trifluoromethyl)-1H-pyrazole, MS(ES): 429 [M+H]$^+$.

Example 1c

Preparation of 3-{5-[2-(2,5-Dichloro-phenyl)-5-trifluoromethyl-2H-pyrazol-3-yl]-thiophen-2-yl}-benzenesulfonamide

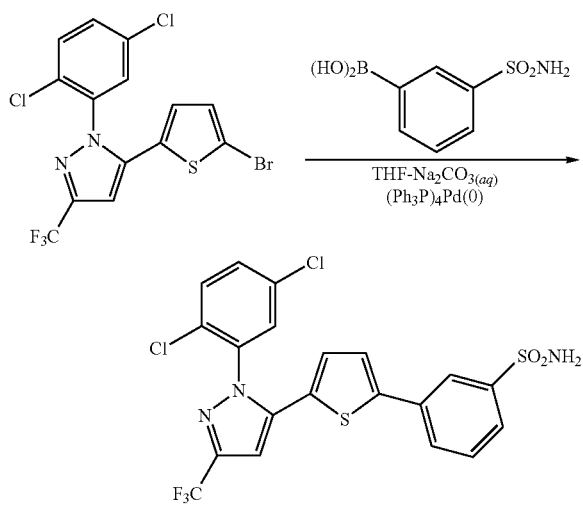

Into a 50 mL flask was weighed 439 mg of bromide (993 μmol), 207.9 mg of boronic acid (1.03 mmol), and 5 mL of THF. The resulting solution was placed in an oil bath and was heated at 80-85° C. As the solution approached reflux c.a. 50 mg of tetrakis(triphenylphosphine)palladium (0) was added followed by 500 L of 1.0 M sodium carbonate. The reaction was maintained at reflux for 2 h then was washed into a separatory funnel with ethyl acetate and 1.0 M sodium carbonate. The ethyl acetate was separated, dried (Na$_2$SO$_4$), and was concentrated in vacuo. The reaction was purified by silica gel flash chromatography (Jones Flashmaster, 50 g SiO$_2$, gradient elution from 100% hexanes to 40% ethyl acetate over 45 minutes). Appropriate fractions were combined and concentrated in vacuo affording the product as a faintly yellow solid, yield: 131 mg (25%). $^1$H NMR (400 MHz, DMSO-d$_6$): δ 8.20 (s, 1H), 7.98 (s, 1H), 7.87 (m, 2H), 7.82 (t, J=8 Hz, 2H), 7.67 (d, J=8 Hz, 1H), 7.64 (d, J=4 Hz, 1H), 7.56 (s, 1H), 7.49 (s, 2H), 7.32 (d, J=4 Hz, 1H).

The following compounds are prepared essentially according to the previous examples:

1-(2,5-dichlorophenyl)-5-(5-{3-[(1-methylethyl)sulfonyl]phenyl}-2-thienyl)-3-(trifluoromethyl)-1H-pyrazole, MS (ES): 547 [M+H]$^+$;

5-{5-[1-(2-chlorophenyl)-3-(trifluoromethyl)-1H-pyrazol-5-yl]-2-thienyl}-3-methyl-2-(methylthio)pyridine, MS (ES): 4662 [M+H]$^+$;

5-{5-[1-(2-chlorophenyl)-3-(trifluoromethyl)-1H-pyrazol-5-yl]-2-thienyl}-2-(ethylthio)-3-methylpyridine; MS (ES): 480.2 [M+H]$^+$;

3-methyl-5-(5-{1-[2-(methyloxy)phenyl]-3-(trifluoromethyl)-1H-pyrazol-5-yl}-3-thienyl)-2-(methylthio)pyridine, MS (ES): 462.3 [M+H]$^+$;

4-(5-{5-[1-(2-chlorophenyl)-3-(trifluoromethyl)-1H-pyrazol-5-yl]-2-thienyl}pyridin-2-yl)morpholine; MS (ES): 491.2, [M+H]$^+$;

1,1-dimethylethyl 4-(5-{5-[1-(2-chlorophenyl)-3-(trifluoromethyl)-1H-pyrazol-5-yl]-2-thienyl}pyridin-2-yl)piperazine-1-carboxylate, MS (ES): 590.2 [M+H]$^+$;

methyl (5-{5-[1-(2-chlorophenyl)-3-(trifluoromethyl)-1H-pyrazol-5-yl]-2-thienyl}pyridin-3-yl)acetate; MS (ES): 478.1 [M+H]$^+$;

methyl (4-{5-[1-(2-chlorophenyl)-3-(trifluoromethyl)-1H-pyrazol-5-yl]-2-thienyl}-3-methylphenyl)acetate; MS (ES): 490.0 [M+H]$^+$;

methyl (3-{5-[1-(2-chlorophenyl)-3-(trifluoromethyl)-1H-pyrazol-5-yl]-2-thienyl}-4-fluorophenyl)acetate; MS (ES): 495.2 [M+H]$^+$;

methyl 2-(5-{5-[1-(2-chlorophenyl)-3-(trifluoromethyl)-1H-pyrazol-5-yl]-2-thienyl}pyridin-3-yl)-2-methylpropanoate; MS (ES): 506.3 [M+H]$^+$;

3-(3-{5-[1-(2-chlorophenyl)-3-(trifluoromethyl)-1H-pyrazol-5-yl]-2-thienyl}phenyl)propanoic acid; MS (ES): 477.0 [M+H]$^+$;

3-(4-{5-[1-(2-chlorophenyl)-3-(trifluoromethyl)-1H-pyrazol-5-yl]-2-thienyl}phenyl)propanoic acid; MS (ES): 477.3 [M+H]$^+$;

4-{5-[1-(2-chlorophenyl)-3-(trifluoromethyl)-1H-pyrazol-5-yl]-2-thienyl}benzoic acid; MS (ES): 449.0 [M+H]$^+$;

3-{5-[1-(2-chlorophenyl)-3-(trifluoromethyl)-1H-pyrazol-5-yl]-2-thienyl}benzoic acid; MS (ES): 449.0 [M+H]$^+$, 471.0 [M+Na]$^+$;

(2E)-3-(4-{5-[1-(2-chlorophenyl)-3-(trifluoromethyl)-1H-pyrazol-5-yl]-2-thienyl}phenyl)prop-2-enoic acid; MS (ES): 474.9 [M+H]$^+$, 497.3 [M+Na]$^+$;

[4-fluoro-3-(5-{3-(trifluoromethyl)-1-[3-(trifluoromethyl)pyridin-2-yl]-1H-pyrazol-5-yl}-2-thienyl)phenyl]acetic acid; MS (ES): 516.3 [M+H]$^+$;

methyl [3-methyl-4-(5-{3-(trifluoromethyl)-1-[3-(trifluoromethyl)pyridin-2-yl]-1H-pyrazol-5-yl}-2-thienyl)phenyl]acetate; MS (ES): 526.5 [M+H]$^+$;

2-(ethylthio)-3-methyl-5-(5-{3-(trifluoromethyl)-1-[2-trifluoromethyl)phenyl]-1H-pyrazol-5-yl}-2-thienyl)pyridine; MS (ES): 514.2 [M+H]$^+$;

5-{5-[1-(2,5-dichlorophenyl)-3-(trifluoromethyl)-1H-pyrazol-5-yl]-2-thienyl}-3-methyl-2-(methylthio)pyridine; MS (ES): 500.4, [M+H]$^+$;

3-methyl-2-(methylthio)-5-(5-{3-(trifluoromethyl)-1-[2-(trifluoromethyl)phenyl]-1H-pyrazol-5-yl}-2-thienyl)pyridine; MS (ES): 500.4 [M+H]$^+$;

5-{5-[1-(2,5-dichlorophenyl)-3-(trifluoromethyl)-1H-pyrazol-5-yl]-3-thienyl}-3-methyl-2-(methylthio)pyridine; MS (ES): 500.3 [M+H]$^+$;

1-(2-chlorophenyl)-5-{5-[3-(ethylsulfonyl)-5-(1-methylethyl)phenyl]-2-thienyl}-3-(trifluoromethyl)-1H-pyrazole, MS (ES): 539.4 [M+H]$^+$;

(3-{5-[1-(2-chlorophenyl)-3-(trifluoromethyl)-1H-pyrazol-5-yl]-2-thienyl}phenyl)acetic acid, MS (ES): 463.3 ([M+H]$^+$ for $^{35}$Cl);

(4-{5-[1-(2-chlorophenyl)-3-(trifluoromethyl)-1H-pyrazol-5-yl]-2-thienyl}phenyl)acetic acid, MS (ES): 463.2 ([M+H]$^+$ for $^{35}$Cl);

2-(3-{5-[1-(2-chlorophenyl)-3-(trifluoromethyl)-1H-pyrazol-5-yl]-2-thienyl}phenyl)-2-methylpropanoic acid, = MS (ES): 491.1 ([M+H]$^+$ for $^{35}$Cl);

1-(3-{5-[1-(2-chlorophenyl)-3-(trifluoromethyl)-1H-pyrazol-5-yl]-2-thienyl}phenyl)cyclobutanecarboxylic acid MS (ES): 503.3 [M+H]$^+$;

2-(3-{5-[1-(2-chlorophenyl)-3-(trifluoromethyl)-1H-pyrazol-5-yl]-2-thienyl}phenyl)-2-ethylbutanoic acid, MS (ES): 519.2 [M+H]$^+$;

2-(4-{5-[1-(2-chlorophenyl)-3-(trifluoromethyl)-1H-pyrazol-5-yl]-2-thienyl}phenyl)-2-methylpropanoic acid, MS (ES): 491.4 [M+H]+;

1-(2,5-dichlorophenyl)-5-(5-{3-[(1-methylethyl)sulfonyl]phenyl}-2-thienyl)-3-(rifluoromethyl)-1H-pyrazole, MS (ES): 547 [M+H]+;

2-[5-{5-[3-(methylsulfonyl)phenyl]-2-thienyl}-3-(trifluoromethyl)-1H-pyrazol-1-yl]-3-(trifluoromethyl)pyridine MS (ES): 518.3 [M+H]+.

1-[5-chloro-2-(methyloxy)phenyl]-5-{5-[3-(methylsulfonyl)phenyl]-2-thienyl}-3-(trifluoromethyl)-1H-pyrazole; $^1$H-NMR (CDCl$_3$): δ 8.07 (1H, m), 7.85 (1H, m), 7.75 (1H, m), 7.58 (1H, t), 7.50-7.45 (2H, m), 7.25 (1H, d), 6.94 (1H, d), 6.88 (1H, d), 6.85 (1H, s), 3.65 (3H, s), 3.09 (3H, s). MS (ES): 513 [M+H]+.

1-[5-chloro-2-(phenyloxy)phenyl]-5-{5-[3-(methylsulfonyl)phenyl]-2-thienyl}-3-(trifluoromethyl)-1H-pyrazole; $^1$H-NMR (CDCl$_3$): δ 8.09 (1H, m), 7.88 (1H, m), 7.77 (1H, m), 7.66 (1H, d), 7.60 (1-H, t), 7.39 (1H, dd), 7.29 (1H, d), 7.24-7.15 (2H, m), 7.07 (1H, t), 6.93 (1H, d), 6.82 (1H, d), 6.79 (1H, s), 6.70-6.64 (2H, m), 3.10 (3H, s). MS (ES): 575 [M+H]+.

1-(2-chloro-5-fluorophenyl)-5-{5-[3-(methylsulfonyl)phenyl]-2-thienyl}-3-(trifluoromethyl)-1H-pyrazole; $^1$H-NMR (CDCl$_3$): δ 8.07 (1H, m), 7.86 (1H, m), 7.75 (1H, m), 7.63-7.49 (21-, m), 7.33 (1H, m), 7.31-7.23 (2H, m), 6.91-6.85 (2H, m), 3.08 (3H, s). MS (ES): 501 [M+H]+.

1-(5-chloro-2-fluorophenyl)-5-{5-[3-(methylsulfonyl)phenyl]-2-thienyl}-3-(trifluoromethyl)-1H-pyrazole; $^1$H-NMR (CDCl$_3$): δ 8.09 (1H, m), 7.87 (1H, m), 7.77 (1H, m), 7.64-7.56 (2H, m), 7.50 (1H, m), 7.28 (1H, d), 7.17 (1H, t), 6.92 (1H, d), 6.88 (1H, s), 3.09 (3H, s). MS (ES): 501 [M+H]+.

1-[2-chloro-5-(methyloxy)phenyl]-5-{5-[3-(methylsulfonyl)phenyl]-2-thienyl}-3-(trifluoromethyl)-1H-pyrazole; $^1$H-NMR (CDCl$_3$): δ 8.06 (1H, m), 7.85 (1H, m), 7.75 (1H, m), 7.58 (1H, t), 7.43 (1H, m), 7.25 (1H, d), 7.14-7.02 (2H, m), 6.89 (1H, s), 6.87 (1H, d), 3.85 (3H, s), 3.08 (3H, s). MS (ES): 513 [M+H]+.

1-[2-chloro-5-(rifluoromethyl)phenyl]-5-{5-[3-(methylsulfonyl)phenyl]-2-thienyl}-3-(trifluoromethyl)-1H-pyrazole; $^1$H-NMR (CDCl$_3$): δ 8.06 (1H, m), 7.90-7.83 (2H, m), 7.79 (1H, m), 7.76-7.67 (2H, m), 7.59 (1H, t), 7.25 (1H, m), 6.92 (1H, m), 6.84 (1H, d), 3.08 (3H, s); MS (ES): 551 and 553 [each M+H]+.

4-chloro-3-[5-{5-[3-(methylsulfonyl)phenyl]-2-thienyl}-3-(trifluoromethyl)-1H-pyrazol-1-yl]phenol; $^1$H-NMR (CDCl$_3$): δ 8.04 (1H, m), 7.84 (1H, d), 7.74 (11, d), 7.57 (1H, t), 7.30 (1H, d), 7.24 (1H, d), 6.99 (1H, m), 6.93 (1H, m), 6.91-6.87 (2H, m), 3.09 (3H, s). MS(ES): 499 [M+H]+.

4-chloro-3-[5-{5-[3-(methylsulfonyl)phenyl]-2-thienyl}-3-(trifluoromethyl)-1H-pyrazol-1-yl]benzamide; $^1$H-NMR (DMSO-d$_6$): δ 8.29 (1H, d), 8.25-8.15 (2H, m), 8.04 (1H, d), 7.96-7.79 (3H, m), 7.75-7.64 (3H, m), 7.56 (1H, m), 7.28 (1H, m), 3.28 (3H, s). MS (ES): 526 [M+H]+.

3-{5-[1-(2-chlorophenyl)-3-(trifluromethyl)-1H-pyrazol-5-yl]-3-thienyl}benzenesulfonamide; 1H-NMR (DMSO-d$_6$): δ 8.07 (1H, m), 8.01-7.96 (2H, m), 7.90-7.70 (5H, m), 7.67-7.57 (3H, m), 739 (2H, s). MS (ES): 484 [M+H]+.

4-{5-[1-(2-chlorophenyl)-3-(trifluoromethyl)-1H-pyrazol-5-yl]-3-thienyl}benzenesulfonamide; $^1$H-NMR (CDCl$_3$): δ 7.96-7.88 (2H, m), 7.61-7.52 (5H, m), 7.51-7.44 (2H, m), 7.18 (1H, d), 6.94 (1H, s), 4.89 (2H, s). MS (ES): 484 [M+H]+.

3-{5-[1-(2-chlorophenyl)-3-(trifluoromethyl)-1H-pyrazol-5-yl]-2-thienyl}benzenesulfonamide; $^1$H-NMR (DMSO-d$_6$): δ 7.89 (1H, m), 7.85 (1H, m), 7.81-7.69 (4H, m), 7.68-7.55 (3H, m), 7.51 (1H, s), 7.45 (2H, s), 7.28 (1H, d). MS (ES): 484 [M+H]+.

4-{5-[1-(2-chlorophenyl)-3-(trifluoromethyl)-1H-pyrazol-5-yl]-2-thienyl}benzenesulfonamide; $^1$H-NMR (DMSO-d$_6$): δ 7.87-7.60 (9H, m), 7.51 (1H, s), 7.43-7.37 (2H, s), 7.28 (1H, d), MS (ES): 484 [M+H]+.

3-{5-[1-(2-chloro-5-hydroxyphenyl)-3-(trifluoromethyl)-1H-pyrazol-5-yl]-2-thienyl}benzenesulfonamide; $^1$H-NMR (DMSO-d$_6$): δ 10.02 (1H, s), 7.94 (1H, s), 7.78 (2H, m), 7.58-7.65 (1H, m), 7.54 (1H, d), 7.47 (2H, s), 7.36 (1H, t), 7.21-7.25 (1H, m), 7.13-7.09 (2H, m), 6.96 (1H, m), MS (ES): 500 [M+H]+.

4-chloro-2-[5-{5-[3-(methylsulfonyl)phenyl]-2-thienyl}-3-(trifluoromethyl)-1H-pyrazol-1-yl]phenol; MS (ES): 499 [M+H]+.

3-(5-{3-(trifluoromethyl)-1-[3-(trifluoromethyl)pyridin-2-yl]-1H-pyrazol-5-yl}-2-thienyl)benzenesulfonamide; MS (ES): 519 [M+H]+.

3-(5-({3-(trifluoromethyl)-1-[2-(trifluoromethyl)phenyl]-1H-pyrazol-5-yl}-2-thienyl)benzenesulfonamide; MS (ES): 518 [M+H]+.

2-[5-{5-[3-(methylsulfonyl)phenyl]-2-thienyl}-3-(trifluoromethyl)-1H-pyrazol-1-yl]benzenesulfonamide; MS (ES): 528 [M+H]+.

3-(5-{1-[5-chloro-2-(phenyloxy)phenyl]-3-(trifluoromethyl)-1H-pyrazol-5-yl}-2-thienyl)benzenesulfonamide; MS (ES): 576 [M+H]+.

5-{5-[3-(Methylsulfonyl)phenyl]-2-thienyl}-1-[2-(phenyloxy)phenyl]-3-(trifluoromethyl)-1H-pyrazole; MS (ES): 541 [M+H]+.

2-Chlor-6-methyl-3-[5-{5-[3-(methylsulfonyl)phenyl]-2-thienyl}-3-(trifluoromethyl)-1H-pyrazol-1-yl]phenol; MS (ES): 513 [M+H]+.

N-(3-{5-[1-(2,5-dichlorophenyl)-3-(trifluoromethyl)-1H-pyrazol-5-yl]-2-thienyl}phenyl)methanesulfonamide; MS (ES): 534 [M+H]+.

1-(2-chlorophenyl)-5-[3'-(methylsulfonyl)biphenyl-3-yl]-3-(triflurmethyl)-1H-pyrazole, MS(ES): 477.0 [M+H]+;

1-(2-chlorophenyl)-5-[3'-(methylsulfonyl)biphenyl-4-yl]-3-(trifluoromethyl)-1H-pyrazole, MS(ES): 477 [M+H]+.

2-{5-[3'-(methylsulfonyl)biphenyl-4-yl]-3-(trifluoromethyl)-1H-pyrazol-1-yl}-3-(trifluoromethyl)pyridine, MS(ES): 512 [M+H]+.

4'-[1-(2-chlorophenyl)-3-(trifluoromethyl)-1H-pyrazol-5-yl]biphenyl-3-sulfonamide, MS(ES): 478 [M+H]+

1-(2-chlorophenyl)-5-{3'-[(1-methylethyl)sulfonyl]biphenyl-4-yl}-3-(trifluoromethyl)-1H-pyrazole, MS(ES): 505 [M+H]+.

5-{3'-[(1-methylethyl)sulfonyl]biphenyl-4-yl}-3-(trifluoromethyl)-1-[2-(trifluoromethyl)phenyl]-1H-pyrazole, MS(ES): 539 [M+H]+.

1-(2,6-dichlorophenyl)-5-(5-[3-(methylsulfonyl)phenyl]-2-thienyl)-3-(trifluoromethyl)-1H pyrazole, MS(ES): 517 [M+H]+

2-methyl-2-(3-(5-(3-(trifluoromethyl)-1-(3-(trifluoromethyl)pyridin-2-yl)-1H-pyrazol-5-yl)thiophen-2-yl)phenyl)propanoic acid. MS (ES): 526 [M+H]+.

methyl 3-(5-(5-(3-(methylsulfonyl)phenyl)thiophen-2-yl)-3-(trifluoromethyl)-1H-pyrazol-1-yl)benzoate. MS (ES): 507 [M+H]+.

2-(3-(5-(5-(3-(methylsulfonyl)phenyl)thiophen-2-yl)-3-(trifluoromethyl)-1H-pyrazol-1-yl)phenyl)propan-2-ol. MS (ES): 507 [M+H]+.

2-(5-(5-(3-(methylsulfonyl)phenyl)thiophen-2-yl)-3-(trifluoromethyl)-1H-pyrazol-1-yl)ethanol. MS (ES): 417 [M+H]+.

3-chloro-2-[5-{5-[3-(methylsulfonyl)phenyl]-2-thienyl}-3-(trifluoromethyl)-1H-pyrazol-1-yl]pyridine: $^1$H-NMR (DMSO-d$_6$): δ 8.73 (1H, dd), 8.39 (1H, dd), 8.03 (1H, m), 7.90-7.83 (3H, m), 7.72-7.65 (2H, m), 7.55 (1H, s), 7.26 (1H, d), 3.27 (3H, s). MS (ES): 484 [M+H]$^+$.

1-(2-chlorophenyl)-5-{5-[3-(methylsulfonyl)phenyl]-2-thienyl}-3-(trifluoromethyl)-1H-pyrazole; MS (ES): 483 [M+H]$^+$;

2-{5-[5-(3-Methanesulfonyl-phenyl)-thiophen-2-yl]-3-trifluoromethyl-pyrazol-1-yl}-3-trifluoromethyl-pyridine; MS (ES): 518 [M+H]$^+$;

5-{5-[3-(methylsulfonyl)phenyl]-2-thienyl}-3-(trifluoromethyl)-1-[2-(trifluoromethyl)phenyl]-1H-pyrazole; MS (ES): 517 [M+H]$^+$;

1-(2-methylphenyl)-5-{5-[3-(methylsulfonyl)phenyl]-2-thienyl}-3-(trifluoromethyl)-1H-pyrazole; MS (ES): 463 [M+H]$^+$;

1-[2-(methyloxy)phenyl]-5-{5-[3-(methylsulfonyl)phenyl]-2-thienyl}-3-(trifluoromethyl)-1H-pyrazole; MS (ES): 479 [M+H]$^+$;

1-(2-fluorophenyl)-5-{5-[3-(methylsulfonyl)phenyl]-2-thienyl}-3-(trifluoromethyl)-1H-pyrazole; MS(ES): 467 [M+H]$^+$;

1-(2-ethylphenyl)-5-{4-[3-(methylsulfonyl)phenyl]-2-thienyl}-3-(trifluoromethyl)-1H-pyrazole, MS (ES) 477.3 [M+H]$^+$ 1-(2-chlorophenyl)-5-{4-[3-(methylsulfonyl)phenyl]-2-thienyl}-3-(trifluoromethyl)-1H-pyrazole, MS (ES) 483.2, 485.2 [M+H]$^+$ 1-(2-chlorophenyl)-3-(trifluoromethyl)-5-{4-[3-(trifluoromethyl)phenyl]-2-thienyl}-1H-pyrazole, MS (ES) 472.3, 474.3 [M+H]$^+$.

Example 2

1-(2,5-Dichloro-phenyl)-5-[5-(3-methanesulfonyl-phenyl)-thiophen-2-yl]-3-trifluoromethyl-1H-pyrazole Example 2a Preparation of 1-[5-(3-Methanesulfonyl-phenyl)-thiophen-2-yl]-ethanone

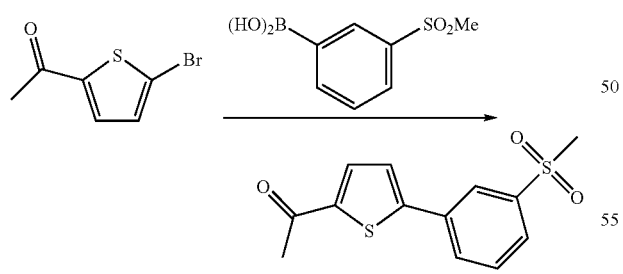

Into a 500 mL flask was weighed 5.04 g of 2-acetyl-5-bromothiophene (24.6 mmol), 6.14 g (30.7 mmol) of boronic acid, 604 mg (523 μmol) of tetrakis(triphenylphosphine)palladium (0), 300 mL of THF, and 30 mL of 1.0 M Na$_2$CO$_3$. The resulting solution was heated at 80-85° C. overnight during which time much of the THF evaporated. The residue was washed into a separatory funnel with ethyl acetate and 1.0 M Na$_2$CO$_3$. The ethyl acetate was separated and filtered of the insoluble product. The solids were washed with ethyl acetate and the filtrate was combined with the ethyl acetate extracts, was dried (MgSO$_4$), and concentrated in vacuo. The residue was then crystallized from ethyl acetate affording the product as a faintly yellow powder, yield: 1.14 g (16.5%). The product filtered from the extraction was recovered as a colorless powder, yield: 430 g (62.4%). $^1$H NMR (400 MHz, CDCl$_3$): δ 8.21 (s, 1H), 7.92 (t, J=7 Hz, 2H), 7.70 (d, J=4.0 Hz, 1H), 7.65 (t, J=7 Hz, 1H), 7.44 (d, J=4 Hz, 1H), 3.10 (s, 3H), 2.59 (s, 3H).

Example 2b

Preparation of 4,4,4-Trifluoro-1-[5-(3-methanesulfonyl-phenyl)-thiophen-2-yl]-butane-1,3-dione

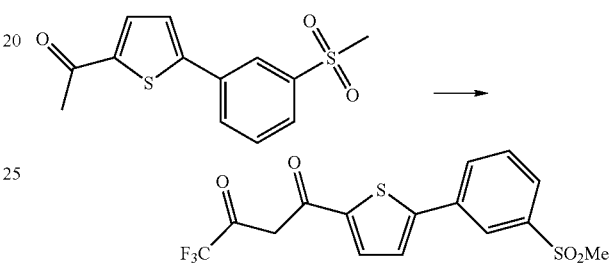

Into a 250 mL flask was weighed 5.42 g (19.3 mmol) of 1-(5-(3-(methylsulfonyl)phenyl)thiophen-2-yl)ethanone and 42 mL of THF. The resulting suspension was stirred and cooled to 0-3° C. in an ice bath and 23 mL of a lithium bis(trimethylsilyl)amide solution (1.0 M in THF) was added. The resulting thick yellow suspension was stirred and allowed to warm to room temperature then ethyl trifluoroacetate (3.46 mL, 29 mmol) was added. After stirring at room temperature overnight the reaction was concentrated in vacuo to remove THF. The residue was washed into a separatory funnel with ethyl acetate and 1 M HCl. The ethyl acetate was separated, washed with brine, dried (MgSO$_4$), and concentrated in vacuo. The resulting amorphous yellow powder was pure enough for further synthetic transformations, yield: 72 g (99%). $^1$H NMR (400 MHz, DMSO-d$_6$): δ 8.20 (d, J=7 Hz, 1H), 8.08 (t, J=7 Hz, 1H), 7.95 (d, J=4.0 Hz, 1H), 7.89 (d, J=7 Hz, 1H), 7.78 (d, J=4 Hz, 1H), 7.69 (t, J=7 Hz, 1H), 6.22 (broad s, 1H), 3.26 (s, 3H).

Example 2c

Preparation of 1-(2,5-Dichloro-phenyl)-5-[5-(3-methanesulfonyl-phenyl)-thiophen-2-yl]-3-trifluoromethyl-1H-pyrazole

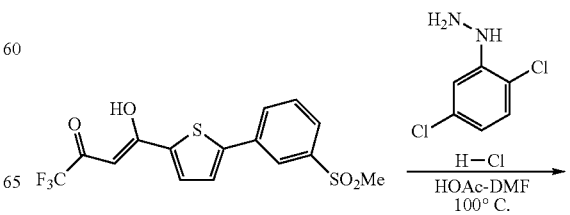

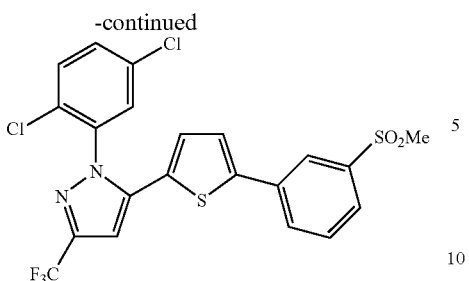

Into an 8 mL vial was weighed 202.7 mg (539 µmol) of (Z)-1,1,1-trifluoro-4-hydroxy-4-(5-(3-(methylsulfonyl)phenyl)thiophen-2-yl)but-3-en-2-one, 117.4 mg (550 µmol) of 2,5-dichlorophenylhydrazine hydrochloride, 3 mL of acetic acid, and 1 mL of DMF. The resulting reaction was stirred at 100-105° C. for 3 h then was concentrated to dryness in vacuo. The residue was purified by silica gel flash chromatography (3×23 cm, 1:1 ethyl acetate-hexanes) and was dried affording the product as a faintly yellow solid, yield: 89 mg (55%). $^1$H NMR (400 MHz, CDCl$_3$): δ 8.08 (s, 1H), 7.87 (d, J=9 Hz, 1H), 7.75 (d, J=9 Hz, 1H), 7.6 (m, 2H), 7.5 (m, 2H), 7.27 (d, J=4 Hz, 1H), 6.90 (s, 1H), 6.87 (d, J=4 Hz, 1H), 3.09 (s, 3H).

The following compounds are prepared essentially according to the previous examples:

1-(2,5-dimethylphenyl)-5-{5-[3-(methylsulfonyl)phenyl]-2-thienyl}-3-(trifluoromethyl)-1H-pyrazole; $^1$H-NMR (DMSO-d$_6$): δ 8.02 (1H, m), 7.90-7.79 (2H, m), 7.73-7.61 (2H, m), 7.47 (1H, s), 7.44-7.32 (3H, m), 7.23 (1H, d), 3.27 (3H, s) 2.36 (3H, s), 1.89 (3H, s). MS (ES): 477 [M+H]$^+$.

5-{5-[3-(methylsulfonyl)phenyl]-2-thienyl}-1-(phenylmethyl)-3-(trifluoromethyl)-1H-pyrazole; $^1$H-NMR (CDCl$_3$): δ 8.13 (1H, m), 7.93-7.77 (2H, m), 7.62 (1H, t), 7.38-7.28 (4H, m), 7.13-7.06 (2H, m), 7.01 (1H, d), 6.73 (1H, s), 5.54 (2H, s), 3.10 (3H, s). MS (ES): 463 [M+H]$^+$.

1-(2,6-dichlorophenyl)-5-{5-[3-(methylsulfonyl)phenyl]-2-thienyl}-3-(trifluoromethyl)-1H-pyrazole, MS(ES): 517 [M+H]$^+$.

Pyrazole Ib

A general synthesis of pyrazole Ib (0037) is depicted in Scheme 3. First, an aryl-oxirane (0031) can be reacted with a bromoaryl-magnesium bromide (0032) to yield an alcohol intermediate (0033), which can be oxidized under standard conditions to give the corresponding ketone (0034). Oxiranes 0031 can be prepared readily from epoxidation of styrenes or treatment of aryl-carboxaldehydes with trimethylsulfonium iodide under basic conditions. Intermediate 0034 can be condensed with N,N-dimethyl-formamide dimethyl acetal (DMFDMA) and then a hydrazine, for example, an alkylhydrazine, R$^2$NHNH$_2$, to provide a mixture of two pyrazole isomers, 0035 and 0036. Resolution of the two pyrazole isomers should be possible via typical chromatography methods. Next, pyrazole 0035 can undergo Suzuki cross-coupling with a boronic acid, R$^4$B(OH)$_2$, to afford the desired product (0037).

Scheme 3

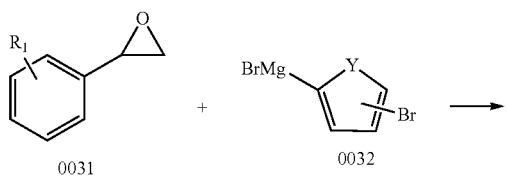

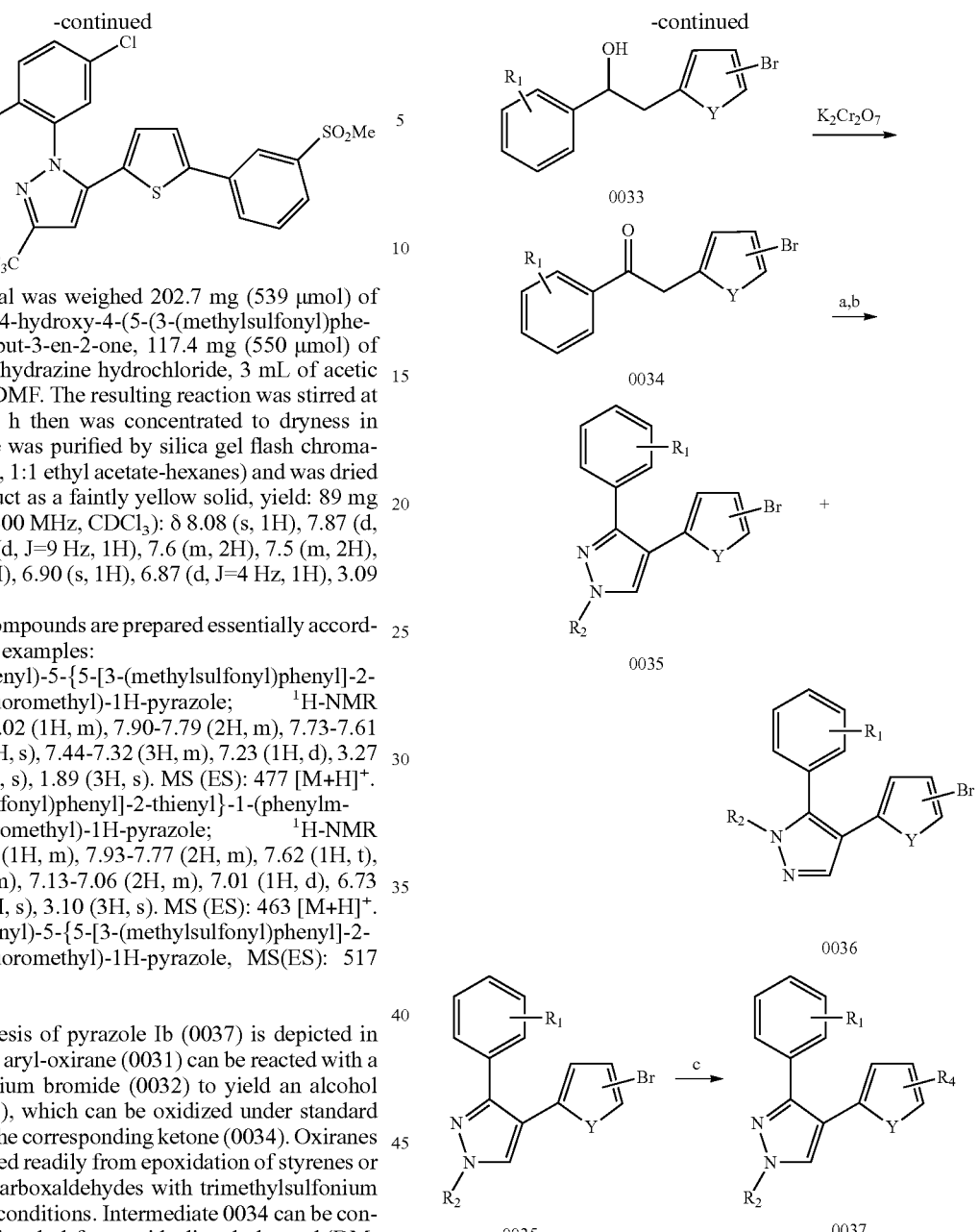

Reactions and conditions: (a) DMFDMA, reflux; (b) R$^2$NHNH$_2$, EtOH, reflux; (c) R$^4$B(OH)$_2$, K$_2$CO$_3$, 10 mol % PdCl$_2$(dppf), H$_2$O, dioxane, 80° C.

Pyrazole Ic

A general synthesis of pyrazole Ic (00414) is shown in Scheme 4. First, an acetyl-bromoarene (0048), for example, where Y is S, O or CH$_2$=CH$_2$, can be condensed with DMFDMA followed by hydrazine, for example an alkylhydrazine, R$^2$NHNH$_2$, to afford a mixture of two pyrazole isomers, 00410 and 00411. Resolution of the two pyrazole isomers should be possible via typical chromatography methods. Suzuki cross-coupling of 00410 with a boronic acid, R$^4$B(OH)$_2$, under standard conditions can provide intermediate 00412. Pyrazole 00412 can be brominated, such as with NBS, and then cross-coupled with an arylboronic acid, R$^4$B(OH)$_2$, to yield the desired product (00414).

Scheme 4

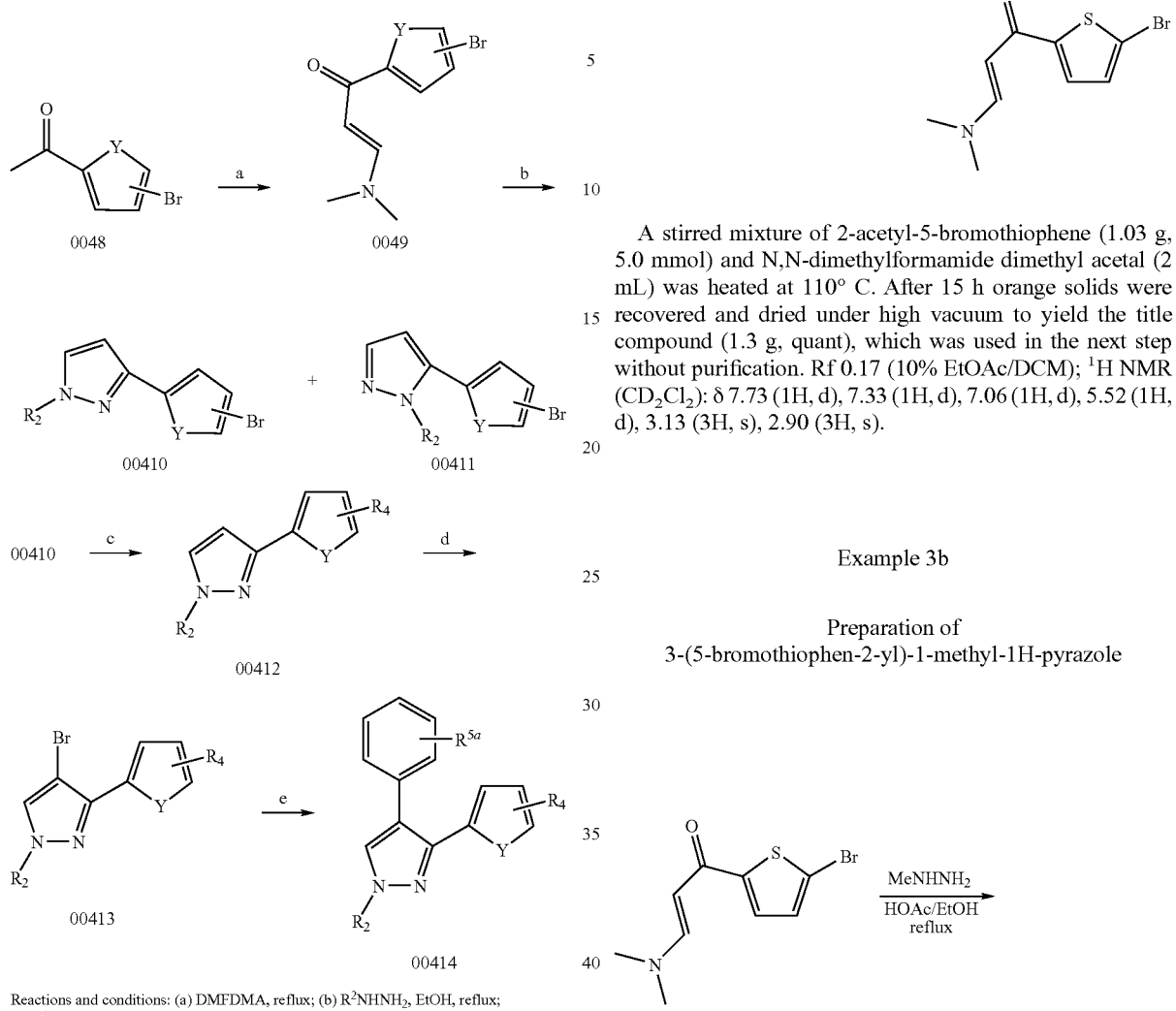

Reactions and conditions: (a) DMFDMA, reflux; (b) R²NHNH₂, EtOH, reflux; (c) R⁴B(OH)₂, K₂CO₃, 10 mol % PdCl₂(dppf), H₂O, dioxane, 80° C.; (d) NBS, THF; (e) R⁵ᵃPhB(OH)₂, K₂CO₃, 10 mol % PdCl₂(dppf), H₂O, dioxane, 80° C.

Example 3

4-(2-chlorophenyl)-3-[5-(3-methanesulfonyl-phenyl)-thiophen-2-yl]-1-methyl-1H-pyrazole

Example 3a

Preparation of 1-(5-bromothiophen-2-yl)-3-dimethylaminopropenone

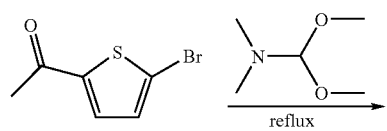

A stirred mixture of 2-acetyl-5-bromothiophene (1.03 g, 5.0 mmol) and N,N-dimethylformamide dimethyl acetal (2 mL) was heated at 110° C. After 15 h orange solids were recovered and dried under high vacuum to yield the title compound (1.3 g, quant), which was used in the next step without purification. Rf 0.17 (10% EtOAc/DCM); ¹H NMR (CD₂Cl₂): δ 7.73 (1H, d), 7.33 (1H, d), 7.06 (1H, d), 5.52 (1H, d), 3.13 (3H, s), 2.90 (3H, s).

Example 3b

Preparation of 3-(5-bromothiophen-2-yl)-1-methyl-1H-pyrazole

To a stirred solution of 1-(5-bromothiophen-2-yl)-3-dimethylaminopropenone (0.70 g, 2.7 mmol) in EtOH (15 mL) was added methylhydrazine (0.16 mL, 3.0 mmol) and then acetic acid (0.45 mL, 8.0 mmol). The resulting mixture was heated at reflux for 2 h, allowed to cool to ambient temperature and then concentrated under reduced pressure. The residue was diluted with DCM (50 mL), washed with H₂O and brine, then dried (Na₂SO₄), concentrated and purified by chromatography (silica, DCM) to yield the title compound 10a (0.21 g) as a white solid and regioisomer, 5-(5-bromothiophen-2-yl)-1-methyl-1H-pyrazole, 11a (035 g) as a pale yellow solid. 10a: Rf 0.42 (DCM); ¹H-NMR (CD₂Cl₂): δ 7.36 (1H, d), 7.01 (2H, m), 6.41 (1H, d), 3.87 (3H, s); 11a: Rf 0.19 (DCM); ¹H-NMR (CD₂Cl₂): δ 7.42 (1H, d), 7.10 (1H, d), 6.94 (1H, m), 6.36 (1H, d), 3.92 (3H, s).

Example 3c

Preparation of 3-[5-(3-methanesulfonyl-phenyl)-thiophen-2-yl]-1-methyl-1H-pyrazole

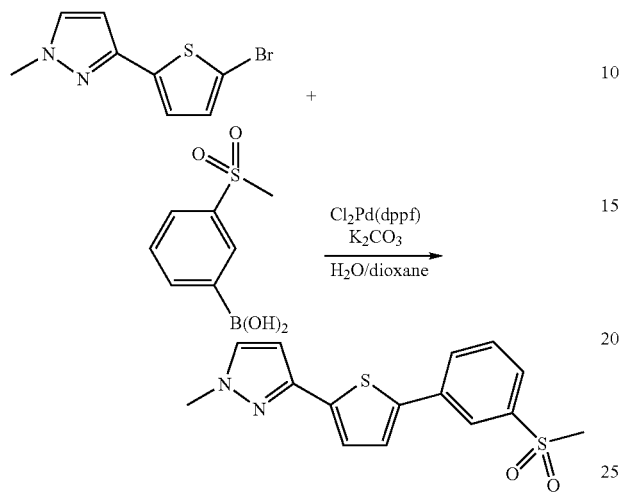

A stirred mixture of 3-(5-bromothiophen-2-yl)-1-methyl-1H-pyrazole (0.20 g, 0.83 mmol), 3-methanesulfonyl-phenylboronic acid (0.20 g, 1.0 mmol), $K_2CO_3$ (345 mg, 2.5 mmol), $Cl_2Pd(dppf) \cdot DCM$ (82 mg, 10 mol %) and $H_2O$ (0.6 mL) in dioxane (6 mL) was sparged with Argon for 5 min and then heated at 85° C. as a sealed flask. After 6 h the reaction mixture was allowed to cool to ambient temperature, filtered (Celite™) and the filter agent rinsed with EtOAc. The combined filtrates were concentrated under reduced pressure and purified by chromatography (silica, EtOAc/DCM, 2:98 to 5:95) to give the title compound (0.11 g, 42%) as a white solid. $^1$H-NMR ($CD_2Cl_2$): δ 8.15 (1H, m), 7.89 (1H, m), 7.80 (1H, m), 7.60 (1H, m), 7.40 (2H, m), 7.29 (1H, d), 6.50 (1H, d), 3.91 (3H, s), 3.07 (3H, s).

Example 3d

Preparation of 4-bromo-3-[5-(3-methanesulfonyl-phenyl)-thiophen-2-yl]-1-methyl-1H-pyrazole

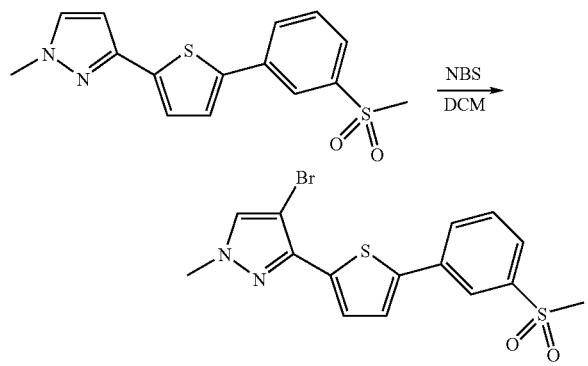

To a stirred solution of 3-[5-(3-methanesulfonyl-phenyl)-thiophen-2-yl]-1-methyl-1H-pyrazole (0.10 g, 0.31 mmol) in DCM (3 mL, anhyd) was added N-bromosuccinimide (NBS) (56 mg, 0.31 mmol). After 22 h additional NBS (56 mg) was added and stirring was continued at ambient temperature. After 46 h (total) the reaction mixture was concentrated under reduced pressure and purified by chromatography (silica, EtOAc/Hex, 20:80 to 40:60) to give the title compound (98 mg, 79%) as a white solid. $^1$H-NMR ($CD_2Cl_2$): δ 8.17 (1H, m), 7.91 (1H, m), 7.82 (1H, m), 7.72 (1H, d), 7.61 (1H, m), 7.50 (1H, s), 7.44 (1H, d), 3.91 (3H, s), 3.08 (3H, s).

Example 3e

Preparation of 4-(2-chlorophenyl)-3-[5-(3-methanesulfonyl-phenyl)-thiophen-2-yl]-1-methyl-1H-pyrazole

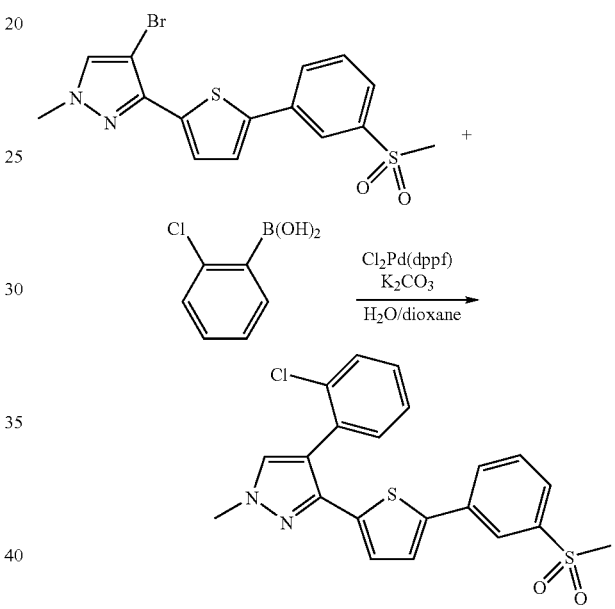

A mixture of 4-bromo-3-[5-(3-methanesulfonyl-phenyl)-thiophen-2-yl]-1-methyl-1H-pyrazole (88 mg, 022 mmol), 2-chlorophenylboronic acid (41 mg, 0.26 mmol), $K_2CO_3$ (91 mg, 0.66 mmol), $Cl_2Pd(dppf) \cdot DCM$ (18 mg, 10 mol %) and $H_2O$ (0.25 mL) in dioxane (2.5 mL) was sparged with Argon for 5 min and then heated at 80° C. as a sealed flask. After 4 h the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 30:70 to 40:60) to give the title compound (64 mg, 67%). Rf 0.14 (40% EtOAc/Hex); $^1$H NMR ($CD_2Cl_2$): δ 8.09 (1H, m), 7.85-7.76 m), 7.60-7.49 (2H, m), 7.45 (1H, s), 7.41-7.30 (3H, m), 7.21 (1H, d), 6.70 (1H, d), 3.97 (3H, s), 3.05 (3H, s); MS (ES): 429 [M+H]$^+$.

The following compounds were prepared from appropriate reagents in a similar manner:

4-(2-Chlorophenyl)-5-[5-(3-methanesulfonyl-phenyl)-thiophen-2-yl]-1-methyl-1H-pyrazole: $^1$H-NMR (DMSO-$d_6$): δ 8.05 (1H, m), 7.93 (1H, d), 7.85 (1H, d), 7.75-7.63 (3H, m), 7.50 (1H, m), 7.38-7.26 (4H, m), 3.97 (3H, s), 3.27 (3H, s); MS (ES): 429 [M+H]$^+$.

4-(2-Chlorophenyl)-3-[5-(3-methanesulfonyl-phenyl)-thiophen-2-yl]-1-(2,2,2-trifluoro-ethyl)-1H-pyrazole:
$^1$H-NMR (CD$_2$Cl$_2$): δ 8.10 (1H, m), 7.87-7.76 (2H, m), 7.64-7.50 (3H, m), 7.45-7.31 (3H, m), 7.23 (1H, d), 6.75 (1H, d), 4.86-4.76 (2H, m), 3.05 (3H, s); MS (ES): 497 [M+H]$^+$.

4-(2-Chlorophenyl)-5-[5-(3-methanesulfonyl-phenyl)-thiophen-2-yl]-1-(2,2,2-trifluoro-ethyl)-1H-pyrazole:
$^1$H-NMR (CD$_2$Cl$_2$): δ 8.08 (1H, m), 7.87-7.78 (3H, m), 7.60 (1H, m), 7.46-7.39 (2H, m), 7.29-7.17 (3H, m), 7.09 (1H, d), 4.89-4.80 (2H, m), 3.06 (3H, s); MS (ES): 497 [M+H]$^+$.

Pyrazole Id

Scheme 5

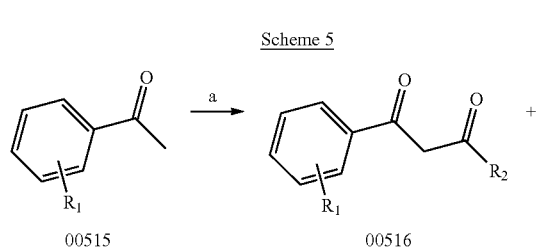

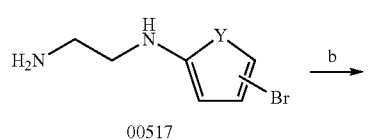

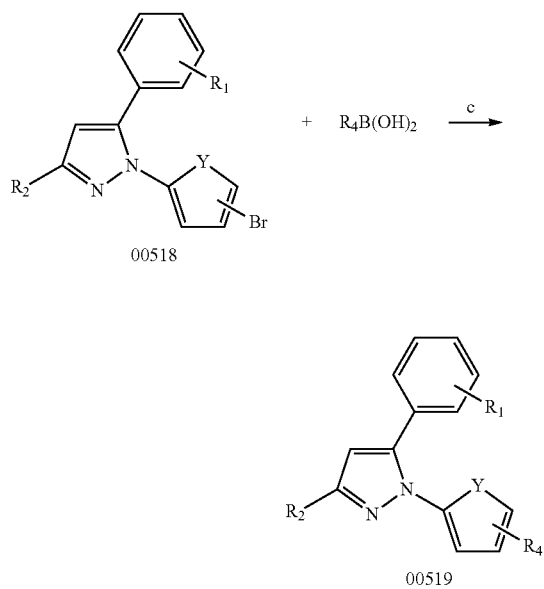

Reaction and conditions: (a) LiHMDS, THF; R$^2$CO$_2$Et, -78 to 20° C.; (b) HOAc, EtOH, reflux; (c) K$_2$CO$_3$, 10 mol % PdCl$_2$(dppf), H$_2$O, dioxane, 80° C.

A general synthesis of pyrazole Id (00519) is shown in Scheme 5. First, an acetyl-arene (00515) can be treated with an ester, R$^2$CO$_2$Et, under Claisen conditions to yield the corresponding 1,3-diketone (00516). Diketone 00516 can be condensed with an arylhydrazine (00517), for example, where Y is S, O or CH$_2$=CH$_2$, to afford the corresponding 1-aryl-pyrazole (00518). Intermediate 00518 then can undergo Suzuki cross-coupling with a boronic acid, R$^4$B(OH)$_2$, to give the desired product (00519).

For example, 2'-trifluoromethyl-acetophenone 00515a (R$^2$=2-CF$_3$) was condensed with ethyl trifluoroacetate to yield diketone 00516a (R$^2$=2-CF$_3$; R$^1$=2-CF$_3$). Intermediate 00516a was condensed with 4-bromo-phenylhydrazine hydrochloride 00517a (Y=CH$_2$=CH$_2$) to provide pyrazole 00518a (R$^2$=CF$_3$; R$^1$=2-CF$_3$; Y=CH$_2$=CH$_2$), which underwent cross-coupling with 3-methanesulfonyl-phenyl-boronic acid to afford pyrazole 00519a (R$^2$=CF$_3$; R$^1$=2-CF$_3$; R$^4$=3-MeSO$_2$Ph; Y=CH$_2$=CH$_2$).

00519a

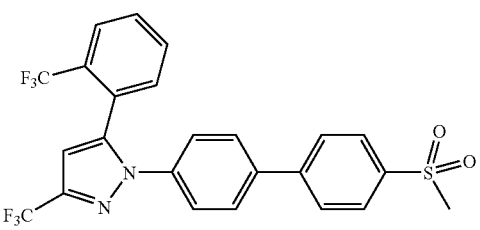

Example 4

1-(3'-methanesulfonyl-biphenyl-4-yl)-3-trifluoromethyl-5-(2-trifluoromethyl-phenyl)-1H-pyrazole Example 4a Preparation of 4,4,4-trifluoro-1-(2-trifluoromethyl-phenyl)-butane-1,3-dione

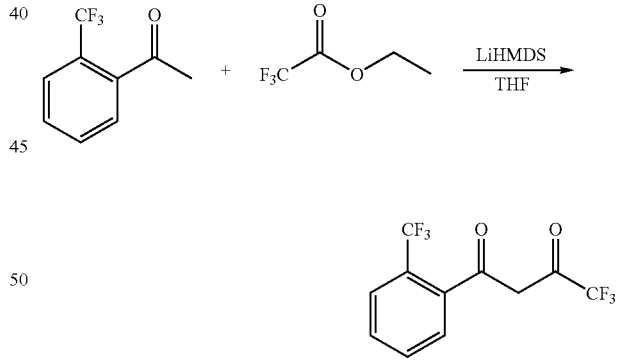

To a stirred solution of 2'-trifluoromethyl-acetophenone (225 mL, 15.0 mmol) in THF (20 mL, anhyd) at −78° C. added dropwise a 1.0M solution of lithium hexamethyldisilazide (LiHMDS) (15.8 mL, 15.8 mmol). After 1 h the reaction mixture was cooled to −78° C. and charged dropwise with ethyl trifluoroacetate (3.6 mL, 30 mmol). After addition was complete, the reaction mixture was allowed to warm to ambient temperature. The reaction mixture was quenched by slow addition of H$_2$O (20 mL) and concentrated under reduced pressure. The resulting material was transferred to a separatory funnel, diluted with Et$_2$O (60 mL), washed with 1N HCl and brine, then dried (MgSO$_4$) and concentrated to yield the title compound (4.2 g, 99%) as an amber liquid, which was used in the next step without purification. Rf: 0.15 (20% EtOAc/Hex).

Example 4b

Preparation of 1-(4-bromophenyl)-3-trifluoromethyl-5-(2-trifluoromethyl)phenyl)-1H-pyrazole

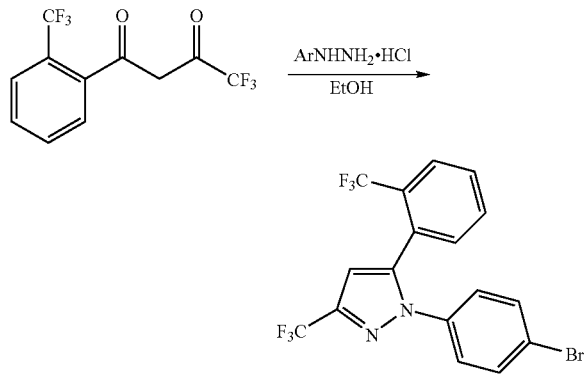

To a stirred solution of 4,4,4-trifluoro-1-(2-trifluoromethyl-phenyl)-butane-1,3-diose (0.40 g, 1.4 mmol) in EtOH (10 mL) was added 4-bromophenylhydrazine hydrochloride (335 mg, 1.5 mmol) and acetic acid (0.4 mL). The resulting mixture was heated at reflux for 20 h, allowed to cool to ambient temperature and concentrated under reduced pressure. The resulting residue was diluted with DCM (80 mL), washed with satd NaCO₃ and brine, then dried (Na₂SO₄), concentrated and purified by chromatography (silica, EtOAc/Hex, 0:100 to 20:80) to give the title compound (0.54 g, 89%) as a pale yellow liquid. $^1$H-NMR (CD$_3$CN): δ 7.85 (d, 1H), 7.63 (m, 2H), 7.50 (d, 2H), 7.37 (m, 1H), 7.17 (d, 2H), 6.92 (s, 1H).

Example 4c

Preparation of 1-(3'-methanesulfonyl-biphenyl-4-yl)-3-trifluoromethyl-5-(2-trifluoromethyl-phenyl)-1H-pyrazole

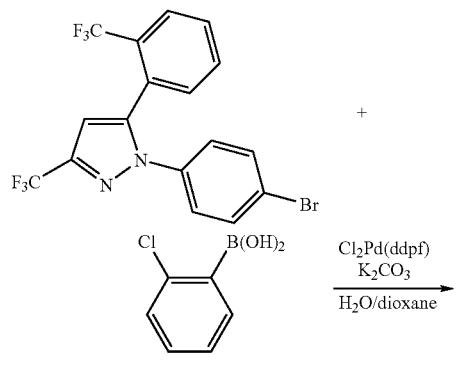

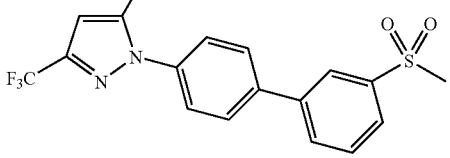

A mixture of 1-(4-bromophenyl)-3-trifluoromethyl-5-(2-trifluoromethyl-phenyl)-1H-pyrazole (135 mg, 0.31 mmol), 3-methanesulfonyl-phenylboronic acid (74 mg, 0.37 mmol), K$_2$CO$_3$ (0.13 g, 0.93 mmol), Cl$_2$Pd(dppf).DCM (24 mg, 10 mol %) and H$_2$O (0.2 mL) in dioxane (2 mL) was sparged with Argon for 5 min and then heated at 80° C. as a sealed flask. After 16 h the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 0:100 to 40:60) to give the title compound (121 mg, 76%). $^1$H NMR (DMSO-d$_6$): δ 8.15 (m, 1H), 8.03 (d, 1H), 7.91 (m, 2H), 7.83 (d, 2H), 7.71-7.76 (m, 3H), 7.66 (m, 1H), 7.40 (d, 2H), 7.18 (s, 1H); MS(ES): 511 [M+H]$^+$.

The following compounds were prepared from appropriate reagents in a similar manner:

4'-{3-(trifluoromethyl)-5-[2-(trifluoromethyl)phenyl]-1H-pyrazol-1-yl}biphenyl-3-sulfonamide, MS(ES): 512 [M+H]$^+$ 3-(trifluoromethyl)-1-[3'-(trifluoromethyl)biphenyl-4-yl]-5-[2-(trifluoromethyl)phenyl]-1H-pyrazole, MS(ES): 501 [M+H]$^+$ 3-(trifluoromethyl)-1-{3'-[(trifluoromethyl)oxy]biphenyl-4-yl}-5-[2-(trifluoromethyl)phenyl]-1H-pyrazole, MS(ES): 517 [M+H]$^+$ 1-[3'-(methylsulfonyl)biphenyl-3-yl]-3-(trifluoromethyl)-5-[2-(trifluoromethyl)phenyl]-1H-pyrazole, MS(ES): 511 [M+H]$^+$ 5-[3-(methylsulfonyl)phenyl]-2-{3-(trifluoromethyl)-5-[2-(trifluoromethyl)phenyl]-1H-pyrazol-1-yl}-1,3-thiazole, MS(ES): 518 [M+H]$^+$ 3-(2-{3-(trifluoromethyl)-5-[2-(trifluoromethyl)phenyl]-1H-pyrazol-1-yl})-1,3-thiazol-5-yl)-benzenesulfonamide, MS(ES): 519 [M+H]$^+$ 5-[3-(methylsulfonyl)phenyl]-2-{3-(rifluoromethyl)-5-[2-(trifluoromethyl)phenyl]-1H-pyrazol-1-yl}pyridine, MS(ES): 512 [M+H]$^+$ The following compounds were prepared in a similar manner from appropriate reagents and by replacing ethyl trifluoroacetate with dimethyl oxalate:

methyl 5-(2-chlorophenyl)-1-[3'-(methylsulfonyl)biphenyl-4-yl]-1H-pyrazole-3-carboxylate, MS(ES): 467 [M+H]+ methyl 5-(2-chlorophenyl)-1-{5-[3-(methylsulfonyl)phenyl]pyridin-2-yl}-1H-pyrazole-3-carboxylate, MS(ES): 468 [M+H]$^+$ methyl 5-(2-chlorophenyl)-1-{6-[3-(methylsulfonyl)phenyl]pyridin-3-yl}-1H-pyrazole-3-carboxylate, MS(ES): 468 [M+H]$^+$ methyl 5-{5-[3-(aminosulfonyl)phenyl]-2-thienyl}—(2,5-dichlorophenyl)-H-pyrazole-3-carboxylate; MS(ES): 508 [M+H]⁺;

Example 5
Preparation of 2-{5-(2-chlorophenyl)-1-[6-(3-methanesulfonyl-phenyl)-pyridin-3-yl]-1H-pyrazol-3-yl}-propan-2-ol

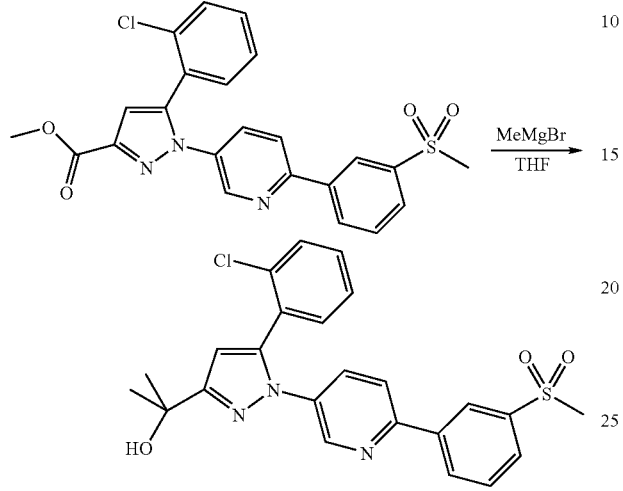

To a stirred solution of methyl 5-(2-chlorophenyl)-1-{6-[3-(methylsulfonyl)phenyl]pyridin-3-yl}-1H-pyrazole-3-carboxylate (0.14 g, 0.30 mmol) in THF (3 mL, anhyd) at 0° C. was added slowly a 1.4M solution of methylmagnesium bromide in 3:1 toluene/THE (0.68 mL, 0.95 mmol). After addition was complete the flask was removed from an ice-water bath and allowed to warm to ambient temperature. After 2 h the reaction mixture was quenched with satd NH₄Cl and extracted with EtOAc (50 mL). The combined extracts were washed with brine, dried (Na₂SO₄), concentrated and purified by chromatography (silica, EtOAc/Hex, 35:65 to 65:35) to yield the title compound (50 mg, 36%) as a white solid. ¹H-NMR (DCM-d₂): δ 8.54 (m, 2H), 8.28 (m, 1H), 7.95 (m, 1H), 7.72-7.81 (m, 2H), 7.68 (m, 1H), 7.34-7.46 (m, 4H), 6.52 (s, 1H), 3.07 (s, 3H), 2.64 (s, 1H), 1.66 (s, 6H); MS(ES): 468 [M+H]⁺. The following compounds were prepared from appropriate reagents in a similar manner.
2-[5-(2-chlorophenyl)-1-{5-[3-(methylsulfonyl)phenyl]pyridin-2-yl}-1H-pyrazol-3-yl]propan-2-ol, MS(ES): 468 [M+H]⁺
2-{5-(2-chlorophenyl)-1-[3'-(methylsulfonyl)biphenyl-4-yl]-1H-pyrazol-3-yl}propan-2-ol, MS(ES): 467 [M+H]⁺

Example 6
Preparation of 1-{5-(2-chlorophenyl)-1-[6-(3-methanesulfonyl-phenyl)-pyridin-3-yl]-1H-pyrazol-3-yl}-ethanone

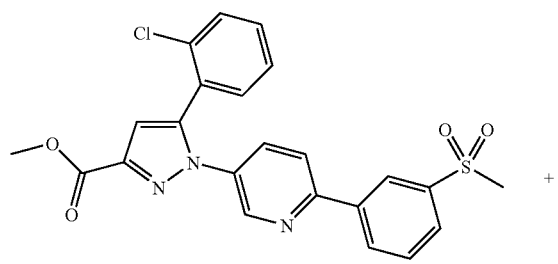

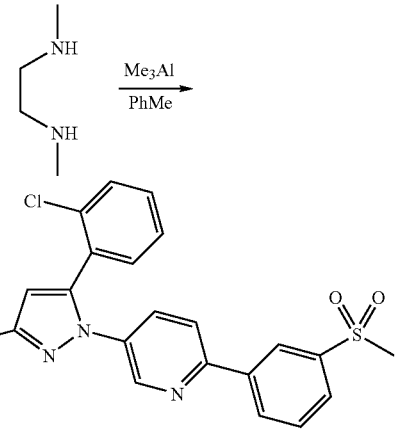

To a stirred solution of N,N'-dimethylethylenediamine (56 μL, 0.52 mmol) in toluene (3 mL, anhyd) at 0° C. was added dropwise a 2.0M solution of trimethylaluminum in hexanes (0.75 mL, 1.5 mmol). After addition was complete the flask was removed from the ice-water bath and allowed to warm to ambient temperature. After 50 min the reaction mixture was charged slowly with a solution of methyl 5-(2-chlorophenyl)-1-{6-[3-(methylsulfonyl)phenyl]pyridin-3-yl}-1H-pyrazole-3-carboxylate (0.22 g, 0.47 mmol) in toluene (3 mL, anhyd) and then heated at reflux. After 90 min the reaction mixture was allowed to cool to ambient temperature and quenched by addition of 1N HCl. The resulting mixture was extracted with EtOAc (2×50 mL). The combined extracts were washed with brine, dried (Na₂SO₄), concentrated and purified by chromatography (silica, EtOAc/Hex, 30:70 to 60:40) to yield the title compound (47 mg, 22%) as a white solid. ¹H-NMR (DCM-d₂): δ 8.65 (m, 1H), 8.57 (m, 1H), 8.30 (m, 1H), 7.99 (m, 1H), 7.79-7.87 (m, 2H), 7.71 (m, 1H), 7.36-7.47 (m, 4H), 7.02 (s, 1H), 3.09 (s, 3H), 2.68 (s, 3H); MS(ES): 452 [M+H]⁺.

The following compounds were prepared from appropriate reagents in a similar manner:
1-[5-(2-chlorophenyl)-1-{5-[3-(methylsulfonyl)phenyl]pyridin-2-yl}-1H-pyrazol-3-yl]ethanone, MS(ES): 452 [M+H]⁺
1-{5-(2-chlorophenyl)-1-[3'-(methylsulfonyl)biphenyl-4-yl]-1H-pyrazol-3-yl}ethanone, MS(ES): 451 [M+H]⁺

Example 7

2-[1-(4-bromophenyl)-5-(2-chlorophenyl)-1H-pyrazol-3-yl]-1,1,1,3,3,3-hexafluoro-propan-2-ol

Example 7a

Preparation of 2-[1-(4-bromophenyl)-5-(2-chlorophenyl)-1H-pyrazol-3-yl]-1,1,1,3,3,3-hexafluoro-propan-2-ol

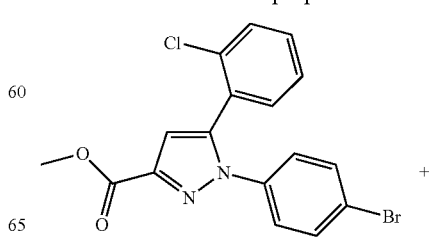

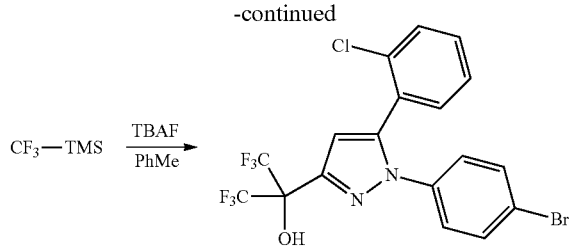

To a stirred solution of 1-(4-bromophenyl)-5-(2-chlorophenyl)-1H-pyrazole-3-carboxylic acid methyl ester (504 mg, 129 mmol) and trifluoromethyl-trimethylsilane (CF$_3$-TMS) (0.77 mL, 5.2 mmol) in toluene (8 mL, anhyd) was added dropwise a 1.0M solution of tetrabutylammonium fluoride (TBAF) in THF (026 mL, 20 mol %, dried over 4 Å molecular sieves). After 20 h the reaction mixture was charged with additional CF$_3$-TMS (0.57 mL) and TBAF (0.2 mL), then heated at 50° C. After 2 h the reaction mixture was allowed to cool to ambient temperature, diluted with DCM (50 mL), washed with H$_2$O and brine, then dried (Na$_2$SO$_4$) and concentrated under reduced pressure. The resulting residue was purified by chromatography (silica, EtOAc/Hex, 0:100 to 20:80) to give the title compound (0.10 g, 16%) as a white solid. $^1$H-NMR (DCM-d$_2$): δ 7.40-7.49 (m, 4H), 7.31-7.36 (m, 2H), 7.16 (d, 2H), 6.71 (s, 1H), 5.18 (s, 1H).

Example 7b

Preparation of 2-[5-(2-chlorophenyl)-1-(3'-methanesulfonyl-biphenyl-4-yl)-1H-pyrazol-3-yl]-1,1,1,3,3,3-hexafluoro-propan-2-ol

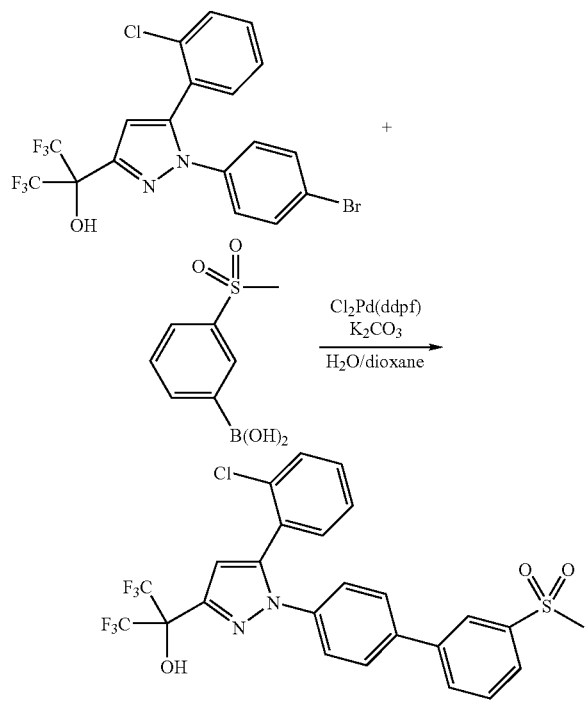

A mixture of 2-[1-(4-bromophenyl)-5-(2-chlorophenyl)-1H-pyrazol-3-yl]-1,1,1,3,3,3-hexafluoro-propan-2-ol (100 mg, 020 mmol), 3-methanesulfonyl-phenylboronic acid (48 mg, 0.24 mmol), K$_2$CO$_3$ (83 mg, 0.60 mmol), Cl$_2$Pd(dppf).DCM (16 mg, 10 mol %) and H$_2$O (0.2 mL) in dioxane (2 mL) was sparged with Argon for 5 min and then heated at 80° C. as a sealed flask. After 3 h the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 0:100 to 50:50) to give the title compound (94 mg, 82%) as a white solid. $^1$H-NMR (DCM-d$_2$): δ 8.12 (m, 1H), 7.92 (m, 1H), 7.87 (m, 1H), 7.67 (m, 1H), 7.61 (d, 2H), 7.33-7.47 (m, 6H), 6.74 (s, 1H), 5.25 (s, 1H), 3.07 (s, 3H); MS(ES): 575 [M+H]$^+$.

Pyrazole 1a Carbinols

The synthesis of pyrazole carbinols are depicted in Scheme 6. Bromothienyl ketone (006A) was treated with a base and then dimethyl oxalate to form a diketo ester (006B), which condensed with a hydrazine salt to form bromothienylpyrazole product (006C). Suzuki coupling of the bromothienylpyrazole with a boronic acid mediated with palladium tetrakis(triphenylphosphine) affords a phenylthienylpyrazole ester (006D). It was submitted to Grignard reaction to afford a carbinol product (006E). Bromo or chloro groups were introduced onto the pyrazole ring via reactions with NBS or NCS.

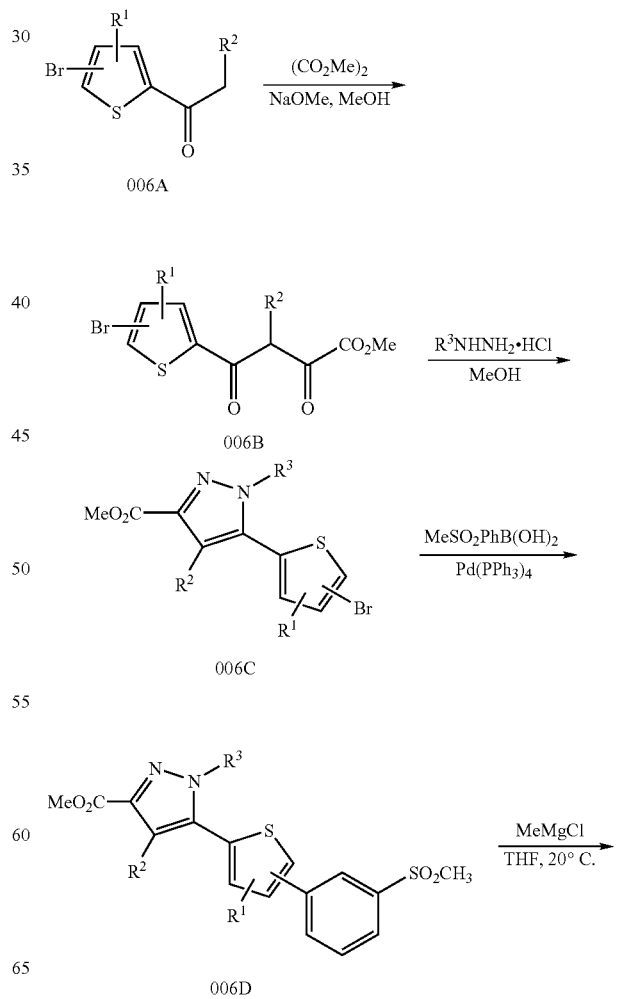

Scheme 6

-continued

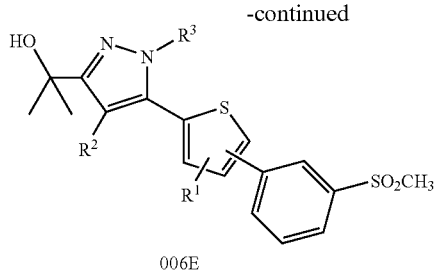

006E

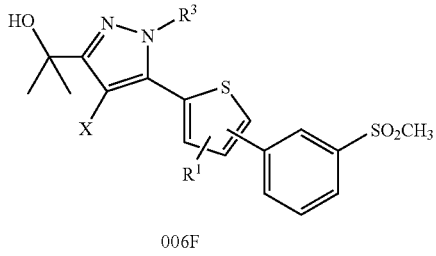

006F

Example 8

2-{1-(2-chloro-phenyl)-5-[5-(3-methanesulfonyl-phenyl)-thiophen-2-yl]-1H-pyrazol-3-yl}-propan-2-ol

Example 8a

Preparation of 4-(5-bromo-thiophen-2-yl)-2,4-dioxo-butyric acid methyl ester

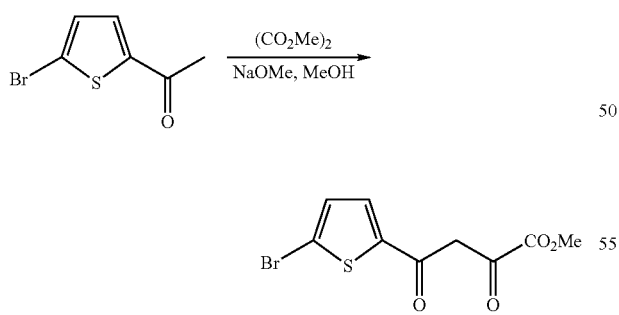

To a solution of 2-acetyl-5-bromothiophene (25 g, 122 mmol) and dimethyl oxalate (23 g, 194 mmol) in dry methanol (800 mL) was added a solution of NaOMe in MeOH (25%, 51 mL, 224 mmol) at ambient temperature. The reaction mixture was stirred at 20° C. for 4 h and then acidified to pH 1 with 6 N aqueous HCl. The yellow solid was collected by filtration, washed with $H_2O$, and dried under high vacuum to afford 4-(5-bromo-thiophen-2-yl)-2,4-dioxo-butyric acid methyl ester (31.3 g, 88%). $^1$H-NMR (DMSO-$d_6$): δ 8.14 (s, 1H), 7.46 (d, 1H), 7.05 (s, 1H), 3.85 (s, 3H).

Example 8b

Preparation of 5-(5-bromo-thiophen-2-yl)-1-(2-chloro-phenyl)-1H-pyrazole-3-carboxylic acid methyl ester

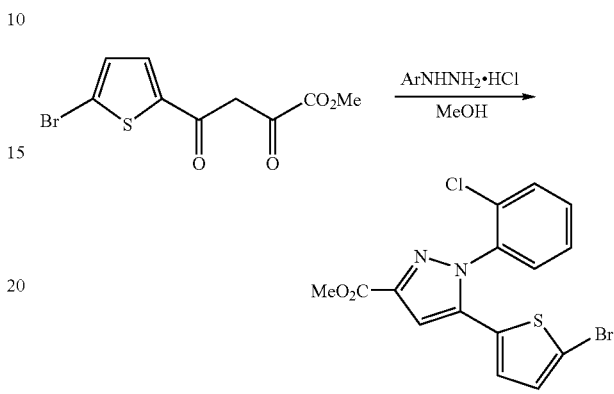

A solution of 4-(5-bromo-thiophen-2-yl)-2,4-dioxo-butyric acid methyl ester (15 g, 50 mmol) and 2-chlorophenylhydrazine hydrochloride (10.75 g, 60 mmol) in dry MeOH (200 mL) was heated to reflux for 6 h. After cooling to 20° C., a white solid precipitated and was collected by filtration, washed with a small volume of cold MeOH and dried under high vacuum to afford 5-(5-bromo-thiophen-2-yl)-1-(2-chloro-phenyl)-1H-pyrazole-3-carboxylic acid methyl ester (20 g, 100%). $^1$H-NMR (CDCl$_3$): δ 7.48-7.55 (m, 3H), 7.43 (m, 1H), 7.11 (s, 1H), 6.90 (d, 2H), 6.65 (s, 1H), 3.95 (s, 3H).

Example 8c

Preparation of 1-(2-chloro-phenyl)-5-[3-(3-methanesulfonyl-phenyl)-thiophen-2-yl]-1H-pyrazole-3-carboxylic acid methyl ester

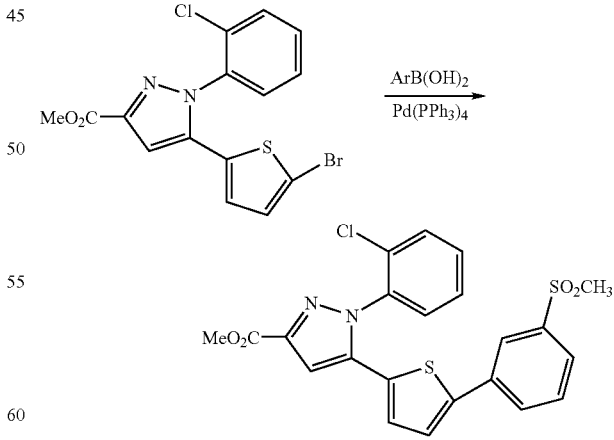

A mixture of 5-(5-bromo-thiophen-2-yl)-1-(2-chloro-phenyl)-1H-pyrazole-3-carboxylic acid methyl ester (8.0 g, 20 mmol), 3-methylsulfonylphenylboronic acid (5.0 g, 24 mmol), sodium carbonate (6.0 g, 56 mmol) and palladium tetrakis(triphenylphosphine) (1.2 g, 1.04 mmol) in 1,4-dioxane (100 mL) and H$_2$O (5 mL) was stirred at 90° C. under N$_2$ for 16 h. Solid was filtered off and washed with ethyl acetate. The filtrate was concentrated under vacuum to give a residue, which was partitioned between ethyl acetate and water. The aqueous layer was separated and extracted with ethyl acetate. The combined organic layers were washed with brine, dried over sodium sulfate and evaporated to give a crude. It was triturated by DCM to afford 1-(2-chloro-phenyl)-5-[5-(3-methanesulfonyl-phenyl)-thiophen-2-yl]-1H-pyrazole-3-carboxylic acid methyl ester (4.8 g). The mother liquors from trituration were combined and concentrated to give a solid, which was purified by flash chromatography on silica gel eluted with EtOAc-hexane (0-60%) to afford another 2.8 g of product. The total yield was 7.6 g (80%). $^1$H-NMR (CDCl$_3$): δ 8.04 (m, 1H), 7.84 (m, 1H), 7.73 (m, 1H), 7.50-7.58 (m, 4H), 7.47 (m, 1H), 7.23 (d, 1H), 7.20 (s, 1H), 6.82 (d, 1H), 3.98 (s, 3H), 3.07 (s, 3H).

Example 8d

Preparation of 2-{1-(2-chlorophenyl-5-[5-(3-methanesulfonyl-phenyl)-thiophen-2-yl]-1H-pyrazol-3-yl}-propan-2-ol and 1-[1-(2-chlorophenyl)-5-{5-[3-(methylsulfonyl)phenyl]-2-thienyl}-1H-pyrazol-3-yl]ethanone

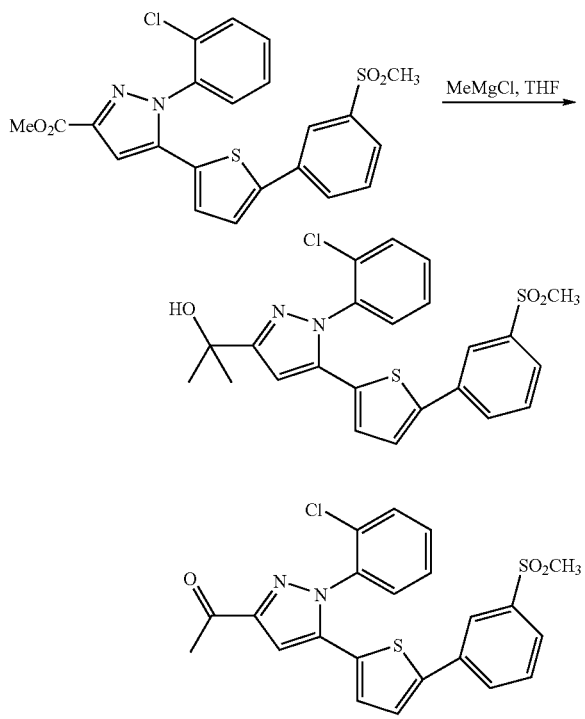

To a stirred solution of 1-(2-chloro-phenyl)-5-[5-(3-methanesulfonyl-phenyl)-thiophen-2-yl]-1H-pyrazole-3-carboxylic acid methyl ester (5.22 g, 11.036 mmol) in dry THF (200 mL) was added dropwise a solution of MeMgCl in THF (3.0 M, 18 mL, 54 mmol) at −78° C. under N$_2$. The reaction solution was allowed to warm to rt overnight and then quenched with saturated aqueous NH$_4$Cl at 0° C. The aqueous layer was separated and extracted with EtOAc. The combined organic layers were washed with brine, dried with sodium sulfate and evaporated in vacuo. The residue was purified by flash chromatography (0-60% EtOAc/hexanes) to afford 2-{1-(2-chloro-phenyl)-5-[5-(3-methanesulfonylphenyl)-thiophen-2-yl]-1H-pyrazol-3-yl}-propan-2-ol as a white solid (2.74 g, 52%) and 1-[1-(2-chlorophenyl)-5-{5-[3-(methylsulfonyl)phenyl]-2-thienyl}-1H-pyrazol-3-yl]ethanone as a white solid (1.5 g, 30%). $^1$H-NMR (CDCl$_3$): δ 8.04 (s, 1H), 7.83 (m, 1H), 7.71 (m, 1H), 7.57-7.53 (m, 3H), 7.50-7.43 (m, 2H), 7.20 (d, 1H), 6.73 (d, 1H), 6.62 (s, 1H), 3.07 (s, 3H), 2.61 (s, 1H), 1.68 (s, 6H). MS(ES): 473 [M+H]$^+$, $^1$H-NMR (CDCl$_3$): δ 8.04 (s, 1H), 7.83 (m, 1H), 7.72 (m, 1H), 7.59-7.49 (m, 5H), 7.22 (d, 1H), 7.15 (s, 1H), 6.80 (d, 1H), 3.07 (s, 3H), 2.65 (s, 3H). MS(ES): 457 [M+H]$^+$.

The following compounds are prepared essentially according to the previous examples:

3-[1-(2-chlorophenyl)-5-{5-[3-(methylsulfonyl)phenyl]-2-thienyl}-1H-pyrazol-3-yl]pentan-3-ol: $^1$HNMR (CDCl$_3$): δ 8.04 (d, 1H), 7.82 (m, 1H), 7.73 (m, 1H), 7.57-7.42 (m, 5H), 7.20 (d, 1H), 6.74 (d, 1H), 6.52 (s, 1H), 3.08 (s, 3H), 2.81 (brs, 1H), 1.89 (q, 4H), 0.92 (t, 6H). MS(ES) 501 [M+H]$^+$, 483 (M-OH).

1-[1-(2-chlorophenyl)-5-{5-[3-(methylsulfonyl)phenyl]-2-thienyl}-1H-pyrazol-3-yl]propan-1-one: $^1$HNMR (CDCl$_3$): δ 8.04 (d, 1H), 7.83 (m, 1H), 7.73 (m, 1H), 7.59-7.48 (m, 5H), 7.22 (d, 1H), 7.15 (s, 1H), 6.80 (d, 1H). 3.13-3.07 (m, 5H), 1.24 (t, 3H). MS(ES) 471 [M+H]$^+$.

1-[1-(2-chlorophenyl)-5-{5-[3-(methylsulfonyl)phenyl]-2-thienyl}-1H-pyrazol-3-yl]propan-1-ol: $^1$HNMR (CDCl$_3$): δ 8.04 (d, 1H), 7.81 (m, 1H), 7.72 (m, 1H), 7.57-7.42 (m, 5H), 7.20 9d, 1H), 6.75 (d, 1H), 6.63 (s, 1H), 4.81 (t, 1H), 3.07 (s, 3H), 2.6 (brs, 1H), 1.94 (m, 2H), 1.04 (t, 3H). MS(ES) 473 [M+H]$^+$, 455 (M-OH).

2-(5-{5-[3-(methylsulfonyl)phenyl]-2-thienyl}-1-[2-(trifluoromethyl)phenyl]-1H-pyrazol-3-yl)propan-2-ol, MS(ES): 507 [M+H]$^+$ 2-(5-{5-[3-(methylsulfonyl)phenyl]-2-thienyl}-1-[3-(trifluoromethyl)pyridin-2-yl]-1H-pyrazol-3-yl)propan-2-ol, MS(ES): 508 [M+H]$^+$ 1-(5-{5-[3-(methylsulfonyl)phenyl]-2-thienyl}-1-[3-(trifluoromethyl)pyridin-2-yl]-1H-pyrazol-3-yl)ethanone, MS(ES): 492 [M+4H]$^+$ 2-[1-(3-fluorophenyl)-5-{5-[3-(methylsulfonyl)phenyl]-2-thienyl}-1H-pyrazol-3-yl]propan-2-ol, MS(ES): 473 [M+H]$^+$ 2-[1-(4-chlorophenyl)-5-{5-[3-(methylsulfonyl)phenyl]-2-thienyl}-1H-pyrazol-3-yl]propan-2-ol, MS(ES): 473 [M+H]$^+$ 2-[1-(3-fluorophenyl)-5-{5-[3-(methylsulfonyl)phenyl]-2-thienyl}-1H-pyrazol-3-yl]propan-2-ol, MS(ES): 457 [M+H]$^+$ 2-[1-(2-fluorophenyl)-5-{5-[3-(methylsulfonyl)phenyl]-2-thienyl}-1H-pyrazol-3-yl]propan-2-ol, MS(ES): 457 [M+H]$^+$ 2-[1-(2-fluorophenyl)-5-{5-[3-(methylsulfonyl)phenyl]-2-thienyl}-1H-pyrazol-3-yl]propan-2-ol, MS(ES): 457 [M+H]$^+$ 1-(5-{5-[3-(methylsulfonyl)phenyl]-2-thienyl}-1-phenyl-1H-pyrazol-3-yl)ethanone, MS(ES): 439 [M+H]$^+$ 1-(5-{5-[3-(methylsulfonyl)phenyl]-2-thienyl}-1-phenyl-1H-pyrazol-3-yl)ethanone MS(ES): 423 [M+H]$^+$ 2-[1-(2,5-dichlorophenyl)-5-{5-[3-(methylsulfonyl)phenyl]-2-thienyl}-1H-pyrazol-3-yl]propan-2-ol; MS(ES): 507 [M+H]$^+$ 2-[1-(2-chloro-3-fluorophenyl)-5-{5-[3-(methylsulfonyl)phenyl]-2-thienyl}-1H-pyrazol-3-yl]propan-2-ol, MS(ES): 491 [M+H]$^+$ 2-[3-(1-hydroxy-1-methylethyl)-5-{5-[3-(methylsulfonyl)phenyl]-2 thienyl}-1H pyrazol-1-yl]-6-(trifluoromethyl)phenol, MS(ES): 523 [M+H]$^+$ 2-(5-{5-[3-(methylsulfonyl)phenyl]-2-thienyl}-1-[4-(trifluoromethyl)pyridin-3-yl]—1H-pyrazol-3-yl)propan-2-ol, MS(ES): 508 [M+H]⁺

2-(5-{5-[3-(methylsulfonyl)phenyl]-2-thienyl}-1-[2-(trifluoromethyl)pyridin-3-yl]-1H-pyrazol-3-yl)propan-2-ol, MS(ES): 508 [M+H]⁺

2-[1-(2-chlorophenyl)-5-{5-[4-(methylsulfonyl)phenyl]-2-thienyl}-1H-pyrazol-3-yl]propan-2-ol, MS(ES): 473 [M+H]⁺

2-[1-(2,6-chloro-3-methylphenyl)-5-{5-[3-(methylsulfonyl)phenyl]-2-thienyl}-1H-pyrazol-3-yl]propan-2-ol, MS(ES): 521 [M+H]⁺, 503 (M-OH)

2-[1-(2,6-dichlorophenyl)-5-{5-[3-(methylsulfonyl)phenyl]-2-thienyl}-1H-pyrazol-3-yl]propan-2-ol, MS(ES): 507 [M+H]⁺, 489 (M-OH)

2-[1-(2-chlorophenyl)-5-{1-methyl-5-[3-(methylsulfonyl)phenyl]1H-pyrrol-2-yl}-1H-pyrazol-3-yl]propan-2-ol, MS(ES): 470 [M+H]⁺, 452 (M-OH)

2-[1-(2,6-dichlorophenyl)-5-{1-methyl-5-[3-(methylsulfonyl)phenyl]-1H-pyrrol-2-yl}-1H pyrazol-3-yl]propan-2-ol, MS(ES): 504 [M+H]⁺, 486 (M-OH)

2-{1-(2-chlorophenyl)-7-[3-(methylsulfonyl)phenyl]-1,4-dihydroindeno[1,2-c]pyrazol-3-yl}propan-2-ol, MS(ES): 479 [M+H]⁺, 461 (M-OH)

2-{1-(2-chlorophenyl)-6-[3-(methylsulfonyl)phenyl]-1,4-dihydroindeno[1,2-c]pyrazol-3-yl}propan-2-ol, MS(ES): 479 [M+H⁺, 461 (M-OH)

2-[1-(2,6-dichlorophenyl)-5-{3-methyl-5-[3-(methylsulfonyl)phenyl]-2-thienyl}-1H-pyrazol-3-yl]propan-2-ol, MS(ES): 521 [M+H]⁺.

2-[5-{5-[3,4-bis(methyloxy)phenyl]-2-thienyl}-1-(2-chlorophenyl)-1H-pyrazol-3-yl]propan-2-ol; MS (ES): 455 [M+H]⁺;

2-chloro-4-{5-[1-(2-chlorophenyl)-3-(1-hydroxy-1-methylethyl)-1H-pyrazol-5-yl]-2-thienyl}-N-(1-methylethyl)benzamide; MS (ES): 514 [M+H]⁺;

2-[1-(2-chlorophenyl)-5-{5-[2-(methylthio)phenyl]-2-thienyl}-1H-pyrazol-3-yl]propan-2-ol; MS (ES): 441 [M+H]⁺;

2-{1-(2-chlorophenyl)-5-[5-(2-fluorobiphenyl-4-yl)-2-thienyl]-1H-pyrazol-3-yl}propan-2-ol; MS (ES): 489 [M+H]⁺;

2-{1-(2-chlorophenyl)-5-[5-(3-fluorophenyl)-2-thienyl]-1H-pyrazol-3-yl}propan-2-ol; MS (ES): 413 [M+H]⁺;

N-(3-{5-[1-(2-chlorophenyl)-3-(1-hydroxy-1-methylethyl)-1H-pyrazol-5-yl]-2-thienyl}phenyl)acetamide; MS (ES): 452 [M+H]⁺;

2-[1-(2-chlorophenyl)-5-(5-{4-[(1-methylethyl)oxy]phenyl}-2-thienyl)-1H-pyrazol-3-yl]propan-2-ol; MS (ES): 453 [M+H]⁺;

2-[1-(2-chlorophenyl)-5-{5-[2-fluoro-3-(methyloxy)phenyl]-2-thienyl}-1H-pyrazol-3-yl]propan-2-ol; MS (ES): 443 [M+H]⁺;

2-{1-(2-chlorophenyl)-5-[5-(4-chlorophenyl)-2-thienyl]-1H-pyrazol-3-yl}propan-2-ol; MS (ES): 429 [M+H]⁺;

2-[1-(2-chlorophenyl)-5-{5-[5-fluoro-2-(methyloxy)phenyl]-2-thienyl}-1H-pyrazol-3-yl]propan-2-ol; MS (ES): 443 [M+H]⁺;

2-[1-(2-chlorophenyl)-5-{5-[4-(ethyloxy)-3-(trifluoromethyl)phenyl]-2-thienyl}-1H-pyrazol-3-yl]propan-2-ol; MS (ES): 507 [M+H]⁺;

2-{1-(2-chlorophenyl)-5-[5-(2,3-dichlorophenyl)-2-thienyl]-1H-pyrazol-3-yl}propan-2-o; MS (ES): 463 [M+H]⁺;

2-[1-(2-chlorophenyl)-5-(5-pyrimidin-5-yl-2-thienyl)-1H-pyrazol-3-yl]propan-2-ol; MS (ES): 397 [M+H]⁺;

4-{5-[1-(2-chlorophenyl)-3-(1-hydroxy-1-methylethyl)-1H-pyrazol-5-yl]-2-thienyl}benzoic acid; MS (ES): 439 [M+H]⁺;

N-(4-{5-[1-(2-chlorophenyl)-3-(1-hydroxy-1-methylethyl)-1H-pyrazol-5-yl]-2-thienyl}phenyl)methanesulfonamide; MS (ES): 488 [M+H]⁺;

2-{5-[1-(2-chlorophenyl)-3-(1-hydroxy-1-methylethyl)-1H-pyrazol-5-yl]-2-thienyl}-5-fluorophenol; MS (ES): 429 [M+H]⁺;

2-[1-(2-chlorophenyl)-5-(5-{4-fluoro-2-[(phenylmethyl)oxy]phenyl}-2-thienyl)-1H-pyrazol-3-yl]propan-2-ol; MS (ES): 519 [M+H]⁺;

3-{5-[1-(2-chlorophenyl)-3-(1-hydroxy-1-methylethyl)-1H-pyrazol-5-yl]-2-thienyl}-5-fluorobenzoic acid; MS (ES): 457 [M+H]⁺;

2-{1-(2-chlorophenyl)-5-[5-(1-methyl-1H-indol-5-yl)-2-thienyl]-1H-pyrazol-3-yl}propan-2-ol; MS (ES): 448 [M+H]⁺;

2-[1-(2-chlorophenyl)-5-(5-{2-[(1-methylethyl)oxy]-5-(trifluoromethyl)phenyl}-2-thienyl)-1H-pyrazol-3-yl]propan-2-ol; MS (ES): 521 [M+H]⁺;

2-chloro-5-{5-[1-(2-chlorophenyl)-3-(1-hydroxy-1-methylethyl)-1H-pyrazol-5-yl]-2-thienyl}benzamide; MS (ES): 472 [M+H]⁺;

2-{5-[5-(2-chloro-6-fluorophenyl)-2-thienyl]-1-(2-chlorophenyl)-1H-pyrazol-3-yl}propan-2-ol; MS (ES): 447 [M+H]⁺;

3-{5-[1-(2-chlorophenyl)-3-(1-hydroxy-1-methylethyl)-1H-pyrazol-5-yl]-2-thienyl}-N,N-dimethylbenzenesulfonamide; MS (ES): 502 [M+H]⁺;

2-chloro-4-{5-[1-(2-chlorophenyl)-3-(1-hydroxy-1-methylethyl)-1H-pyrazol-5-yl]-2-thienyl}-N-methylbenzamide; MS (ES): 486 [M+H]⁺;

2-[1-(2-chlorophenyl)-5-(5-{2-methyl-4-[(1-methylethyl)oxy]phenyl}-2-thienyl)-1H-pyrazol-3-yl]propan-2-ol; MS (ES): 467 [M+H]⁺;

4-{5-[1-(2-chlorophenyl)-3-(1-hydroxy-1-methylethyl)-1H-pyrazol-5-yl]-2-thienyl}-N-(furan-2-ylmethyl)benzamide; MS (ES): 518 [M+H]⁺;

methyl 2-{5-[1-(2-chlorophenyl)-3-(1-hydroxy-1-methylethyl)-1H-pyrazol-5-yl]-2-thienyl}benzoate; MS (ES): 453 [M+H]⁺;

2-[5-{5-[3-chloro-4-(methyloxy)phenyl]-2-thienyl)}1-(2-chlorophenyl)-1H-pyrazol-3-yl]propan-2-ol; MS (ES): 459 [M+H]⁺;

2-[5-(5-{3-chloro-4-[(1-methylethyl)oxy]phenyl}-2-thienyl)-1-(2-chlorophenyl)-1H-pyrazol-3-yl]propan-2-ol; MS (ES): 487 [M+H]⁺;

2-[1-(2-chlorophenyl)-5-{5-[4-(1,3-thiazolidin-3-ylcarbonyl)phenyl]-2-thienyl}-1H-pyrazol-3-yl]propan-2-ol; MS (ES): 510 [M+H]⁺;

2-chloro-4-{5-[1-(2-chlorophenyl)-3-(1-hydroxy-1-methylethyl)-1H-pyrazol-5-yl]-2-thienyl}-N-cyclopropylbenzamide; MS (ES): 512 [M+H]⁺;

2-{5-[1-(2-chlorophenyl)-3-(1-hydroxy-1-methylethyl)-1H-pyrazol-5-yl]-2-thienyl}-4-fluorophenol; MS (ES): 429 [M+H]⁺;

N-(2-{5-[1-(2-chlorophenyl)-3-(1-hydroxy-1-methylethyl)-1H-pyrazol-5-yl]-2-thienyl}phenyl)methanesulfonamide; MS (ES): 488 [M+H]⁺

4-{5-[1-(2-chlorophenyl)-3-(1-hydroxy-1-methylethyl)-1H-pyrazol-5-yl]-2-thienyl}-2-fluorobenzoic acid; MS (ES): 457 [M+H]⁺;

2-[1-(2-chlorophenyl)-5-{5-[4-(methylthio)-3-(trifluoromethyl)phenyl]-2-thienyl}-H-pyrazol-3-yl]propan-2-ol; MS (ES): 509 [M+H]⁺;

2-[1-(2-chlorophenyl)-5-{5-[2-methyl-5-(methyloxy)phenyl]-2-thienyl}-1H-pyrazol-3-yl]propan-2-ol; MS (ES): 439 [M+H]$^+$;

2-[1-(2-chlorophenyl)-5-{5-[2-(methyloxy)pyridin-3-yl]-2-thienyl}-1H-pyrazol-3-yl]propan-2-ol MS (ES): 426 [M+H]$^+$;

2-[1-(2-chlorophenyl)-5-{5-[6-(methyoxy)pyridin-3-yl]-2-thienyl}-1H-pyrazol-3-yl]propan-2-ol; MS (ES): 426 [M+H]$^+$;

2-[1-(2-chlorophenyl)-5-{5-[4-(methyloxy)-3-(trifluoromethyl)phenyl]-2-thienyl}-1H-pyrazol-3-yl]propan-2-ol; MS (ES): 493 [M+H]$^+$;

2-[1-(2-chlorophenyl)-5-(5-pyridin-3-yl-2 thienyl)-1H-pyrazol-3-yl]propan-2-ol; MS (ES): 396 [M+H]$^+$;

2-{1-(2-chlorophenyl)-5-[5-(1H-indol-6-yl)-2-thienyl]-1H-pyrazol-3-yl}propan-2-ol; MS (ES): 434 [M+H]$^+$;

2-[1-(2-chlorophenyl)-5-{5-[(1E)-3,3-dimethylbut-1-en-1-yl]-2-thienyl}-1H-pyrazol-3-yl]propan-2-ol; MS (ES): 401 [M+H]$^+$;

1,1-dimethylethyl 2-{5-[1-(2-chlorophenyl)-3-(1-hydroxy-1-methylethyl)-1H-pyrazol-5-yl]-2-thienyl}-1H-pyrrole-1-carboxylate; MS (ES): 484 [M+H]$^+$;

2-[1-(2-chlorophenyl)-5-(5-{2-[(1-methylethyl)oxy]pyridin-3-yl}-2-thienyl)-1H-pyrazol-3-yl]propan-2-ol; MS (ES): 454 [M+H]$^+$;

2-[1-(2-chlorophenyl)-5-{5-[2-(cyclopentyloxy)pyridin-3-yl]-2-thienyl}-1H-pyrazol-3-yl]propan-2-ol; MS (ES): 480 [M+H]$^+$;

ethyl 4-{5-[1-(2-chlorophenyl)-3-(1-hydroxy-1-methylethyl)-1H-pyrazol-5-yl]-2-thienyl}benzoate; MS (ES): 467 [M+H]$^+$;

2-{1-(2-chlorophenyl)-5-[5-(5-methylfuran-2-yl)-2-thienyl]-1H-pyrazol-3-yl}propan-2-ol; MS (ES): 399 [M+H]$^+$;

4-{5-[1-(2-chlorophenyl)-3-(1-hydroxy-1-methylethyl)-1H-pyrazol-5-yl]-2-thienyl}benzamide; MS (ES): 438 [M+H]$^+$;

methyl N-[(4-{5-[1-(2-chlorophenyl)-3-(1-hydroxy-1-methylethyl)-1H-pyrazol-5-yl]-2-thienyl}phenyl)carbonyl]glycinate; MS (ES): 510 [M+H]$^+$;

3-{5-[1-(2-chlorophenyl)-3-(1-hydroxy-1-methylethyl)-1H-pyrazol-5-yl]-2-thienyl}benzamide; MS (ES): 438 [M+H]$^+$;

2-[1-(2-chlorophenyl)-5-{5-[3-(thiomorpholin-4-ylcarbonyl)phenyl]-2-thienyl}-1H-pyrazol-3-yl]propan-2-ol; MS (ES): 524 [M+H]$^+$;

2-{5-[5-(1,3-benzodioxol-5-yl)-2-thienyl]-1-(2-chlorophenyl)-1H-pyrazol-3-yl}propan-2-ol; MS (ES): 439 [M+H]$^+$;

2-[1-(2-chlorophenyl)-5-{5-[2-methyl-5-(morpholin-4-ylsulfonyl)phenyl]-2-thienyl}-1H-pyrazol-3-yl]propan-2-ol; MS (ES): 558 [M+H]$^+$;

2-[5-{5-[2,4-bis(trifluoromethyl)phenyl]-2-thienyl}-1-(2-chlorophenyl)-1H-pyrazol-3-yl]propan-2-ol; MS (ES): 531 [M+H]$^+$;

2-[5-{5-[2,3-bis(methyloxy)phenyl]-2-thienyl}-1-(2-chlorophenyl)-1H-pyrazol-3-yl]propan-2-ol; MS (ES): 455 [M+H]$^+$;

2-[1-(2-chlorophenyl)-5-{5-[3,5-difluoro-2-(methyloxy)phenyl]-2-thienyl}-1H-pyrazol-3-yl]propan-2-ol; MS (ES): 461 [M+H]$^+$;

2-[1-(2-chlorophenyl)-5-{5-[2-(phenyloxy)phenyl]-2-thienyl}-1H-pyrazol-3-yl]propan-2-ol; MS (ES): 487 [M+H]$^+$;

2-[1-(2-chlorophenyl)-5-{5-[3-(trifluoromethyl)phenyl]-2-thienyl}-1H-pyrazol-3-yl]propan-2-ol; MS (ES): 463 [M+H]$^+$;

2-{1-(2-chlorophenyl)-5-[5-(3,5-dichlorophenyl)-2-thienyl]-1H-pyrazol-3-yl}propan-2-ol; MS (ES): 463 [M+H]$^+$;

2-{1-(2-chlorophenyl)-5-[5-(2,4,5-trimethylphenyl)-2-thienyl]-1H-pyrazol-3-yl}propan-2-ol; MS (ES): 437 [M+H]$^+$;

2-[1-(2-chlorophenyl)-5-(5-naphthalen-2-yl-2-thienyl)-1H-pyrazol-3-yl]propan-2-ol; MS (ES): 445 [M+H]$^+$;

2-[1-(2-chlorophenyl)-5-(5-{2-[(1-methylethyl)oxy]phenyl}-2-thienyl)-1H-pyrazol-3-yl]propan-2-ol; MS (ES): 453 [M+H]$^+$;

2-[1-(2-chlorophenyl)-5-{5-[2-fluoro-5-(methyloxy)phenyl]-2-thienyl}-1H-pyrazol-3-yl]propan-2-ol; MS (ES): 443 [M+H]$^+$;

2-{1-(2-chlorophenyl)-5-[5-(1-phenylethenyl)-2-thienyl]-1H-pyrazol-3-yl}propan-2-ol; MS (ES): 421 [M+H]$^+$;

2-[1-(2-chlorophenyl)-5-{5-[(1E)-prop-1-en-1-yl]-2-thienyl}-1H-pyrazol-3-yl]propan-2-ol; MS (ES): 359 [M+H]$^+$;

2-{1-(2-chlorophenyl)-5-[5-(5-fluoro-2-methylphenyl)-2-thienyl]-1H-pyrazol-3-yl}propan-2-ol; MS (ES): 427 [M+H]$^+$;

2-[1-(2-chlorophenyl)-5-{5-[2-(hydroxymethyl)phenyl]-2-thienyl}-1H-pyrazol-3-yl]propan-2-ol; MS (ES): 425 [M+H]$^+$;

2-[1-(2-chlorophenyl)-5-(5-{5-methyl-2-[(1-methylethyl)oxy]phenyl}-2-thienyl)-1H-pyrazol-3-yl]propan-2-ol; MS (ES): 467 [M+H]$^+$;

2-[5-(2,2'-bithien-5-yl)-1-(2-chlorophenyl)-1H-pyrazol-3-yl]propan-2-ol; MS (ES): 401 [M+H]$^+$;

2-[5-(5-biphenyl-3-yl-2-thienyl)-1-(2-chlorophenyl)-1H-pyrazol-3-yl]propan-2-ol; MS (ES): 471 [M+H]$^+$;

2-[1-(2-chlorophenyl)-5-{5-[5-methyl-2-(propyloxy)phenyl]-2-thienyl}-1H-pyrazol-3-yl]propan-2-ol; MS (ES): 467 [M+H]$^+$;

2-{1-(2-chlorophenyl)-5-[5-(4-propylphenyl)-2-thienyl]-1H-pyrazol-3-yl}propan-2-ol; MS (ES): 437 [M+H]$^+$;

2-[1-(2-chlorophenyl)-5-(5-{4-[(trifluoromethyl)oxy]phenyl}-2-thienyl)-1H-pyrazol-3-yl]propan-2-ol; MS (ES): 479 [M+H]$^+$;

4-{5-[1-(2-chlorophenyl)-3-(1-hydroxy-1-methylethyl)-1H-pyrazol-5-yl]-2-thienyl}-N-(2-methylpropyl)benzamide; MS (ES): 494 [M+H]$^+$;

2-[1-(2-chlorophenyl)-5-{5-[3-(ethyloxy)phenyl]-2-thienyl}-1H-pyrazol-3-yl]propan-2-ol; MS (ES): 439 [M+H]$^+$;

2-{1-(2-chlorophenyl)-5-[5-(4-ethylphenyl)-2-thienyl]-1H-pyrazol-3-yl}propan-2-ol; MS (ES): 423 [M+H]$^+$;

2-{1-(2-chlorophenyl)-5-[5-(3,4-dichlorophenyl)-2-thienyl]-1H-pyrazol-3-yl}propan-2-ol; MS (ES): 463 [M+H]$^+$;

2-[1-(2-chlorophenyl)-5-{5-[6-(methyloxy)naphthalen-2-yl]-2-thienyl}-1H-pyrazol-3-yl]propan-2-ol; MS (ES): 475 [M+H]$^+$;

2-{1-(2-chlorophenyl)-5-[5-(2-ethylphenyl)-2-thienyl]-1H-pyrazol-3-yl}propan-2-ol; MS (ES): 423 [M+H]$^+$;

2-[1-(2-chlorophenyl)-5-{5-[4-(dimethylamino)phenyl]-2-thienyl}-1H-pyrazol-3-yl]propan-2-ol; MS (ES): 438 [M+H]$^+$;

2-{1-(2-chlorophenyl)-5-[5-(2,4,5-trifluorophenyl)-2-thienyl]-1H-pyrazol-3-yl}propan-2-ol; MS (ES): 449 [M+H]$^+$;

2-[1-(2-chlorophenyl)-5-{5-[2-fluoro-5-(trifluoromethyl)phenyl]-2-thienyl}-1H-pyrazol-3-yl]propan-2-ol; MS (ES): 481 [M+H]$^+$;

2-{1-(2-chlorophenyl)-5-[5-(2,3,4-trifluorophenyl)-2-thienyl]-1H-pyrazol-3-yl}propan-2-ol; MS (ES): 449 [M+H]$^+$;

N-(4-{5-[1-(2-chlorophenyl)-3-(1-hydroxy-1-methylethyl)-1H-pyrazol-5-yl]-2-thienyl}phenyl)acetamide; MS (ES): 452 [M+H]$^+$;

2-[1-(2-chlorophenyl)-5-{5-[3-(hydroxymethyl)phenyl]-2-thienyl}-1H-pyrazol-3-yl]propan-2-ol; MS (ES): 425 [M+H]$^+$;

2-[5-{5-[5-chloro-2-(methyloxy)phenyl]-2-thienyl}-1-(2-chlorophenyl)-1H-pyrazol-3-yl]propan-2-ol; MS (ES): 459 [M+H]$^+$;

2-[1-(2-chlorophenyl)-5-{5-[2,3,4-tris(methyloxy)phenyl]-2-thienyl}-1H-pyrazol-3-yl]propan-2-ol; MS (ES): 485 [M+H]$^+$;

2-[1-(2-chlorophenyl)-5-{5-[2-(trifluoromethyl)phenyl]-2-thienyl}-1H-pyrazol-3-yl]propan-2-ol; MS (ES): 463 [M+H]$^+$;

2-{1-(2-chlorophenyl)-5-[5-(1H-indol-5-yl)-2-thienyl]-1H-pyrazol-3-yl}propan-2-ol; MS (ES): 434 [M+H]$^+$;

2-[1-(2-chlorophenyl)-5-{5-[6-(ethyloxy)naphthalen-2-yl]-2-thienyl}-1H-pyrazol-3-yl]propan-2-ol; MS (ES): 489 [M+H]$^+$;

2-[1-(2-chlorophenyl)-5-{5-[4-(hydroxymethyl)phenyl]-2-thienyl}-1H-pyrazol-3-yl]propan-2-ol; MS (ES): 425 [M+H]$^+$;

2-{1-(2-chlorophenyl)-5-[5-(2,3-difluorophenyl)-2-thienyl]-1H-pyrazol-3-yl}propan-2-ol; MS (ES): 431 [M+H]$^+$;

2-{1-(2-chlorophenyl)-5-[5-(2,4-difluorophenyl)-2-thienyl]-1H-pyrazol-3-yl}propan-2-ol; MS (ES): 431 [M+H]$^+$;

2-[5-[5-(2-chloro-6-fluoro-3-methylphenyl)-2-thienyl]-1-(2-chlorophenyl)-1H-pyrazol-3-yl}propan-2-ol; MS (ES): 461 [M+H]$^+$;

2-[1-(2-chlorophenyl)-5-{5-[4-(methylthio)phenyl]-2-thienyl}-1H-pyrazol-3-yl]propan-2-ol; MS (ES): 441 [M+H]$^+$;

2-[1-(2-chlorophenyl)-5-{5-[4-(trifluoromethyl)phenyl]-2-thienyl}-1H-pyrazol-3-yl]propan-2-ol; MS (ES): 463 [M+H]$^+$;

±2-{5-[5-(6-chloro-2-fluoro-3-methylphenyl)-2-thienyl]-1-(2-chlorophenyl)-1H-pyrazol-3-yl}propan-2-ol; MS (ES): 461 [M+H]$^+$;

2-{1-(2-chlorophenyl)-5-[5-(4-fluoro-3-methylphenyl)-2-thienyl]-1H-pyrazol-3-yl}propan-2-ol; MS (ES): 427 [M+H]$^+$;

2-{1-(2-chlorophenyl)-5-[5-(3,4-difluorophenyl)-2-thienyl]-1H-pyrazol-3-yl}propan-2-ol; MS (ES): 431 [M+H]$^+$;

2-[1-(2-chlorophenyl)-5-{5-[4-(phenyloxy)phenyl]-2-thienyl}-1H-pyrazol-3-yl]propan-2-ol; MS (ES): 487 [M+H]$^+$;

2-[1-(2-chlorophenyl)-5-{5-[4-chloro-2-(trifluoromethyl)phenyl]-2-thienyl}-1H-pyrazol-3-yl]propan-2-ol; MS (ES): 497 [M+H]$^+$;

2-{1-(2-chlorophenyl)-5-[5-(2,5-dichlorophenyl)-2-thienyl]-1H-pyrazol-3-yl}propan-2-ol; MS (ES): 463 [M+H]$^+$;

2-[5-{5-[2-chloro-4-(ethyloxy)phenyl]-2-thienyl}-1-(2-chlorophenyl)-1H-pyrazol-3-yl]propan-2-ol; MS (ES): 473 [M+H]$^+$;

2-{1-(2-chlorophenyl)-5-[5-(3-chlorophenyl)-2-thienyl]-1H-pyrazol-3-yl}propan-2-ol; MS (ES): 429 [M+H]$^+$;

2-{1-(2-chlorophenyl)-5-[5-(1H-indol-4-yl)-2-thienyl]-1H-pyrazol-3-yl}propan-2-ol; MS (ES): 434 [M+H]$^+$;

2-[1-(2-chlorophenyl)-5-{5-[2-chloro-4-(trifluoromethyl)phenyl]-2-thienyl}-1H-pyrazol-3-yl]propan-2-ol; MS (ES): 497 [M+H]$^+$;

N-(3-{5-[1-(2-chlorophenyl)-3-(1-hydroxy-1-methylethyl)-1H-pyrazol-5-yl]-2-thienyl}phenyl)methanesulfonamide; MS (ES): 488 [M+H]$^+$;

3-{5-[1-(2-chlorophenyl)-3-(1-hydroxy-1-methylethyl)-1H-pyrazol-5-yl]-2-thienyl}benzenesulfonamide; MS (ES): 474 [M+H]$^+$;

3-{5-[1-(2-chlorophenyl)-3-(1-hydroxy-1-methylethyl)-1H-pyrazol-5-yl]-2-thienyl}-N-(1-methylethyl)benzamide; MS (ES): 480 [M+H]$^+$;

2-[1-(2-chlorophenyl)-5-{5-[4-fluoro-3-(trifluoromethyl)phenyl]-2-thienyl}-1H-pyrazol-3-yl]propan-2-ol; MS (ES): 481 [M+H]$^+$;

2-[5-{5-[3,5-bis(trifluoromethyl)phenyl]-2-thienyl}-1-(2-chlorophenyl)-1H-pyrazol-3-yl]propan-2-ol; MS (ES): 531 [M+H]$^+$;

2-[5-(5-biphenyl-4-yl-2-thienyl)-1-(2-chlorophenyl)-1H-pyrazol-3-yl]propan-2-ol; MS (ES): 471 [M+H]$^+$;

2-[1-(2-chlorophenyl)-5-{5-[4-(1-methylethyl)phenyl]-2-thienyl}-1H-pyrazol-3-yl]propan-2-ol; MS (ES): 437 [M+H]$^+$;

2-[1-(2-chlorophenyl)-5-(5-ethyl-2-thienyl)-1H-pyrazol-3-yl]propan-2-ol; MS (ES): 347 [M+H]$^+$;

2-[1-(2-chlorophenyl)-5-(5-{3-fluoro-4-[(phenylmethyl)oxy]phenyl}-2-thienyl)-1H-pyrazol-3-yl]propan-2-ol; MS (ES): 519 [M+H]$^+$;

2-[1-(2-chlorophenyl)-5-{5-[3-chloro-4-(trifluoromethyl)phenyl]-2-thienyl}-1H-pyrazol-3-yl]propan-2-ol; MS (ES): 497 [M+H]$^+$;

2-[1-(2-chlorophenyl)-5-{5-[4-(ethylsulfonyl)phenyl]-2-thienyl}-1H-pyrazol-3-yl]propan-2-ol; MS (ES): 487 [M+H]$^+$;

2-(5-{3-methyl-5-[3-(methylsulfonyl)phenyl]-2-thienyl}-1-[4-(trifluoromethyl)pyridin-3-yl]-1H-pyrazol-3-yl)propan-2-ol, MS(ES): 522 [M+H]$^+$, 504 (M-OH)

2-[1-(2-chlorophenyl)-5-{4-methyl-5-[3-(methylsulfonyl)phenyl]-2-thienyl}-1H-pyrazol-3-yl]propan-2-ol, MS(ES): 487 [M+H]$^+$, 469 (M-OH)

2-[1-(2-chlorophenyl)-5-{3-ethyl-5-[3-(methylsulfonyl)phenyl]-2-thienyl}-1H-pyrazol-3-yl]propan-2-ol, MS(ES): 501 [M+H]$^+$, 483 (M-OH)

2-[1-(2-chloro-3-fluorophenyl)-5-{3-ethyl-5-[3-(methylsulfonyl)phenyl]-2-thienyl}-1H-pyrazol-3-yl]propan-2-ol, MS(ES): 519 [M+H]$^+$, 501 (M-OH)

2-[5-{4-bromo-5-[3-(methylsulfonyl)phenyl]-2-thienyl}-1-(2-chlorophenyl)-1H-pyrazol-3-yl]propan-2-ol, MS(ES): 553 [M+H]$^+$.

2-[5-{4-bromo-3-methyl-5-[3-(methylsulfonyl)phenyl]-2-thienyl}-1-(2-chlorophenyl)-1H-pyrazol-3-yl]propan-2-ol, MS(ES): 567 [M+H]$^+$.

2-[1-(2-chlorophenyl)-5-{3-methyl-5-[3-(methylsulfonyl)phenyl]-2-thienyl}-1H-pyrazol-3-yl]propan-2-ol, MS(ES): 487 [M+H]$^+$.

2-[1-(2-chlorophenyl)-5-{3-methyl-4-[3-(methylsulfonyl)phenyl]-2-thienyl}-1H-pyrazol-3-yl]propan-2-ol, MS(ES): 487 [M+H]$^+$.

2-(1-[3-fluoro-2-(trifluoromethyl)phenyl]-5-{3-methyl-5-[3-(methylsulfonyl)phenyl]-2-thienyl}-1H-pyrazol-3-yl)propan-2-ol, MS(ES): 539 [M+H]$^+$.

2-[5-{3-bromo-5-[3-(methylsulfonyl)phenyl]-2-thienyl}-1-(2-chlorophenyl)-1H-pyrazol-3-yl]propan-2-ol MS(ES): 553 [M+H]$^+$.

2-[5-{3-chloro-5-[3-(methylsulfonyl)phenyl]-2-thienyl}-1-(2-chlorophenyl)-1H-pyrazol-3-yl]propan-2-ol, MS(ES): 507 [M+H]$^+$.

2-[1-(2-chloro-3-fluorophenyl)-5-{3-methyl-5-[3-(methylsulfonyl)phenyl]-2-thienyl}-1H-pyrazol-3-yl]propan-2-ol, MS(ES): 505 [M+H]$^+$.

methyl 5-(5-{3-[(1-methylethyl)sulfonyl]phenyl}-2-thienyl)-1-[3-(trifluoromethyl)pyridin-2-yl]-1H-pyrazole-3-carboxylate, MS(ES): 5536 [M+H]$^+$.

1-{5-(5-{3-[1-methylethyl)sulfonyl]phenyl}-2-thienyl)-1-[3-(trifluoromethyl)pyridin-2-yl]-1H-pyrazol-3-yl}ethanone, MS(ES): 520 [M+H]$^+$.

2-(5-(5-{3-[(1-methylethyl)sulfonyl]phenyl}-2-thienyl)-1-[3-(trifluoromethyl)pyridin-2-yl]-1H-pyrazol-3-yl)propan-2-ol, MS(ES): 536 [M+H]$^+$.

2-[1-(2-chlorophenyl)-5-(5-{3-[(1-methylethyl)sulfonyl]phenyl)-2-thienyl}-1H-pyrazol-3-yl]propan-2-ol, MS(ES): 501 [M+H]$^+$.

2-[1-(3-fluoropyridin-2-yl)-5-(5-[3-(methylsulfonyl)phenyl]-2-thienyl)-1H-pyrazol-3-yl]propan-2-ol, MS(ES): 458 [M+H]$^+$.

2-[1-(2-chloropyridin-3-yl)-5-{5-[3-(methylsulfonyl)phenyl]-2-thienyl}-1H-pyrazol-3-yl]propan-2-ol, MS(ES): 474 [M+H]$^+$.

2-[1-(2-bromophenyl)-5-{5-[4-(methylsulfonyl)phenyl]-2-thienyl}-1H-pyrazol-3-yl]propan-2-ol, MS(ES): 517 [M+H]$^+$.

2-[1-(2,3-difluorophenyl)-5-{5-[3-(methylsulfonyl)phenyl]-2-thienyl}-1H-pyrazol-3-yl]propan-2-ol, MS(ES): 475 [M+H]$^+$.

2-(5-{5-[3-(methylsulfonyl)phenyl]-2-thienyl}-1-{2-[(trifluoromethyl)oxy]phenyl}-1H-pyrazol-3-yl)propan-2-ol, MS(ES): 523 [M+H]$^+$.

2-[4-(3-chloro-2-fluorophenyl)-5-{5-[3-(methylsulfonyl)phenyl]-2-thienyl}-1H-pyrazol-3-yl]propan-2-ol, MS(ES): 491 [M+H]$^+$.

2-[1-(2,2-difluoro-1,3-benzodioxol-4-yl)-5-{5-[3-(methylsulfonyl)phenyl]-2-thienyl}-1H-pyrazol-3-yl]propan-2-ol, MS(ES): 519 [M+H]$^+$.

2-[1-[2-chloro-5-(trifluoromethyl)phenyl]-5-{5-[3-(methylsulfonyl)phenyl]-2-thienyl}-1H-pyrazol-3-yl]propan-2-ol, MS(ES): 565 [M+H]$^+$.

2-[1-(2,6-difluorophenyl)-5-{5-[3-(methylsulfonyl)phenyl]-2-thienyl}-1H-pyrazol-3-yl]propan-2-ol, MS(ES): 475 [M+H]$^+$.

2-[1-(3-fluoro-2-methylphenyl)-5-{5-[3-(methylsulfonyl)phenyl]-2-thienyl}-1H-pyrazol-3-yl]propan-2-ol, MS(ES): 471 [M+H]$^+$.

2-[1-(5-fluoropyridin-3-yl)-5-{5-[3-(methylsulfonyl)phenyl]-2-thienyl}-1H-pyrazol-3-yl]propan-2-ol, MS(ES): 458 [M+H]$^+$.

2-[4-chloro-1-(5-fluoropyridin-3-yl)-5-{5-[3-(methylsulfonyl)phenyl]-2-thienyl}-1H-pyrazol-3-yl]propan-2-ol, MS(ES): 492 [M+H]$^+$.

2-[4-bromo-1-(5-fluoropyridin-3-yl)-5-{5-[4-(methylsulfonyl)phenyl]-2-thienyl}-1H-pyrazol-3-yl]propan-2-ol, MS(ES): 538 [M+H]$^+$.

2-(5-{5-[3-(methylsulfonyl)phenyl]-2-thienyl}-1-[3-(trifluoromethyl)pyridin-4-yl]-1H-pyrazol-3-yl)propan-2-ol, MS(ES): 508 [M+H]$^+$.

2-[1-(3-fluoropyridin-4-yl)-5-{5-[3-(methylsulfonyl)phenyl]-2-thienyl}-1H-pyrazol-3-yl]propan-2-ol, MS(ES): 458 [M+H]$^+$.

2-[1-(3,5-dichloropyridin-4-yl)-5-{5-[3-(methylsulfonyl)phenyl]-2-thienyl}-1H-pyrazol-3-yl]propan-2-ol, MS(ES): 508 [M+H]$^+$.

2-[1-(3-chloropyridin-4-yl)-5-{5-[4-(methylsulfonyl)phenyl]-2-thienyl}-1H-pyrazol-3-yl]propan-2-ol, MS(ES): 474 [M+H]$^+$.

2-(1-[5-chloro-2-(phenyloxy)phenyl]-5-{5-[3-(methylsulfonyl)phenyl]-2-thienyl}-1H-pyrazol-3-yl)propan-2-ol; MS (ES): 565 [M+H]$^+$.

1-(1-[5-chloro-2-(phenyloxy)phenyl]-5-{5-[3-(methylsulfonyl)phenyl]-2-thienyl}-1H-pyrazol-3-yl)ethanone; MS (ES): 549 [M+H]$^+$.

3-{5-[1-(2,5-dichlorophenyl)-3-(1-hydroxy-1-methylethyl)-1H-pyrazol-5-yl]-2-thienyl}benzenesulfonamide; MS (ES): 508 and 510 [each M+H]$^+$.

3-{5-[3-acetyl-1-(2,5-dichlorophenyl)-1H-pyrazol-5-yl]-2-thienyl}benzenesulfonamide; MS (ES): 492 and 494 [each M+H]$^+$.

2-(3-(3-(2-hydroxypropan-2-yl)-5-(3-(methylsulfonyl)phenyl)thiophen-2-yl)-1H-pyrazol-1-yl)phenyl)propan-2-ol. MS (ES): 497 [M+H]$^+$.

2-(1-(2,4-difluorophenyl)-5-(5-(3-(methylsulfonyl)phenyl)thiophen-2-yl)-1H-pyrazol-3-yl)propan-2-ol. MS (ES): 475 [M+H]$^+$.

2-(1-(3,5-difluorophenyl)-5-(5-(3-(methylsulfonyl)phenyl)thiophen-2-yl)-1H-pyrazol-3-yl)propan-2-ol. MS (ES): 475 [M+H]$^+$.

2-(1-(3,4-difluorophenyl)-5-(5-(3-(methylsulfonyl)phenyl)thiophen-2-yl)-1H-pyrazol-3-yl)propan-2-ol. MS (ES): 475 [M+H]$^+$.

2-(1-(2,4-dichlorophenyl)-5-(5-(3-(methylsulfonyl)phenyl)thiophen-2-yl)-1H-pyrazol-3-yl)propan-2-ol. MS (ES): 507 [M+H]$^+$.

2-(1-(2,3-dichlorophenyl)-5-(5-(3-(methylsulfonyl)phenyl)thiophen-2-yl)-1H-pyrazol-3-yl)propan-2-ol. MS (ES): 507 [M+H]$^+$.

2-(1-(2,5-difluorophenyl)-5-(5-(3-(methylsulfonyl)phenyl)thiophen-2-yl)-1H-pyrazol-3-yl)propan-2-ol. MS (ES): 475 [M+H]$^+$.

2-(1-(3,5-dichlorophenyl)-5-(5-(3-(methylsulfonyl)phenyl)thiophen-2-yl)-1H-pyrazol-3-yl)propan-2-ol. MS (ES): 507 [M+H]$^+$.

2-(1-(3,4-dichlorophenyl)-5-(5-(3-(methylsulfonyl)phenyl)thiophen-2-yl)-1H-pyrazol-3-yl)propan-2-ol. MS (ES): 507 [M+H]$^+$.

2-(1-(2-ethylphenyl)-5-(5-(3-(methylsulfonyl)phenyl)thiophen-2-yl)-1H-pyrazol-3-yl)propan-2-ol. MS (ES): 467 [M+H]$^+$.

2-(5-(5-(3-(methylsulfonyl)phenyl)thiophen-2-yl)-1-(2-propylphenyl)-1H-pyrazol-3-yl)propan-2-ol. MS (ES): 481 [M+H]$^+$.

2-(1-(5-fluoro-2-methylphenyl)-5-(5-(3-(methylsulfonyl)phenyl)thiophen-2-yl)-1H-pyrazol-3-yl)propan-2-ol. MS (ES): 471 [M+H]$^+$.

2-O-(3-chloro-2-methylphenyl)-5-(5-(3-(methylsulfonyl)phenyl)thiophen-2-yl)-1H-pyrazol-3-yl)propan-2-ol. MS (ES): 487 [M+H]$^+$.

2-O-(2,4-dichloro-6-(trifluoromethyl)phenyl)-5-(5-(3-(methylsulfonyl)phenyl)-thiophen-2-yl)-1H-pyrazol-3-yl)propan-2-ol. MS (ES): 575 [M+H]$^+$.

2-(1-(2-isopropylphenyl)-5-(5-(3-(methylsulfonyl)phenyl)thiophen-2-yl)-1H-pyrazol-3-yl)propan-2-ol. MS (ES): 481[M+H]$^+$.

2-(5-(5-(3-(methylsulfonyl)phenyl)thiophen-2-yl)-1-(pyridin-3-yl)-1H-pyrazol-3-yl)propan-2-ol. MS (ES): 440 [M+H]$^+$.

2-(1-(2,6-dimethylphenyl)-5-(5-(3-(methylsulfonyl)phenyl)thiophen-2-yl)-1H-pyrazol-3-yl)propan-2-01. MS (ES): 467[M+H]$^+$.

2-(1-(2-fluoro-6-(trifluoromethyl)phenyl)-5-(5-(3-(methylsulfonyl)phenyl)thiophen-2-yl)-1H-pyrazol-3-yl)propan-2-ol. MS (ES): 525[M+H]$^+$ 2-(1-(2-(difluoromethoxy)phenyl)-5-(5-(3-(methylsulfonyl) phenyl)thiophen-2-yl)-1H-pyrazol-3-yl)propan-2-ol. MS (ES): 505 [M+H]⁺.

2-(1-(3-fluoro-2-trifluoromethyl)phenyl)-5-(5-(3-(methylsulfonyl)phenyl)thiophen-2-yl)-1H-pyrazol-3-yl)propan-2-ol. MS (ES): 525 [M+H]⁺.

3-(5-(1-(2-chlorophenyl)-3-(2-hydroxypropan-2-yl)-1H-pyrazol-5-yl)thiophen-2-yl)-N-(2-(dimethylamino)ethyl) benzenesulfonamide. MS (ES): 545 [M+H]⁺.

2-(5-(3-bromo-5-(3-(methylsulfonyl)phenyl)thiophen-2-yl)-1-(3-fluoro-2-methylphenyl)-1H-pyrazol-3-yl)propan-2-ol. MS (ES): 549 [M+H]⁺.

2-(5-(3-bromo-5-(3-(methylsulfonyl)phenyl)thiophen-2-yl)-1-(2-chloro-3-fluorophenyl)-1H-pyrazol-3-yl)propan-2-ol. MS (ES): 569 [M+H]⁺.

2-(1-(2-chloro-3-fluorophenyl)-5-(3-chloro-5-(3-(methylsulfonyl)phenyl)thiophen-2-yl)-1H-pyrazol-3-yl)propan-2-ol. MS (ES): 525 [M+H]⁺.

2-(5-(3-chloro-5-(3-(methylsulfonyl)phenyl)thiophen-2-yl)-1-(3-fluoro-2-(trifluoromethyl)phenyl)-1H-pyrazol-3-yl) propan-2-ol. MS (ES): 559 [M+H]⁺.

2-(5-(3-bromo-5-(3-(methylsulfonyl)phenyl)thiophen-2-yl)-1-(3-fluoro-2-(trifluoromethyl)phenyl)-1H-pyrazol-3-yl) propan-2-ol. MS (ES): 603 [M+H]⁺.

2-(1-(3-fluoro-2-methylphenyl)-5-(3-methyl-5-(3-(methylsulfonyl)phenyl)thiophen-2-yl)-1H-pyrazol-3-yl)propan-2-ol. MS (ES): 485 [M+H]⁺.

2-(5-{3-methyl-5-[3-(methylsulfonyl)phenyl]-2-thienyl}-1-[2-(trifluoromethyl)pyridin-3-yl]-1H-pyrazol-3-yl)propan-2-ol, MS(ES): 522 [M+H]⁺.

Example 9

2-[1-(2-chlorophenyl)-5-{5-[3-(methylsulfonyl)phenyl]-2-thienyl}-1H-pyrazol-3-yl]-1,1,1,3,3,3-hexafluoropropan-2-ol Example 9a Preparation of 2-[5-(5-bromothiophen-2-yl)-1-(2-chlorophenyl)-1H-pyrazol-3-yl]-1,1,1,3,3,3-hexafluoro-propan-2-ol

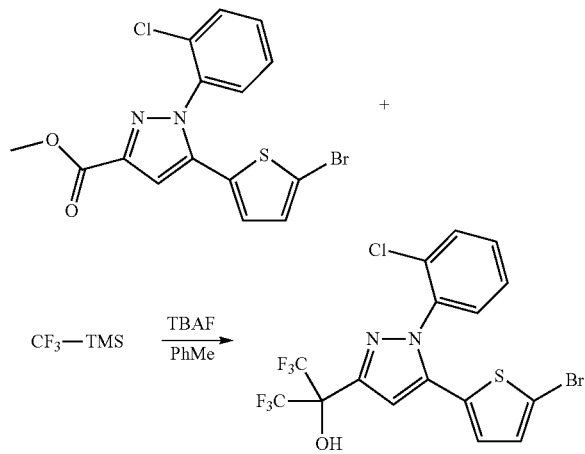

To a stirred solution of 5-(5-bromothiophen-2-yl)-1-(2-chlorophenyl)-1H-pyrazole-3-carboxylic acid methyl ester (0.40 g, 1.0 mmol) and trifluoromethyl-trimethylsilane (CF₃-TMS) (0.59 mL, 4.0 mmol) in toluene (4 mL, anhyd) was added dropwise a 1.0M solution of tetrabutylammonium fluoride (TBAF) in THF (0.20 mL, 20 mol %, dried over 4 Å molecular sieves). After 2 h the reaction mixture was charged with additional CF₃-TMS (0.3 mL) and TBAF (50 µL), then heated at 45° C. After 20 h (total) the reaction mixture was allowed to cool to ambient temperature, diluted with DCM (50 mL), washed with H₂O and brine, then dried (Na₂SO₄) and concentrated under reduced pressure. The resulting residue was purified by chromatography (silica, EtOAc/Hex, 0:100 to 30:70) to give the title compound (86 mg). Rf 0.38 (20% EtOAc/Hex); GC-MS (EI): 504, 506 [M⁺].

Example 9b

Preparation of 2-[1-(2-chlorophenyl)-5-{5-[3-(methylsulfonyl)phenyl]-2-thienyl}-1H-pyrazol-3-yl]-1,1,1,3,3,3-hexafluoropropan-2-ol

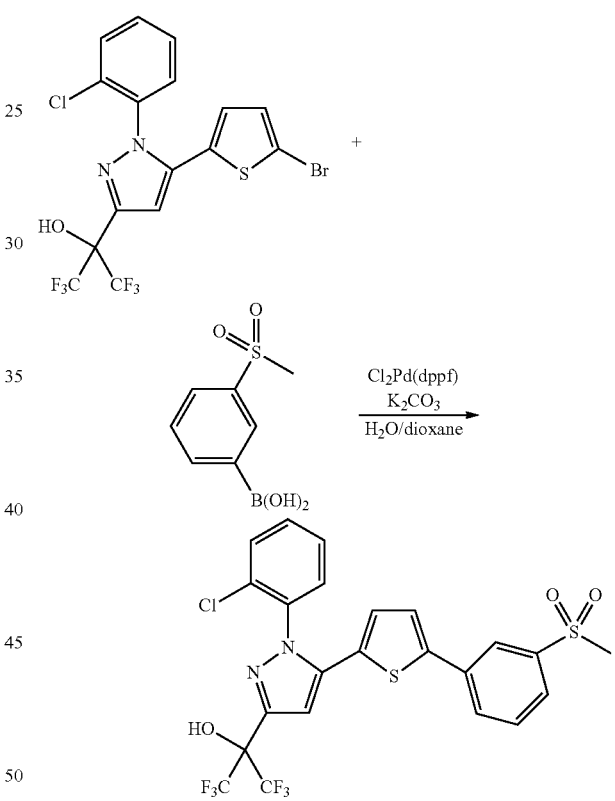

A mixture of 2-[5-(5-bromothiophen-2-yl)-1-(2-chlorophenyl)-1H-pyrazol-3-yl]-1,1,1,3,3,3-hexafluoro-propan-2-ol (84 mg, 0.17 mmol), 3-methanesulfonyl-phenylboronic acid (42 mg, 0.21 mmol), K₂CO₃ (70 mg, 0.51 mmol), Cl₂Pd (dppf).DCM (21 mg, 15 mol %) and H₂O (0.2 mL) in dioxane (2 mL) was sparged with Argon for 5 min and then heated at 80° C. as a sealed flask. After 3 h the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 0:100 to 50:50) to give the title compound (34 mg) as a white solid. ¹H-NMR (DCM-d₂): δ 8.03 (m, 1H), 7.83 (m, 1H), 7.76 (m, 1H), 7.55-7.62 (m, 4H), 7.49-7.54 (m, 1H), 7.29 (d, 1H), 6.91 (d, 1H), 6.86 (s, 1H), 5.10 (s, 1H), 3.05 (s, 3H); MS(ES): 581 [M+H]⁺.

The following compound was prepared from the appropriate methyl ketone intermediate in a similar manner:

2-[1-(2-chlorophenyl)-5-{5-[3-(methylsulfonyl)phenyl]-2-thienyl}-1H-pyrazol-3-yl]-1,1,1-trifluoropropan-2-ol, MS(ES): 527 [M+H]+

The following compound was prepared from the appropriate carboxaldehyde intermediate in a similar manner:

1-[1-(2-chlorophenyl)-5-{5-[3-(methylsulfonyl)phenyl]-2-thienyl}-1H-pyrazol-3-yl]-2,2,2-trifluoroethanol, GC-MS (EI): 512 [M+].

Example 10

2-{1-(2-Chloro-phenyl)-4-fluoro-5-[5-(3-methanesulfonyl-phenyl)-thiophen-2-yl]-1H-pyrazol-3-yl}-propan-2-ol

Example 10a

Preparation of 2-bromo-5-(2-fluoro-1,1-dimethoxy-ethyl)-thiophene

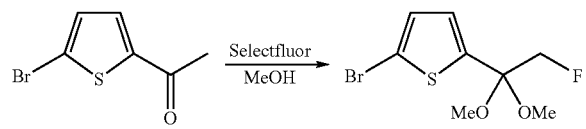

To a solution of 2-acetyl-5-bromothiophene (10.3 g, 50 mmol) in city methanol (300 mL) was added selectfluor (25 g, 70.57 mmol). The suspension was stirred at reflux for 50 h. Evaporation of solvent gave a residual solid, which was taken up in DCM. The insoluble material was filtered off and the filtrate was washed with water, dried over sodium sulfate and evaporated in vacuo. The crude product was purified by flash chromatography on silica gel eluted with EtOAc-hexane (0-30%) to afford 2-bromo-5-(2-fluoro-1,-dimethoxy-ethyl)-thiophene as a white solid (4.8 g, 36%). $^1$H-NMR (CDCl$_3$): δ 6.98 (d, 1H), 6.84 (d, 1H), 4.51 (d, 2H), 3.29 (s, 6H).

Example 10b

Preparation of 1-(5-bromo-thiophen-2-yl)-2-fluoro-ethanone

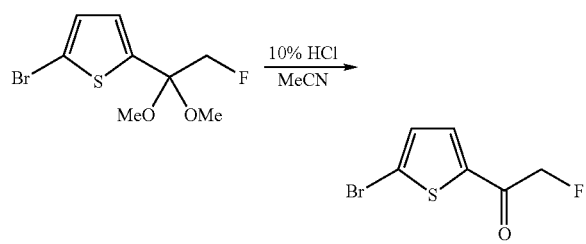

To a stirred solution of 2-bromo-5-(2-fluoro-1,1-dimethoxy-ethyl)-thiophene (9.4 g, 35 mmol) in MeCN (100 mL) was added 10% aq. HCl (50 mL) at 20° C. and the reaction mixture was stirred at ° C. for 3 h. Solvent was removed in vacuo to afford a residue, which was partitioned between DCM and water, the aqueous layer was extracted with DCM. The combined organic layers were washed with water, sat aq. NaHCO$_3$ and brine, dried over sodium sulfate and evaporated in vacuo to give a white solid. It was dissolved in minimum volume of DCM, and a large volume of hexane was added. After evaporation of most of the solvent, solid precipitated and was then collected with filtration, washed with hexane and dried under high vacuum to afford 1-(5-bromo-thiophen-2-yl)-2-fluoro-ethanone (6.52 g, 84%). $^1$H-NMR (CDCl$_3$): δ 7.64 (d, 1H), 7.15 (d, 1H), 5.26 (d, 2H).

Example 10c

Preparation of 5-(5-bromo-thiophen-2-yl)-1-(2-chloro-phenyl)-4-fluoro-1H-pyrazole-3-carboxylic acid methyl ester

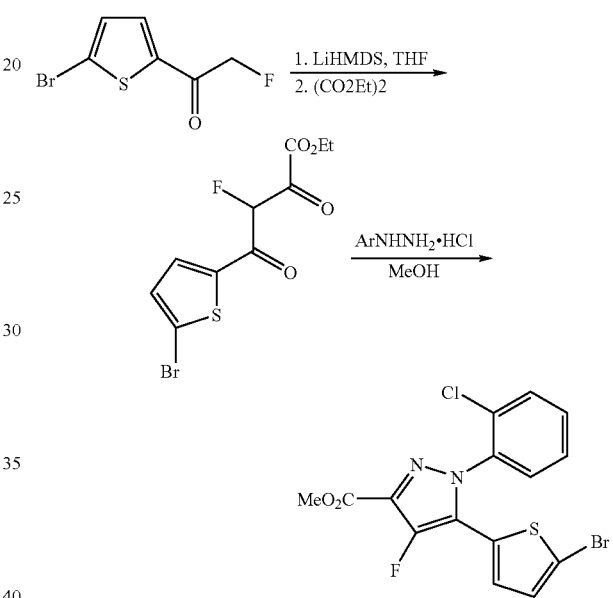

To a stirred solution of 1-(5-bromo-thiophen-2-yl)-2-fluoro-ethanone (6.59 g, 29.54 mmol) in dry THF (200 mL) was added a solution of LiHMDS in THF (1.0 M, 36 mL, 36 mmol) under nitrogen at −78° C. and the reaction mixture was stirred at −78° C. for 40 min, then a solution of diethyl oxalate (6 mL, 4425 mmol) in dry THF (50 mL) was added dropwise. The mixture was allowed to warm to 20° C. overnight, then quenched with 2 N aq. HCl and extracted with ether. The combined organic layers were washed with brine, dried over sodium sulfate and evaporated in vacuo to afford 5-(5-bromo-thiophen-2-yl)-1-(2-chloro-phenyl)-4-fluoro-1H-pyrazole-3-carboxylic acid methyl ester as a dark-red oil (10.4 g, 100%), which was used in the next reaction without further purification.

A mixture of the above oil (6.4 g, 19.81 mmol) and 2-chlorophenylhydrazine hydrochloride (4.0 g, 22.3 mmol) in dry EtOH (100 mL) was refluxed for 12 h. Solvent was then removed in vacuo to give a residue, which was partitioned between EtOAc and water and aqueous layer was separated and extracted with EtOAc. The combined organic layers were washed with sat. NaHCO$_3$ and brine, dried over sodium sulfate and evaporated in vacuo to give a crude. The crude product was purified by flash chromatography on silica gel eluted with EtOAc-hexane (0-30%) to afford 5-(5-bromo-thiophen-2-yl)-1-(2-chloro-phenyl)-4-fluoro-1H-pyrazole- 3-carboxylic acid methyl ester as a dark-red syrup (4.27 g, 50%). MS(ES): 431 [M+1-1]+.

Example 10d

Preparation of 2-{1-(2-Chloro-phenyl)-4-fluoro-5-[5-(3-methanesulfonyl-phenyl)-thiophen-2-yl]-1H-pyrazol-3-yl-}-propan-2-ol

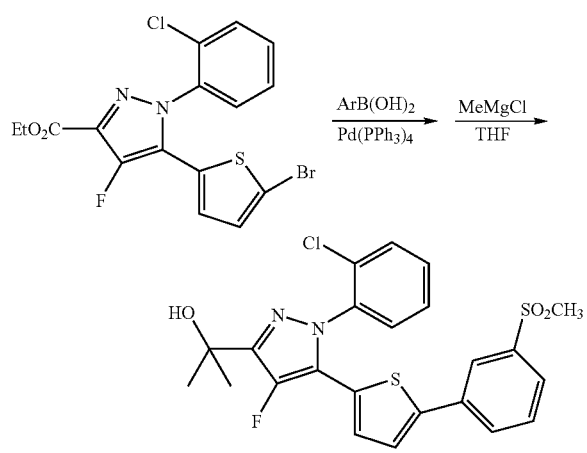

The title compound was prepared in a manner similar to that described in Examples 8c and 8d by using 5-(5-bromo-thiophen-2-yl)-1-(2-chloro-phenyl)-4-fluoro-1H-pyrazole-3-carboxylic acid ethyl ester. $^1$H-NMR (CDCl$_3$): δ 8.03 (m, 1H), 7.82 (m, 1H), 7.72 (m, 1H), 7.57-7.45 (m, 5H), 7.27 (d, 1H), 6.99 (d, 1H), 3.07 (s, 3H), 2.74 (s, 1H), 1.72 (s, 6H).

Example 11

Preparation of 2-[4-Bromo-5-[5-(3-methanesulfonyl-phenyl)-thiophen-2-yl]-1-(2-trifluoromethyl-phenyl)-1H-pyrazol-3-yl]-propan-2-ol

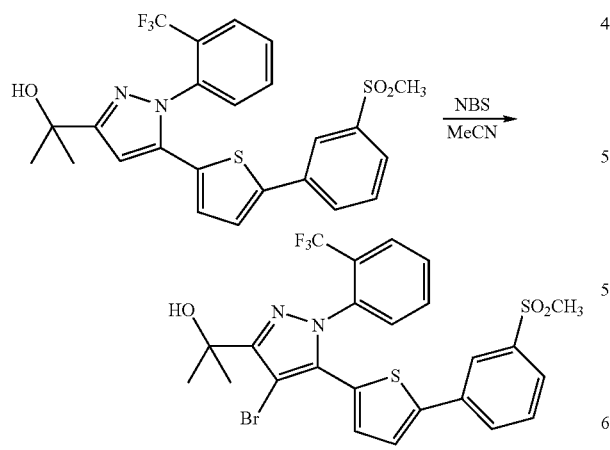

To a stirred solution of 2-[5-[5-(3-methanesulfonyl-phenyl)-thiophen-2-yl]-1-(2-trifluoromethyl-phenyl)-1H-pyrazol-3-yl]-propan-2-ol (254 mg, 0.5 mmol) in dry MeCN was added N-bromosuccinimide (94 mg, 0.53 mmol) at 20° C. and the reaction mixture was stirred at 20° C. overnight. Evaporation of solvent gave a residue, which was purified by flash chromatography on silica gel eluted with EtOAC-hexane (0-60%) to afford the title compound as a white solid (286 mg, 98%). $^1$H-NMR (CDCl$_3$): δ 8.05 (m, 1H), 7.85-7.81 (m, 2H), 7.76 (m, 1H), 7.63-7.61 (m, 2H), 7.56 (t, 1H), 7.39 (m, 1H), 7.25 (d, 1H), 6.98 (d, 1H), 3.09 (s, 1H), 3.07 (s, 3H), 1.74 (s, 6H).

The following compounds are prepared essentially according to the previous examples:

4-bromo-1-(2,6-dichlorophenyl)-5-{5-[3-(methylsulfonyl)phenyl]-2-thienyl}-3-(trifluoromethyl)-1H-pyrazole, MS(ES): 597 [M+H]+

2-[4-bromo-1-(2-chlorophenyl)-5-{5-[3-(methylsulfonyl)phenyl]-2-thienyl}-1H-pyrazol-3-yl]propan-2-ol, MS(ES): 553 [M+H]+, 535 (M-OH)

2-[4-bromo-1-(2,6-dichlorophenyl)-5-{5-[3-(methylsulfonyl)phenyl]-2-thienyl}-1H-pyrazol-3-yl]propan-2-ol, MS(ES): 569 (M-OH)

2-[4-bromo-1-(3-chloro-2-fluorophenyl)-5-{5-[3-(methylsulfonyl)phenyl]-2-thienyl}-1H-pyrazol-3-yl]propan-2-ol, MS(ES): 551 (M-OH)

2-[4-bromo-1-(2-ethylphenyl)-5-{5-[4-(methylsulfonyl)phenyl]-2-thienyl}-1H-pyrazol-3-yl]propan-2-ol, MS(ES): 545 [M+H]+, 527 (M-OH)

2-(4-bromo-5-{5-[3-(methylsulfonyl)phenyl]-2-thienyl}-1-{2-[(trifluoromethyl)oxy]phenyl}-1H-pyrazol-3-yl)propan-2-ol, MS(ES): 601 [M+H]+, 584 (M-OH)

2-[4-bromo-1-(2-bromophenyl)-5-{5-[3-(methylsulfonyl)phenyl]-2-thienyl}-1H-pyrazol-3-yl]propan-2-ol, MS(ES): 595 [M+H]+, 577 (M-OH)

2-(4-bromo-5-{5-[3-(methylsulfonyl)phenyl]-2-thienyl}-1-[4-(trifluoromethyl)pyridin-3-yl]-1H-pyrazol-3-yl)propan-2-ol, MS(ES): 586 [M+H]+, 568 (M-OH)

2-(4-Bromo-5-{5-[3-(methylsulfonyl)phenyl]-2-thienyl}-1-[3-(trifluoromethyl)pyridin-2-yl]-1H-pyrazol-3-yl)propan-2-ol, MS(ES): 586 [M+H]+, 568 (M-OH)

2-(4-Bromo-5-{5-[4-(methylsulfonyl)phenyl]-2-thienyl}-1-[2-(trifluoromethyl)pyridin-3-yl]-1H-pyrazol-3-yl)propan-2-ol, MS(ES): 586 [M+H]+, 568 (M-OH)

2-[4-Bromo-1-(3-fluoro-2-methylphenyl)-5-{5-[3-(methylsulfonyl)phenyl]-2-thienyl}-1H-pyrazol-3-yl]propan-2-ol, MS(ES): 550 [M+H]+, 531 (M-OH)

2-[4-Bromo-1-(2-chloro-3-fluorophenyl)-5-{5-[3-(methylsulfonyl)phenyl]-2-thienyl}-1H-pyrazol-3-yl]propan-2-ol, MS(ES): 569 [M+H]+, 551 (M-OH)

Example 12

Preparation of 2-{4-Chloro-1-(2-fluoro-phenyl)-5-[5-(3-methanesulfonyl-phenyl)-thiophen-2-yl]-1H-pyrazol-3-yl}-propan-2-ol

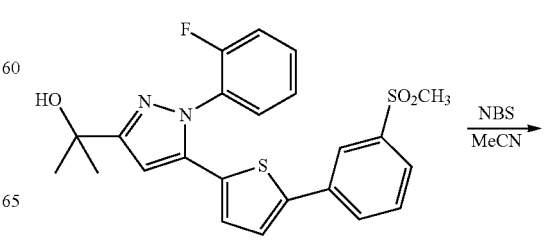

-continued

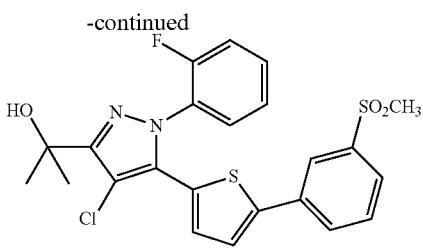

To a stirred solution of 2-{1-(2-Fluoro-phenyl)-5-[5-(3-methanesulfonyl-phenyl)-thiophen-2-yl]-1H-pyrazol-3-yl}-propan-2-ol (115 mg, 0.25 mmol) in dry MeCN was added N-chlorosuccinimide (35 mg, 026 mmol) at 20° C. and the reaction mixture was stirred in a sealed vial at 75° C. overnight. Evaporation of solvent gave a residue, which was purified by flash chromatography on silica gel eluting with EtOAC-hexane (0-60%) to afford the title compound as a white solid (123 mg, 100%). $^1$H-NMR (CDCl$_3$): δ 8.08 (m, 1H), 7.84 (m, 1H), 7.78 (m, 1H), 7.59-7.49 (m, 3H), 7.30-7.28 (m, 2H), 7.17 (t, 1H), 7.03 (d, 1H), 3.08 (s, 4H), 1.74 (s, 6H).

The following compounds are prepared essentially according to the previous examples:

2-(4-chloro-5-{5-[4-(methylsulfonyl)phenyl]-2-thienyl}-1-[3-(trifluoromethyl)pyridin-4-yl]-1H-pyrazol-3-yl)propan-2-ol, MS(ES): 542 [M+H]$^+$.

2-[4-chloro-1-(3-fluoropyridin-4-yl)-5-{5-[3-(methylsulfonyl)phenyl]-2-thienyl}-1H-pyrazol-3-yl]propan-2-ol, MS(ES): 492 [M+H]$^+$.

2-[4-chloro-1-(3-chloropyridin-4-yl)-5-{5-[3-(methylsulfonyl)phenyl]-2-thienyl}-1H-pyrazol-3-yl]propan-2-ol, MS(ES): 508 [M+H]$^+$.

2-[4-chloro-1-(3,5-dichloropyridin-4-yl)-5-{5-[3-(methylsulfonyl)phenyl]-2-thienyl}-1H-pyrazol-3-yl]propan-2-ol, MS(ES): 544 [M+H]$^+$.

2-[4-Chloro-1-(2-chlorophenyl)-5-{5-[3-(methylsulfonyl)phenyl]-2-thienyl}-1H-pyrazol-3-yl]propan-2-ol, MS(ES): 507 [M+H]$^+$, 489 (M-OH)

2-[4-chloro-1-(2,6-dichlorophenyl)-5-{5-[3-(methylsulfonyl)phenyl]-2-thienyl}-1H-pyrazol-3-yl]propan-2-ol, MS(ES): 541 [M+H]$^+$, 523 (M-OH)

2-(4-chloro-5-{5-[3-(methylsulfonyl)phenyl]-2-thienyl}-1-[2-(trifluoromethyl)phenyl]-1H-pyrazol-3-yl)propan-2-ol, MS(ES): 541 [M+H]$^+$, 523 (M-OH)

2-[4-chloro-1-(3-chloro-2-fluorophenyl)-5-{5-[3-(methylsulfonyl)phenyl]-2-thienyl}-1H-pyrazol-3-yl]propan-2-ol, MS(ES): 525 [M+H]$^+$, 507 (M-OH)

2-[4-chloro-1-(2-ethylphenyl)-5-{5-[4-(methylsulfonyl)phenyl]-2-thienyl}-1H-pyrazol-3-yl]propan-2-ol, MS(ES): 501 [M+H]$^+$, 483 (M-OH)

2-(4-chloro-5-{5-[3-(methylsulfonyl)phenyl]-2-thienyl}-1-{2-[(trifluoromethyl)oxy]phenyl}-1H-pyrazol-3-yl)propan-2-ol, MS(ES): 557 [M+H]$^+$, 539 (M-OH)

2-[4-Chloro-1-(2-bromophenyl)-5-{5-[4-(methylsulfonyl)phenyl]-2-thienyl}-1H-pyrazol-3-yl]propan-2-ol, MS(ES): 551 [M+H]$^+$, 533 (M-OH)

2-(4-Chloro-5-{5-[3-(methylsulfonyl)phenyl]-2-thienyl}-1-[4-(trifluoromethyl)pyridin-3-yl]-1H-pyrazol-3-yl)propan-2-ol, MS(ES): 542 [M+H]$^+$, 524 (M-OH)

2-(4-Chloro-5-{5-[3-(methylsulfonyl)phenyl]-2-thienyl}-1-[2-(trifluoromethyl)pyridin-3-yl]-1H-pyrazol-3-yl)propan-2-ol, MS(ES): 542 [M+H]$^+$, 524 (M-OH)

2-(4-Chloro-5-{5-[3-(methylsulfonyl)phenyl]-2-thienyl}-1-[3-(trifluoromethyl)pyridin-2-yl]-1H-pyrazol-3-yl)propan-2-ol, MS(ES): 542 [M+H]$^+$, 524 (M-OH)

2-[4-Chloro-1-(3-fluoro-2-methylphenyl)-5-{5-[3-(methylsulfonyl)phenyl]-2-thienyl}-1H-pyrazol-3-yl]propan-2-ol, 505 [M+H]$^+$, 487 (M-OH)

2-[4-Chloro-1-(2-chloro-3-fluorophenyl)-5-{5-[3-(methylsulfonyl)phenyl]-2-thienyl}-1H-pyrazol-3-yl]propan-2-ol, MS(ES): 525 [M+H]$^+$, 507 (M-OH)

2-[4-Chloro-1-(2,3-difluorophenyl)-5-{5-[3-(methylsulfonyl)phenyl]-2-thienyl}-1H-pyrazol-3-yl]propan-2-ol, MS(ES): 509 [M+H]$^+$, 491 (M-OH)

2-[4-Chloro-1-(2,6-dimethylphenyl)-5-{5-[3-(methylsulfonyl)phenyl]-2-thienyl}-1H-pyrazol-3-yl]propan-2-ol, MS(ES): 501 [M+H]$^+$, 483 (M-OH)

2-[4-Chloro-1-(2,6-difluorophenyl)-5-{5-[3-(methylsulfonyl)phenyl]-2-thienyl}-1H-pyrazol-3-yl]propan-2-ol, MS(ES): 509 [M+H]$^+$, 491 (M-OH)

2-[4-Chloro-1-(2-chloro-6-fluorophenyl)-5-{5-[3-(methylsulfonyl)phenyl]-2-thienyl}-1H-pyrazol-3-yl]propan-2-ol, MS(ES): 525 [M+H]$^+$, 507 (M-OH)

2-[4-Chloro-1-(2-chloro-6-dimethylphenyl)-5-{5-[3-(methylsulfonyl)phenyl]-2-thienyl}-1H-pyrazol-3-yl]propan-2-ol, MS(ES): 521 [M+H]$^+$, 503 (M-OH)

2-[4-Chloro-1-(2,4-difluorophenyl)-5-{5-[4-(methylsulfonyl)phenyl]-2-thienyl}-1H-pyrazol-3-yl]propan-2-ol, MS(ES): 509 [M+H]$^+$, 491 (M-OH)

2-(4-chloro-5-{3-methyl-5-[3-(methylsulfonyl)phenyl]-2-thienyl}-1-[4-(trifluoromethyl)pyridin-3-yl]-1H-pyrazol-3-yl)propan-2-ol, MS(ES): 556 [M+H]$^+$, 538 (M-OH)

2-[4-chloro-3-(1-hydroxy-1-methylethyl)-5-{5-[3-(methylsulfonyl)phenyl]-2-thienyl}-1H-pyrazol-1-yl]-6-(trifluoromethyl)phenol, MS(ES): 557 [M+H]$^+$, 539 (M-OH)

2-[4-chloro-1-(2-chlorophenyl)-5-{1-methyl-5-[3-(methylsulfonyl)phenyl]-1H-pyrrol-2-yl}-1H-pyrazol-3-yl]propan-2-ol, MS(ES): 504 [M+H]$^+$, 486 (M-OH)

2-(4-chloro-5-{3-methyl-5-[3-(methylsulfonyl)phenyl]-2-thienyl}-1-[4-(trifluoromethyl)pyridin-3-yl]-1H-pyrazol-3-yl)propan-2-ol, MS(ES): 604 [M+H]$^+$, 524 (M-79).

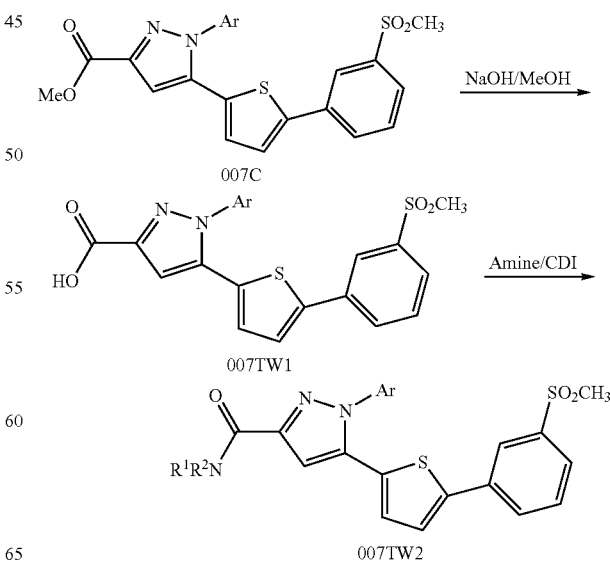

As depicted in Scheme 7 ester 007C was transformed into amides. Ester 007C was hydrolyzed to give acid 007TW1, which treated with carbonyldiimidazole and then an amine to afford amide 007TW2.

Example 13

1-(2-chlorophenyl)-N-ethyl-5-{5-[3-(methylsulfonyl)phenyl]-2-thienyl}-1H-pyrazole-3-carboxamide

Example 13a

Preparation of 1-(2-chlorophenyl)-5-{5-[3-(methylsulfinyl)phenyl]-2-thienyl}-1H-pyrazole-3-carboxylic acid

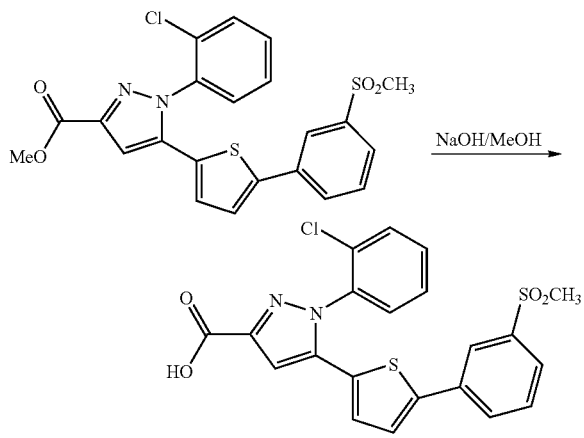

To a solution of 1-(2-chloro-phenyl)-5-[5-(3-methanesulfonyl-phenyl)-thiophen-2-yl]-1H-pyrazole-3-carboxylic acid methyl ester (5.8 g, 123 mmol) in MeOH (50 mL) was added aqueous NaOH (4 N, 25 mL) and the mixture was refluxed for 2 h. After cooling to 20° C., solvent was removed. Water was added to dissolve the crude and then the solution was acidified with acetic acid. Solid was collected by filtration and washed with water and dried under high vacuum to give 1-(2-chlorophenyl)-5-{5-[3-(methylsulfonyl)phenyl]-2-thienyl}-1H-pyrazole-3-carboxylic acid (5.1 g). MS(ES): 459 [M+H]$^+$.

Example 13b

Preparation of 1-(2-chlorophenyl)-N-ethyl-5-{5-[3-(methylsulfonyl)phenyl]-2-thienyl}-1H-pyrazole-3-carboxamide

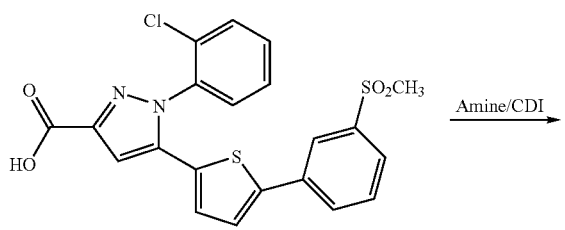

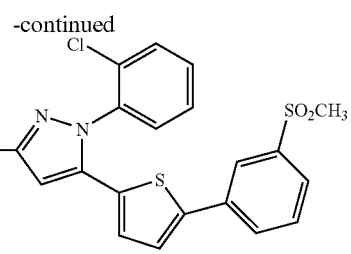

To a suspension of 1-(2-chlorophenyl)-5-{5-[3-(methylsulfonyl)phenyl]-2-thienyl}-1H-pyrazole-3-carboxylic acid (92 mg, 0.2 mmol) in DCM (2 mL) was added carbonyldiimidazole (39 mg, 1.2 equiv) and stirring was continued for 2 h at 20° C. A solution of ethylamine in THF (1.8 M, 0.17 mL, 1.5 equiv) was added and the mixture was stirred overnight at 20° C. Evaporation of solvent gave a crude, which was purified by column chromatography on silica gel eluting with MeOH-DCM (1:19) to afford 1-(2-chlorophenyl)-N-ethyl-5-{5-[3-(methylsulfonyl)phenyl]-2-thienyl}-1H-pyrazole-3-carboxamide (84 mg). $^1$H-NMR (CDCl$_3$): δ 8.03 (m, 1H), 7.83 (m, 1H), 7.74 (m, 1H), 7.62-7.45 (m, 5H), 7.22 (m, 1H), 7.19 (s, 1H), 6.91 (m, 1H), 6.82 (d, 1H), 3.55-3.43 (m, 2H), 3.07 (3 s, H), 1.25 (s, 3H). MS(ES): 486 [M+H]$^+$.

The following compounds are prepared essentially according to the previous examples:

1-{[1-(2-chlorophenyl)-5-{5-[3-(methylsulfonyl)phenyl]-2-thienyl}-1H-pyrazol-3-yl]carbonyl}piperidine, MS(ES): 526 [M+H]$^+$.

1-(2,6-dichlorophenyl)-5-{3-methyl-5-[3-(methylsulfonyl)phenyl]-2-thienyl}-N-(2,2,2-trifluoroethyl)-1H-pyrazole-3-carboxamide, MS(ES): 588 [M+H]$^+$.

1-(2,6-dichlorophenyl)-5-{3-methyl-5-[3-(methylsulfonyl)phenyl]-2-thienyl}-3-(pyrrolidin-1-ylcarbonyl)-1H-pyrazole, MS(ES): 560 [M+H]$^+$.

1-(2-chlorophenyl)-N-[2-(diethylamino)ethyl]-N-methyl-5-{5-[3-(methylsulfonyl)phenyl]-2-thienyl}-1H-pyrazole-3-carboxamide, MS (ES) 571.3, 573.3 [M+H]$^+$ 1-(2-chlorophenyl)-N-[2-(diethylamino)ethyl]-N-ethyl-5-{5-[3-(methylsulfonyl)phenyl]-2-thienyl}-1H-pyrazole-3-carboxamide, MS (ES) 585.3, 587.3 [M+H]$^+$ 1-(2-chlorophenyl)-N-[2-(dimethylamino)ethyl]-N-methyl-5-{5-[3-(methylsulfonyl)phenyl]-2-thienyl}-1H-pyrazole-3-carboxamide, MS (ES) 543.3, 545.3 [M+H]$^+$ 1-(2-chlorophenyl)-N-[3-(dimethylamino)propyl]-N-methyl-5-{5-[3-(methylsulfonyl)phenyl]-2-thienyl}-1H-pyrazole-3-carboxamide, MS (ES) 557.2, 559.2 [M+H]$^+$ methyl N-{[1-(2-chlorophenyl)-5-{5-[4-(methylsulfonyl)phenyl]-2-thienyl}-1H-pyrazol-3-yl]carbonyl}-N-methylglycinate, MS (ES) 544.2, 546.2 [M+H]$^+$ N-{[1-(2-chlorophenyl)-5-{5-[3-(methylsulfonyl)phenyl]-2-thienyl}-1H-pyrazol-3-yl]carbonyl}-N-methylglycine, MS (ES) 530.2, 532.2 [M+H]$^+$.

1-(2-chlorophenyl)-5-{5-[3-(methylsulfonyl)phenyl]-2-thienyl}-N-(2-morpholin-4-ylethyl)-1H-pyrazole-3-carboxamide, MS (ES) 571.3, 573.3 [M+H]$^+$ 1-{[1-(2-chlorophenyl)-5-{5-[3-(methylsulfonyl)phenyl]-2-thienyl}-1H-pyrazol-3-yl]carbonyl}-N,N-dimethylpiperidin-4-amine, MS (ES) 569.3, 5713 [M+H]$^+$ 1-{[1-(2-chlorophenyl)-5-{5-[3-(methylsulfonyl)phenyl]-2-thienyl}-1H-pyrazol-3-yl]carbonyl}piperidine 4 carboxylic acid, MS(ES) 570.0, 572.0. [M+H]$^+$ 5-{5-[3-(methylsulfonyl)phenyl]-2-thienyl}-1-[2-(trifluoromethyl)phenyl]-1H-pyrazole-3-carboxylic acid, MS (ES) 493.1 [M+H]$^+$ 5-{5-[3-(methylsulfonyl)phenyl]-2-thienyl}-3-(pyrrolidin-1-ylcarbonyl)-1-[2-(trifluoromethyl)phenyl]-1H-pyrazole, MS (ES) 546.3 [M+H]+

1-(2-chlorophenyl)-N-methyl-N-(methyloxy)-5-{5-[3-(methylsulfonyl)phenyl]-2-thienyl}-1H-pyrazole-3-carboxamide, MS (ES) 502.1, 504.1 [M+H]+

1-(2-chlorophenyl)-N-(methyloxy)-5-{5-[3-(methylsulfonyl)phenyl]-2-thienyl}-1H-pyrazole-3-carboxamide, MS (ES) 488.0, 490.0 [M+H]+

N-methyl-N-(methyloxy)-5-{5-[3-(methylsulfonyl)phenyl]-2-thienyl}-1-[3-(trifluoromethyl)pyridin-2-yl]-1H-pyrazole-3-carboxamide, MS (ES) 537.3 [M+H]+

5-{5-[3-(methylsulfonyl)phenyl]-2-thienyl}-N-(2,2,2-trifluoroethyl)-1-[3-(trifluoromethyl)pyridin-2-yl]-1H-pyrazole-3-carboxamide, MS (ES) 575.3 [M+H]+

1-(2-chlorophenyl)-5-{5-[3-(methylsulfonyl)phenyl]-2-thienyl}-N-(2,2,2-trifluoroethyl)-1H-pyrazole-3-carboxamide, MS (ES) 540.3, 542.3 [M+H]+

5-{5-[3-(methylsulfonyl)phenyl]-2-thienyl}-N-(2,2,2-trifluoroethyl)-1-[2-(trifluoromethyl)phenyl]-1H-pyrazole-3-carboxamide, MS (ES) 574.3 [M+H]+ methyl 3-{5-[1-(2-chlorophenyl)-3-{[(2,2,2-trifluoroethyl)amino]carbonyl}-1H-pyrazol-5-yl]-2-thienyl}benzoate, MS (ES) 519.3, 521.3 [M+H]+

1-(2-chlorophenyl)-5-{5-[3-(1-hydroxy-1-methylethyl)phenyl]-2-thienyl}-N-(2,2,2-trifluoroethyl)-1H-pyrazole-3-carboxamide, MS (ES) 519.3, 521.3 [M+H]+

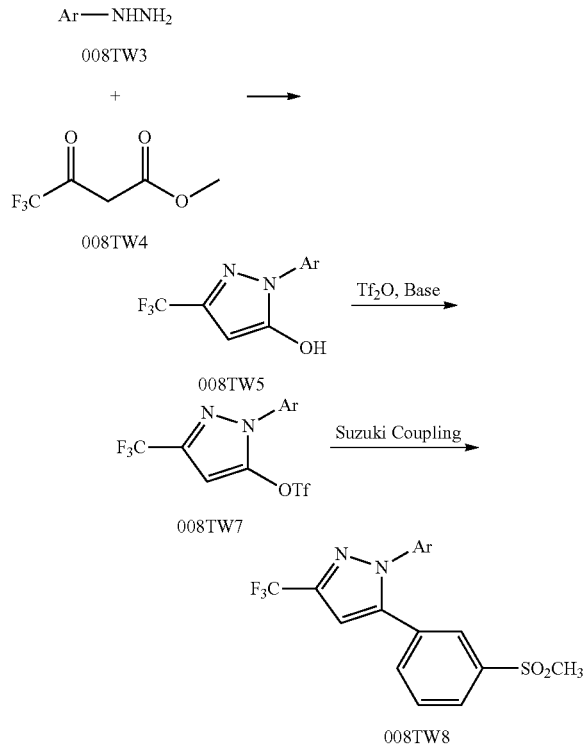

Scheme 8

As depicted in Scheme 8, 1H-pyrazol-5-ol 008TW5 was prepared and the hydroxy group was substituted with other groups. Ketoester 008TW4 reacted with hydrozine 0081W3 to form 1H-Pyrazol-5-ol 008TW5, which was converted to the corresponding triflate 008TW7. 008TW7 was submitted to Suzuki coupling reaction with a boronic acid to introduce a phenyl group to afford product 008TW8.

Example 14

1-(2-chlorophenyl)-5-[3-(methylsulfonyl)phenyl]-3-(trifluoromethyl)-1H-pyrazole

Example 14a

Preparation of 1-(2-chlorophenyl)-3-(trifluoromethyl)-1H-pyrazol-5-yl-trifluoromethanesulfonate

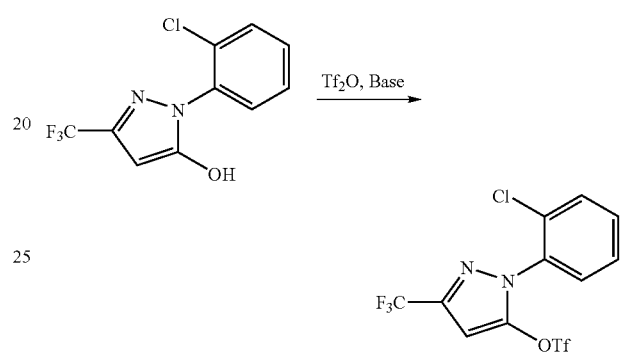

To a mixture of 1-(2-chlorophenyl)-3-(trifluoromethyl)-1H-pyrazol-5-ol (0.52 g, 2 mmol) and 2,6-di-tert-butyl-4-methylpyridine (0.51 g, 1.25 equiv) in DCM (8 mL) was added triflic anhydride (374 µL, 1.1 equiv) at −78° C. The mixture was warmed to 20° C. and stirred overnight at 20° C. It was quenched with sat. aqueous NaHCO3 and the aqueous layer was separated and extracted with DCM. The combined organic layers were washed water and dried over Na2SO4. Evaporation of solvent gave a crude, which was purified by column chromatography on silica gel eluting with EtOAc-hexane (1:4) to give the title compound (620 mg). 1H-NMR (CDCl3): δ 7.60-7.44 (m, 4H), 6.61 (s, 1H).

Example 14b

Preparation of 1-(2-chlorophenyl)-5-[3-(methylsulfonyl)phenyl]-3-(trifluoromethyl)-1H-pyrazole

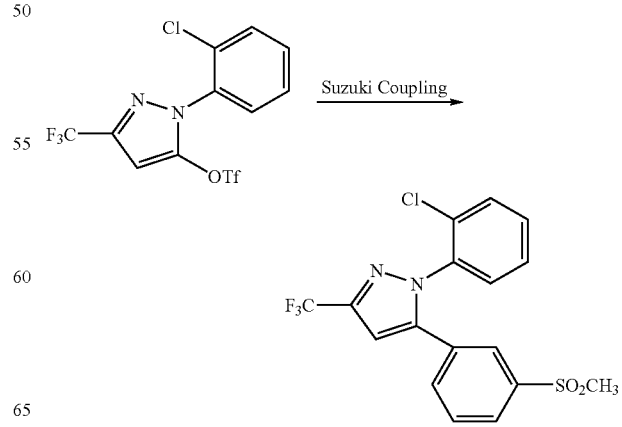

1-(2-chlorophenyl)-5-[3-(methylsulfonyl)phenyl]-3-(trifluoromethyl)-1H-pyrazole was prepared in a manner similar to that described in Examples 1c by using 1-(2-chlorophenyl)-3-(trifluoromethyl)-1H-pyrazol-5-yl trifluoromethanesulfonate and 3-(methylsulfonyl)phenylboronic acid. $^1$H-NMR (CDCl$_3$): δ 7.90 (1H, m), 7.76 (1H, d), 7.57-7.47 (3H, m), 7.46-7.42 (3H, m), 6.92 (1H, s), 2.92 (3H, s). MS (ES): 401 [M+H]$^+$.

Scheme 9

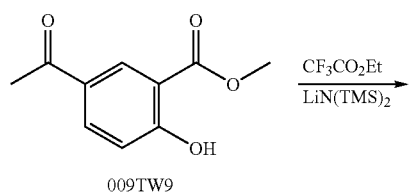

009TW9

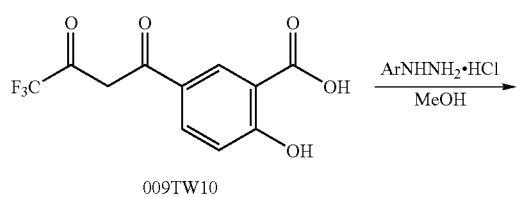

009TW10

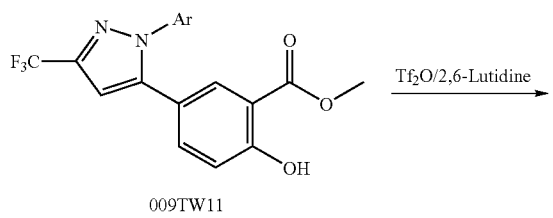

009TW11

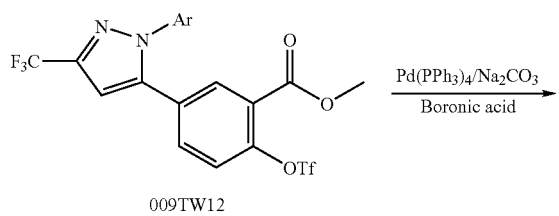

009TW12

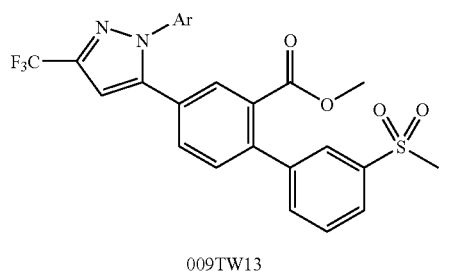

009TW13

-continued

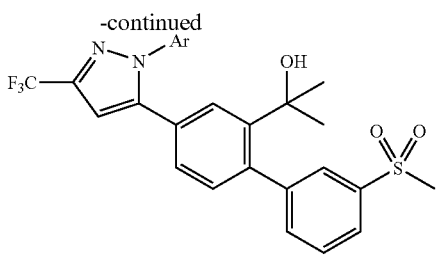

009TW14

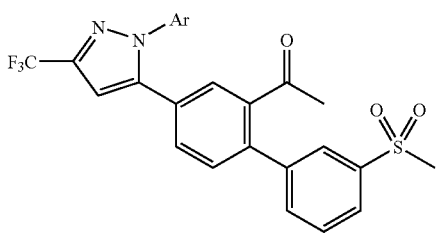

009TW15

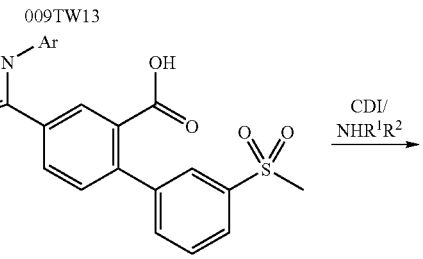

009TW13

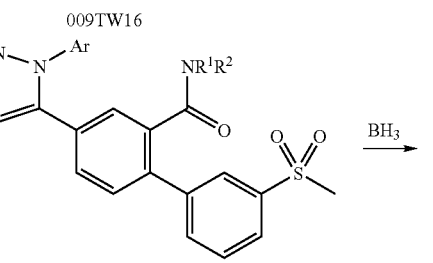

009TW16

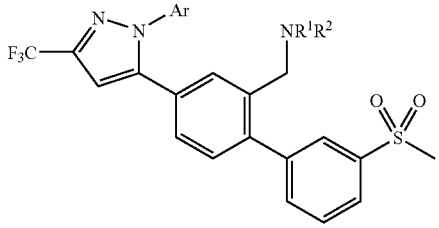

009TW17

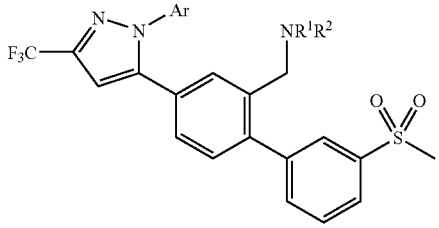

009TW18

As depicted in Scheme 9, ester group on 6-phenyl ring can be transformed into other functional groups such as carbinols and amides, ketones and methylamines. Claisen condensation of 009TW9 with an ester to form diketone 009TW10 was followed by condensation of 009TW10 with a hydrazine to form pyrazole product 009TW11. Treatment of 009TW11 with triflic anhydride to form inflate 009TW12. Suzuki coupling of 009TW12 with a boronic acid afforded product 009TW13, which was treated with Grignard reagent to form carbinol 009TW16, together with ketone 009TW15 as a minor product. Ester 009TW13 was hydrolyzed to give acid 009TW16, which was transformed into amide 009TW17 via cabonyldiimidazole coupling. Reduction of 009TW17 with borane afforded amine 009TW18.

Example 15 and 16

2-{4-[1-(2-chlorophenyl)-3-(trifluoromethyl)-1H-pyrazol-5-yl]-3'-(methylsulfonyl)biphenyl-2-yl}propan-2-ol (15) and 1-{4-[7-(2-chlorophenyl)-3-(trifluoromethyl)-1H-pyrazol-5-yl]-3'-(methylsulfonyl)biphenyl-2-yl}ethanone (16)

Example 15a

Preparation of methyl 5-(1-(2-chlorophenyl)-3-(trifluoromethyl)-1H-pyrazol-5-yl)-2-hydroxybenzoate

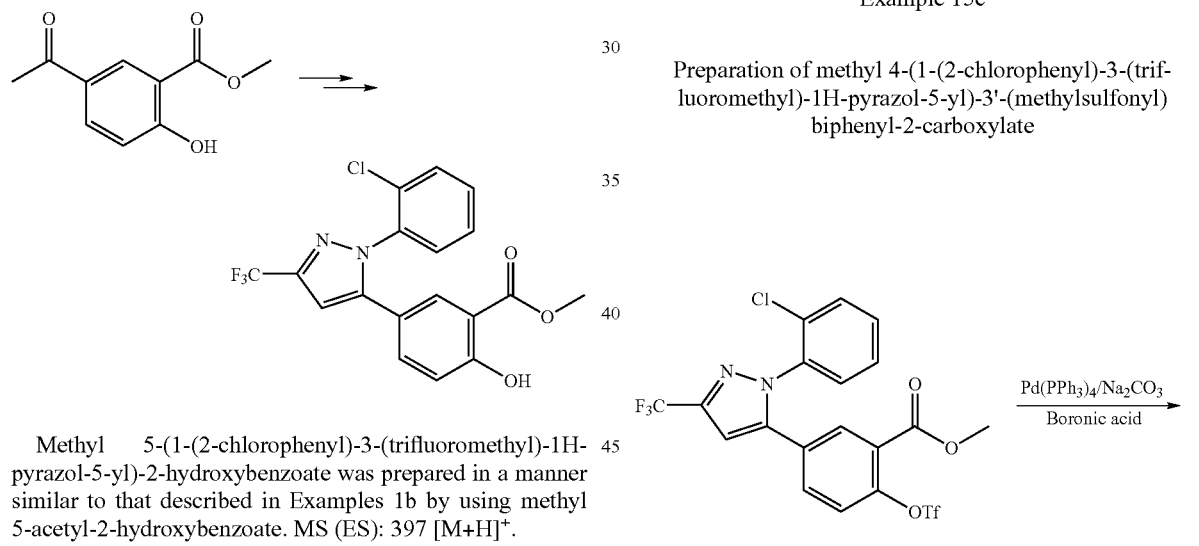

Methyl 5-(1-(2-chlorophenyl)-3-(trifluoromethyl)-1H-pyrazol-5-yl)-2-hydroxybenzoate was prepared in a manner similar to that described in Examples 1b by using methyl 5-acetyl-2-hydroxybenzoate. MS (ES): 397 [M+H]$^+$.

Example 15b

Preparation of methyl 5-(1-(2-chlorophenyl)-3-(trifluoromethyl)-1H-pyrazol-5-yl)-2-(trifluoromethylsulfonyloxy)benzoate

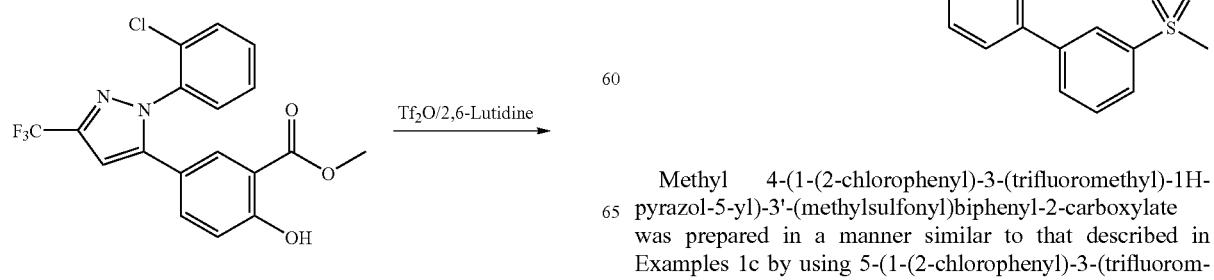

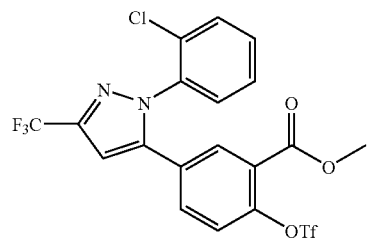

To a solution of methyl 5-(1-(2-chlorophenyl)-3-(trifluoromethyl)-1H-pyrazol-5-yl)-2-hydroxybenzoate (1.29 g, 3.25 mmol) and 2,6-lutidine (0.5 mL, 1.2 equiv) in DCM (15 mL) was added triflic anhydride (0.663 mL, 1.2 equiv) at −78° C. and the reaction solution was stirred for 1 h at −78° C. After quenching with water, aqueous layer was separated and extracted with DCM. The combined organic layers were washed with saturated aqueous NaHCO$_3$ and water and dried over Na$_2$SO$_4$. Evaporation of solvent gave a crude, which was purified by column chromatography on silica gel eluting with EtOAc-hexane (1:4) to afford methyl 5-(1-(2-chlorophenyl)-3-(trifluoromethyl)-1H-pyrazol-5-yl)-2-(trifluoromethylsulfonyloxy)benzoate (1.64 g). MS 529 [M+H]$^+$.

Example 15c

Preparation of methyl 4-(1-(2-chlorophenyl)-3-(trifluoromethyl)-1H-pyrazol-5-yl)-3'-(methylsulfonyl)biphenyl-2-carboxylate

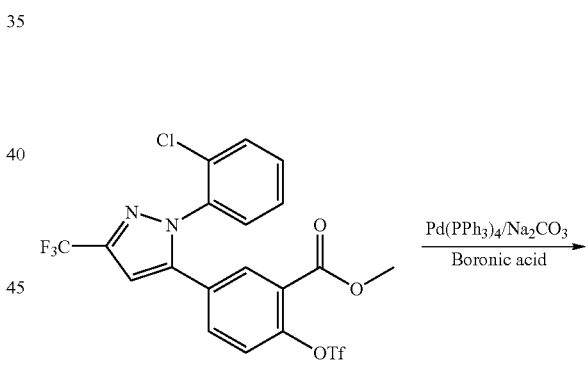

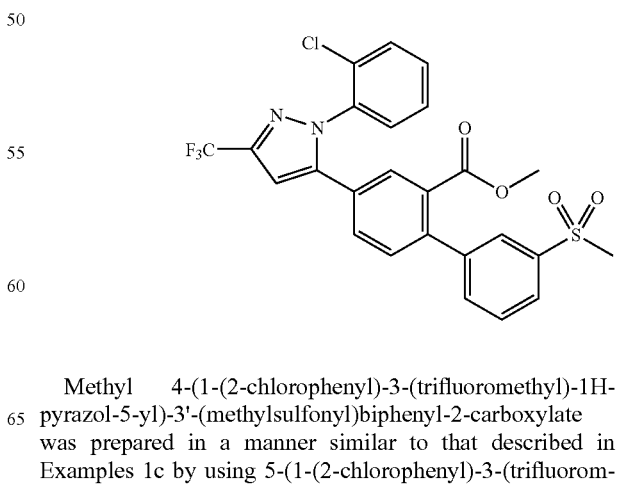

Methyl 4-(1-(2-chlorophenyl)-3-(trifluoromethyl)-1H-pyrazol-5-yl)-3'-(methylsulfonyl)biphenyl-2-carboxylate was prepared in a manner similar to that described in Examples 1c by using 5-(1-(2-chlorophenyl)-3-(trifluoromethyl)-1H-pyrazol-5-yl)-2-(trifluoromethylsulfonyloxy)benzoate and 3-(methylsulfonyl)phenylboronic acid. MS (ES): 535 [M+H]+.

Example 15d and 16

Preparation of 2-{4-[1-(2-chlorophenyl)-3-(trifluoromethyl)-1H-pyrazol-5-yl]-3'-(methylsulfinyl)biphenyl-2-yl}propan-2-ol (15) and 1-{4-[1-(2-chlorophenyl)-3-(trifluoromethyl)-1H-pyrazol-5-yl]-3'-(methylsulfonyl)biphenyl-2-yl}ethanone (16)

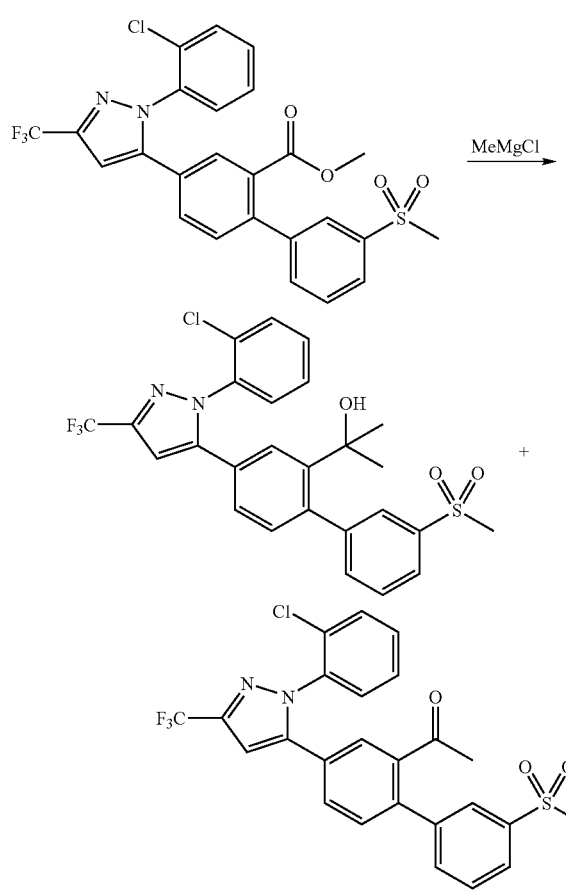

2-{4-[1-(2-chlorophenyl)-3-(trifluoromethyl)-1H-pyrazol-5-yl]-3'-(methylsulfonyl)biphenyl-2-yl}propan-2-ol and 1-{4-[1-(2-chlorophenyl)-3-(trifluoromethyl)-1H-pyrazol-5-yl]-3'-(methylsulfonyl)biphenyl-2-yl}ethanone were prepared in a manner similar to that described in Examples 8d by using methyl 4-(1-(2-chlorophenyl)-3-(trifluoromethyl)-1H-pyrazol-5-yl)-3'-(methylsulfonyl)biphenyl-2-carboxylate. 15d: $^1$H-NMR (CDCl$_3$): δ 7.91 (m, 1H), 7.85 (d, 1H), 7.57-7.50 (m, 4H), 7.47-7.41 (m, 2H), 7.37 (d, 1H), 7.20 (dd, 1H), 7.01 (s, 1H), 6.88 (s, 1H), 3.07 (s, 3H), 2.05 (s, 1H), 1.25 (s, 6H). MS(ES): 536 [M+H]+. 16: $^1$H-NMR (CDCl$_3$): δ 7.95 (m, 1H), 7.87 (m, 1H), 7.61 (m, 1H), 7.57-7.43 (m, TH), 7.38 (dd, 1H), 7.30 (d, 1H), 6.92 (s, 1H), 3.08 (s, 3H), 2.13 (s, 3H). MS(ES): 518 [M+H]+

Example 17

(4-(1-(2-chlorophenyl)-3-(trifluoromethyl)-1H-pyrazol-5-yl)-3'(methylsulfonyl)biphenyl-2-yl)(morpholino)methanone Example 17a Preparation of 4-(1-(2-chlorophenyl)-3-(trifluoromethyl)-1H-pyrazol-5-yl)-3'-(methylsulfonyl)biphenyl-2-carboxylic acid

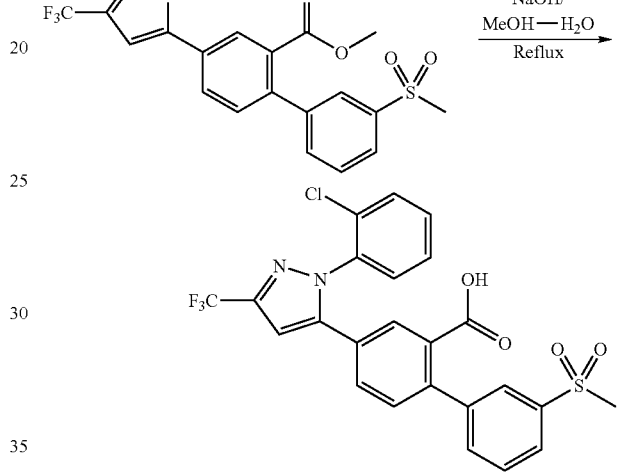

A solution of methyl 4-(1-(2-chlorophenyl)-3-(trifluoromethyl)-1H-pyrazol-5-yl)-3'-(methylsulfonyl)biphenyl-2-carboxylate (1.37 g, 2.6 mmol) and NaOH (1 g, 25 mmol) in MeOH—H2O (2:1, 16 mL) was refluxed for 2 h. After cooling, solid was removed and the filtrate was acidified with formic acid. Solid was collected by filtration and washed with water and dried under high vacuum to afford 4-(1-(2-chlorophenyl)-3-(trifluoromethyl)-1H-pyrazol-5-yl)-3'-(methylsulfonyl)biphenyl-2-carboxylic acid (1.05 g). MS(ES): 521 [M+H]+.

Example 17b

Preparation of (4-(1-(2-chlorophenyl)-3-(trifluoromethyl)-1H-pyrazol-5-yl)-3'-(methylsulfonyl)biphenyl-2-yl)(morpholino)methanone

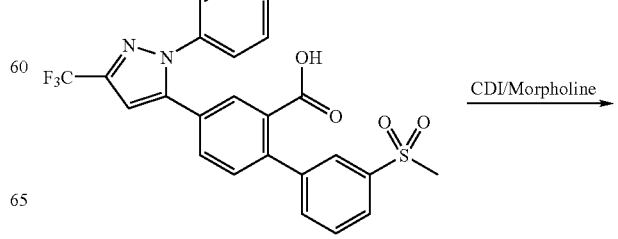

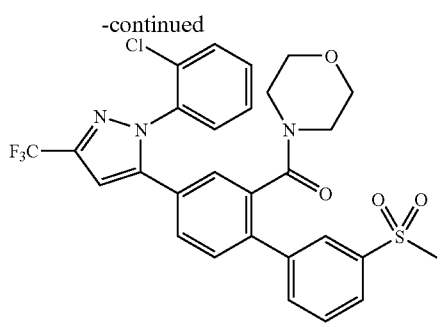

To a suspension of 4-(1-(2-chlorophenyl)-3-(trifluoromethyl)-1H-pyrazol-5-yl)-3'-(methylsulfonyl)biphenyl-2-carboxylic acid (0.52 g, 1 mmol) in DCM (6 mL) was added carbonyldimidazole (2.43 mg, 1.5 mmol) and the mixture was stirred for 2 h at 20° C. Morpholine (0.175 mL, 2 mmol) was added and the mixture was stirred overnight at 20° C. Evaporation of solvent gave a crude, which was purified by column chromatography on silica gel eluting with EtOAc-hexane (1:4 to 4:1) to afford (4-(1-(2-chlorophenyl)-3-(trifluoromethyl)-1H-pyrazol-5-yl)-3'-(methylsulfonyl)biphenyl-2-yl)(morpholino)methanone (0.52 g). $^1$H-NMR (CDCl$_3$): δ 7.97 (m, 2H), 7.77 (d, 1H), 7.64 (m, 1H), 7.58 (m, 1H), 7.46-7.24 (m, 5H), 6.89 (s, 1H), 3.55 (m, 3H), 3.33 (m, 2H), 3.08 (s, 3H), 2.87 (m, 2H), 2.69 (m, 1H). MS(ES): 590 [M+H]$^+$.

Example 18

Preparation of 4-((4-(1-(2-chlorophenyl)-3-(trifluoromethyl)-1H-pyrazol-5-yl)-3'-(methylsulfonyl)biphenyl-2-yl)methyl)morpholine

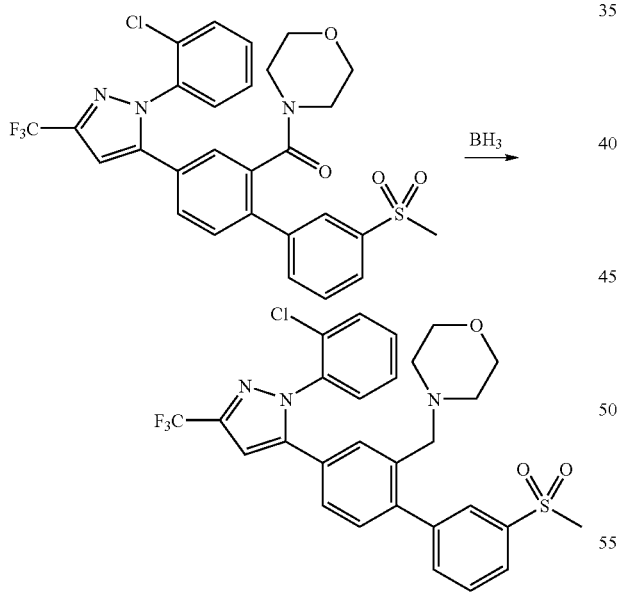

To a solution of BH$_3$ (1 M, 4 mL) in THF was added (4-(1-(2-chlorophenyl)-3-(trifluoromethyl)-1H-pyrazol-5-yl)-3'-(methylsulfonyl)biphenyl-2-yl)(morpholino)-methanone (4.60 mg, 0.78 mmol) and the solution was stirred overnight at 20° C. MeOH was added to quench borane and solvent was evaporated to afford a crude, which was purified by column chromatography on silica gel eluting with MeOH-DCM (1:19) to afford 4-((4-(1-(2-chlorophenyl)-3-(trifluoromethyl)-1H-pyrazol-5-yl)-3'-(methylsulfonyl)biphenyl-2-yl)methyl)morpholine (0.2 g). $^1$H-NMR (CDCl$_3$): δ 8.25 (m, 1H), 7.93 (m, 1H), 7.72 (m, 1H), 7.60 (m, 1H), 7.55 (m, 1H), 7.49-7.39 (m, 3H), 7.33-7.26 (m, 2H), 7.18 (m, 1H), 6.85 (s, 1H), 3.58 (m, 4H), 3.16 (s, 3H), 3.07 (s, 3H), 2.14 (m, 4H). MS(ES): 576 [M+H]$^+$.

Scheme 10

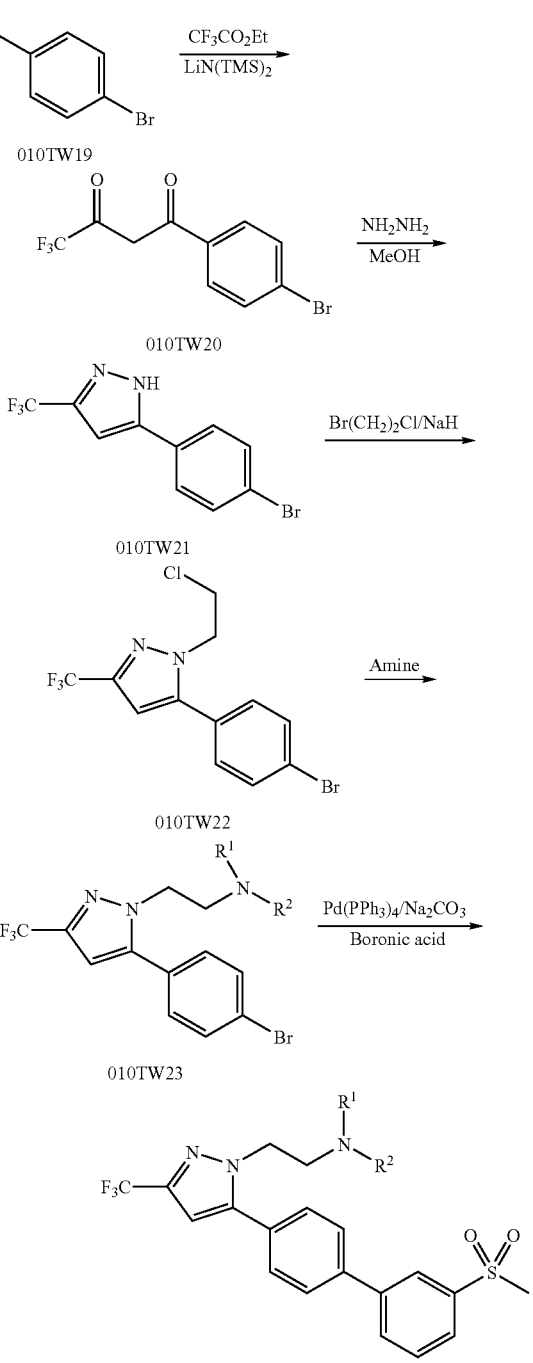

X = O, NMe

As depicted in Scheme 10, aminoethylpyrazoles were synthesized via alkylation of pyrazole with 1,2-dihaloethane followed by subsequent alkylation of amines. Claisen condensation of ketone 010TW19 with an ester to form diketone 010TW20 was followed by addition-cyclization with hydrazine to give pyrazole 010TW21. Alkylation of 010TW21 afforded chloroethylpyrazole 010TW22, which was used for alkylation of amines to form amines 010TW23. Final Suzuki coupling of 010TW23 with a boronic acid afforded 010TW24.

Example 19

4-(2-{5-[3'-methylsulfonyl)biphenyl-4-yl]-3-(trifluoromethyl)-1H-pyrazol-1-yl}ethyl)morpholine

Example 19a

Preparation of 5-(4-bromophenyl)-3-(trifluoromethyl)-1H-pyrazole

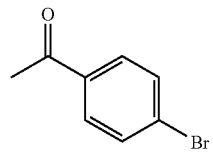

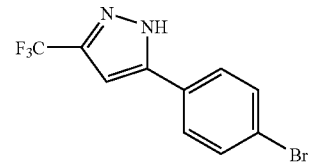

5-(4-bromophenyl)-3-(trifluoromethyl)-1H-pyrazole was prepared in a manner similar to that described in Examples 1b by using 4'-bromoacetophenone. MS (ES): 291 [M+H]+.

Example 19b

Preparation of 5-(4-bromophenyl)-1-(2-chloroethyl)-3-(trifluoromethyl)-1H-pyrazole

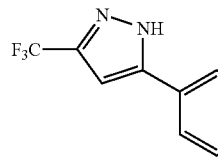

To a solution of 5-(4-bromophenyl)-3-(trifluoromethyl)-1H-pyrazole (2.05 g, 7 mmol) and 1-bromo-2-chloroethane (0.71 mL, 1.2 equiv) in DMF (30 mL) was added NaH (0.42 g, 60%, 1.5 equiv) and the mixture was stirred overnight at 20° C. The reaction was quenched by water. Solid was collected and washed by water and dried under high vacuum to give a crude, which was purified by column chromatography eluting with MeOH-DCM (6:96) to give 5-(4-bromophenyl)-1-(2-chloroethyl)-3-(trifluoromethyl)-1H-pyrazole (400 mg) as a minor product. $^1$H-NMR (CDCl$_3$): δ 7.64 (d, 1H), 7.31 (d, 1H), 6.54 (s, 1H), 4.41 (t, 2H), 3.93 (t, 2H).

Example 19c

Preparation of 4-(2-(5-(4-bromophenyl)-3-(trifluoromethyl)-1H-pyrazol-1-yl)ethyl)morpholine

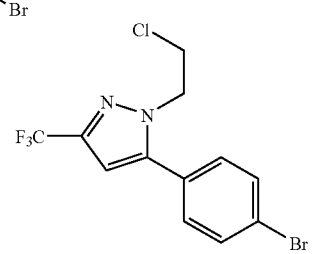

A solution of 5-(4-bromophenyl)-1-(2-chloroethyl)-3-(trifluoromethyl)-1H-pyrazole (200 mg, 0.56 mmol) and morpholine (0.245 mL, 5 equiv) in acetonitrile (2 mL) was stirred overnight at 90° C. Evaporation of solvent gave of 4-(2-(5-(4-bromophenyl)-3-(trifluoromethyl)-1H-pyrazol-1-yl)ethyl)morpholine. MS (ES): 404 [M+H]+.

Example 19d

Preparation of 4-(2-(5-(3'-(methylsulfonyl)biphenyl-4-yl)-3-(trifluoromethyl)-1H-pyrazol-1-yl)ethyl)morpholine

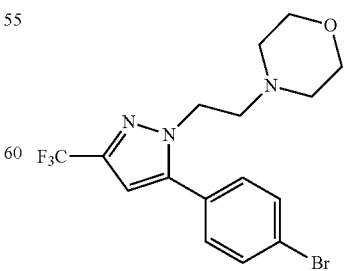

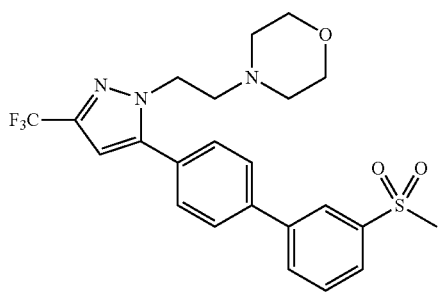

4-(2-{5-[3'-(methylsulfonyl)biphenyl-4-yl]-3-(trifluoromethyl)-1H-pyrazol-1-yl}ethyl)morpholine was prepared in a manner similar to that described in Examples 1c by using the above crude product and (3-methylsulfonyl)phenylboronic acid. $^1$H-NMR (CDCl$_3$): δ 8.21 (m, 1H), 7.95 (m, 2H), 7.76-7.53 (m, 4H), 7.46 (m, 1H), 6.58 (s, 1H), 4.30 (t, 2H), 3.59 (m, 4H), 3.13 (t, 3H), 2.84 (t, 2H), 2.36 (m, 4H). MS (ES): 480 [M+H]$^+$.

The following compound is prepared essentially according to the previous examples:

1-methyl-4-(2-{5-[3'-(methylsulfonyl)biphenyl-4-yl]-3-(trifluoromethyl)-1H-pyrazol-1-yl}ethyl)piperazine MS(ES): 493 [M+H]$^+$.

Scheme 11

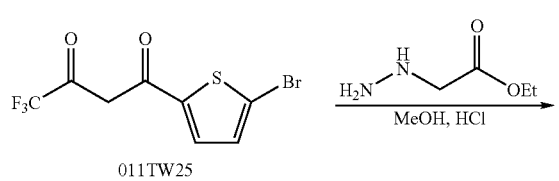

011TW25

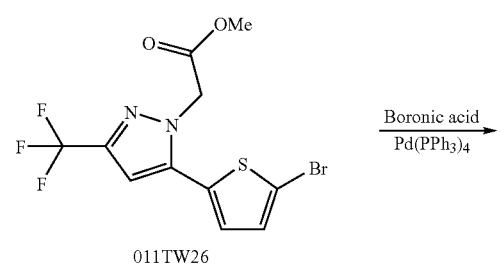

011TW26

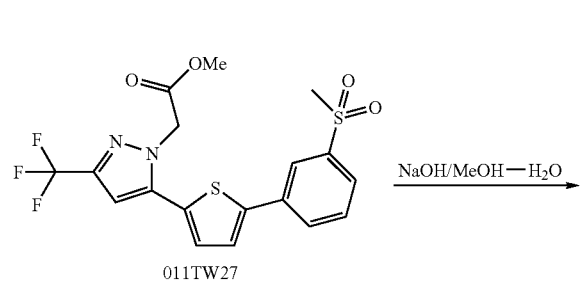

011TW27

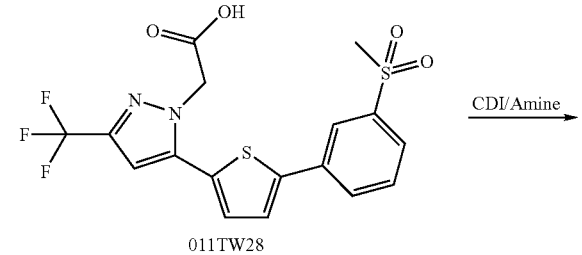

011TW28

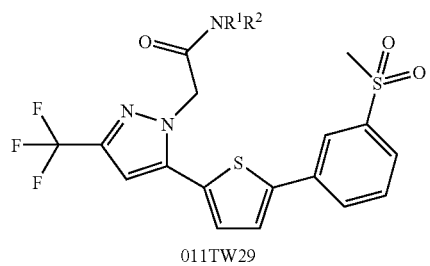

011TW29

As depicted in Scheme 11, a carbonyl group can be introduced into the pyrazole system. Diketone 011TW25 reacted with a hydrazine to form pyrazole 011TW26. Suzuki coupling of 011TW26 with a boronic acid afforded 011TW27, whose ester group was then hydrolyzed to give acid 011TW28. CDI coupling of acid 011TW28 with amines afforded amides 011TW29

Example 20

4-{[5-{5-[3-(methylsulfonyl)phenyl]-2-thienyl}-3-(trifluoromethyl)-1H-pyrazol-1-yl]acetyl}morpholine Example 20a Preparation of Methyl 2-(5-(5-(3-(methylsulfonyl)phenyl)thiophen-2-yl)-3-(trifluoromethyl)-1H-pyrazol-1-yl)acetate

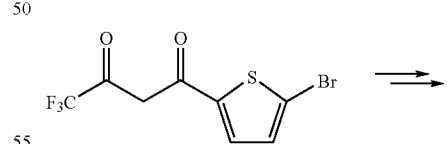

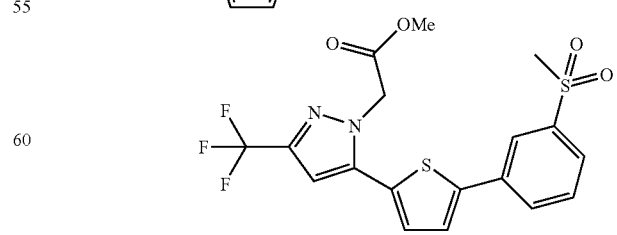

Methyl 2-(5-(5-(3-(methylsulfonyl)phenyl)thiophen-2-yl)-3-(trifluoromethyl)-1H-pyrazol-1-yl)acetate was prepared in a manner similar to that described in Examples 1c by using methyl 2-hydrazinoacetate (in MeOH). MS(ES): 445 [M+H]⁺.

Example 20b

Preparation of 2-(5-(5-(3-(methylsulfinyl)phenyl)thiophen-2-yl)-3-(trifluoromethyl)-1H-pyrazol-1-yl)acetic acid

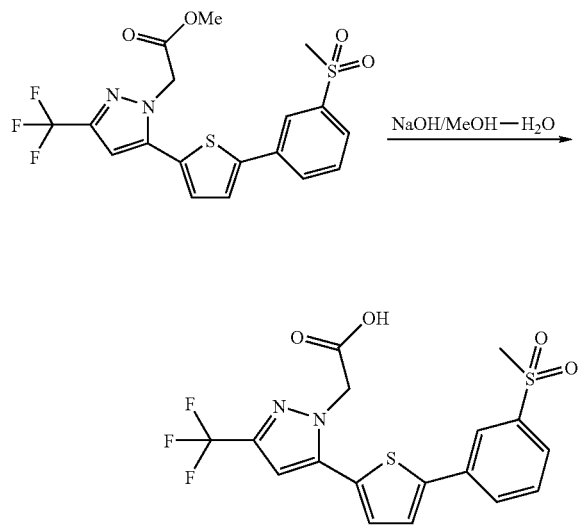

2-(5-(5-(3-(methylsulfonyl)phenyl)thiophen-2-yl)-3-(trifluoromethyl)-1H-pyrazol-1-yl)acetic acid was prepared in a manner similar to that described in Example 17a MS(ES): 431 [M+H]⁺.

Example 20c

Preparation of 4-{[5-{5-[3-(methylsulfonyl)phenyl]-2-thienyl}-3-(trifluoromethyl)-1H-pyrazol-1-yl]acetyl}morpholine

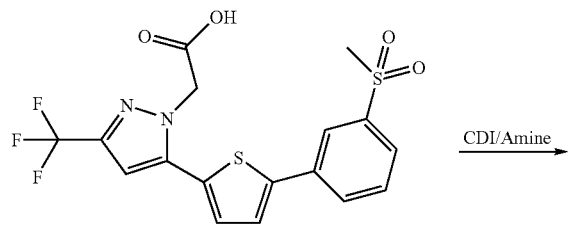

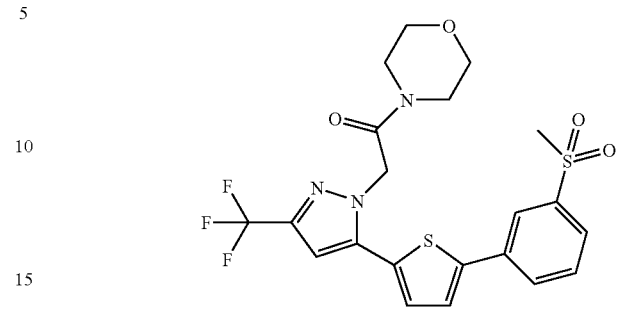

4-{[5-{5-[3-(methylsulfonyl)phenyl]-2-thienyl}-3-(trifluoromethyl)-1H-pyrazol-1-yl]acetyl}morpholine was prepared in a manner similar to that described in Examples 19.
¹H-NMR (CDCl₃): δ 8.15 (s, 1H), 7.90 (m, 1H), 7.86 (m, 1H), 7.63 (m, 1H), 7.42 (d, 1H), 7.32 (d, 1H), 6.73 (s, 1H), 5.12 (s, 2H), 3.76-3.72 (m, 4H), 3.66 (t, 2H), 3.57 (t, 2H), 3.11 (s, 3H). MS (ES): 500 [M+H]⁺.
The following compounds are prepared essentially according to the previous examples:
5-{5-[3-(methylsulfonyl)phenyl]-2-thienyl}-1-(2-oxo-2-pyrrolidin-1-ylethyl)-3-(trifluoromethyl)-1H-pyrazole, MS(ES: 484 [M+H]⁺.
1-{[5-{5-[3-(methylsulfonyl)phenyl]-2-thienyl}-3-(trifluoromethyl)-1H-pyrazol-1-yl]acetyl}piperidine, MS(ES: 498 [M+H]⁺.
5-{5-[3-(methylsulfonyl)phenyl]-2-thienyl}-1-(2-oxo-2-pyrrolidin-1-ylethyl)-3-(trifluoromethyl)-1H-pyrazole, MS(ES): 484 [M+H]⁺.

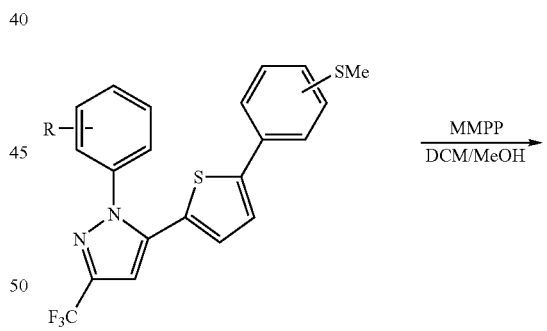

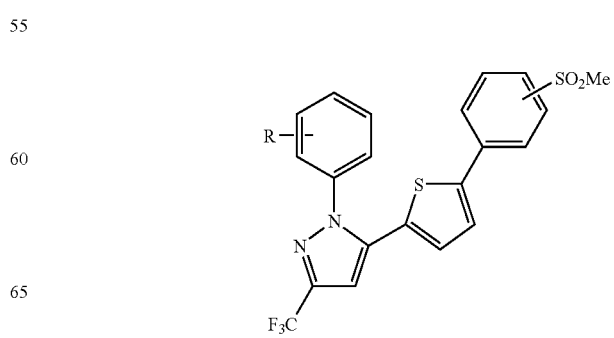

The starting materials (012vi) were prepared in similar manner of Scheme 1, followed by further transformations to make final products as described in Scheme 12.

Example 21

5-{5-[2-(2-Chloro-phenyl)-5-trifluoromethyl-2H-pyrazol-3-yl]-thiophen-2-yl}-2-methanesulfonyl-3-methyl-pyridine

Example 21a

Preparation of 5-{5-[2-(2-Chloro-phenyl)-5-trifluoromethyl-2H-pyrazol-3-yl]-thiophen-2-yl}-2-methanesulfonyl-3-methyl-pyridine

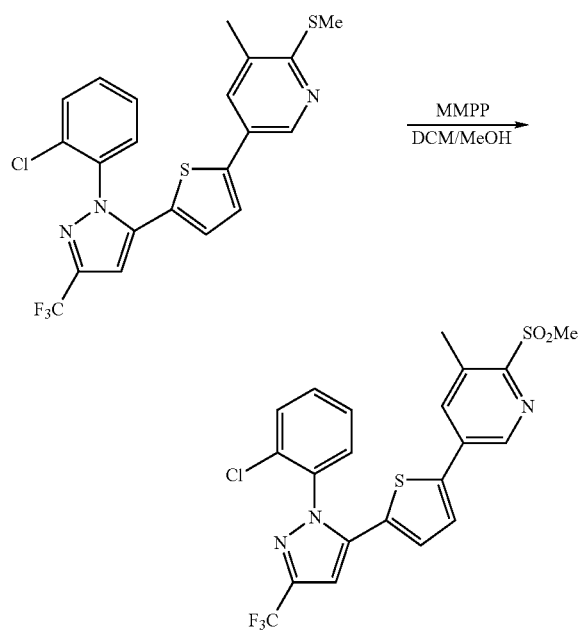

5-{5-[2-(2-Chloro-phenyl)-5-trifluoromethyl-2H-pyrazol-3-yl]-thiophen-2-yl}-3-methyl-2-methylsulfanyl-pyridine (158 mg, 0.34 mmol) was dissolved in 15 mL mixture of dichloromethane and methanol (5:1, V/V). MMPP (magnesium monoperoxyphthalate hexahydrate, 424 mg, 0.75 mmol, 80% tech.) was added then. The mixture was stirred at room temperature for 2 hrs, then diluted with dichloromethane, and filtered. The filtrate was washed with saturated NaHCO$_3$ and brine, dried over Na$_2$SO$_4$, and concentrated in vacuo. The crude product was purified by column chromatography on silica gel (10→40% EtOAc/Hexane) to give a white solid (116 mg, 69% yield). $^1$H-NMR (400 MHz, CDCl$_3$): δ 2.73 (s, 3H), 3.36 (s, 3H), 6.89 (d, J=3.9, 1H), 6.93 (s, 1H), 7.27 (m, 1H), 7.58-7.49 (m, 4H), 7.70-7.69 (m, 1H), 8.52-8.51 (m, 1H). MS (ES): 498.3 [M+H]$^+$.

The following compounds were made in similar manner by oxidation of appropriate sulfides:
2-(ethylsulfonyl)-3-methyl-5-(5-{3-(trifluoromethyl)-1-[2-(trifluoromethyl)phenyl]-1H-pyrazol-5-yl}-2-thienyl)pyridine; MS (ES): 546.2 [M+H]$^+$;
3-methyl-5-(5-{1-[2-(methyloxy)phenyl]-3-(trifluoromethyl)-1H-pyrazol-5-yl}-3-thienyl)-2-(methylsulfonyl)pyridine; MS (ES): 494.3 [M+H]$^+$;
5-{5-[1-(2-chlorophenyl)-3-(trifluoromethyl)-1H-pyrazol-5-yl]-2-thienyl}-2-(ethylsulfonyl)-3-methylpyridine; MS (ES): 512.3 [M+H]$^+$;
5-{5-[1-(2,5-dichlorophenyl)-3-(trifluoromethyl)-1H-pyrazol-5-yl]-2-thienyl}-3-methyl-2-(methylsulfonyl)pyridine; MS (ES): 532.4 546.1 [M+H]$^+$;
3-methyl-2-(methylsulfonyl)-5-(5-(3-(trifluoromethyl)-{[2-(trifluoromethyl)phenyl]-1H-pyrazol-5-yl}-2-thienyl)pyridine; MS (ES): 532.2[M+H]$^+$;
5-{5-[1-(2,5-dichlorophenyl)-3-(trifluoromethyl)-1H-pyrazol-5-yl]-3-thienyl}-3-methyl-2-(methylsulfonyl)pyridine; MS (ES): 532.4, 536.2 [M+H]$^+$;

Scheme 13

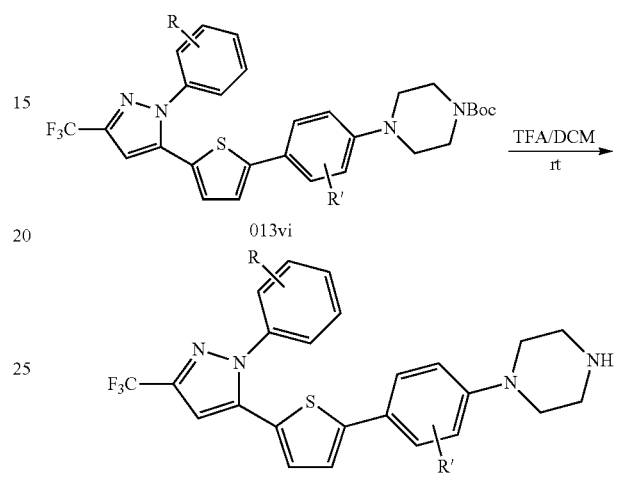

The starting materials (013vi) were prepared in similar manner of Scheme 1 followed by further transformations to make final products as described in Scheme 13.

Example 22

Preparation of 1-(5-{5-[2-(2-Chloro-phenyl)-5-trifluoromethyl-2H-pyrazol-3-yl]-thiophen-2-yl}-pyridin-2-yl)-piperazine

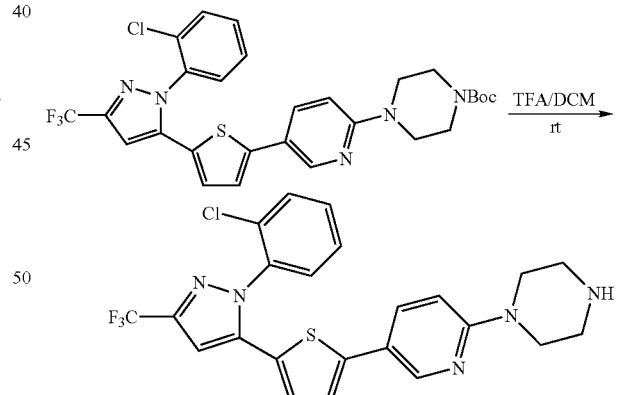

4-(5-{5-[2-(2-Chloro-phenyl)-5-trifluoromethyl-2H-pyrazol-3-yl]-thiophen-2-yl}-pyridin-2-yl)-piperazine-1-carboxylic acid tert-butyl ester (196 mg, 0.33 mmol) was mixed with 4 mL 50% trifluoromethylacetic acid in dichloromethane, and stirred at room temperature for 2 hrs. All solvent was removed; the residue was redissolved in dichloromethane and neutralized to pH 7 by saturated NaHCO$_3$. The organic layer was washed with brine, dried over Na$_2$SO$_4$, and concentrated in vacuo to give a solid that was washed several times with dichloromethane to give yellow solid (75 mg, 47% yield). 1H-NMR (400 MHz, CDCl$_3$): δ 3.32-329 (m, 4H), 3.94-3.91 (m, 4H), 6.67 (d, J=8.8, 1H), 6.79 (d, J=3.8, 1H), 6.87 (s, 1H), 7.02 (d, J=3.8, 1H), 7.57-7.45 (m, 4H), 7.63 (dd, J=8.8, J=2.5, 1H), 8.34 (d, J=2.2, 1H). MS (ES) 490.3, 492.3, [M+H]$^+$.

Scheme 14

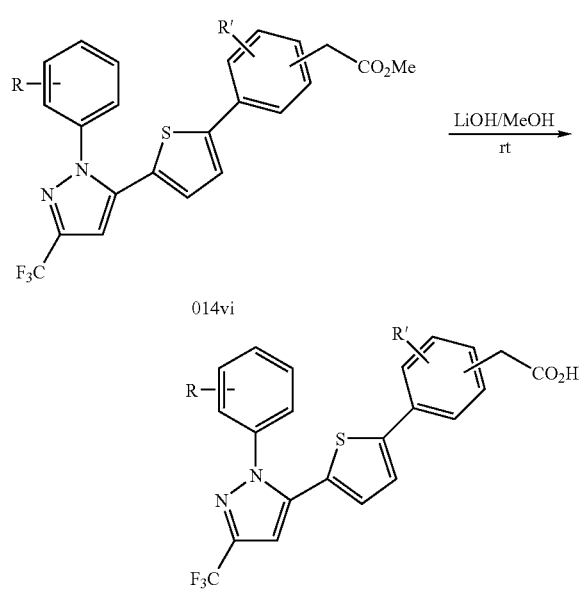

014vi

The starting materials (014vi) were prepared in similar manner of Scheme 1 by further transformations to make final products as described in Scheme 14

Example 23

Preparation of (4-{5-[2-(2-Chloro-phenyl)-5-trifluoromethyl-2H-pyrazol-3-yl]-thiophen-2-yl}-3-methylphenyl)-acetic acid

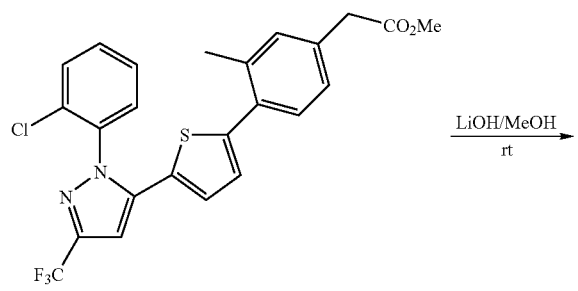

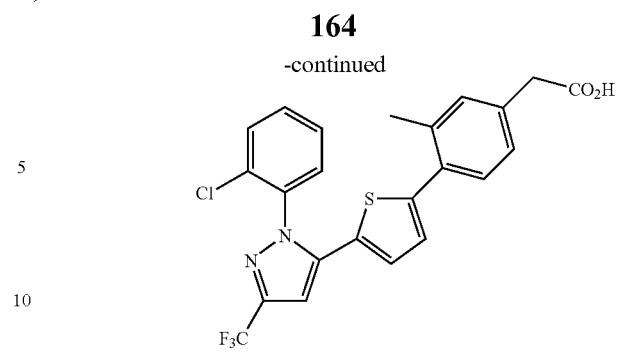

(4-{5-[2-(2-Chloro-phenyl)-5-trifluoromethyl-2H-pyrazol-3-yl]-thiophen-2-yl}-3-methylphenyl)-acetic acid methyl ester (122 mg, 025 mmol) was dissolved in 6 mL mixture of THF and water (3:1, V/V). Lithium hydroxide monohydrate (23 mg, 0.55 mmol) was then added. After stirring at room temperature for 2 hrs, the mixture was neutralized to pH 7 by 1N HCl, and then extracted with ethyl acetate. The combined organic layers were washed with brine, dried over Na$_2$SO$_4$, and concentrated in vacuo. The crude product was purified by reverse HPLC to give a white solid (66 mg, 55% yield). 1H-NMR (400 MHz, CDCl$_3$): δ 2.33 (s, 3H), 3.65 (s, 2H), 6.88-6.84 (m, 3H), 7.17-7.11 (m, 1H), 7.17 (m, 1H), 7.27 (m, 1H), 7.56-7.42 (m, 4H). MS (ES) 477.2, [M+H]$^+$.

The following compounds were made in similar manner by hydrolysis of corresponding phenylacetate ester precursors.

(3-{5-[1-(2-chlorophenyl)-3-(trifluoromethyl)-1H-pyrazol-5-yl]-2-thienyl}-4-fluorophenyl)acetic acid; MS (ES): 481.1, 484.4 [M+H]$^+$;

2-(5-{5-[1-(2-chlorophenyl)-3-(trifluoromethyl)-1H-pyrazol-5-yl]-2-thienyl}pyridin-3-yl)-2-methylpropanoic acid; MS (ES): 492.1, 494.3 [M+H]$^+$;

(5-{5-[1-(2-chlorophenyl)-3-(trifluoromethyl)-1H-pyrazol-5-yl]-2-thienyl}pyridin-3-yl)acetic acid; MS (ES): 464.0, 466.1 [M+H]$^+$;

[3-methyl-4-(5-{3-(trifluoromethyl)-1-[3-(trifluoromethyl)pyridin-2-yl]-1H-pyrazol-5-yl}-2-thienyl)phenyl]acetic acid; MS (ES): 512.3 [M+H]$^+$;

Scheme 15

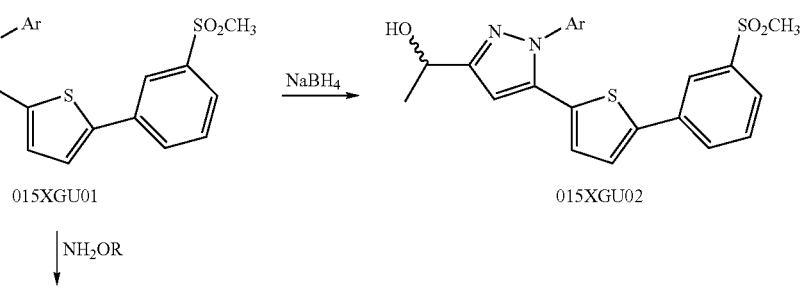

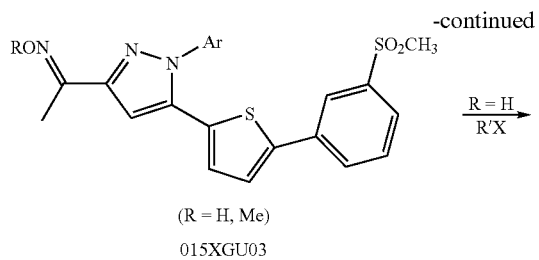
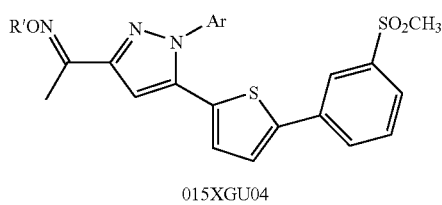

(R = H, Me)
015XGU03

015XGU04

As depicted in Scheme 15, a ketone can be transformed into alcohols and oximes, which can be alkylated. Ketone 015XGU01 was reduced with NaBH$_4$ to a secondary alcohol 015XGU02. Oxime 015XGU03 was obtained by treatment of ketone 015XGU01 with hydroxylamine in the presence of a base. Oxime 015XGU03 was alkylated with alkyl chloride or alkyl bromide to give the O-alkylated oxime 015XGU04.

Example 24

Preparation of 1-[1-(2-Chlorophenyl)-5-{5-[3-(methylsulfonyl)phenyl]-2-thienyl}-1H-pyrazol-3-yl]ethanol

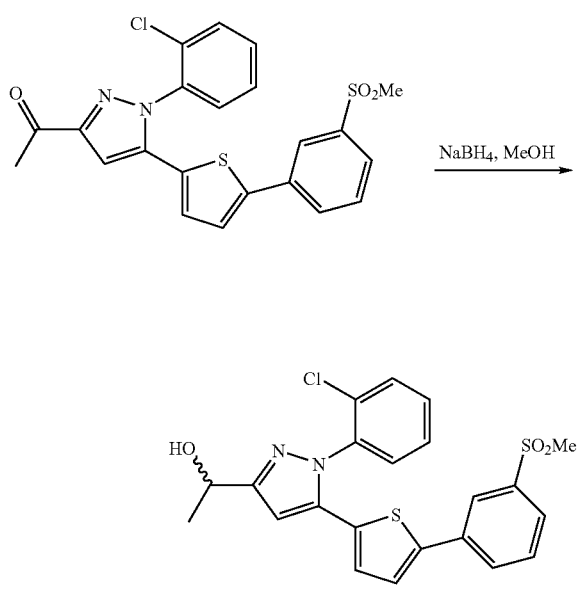

NaBH$_4$ (600 mg) was added at 0° C. to a suspension of 1-[1-(2-chlorophenyl)-5-{5-3-(methylsulfonyl)phenyl]-2-thienyl}-1H-pyrazol-3-yl]ethanone (460 mg, 1 mmol) in a mixture of MeOH-THF (1:3, 100 mL), and the resulting mixture was stirred at rt for 4 h. Water was added, and the solvent was removed in vacuo. The residue was partitioned between water and DCM, the aqueous was extracted with DCM. The combined extracts were washed with brine, dried over Na$_2$SO$_4$, and evaporated in vacuo. The crude product was purified by flash chromatography (0-80% EtOAc/hexanes) to give the title compound as a white solid (423 mg, 92%). $^1$HNMR (CDCl$_3$): δ 8.04 (m, 1H), 7.83-7.81 (m, 1H), 7.74-7.71 (m, 1H), 7.57-7.43 (m, 5H), 7.21 (d, 1H), 6.75 (d, 1H), 6.64 (s, 1H), 5.05 (q, 1H), 3.07 (s, 3H), 2.05 (brs, 1H), 1.63 (d, 3H). MS(ES): 459 [M+H]$^+$, 441 (M-OH).

Example 25

Preparation of 1-[1-(2-chlorophenyl)-5-{5-[3-(methylsulfonyl)phenyl]-2-thienyl}-1H-pyrazol-3-yl]ethanone oxime

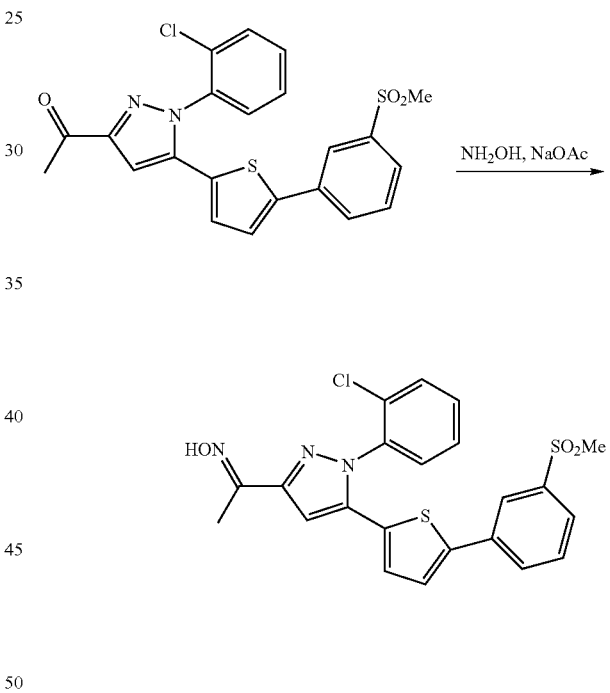

A mixture of 1-[1-(2-chlorophenyl)-5-{5-3-(methylsulfonyl)phenyl]-2-thienyl}-1H-pyrazol-3-yl]ethanone (120 mg, 0.263 mmol), NH$_2$OH.HCl (92 mg, 1.32 mmol), and NaOAc (132 mg, 1.6 mmol) in a mixture of MeOH—H$_2$O (2:1, 15 mL) was stirred at 85° C. in a sealed vial for 11 h. The solvent was removed in vacuo, and the residue was purified by flash chromatography (0-60% EtOAc/hexanes) to give the title compound as a white solid (115 mg, 93%). $^1$HNMR (CDCl$_3$): δ 8.04 (m, 1H), 7.83-7.81 (m, 1H), 7.73-7.71 (m, 1H), 7.57-7.43 (m, 5H), 7.21 (d, 1H), 6.97 (s, 1H), 6.76 (d, 1H), 3.09 (s, 3H), 2.37 (s, 3H). MS(ES): 472 [M+H]$^+$.

The following compound is prepared essentially according to the previous examples:

1-[1-(2-chlorophenyl)-5-{5-[3-(methylsulfonyl)phenyl]-2-thienyl}-1H-pyrazol-3-yl]ethanone O-methyloxime MS(ES): 486 [M+H]$^+$

Example 26

Preparation of 1-[1-(2-chlorophenyl)-5-{5-[3-(methylsulfonyl)phenyl]-2-thienyl}-1H-pyrazol-3-yl]ethanone O-[2-(dimethylamino)ethyl]oxime

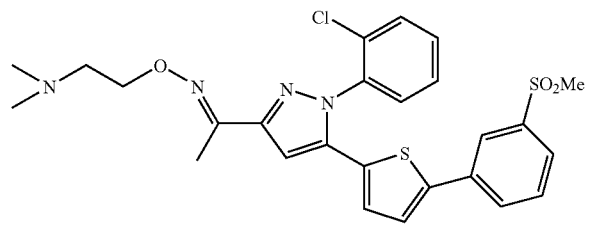 [SMILES: C/C(=N\OCCN(C)C)c1cc(-c2ccc(-c3cccc(S(C)(=O)=O)c3)s2)n(-c2ccccc2Cl)n1]

A mixture of 1-[1-(2-chlorophenyl)-5-{5-[3-(methylsulfonyl)phenyl]-2-thienyl}-1H-pyrazol-3-yl]ethanone oxime (196 mg, 0.415 mmol), KOH (142 mg, 2.3 mmol), 2-(dimethylamino)ethyl chloride hydrochloride (185 mg, 1.3 mmol), and anhydrous DMSO (5 mL) was stirred at 60° C. in a sealed vial for 3 h. The reaction mixture was diluted with water, extracted with ether. The combined extracts were washed with brine, dried over $Na_2SO_4$, and evaporated in vacuo. The residue was purified by flash chromatography (0-30% MeOH/DCM) to give the title compound as a white solid (50 mg, 22%). $^1$HNMR (CDCl$_3$): δ8.04 (d, 1H), 7.83-7.81 (m, 1H), 7.74-7.71 (m, 1H), 7.57-7.43 (m, 5H), 7.21 (d, 1H), 7.00 (s, 1H), 6.76 (d, 1H), 4.38 (t, 2H), 3.07 9s, 3H), 2.78 (m, 2H), 2.40 (brs, 6H), 2.31 (s, 3H).

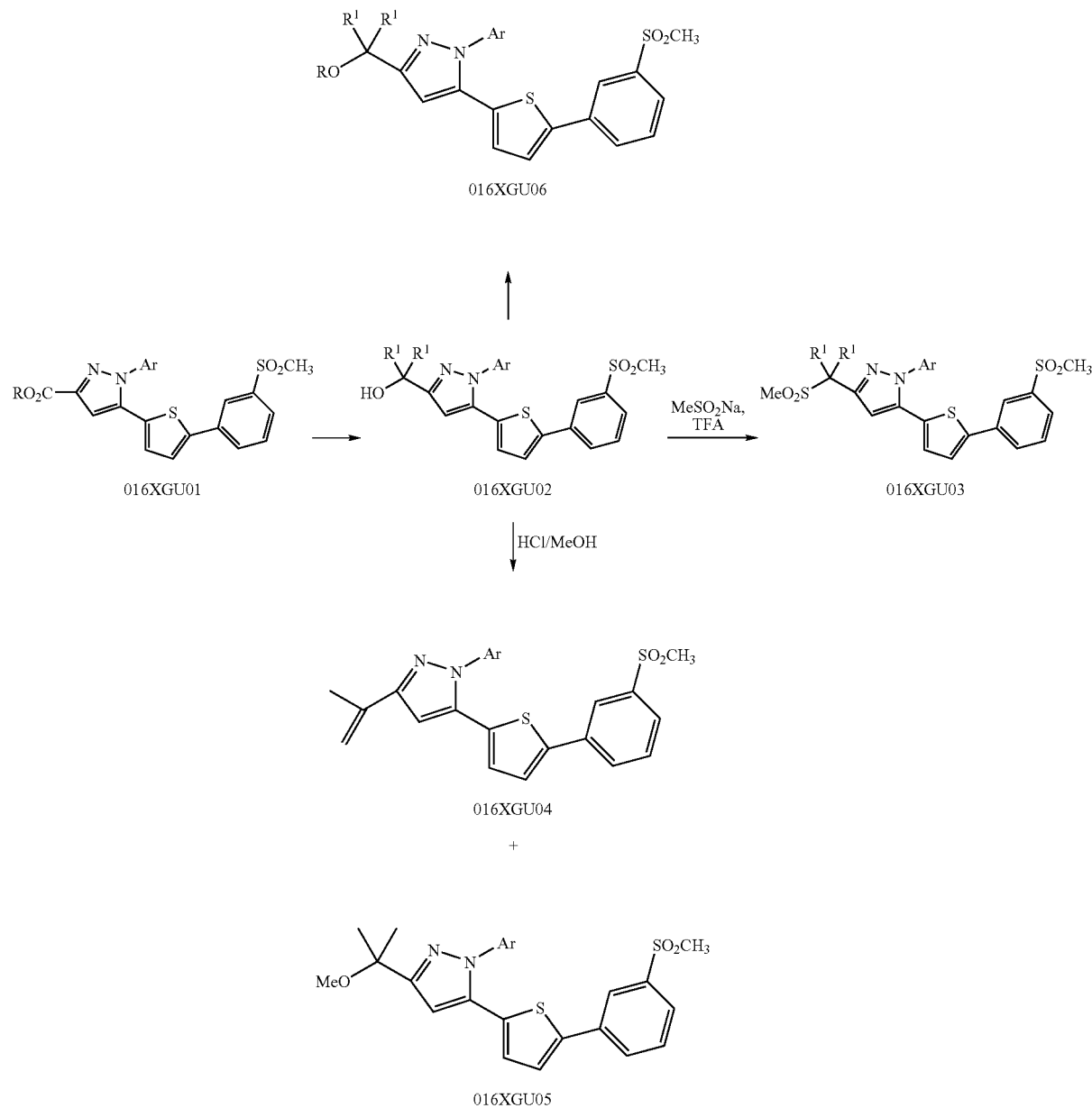

Scheme 16

As depicted in Scheme 16, A carbinol can be transformed into ethers, alkenes and sulfoxide. Ester 016XGU01 was treated with EtMgBr in the presence of Ti(OPr-i)$_4$ or 1,4-butane dimagnesiumbromide to give the cyclopropanol or cyclopentanol 016XGU02. The carbinol was alkylated with RX to give 016XGU06. The carbinol reacted with MeSO$_2$Na in the presence of acid such as TFA to give 016XGU03 and the corresponding olefin 016XGU04. The olefin 016XGU04 and methyl ether 016XGU05 were obtained by treatment of the carbinol with HCl/MeOH.

Example 27

Preparation of 1-[1-(2-chlorophenyl)-5-{5-[3-(methylsulfonyl)phenyl]-2-thienyl}-1H-pyrazol-3-yl]cyclopentanol

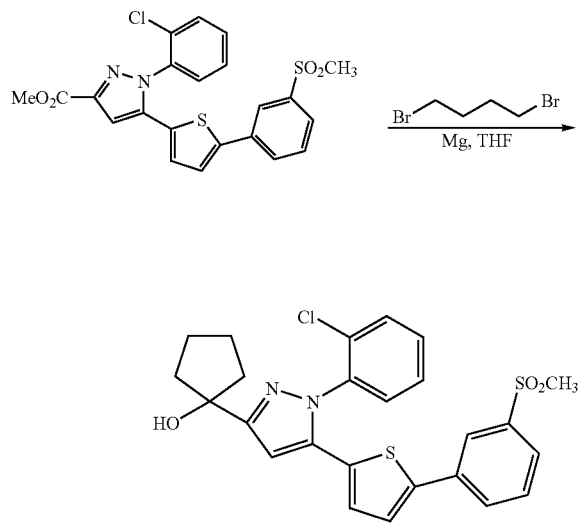

Magnesium turnings (300 mg, 12.5 mmol) was introduced into a oven-dried flask under N$_2$, covered with anhydrous THF (150 mL), and a solution of dibromobutane (0.72 mL, 6.08 mmol) in anhydrous THF (20 mL) was added dropwise at ambient temperature at such a rate that the temperature of the reaction mixture did not rise above 40° C. The mixture was stirred at ambient temperature for 1 h, and the magnesium turnings disappeared. 1-(2-chloro-phenyl)-5-[5-(3-methanesulfonyl-phenyl)thiophen-2-yl]-1H-pyrazole-3-carboxylic acid methyl ester (2.37 g, 5 mmol) was added as a solid, and the resulting dark-purple solution was stirred at room temperature under N$_2$ for 1 h, At 0° C. aqueous NH$_4$Cl solution was added, and then extracted with EtOAc, The combined extracts were washed with brine, dried over Na$_2$SO$_4$. and evaporated in vacuo. The crude product was purified by flash chromatography (0-60% EtOc/hexanes) to afford the title compound as a white solid (1.4 g, 56%). $^1$HNMR (CDCl$_3$): δ 8.04 (d, 1H), 7.83-7.81 (m, 1H), 7.74-7.71 (m, 1H), 7.57-7.52 (m, 3H), 7.48-7.44 (m, 2H), 7.20 (d, 1H), 6.74 (d, 1H), 6.63 (s, 1H), 3.07 (s, 3H), 2.42 (brs, 1H), 2.20-1.83 (m, 8H). MS(ES) 499 [M+H]$^+$, 481 (M-OH).

Example 28

Preparation of 1-[1-(2-chlorophenyl)-5-{5-[3-(methylsulfonyl)phenyl]-2-thienyl}-1H-pyrazol-3-yl]cyclopropanol

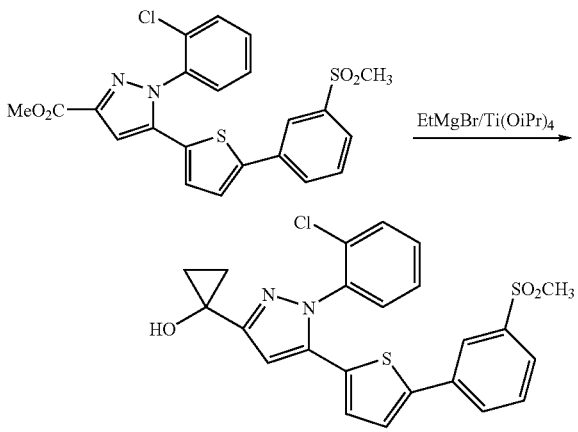

A solution of EtMgBr in THF (1.0M, 11 mL) was added dropwise at it to a stirred solution of 1-(2-chloro-phenyl)-5-[5-(3-methanesulfonyl-phenyl)-thiophen-2-yl]-1H-pyrazole-3-carboxylic acid methyl ester (950 mg, 2 mmol) and Ti(OiPr)$_4$ (0.7 mL, 2.4 mmol) in anhydrous THF (50 mL) under N$_2$. The resulting dark mixture was stirred at it for 2 h. At 0° C. aqueous NH$_4$Cl solution was added, extracted with Et$_2$O. The combined extracts were washed with brine, dried over Na$_2$SO$_4$, and evaporated in vacuo. The crude product was purified first by flash chromatography (0-60% EtOAc/hexanes) and then by reverse HPLC to give the title compounds as a white solid (85 mg, 0.1%). $^1$HNMR (CDCl$_3$): δ 8.04 (d, 1H), 7.83-7.81 (m, 1H), 7.74-7.71 (m, 1H), 7.57-7.43 (m, 5H), 7.2 (d, 1H), 6.72 (d, 1H), 6.50 9s, 1H), 3.07 (s, 3H), 2.92 (brs, 1H), 1.31 (m, 2H), 1.17 (m, 2H). MS(ES): 471[M+H]$^+$, 453 (M-OH).

Example 29

Preparation of 3-[1-methyl-1-(methylsulfonyl)ethyl]-5-{5-[3-(methylsulfonyl)phenyl]-2-thienyl}-1-[2-(trifluoromethyl)phenyl]-1H-pyrazole, and 3-(1-methylethenyl)-5-{5-[3-(methylsulfonyl)phenyl]-2-thienyl}-1-[2-(trifluoromethyl)phenyl]-1H-pyrazole)

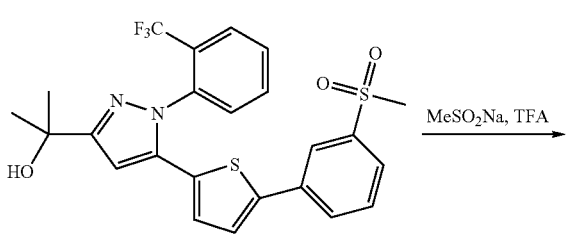

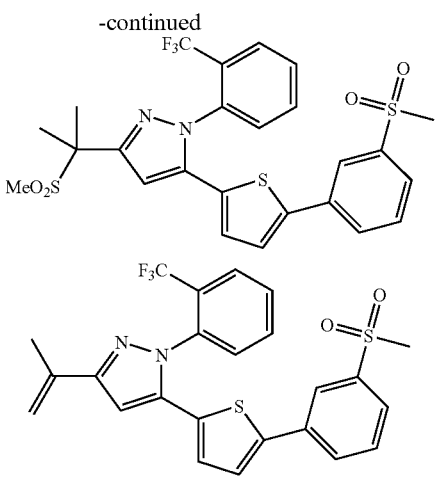

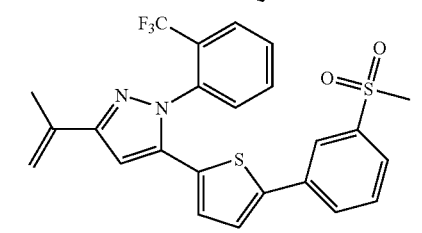

TFA (1 mL) was added dropwise at 0° C. to a stirred mixture of the carbinol (270 mg, 0.533 mmol) and MeSO$_2$Na (280 mg, 2.74 mmol) in CHCl$_3$ (8 mL), the resulting mixture was stirred at rt overnight. After dilution with water, the mixture was poured into 12% aqueous NH$_4$OH solution, and extracted with DCM. The combined extracts were washed with water and brine, dried over Na$_2$SO$_4$, and evaporated in vacuo. The crude product was purified by flash chromatography (0-80% EtOAc/hexanes) to give the title compounds as white solid. (152 mg, 50%). $^1$HNMR (CDCl$_3$): δ 8.02 (d, 1H), 7.9 (m, 1H), 7.83 (m, 1H), 7.71 (m, 3H), 7.55 (m, 1H), 7.46 (m, 1H), 7.20 (d, 1H), 6.88 (s, 1H), 6.74 (d, 1H), 3.07 (s, 3H), 2.77 (s, 3H), 1.88 (s, 61-1). MS(ES): 569 [M+H]$^+$; (40 mg). $^1$HNMR (CDCl$_3$): δ 8.03 (d, 1H), 7.87-7.81 (m, 2H), 7.73-7.66 (m, 3H), 7.57-7.17 (m, 2H), 7.17 (d, 1H), 6.78 (s, 1H), 6.65 (d, 1H), 5.62 (s, 1H), 5.18 (m, 1H), 3.07 (s, 3H), 2.19 (s, MS(ES): 489 [M+H]$^+$.

The following compounds are prepared essentially according to the previous examples:

2-(3-[1-methyl-1-(methylsulfonyl)ethyl]-5-{5-[3-(methylsulfonyl)phenyl]-2-thienyl}-1H-pyrazol-1-yl)-3-(trifluoromethyl)pyridine, MS(ES): 570 [M+H]$^+$ 2-[3-(1-methyl ethenyl)-5-{5-[3-methylsulfonyl)phenyl]-2-thienyl}-1H-pyrazol-1-yl]-3-(trifluoromethyl)pyridine, MS(ES): 490 [M+H]$^+$ 3-(3-[1-methyl-1-(methylsulfonyl)ethyl]-5-{5-[3-(methylsulfonyl)phenyl]-2-thienyl}-1H-pyrazol-1-yl)-2-(trifluoromethyl)pyridine MS(ES): 570 [M+H]$^+$ 3-(1-methylethenyl)-5-{5-[3-(methylsulfonyl)phenyl]-2-thienyl}-1-[2-trifluoromethyl)phenyl]-1H-pyrazole, MS(ES): 490 [M+H]$^+$ 3-(3-[1-methyl-1-methylsulfonyl)ethyl]-5-{5-[3-(methylsulfonyl)phenyl]-2-thienyl}-1H-pyrazol-1-yl)-2-(trifluoromethyl)pyridine, MS(ES): 570 [M+H]$^+$

Example 30

Preparation of 1-(2-chlorophenyl)-3-(1-methylethenyl)-5-{5-[3-(methylsulfonyl)phenyl]-2-thienyl}-1H-pyrazole and 1-(2-chlorophenyl)-3-[1-methyl-1-(methyloxy)ethyl]-5-{5-[3-(methylsulfonyl)phenyl]-2-thienyl}-1H-pyrazole

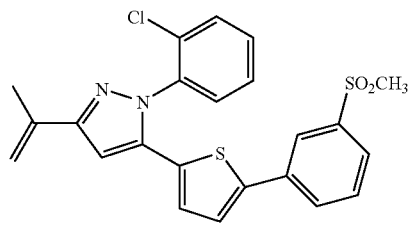

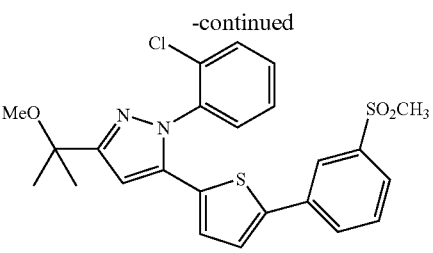

A solution of HCl/MeOH (1.25M, 8 mL) was added to stirred solution of 2-{1-(2-chlorophenyl)-5-[5-(3-methanesulfonyl-phenyl)-thiophen-2-yl]-1H-pyrazol-3-yl}-propan-2-ol (430 mg, 0.864 mmol) in CHCl$_3$, and the reaction mixture was stirred at 85° C. in a sealed vial for 6 h. The solvent was removed in vacuo, and the residue was purified by flash chromatography (0-50% EtOAc/hexanes) to give the title compounds as white solid. (110 mg, 28%): $^1$HNMR (CDCl$_3$): δ 8.05 (m, 1H), 7.83-7.81 (m, 1H), 7.74-7.72 (m, 1H), 7.57-7.52 (m, 3H), 7.49-7.41 (m, 2H), 7.20 (d, 1H), 6.79 (s, 1H), 6.72 (d, 1H), 5.64 (s, 1H), 5.18 (m, 1H), 3.07 (s, 3H), 2.21 (s, 3H). MS(ES): 455 [M+H]$^+$. (94 mg, 22%): $^1$HNMR (CDCl$_3$): δ 8.04 (m, 1H), 7.83-7.80 (m, 1H), 7.74-7.71 (m, 1H), 7.57-7.52 (m, 3H), 7.50-7.41 (m, 2H), 7.20 (d, 1H), 6.74 (d, 1H), 6.67 (s, 1H), 3.23 (d, 3H), 3.07 (s, 3H), 1.63 (s, 6H). MS(ES): 455 (M-OMe).

Example 31

Preparation of 5-{5-[3-(methylsulfonyl)phenyl]-2-thienyl}-3-[1-methyl-1-(methyloxy)ethyl]-1-[2-(trifluoro-methyl)phenyl]-1H-pyrazole and 5-{5-[3-(ethylsulfonyl)phenyl]-2-thienyl}-3-[1-methyl-1-(methyloxy)ethyl]-1-[2-(trifluoromethyl)phenyl]-1H-pyrazole

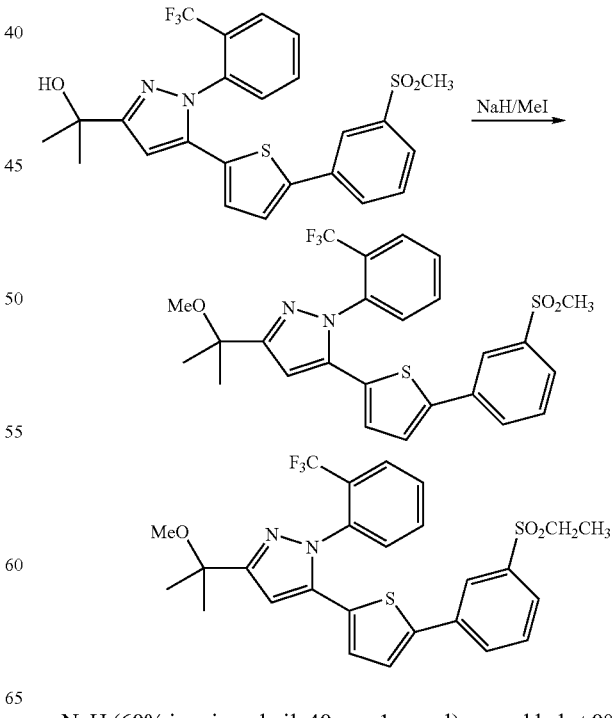

NaH (60% in mineral oil, 40 mg, 1 mmol) was added at 0° C. to a stirred mixture of 2-(5-{5-[3-(methylsulfonyl)phenyl]-2-thienyl}-1-[2-(trifluoromethyl)phenyl]-1H-pyrazol-3-yl)propan-2-ol (260 mg, 0.5 mmol), MeI (47 μL, 0.75 mmol) and anhydrous DMF (8 mL), and the resulting mixture was stirred at rt for 3 h. At 0° C. water was added to quench the reaction, then extracted with DCM. The combined extracts were washed with water and brine, dried over Na₂SO₄, and evaporated in vacuo. The crude product was purified first by flash chromatography (0-40% EtOAc/hexanes), then by normal phase HPLC to give the two title compounds as white solid. (110 mg, 41%). ¹HNMR (CDCl₃): δ 8.03 (m, 1H), 7.87-7.81 (m, 2H), 7.73-7.66 (m, 3H), 7.57-7.50 (m, 2H), 7.18 (d, 1H), 6.66 (m, 2H), 3.21 (s, 3H), 3.07 (s, 3H), 1.63 (s, 6H). MS(ES): 521 [M+H]⁺. (71 mg, 26%). ¹HNMR (CDCl₃): δ 7.98 (m, 1H), 7.87-7.85 (m, 1H), 7.79-7.76 (m, 1H), 7.72-7.66 (m, 3H), 7.56-7.50 (m, 2H), 7.18 (d, 1H), 6.66 (m, 2H), 3.21 (s, 3H), 3.13 (q, 2H), 1.63 (s, 6H), 1.29 (t, 3H). MS(ES): 535 [M+H]⁺.

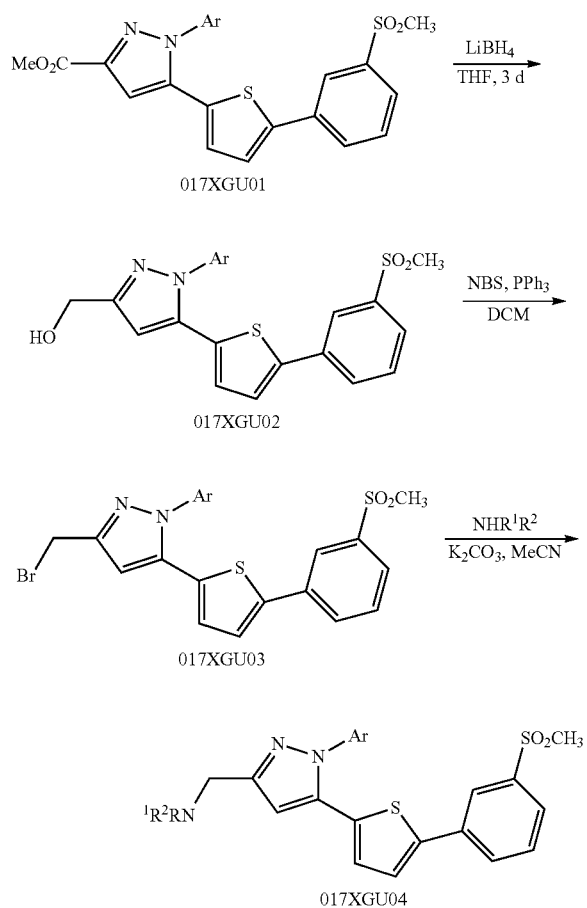

As depicted in Scheme 17, An ester can be transformed into alcohols and amines. Ester 017XGU01 was reduced with lithium borohydride to give primary alcohol 017XGU02 in good yields. Alcohol 017XGU02 was converted to the corresponding bromide 017XGU03 by treatment with NBS/PPh₃. Amine 017XGU04 was obtained by treatment of bromide 017GU03 with the corresponding an amine.

Example 32

Preparation of [1-(2-chlorophenyl)-5-{5-[3-(methylsulfonyl)phenyl]-2-thienyl}-1H-pyrazol-3-yl]methanol

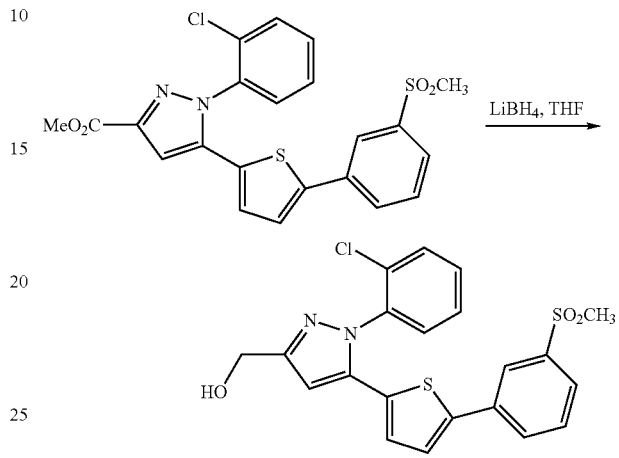

LiBH₄ (1.0M in THF, 14 mL, 28 mmol) was added dropwise at rt to a stirred solution of 1-(2-chloro-phenyl)-5-[5-(3-methanesulfonyl-phenyl)-thiophen-2-yl]-1H-pyrazole-3-carboxylic acid methyl ester (4.38 g, 9.26 mmol) in anhydrous THF (100 mL) under N₂, and the resulting mixture was stirred at rt for 3d. Acetone (2 mL) and water (2 mL) was added successively at 0° C. and the solid was filtered off. The filtrate was concentrated in vacuo. The residue was taken up in EtOAc (200 mL), washed with water and brine, dried over Na₂SO₄ and evaporated in vacuo. The crude product was purified by flash chromatography (0-90% EtOAc/hexanes) to give the title compound as a white solid (3.1 g, 75%). ¹HNMR (CDCl₃): δ 8.04 (m, 1H), 7.84-7.81 (m, 1H), 7.74-7.72 (m, 1H), 7.58-7.44 (m, 5H), 7.21 (d, 1H), 6.76 (d, 1H), 6.69 (s, 1H), 4.80 (s, 2H), 3.07 (s, 3H), 1.65 (brs, 1H). MS(ES): 445 [M+H]⁺.

Example 33

Preparation of 4-{[1-(2-chlorophenyl)-5-{5-[3-(methylsulfonyl)phenyl]-2-thienyl}-1H-pyrazol-3-yl]methyl}morpholine

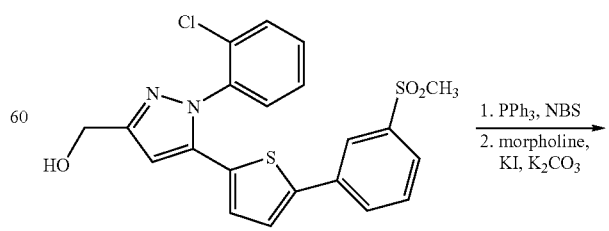

-continued

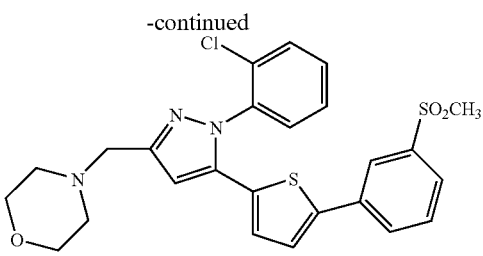

PPh$_3$ (4.36 g, 16.62 mmol) was added at 0° C. to a stirred solution of [1-(2-chlorophenyl)-5-{5-[3-(methylsulfonyl)phenyl]-2-thienyl}-1H-pyrazol-3-yl]methanol (6.15 g, 13.85 mmol) in dry DCM. After 30 min, NBS (2.72 g, 15.28 mmol) was added portionwise at 0° C., and the mixture was stirred at it overnight. The solvent was removed in vacuo, and the crude product was purified by flash chromatography (0-50% EtOAc/hexanes) to afford 3-bromomethyl-1-(2-chlorophenyl)-5-{5-[3-(methylsulfonyl)phenyl]-thiophen-2-yl]-1H-pyrazole as a pale-yellow solid (3.6 g, 54%).

A mixture of 3-bromomethyl-1-(2-chlorophenyl)-5-{5-[3-(methylsulfonyl)phenyl]-thiophen-2-yl]-1H-pyrazole (51 mg, 0.1 mmol), K$_2$CO$_3$ (42 mg, 0.3 mmol), KI (10 mg), and morpholine (0.3 mmol) in anhydrous MeCN (5 mL) was stirred at 90° C. for 6 h under N$_2$. The solid was filtered off, and the filtrate was concentrated in vacuo. The crude product was purified by flash chromatography (0-80% EtOAc/hexanes) to give the title compound as a pale-yellow solid (50 mg, 96%). $^1$HNMR (CDCl$_3$): δ 8.04 (m, 1H), 7.82 (m, 1H), 7.72 (m, 1H), 7.57-7.43 (m, 5H), 7.20 (d, 1H), 6.75 (d, 1H), 6.66 (s, 1H), 3.77 (m, 4H), 3.66 (s, 2H), 3.07 (s, 3H), 2.60 (m, 4H). MS(ES): 514 [M+H]$^+$.

The following compounds are prepared essentially according to the previous examples:

1-{[1-(2-chlorophenyl)-5-{5-[3-(methylsulfonyl)phenyl]-2-thienyl}-1H-pyrazol-3-yl]methyl}-4-methylpiperazine, MS(ES): 527 [M+H]$^+$ 1-(2-chlorophenyl)-5-{5-[3-(methylsulfonyl)phenyl]-2-thienyl}-3-(pyrrolidin-1-ylmethyl)-1H-pyrazole, MS(ES): 498 [M+H]$^+$ 2-(4-{[1-(2-chlorophenyl)-5-{5-[3-(methylsulfonyl)phenyl]-2-thienyl}-1H-pyrazol-3-yl]methyl}piperazin-1-yl)pyrimidine, MS(ES): 591 [M+H]$^+$ 1-[1-(2-chlorophenyl)-5-{5-[3-(methylsulfonyl)phenyl]-2-thienyl}-1H-pyrazol-3-yl]-N-(furan-2-ylmethyl)-N-methylmethanamine, MS(ES): 538 [M+H]$^+$ 1-[1-(2-chlorophenyl)-5-{5-[3-(methylsulfonyl)phenyl]-2-thienyl}-1H-pyrazol-3-yl]-N-(pyridin-2-ylmethyl)methanamine, MS(ES): 535 [M+H]$^+$ Phenylmethyl 4-{[1-(2-chlorophenyl)-5-{5-[3-(methylsulfonyl)phenyl]-2-thienyl}-1H-pyrazol-3-yl]methyl}-3-oxopiperazine-1-carboxylate, MS(ES): 661 [M+H]$^+$ 1-(2-chlorophenyl)-3-(1H-imidazol-1-ylmethyl)-5-{5-[3-(methylsulfonyl)phenyl]-2-thienyl}-1H-pyrazole, MS(ES): 495 [M+H]$^+$ 1-[1-(2-chlorophenyl)-5-{5-[3-(methylsulfonyl)phenyl]-2-thienyl}-1H-pyrazol-3-yl]-N-methyl-N-(2-thienylmethyl)methanamine, MS(ES): 554 [M+H]$^+$ 3-[{[1-(2-chlorophenyl)-5-{5-[3-(methylsulfonyl)phenyl]-2-thienyl}-1H-pyrazol-3-yl]methyl}(furan-2-ylmethyl)amino]propanenitrile, MS(ES): 577 [M+H]$^+$ N-{([1-(2-chlorophenyl)-5-{5-[3-(methylsulfonyl)phenyl]-2-thienyl}-1H-pyrazol-3-yl]methyl}-2,2,2-trifluoro-N-(furan-2-ylmethyl)ethanamine, MS(ES): 606 [M+H]$^+$ N-{[1-(2-chlorophenyl)-5-{5-[3-(methylsulfonyl)phenyl]-2-thienyl}-1H-pyrazol-3-yl]methyl}-N-(furan-2-ylmethyl)propan-2-amine, MS(ES): 566 [M+H]$^+$ N-{[1-(2-chlorophenyl)-5-{5-[3-(methylsulfonyl)phenyl]-2-thienyl}-1H-pyrazol-3-yl]methyl}-N-(furan-2-ylmethyl)cyclopropanamine, MS(ES): 564 [M+H]$^+$ N-{[1-(2-chlorophenyl)-5-{5-[3-(methylsulfonyl)phenyl]-2-thienyl}-1H-pyrazol-3-yl]methyl}-N-(furan-2-ylmethyl)-2-methylpropan-2-amine, MS(ES): 580 [M+H]$^+$ N-{[1-(2-chlorophenyl)-5-{5-[3-(methylsulfonyl)phenyl]-2-thienyl}-1H-pyrazol-3-yl]-methyl}-N-(furan-2-ylmethyl)cyclohexanamine, MS(ES): 606 [M+H]$^+$ 1-[1-(2-chlorophenyl)-5-{5-[3-(methylsulfonyl)phenyl]-2-thienyl}-1H-pyrazol-3-yl]-N-[(3,5-dimethylisoxazol-4-yl)methyl]-N-methylmethanamine, MS(ES): 567 [M+H]$^+$ N-{[1-(2-chlorophenyl)-5-{5-[3-(methylsulfonyl)phenyl]-2-thienyl}-1H-pyrazol-3-yl]methyl}-N-(pyridin-4-ylmethyl)ethanamine, MS(ES): 563[M+H]$^+$ N-{[1-(2-chlorophenyl)-5-{5-[3-(methylsulfonyl)phenyl]-2-thienyl}-1H-pyrazol-3-yl]methyl}-N-(pyridin-4-ylmethyl)methanamine, MS(ES): 549 [M+H]$^+$ 1-[1-(2-chlorophenyl)-5-{5-[3-(methylsulfonyl)phenyl]-2-thienyl}-1H-pyrazol-3-yl]-N-methyl-N-(1,3-oxazol-2-ylmethyl)methanamine, MS(ES): 539 [M+H]$^+$ N-{[1-(2-chlorophenyl)-5-{5-[3-(methylsulfonyl)phenyl]-2-thienyl}-1H-pyrazol-3-yl]methyl}-N-methyl-2-pyridin-2-ylethanamine, MS(ES): 563 [M+H]$^+$.

N-{[1-(2-chlorophenyl)-5-{5-[3-(methylsulfonyl)phenyl]-2-thienyl}-1H-pyrazol-3-yl]methyl}-2-methyl-N-(1-methylethyl)propan-2-amine MS(ES): 542 [M+H]$^+$.

3-[{[1-(2-chlorophenyl)-5-{5-[3-(methylsulfonyl)phenyl]-2-thienyl}-1H-pyrazol-3-yl]methyl}(ethyl)amino]propanenitrile, MS(ES): 525 [M+H]$^+$, (1S)—N-{[1-(2-chlorophenyl)-5-{5-[3-(methylsulfonyl)phenyl]-2-thienyl}-1H-pyrazol-3-yl]methyl}-N-methyl-1-phenylethanamine, MS(ES): 562 [M+H]$^+$.

N-{[1-(2-chlorophenyl)-5-{5-[3-(methylsulfonyl)phenyl]-2-thienyl}-1H-pyrazol-3-yl]methyl}-N-methyl-2-phenylethanamine, MS(ES): 562 [M+H]$^+$.

1-{[1-(2-chlorophenyl)-5-{5-[3-(methylsulfonyl)phenyl]-2-thienyl}-1H-pyrazol-3-yl]methyl}-4-(phenylmethyl)piperidine; MS (ES): 602 [M+H]$^+$;

ethyl N-{[1-(2-chlorophenyl)-5-{5-[3-(methylsulfonyl)phenyl]-2-thienyl}-1H-pyrazol-3-yl]methyl}piperidine-2-carboxylate; MS (ES): 584 [M+H]$^+$;

1-{[1-(2-chlorophenyl)-5-{5-[3-(methylsulfonyl)phenyl]-2-thienyl}-1H-pyrazol-3-yl]methyl}-4-(phenylmethyl)piperazine; MS (ES): 603 [M+H]$^+$;

ethyl N-{[1-(2-chlorophenyl)-5-{5-[3-(methylsulfonyl)phenyl]-2-thienyl}-1H-pyrazol-3-yl]methyl}-N-(phenylmethyl)glycinate; MS (ES): 620 [M+H]$^+$;

4-[(4-{[1-(2-chlorophenyl)-5-{5-[3-(methylsulfonyl)phenyl]-2-thienyl}-1H-pyrazol-3-yl]methyl}piperazin-1-yl)acetyl]morpholine; MS (ES): 640 [M+H]$^+$;

2-{[1-(2-chlorophenyl)-5-{5-[3-(methylsulfonyl)phenyl]-2-thienyl}-1H-pyrazol-3-yl]methyl}decahydroisoquinoline; MS (ES): 566 [M+H]$^+$;

2-[3,4-bis(methyloxy)phenyl]-N-{[1-(2-chlorophenyl)-5-{5-[3-(methylsulfonyl)phenyl]-2-thienyl}-1H-pyrazol-3-yl]methyl}-N-methylethanamine; MS (ES): 622 [M+H]$^+$;

ethyl 1-{[1-(2-chlorophenyl)-5-{5-[3-(methylsulfonyl)phenyl]-2-thienyl}-1H-pyrazol-3-yl]methyl}piperidine-4-carboxylate; MS (ES): 584 [M+H]$^+$;

ethyl 4-{[1-(2-chlorophenyl)-5-{5-[3-(methylsulfonyl)phenyl]-2-thienyl}-1H-pyrazol-3-yl]methyl}piperazine-1-carboxylate; MS (ES): 585 [M+H]$^+$, N-{[1-(2-chlorophenyl)-5-{5-[3-(methylsulfonyl)phenyl]-2-thienyl}-1H-pyrazol-3-yl]methyl}-N-propylpropan-1-amine; MS (ES): 528 [M+H]+;

1-{[1-(2-chlorophenyl)-5-{5-[3-(methylsulfonyl)phenyl]-2-thienyl}-1H-pyrazol-3-yl]methyl}-3-methylpiperidine; MS (ES): 526 [M+H]+;

4-{[1-(2-chlorophenyl)-5-{5-[3-(methylsulfonyl)phenyl]-2-thienyl}-1H-pyrazol-3-yl]methyl}-2,6-dimethylmorpholine; MS (ES): 542 [M+H]+;

1,1-dimethylethyl 4-{[1-(2-chlorophenyl)-5-{5-[3-(methylsulfonyl)phenyl]-2-thienyl}-1H-pyrazol-3-yl]methyl}piperazine-1-carboxylate; MS (ES): 613 [M+H]+;

1-{[1-(2-chlorophenyl)-5-{5-[3-(methylsulfonyl)phenyl]-2-thienyl}-1H-pyrazol-3-yl]methyl}-4-(2-oxo-2-pyrrolidin-1-ylethyl)piperazine; MS (ES): 624 [M+H]+;

N-{[1-(2-chlorophenyl)-5-{5-[3-(methylsulfonyl)phenyl]-2-thienyl}-1H-pyrazol-3-yl]methyl}-2-(methyloxy)-N-[2-(methyloxy)ethyl]ethanamine; MS (ES): 560 [M+H]+;

1-{4-[1-(2-chlorophenyl)-5-{5-[3-(methylsulfonyl)phenyl]-2-thienyl}-1H-pyrazol-3-yl]methyl}-4-(3,4-dichlorophenyl)piperazine; MS (ES): 657 [M+H]+;

1-{[1-(2-chlorophenyl)-5-{5-[3-(methylsulfonyl)phenyl]-2-thienyl}-1H-pyrazol-3-yl]methyl}-4-phenylpiperazine; MS (ES): 589 [M+H]+;

3-{[1-(2-chlorophenyl)-5-{5-[3-(methylsulfonyl)phenyl]-2-thienyl}-1H-pyrazol-3-yl]methyl}-1,3-thiazolidine; MS (ES): 516 [M+H]+;

1-[1-(2-chlorophenyl)-5-{5-[3-(methylsulfonyl)phenyl]-2-thienyl}-1H-pyrazol-3-yl]-N,N-bis(pyridin-2-ylmethyl)methanamine; MS (ES): 626 [M+H]+;

N-{[1-(2-chlorophenyl)-5-{5-[3-(methylsulfonyl)phenyl]-2-thienyl}-1H-pyrazol-3-yl]methyl}-N,N',N'-triethylethane-1,2-diamine; MS (ES): 571 [M+H]+;

1-{[1-(2-chlorophenyl)-5-{5-[3-(methylsulfonyl)phenyl]-2-thienyl}-1H-pyrazol-3-yl]methyl}-4-ethylpiperazine; MS (ES): 541 [M+H]+;

1-[1-(2-chlorophenyl)-5-{5-[3-(methylsulfonyl)phenyl]-2-thienyl}-1H-pyrazol-3-yl]-N,N-bis(phenylmethyl)methanamine; MS (ES): 624 [M+H]+;

1-{[1-(2-chlorophenyl)-5-{5-[3-(methylsulfonyl)phenyl]-2-thienyl}-1H-pyrazol-3-yl]methyl}-4-pyrrolidin-1-ylpiperidine; MS (ES): 581 [M+H]+;

1-(1,3-benzodioxol-5-ylmethyl)-4-{[1-(2-chlorophenyl)-5-{5-[3-(methylsulfonyl)phenyl]-2-thienyl}-1H-pyrazol-3-yl]methyl}piperazine; MS (ES): 647 [M+H]+;

N-{[1-(2-chlorophenyl)-5-{5-[3-(methylsulfonyl)phenyl]-2-thienyl}-1H-pyrazol-3-yl]methyl}-N-methylhexan-1-amine; MS (ES): 542 [M+H]+;

1-{[1-(2-chlorophenyl)-5-{5-[3-(methylsulfonyl)phenyl]-2-thienyl}-1H-pyrazol-3-yl]methyl}-3,5-dimethylpiperidine; MS (ES): 540 [M+H]+;

1-{[1-(2-chlorophenyl)-5-{5-[3-(methylsulfonyl)phenyl]-2-thienyl}-1H-pyrazol-3-yl]methyl}-2-ethylpiperidine; MS (ES): 540 [M+H]+;

1-{[1-(2-chlorophenyl)-5-{5-[3-(methylsulfonyl)phenyl]-2-thienyl}-1H-pyrazol-3-yl]methyl}-2,5-dimethylpiperazine; MS (ES): 541 [M+H]+;

1-{[1-(2-chlorophenyl)-5-{5-[3-(methylsulfonyl)phenyl]-2-thienyl}-1H-pyrazol-3-yl]methyl}-1,4,5,6-tetrahydropyrimidine; MS (ES): 511 [M+H]+;

1-{[1-(2-chlorophenyl)-5-{5-[3-(methylsulfonyl)phenyl]-2-thienyl}-1H-pyrazol-3-yl]methyl}azepane; MS (ES): 526 [M+H]+;

1-{[1-(2-chlorophenyl)-5-{5-[3-(methylsulfonyl)phenyl]-2-thienyl}-1H-pyrazol-3-yl]methyl}-4-[5-(trifluoromethyl)pyridin-2-yl]piperazine; MS (ES): 658 [M+H]+;

1-{[1-(2-chlorophenyl)-5-{5-[3-(methylsulfonyl)phenyl]-2-thienyl}-1H-pyrazol-3-yl]methyl}-4-[3-(trifluoromethyl)phenyl]piperazine; MS (ES): 657 [M+H]+;

N-{[1-(2-chlorophenyl)-5-{5-[3-(methylsulfonyl)phenyl]-2-thienyl}-1H-pyrazol-3-yl]methyl}-N-cyclohexylcyclohexanamine; MS (ES): 608 [M+H]+;

methyl 1-([1-(2-chlorophenyl)-5-{5-[3-(methylsulfonyl)phenyl]-2-thienyl}-1H-pyrazol-3-yl]methyl}-L-prolinate; MS (ES): 556 [M+H]+;

1-([1-(2-chlorophenyl)-5-{5-[3-(methylsulfonyl)phenyl]-2-thienyl)-1H-pyrazol-3-yl]methyl}-1,4-diazepane; MS (ES): 527 [M+H]+;

1-(2-chlorophenyl)-3-({2-[4-(ethyloxy)phenyl]pyrrolidin-1-yl}methyl)-5-{5-[3-(methylsulfonyl)phenyl]-2-thienyl}-1H-pyrazole; MS (ES): 618 [M+H]+;

1-[1-(2-chlorophenyl)-5-{5-[3-(methylsulfonyl)phenyl]-2-thienyl}-1H-pyrazol-3-yl]-N-[(4-fluorophenyl)methyl]-N-methylmethanamine; MS (ES): 566 [M+H]+;

N-{[1-(2-chlorophenyl)-5-{5-[3-(methylsulfonyl)phenyl]-2-thienyl}-1H-pyrazol-3-yl]methyl}-N-methyl-2-morpholin-4-yl-1-phenylethanamine; MS (ES): 647 [M+H]+;

1-{[1-(2-chlorophenyl)-5-{5-[3-(methylsulfonyl)phenyl]-2-thienyl}-1H-pyrazol-3-yl]methyl}-2-phenylazepane; MS (ES): 602 [M+H]+;

1-(2-chlorophenyl)-3-{[2-(2-methylphenyl)pyrrolidin-1-yl]methyl}-5-{5-[3-(methylsulfonyl)phenyl]-2-thienyl}-1H-pyrazole; MS (ES): 588 [M+H]+;

1-(2-chlorophenyl)-3-({2-[4-(methyloxy)phenyl]pyrrolidin-1-yl}methyl)-5-{5-[3-(methylsulfonyl)phenyl]-2-thienyl}-1H-pyrazole; MS (ES): 604 [M+H]+;

1-(2-chlorophenyl)-3-{[2-(4-methylphenyl)pyrrolidin-1-yl]methyl}-5-{5-[3-(methylsulfonyl)phenyl]-2-thienyl}-1H-pyrazole; MS (ES): 588 [M+H]+;

1-(2-chlorophenyl)-3-({2-[4-(1,1-dimethylethyl)phenyl]pyrrolidin-1-yl}methyl)-5-{5-[3-(methylsulfonyl)phenyl]-2-thienyl}-1H-pyrazole; MS (ES): 630 [M+H]+;

1-{[1-(2-chlorophenyl)-5-{5-[3-(methylsulfonyl)phenyl]-2-thienyl}-1H-pyrazol-3-yl]methyl}-2-pyridin-2-ylazepane; MS (ES): 603 [M+H]+;

1-{[1-(2-chlorophenyl)-5-{5-[3-(methylsulfonyl)phenyl]-2-thienyl}-1H-pyrazol-3-yl]methyl}-2-(4-methylphenyl)azepane; MS (ES): 616 [M+H]+;

1-{[1-(2-chlorophenyl)-5-{5-[3-(methylsulfonyl)phenyl]-2-thienyl}-1H-pyrazol-3-yl]methyl}-2-(4-fluorophenyl)azepane; MS (ES): 620 [M+H]+;

N-{[1-(2-chlorophenyl)-5-{5-[3-(methylsulfonyl)phenyl]-2-thienyl}-1H-pyrazol-3-yl]methyl}-N-methyl-1-phenylethanamine; MS (ES): 562 [M+H]+;

1-{[1-(2-chlorophenyl)-5-{5-[3-(methylsulfonyl)phenyl]-2-thienyl}-1H-pyrazol-3-yl]methyl}-2-(3,4-dichlorophenyl)azepane; MS (ES): 670 [M+H]+;

1-{[1-(2-chlorophenyl)-5-{5-[3-(methylsulfonyl)phenyl]-2-thienyl}-1H-pyrazol-3-yl]methyl}-2-[4-(methyloxy)phenyl]azepane; MS (ES): 632 [M+H]+;

1-(2-chlorophenyl)-3-{[2-(3-chlorophenyl)pyrrolidin-1-yl]methyl}-5-{5-[3-(methylsulfonyl)phenyl]-2-thienyl}-1H-pyrazole; MS (ES): 608 [M+H]+;

3-{[2-(4-bromophenyl)pyrrolidin-1-yl]methyl}-1-(2-chlorophenyl)-5-{5-[3-(methylsulfonyl)phenyl]-2-thienyl}-1H-pyrazole; MS (ES): 652 [M+H]+;

1-(2-chlorophenyl)-3-({2-[3-(methyloxy)phenyl]pyrrolidin-1-yl}methyl)-5-{5-[3-(methylsulfonyl)phenyl]-2-thienyl}-1H-pyrazole; MS (ES): 604 [M+H]+;

1-(2-chlorophenyl)-3-({2-[2-(methyloxy)phenyl]pyrrolidin-1-yl}methyl)-5-{5-[3-(methylsulfonyl)phenyl]-2-thienyl}-1H-pyrazole; MS (ES): 604 [M+H]+;

1-{[1-(2-chlorophenyl)-5-{5-[3-(methylsulfonyl)phenyl]-2-thienyl}-1H-pyrazol-3-yl]methyl}-2-[3-(methyloxy)phenyl]azepane; MS (ES): 632 [M+H]$^+$;

1-{[1-(2-chlorophenyl)-5-{5-[3-(methylsulfonyl)phenyl]-2-thienyl}-1H-pyrazol-3-yl]methyl}-2-(2-thienyl)azepane; MS (ES): 608 [M+H]$^+$;

1-[1-(2-chlorophenyl)-5-{5-[3-(methylsulfonyl)phenyl]-2-thienyl}-1H-pyrazol-3-yl]-N-methyl-N-(3-thienylmethyl)methanamine; MS (ES): 554 [M+H]$^+$;

4-({[1-(2-chlorophenyl)-5-{5-[3-(methylsulfonyl)phenyl]-2-thienyl}-1H-pyrazol-3-yl]methyl}amino)pyrimidine-2(1H)-thione; MS (ES): 554 [M+H]$^+$;

1-[1-(2-chlorophenyl)-5-{5-[3-(methylsulfonyl)phenyl]-2-thienyl}-1H-pyrazol-3-yl]-N-methyl-N-[(3-methylisoxazol-5-yl)methyl]methanamine; MS (ES): 553 [M+H]$^+$;

N-({1-(2-chlorophenyl)-5-{5-[3-(methylsulfonyl)phenyl]-2-thienyl)-1H-pyrazol-3-yl]methyl}-N-methyl-1-(2-thienyl)ethanamine; MS (ES): 568 [M+H]$^+$;

(1-{[1-(2-chlorophenyl)-5-{5-[3-(methylsulfonyl)phenyl]-2-thienyl}-1H-pyrazol-3-yl]methyl}piperidin-3-yl)methanol; MS (ES): 542 [M+H]$^+$;

4-{[1-(2-chlorophenyl)-5-{5-[3-(methylsulfonyl)phenyl]-2-thienyl}-1H-pyrazol-3-yl]methyl}-3-[4-(trifluoromethyl)phenyl]thiomorpholine; MS (ES): 674 [M+H]$^+$;

1-{[1-(2-chlorophenyl)-5-{5-[3-(methylsulfonyl)phenyl]-2-thienyl}-1H-pyrazol-3-yl]methyl}-2-(3-methylphenyl)azepane; MS (ES): 616 [M+H]$^+$;

1-[1-(2-chlorophenyl)-5-{5-[3-(methylsulfonyl)phenyl]-2-thienyl}-1H-pyrazol-3-yl]-N,N-dimethylmethanamine; MS (ES): 472 [M+H]$^+$;

1-(1,1-dimethylethyl) 3-methyl 4-{[1-(2-chlorophenyl)-5-{5-[3-(methylsulfonyl)phenyl]-2-thienyl}-1H-pyrazol-3-yl]methyl}piperazine-1,3-dicarboxylate; MS (ES): 671 [M+H]$^+$;

2-(4-{[1-(2-chlorophenyl)-5-{5-[3-(methylsulfonyl)phenyl]-2-thienyl}-1H-pyrazol-3-yl]methyl}piperazin-1-yl)-N,N-diethylethanamine; MS (ES): 612 [M+H]$^+$;

1-{[1-(2-chlorophenyl)-5-{5-[3-(methylsulfonyl)phenyl]-2-thienyl}-1H-pyrazol-3-yl]methyl}-4-(3-phenylpropyl)piperazine; MS (ES): 631 [M+H]$^+$;

1-[1-(2-chlorophenyl)-5-{5-[3-(methylsulfonyl)phenyl]-2-thienyl}-1H-pyrazol-3-yl]-N-[(4-ethylphenyl)methyl]-N-methylmethanamine; MS (ES): 576 [M+H]$^+$;

1-[1-(2-chlorophenyl)-5-{5-[3-(methylsulfonyl)phenyl]-2-thienyl}-1H-pyrazol-3-yl]-N-methyl-N-[(4-methyl-1H-imidazol-2-yl)methyl]methanamine; MS (ES): 552 [M+H]$^+$;

[{[1-(2-chlorophenyl)-5-{5-[3-(methylsulfonyl)phenyl]-2-thienyl}-1H-pyrazol-3-yl]methyl}(methyl)amino]acetonitrile; MS (ES): 497 [M+H]$^+$;

1-{[1-(2-chlorophenyl)-5-{5-[3-(methylsulfonyl)phenyl]-2-thienyl}-1H-pyrazol-3-yl]methyl}piperidine; MS (ES): 512 [M+H]$^+$;

N-{[1-(2-chlorophenyl)-5-{5-[3-(methylsulfonyl)phenyl]-2-thienyl}-1H-pyrazol-3-yl]methyl}-2-methyl-N-(phenylmethyl)propan-2-amine; MS (ES): 590 [M+H]$^+$;

1-[1-(2-chlorophenyl)-5-{5-[3-(methylsulfonyl)phenyl]-2-thienyl}-1H-pyrazol-3-yl]-N-(1H-imidazol-2-ylmethyl)-N-methylmethanamine; MS (ES): 538 [M+H]$^+$;

1-[1-(2-chlorophenyl)-5-{5-[3-(methylsulfonyl)phenyl]-2-thienyl}-1H-pyrazol-3-yl]-N-methyl-N-[(5-methyl-1H-pyrazol-3-yl)methyl]methanamine; MS (ES): 552 [M+H]$^+$;

1-[1-(2-chlorophenyl)-5-{5-[3-(methylsulfonyl)phenyl]-2-thienyl}-1H-pyrazol-3-yl]-N-methyl-N-[(4-methylphenyl)methyl]methanamine; MS (ES): 562 [M+H]$^+$;

1-{[1-(2-chlorophenyl)-5-{5-[3-(methylsulfonyl)phenyl]-2-thienyl}-1H-pyrazol-3-yl]methyl}-2-(2-methylphenyl)azepane; MS (ES): 616 [M+H]$^+$;

1-(2-chlorophenyl)-5-{5-[3-(methylsulfonyl)phenyl]-2-thienyl}-3-({2-[2-(trifluoromethyl)phenyl]pyrrolidin-1-yl}methyl)-1H-pyrazole; MS (ES): 642 [M+H]$^+$;

1-[1-(2-chlorophenyl)-5-{5-[3-(methylsulfonyl)phenyl]-2-thienyl}-1H-pyrazol-3-yl]-N-methyl-N-(quinolin-8-ylmethyl)methanamine; MS (ES): 599 [M+H]$^+$;

4-(1-{[1-(2-chlorophenyl)-5-{5-[3-(methylsulfonyl)phenyl]-2-thienyl}-1H-pyrazol-3-yl]methyl}pyrrolidin-2-yl)-N,N-dimethylaniline; MS (ES): 617 [M+H]$^+$;

1-[1-(2-chlorophenyl)-5-{5-[3-(methylsulfonyl)phenyl]-2-thienyl}-1H-pyrazol-3-yl]-N-[(3,5-dimethyl-1H-pyrazol-4-yl)methyl]-N-methylmethanamine; MS (ES): 566 [M+H]$^+$;

1-(1,3-benzothiazol-2-yl)-N-{[1-(2-chlorophenyl)-5-{5-[3-(methylsulfonyl)phenyl]-2-thienyl}-1H-pyrazol-3-yl]methyl}-N-methylmethanamine; MS (ES): 605 [M+H]$^+$;

N~1~-{[1-(2-chlorophenyl)-5-{5-[3-(methylsulfonyl)phenyl]-2-thienyl}-1H-pyrazol-3-yl]methyl}-N~1~,N~2~,N~2~-trimethyl-1-phenylethane-1,2-diamine; MS (ES): 605 [M+H]$^+$;

1-[1-(2-chlorophenyl)-5-{5-[3-(methylsulfonyl)phenyl]-2-thienyl}-1H-pyrazol-3-yl]-methyl-N-[(2-methyl-1,3-thiazol-4-yl)methyl]methanamine; MS (ES): 569 [M+H]$^+$;

1-(1-benzothien-2-yl)-N-{[1-(2-chlorophenyl)-5-{5-[3-(methylsulfonyl)phenyl]-2-thienyl}-1H-pyrazol-3-yl]methyl}-N-methylmethanamine; MS (ES): 604 [M+H]$^+$;

2-(1-{[1-(2-chlorophenyl)-5-{5-[3-(methylsulfonyl)phenyl]-2-thienyl}-1H-pyrazol-3-yl]methyl}pyrrolidin-2-yl)-1H-indole; MS (ES): 613 [M+H]$^+$;

3-{[2-(2-bromophenyl)pyrrolidin-1-yl]methyl}-1-(2-chlorophenyl)-5-{5-[3-(methylsulfonyl)phenyl]-2-thienyl}-1H-pyrazole; MS (ES): 652 [M+H]$^+$;

1-[1-(2-chlorophenyl)-5-{5-[3-(methylsulfonyl)phenyl]-2-thienyl}-1H-pyrazol-3-yl]-N-methyl-N-(quinolin-5-ylmethyl)methanamine; MS (ES): 599 [M+H]$^+$;

N-butyl-N-{[1-(2-chlorophenyl)-5-{5-[3-(methylsulfonyl)phenyl]-2-thienyl}-1H-pyrazol-3-yl]methyl}butan-1-amine; MS (ES): 556 [M+H]$^+$;

1-{[1-(2-chlorophenyl)-5-{5-[3-(methylsulfonyl)phenyl]-2-thienyl}-1H-pyrazol-3-yl]methyl}-4-phenylpiperidine-4-carbonitrile; MS (ES): 613 [M+H]$^+$;

2-{[1-(2-chlorophenyl)-5-{5-[3-(methylsulfonyl)phenyl]-2-thienyl}-1H-pyrazol-3-yl]methyl}-6,7-bis(methyloxy)-1,2,3,4-tetrahydroisoquinoline; MS (ES): 620 [M+H]$^+$;

4-(4-chlorophenyl)-1-{[1-(2-chlorophenyl)-5-{5-[3-(methylsulfonyl)phenyl]-2-thienyl}-1H-pyrazol-3-yl]methyl}-1,2,3,6-tetrahydropyridine; MS (ES): 620 [M+H]$^+$;

1-[1-(2-chlorophenyl)-5-{5-[3-(methylsulfonyl)phenyl]-2-thienyl}-1H-pyrazol-3-yl]-N-methyl-N-[(5-phenylisoxazol-3-yl)methyl]methanamine; MS (ES): 615 [M+H]$^+$;

4-bromo-1-{[1-(2-chlorophenyl)-5-{5-[3-(methylsulfonyl)phenyl]-2-thienyl}-1H-pyrazol-3-yl]methyl}piperidine; MS (ES): 590 [M+H]$^+$;

methyl N-{[1-(2-chlorophenyl)-5-{5-[3-(methylsulfonyl)phenyl]-2-thienyl}-1H-pyrazol-3-yl]methyl}-N-methylglycinate; MS (ES): 530 [M+H]$^+$;

1-({1-(2-chlorophenyl)-5-{5-[3-(methylsulfonyl)phenyl]-2-thienyl}-1H-pyrazol-3-yl]methyl)piperidin-3-ol; MS (ES): 528 [M+H]$^+$;

N-{[1-(2-chlorophenyl)-5-(5-[3-(methylsulfonyl)phenyl]-2-thienyl}-1H-pyrazol-3-yl]methyl)-N-methyl-2-phenylpropan-2-amine; MS (ES): 576 [M+H]$^+$;

4-{[1-(2-chlorophenyl)-5-{5-[3-(methylsulfonyl)phenyl]-2-thienyl}-1H-pyrazol-3-yl]methyl}-3-(4-fluorophenyl)thiomorpholine; MS (ES): 624 [M+H]+;

N-{[1-(2-chlorophenyl)-5-{5-[3-(methylsulfonyl)phenyl]-2-thienyl}-1H-pyrazol-3-yl]methyl}-N-methylpropan-2-amine; MS (ES): 500 [M+H]+;

N-{[1-(2-chlorophenyl)-5-{5-[3-(methylsulfonyl)phenyl]-2-thienyl}-1H-pyrazol-3-yl]methyl}-N,N',N'-trimethyl-propane-1,3-diamine; MS (ES): 543 [M+H]+;

1-{[1-(2-chlorophenyl)-5-{5-[3-(methylsulfonyl)phenyl]-2-thienyl}-1H-pyrazol-3-yl]methyl}-4-(1-methylpropyl)piperazine; MS (ES): 569 [M+H]+;

(2R,6S)-1-{[1-(2-chlorophenyl)-5-{5-[3-(methylsulfonyl)phenyl]-2-thienyl}-1H-pyrazol-3-yl]methyl}-2,6-dimethylpiperidine; MS (ES): 540 [M+H]+;

N-{[1-(2-chlorophenyl)-5-{5-[3-(methylsulfonyl)phenyl]-2-thienyl}-1H-pyrazol-3-yl]methyl}-N-(cyclopropylmethyl)propan-1-amine; MS (ES): 540 [M+H]+;

1-{[1-(2-chlorophenyl)-5-{5-[3-(methylsulfonyl)phenyl]-2-thienyl}-1H-pyrazol-3-yl]methyl}decahydroquinoline; MS (ES): 566 [M+H]+;

N-{[1-(2-chlorophenyl)-5-{5-[3-(methylsulfonyl)phenyl]-2-thienyl}-1H-pyrazol-3-yl]methyl}-N-ethylethanamine; MS (ES): 500 [M+H]+;

1,1-dimethylethyl 4-{[1-(2-chlorophenyl)-5-{5-[3-(methylsulfonyl)phenyl]-2-thienyl}-1H-pyrazol-3-yl]methyl}-1,4-diazepane-1-carboxylate; MS (ES): 627 [M+H]+;

N-{[1-(2-chlorophenyl)-5-{5-[3-(methylsulfonyl)phenyl]-2-thienyl}-1H-pyrazol-3-yl]methyl}-N-methyl-2,2-bis(methyloxy)ethanamine; MS (ES): 546 [M+H]+;

1-({1-(2-chlorophenyl)-5-{5-[3-(methylsulfonyl)phenyl]-2-thienyl)-1H-pyrazol-3-yl]methyl}piperidin-4-ol; MS (ES): 528 [M+H]+;

[(2S)-1-{[1-(2-chlorophenyl)-5-(5-[3-(methylsulfonyl)phenyl]-2-thienyl}-1H-pyrazol-3-yl]methyl)pyrrolidin-2-yl]methanol; MS (ES): 528 [M+H]+;

1-{[1-(2-chlorophenyl)-5-(5-[3-(methylsulfonyl)phenyl]-2-thienyl)-1H-pyrazol-3-yl]methyl}-4-methyl-1,4-diazepane; MS (ES): 541 [M+H]+;

1-{[1-(2-chlorophenyl)-5-(5-[3-(methylsulfonyl)phenyl]-2-thienyl)-1H-pyrazol-3-yl]methyl}-2-methylpiperazine; MS (ES): 527 [M+H]+;

N-{[1-(2-chlorophenyl)-5-{5-[3-(methylsulfonyl)phenyl]-2-thienyl}-1H-pyrazol-3-yl]methyl}-N-ethylcyclohexanamine; MS (ES): 554 [M+H]+;

N-{[1-(2-chlorophenyl)-5-{5-[3-(methylsulfonyl)phenyl]-2-thienyl}-1H-pyrazol-3-yl]methyl}-N,N-diethyl-N-methylethane-1,2-diamine; MS (ES): 557 [M+H]+;

1-butyl-4-{[1-(2-chlorophenyl)-5-{5-[3-(methylsulfonyl)phenyl]-2-thienyl}-1H-pyrazol-3-yl]methyl}piperazine; MS (ES): 569 [M+H]+;

N-{[1-(2-chlorophenyl)-5-{5-[3-(methylsulfonyl)phenyl]-2-thienyl}-1H-pyrazol-3-yl]methyl}-N,1-dimethylpiperidin-4-amine; MS (ES): 555 [M+H]+;

N-{[1-(2-chlorophenyl)-5-{5-[3-(methylsulfonyl)phenyl]-2-thienyl}-1H-pyrazol-3-yl]methyl}-N-methylpropan-1-amine; MS (ES): 500 [M+H]+;

N-{[1-(2-chlorophenyl)-5-{5-[3-(methylsulfonyl)phenyl]-2-thienyl}-1H-pyrazol-3-yl]methyl}-N-ethylpropan-2-amine; MS (ES): 514 [M+H]+;

1-{[1-(2-chlorophenyl)-5-{5-[3-(methylsulfonyl)phenyl]-2-thienyl}-1H-pyrazol-3-yl]methyl}-4-[2-(methyloxy)ethyl]piperazine; MS (ES): 571 [M+H]+;

N-{[1-(2-chlorophenyl)-5-(5-[3-(methylsulfonyl)phenyl]-2-thienyl}-1H-pyrazol-3-yl]methyl)-N-(1-methylethyl)propan-2-amine; MS (ES): 528 [M+H]+;

1-{[1-(2-chlorophenyl)-5-{5-[3-(methylsulfonyl)phenyl]-2-thienyl}-1H-pyrazol-3-yl]methyl}-4-methylpiperidine; MS (ES): 526 [M+H]+;

4-{[1-(2-chlorophenyl)-5-{5-[3-(methylsulfonyl)phenyl]-2-thienyl}-1H-pyrazol-3-yl]methyl}thiomorpholine; MS (ES): 530 [M+H]+;

2-{[1-(2-chlorophenyl)-5-{5-[3-(methylsulfonyl)phenyl]-2-thienyl}-1H-pyrazol-3-yl]methyl}-1,2,3,4-tetrahydroisoquinoline; MS (ES): 560 [M+H]+;

N-{[1-(2-chlorophenyl)-5-{5-[3-(methylsulfonyl)phenyl]-2-thienyl}-1H-pyrazol-3-yl]methyl}-N-(phenylmethyl)propan-2-amine; MS (ES): 576 [M+H]+;

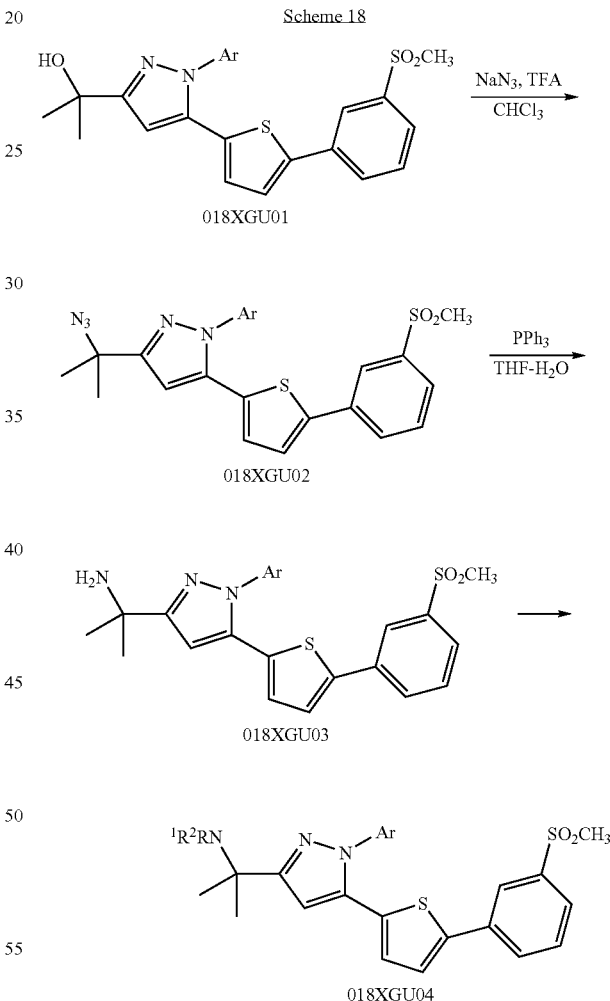

Scheme 18

As depicted in Scheme 18, Dimethylcarbinol can be transformed into the corresponding amines. Carbinol 018XGU01 reacted with sodium azide in the presence of TFA to give azide 018XGU02 in good yield. Azide 018XGU02 was reduce to the amine 018XGU03 by treatment with PPh₃ in THF—H₂O. Amine 018XGU03 was converted to 018XGU04 by alkylation with a halide or reductive-amination of aldehydes.

Example 34

Preparation of 1-(2-chlorophenyl)-5-{5-[3-(methylsulfonyl)phenyl]-2-thienyl}-3-[1-methyl-1-(2lambda~5-triaz-1-en-2-yn-1-yl)ethyl]-1H-pyrazole

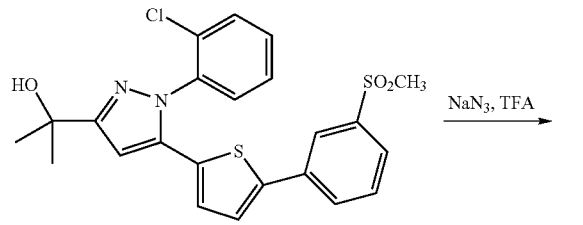

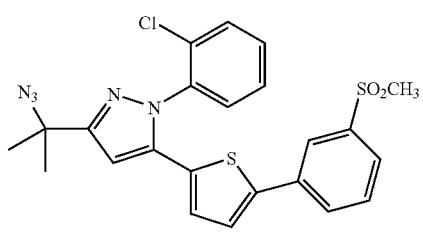

NaN₃ (200 mg, 3 mmol) was added to a stirred solution of 2-{1-(2-chlorophenyl)-5-[5-(3-methanesulfonyl-phenyl)-thiophen-2-yl]-1H-pyrazol-3-yl}-propan-2-ol (474 mg, 1 mmol) in CHCl₃ (9 mL) at rt. And the mixture was cooled to 0° C. To this slurry was added dropwise TFA (0.6 mL, 7.8 mmol) over 5 min. The reaction was allowed to warm to rt overnight. The mixture was partitioned between aqueous NH₄OH (1N) and CHCl₃. The organic layer was washed with water and brine, then dried over Na₂SO₄, and evaporated in vacuo. The residue was purified by flash chromatography (0-40% EtOAc/hexanes) to give the title compound as a white solid (380 mg, 76%). ¹HNMR (CDCl₃): δ 8.04 (m, 1H), 7.84-7.81 (m, 1H), 7.74-7.71 (m, 1H), 7.57-7.42 (m, 5H), 7.21 (d, 1H), 6.75 (d, 1H), 6.66 (s, 1H), 3.07 (s, 3H), 1.73 (s, 6H). MS(ES): 498 [M+H]⁺.

Example 35

Preparation of 2-[1-(2-chlorophenyl)-5-{5-[3-(methylsulfonyl)phenyl]-2-thienyl}-1H-pyrazol-3-yl]propan-2-amine

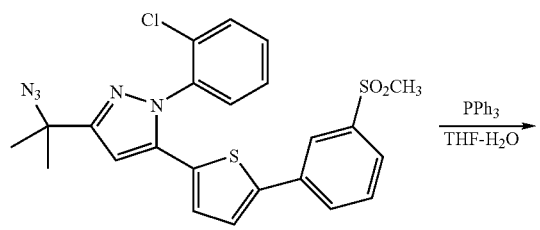

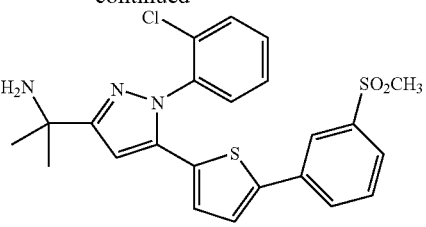

PPh₃ (3.3 g, 12.58 mmol) was added at rt to a solution of the 3-(2-azidopropan-2-yl)-1-(2-chlorophenyl)-5-(5-(3-(methylsulfonyl)phenyl)thiophen-2-yl)-1H-pyrazole) (3.08 g, 6.185 mmol) in a mixture of THF—H₂O (6:1, 70 mL), and the resulting mixture was stirred at it under N₂ for 8d. The solvent was removed in vacuo, and the residue was partitioned between water and EtOAc. The two phases were separated, and the aqueous phase was extracted with EtOAc. The combined extracts were washed with brine, dried over Na₂SO₄, and evaporated in vacuo. The crude product was purified by flash chromatography (0-60% 20% MeOH/DCM) to give the title compound as a light-yellow solid (2.43 g, 89%). ¹HNMR (CDCl₃): δ 8.04 (m, 1H), 7.83-7.80 (m, 1H), 7.73-7.71 (m, 1H), 7.56-7.41 (m, 5H), 7.19 9d, 1H), 6.72 9d, 1H), 6.63 (s, 1H), 3.07 (s, 3H), 2.43 (brs, 2H), 1.61 (s, 6H). MS(ES) 455 (M-NH₂).

Example 36

Preparation of 1-(2-chlorophenyl)-3-(1-methyl-1-pyrrolidin-1-ylethyl)-5-{5-[3-(methylsulfinyl)phenyl]-2-thienyl}-1H-pyrazole

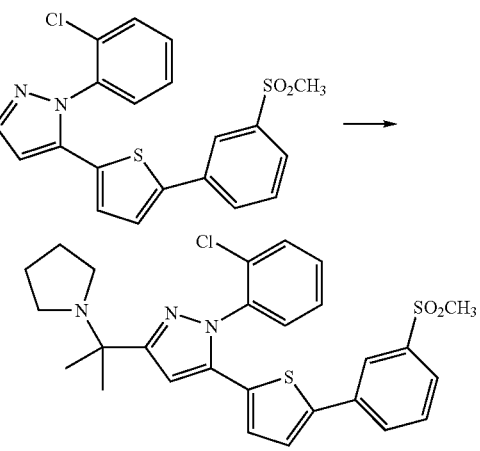

A mixture of the 2-[1-(2-chlorophenyl)-5-{5-[3-(methylsulfonyl)phenyl]-2-thienyl}-1H-pyrazol-3-yl]propan-2-amine (142 mg, 0.3 mmol), K₂CO₃ (83 mg, 0.6 mmol), 1,4-dibromobutane (0.1 mL, 0.7 mmol) and anhydrous EtOH was stirred at 100° C. in a sealed vial for 18 h. The solvent was removed in vacuo, and the residue was purified by flash chromatography (0-40% 20% MeOH/DCM) to give the title compound as a pale-yellow solid. ¹HNMR (CDCl₃): Et 8.03 (m, 1H), 7.86-7.83 (m, 1H), 7.74-7.71 (m, 1H), 7.61-7.47 (m, 5H), 7.23 (d, 1H), 6.93 (s, 1H), 6.83 (d, 1H), 3.68 (m, 2H), 3.08 (s, 3H), 2.17 (m, 2H), 2.04 (s, 6H), 1.83 (m, 2H). MS(ES): 526 [M+H]⁺.

The following compound is prepared essentially according to the previous examples:

4-{1-[1-(2-chlorophenyl)-5-{5-[3-(methylsulfonyl)phenyl]-2-thienyl}-1H-pyrazol-3-yl]-1-methylethyl}morpholine, MS(ES): 542 [M+H]⁺

Example 37

Preparation of 2-[1-(2-chlorophenyl)-5-{5-[3-(methylsulfonyl)phenyl]-2-thienyl}-1H-pyrazol-3-yl]-N,N-dimethylpropan-2-amine

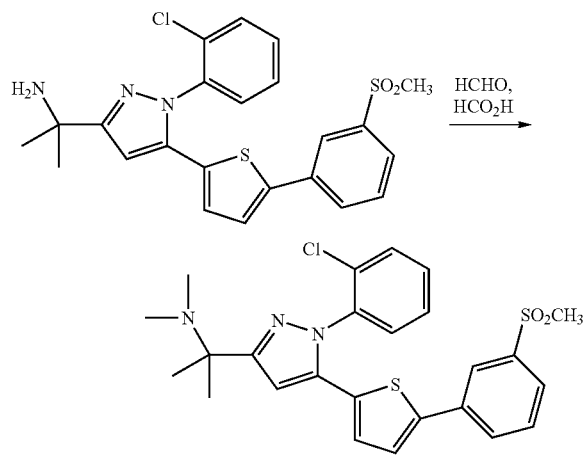

37% HCHO (80 mg, 0.986 mmol) was added to a solution of 2-[1-(2-chlorophenyl)-5-{5-[3-(methylsulfonyl)phenyl]-2-thienyl}-1H-pyrazol-3-yl]propan-2-amine (182 mg, 03872 mmol) in formic acid (2 mL), and the mixture was stirred at 95° C. in a sealed vial overnight. The reaction mixture was basified with aqueous NaOH (2N), and then extracted with DCM. The combined extracts were washed with brine, dried over Na₂SO₄, and evaporated in vacuo. The residue was purified by flash chromatography (0-70% 20% MeOH/DCM) to give the title compound as a pale-yellow solid (62 mg, 32%). ¹HNMR (CDCl₃): δ 8.03 (m, 1H), 7.82 (m, 1H), 7.71 (m, 1H), 7.57-7.42 (m, 5H), 7.20 (d, 1H), 6.76 (m, 2H), 3.07 (s, 3H), 2.33 (brs, 6H), 1.57 (brs, 6H).

Scheme 19

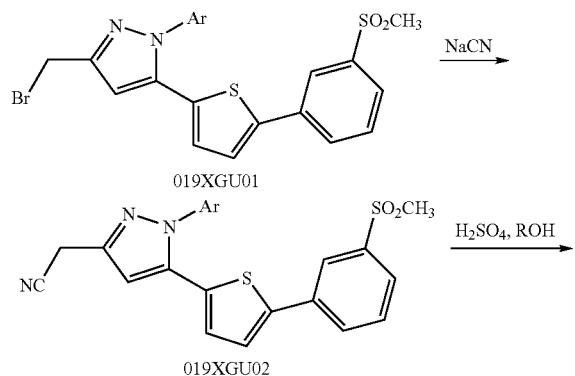

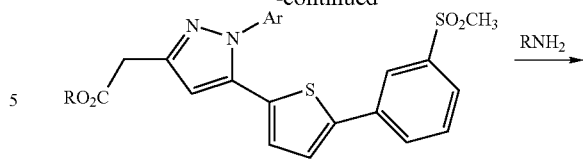

As depicted in Scheme 19, pyrazole-methyl bromide can be converted to the corresponding pyrazole-amides. Bromide 019XGU01 was converted to the cyanide 019XGU02 by reacting with sodium cyanide. The cyanide was hydrolyzed to afford ester 019XGU03, which was converted to the corresponding amides by treatment with the amine in the presence of the corresponding ammonium chloride.

Example 38

Preparation of [1-(2-chlorophenyl)-5-{5-[3-(methylsulfonyl)phenyl]-2-thienyl}-1H-pyrazol-3-yl]acetonitrile

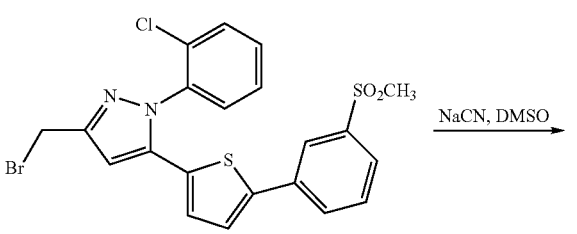

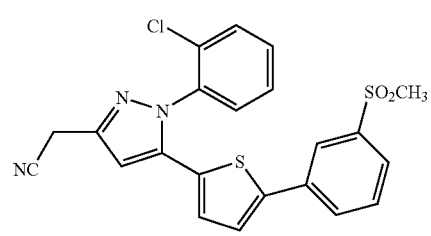

A mixture of the 3-bromomethyl-1-(2-chlorophenyl)-5-{5-[3-(methylsulfonyl)phenyl]-thiophen-2-yl]-1H-pyrazole (720 mg, 1.42 mmol), NaCN (250 mg, 5.1 mmol), and DMSO (10 mL) was stirred in a sealed vial at 100° C. for 5 h, diluted with water, and extracted with EtOAc. The combined extracts were washed with water, brine, dried over Na₂SO₄, and evaporated in vacuo. The crude product was purified by flash chromatography (0-80% EtOAc/hexanes) to give the title compound as a white solid (350 mg, 54%). ¹HNMR (CDCl₃):

δ 8.03 (d, 1H), 7.84 (m, 1H), 7.72 (m, 1H), 7.58-7.44 (m, 5H), 7.22 (d, 1H), 6.79 (d, 1H), 6.73 (s, 1H), 3.87 (s, 2H), 3.09 (s, 3H). MS(ES): 454 [M+H]+.

Example 39

Preparation of Methyl [1-(2-chlorophenyl)-5-{5-[3-(methylsulfonyl)phenyl]-2-thienyl}-1H-pyrazol-3-yl]acetate

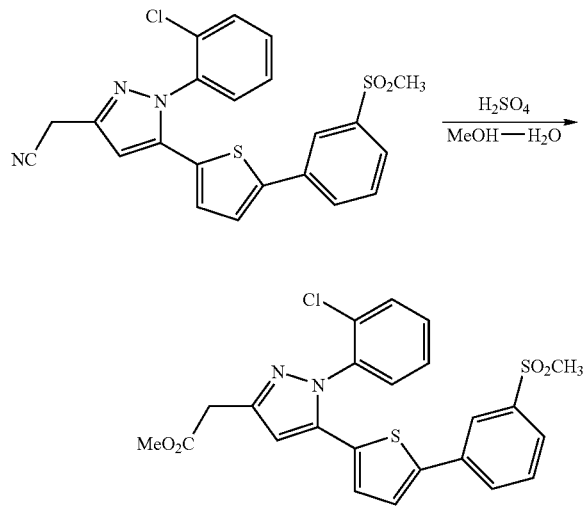

Concentrated H$_2$SO$_4$ (4 mL) was added dropwise at 0° C. to a stirred solution of the [1-(2-chlorophenyl)-5-{5-[3-(methylsulfonyl)phenyl]-2-thienyl}-1H-pyrazol-3-yl]acetonitrile (148 mg, 0.33 mmol) in a mixture of MeOH—H$_2$O (10:1, 11 mL), and the resulting mixture was stirred at 90° C. overnight. The mixture was diluted with cold water, then basified with Na$_2$CO$_3$ solid, extracted with EtOAc. The combined extracts were washed with brine, dried over Na$_2$SO$_4$, and evaporated in vacuo. The crude product was purified by flash chromatography (0-40% 20% MeOH/DCM) to afford the title compound as a white solid (131 mg, 82%). $^1$HNMR (CDCl$_3$): δ 8.04 (m, 1H), 7.83-7.81 (m, 1H), 7.73-7.71 (m, 1H), 7.57-7.41 (m, 5H), 7.20 (d, 1H), 6.75 (d, 1H), 6.69 9s, 1H), 3.82 9s, 2H), 3.79 (s, 3H), 3.08 (s, 3H). MS(ES): 487 [M+H]+.

Example 40

Preparation of 2-[1-(2-chlorophenyl)-5-{5-[3-(methylsulfonyl)phenyl]-2-thienyl}-1H-pyrazol-3-yl]-N-ethylacetamide

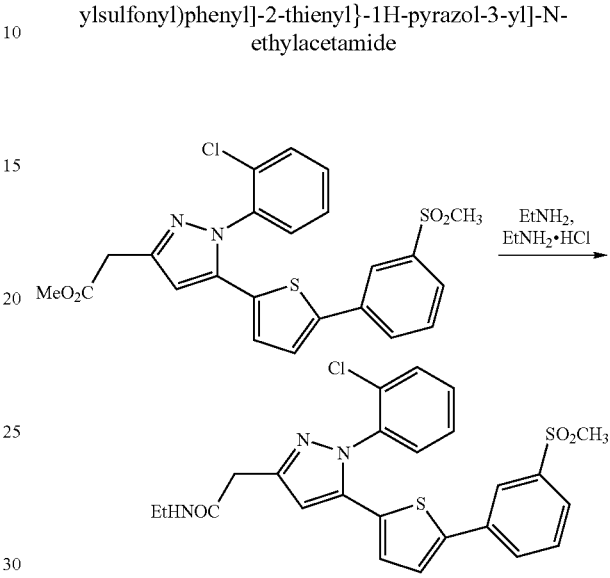

A mixture of the methyl [1-(2-chlorophenyl)-5-{5-[3-(methylsulfonyl)phenyl]-2-thienyl}-1H-pyrazol-3-yl]acetate (100 mg, 0.2 mmol), EtNH$_2$ (2.0M in THF, 5 mL) and ethylamine hydrochloride (200 mg) was stirred at 70° C. in a sealed vial for 8 h. The solvent was removed in vacuo, another EtNH$_2$/THF (2.0M, 5 mL) was added, the mixture was stirred at 78° C. for another 24 h. Another 3 mL of EtNH$_2$/THF was added, and the mixture was stirred at 78° C. for another 20 h. The solvent was removed in vacuo, and the crude product was purified by flash chromatography (0-30% 20% MeOH/DCM) to give the title compound as a white solid (85 mg, 83%). $^1$HNMR (CDCl$_3$): δ 8.04 (m, 1H), 7.84-7.82 (m, 1H), 7.74-7.71 (m, 1H), 7.60-7.46 (m, 5H), 7.21 (d, 1H), 6.78 (d, 1H), 6.61 (s, 1H), 6.45 (brs, 1H), 3.69 (s, 2H), 3.30 (q, 2H), 3.07 (s, 3H), 1.14 (t, 3H). MS(ES): 500 [M+H]+.

Scheme 20

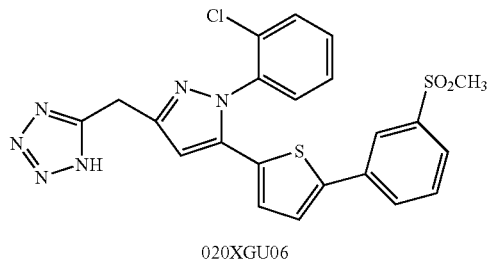

020XGU06

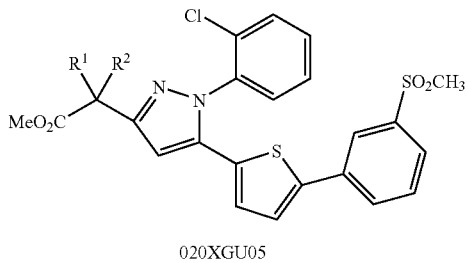

020XGU05

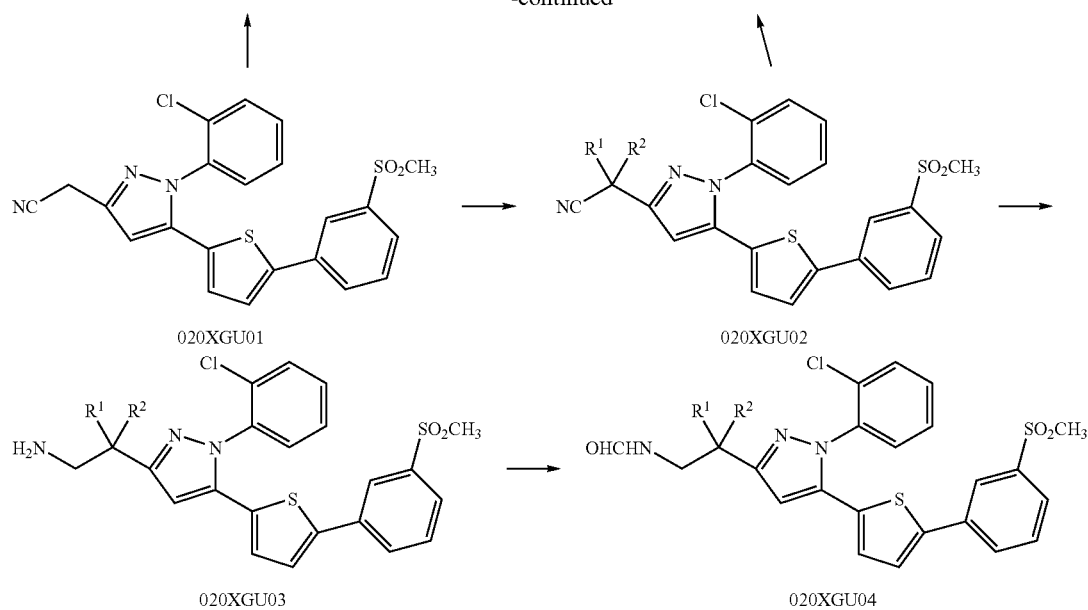

As depicted in Scheme 20, nitriles can be transformed into tetrazoles, esters and amides. The cyanide 020XGU01 was alkylated to give 020XGU02, which was reduced with DIBAL-H to give the primary 020XGU03. 020XGU04 was obtained by formylation of the primary amine 020XGU03 with HCO₂Et. Treatment of the cyanide 020XGU01 with NaN₃ and NH₄Cl gave the tetrazole 020XGU06. 020XGU02 was hydrolyzed to give the ester 020XGU05.

Example 41

Preparation of 5-{[1-(2-chlorophenyl)-5-{5-[3-(methylsulfonyl)phenyl]-2-thienyl}-1H-pyrazol-3-yl]methyl}-1H-tetrazole

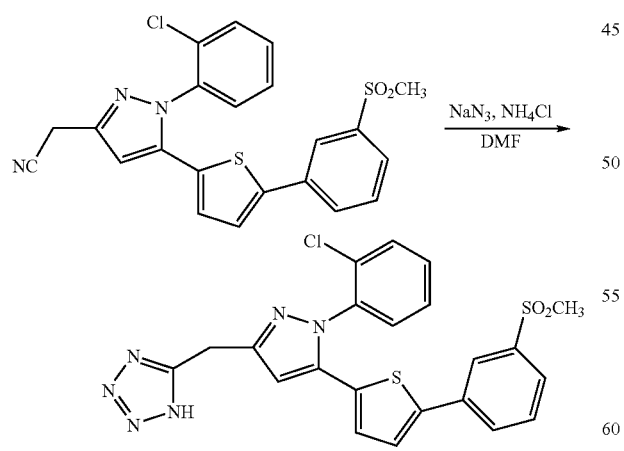

A mixture of [1-(2-chlorophenyl)-5-{5-[3-(methylsulfonyl)phenyl]-2-thienyl}-1H-pyrazol-3-yl]acetonitrile (136 mg, 0.3 mmol), NaN₃ (59 mg, 0.9 mmol), NH₄Cl (49 mg, 0.9 mmol), and anhydrous DMF (5 mL) was stirred in a sealed vial at 120° C. for 24 h. The mixture was poured into water, and extracted with DCM. The combined extracts were washed with water and brine, dried over Na₂SO₄, and evaporated in vacuo. The crude product was purified by flash chromatography (0-80% 20% MeOH/DCM) to give the title compound as a white solid (116 mg, 78%). ¹HNMR (CDCl₃): δ 8.04 (m, 1H), 7.85-7.83 (m, 1H), 7.74-7.71 (m, 1H), 7.62-7.46 (m, 5H), 7.22 (d, 1H), 6.8 (d, 1H), 6.66 (s, 1H), 4.52 (s, 2H), 3.08 (s, 3H). MS(ES): 497 [M+H]⁺.

Example 42

Preparation of 2-[1-(2-chlorophenyl)-5-{5-[3-(methylsulfonyl)phenyl]-2-thienyl}-1H-pyrazol-3-yl]-2-methyl propanenitrile and 2-[1-(2-chlorophenyl)-5-{5-[3-(ethylsulfonyl)phenyl]-2-thienyl}-1H-pyrazol-3-yl]-2-methylpropanenitrile

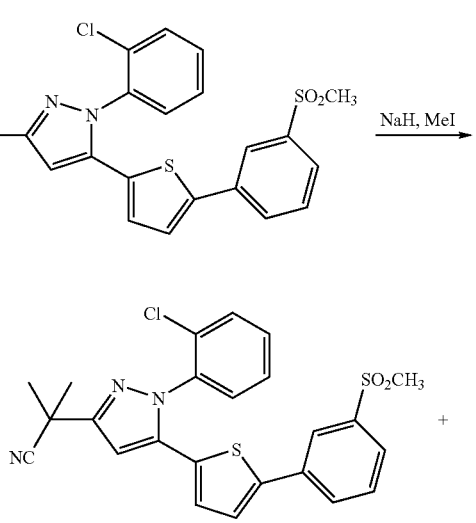

-continued

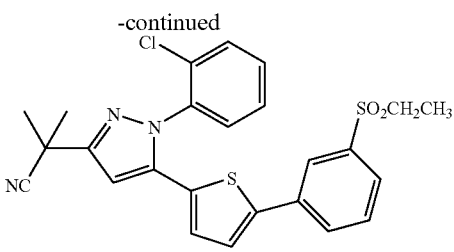

NaH (60% in mineral oil, 120 mg, 3 mmol) was added at 0° C. to a stirred solution of the [1-(2-chlorophenyl)-5-{5-[3-(methylsulfonyl)phenyl]-2-thienyl}-1H-pyrazol-3-yl]acetonitrile (453 mg, 1 mmol) and MeI (160 µL, 2.56 mmol) in anhydrous DMF (15 mL) under $N_2$. The reaction mixture was allowed to warm to rt and stirred at rt for 4 h. The reaction mixture was quenched with aqueous $NH_4Cl$ solution, and extracted with EtOAc. The combined extracts were washed with water and brine, dried over $Na_2SO_4$, and evaporated in vacuo. The crude product was purified first by flash chromatography (0-70% EtOAc/hexanes), again by preparative HPLC (normal phase) to give the two title compounds as white solid. (236 mg, 49%). $^1$HNMR (CDCl$_3$): δ 8.04 (m, 1H), 7.84-7.82 (m, 1H), 7.74-7.71 (m, 1H), 7.58-7.43 (m, 5H), 7.21 (d, 1H), 6.77 (d, 1H), 6.72 (s, 1H), 3.07 (s, 3H), 1.83 (s, 6H). MS(ES): 482 [M+H]$^+$. (227 mg, 46%). $^1$HNMR (CDCl$_3$): δ 8.00 (m, 1H), 7.80-7.78 (m, 1H), 7.73-7.71 (m, 1H), 7.57-7.45 (m, 5H), 7.21 (d, 1H), 6.76 (d, 1H), 6.71 (s, 1), 3.13 (q, 2H), 1.83 (s, 6H), 1.30 (t, 3H). MS(ES): 496 [M+H]$^+$.

Example 43

Preparation of 1-[1-(2-chlorophenyl)-5-{5-[3-(methylsulfonyl)phenyl]-2-thienyl}-1H-pyrazol-3-yl]cyclopropanecarbonitrile

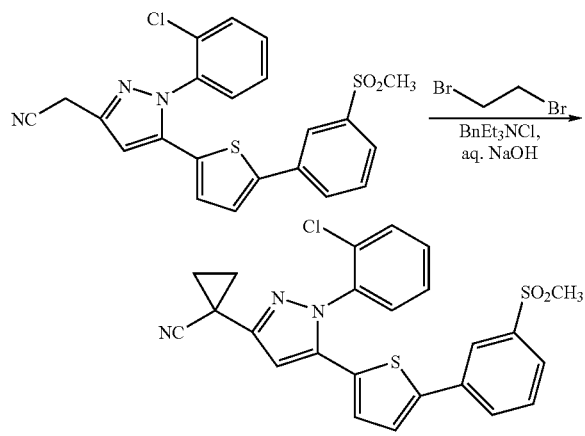

1,2-dibromoethane (40 µL, 0.46 mmol) was added to a stirred suspension of the [1-(2-chlorophenyl)-5-{5-[3-(methylsulfonyl)phenyl]-2-thienyl}-1H-pyrazol-3-yl]acetonitrile (68 mg, 0.15 mmol), benzyltriethylammonium chloride (20 mg, 0.088 mmol), and 50% aqueous NaOH (2 mL) at 0° C., the resulting mixture was stirred at rt overnight. After diluted with water, the mixture was extracted with ether. The combined extracts were washed with brine, dried over $Na_2SO_4$, and evaporated in vacuo. The crude product was purified by flash chromatography (0-70% EtOAc/hexanes) to give the title compound as a white solid (59 mg, 82%). $^1$HNMR (CDCl$_3$): δ 8.04 (m, 1H), 7.84-7.82 (m, 1H), 7.74-7.71 (m, 1H), 7.58-7.43 (m, 5H), 7.21 (d, 1H), 6.79-6.77 (m, 2H), 3.07 9d, 3H), 1.73-1.68 (m, 4H). MS(ES): 480 [M+H]$^+$.

The following compounds are prepared essentially according to the previous examples:

1-[1-(2-chlorophenyl)-5-{5-[3-(methylsulfonyl)phenyl]-2-thienyl}-1H-pyrazol-3-yl]cyclopeantanecarbonitrile MS(ES): 508 [M+H]$^+$ Example 44

Preparation of 2-[1-(2-chlorophenyl)-5-{5-[3-(methylsulfonyl)phenyl]-2-thienyl}-1H-pyrazol-3-yl]-2-methylpropan-1-amine

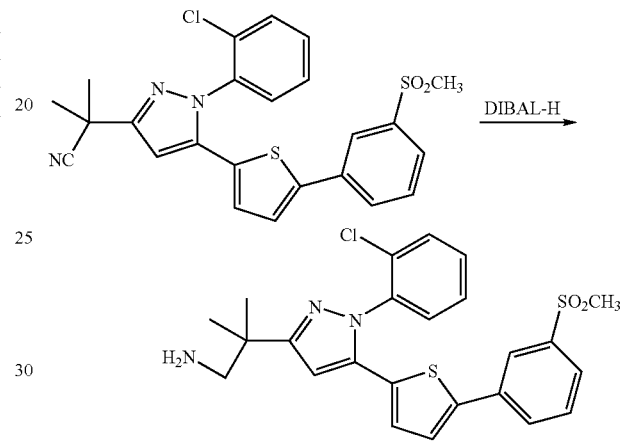

DIBAL-H (1.0M in hexanes, 1.5 mL, 1.5 mmol) was added dropwise at −78° C. to a stirred solution of 2-[1-(2-chlorophenyl)-5-{5-[3-(methylsulfonyl)phenyl]-2-thienyl}-1H-pyrazol-3-yl]-2-methyl propanenitrile (210 mg, 0.436 mmol) in dry DCM (10 mL) under $N_2$, the resulting mixture was stirred at −78° C. for 3 h. At −78° C. 10% aqueous Rochelle's salt solution was added dropwise to quench the reaction, the mixture was allowed to warm to rt, and extracted with DCM. The combined extracts were washed with brine, dried over $Na_2SO_4$, and evaporated in vacuo. The crude product was purified by flash chromatography (0-60% 20% MeOH/DCM) to give the title compound as a white solid (160 mg, 76%). $^1$HNMR (CDCl$_3$): δ 8.04 (m, 1H), 7.83-7.80 (m, 1H), 7.74-7.71 (m, 1H), 7.57-7.42 (m, 5H), 7.20 (d, 1H), 6.71 (d, 1H), 6.52 (s, 1H0, 3.07 (s, 3H), 2.90 (s, 2H), 2.17 (brs, 2H), 1.39 (s, 6H). MS(ES): 486 [M+H]$^+$.

Example 45

Preparation of N-{2-[7-(2-chlorophenyl)-5-{5-[3-(methylsulfonyl)phenyl]-2-thienyl}-1H-pyrazol-3-yl]-2-methylpropyl}formamide

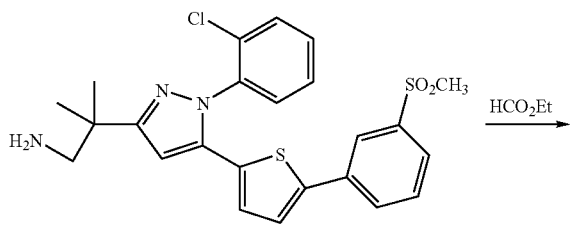

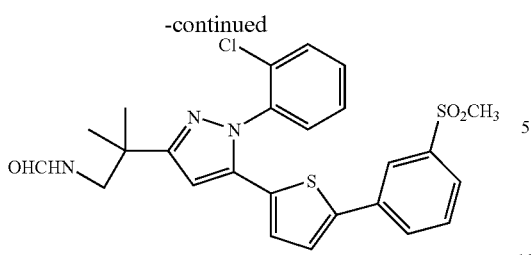

A mixture of 2-[1-(2-chlorophenyl)-5-{5-[3-(methylsulfonyl)phenyl]-2-thienyl}-1H-pyrazol-3-yl]-2-methylpropan-1-amine (82 mg, 0.1687 mmol) and HCO₂Et (1.5 mL) was stirred at 75° C. in a sealed vial overnight. The solvent was removed in vacuo, and the residue was purified by flash chromatography (0-40% 20% MeOH/DCM) to give the title compound as a white solid (72 mg, 83%). ¹HNMR (CDCl₃): δ 8.21 (s, 1H), 8.04 (m, 1H), 7.84-7.80 (m, 1H), 7.74-7.71 (m, 1H), 7.57-7.42 (m, 5H), 7.21 (d, 1H), 6.73 (d, 1H), 6.53 (s, 1H), 6.50 (brs, 1H), 3.56 (d, 2H), 3.07 (s, 3H), 1.40 (s, 6H). MS(ES): 514 [M+H]⁺.

The following compounds are prepared essentially according to the previous examples:

N-{1-[1-(2-chlorophenyl)-5-{5-[3-(methylsulfonyl)phenyl]-2-thienyl}-1H-pyrazol-3-yl]-1-methylethyl}formamide, MS(ES): 500 [M+H]⁺

Example 46

Preparation of 4-{[1-(2-chlorophenyl)-5-{5-[3-(methylsulfonyl)phenyl]-2-thienyl}-1H-pyrazol-3-yl]methyl}morpholine

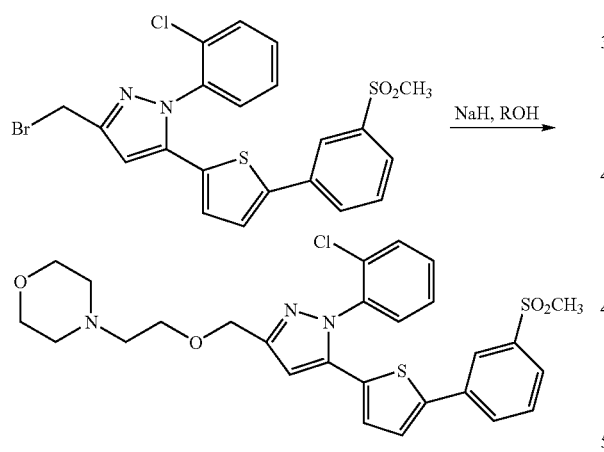

NaH (60% in mineral oil, 40 mg, 1 mmol) was added to a stirred mixture of the bromide (102 mg, 0.2 mmol), 4-(2-hydroxyethyl)morpholine (40 µL, 0.3 mmol) and anhydrous DMF (10 mL) at 0° C. under N₂. The mixture was stirred at rt overnight, and the solvent was removed in vacuo. The residue was dissolved in EtOAc, washed with water and brine, dried over Na₂SO₄, and evaporated in vacuo. The crude product was purified first by flash chromatography (0-15% MeOH/DCM), again by reverse phase preparative HPLC to give the title compound as a white solid (58 mg, 52%). ¹HNMR (CDCl₃): δ 8.04 (m, 1H), 7.83-7.81 (m, 1H), 7.74-7.72 (m, 1H), 7.57-7.44 (m, 5H), 7.21 (d, 1H), 6.75 (d, 1H), 6.71 (s, 1H), 4.66 (s, 2H), 3.75-3.70 (m, 6H), 3.08 (s, 3H), 2.66 (m, 2H), 2.52 (m, 4H). MS(ES): 558 [M+H]⁺.

The following compound is prepared essentially according to the previous examples:

N-{[1-(2-chlorophenyl)-5-{5-[3-(methylsulfonyl)phenyl]-2-thienyl}-1H-pyrazol-3-yl]methyl}-2-morpholin-4-ylethanamine, MS(ES): 557 [M+H]⁺

Scheme 21

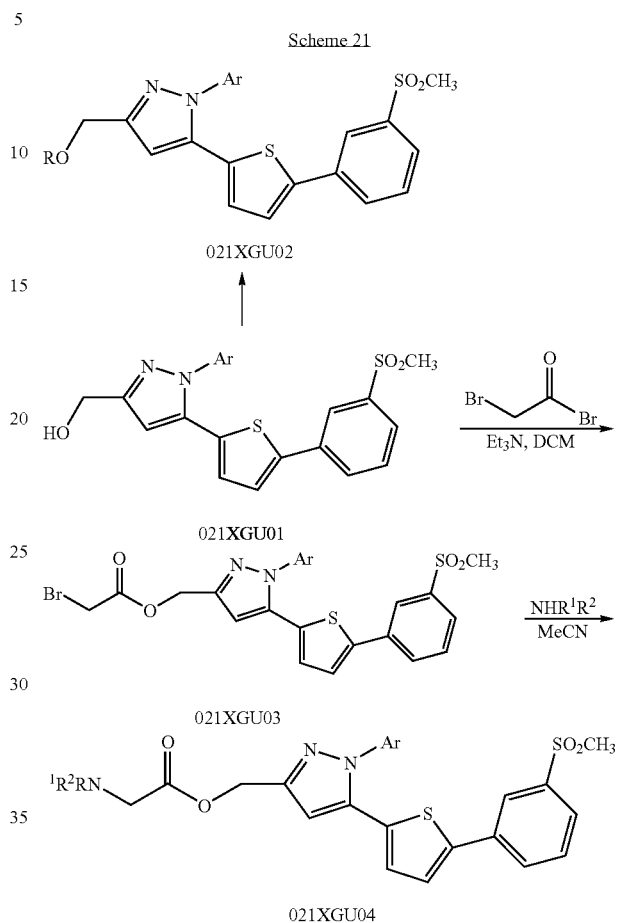

As depicted in Scheme 21, alcohol 021XG01 can be transformed into the corresponding ethers and esters containing amino groups. Alcohol 021XGU01 was converted to 021XGU02 by alkylation with alkyl halides. Ester 021XGU03 was obtained by acylation of 021XGU01 with bromoacetyl bromide. Replacement of the bromide with amines afforded 021XGU04.

Example 47

Preparation of [1-(2-chlorophenyl)-5-{5-[3-(methylsulfonyl)phenyl]-2-thienyl}-1H-pyrazol-3-yl]methyl morpholin-4-ylacetate

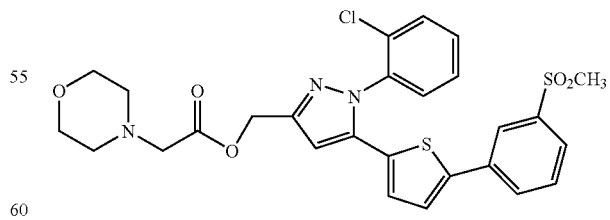

iPr₂NEt (0.8 mL, 4.6 mmol) was added at 0° C. to a stirred solution of [1-(2-chlorophenyl)-5-{5-[3-(methylsulfonyl)phenyl]-2-thienyl}-1H-pyrazol-3-yl]methanol (450 mg, 1 mmol) in dry DCM (10 mL) under N₂ followed by bromoacetyl bromide (0.2 mL, 2.3 mmol), the resulting dark mixture was stirred at it overnight under N₂. The mixture was diluted with DCM, washed with water, dried over Na₂SO₄, and evaporated in vacuo. The residue was purified by flash chromatography (0-80% EtOAc/hexanes) to give the ester as a pale-yellow solid (465 mg, 82%). A mixture of the ester (114 mg, 0.2 mmol), K₂CO₃ (90 mg, 0.6 mmol), morpholine (0.1 mL), and anhydrous MeCN (5 mL) was stirred in a sealed vial at 60° C. overnight. The solvent was removed in vacuo, and the residue was purified by flash chromatography (0-100% EtOAc/hexanes) to give the title compound as a white solid (82 mg, 72%). ¹HNMR (CDCl₃): δ 8.04 (m, 1H), 7.83-7.81 (m, 1H), 7.74-7.71 (m, 1H), 7.58-7.44 (m, 5H), 7.21 (d, 1H), 6.76 (d, 1H), 6.71 (s, 1H), 5.27 (s, 2H), 3.77 (t, 4H), 3.32 (d, 2H), 3.08 (s, 3H), 2.63 (t, 4H). MS(ES): 572 [M+H]⁺.

The following compound is prepared essentially according to the previous examples:

1-(2-chlorophenyl)-5-{5-[3-(methylsulfonyl)phenyl]-2-thienyl}-1H-pyrazol-3-yl]methyl (4-methylpiperazin-1-yl)acetate, MS(ES): 585 [M+H]⁺

Example 48

Preparation of 2-[({[1-(2-chlorophenyl)-5-{5-[3-(methylsulfonyl)phenyl]-2-thienyl}-1H-pyrazol-3-yl]methoxy}oxy)methyl]pyridine

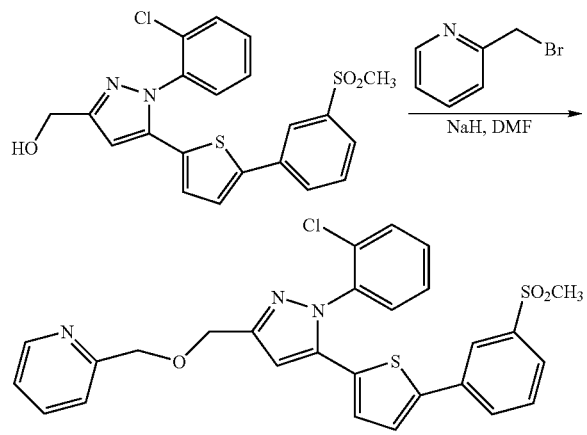

NaH (60% in mineral oil, 90 mg, 2.25 mmol) was added at 0° C. to a stirred mixture of [1-(2-chlorophenyl)-5-{5-[3-(methylsulfonyl)phenyl]-2-thienyl}-1H-pyrazol-3-yl]methanol (222 mg, 0.5 mmol), 2-(bromomethyl)pyridine hydrobromide (190 mg, 0.75 mmol), and anhydrous DMF (5 mL) under N₂, the resulting mixture was stirred at it for 4 h. The reaction mixture was poured into ice-water, and extracted with EtOAc. The combined extracts were washed with brine, dried over Na₂SO₄, and evaporated in vacuo. The crude product was purified by flash chromatography (0-100% EtOAc/hexanes) to give the title compound as a colorless semi-solid (179 mg, 67%). ¹HNMR (CDCl₃): δ 8.58 (m, 1H), 8.04 (m, 1H), 7.82 (m, 1H), 7.74-7.71 (m, 2H), 7.57-7.44 (m, 6H), 7.20 (m, 2H), 6.76 (m, 2H), 4.78 (m, 4H), 3.08 (s, 3H). MS(ES): 536 [M+H]⁺.

The following compound is prepared essentially according to the previous examples:

1-(2-chlorophenyl)-5-{5-[3-(methylsulfonyl)phenyl]-2-thienyl}-3-[({[5-trifluoromethyl)furan-2-yl]methyl}oxy)methyl]-1H-pyrazole, MS(ES): 593 [M+H]⁺

Example 50

Preparation of 1-(2-chloro-phenyl)-5-[5-(3-methanesulfonyl-phenyl)-thiophen-2-yl]-1H-pyrazole-3-carboxylic acid

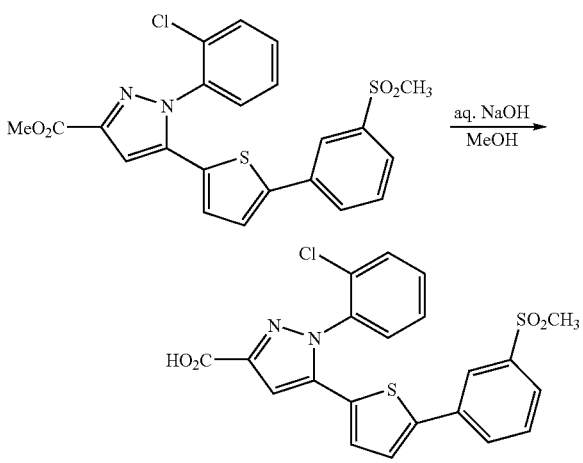

Aqueous NaOH solution (2N, 80 mL) was added to a suspension of 1-(2-chloro-phenyl)-5-[5-(3-methanesulfonyl-phenyl)-thiophen-2-yl]-1H-pyrazole-3-carboxylic acid methyl ester (5 g, 10.57 mmol) in MeOH (80 mL), and the resulting mixture was stirred at reflux for 10 h. The volatiles was removed in vacuo, the residual solution was acidified with aqueous HCl (6N) to pH 2, extracted with EtOAc. The combined extracts were washed with water and brine, dried over Na₂SO₄, and evaporated in vacuo. The crude product was recrystallized from DCM/hexane to give the title compound as a white solid (4.1 g, 86%). ¹H-NMR (DMSO-d₆): δ 12.73 (s, 1H), 7.98 (m, 1H), 7.83 (m, 2H), 7.77 (m, 2H), 7.71 (m, 1H), 7.67 (d, 1H), 7.62 (m, 2H), 7.34 (s, 1H), 7.19 (s, 1H), 3.26 (s, 3H). MS(ES): 459 [M+H]⁺.

The following compounds are prepared essentially according to the previous examples:

2-[1-(2-chlorophenyl)-5-{5-[3-(ethylsulfonyl)phenyl]-2-thienyl}-1H-pyrazol-3-yl]-2-methylpropanoic acid, MS(ES): 501 [M+H]⁺

Scheme 21A

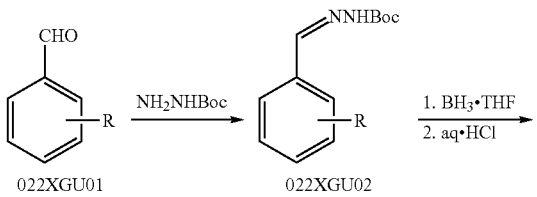

-continued

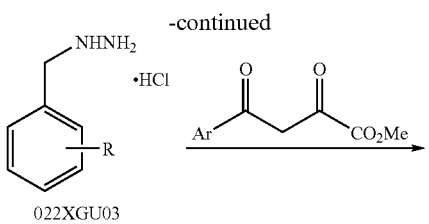

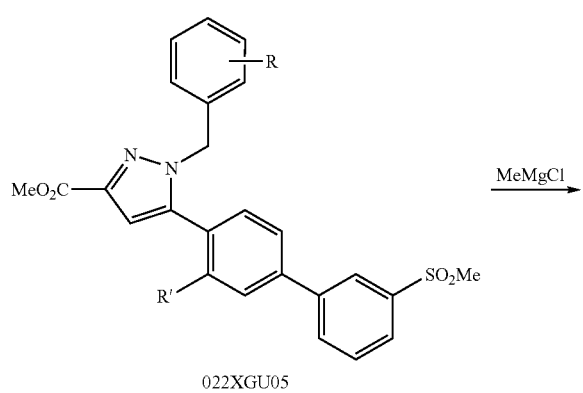

with a boronic acid afforded 022XGU05, which was converted to the carbinol 022XGU06 by treatment with methylmagnesium chloride.

Example 51

Preparation of 2-{1-[(2,3-dichlorophenyl)methyl]-5-[3-methyl-3'-(methylsulfonyl)biphenyl-4-yl]-1H-pyrazol-3-yl}propan-2-ol

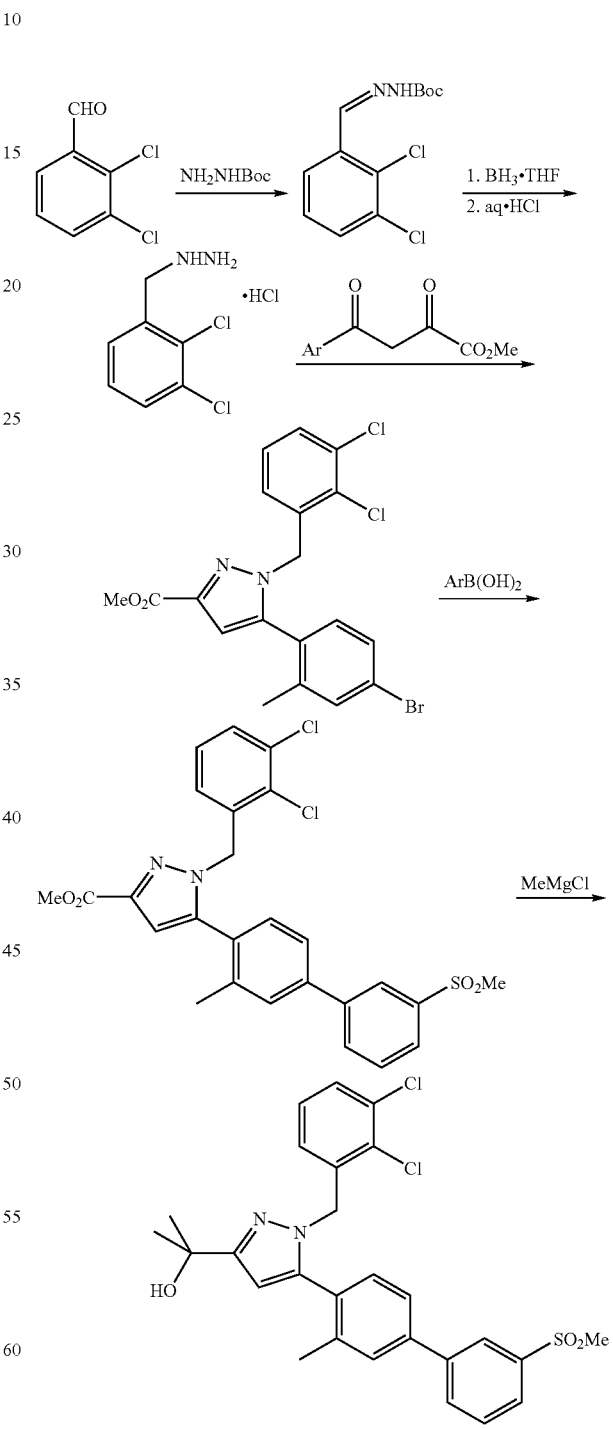

2-{1-[(2,3-dichlorophenyl)methyl]-5-[3-methyl-3'-(methylsulfonyl)biphenyl-4-yl]-1H-pyrazol-3-yl}propan-2-ol was prepared in a manner similar to that as described in Example As depicted in Scheme 21A, a-ring benzyl pyrazoles was synthesized. Aldehyde 022XGU01 reacted with tert-butyl carbazate to give 022XGU02; which was reduced with diborane to give benzylhydrazine 022XGU03. Treatment of the benzylhydrazine with a diketone ester gave pyrazole 022XGU04 in high yield. Suzuki coupling of 022XGU04

8 using the appropriate benzylhydrazine hydrochloride prepared by the reported procedure (Ghali, N J. et al *J. Org. Chem.* 1981, 46, 5413-5414) $^1$HNMR (CDCl$_3$): δ 8.16 (m, 1H), 7.93 (m, 1H), 7.87 (m, 1H), 7.66 (t, 1H), 7.51 (m, 1H), 7.41-7.34 (m, 2H), 7.17-7.10 (m, 2H), 6.57 (m, 1H), 6.28 (s, 1H), 5.25 (s, 2H), 3.10 (s, 3H), 2.68 (s, 1H), 2.23 (s, 3H), 1.66 (s, 6H). MS(ES): 529 [M+H]$^+$, 511 (M-OH)

The following compounds are prepared essentially according to the previous examples:

2-{1-[(2,3-dichlorophenyl)methyl]-5-[3'-(methylsulfonyl)biphenyl-4-yl]-1H-pyrazol-3-yl}propan-2-ol, MS(ES): 515 [M+H]$^+$, 497 (M-OH)

2-{5-[3-chloro-3'-(methylsulfonyl)biphenyl-4-yl]-1-[(2,3-dichlorophenyl)methyl]-1H-pyrazol-3-yl}propan-2-ol, MS(ES): 549 [M+H]$^+$, 531 (M-OH)

2-{1-[(4-chlorophenyl)methyl]-5-[3-methyl-3'-(methylsulfonyl)biphenyl-4-yl]-1H-pyrazol-3-yl}propan-2-ol, MS(ES): 495 [M+H]$^+$, 5-(5-{1-[(2,4-difluorophenyl)methyl]-3-(trifluoromethyl)-1H-pyrazol-5-yl}-2-thienyl)-3-methyl-2-(methylsulfonyl)pyridine; 514.2 [M+H]$^+$ Scheme 21B

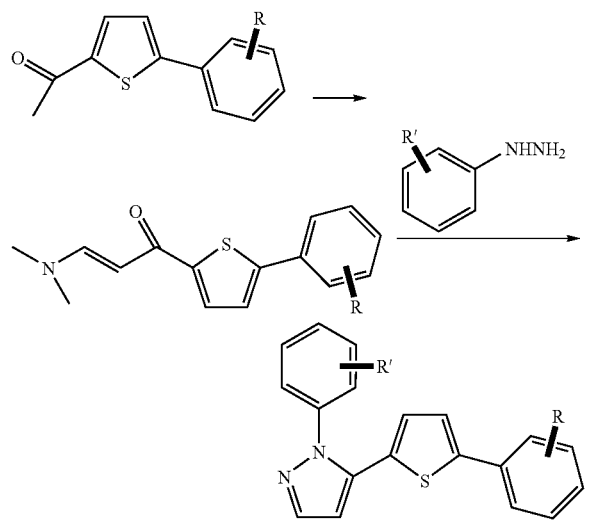

As depicted in Scheme 21B, pyrazoles can be prepared via an enamine intermediate. Most aryl-methyl-ketones will react with a reagent such as Bredereck's reagent or N,N-dimethylformamide diethyl acetal to form an enamine. Under mild conditions, such eneamines react with arylhydrazines to regioselectively afford a single pyrazole isomer.

Example 52

Preparation of 1-(2,5-Dichloro-phenyl)-5-[5-(3-methanesulfinyl-phenyl)-thiophen-2-yl]-1H-pyrazole

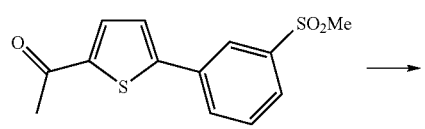

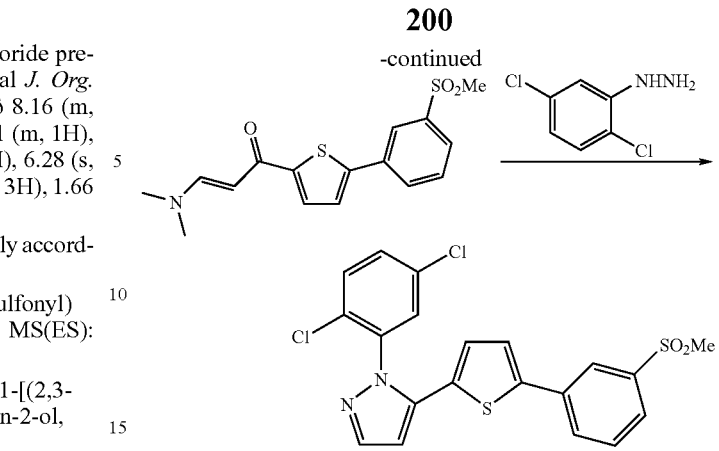

Into a 100 mL flask was weighed 1.34 g of 1-[5-(3-Methanesulfonyl-phenyl)-thiophen-2-yl]-ethanone, 13 mL of DMF, and 988 μL (1.2 eq) of N,N-dimethylformamide diethyl acetal. The reaction was heated at ~80° C. for 18 h then was washed into a separatory funnel with ethyl acetate and water. The resulting precipitate was collected by filtration and was dried under high vacuum affording the eneamine product as a yellow powder, yield: 1.27 g (79%). $^1$H NMR (400 MHz, DMSO-d$_6$): δ 8.30 (s, 1H), 8.17 (d, J=8 Hz, 1H), 7.99 (d, J=8 Hz, 1H), 7.94 (d, J=4 Hz, 1H), 7.75-7.85 (m, 3H), 5.93 (d, J=12 Hz, 1H), 3.43 (s, 3H), 3.41 (s, 3H), 3.04 (s, 3H).

Into a 50 mL flask was weighed 105.7 mg of eneamine, 97.0 mg of 2,5-dichlorophenylhydrazine hydrochloride, 1 mL of DMF and 1 mL of acetic acid. The resulting solution was heated at 95-100° C. for 20 h then was washed into a separatory funnel with ethyl acetate and water. The ethyl acetate was separated, washed with brine, was dried (MgSO$_4$), and concentrated in vacuo. The residue was purified by silica gel flash chromatography (Jones Flashmaster, 20 g SiO$_2$, gradient from 20% ethyl acetate to 50% ethyl acetate-hexanes over 30 minutes). Appropriate fractions were combined and concentrated in vacuo affording the product as a colorless powder, yield: 115 mg (81%). $^1$H-NMR (400 MHz, CDCl$_3$): δ 8.07 (1H, m), 7.84 (1H, m), 7.78 (1H, d), 7.75 (1H, m), 7.60-7.53 (2H, m), 7.49-7.46 (2H, m), 7.24 (1H, d), 6.79 (1H, d), 6.67 (1H, d), 3.08 (3H, s). MS (ES): 451 [M+H]$^+$.

Example 53

Preparation of 4-{5-[1-(2,5-dichlorophenyl)-3-(trifluoromethyl)-1H-pyrazol-5-yl]-2-thienyl}-2-(methylsulfonyl)benzoic acid

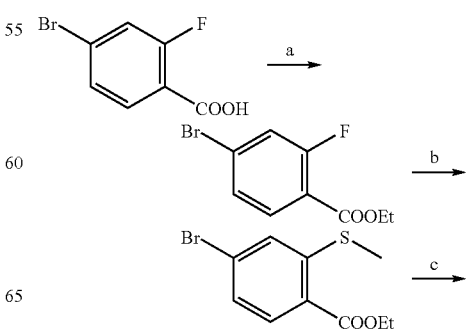

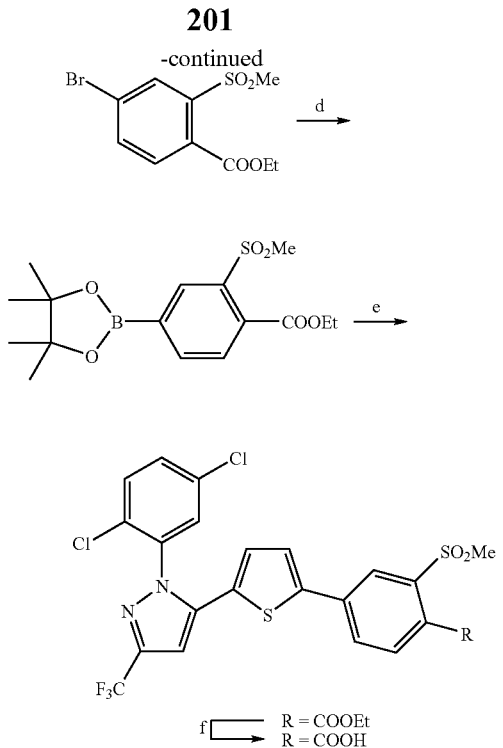

a) EDCI, DMAP, EtOH, CH₂Cl₂, 45° C.; b) NaSMe, THF, 80° C.; c) MCPBA, CH₂Cl₂, 25° C.; d) Bis(pinacolato)diboron, Pd(dppf), KOAc, DMSO, 85° C.; e) (Ph₃P)₄Pd, v where R₁=2,5-Cl, Na₂CO₃, THF-water, 80° C.; f) LiOH, THF-MeOH—H₂O, 25° C.

Into a 1 L flask was weighed 24.66 g (113 mmol) of acid, 26.5 g (138 mmol) of EDCI, 1.7 g of DMAP, 425 mL of dichloromethane, and 25 mL of ethanol. The resulting solution was heated at 40-45° C. for 24 h then was concentrated in vacuo to remove dichloromethane. The residue was washed into a separatory funnel with ethyl acetate and 1 M HCl. The ethyl acetate was separated, washed with brine, was dried (Na₂SO₄) and was concentrated in vacuo. The intermediate 4-Bromo-2-fluoro-benzoic acid ethyl ester was recovered as a colorless oil, yield: 24.99 g (89.8%).

The ester was treated with 12.2 g of sodium thiomethoxide and 200 mL of THF and the resulting suspension was heated at 80-85° C. for 5 h. The reaction was then concentrated to remove THF and was washed into a separatory funnel with ethyl acetate and 1 M HCl. The ethyl acetate was separated, washed with brine, was dried (Na₂SO₄), and concentrated in vacuo affording the intermediate 4-Bromo-2-methylsulfanyl-benzoic acid ethyl ester as a light gray solid, yield: 27.5 g (99%). ¹H NMR (400 MHz, CDCl₃): δ 7.86 (d, J=8 Hz, 1H), 7.36 (s, 1H), 7.28 (d, J=8 Hz, 1H), 4.38 (q, J=7 Hz, 2H), 2.45 (s, 3H), 1.39 (t, J=7 Hz, 3H).

Into a 1 L flask was weighed 15.0 g of 4-Bromo-2-methylsulfanyl-benzoic acid ethyl ester (54.5 mmol), 200 mL of dichloromethane, and 28.0 g of MCPBA (77% max., Aldrich) was added portionwise at room temperature. The resulting suspension was stirred at room temperature for three days then was concentrated in vacuo to remove dichloromethane. The residue was washed into a separatory funnel with ethyl acetate and 1.0 M NaOH. The ethyl acetate was separated, washed with brine, was dried (Na₂SO₄), and concentrated in vacuo. The intermediate 4-Bromo-2-methanesulfonyl-benzoic acid ethyl ester was recovered as a colorless oil which crystallized on standing, yield: 16.3 g (97%). ¹H NMR (400 MHz, CDCl₃): δ 8.27 (s, 1H), 7.82 (d, J=8 Hz, 1H), 7.60 (d, J=8 Hz, 1H), 4.44 (q, J=7 Hz, 2H), 3.38 (s, 3H), 1.41 (t, J=7 Hz, 3H).

The 4-Bromo-2-methanesulfonyl-benzoic acid ethyl ester (16.3 g, 53 mmol) was weighed into a flask with 21 g of bis(pinacolato)diboron, 19 g of potassium acetate, 5 g of dichloro[1,1'-bis(diphenylphosphino)ferrocene]palladium (II) dichloromethane adduct, and 150 mL of DMSO. The resulting suspension was heated at 80-85° C. for 20 h then was diluted with 200 mL of water, 200 mL of ethyl acetate, and the reaction mixture was filtered through celite to remove solids. The filtrate was transferred to a separatory funnel and the aqueous phase was separated and washed with ethyl acetate. The ethyl acetate washings were combined, washed with brine, were dried (Na₂SO₄) and concentrated in vacuo. The residue was purified by silica gel flash chromatography (Biotage, 65×200 mm SiO₂, gradient elution from 100% hexanes to 40% ethyl acetate over 1 h). Appropriate fractions were combined and concentrated in vacuo affording the 2-Methanesulfonyl-4-(4,4,5,5-tetramethyl-[1,3,2]dioxaborolan-2-yl)-benzoic acid ethyl ester as a colorless solid, yield: 12.65 g (67%). ¹H-NMR (400 MHz, CDCl₃): δ 8.52 (s, 1H), 8.08 (d, J=8 Hz, 1H), 7.65 (d, J=8 Hz, 1H), 4.45 (q, J=7 Hz, 2H), 3.33 (s, 3H), 1.42 (t, J=7 Hz, 3H), 1.35 (s, 2H).

Into a 100 mL flask was weighed 865 mg (1.96 mmol) of bromide v (where R¹=2,5-Cl), 693.5 mg (1.96 mmol) of boronate, and 20 mL of THF. The resulting solution was heated at 80-85° C. and ~250 mg of tetrakistriphenylphosphine palladium (0) was added followed by 2.0 mL of 1.0 M Na₂CO₃. The reaction was maintained at 80-85° C. for 3 h then was concentrated to remove THF. The residue was washed into a separatory funnel with ethyl acetate and 1.0 M sodium carbonate. The ethyl acetate was separated, washed with brine, was dried (Na₂SO₄), and concentrated in vacuo. Crude product was purified by silica gel flash chromatography (Jones Flashmaster, 50 g SiO₂, gradient elution from 100% hexanes to 40% ethyl acetate over 30 minutes). Appropriate fractions were combined and concentrated in vacuo affording the intermediate ethyl 4-{5-[1-(2,5-dichlorophenyl)-3-(trifluoromethyl)-1H-pyrazol-5-yl]-2-thienyl}-2-(methylsulfonyl)benzoate as a colorless powder, yield: 256.4 mg (222%); MS (ES): 589 and 591 [each M+H]⁺.

Into a 50 mL flask was weighed 120.2 mg of ester, 1 mL of THF, and 1 mL of methanol. To the solution was added 204 µL of a 3.0 M LiOH solution. The reaction was stirred at room temperature for 3 h then was washed into a separatory funnel with ethyl acetate and 1 M HCl. The ethyl acetate was separated, washed with brine, was dried (Na₂SO₄), and concentrated in vacuo. The crude acid was purified by reverse-phase HPLC to afford 4-{5-[1-(2,5-dichlorophenyl)-3-(trifluoromethyl)-1H-pyrazol-5-yl]-2-thienyl}-2-(methylsulfonyl)benzoic acid as a colorless powder, yield 43.0 mg (38%); ¹H-NMR (400 MHz, DMSO-d₆): δ 8.20 (s, 1H), 8.09 (s, 1H), 7.98 (d, J=8 Hz, 1H), 7.86 (m, 2H), 7.81 (d, J=8 Hz, 1H), 7.74 (d, J=4 Hz, 1H), 7.58 (s, 1H), 7.32 (d, J=4 Hz, 1H), 3.46 (s, 3H); MS (ES): 561 and 563 [M+H]⁺.

The following compounds are prepared essentially according to the previous examples:

3-{5-[5-(3-Methanesulfonyl-phenyl)-thiophen-2-yl]-3-trifluoromethyl-pyrazol-1-yl}-thiophene-2-carboxylic acid. ¹H-NMR (400 MHz, CDCl₃): δ 8.05 (1H, m), 7.88-7.81 (1H, m), 7.77-7.69 (2H, m), 7.57 (1H, m), 7.26-722 (2H, m), 6.89 (1H, d), 6.86 (1H, s), 3.08 (3H, s). MS (ES): 499 [M+H]⁺.

2-(3-{5-[1-(2,5-dichlorophenyl)-3-(trifluoromethyl)-1H-pyrazol-5-yl]-2-thienyl}phenyl)-2-methylpropanoic acid. $^{1}$H-NMR (400 MHz, CDCl$_{3}$): δ 7.59 (1H, d), 7.53 (1H, m), 7.51-7.43 (2H, m), 7.42-7.32 (3H, m), 7.14 (1H, d), 6.87 (1H, s), 6.80 (1H, d), 1.62 (6H, s). MS (ES): 525 [M+H]$^{+}$.

Ethyl 3-{5-[1-(2,5-dichlorophenyl)-3-(trifluoromethyl)-1H-pyrazol-5-yl]-2-thienyl}-5-(methylsulfonyl)benzoate; MS (ES): 589 and 591 [each M+H]$^{+}$.

Example 54

Preparation of 1-[5-Chloro-2-(4-fluoro-phenoxy)-phenyl]-[5-(3-methanesulfonyl-phenyl)-thiophen-2-yl]-3-trifluoromethyl-1H-pyrazole

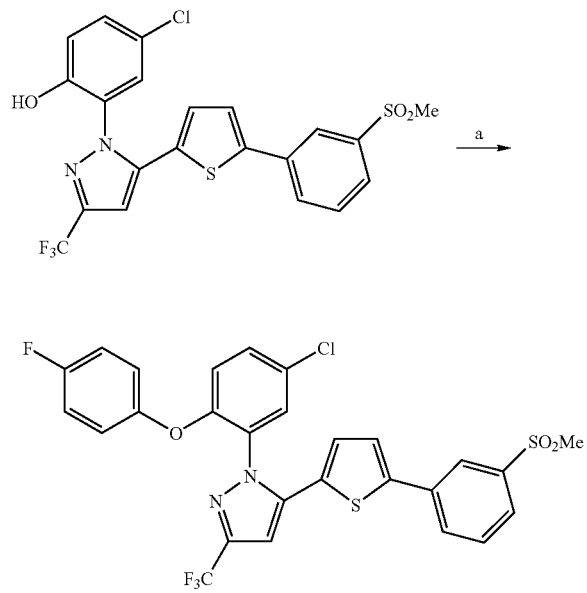 [SMILES: CS(=O)(=O)c1cccc(-c2ccc(-c3cc(C(F)(F)F)nn3-c3cc(Cl)ccc3O)s2)c1 ; CS(=O)(=O)c1cccc(-c2ccc(-c3cc(C(F)(F)F)nn3-c3cc(Cl)ccc3Oc3ccc(F)cc3)s2)c1]

a) 4-F-phenylboronic acid, Cu(OAc)$_{2}$, $^{i}$(Pr)$_{2}$EtN, CH$_{2}$Cl$_{2}$, 25° C.

4-Chloro-2-{5-[5-(3-methanesulfonyl-phenyl)-thiophen-2-yl]-3-trifluoromethyl-pyrazol-1-yl}-phenol was prepared as described in Example 1. Into a 50 mL flask was weighed 194 mg (388 μmol) of phenol, 159 mg of copper (II) acetate, 113.8 mg of 4-fluoroboronic acid, ~50 mg of activated 4 angstrom molecular sieves, 4 mL of dichloromethane, and 500 μL of diisopropylethylamine. The resulting suspension was stirred at room temperature for 21 h then was poured into a separatory funnel with ethyl acetate and 1 M NaOH. The ethyl acetate was separated, washed with brine, was dried (Na$_{2}$SO$_{4}$), and concentrated in vacuo. The residue was purified by silica gel flash chromatography (Jones Flashmaster, 50 g SiO$_{2}$, gradient elution from 100% hexanes to 40% ethyl acetate). Appropriate fractions were combined and concentrated in vacuo affording the product as a colorless solid, yield: 89 mg (39%). $^{1}$H-NMR (400 MHz, CDCl$_{3}$): δ 8.09 (s, 1H), 7.88 (d, J=8 Hz, 1H), 7.76 (d, J=8 Hz, 1H), 7.66 (d, J=4 Hz, 1H), 7.61 (t, J=8 Hz, 1H), 7.40 (d, J=8 Hz, 1H), 7.30 (d, J=4 Hz, 1H), 6.90 (m, 2H), 6.79 (d, J=9 Hz, 2H), 6.64 (m, 2H), 3.10 (s, 3H); MS (ES): 593 [M+H]$^{+}$.

Example 55

Preparation of 3-{5-[1-(2,5-dichlorophenyl)-3-(trifluoromethyl)-1H-pyrazol-5-yl]-2-thienyl}benzenesulfonamide

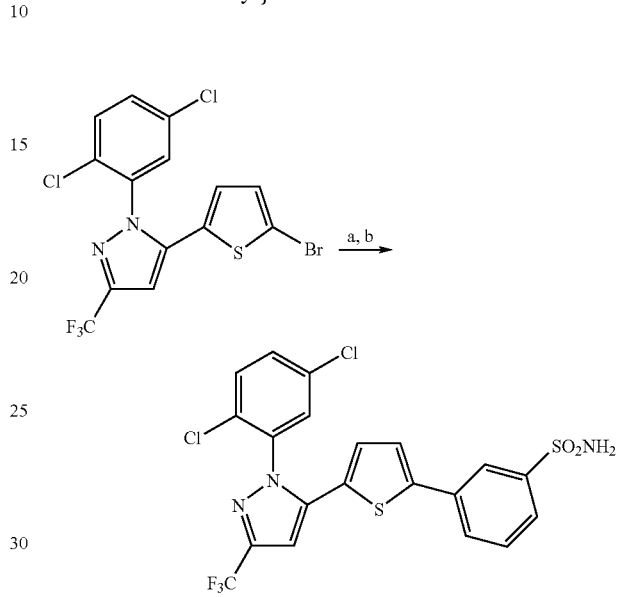

a) Bis(pinacolato)diboron, Pd(dppf), KOAc, DMSO, 85° C.;
b) (Ph$_{3}$P)$_{4}$Pd, 3-Br-Benzenesulfonamide, Na$_{2}$CO$_{3}$, THF-water, 80° C.

Into a 100 mL flask was weighed 4.43 g (10.0 mmol) of bromide, 3.14 g of bis(pinacolato)diboron, 3.12 g of potassium acetate, 29 mL of DMSO and 516 mg of dichloro[1,1'-bis(diphenylphosphino)ferrocene]palladium dichloromethane adduct. The resulting suspension was heated at 100° C. for 18 h then was washed into a separatory funnel with ethyl acetate and water. The ethyl acetate was separated, washed with water, brine, was dried (MgSO$_{4}$), and concentrated in vacuo. The residue was purified by silica gel flash chromatography (Jones Flashmaster, two 70 g columns, gradient elution from 100% hexanes to 20% ethyl acetate over 40 minutes). Appropriate fractions were combined and concentrated in vacuo to afford the product as an off-white solid mixture of boronic acid and boronate, yield: 1.8 g (~35%).

The crude boronate (601 mg) was weighed into a 50 mL flask with 312 mg of 3-bromosulfonamide and 10 mL of THF. The resulting solution was heated at 80-85° C. and ~50 mg of tetrakistriphenylphosphine palladium (0) was added followed by 1.0 mL of 1.0 M sodium carbonate. The reaction was maintained at 80-85° C. for three hours then was cooled and concentrated in vacuo. The residue was washed into a separatory funnel with ethyl acetate and 1.0 M sodium carbonate. The ethyl acetate was separated, washed with brine, was dried (MgSO$_{4}$), and concentrated in vacuo. The product was purified by silica gel flash chromatography (Jones Flashmaster, 70 g SiO$_{2}$, gradient elution from 100% hexanes to 40% ethyl acetate over 30 minutes). Appropriate fractions were combined and concentrated in vacuo affording the product as a faintly yellow powder, yield: 75 mg (11%). $^{1}$H-NMR. (400 MHz, CDCl$_{3}$): δ 8.07 (1H, m), 7.84 (1H, m), 7.68 (1H, m), 7.59 (1H, m), 7.56-7.45 (3H, m), 7.22 (1H, d), 6.88 (1H, s), 6.85 (1H, d), 4.98 (2H, s). MS (ES): 518 [M+H]$^+$.

Example 56

Preparation of N-[(3-{5-[1-(2-chlorophenyl)-3-(trifluoromethyl)-1H-pyrazol-5-yl]-2-thienyl}phenyl)sulfonyl]acetamide

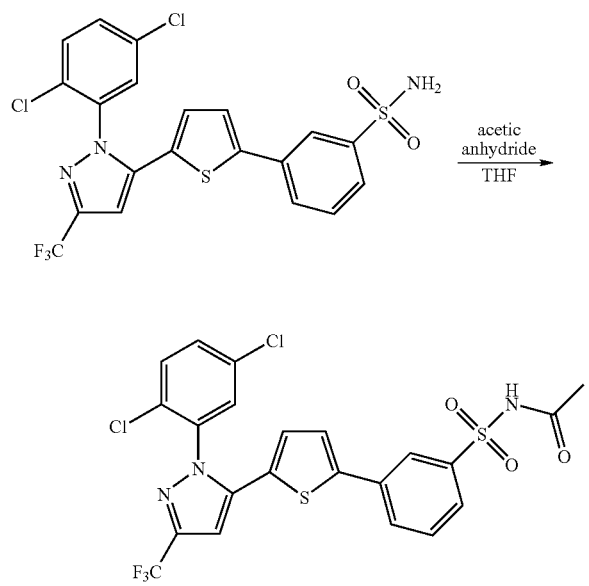

3-{5-[2-(2-Chloro-phenyl)-5-trifluoromethyl-2H-pyrazol-3-yl]-thiophen-2-yl}-benzenesulfonamide was prepared as described in Example 1. Into a 250 mL flask was weighed 209.6 mg (433 μmol) of the sulfonamide and 866 μL of 1.0 M lithium bis(trimethylsilyl)amide. To the solution was added 123 μL of acetic anhydride. The reaction was stirred at mom temperature for 1 h then was washed into a separatory funnel with 1.0 M HCl and ethyl acetate. The ethyl acetate was separated, washed with brine, was dried (Na$_2$SO$_4$), and was concentrated in vacuo. The crude product was purified by reverse-phase HPLC affording the product as a colorless powder, yield: 47.0 mg (20%); $^1$H NMR (400 MHz, CDCl$_3$): δ 8.16 (s, 1H), 7.91 (d, J=8 Hz, 1H), 7.66 (d, J=8 Hz, 1H), 7.4-7.6 (m, 5H), 7.21 (d, J=4 Hz, 1H), 6.89 (s, 1H), 6.79 (d, J=4 Hz, 1H), 2.04 (s, 3H); MS (ES): 526 [M+H]$^+$.

The following compounds are prepared essentially according to the previous examples by substituting the appropriate anhydride:

N-[(3-{5-[1-(2,5-dichlorophenyl)-3-(trifluoromethyl)-1H-pyrazol-5-yl]-2-thienyl}phenyl)sulfonyl]-2,2-dimethyl-propanamide; MS (ES): 602 and 604 [each M+H]$^+$.

Example 57

Preparation of 2-[4-{5-[1-(2,5-dichlorophenyl)-3-(trifluoromethyl)-1H-pyrazol-5-yl]-2-thienyl}-2-(methylsulfonyl)phenyl]propan-2-ol and [4-{5-[1-(2,5-dichlorophenyl)-3-(trifluoromethyl)-1H-pyrazol-5-yl]-2-thienyl}-2-(methylsulfonyl)phenyl]methanol

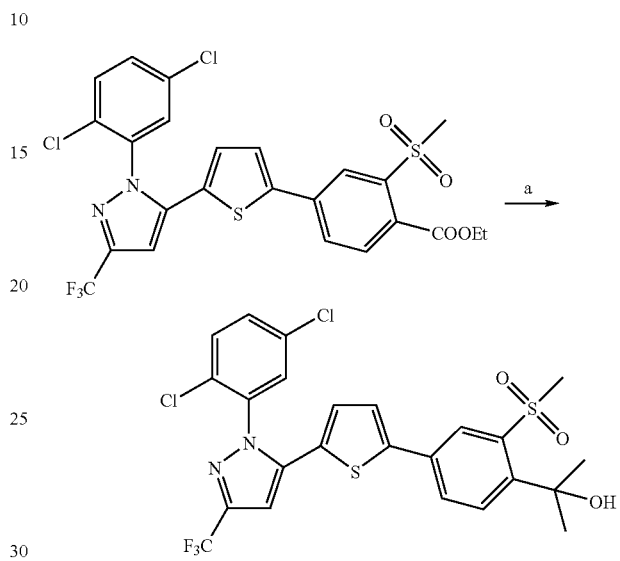

a) MeMgBr, THF, 0-25° C.

Ethyl 4-{5-[1-(2,5-dichlorophenyl)-3-(trifluoromethyl)-1H-pyrazol-5-yl]-2-thienyl}-2(methylsulfonyl)benzoate was prepared as described in Example 53. Into a 50 mL flask was weighed 209.4 mg of ester and 2.0 mL of anhydrous THF. The solution was cooled under nitrogen in an ice bath and 1.0 mL of 1.4 M MeMgBr in THF (Aldrich) was added. The reaction was removed from cooling and was stirred at room temperature for 1 h then was quenched by addition of saturated ammonium chloride. The reaction was washed into a separatory funnel with ethyl acetate and saturated ammonium chloride. The ethyl acetate was separated, washed with brine, was dried (Na$_2$SO$_4$), and concentrated in vacuo. The residue was purified by silica gel flash chromatography (Biotage, 25×150 mm SiO$_2$, gradient elution from 100% hexanes to 100% ethyl acetate over 45 minutes). Appropriate fractions were combined and concentrated in vacuo affording the product as a cream colored semi-solid, yield: 157.1 mg (77%); $^1$HNMR (400 MHz, CDCl$_3$): δ 8.34 (s, 1H), 7.65 (d, J=8 Hz, 1H), 7.59 (s, 1H), 7.45-7.53 (m, 3H), 7.26 (d, J=4 Hz, 1H), 6.89 (s, 1H), 6.85 (d, J=4 Hz, 1H), 4.82 (br s, 1H), 3.43 (s, 3H), 1.71 (s, 6H); MS (ES): 575 and 577 [each M+H]$^+$.

The following compounds are prepared essentially according to the previous examples by substituting 3-Bromo-5-fluoro-benzoic acid for 4-Bromo-2-fluoro-benzoic acid:

2-[3-{5-[1-(2,5-dichlorophenyl)-3-(trifluoromethyl)-1H-pyrazol-5-yl]-2-thienyl}-5-(methylsulfonyl)phenyl]propan-2-ol; MS (ES): 575 and 577 [each M+H]$^+$.

2-[3-{5-[1-(2,6-dichlorophenyl)-3-(trifluoromethyl)-1H-pyrazol-5-yl]-2-thienyl}-5-(methylsulfonyl)phenyl]propan-2-ol; MS (ES): 575 and 577 [each M+H]$^+$.

2-[3-{5-[1-(2-chlorophenyl)-3-(trifluoromethyl)-1H-pyrazol-5-yl]-2-thienyl}-5-(methylsulfonyl)phenyl]propan-2-ol; MS (ES): 541 [M+H]$^+$.

Example 58

Preparation of [4-{5-[1-(2,5-dichlorophenyl)-3-(trifluoromethyl)-1H-pyrazol-5-yl]-2-thienyl}-2-(methylsulfonyl)phenyl]methanol

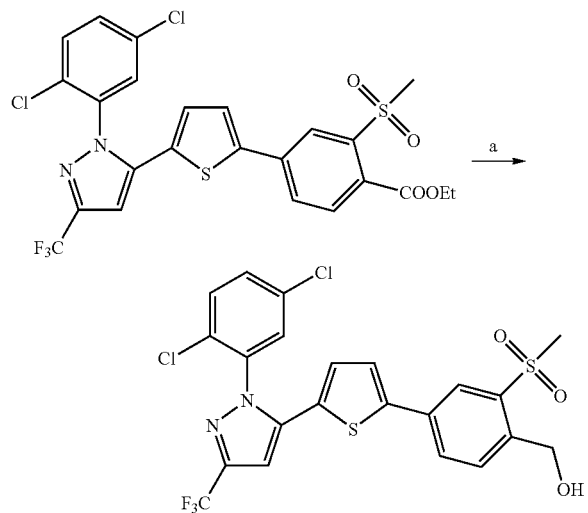

a) LiBH₄, THF, 25° C.

Into a 4 mL vial was weighed 102.0 mg of ester and 1.0 mL of anhydrous THF. The resulting solution was cooled in an ice bath and 200 μL of 2.0 M LiBH₄ in THF (Aldrich) was added. The reaction was allowed to warm to room temperature where it remained for 3 days. The reaction was then washed into a separatory funnel with ethyl acetate and 1 M HCl. The ethyl acetate was separated, washed with brine, was dried (Na₂SO₄), and concentrated in vacuo. The crude material was purified by reverse-phase HPLC to afford the product as a colorless solid, yield: 14.0 mg (15%); ¹H NMR (400 MHz, CDCl₃): δ 8.17 (s, 1H), 7.72 (d, J=8 Hz, 1H), 7.5-7.6 (m, 2H), 7.50 (m, 2H), 7.26 (s, 1H), 6.89 (s, 1H), 6.85 (d, J=4 Hz 1H), 4.96 (s, 2H), 3.20 (s, 3H); MS (ES): 547 and 549 [each M+H]⁺.

Example 59

Preparation of 4-(2-{[4-{5-[1-(2,5-dichlorophenyl)-3-(trifluoromethyl)-1H-pyrazol-5-yl]-2-thienyl}-2-(methylsulfonyl)phenyl]oxy}ethyl)morpholine

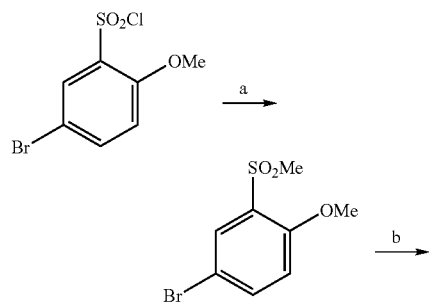

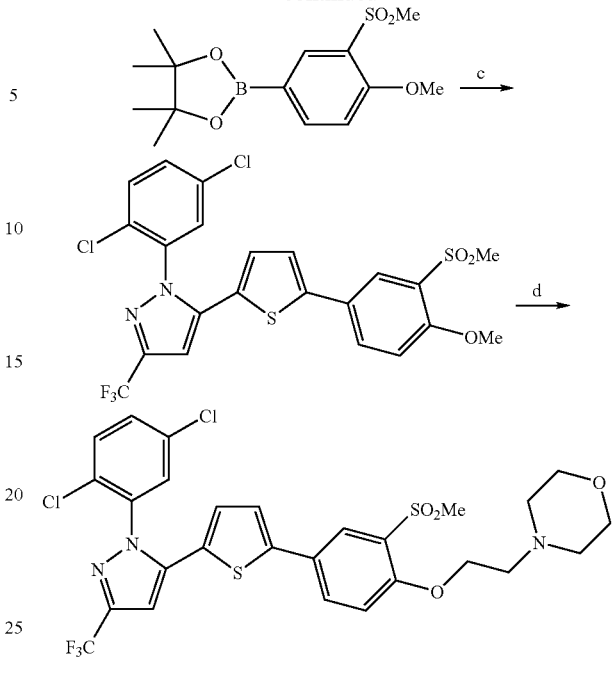

a) NaHCO₃, Na₂SO₃, H₂O, 85° C., then Me₂SO₂, NaHCO₃, H₂O, 120° C.; b) Bis(pinacolato)diboron, Pd(dppf), KOAc, DMSO, 100° C. c) (Ph₃P)₄Pd, 5-(5-Bromothiophen-2-yl)-1-(2,5-dichlorophenyl)-3-trifluoromethyl-1H-pyrazole, Na₂CO₃, THF water, 80° C.; d) BBr₃, CH₂Cl₂, 25° C.; K₂CO₃, 4-(2-Chloroethyl)morpholine hydrochloride, DMF, 100° C.

Into a 1 L flask was weighed 41.4 g of sodium sulfite, 29 g of sodium bicarbonate, and 175 mL of water. The suspension was stirred at 80-85° C. and sulfonyl chloride (50 g) was added portionwise over 3 h. Heating was continued for 3 h then the reaction was allowed to stand at room temperature for 3 days. The intermediate sulfinate was collected by filtration with added water then was dried under high vacuum. The dry solids (45 g) were returned to a 1 L flask along with 28.0 g of sodium bicarbonate, 25 mL of dimethylsulfate, and 63.75 mL of water. The resulting suspension was heated at 120-125° C., where it became a solution, for 20 h then was cooled and washed into a separatory funnel with ethyl acetate and water. The ethyl acetate was separated, washed with brine, was dried (Na₂SO₄), and concentrated in vacuo. The product was precipitated from dichloromethane with hexanes and was dried under high vacuum to afford the intermediate 4-Bromo-2-methanesulfonyl-1-methoxy-benzene as a colorless powder, yield: 31.1 g (67%). ¹H NMR (400 MHz, CDCl₃): δ 8.08 (2, 1H), 7.69 (d, J=8 Hz, 1H), 6.96 (d, J=8 Hz, 1H), 4.00 (s, 3H), 3.21 (s, 3H).

Into a 500 mL flask was weighed 15.48 g (58.4 mmol) of bromide, 23 g of boronate, 21 g of potassium acetate, 5 g of dichloro[1,1'-bis(diphenylphosphino)ferrocene]palladium (II) dichloromethane adduct, and 150 mL of DMSO. The resulting suspension was heated at ~100° C. for 20 h then was cooled and diluted with 200 mL of ethyl acetate and 200 mL of water. The suspension was filtered through celite to remove solids and the filtrate was transferred to a separatory funnel. The aqueous phase was separated and washed with ethyl acetate. The ethyl acetate washings were combined, washed with brine, were dried (Na₂SO₄) and concentrated in vacuo. The residue was purified by silica gel flash chromatography (Biotage, 65×200 mm SiO₂, gradient elution from 100% hexanes to 100% ethyl acetate over 1 h). Appropriate fractions were combined and concentrated in vacuo. The partially purified product was dissolved in ethyl acetate and was precipitated with hexanes. The intermediate 2-(3-Methanesulfonyl-4-methoxy-phenyl)-4,4,5,5-tetramethyl-[1,3,2]dioxaborolane was recovered as a faintly yellow powder, yield: 12.56 g (77%). ¹H NMR (400 MHz, CDCl₃): δ 8.43 (s, 1H), 8.01 (d, J=8 Hz, 1H), 7.03 (d, J=8 Hz, 1H), 4.02 (s, 3H), 3.20 (s, 3H), 1.33 (s, 12H).

Into a 250 mL flask was weighed 5.0 g (11.3 mmol) of 5-(5-Bromothiophen-2-yl)-1-(2,5-dichlorophenyl)-3-trifluoromethyl-1H-pyrazole, (4.43 g (14.2 mmol) of boronate, and 100 mL of THF. The resulting solution was heated at 80-85° C. and ~1 g of tetrakistriphenylphosphine palladium (0) was added followed by 10 mL of 1.0 M Na₂CO₃. The reaction was maintained at 80-85° C. for 3 h then was concentrated to remove THF. The residue was washed into a separator), funnel with ethyl acetate and 1.0 M sodium carbonate. The ethyl acetate was separated, washed with brine, was dried (Na₂SO₄), and concentrated in vacuo. Crude product was purified by silica gel flash chromatography (Biotage, 65×200 mm SiO₂, gradient elution from 100% hexanes to 60% ethyl acetate over 1 h). Appropriate fractions were combined and concentrated in vacuo affording the intermediate methoxy compound as a yellow solid, yield: 2.75 g (44%).

The methoxy compound described, 2.60 g, (4.75 mmol) was weighed into a 250 mL flask along with 75 mL of dichloromethane. The resulting solution was cooled to ~70° C. and 14 mL of 1.0 M BBr3 in dichloromethane was added. The reaction was allowed to warm to room temperature where it remained for 4 h. The reaction was then quenched by addition of methanol and was concentrated in vacuo. The residue was washed into a separatory funnel with ethyl acetate and 1 M HCl. The ethyl acetate was separated, washed with brine, was dried (Na₂SO₄), and concentrated in vacuo. The residue was purified by silica gel flash chromatography (Biotage, 40×150 ram SiO₂, gradient elution from 100% hexanes to 60% ethyl acetate over 1 h). Appropriate fractions were combined and concentrated in vacuo affording the intermediate 4-{5-[1-(2,5-dichlorophenyl)-3-(trifluoromethyl)-1H-pyrazol-5-yl]-2-thienyl}-2-(methylsulfonyl)phenol as a colorless solid, yield: 1.39 g (54.9%); MS (ES): 533 and 535 [each M+H]⁺.

Into a 50 mL flask was weighed 249.2 mg (467 mmol) of phenol, 263 mg of potassium carbonate, 368 mg (1.98 mmol) of 4-(2-Chloroethyl)morpholine hydrochloride, and 3 mL of DMF. The resulting suspension was heated at 100-105° C. for 30 minutes then was washed into a separatory funnel with ethyl acetate and 1.0 M sodium carbonate. The ethyl acetate was separated, washed with brine, was dried (Na₂SO₄), and concentrated in vacuo. The residue was purified by silica gel flash chromatography (Biotage, 25×150 mm SiO₂, gradient elution from 100% dichloromethane to 89:10:1 dichloromethane-methanol-ammonium hydroxide over 45 minutes). Appropriate fractions were combined and concentrated in vacuo then were dissolved in dichloromethane and product was precipitated by addition of hexanes. The precipitate was collected by filtration and was dried affording the product as an off-white solid, yield: 78 mg (26%). ¹H NMR (400 MHz, CDCl₃): δ 8.11 (s, 1H), 7.67 (d, J=8 Hz, 1H), 7.59 (s, 1H), 7.49 (m, 2H), 7.12 (d, J=4 Hz, 1H), 7.04 (d, J=8 Hz, 1H), 6.86 (s, 1H), 6.81 (d, J=4 Hz, 1H), 4.26 (t, J=5 Hz, 2H), J=5 Hz, 4H), 3.33 (s, 3H), 2.87 (t, J=5 Hz, 2H), 2.58 (t, J=5 Hz, 4H); MS (ES): 646 and 648 [each M+H]⁺.

The following compounds are prepared essentially according to the previous examples by substituting an alkyl halide for 4-(2-Chloroethyl)morpholine hydrochloride:

5-(2-{[4-{5-[1-(2,5-dichlorophenyl)-3-(trifluoromethyl)-1H-pyrazol-5-yl]-2-thienyl}-2-(methylsulfonyl)phenyl]oxy}ethyl)-1H-tetrazole; MS (ES): 629 and 631 [each M+H]⁺.

2-{[4-{5-[1-(2,5-dichlorophenyl)-3-(trifluoromethyl)-1H-pyrazol-5-yl]-2-thienyl}-2-(methylsulfonyl)phenyl]oxy}ethanol; MS (ES): 577 and 579 [each M+H]⁺.

Scheme 22

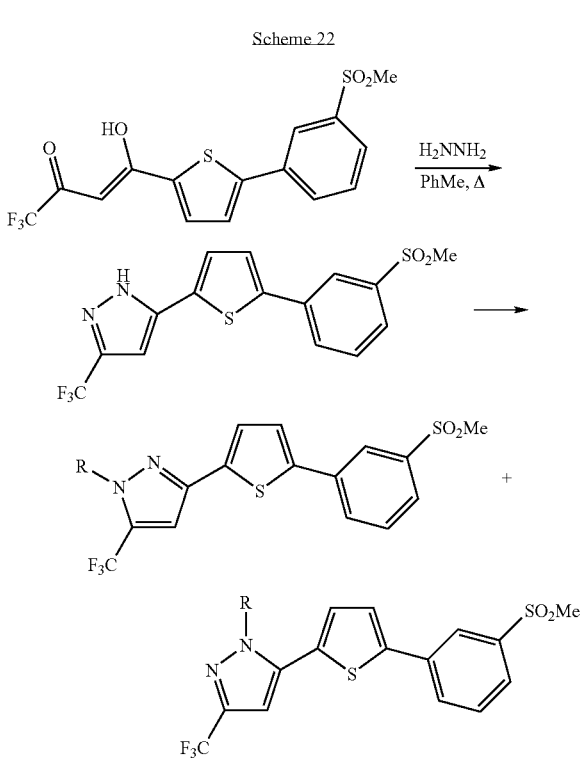

Another method used for preparing examples of the invention is shown as Example 60. 4,4,4-Trifluoro-1-[5-(3-methanesulfonyl-phenyl)-thiophen-2-yl]-butane-1,3-dione was condensed directly with hydrazine to form pyrazole 3-[5-(3-Methanesulfonyl-phenyl)-thiophen-2-yl]-5-trifluoromethyl-1H-pyrazole. Alkylation of a pyrazole such as 3-[5-(3-Methanesulfonyl-phenyl)-thiophen-2-yl]-5-trifluoromethyl-1H-pyrazole could result in a mixture of positional isomers which could be separated by one skilled in the art Example 60

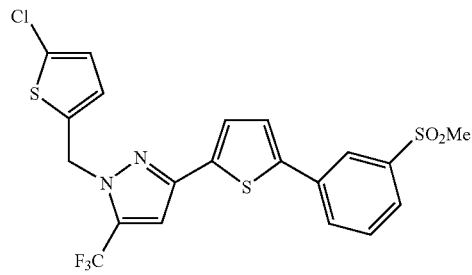 [SMILES: CS(=O)(=O)c1cccc(-c2ccc(-c3cc(C(F)(F)F)n(Cc4ccc(Cl)s4)n3)s2)c1]

Preparation of 1-[(5-chloro-2-thienyl)methyl]-3-{5-[3-(methylsulfonyl)phenyl]-2-thienyl}-5-(trifluoromethyl)-1H-pyrazole Into a 100 mL flask was weighed 5.18 g (13.8 mmol) of 4,4,4-Trifluoro-1-[5-(3-methanesulfonyl-phenyl)-thiophen-2-yl]-butane-1,3-dione, 50 mL of toluene, and 450 µL (14.3 mmol) of hydrazine. The resulting solution was heated at 100° C. for 21 h. The reaction was then concentrated in vacuo and was partially purified by silica gel flash chromatography (Jones Flashmaster, 70 g SiO$_2$, gradient elution from 100% hexanes to 20% ethyl acetate over 30 minutes. Appropriate fractions were combined, concentrated in vacuo, and were precipitated from ethyl acetate with hexanes to afford the intermediate 3-[5-(3-Methanesulfonyl-phenyl)-thiophen-2-yl]-5-trifluoromethyl-1H-pyrazole as a faintly yellow, semi-crystalline solid, yield: 1.24 g (24%). $^1$H NMR (400 MHz, CDCl$_3$): δ 8.15 (s, 1H), 7.86 (d, J=8 Hz, 2H), 7.62 (t, J=8 Hz, 1H), 7.45 (d, J=4 Hz, 1H), 7.39 (d, J=4 Hz, 1H), 6.70 (s, 1H), 3.12 (s, 3H); MS (ES): 373 [M+H]$^+$.

Into an 8 mL vial was weighed 96.6 mg (259 µmol) of pyrazole, 93.5 mg of potassium carbonate, 1 mL of DMF, and 35.6 µL of 2-Chloro-5-chloromethylthiophene. The reaction was heated at 80-85° C. for 3 h then was washed into a separatory funnel with ethyl acetate and water. The ethyl acetate was separated, was dried (MgSO$_4$), and concentrated in vacuo. HPLC analysis showed the product to be a 1:1 mixture of isomers. Each was purified by reverse-phase HPLC purification to afford the products as colorless waxes.

1-[(5-chloro-2-thienyl)methyl]-3-{5-[3-(methylsulfonyl)phenyl]-2-thienyl}-5-(trifluoromethyl)-1H-pyrazole: $^1$H NMR (400 MHz, CDCl$_3$): δ 8.19 (s, 1H), 7.86 (m, 2H), J=8 Hz, 1H), 7.39 (d, J=4 Hz, 1H), 7.34 (d, J=4 Hz, 1H), 6.86 (m, 2H), 6.78 (d, J=4 Hz, 1H), 5.47 (s, 2H), 3.11 (s, 3H); MS (ES): 503 [M+H]$^+$.

1-[(5-chloro-2-thienyl)methyl]-5-{5-[3-(methylsulfonyl)phenyl]-2-thienyl}-3-(trifluoromethyl)-1H-pyrazole: $^1$H NMR (400 MHz, CDCl$_3$): δ 8.18 (s, 1H), 7.88 (m, 2H), 7.64 (t, J=8 Hz, 1H), 7.44 (d, J=4 Hz, 1H), 7.17 (d, J=4 Hz, 1H), 6.75 (d, J=4 Hz, 1H), 6.71 (m, 2H), 5.56 (s, 2H), 3.13 (s, 3H); MS (ES): 503 [M+H]$^+$.

The following compounds are prepared essentially according to the previous examples by substituting an appropriate reagent for 2-Chloro-5-chloromethylthiophene.

3-{5-[3-(methylsulfonyl)phenyl]-2-thienyl}-1-(2-thienylcarbonyl)-5-(trifluoromethyl)-1H-pyrazole; $^1$H-NMR (400 MHz, CDCl$_3$): δ 8.43 (0.5H, dd, J=1.4 Hz), 8.33 (0.5H, dd, J=1.4 Hz), 8.23 (0.5H, t, J=1 Hz), 8.18 (0.5H, t, J=1 Hz), 7.86-7.96 (m, 3H), 7.63 (1H, q, J=8 Hz), 7.49 (1H, m), 7.44 (0.5H, d, J=4 Hz), 7.40 (0.5H, d, J=4 Hz), 7.21-7.28 (1H, m), 7.20 (0.5H, s), 6.89 (0.5H, s), 3.13 (1.5H, s), 3.11 (1.5H, s); MS (ES): 483 [M+H]$^+$.

5-{5-[3-(methylsulfonyl)phenyl]-2-thienyl}-1-(2-thienylcarbonyl)-3-(trifluoromethyl)-1H-pyrazole; $^1$H-NMR (400 MHz, CDCl$_3$): δ 8.43 (0.5H, dd, J=1.4 Hz), 8.33 (0.5H, dd, J=1.4 Hz), 8.23 (0.5H, t, J=1 Hz), 8.18 (0.5H, t, J=1 Hz), 7.86-7.96 (m, 3H), 7.63 (1H, q, J=8 Hz), 7.49 (1H, m), 7.44 (0.5H, d, J=4 Hz), 7.40 (0.5H, d, J=4 Hz), 7.21-7.28 (1H, m), 7.20 (0.5H, s), 6.89 (0.5H, s), 3.13 (1.5H, s), 3.11 (1.5H, s); MS (ES): 483 [M+H]$^+$.

5-{5-[3-(methylsulfonyl)phenyl]-2-thienyl}-1-(phenylsulfonyl)-3-(trifluoromethyl)-1H-pyrazole; $^1$H-NMR (400 MHz, CDCl$_3$): δ 8.18 (1H, m), 7.96-7.81 (4H, m), 7.74-7.60 (2H, m), 7.58-7.48 (2H, m), 7.45 (1H, d), 7.40 (1H, d), 6.67 (1H, s), 3.13 (3H, s), MS (ES): 513 [M+H]$^+$.

3-{5-[3-(methylsulfonyl)phenyl]-2-thienyl}-1-(phenylsulfonyl)-5-(trifluoromethyl)-1H-pyrazole; $^1$H-NMR (400 MHz, CDCl$_3$): δ 8.18 (1H, s), 8.14 (2H, d, J=8 Hz), 7.88 (2H, d, J=8 Hz), 7.60 (4H, m), 7.38 (2H, m), 7.00 (1H, s), 3.11 (3H, s); MS (ES): 513 [M+H]$^+$.

1-[(2,4-difluorophenyl)methyl]-5-{5-[3-(methylsulfonyl)phenyl]-2-thienyl}-3-(trifluoromethyl)-1H-pyrazole; $^1$H-NMR (400 MHz, CDCl$_3$): δ 8.14 (1H, m), 7.89 (1H, m), 7.83 (1H, m), 7.63 (1H, t), 7.39 (1H, d), 7.06 (1H, d), 6.95 (1H, m), 6.89-6.79 (2H, m), 6.74 (1H, s), 5.54 (2H, s), 3.11 (3H, s). MS (ES): 499 [M+H]$^+$.

1-[(2,4-difluorophenyl)methyl]-3-{5-[3-(methylsulfonyl)phenyl]-2-thienyl}-5-(trifluoromethyl)-1H-pyrazole; $^1$H-NMR (400 MHz, CDCl$_3$): δ 8.18 (1H, m), 7.91-7.81 (2H, m), 7.60 (1H, t), 7.39 (1H, d), 7.34 (1H, d), 7.10 (1H, m), 6.92-6.79 (3H, m), 5.48 (2H, s), 3.10 (3H, s). MS (ES): 499 [M+H]$^+$.

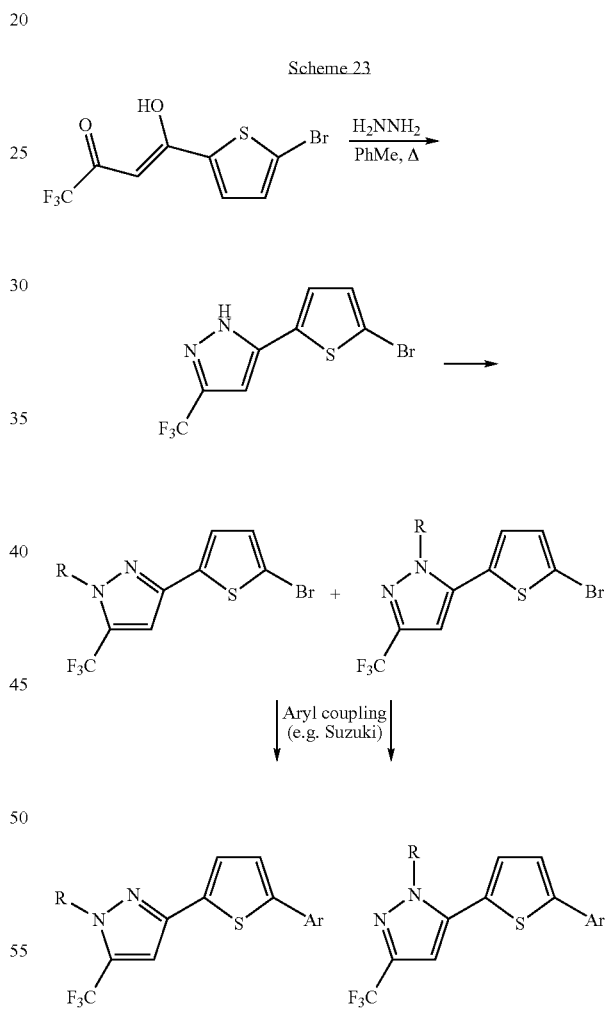

Scheme 23

Other examples of the invention were prepared by a different route of assembly as shown in Scheme 23. Similar to Example 60, 1-(5-Bromothiophen-2-yl)-4,4,4-trifluoro-butane-1,3-dione can be condensed with hydrazine directly to form a pyrazole. As in Example 60, acylation or alkylation can produce a mixture of isomers which could be separated at the stage of the bromide or such a mixture could be separated after aryl coupling.

Example 61

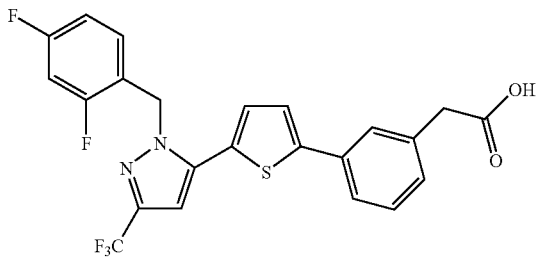 [SMILES: O=C(O)Cc1cccc(-c2ccc(-c3cc(C(F)(F)F)nn3Cc3ccc(F)cc3F)s2)c1]

Preparation of [3-(5-{1-{1-[(2,4-difluorophenyl)methyl]-3-(trifluoromethyl)-1H-pyrazol-5-yl}-2-thienyl}phenyl]acetic acid Into a 250 mL flask was weighed 5.00 g (23.2 mmol) of (3-Bromophenyl)acetic acid, 50 mL of methanol, and 50 mL of 4.0 M HCl in dioxane (Aldrich). The reaction was stirred at room temperature for 3 h then was concentrated in vacuo. The residue was washed into a separatory funnel with ethyl acetate and 10% ammonium hydroxide. The ethyl acetate was separated, was dried (MgSO$_4$), and was concentrated in vacuo. The intermediate (3-Bromophenyl)acetic acid methyl ester was recovered as a colorless oil, yield, 5.2 g (98%).

Into a 250 mL flask was weighed 5.18 g of ester (22.6 mmol) along with 7.51 g of bis(pinacolato)diboron, 6.6 g of potassium carbonate, 68 mL of DMSO, and 1.1 g of dichloro[1,1'-bis(diphenylphosphino)ferrocene]palladium (II) dichloromethane adduct. The resulting suspension was heated at 80-85° C. overnight then was washed into a separatory funnel with water and ether. The ether was separated, washed with brine, was dried (MgSO$_4$), and was concentrated in vacuo. The residue was purified by silica gel flash chromatography (Jones Flashmaster, two 70 g columns, gradient elution from 100% hexanes to 40% ethyl acetate over 1 h). Appropriate fractions were combined and concentrated in vacuo to afford the intermediate [3-(4,4,5,5-Tetramethyl-[1,3,2]dioxaborolan-2-yl)phenyl]acetic acid methyl ester as a faintly yellow oil, yield: 3.02 g (47%). $^1$H NMR (400 MHz, CDCl$_3$): δ 7.73 (m, 2H), 7.3-7.4 (m, 2H), 3.70 (s, 3H), 3.65 (s, 2H), 1.36 (s, 12H).

Into a 500 mL flask was weighed 15.1 g (50.15 mmol) of 4,4,4-Trifluoro-1-[5-(3-methanesulfonyl-phenyl)-thiophen-2-yl]-butane-1,3-dione, 150 mL of toluene, and 1.575 mL (1.1 eq) of hydrazine. The intermediate hydrazone precipitated from solution over 15 minutes then the reaction was heated to 100-105° C. where it remained for 18 h. The reaction was then concentrated to dryness in vacuo and the residue was dissolved in dichloromethane and precipitated with hexanes. The semicrystalline precipitate was collected by filtration and was dried under high vacuum to afford the intermediate 5-(5-Bromothiophen-2-yl)-3-trifluoromethyl-1H-pyrazole as a colorless solid, yield: 9.90 g (66%).

Into a 500 mL flask was weighed 5.0 g (16.8 mmol) of pyrazole, 5.4 g of potassium carbonate, 4.7 g (22.7 mmol) of 1-Bromomethyl-2,4-difluorobenzene, and 50 mL of DMF. The resulting suspension was stirred at 100-105° C. for 1 h then was allowed to cool to room temperature. The reaction was washed into a separatory funnel with ethyl acetate and water. The ethyl acetate was separated, washed with water, brine, was dried (MgSO$_4$), and concentrated in vacuo. The resulting mixture of isomers was purified by silica gel flash chromatography (5×30 cm, 5% ethyl acetate-hexanes) to afford the 5-(5-Bromothiophen-2-yl)-1-(2,4-difluoro-benzyl)-3-trifluoromethyl-1H-pyrazole as a colorless oil, yield: 2.21 g (31%) and 3-(5-Bromo-thiophen-2-yl)-1-(2,4-difluorobenzyl)-5-trifluoromethyl-1H-pyrazole as a colorless oil, yield: 4.62 g (65%).

Into a 250 mL flask was weighed 1.124 g (2.66 mmol) of 5-(5-Bromothiophen-2-yl)-1-(2,4-difluoro-benzyl)-3-trifluoromethyl-1H-pyrazole, 1.5 g of boronate (5.43 mmol), 100 mL of THF, and 10 mL of 1.0 M sodium carbonate. The resulting solution was heated at 80-85° C. in an oil bath and 318 mg of tetrakistriphenylphosphine palladium (0) was added. The reaction was heated for 18 h then was concentrated in vacuo to remove THF. The residue was washed into a separator), funnel with ethyl acetate and 1.0 M sodium carbonate. The ethyl acetate was separated, washed with brined, was dried (MgSO$_4$), and concentrated in vacuo. The residue was purified by silica gel flash chromatography (Jones Flashmaster, 70 g SiO$_2$, gradient elution from 100% hexanes to 40% ethyl acetate over 1 h). Appropriate fractions were combined and concentrated in vacuo to afford the intermediate (3-{5-[1-(2,4-Difluorobenzyl)-5-trifluoromethyl-1H-pyrazol-3-yl]-thiophen-2-yl}-phenyl)acetic acid methyl ester as a colorless oil, yield: 445 mg (34%).

The intermediate ester was dissolved in 10 mL of THF, 10 mL of methanol, and a solution of LiOH—H$_2$O (150 mg in 2 mL of water) was added. The resulting solution was stirred at 60-65° C. for 3 h then was concentrated in vacuo to remove methanol. The residue was washed into a separatory funnel with dichloromethane and water. The aqueous phase was separated and was acidified by addition of concentrated HCl. The aqueous phase was then washed with dichloromethane three times and the Washings were combined, dried (Na$_2$SO$_4$), and concentrated in vacuo. The residue was purified by reverse-phase HPLC to afford the acid as a colorless solid, yield: 52 mg (12%). $^1$H NMR (400 MHz, DMSO-d$_6$): δ 7.5-7.55 (m, 3H), 7.40 (d, J=4 Hz, 1H), 7.34 (t, J=8 Hz, 1H), 7.23 (m, 2H), 7.09 (s, 1H), 7.0-7.08 (m, 2H), 5.59 (s, 2H), 3.59 (s, 2H); MS (ES): 479 [M+H]$^+$.

The following compounds are prepared essentially according to the previous examples by substituting the appropriate reagents:

[3-(5-{1-[(5-chloro-2-thienyl)methyl]-3-(trifluoromethyl)-1H-pyrazol-5-yl}-2-thienyl)phenyl]acetic acid; $^1$H-NMR (400 MHz, CDCl$_3$): δ 7.55-7.49 (2H, m), 7.38 (1H, m), 7.31 (1H, d), 7.27 (1H, m), 7.11 (1H, d), 6.73 (1H, d), 6.68 (1H, d), 6.66 (1H, s), 5.54 (2H, s), 3.70 (2H, s). MS (ES): 483 [M+H]$^+$.

Example 62

Preparation of 1-methylethyl 5-{5-[3-(aminosulfonyl)phenyl]-2-thienyl}-1-(2,5-dichlorophenyl)-1H-pyrazole-3-carboxylate

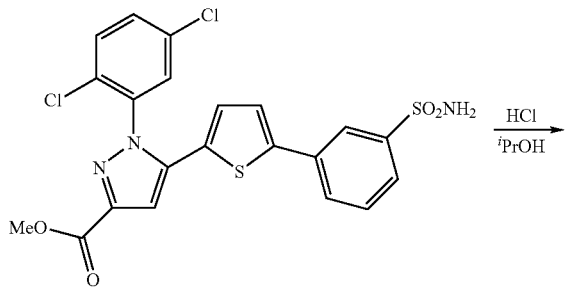

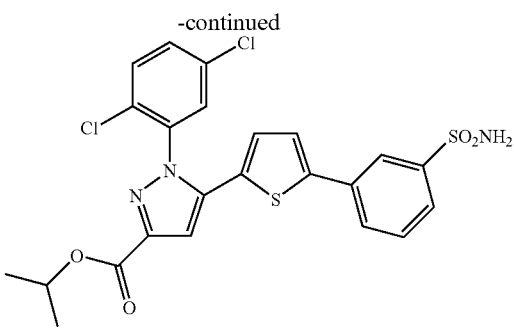

Into a 25 mL flask was weighed 114 mg (224 mmol) of methyl 1-(2,5-dichlorophenyl)-5-(5-(3-sulfamoylphenyl)thiophen-2-yl)-1H-pyrazole-3-carboxylate, 156 mg of KF, 4 mL of isopropyl alcohol, and 200 μL of concentrated HCl. The reaction was heated at 80-85° C. for 3 days. The reaction was then washed into a separatory funnel with ethyl acetate and water. The ethyl acetate was separated, washed with brine, was dried ($Na_2SO_4$), and concentrated in vacuo. Product was further purified by silica gel flash chromatography (Jones Flashmaster, 25 g $SiO_2$, gradient elution from 20% ethyl acetate to 60% ethyl acetate over 30 minutes). Appropriate fractions were combined and concentrated in vacuo to afford the product as a colorless powder, yield: 53.3 mg (44%). $^1$H NMR (400 MHz, $CDCl_3$): δ 8.05 (s, 1H), 7.83 (d, J=8 Hz, 1H), 7.66 (d, J=8 Hz, 1H), 7.59 (s, 1H), 7.44-7.51 (m, 3H), 7.21 (d, J=4 Hz, 1H), 7.13 (s, 1H), 6.81 (d, J=4 Hz, 1H), 5.33 (heptet, J=6 Hz, 1H), 5.08 (s, 2H), 1.41 (d, J=7 Hz, 6H); MS (ES): 536 [M+H]$^+$.

Example 63

Preparation of [4-{5-[1-(2,5-dichlorophenyl)-3-(trifluoromethyl)-1H-pyrazol-5-yl]-2-thienyl}-2-(methylsulfonyl)phenyl]methanol

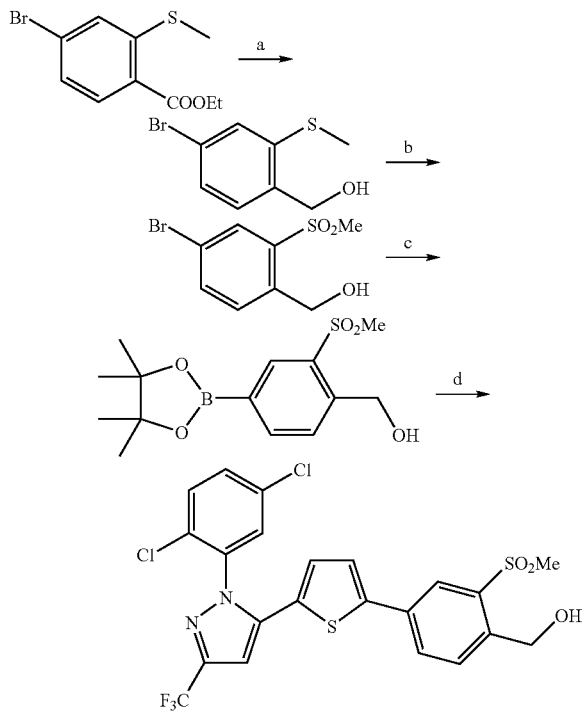

a) $LiBH_4$, THF, 85° C.; b) MCPBA, $CH_2Cl_2$, 25° C.; c) Bis(pinacolato)diboron, Pd(dppf), KOAc, DMSO, 100° C. C) $(Ph_3P)_4Pd$, 5-(5-Bromothiophen-2-yl)-1-(2,5-dichlorophenyl)-3-trifluoromethyl-1H-pyrazole, $Na_2CO_3$, THF-water, 80° C.

4-Bromo-2-methylsulfanyl-benzoic acid ethyl ester was prepared as described in Example 53. Into a 1 L flask was weighed 27.5 g of ester (99.9 mmol) and 150 mL of THF. A solution of 2.0 M $LiBH_4$ in THF (50 mL, 100 mmol) was then added and the reaction was heated to 80-85° C. where it remained for 23 h. The reaction was then removed from heat and was cooled in an ice bath as it was quenched by addition of acetone. The reaction was then concentrated in vacuo and was washed into a separatory funnel with ethyl acetate and 1 M HCl. The ethyl acetate was separated, washed with brine, was dried ($Na_2SO_4$), and concentrated in vacuo. The intermediate (4-Bromo-2-methylsulfanyl-phenyl)-methanol was recovered as a colorless oil that solidified on standing, yield: 25.5 g (100$^+$%). $^1$H NMR (400 MHz, $CDCl_3$): δ 7.24-7.34 (m, 3H), 4.69 (s, 2H), 2.50 (s, 3H).

The alcohol was then dissolved in 250 mL of dichloromethane, was cooled to 0-3° C. in an ice bath, and 44 g of 3-chloroperbenzoic acid (77% max., Aldrich) was added portionwise. The reaction was then allowed to warm to room temperature where it remained for 22 h. The reaction was then concentrated in vacuo to remove dichloromethane and the residue was washed into a separatory funnel with ethyl acetate and 1 M NaOH. The ethyl acetate was separated, washed with 1 M NaOH, was dried ($Na_2SO_4$), and concentrated in vacuo. The residue was purified by silica gel flash chromatography (Biotage, 65×200 mm $SiO_2$, gradient elution from 100% hexanes to 100% ethyl acetate over 1 h). Appropriate fractions were combined and concentrated in vacuo to afford the intermediate (4-Bromo-2-methanesulfonyl-phenyl)-methanol as a colorless, semi-crystalline solid, yield: 17.13 g (65%). $^1$H NMR (400 MHz, $CDCl_3$): δ 8.18 (s, 1H), 7.77 (d, J=8 Hz, 1H), 7.46 (d, J=8 Hz, 1H), 4.92 (s, 2H), 3.19 (s, 3H), 2.94 (br s, 1H).

Into a 1 L flask was weighed 17.13 g of bromide, 25 g of bis(pinacolato)diboron, 5.0 g of dichloro[1,1'-bis(diphenylphosphino)ferrocene]palladium (II) dichloromethane adduct, 23 g of potassium acetate, and 175 mL of DMSO. The resulting suspension was heated at 98-102° C. for 18 h then was diluted with 200 mL of ethyl acetate and 200 mL of water. The resulting suspension was filtered through celite to remove solids and the filtrate was transferred to a separatory funnel. The aqueous phase was separated and washed with ethyl acetate. The ethyl acetate washings were combined, washed with brine, were dried ($Na_2SO_4$) and concentrated in vacuo. The residue was purified by silica gel flash chromatography (Biotage, 65×200 mm $SiO_2$, gradient elution from 100% hexanes to 40% ethyl acetate over 1 h). Appropriate fractions were combined and concentrated in vacuo. The partially purified product was dissolved in dichloromethane and was precipitated with hexanes. The intermediate [2-Methanesulfonyl-4-(4,4,5,5-tetramethyl-[1,3,2]dioxaborolan-2-yl)-phenyl]-methanol was recovered as an off-white powder, yield: 8.78 g (43%). $^1$H NMR (400 MHz, $CDCl_3$): δ 8.45 (s, 1H), 8.04 (d, J=8 Hz, 1H), 7.57 (d, J=8 Hz, 1H), 4.96 (s, 1H), 3.17 (s, 3H), 1.35 (s, 6H), 1.24 (s, 6H).

Into a 250 mL flask was weighed 2.52 g (5.7 mmol) of 5-(5-Bromothiophen-2-yl)-1-(2,5-dichlorophenyl)-3-trifluoromethyl-1H-pyrazole, 3.6 g of boronate, and 100 mL of THF. The resulting solution was heated at 80-85° C. and ~200 mg of tetrakistriphenylphosphine palladium (0) was added. The reaction was heated for 3 h then was cooled and concentrated to remove THF. The residue was washed into a separatory funnel with ethyl acetate and 1.0 M sodium carbonate. The ethyl acetate was separated, washed with brine, was dried (Na$_2$SO$_4$), and concentrated in vacuo. The crude product was purified by silica gel flash chromatography (Biotage, 25×150 mm SiO$_2$, gradient elution from 100% hexanes to 100% ethyl acetate over 1 h). Appropriate fractions were combined and concentrated in vacuo to afford the product as a colorless solid, yield: 348 mg (11%); $^1$HNMR (400 MHz, CDCl$_3$): δ 8.17 (s, 1H), 7.72 (d, J=8 Hz, 1H), 7.5-7.6 (m, 2H), 7.50 (m, 2H), 7.26 (s, 1H), 6.89 (s, 1H), 6.85 (d, J=4 Hz, 1H), 4.96 (s, 2H), 3.20 (s, 3H); MS (ES): 547 and 549 [each M+H]$^+$.

The following compound is prepared essentially according to the previous examples by substituting the appropriate reagents:

[2-(methylsulfonyl)-4-(5-{3-(trifluoromethyl)-1-[3-(trifluoromethyl)pyridin-2-yl]-1H-pyrazol-5-yl}-2-thienyl)phenyl]methanol; MS (ES): 548 [M+H]$^+$.

Example 64

Preparation of 2-(3-(5-(1-(2-chlorophenyl)-3-(trifluoromethyl)-1H-pyrazol-5-yl)thiophen-2-yl)phenoxy)-2-methylpropanoic acid)

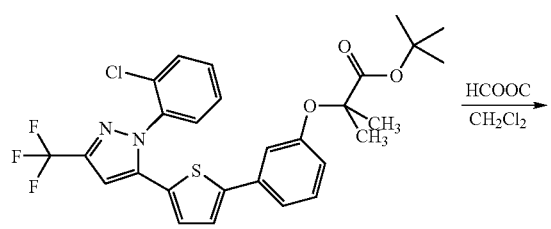

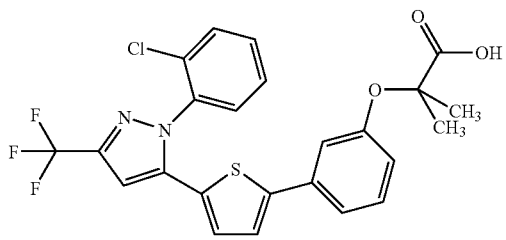

To a solution of tert-butyl 2-(3-(5-(1-(2-chlorophenyl)-3-(trifluoromethyl)-1H-pyrazol-5-yl)thiophen-2-yl)phenoxy)-2-methylpropanoate (47 mg, 84 µmol) in dichloromethane (0.5 mL) was added formic acid (1.0 mL). The resulting pale orange solution was allowed to stir at ambient temperature. After 5 hours at ambient temperature, LC/MS analysis of the reaction showed ~5% of the starting ester remaining. After 7 hours stirring at ambient temperature the reaction mixture was concentrated under reduced pressure to afford crude product. This material was purified by flash column chromatography eluting with a gradient from CH$_2$Cl$_2$ to 10% MeOH/CH$_2$Cl$_2$ to afford 2-(3-(5-(1-(2-chlorophenyl)-3-(trifluoromethyl)-1H-pyrazol-5-yl)thiophen-2-yl)phenoxy)-2-methylpropanoic acid (21.7 mg, 51% yield) as an off white foam. MS(ES): 509 [M+H]$^+$.

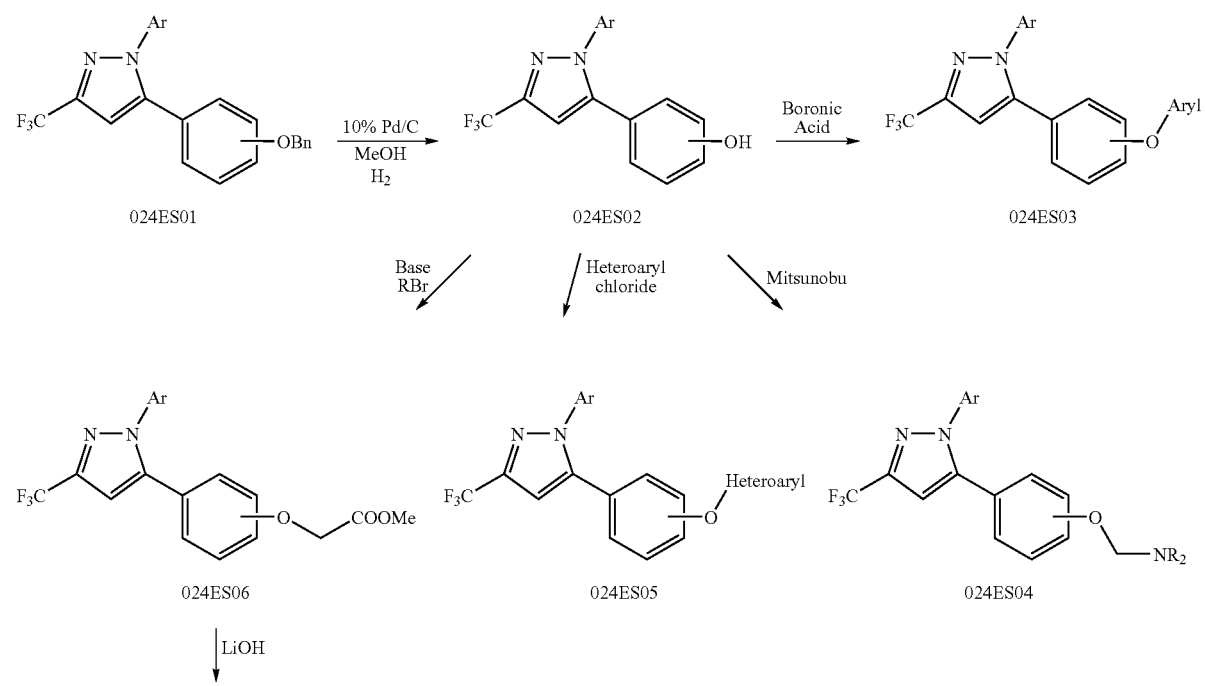

Scheme 24

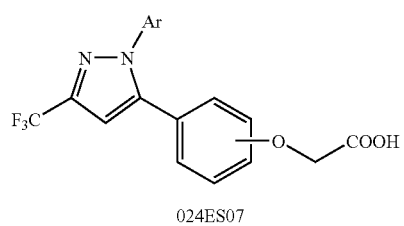

024ES07

As depicted in Scheme 24, hydroxyl group on C-phenyl can be transformed into other groups. Benzyloxyphenyl pyrazoles 024ES01 (prepared in a manner similar to Example 2c) can be deprotected to afford hydroxyphenyl pyrazoles 024ES02. The free hydroxyl group can be derivatized via: copper-mediated arylboronic acid coupling to afford diaryl ethers 024ES03, Mitsunobu reaction with alcohols to afford aryl-alkyl ethers 024ES04, reaction with heteroaryl halides to afford aryl-heteroaryl ethers 024ES05, or alkylated with alkyl halides to afford aryl alkyl ethers 024ES06, which may be further derivatized or transformed (See 024ES07).

Example 65

2-(4-(1-(2-chlorophenyl)-3-(trifluoromethyl)-1H-pyrazol-5-yl)phenoxy)pyrimidine

Example 65a

Preparation of 3-(1-(2-chlorophenyl)-3-(trifluoromethyl)-1H-pyrazol-5-yl)phenol

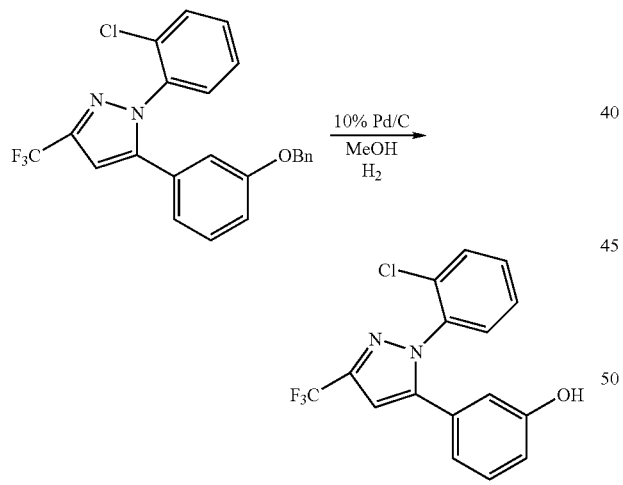

To a solution of 5-(3-(benzyloxy)phenyl)-1-(2-chlorophenyl)-3-(trifluoromethyl)-1H-pyrazole in MeOH (100 mL) was added 10% palladium on carbon (1.04 g). The black suspension was shaken on the Parr hydrogenator at 40-50 psi hydrogen pressure for 5 hours. At this time the reaction was incomplete as evidenced by HPLC analysis. The reaction suspension was treated with additional Pd/C and shaken under 60 psi hydrogen pressure for an additional 16 hours. At this time HPLC showed no remaining starting 5-(3-(benzyloxy)phenyl)-1-(2-chlorophenyl)-3-(trifluoromethyl)-1H-pyrazole. The reaction mixture was filtered through a pad of Celite that was then washed thoroughly with MeOH. The filtrate was concentrated under reduced pressure to afford 3-(1-(2-chlorophenyl)-3-(trifluoromethyl)-1H-pyrazol-5-yl) phenol as a brittle foam. This material was pure enough for use in subsequent transformations. MS(ES): 339 [M+H]$^+$.

The following compound is prepared essentially according to the previous examples:
4-[1-(2-chlorophenyl)-3-(trifluoromethyl)-1H-pyrazol-5-yl] phenol, MS(ES): 339 [M+H]$^+$.

Example 65b

Preparation of 2-(4-(1-(2-chlorophenyl)-3-(trifluoromethyl)-1H-pyrazol-5-yl)phenoxy)pyrimidine

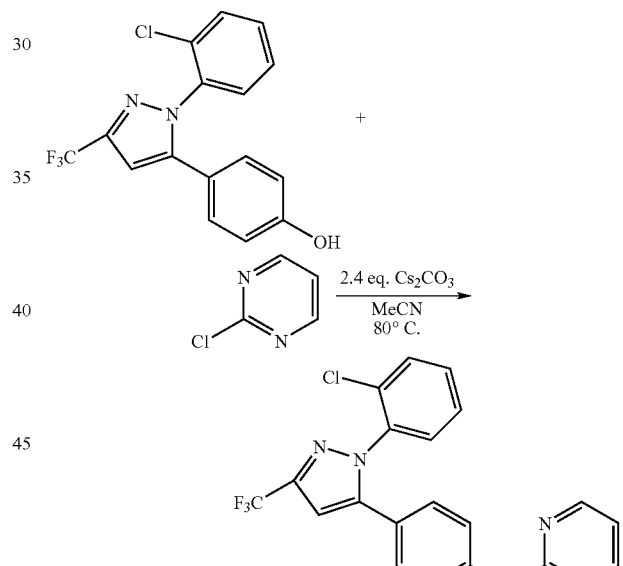

To a suspension of 4-(1-(2-chlorophenyl)-3-(trifluoromethyl)-1H-pyrazol-5-yl)phenol (ref hydrogenation below) (60 mg, 180 μmol) and Cs$_2$CO$_3$ (140 mg, 400 μmol) in acetonitrile (2 mL) was added 2-chloropyrimidine (66 mg, 580 μmol). The suspension was then heated to 80° C. in an oil bath. After stirring for 16 hours at 80° C. the suspension was filtered through a plug of silica gel (1 g), which was eluted with EtOAc. The filtrate was concentrated under reduced pressure and purified by flash column chromatography eluting with a gradient from 10% to 30% EtOAc/hexane to afford 2-(4-(1-(2-chlorophenyl)-3-(trifluoromethyl)-1H-pyrazol-5-yl)phenoxy)pyrimidine (55 mg, 75% yield) as a white powder. MS(ES): 417 [M+H]$^+$.

The following compound is prepared essentially according to the previous examples:

2-({-4-[1-(2-chlorophenyl)-3-(trifluoromethyl)-1H-pyrazol-5-yl]phenyl}oxy)pyrazine MS(ES): 417 [M+H]+.

Example 66

2-(3-(1-(2-chlorophenyl)-3-(trifluoromethyl)-1H-pyrazol-5-yl)phenoxy)acetic acid

Example 66a

Preparation of methyl 2-(3-(1-(2-chlorophenyl)-3-(trifluoromethyl)-1H-pyrazol-5-yl)phenoxy)acetate

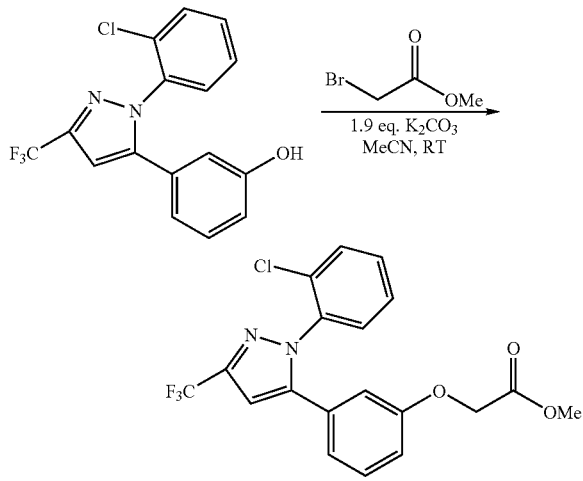

To a suspension of 3-(1-(2-chlorophenyl)-3-(trifluoromethyl)-1H-pyrazol-5-yl)phenol (229 mg, 0.68 mmol) and K$_2$CO$_3$ (179 mg, 1.3 mmol) in acetonitrile (3.0 mL) was added methyl bromoacetate (85 μL, 0.90 mmol). The suspension was stirred at ambient temperature for 16 hours at which time HPLC analysis showed conversion to a product with a slightly longer retention time. The reaction suspension was filtered through a plug of Celite that was then washed thoroughly with EtOAc. The filtrate was concentrated to afford a pale yellow oil. This material was further purified by flash column chromatography eluting with a gradient from 0% to 28% EtOAc/hexane to afford methyl 2-(3-(1-(2-chlorophenyl)-3-(trifluoromethyl)-1H-pyrazol-5-yl)phenoxy)acetate (158 mg, 57% yield) as an oil. MS(ES): 411 [M+H]+.

The following compounds are prepared essentially according to the previous examples:

2-({-4-[1-(2-chlorophenyl)-3-(trifluoromethyl)-1H-pyrazol-5-yl]phenyl}oxy)ethanol, MS(ES): 383 [M+H]+.

ethyl ({4'-[1-(2-chlorophenyl)-3-(1-hydroxy-1-methylethyl)-1H-pyrazol-5-yl]biphenyl-3-yl}oxy)acetate, MS(ES): 512 [M+Na]+.

2-({4-[1-(2-chlorophenyl)-3-(1-hydroxy-1-methylethyl)-1H-pyrazol-5-yl]biphenyl-3-yl}oxy)-N,N-diethylacetamide, MS(ES): 540 [M+Na]+.

4'-[1-(2-chlorophenyl)-3-(1-hydroxy-1-methylethyl)-1H-pyrazol-5-yl]biphenyl-3-yl (1-methylethyl)carbamate, MS(ES): 512 [M+Na]+.

Example 66b

Preparation of 2-(3-(1-(2-chlorophenyl)-3-(trifluoromethyl)-1H-pyrazol-5-yl)phenoxy)acetic acid

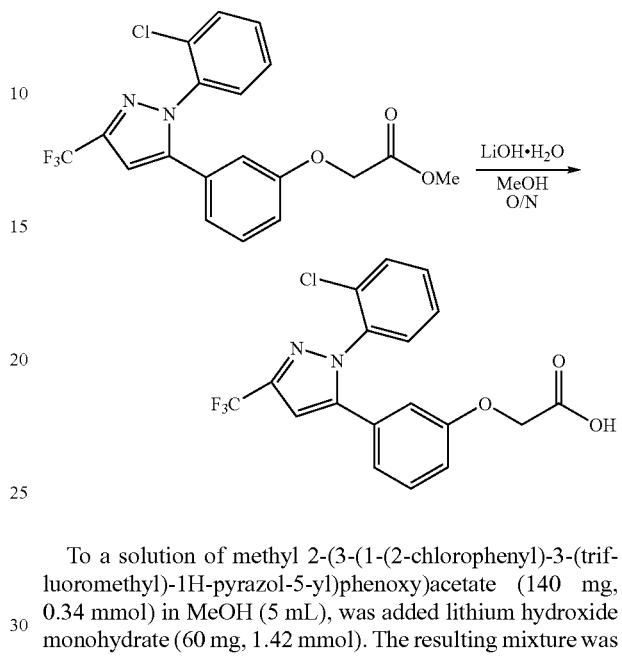

To a solution of methyl 2-(3-(1-(2-chlorophenyl)-3-(trifluoromethyl)-1H-pyrazol-5-yl)phenoxy)acetate (140 mg, 0.34 mmol) in MeOH (5 mL), was added lithium hydroxide monohydrate (60 mg, 1.42 mmol). The resulting mixture was stirred at ambient temperature for 18 hours. The reaction mixture was then concentrated under reduced pressure and the residue was taken up in CH$_2$Cl$_2$ and H$_2$O. The aqueous was made acidic by the addition of 1 N HCl. The layers were separated and the acidic aqueous was further extracted with CH$_2$Cl$_2$ (3×). The combined organic extracts were dried over Na$_2$SO$_4$, filtered, and concentrated under reduced pressure. This white solid was taken up in warm CH$_2$Cl$_2$ and hexane and the resulting solution was cooled in an ice bath. Filtration, washing with hexane and drying of the precipitated solids afforded 2-(3-(1-(2-chlorophenyl)-3-(trifluoromethyl)-1H-pyrazol-5-yl)phenoxy)acetic acid (69 mg, 51% yield) as a white solid. MS(ES): 397 [M+H]+.

The following compound is prepared essentially according to the previous examples:

({4-[1-(2-chlorophenyl)-3-(trifluoromethyl)-1H-pyrazol-5-yl]phenyl}oxy)acetic acid, MS(ES): 397 [M+H]+.

Example 67

Preparation of 4-(2-(3-(1-(2-chlorophenyl)-3-(trifluoromethyl)-1H-pyrazol-5-yl)phenoxy)-ethyl)morpholine

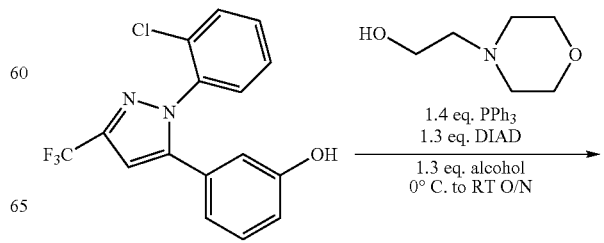

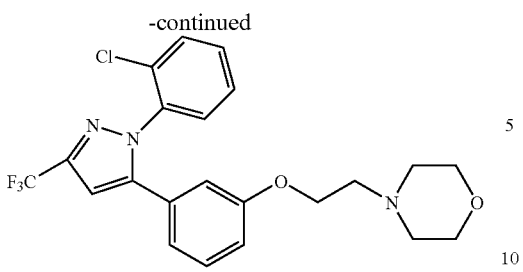

To a solution of 3-(1-(2-chlorophenyl)-3-(trifluoromethyl)-1H-pyrazol-5-yl)phenol (155 mg, 0.5 mmol) and triphenylphosphine (170 mg, 0.65 mmol) in THF (2 mL) was added 2-morpholinoethanol (72 μL, 0.59 mmol). The solution was cooled in an ice bath and treated with diisopropylazodicarboxylate (125 μL, 0.64 mmol). After a few minutes the ice bath was removed and the reaction was allowed to stir while warming to ambient temperature. After stirring for 16 hours LC/MS analysis showed desired product and triphenylphosphine oxide as the major peaks. The reaction solution was concentrated under reduced pressure and the resulting yellow oil was purified by flash column chromatography eluting with 30% followed by 40% EtOAc/hexane, and then a gradient of CH$_2$Cl$_2$ to 4% MeOH/CH$_2$Cl$_2$. The white solid that was obtained was found to be contaminated with triphenylphosphine oxide. This crude product was further purified by normal phase preparative HPLC eluting with a gradient from CH$_2$Cl$_2$ to 10% isopropanol/CH$_2$Cl$_2$ to afford 4-(2-(3-(1-(2-chlorophenyl)-3-(trifluoromethyl)-1H-pyrazol-5-yl)phenoxy)ethyl)morpholine (139 mg, 67% yield) as a thick syrup. MS(ES): 452 [M+H]$^+$.

The following compounds are prepared essentially according to the previous examples:

2-({3-[1-(2-chlorophenyl)-3-(trifluoromethyl)-1H-pyrazol-5-yl]phenyl}oxy)-N,N-dimethylethanamine. MS(ES): 410 [M+H]$^+$.

1-[2-({3-[1-(2-chlorophenyl)-3-(trifluoromethyl)-1H-pyrazol-5-yl]phenyl}oxy)ethyl]piperidine MS(ES): 450 [M+H]$^+$.

2-({4-[1-(2-chlorophenyl)-3-(trifluoromethyl)-1H-pyrazol-5-yl]phenyl}oxy)-N,N-dimethylethanamine, MS(ES): 410 [M+H]$^+$.

4-[2-({4-[1-(2-chlorophenyl)-3-(trifluoromethyl)-1H-pyrazol-5-yl]phenyl}oxy)ethyl]morpholine, MS(ES): 452 [M+H]$^+$.

1-[2-({4-[1-(2-chlorophenyl)-3-(trifluoromethyl)-1H-pyrazol-5-yl]phenyl}oxy)ethyl]piperidine, MS(ES): 450 [M+H]$^+$.

Example 68

1-(2-chlorophenyl)-5-(4-{[3-(methylsulfonyl)phenyl]oxy}phenyl)-3-(trifluoromethyl)-1H-pyrazole

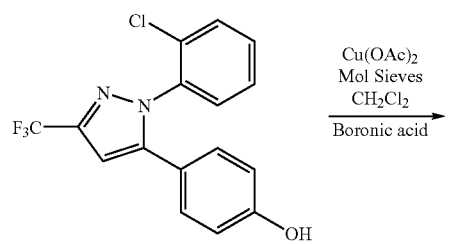

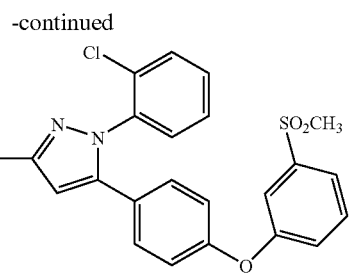

A mixture of 4-(1-(2-chlorophenyl)-3-(trifluoromethyl)-1H-pyrazol-5-yl)phenol (169 mg, 0.5 mmol), 3-methylsulfonylphenylboronic acid (200 mg, 1 mmol), Cu(OAc)$_2$ (181 mg, 1 mmol), and NEt$_3$ (35 μL, 2.5 mmol) and molecule sieves (4A) in DCM was shaken overnight at 20° C. Solid was removed by filtration and filtrate was evaporated to give a crude, which was purified by column chromatography on silica gel eluting with EtOAc-hexane (1:4 to 1:2) to afford 1-(2-chlorophenyl)-5-(4-{[3-(methylsulfonyl)phenyl]oxy}phenyl)-3-(trifluoromethyl)-1H-pyrazole (88 mg). $^1$H-NMR: CDCl3: 7.68 (m, 1H), 7.55 (m, 2H), 7.48 (m, 1H), 7.62-7.40 (m, 2H), 7.27 (m, 2H), 7.21 (m, 1H), 6.93 (m, 1H), 6.80 (s, 1H), 3.04 (s, 3H), MS(ES): 493 [M+H]$^+$.

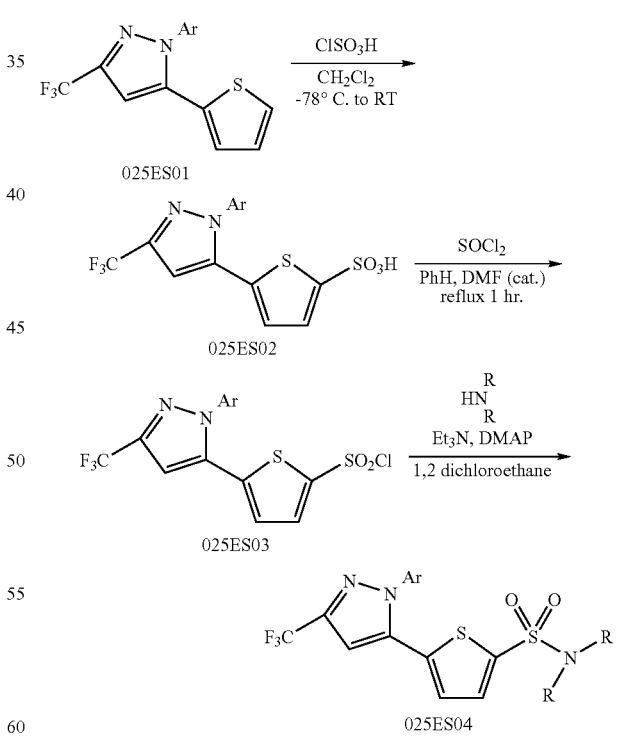

Scheme 25

As depicted in Scheme 25, aminosulfonyl groups can be introduced to the thiophene ring. Thiophene pyrazoles 025ES01 (Prepared in a manner similar to Example 2c) can be sulfonated by the action of chlorosulfonic acid to afford sulfonic acids 025ES02. Conversion to the sulfonyl chlorides 025ES03 followed by derivatization with amines under basic conditions affords sulfonamides 0025ES04.

Example 69

1-(5-(1-(2-chlorophenyl)-3-(trifluoromethyl)-1H-pyrazol-5-yl)thiophen-2-ylsulfonyl)-4-methylpiperazine

Example 69a

Preparation of 5-(1-(2-chlorophenyl)-3-(trifluoromethyl)-1H-pyrazol-5-yl)thiophene-2-sulfonic acid

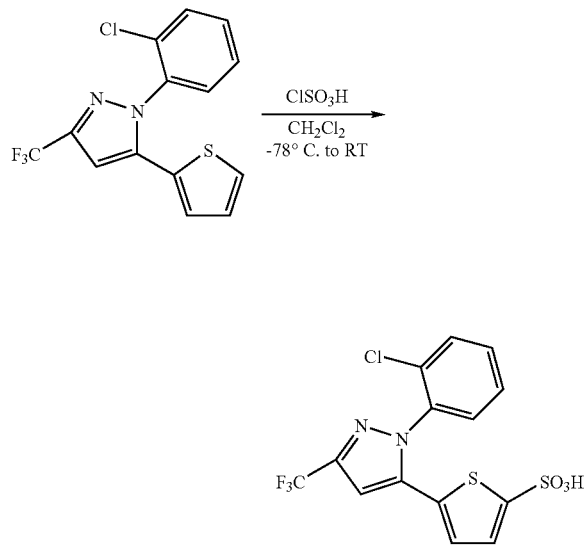

Chlorosulfonic acid (1.0 mL, 15 mmol) was added dropwise to a cold (−78° C.) solution of 1-(2-chlorophenyl)-5-(thiophen-2-yl)-3-(trifluoromethyl)-1H-pyrazole (1.0 g, 3.2 mmol) in CH$_2$Cl$_2$ (22 mL) After 75 minutes stirring at −78° C. the cooling bath was removed and the brown solution was allowed to warm to ambient temperature. After 3½ hours stirring at ambient temperature, the reaction mixture was poured onto ice and diluted with CH$_2$Cl$_2$. The milky lower organic phase was separated and dried over Na$_2$SO$_4$. Filtration and concentration under reduced pressure of the organics gave a biphasic mixture that was further pumped down under high vacuum. NMR and GC/MS analysis of this material showed it not to be the product. The aqueous phase from the workup was saturated with Na$_2$SO$_4$ and extracted with EtOAc (3×). These organic extract were dried over Na$_2$SO$_4$, filtered and concentrated under reduced pressure to afford 5-(1-(2-chlorophenyl)-3-(trifluoromethyl)-1H-pyrazol-5-yl)thiophene-2-sulfonic acid as a yellow syrup. This crude material was carried on to the sulfonyl chloride formation without purification. MS(ES): 409[M+H]$^+$.

Example 69b

Preparation of 5-(1-(2-chlorophenyl)-3-(trifluoromethyl)-1H-pyrazol-5-yl)thiophene-2-sulfonyl chloride

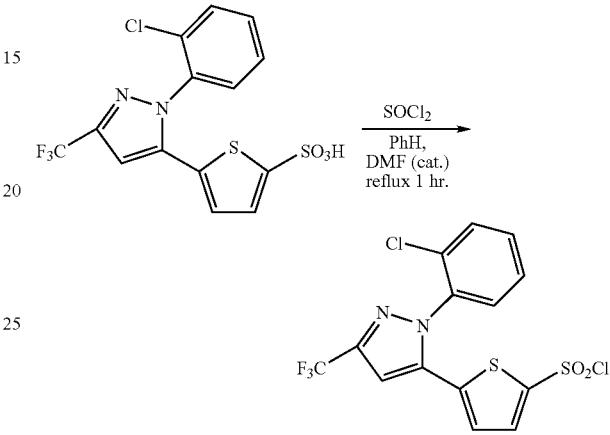

5-(1-(2-Chlorophenyl)-3-(trifluoromethyl)-1H-pyrazol-5-yl)thiophene-2-sulfonic acid (~3.2 mmol from previous step) was combined with benzene (5.0 mL) in a reaction vial. This mixture was treated with thionyl chloride (5.0 mL, 69 mmol) and a catalytic amount of dimethylformamide (0.1 mL). The reaction was then heated to reflux in an oil bath. After refluxing for 1 hour the reaction mixture was concentrated under reduced pressure to afford a yellow oil that partially solidified under reduced pressure. This crude material was purified by flash column chromatography eluting with a gradient from 10% to 30% EtOAc/hexane. Product-containing fractions were collected and concentrated to afford 5-(1-(2-chlorophenyl)-3-(trifluoromethyl)-1H-pyrazol-5-yl)thiophene-2-sulfonyl chloride as a pale yellow oil. The mostly pure material was carried on to subsequent transformations without further purification.

Example 69c

Preparation of 1-(5-(1-(2-chlorophenyl)-3-(trifluoromethyl)-1H-pyrazol-5-yl)thiophen-2-ylsulfonyl)-4-methylpiperazine

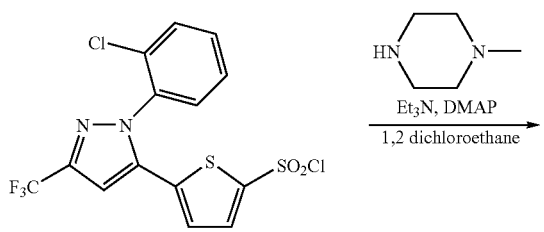

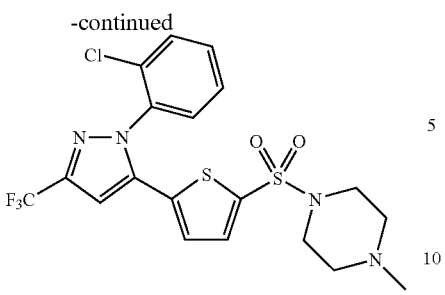

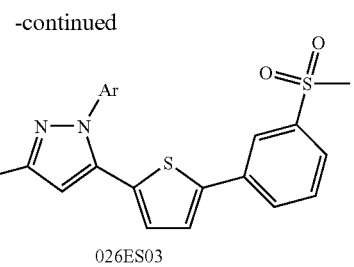

Triethylamine (0.15 mL, 1.1 mmol) and a small amount of DMAP were dissolved in 1,2-dichloroethane (2 mL) in a reaction vial. This solution was treated with 1-methyl piperazine (50 µL, 0.45 mmol) followed by 5-(1-(2-chlorophenyl)-3-(trifluoromethyl)-1H-pyrazol-5-yl)thiophene-2-sulfonyl chloride (145 mg, 0.34 mmol) as a solution in 1,2-dichloroethane (1 mL). After stirring 4½ hours at ambient temperature the reaction was quenched by dilution with CH$_2$Cl$_2$ and water. Saturated NaHCO$_3$ was added and the basic aqueous was extracted with CH$_2$Cl$_2$ (3×). The combined organic extracts were dried over Na$_2$SO$_4$, filtered and concentrated under reduced pressure to afford crude product as a pale yellow oil. This crude product was purified by flash column chromatography eluting with a gradient from CH$_2$Cl$_2$ to 16% acetonitrile/CH$_2$Cl$_2$ to afford 1-(5-(1-(2-chlorophenyl)-3-(trifluoromethyl)-1H-pyrazol-5-yl)thiophen-2-ylsulfonyl)-4-methylpiperazine (90.5 mg, 54% yield) as a brittle white foam. MS(ES): 491 [M+H]$^+$.

The following compound is prepared essentially according to the previous examples:
1-({5-[1-(2-chlorophenyl)-3-(trifluoromethyl)-1H-pyrazol-5-yl]-2-thienyl}sulfonyl)piperidine MS(ES): 476[M+H]$^+$.

As depicted in Scheme 26, pyrazole-carboxylic acid can be transformed into pyrazole-amides. Carboxylic acid 0026ES01 (prepared in a manner similar to Example 2c) can be converted to its corresponding acid chloride 026ES02 by the action of oxalyl chloride. Reaction with various amines under basic conditions leads to the corresponding amides 026ES03.

Example 70

Methyl 1-{[1-(2-chlorophenyl)-5-{5-[3-(methylsulfonyl)phenyl]-2-thienyl}-1H-pyrazol-3-yl]carbonyl}piperidine-4-carboxylate Example 70a Preparation of 1-(2-chlorophenyl)-5-(5-(3-(methylsulfonyl)phenyl)thiophen-2-yl)-1H-pyrazole-3-carbonyl chloride

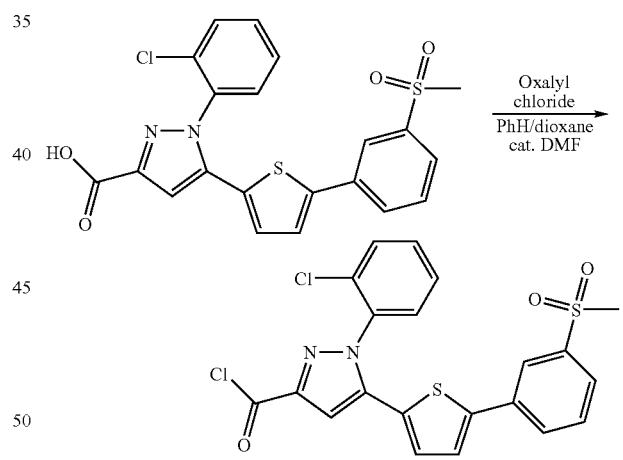

To a suspension of 1-(2-chlorophenyl)-5-(5-(3-(methylsulfonyl)phenyl)thiophen-2-yl)-1H-pyrazole-3-carboxylic acid (160 mg, 0.35 mmol) in PhH (1.0 mL) was added a small amount of DMF. Oxalyl chloride (60 µL, 0.69 mmol) was added to the suspension. After stirring for 15 minutes at ambient temperature, gas evolution had ceased and only part of the solids had dissolved. After 25 minutes dioxane (2.0 mL) was added. There was renewed gas evolution and most of the solids dissolved. After 30 minutes additional oxalyl chloride (50 µL, 0.57 mmol) was added. There was vigorous gas evolution and after a total of 90 minutes stirring the reaction mixture was concentrated under reduced pressure to afford 1-(2-chlorophenyl)-5-(5-(3-(methylsulfonyl)phenyl)thiophen-2-yl)-1H-pyrazole-3-carbonyl chloride as a pale Scheme 26

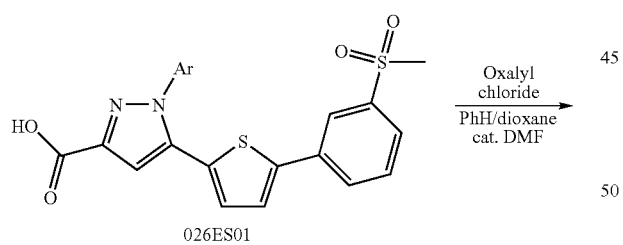

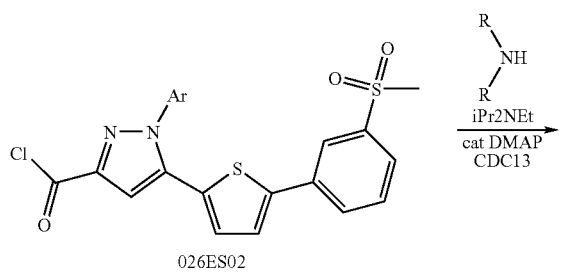

Example 70b

Preparation of methyl 1-{[1-(2-chlorophenyl)-5-{5-[3-(methylsulfonyl)phenyl]-2-thienyl}-1H-pyrazol-3-yl]carbonyl}piperidine-4-carboxylate

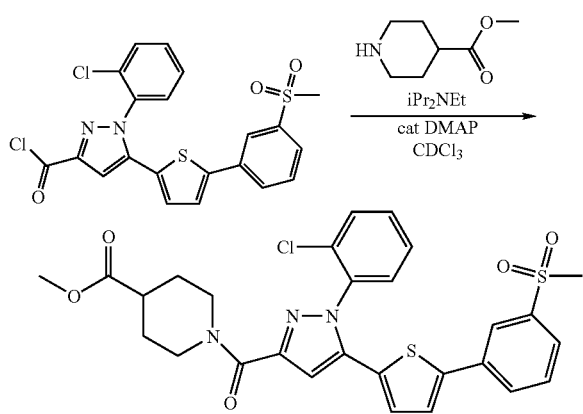

To a solution of 1-(2-chlorophenyl)-5-(5-(3-(methylsulfonyl)phenyl)thiophen-2-yl)-1H-pyrazole-3-carbonyl chloride (0.23 mmol crude from previous step) in CDCl$_3$ (12 ml) was added N,N-diisopropylethylamine (150 μL, 0.86 mmol) and a small amount of DMAP. The resulting mixture was treated with methyl isonipecotate (62 μL, 0.46 mmol). After stirring for 3 hours at ambient temperature the reaction was quenched by dilution with H2O, and dilution with CH$_2$Cl$_2$. The layers were separated and the basic aqueous layer was extracted with CH$_2$Cl$_2$. The combined organic extracts were dried over Na$_2$SO$_4$, filtered and concentrated under reduced pressure to afford crude product. This material was purified by flash column chromatography eluting with a gradient from 0% to 16% MeCN in CH$_2$Cl$_2$ to afford methyl 1-{[1-(2-chlorophenyl)-5-{5-[3-(methylsulfonyl)phenyl]-2-thienyl}-1H-pyrazol-3-yl]carbonyl}piperidine-4-carboxylate (11 mg, 8% yield) as a white powder. MS(ES): 584 [M+H]$^+$.

The following compounds are prepared essentially according to the previous examples:

1-(2-chlorophenyl)-5-{5-[3-(methylsulfonyl)phenyl]-2-thienyl}-N-piperidin-1-yl-1H-pyrazole-3-carboxamide, MS(ES): 541.3 [M+H]$^+$.

1-(2-chlorophenyl)-5-{5-[3-(methylsulfonyl)phenyl]-2-thienyl}-3-(pyrrolidin-1-ylcarbonyl)-1H pyrazole, MS(ES): 512 [M+H]$^+$.

1-{[1-(2-chlorophenyl)-5-{5-[3-(methylsulfonyl)phenyl]-2-thienyl}-1H-pyrazol-3-yl]carbonyl}-4-methylpiperidine, MS(ES): 540 [M+H]$^+$.

1-{[1-(2-chlorophenyl)-5-{5-[3-(methylsulfonyl)phenyl]-2-thienyl}-1H-pyrazol-3-yl]carbonyl}-4-methylpiperazine, (ES): 541 [M+H]$^+$.

1-(2-chlorophenyl)-5-{5-[3-(methylsulfonyl)phenyl]-2-thienyl}-N-[3-(trifluoromethyl)phenyl]-1H-pyrazole-3-carboxamide, MS(ES): 602 [M+H]$^+$.

5-[3-chloro-3'-(methylsulfonyl)biphenyl-4-yl]-1-(2,6-dichlorophenyl)-N-(2,2,2-trifluoroethyl)-1H-pyrazole-3-carboxamide MS(ES): 604 [M+H]$^+$.

5-[3-chloro-3'-(methylsulfonyl)biphenyl-4-yl]-N-(2,2,2-trifluoroethyl)-1-[2-(trifluoromethyl)pyridin-3-yl]-1H-pyrazole-3-carboxamide MS(ES): 603 [M+H]$^+$.

4-chloro-5-[3-chloro-3'-(methylsulfonyl)biphenyl-4-yl]-N-(2,2,2-trifluoroethyl)-1-[2-(trifluoromethyl)pyridin-3-yl]-1H-pyrazole-3-carboxamide MS(ES): 637 [M+H]$^+$.

5-[3-chloro-3'-(methylsulfonyl)biphenyl-4-yl]-1-(2,6-dichlorophenyl)-N-(2-hydroxy-1,1-dimethylethyl)-1H-pyrazole-3-carboxamide MS(ES): 592 [M+H]$^+$.

5-[3-chloro-3'-(methylsulfonyl)biphenyl-4-yl]-1-(2,6-dichlorophenyl)-N-(1,1-dimethylethyl)-1H-pyrazole-3-carboxamide MS(ES): 578 [M+H]$^+$.

5-[3-chloro-3'-(methylsulfonyl)biphenyl-4-yl]-N-cyclopropyl-1-(2,6-dichlorophenyl)-1H-pyrazole-3-carboxamide MS(ES): 560 [M+H]$^+$.

5-[3-chloro-3'-(methylsulfonyl)biphenyl-4-yl]-N-cyclobutyl-1-(2,6-dichlorophenyl)-1H-pyrazole-3-carboxamide MS(ES): 576 [M+H]$^+$.

5-[3-chloro-3'-(methylsulfonyl)biphenyl-4-yl]-N-cyclopentyl-1-(2,6-dichlorophenyl)-1H-pyrazole-3-carboxamide MS(ES): 590 [M+H]$^+$.

Scheme 27

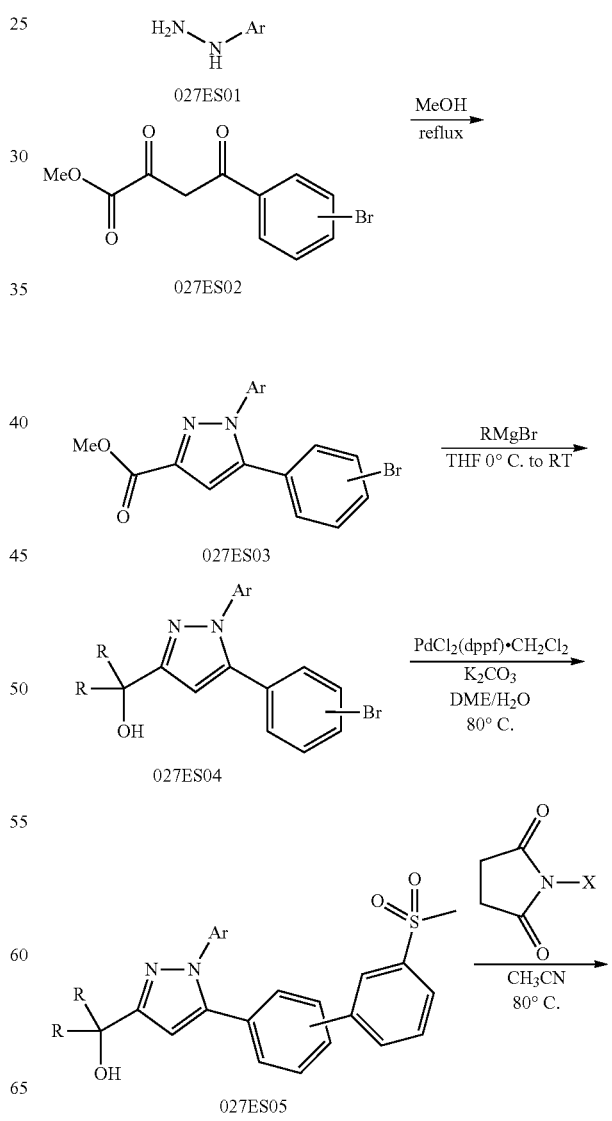

-continued

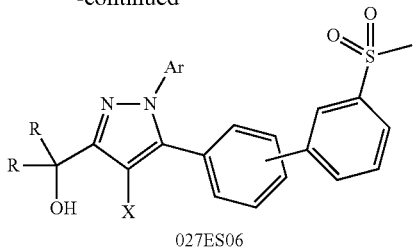

027ES06

As depicted in Scheme 27, biphenylpyrazoles can be prepared starting from the condensation of a hydrazine with a diketo ester and can be chlorinated on the pyrazole ring. Hydrazines 027ES01 can be condensed with diketones 027ES02 as in Example 2c to afford pyrazoles 027ES03. The ester functionality of 027ES03 can then be converted to a tertiary alcohol 027ES04 by the action of alkylmagnesium halides in a manner similar to Example 5. The resulting aryl bromide can then be coupled to a boronic acid under palladium catalyzed coupling conditions similar to those in Example 1c to afford biaryls 027ES05. The pyrazole nucleus of 027ES05 can then be halogenated by treatment with NBS or NCS to afford the halo-pyrazoles 027ES06.

Example 71

2-(5-(3'-(Methylsulfonyl)biphenyl-4-yl)-1-(2-(trifluoromethyl)phenyl)-1H-pyrazol-3-yl)propan-2-ol

Example 71a

Preparation of 2-(5-(4-bromophenyl)-1-(2-(trifluoromethyl)phenyl)-1H-pyrazol-3-yl)propan-2-ol

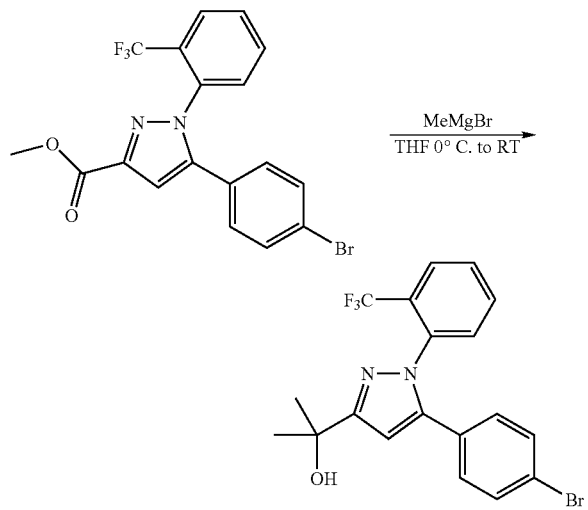

To a suspension of methyl 5-(4-bromophenyl)-1-(2-(trifluoromethyl)phenyl)-1H-pyrazole-3-carboxylate (393 mg, 0.9 mmol) in dry toluene (9 mL) stirred at ambient temperature was added methylmagnesium bromide (1.4 mL of a 3.0M solution in ether, 4.2 mmol) dropwise. After 2¼ hours stirring at ambient temperature the reaction mixture was quenched by the addition of saturated ammonium chloride and EtOAc. The aqueous layer was extracted with EtOAc (3×). The combined organic extract were dried over Na₂SO₄, filtered and concentrated under reduced pressure to afford 2-(5-(4-bromophenyl)-1-(2-(trifluoromethyl)phenyl)-1H-pyrazol-3-yl)propan-2-ol as an orange-yellow oil, which was carried on to the subsequent step. GC/MS (EI, =426 [M⁺]

Example 71b

Preparation of 2-(5-(3'-(methylsulfonyl)biphenyl-4-yl)-1-(2-(trifluoromethyl)phenyl)-1H-pyrazol-3-yl)propan-2-ol

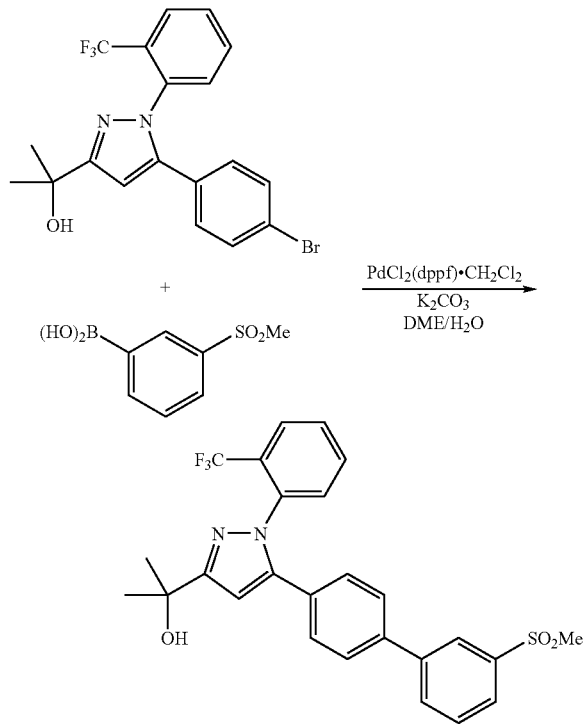

To a solution of 2-(5-(4-bromophenyl)-1-(2-(trifluoromethyl)phenyl)-1H-pyrazol-3-yl)propan-2-ol (115 mg, 0.27 mmol) and 3-(methylsulfonyl)phenylboronic acid (66 mg, 033 mmol) in 1,2-dimethoxyethane (1.5 mL) was added K₂CO₃ (110 mg, 0.80 mmol) and H₂O (1.5 mL). The resulting biphasic suspension was stirred at ambient temperature and sparged with nitrogen for 10 minutes. The reaction was then treated with dichloro[1,1'-bis(diphenylphosphino)ferrocene] palladium (11) dichloromethane adduct (15 mg, 18 μmol) and heated to 80° C. in an oil bath. The reaction was heated at 80° C. for three hours and then allowed to cool to ambient temperature overnight. The cooled reaction mixture was diluted with EtOAc and H₂O. The aqueous layer was extracted with EtOAc (3×). The combined organic extracts were washed with brine, dried over Na₂SO₄, filtered and concentrated to afford crude product as a dark oil. The crude product was purified by flash-column chromatography eluting with a gradient from 10% to 100% EtOAc/hexane to afford 2-(5-(3'-(methylsulfonyl)biphenyl-4-yl)-1-(2-(trifluoromethyl)phenyl)-1H-pyrazol-3-yl)propan-2-ol (122 mg, 90% yield) as an off-white powder. MS(ES): 501 [M+H]⁺.

The following compounds are prepared essentially according to the previous examples:

2-{5-[3'-(methylsulfonyl)biphenyl-4-yl]-1-[3-(trifluorom-
ethyl)pyridin-2-yl]-1H-pyrazol-3-yl}propan-2-ol,
MS(ES): 502 [M+H]+.
2-{1-(2-chlorophenyl)-5-[3'-(methylsulfonyl)biphenyl-4-
yl]-1H-pyrazol-3-yl}propan-2-ol, MS(ES): 467 [M+H]+.
4'-[1-(2-chlorophenyl)-3-(1-hydroxy-1-methylethyl)-1H-
pyrazol-5-yl]-N-(1-methylethyl)biphenyl-3-carboxamide,
MS(ES): 474 [M+H]+.
4'-[1-(2-chlorophenyl)-3-(1-hydroxy-1-methylethyl)-1H-
pyrazol-5-yl]-N-[2-(dimethylamino)ethyl]biphenyl-3-
carboxamide, MS(ES): 503 [M+H]+.
2-{1-(2-chlorophenyl)-5-[4'-(ethylsulfonyl)biphenyl-4-yl]-
1H-pyrazol-3-yl}propan-2-ol, MS(ES): 481 [M+H]+.
2-{1-(2-chlorophenyl)-5-[3-methyl-3'-(methylsulfonyl)bi-
phenyl-4-yl]-1H-pyrazol-3-yl}propan-2-ol MS(ES): 481
[M+H]+.
2-{1-(2-chlorophenyl)-5-[3-fluoro-3'-(methylsulfonyl)bi-
phenyl-4-yl]-1H-pyrazol-3-yl}propan-2-ol MS(ES): 485
[M+H]+.
2-{5-[3-chloro-3'-(methylsulfonyl)biphenyl-4-yl]-1-(2-
chlorophenyl)-1H-pyrazol-3-yl}propan-2-ol MS(ES): 501
[M+H]+.
1-(5-{4-[1-(2-chlorophenyl)-3-(1-hydroxy-1-methylethyl)-
1H-pyrazol-5-yl]phenyl}-2-thienyl)ethanone MS(ES):
419 (M-OH)
5-{4-[1-(2-chlorophenyl)-3-(1-hydroxy-1-methylethyl)-1H-
pyrazol-5-yl]phenyl}thiophene-2-carbaldehyde, MS(ES):
405 (M-OH)
2-[1-(2-chlorophenyl)-5-{4-[2-(methyloxy)pyrimidin-5-yl]
phenyl}-1H-pyrazol-3-yl]propan-2-ol, MS(ES): 421
[M+H]+

Example 72

2-[1-(2-chlorophenyl)-5-{4-[3-(methylsulfonyl)phe-
nyl]furan-2-yl}-1H-pyrazol-3-yl]propan-2-ol Example 72a Preparation of 4-bromo-furan-2-carboxylic acid

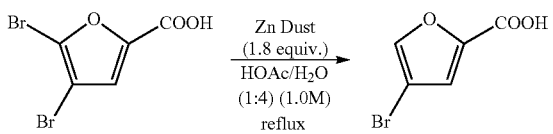

A 500 mL three-necked round-bottom flask fitted with an overhead mechanical stirrer and reflux condenser was charged with 4,5-dibromo-furan-2-carboxylic acid (57.0 g, 211 mmol), H₂O (168 mL), and HOAc (42 mL). The third neck of the flask was stoppered and the suspension was heated to reflux with a temperature controlled heating mantle held at 125-130° C. Zn dust (24.9 g, 381 mmol) (previously ground in a mortar and pestle to break up lumps) was added portionwise over 50 minutes. Subsequent portions are added after most of the previously added portion has disappeared. After the first portions of the Zn were added, all of the 4,5-dibromofuran-2-carboxylic acid dissolves to give a pale brown solution. Twenty-five minutes after the conclusion of the zinc addition a thick grey-white slurry had formed. HPLC analysis of the reaction slurry at this time indicated complete consumption of the starting 4,5-dibromofuran-2-carboxylic acid and conversion to the desired product. After 35 minutes, heating was discontinued, and the slurry was allowed to cool to ambient temperature. After cooling to ambient temperature the reaction slurry was diluted with cold H₂O (175 mL), cooled in an ice bath, and then filtered. The white and grey solids were rinsed with cold H₂O, and dried on the filter for 3 hours. The product/Zn mixture was then pumped down under high vacuum with gentle heating to afford white-grey flakes. A portion of the resulting solids (37.3 g) was dissolved in warm acetone (1.8 L, solubility about 20 g/L). The resulting solution was filtered to remove residual zinc dust, and then concentrated under reduced pressure to afford 4-bromo-furan-2-carboxylic acid as a white powder. This material was carried on to the acid chloride formation without purification. ¹H-NMR (400 MHz, DMSO-d₆): δ 7.96 (1H, d, J=0.8 Hz), 7.04 (1H, d, J=0.8 Hz).

Example 72b

Preparation of 4-bromofuran-2-carbonyl chloride

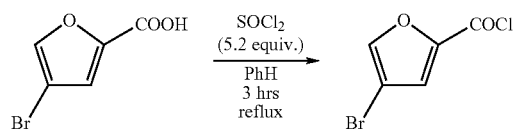 [SMILES: O=C(O)c1cc(Br)co1 ; O=C(Cl)c1cc(Br)co1]

The crude 4-bromo-furan-2-carboxylic acid (30 g, 157 mmol) was placed in a 500 mL round bottom flask equipped with a magnetic stirring bar and a reflux condenser, and the flask was alternately evacuated and filled with nitrogen several times. The solids were suspended in benzene (400 mL), treated with SOCl₂ (60 mL, 823 mmol) and the mixture was heated to reflux in a heating mantle. Dark tarry materials form on the walls of the reaction flask during the course of the reaction. After ~135 minutes at reflux a sample of the reaction was concentrated under reduced pressure and analyzed by ¹³C NMR. The NMR was quite clean and showed the reaction to be complete. [¹³C-NMR (400 MHz, CDCl₃): δ 154.9, 147.6, 146.3, 126.0, 102.5] After ~3 hours at reflux the reaction mixture was allowed to cool to ambient temperature. The pale brown supernatant solution of the acid chloride was decanted from the dark solids, and the solids were rinsed with additional benzene. The benzene solutions were combined and concentrated under reduced pressure to afford 4-bromo-furan-2-carbonyl chloride as a pale brown oil. This crude material was carried on to the amide formation without purification.

Example 72c

Preparation of 4-bromo-furan-2-carboxylic acid methoxy-methyl-amide

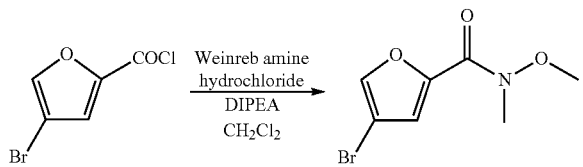

The crude 4-bromofuran-2-carbonyl chloride (157 mmol theoretical) was dissolved in CH₂Cl₂ (500 mL) in a 1 L round bottomed flask. The flask was immersed in an ice bath and N,O-dimethyl-hydroxylamine hydrochloride (19.5 g, 200 mmol) was added. The cold suspension was then treated with N,N-diisopropylethylamine (75 mL, 430 mmol), and a small amount of 4-(N,N-dimethylamino)pyridine (catalytic). Several minutes after the addition of the 4-(N,N-dimethylamino) pyridine the ice bath was removed and the pale orange solution was allowed to warm to ambient temperature. After standing at ambient temperature for ~16 hours the pale brown reaction mixture was quenched with water (100 mL) and diluted with CH$_2$Cl$_2$ (500 mL). The layers were separated and the organic layer was washed with 1N HCl (2×100 mL), H$_2$O (100 mL), and saturated NaHCO$_3$ (50 mL). The organics were dried over Na$_2$SO$_4$, filtered, and concentrated under reduced pressure to afford 4-bromo-furan-2-carboxylic acid methoxy-methyl-amide (25.7 g, 70% yield from crude acid) as a pale brown solid. 1H NMR of the material showed it to be very clean. $^1$H-NMR (400 MHz, CDCl$_3$): δ 7.60 (1H, d, J=0.8 Hz), 7.14 (1H, d, J=0.8 Hz), 3.77 (3H, s), 3.35 (3H, s).

Example 72d

Preparation of 1-(4-bromo-furan-2-yl)-ethanone

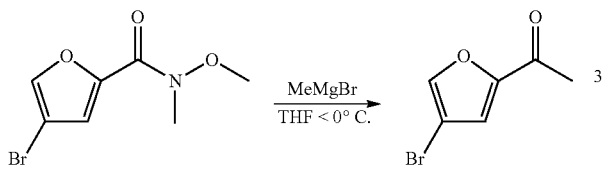

A solution of 4-bromo-furan-2-carboxylic acid methoxy-methyl-amide (27.5 g, 117 mmol) in THF (350 mL) was prepared and cooled in an ice-salt bath (<0° C.) to this solution was added methylmagnesium bromide (51 mL of a 3.0 M solution in Et$_2$O, 153 mmol) slowly so as to maintain the temperature below 0° C. The resulting off-white/brown suspension was stirred at ~-10° C. TLC analysis of an NH$_4$Cl-quenched aliquot after 1 hour showed no starting amide present. After 75 minutes at -10° C. the reaction was quenched by the addition of saturated aqueous NH$_4$Cl (100 mL). Additional H$_2$O was added followed by 3N aqueous HCl (~40 mL) to dissolve the solids. The resulting biphasic solution was concentrated on the rotary evaporator to remove most of the THF. The resulting aqueous slurry was diluted with Et$_2$O, and 3N aqueous HCl was added to bring the pH <7. The layers were separated and the aqueous layer was extracted with Et$_2$O (3×100 mL). The combined organic layers were washed with saturated aqueous NaHCO$_3$, brine, dried over Na$_2$SO$_4$, filtered and concentrated under reduced pressure to afford 1-(4-bromo-furan-2-yl)-ethanone (20.4 g, 92% yield) as a pale brown solid. $^1$H-NMR (400 MHz, CDCl$_3$): δ 7.58 (1H, d, J=0.8 Hz), 7.18 (1H, d, J=0.8 Hz), 2.47 (3H, s).

The following compounds are prepared essentially according to the previous examples:

methyl 1-(2-chlorophenyl)-5-{4-[3-(methylsulfonyl)phenyl]furan-2-yl}-1H-pyrazole-3-carboxylate, MS(ES): 457 [M+H]$^+$.

2-[1-(2-chlorophenyl)-5-{4-[3-(methylsulfonyl)phenyl]furan-2-yl}-1H-pyrazol-3-yl]propan-2-ol, MS(ES): 457 [M+H]$^+$.

2-[1-(2-chlorophenyl)-5-{4-[3-(methylsulfonyl)phenyl]-2-thienyl}-1H-pyrazol-3-yl]propan-2-ol, MS(ES): 473 [M+H]$^+$ Scheme 28

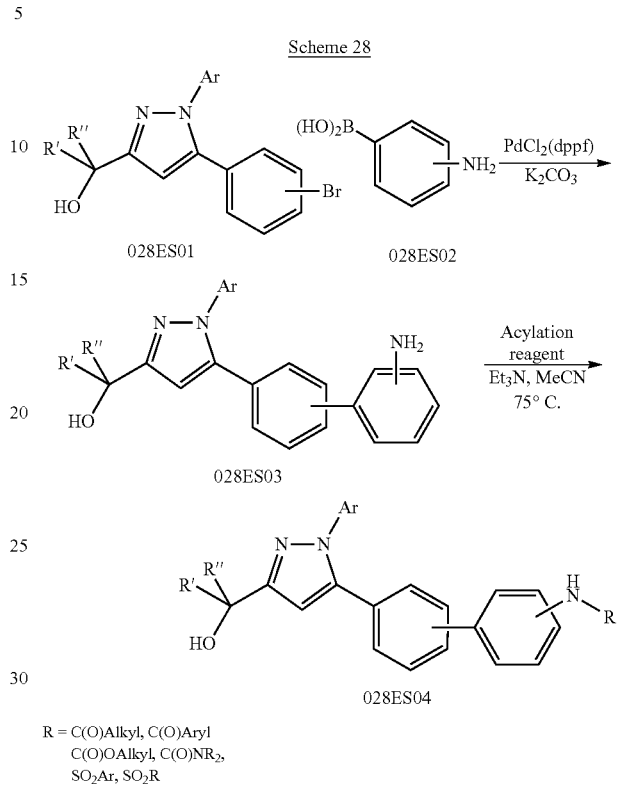

R = C(O)Alkyl, C(O)Aryl
C(O)OAlkyl, C(O)NR$_2$,
SO$_2$Ar, SO$_2$R

As depicted in Scheme 28, amides and sulfonamides can be prepared via acylation of a free amino groups. Carbinols 028ES01 (prepared in a manner similar to Example 5) can be coupled under palladium-catalyzed coupling conditions similar to Example 1c with aminophenyl boronic acids to afford amino biaryls 028ES03. The amine functionality of these can then be further derivatized under basic conditions to afford acylated or sulfonylated derivatives 028ES04.

Example 73

Preparation of N-(4'-(1-(2-chlorophenyl)-3-(2-hydroxypropan-2-yl)-1H-pyrazol-5-yl)biphenyl-3-yl)acetamide

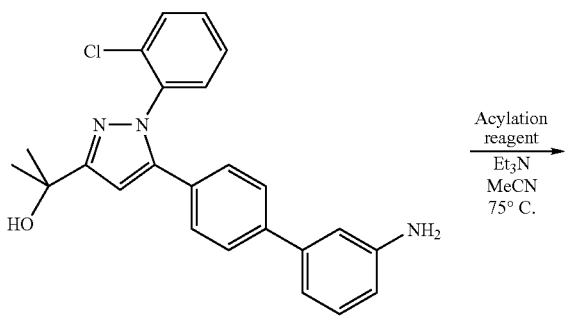

-continued

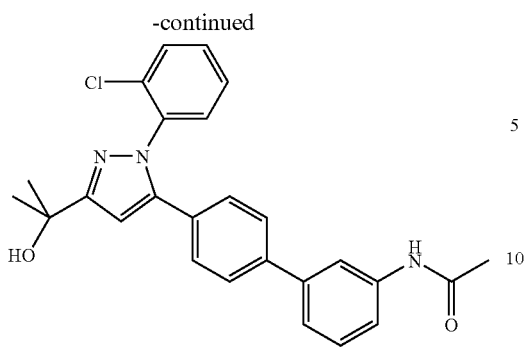

To a solution of 2-(5-(3'-aminobiphenyl-4-yl)-1-(2-chlorophenyl)-1H-pyrazol-3-yl)propan-2-ol (370 mg, 037 mmol) in acetonitrile (1.6 mL) was added triethylamine (0.12 mL, 0.86 mmol) followed by acetyl chloride (27 μL, 380 μmol). The reaction vial was then shaken at 75° C. overnight. After cooling the reaction solution was concentrated under reduced pressure and the crude product was purified by flash column chromatography eluting with a gradient from 0% to 100% EtOAc/hexane to afford N-(4'-(1-(2-chlorophenyl)-3-(2-hydroxypropan-2-yl)-1H-pyrazol-5-yl)biphenyl-3-yl)acetamide (82 mg, 49% yield) as an oil. $^1$H NMR (400 MHz CDCl$_3$): δ 7.79 (1H, s), 7.49-7.42 (4H, m), 7.41-732 (4H, m), 7.31-7.21 (3H, m), 6.54 (1H, s), 2.68 (1H, s), 2.19 (3H, s), 1.69 (6H, s). MS(ES): 445[M+H]$^+$. The following compounds are prepared essentially according to the previous examples:

N-{4'-[1-(2-chlorophenyl)-3-(1-hydroxy-1-methylethyl)-1H-pyrazol-5-yl]biphenyl-3-yl}methanesulfonamide MS(ES): 482 [M+H]$^+$.

N-{4'-[1-(2-chlorophenyl)-3-(1-hydroxy-1-methylethyl)-1H-pyrazol-5-yl]biphenyl-3-yl}-1,1,1-trifluoromethanesulfonamide MS(ES): 535 [M+H]$^+$.

Example 74

2-(5-(5-(3-(methylsulfonyl)phenyl)thiophen-2-yl)-1-(pyridin-4-yl)-1H-pyrazol-3-yl)propan-2-ol Example 74a Preparation of methyl 4-(5-bromothiophen-2-yl)-4-oxo-2-(2-(pyridin-4-yl)hydrazono)butanoate

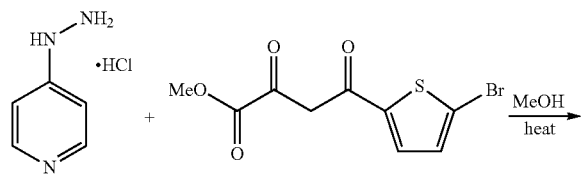

-continued

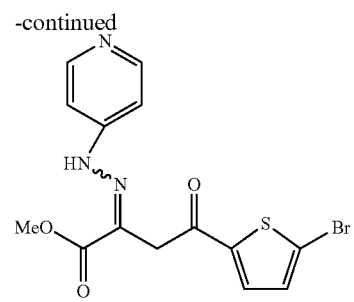

4-Hydrazinopyridine hydrochloride (366 mg, 2.51 mmol) and methyl 4-(5-bromothiophen-2-yl)-2,4-dioxobutanoate (724 mg, 2.5 mmol) were suspended in MeOH (12 mL) and heated to reflux to afford a yellow solution. After refluxing for 24 hours the reaction was allowed to cool to ambient temperature and was concentrated under reduced pressure to afford an orange oil. LC/MS analysis showed it to be a mixture of two isomers of the hydrazone with a small amount of cyclized pyrazole present. This material was carried on the dehydrative cyclization to prepare the cyclized pyrazole. MS(ES): 384 [M+H]$^+$.

Example 74b

Preparation of methyl 5-(5-(3-(methylsulfonyl)phenyl)thiophen-2-yl)-1-(pyridin-4-yl)-1H-pyrazole-3-carboxylate

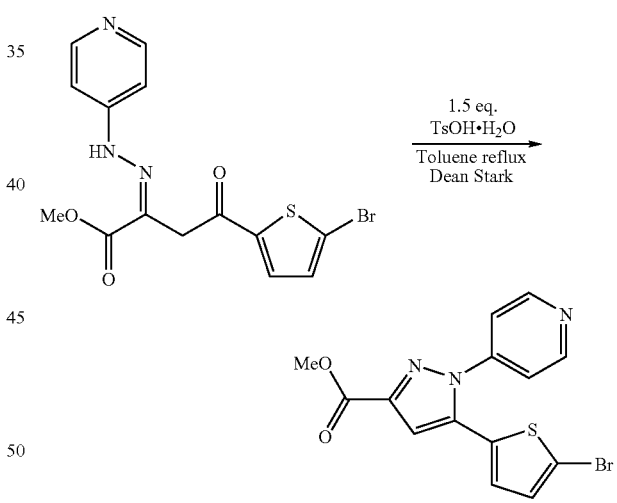

The crude (E-Z)-methyl 4-(5-bromothiophen-2-yl)-4-oxo-2-(2-(pyridin-4-yl)hydrazono)-butanoate (2.5 mmol from previous step) was suspended in toluene (40 mL), treated with p-toluenesulfonic acid monohydrate (735 mg, 3.9 mmol) and heated to reflux under a Dean-Stark water separator overnight. LC/MS analysis at this time showed two regioisomers of the cyclized pyrazole product. The reaction was cooled and diluted with EtOAc, H$_2$O, and basified by careful addition of solid Na$_2$CO$_3$. The basic aqueous was extracted with EtOAc (3×), and the combined organic extracts were washed with water, brine, dried over Na$_2$SO$_4$, filtered and concentrated under reduced pressure to afford an orange film. This material was purified by flash column chromatography eluting with a gradient from 0% to 100% EtOAc/hexane to afford a mixture of two isomeric pyrazoles. This mixture was carried on to the Suzuki coupling with no further purification.

Example 74e

Preparation of methyl 5-(5-(3-(methylsulfonyl)phenyl)thiophen-2-yl)-1-(pyridin-4-yl)-1H-pyrazole-3-carboxylate

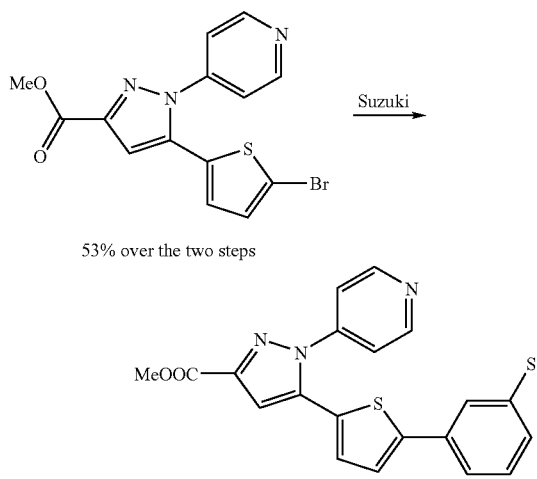

53% over the two steps

A mixture of methyl 5-(5-bromothiophen-2-yl)-1-(pyridin-4-yl)-1H-pyrazole-3-carboxylate (480 mg, 1.3 mmol) and 3-(methylsulfonyl)phenylboronic acid (390 mg, 1.9 mmol) was suspended in THF (6 mL) with Na$_2$CO$_3$ (1.0 mL of a 2M aqueous solution, 2.0 mmol). The mixture was sparged with nitrogen for ~10 minutes, treated with Pd(PPh$_3$)$_4$ (54 mg, 47 mol), and heated to 65° C. After 4 hours at 65° C. there was still starting methyl 5-(5-bromothiophen-2-yl)-1-(pyridin-4-yl)-1H-pyrazole-3-carboxylate visible as evidenced by LC/MS. Additional palladium catalyst was added and heating was continued. After heating at 65° C. overnight the reaction mixture was concentrated under reduced pressure to afford a dark semi-solid that was triturated with EtOAc and filtered to remove the solids. The filtrate was concentrated under reduced pressure and purified by flash column chromatography eluting with a gradient from 0% to 50% MeCN/CH$_2$Cl$_2$ to afford methyl 5-(5-(3-(methylsulfonyl)phenyl)-thiophen-2-yl)-1-(pyridin-4-yl)-1H-pyrazole-3-carboxylate (137 mg, 24% yield) as a mixture with triphenylphosphine oxide. This colorless film will be carried on to the Grignard addition without further purification.

The following compounds are prepared essentially according to Example 8:

2-(5-{5-[3-(methylsulfonyl)phenyl]-2-thienyl}-1-pyridin-4-yl-1H-pyrazol-3-propan-2-ol, $^1$H NMR (400 MHz CDCl$_3$): δ 8.68-8.57 (2H, m), 8.14 (1H, m), 7.92-7.78 (2H, m), 7.61 (1H, t), 7.43-7.36 (2H, m), 7.34 (1H, d), 6.93 (1H, d), 6.60 (1H, s), 3.11 (3H, s), 2.75 (1H, s), 1.67 (6H, s). MS(ES): 440 [M+H]$^+$.

2-[1-(4-methylpyridin-3-yl)-5-{5-[3-(methylsulfonyl)phenyl]-2-thienyl}-1H-pyrazol-3-yl]propan-2-ol, MS(ES): 454 [M+H]$^+$.

2-[1-(2,6-dimethylpyridin-3-yl)-5-{5-[3-(methylsulfonyl)phenyl]-2-thienyl}-1H-pyrazol-3-yl]propan-2-ol, MS(ES): 468 [M+H]$^+$.

2-[1-(2-methylphenyl)-5-{5-[3-(methylsulfonyl)phenyl]-2-thienyl}-1H-pyrazol-3-yl]propan-2-ol, MS(ES): 453 [M+H]$^+$.

2-[1-(2,5-dimethylphenyl)-5-{5-[3-(methylsulfonyl)phenyl]-2-thienyl}-1H-pyrazol-3-yl]propan-2-ol, MS(ES): 467 [M+H]$^+$.

2-[1-(2,3-dimethylphenyl)-5-{5-[3-(methylsulfonyl)phenyl]-2-thienyl}-1H-pyrazol-3-yl]propan-2-ol, MS(ES): 467 [M+H]$^+$.

2-(1-[2-fluoro-3-(trifluoromethyl)phenyl]-5-{5-[3-(methylsulfonyl)phenyl]-2-thienyl}-1H-pyrazol-3-yl)propan-2-ol, MS(ES): 525 [M+H]$^+$.

2-[1-(2-chloro-5-fluorophenyl)-5-{5-[3-(methylsulfonyl)phenyl]-2-thienyl}-1H-pyrazol-3-yl]propan-2-ol, MS(ES): 491 [M+H]$^+$.

2-[1-(2-chloro-6-methylphenyl)-5-{5-[3-(methylsulfonyl)phenyl]-2-thienyl}-1H-pyrazol-3-yl]propan-2-ol, MS(ES): 487 [M+H]$^+$.

2-[1-(5-chloro-2-fluorophenyl)-5-{5-[3-(methylsulfonyl)phenyl]-2-thienyl}-1H-pyrazol-3-yl]propan-2-ol, MS(ES): 491 [M+H]$^+$ 2-[1-(2-chloro-6-fluorophenyl)-5-{5-[3-(methylsulfonyl)phenyl]-2-thienyl}-1H-pyrazol-3-yl]propan-2-ol, MS(ES): 491 [M+H]$^+$.

2-{1-(2,6-dichlorophenyl)-5-[3-methyl-3'-(methylsulfonyl)biphenyl-4-yl]-1H-pyrazol-3-yl}propan-2-ol, MS(ES): 515 [M+H]$^+$.

2-{1-(2,6-dichlorophenyl)-5-[2-methyl-3'-(methylsulfonyl)biphenyl-4-yl]-1H-pyrazol-3-yl}propan-2-ol, MS(ES): 537 [M+Na]$^+$.

2-{5-[3-methyl-3'-(methylsulfonyl)biphenyl-4-yl]-1-[2-(trifluoromethyl)pyridin-3-yl]-1H-pyrazol-3-yl}propan-2-ol, 516 [M+H]$^+$.

2-{5-[3-methyl-3'-(methylsulfonyl)biphenyl-4-yl]-1-[4-(trifluoromethyl)pyridin-3-yl]-1H-pyrazol-3-yl}propan-2-ol MS(ES): 516 [M+H]$^+$.

2-{5-[3'-(methylsulfonyl)biphenyl-4-yl]-1-[4-(trifluoromethyl)pyridin-3-yl]-1H-pyrazol-3-yl}propan-2-ol MS(ES): 502 [M+H]$^+$.

2-{5-[3-chloro-3'-(methylsulfonyl)biphenyl-4-yl]-1-[4-(trifluoromethyl)pyridin-3-yl]-1H-pyrazol-3-yl}propan-2-ol MS(ES): 536 [M+H]$^+$.

2-{1-(2,6-dichlorophenyl)-5-[3'-(methylsulfonyl)biphenyl-4-yl]-1H-pyrazol-3-yl}propan-2-ol MS(ES): 501 [M+H]$^+$.

2-{5-[3-chloro-3'-(methylsulfonyl)biphenyl-4-yl]-1-(2,6-dichlorophenyl)-1H-pyrazol-3-yl}propan-2-ol MS(ES): 537 [M+H]$^+$ 2-{5-[3-chloro-3'-(methylsulfonyl)biphenyl-4-yl]-1-[2-(trifluoromethyl)pyridin-3-yl]-1H-pyrazol-3-yl}propan-2-ol MS(ES): 536 [M+H]$^+$.

2-{3'-chloro-4'-[1-(2,6-dichlorophenyl)-3-(trifluoromethyl)-1H-pyrazol-5-yl]biphenyl-3-yl}propan-2-ol MS(ES): 525 [M+H]$^+$.

2-{1-(2-chlorophenyl)-5-[4-(1H-indol-6-yl)phenyl]-1H-pyrazol-3-yl}propan-2-ol, MS(ES): 450 [M+Na]$^+$.

2-{1-(2-chlorophenyl)-5-[4-(1H-indol-5-yl)phenyl]-1H-pyrazol-3-yl}propan-2-ol, MS(ES): 428 [M+H]$^+$.

2-{1-(2-chlorophenyl)-5-[4-(1-methyl-1H-indol-5-yl)phenyl]-1H-pyrazol-3-yl}propan-2-ol MS(ES): 442 [M+H]$^+$.

2-{1-(2-chlorophenyl)-5-[4-(1H-indol-4-yl)phenyl]-1H-pyrazol-3-yl}propan-2-ol, MS(ES): 450 [M+Na]$^+$.

2-(1-(2-chlorophenyl)-5-(3'-(trifluoromethyl)biphenyl-4-yl)-1H-pyrazol-3-yl)propan-2-ol. MS (ES): 457 [M+H]$^+$.

2-(5-(2'-chloro-4'-(trifluoromethyl)biphenyl-4-yl)-1-(2-chlorophenyl)-1H-pyrazol-3-yl)propan-2-ol. MS (ES): 491[M+H]$^+$.

2-(1-(2-chlorophenyl)-5-(4'-fluoro-3'-(trifluoromethyl)biphenyl-4-yl)-1H-pyrazol-3-yl)propan-2-ol. MS (ES): 475 [M+H]⁺.

4'-(1-(2-chlorophenyl)-3-(2-hydroxypropan-2-yl)-1H-pyrazol-5-yl)biphenyl-3-sulfonamide. MS (ES): 468[M+H]⁺.

2-(1-(2-chlorophenyl)-5-(4'-(methylsulfonyl)biphenyl-4-yl)-1H-pyrazol-3-yl)propan-2-ol. (ES): 467[M+H]⁺.

4'-(1-(2-chlorophenyl)-3-(2-hydroxypropan-2-yl)-1H-pyrazol-5-yl)biphenyl-4-sulfonamide. MS (ES): 468[M+H]⁺.

2-(4'-(1-(2-chlorophenyl)-3-(2-hydroxypropan-2-yl)-1H-pyrazol-5-yl)biphenyl-3-yl)propan-2-ol. MS (ES): 447 [M+H]⁺.

4'-(1-(2-chlorophenyl)-3-(2-hydroxypropan-2-yl)-1H-pyrazol-5-yl)-N-(2-(dimethylamino)ethyl)biphenyl-3-sulfonamide. MS (ES): 539[M+H]⁺.

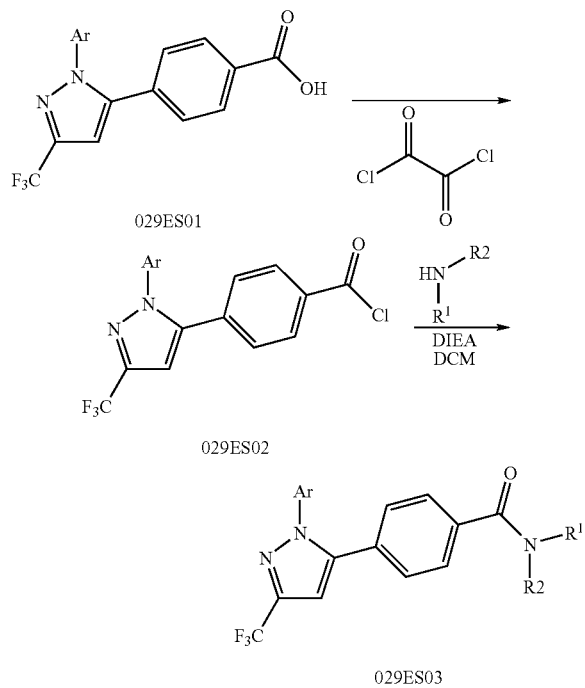

As depicted in Scheme 29, carboxylic acids can be transformed into amides via acylation. Carboxylic acids 029ES01 (Made in a manner similar to Example 2c) can be converted to their corresponding acid chlorides, 029ES02, by the action of oxalyl chloride in a manner similar to Example 70a. The resulting acid chloride can then be reacted with various amines under basic conditions similar to Example 70b to afford the corresponding amides 029ES03.

Example 75

4-[2-(2-Chloro-phenyl)-5-trifluoromethyl-2H-pyrazol-3-yl]-N,N-dimethyl-benzamide Example 75a Preparation of 4-[2-(2-Chloro-phenyl)-5-trifluoromethyl-2H-pyrazol-3-yl]-benzoyl chloride 4-[2-(2-Chloro-phenyl)-5-trifluoromethyl-2H-pyrazol-3-yl]-benzoic acid was prepared in a similar manner as described previously. To a 500 ml round bottom flask was added 2 g of the acid, ~150 ml of dry THF, 300 μL of DMF and 1500 μL of oxalyl chloride. The reaction was stirred at room temperature for 30 minutes. The solvent was removed under reduced pressure and the resulting yellow solid was dissolved in dichloromethane and dried under reduced pressure two more times. The resulting yellow solid was then dissolved to 0.1M in dry dichloromethane and used without further purification.

Example 75b

Preparation of 4-[2-(2-Chloro-phenyl)-5-trifluoromethyl-2H-pyrazol-3-yl]-N,N-dimethyl-benzamide

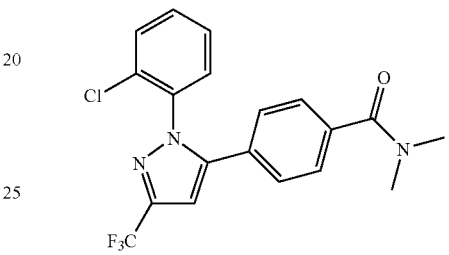

In a 1 dram vial was added 4-[2-(2-Chloro-phenyl)-5-trifluoromethyl-2H-pyrazol-3-yl]-benzoyl chloride (300 mL, 0.3 mmol) as a 0.1M solution in Dichloromethane, Dimethylamine (27 mg, 0.6 mmol) and N,N-Diisopropylethylamine (77.4 mg, 0.6 mmol). The reaction was stirred at room temperature for 30 min and then placed directly on silica and purified using a gradient of Hexane to Ethyl Acetate 0-50% over 10 CV. The relevant fractions were combined and dried in vacuo to give 108.6 mg (92%) of an off white solid; MS (ES): 394 [M+H]⁺; ¹H NMR (400 MHz, DMSO-d₆): δ 7.84 (dd, J=7.8 Hz; 1.7 Hz 1H), 7.73-7.58 (m, 3H), 7.45-7.35 (m, 5H), 3.00 (s, 3H), 2.89 (s, 3H).

The following compounds were synthesized in a similar manner:

4-[1-(2-chlorophenyl)-3-(trifluoromethyl)-1H-pyrazol-5-yl]-N-(2-morpholin-4-ylethyl)benzamide, MS(ES): 479 [M+H]⁺.

methyl N-({44-[1-(2-chlorophenyl)-3-(trifluoromethyl)-1H-pyrazol-5-yl]phenyl}carbonyl)glycinate, MS(ES): 438 [M+H]⁺.

4-[1-(2-chlorophenyl)-3-(trifluoromethyl)-1H-pyrazol-5-yl]-N-(2-oxotetrahydro-3-thienyl)benzamide, MS(ES): 466 [M+H]⁺.

methyl N-({4-[1-(2-chlorophenyl)-3-(trifluoromethyl)-1H-pyrazol-5-yl]phenyl}carbonyl)-beta-alaninate, MS(ES): 452 [M+H]⁺.

4-[1-(2-chlorophenyl)-3-(trifluoromethyl)-1H-pyrazol-5-yl]-N4-[2-(methylsulfonyl)ethyl]benzamide, MS(ES): 472 [M+H]⁺.

1-({4-[1-(2-chlorophenyl)-3-(trifluoromethyl)-1H-pyrazol-5-yl]phenyl}carbonyl)-4-[2-(methylsulfonyl)ethyl]piperazine, MS(ES): 541 [M+H]⁺.

4-[1-(2-chlorophenyl)-3-(trifluoromethyl)-1H-pyrazol-5-yl]-N-(1,1-dioxidotetrahydro-3-thienyl)benzamide, MS(ES): 484 [M+H]⁺.

4-[1-(2-chlorophenyl)-3-(trifluoromethyl)-1H-pyrazol-5-yl]-N-[3-(methylsulfonyl)phenyl]benzamide, MS(ES): 520 [M+H]⁺.

4-[1-(2-chlorophenyl)-3-(1-hydroxy-1-methylethyl)-1H-pyrazol-5-yl]-N,N-dimethylbenzamide, MS(ES): 384 [M+H]$^+$.

1-(2-chlorophenyl)-5-{5-[3-(methylsulfonyl)phenyl]-2-thienyl}-N-pyridin-3-yl-1H-pyrazole-3-carboxamide; MS (ES): 535 [M+H]$^+$ 1-(2-chlorophenyl)-5-{5-[3-(methylsulfonyl)phenyl]-2-thienyl}-N-pyridin-4-yl-1H-pyrazole-3-carboxamide; MS (ES): 535 [M+H]$^+$ 1-(2-chlorophenyl)-N-[2-(dimethylamino)ethyl]-5-{5-[3-(methylsulfonyl)phenyl]-2-thienyl}-1H-pyrazole-3-carboxamide; MS (ES): 529 [M+H]$^+$;

1-(2-chlorophenyl)-N-[3-(methyloxy)propyl]-5-{5-[3-(methylsulfonyl)phenyl]-2-thienyl}-1H-pyrazole-3-carboxamide; MS (ES): 530 [M+H]$^+$;

4-([1-(2-chlorophenyl)-5-{5-[3-(methylsulfonyl)phenyl]-2-thienyl)-1H-pyrazol-3-yl]carbonyl}morpholine; MS (ES): 528 [M+H]$^+$;

1-(2-chlorophenyl)-N-[6-(methyloxy)pyridin-3-yl]-5-{5-[3-(methylsulfonyl)phenyl]-2-thienyl}-1H-pyrazole-3-carboxamide; MS (ES): 565 [M+H]$^+$;

1-(2-chlorophenyl)-N,N-dimethyl-5-{5-[3-(methylsulfonyl)phenyl]-2-thienyl}-1H-pyrazole-3-carboxamide; MS (ES): 486 [M+H]$^+$;

1-{([1-(2-chlorophenyl)-5-{5-[3-(methylsulfonyl)phenyl]-2-thienyl}-1H-pyrazol-3-yl]carbonyl}-4-cyclopentylpiperazine; MS (ES): 595 [M+H]$^+$;

1-(2-chlorophenyl)-N-methyl-N-(1-methylpiperidin-4-yl)-5-{5-[3-(methylsulfonyl)phenyl]-2-thienyl}-1H-pyrazole-3-carboxamide; MS (ES): 569 [M+H]$^+$;

1-(2-chlorophenyl)-N-[3-(dimethylamino)propyl]-N-methyl-5-{5-[3-(methylsulfonyl)phenyl]-2-thienyl}-1H-pyrazole-3-carboxamide; MS (ES): 557 [M+H]$^+$;

1-(2-chlorophenyl)-5-{5-[3-(methylsulfonyl)phenyl]-2-thienyl}-N-(3-pyrrolidin-1-ylpropyl)-1H-pyrazole-3-carboxamide; MS (ES): 569 [M+H]$^+$;

1-(2-chlorophenyl)-N-[(1-ethylpyrrolidin-3-yl)methyl]-5-{5-[3-(methylsulfonyl)phenyl]-2-thienyl}-1H-pyrazole-3-carboxamide; MS (ES): 569 [M+H]$^+$;

N-(5-chloro-2-hydroxyphenyl)-4-[1-(2-chlorophenyl)-3-(trifluoromethyl)-1H-pyrazol-5-yl]benzamide; MS (ES): 492 [M+H]$^+$;

4-[1-(2-chlorophenyl)-3-(trifluoromethyl)-1H-pyrazol-5-yl]-N-quinolin-6-ylbenzamide; MS (ES): 493 [M+H]$^+$;

4-[1-(2-chlorophenyl)-3-(trifluoromethyl)-1H-pyrazol-5-yl]-N-(2,3-dihydro-1,4-benzodioxin-6-yl)benzamide; MS (ES): 500 [M+H]$^+$;

4-[1-(2-chlorophenyl)-3-(trifluoromethyl)-1H-pyrazol-5-yl]-N-{4-[2,2,2-trifluoro-1-hydroxy-1-(trifluoromethyl)ethyl]phenyl}benzamide; MS (ES): 608 [M+H]$^+$;

4-[1-(2-chlorophenyl)-3-(trifluoromethyl)-1H-pyrazol-5-yl]-N-(3-cyanophenyl)benzamide; MS (ES): 467 [M+H]$^+$;

2-[({4-[1-(2-chlorophenyl)-3-(trifluoromethyl)-1H-pyrazol-5-yl]phenyl}carbonyl)amino]-5-methylbenzoic acid; MS (ES): 500 [M+H]$^+$;

2-[({4-[1-(2-chlorophenyl)-3-(trifluoromethyl)-1H-pyrazol-5-yl]phenyl}carbonyl)amino]benzoic acid; MS (ES): 486 [M+H]$^+$;

4-[1-(2-chlorophenyl)-3-(trifluoromethyl)-1H-pyrazol-5-yl]-N-[2-(ethyloxy)phenyl]benzamide; MS (ES): 486 [M+H]$^+$;

4-[1-(2-chlorophenyl)-3-(trifluoromethyl)-1H-pyrazol-5-yl]-N-(2-cyanophenyl)benzamide; MS (ES): 467 [M+H]$^+$;

2-[({4-[1-(2-chlorophenyl)-3-(trifluoromethyl)-1H-pyrazol-5-yl]phenyl}carbonyl)amino]pyridine-3-carboxylic acid; MS (ES): 487 [M+H]$^+$;

N-[4-(aminocarbonyl)phenyl]-4-[1-(2-chlorophenyl)-3-(trifluoromethyl)-1H-pyrazol-5-yl]benzamide; MS (ES): 485 [M+H]$^+$;

4-[1-(2-chlorophenyl)-3-(trifluoromethyl)-1H-pyrazol-5-yl]-N-quinolin-5-ylbenzamide; MS (ES): 493 [M+H]$^+$;

4-[1-(2-chlorophenyl)-3-(trifluoromethyl)-1H-pyrazol-5-yl]-N-(2-piperidin-1-ylphenyl)benzamide; MS (ES): 525 [M+H]$^+$;

N-(5-chloro-2-morpholin-4-ylphenyl)-4-[4-(2-chlorophenyl)-3-(trifluoromethyl)-1H-pyrazol-5-yl]benzamide; MS (ES): 561 [M+H]$^+$;

4-[1-(2-chlorophenyl)-3-(trifluoromethyl)-1H-pyrazol-5-yl]-N-isoxazol-3-ylbenzamide; MS (ES): 433 [M+H]$^+$;

4-[1-(2-chlorophenyl)-3-(trifluoromethyl)-1H-pyrazol-5-yl]-N-[5-(1,1-dimethylethyl)-1,3,4-thiadiazol-2-yl]benzamide; MS (ES): 506 [M+H]$^+$;

2-[({4-[1-(2-chlorophenyl)-3-(trifluoromethyl)-1H-pyrazol-5-yl]phenyl}carbonyl)amino]-4-methylbenzoic acid; MS (ES): 500 [M+H]$^+$;

4-[1-(2-chlorophenyl)-3-(trifluoromethyl)-1H-pyrazol-5-yl]-N-1H-indazol-5-ylbenzamide; MS (ES): 482 [M+H]$^+$;

4-[1-(2-chlorophenyl)-3-(trifluoromethyl)-1H-pyrazol-5-yl]-N-{4-[(1-methylethyl)oxy]phenyl}benzamide; MS (ES): 500 [M+H]$^+$;

4-[1-(2-chlorophenyl)-3-(trifluoromethyl)-1H-pyrazol-5-yl]-N-(4-methyl-1,3-thiazol-2-yl)benzamide; MS (ES): 463 [M+H]$^+$;

N-(2-chloro-3-hydroxy-4-methylphenyl)-4-[1-(2-chlorophenyl)-3-(trifluoromethyl)-1H-pyrazol-5-yl]benzamide; MS (ES): 506 [M+H]$^+$;

{4-[({4-[1-(2-chlorophenyl)-3-(trifluoromethyl)-1H-pyrazol-5-yl]phenyl}carbonyl)amino]phenyl}acetic acid; MS (ES): 500 [M+H]$^+$;

4-[1-(2-chlorophenyl)-3-(trifluoromethyl)-1H-pyrazol-5-yl]-N-(furan-2-ylmethyl)-N-methylbenzamide; MS (ES): 460 [M+H]$^+$;

4-({4-[1-(2-chlorophenyl)-3-(trifluoromethyl)-1H-pyrazol-5-yl]phenyl}carbonyl)-2,6-dimethylmorpholine; MS (ES): 464 [M+H]$^+$;

1-({4-[1-(2-chlorophenyl)-3-(trifluoromethyl)-1H-pyrazol-5-yl]phenyl}carbonyl)-4-(ethylsulfonyl)piperazine; MS (ES): 527 [M+H]$^+$;

1-({4-[1-(2-chlorophenyl)-3-(trifluoromethyl)-1H-pyrazol-5-yl]phenyl}carbonyl)-1,4-diazepane; MS (ES): 449 [M+H]$^+$;

4-[1-(2-chlorophenyl)-3-(trifluoromethyl)-1H-pyrazol-5-yl]-N-methyl-N-(pyridin-4-ylmethyl)benzamide; MS (ES): 471 [M+H]$^+$;

4-({4-[1-(2-chlorophenyl)-3-(trifluoromethyl)-1H-pyrazol-5-yl]phenyl}carbonyl)thiomorpholine; MS (ES): 452 [M+H]$^+$;

1-({4-[1-(2-chlorophenyl)-3-(trifluoromethyl)-1H-pyrazol-5-yl]phenyl}carbonyl)piperidin-3-ol; MS (ES): 450 [M+H]$^+$;

[1-({4-[1-(2-chlorophenyl)-3-(trifluoromethyl)-1H-pyrazol-5-yl]phenyl}carbonyl)pyrrolidin-2-yl]methanol; MS (ES): 450 [M+H]$^+$;

1-({4-[1-(2-chlorophenyl)-3-(trifluoromethyl)-1H-pyrazol-5-yl]phenyl}carbonyl)piperidin-4-ol; MS (ES): 450 [M+H]$^+$;

1-({4-[1-(2-chlorophenyl)-3-(trifluoromethyl)-1H-pyrazol-5-yl]phenyl}carbonyl)-4-methyl-1,4-diazepane; MS (ES): 463 [M+H]$^+$;

1-({4-[1-(2-chlorophenyl)-3-(trifluoromethyl)-1H-pyrazol-5-yl]-phenyl}carbonyl)-4-[2-(trifluoromethyl)phenyl]piperazine; MS (ES): 579 [M+H]$^+$;

4-[1-(2-chlorophenyl)-3-(trifluoromethyl)-1H-pyrazol-5-A-N42-(dimethylamino)ethyl]-N-methylbenzamide; MS (ES): 451 [M+H]$^+$;

4-[1-(2-chlorophenyl)-3-(trifluoromethyl)-1H-pyrazol-5-yl]-N-methyl-N-(2-thienylmethyl)benzamide; MS (ES): 476 [M+H]$^+$;

4-[1-(2-chlorophenyl)-3-(trifluoromethyl)-1H-pyrazol-5-yl]-N-(4-piperidin-1-ylphenyl)benzamide; MS (ES): 525 [M+H]$^+$;

1-({4-[1-(2-chlorophenyl)-3-(trifluoromethyl)-1H-pyrazol-5-yl]phenyl}carbonyl)piperidine-4-carboxylic acid; MS (ES): 478 [M+H]$^+$;

4-({4-[1-(2-chlorophenyl)-3-(trifluoromethyl)-1H-pyrazol-5-yl]phenyl}carbonyl)morpholine; MS (ES): 436 [M+H]$^+$;

4-[1-(2-chlorophenyl)-3-(trifluoromethyl)-1H-pyrazol-5-yl]-N-1,3,4-thiadiazol-2-ylbenzamide; MS (ES): 450 [M+H]$^+$;

4-[1-(2-chlorophenyl)-3-(trifluoromethyl)-1H-pyrazol-5-yl]-N-(4-hydroxy-3-methylphenyl)benzamide; MS (ES): 472 [M+H]$^+$;

4-[1-(2-chlorophenyl)-3-(trifluoromethyl)-1H-pyrazol-5-yl]-N-[4-(5-methyl-3-oxo-2,3-dihydro-1H-pyrazol-1-yl)phenyl]benzamide; MS (ES): 538 [M+H]$^+$;

2-[4-({4-[1-(2-chlorophenyl)-3-(trifluoromethyl)-1H-pyrazol-5-yl]phenyl}carbonyl)piperazin-1-yl]benzonitrile; MS (ES): 536 [M+H]$^+$;

1-({4-[1-(2-chlorophenyl)-3-(trifluoromethyl)-1H-pyrazol-5-yl]phenyl}carbonyl)-4-pyridin-4-ylpiperazine; MS (ES): 512 [M+H]$^+$;

1-({4-[1-(2-chlorophenyl)-3-(trifluoromethyl)-1H-pyrazol-5-yl]phenyl}Carbonyl)-4-[4-(methyloxy)phenyl]piperazine; MS (ES): 541 [M+H]$^+$;

2-[4-({4-[1-(2-chlorophenyl)-3-(trifluoromethyl)-1H-pyrazol-5-yl]phenyl}carbonyl)piperazin-1-yl]phenol; MS (ES): 527 [M+H]$^+$;

4-({4-[1-(2-chlorophenyl)-3-(trifluoromethyl)-1H-pyrazol-5-yl]phenyl}carbonyl)piperazin-2-one; MS (ES): 449 [M+H]$^+$;

3-({4-[1-(2-chlorophenyl)-3-(trifluoromethyl)-1H-pyrazol-5-yl]phenyl}carbonyl)-4,4-dimethyl-1,3-oxazolidine; MS (ES): 450 [M+H]$^+$;

1-({4-[1-(2-chlorophenyl)-3-(trifluoromethyl)-1H-pyrazol-5-yl]phenyl}carbonyl)-4-(tetrahydrofuran-2-ylmethyl)piperazine; MS (ES): 519 [M+H]$^+$;

1-({4-[1-(2-chlorophenyl)-3-(trifluoromethyl)-1H-pyrazol-5-yl]phenyl}carbonyl)-4-propanoyl piperazine; MS (ES): 491 [M+H]$^+$;

1-({4-[1-(2-chlorophenyl)-3-(trifluoromethyl)-1H-pyrazol-5-yl]phenyl}carbonyl)-4-methylpiperazine; MS (ES): 449 [M+H]$^+$;

1,1-dimethylethyl [1-({4-[1-(2-chlorophenyl)-3-(trifluoromethyl)-1H-pyrazol-5-yl]phenyl}carbonyl)pyrrolidin-3-yl]carbamate; MS (ES): 535 [M+H]$^+$;

1-({4-[1-(2-chlorophenyl)-3-(trifluoromethyl)-1H-pyrazol-5-yl]phenyl}carbonyl)azetidine-3-carboxylic acid; MS (ES): 450 [M+H]$^+$;

4-[4-({4-[1-(2-chlorophenyl)-3-(trifluoromethyl)-1H-pyrazol-5-yl]phenyl}carbonyl)piperazin-1-yl]phenol; MS (ES): 527 [M+H]$^+$;

4-[1-(2-chlorophenyl)-3-(trifluoromethyl)-1H-pyrazol-5-yl]-N-[2-(methyloxy)ethyl]-N-(1-methylpiperidin-4-yl)benzamide; MS (ES): 521 [M+H]$^+$;

4-[1-(2-chlorophenyl)-3-(trifluoromethyl)-1H-pyrazol-5-yl]-N-methyl-N-(1-methylpyrrolidin-3-yl)benzamide; MS (ES): 463 [M+H]$^+$;

1-({4-[1-(2-chlorophenyl)-3-(trifluoromethyl)-1H-pyrazol-5-yl]phenyl}carbonyl)-1,2,5,6-tetrahydropyridine-3-carboxylic acid; MS (ES): 476 [M+H]$^+$;

1-({4-[1-(2-chlorophenyl)-3-(trifluoromethyl)-1H-pyrazol-5-yl]phenyl}carbonyl)-4-(1-methylpropyl)piperazine; MS (ES): 491 [M+H]$^+$;

3-[1-({4-[1-(2-chlorophenyl)-3-(trifluoromethyl)-1H-pyrazol-5-yl]phenyl}carbonyl)piperidin-4-yl]-1H-indole; MS (ES): 549 [M+H]$^+$;

4-[1-(2-chlorophenyl)-3-(trifluoromethyl)-1H-pyrazol-5-yl]-N-cyclopropyl-N-(1-methylpiperidin-4-yl)benzamide; MS (ES): 503 [M+H]$^+$;

4-[1-(2-chlorophenyl)-3-(trifluoromethyl)-1H-pyrazol-5-yl]-N-[2-(dimethylamino)ethyl]-N-ethylbenzamide; MS (ES): 465 [M+H]$^+$;

2-[4-({4-[1-(2-chlorophenyl)-3-(trifluoromethyl)-1H-pyrazol-5-yl]phenyl}carbonyl)piperazin-1-yl]pyrazine; MS (ES): 513 [M+H]$^+$;

4-[1-(2-chlorophenyl)-3-(trifluoromethyl)-1H-pyrazol-5-yl]-N-(1,3-dioxolan-2-ylmethyl)-N-methylbenzamide; MS (ES): 466 [M+H]$^+$;

N-(1-acetylpiperidin-4-yl)-4-[1-(2-chlorophenyl)-3-(trifluoromethyl)-1H-pyrazol-5-yl]-N-cyclopropylbenzamide; MS (ES): 531 [M+H]$^+$;

1-({4-[1-(2-chlorophenyl)-3-(trifluoromethyl)-1H-pyrazol-5-yl]phenyl}carbonyl)-4-(6-methylpyridin-2-yl)piperazine; MS (ES): 526 [M+H]$^+$;

ethyl 1-({4-[1-(2-chlorophenyl)-3-(trifluoromethyl)-1H-pyrazol-5-yl]phenyl}carbonyl)piperidine-2-carboxylate; MS (ES): 506 [M+H]$^+$;

1-({4-[1-(2-chlorophenyl)-3-(trifluoromethyl)-1H-pyrazol-5-yl]phenyl}carbonyl)-4-(3-methylphenyl)piperazine; MS (ES): 525 [M+H]$^+$;

4-[1-(2-chlorophenyl)-3-(trifluoromethyl)-1H-pyrazol-5-yl]-N-cyclopropyl-N-(1-propylpiperidin-4-yl)benzamide; MS (ES): 531 [M+H]$^+$;

ethyl 1-({4-[1-(2-chlorophenyl)-3-(trifluoromethyl)-1H-pyrazol-5-yl]phenyl}carbonyl)piperidine-4-carboxylate; MS (ES): 506 [M+H]$^+$;

1-({4-[1-(2-chlorophenyl)-3-(trifluoromethyl)-1H-pyrazol-5-yl]phenyl}carbonyl)-4-[4-(trifluoromethyl)pyrimidin-2-yl]-1,4-diazepane; MS (ES): 595 [M+H]$^+$;

4-[1-(2-chlorophenyl)-3-(trifluoromethyl)-1H-pyrazol-5-yl]-methyl-N-(pyridin-3-ylmethyl)benzamide; MS (ES): 471 [M+H]$^+$;

N-butyl-4-[1-(2-chlorophenyl)-3-(trifluoromethyl)-1H-pyrazol-5-yl]-N-(2-thienylmethyl)benzamide; MS (ES): 518 [M+H]$^+$;

1-({4-[1-(2-chlorophenyl)-3-(trifluoromethyl)-1H-pyrazol-5-yl]phenyl}carbonyl)-4-ethylpiperazine; MS (ES): 463 [M+H]$^+$;

1-({4-[1-(2-chlorophenyl)-3-(trifluoromethyl)-1H-pyrazol-5-yl]phenyl}carbonyl)-4-[3-(methyloxy)phenyl]piperazine; MS (ES): 541 [M+H]$^+$;

4-[1-(2-chlorophenyl)-3-(trifluoromethyl)-1H-pyrazol-5-yl]-N-methyl-N-(1-methylpiperidin-4-yl)benzamide; MS (ES): 477 [M+H]$^+$;

N-(2-amino-2-oxoethyl)-4-[1-(2-chlorophenyl)-3-(trifluoromethyl)-1H-pyrazol-5-yl]-N-methylbenzamide; MS (ES): 437 [M+H]$^+$;

1-({4-[1-(2-chlorophenyl)-3-(trifluoromethyl)-1H-pyrazol-5-yl]phenyl}carbonyl)-4-(furan-2-ylcarbonyl)piperazine; MS (ES): 529 [M+H]$^+$;

1-({4-[1-(2-chlorophenyl)-3-(trifluoromethyl)-1H-pyrazol-5-yl]phenyl}carbonyl)-4-(2-fluorophenyl)piperazine; MS (ES): 529 [M+H]$^+$;

1-({4-[1-(2-chlorophenyl)-3-(trifluoromethyl)-1H-pyrazol-5-yl]phenyl}carbonyl)-4-[2-(methyloxy)phenyl]piperazine; MS (ES): 541 [M+H]$^+$;

1-({4-[1-(2-chlorophenyl)-3-(trifluoromethyl)-1H-pyrazol-5-yl]phenyl}carbonyl)-4-[2-(2-thienyl)ethyl]piperazine; MS (ES): 545 [M+H]$^+$;

4-[({4-[1-(2-chlorophenyl)-3-(trifluoromethyl)-1H-pyrazol-5-yl]phenyl}carbonyl)amino]benzoic acid; MS (ES): 486 [M+H]$^+$;

4-[1-(2-chlorophenyl)-3-(trifluoromethyl)-1H-pyrazol-5-yl]-N-[3-(piperidin-1-ylsulfonyl)phenyl]benzamide; MS (ES): 589 [M+H]$^+$;

4-[1-(2-chlorophenyl)-3-(trifluoromethyl)-1H-pyrazol-5-yl]-1,3-thiazol-2-ylbenzamide; MS (ES): 449 [M+H]$^+$;

4-[1-(2-chlorophenyl)-3-(trifluoromethyl)-1H-pyrazol-5-yl]-N-[3-(pyrrolidin-1-ylsulfonyl)phenyl]benzamide; MS (ES): 575 [M+H]$^+$;

4-[1-(2-chlorophenyl)-3-(trifluoromethyl)-1H-pyrazol-5-yl]-N-[2-methyl-4-(methyloxy)phenyl]benzamide; MS (ES): 486 [M+H]$^+$;

4-[1-(2-chlorophenyl)-3-(trifluoromethyl)-1H-pyrazol-5-yl]-N-{2-[(difluoromethyl)oxy]phenyl}benzamide; MS (ES): 508 [M+H]$^+$;

4-[1-(2-chlorophenyl)-3-(trifluoromethyl)-1H-pyrazol-5-yl]-N-{4-[(difluoromethyl)oxy]phenyl}benzamide; MS (ES): 508 [M+H]$^+$;

4-[1-(2-chlorophenyl)-3-(trifluoromethyl)-1H-pyrazol-5-yl]-N-(3-fluorophenyl)benzamide; MS (ES): 460 [M+H]$^+$;

4-[1-(2-chlorophenyl)-3-(trifluoromethyl)-1H-pyrazol-5-yl]-N-[3-(morpholin-4-ylsulfonyl)phenyl]benzamide; MS (ES): 591 [M+H]$^+$;

4-[1-(2-chlorophenyl)-3-(trifluoromethyl)-1H-pyrazol-5-yl]-N-[4-(trifluoromethyl)phenyl]benzamide; MS (ES): 510 [M+H]$^+$;

N-(3-chlorophenyl)-4-[1-(2-chlorophenyl)-3-(trifluoromethyl)-1H-pyrazol-5-yl]benzamide; MS (ES): 476 [M+H]$^+$;

4-[1-(2-chlorophenyl)-3-(trifluoromethyl)-1H-pyrazol-5-yl]-N-[6-(methylsulfonyl)pyridin-3-yl]benzamide; MS (ES): 521 [M+H]$^+$;

4-[1-(2-chlorophenyl)-3-(trifluoromethyl)-1H-pyrazol-5-yl]-N-[2-(trifluoromethyl)phenyl]benzamide; MS (ES): 510 [M+H]$^+$;

4-[1-(2-chlorophenyl)-3-(trifluoromethyl)-1H-pyrazol-5-yl]-N-[2-(methyloxy)phenyl]benzamide; MS (ES): 472 [M+H]$^+$;

4-[1-(2-chlorophenyl)-3-(trifluoromethyl)-1H-pyrazol-5-yl]-N-[2-fluoro-5-(trifluoromethyl)phenyl]benzamide; MS (ES): 528 [M+H]$^+$;

N-(2-chlorophenyl)-4-[1-(2-chlorophenyl)-3-(trifluoromethyl)-1H-pyrazol-5-yl]benzamide; MS (ES): 476 [M+H]$^+$;

4-[1-(2-chlorophenyl)-3-(trifluoromethyl)-1H-pyrazol-5-yl]-N-[3-(methyloxy)phenyl]benzamide; MS (ES): 472 [M+H]$^+$;

4-[1-(2-chlorophenyl)-3-(trifluoromethyl)-1H-pyrazol-5-yl]-N-[3-(trifluoromethyl)phenyl]benzamide; MS (ES): 510 [M+H]$^+$;

4-[1-(2-chlorophenyl)-3-(trifluoromethyl)-1H-pyrazol-5-yl]-N-{2-[(trifluoromethyl)oxy]phenyl}benzamide; MS (ES): 526 [M+H]$^+$;

4-[1-(2-chlorophenyl)-3-(trifluoromethyl)-1H-pyrazol-5-yl]-N-[4-(pyridin-4-ylcarbonyl)phenyl]benzamide; MS (ES): 547 [M+H]$^+$;

N-[3,5-bis(methyloxy)phenyl]-4-[1-(2-chlorophenyl)-3-(trifluoromethyl)-1H-pyrazol-5-yl]benzamide; MS (ES): 502 [M+H]$^+$;

4-[1-(2-chlorophenyl)-3-(trifluoromethyl)-1H-pyrazol-5-yl]-N-pyridin-3-ylbenzamide; MS (ES): 443 [M+H]$^+$;

N-(2-chloro-5-hydroxyphenyl)-4-[1-(2-chlorophenyl)-3-(trifluoromethyl)-1H-pyrazol-5-yl]benzamide; MS (ES): 492 [M+H]$^+$;

4-[1-(2-chlorophenyl)-3-(trifluoromethyl)-1H-pyrazol-5-yl]-N-pyridin-4-ylbenzamide; MS (ES): 443 [M+H]$^+$;

N-1,3-benzodioxol-5-yl-4-[1-(2-chlorophenyl)-3-(trifluoromethyl)-1H-pyrazol-5-yl]benzamide; MS (ES): 486 [M+H]$^+$;

3-[({4-[1-(2-chlorophenyl)-3-(trifluoromethyl)-1H-pyrazol-5-yl]phenyl}carbonyl)amino]benzoic acid; MS (ES): 486 [M+H]$^+$;

4-[1-(2-chlorophenyl)-3-(trifluoromethyl)-1H-pyrazol-5-yl]-N-[2-methyl-6-(methyloxy)phenyl]benzamide; MS (ES): 486 [M+H]$^+$;

4-[1-(2-chlorophenyl)-3-(trifluoromethyl)-1H-pyrazol-5-yl]-N-(3-methylpyridin-2-yl)benzamide; MS (ES): 457 [M+H]$^+$;

4-[1-(2-chlorophenyl)-3-(trifluoromethyl)-1H-pyrazol-5-yl]-N-{4-[(trifluoromethyl)oxy]phenyl}benzamide; MS (ES): 526 [M+H]$^+$;

4-[1-(2-chlorophenyl)-3-(trifluoromethyl)-1H-pyrazol-5-yl]-N-(3-cyclopropyl-1H-pyrazol-5-yl)benzamide; MS (ES): 472 [M+H]$^+$;

N-[3,4-bis(methyloxy)phenyl]-4-[1-(2-chlorophenyl)-3-(trifluoromethyl)-1H-pyrazol-5-yl]benzamide; MS (ES): 502 [M+H]$^+$;

4-[1-(2-chlorophenyl)-3-(trifluoromethyl)-1H-pyrazol-5-yl]-N-quinolin-8-ylbenzamide; MS (ES): 493 [M+H]$^+$;

4-chloro-3-[({4-[1-(2-chlorophenyl)-3-(trifluoromethyl)-1H-pyrazol-5-yl]phenyl}carbonyl)amino]benzoic acid; MS (ES): 520 [M+H]$^+$;

1-({4-[1-(2-chlorophenyl)-3-(trifluoromethyl)-1H-pyrazol-5-yl]phenyl}carbonyl)azetidine-2-carboxylic acid; MS (ES): 450 [M+H]$^+$;

4-[1-(2-chlorophenyl)-3-(trifluoromethyl)-1H-pyrazol-5-yl]-N-{3-[(trifluoromethyl)oxy]phenyl}benzamide; MS (ES): 526 [M+H]$^+$;

4-[1-(2-chlorophenyl)-3-(trifluoromethyl)-1H-pyrazol-5-yl]-N-{4-[(trifluoromethyl)thio]phenyl}benzamide; MS (ES): 542 [M+H]$^+$;

4-[1-(2-chlorophenyl)-3-(trifluoromethyl)-1H-pyrazol-5-yl]-N-[6-(methyloxy)pyridin-3-yl]benzamide; MS (ES): 473 [M+H]$^+$;

4-[1-(2-chlorophenyl)-3-(trifluoromethyl)-1H-pyrazol-5-yl]-N-(4-methylpyridin-2-yl)benzamide; MS (ES): 457 [M+H]$^+$;

4-[1-(2-chlorophenyl)-3-(trifluoromethyl)-1H-pyrazol-5-yl]-N-[2-methyl-5-(methyloxy)phenyl]benzamide; MS (ES): 486 [M+H]$^+$;

4-[1-(2-chlorophenyl)-3-(trifluoromethyl)-1H-pyrazol-5-yl]-N-(1-methyl-1H-pyrazol-5-yl)benzamide; MS (ES): 446 [M+H]$^+$;

N-[5-(acetylamino)-2-chlorophenyl]-4-[1-(2-chlorophenyl)-3-(trifluoromethyl)-1H-pyrazol-5-yl]benzamide; MS (ES): 533 [M+H]$^+$;

4-[1-(2-chlorophenyl)-3-(trifluoromethyl)-1H-pyrazol-5-yl]-N-[5-(trifluoromethyl)-1,3,4-thiadiazol-2-yl]benzamide; MS (ES): 518 [M+H]$^+$;

4-[1-(2-chlorophenyl)-3-(trifluoromethyl)-1H-pyrazol-5-yl]-N-[4-chloro-2-(trifluoromethyl)phenyl]benzamide; MS (ES): 544 [M+H]$^+$;

4-[1-(2-chlorophenyl)-3-(trifluoromethyl)-1H-pyrazol-5-yl]-N-(5-methylpyridin-2-yl)benzamide; MS (ES): 457 [M+H]+;

4-[1-(2-chlorophenyl)-3-(trifluoromethyl)-1H-pyrazol-5-yl]-N-[2-(methyloxy)-5-(trifluoromethyl)phenyl]benzamide; MS (ES): 540 [M+H]+;

4-[1-(2-chlorophenyl)-3-(trifluoromethyl)-1H-pyrazol-5-yl]-N-(6-methylpyridin-2-yl)benzamide; MS (ES): 457 [M+H]+;

4-[1-(2-chlorophenyl)-3-(trifluoromethyl)-1H-pyrazol-5-yl]-N-[4-(methyloxy)biphenyl-3-yl]benzamide; MS (ES): 548 [M+H]+;

N-(3-chloro-4-fluorophenyl)-4-[1-(2-chlorophenyl)-3-(trifluoromethyl)-1H-pyrazol-5-yl]benzamide; MS (ES): 494 [M+H]+;

4-[1-(2-chlorophenyl)-3-(trifluoromethyl)-1H-pyrazol-5-yl]-N-{6-[(trifluoromethyl)oxy]-1,3-benzothiazol-2-yl}benzamide; MS (ES): 583 [M+H]+;

4-[1-(2-chlorophenyl)-3-(trifluoromethyl)-1H-pyrazol-5-yl]-N-[2-fluoro-3-(trifluoromethyl)phenyl]benzamide; MS (ES): 528 [M+H]+;

4-[1-(2-chlorophenyl)-3-(trifluoromethyl)-1H-pyrazol-5-yl]-N-[2-(1H-pyrrol-1-yl)phenyl]benzamide; MS (ES): 507 [M+H]+;

4-[1-(2-chlorophenyl)-3-(trifluoromethyl)-1H-pyrazol-5-yl]-N-[2-chloro-5-(trifluoromethyl)phenyl]benzamide; MS (ES): 544 [M+H]+;

4-[1-(2-chlorophenyl)-3-(trifluoromethyl)-1H-pyrazol-5-yl]-N-(1-methyl-1H-pyrazol-3-yl)benzamide; MS (ES): 446 [M+H]+;

4-[1-(2-chlorophenyl)-3-(trifluoromethyl)-1H-pyrazol-5-yl]-N-[5-(1,1-dimethylethyl)-2-(methyloxy)phenyl]benzamide; MS (ES): 528 [M+H]+;

N-[5-chloro-2-(methyloxy)phenyl]-4-[1-(2-chlorophenyl)-3-(trifluoromethyl)-1H-pyrazol-5-yl]benzamide; MS (ES): 506 [M+H]+;

4-[1-(2-chlorophenyl)-3-(trifluoromethyl)-1H-pyrazol-5-yl]-N-(5-methyl-1,3,4-thiadiazol-2-yl)benzamide; MS (ES): 464 [M+H]+;

4-[1-(2-chlorophenyl)-3-(trifluoromethyl)-1H-pyrazol-5-yl]-N-(2,6-dichlorophenyl)benzamide; MS (ES): 510 [M+H]+;

4-[1-(2-chlorophenyl)-3-(trifluoromethyl)-1H-pyrazol-5-yl]-N-(3-hydroxyphenyl)benzamide; MS (ES): 458 [M+H]+;

2-[({4-[1-(2-chlorophenyl)-3-(trifluoromethyl)-1H-pyrazol-5-yl]phenyl}carbonyl)amino]-6-(methyloxy)benzoic acid; MS (ES): 516 [M+H]+;

4-[1-(2-chlorophenyl)-3-(trifluoromethyl)-1H-pyrazol-5-yl]-N-(5-methylisoxazol-3-yl)benzamide; MS (ES): 447 [M+H]+;

4-[1-(2-chlorophenyl)-3-(trifluoromethyl)-1H-pyrazol-5-yl]-N-[3-fluoro-4-(methyloxy)phenyl]benzamide; MS (ES): 490 [M+H]+;

4-[1-(2-chlorophenyl)-3-(trifluoromethyl)-1H-pyrazol-5-yl]-N-[4-(dimethylamino)phenyl]benzamide; MS (ES): 485 [M+H]+;

4-[1-(2-chlorophenyl)-3-(trifluoromethyl)-1H-pyrazol-5-yl]-N-(furan-2-ylmethyl)benzamide; MS (ES): 446 [M+H]+;

ethyl 4-[({4-[1-(2-chlorophenyl)-3-(trifluoromethyl)-1H-pyrazol-5-yl]phenyl}carbonyl)amino]piperidine-1-carboxylate; MS (ES): 521 [M+H]+;

4-[1-(2-chlorophenyl)-3-(trifluoromethyl)-1H-pyrazol-5-yl]-N-(tetrahydrofuran-2-ylmethyl)benzamide; MS (ES): 450 [M+H]+;

4-[1-(2-chlorophenyl)-3-(trifluoromethyl)-1H-pyrazol-5-yl]-N-(2-thienylmethyl)benzamide; MS (ES): 462 [M+H]+;

4-[1-(2-chlorophenyl)-3-(trifluoromethyl)-1H-pyrazol-5-yl]-N-[2-(dimethylamino)ethyl]benzamide; MS (ES): 437 [M+H]+;

4-[1-(2-chlorophenyl)-3-(trifluoromethyl)-1H-pyrazol-5-yl]-N-[3-(dimethylamino)-2,2-dimethylpropyl]benzamide; MS (ES): 479 [M+H]+;

4-[1-(2-chlorophenyl)-3-(trifluoromethyl)-1H-pyrazol-5-yl]-N-(2-pyrrolidin-1-ylethyl)benzamide; MS (ES): 463 [M+H]+;

4-[1-(2-chlorophenyl)-3-(trifluoromethyl)-1H-pyrazol-5-yl]-N-{3-[(1-methylethyl)oxy]propyl}benzamide; MS (ES): 466 [M+H]+;

4-[1-(2-chlorophenyl)-3-(trifluoromethyl)-1H-pyrazol-5-yl]-N-{[2-(methyloxy)phenyl]methyl}benzamide; MS (ES): 486 [M+H]+;

4-[1-(2-chlorophenyl)-3-(trifluoromethyl)-1H-pyrazol-5-yl]-N-(3-morpholin-4-ylpropyl)benzamide; MS (ES): 493 [M+H]+;

4-[1-(2-chlorophenyl)-3-(trifluoromethyl)-1H-pyrazol-5-yl]-N-[2-(2-thienyl)ethyl]benzamide; MS (ES): 476 [M+H]+;

4-[1-(2-chlorophenyl)-3-(trifluoromethyl)-1H-pyrazol-5-yl]-N-(pyridin-4-ylmethyl)benzamide; MS (ES): 457 [M+H]+;

4-[1-(2-chlorophenyl)-3-(trifluoromethyl)-1H-pyrazol-5-yl]-N-{2-[3-(methyloxy)phenyl]ethyl}benzamide; MS (ES): 500 [M+H]+;

N-{[3,4-bis(methyloxy)phenyl]methyl}-4-[1-(2-chlorophenyl)-3-(trifluoromethyl)-1H-pyrazol-5-yl]benzamide; MS (ES): 516 [M+H]+;

4-[1-(2-chlorophenyl)-3-(trifluoromethyl)-1H-pyrazol-5-yl]-N-{2-[4-(methyloxy)phenyl]ethyl}benzamide; MS (ES): 500 [M+H]+;

2-piperidin-1-ylethyl 4-[1-(2-chlorophenyl)-3-(trifluoromethyl)-1H-pyrazol-5-yl]benzoate, MS(ES): 478 [M+H]+.

2-(dimethylamino)ethyl 4-[1-(2-chlorophenyl)-3-(trifluoromethyl)-1H-pyrazol-5-yl]benzoate, MS(ES): 438 [M+H]+.

2-piperidin-1-ylethyl 4-[1-(2-chlorophenyl)-3-(trifluoromethyl)-1H-pyrazol-5-yl]benzoate, MS(ES): 478 [M+H]+.

2-morpholin-4-ylethyl 4-[1-(2-chlorophenyl)-3-(trifluoromethyl)-1H-pyrazol-5-yl]benzoate, MS(ES): 480 [M+H]+.

3-(dimethylamino)propyl 4-[1-(2-chlorophenyl)-3-(trifluoromethyl)-1H-pyrazol-5-yl]benzoate, MS(ES): 452 [M+H]+.

2-(methylsulfonyl)ethyl 4-[1-(2-chlorophenyl)-3-(trifluoromethyl)-1H-pyrazol-5-yl]benzoate, MS(ES): 473 [M+H]+.

2-(4-methylpiperazin-1-yl)ethyl 4-[1-(2-chlorophenyl)-3-(trifluoromethyl)-1H-pyrazol-5-yl]benzoate, MS(ES): 493 [M+H]+.

3-(methylsulfonyl)propyl 4-[1-(2-chlorophenyl)-3-(trifluoromethyl)-1H-pyrazole-5-yl]benzoate, MS(ES): 487 [M+H]+.

2-(dimethylamino)ethyl 4-[1-(2-chlorophenyl)-3-(trifluoromethyl)-1H-pyrazol-5-yl]benzoate; MS(ES): 438 [M+H]+;

2-pyridin-2-ylethyl 4-[1-(2-chlorophenyl)-3-(trifluoromethyl)-1H-pyrazol-5-yl]benzoate; MS (ES): 472 [M+H]+;

[3,5-dimethyl-4-(methyloxy)pyridin-2-yl]methyl 4-[1-(2-chlorophenyl)-3-(trifluoromethyl)-1H-pyrazol-5-yl]benzoate; MS (ES): 516 [M+H]+;

2-(propylthio)ethyl 4-[1-(2-chlorophenyl)-3-(trifluoromethyl)-1H-pyrazol-5-yl]benzoate; MS (ES): 469 [M+H]+;

furan-3-ylmethyl 4-[1-(2-chlorophenyl)-3-(trifluoromethyl)-1H-pyrazol-5-yl]benzoate; MS (ES): 447 [M+H]+;

(2,4-difluorophenyl)methyl 4-[1-(2-chlorophenyl)-3-(trifluoromethyl)-1H-pyrazol-5-yl]benzoate; MS (ES): 493 [M+H]+;

furan-2-ylmethyl 4-[1-(2-chlorophenyl)-3-(trifluoromethyl)-1H-pyrazol-5-yl]benzoate; MS (ES): 447 [M+H]+;

2-(2-methylphenyl)ethyl 4-[1-(2-chlorophenyl)-3-(trifluoromethyl)-1H-pyrazol-5-yl]benzoate; MS (ES): 485 [M+H]+;

2-[3-(trifluoromethyl)phenyl]ethyl 4-[1-(2-chlorophenyl)-3-(trifluoromethyl)-1H-pyrazol-5-yl]benzoate; MS (ES): 539 [M+H]+;

3-(methylthio)propy 4-[1-(2-chlorophenyl)-3-(trifluoromethyl)-1H-pyrazol-5-yl]benzoate; MS (ES): 455 [M+H]+;

2-oxo-2-phenylethyl 4-[1-(2-chlorophenyl)-3-(trifluoromethyl)-H-1-pyrazol-5-yl]benzoate; MS (ES): 485 [M+H]+;

pyridin-3-ylmethyl 4-[1-(2-chlorophenyl)-3-(trifluoromethyl)-1H-pyrazol-5-yl]benzoate; MS (ES): 458 [M+H]+;

2-(phenylsulfonyl)ethyl 4-[1-(2-chlorophenyl)-3-(trifluoromethyl)-1H-pyrazol-5-yl]benzoate; MS (ES): 535 [M+H]+;

(2,5-dichlorophenyl)methyl 4-[1-(2-chlorophenyl)-3-(trifluoromethyl)-1H-pyrazol-5-yl]benzoate; MS (ES): 525 [M+H]+;

[4-(methylthio)phenyl]methyl 4-[1-(2-chlorophenyl)-3-(trifluoromethyl)-1H-pyrazol-5-yl]benzoate; MS (ES): 503 [M+H]+;

cyanomethyl 4-[1-(2-chlorophenyl)-3-(trifluoromethyl)-1H-pyrazol-5-yl]benzoate; MS (ES): 406 [M+H]+;

3-[3-(trifluoromethyl)-1H-pyrazol-4-yl]propyl 4-[1-(2-chlorophenyl)-3-(trifluoromethyl)-1H-pyrazol-5-yl]benzoate; MS (ES): 543 [M+H]+;

2-isoxazol-4-ylethyl 4-[1-(2-chlorophenyl)-3-(trifluoromethyl)-1H-pyrazol-5-yl]benzoate; MS (ES): 462 [M+H]+;

2-(2-thienyl)ethyl-4-[1-(2-chlorophenyl)-3-(trifluoromethyl)-1H-pyrazol-5-yl]benzoate; MS (ES): 477 [M+H]+;

(5-methyl-1-phenyl-1H-pyrazol-4-yl)methyl 4-[1-(2-chlorophenyl)-3-(trifluoromethyl)-1H-pyrazol-5-yl]benzoate; MS (ES): 537 [M+H]+;

2,2'-bithien-5-ylmethyl 4-[1-(2-chlorophenyl)-3-(trifluoromethyl)-1H-pyrazol-5-yl]benzoate; MS (ES): 545 [M+H]+;

3-pyridin-2-ylpropyl 4-[1-(2-chlorophenyl)-3-(trifluoromethyl)-1H-pyrazol-5-yl]benzoate; MS (ES): 486 [M+H]+;

2-(methylthio)ethyl 4-[1-(2-chlorophenyl)-3-(trifluoromethyl)-1H-pyrazol-5-yl]benzoate; MS (ES): 441 [M+H]+;

pyridin-4-ylmethyl 4-[1-(2-chlorophenyl)-3-(trifluoromethyl)-1H-pyrazol-5-yl]benzoate; MS (ES): 458 [M+H]+;

1,3-benzothiazol-2-ylmethyl 4-[1-(2-chlorophenyl)-3-(trifluoromethyl)-1H-pyrazol-5-yl]benzoate; MS (ES): 514 [M+H]+;

3-thienylmethyl 4-[1-(2-chlorophenyl)-3-(trifluoromethyl)-1H-pyrazol-5-yl]benzoate; MS (ES): 463 [M+H]+;

2-[(4-methylphenyl)sulfonyl]ethyl 4-[1-(2-chlorophenyl)-3-(trifluoromethyl)-1H-pyrazol-5-yl]benzoate; MS (ES): 549 [M+H]+;

2-(4-methyl-1,3-thiazol-5-yl)ethyl 4-[1-(2-chlorophenyl)-3-(trifluoromethyl)-1H-pyrazol-5-yl]benzoate; MS (ES): 492 [M+H]+;

(2-phenyl-1,3-thiazol-4-yl)methyl 4-[1-(2-chlorophenyl)-3-(trifluoromethyl)-1H-pyrazol-5-yl]benzoate; MS (ES): 540 [M+H]+;

2-cyanoethyl 4-[1-(2-chlorophenyl)-3-(trifluoromethyl)-1H-pyrazol-5-yl]benzoate; MS (ES): 420 [M+H]+;

4-[1-(2-chlorophenyl)-3-(trifluoromethyl)-1H-pyrazol-5-yl]benzoic hydroxyacetic anhydride; MS (ES): 425 [M+H]+;

[1-(phenylmethyl)-1H-imidazol-2-yl]methyl 4-[1-(2-chlorophenyl)-3-(trifluoromethyl)-1H-pyrazol-5-yl]benzoate; MS (ES): 537 [M+H]+;

(5-methyl-3-phenylisoxazol-4-yl)methyl 4-[1-(2-chlorophenyl)-3-(trifluoromethyl)-1H-pyrazol-5-yl]benzoate; MS (ES): 538 [M+H]+;

[4-(1H-pyrazol-1-yl)phenyl]methyl 4-[1-(2-chlorophenyl)-3-(trifluoromethyl)-1H-pyrazol-5-yl]benzoate; MS (ES): 523 [M+H]+;

[2,3-bis(methyloxy)phenyl]methyl 4-[1-(2-chlorophenyl)-3-(trifluoromethyl)-1H-pyrazol-5-yl]benzoate; MS (ES): 517 [M+H]+;

(5-methyl-2-phenyl-2H-1,2,3-triazol-4-yl)methyl 4-[1-(2-chlorophenyl)-3-(trifluoromethyl)-1H-pyrazol-5-yl]benzoate; MS (ES): 538 [M+H]+;

[4-(1H-1,2,4-triazol-1-yl)phenyl]methyl 4-[1-(2-chlorophenyl)-3-(trifluoromethyl)-1H-pyrazol-5-yl]benzoate; MS (ES): 524 [M+H]+;

[6-(phenyloxy)pyridin-3-yl]methyl 4-[1-(2-chlorophenyl)-3-(trifluoromethyl)-1H-pyrazol-5-yl]benzoate; MS (ES): 550 [M+H]+;

2-{[4-(trifluoromethyl)pyridin-2-yl]oxy}ethyl 4-[1-(2-chlorophenyl)-3-(trifluoromethyl)-1H-pyrazol-5-yl]benzoate; MS (ES): 556 [M+H]+;

2-(3-methyl-5-oxo-4,5-dihydro-1H-pyrazol-4-yl)ethyl 4-[1-(2-chlorophenyl)-3-(trifluoromethyl)-1H-pyrazol-5-yl]benzoate; MS (ES): 491 [M+H]+;

(2-butyl-5-chloro-1H-imidazol-4-yl)methyl 4-[1-(2-chlorophenyl)-3-(trifluoromethyl)-1H-pyrazol-5-yl]benzoate; MS (ES): 537 [M+H]+;

(5-pyridin-2-yl-2-thienyl)methyl 4-[1-(2-chlorophenyl)-3-(trifluoromethyl)-1H-pyrazol-5-yl]benzoate; MS (ES): 540 [M+H]+;

(5-methyl-1H-imidazol-4-yl)methyl 4-[1-(2-chlorophenyl)-3-(trifluoromethyl)-1H-pyrazol-5-yl]benzoate; MS (ES): 461 [M+H]+;

3-pyridin-3-ylpropyl 4-[1-(2-chlorophenyl)-3-(trifluoromethyl)-1H-pyrazol-5-yl]benzoate; MS (ES): 486 [M+H]+;

2-[(2-methylpropyl)thio]ethyl 4-[1-(2-chlorophenyl)-3-(trifluoromethyl)-1H-pyrazol-5-yl]benzoate; MS (ES): 483 [M+H]+;

[5-(2-methyl-1,3-thiazol-4-yl)-2-thienyl]methyl 4-[1-(2-chlorophenyl)-3-(trifluoromethyl)-1H-pyrazol-5-yl]benzoate; MS (ES): 560 [M+H]+;

2-(2-chlorophenyl)ethyl 4-[1-(2-chlorophenyl)-3-(trifluoromethyl)-1H-pyrazol-5-yl]benzoate; MS (ES): 505 [M+H]+;

pyridin-2-ylmethyl 4-[1-(2-chlorophenyl)-3-(trifluoromethyl)-1H-pyrazol-5-yl]benzoate; MS (ES): 458 [M+H]+;

1H-imidazol-4-ylmethyl 4-[1-(2-chlorophenyl)-3-(trifluoromethyl)-1H-pyrazol-5-yl]benzoate; MS (ES): 447 [M+H]+;

(2-methylpyridin-3-yl)methyl 4-[1-(2-chlorophenyl)-3-(trifluoromethyl)-1H-pyrazol-5-yl]benzoate; MS (ES): 472 [M+H]+;

[1-(phenylsulfonyl)-1H-indol-3-yl]methyl 4-[1-(2-chlorophenyl)-3-(trifluoromethyl)-1H-pyrazol-5-yl]benzoate; MS (ES): 636 [M+H]+;

2-(1H-imidazol-1-yl)ethyl 4-[1-(2-chlorophenyl)-3-(trifluoromethyl)-1H-pyrazol-5-yl]benzoate; MS (ES): 461 [M+H]+;

2-(diethylamino)ethyl 4-[1-(2-chlorophenyl)-3-(trifluoromethyl)-1H-pyrazol-5-yl]benzoate; MS (ES): 466 [M+H]+;

N-({4-[1-(2-chlorophenyl)-3-(trifluoromethyl)-1H-pyrazol-5-yl]phenyl}carbonyl)glycine, MS(ES): 424 [M+H]+.

N-({4-[1-(2-chlorophenyl)-3-(trifluoromethyl)-1H-pyrazol-5-yl]phenyl}carbonyl)-beta-alanine, MS(ES): 438 [M+H]+.

Example 76

Preparation of 3-(methylsulfonyl)propyl 4-(1-(2-chlorophenyl)-3-(trifluoromethyl)-1H-pyrazol-5-yl)benzoate

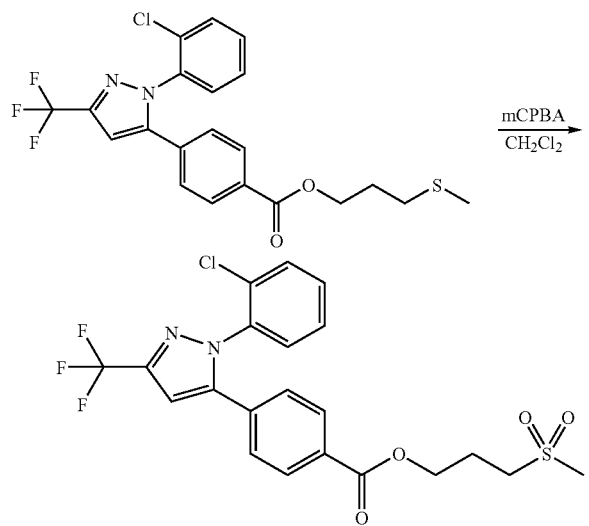

To a solution of 3-(methylthio)propyl 4-(1-(2-chlorophenyl)-3-(trifluoromethyl)-1H-pyrazol-5-yl)benzoate (382 mg, 0.84 mmol) in CH$_2$Cl$_2$ (10 mL) was added 3-chloroperoxybenzoic acid (429 mg of 77% technical grade, 1.9 mmol). After stirring at ambient temperature for 1 hour LC/MS indicated complete conversion to product. At this time the reaction was quenched by the addition of 10% aqueous sodium thiosulfate solution and saturated aqueous NaHCO$_3$. The basic aqueous was extracted with CH$_2$Cl$_2$ (3×). The combined organic extracts were dried over Na$_2$SO$_4$, filtered and the filtrate concentrated under reduced pressure to afford a thin film. This crude product was purified by flash column chromatography eluting with a gradient from 0% to 100% EtOAc/hexane to afford 3-(methylsulfonyl)propyl 4-(1-(2-chlorophenyl)-3-(trifluoromethyl)-1H-pyrazol-5-yl)benzoate (345 mg, 84% yield) as a sticky white solid. $^1$H NMR (400 MHz CDCl$_3$): δ 7.98-7.91 (2H, m), 7.50 (1H, m), 7.48-7.36 (3H, m), 7.33-7.27 (2H, m), 6.88 (1H, s), 4.77 (2H, t), 3.45 (2H, t), 3.00 (3H, s). MS(ES): 487 [M+H]+.

Example 77

Preparation of 2-(4-chloro-5-{5-[3-(methylsulfonyl)phenyl]-2-thienyl}-1-[2-(trifluoromethyl)pyridin-3-yl]-1H-pyrazol-3-yl)propan-2-ol

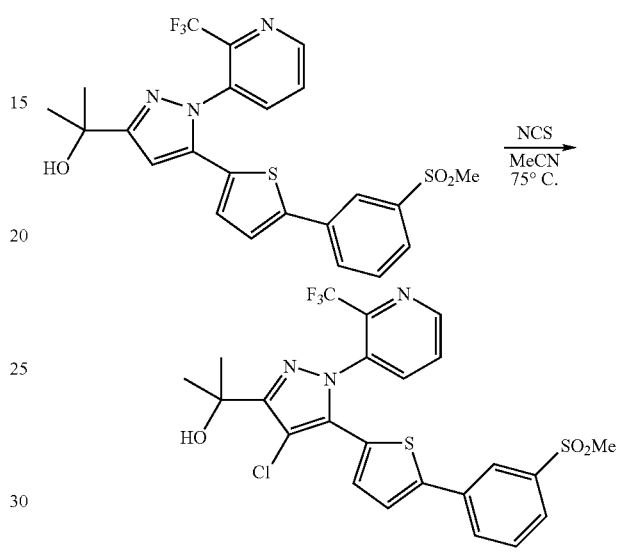

To a solution of 2-(5-(5-(3-(methylsulfonyl)phenyl)thiophen-2-yl)-1-(2-(trifluoromethyl)-pyridin-3-yl)-1H-pyrazol-3-yl)propan-2-ol (10.6 g, 21 mmol) in MeCN (200 mL) was added N-chlorosuccinimide. The resulting solution was heated to 75° C. in a heating mantle. After stirring for 3 hours at 75° C. heating was discontinued and the solution was concentrated under reduced pressure to afford a yellow foam. This crude product was purified by flash column chromatography eluting with a gradient from 0% to 100% EtOAc/hexane. Fractions that Were pure by TLC analysis were combined and concentrated under reduced pressure to afford a white sticky foam that was contaminated with succinimide as evidenced by NMR analysis. This material was taken up in CH$_2$Cl$_2$ and washed with saturated aqueous Na$_2$CO$_3$ (2×). The organic layer was dried over Na$_2$SO$_4$, filtered and concentrated under reduced pressure to afford 2-(4-chloro-5-{5-[3-(methylsulfonyl)phenyl]-2-thienyl}-1-[2-(trifluoromethyl)pyridin-3-yl]-1H-pyrazol-3-yl)propan-2-ol (6.7 g, 60% yield) as an off-white foam. $^1$H NMR (400 MHz CDCl$_3$): δ 8.85 (1H, m), 8.06 (1H, t), 7.86 (1H, m), 7.82-7.73 (2H, m), 7.67-7.62 (1H, m), 7.58 (1H, t), 7.28 (1H, d), 7.01 (1H, d), 3.08 (3H, s), 2.93 (1H, s), 1.73 (6H, s). MS(ES): 542 [M+H]+.

The following compounds are prepared essentially according to the previous examples:

2-(4-chloro-5-{3-methyl-5-[3-(methylsulfonyl)phenyl]-2-thienyl}-1-[2-(trifluoromethyl)pyridin-3-yl]-1H-pyrazol-3-yl)propan-2-ol, MS(ES): 556 [M+H]+.

2-{4-chloro-1-(2,6-dichlorophenyl)-5-[3-methyl-3'-(methylsulfonyl)biphenyl-4-yl]-1H-pyrazol-3-yl}propan-2-ol, MS(ES): 549 [M+H]+.

2-{4-chloro-5-[3-methyl-3'-(methylsulfonyl)biphenyl-4-yl]-1-[2-(trifluoromethyl)pyridin-3-yl]-1H-pyrazol-3-yl}propan-2-ol, MS(ES): 550 [M+H]+.

2-{4-chloro-5-[3-methyl-3'-(methylsulfonyl)biphenyl-4-yl]-1-[4-(trifluoromethyl)pyridin-3-yl]-1H-pyrazol-3-yl}propan-2-ol MS(ES): 550 [M+H]+.

2-{4-chloro-5-[3'-(methylsulfonyl)biphenyl-4-yl]-1-[4-(trifluoromethyl)pyridin-3-yl]-1H-pyrazol-3-yl}propan-2-ol MS(ES): 536 [M+H]+.

2-{4-chloro-1-(2,6-dichlorophenyl)-5-[3'-(methylsulfonyl)biphenyl-4-yl]-1H-pyrazol-3-yl}propan-2-ol MS(ES): 537 [M+H]+.

2-{4-chloro-5-[3-chloro-3'-(methylsulfonyl)biphenyl-4-yl]-1-(2,6-dichlorophenyl)-1H-pyrazol-3-yl}propan-2-ol MS(ES): 571 [M+H]+.

2-{4-chloro-5-[3-chloro-3'-(methylsulfonyl)biphenyl-4-yl]-1-[2-(trifluoromethyl)pyridin-3-yl]-1H-pyrazol-3-yl}propan-2-ol MS(ES): 570 [M+H]+.

Example 78

Preparation of azetidin-1-yl(4-(1-(2-chlorophenyl)-3-(2-hydroxypropan-2-yl)-1H-pyrazol-5-yl)-phenyl)methanone

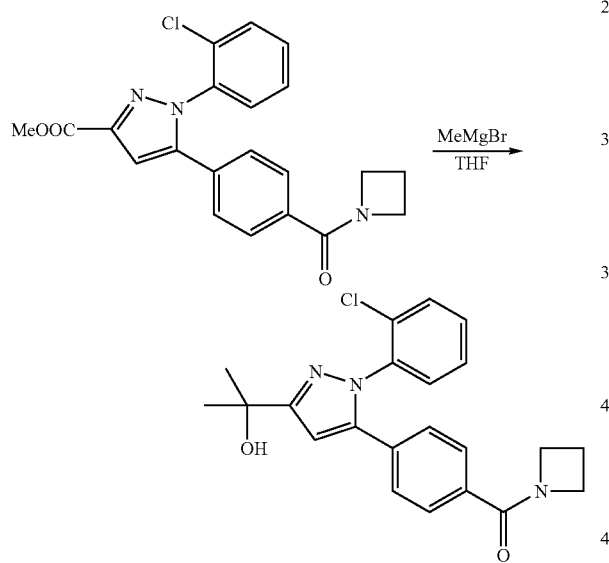

To a cooled (−78° C.) solution of methyl 5-(4-(azetidine-1-carbonyl)phenyl)-1-(2-chlorophenyl)-1H-pyrazole-3-carboxylate (138 mg, 0.35 mmol) in THF (5 mL) was added methylmagnesium bromide (0.3 mL of a 3.0M solution in ether, 0.9 mmol). The resulting brown solution was allowed to slowly warm to ambient temperature overnight. The reaction was then quenched by the addition of saturated aqueous ammonium chloride solution and EtOAc. The aqueous was extracted with EtOAc (3×) and the combined organic extracts were washed with brine, dried (Na2SO4), filtered and concentrated under reduced pressure to afford a yellow film. This crude product was purified by flash column chromatography eluting with a gradient of 0% to 10% MeOH in CH2Cl2. The main peak was collected and was ~85% pure by HPLC. This material was further purified by reverse phase preparative HPLC eluting with MeCN/H2O with 0.1% TFA. The product fractions from the HPLC were made basic by the careful addition of solid Na2CO3. The resulting mixture was concentrated to remove most of the MeCN. The resulting aqueous suspension was extracted with CH2Cl2 (3×), and the combined extracts were dried over Na2SO4 overnight, filtered and concentrated under reduced pressure to afford azetidin-1-yl(4-(1-(2-chlorophenyl)-3-(2-hydroxypropan-2-yl)-1H-pyrazol-5-yl)phenyl)methanone (43 mg, 31% yield) as a pale brown powder. 1H NMR (400 MHz CDCl3): δ 7.54-7.48 (2H, m), 7.46-7.40 (2H, m), 7.39-731 (2H, m), 7.24-7.19 (2H, m), 6.54 (1H, s), 4.32-4.16 (4H, m), 2.63 (1H, s), 2.38-2.28 (2H, m), 1.68 (6H, s). MS(ES): 396 [M+H]+.

The following compounds are prepared essentially according to the previous examples:

2-{1-(2-chlorophenyl)-5-[4-(pyrrolidin-1-ylcarbonyl)phenyl]-1H-pyrazol-3-yl}propan-2-ol, MS(ES): 410 [M+H]+.

Example 79

2-[1-(2-chlorophenyl)-5-{5-[3-(methylsulfonyl)phenyl]pyridin-2-yl}-1H-pyrazol-3-yl]propan-2-ol Example 79a Preparation of methyl 5-(5-bromopyridin-2-yl)-1-(2-chlorophenyl)-1H-pyrazole-3-carboxylate

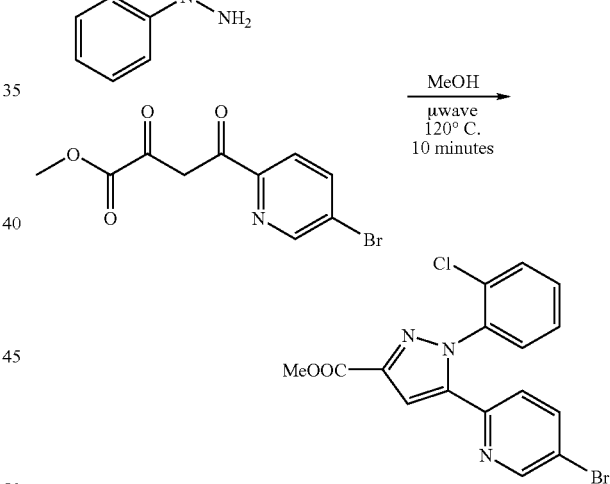

A mixture of (2-chlorophenyl)hydrazine hydrochloride (1.1 g, 6.1 mmol) and methyl 4-(5-bromopyridin-2-yl)-2,4-dioxobutanoate (1.7 g, 6.0 mmol) in MeOH (30 mL) was divided into two microwave reaction vessels. Each reaction vessel was then heated in the microwave at 120° C. for ten minutes. LC/MS analysis at this time showed the reaction to be essentially complete. The solutions were concentrated under reduced pressure to afford a dark brown semi-solid. This material was taken up in EtOAc and saturated aqueous NaHCO3. The layers were separated and the basic aqueous was extracted with EtOAc (3×). Combined organic extracts were washed with brine, dried over Na2SO4, filtered and concentrated to afford a dark oil. This crude product was purified by flash column chromatography eluting with a gradient from 0% to 100% EtOAc in hexane to afford methyl 5-(5-bromopyridin-2-yl)-1-(2-chlorophenyl)-1H-pyrazole-3-carboxylate (300 mg, 13% yield) as an oil.

Example 79b

Preparation of methyl 1-(2-chlorophenyl)-5-(5-(3-(methylsulfonyl)phenyl)pyridin-2-yl)-1H-pyrazole-3-carboxylate

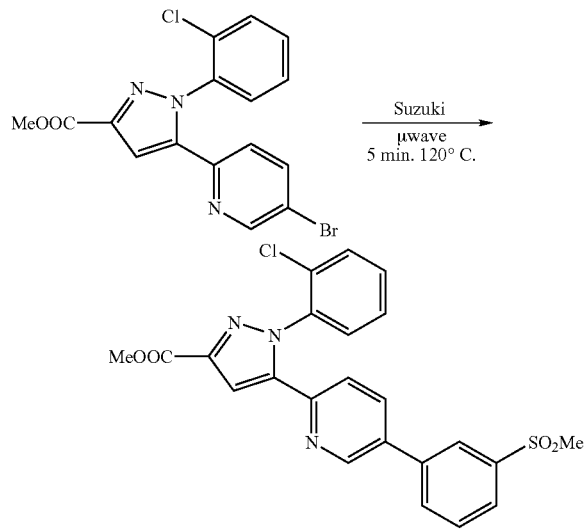

Methyl 5-(5-bromopyridin-2-yl)-1-(2-chlorophenyl)-1H-pyrazole-3-carboxylate (200 mg, 0.51 mmol), 3-(methylsulfonyl)phenylboronic acid (120 mg, 0.60 mmol) and dichloro[1,1'-bis(diphenylphosphino)ferrocene]palladium (11) dichloromethane adduct (20 mg, 24 µmol), and $K_2CO_3$ (0.45 mL of a 3.5M aqueous solution, 1.6 mmol) were combined in DME (2.5 mL) in a microwave reaction vessel. The dark mixture was heated at 120° C. for 5 minutes. The reaction mixture was diluted with EtOAc and $H_2O$. The aqueous layer was removed and extracted with additional EtOAc. The combined organics were dried over $Na_2SO_4$, treated with some decolorizing carbon and filtered through a pad of Celite. Concentration of the filtrates under reduced pressure and purification by flash column chromatography eluting with 0% to 50% $MeCN/CH_2Cl_2$ afforded methyl 1-(2-chlorophenyl)-5-(5-(3-(methylsulfonyl)phenyl)pyridin-2-yl)-1H-pyrazole-3-carboxylate as a pale yellow foam. This material was carried on to the subsequent step. MS(ES): 468 [M+H]$^+$.

The following compounds are prepared essentially according to the previous examples:

2-[1-(2-chlorophenyl)-5-{5-[3-(methylsulfonyl)phenyl]pyridin-2-yl}-1H-pyrazol-3-yl]propan-2-ol, $^1$H NMR (400 MHz $CDCl_3$): δ 8.70 (1H, m), 8.11 (1H, m), 7.96 (1H, m), 7.87-7.80 (2H, m), 7.68 (1H, t), 7.57 (1H, m), 7.49-7.37 (3H, m), 7.32 (1H, d), 6.89 (1H, s), 3.09 (3H, s), 1.70 (6H, s). MS(ES): 468 [M+H]$^+$.

2-[1-(2-chlorophenyl)-5-{6-[3-(methylsulfonyl)phenyl]pyridin-3-yl}-1H-pyrazol-3-yl]propan-2-ol, MS(ES): 468 [M+H]$^+$.

2-[4-chloro-1-(2-chlorophenyl)-5-{5-[3-(methylsulfonyl)phenyl]pyridin-2-yl}-1H-pyrazol-3-yl]propan-2-ol, MS(ES): 502 [M+H]$^+$.

2-[4-chloro-1-(2-chlorophenyl)-5-{6-[3-(methylsulfonyl)phenyl]pyridin-3-yl}-1H-pyrazol-3-yl]propan-2-ol, MS(ES): 502 [M+H]$^+$.

Example 80

Preparation of (1-(2,6-dichlorophenyl)-5-(3-methyl-3'-(methylsulfonyl)biphenyl-4-yl)-1H-pyrazol-3-yl)(pyrrolidin-1-yl)methanone

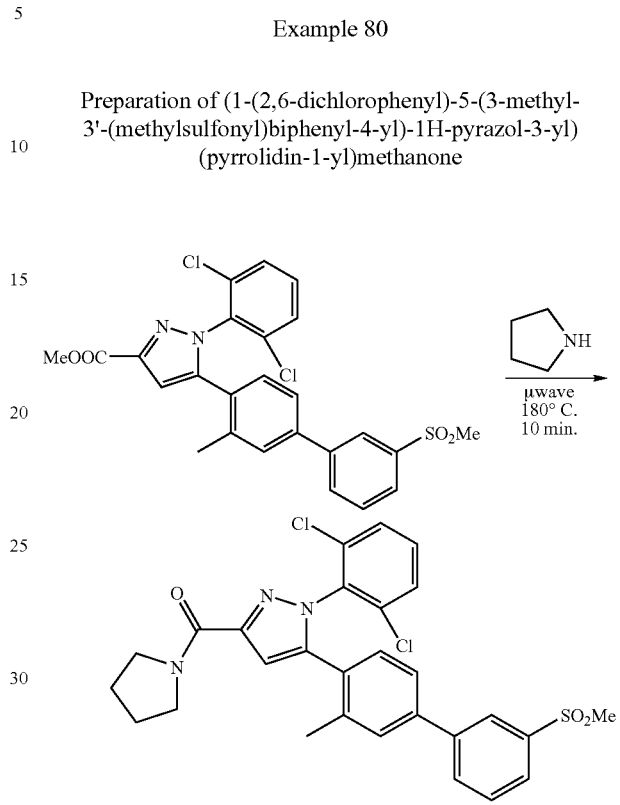

Methyl 1-(2,6-dichlorophenyl)-5-(3-methyl-3'-(methylsulfonyl)biphenyl-4-yl)-1H-pyrazole-3-carboxylate (102 mg, 0.20 mmol) was suspended in pyrrolidine (0.6 mL, 7.2 mmol) and heated in the microwave at 180° C. for 10 minutes. The dark reaction mixture was concentrated under reduced pressure and azeotroped with toluene to remove most of the pyrrolidine. The resulting crude product was purified by preparative reverse phase HPLC eluting with $MeCN/H_2O$ with 0.05% TFA. The product fractions from the HPLC were made basic by the careful addition of saturated aqueous $NaHCO_3$. The resulting mixture was concentrated to remove most of the MeCN. The resulting aqueous suspension was extracted with $CH_2Cl_2$ (3×), and the combined extracts were dried over $Na_2SO_4$ overnight, filtered and concentrated under reduced pressure to afford (1-(2,6-dichlorophenyl)-5-(3-methyl-3'-(methylsulfonyl)biphenyl-4-yl)-1H-pyrazol-3-yl)(pyrrolidin-1-yl)methanone (15 mg, 14% yield) as a brown solid. $^1$H NMR (400 MHz $CDCl_3$): δ 8.10 (1H, m), 7.91 (1H, m), 7.83 (1H, m), 7.62 (1H, t), 7.49 (1H, d), 7.42-7.34 (2H, m), 7.33-7.21 (2H, m), 7.13 (1H, d), 7.06 (1H, s), 3.99 (2H, t), 3.71 (2H, t), 3.08 (3H, s), 2.50 (3H, s), 2.03-1.86 (4H, m). MS(ES): 554 [M+H]$^+$.

The following compounds are prepared essentially according to the previous examples:

5-[3-chloro-3'-(methylsulfonyl)biphenyl-4-yl]-1-(2,6-dichlorophenyl)-3-(pyrrolidin-1-ylcarbonyl)-1H-pyrazole MS(ES): 576 [M+H]$^+$.

5-[3-chloro-3'-(methylsulfonyl)biphenyl-4-yl]-N-(2-methylpropyl)-1-[2-(trifluoromethyl)pyridin-3-yl]-1H-pyrazole-3-carboxamide MS(ES): 577 [M+H]$^+$.

5-[3-chloro-3'-(methylsulfonyl)biphenyl-4-yl]-1-(2,6-dichlorophenyl)-N-(2-methylpropyl)-1H-pyrazole-3-carboxamide MS(ES): 578 [M+H]+.

Example 81

(E)-3-(4-(1-(2,6-dichlorophenyl)-3-(2-hydroxypropan-2-yl)-1H-pyrazol-5-yl)-3-methylstyryl)benzoic acid Example 81a Preparation of 4-(1-(2,6-dichlorophenyl)-3-(2-hydroxypropan-2-yl)-1H-pyrazol-5-yl)-3-methylbenzaldehyde

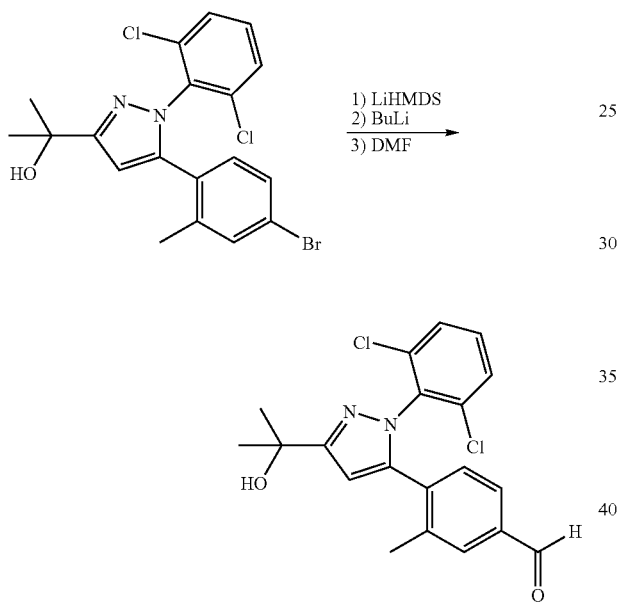

To a cold (−78° C.) solution of 2-(5-(4-bromo-2-methylphenyl)-1-(2,6-dichlorophenyl)-1H-pyrazol-3-yl)propan-2-ol (215 mg, 0.49 mmol) in a mixture of THF (4 mL) and Et₂O (4 mL) was added lithium bis(trimethylsilyl)amide (0.5 mL of a 1.0M solution in THF, 0.5 mmol). After several minutes stirring at −78° C. the resulting alkoxide solution was treated with n-butyllithium (1.0 mL of a 1.6M solution in hexane, 1.6 mmol). After 10 minutes stirring at −78° C., LC/MS showed some starting bromide present in a quenched aliquot of the reaction. After 30 minutes additional n-butyllithium was added (0.5 mL of a 1.6M solution in hexane, 0.8 mmol). After an additional 15 minutes stirring at −78° C. the reaction mixture was treated with dry N,N-dimethylformamide (0.4 mL, 5.2 mmol). Several minutes after the addition of the DMF, the −78° C. bath was replaced with an ice bath and the reaction mixture was allowed to come to ambient temperature overnight. The reaction was quenched by the addition of saturated NH4Cl and diluted with EtOAc. The layers were separated and the aqueous was extracted with EtOAc (3×). Combined organic extracts were washed with brine, dried (Na₂SO₄), filtered and concentrated under reduced pressure to afford a yellow syrup. The crude product was purified by flash column chromatography eluting with 0% to 100% EtOAc/hexane to afford 4-(1-(2,6-dichlorophenyl)-3-(2-hydroxypropan-2-yl)-1H-pyrazol-5-yl)-3-methylbenzaldehyde which was carried on to the next step without further purification. MS(ES): 389 [M+H]+.

Example 81b

Preparation of (E)-methyl 3-(4-(1-(2,6-dichlorophenyl)-3-(2-hydroxypropan-2-yl)-1H-pyrazol-5-yl)-3-methylstyryl)benzoate

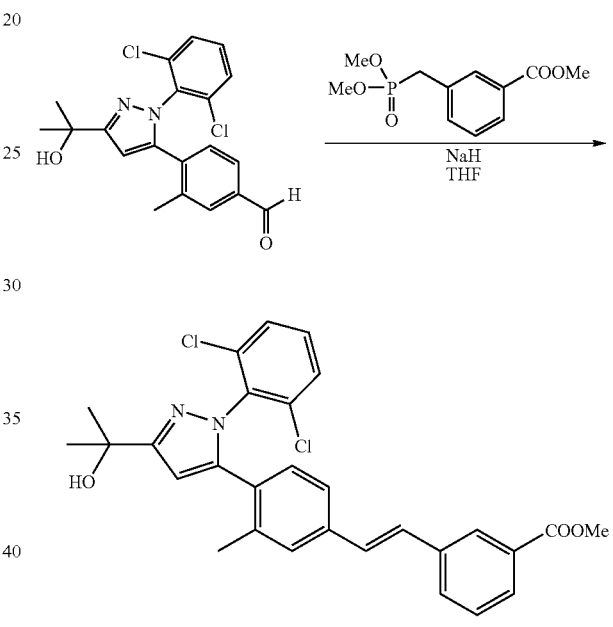

To a suspension of NaH (52 mg of a 60% dispersion in mineral oil) in THF (7.5 mL) cooled to 0° C. in an ice bath was added methyl 3-((dimethoxyphosphoryl)methyl)benzoate as a solution in THF (1 mL) followed by a THF (1 mL) rinse of the phosphonate vial and syringe to insure complete transfer. The ice bath was removed and the reaction was allowed to warm to ambient temperature. After 90 minutes at ambient temperature, 4-(1-(2,6-dichlorophenyl)-3-(2-hydroxypropan-2-yl)-1H-pyrazol-5-yl)-3-methylbenzaldehyde (0.49 mmol impure from previous step) was added via cannula to the reaction mixture followed by a THF (1 mL) rinse of the flask and cannula after 1 hour-45 minutes at ambient temperature the reaction was quenched by addition of saturated aqueous NH4Cl and EtOAc. The layers were separated and the aqueous was extracted with EtOAc (3×). Combined organic extracts were washed with brine, dried (Na₂SO₄), filtered and concentrated under reduced pressure to afford a yellow syrup. The crude product was purified by flash column chromatography eluting with a gradient from 0% to 40% MeCN/CH₂Cl₂ to afford (E)-methyl 3-(4-(1-(2,6-dichlorophenyl)-3-(2-hydroxypropan-2-yl)-1H-pyrazol-5-yl)-3-methylstyryl)benzoate (180 mg, 70% yield) of slightly impure product. This material was carried on to the ester hydrolysis without further purification. MS(ES): 521 [M+H]+.

Example 81c

Preparation of (E)-3-(4-(1-(2,6-dichlorophenyl)-3-(2-hydroxypropan-2-yl)-1H-pyrazol-5-yl)-3-methylstyryl)benzoic acid

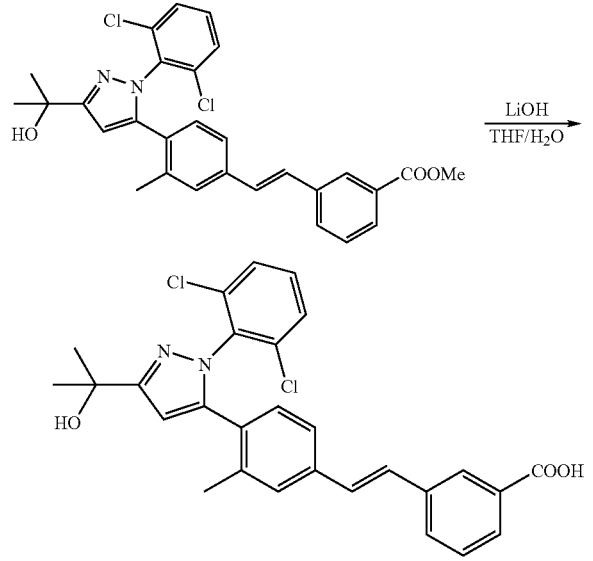

To a solution of (E)-methyl 3-(4-(1-(2,6-dichlorophenyl)-3-(2-hydroxypropan-2-yl)-1H-pyrazol-5-yl)-3-methylstyryl)benzoate (180 mg of impure material from previous step, 0.35 mmol) in THF (2.0 mL) was added H2O (0.4 mL) followed by lithium hydroxide monohydrate (25.3 mg, 0.6 mmol). After stirring for 1 hour at ambient temperature a biphasic mixture had formed, and LC/MS analysis of the reaction showed no reaction. a small amount of MeOH was added to homogenize the mixture, and the reaction was then heated to 50° C. in an oil bath. After 2 hours stirring at 50° C., LC/MS analysis showed the reaction to be complete. Heating was discontinued, and after stirring at ambient temperature overnight, the reaction was quenched by the addition of 5% aqueous citric acid, and EtOAc. The layers were separated and the aqueous was extracted with EtOAc (3×). Combined organic extracts were washed with brine, dried (Na2SO4), filtered and concentrated under reduced pressure to afford a clear film. This material was purified by reverse phase preparative HPLC eluting with a gradient of MeCN/H2O with 0.05% TFA. The major peak from the HPLC was concentrated under reduced pressure to remove most of the solvents, and the resulting acidic aqueous was extracted with CH2Cl2 (3×). The combined organic extracts were washed with H2O until the washings were no longer acidic (2×), dried over Na2SO4, filtered, and concentrated under reduced pressure to afford (E)-3-(4-(1-(2,6-dichlorophenyl)-3-(2-hydroxypropan-2-yl)-1H-pyrazol-5-yl)-3-methylstyryl)benzoic acid (45.4 mg, 26% yield) as a white powder. 1H NMR (400 MHz CDCl3): δ 821 (1H, s), 7.98 (1H, d, 7.69 (1H, d), 7.45 (1H, t), 7.39 (1H, d), 7.37-7.31 (2H, m), 7.23 (1H, m), 7.15 (1H, m), 7.12-7.07 (2H, m), 7.06 (1H, m), 6.46 (1H, s), 2.45 (3H, s), 1.71 (6H, s). MS(ES): 529 [M+H]+.

Example 82

Preparation of 2-(1-(2,6-dichlorophenyl)-5-(2-methyl-4-(2-morpholinoethylamino)phenyl)-1H-pyrazol-3-yl)propan-2-ol

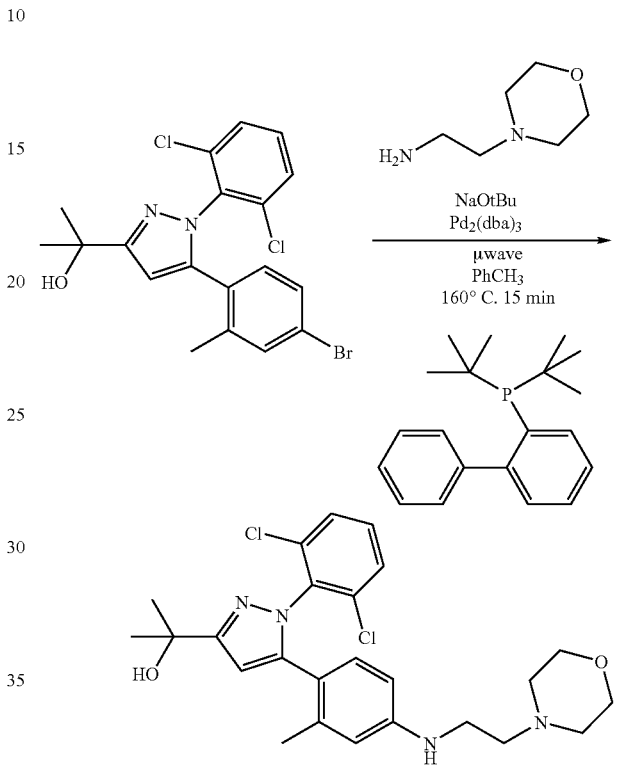

A mixture of 2-(5-(4-bromo-2-methylphenyl)-1-(2,6-dichlorophenyl)-1H-pyrazol-3-yl)propan-2-ol ((160 mg, 0.36 mmol), 2-morpholinoethanamine (75 mL, 0.57 mmol), sodium tert-butoxide (54 mg, 0.57 mmol), biphenyl-2-yldi-tert-butylphosphine (13.1 mg, 44 µmol), and Pd2(dba)3 (19.8 mg, 22 µmol) was placed in a microwave reaction vial and heated at 160° C. for 15 minutes. After cooling, the reaction was diluted with saturated aqueous NaHCO3, and EtOAc. The layers were separated and the aqueous was extracted with EtOAc (3×). Combined organic extracts were washed with brine, dried (Na2SO4), filtered and concentrated under reduced pressure to afford a dark oil. This material was purified by reverse phase preparative HPLC eluting with a gradient of MeCN/H2O with 0.05% TFA. The product peak from the HPLC was basified by addition of saturated aqueous NaHCO3, and concentrated under reduced pressure to remove most of the solvents. The basic aqueous was extracted with CH2Cl2 (3×). The combined organic extracts were dried over Na2SO4, filtered, and concentrated under reduced pressure to afford 2-(1-(2,6-dichlorophenyl)-5-(2-methyl-4-(2-morpholinoethylamino)phenyl)-1H-pyrazol-3-yl)propan-2-ol (67 mg, 38% yield) as a white foam. 1H NMR (400 MHz CDCl3): δ 7.34-7.29 (2H, m), 7.20 (1H, m), 6.84 (1H, d), 6.46 (1H, d), 6.32 (1H, s), 6.23 (1H, m), 4.32 (1H, s), 3.74-3.66 (4H, m), 3.15-3.07 (2H, m), 2.66 (1H, s), 2.63-2.55 (2H, t), 2.48-2.40 (4H, m), 2.33 (3H, s), 1.67 (6H, s). MS(ES): 489 [M+H]+.

The following compounds are prepared essentially according to the previous examples:

2-[1-(2,6-dichlorophenyl)-5-{2-methyl-4-[(2-piperidin-1-ylethyl)amino]phenyl}-1H-pyrazol-3-yl]propan-2-ol MS(ES): 487 [M+H]+.

2-[1-(2,6-dichlorophenyl)-5-(2-methyl-4-{[2-(methylsulfonyl)ethyl]amino}phenyl)-1H-pyrazol-3-yl]propan-2-ol MS(ES): 504 [M+Na]+.

2-[1-(2,6-dichlorophenyl)-5-{4-[(1,1-dioxidotetrahydro-3-thienyl)amino]-2-methylphenyl}-1H-pyrazol-3-yl]propan-2-ol MS(ES): 516 [M+Na]+.

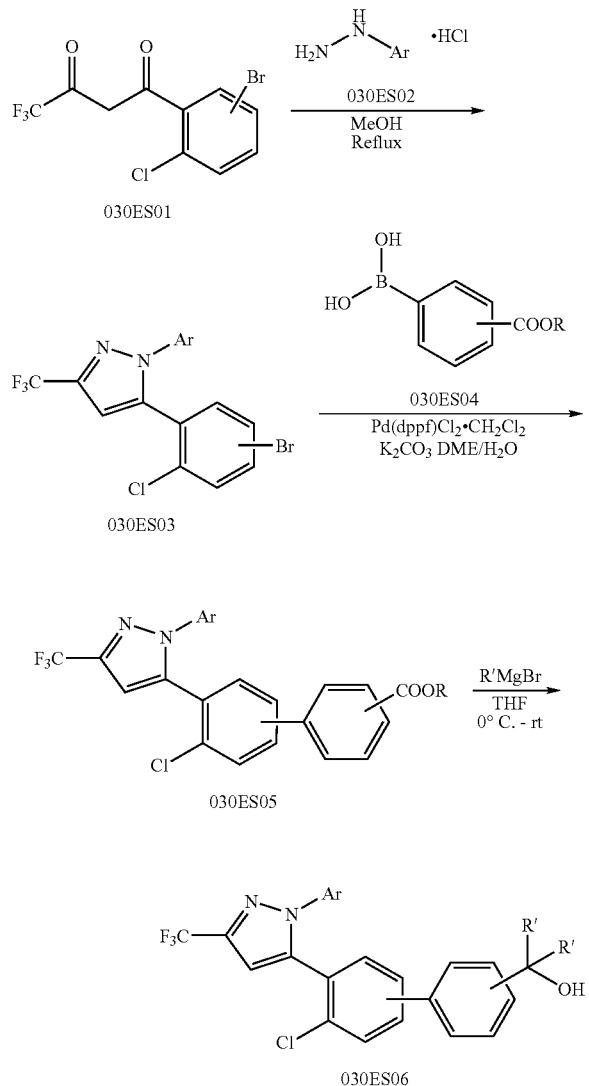

As depicted in Scheme 30, alkoxycarbonylbiphenylpyrazoles were prepared from the condensation of a hydrazine with a acetone and were further transformed into carbinols. Diketone 030ES01 can be condensed with hydrazine 030ES02 in a manner similar to Example 2c to afford pyrazole 030ES03. The resulting pyrazole can then be coupled with boronic acid 030ES04 under palladium-catalyzed coupling conditions in a manner similar to Example 1c to afford biaryl ester 030ES05. Treatment of the ester with an alkylmagnesium halide in a manner similar to Example 5 affords alcohol 030ES06.

Example 82

2-{3'-chloro-4'-[1-(2,6-dichlorophenyl)-3-(trifluoromethyl)-1H-pyrazol-5-yl]biphenyl-3-yl}propan-2-ol Example 82a Preparation of methyl 3'-chloro-4'-(1-(2,6-dichlorophenyl)-3-(trifluoromethyl)-1H-pyrazol-5-yl)biphenyl-3-carboxylate

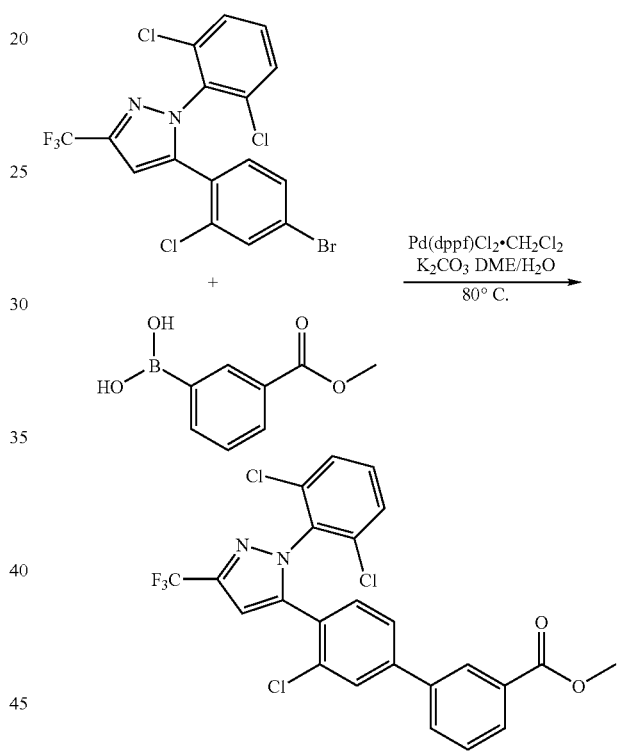

To a solution of 5-(4-bromo-2-chlorophenyl)-1-(2,6-dichlorophenyl)-3-(trifluoromethyl)-1H-pyrazole (3.55 g, 7.55 mmol) and 3-(methoxycarbonyl)phenylboronic acid (1.77 g, 9.83 mmol) in 1,2-dimethoxyethane (36 mL) was added $K_2CO_3$ (3.126 g, 22.65 mmol) and $H_2O$ (4 mL). The resulting biphasic suspension was stirred at ambient temperature and sparged with nitrogen for 10 minutes. The reaction was then treated with dichloro[1,1'-bis(diphenylphosphino)ferrocene]palladium (II) dichloromethane adduct (600 mg, 0.734 mmol) and heated to 80° C. in an oil bath. The reaction was heated at 80° C. for 10 hours and then allowed to cool to ambient temperature. The cooled reaction mixture was diluted with EtOAc and $H_2O$. The aqueous layer was extracted with EtOAc (3×). The combined organic extracts were washed with brine, dried over $Na_2SO_4$, filtered and concentrated to afford crude product as a dark oil. The crude product was purified by flash-column chromatography eluting with a gradient from 0% to 40% EtOAc/hexane to afford methyl 3'-chloro-4'-(1-(2,6-dichlorophenyl)-3-(trifluoromethyl)-1H-pyrazol-5-yl)biphenyl-3-carboxylate (3.50 g, 88% yield) solid. MS(ES): 525 [M+H]+.

Example 82b

Preparation of 2-{3'-chloro-4'-[1-(2,6-dichlorophenyl)-3-(trifluoromethyl)-1H-pyrazol-5-yl]biphenyl-3-yl}propan-2-ol

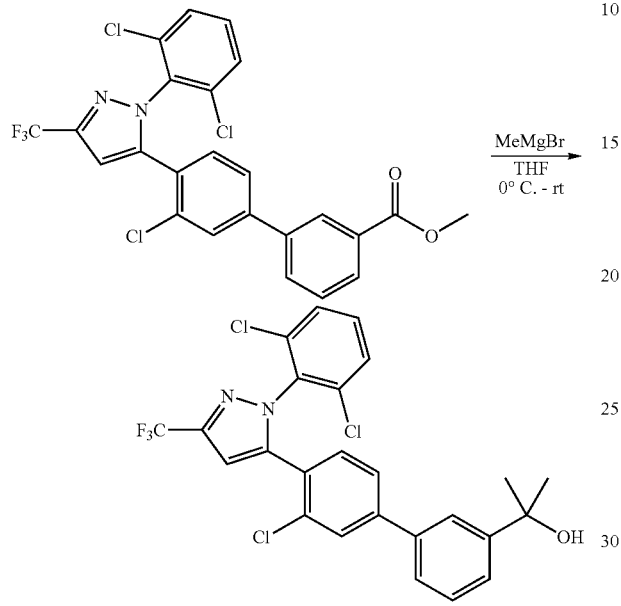

To a suspension of methyl 3'-chloro-4'-(1-(2,6-dichlorophenyl)-3-(trifluoromethyl)-1H-pyrazol-5-yl)biphenyl-3-carboxylate (1.15 g, 2.19 mmol) in dry tetrahydrofuran (10 mL) stirred at 0° C. in icebath was added methylmagnesium bromide (2.04 mL of a 3.0M solution in tetrahydrofuran, 6.12 mmol) dropwise. After adding the methylmagnesium bromide, the icebath was removed. After 2 hours stirring at ambient temperature the reaction mixture was quenched by the addition of saturated ammonium chloride and EtOAc. The aqueous layer was extracted with EtOAc (3×). The combined organic extract were dried over $Na_2SO_4$, filtered and concentrated under reduced pressure to afford brown oil. The crude product was purified by flash-column chromatography eluting with a gradient from 0% to 100% EtOAc/hexane to afford (450 mg, 39% yield) foamed white solid. MS(ES): 525 [M+H]+. 1H-NMR (CDCl3): δ 7.73-7.67 (2H, m), 7.48 (1H, m), 7.44-7.28 (6H, m), 7.19 (1H, d), 6.98 (1H, s), 1.74 (1H, s), 1.62 (6H, s).

The following compounds are prepared essentially according to the previous examples:
2-(3-{5-[1-(2-chlorophenyl)-3-(trifluoromethyl)-1H-pyrazol-5-yl]-2-thienyl}phenyl)propan-2-ol, MS(ES): 463 [M+H]+.
2-(4-{5-[1-(2-chlorophenyl)-3-(trifluoromethyl)-1H-pyrazol-5-yl]-2-thienyl}phenyl)propan-2-ol, MS(ES): 463 [M+H]+.
2-[3-(5-{3-(trifluoromethyl)-1-[3-(trifluoromethyl)pyridin-2-yl]-1H-pyrazol-5-yl}-2-thienyl)phenyl]propan-2-ol, MS(ES): 498 [M+H]+.
2-[4-(5-{3-(trifluoromethyl)-1-[3-(trifluoromethyl)pyridin-2-yl]-1H-pyrazol-5-yl}-2-thienyl)phenyl]propan-2-ol, MS(ES): 498 [M+H]+.

Scheme 31

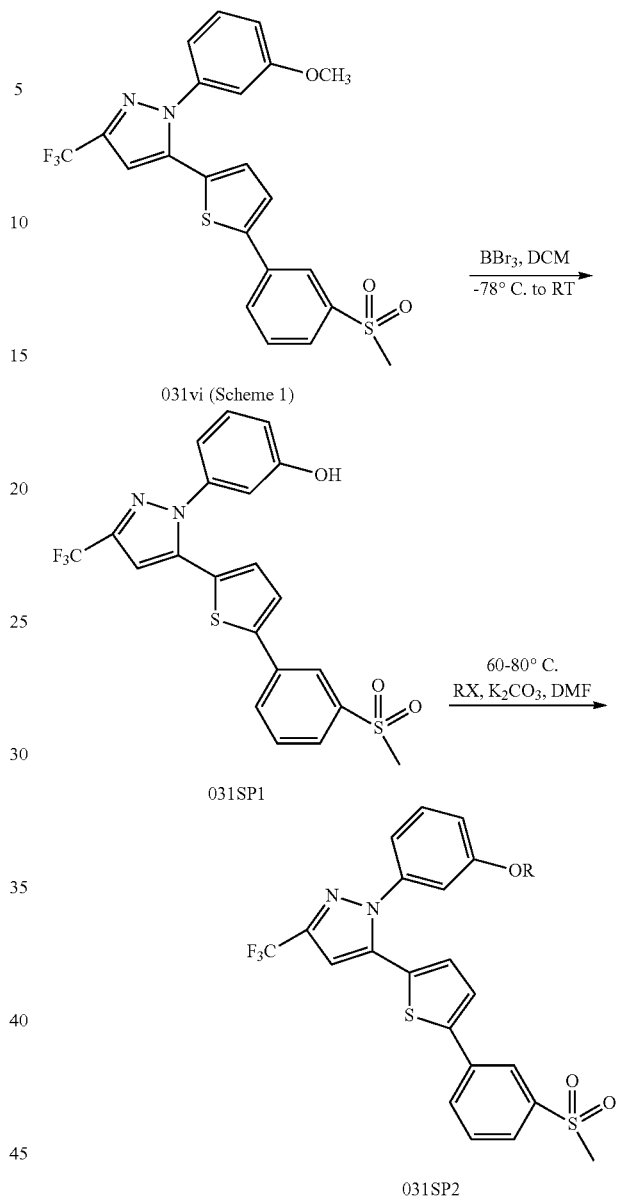

As depicted in Scheme 31, 3-methoxy substituted pyrazole (031vi) prepared as described in Scheme 1 was transformed into phenol 031SP1, which was treated with alkyl halide in the presence of a base to afford 3-alkoxy substituted pyrazole 031SP2.

Example 83

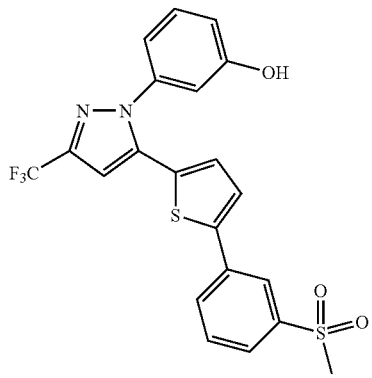 [SMILES: CS(=O)(=O)c1cccc(-c2ccc(-c3cc(C(F)(F)F)nn3-c3cccc(O)c3)s2)c1]

Preparation of 3-(5-(5-(3-(methylsulfonyl)phenyl)thiophen-2-yl)-3-(trifluoromethyl)-1H-pyrazol-1-yl)phenol 1-(3-methoxyphenyl)-5-(5-(3-(methylsulfonyl)phenyl)thiophen-2-yl)-3-(trifluoromethyl)-1H-pyrazole (031vi) was prepared as described in Scheme 1. A solution of 1.0 M boron tribromide (59.33 mL, 59.33 mmol) in anhydrous DCM was slowly added to a solution of the 3-methoxy substituted pyrazole (9.464 g, 19.78 mmol) in 20 mL of anhydrous DCM at −78° C. under nitrogen. The mixture was vigorously stirred and allowed to warn to ambient temperature overnight. The reaction mixture was then cooled to 0° C. with an ice/water bath and about 50.0 mL of MeOH was added in portion. The mixture was stirred at mom temperature for 1 h and concentrated in vacuo. The residue was dissolved in dichloromethane and neutralized to pH 7 by adding 1 N NaOH. The organic layer was washed with brine, water, separated and dried with anhydrous $Na_2SO_4$. The dichloromethane was concentrated in vacuo. The resulting crude product was purified by column chromatography (30-60% EtOAc/hexane), providing the product 3-hydroxy substituted pyrazole (4.13 g, 45% yield). $^1$H-NMR (Acetone-$d_6$): δ 8.83 (s, 1H), 8.04 (m, 1H), 7.85 (m, 1H), 7.81 (m, 1H), 7.61 (m, 1H) 7.51 (m, 1H), 7.30 (m, 1H), 7.06 (m, 2H), 6.95 (m, 1H), 6.92 (m, 1H), 6.90 (m 1H), 3.08 (s, 3H); MS (ES): 465 [M+H]$^+$.

Example 84

Preparation of 1-(3-ethoxyphenyl)-5-(5-(3-(methylsulfonyl)phenyl)thiophen-2-yl)-3-(trifluoromethyl)-1H-pyrazole

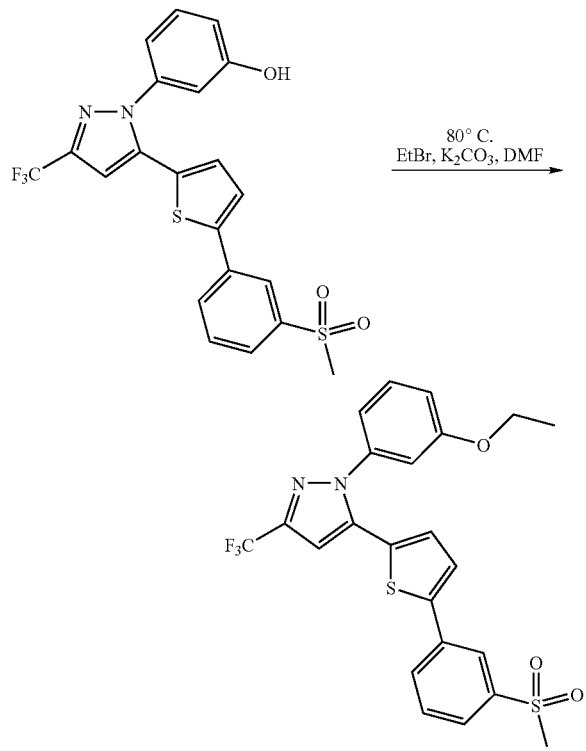

3-(5-(5-(3-(methylsulfonyl)phenyl)thiophen-2-yl)-3-(trifluoromethyl)-1H-pyrazol-1-yl)phenol (80 mg, 0.17 mmol) was dissolved in anhydrous DMF (3 mL). To this solution was added potassium carbonate (29 mg, 0.20 mmol) and ethyl bromide (38 mg, 0.34 mmol) in anhydrous DMF (3.0 mL). The reaction mixture was heated at 80° C. under nitrogen atmosphere for overnight. After the mixture was cooled off, it was poured into 20.0 mL of water and extract with ethyl acetate. The combined organic layer was washed with brine and water and concentrated in vacuo. The crude product was purified by flash column chromatography (60% ethyl acetate in hexane), providing the product 3-ethoxy substituted pyrazole (65 mg, 77% yield). $^1$H-NMR (CDCl$_3$): δ 8.08 (m, 1H), 7.86 (m, 1H), 7.77 (m, 1H), 7.59 (m, 1H), 7.34 (m, 1H), 7.27 (m, 1H), 7.01 (m, 1H), 6.99 (m, 1H), 6.98 (m, 1H), 6.87 (m, 1H), 6.84 (m, 1H), 4.04 (q, J=6.8 Hz, 2H), 3.09 (s, 3H), 1.40 (t, J=6.8 Hz, 3H). MS (ES): 493 [M+H]$^+$.

The following compounds are prepared essentially according to the previous examples:

1-(3-isopropoxyphenyl)-5-(5-(3-(methylsulfonyl)phenyl)thiophen-2-yl)-3-(trifluoromethyl)-1H-pyrazole. MS (ES): 507 [M+H]$^+$ 1-(3-isobutoxyphenyl)-5-(5-(3-(methylsulfonyl)phenyl)thiophen-2-yl)-3-(trifluoromethyl)-1H-pyrazole. MS (ES): 521 [M+H]$^+$ tert-Butyl 2-methyl-2-(3-(5-(5-(3-(methylsulfonyl)phenyl)thiophen-2-yl)-3-(trifluoromethyl)-1H-pyrazol-1-yl)phenoxy)propanoate. MS (ES): 607 [M+H]$^+$.

2-{5-[4-(3-Methanesulfonyl-phenyl)-thiophen-2-yl]-3-trifluoromethyl-pyrazol-1-yl}-phenol. MS(ES) 465.0 [M+H]$^+$, Diethyl-[2-(2-{5-[4-(3-methanesulfonyl-phenyl)-thiophen-2-yl]-3-trifluoromethyl-pyrazol-1-yl}-phenoxy)-ethyl]amine. MS(ES) 564.3 [M+H]$^+$, (2-{5-[4-(3-Methanesulfonyl-phenyl)-thiophen-2-yl]-3-trifluoromethyl-pyrazol-1-yl}-phenoxy)-acetic acid tert-butyl ester. MS (ES) 579.4 [M+H]$^+$, 1-[2-(2-{5-[4-(3-Methanesulfonyl-phenyl)-thiophen-2-yl]-3-trifluoromethyl-pyrazol-1-yl}-phenoxy)-ethyl]-piperidine. MS (ES) 576.3 [M+H]$^+$, 4-[2-(2-{5-[4-(3-Methanesulfonyl-phenyl)-thiophen-2-yl]-3-trifluoromethyl-pyrazol-1-yl}-phenoxy)-ethyl]-morpholine. MS (ES) 578.4 [M+H]$^+$, 2-(2-{5-[4-(3-Methanesulfonyl-phenyl)-thiophen-2-yl]-3-trifluoromethyl-pyrazol-1-yl}-phenoxymethyl)-pyridine. MS (ES) 556.3 [M+H]$^+$, 4-[3-(2-{5-[4-(3-Methanesulfonyl-phenyl)-thiophen-2-yl]-3-trifluoromethyl-pyrazol-1-yl}-phenoxy)-propyl]-morpholine. MS (ES) 592.0 [M+H]$^+$, 1-[3-(2-{5-[4-(3-Methanesulfonyl-phenyl)-thiophen-2-yl]-3-trifluoromethyl-pyrazol-1-yl}-phenoxy)-propyl]-4-methyl-piperazine. MS (ES) 605.0 [M+H]$^+$, 1-[2-(2,2-Dimethyl-propoxy)-phenyl]-5-[4-(3-methanesulfonyl-phenyl)-thiophen-2-yl]-3-trifluoromethyl-1H-pyrazole. MS (ES) 535.3 [M+H]$^+$, 557.3 [M+Na]$^+$ 2-(2-{5-[4-(3-Methanesulfonyl-phenyl)-thiophen-2-yl]-3-trifluoromethyl-pyrazol-1-yl}-phenoxy)-ethanol. MS (ES) 509.3 [M+H]$^+$ 1-[2-(3-Chloro-propoxy)-phenyl]-5-[4-(3-methanesulfonyl-phenyl)-thiophen-2-yl]-3-trifluoromethyl-1H-pyrazole. MS (ES) 541.3, 543.3 [M+H]$^+$ 1-(2-Ethoxy-phenyl)-5-[4-(3-methanesulfonyl-phenyl)-thiophen-2-yl]-3-trifluoromethyl-1H-pyrazole, MS (ES) 493.3 [M+H]$^+$ 1-(2-isopropoxy-phenyl)-5-[4-(3-methanesulfonyl-phenyl)-thiophen-2-yl]-3-trifluoromethyl-1H-pyrazole, MS (ES) 507.3 [M+H]$^+$ 1-(2-Isobutoxy-phenyl)-5-[4-(3-methanesulfonyl-phenyl)-thiophen-2-yl]-3-trifluoromethyl-1H-pyrazole, MS (ES) 521.4 [M+H]+

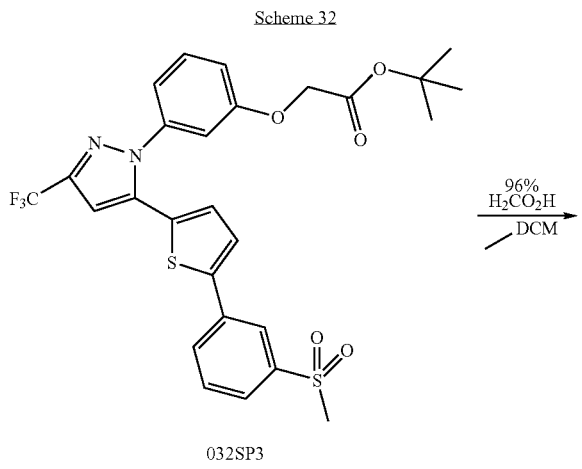

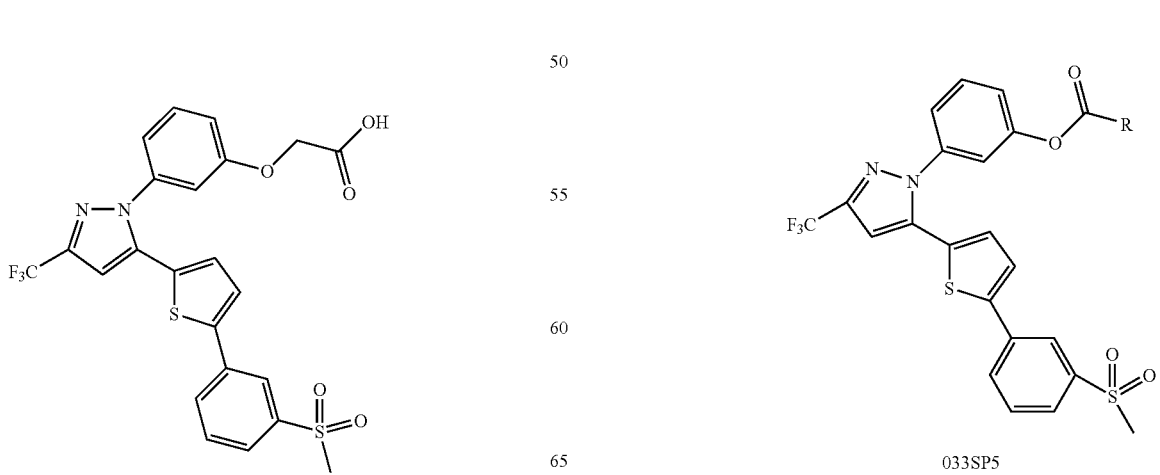

As depicted in Scheme 32, t-butyl ester 032SP3 was treated with formic acid in DCM to afford acid 032SP4.

Example 85

Preparation of 2-(3-(5-(5-(3-(methylsulfonyl)phenyl)thiophen-2-yl)-3-(trifluoromethyl)-1H-pyrazol-1-yl)phenoxy)acetic acid tert-Butyl 2-(3-(5-(5-(3-(methylsulfonyl)phenyl)thiophen-2-yl)-3-(trifluoromethyl)-1H-pyrazol-1-yl)phenoxy)acetate was prepared in a manner described in Scheme 31. To a solution of the t-butyl ester (70 mg, 0.12 mmol) in anhydrous DCM (2.0 mL) was added 2.0 mL of 96% formic acid. The reaction mixture was stirred at room temperature for overnight. It was concentrated and the residue was purified by flash silica gel column chromatography (10% MeOH/DCM), providing the product (28 mg, 45% yield). ¹H-NMR (Acetone-d6): δ 8.01 (s, 1H), 7.82 (m, 1H), 7.77 (m, 1H), 7.57 (m, 1H), 7.45 (m, 1H), 7.37 (m, 1H), 7.08-7.01 (br, 5H), 4.68 (s, 2H), 3.05 (s, 3H). MS (ES): 523 [M+H]+.

The following compounds are prepared essentially according to the previous examples:
(2-{5-[4-(3-Methanesulfonyl-phenyl)-thiophen-2-yl]-3-trifluoromethyl-pyrazol-1-yl}-phenoxy)-acetic acid. MS (ES) 523.3 [M+H]+

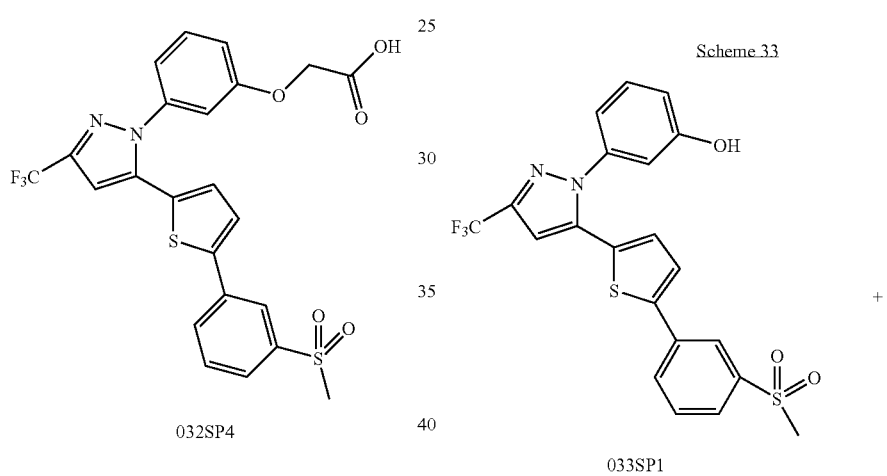

As depicted in Scheme 33, 3-hydroxy substituted pyrazole 033SP1 was treated with dialkyl carbamic chloride or acyl chloride in the presence of base to afford carbamate or ester, 033SP5.

Example 86

Preparation of 3-(5-(5-(3-(methylsulfonyl)phenyl)thiophen-2-yl)-3-(trifluoromethyl)-1H-pyrazol-1-yl)phenyl dimethylcarbamate

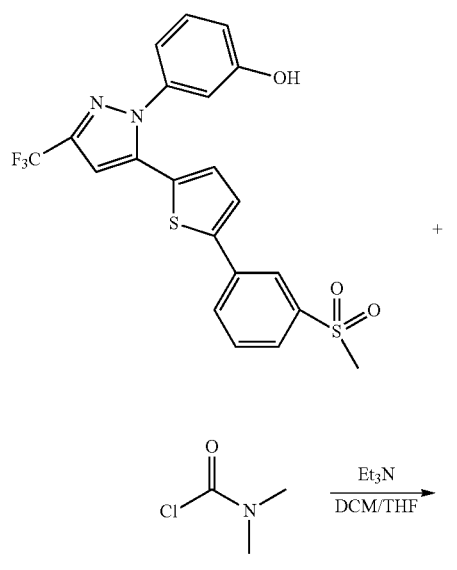

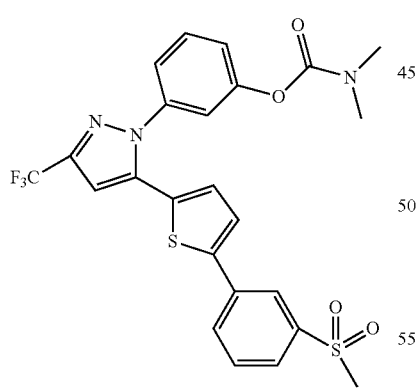

To a solution of 3-(5-(5-(3-(methylsulfonyl)phenyl)thiophen-2-yl)-3-(trifluoromethyl)-1H-pyrazol-1-yl)phenol (80 mg, 0.17 mmol) and triethylamine (35 mg, 0.34 mmol) in anhydrous DCM (1.5 mL) and THF (1.5 mL) was added dimethyl carbamic chloride (28 mg, 026 mmol). The reaction mixture was heated to reflux at 85° C. under nitrogen atmosphere for overnight. It was cooled off and concentrated in vacuo. The residue was purified by column chromatography (60% ethyl acetate in hexane) to yield product carbamate (24 mg, 26% yield). $^1$H-NMR (CDCl$_3$): δ8.10 (m, 1H), 7.85 (m, 1H), 7.79 (m, 1H), 7.58 (m, 1H), 7.42 (m, 1H), 7.35 (m, 1H), 7.28 (m, 1H), 7.26 (m, 1H), 7.22 (m, 1H), 6.91 (m, 1H), 6.84 (s, 1H), 3.09 (s, 6H), 3.00 (s, 3H). MS (ES): 536 [M+H]$^+$.

The following compounds are prepared essentially according to the previous examples:

3-(5-(5-(3-(methylsulfonyl)phenyl)thiophen-2-yl)-3-(trifluoromethyl)-1H-pyrazol-1-yl)phenyl diethylcarbamate. MS (ES): 564 [M+H]$^+$.

Isobutyric acid 2-{5-[1-(3-methanesulfonyl-phenyl)-thiophen-2-yl]-3-trifluoromethyl-pyrazol-1-yl}-phenyl ester, MS (ES) 535.3 [M+H]

2,2-Dimethyl-propionic acid 2-{5-[4-(3-methanesulfonyl-phenyl)-thiophen-2-yl]-3-trifluoromethyl-pyrazol-1-yl}-phenyl ester. MS (ES) 549.3 [M+H]$^+$ Dimethyl-carbamic acid 2-{5-[4-(3-methanesulfonyl-phenyl)-thiophen-2-yl]-3-trifluoromethyl-pyrazol-1-yl}-phenyl ester. MS (ES) 536.3 [M+H]$^+$ Scheme 34

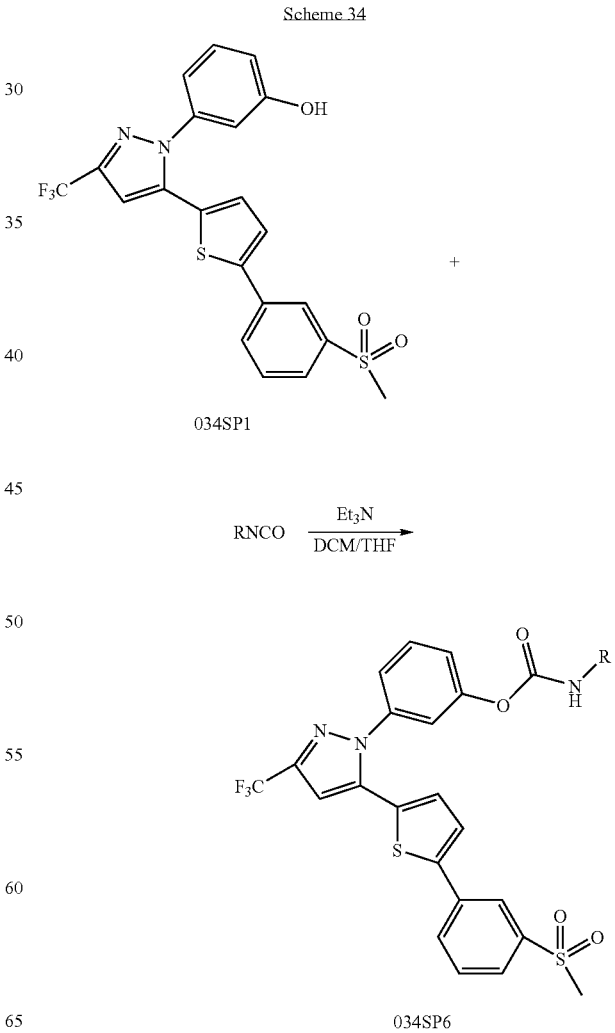

As depicted in Scheme 34, 3-hydroxy substituted pyrazole 034SP1 was treated with alkyl isocyanate in the presence of base to afford carbamate 034SP6.

Example 87

Preparation of 3-(5-(5-(3-(methylsulfonyl)phenyl)thiophen-2-yl)-3-(trifluoromethyl)-1H-pyrazol-1-yl)phenyl methylcarbamate

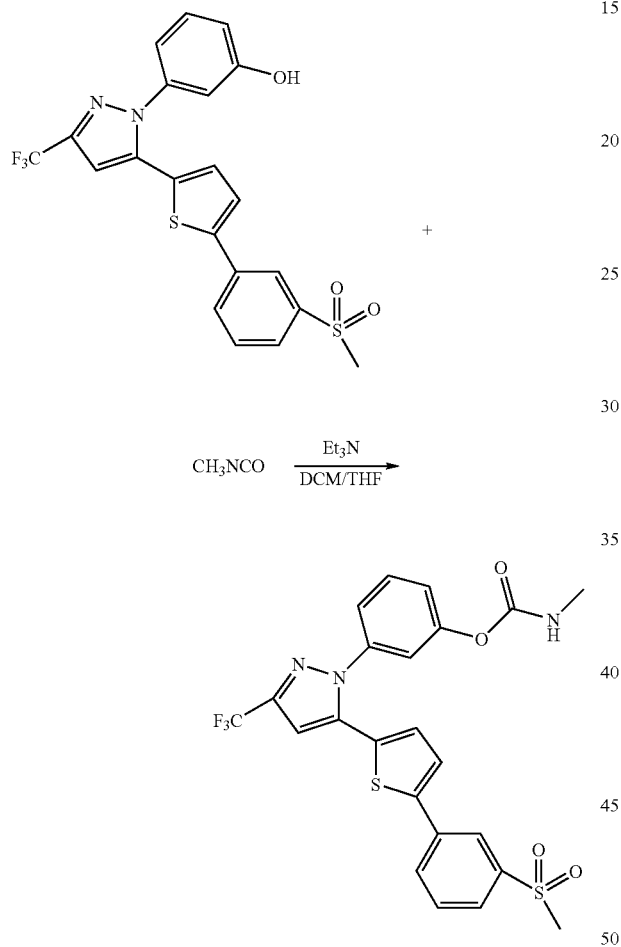

3-(5-(5-(3-(methylsulfonyl)phenyl)thiophen-2-yl)-3-(trifluoromethyl)-1H-pyrazol-1-yl)phenol (80 mg, 0.17 mmol) was dissolved in anhydrous DCM (1.5 mL) and THF (1.5 mL). To this solution was added triethylamine (35 mg, 0.34 mmol) and methyl isocyanate (15 mg, 0.26 mmol). The reaction mixture was stirred at room temperature under nitrogen atmosphere for overnight. The solvent was evaporated in vacuo. The residue was purified by column chromatography (60% ethyl acetate in hexane) to yield the product methylcarbamate (56 mg, 95% yield). $^1$H-NMR (CDCl$_3$): δ8.10 (m, 1H), 7.86 (m, 1H), 7.79 (m, 1H), 7.59 (m, 1H), 7.43 (m, 1H), 7.32 (m, 1H), 7.29-724 (br, 3H), 6.91 (m, 1H), 6.84 (m, 1H), 5.02 (br, 1H), 3.10 (s, 3H), 2.89 (s, 3H), 2.88 (s, 3H). MS (ES): 522 [M+H]$^+$ The following compounds are prepared essentially according to the previous examples:

3-(5-(5-(3-(methylsulfonyl)phenyl)thiophen-2-yl)-3-(trifluoromethyl)-1H-pyrazol-1-yl)phenyl propylcarbamate. MS (ES): 550 [M+H]$^+$ Methyl-carbamic acid 2-(5-[4-(3-methanesulfonyl-phenyl)-thiophen-2-yl]-3-trifluoromethyl-pyrazol-1-yl)-phenyl ester. MS (ES) 522.3 [M+H]$^+$ Propyl-carbamic acid 2-{5-[4-(3-methanesulfonyl-phenyl)-thiophen-2-yl]-3-trifluoromethyl-pyrazol-1-yl}-phenyl ester. MS (ES) 550.3 [M+H]$^+$ Isopropyl-carbamic acid 2-{5-[4-(3-methanesulfonyl-phenyl)-thiophen-2-yl]-3-trifluoromethyl-pyrazol-1-yl}-phenyl ester. MS (ES) 550.3 [M+H]$^+$

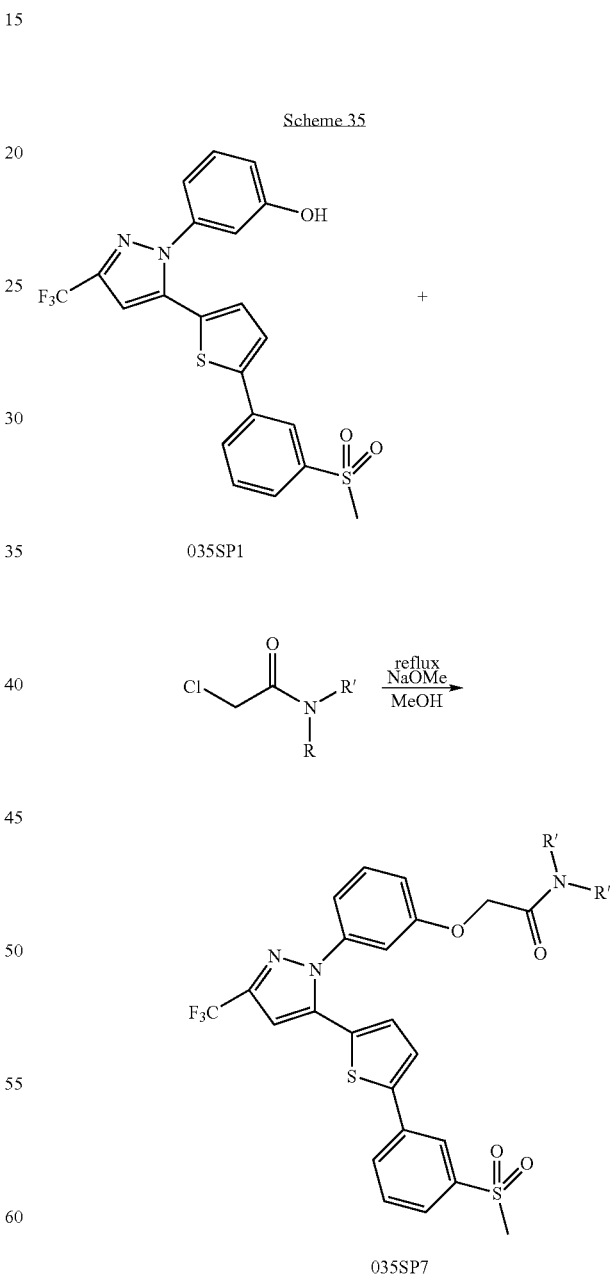

Scheme 35

As depicted in Scheme 35, 3-hydroxy substituted pyrazole 035SP1 was treated with 2-chloroacetamide in the presence of base to afford acetamide 035SP7.

Example 88

Preparation of N,N-dimethyl-2-(3-(5-(5-(3-(methylsulfonyl)phenyl)thiophen-2-yl)-3-(trifluoromethyl)-1H-pyrazol-1-yl)phenoxy)acetamide

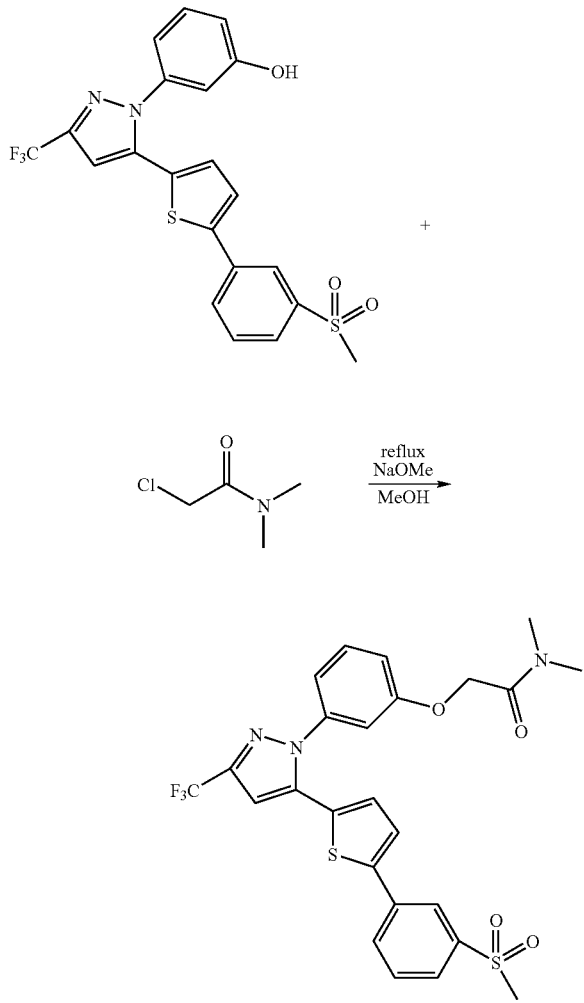

3-(5-(5-(3-(methylsulfonyl)phenyl)thiophen-2-yl)-3-(trifluoromethyl)-1H-pyrazol-1-yl)phenol (120 mg, 0.26 mmol) was dissolved in anhydrous methanol (10.0 mL). To this solution was added a 25 wt % solution of NaOMe in methanol (130 μL, 0.57 mmol) and 2-chloro-N,N-dimethyl-acetamide (156 mg, 128 mmol). The reaction mixture was heated to reflux at 80° C. under nitrogen atmosphere for overnight. It was cooled off and concentrated in vacuo. The residue was purified by column chromatography (50% ethyl acetate in hexane) to yield the product (87 mg, 61% yield). $^1$H-NMR (Acetone-d6): δ 8.21 (m, 1H), 8.03 (m, 1H), 7.96 (m, 1H), 7.76 (m, 1H), 7.65 (m, 1H), 7.52 (m, 1H), 7.25-7.16 (br, 5H), 4.94 (s, 2H), 3.25 (s, 3H), 3.09 (s, 3H), 2.90 (s, 3H), 2.88 (s, 3H). MS (ES): 550 [M+H]$^+$ The following compounds were prepared in a similar manner:

2-(3-(5-(5-(3-(methylsulfonyl)phenyl)thiophen-2-yl)-3-(trifluoromethyl)-1H-pyrazol-1-yl)phenoxy)-1-morpholinoethanone. MS (ES): 592 [M+H]$^+$ N,N-diethyl-2-({2-[5-{4-[3-(methylsulfonyl)phenyl]-2-thienyl}-3-(trifluoromethyl)-1H-pyrazol-1-yl]phenyl}oxy)acetamide; MS (ES): 578 [M+H]$^+$;

4-[({2-[5-{4-[3-(methylsulfonyl)phenyl]-2-thienyl}-3-(trifluoromethyl)-1H-pyrazol-1-yl]phenyl}oxy)methyl]pyridine; MS (ES): 556 [M+H]$^+$;

N-(1-methylethyl)-2-({2-[5-{4-[3-(methylsulfonyl)phenyl]-2-thienyl}-3-(trifluoromethyl)-1H-pyrazol-1-yl]phenyl}oxy)acetamide; MS (ES): 564 [M+H]$^+$;

5-({2-[5-{4-[3-(methylsulfonyl)phenyl]-2-thienyl}-3-(trifluoromethyl)-1H-pyrazol-1-yl]phenyl}oxy)pentanenitrile; MS (ES): 546 [M+H]$^+$;

5-{4-[3-(methylsulfonyl)phenyl]-2-thienyl}-1-[2-({[1-(phenylmethyl)-1H-imidazol-2-yl]methyl}oxy)phenyl]-3-(trifluoromethyl)-1H-pyrazole; MS (ES): 635 [M+H]$^+$;

2-[2-({2-[5-{4-[3-(methylsulfonyl)phenyl]-2-thienyl}-3-(trifluoromethyl)-1H-pyrazol-1-yl]phenyl}oxy)ethyl]-1H-isoindole-1,3(2H)-dione; MS (ES): 638 [M+H]$^+$;

2-({2-[5-{4-[3-(methylsulfonyl)phenyl]-2-thienyl}-3-(trifluoromethyl)-1H-pyrazol-1-yl]phenyl}oxy)-N-phenylacetamide; MS (ES): 598 [M+H]$^+$;

6-({2-[5-{4-[3-(methylsulfonyl)phenyl]-2-thienyl}-3-(trifluoromethyl)-1H-pyrazol-1-yl]phenyl}oxy)hexan-2-one; MS (ES): 563 [M+H]$^+$;

1-{4-[({2-[5-{4-[3-(methylsulfonyl)phenyl]-2-thienyl}-3-(trifluoromethyl)-1H-pyrazol-1-yl]phenyl}oxy)methyl]phenyl}-1H-1,2,4-triazole; MS (ES): 622 [M+H]$^+$;

5-{4-[3-(methylsulfonyl)phenyl]-2-thienyl}-1-(2-{[(3-nitrophenyl)methyl]oxy}phenyl)-3-(trifluoromethyl)-1H-pyrazole; MS (ES): 600 [M+H]$^+$;

N,N-diethyl-2-({2-[5-{4-[3-(methylsulfonyl)phenyl]-2-thienyl}-3-(trifluoromethyl)-1H-pyrazol-1-yl]phenyl}oxy)acetamide; MS (ES): 578 [M+H]$^+$.

4-[({2-[5-{4-[3-(methylsulfonyl)phenyl]-2-thienyl}-3-(trifluoromethyl)-1H-pyrazol-1-yl]phenyl}oxy)methyl]pyridine; MS (ES): 556 [M+H]$^+$.

N-(1-methylethyl)-2-({2-[5-{4-[3-(methylsulfonyl)phenyl]-2-thienyl}-3-(trifluoromethyl)-1H-pyrazol-1-yl]phenyl}oxy)acetamide; MS (ES): 564 [M+H]$^+$.

5-({2-[5-{4-[3-(methylsulfonyl)phenyl]-2-thienyl}-3-(trifluoromethyl)-1H-pyrazol-1-yl]phenyl}oxy)pentanenitrile; MS (ES): 546 [M+H]$^+$.

5-{4-[3-(methylsulfonyl)phenyl]-2-thienyl}-1-[2-({[1-(phenylmethyl)-1H-imidazol-2-yl]methyl}oxy)phenyl]-3-(trifluoromethyl)-1H-pyrazole; MS (ES): 635 [M+H]$^+$.

2-[2-({2-[5-{4-[3-(methylsulfonyl)phenyl]-2-thienyl}-3-(trifluoromethyl)-1H-pyrazol-1-yl]phenyl}oxy)ethyl]-1H-isoindole-1,3(2H)-dione; MS (ES): 638 [M+H]$^+$.

2-({2-[5-{4-[3-(methylsulfonyl)phenyl]-2-thienyl}-3-(trifluoromethyl)-1H-pyrazol-1-yl]phenyl}oxy)-N-phenylacetamide; MS (ES): 598 [M+H]$^+$.

6-({2-[5-{4-[3-(methylsulfonyl)phenyl]-2-thienyl}-3-(trifluoromethyl)-1H-pyrazol-1-yl]phenyl}oxy)hexan-2-one; MS (ES): 563 [M+H]$^+$.

1-{4-[({2-[5-(4-[3-(methylsulfonyl)phenyl]-2-thienyl)-3-(trifluoromethyl)-1H-pyrazol-1-yl]phenyl}oxy)methyl]phenyl}-1H-1,2,4-triazole; MS (ES): 622 [M+H]$^+$.

5-{4-[4-(methylsulfonyl)phenyl]-2-thienyl}-1-(2-{[(3-nitrophenyl)methyl]oxy}phenyl)-3-(trifluoromethyl)-1H-pyrazole; MS (ES): 600 [M+H]$^+$.

Scheme 36

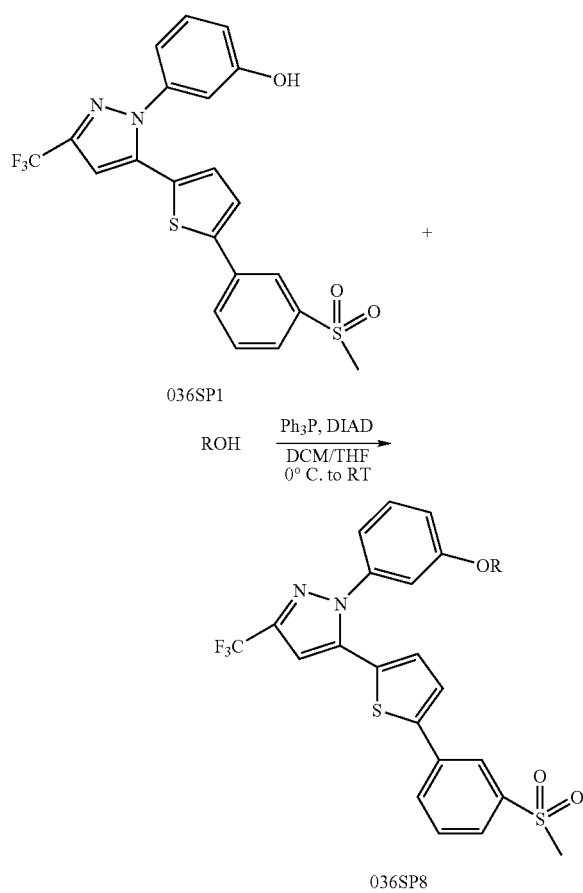

As depicted in Scheme 36, 3-hydroxy substituted pyrazole 036SP1 was treated with an alcohol in the presence of triphenyl phosphine and diisopropyl azodicarboxylate to afford 3-alkoxy substituted pyrazole 036SP8.

Example 89

Preparation of N,N-dimethyl-2-(3-(5-(5-(3-(methylsulfonyl)phenyl)thiophen-2-yl)-3-(trifluoromethyl)-1H-pyrazol-1-yl)phenoxy)ethanamine

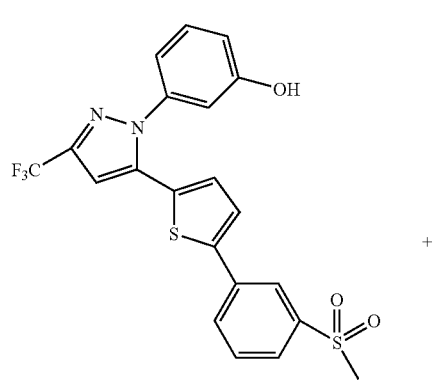

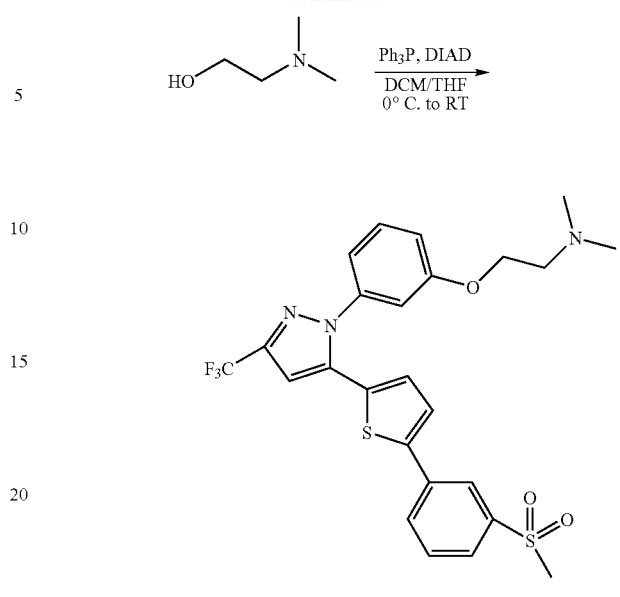

3-(5-(5-(3-(methylsulfonyl)phenyl)thiophen-2-yl)-3-(trifluoromethyl)-1H-pyrazol-1-yl)phenol (120 mg, 0.26 mmol), 2-(dimethylamino)ethanol (46 mg, 0.52 mmol) and triphenylphosphine (138 mg, 0.52 mmol) were dissolved in a mixture solvent of anhydrous THF (2.5 mL) and DCM (2.5 mL) and cooled off at 0° C. under nitrogen atmosphere. To this solution was added diisopropyl azodicarboxylate (111 mg, 0.52 mmol). The reaction mixture was stirred vigorously and warmed up to mom temperature overnight. The solvent was evaporated in vacuo and the residue was purified by HPLC, providing the product (61 mg, 44%). $^1$H-NMR (Acetone-d6): δ 8.13 (m, 1H), 7.93 (m, 1H), 7.90 (m, 1H), 7.71 (m, 1H), 7.60 (m, 1H), 7.47 (m, 1H), 7.17-7.09 (br, 5H), 4.12 (t, J=5.8 Hz, 2H), 3.18 (s, 3H), 2.65 (t, J=5.8 Hz, 2H), 2.21 (s, 6H). MS (ES): 536 [M+H]$^+$.

Example 90

Preparation of 4-(3-(5-(5-(3-(methylsulfonyl)phenyl)thiophen-2-yl)-3-(trifluoromethyl)-1H-pyrazol-1-yl)phenoxy)piperidine

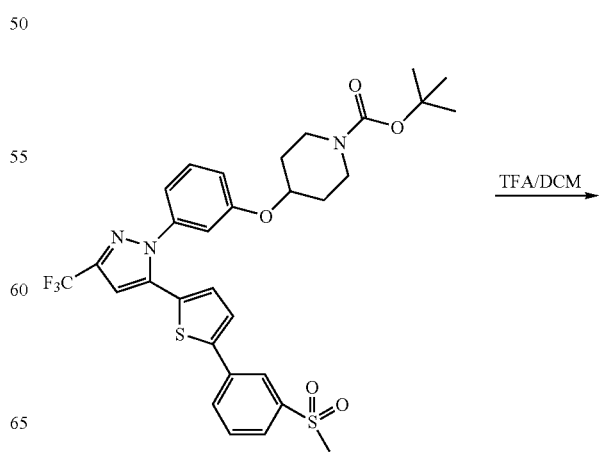

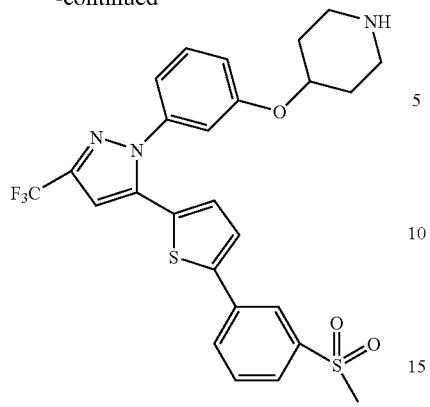

tert-Butyl 4-(3-(5-(5-(3-(methylsulfonyl)phenyl)thiophen-2-yl)-3-(trifluoromethyl)-1H-pyrazol-1-yl)phenoxy)piperidine-1-carboxylate was prepared as described in Scheme 36. The t-butyl carbamate (83 mg, 0.13 mmol) was dissolved in trifluoroacetic acid (0.5 mL) and anhydrous DCM (4.0 mL). It was stirred at room temperature under nitrogen atmosphere for overnight. The reaction mixture was concentrated in vacuo and the residue was taken into DCM. Potassium carbonate was added into the DCM solution and it was stirred for 2 hours. The salt was filtered and the filtrate was concentrated in vacuo. The residue was purified by column chromatography (10% isopropyl alcohol in DCM), providing the product amine (45 mg, 64%). %). $^1$H-NMR (DMSO-d6): δ 8.01 (m, 1H), 7.89 (m, 1H), 7.69 (m, 1H), 7.49 (m, 1H), 7.41 (m, 1H), 7.26 (m, 1H), 7.23 (m, 2H), 7.13 (m, 1H), 4.63 (m, 1H), 3.28 (s, 3H), 3.11 (m, 2H), 2.87 (m, 2H), 1.99 (m, 2H), 1.71 (m, 2H). MS (ES): 548 [M+H]$^+$.

The following compounds are prepared essentially according to the previous examples:

4-(2-(3-(5-(5-(3-(methylsulfonyl)phenyl)thiophen-2-yl)-3-(trifluoromethyl)-1H-pyrazol-1-yl)phenoxy)ethyl)morpholine. MS (ES): 578 [M+H]$^+$ 1-(2-(3-(5-(5-(3-(methylsulfonyl)phenyl)thiophen-2-yl)-3-(trifluoromethyl)-1H-pyrazol-1-yl)phenoxy)ethyl)piperidine. MS (ES): 576 [M+H]$^+$.

5-(5-(3-(methylsulfonyl)phenyl)thiophen-2-yl)-1-(3-(tetrahydrofuran-3-yloxy)phenyl)-3-(trifluoromethyl)-1H-pyrazole. MS (ES): 535 [M+H]$^+$.

Scheme 37

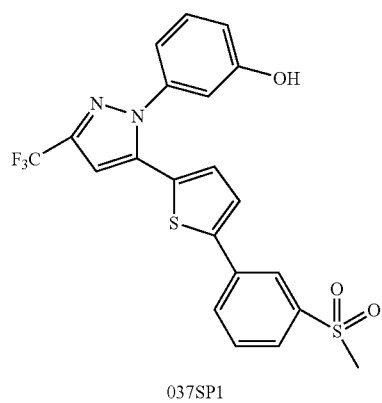

037SP1

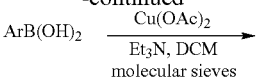

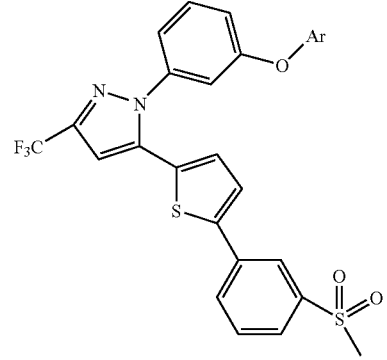

037SP9

As depicted in Scheme 37, the hydroxyl substituted pyrazole 037SP1 was treated with arylboronic acid in the presence of triethylamine and copper (II) acetate to afford the product diaryl ether 037SP9.

Example 91

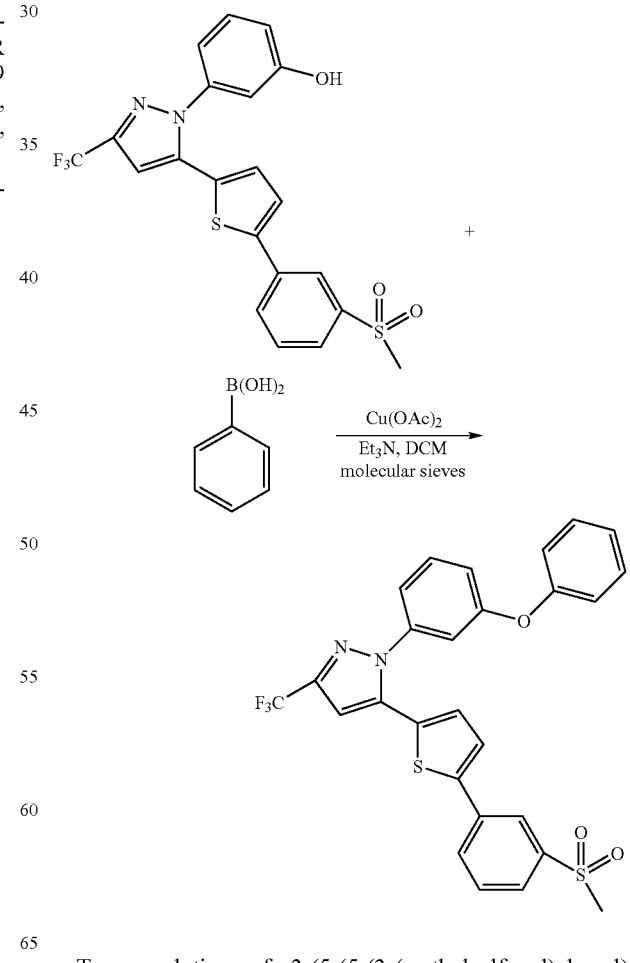

To a solution of 3-(5-(5-(3-(methylsulfonyl)phenyl)thiophen-2-yl)-3-(trifluoromethyl)-1H-pyrazol-1-yl)phenol (120 mg, 0.26 mmol) in anhydrous DCM (6.0 mL) was added Cu(OAc)$_2$ (94 mg, 0.52 mmol), phenylboronic acid (63 mg, 0.52 mmol) and powdered 4 Å molecular sieves and triethylamine (131 mg, 1.29 mmol). The heterogeneous reaction mixture was stirred at ambient temperature for overnight. The resulting slurry was filtered through celite and the solvent was evaporated in vacuo. The crude product was purified by column chromatography (40% ethyl acetate in hexane), providing product diary ether (73 mg, 52% yield). $^1$H-NMR (CDCl$_3$): δ8.10 (m, 1H), 7.88 (m, 1H), 7.79 (m, 1H), 7.61 (m, 1H), 7.31-7.27 (m, 3H), 7.20 (m, 1H), 7.12 (m, 1H), 7.04 (m, 1H), 7.00 (m, 2H), 6.89 (m, 1H), 6.82 (s, 1H), 3.10 (s, 3H). MS (ES): 541 [M+H]$^+$.

coupled with 3-methylsulfonylphenyl boronic acid in the presence of PdCl$_2$dppf, Na$_2$CO$_3$ to afford the product 038SP12.

Example 92

4-(1-(2-chlorophenyl)-3-(trifluoromethyl)-1H-pyrazol-5-yl)-N-(2-morpholinoethyl)benzamide Example 92a Preparation of 3-(5-(5-bromothiophen-2-yl)-3-(trifluoromethyl)-1H-pyrazol-1-yl)aniline

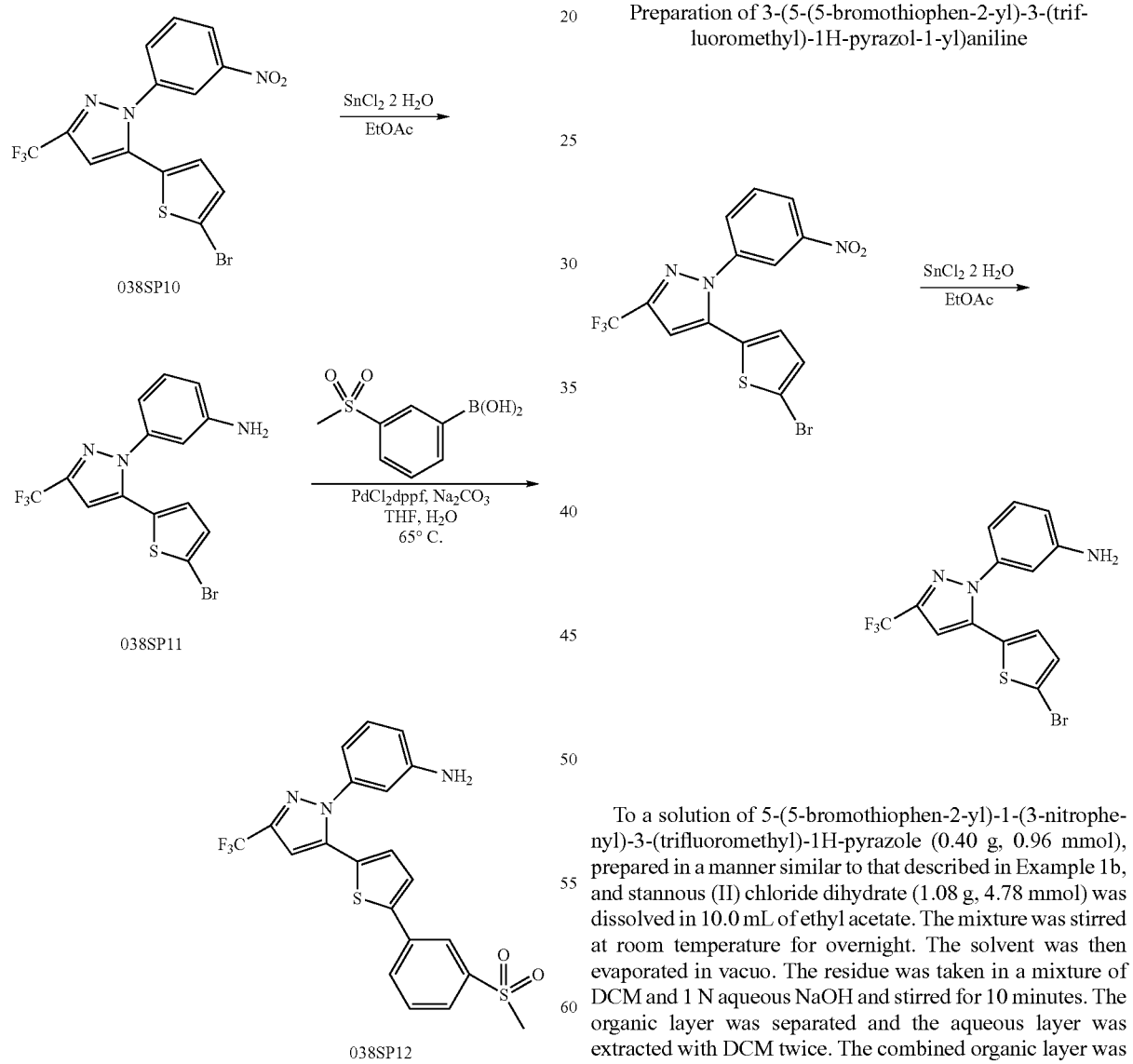

As depicted in Scheme 38, the 3-nitrophenyl substituted pyrazole 038SP10 was reduced with SnCl$_2$ to aniline, which To a solution of 5-(5-bromothiophen-2-yl)-1-(3-nitrophenyl)-3-(trifluoromethyl)-1H-pyrazole (0.40 g, 0.96 mmol), prepared in a manner similar to that described in Example 1b, and stannous (II) chloride dihydrate (1.08 g, 4.78 mmol) was dissolved in 10.0 mL of ethyl acetate. The mixture was stirred at room temperature for overnight. The solvent was then evaporated in vacuo. The residue was taken in a mixture of DCM and 1 N aqueous NaOH and stirred for 10 minutes. The organic layer was separated and the aqueous layer was extracted with DCM twice. The combined organic layer was dried with anhydrous Na$_2$SO$_4$ and concentrated in vacuo. The residue was purified by column chromatography (30% ethyl acetate in hexane) providing the product aniline (327 mg, 88% yield). $^1$H-NMR (CDCl$_3$): 026 (m, 1H), 6.90 (m, 1H), 6.76 (m, 5H), 3.84 (s, 2H).

Example 92b

Preparation of 3-(5-(5-(3-methylsulfonyl)phenyl)thiophen-2-yl)-3-(trifluoromethyl)-1H-pyrazol-1-yl)aniline

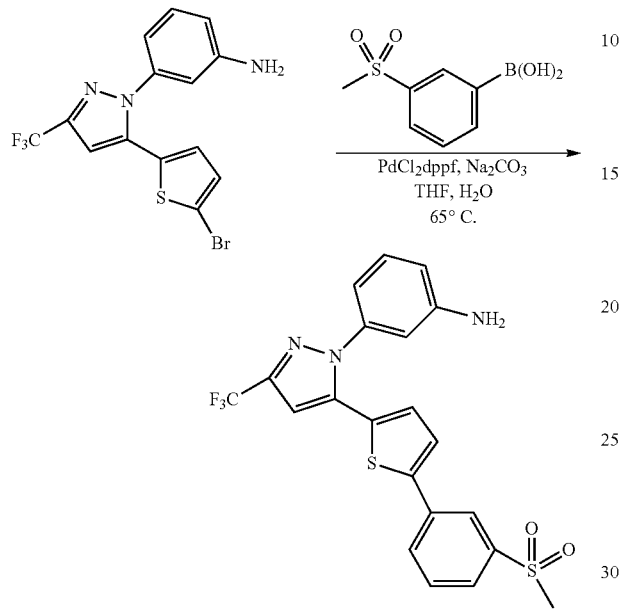

To a solution of the 3-(5-(5-bromothiophen-2-yl)-3-(trifluoromethyl)-1H-pyrazol-1-yl)aniline (1.55 g, 4.0 mmol) in anhydrous THF (20.0 mL) was added 3-(methylsulfonyl)phenylboronic acid (0.88 g, 4.4 mmol), PdCl$_2$dppf (163 mg, 020 mmol), Na$_2$CO$_3$ (0.85, 8.0 mmol) and water (2.0 mL). The reaction mixture was heated to reflux at 55° C. under nitrogen atmosphere for 15 hours. It was cooled off and passed through a pad of celite. The solvent was evaporated in vacuo and the resulting residue was purified by column chromatography (50% ethyl acetate in hexane), providing the product (778 mg, 42%). $^1$H-NMR (Acetone-d6): 0.98 (m, 1H), 7.78 (m, 2H), 7.55 (m, 2H), 7.47 (m, 1H), 7.41 (m, 1H), 7.28 (m, 1H), 7.11 (m, 1H), 7.02 (m, 1H), 6.97 (m, 1H), 5.49 (s, 2H), 3.05 (s, 3H). MS (ES): 464 [M+H]$^+$.

Scheme 39

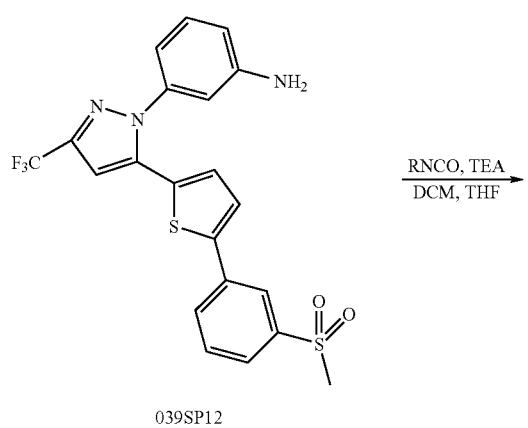

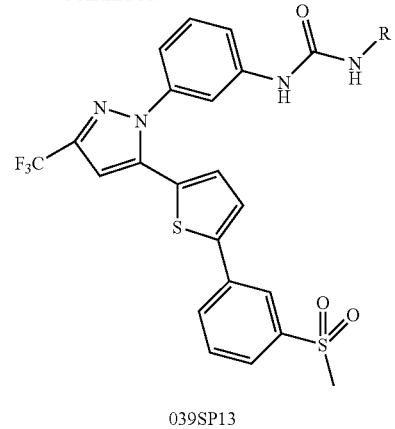

039SP13

As depicted in Scheme 39, the aniline 039P12 was treated with alkyl isocyanate in the presence of triethylamine to afford urea 039SP13.

Example 93

Preparation of 1-(3-(5-(5-(3-(methylsulfonyl)phenyl)thiophen-2-yl)-3-(trifluoromethyl)-1H-pyrazol-1-yl)phenyl)urea

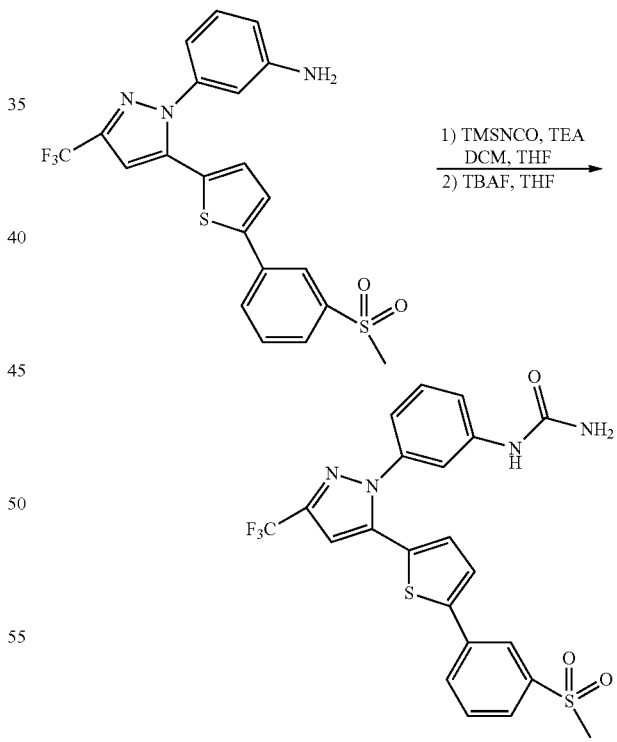

To a solution of the 3-(5-(5-(3-(methylsulfonyl)phenyl)-thiophen-2-yl)-3-(trifluoromethyl)-1H-pyrazol-1-yl)aniline in anhydrous DCM (1.0 mL) and THF (3.0 mL) was added trimethylsilyl isocyanate (112 mg, 0.85 mmol) and triethyl amine (29 mg, 0.28 mmol). The reaction mixture was stirred under nitrogen atmosphere for overnight. A 1.0 M solution of tetra-butylammonium fluoride (1.42 mL, 1.42 mmol) in THF was added and the mixture was stirred at room temperature for overnight. The solvent was evaporated in vacuo and the resulting residue was purified by HPLC, providing the urea product (70 mg, 49%). ¹H-NMR (Acetone-d6): δ 8.56 (s, 1H), 8.13 (m, 1H), 7.98 (m, 1H), 7.91 (m, 1H), 7.69 (m, 1H), 7.60 (m, 1H), 7.49 (m, 1H), 7.20 (m, 1H), 7.17 (m, 1H), 6.44 (br, 2H), 3.18 (s, 3H). MS (ES): 507 [M+H]⁺.

Scheme 40

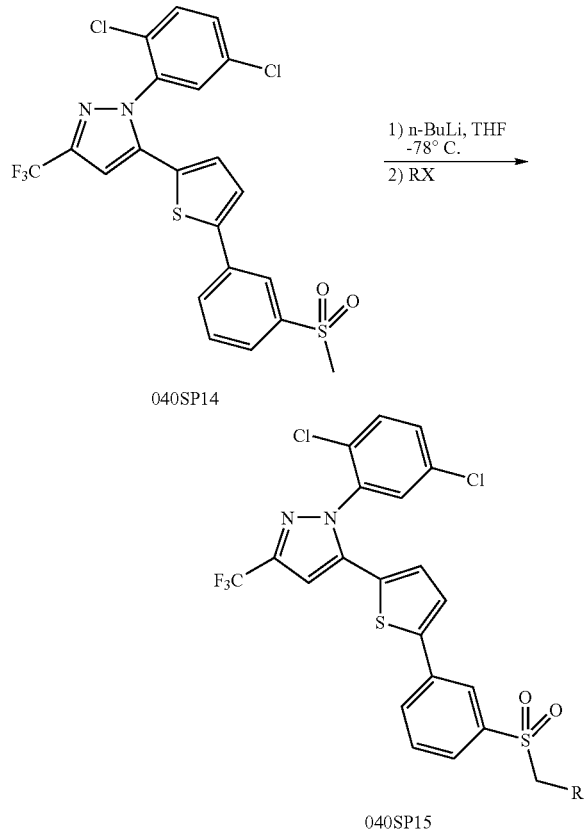

040SP14

040SP15

As depicted in Scheme 40, the methylsulfonyl substituted pyrazole 040SP14 was treated with n-butyl lithium and then alkyl halide to afford the alkyl sulfonyl substituted pyrazole 040SP15.

Example 94

Preparation of 1-(2,5-dichlorophenyl)-5-(5-(3-ethylsulfonyl)phenyl)thiophen-2-yl)-3-(trifluoromethyl)-1H-pyrazole

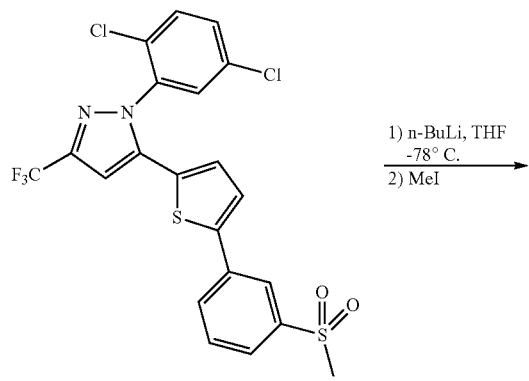

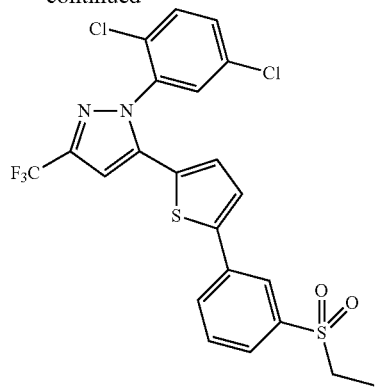

1-(2,5-dichlorophenyl)-5-(5-(3-(methylsulfonyl)phenyl)thiophen-2-yl)-3-(trifluoromethyl)-1H-pyrazole (0.5 g, 0.97 mmol), prepared as described in Example 1c, was dissolved in anhydrous THF (8.0 mL) and cooled at −78° C. under nitrogen atmosphere. To this solution a 1.6 M solution n-BuLi (0.78 mL, 1.28 mmol) in hexane was added. The mixture was stirred at −78° C. for 15 min and iodomethane (608 mg, 428 mmol) was added and it was stirred for overnight while it warmed up to room temperature. The reaction was quenched carefully with water and the product was extracted with ethyl acetate. The organic layer was washed with brine and water and dried over anhydrous Na₂SO₄ and concentrated in vacuo. The residue was purified by column chromatography (50% ethyl acetate in hexane), providing the product (153 mg, 30%). ¹H-NMR (CDCl₃): δ8.04 (m, 1H), 7.83 (m, 1H), 7.76 (m, 1H), 7.60 (m, 1H), 7.51 (m, 2H), 7.26 (m, 1H), 6.90 (s, 1H), 6.87 (m, 1H), 3.15 (q, J=7.5 Hz, 2H), 1.31 (t, J=7.5 Hz, 3H). MS (ES): 531 [M+H]⁺.

The following compounds are prepared essentially according to the previous examples:

1-(2,5-dichlorophenyl)-5-(5-(3-(propylsulfonyl)phenyl)thiophen-2-yl)-3-(trifluoromethyl)-1H-pyrazole.
¹H-NMR (CDCl₃): δ 7.73 (m, 1H), MS (ES): 545 [M+H]⁺.

1-(2,5-dichlorophenyl)-5-(5-{3-[(1,1-dimethylethyl)sulfonyl]phenyl}-2-thienyl)-3-(trifluoromethyl)-1H-pyrazole, MS(ES): 559 [M+H]⁺.

Scheme 41

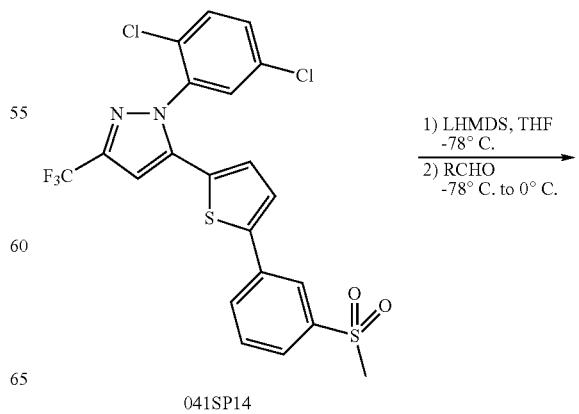

041SP14

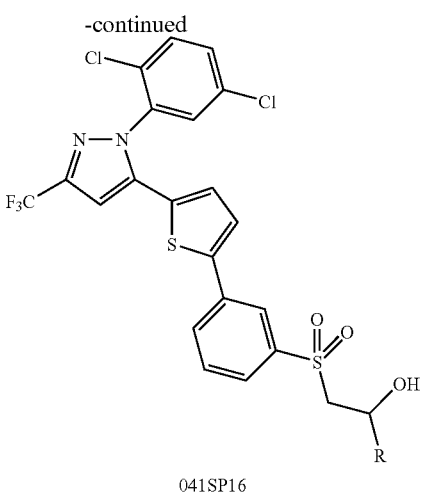

041SP16

As depicted in Scheme 41, the methylsulfonyl substituted pyrazole 041SP14 was treated with LHMDS and then an aldehyde to afford the alcohol 041SP16.

Example 95

Preparation of 1-(3-(5-(1-(2,5-dichlorophenyl)-3-(trifluoromethyl)-1H-pyrazol-5-yl)thiophen-2-yl)phenylsulfonyl)butan-2-ol To a solution of 1-(2,5-dichlorophenyl)-5-(5-(3-(methylsulfonyl)phenyl)thiophen-2-yl)-3-(trifluoromethyl)-1H-pyrazole (0.20 g, 0.39 mmol) in anhydrous TIE (4.0 mL) cooled at −78° C. under nitrogen atmosphere was added slowly a 1.6 M solution LHMDS (0.27 mL, 0.43 mmol) in THF. The mixture was stirred at −78° C. for 15 min. and propionaldehyde (45 mg, 0.77 mmol) was added and it was stirred for overnight while it warmed up to room temperature. The reaction was quenched with water and the product was extracted with ethyl acetate. The organic layer was washed with brine and water and dried over anhydrous $Na_2SO_4$ and concentrated in vacuo. The residue was purified by column chromatography (60% ethyl acetate in hexane), providing the product (156 mg, 70%). $^1$H-NMR. (Acetone-d6): δ 8.12 (m, 1H), 7.98 (m, 1H), 7.90 (m, 1H), 7.88 (m, 1H), 7.77 (m, 2H), 7.68 (m, 1H), 7.58 (m, 1H), 7.28 (s, 1H), 7.20 (m, 1H), 4.02 (m, 1H), 3.39 (m, 2H), 1.58 (m, 1H), 1.48 (m, 1H), 0.9 (t, J=7.1 Hz, 3H). MS (ES): 575 [M+H]$^+$.

Scheme 42

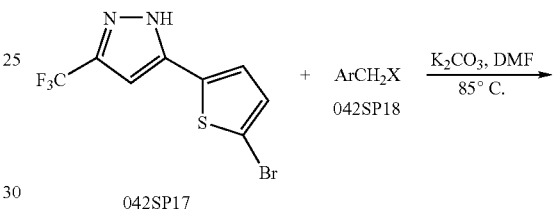

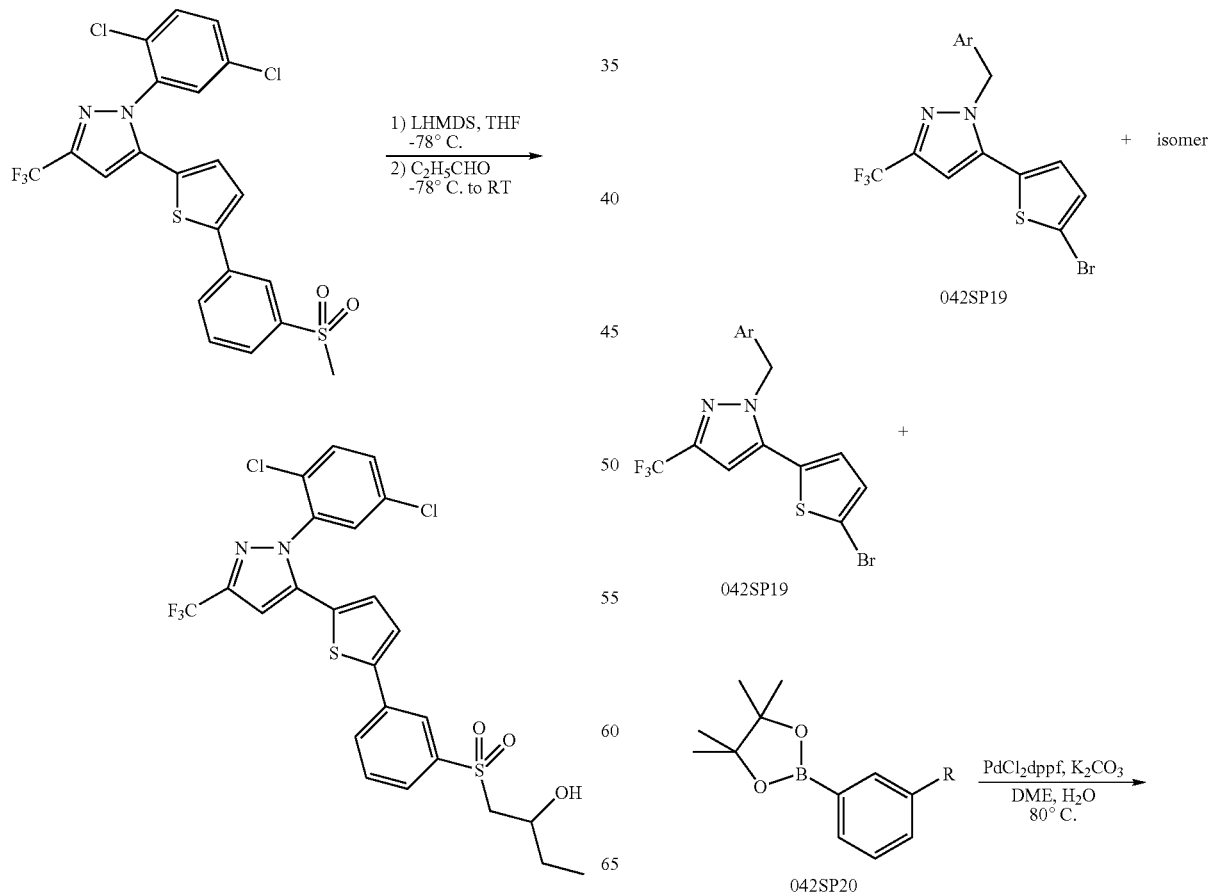

289

-continued

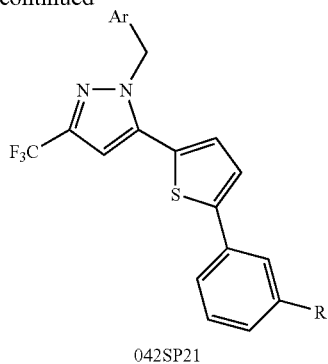
042SP21

As depicted in Scheme 42, pyrazole 042SP17 prepared as described in Example 1b was treated with alkyl halide 042SP18 and $K_2CO_3$ at 85° C. to afford 5-(5-bromothiophen-2-yl)-1-arylmethyl-3-(trifluoromethyl)-1H-pyrazole 042SP19, which was coupled with an aryl boronic eater 042SP20 in the presence of $PdCl_2(dppf)$, $K_2CO_3$, resulting in the pyrazole 042SP21.

Example 96

Preparation of 2-(3-(5-(1-((5-chlorothiophen-2-yl)methyl)-3-(trifluoromethyl)-1H-pyrazol-5-yl)thiophen-2-yl)phenyl)-2-methylpropanoic acid

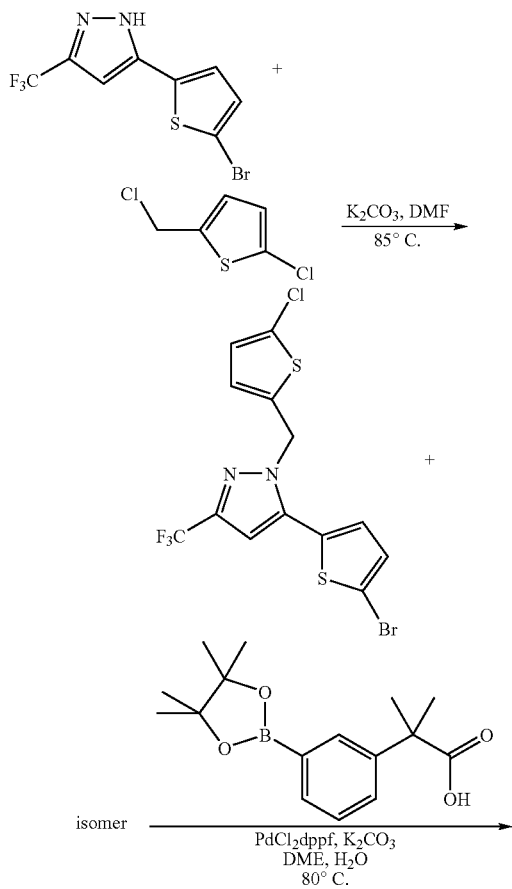

290

-continued

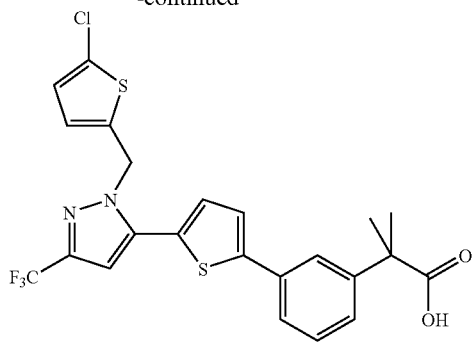

5-(5-bromothiophen-2-yl)-3-(trifluoromethyl)-1H-pyrazole (3.23 g, 10.88 mmol), prepared in a manner similar to that described in Example 1b, was dissolved in anhydrous DMF (40 mL). To this solution was added 2-chloro-5-(chloromethyl)thiophene (2.0 g, 11.97 mmol) and $K_2CO_3$ (2.25 g, 16.32 mmol). The reaction mixture was heated at 85° C. under nitrogen atmosphere for overnight. The solvent was evaporated and the resulting residue was taken into ethyl acetate. The reaction mixture was washed with water and brine and dried over anhydrous $Na_2SO_4$. It was concentrated in vacuo. The residue was purified by column chromatography (10% ethyl acetate in hexane), providing the product 5-(5-bromothiophen-2-yl)-1-(5-chlorothiophen-2-yl)methyl)-3-(trifluoromethyl)-1H-pyrazole (1.39 g, 30%). $^1$H-NMR ($CDCl_3$): δ 7.11 (m, 1H), 6.90 (m, 1H), 6.75 (m, 1H), 6.67 (m, 1H), 6.61 (s, 1H), 5.46 (s, 2H). The above product was coupled with an aryl boronic ester in a manner similar to that described in Example 1c, providing the title compound (161 mg, 45%). $^1$H-NMR ($CDCl_3$): δ 7.63 (s, 1H), 7.50 (m, 1H), 7.40 (m, 2H), 7.32 (m, 1H), 7.12 (m, 1H), 6.74 (m, 1H), 6.69 (m, 1H), 6.66 (s, 1H), 5.54 (s, 2H), 1.66 (s, 6H). MS (ES): 511 [M+H]$^+$.

The following compounds are prepared essentially according to the previous examples:
2-(3-(5-(1-(2,4-difluorobenzyl)-3-(trifluoromethyl)-1H-pyrazol-5-yl)thiophen-2-yl)phenyl)-2-methylpropanoic acid. MS (ES): 507 [M+H]$^+$.
1-(5-(5-(1-(2,4-difluorobenzyl)-3-(trifluoromethyl)-1H-pyrazol-5-yl)thiophen-2-yl)pyridin-2-yl)piperazine. MS (ES): 506 [M+H]$^+$.
2-(1-(2,4-difluorobenzyl)-5-(5-(3-(methylsulfonyl)phenyl)thiophen-2-yl)-1H-pyrazol-3-yl)propan-2-ol. MS (ES): 489 [M+H]$^+$.

Scheme 43

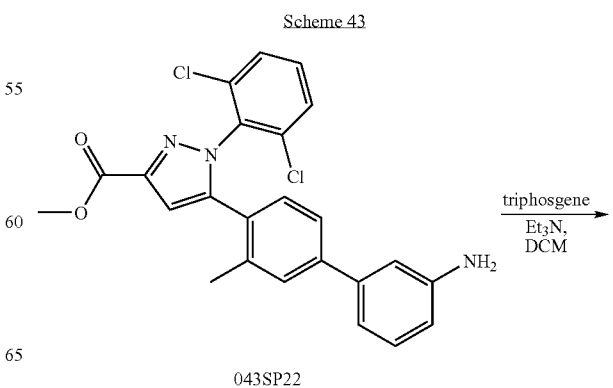
043SP22

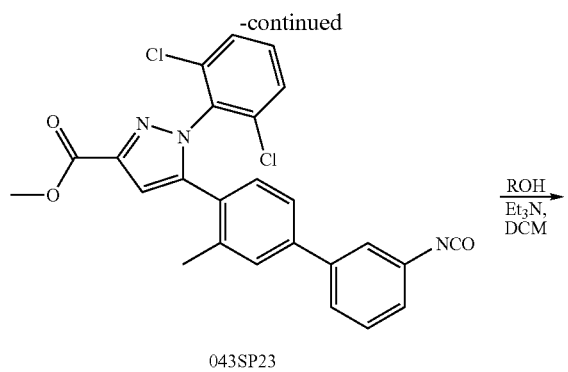

043SP23

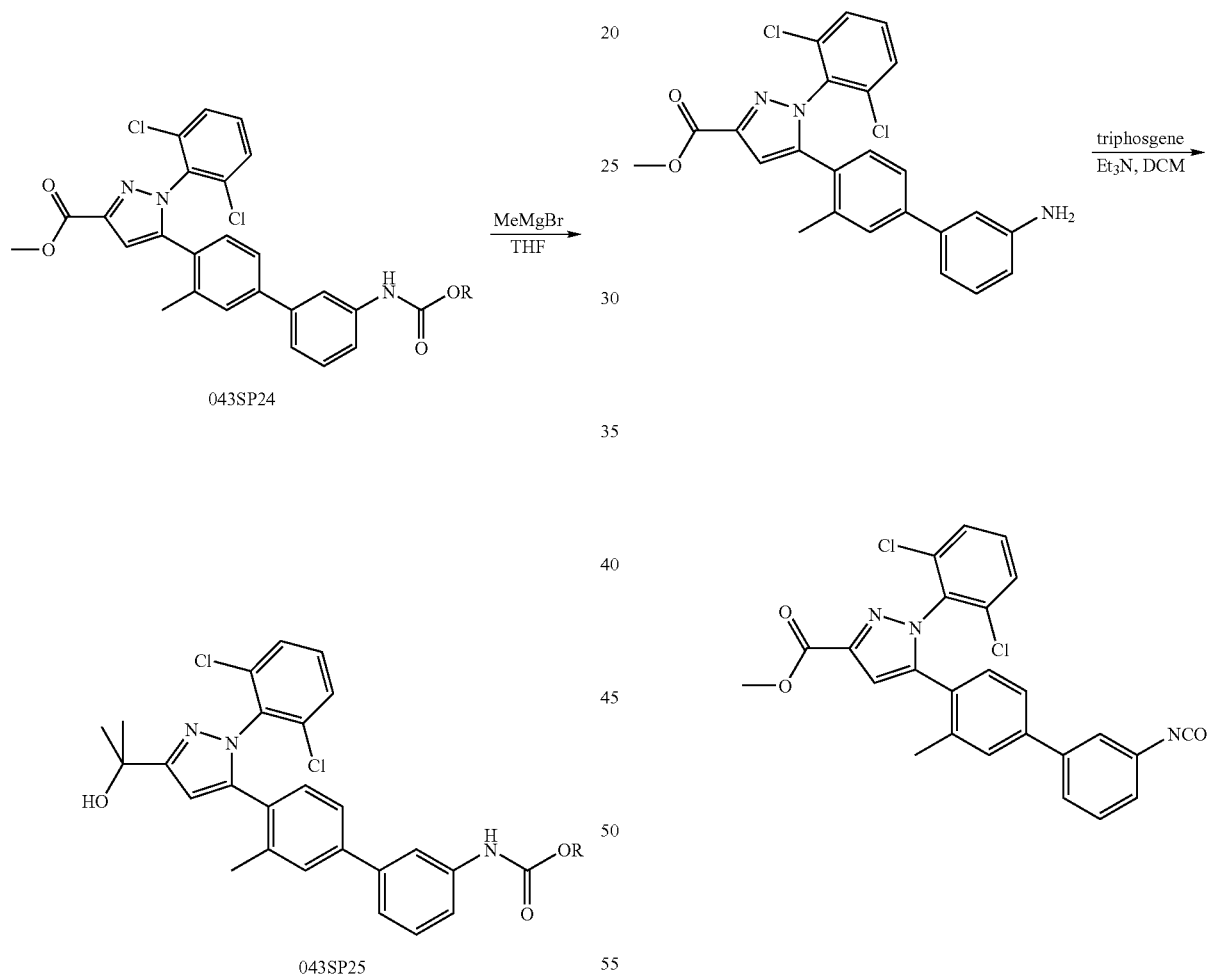

As depicted in Scheme 43, the aniline 043SP22 was treated with triphosgene and triethylamine to afford isocyanate 043SP23, which was reacted with alcohol, providing the carbamate 043SP24. The cabarmate 043SP24 was treated with MeMgBr to produce the carbinol 043SP25.

Example 97

3-(4-methylpiperazin-1-yl)propyl 4'-(1-(2,6-dichlorophenyl)-3-(2-hydroxypropan-2-yl)-1H-pyrazol-5-yl)-3'-methylbiphenyl-3-ylcarbamate Example 97a Preparation of methyl 1-(2,6-dichlorophenyl)-5-(3'-isocyanato-3-methylbiphenyl-4-yl)-1H-pyrazole-3-carboxylate methyl 5-(3'-amino-3-methylbiphenyl-4-yl)-1-(2,6-dichlorophenyl)-1H-pyrazole-3-carboxylate (0.276 g, 0.61 mmol) was dissolved in anhydrous DCM (6.0 mL) and cooled off under nitrogen atmosphere at 0° C. with an ice/water bath. To this solution was added triethyl amine (74 mg, 0.73 mmol) and triphosgene (181 mg, 0.61 mmol). The reaction mixture was stirred for 4 hours while it warmed up to room temperature. It was quenched carefully with water and the reaction mixture was extracted with DCM. The organic layer was washed with water and brine and dried over anhydrous Na$_2$SO$_4$. The residue was concentrated in vacuo, providing the crude product isocyanate, which was used for the next reaction without purification.

Example 97b

Preparation of methyl 1-(2,6-dichlorophenyl)-5-(3-methyl-3'43-(4-methylpiperazin-1-yl)propoxy)carbonylamino)biphenyl-4-yl)-1H-pyrazole-3-carboxylate

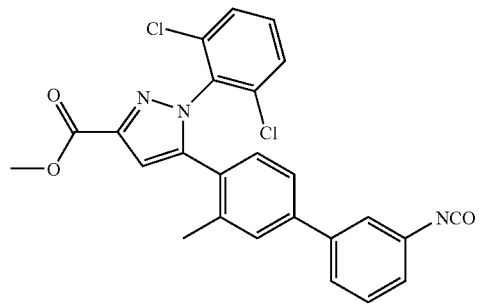

+

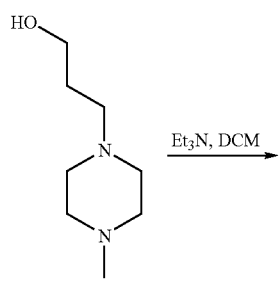

Et$_3$N, DCM →

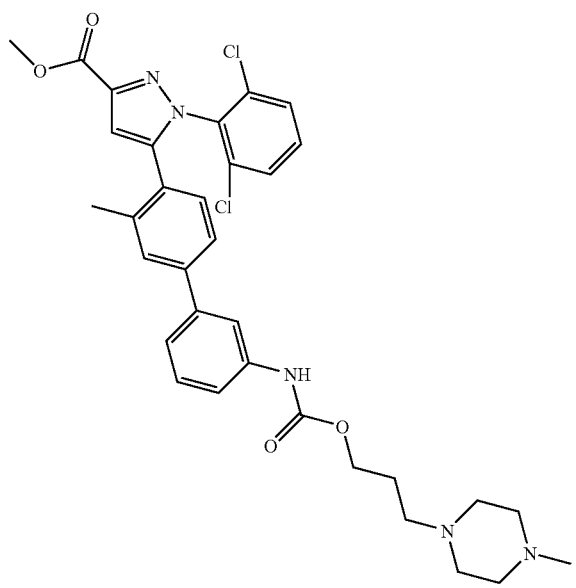

To a solution of the crude isocyanate in anhydrous DCM (6.0 mL) was added triethyl amine (74 mg, 0.73 mmol) and 3-(4-methylpiperazin-1-yl)propan-1-ol (97 mg, 0.61 mmol). The reaction mixture was stirred under nitrogen atmosphere at room temperature for overnight. It was concentrated in vacuo. The crude product carbamate was used for the next reaction without purification.

Example 97c

Preparation of 3-(4-methylpiperazin-1-yl)propyl 4'-(1-(2,6-dichlorophenyl)-3-(2-hydroxypropan-2-yl)-1H-pyrazol-5-yl)-3'-methylbiphenyl-3-ylcarbamate

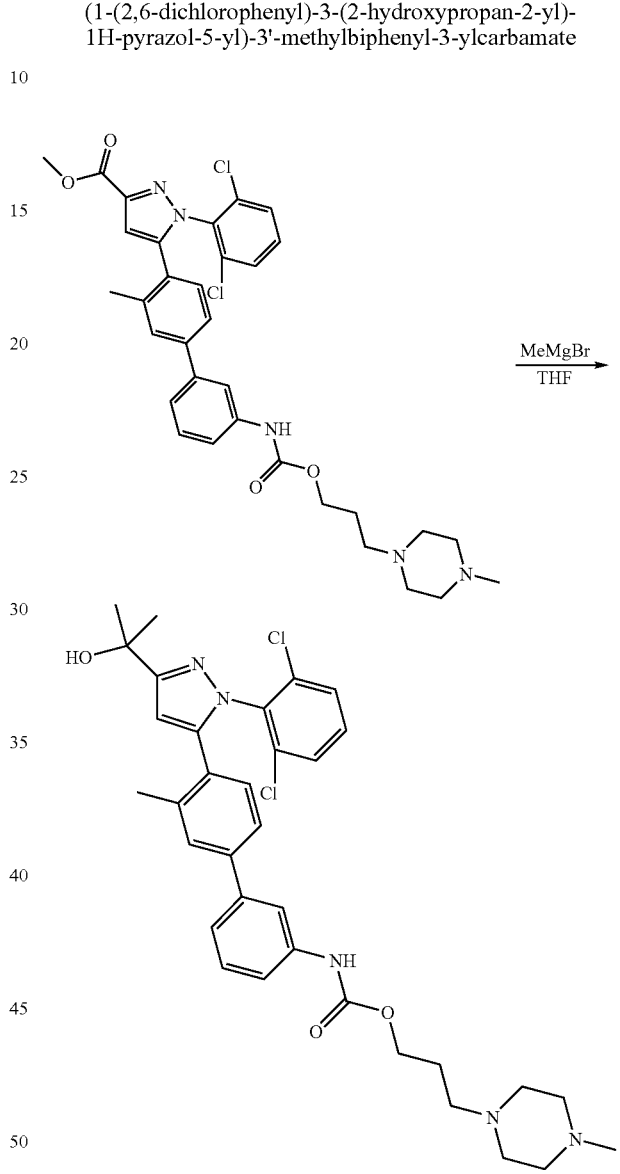

To a solution of the crude carbamate in anhydrous THF (6.0 mL) cooled off under nitrogen atmosphere at −78° C. was added a 3.0 M solution of MeMgBr (1.0 mL, 3.0 mmol). It was stilled at −78° C. for 30 minutes and the cold bath was then removed. The mixture was stirred for 4 hours while it warmed up to room temperature. It was quenched with water and aq. NH$_4$Cl. The reaction mixture was extracted with ethyl acetate. The organic layer was washed with brine and water and dried over anhydrous Na$_2$SO$_4$. The solvent was evaporated in vacuo and the residue was purified by HPLC, providing the product (74 mg, 19% over 3 steps). $^1$H-NMR (CDCl$_3$): δ 7.68 (br, 1H), 7.45 (m, 1H), 7.33 (m, 3H), 7.23 (m, 3H), 7.10 (m, 1H), 6.64 (s, 1H), 6.46 (s, 1H), 4.22 (m, 1H), 2.66 (s, 1H), 2.46 (br, 11H), 2.29 (s, 3H), 1.87 (m, 2H), 1.70 (s, 6H), 1.61 (s, 3H). MS (ES): 636 [M+H]$^+$.

Scheme 44

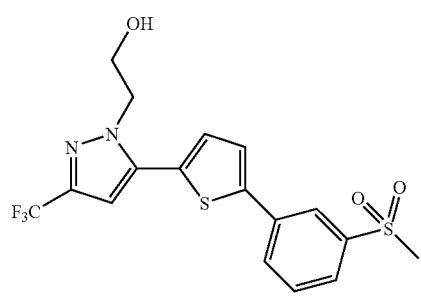

044SP26

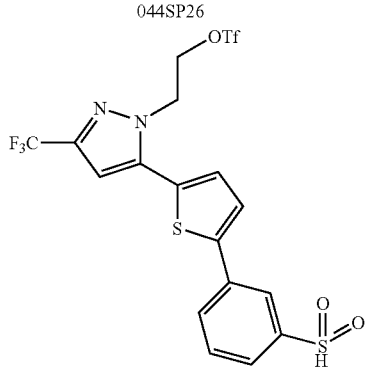

044SP27

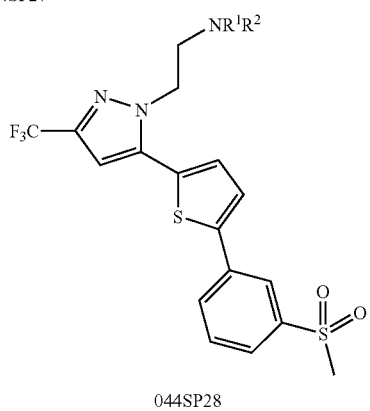

044SP28

As depicted in Scheme 44, the hydroxyethyl substituted pyrazole 044P26 was treated with triflic anhydride and DIEA to afford the triflate 044SP27, which was reacted with amine, resulting in the aminoethyl substituted pyrazole 044SP28.

Example 98

Preparation of N-(2-(5-(5-(3-(methylsulfonyl)phenyl)thiophen-2-yl)-3-(trifluoromethyl)-1H-pyrazol-1-yl)ethyl)propan-2-amine

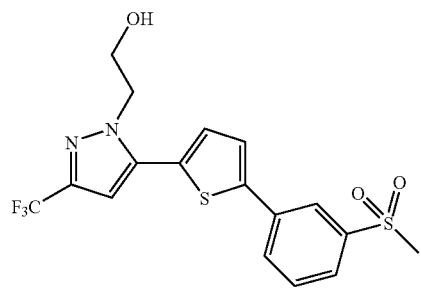

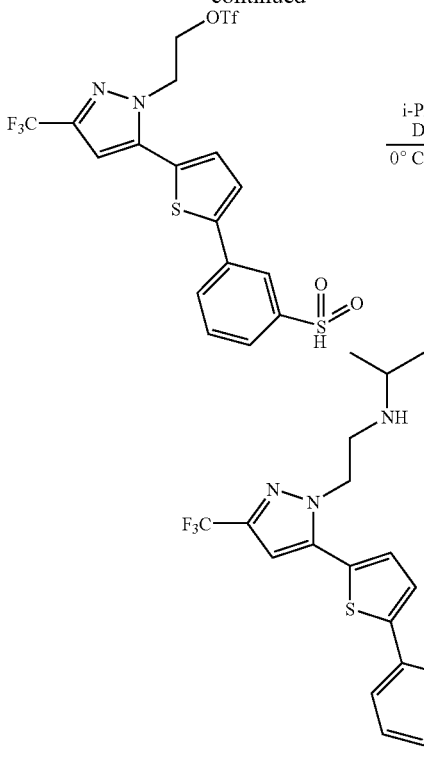

2-(5-(5-(3-(methylsulfonyl)phenyl)thiophen-2-yl)-3-(trifluoromethyl)-1H-pyrazol-1-yl)ethanol (208 mg, 0.50 mmol), prepared in a manner similar to that describes Example 1c, was dissolved in anhydrous DCM (4.0 mL) and cooled off at 0° C. under nitrogen atmosphere with an ice/water bath. To this solution was added DIEA (97 mg, 0.75 mmol) and trine anhydride (169 mg, 0.60 mmol). The reaction mixture was stirred at 0° C. for an hour and isopropyl amine (148 mg, 2.5 mmol) was added. It was stirred for overnight while it warmed up to room temperature. The reaction mixture was concentrated in vacuo and the residue was purified by HPLC, providing the product amine (148 mg, 65%). %). $^1$H-NMR (CDCl$_3$): δ 8.17 (m, 1H), 7.90 (m, 1H), 7.87 (m, 1H), 7.64 (m, 1H), 7.44 (m, 1H), 7.30 (m, 1H), 6.67 (s, 1H), 4.39 (m, 2H), 3.15 (m, 2H), 3.13 (s, 3H), 2.79 (m, 1H), 1.03 (d, 6H). MS (ES): 458 [M+H]$^+$.

The following compounds are prepared essentially according to the previous examples:

N-(2-(5-(5-(3-(methylsulfonyl)phenyl)thiophen-2-yl)-3-(trifluoromethyl)-1H-pyrazol-1-yl)ethyl)cyclopentanamine. MS (ES): 484 [M+H]$^+$.

N-benzyl-N-methyl-2-(5-(5-(3-(methylsulfonyl)phenyl)thiophen-2-yl)-3-(trifluoromethyl)-1H-pyrazol-1-yl)ethanamine. MS (ES): 520 [M+H]$^+$.

N-methyl-2-(5-(5-(3-(methylsulfonyl)phenyl)thiophen-2-yl)-3-(trifluoromethyl)-1H-pyrazol-1-yl)-N-(thiophen-2-ylmethyl)ethanamine. MS (ES): 526 [M+H]$^+$.

N-(furan-2-ylmethyl)-N-methyl-2-(5-(5-(3-(methylsulfonyl)phenyl)thiophen-2-yl)-3-(trifluoromethyl)-1H-pyrazol-1-yl)ethanamine. MS (ES): 510 [M+H]$^+$ N-methyl-2-(5-(5-(3-(methylsulfonyl)phenyl)thiophen-2-yl)-3-(trifluoromethyl)-1H-pyrazol-1-yl)-N-(pyridin-4-ylmethyl)ethanamine. MS (ES): 521 [M+H]$^+$.

1-(2-(1H-imidazol-1-yl)ethyl)-5-(5-(3-(methylsulfonyl)phenyl)thiophen-2-yl)-3-(trifluoromethyl)-1H-pyrazole. MS (ES): 467 [M+H]$^+$.

1-methyl-4-(2-(5-(5-(3-(methylsulfonyl)phenyl)thiophen-2-yl)-3-(trifluoromethyl)-1H-pyrazol-1-yl)ethyl)piperazine. MS (ES): 499 [M+H]$^+$.

1-(2-(5-(5-(3-(methylsulfonyl)phenyl)thiophen-2-yl)-3-(trifluoromethyl)-1H-pyrazol-1-yl)ethyl)pyrrolidin-3-ol. MS (ES): 486 [M+H]$^+$.

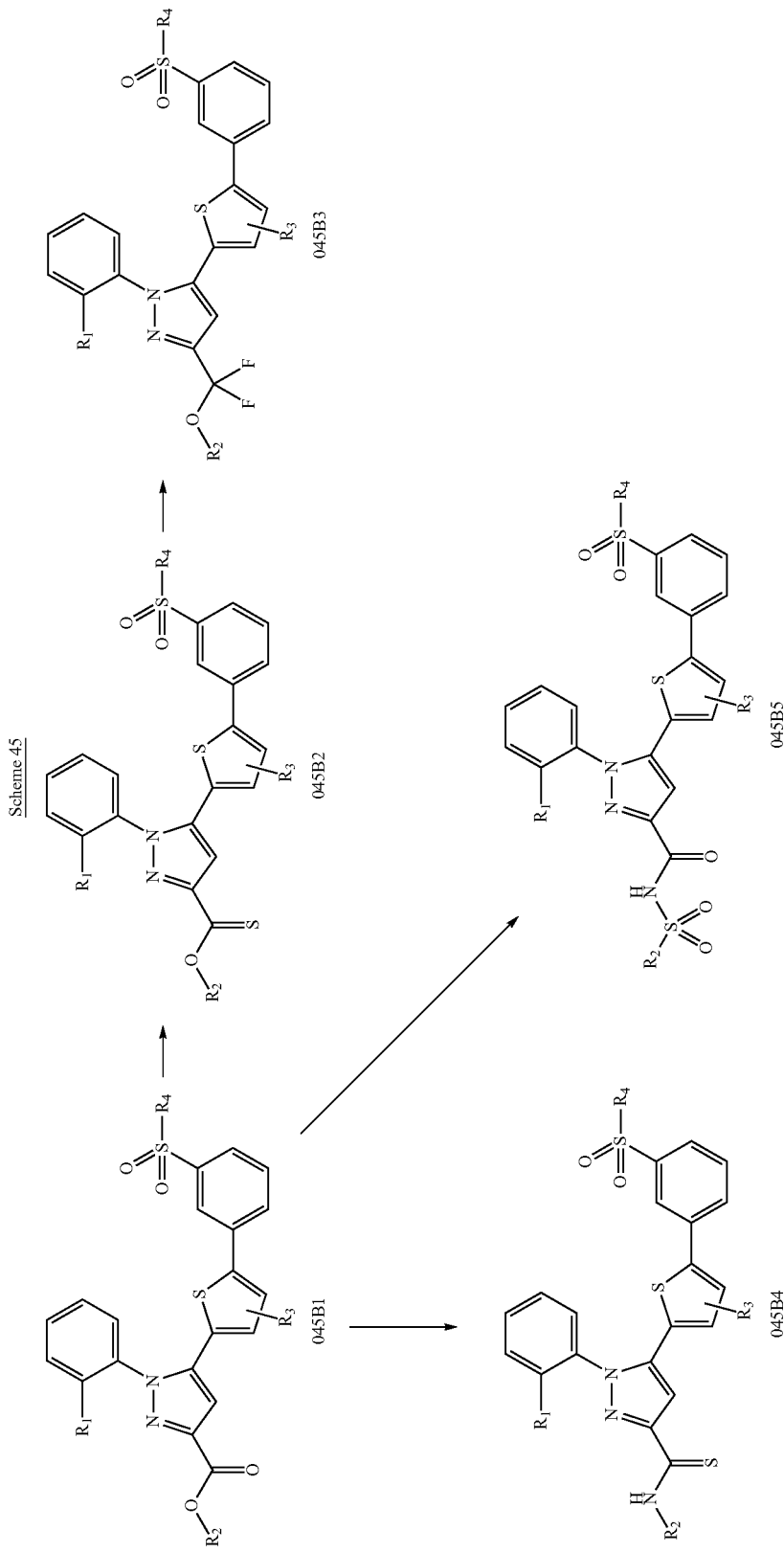

Additional methods for function group conversion on the pyrazole ring are illustrated in Scheme 45. Ester substituted pyrazole compound, such as formula (045B1) can be converted to thioesters, such as compound (045B2) using standard techniques that use known reagents of thiation such as Lawesson's reagent. Thioester (045B2) can be converted to difluoroethers compounds, such as formula (045B3), with the aid of known reagents of gem difluorination such as DAST. Ester substituted pyrazole compound (045B1) can also be converted to amides, thioamides, such as compound (045B4), carboxylic acids, sulfonamides such as compound (045B5), and amines using techniques that are readily apparent to one skilled in the arts.

Example 99

3-(Difluoro-methoxy-methyl)-5-[5-(3-methanesulfonyl-phenyl)-thiophen-2-yl]-1-(2-trifluoromethyl-phenyl)-1H-pyrazole Example 99a Preparation of 5-[5-(3-Methanesulfonyl-phenyl)-thiophen-2-yl]-1-(2-trifluoromethyl-phenyl)-1H-pyrazole-3-carbothioic acid O-methyl ester

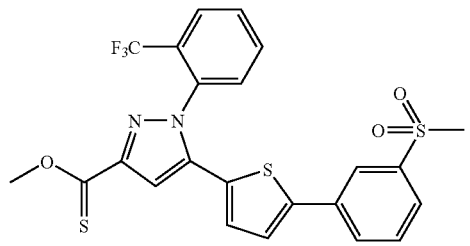

To a 50 mL round bottom flask attached with condenser was added 5-[5-(3-Methanesulfonyl-phenyl)-thiophen-2-yl]-1-(2-trifluoromethyl-phenyl)-1H-pyrazole-3-carboxylic acid methyl ester (326 mg, 644 μmmol), Lawesson's reagent (520 mg, 129 mmol) and anhydrous toluene (23 mL). The reaction solution was stirred at reflux for 1 day. The reaction solution was concentrated in vacuo, and the crude material was chromatographed through a 25 g SiO$_2$ column using a gradient of 100% Hx to 50% EtOAc to afford 302 mg (90% yield) of the title compound. MS (ES) 523.3 [M+H]$^+$, 545.0 (M+Na)$^+$.

Example 99b

Preparation of 3-(Difluoro-methoxy-methyl)-5-[5-(3-methanesulfonyl-phenyl)-thiophen-2-yl]-1-(2-trifluoromethyl-phenyl)-1H-pyrazole

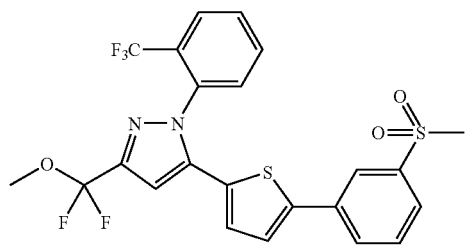

To a dry, N$_2$ purged round bottom flask was added 5-[5-(3-Methanesulfonyl-phenyl)-thiophen-2-yl]-1-(2-trifluoromethyl-phenyl)-1H-pyrazole-3-carbothioic acid O-methyl ester (280 mg, 535 μmol) in a solution of anhydrous DCM (15 mL). To the reaction solution was added DAST (200 mL, 1.53 mmol), and the reaction solution was stirred at room temperature for 14 hrs. The reaction solution was diluted with DCM (100 mL) and washed with aq. NaCl, partitioned, dried over Na$_2$SO$_4$, filtered, and concentrated in vacuo. The crude residue was chromatographed through a 25 g SiO$_2$ column using a mobile phase of 100 Hx to 50% EtOAc to afford 64 mg (23% yield) of the title compound. $^1$H NMR (400 MHz, CDCl$_3$) δ 8.02 (s, 1H), 7.80-7.89 (m, 2H), 7.66-7.75 (m, 3H), 7.50-7.58 (m, 2H), 7.18 (d, 1H), 6.83 (s, 1H), 6.74 (d, 1H), 3.47 (s, 3H), 3.06 (s, 3H); $^{19}$F NMR (400 MHz, CDCl$_3$) δ −61, −71 ppm. MS (ES) 529.3 [M+H].

Example 100

N-[5-[5-(3-Methanesulfonyl-phenyl)-thiophen-2-yl]-1-(2-trifluoromethyl-phenyl)-1H-pyrazole-3-carbonyl]-methanesulfonamide Example 100a 5-[5-(3-Methanesulfonyl-phenyl)-thiophen-2-yl]-1-(2-trifluoromethyl-phenyl)-1H-pyrazole-3-carboxylic acid

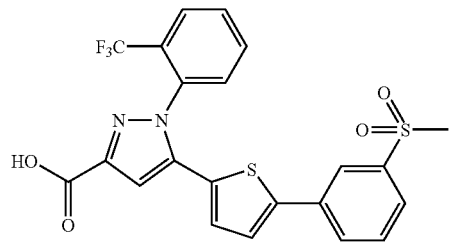 [SMILES: CS(=O)(=O)c1cccc(-c2ccc(-c3cc(C(=O)O)nn3-c3ccccc3C(F)(F)F)s2)c1]

To a 100 mL round bottom flask attached with condenser was added 5-[5-(3-Methanesulfonyl-phenyl)-thiophen-2-yl]-1-(2-trifluoromethyl-phenyl)-1H-pyrazole-3-carboxylic acid ethyl ester (2.52 g, 4.98 mmol), 1N aq NaOH (30 mL), and MeOH (25 mL). The reaction solution was stared at 55° C. for 1.5 hr prior to TLC analysis. The reaction solution was diluted with EtOAc (200 mL), poured into a separately funnel and the organic phase was partitioned. The aqueous phase was neutralized by the addition of aq 1 N HCl and extracted with EtOAc (70 mL×2). The combined organic phase was dried over Na$_2$SO$_4$, filtered into a round bottom flask and concentrated on the Rotavapor. The crude residue was chromatographed thru a 25 g SiO$_2$ column using a mobile phase gradient of 100% Hx to 85% EtOAc to afford 1.35 g (55% yield) title compound. MS (ES) 493.1 [M+H]$^+$.

Example 100b

N-[5-[5-(3-Methanesulfonyl-phenyl)-thiophen-2-yl]-1-(2-trifluoromethyl-phenyl)-1H-pyrazole-3-carbonyl]-methanesulfonamide

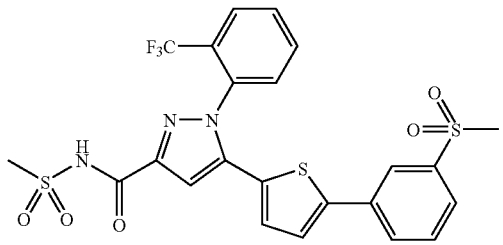

To round bottom flask was added 5-[5-(3-Methanesulfonyl-phenyl)-thiophen-2-yl]-1-(2-trifluoromethyl-phenyl)-1H-pyrazole-3-carboxylic acid (302 mg, 615 mmol), oxalyl chloride (0.54 mL), anhydrous DCM (10 mL), and anhydrous DMF (100 µL). The reaction solution was stirred at room temperature for approximately 1 hr prior to concentration in vacuo. The resulting crude acid chloride intermediate was used in the next reaction without further purification. To a glass vial was added acid chloride (615 µmol theoretical), methanesulfonamide (117 mg, 1.23 mmol), 1,2-dichloroethane (9 mL), DIEA (200 µL), and DMAP (10 mg). The reaction solution was stirred at 45° C. for 3 hrs. The reaction solution was diluted with DCM (60 mL) and transferred to a separatory funnel. The solution was washed with aq NH$_4$Cl (50 mL×2) and with aq NaCl (50 mL). The organic phase was dried over Na$_2$SO$_4$, filtered, concentrated on the Rotavapor and chromatographed through a 25 g SiO$_2$ column using a mobile phase gradient of 100% Hx to 70% EtOAc to afford 182 mg (52% yield) of the title compound. $^1$H NMR (400 MHz, CDCl$_3$) δ 9.07 (s, 1H), 8.02 (s, 1H), 7.91 (m, 1H), 7.84 (d, 1H), 7.74-7.80 (m, 2H), 7.69 (d, 1H), 7.55 (t, 1H), 7.48 (m, 1H), 7.23 (s, 1H), 7.21 (d, 1H), 6.77 (d, 1H), 3.42 (s, 3H), 3.07 (s, 3H); $^{19}$F NMR (400 MHz, CDCl$_3$) δ −60.5 ppm MS (ES) 570.2 [M+H]$^+$.

Example 101

Preparation of 1-(2-Chloro-phenyl)-5-[5-(3-methanesulfonyl-phenyl)-thiophen-2-yl]-1H-pyrazole-3-carbothioic acid ethylamide

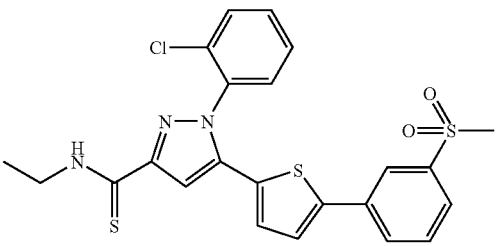 [SMILES: CCNC(=S)c1cc(-c2ccc(-c3cccc(S(C)(=O)=O)c3)s2)n(-c2ccccc2Cl)n1]

To a dry, N$_2$ purged 50 mL round bottom flask attached with condenser was added 1-(2-Chloro-phenyl)-5-[5-(3-methanesulfonyl-phenyl)-thiophen-2-yl]-1H-pyrazole-3-carboxylic acid ethylamide (100 mg, 206 µmol), Lawesson's reagent (200 mg, 494 µmol), and anhydrous toluene (8 mL). The reaction solution was allowed to stir at reflux for 14 hrs. The reaction solution was allowed to cool to room temperature prior to addition of a 1:1 mixture of benzene and Et$_2$O. The resulting precipitate was removed by vacuum filtration through a Buchner funnel. The filtrate was concentrated on the Rotavapor and the crude residue was chromatographed through a 12 g SiO$_2$ column using a mobile phase gradient of 100% Hx to 50% EtOAc to afford 39 mg (38% yield) of the title compound. $^1$H NMR (400 MHz, CDCl$_3$) δ 8.68 (br s, 1H), 8.02 (s, 1H), 7.83 (d, 1H), 7.72 (d, 1H), 7.48-7.70 (m, 5H), 7.42 (s, 1H), 7.22 (d, 1H), 6.83 (d, 1H), 3.87 (m, 2H), 3.07 (s, 3H), 1.36 (t, 3H). MS (ES) 502.3, 504.3 [M+H]$^+$.

The following compound was prepared in a similar manner to, that described above:

1-(2-chlorophenyl)-5-{5-[3-(methylsulfonyl)phenyl]-2-thienyl}-N-(2,2,2-trifluoroethyl)-1H-pyrazole-3-carbothioamide, MS (ES) 556.0, 558.0 [M+H]$^+$ Scheme 46

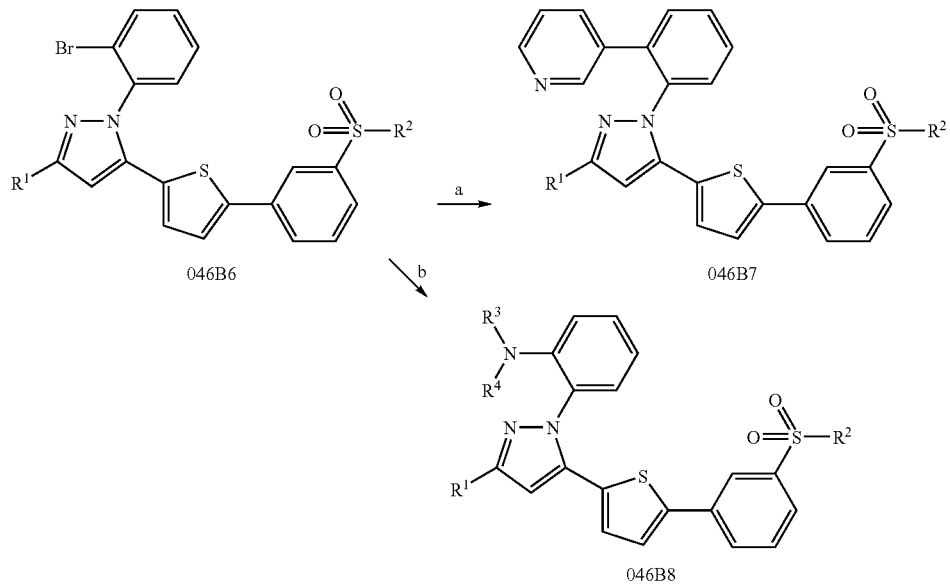

(a) 3-Pyr-boronic acid, PdCl$_2$dppf, K$_2$CO$_3$; (b) R$_3$R$_4$NH, Pd cat

Additional methods for A-ring substitution which use metal catalyzed carbon-carbon bond coupling methodology are illustrated in Scheme 46. The pyrazole-phenyl bromide intermediate (046B6) can be reacted under Suzuki coupling conditions to prepare the ortho-aryl products, such as compound (046B7). The aryl bromide intermediate (046B6) can also be used in Buchwald amination reaction to prepare alkylamino substituted compounds, such as formula (046B8).

Example 102

Preparation of 3-(2-{5-[5-(3-Methanesulfonyl-phenyl)-thiophen-2-yl]-3-trifluoromethyl-pyrazol-1-yl}-phenyl)-pyridine

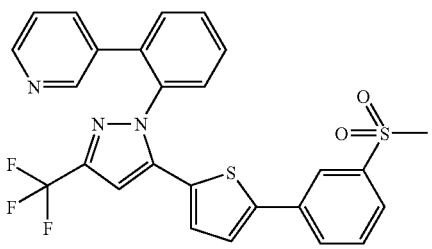 [SMILES: CS(=O)(=O)c1cccc(-c2ccc(-c3cc(C(F)(F)F)nn3-c3ccccc3-c3cccnc3)s2)c1]

To a 50 mL round bottom flask attached with condenser was added 1-(2-Bromo-phenyl)-5-[5-(3-methanesulfonyl-phenyl)-thiophen-2-yl]-3-trifluoromethyl-1H-pyrazole (prepared following the described in Example 1c) (110 mg, 210 µmol), 3-pyridylboronic acid (31 mg, 525 µmol), PdCl$_2$dppf (25 mg, 10 mol %), K$_2$CO$_3$ (58 mg, 410 µmol), 1,4-dioxane (8 mL) and H$_2$O (1.5 mL). The reaction solution was allowed to stir at 75° C. for 20 hrs. The reaction solution was diluted with EtOAc (150 mL) and transferred to a separator), funnel and washed with aq NH$_4$Cl (100 mL) and aq NaCl (100 mL). The organic phase was dried over Na$_2$SO$_4$, filtered, concentrated on the Rotavapor and chromatographed through a 25 g SiO$_2$ column using a mobile phase gradient of 100% Hx to 90% EtOAc to afford 45 mg (41% yield) of the title compound. $^1$H NMR (400 MHz, DMSO-d$_6$) δ 8.41 (m, 1H), 7.99 (m, 2H), 7.51-7.90 (m, 8H), 7.24 (s, 1H), 7.17-7.23 (m, 2H), 6.87 (d, 1H), 3.28 (s, 3H); $^{19}$F NMR (400 MHz, DMSO-d$_6$) δ −61.2 ppm. MS (ES) 526.5 [M+H]$^+$.

Scheme 47

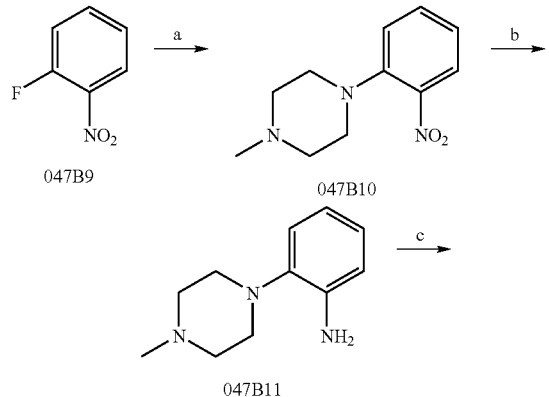

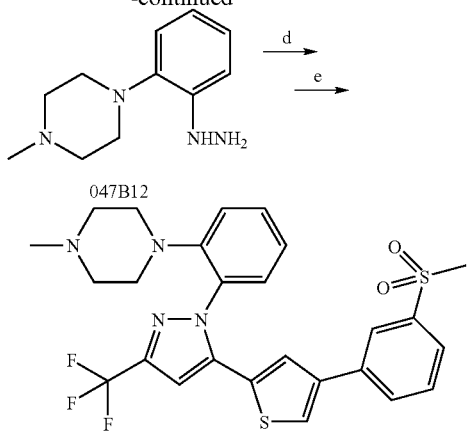

(a) 4-Me-piperazine, THF, reflux; (b) 30 psi H2, 10% Pd/C; (c) (i) NaNO2, HCl, (ii) SnCl2•2H2O, HCl' (d) diketone, tol, HCl; (e) Suzuki coupling Additional methods for synthesizing substituted arylhydrazines, such as compound (047B12) are shown in Scheme 47. The hydrazines can be used to prepare pyrazole compounds, similar to those described in Example 1c, and the method in Scheme 47 is a complementary method to that described in Scheme 46. 2-Fluoro-nitrobenzene (047B9) can be reacted with alkylamines to undergo a S$_N$Ar reaction to yield substituted arylnitro compounds (047B10). The nitro intermediate (047B10) can be converted to the corresponding aniline (047B11) using known hydrogenation methods. The resulting aniline (047B11) can be converted to the arylhydrazine (047B12) by reaction through the diazonium salt followed by reduction. When these hydrazines are applied to the pyrazole synthesis methodology described in Example 1c, final pyrazole compounds containing larger and more complex aminoalkyl substituents, such as compound (047B13) are available.

Example 103

1-(2-{5-[4-(3-Methanesulfonyl-phenyl)-thiophen-2-yl]-3-trifluoromethyl-pyrazol-1-yl}-phenyl)-4-methyl-piperazine

Example 103a

Preparation of 1-Methyl-4-(2-nitro-phenyl)-piperazine

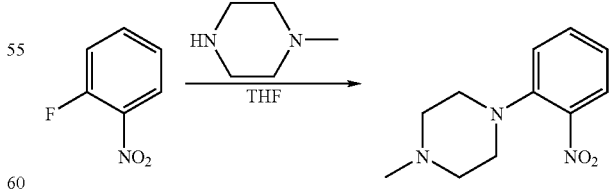

To a Kontes glass tube was added 2-fluoro-nitrobenzene (3.34 g, 23.7 mmol), 1-methyl-piperazine (3.90 mL, 35.6 mmol), and anhydrous THF (10 mL). The tube was sealed and the reaction mixture was allowed to stir at 60° C. for 1 day. The reaction solution was diluted with EtOAc (150 mL), washed with aq NaHCO$_3$, dried over Na$_2$SO$_4$, filtered, and concentrated in vacuo to afford 5.07 g (97% yield) of the title product. MS (ES) 222.3 [M+H]⁺.

Example 103b

Preparation of 2-(4-Methyl-piperazin-1-yl)-phenylhydrazine-HCl

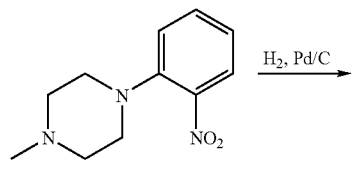

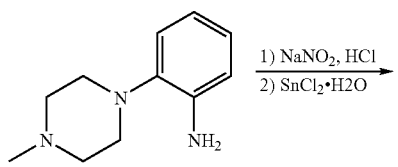

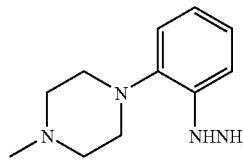

To a Parr Hydrogenation flask was added 1-Methyl-4-(2-nitro-phenyl)-piperizine (2.72 g, 12.3 mmol), EtOAc (50 mL), MeOH (50 mL). The flask was purged with dry $N_2$ for 5 min prior to addition of 10% Pd/carbon (1.00 g). The flask was placed onto the Parr hydrogenation apparatus and exposed to $H_2$ at 30 psi. The reaction was allowed to shake under $H_2$ pressure for 2 hrs. The flask was vented and the solution was filtered through a silica gel padded Buchner funnel. The filtrate was concentrated in vacuo to afford 2.0 g aniline product. The crude aniline was added to a 100 mL round bottom flask along with sodium nitrite (940 mg, 13.6 mmol), and conc. HCl (13 mL). The reaction was stirred at −10° C. for approximately 1 hr prior to addition of tin(II) chloride-dihydrate (10 g, 45 mmol) in a solution of conc. HCl (8 mL). The reaction solution was stirred at −10° C. for 1 hr. The solution was diluted with EtOAc (200 mL) and 2N aq NaOH was added until all tin byproduct was water soluble. The EtOAc phase was partitioned and the aq phase was extracted with EtOAc (150×2). The combined organic phase was dried over $Na_2SO_4$, filtered, and concentrated in vacuo to afford 1.69 g (79% yield) of product MS (ES) 237.3 [M+H]⁺, 259.3 (M+Na)⁺.

Example 103c 1-(2-{5-[4-(3-Methanesulfonyl-phenyl)-thiophen-2-yl]-3-trifluoromethyl-pyrazol-1-yl}-phenyl)-4-methyl-piperazine

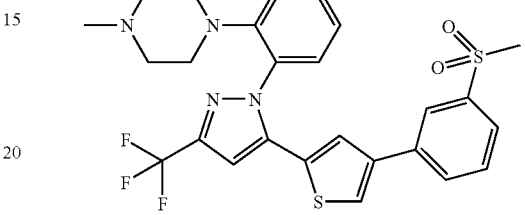

The compound 1-(2-{5-[4-(3-Methanesulfonyl-phenyl)-thiophen-2-yl]-3-trifluoromethyl-pyrazol-1-yl}-phenyl)-4-methyl-piperazine was prepared in a manner similar to that described in Example 1c by using 2-(4-Methyl-piperazin-1-yl)-phenylhydrazine-HCl. ¹H NMR (400 MHz, DMSO-$d_6$) δ 8.16 (s, 1H), 7.97-8.08 (m, 3H), 7.84 (d, 1H), 7.69 (t, 1H), 7.57 (t, 1H), 7.44-7.57 (m, 2H), 7.17-7.28 (m, 2H), 3.28 (s, 3H), 2.67 (br s, 2H), 2.03 (s, 3H), 1.86-2.14 (m, 6H); ¹⁹F NMR (400 MHz, DMSO-$d_6$) δ −61.1 ppm. MS (ES) 547.3 [M+H]⁺, 569.3 (M+Na)⁺.

The following compounds were synthesized in a manner similar to that described in Example 103:

3-{5-[1-[2-(4-methylpiperazin-1-yl)phenyl]-3-(trifluoromethyl)-1H-pyrazol-5-yl]-3-thienyl}benzenesulfonamide, MS (ES) 548.3 [M+H]⁺, 570.0 (M+Na)⁺

4-{2-[5-{4-[3-(methylsulfonyl)phenyl]-2-thienyl}-3-(trifluoromethyl)-1H-pyrazol-1-yl]phenyl}morpholine, MS (ES) 534.2 [M+H]⁺

4-{2-[5-(4-bromo-2-thienyl)-3-(trifluoromethyl)-1H-pyrazol-1-yl]phenyl}morpholine, MS(ES) 458.2, 460.2 [M+H]⁺

5-{4-[3-(methylsulfonyl)phenyl]-2-thienyl}-1-(2-propylphenyl)-3-(trifluoromethyl)-1H-pyrazole, MS (ES) 491.2 [M+H]⁺

1-[2-(1-methylethyl)phenyl]-5-{4-[3-(methylsulfonyl)phenyl]-2-thienyl}-3-(trifluoromethyl)-1H-pyrazole, MS (ES) 491.4 [M+H]⁺

1-methyl-4-({2-[5-{4-[3-(methylsulfonyl)phenyl]-2-thienyl}-3-(trifluoromethyl)-1H-pyrazol-1-yl]phenyl}methyl)piperazine, MS (ES) 560.8 [M+H]⁺

Scheme 48

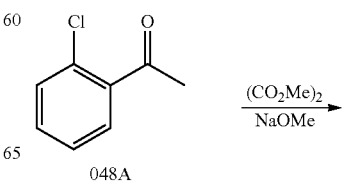

048A

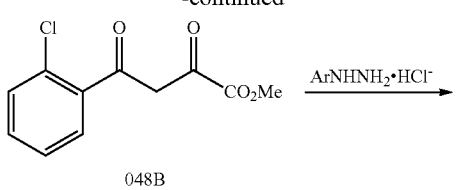

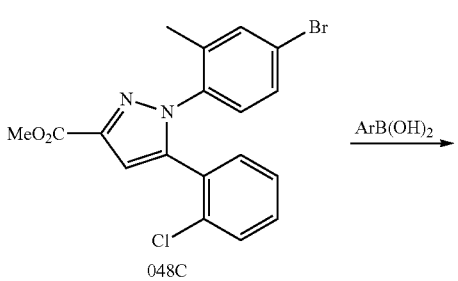

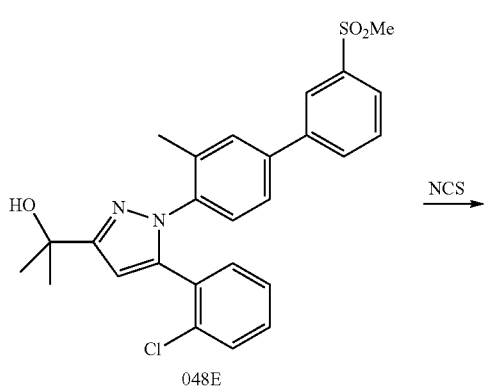

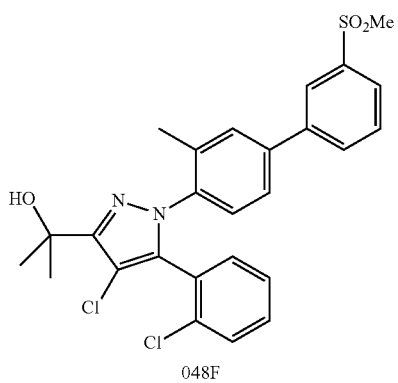

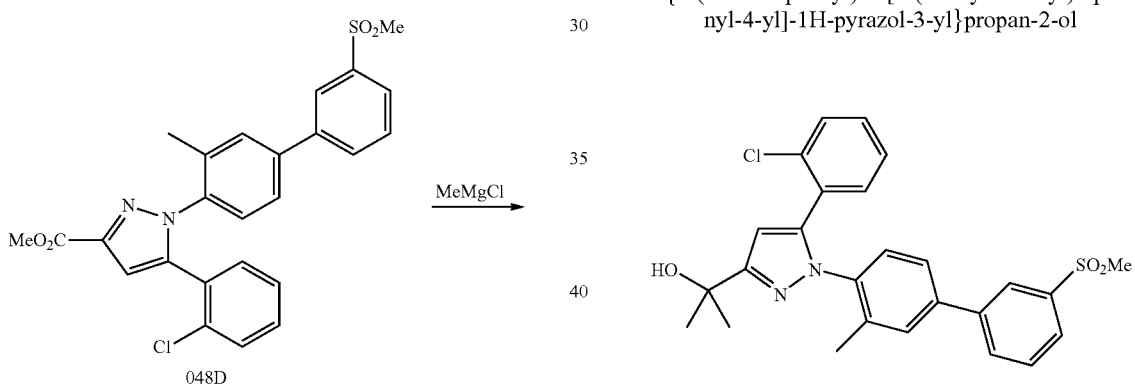

As depicted in Scheme 48, biphenyl pyrazole 048E and 048F were prepared from acetophenone 048A in a manner similar to that described in Scheme 6.

Example 104

2-{5-(2-chlorophenyl)-1-[3-(methylsulfonyl)biphenyl-4-yl]-1H-pyrazol-3-yl}propan-2-ol 2-{5-(2-chlorophenyl)-1-[3-methyl-3'-(methylsulfonyl) biphenyl-4-yl]-1H-pyrazol-3-yl}propan-2-ol was prepared in a manner similar to that as described in Example 8d by using 2'-chloroacetophenone. $^1$H-NMR (CDCl$_3$): δ 8.10 (s, 1H), 7.91 (m, 1H), 7.89 (m, 1H), 7.83 (m, 1H), 7.62 (m, 1H), 7.46 (d, 1H), 7.38 (d, 1H), 7.34-7.16 (m, 4H), 6.53 (s, 1H), 3.09 (s, 3H), 2.71 (s, 1H), 2.23 (s, 3H), 1.70 (s, 6H). MS(ES): 481 [M+H]$^+$, 463 (M-OH).

The following compounds are prepared essentially according to the previous examples:

5-((2-chlorophenyl)-1-(4-bromo-2-chlorophenyl)-1H-pyrazole-3-carboxylic acid methyl ester was prepared in a manner similar to that as described in Example 8b by using 4-(2-chlorophenyl)-2,4-dioxo-butyric acid methyl ester. MS(ES): 405 [M+H]$^+$.

5-((2-chlorophenyl)-1-[3-methyl-3'-(methylsulfonyl)biphenyl-4-yl]-1H-pyrazole-3-carboxylic acid methyl ester was prepared in a manner similar to that as described in Example 8c. by using 5-((2-chlorophenyl)-1-(4-bromo-2-chlorophenyl)-1H-pyrazole-3-carboxylic acid methyl ester MS(ES): 481 [M+H]$^+$.

2-{5-(2-chlorophenyl)-1-[3-methyl-3'-(methylsulfonyl)biphenyl-4-yl]-1H-pyrazol-3-yl}propan-2-ol was prepared in a manner similar to that as described in Example 8d by using 5-((2-chlorophenyl)-1-[3-methyl-3'-(methylsulfonyl)biphenyl-4-yl]-1H-pyrazole-3-carboxylic acid methyl ester. $^1$H-NMR (CDCl$_3$): δ 8.10 (s, 1H), 7.91 (m, 1H), 7.89 (M, 1H), 7.83 (m, 1H), 7.62 (m, 1H), 7.46 (d, 1H), 7.38 (d, 1H), 7.34-7.16 (m, 4H), 6.53 (s, 1H), 3.09 (s, 3H), 2.71 (s, 1H), 2.23 (s, 3H), 1.70 (s, 6H). MS(ES): 481 [M+H]$^+$, 463 (M-OH).

2-{1-[3-chloro-3'-(methylsulfonyl)biphenyl-4-yl]-5-(2-chlorophenyl)-1H-pyrazol-3-yl}propan-2-ol, MS(ES): 501 [M+H]$^+$, 483 (M-OH)

2-{5-(2,6-dichlorophenyl)-1-[3-methyl-3'-(methylsulfonyl)biphenyl-4-yl]-1H-pyrazol-3-yl}propan-2-ol, MS(ES): 515 [M+H]$^+$, 497 (M-OH)

2-{1-[3-chloro-3'-(methylsulfonyl)biphenyl-4-yl]-5-(2,6-dichlorophenyl)-1H-pyrazol-3-yl}propan-2-ol, MS(ES): 535 [M+H]$^+$, 517 (M-OH)

2-{5-(2,6-dichlorophenyl)-1-[3'-(methylsulfonyl)biphenyl-4-yl]-1H-pyrazol-3-yl}propan-2-ol, MS(ES): 501 [M+H]$^+$, 483 (M-OH)

2-{5-(2,3-dichlorophenyl)-1-[3'-(methylsulfonyl)biphenyl-4-yl]-1H-pyrazol-3-yl}propan-2-ol, MS(ES): 501 [M+H]$^+$, 483 (M-OH)

2-{5-(2,3-dichlorophenyl)-1-[3-methyl-3'-(methylsulfonyl)biphenyl-4-yl]-1H-pyrazol-3-yl}propan-2-ol, MS(ES): 515 [M+H]$^+$, 497 (M-OH)

2-{1-[3-chloro-3'-(methylsulfonyl)biphenyl-4-yl]-5-(2,3-dichlorophenyl)-1H-pyrazol-3-yl}propan-2-ol, MS(ES): 535 [M+H]$^+$, 517 (M-OH)

2-[5-(2-chlorophenyl)-1-{3-methyl-5-[3-(methylsulfonyl)phenyl]pyridin-2-yl}-1H-pyrazol-3-yl]propan-2-ol, MS(ES): 482 [M+H]$^+$, 464 (M-OH)

2-{5-(2-chlorophenyl)-1-[3,5-dimethyl-3'-(methylsulfonyl)biphenyl-4-yl]-1H-pyrazol-3-yl}propan-2-ol, MS(ES): 495 [M+H]$^+$, 477 (M-OH)

2-(5-(2-chloro-6-fluorophenyl)-1-(3'-(methylsulfonyl)biphenyl-4-yl)-1H-pyrazol-3-yl)propan-2-ol. MS(ES): 485 [M+H]$^+$.

2-(5-(2,3-difluorophenyl)-1-(3'-(methylsulfonyl)biphenyl-4-yl)-1H-pyrazol-3-yl)propan-2-ol. MS (ES): 469 [M+H]$^+$.

2-(5-(2-chloro-6-fluorophenyl)-1-(3-fluoro-3'-(methylsulfonyl)biphenyl-4-yl)-1H-pyrazol-3-yl)propan-2-ol. MS (ES): 503 [M+H]$^+$.

2-(5-(2,3-difluorophenyl)-1-(3-fluoro-3'-(methylsulfonyl)biphenyl-4-yl)-1H-pyrazol-3-yl)propan-2-ol. MS (ES): 487 [M+H]$^+$.

2-(5-(2-chloro-6-fluorophenyl)-1-(3-methyl-3'-(methylsulfonyl)biphenyl-4-yl)-1H-pyrazol-3-yl)propan-2-ol. MS (ES): 499 [M+H]$^+$.

2-(5-(2,3-difluorophenyl)-1-(3-methyl-3'-(methylsulfonyl)biphenyl-4-yl)-1H-pyrazol-3-yl)propan-2-ol. MS (ES): 483 [M+H]$^+$.

2-(1-(3-chloro-3'-(methylsulfonyl)biphenyl-4-yl)-5-(2-chloro-6-fluorophenyl)-1H-pyrazol-3-yl)propan-2-ol. MS (ES): 519 [M+H]$^+$.

2-(1-(3-chloro-3'-(methylsulfonyl)biphenyl-4-yl)-5-(2,3-difluorophenyl)-1H-pyrazol-3-yl)propan-2-ol. MS (ES): 503 [M+H]$^+$.

2-(1-(3-methyl-3'-(methylsulfonyl)biphenyl-4-yl)-5-(2-(trifluoromethyl)phenyl)-1H-pyrazol-3-yl)propan-2-ol. MS (ES): 515 [M+H]$^+$.

2-(1-(3-chloro-3'-(methylsulfonyl)biphenyl-4-yl)-5-(2-(trifluoromethyl)phenyl)-1H-pyrazol-3-yl)propan-2-ol. MS (ES): 535 [M+H]$^+$.

2-(4-chloro-5-(2-chloro-6-fluorophenyl)-1-(2-methyl-3'-(methylsulfonyl)biphenyl-4-yl)-1H-pyrazol-3-yl)propan-2-ol. MS (ES): 499 [M+H]$^+$.

2-(5-(2,6-dichlorophenyl)-1-(2-methyl-3'-(methylsulfonyl)biphenyl-4-yl)-1H-pyrazol-3-yl)propan-2-ol. MS (ES): 515 [M+H]$^+$.

Example 105

2-{4-chloro-5-(2-chlorophenyl)-1-[3-methyl-3'-(methylsulfonyl)biphenyl-4-yl]-1H-pyrazol-3-yl}propan-2-ol

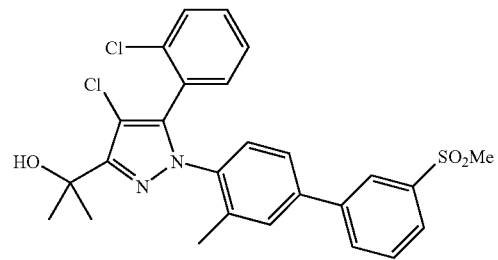 [SMILES: Cc1cc(-c2cccc(S(C)(=O)=O)c2)ccc1-n1nc(C(C)(C)O)c(Cl)c1-c1ccccc1Cl]

2-{4-chloro-5-(2-chlorophenyl)-1-[3-methyl-3'-(methylsulfonyl)biphenyl-4-yl]-1H-pyrazol-3-yl}propan-2-ol was prepared in a manner similar to that as described in Example 12. $^1$H-NMR (CDCl$_3$): δ 8.08 (m, 1H), 7.91 (m, 1H), 7.80 (m, 1H), 7.62 (t, 1H), 7.46 (d, 1H), 7.43 (m, 1H), 7.35-7.25 (m, 5H), 7.13 (d, 1H), 3.18 (s, 1H), 3.08 (s, 3H), 2.29 (s, 3H), 1.76 (s, 3H). MS(ES): 515 [M+H]$^+$, 497 (M-OH)

The following compounds are prepared essentially according to the previous examples:

2-{4-chloro-5-(2-chlorophenyl)-1-[3'-(methylsulfonyl)biphenyl-4-yl]-1H-pyrazol-3-yl}propan-2-ol: $^1$H-NMR (CDCl$_3$): δ 8.10 (s, 1H), 7.91 (m, 1H), 7.81 (m, 1H), 7.64 (m, 1H), 7.53-7.33 (m, 8H), 3.22 (s, 1H), 3.08 (s, 3H), 1.77 (s, 6H). MS(ES): 501 [M+H]$^+$, 483 (M-OH)

2-[4-chloro-5-(2-chlorophenyl)-1-{3-methyl-5-[3-(methylsulfonyl)phenyl]pyridin-2-yl}-1H-pyrazol-3-yl]propan-2-ol, MS(ES): 516 [M+H]$^+$, 498 (M-OH)

2-{4-chloro-1-[3-chloro-3'-(methylsulfonyl)biphenyl-4-yl]-5-(2-chlorophenyl)-1H-pyrazol-3-yl}propan-2-ol, MS(ES): 534 [M+H]$^+$, 517 (M-OH)

2-{4-chloro-5-(2,6-dichlorophenyl)-1-[3-methyl-3'-(methylsulfonyl)biphenyl-4-yl]-1H-pyrazol-3-yl}propan-2-ol, MS(ES): 549 [M+H]$^+$, 531 (M-OH)

2-{4-chloro-5-(2,6-dichlorophenyl)-1-[3-chloro-3'-(methylsulfonyl)biphenyl-4-yl]-1H-pyrazol-3-yl}propan-2-ol, MS(ES): 569 [M+H]$^+$, 551 (M-OH)

2-(4-chloro-5-(2-chloro-6-fluorophenyl)-1-(3-methyl-3'-(methylsulfonyl)biphenyl-4-yl)-1H-pyrazol-3-yl)propan-2-ol. MS (ES): 533 [M+H]$^+$.

2-(4-chloro-1-(3-chloro-3'-(methylsulfonyl)biphenyl-4-yl)-5-(2-chloro-6-fluorophenyl)-1H-pyrazol-3-yl)propan-2-ol. MS (ES): 553 [M+H]$^+$.

2-(4-chloro-5-(2-chloro-6-fluorophenyl)-1-(2-methyl-3'-(methylsulfonyl)biphenyl-4-yl)-1H-pyrazol-3-yl)propan-2-ol. MS (ES): 533 [M+H]$^+$.

2-(4-chloro-5-(2,6-dichlorophenyl)-1-(2-methyl-3'-(methylsulfonyl)biphenyl-4-yl)-1H-pyrazol-3-yl)propan-2-ol. MS (ES): 549[M+H]$^+$.

2-(4-chloro-1-(3-methyl-3'-(methylsulfonyl)biphenyl-4-yl)-5-(2-(trifluoromethyl)-phenyl)-1H-pyrazol-3-yl)propan-2-ol. MS (ES): 549 [M+H]$^+$.

2-(4-chloro-1-(3-chloro-3'-(methylsulfonyl)biphenyl-4-yl)-5-(2-(trifluoromethyl)phenyl)-1H-pyrazol-3-yl)propan-2-ol. MS (ES): 569 [M+H]+.

2-(4-chloro-5-(2-chloro-6-fluorophenyl)-1-(3-fluoro-3'-(methylsulfonyl)biphenyl-4-yl)-1H-pyrazol-3-yl)propan-2-ol. MS (ES): 537 [M+H]+.

2-(4-chloro-5-(2,3-difluorophenyl)-1-(3-fluoro-3'-(Methylsulfonyl)biphenyl-4-yl)-1H-pyrazol-3-yl)propan-2-ol. MS (ES): 521 [M+H]+.

2-(4-chloro-1-(3-chloro-3'-(methylsulfonyl)biphenyl-4-yl)-5-(2,3-difluorophenyl)-1H-pyrazol-3-yl)propan-2-ol. MS (ES): 537 [M+H]+.

Example 106

The following compounds the invention, in Tables 1 and 2, were prepared according to one of the previous Examples 1-105:

TABLE 1

| | | |
|---|---|---|
| 1 | 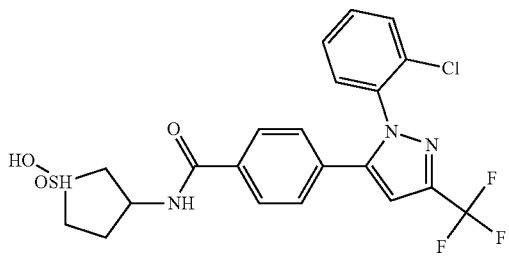 | 4-[1-(2-chlorophenyl)-3-(trifluoromethyl)-1H-pyrazol-5-yl]-N-(1,1-dioxidotetrahydro-3-thienyl)benzamide |
| 2 | 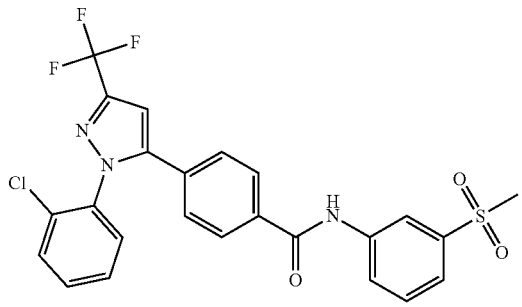 [SMILES: CS(=O)(=O)c1cccc(NC(=O)c2ccc(-c3cc(C(F)(F)F)nn3-c3ccccc3Cl)cc2)c1] | 4-(1-(2-chlorophenyl)-3-(trifluoromethyl)-1H-pyrazol-5-yl)-N-(3-(methylsulfonyl)phenyl)benzamide |
| 3 | 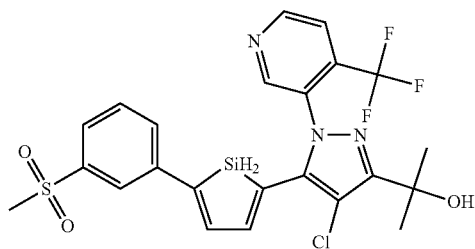 | 2-(4-chloro-5-(5-(3-(methylsulfonyl)phenyl)thiophen-2-yl)-1-(4-(trifluoromethyl)pyridin-3-yl)-1H-pyrazol-3-yl)propan-2-ol |
| 4 | 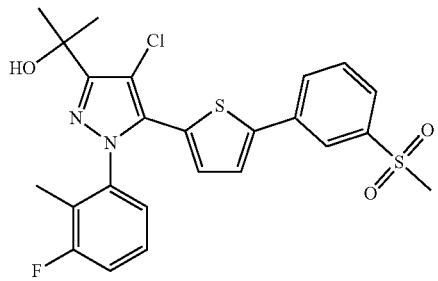 [SMILES: Cc1c(F)cccc1-n1nc(C(C)(C)O)c(Cl)c1-c1ccc(-c2cccc(S(C)(=O)=O)c2)s1] | 2-(4-chloro-1-(3-fluoro-2-methylphenyl)-5-(5-(3-(methylsulfonyl)phenyl)thiophen-2-yl)-1H-pyrazol-3-yl)propan-2-ol |
| 5 | 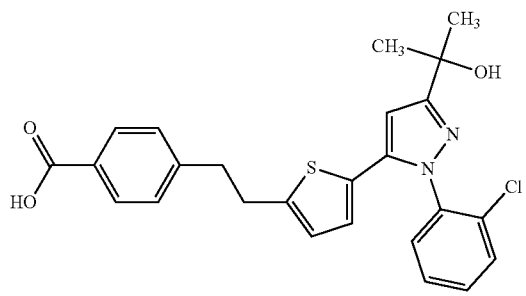 [SMILES: CC(C)(O)c1cc(-c2ccc(CCc3ccc(C(=O)O)cc3)s2)n(-c2ccccc2Cl)n1] | 2-(4-bromo-1-(3-fluoro-2-methylphenyl)-5-(5-(3-(methylsulfonyl)phenyl)thiophen-2-yl)-1H-pyrazol-3-yl)propan-2-ol |

| | | |
|---|---|---|
| 6 | 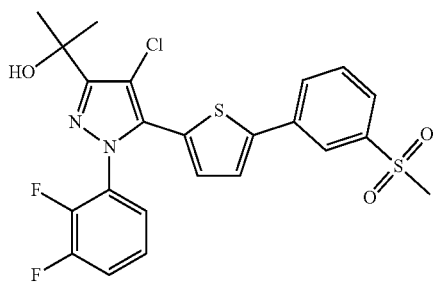 [SMILES: CC(C)(O)c1nn(-c2cccc(F)c2F)c(-c2ccc(-c3cccc(S(C)(=O)=O)c3)s2)c1Cl] | 2-(4-chloro-1-(2,3-difluorophenyl)-5-(5-(3-(methylsulfonyl)phenyl)thiophen-2-yl)-1H-pyrazol-3-yl)propan-2-ol |
| 7 | 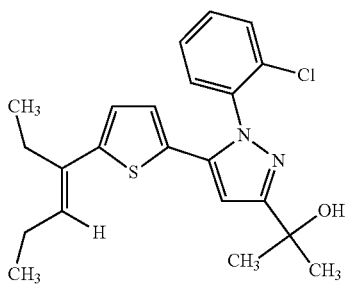 [SMILES: CC/C=C(\CC)c1ccc(-c2cc(C(C)(C)O)nn2-c2ccccc2Cl)s1] | 2-(1-(2-difluoromethoxy)phenyl)-5-(5-(3-(methylsulfonyl)phenyl)thiophen-2-yl)-1H-pyrazol-3-yl)propan-2-ol |
| 8 | 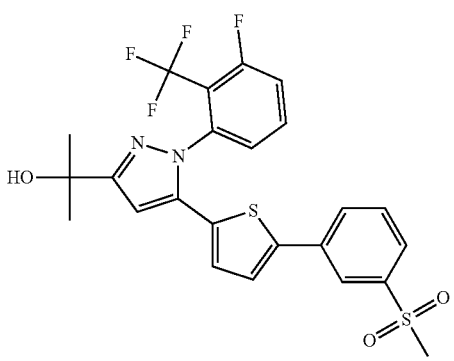 [SMILES: CC(C)(O)c1cc(-c2ccc(-c3cccc(S(C)(=O)=O)c3)s2)n(-c2cccc(F)c2C(F)(F)F)n1] | 2-(1-(3-fluoro-2-(trifluoromethyl)phenyl)-5-(5-(3-(methylsulfonyl)phenyl)thiophen-2-yl)-1H-pyrazol-3-yl)propan-2-ol |
| 9 | 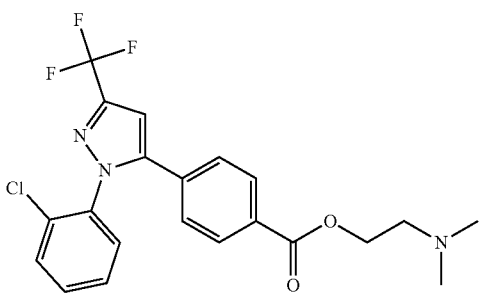 [SMILES: CN(C)CCOC(=O)c1ccc(-c2cc(C(F)(F)F)nn2-c2ccccc2Cl)cc1] | 2-(dimethylamino)ethyl-4-(1-(2-chlorophenyl)-3-(trifluoromethyl)-1H-pyrazol-5-yl)benzoate |
| 10 | 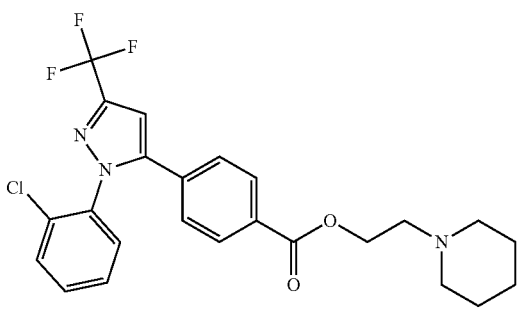 [SMILES: O=C(OCCN1CCCCC1)c1ccc(-c2cc(C(F)(F)F)nn2-c2ccccc2Cl)cc1] | 2-(piperidin-1-yl)ethyl-4-(1-(2-chlorophenyl)-3-(trifluoromethyl)-1H-pyrazol-5-yl)benzoate |

TABLE 1-continued

| | | |
|---|---|---|
| 11 | 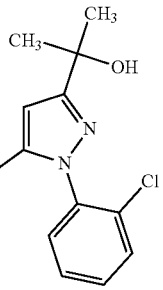 | 2-morpholinoethyl-4-(1-(2-chlorophenyl)-3-(trifluoromethyl)-1H-pyrazol-5-yl)benzoate |
| 12 | 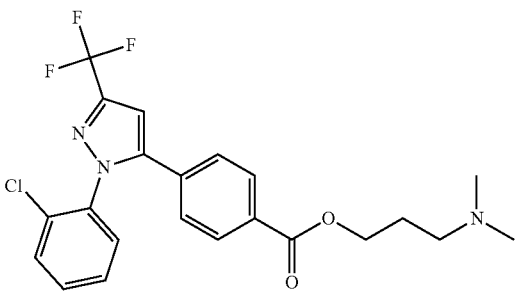 [SMILES: CN(C)CCCOC(=O)c1ccc(-c2cc(C(F)(F)F)nn2-c2ccccc2Cl)cc1] | 3-(dimethylamino)propyl-4-(1-(2-chlorophenyl)-3-(trifluoromethyl)-1H-pyrazol-5-yl)benzoate |
| 13 | 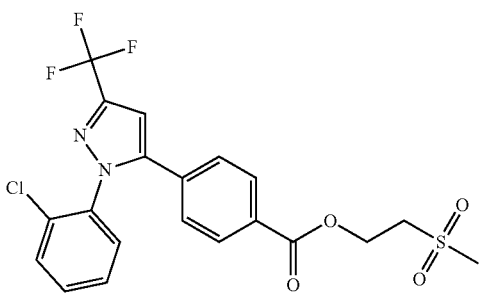 [SMILES: CS(=O)(=O)CCOC(=O)c1ccc(-c2cc(C(F)(F)F)nn2-c2ccccc2Cl)cc1] | 2-(methy6lsulfonyl)ethyl-4-(1-(2-chlorophenyl)-3-(trifluoromethyl)-1H-pyrazol-5-yl)benzoate |
| 14 | 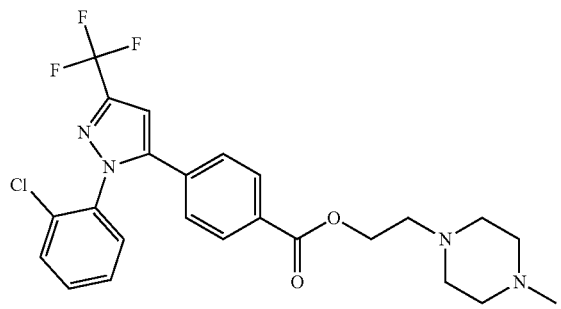 [SMILES: CN1CCN(CCOC(=O)c2ccc(-c3cc(C(F)(F)F)nn3-c3ccccc3Cl)cc2)CC1] | 2-(4-methylpiperazin-1-yl)ethyl 4-(1-(2-chlorophenyl)-3-(trifluoromethyl)-1H-pyrazol-5-yl)benzoate |
| 15 | 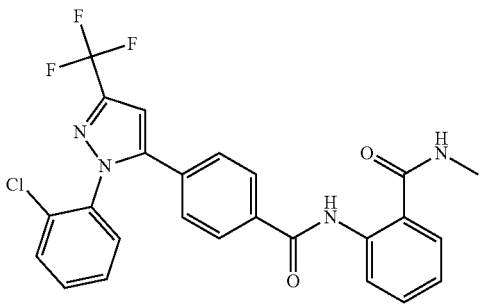 [SMILES: CNC(=O)c1ccccc1NC(=O)c1ccc(-c2cc(C(F)(F)F)nn2-c2ccccc2Cl)cc1] | 2-(4-(1-(2-chlorophenyl)-3-(trifluoromethyl)-1H-pyrazol-5-yl)benzamide)-N-methylbenzamide |

| | | |
|---|---|---|
| 16 | 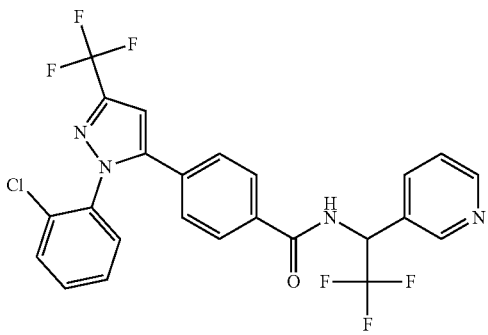 [SMILES: O=C(NC(c1cccnc1)C(F)(F)F)c1ccc(-c2cc(C(F)(F)F)nn2-c2ccccc2Cl)cc1] | 4-(1-(2-chlorophenyl)-3-(trifluoromethyl)-1H-pyrazol-5-yl)-N-(2,2,2-trifluoro-1-(pyridin-3-yl)ethyl)benzamide |
| 17 | 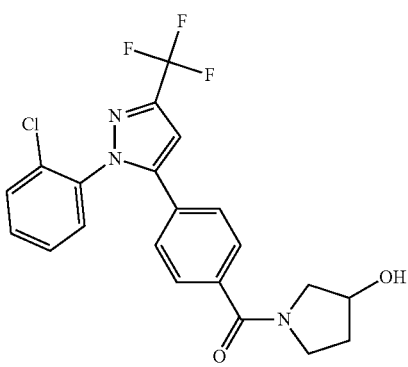 [SMILES: O=C(c1ccc(-c2cc(C(F)(F)F)nn2-c2ccccc2Cl)cc1)N1CCC(O)C1] | (4-(1-(2-chlorophenyl)-3-(trifluoromethyl)-1H-pyrazol-5-yl)phenyl)(3-hydroxypyrrolidin-1-yl)methanone |
| 18 | 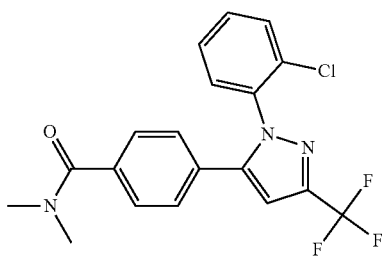 [SMILES: CN(C)C(=O)c1ccc(-c2cc(C(F)(F)F)nn2-c2ccccc2Cl)cc1] | 4-(1-(2-chlorophenyl)-3-(trifluoromethyl)-1H-pyrazol-5-yl)-N,N-dimethylbenzamide |
| 19 | 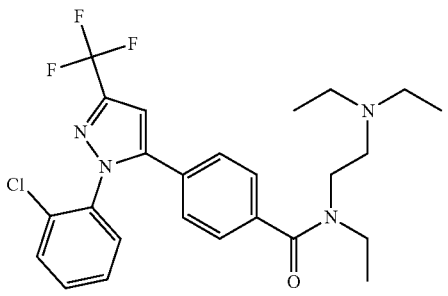 [SMILES: CCN(CC)CCN(CC)C(=O)c1ccc(-c2cc(C(F)(F)F)nn2-c2ccccc2Cl)cc1] | 4-(1-(2-chlorophenyl)-3-(trifluoromethyl)-1H-pyrazol-5-yl)-N-(2-(diethylamino)ethyl)-N-ethylbenzamide |
| 20 | 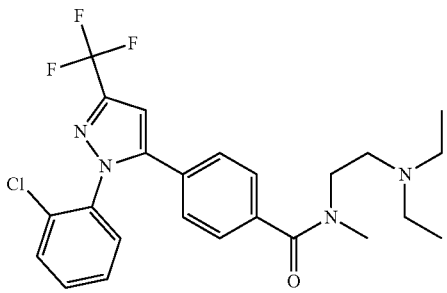 [SMILES: CCN(CC)CCN(C)C(=O)c1ccc(-c2cc(C(F)(F)F)nn2-c2ccccc2Cl)cc1] | 4-(1-(2-chlorophenyl)-3-(trifluoromethyl)-1H-pyrazol-5-yl)-N-(2-(diethylamino)ethyl)-N-methylbenzamide |

| | | |
|---|---|---|
| 21 | 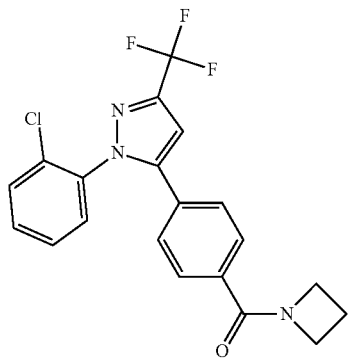 [SMILES: O=C(c1ccc(-c2cc(C(F)(F)F)nn2-c2ccccc2Cl)cc1)N1CCC1] | azetdin-1-yl(4-(1-(2-chlorophenyl)-3-(trifluoromethyl)-1H-pyrazol-5-yl)phenyl)methanone |
| 22 | 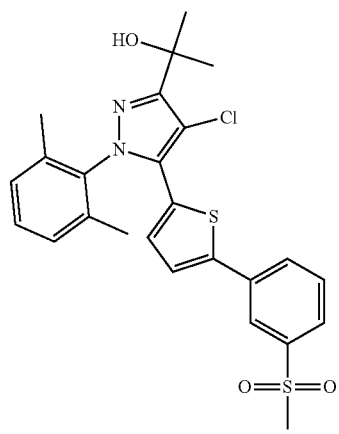 [SMILES: Cc1cccc(C)c1-n1nc(C(C)(C)O)c(Cl)c1-c1ccc(-c2cccc(S(C)(=O)=O)c2)s1] | 2-(4-chloro-1-(2,6-dimethylphenyl)-5-(5-(3-(methylsulfonyl)phenyl)thiophen-2-yl)-1H-pyrazol-3-yl)propan-2-ol |
| 23 | 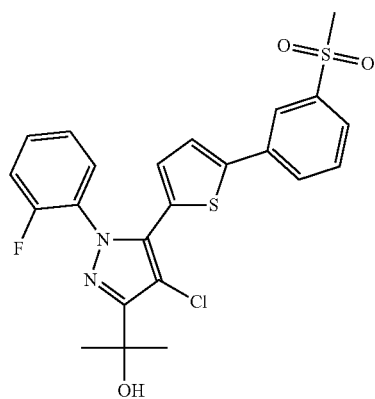 [SMILES: CC(C)(O)c1nn(-c2ccccc2F)c(-c2ccc(-c3cccc(S(C)(=O)=O)c3)s2)c1Cl] | 2-(4-chloro-1-(2-fluorophenyl)-5-(5-(3-(methylsulfonyl)phenyl)thiophen-2-yl)-1H-pyrazol-3-yl)propan-2-ol |
| 24 | 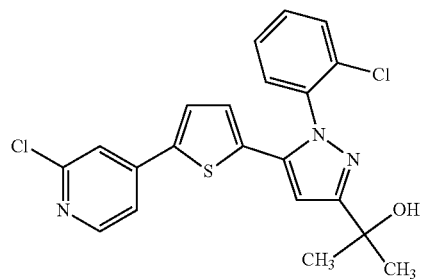 [SMILES: CC(C)(O)c1cc(-c2ccc(-c3ccnc(Cl)c3)s2)n(-c2ccccc2Cl)n1] | 2-(4-chloro-1-(2,6-difluorophenyl)-5-(5-(3-(methylsulfonyl)phenyl)thiophen-2-yl)-1H-pyrazol-3-yl)propan-2-ol |

TABLE 1-continued
| 25 | 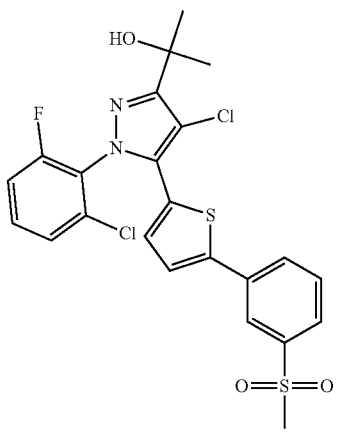 [SMILES: CC(C)(O)c1nn(-c2c(F)cccc2Cl)c(-c2ccc(-c3cccc(S(C)(=O)=O)c3)s2)c1Cl] | 2-(4-chloro-1-(2-chloro-6-fluorophenyl)-5-(5-(3-(methylsulfonyl)phenyl)thiophen-2-yl)-1H-pyrazol-3-yl)propan-2-ol |
| --- | --- | --- |
| 26 | 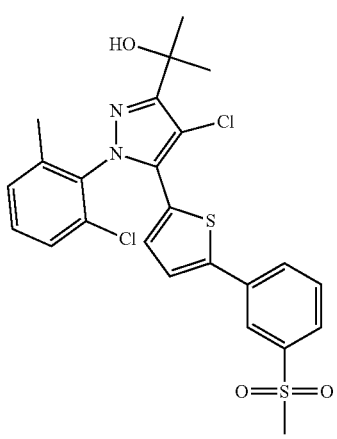 [SMILES: Cc1cccc(Cl)c1-n1nc(C(C)(C)O)c(Cl)c1-c1ccc(-c2cccc(S(C)(=O)=O)c2)s1] | 2-(4-chloro-1-(2-chloro-6-methylphenyl)-5-(5-(3-(methylsulfonyl)phenyl)thiophen-2-yl)-1H-pyrazol-3-yl)propan-2-ol |
| 27 | 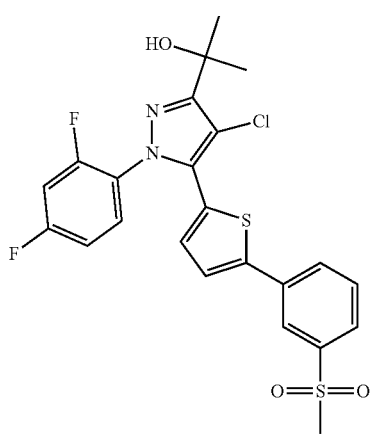 [SMILES: CC(C)(O)c1nn(-c2ccc(F)cc2F)c(-c2ccc(-c3cccc(S(C)(=O)=O)c3)s2)c1Cl] | 2-(4-chloro-1-(2,4-difluorophenyl)-5-(5-(3-(methylsulfonyl)phenyl)thiophen-2-yl)-1H-pyrazol-3-yl)propan-2-ol |
| 28 | 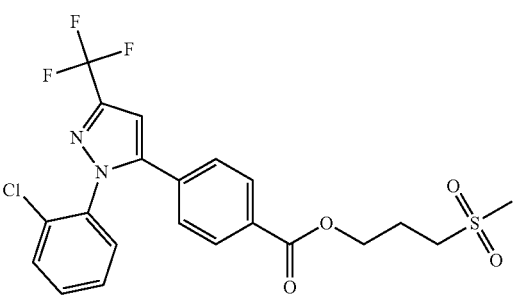 [SMILES: CS(=O)(=O)CCCOC(=O)c1ccc(-c2cc(C(F)(F)F)nn2-c2ccccc2Cl)cc1] | 3-(methylsulfonyl)propyl 4-(1-(2-chlorophenyl)-3-(trifluoromethyl)-1H-pyrazol-5-yl)benzoate |

| | | |
|---|---|---|
| 29 | 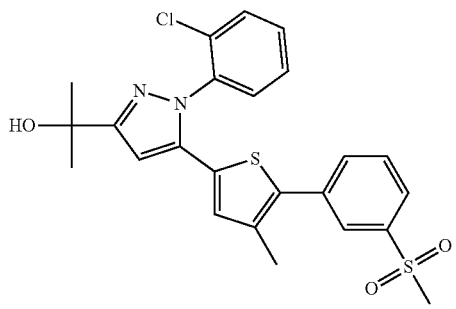 [SMILES: Cc1cc(-c2cc(C(C)(C)O)nn2-c2ccccc2Cl)sc1-c1cccc(S(C)(=O)=O)c1] | 2-(1-(2-chlorophenyl)-5-(4-methyl-5-(3-(methylsulfonyl)phenyl)thiophen-2-yl)-1H-pyrazol-3-yl)propan-2-ol |
| 30 | 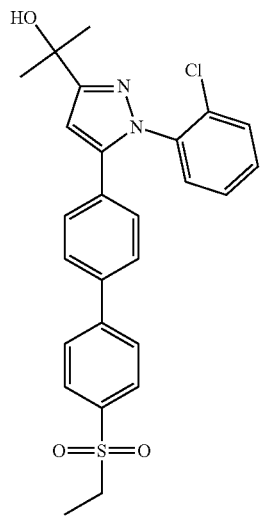 [SMILES: CCS(=O)(=O)c1ccc(-c2ccc(-c3cc(C(C)(C)O)nn3-c3ccccc3Cl)cc2)cc1] | 2-(1-(2-chlorophenyl)-5-(4'-(ethylsulfonyl)biphenyl-4-yl)-1H-pyrazol-3-yl)propan-2-ol |
| 31 | 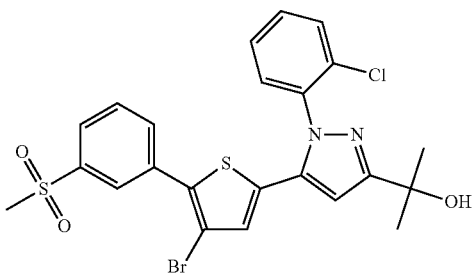 [SMILES: CC(C)(O)c1cc(-c2cc(Br)c(-c3cccc(S(C)(=O)=O)c3)s2)n(-c2ccccc2Cl)n1] | 2-(5-(4-bromo-5-(3-(methylsulfonyl)phenyl)thiophen-2-yl)-1-(2-chlorrophenyl)-1H-pyrazol-3-yl)propan-2-ol |
| 32 | 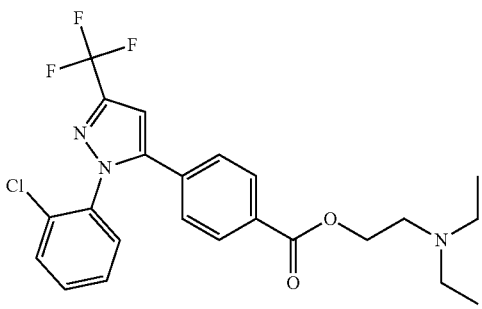 [SMILES: CCN(CC)CCOC(=O)c1ccc(-c2cc(C(F)(F)F)nn2-c2ccccc2Cl)cc1] | 2-(diethylamino)ethyl 4-(1-(2-chlorrophenyl)-3-(trifluoromethyl)-1H-pyrazol-5-yl)benzoate |

TABLE 1-continued

| 33 | 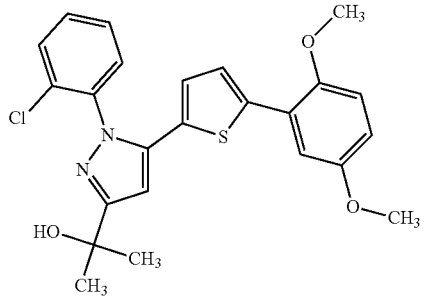 [SMILES: COc1ccc(OC)c(-c2ccc(-c3cc(C(C)(C)O)nn3-c3ccccc3Cl)s2)c1] | 2-(5-(4-bromo-3-methyl-5-(3-(methylsulfonyl)phenyl)thiophen-2-yl)-1-(2-chlorophenyl)-1H-pyrazol-3-yl)propan-2-ol |
| 34 | 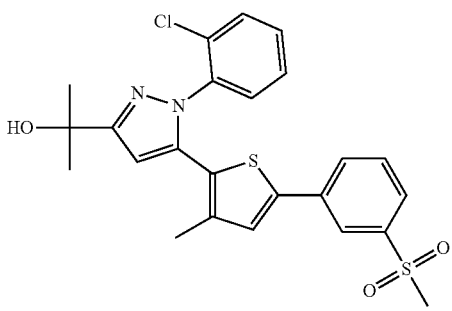 [SMILES: Cc1cc(-c2cccc(S(C)(=O)=O)c2)sc1-c1cc(C(C)(C)O)nn1-c1ccccc1Cl] | 2-(1-(2-chlorophenyl)-5-(3-methyl-5-(3-(methylsulfonyl)phenyl)thiophen-2-yl)-1H-pyrazol-3-yl)propan-2-ol |
| 35 | 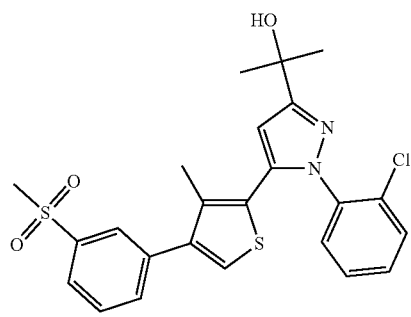 [SMILES: Cc1c(-c2cccc(S(C)(=O)=O)c2)csc1-c1cc(C(C)(C)O)nn1-c1ccccc1Cl] | 2-(1-(2-chlorophenyl)-5-(3-methyl-4-(3-(methylsulfonyl)phenyl)thiophen-2-yl)-1H-pyrazol-3-yl)propan-2-ol |
| 36 | 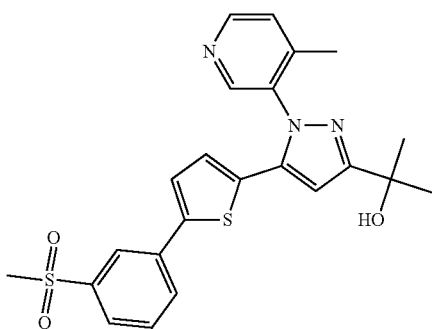 [SMILES: Cc1ccncc1-n1nc(C(C)(C)O)cc1-c1ccc(-c2cccc(S(C)(=O)=O)c2)s1] | 2-(1-(4-methylpyridin-3-yl)-5-(5-(3-(methylsulfonyl)phenyl)thiophen-2-yl)-1H-pyrazol-3-yl)propan-2-ol |
| 37 | 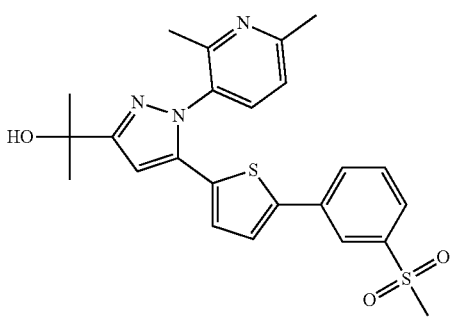 [SMILES: Cc1ccc(-n2nc(C(C)(C)O)cc2-c2ccc(-c3cccc(S(C)(=O)=O)c3)s2)c(C)n1] | 2-(1-(2,6-dimethylpyridin-3-yl)-5-(5-(3-(methylsulfonyl)phenyl)thiophen-2-yl)-1H-pyrazol-3-yl)propan-2-ol |

TABLE 1-continued

| | | |
|---|---|---|
| 38 | 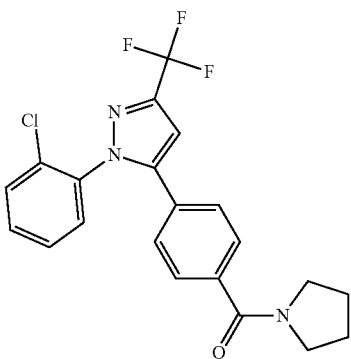 [SMILES: O=C(c1ccc(-c2cc(C(F)(F)F)nn2-c2ccccc2Cl)cc1)N1CCCC1] | (4-(1-(2-chlorophenyl)-3-(trifluoromethyl)-1H-pyrazol-5-yl)phenyl)(pyrrolidin-1-yl)methanone |
| 39 | 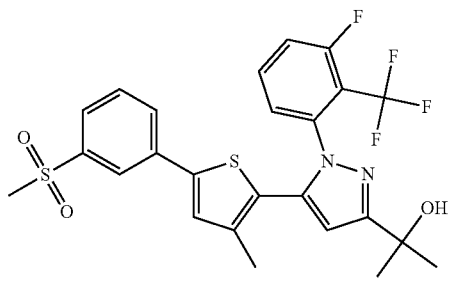 [SMILES: Cc1cc(-c2cccc(S(C)(=O)=O)c2)sc1-c1cc(C(C)(C)O)nn1-c1cccc(F)c1C(F)(F)F] | 2-(1-(3-fluoro-2-(trifluoromethyl)phenyl)-5-(3-methyl-5-(3-(methylsulfonyl)phenyl)thiophen-2-yl)-1H-pyrazol-3-yl)propan-2-ol |
| 40 | 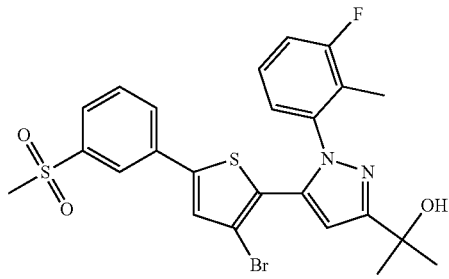 [SMILES: Cc1c(F)cccc1-n1nc(C(C)(C)O)cc1-c1sc(-c2cccc(S(C)(=O)=O)c2)cc1Br] | 2-(5-(3-bromo-5-(3-(methylsulfonyl)phenyl)thiophen-2-yl)-1-(3-fluoro-2-methylphenyl)-1H-pyrazol-3-yl)propan-2-ol |
| 41 | 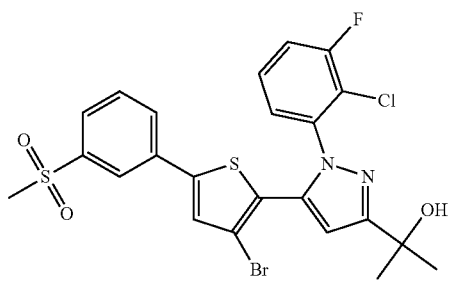 [SMILES: CC(C)(O)c1cc(-c2sc(-c3cccc(S(C)(=O)=O)c3)cc2Br)n(-c2cccc(F)c2Cl)n1] | 2-(5-(3-bromo-5-(3-(methylsulfonyl)phenyl)thiophen-2-yl)-1-(2-chloro-3-fluorophenyl)-1H-pyrazol-3-yl)propan-2-ol |
| 42 | 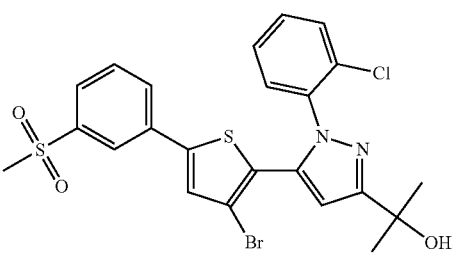 [SMILES: CC(C)(O)c1cc(-c2sc(-c3cccc(S(C)(=O)=O)c3)cc2Br)n(-c2ccccc2Cl)n1] | 2-(5-(3-bromo-5-(3-(methylsulfonyl)phenyl)thiophen-2-yl)-1-(2-chlorophenyl)-1H-pyrazol-3-yl)propan-2-ol |

| | | |
|---|---|---|
| 43 | 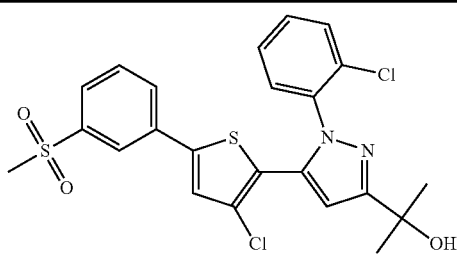 | 2-(5-(3-chloro-5-(3-(methylsulfonyl)phenyl)thiophen-2-yl)-1-(2-chlorophenyl)-1H-pyrazol-3-yl)propan-2-ol |
| 44 | 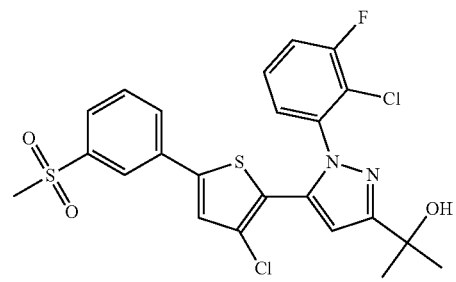 | 2-(1-(2-chloro-3-fluorophenyl)-5-(3-chloro-5-(3-(methylsulfonyl)phenyl)thiophen-2-yl)-1H-pyrazol-3-yl)propan-2-ol |
| 45 | 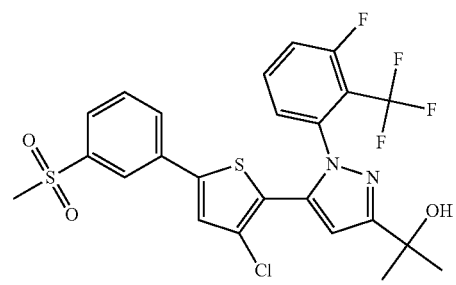 [SMILES: CC(C)(O)c1cc(-c2sc(-c3cccc(S(C)(=O)=O)c3)cc2Cl)n(-c2cccc(F)c2C(F)(F)F)n1] | 2-(5-(3-chloro-5-(3-(methylsulfonyl)phenyl)thiophen-2-yl)-1-(3-fluoro-2-(trifluoromethyl)phenyl)-1H-pyrazol-3-yl)propan-2-ol |
| 46 | 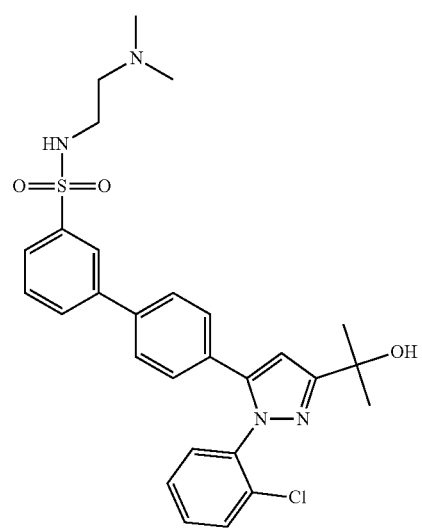 [SMILES: CN(C)CCNS(=O)(=O)c1cccc(-c2ccc(-c3cc(C(C)(C)O)nn3-c3ccccc3Cl)cc2)c1] | 4'-(1-(2-chlorophenyl)-3-(2-hydroxypropan-2-yl)-1H-pyrazol-5-yl)-N-(2-(dimethylamino)ethyl)biphenyl-3-sulfonamide |
| 47 | 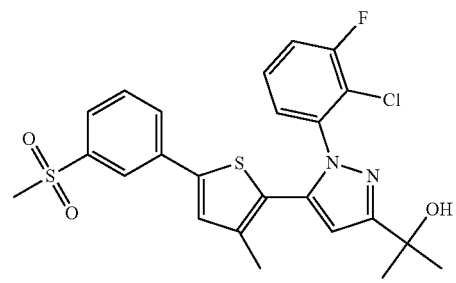 [SMILES: Cc1cc(-c2cccc(S(C)(=O)=O)c2)sc1-c1cc(C(C)(C)O)nn1-c1cccc(F)c1Cl] | 2-(1-(2-chloro-3-fluorophenyl)-5-(3-methyl-5-(3-(methylsulfonyl)phenyl)thiophen-2-yl)-1H-pyrazol-3-yl)propan-2-ol |

TABLE 1-continued

| | | |
|---|---|---|
| 48 | 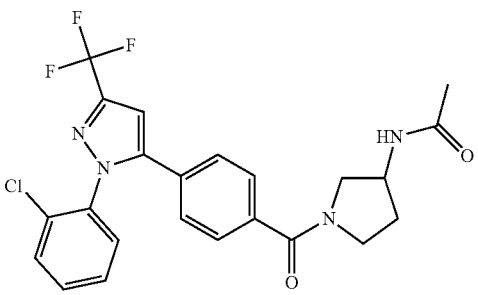 [SMILES: CC(=O)NC1CCN(C(=O)c2ccc(-c3cc(C(F)(F)F)nn3-c3ccccc3Cl)cc2)C1] | N-(1-(4-(1-(2-chlorophenyl)-3-(trifluoromethyl)-1H-pyrazol-5-yl)benzoyl)pyrrolidin-3-yl)acetamide |
| 49 | 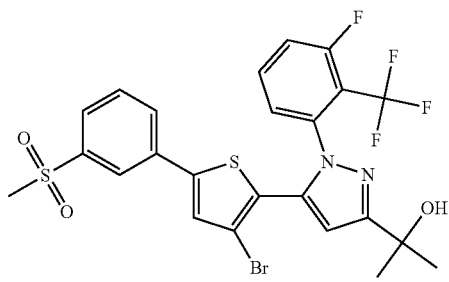 [SMILES: CC(C)(O)c1cc(-c2sc(-c3cccc(S(C)(=O)=O)c3)cc2Br)n(-c2cccc(F)c2C(F)(F)F)n1] | 2-(5-(3-bromo-5-(3-(methylsulfonyl)phenyl)thiophen-2-yl)-1-(3-fluoro-2-(trifluoromethyl)phenyl)-1H-pyrazol-3-yl)propan-2-ol |
| 50 | 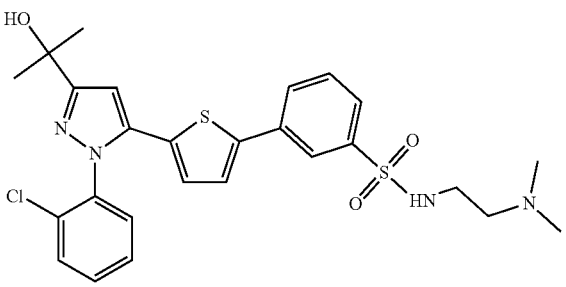 [SMILES: CN(C)CCNS(=O)(=O)c1cccc(-c2ccc(-c3cc(C(C)(C)O)nn3-c3ccccc3Cl)s2)c1] | 3-(5-(1-(2-chlorophenyl)-3-(2-hydroxypropan-2-yl)-1H-pyrazol-5-yl)thiophen-2-yl)-N-(2-(dimethylamino)ethyl)benzenesulfonamide |
| 51 | 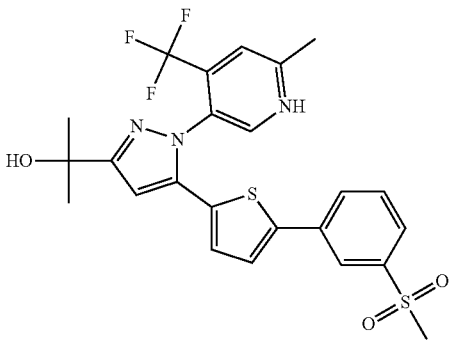 [SMILES: Cc1cc(C(F)(F)F)c(-n2nc(C(C)(C)O)cc2-c2ccc(-c3cccc(S(C)(=O)=O)c3)s2)cn1] | 2-(1-(6-methyl-4-(trifluoromethyl)-1,6-dihydropyridin-3-yl)-5-(5-(3-(methylsufonyl)phenyl)thiophen-2-yl)-1H-pyrazol-3-yl)propan-2-ol |
| 52 | 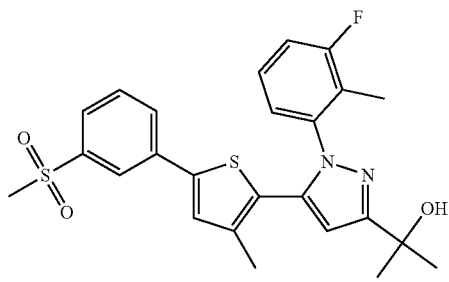 [SMILES: Cc1cc(-c2cccc(S(C)(=O)=O)c2)sc1-c1cc(C(C)(C)O)nn1-c1cccc(F)c1C] | 2-(1-(3-fluoro-2-methylphenyl)-5-(3-methyl-5-(3-(methylsulfonyl)phenyl)thiophen-2-yl)-1H-pyrazol-3-yl)propan-2-ol |

TABLE 1-continued

| | | |
|---|---|---|
| 53 | 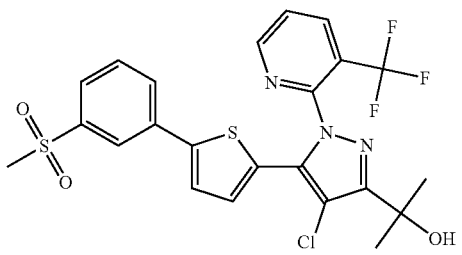 [SMILES: CC(C)(O)c1nn(-c2ncccc2C(F)(F)F)c(-c2ccc(-c3cccc(S(C)(=O)=O)c3)s2)c1Cl] | 2-(4-chloro-5-(5-(3-(methylsulfonyl)phenyl)thiophen-2-yl)-1-(3-(trifluoromethyl)pyridin-2-yl)-1H-pyrazol-3-yl)propan-2-ol |
| 54 | 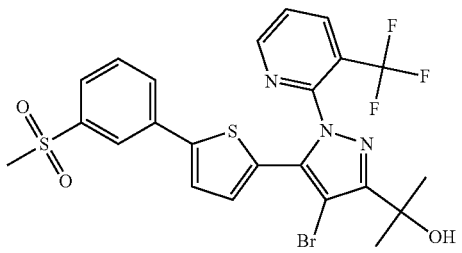 [SMILES: CC(C)(O)c1nn(-c2ncccc2C(F)(F)F)c(-c2ccc(-c3cccc(S(C)(=O)=O)c3)s2)c1Br] | 2-(4-bromo-5-(5-(3-methylsulfonyl)phenyl)thiophen-2-yl)-1-(3-(trifluoromethyl)pyridin-2-yl)-1H-pyrazol-3-yl)propan-2-ol |
| 55 | 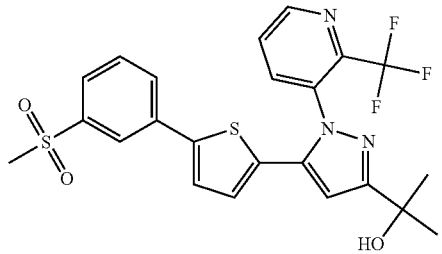 [SMILES: CC(C)(O)c1cc(-c2ccc(-c3cccc(S(C)(=O)=O)c3)s2)n(-c2cccnc2C(F)(F)F)n1] | 2-(5-(5-(3-(methylsulfonyl)phenyl)thiophen-2-yl)-1-(2-(trifluoromethyl)pyridin-3-yl)-1H-pyrazol-3-yl)propan-2-ol |
| 56 | 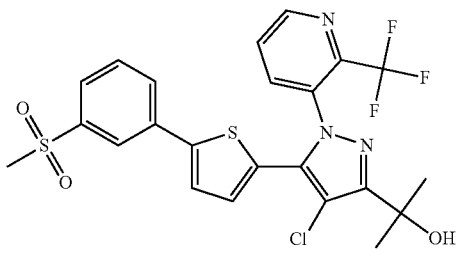 [SMILES: CC(C)(O)c1nn(-c2cccnc2C(F)(F)F)c(-c2ccc(-c3cccc(S(C)(=O)=O)c3)s2)c1Cl] | 2-(4-chloro-5-(5-(3-(methylsulfonyl)phenyl)thiophen-2-yl)-1-(2-(trifluoromethyl)pyridin-3-yl)-1H-pyrazol-3-yl)propan-2-ol |
| 57 | 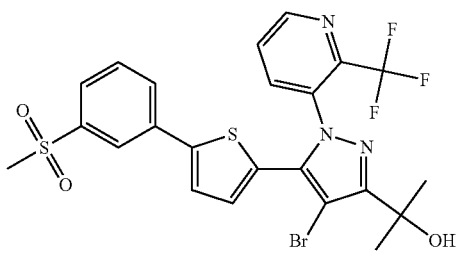 [SMILES: CC(C)(O)c1nn(-c2cccnc2C(F)(F)F)c(-c2ccc(-c3cccc(S(C)(=O)=O)c3)s2)c1Br] | 2-(4-bromo-5-(5-(3-methylsulfonyl)phenyl)thiophen-2-yl)-1-(2-(trifluoromethyl)pyridin-3-yl)-1H-pyrazol-3-yl)propan-2-ol |
| 58 | 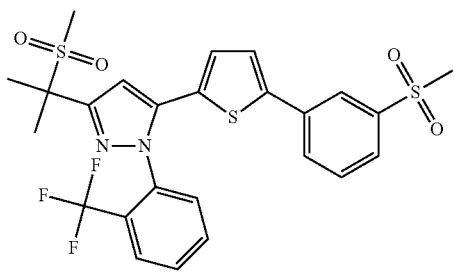 [SMILES: CC(C)(c1cc(-c2ccc(-c3cccc(S(C)(=O)=O)c3)s2)n(-c2ccccc2C(F)(F)F)n1)S(C)(=O)=O] | 5-(5-(3-(methylsulfonyl)phenyl)thiophen-2-yl)-3-(2-(methylsulfonyl)propan-2-yl)-1-(2-(trifluoromethyl)phenyl)-1H-pyrazole |

TABLE 1-continued

| | | |
|---|---|---|
| 59 | 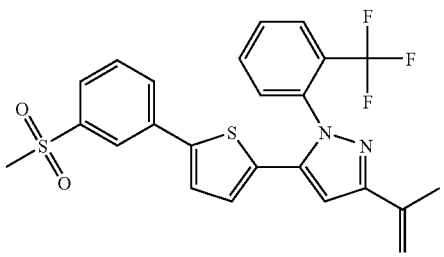 [SMILES: C=C(C)c1cc(-c2ccc(-c3cccc(S(C)(=O)=O)c3)s2)n(-c2ccccc2C(F)(F)F)n1] | 5-(5-(3-(methylsulfonyl)phenyl)thiophen-2-yl)-3-(prop-1-en-2-yl)-1-(2-(trifluoromethyl)phenyl)-1H-pyrazole |
| 60 | 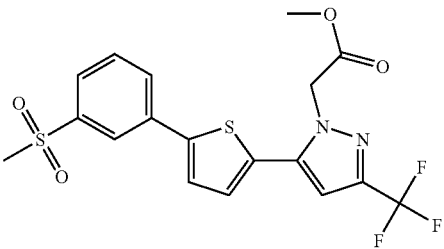 [SMILES: COC(=O)Cn1nc(C(F)(F)F)cc1-c1ccc(-c2cccc(S(C)(=O)=O)c2)s1] | methyl 2-(5-(5-(3-(methylsulfonyl)phenyl)thiophen-2-yl)-3-(trifluoromethyl)-1H-pyrazol-1-yl)acetate |
| 61 | 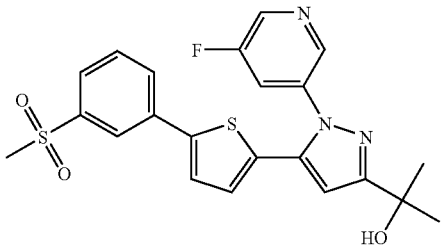 [SMILES: CC(C)(O)c1cc(-c2ccc(-c3cccc(S(C)(=O)=O)c3)s2)n(-c2cncc(F)c2)n1] | 2-(1-(5-fluoropyridin-3-yl)-5-(5-(3-(methylsulfonyl)phenyl)thiophen-2-yl)-1H-pyrazol-3-yl)propan-2-ol |
| 62 | 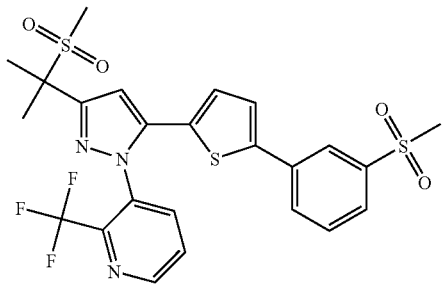 [SMILES: CC(C)(c1cc(-c2ccc(-c3cccc(S(C)(=O)=O)c3)s2)n(-c2cccnc2C(F)(F)F)n1)S(C)(=O)=O] | 3-(5-(5-(3-(methylsulfonyl)phenyl)thiophen-2-yl)-3-(2-(methylsulfonyl)propan-2-yl)-1H-pyrazol-1-yl)-2-(trifluoromethyl)pyridine |
| 63 | 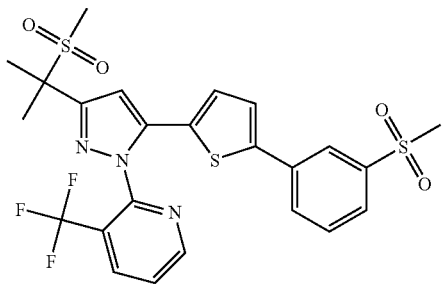 [SMILES: CC(C)(c1cc(-c2ccc(-c3cccc(S(C)(=O)=O)c3)s2)n(-c2ncccc2C(F)(F)F)n1)S(C)(=O)=O] | 2-(5-(5-(3-(methylsulfonyl)phenyl)thiophen-2-yl)-3-(2-(methylsulfonyl)propan-2-yl)-1H-pyrazol-1-yl)-3-(trifluoromethyl)pyridine |
| 64 | 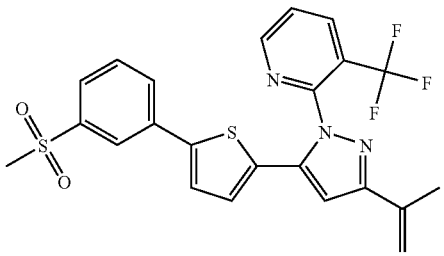 [SMILES: C=C(C)c1cc(-c2ccc(-c3cccc(S(C)(=O)=O)c3)s2)n(-c2ncccc2C(F)(F)F)n1] | 2-(5-(5-(3-(methylsulfonyl)phenyl)thiophen-2-yl)-3-(prop-1-en-2-yl)-1H-pyrazol-1-yl)-3-(trifluoromethyl)pyridine |

TABLE 1-continued

| | | |
|---|---|---|
| 65 | 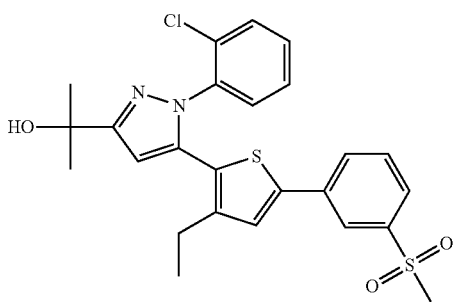 [SMILES: CCc1cc(-c2cccc(S(C)(=O)=O)c2)sc1-c1cc(C(C)(C)O)nn1-c1ccccc1Cl] | 2-(1-(2-chlorophenyl)-5-(3-ethyl-5-(3-(methylsulfonyl)phenyl)thiophen-2-yl)-1H-pyrazol-3-yl)propan-2-ol |
| 66 | 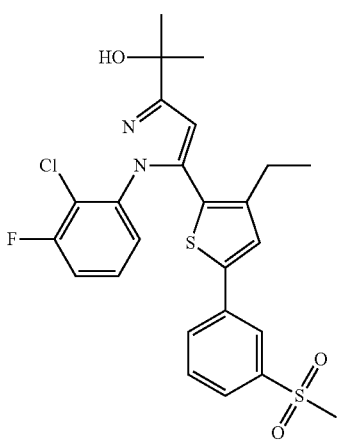 [SMILES: CCc1cc(-c2cccc(S(C)(=O)=O)c2)sc1/C(=C/C(=N)C(C)(C)O)Nc1cccc(F)c1Cl] | 2-(1-(2-chloro-3-fluorophenyl)-5-(3-ethyl-5-(3-(methylsulfonyl)phenyl)thiophen-2-yl)-1H-pyrazol-3-yl)propan-2-ol |
| 70 | 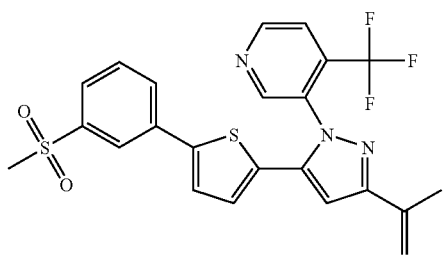 [SMILES: C=C(C)c1cc(-c2ccc(-c3cccc(S(C)(=O)=O)c3)s2)n(-c2cnccc2C(F)(F)F)n1] | 3-(5-(5-(3-(methylsulfonyl)phenyl)thiophen-2-yl)-3-prop-1-en-2-yl)-1H-pyrazol-1-yl)-4-(trifluoromethyl)pyridine |
| 71 | 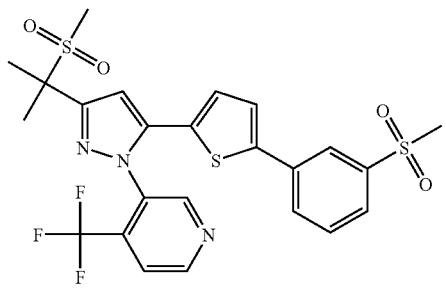 [SMILES: CC(C)(c1cc(-c2ccc(-c3cccc(S(C)(=O)=O)c3)s2)n(-c2cnccc2C(F)(F)F)n1)S(C)(=O)=O] | 3-(5-(5-(3-(methylsulfonyl)phenyl)thiophen-2-yl)-3-(2-(methylsulfonyl)propan-2-yl)-1H-pyrazol-1-yl)-4-(trifluoromethyl)pyridine |
| 72 | 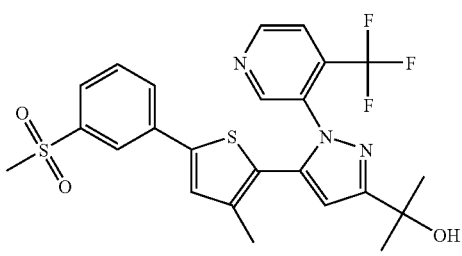 [SMILES: Cc1cc(-c2cccc(S(C)(=O)=O)c2)sc1-c1cc(C(C)(C)O)nn1-c1cnccc1C(F)(F)F] | 2-(5-(3-methyl-5-(3-(methylsulfonyl)phenyl)thiophen-2-yl)-1-(4-(trifluoromethyl)pyridin-3-yl)-1H-pyrazol-3-yl)propan-2-ol |

TABLE 1-continued

| 73 | 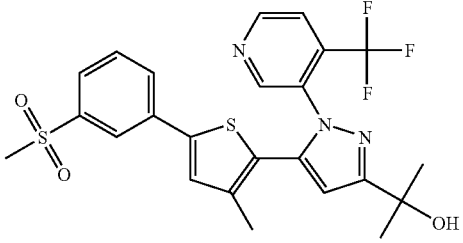 [SMILES: Cc1cc(-c2cccc(S(C)(=O)=O)c2)sc1-c1cc(C(C)(C)O)nn1-c1cnccc1C(F)(F)F] | 2-(5-(3-methyl-5-(3-(methylsulfonyl)phenyl)thiophen-2-yl)-1-(4-(trifluoromethyl)pyridin-3-yl)-1H-pyrazol-3-yl)propan-2-ol |
| --- | --- | --- |
| 74 | 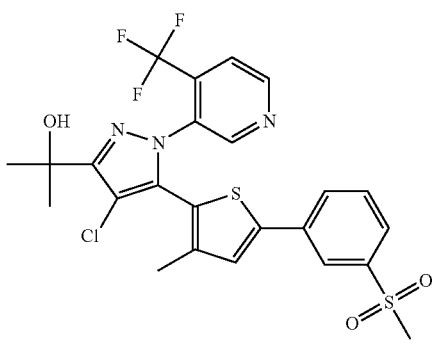 [SMILES: Cc1cc(-c2cccc(S(C)(=O)=O)c2)sc1-c1c(Cl)c(C(C)(C)O)nn1-c1cnccc1C(F)(F)F] | 2-(4-chloro-5-(3-methyl-5-(3-(methylsulfonyl)phenyl)thiophen-2-yl)-1-(4-(trifluoromethyl)pyridin-3-yl)-1H-pyrazol-3-yl)propan-2-ol |
| 75 | 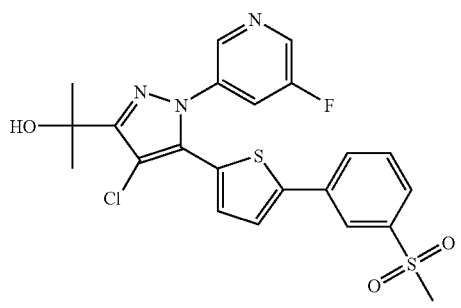 | 2-(4-chloro-1-(5-fluoropyridin-3-yl)-5-(5-(3-(methylsulfonyl)phenyl)thiophen-2-yl)-1H-pyrazol-3-yl)propan-2-ol |
| 76 | 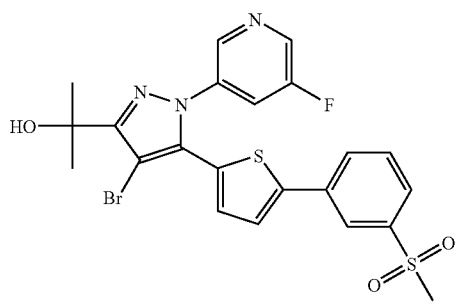 [SMILES: CC(C)(O)c1nn(-c2cncc(F)c2)c(-c2ccc(-c3cccc(S(C)(=O)=O)c3)s2)c1Br] | 2-(4-bromo-1-(5-fluoropyridin-3-yl)-5-(5-(3-(methylsulfonyl)phenyl)thiophen-2-yl)-1H-pyrazol-3-yl)propan-2-ol |
| 77 | 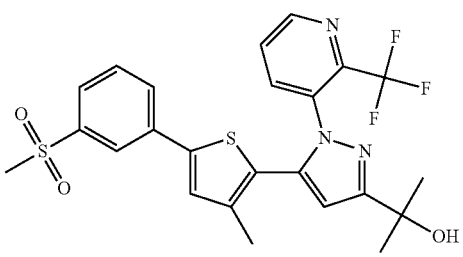 [SMILES: Cc1cc(-c2cccc(S(C)(=O)=O)c2)sc1-c1cc(C(C)(C)O)nn1-c1cccnc1C(F)(F)F] | 2-(5-(3-methyl-5-(3-(methylsulfonyl)phenyl)thiophen-2-yl)-1-(2-(trifluoromethyl)pyridin-3-yl)-1H-pyrazol-3-yl)propan-2-ol |

| | | |
|---|---|---|
| 78 | 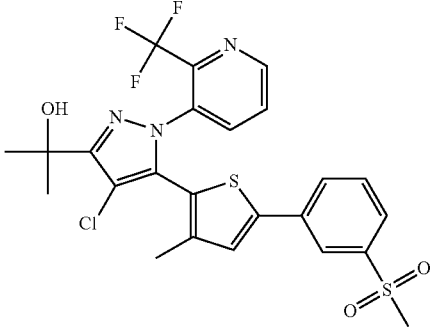 [SMILES: Cc1cc(-c2cccc(S(C)(=O)=O)c2)sc1-c1c(Cl)c(C(C)(C)O)nn1-c1cccnc1C(F)(F)F] | 2-(4-chloro-5-(3-methyl-5-(3-(methylsulfonyl)phenyl)thiophen-2-yl)-1-(2-(trifluoromethyl)pyridin-3-yl)-1H-pyrazol-3-yl)propan-2-ol |
| 80 | 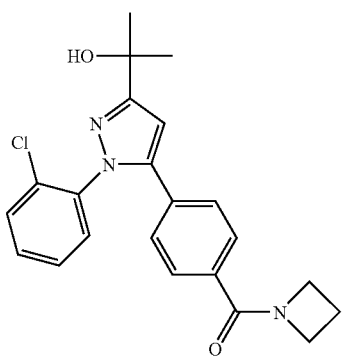 [SMILES: CC(C)(O)c1cc(-c2ccc(C(=O)N3CCC3)cc2)n(-c2ccccc2Cl)n1] | azetidin-1-yl(4-(1-(2-chlorophenyl)-3-(2-hydroxypropan-2-yl)-1H-pyrazol-5-yl)phenyl)methanone |
| 81 | 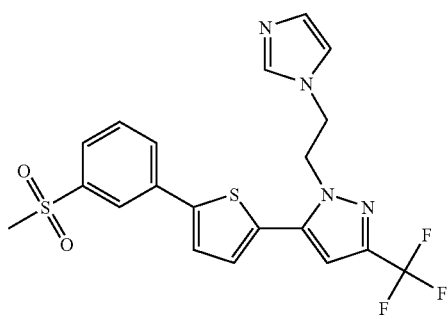 [SMILES: CS(=O)(=O)c1cccc(-c2ccc(-c3cc(C(F)(F)F)nn3CCn3ccnc3)s2)c1] | 1-(2-(1H-imidazol-1-yl)ethyl)-5-(5-(3-(methylsulfonyl)phenyl)thiophen-2-yl)-3-(trifluoromethyl)-1H-pyrazole |
| 82 | 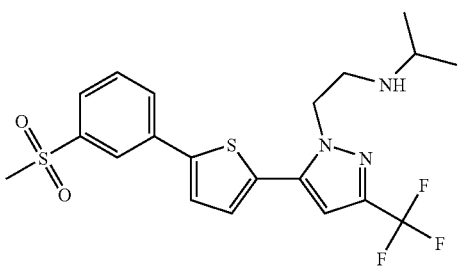 [SMILES: CC(C)NCCn1nc(C(F)(F)F)cc1-c1ccc(-c2cccc(S(C)(=O)=O)c2)s1] | N-(2-(5-(5-(3-(methylsulfonyl)phenyl)thiophen-2-yl)-3-(trifluoromethyl)-1H-pyrazol-1-yl)ethyl)propan-2-amine |
| 83 | 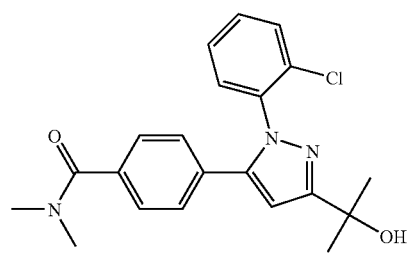 [SMILES: CN(C)C(=O)c1ccc(-c2cc(C(C)(C)O)nn2-c2ccccc2Cl)cc1] | 4-(1-(2-chlorophenyl)-3-(2-hydroxypropan-2-yl)-1H-pyrazol-5-yl)-N,N-dimethylbenzamide |

| | | |
|---|---|---|
| 84 | 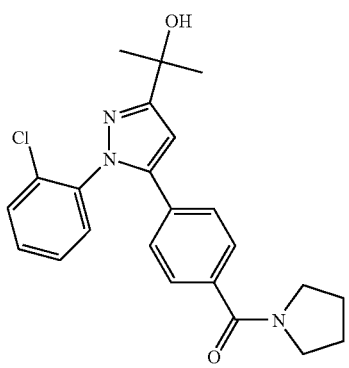 [SMILES: CC(C)(O)c1cc(-c2ccc(C(=O)N3CCCC3)cc2)n(-c2ccccc2Cl)n1] | (4-(1-(2-chlorophenyl)-3-(2-hydroxypropan-2-yl)-1H-pyrazol-5-yl)phenyl)(pyrrolidin-1-yl)methanone |
| 85 | 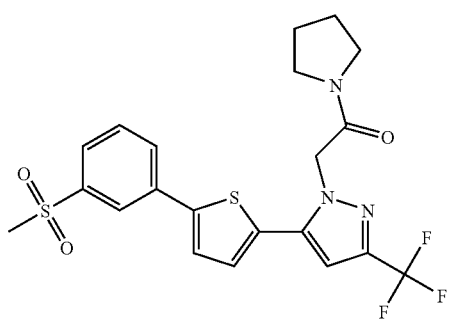 [SMILES: CS(=O)(=O)c1cccc(-c2ccc(-c3cc(C(F)(F)F)nn3CC(=O)N3CCCC3)s2)c1] | 2-(5-(5-(3-(methylsulfonyl)phenyl)thiophen-2-yl)-3-(trifluoromethyl)-1H-pyrazol-1-yl)-1-(pyrrolidin-1-yl)ethanone |
| 86 | 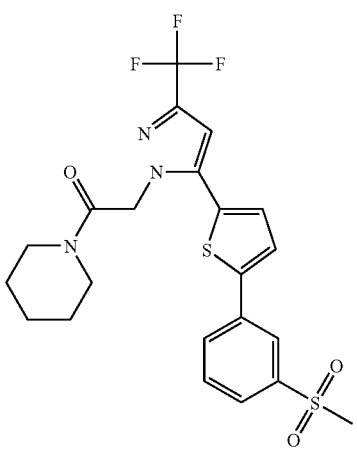 [SMILES: CS(=O)(=O)c1cccc(-c2ccc(/C(=C/C(=N)C(F)(F)F)NCC(=O)N3CCCCC3)s2)c1] | 2-(5-(5-(3-(methylsulfonyl)phenyl)thiophen-2-yl)-3-(trifluoromethyl)-1H-pyrazol-1-yl)-1-(piperidin-1-yl)ethanone |
| 87 | 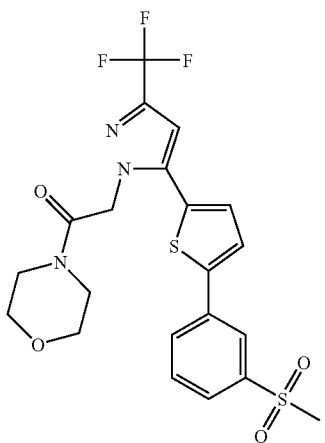 [SMILES: CS(=O)(=O)c1cccc(-c2ccc(/C(=C/C(=N)C(F)(F)F)NCC(=O)N3CCOCC3)s2)c1] | 2-(5-(5-(3-(methylsulfonyl)phenyl)thiophen-2-yl)-3-(trifluoromethyl)-1H-pyrazol-1-yl)-1-morpholinoethanone |

| | | |
|---|---|---|
| 88 | 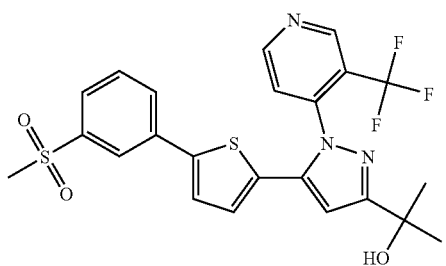 [SMILES: CC(C)(O)c1cc(-c2ccc(-c3cccc(S(C)(=O)=O)c3)s2)n(-c2ccncc2C(F)(F)F)n1] | 2-(5-(5-(3-(methylsulfonyl)phenyl)thiophen-2-yl)-1-(3-(trifluoromethyl)pyridin-4-yl)-1H-pyrazol-3-yl)propan-2-ol |
| 89 | 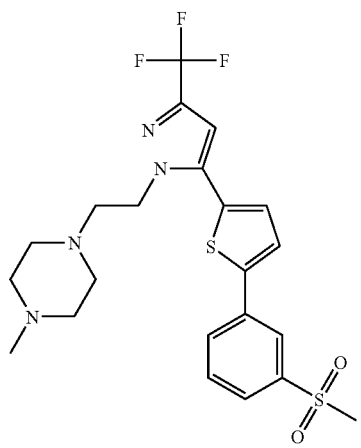 [SMILES: CN1CCN(CCN/C(=C\C(=N)C(F)(F)F)c2ccc(-c3cccc(S(C)(=O)=O)c3)s2)CC1] | 1-methyl-4-(2-(5-(5-(3-(methylsulfonyl)phenyl)thiophen-2-yl)-3-(trifluoromethyl)-1H-pyrazol-1-yl)ethyl)piperazine |
| 90 | 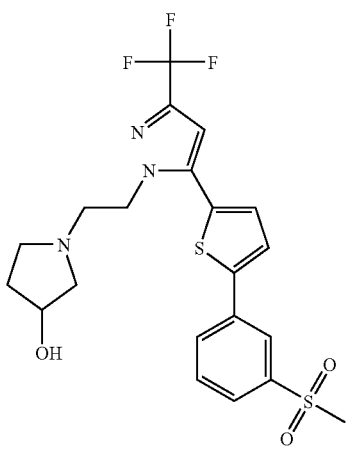 [SMILES: CS(=O)(=O)c1cccc(-c2ccc(/C(=C/C(=N)C(F)(F)F)NCCN3CCC(O)C3)s2)c1] | 1-(2-(5-(5-(3-(methylsulfonyl)phenyl)thiophen-2-yl)-3-(trifluoromethyl)-1H-pyrazol-1-yl)ethyl)pyrrolidin-3-ol |
| 91 | 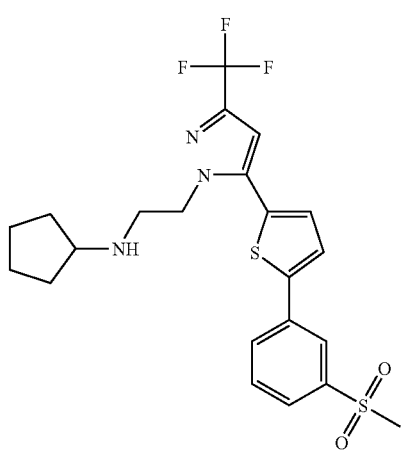 [SMILES: CS(=O)(=O)c1cccc(-c2ccc(/C(=C/C(=N)C(F)(F)F)NCCNC3CCCC3)s2)c1] | N-(2-(5-(5-(3-(methylsulfonyl)phenyl)thiophen-2-yl)-3-(trifluoromethyl)-1H-pyrazol-1-yl)ethyl)cyclopentanamine |

TABLE 1-continued

| | | |
|---|---|---|
| 92 | 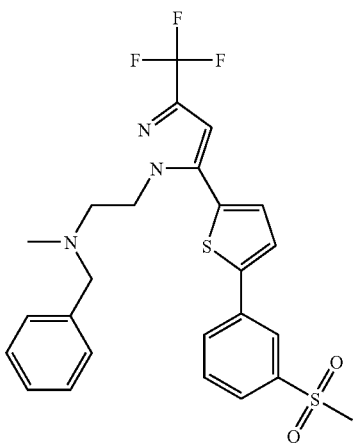 [SMILES: CN(CCN/C(=C\C(=N)C(F)(F)F)c1ccc(-c2cccc(S(C)(=O)=O)c2)s1)Cc1ccccc1] | N-benzyl-N-methyl-2-(5-(5-(3-(methylsulfonyl)phenyl)thiophen-2-yl)-3-(trifluoromethyl)-1H-pyrazol-1-yl)ethanamine |
| 93 | 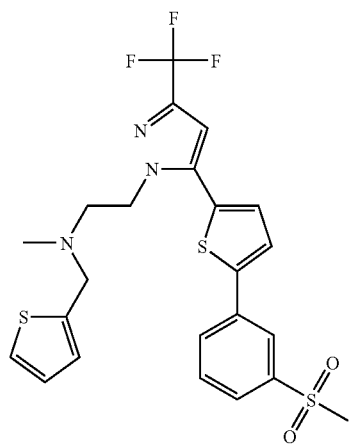 [SMILES: CN(CCN/C(=C\C(=N)C(F)(F)F)c1ccc(-c2cccc(S(C)(=O)=O)c2)s1)Cc1cccs1] | N-methyl-2-(5-(5-(3-(methylsulfonyl)phenyl)thiophen-2-yl)-3-(trifluoromethyl)-1H-pyrazol-1-yl)-N-(thiophen-2-ylmethyl)ethanamine |
| 94 | 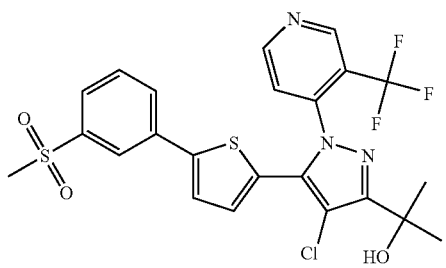 [SMILES: CC(C)(O)c1nn(-c2ccncc2C(F)(F)F)c(-c2ccc(-c3cccc(S(C)(=O)=O)c3)s2)c1Cl] | 2-(4-chloro-5-(5-(3-(methylsulfonyl)phenyl)thiophen-2-yl)-1-(3-(trifluoromethyl)pyridin-4-yl)-1H-pyrazol-3-yl)propan-2-ol |
| 95 | 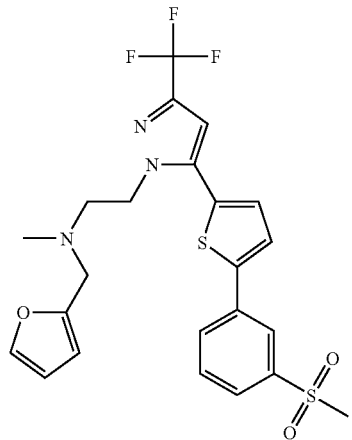 | N-(furan-2-ylmethyl)-N-methyl-2-(5-(5-(3-(methylsulfonyl)phenyl)thiophen-2-yl)-3-(trifluoromethyl)-1H-pyrazol-1-yl)ethanamine |

TABLE 1-continued

| | | |
|---|---|---|
| 96 | 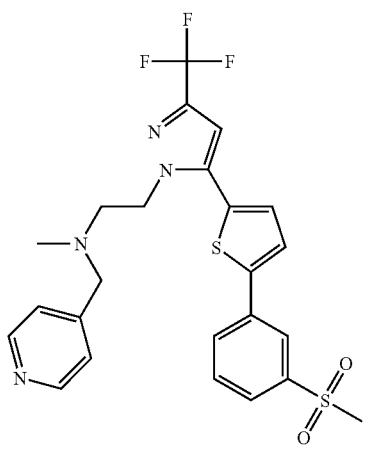 [SMILES: CN(CCN/C(=C\C(=N)C(F)(F)F)c1ccc(-c2cccc(S(C)(=O)=O)c2)s1)Cc1ccncc1] | N-methyl-2-(5-(5-(3-(methylsulfonyl)phenyl)thiophen-2-yl)-3-(trifluoromethyl)-1H-pyrazol-1-yl)-N-(pyridin-4-ylmethyl)ethanamine |
| 97 | 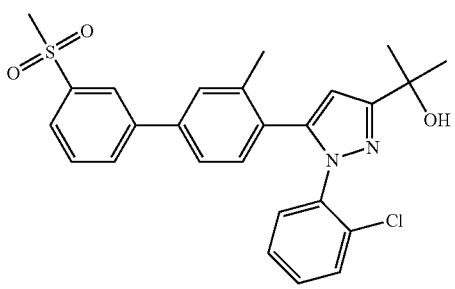 [SMILES: Cc1cc(-c2cccc(S(C)(=O)=O)c2)ccc1-c1cc(C(C)(C)O)nn1-c1ccccc1Cl] | 2-(1-(2-chlorophenyl)-5-(3-methyl-3'-(methylsulfonyl)biphenyl-4-yl)-1H-pyrazol-3-yl)propan-2-ol |
| 98 | 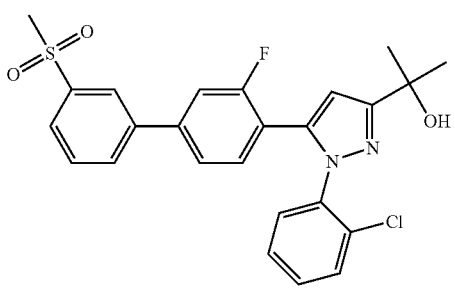 | 2-(1-(2-chlorophenyl)-5-(3-fluoro-3'-(methylsulfonyl)biphenyl-4-yl)-1H-pyrazol-3-yl)propan-2-ol |
| 99 | 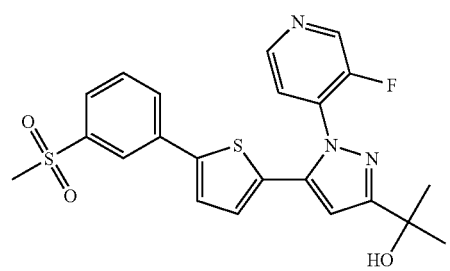 [SMILES: CC(C)(O)c1cc(-c2ccc(-c3cccc(S(C)(=O)=O)c3)s2)n(-c2ccncc2F)n1] | 2-(1-(3-fluoropyridin-4-yl)-5-(5-(3-(methylsulfonyl)phenyl)thiophen-2-yl)-1H-pyrazol-3-yl)propan-2-ol |
| 100 | 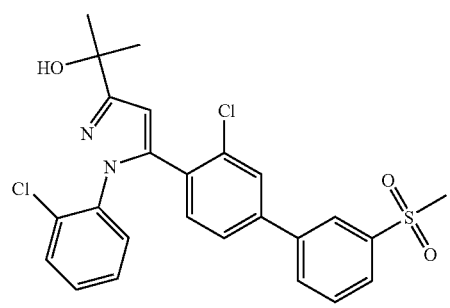 [SMILES: CC(C)(O)C(=N)/C=C(\Nc1ccccc1Cl)c1ccc(-c2cccc(S(C)(=O)=O)c2)cc1Cl] | 2-(5-(3-chloro-3'-(methylsulfonyl)biphenyl-4-yl)-1-(2-chlorophenyl)-1H-pyrazol-3-yl)propan-2-ol |

| | | |
|---|---|---|
| 101 | 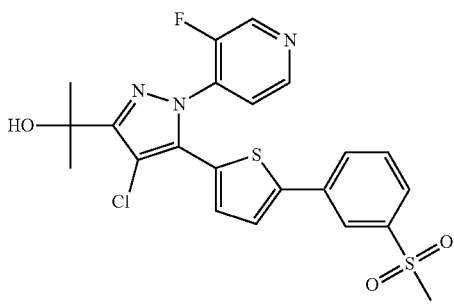 [SMILES: CC(C)(O)c1nn(-c2ccncc2F)c(-c2ccc(-c3cccc(S(C)(=O)=O)c3)s2)c1Cl] | 2-(4-chloro-1-(3-fluoropyridin-4-yl)-5-(5-(3-(methylsulfonyl)phenyl)thiophen-2-yl)-1H-pyrazol-3-yl)propan-2-ol |
| 102 | 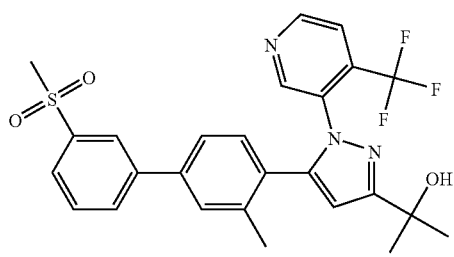 [SMILES: Cc1cc(-c2cccc(S(C)(=O)=O)c2)ccc1-c1cc(C(C)(C)O)nn1-c1cnccc1C(F)(F)F] | 2-(5-(3-methyl-3'-(methylsulfonyl)biphenyl-4-yl)-1-(4-(trifluoromethyl)pyridin-3-yl)-1H-pyrazol-3-yl)propan-2-ol |
| 103 | 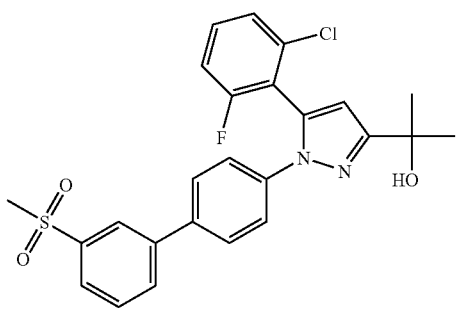 [SMILES: CC(C)(O)c1cc(-c2c(F)cccc2Cl)n(-c2ccc(-c3cccc(S(C)(=O)=O)c3)cc2)n1] | 2-(5-(2-chloro-6-fluorophenyl)-1-(3'-(methylsulfonyl)biphenyl-4-yl)-1H-pyrazol-3-yl)propan-2-ol |
| 104 | 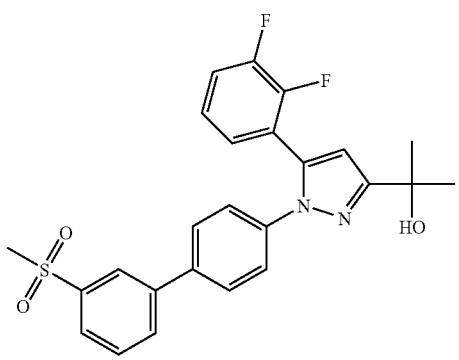 [SMILES: CC(C)(O)c1cc(-c2cccc(F)c2F)n(-c2ccc(-c3cccc(S(C)(=O)=O)c3)cc2)n1] | 2-(5-(2,3-difluorophenyl)-1-(3'-(methylsulfonyl)biphenyl-4-yl)-1H-pyrazol-3-yl)propan-2-ol |
| 105 | 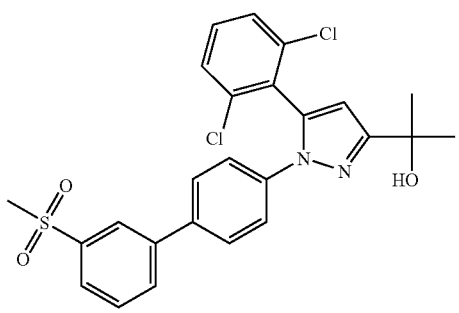 [SMILES: CC(C)(O)c1cc(-c2c(Cl)cccc2Cl)n(-c2ccc(-c3cccc(S(C)(=O)=O)c3)cc2)n1] | 2-(5-(2,6-dichlorophenyl)-1-(3'-(methylsulfonyl)biphenyl-4-yl)-1H-pyrazol-3-yl)propan-2-ol |

TABLE 1-continued

| | | |
|---|---|---|
| 106 | 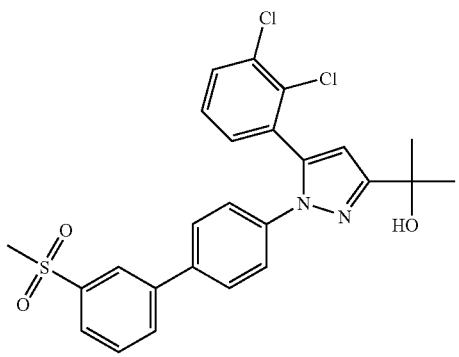 [SMILES: CC(C)(O)c1cc(-c2cccc(Cl)c2Cl)n(-c2ccc(-c3cccc(S(C)(=O)=O)c3)cc2)n1] | 2-(5-(2,3-dichlorophenyl)-1-(3'-(methylsulfonyl)biphenyl-4-yl)-1H-pyrazol-3-yl)propan-2-ol |
| 107 | 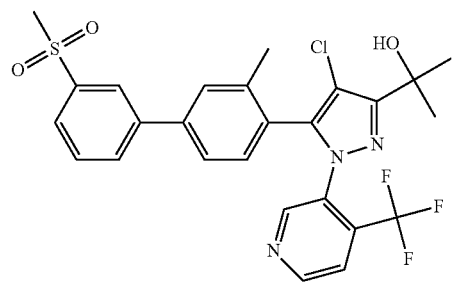 [SMILES: Cc1cc(-c2cccc(S(C)(=O)=O)c2)ccc1-c1c(Cl)c(C(C)(C)O)nn1-c1cnccc1C(F)(F)F] | 2-(4-chloro-5-(3-methyl-3'-(methylsulfonyl)biphenyl-4-yl)-1-(4-(trifluoromethyl)pyridin-3-yl)-1H-pyrazol-3-yl)propan-2-ol |
| 108 | 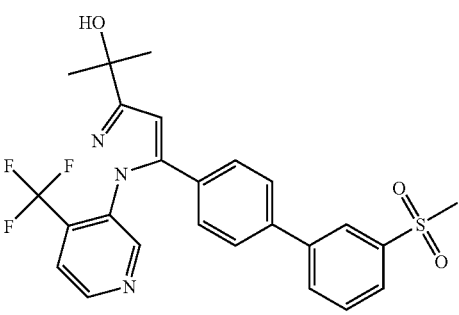 [SMILES: CC(C)(O)C(=N)/C=C(\Nc1cnccc1C(F)(F)F)c1ccc(-c2cccc(S(C)(=O)=O)c2)cc1] | 2-(5-(3'-(methylsulfonyl)biphenyl-4-yl)-1-(4-(trifluoromethyl)pyridin-3-yl)-1H-pyrazol-3-yl)propan-2-ol |
| 109 | 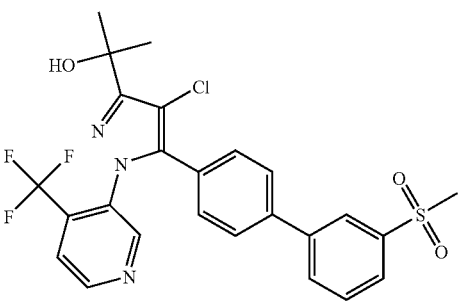 [SMILES: CC(C)(O)C(=N)/C(Cl)=C(\Nc1cnccc1C(F)(F)F)c1ccc(-c2cccc(S(C)(=O)=O)c2)cc1] | 2-(4-chloro-5-(3'-(methylsulfonyl)biphenyl-4-yl)-1-(4-(trifluoromethyl)pyridin-3-yl)-1H-pyrazol-3-yl)propan-2-ol |
| 110 | 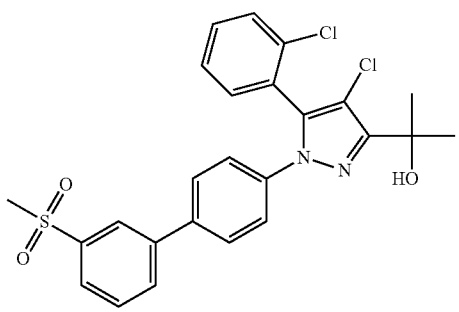 [SMILES: CC(C)(O)c1nn(-c2ccc(-c3cccc(S(C)(=O)=O)c3)cc2)c(-c2ccccc2Cl)c1Cl] | 2-(4-chloro-5-(2-chlorophenyl)-1-(3'-(methylsulfonyl)biphenyl-4-yl)-1H-pyrazol-3-yl)propan-2-ol |

TABLE 1-continued

| | | |
|---|---|---|
| 112 | 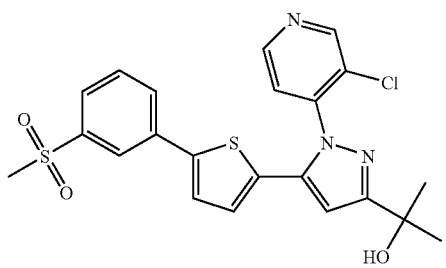 [SMILES: CC(C)(O)c1cc(-c2ccc(-c3cccc(S(C)(=O)=O)c3)s2)n(-c2ccncc2Cl)n1] | 2-(1-(3-chloropyridin-4-yl)-5-(5-(3-(methylsulfonyl)phenyl)thiophen-2-yl)-1H-pyrazol-3-yl)propan-2-ol |
| 113 | 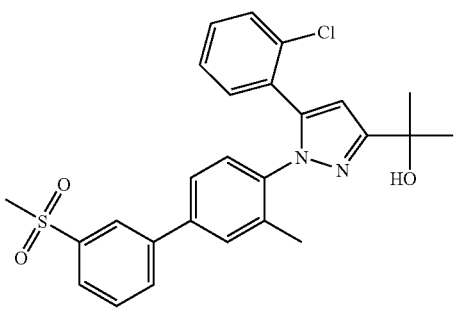 [SMILES: Cc1cc(-c2cccc(S(C)(=O)=O)c2)ccc1-n1nc(C(C)(C)O)cc1-c1ccccc1Cl] | 2-(5-(2-chlorophenyl)-1-(3-methyl-3'-(methylsulfonyl)biphenyl-4-)-1H-pyrazol-3-yl)propan-2-ol |
| 114 | 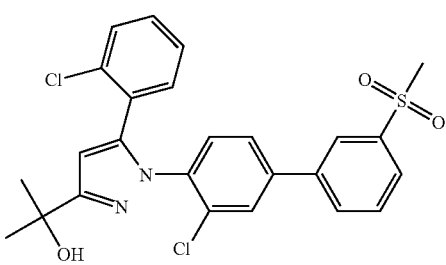 [SMILES: CC(C)(O)C(=N)/C=C(\Nc1ccc(-c2cccc(S(C)(=O)=O)c2)cc1Cl)c1ccccc1Cl] | 2-(1-(3-chloro-3'-(methylsulfonyl)biphenyl-4-yl)-5-(2-chlorophenyl)-1H-pyrazol-3-yl)propan-2-ol |
| 115 | 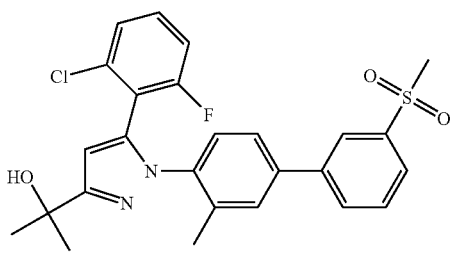 [SMILES: Cc1cc(-c2cccc(S(C)(=O)=O)c2)ccc1N/C(=C\C(=N)C(C)(C)O)c1c(F)cccc1Cl] | 2-(5-(2-chloro-6-fluorophenyl)-1-(3-methyl-3'-(methylsulfonyl)biphenyl-4-yl)-1H-pyrazol-3-yl)propan-2-ol |
| 116 | 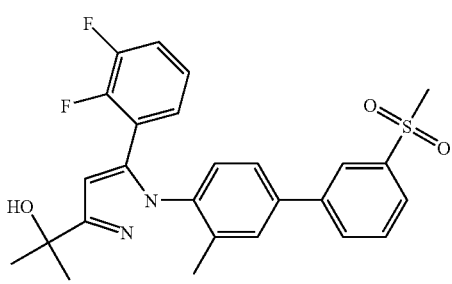 [SMILES: Cc1cc(-c2cccc(S(C)(=O)=O)c2)ccc1N/C(=C\C(=N)C(C)(C)O)c1cccc(F)c1F] | 2-(5-(2,3-difluorophenyl)-1-(3-methyl-3'-(methylsulfonyl)biphenyl-4-yl)-1H-pyrazol-3-yl)propan-2-ol |
| 117 | 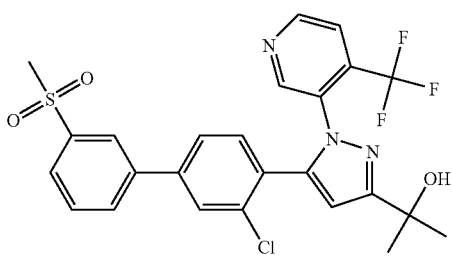 [SMILES: CC(C)(O)c1cc(-c2ccc(-c3cccc(S(C)(=O)=O)c3)cc2Cl)n(-c2cnccc2C(F)(F)F)n1] | 2-(5-(3-chloro-3'-(methylsulfonyl)biphenyl-4-yl)-1-(4-(trifluoromethyl)pyridin-3-yl)-1H-pyrazol-3-yl)propan-2-ol |

| | | |
|---|---|---|
| 118 | 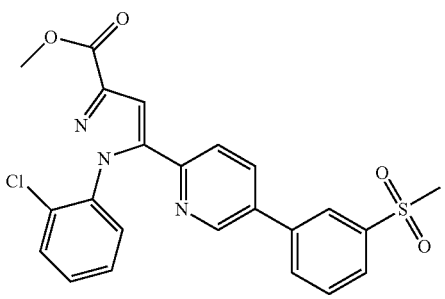 [SMILES: COC(=O)C(=N)/C=C(\Nc1ccccc1Cl)c1ccc(-c2cccc(S(C)(=O)=O)c2)cn1] | methyl 1-(2-chlorophenyl)-5-(5-(3-(methylsulfonyl)phenyl)pyridin-2-yl)-1H-pyrazole-3-carboxylate |
| 119 | 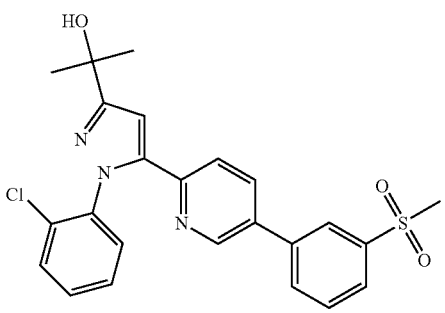 [SMILES: CC(C)(O)C(=N)/C=C(\Nc1ccccc1Cl)c1ccc(-c2cccc(S(C)(=O)=O)c2)cn1] | 2-(1-(2-chlorophenyl)-5-(5-(3-(methylsulfonyl)phenyl)pyridin-2-yl)-1H-pyrazol-3-yl)propan-2-ol |
| 120 | 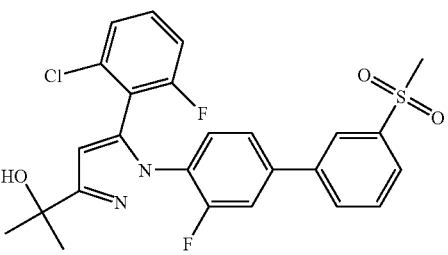 | 2-(5-(2-chloro-6-fluorophenyl)-1-(3-fluoro-3'-(methylsulfonyl)biphenyl-4-yl)-1H-pyrazol-3-yl)propan-2-ol |
| 121 | 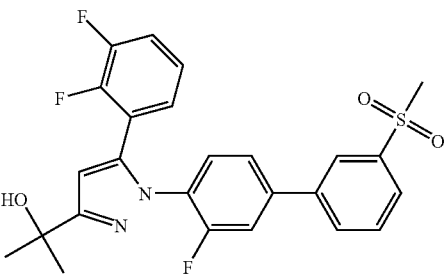 [SMILES: CC(C)(O)C(=N)/C=C(\Nc1ccc(-c2cccc(S(C)(=O)=O)c2)cc1F)c1cccc(F)c1F] | 2-(5-(2,3-difluorophenyl)-1-(3-fluoro-3'-(methylsulfonyl)biphenyl-4-yl)-1H-pyrazol-3-yl)propan-2-ol |
| 122 | 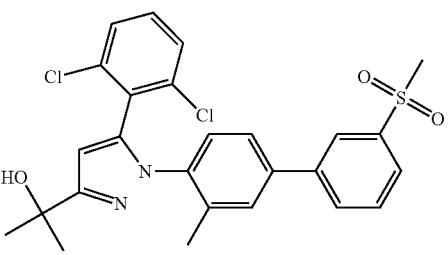 [SMILES: Cc1cc(-c2cccc(S(C)(=O)=O)c2)ccc1N/C(=C\C(=N)C(C)(C)O)c1c(Cl)cccc1Cl] | 2-(5-(2,6-dichlorophenyl)-1-(3-methyl-3'-(methylsulfonyl)biphenyl-4-yl)-1H-pyrazol-3-yl)propan-2-ol |

TABLE 1-continued

| | | |
|---|---|---|
| 123 | 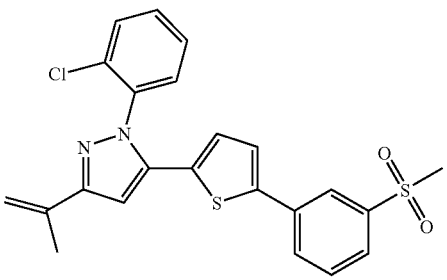 [SMILES: C=C(C)c1cc(-c2ccc(-c3cccc(S(C)(=O)=O)c3)s2)n(-c2ccccc2Cl)n1] | 1-(2-chlorophenyl)-5-(5-(3-(methylsulfonyl)phenyl)thiophen-2-yl)-3-(prop-1-en-2-yl)-1H-pyrazole |
| 124 | 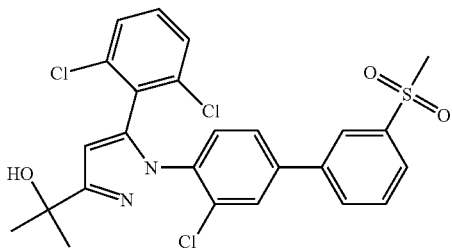 [SMILES: CC(C)(O)C(=N)/C=C(\Nc1ccc(-c2cccc(S(C)(=O)=O)c2)cc1Cl)c1c(Cl)cccc1Cl] | 2-(1-(3-chloro-3'-(methylsulfonyl)nbiphenyl-4-yl)-5-(2,6-dichlorophenyl)-1H-pyrazol-3-yl)propan-2-ol |
| 125 | 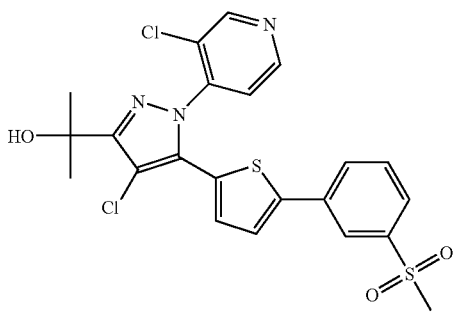 [SMILES: CC(C)(O)c1nn(-c2ccncc2Cl)c(-c2ccc(-c3cccc(S(C)(=O)=O)c3)s2)c1Cl] | 2-(4-chloro-1-(3-chloropyridin-4-yl)-5-(5-(3-(methylsulfonyl)phenyl)thiophen-2-yl)-1H-pyrazol-3-yl)propan-2-ol |
| 126 | 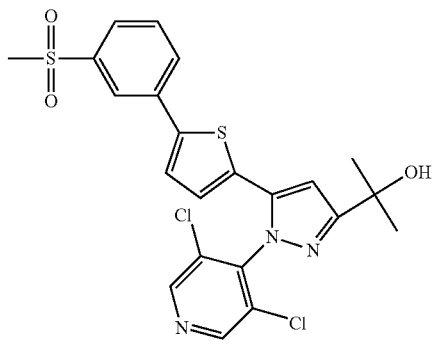 [SMILES: CC(C)(O)c1cc(-c2ccc(-c3cccc(S(C)(=O)=O)c3)s2)n(-c2c(Cl)cncc2Cl)n1] | 2-(1-(3,5-dichloropyridin-4-yl)-5-(5-(3-(methylsulfonyl)phenyl)thiophen-2-yl)-1H-pyrazol-3-yl)propan-2-ol |
| 127 | 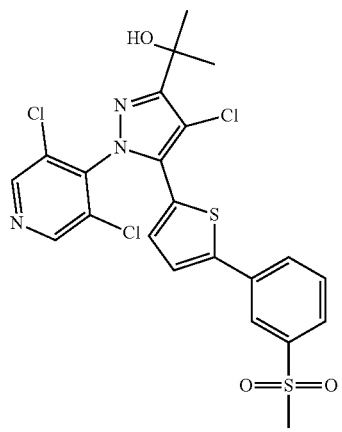 [SMILES: CC(C)(O)c1nn(-c2c(Cl)cncc2Cl)c(-c2ccc(-c3cccc(S(C)(=O)=O)c3)s2)c1Cl] | 2-(4-chloro-1-(3,5-dichloropyridin-4-yl)-5-(5-(3-(methylsulfonyl)phenyl)thiophen-2-yl)-1H-pyrazol-3-yl)propan-2-ol |

TABLE 1-continued

| | | |
|---|---|---|
| 128 | 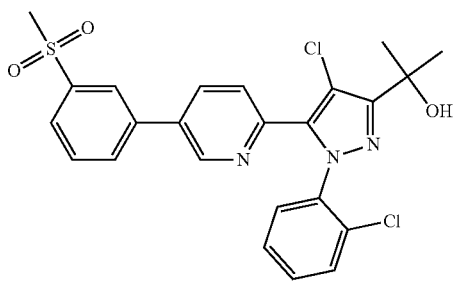 [SMILES: CC(C)(O)c1nn(-c2ccccc2Cl)c(-c2ccc(-c3cccc(S(C)(=O)=O)c3)cn2)c1Cl] | 2-(4-chloro-1-(2-chlorophenyl)-5-(5-(3-(methylsulfonyl)phenyl)pyridin-2-yl)-1H-pyrazol-3-yl)propan-2-ol |
| 129 | 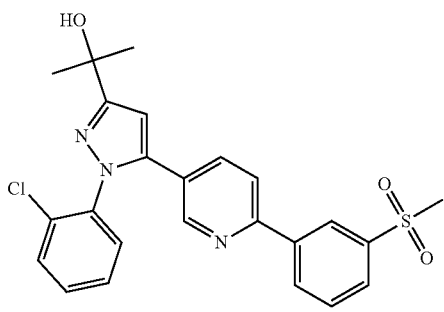 [SMILES: CC(C)(O)c1cc(-c2ccc(-c3cccc(S(C)(=O)=O)c3)nc2)n(-c2ccccc2Cl)n1] | 2-(1-(2-chlorophenyl)-5-(5-(3-(methylsulfonyl)phenyl)pyridin-3-yl)-1H-pyrazol-3-yl)propan-2-ol |
| 130 | 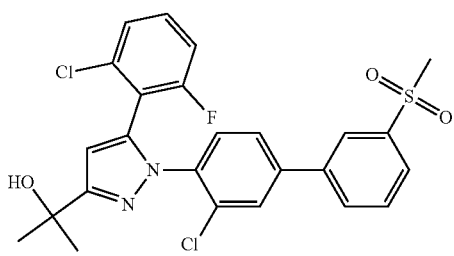 [SMILES: CC(C)(O)c1cc(-c2c(F)cccc2Cl)n(-c2ccc(-c3cccc(S(C)(=O)=O)c3)cc2Cl)n1] | 2-(1-(3-chloro-3'-(methylsulfonyl)biphenyl-4-yl)-5-(2-chloro-6-fluorophenyl)-1H-pyrazol-3-yl)propan-2-ol |
| 131 | 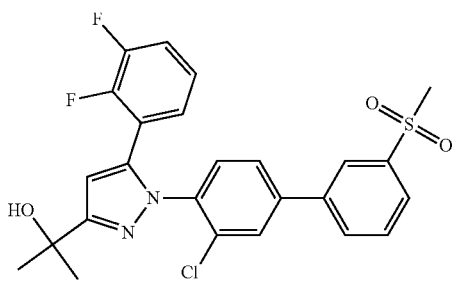 [SMILES: CC(C)(O)c1cc(-c2cccc(F)c2F)n(-c2ccc(-c3cccc(S(C)(=O)=O)c3)cc2Cl)n1] | 2-(1-(3-chloro-3'-(methylsulfonyl)biphenyl-4-yl)-5-(2,3-difluorophenyl)-1H-pyrazol-3-yl)propan-2-ol |
| 132 | 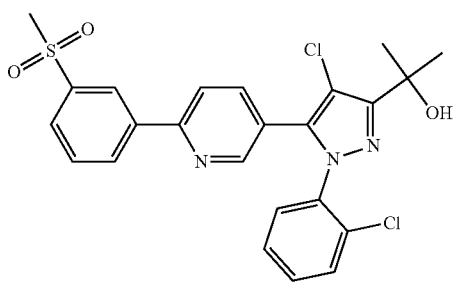 [SMILES: CC(C)(O)c1nn(-c2ccccc2Cl)c(-c2ccc(-c3cccc(S(C)(=O)=O)c3)nc2)c1Cl] | 2-(4-chloro-1-(2-chlorophenyl)-5-(6-(3-(methylsulfonyl)phenyl)pyridin-3-yl)-1H-pyrazol-3-yl)propan-2-ol |

| | | |
|---|---|---|
| 133 | 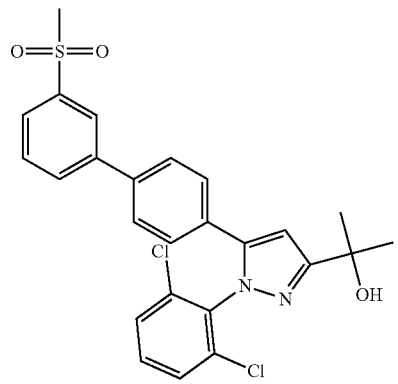 [SMILES: CC(C)(O)c1cc(-c2ccc(-c3cccc(S(C)(=O)=O)c3)cc2)n(-c2c(Cl)cccc2Cl)n1] | 2-(1-(2,6-dichlorophenyl)-5-(3'-(methylsulfonyl)biphenyl-4-yl)-1H-pyrazol-3-yl)propan-2-ol |
| 134 | 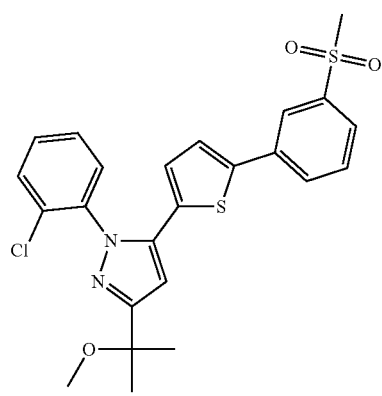 [SMILES: COC(C)(C)c1cc(-c2ccc(-c3cccc(S(C)(=O)=O)c3)s2)n(-c2ccccc2Cl)n1] | 1-(2-chlorophenyl)-3-(2-methoxypropan-2-yl)-5-(5-(3-(methylsulfonyl)phenyl)thiophen-2-yl)-1H-pyrazole |
| 135 | 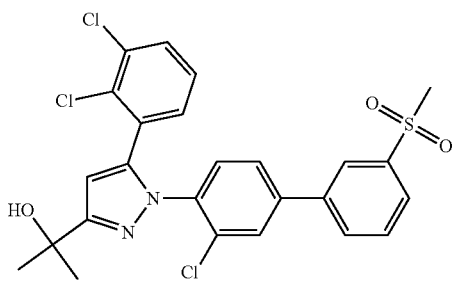 [SMILES: CC(C)(O)c1cc(-c2cccc(Cl)c2Cl)n(-c2ccc(-c3cccc(S(C)(=O)=O)c3)cc2Cl)n1] | 2-(1-(3-chloro-3'-(methylsulfonyl)biphenyl-4-yl)-5-(2,3-dichlorophenyl)-1H-pyrazol-3-yl)propan-2-ol |
| 136 | 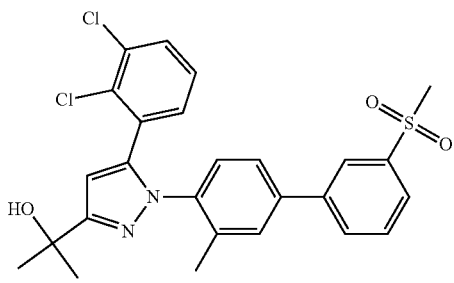 [SMILES: Cc1cc(-c2cccc(S(C)(=O)=O)c2)ccc1-n1nc(C(C)(C)O)cc1-c1cccc(Cl)c1Cl] | 2-(5-(2,3-dichlorophenyl)-1-(3-methyl-3'-(methylsulfonyl)biphenyl-4-yl)1H-pyrazol-3-yl)propan-2-ol |
| 137 | 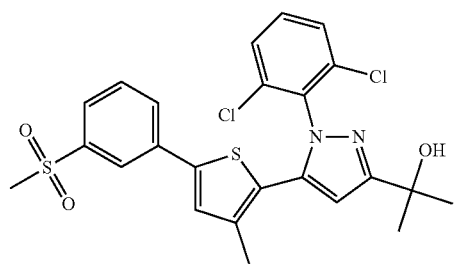 [SMILES: Cc1cc(-c2cccc(S(C)(=O)=O)c2)sc1-c1cc(C(C)(C)O)nn1-c1c(Cl)cccc1Cl] | 2-(1-(2,6-dichlorophenyl)-5-(3-methyl-5-(3-(methylsulfonyl)phenyl)thiophen-2-yl)-1H-pyrazol-3-yl)propan-2-ol |

| | | |
|---|---|---|
| 138 | 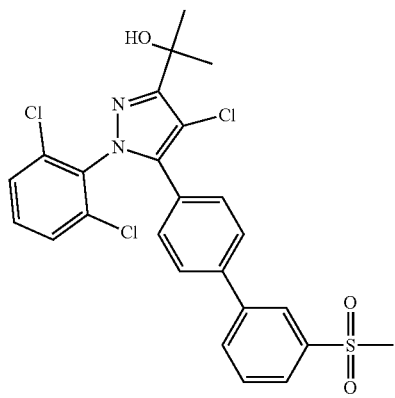 [SMILES: CC(C)(O)c1nn(-c2c(Cl)cccc2Cl)c(-c2ccc(-c3cccc(S(C)(=O)=O)c3)cc2)c1Cl] | 2-(4-chloro-1-(2,6-dichlorophenyl)-5-(3'-(methylsulfonyl)biphenyl-4-yl)-1H-pyrazol-3-yl)propan-2-ol |
| 139 | 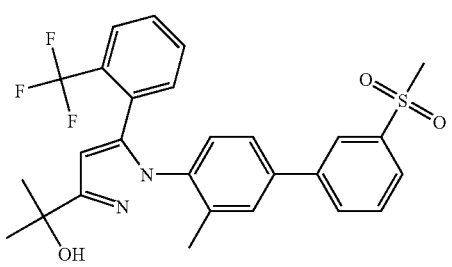 [SMILES: Cc1cc(-c2cccc(S(C)(=O)=O)c2)ccc1N/C(=C\C(=N)C(C)(C)O)c1ccccc1C(F)(F)F] | 2-(1-(3-methyl-3'-(methylsulfonyl)biphenyl-4-yl)-5-(2-(trifluoromethyl)phenyl)-1H-pyrazol-3-yl)propan-2-ol |
| 140 | 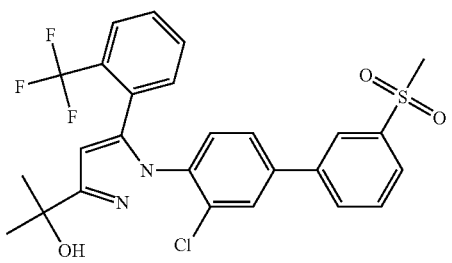 [SMILES: CC(C)(O)C(=N)/C=C(\Nc1ccc(-c2cccc(S(C)(=O)=O)c2)cc1Cl)c1ccccc1C(F)(F)F] | 2-(1-(3-chloro-3'-(methylsulfonyl)biphenyl-4-yl)-5-(2-(trifluoromethyl)phenyl)-1H-pyrazol-3-yl)propan-2-ol |
| 141 | 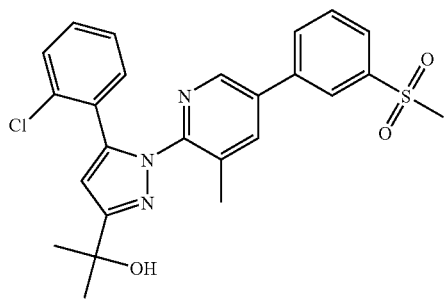 [SMILES: Cc1cc(-c2cccc(S(C)(=O)=O)c2)cnc1-n1nc(C(C)(C)O)cc1-c1ccccc1Cl] | 2-(5-(2-chlorophenyl)-1-(3-methyl-5-(3-(methylsulfonyl)phenyl)pyridin-2-yl)-1H-pyrazol-3-yl)propan-2-ol |
| 142 | 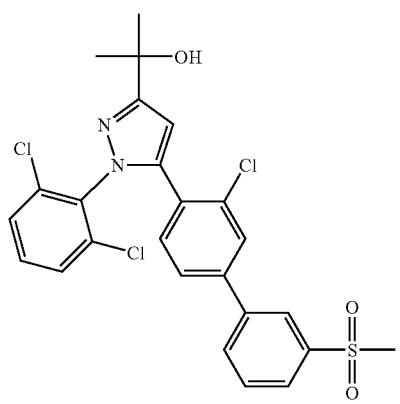 [SMILES: CC(C)(O)c1cc(-c2ccc(-c3cccc(S(C)(=O)=O)c3)cc2Cl)n(-c2c(Cl)cccc2Cl)n1] | 2-(5-(3-chloro-3'-(methylsulfonyl)biphenyl-4-yl)-1-(2,6-dichlorophenyl)-1H-pyrazol-3-yl)propan-2-ol |

TABLE 1-continued

| 143 | 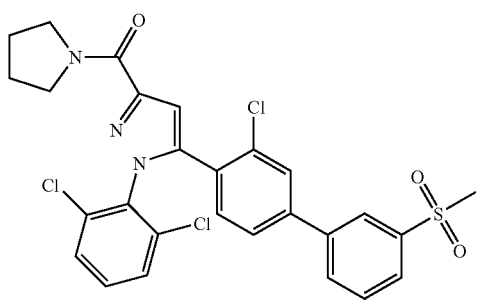 [SMILES: CS(=O)(=O)c1cccc(-c2ccc(/C(=C/C(=N)C(=O)N3CCCC3)Nc3c(Cl)cccc3Cl)c(Cl)c2)c1] | (5-(3-chloro-3'-(methylsulfonyl)biphenyl-4-yl)-1-(2,6-dichlorophenyl)-1H-pyrazol-3-yl)(pyrrolidin-1-yl)methanone |
| 144 | 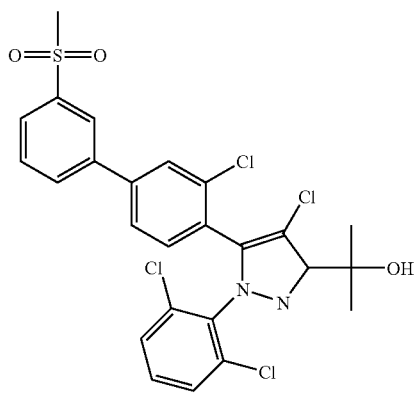 [SMILES: CC(C)(O)C1NN(c2c(Cl)cccc2Cl)C(c2ccc(-c3cccc(S(C)(=O)=O)c3)cc2Cl)=C1Cl] | 2-(4-chloro-5-(3-chloro-3'-(methylsulfonyl)biphenyl-4-yl)-1-(2,6-dichlorophenyl)-1H-pyrazol-3-yl)propan-2-ol |
| 145 | 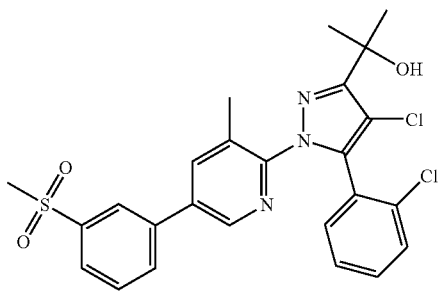 [SMILES: Cc1cc(-c2cccc(S(C)(=O)=O)c2)cnc1-n1nc(C(C)(C)O)c(Cl)c1-c1ccccc1Cl] | 2-(4-chloro-5-(2-chlorophenyl)-1-(3-methyl-5-(3-(methylsulfonyl)phenyl)pyridin-2-yl)-1H-pyrazol-3-yl)propan-2-ol |
| 146 | 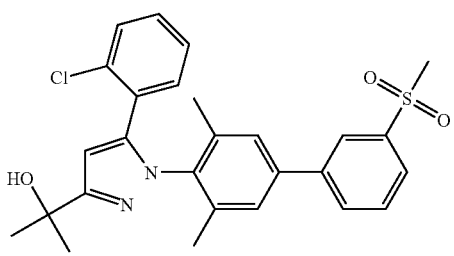 [SMILES: Cc1cc(-c2cccc(S(C)(=O)=O)c2)cc(C)c1N/C(=C\C(=N)C(C)(C)O)c1ccccc1Cl] | 2-(5-(2-chlorophenyl)-1-(3,5-dimethyl-3'-(methylsulfonyl)biphenyl-4-yl)-1H-pyrazol-3-yl)propan-2-ol |
| 147 | 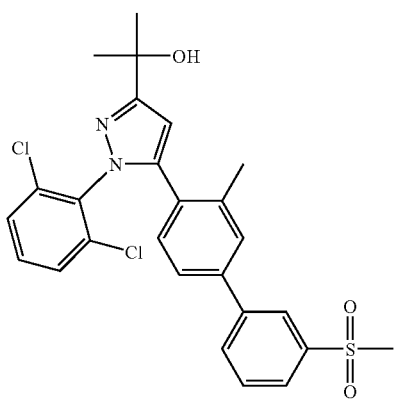 [SMILES: Cc1cc(-c2cccc(S(C)(=O)=O)c2)ccc1-c1cc(C(C)(C)O)nn1-c1c(Cl)cccc1Cl] | 2-(1-(2,6-dichlorophenyl)-5-(3-methyl-3'-(methylsulfonyl)biphenyl-4-yl)-1H-pyrazol-3-yl)propan-2-ol |

TABLE 1-continued

| 148 | 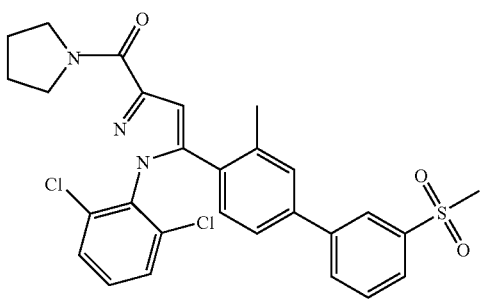 | (1-(2,6-dichlorophenyl)-5-(3-methyl-3'-(methylsulfonyl)biphenyl-4-yl)-1H-pyrazol-3-yl)(pyrrolidin-1-yl)methanone |

| 149 | 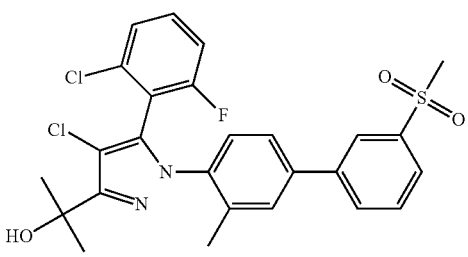 [SMILES: Cc1cc(-c2cccc(S(C)(=O)=O)c2)ccc1N/C(=C(/Cl)C(=N)C(C)(C)O)c1c(F)cccc1Cl] | 2-(4-chloro-5-(2-chloro-6-fluorophenyl)-1-(3-methyl-3'-(methylsulfonyl)biphenyl-4-yl)-1H-pyrazol-3-yl)propan-2-ol |

| 151 | 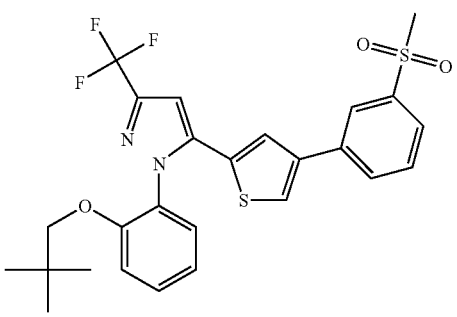 [SMILES: CC(C)(C)COc1ccccc1N/C(=C\C(=N)C(F)(F)F)c1cc(-c2cccc(S(C)(=O)=O)c2)cs1] | 1-{2-[(2,2-dimethylpropyl)oxy]phenyl}-5-{4-[3-(methylsulfonyl)phenyl]-2-thienyl}-3-(trifluoromethyl)-1H-pyrazole |

| 152 | 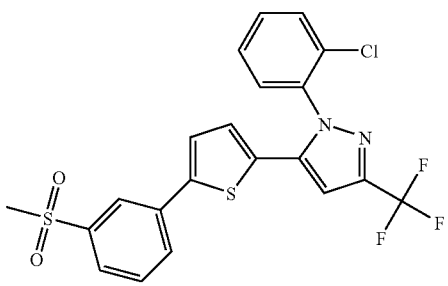 [SMILES: CS(=O)(=O)c1cccc(-c2ccc(-c3cc(C(F)(F)F)nn3-c3ccccc3Cl)s2)c1] | 1-(2-chlorophenyl)-5-{5-[3-(methylsulfonyl)phenyl]-2-thienyl}-3-(trifluoromethyl)-1H-pyrazole |

| 153 | 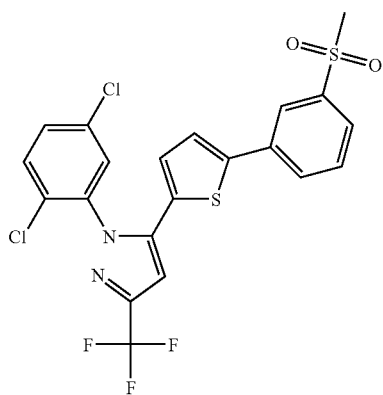 | 1-(2,5-dichlorophenyl)-5-{5-[3-(methylsulfonyl)phenyl]-2-thienyl}-3-(trifluoromethyl)-1H-pyrazole |

TABLE 1-continued

| 154 | 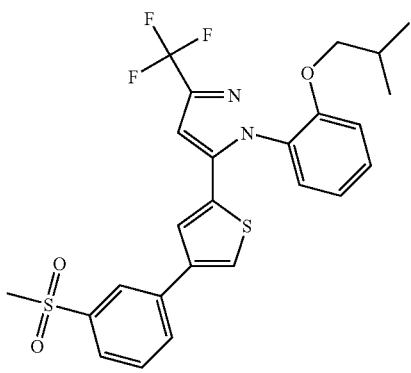 [SMILES: CC(C)COc1ccccc1N/C(=C\C(=N)C(F)(F)F)c1cc(-c2cccc(S(C)(=O)=O)c2)cs1] | 1-{2-[(2-methylpropyl)oxy]phenyl}-5-{4-[3-(methylsulfonyl)phenyl]-2-thienyl}-3-(trifluoromethyl)-1H-pyrazole |
| --- | --- | --- |
| 155 | 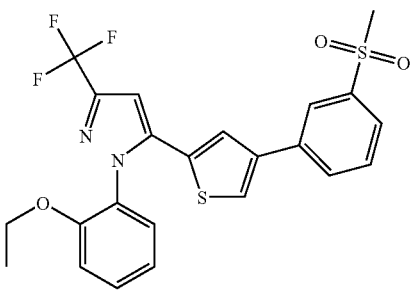 [SMILES: CCOc1ccccc1N/C(=C\C(=N)C(F)(F)F)c1cc(-c2cccc(S(C)(=O)=O)c2)cs1] | 1-[2-(ethyloxy)phenyl]-5-{4-[3-(methylsulfonyl)phenyl]-2-thienyl}-3-(trifluoromethyl)-1H-pyrazole |
| 156 | 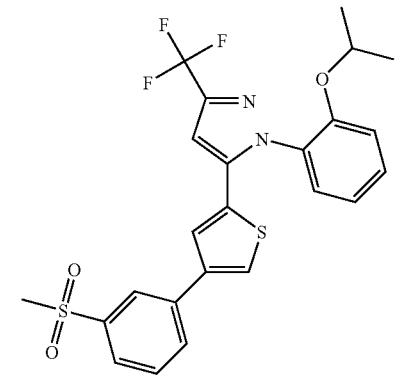 [SMILES: CC(C)Oc1ccccc1N/C(=C\C(=N)C(F)(F)F)c1cc(-c2cccc(S(C)(=O)=O)c2)cs1] | 1-{2-[(1-methylethyl)oxy]phenyl}-5-{4-[3-(methylsulfonyl)phenyl]-2-thienyl}-3-(trifluoromethyl)-1H-pyrazole |
| 157 | 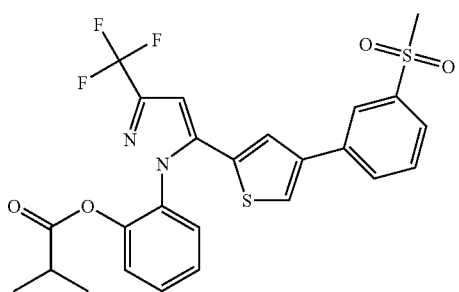 [SMILES: CN(C)C(=O)Oc1ccccc1N/C(=C\C(=N)C(F)(F)F)c1cc(-c2cccc(S(C)(=O)=O)c2)cs1] | 2-[5-{4-[3-(methylsulfonyl)phenyl]-2-thienyl}-3-(trifluoromethyl)-1H-pyrazol-1-yl]phenyl 2-methylpropanoate |
| 158 | 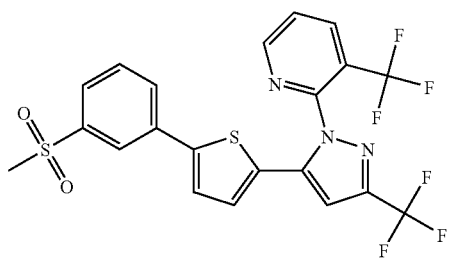 | 2-[5-{5-[3-(methylsulfonyl)phenyl]-2-thienyl}-3-(trifluoromethyl)-1H-pyrazol-1-yl]-3-(trifluoromethyl)pyridine |

| | | |
|---|---|---|
| 159 | 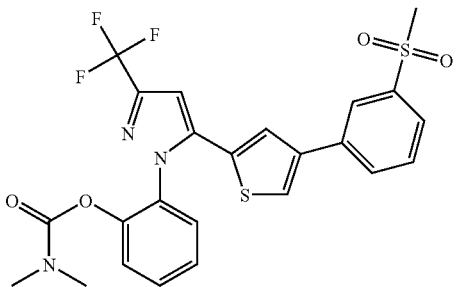 | 2-[5-{4-[3-(methylsulfonyl)phenyl]-2-thienyl}-3-(trifluoromethyl)-1H-pyrazol-1-yl]phenyl dimethylcarbamate |
| 160 | 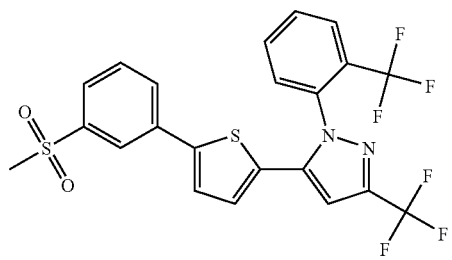 [SMILES: CS(=O)(=O)c1cccc(-c2ccc(-c3cc(C(F)(F)F)nn3-c3ccccc3C(F)(F)F)s2)c1] | 5-{5-[3-(methylsulfonyl)phenyl]-2-thienyl}-3-(trifluoromethyl)-1-[2-(trifluoromethyl)phenyl]-1H-pyrazole |
| 161 | 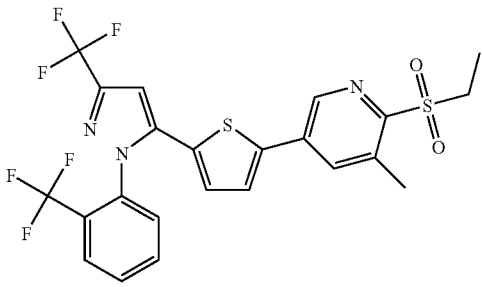 [SMILES: CCS(=O)(=O)c1ncc(-c2ccc(/C(=C/C(=N)C(F)(F)F)Nc3ccccc3C(F)(F)F)s2)cc1C] | 2-(ethylsulfonyl)-3-methyl-5-(6-{3-(trifluoromethyl)-1-[2-(trifluoromethyl)phenyl]-1H-pyrazol-5-yl}-2-thienyl)pyridine |
| 162 | 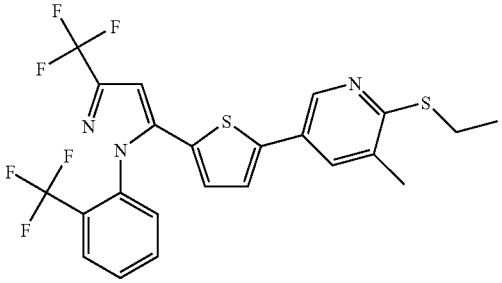 [SMILES: CCSc1ncc(-c2ccc(/C(=C/C(=N)C(F)(F)F)Nc3ccccc3C(F)(F)F)s2)cc1C] | 2-(ethylthio)-3-methyl-5-(6-{3-(trifluoromethyl)-1-[2-(trifluoromethyl)phenyl]-1H-pyrazol-5-yl}-2-thienyl)pyridine |
| 163 | 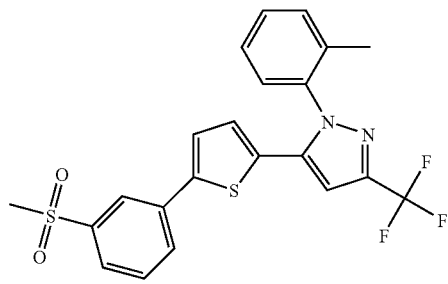 [SMILES: Cc1ccccc1-n1nc(C(F)(F)F)cc1-c1ccc(-c2cccc(S(C)(=O)=O)c2)s1] | 1-(2-methylphenyl)-5-{5-[3-(methylsulfonyl)phenyl]-2-thienyl}-3-(trifluoromethyl)-1H-pyrazole |

| | | |
|---|---|---|
| 164 | 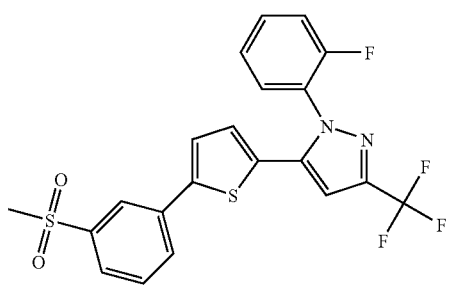 [SMILES: CS(=O)(=O)c1cccc(-c2ccc(-c3cc(C(F)(F)F)nn3-c3ccccc3F)s2)c1] | 1-(2-fluorophenyl)-5-{5-[3-(methylsulfonyl)phenyl]-2-thienyl}-3-(trifluoromethyl)-1H-pyrazole |
| 165 | 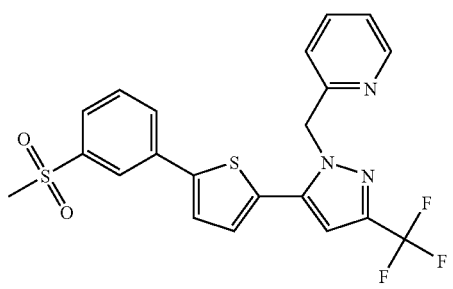 [SMILES: CS(=O)(=O)c1cccc(-c2ccc(-c3cc(C(F)(F)F)nn3Cc3ccccn3)s2)c1] | 2-{[5-{5-[3-(methylsulfonyl)phenyl]-2-thienyl}-3-(trifluoromethyl)-1H-pyrazol-1-yl]methyl}pyridine |
| 166 | 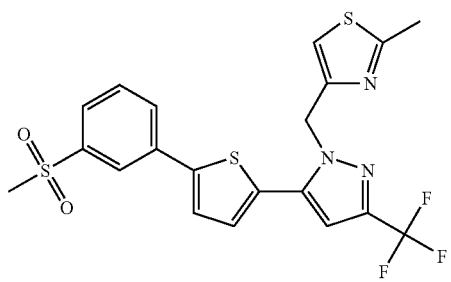 [SMILES: Cc1nc(Cn2nc(C(F)(F)F)cc2-c2ccc(-c3cccc(S(C)(=O)=O)c3)s2)cs1] | 2-methyl-4-{[5-{5-[3-(methylsulfonyl)phenyl]-2-thienyl}-3-(trifluoromethyl)-1H-pyrazol-3-yl]methyl}-1,3-thiazole |
| 167 | 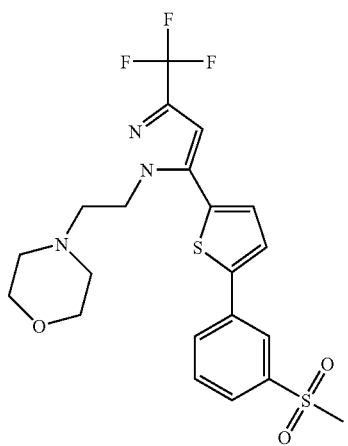 [SMILES: CS(=O)(=O)c1cccc(-c2ccc(/C(=C/C(=N)C(F)(F)F)NCCN3CCOCC3)s2)c1] | 4-{2-[5-{5-[3-(methylsulfonyl)phenyl]-2-thienyl}-3-(trifluoromethyl)-1H-pyrazol-1-yl]ethyl}morpholine |

TABLE 1-continued

| | | |
|---|---|---|
| 168 | | 5-methyl-3-{[5-{5-[3-(methylsulfonyl)phenyl]-2-thienyl}-3-(trifluoromethyl)-1H-pyrazol-1-yl]methyl}isoxazole |
| 169 | | 5-methyl-3-{[3-{5-[3-(methylsulfonyl)phenyl]-2-thienyl}-5-(trifluoromethyl)-1H-pyrazol-1-yl]methyl}isoxazole |
| 170 | | 2-{[3-{5-[3-(methylsulfonyl)phenyl]-2-thienyl}-5-(trifluoromethyl)-1H-pyrazol-1-yl]methyl}pyridine |
| 171 | | 2-methyl-4-{[3-{5-[3-(methylsulfonyl)phenyl]-2-thienyl}-5-(trifluoromethyl)-1H-pyrazol-1-yl]methyl}-1,3-thiazole |
| 172 | | 2-[5-{5-[3-(methylsulfonyl)phenyl]-2-thienyl}-3-(trifluoromethyl)-1H-pyrazol-1-yl]benzoic acid |

TABLE 1-continued
| | | |
|---|---|---|
| 173 | 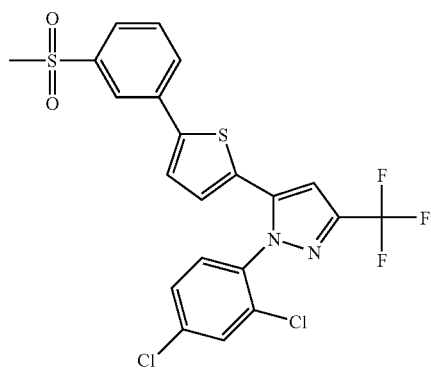 [SMILES: CS(=O)(=O)c1cccc(-c2ccc(-c3cc(C(F)(F)F)nn3-c3ccc(Cl)cc3Cl)s2)c1] | 1-(2,4-difluorophenyl)-5-{5-[3-(methylsulfonyl)phenyl]-2-thienyl}-3-(trifluoromethyl)-1H-pyrazole |
| 174 | 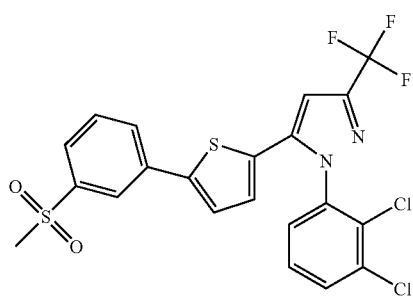 [SMILES: CS(=O)(=O)c1cccc(-c2ccc(/C(=C/C(=N)C(F)(F)F)Nc3cccc(Cl)c3Cl)s2)c1] | 1-(2,3-dichlorophenyl)-5-{5-[3-(methylsulfonyl)phenyl]-2-thienyl}-3-(trifluoromethyl)-1H-pyrazole |
| 175 | 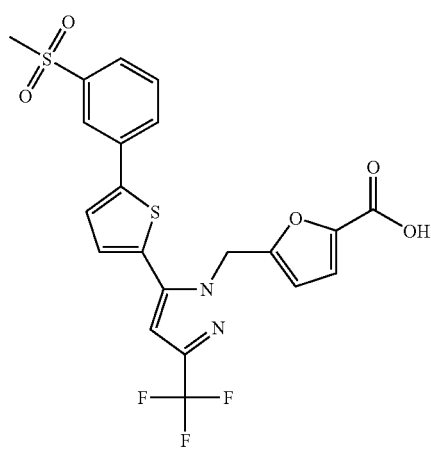 [SMILES: CS(=O)(=O)c1cccc(-c2ccc(/C(=C/C(=N)C(F)(F)F)NCc3ccc(C(=O)O)o3)s2)c1] | 5-{[5-{5-[3-(methylsulfonyl)phenyl]-2-thienyl}-3-(trifluoromethyl)-1H-pyrazol-1-yl]methyl}furan-2-carboxylic acid |
| 176 | 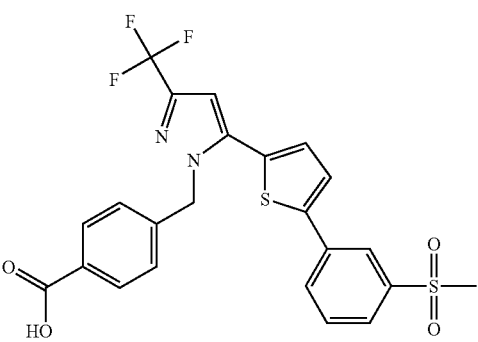 [SMILES: CS(=O)(=O)c1cccc(-c2ccc(/C(=C/C(=N)C(F)(F)F)NCc3ccc(C(=O)O)cc3)s2)c1] | 4-{[5-{5-[3-(methylsulfonyl)phenyl]-2-thienyl}-3-(trifluoromethyl)-1H-pyrazol-1-yl]methyl}benzoic acid |

TABLE 1-continued

| | | |
|---|---|---|
| 177 | 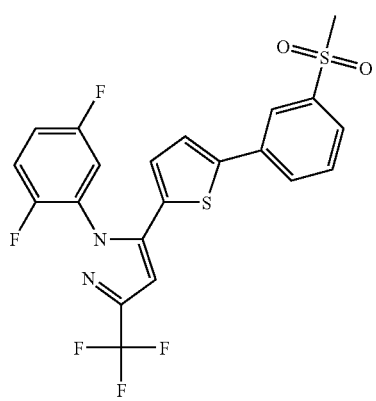 [SMILES: CS(=O)(=O)c1cccc(-c2ccc(/C(=C/C(=N)C(F)(F)F)Nc3cc(F)ccc3F)s2)c1] | 1-(2,5-difluorophenyl)-5-{5-[3-(methylsulfonyl)phenyl]-2-thienyl}-3-(trifluoromethyl)-1H-pyrazole |
| 178 | 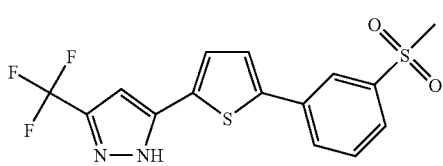 | 5-{5-[3-(methylsulfonyl)phenyl]-2-thienyl}-3-(trifluoromethyl)-1H-pyrazole |
| 179 | 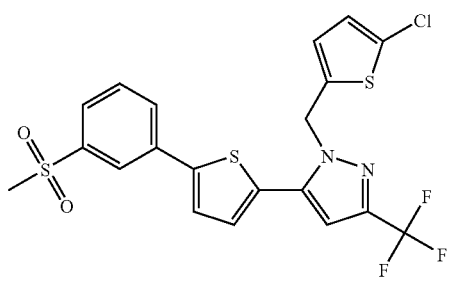 [SMILES: CS(=O)(=O)c1cccc(-c2ccc(-c3cc(C(F)(F)F)nn3Cc3ccc(Cl)s3)s2)c1] | 1-[(5-chloro-2-thienyl)methyl]-5-{5-[3-(methylsulfonyl)phenyl]-2-thienyl}-3-(trifluoromethyl)-1H-pyrazole |
| 180 | 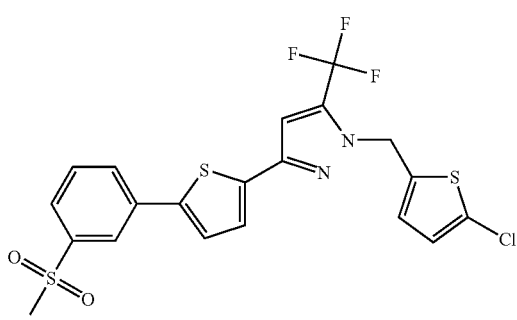 [SMILES: CS(=O)(=O)c1cccc(-c2ccc(C(=N)/C=C(\NCc3ccc(Cl)s3)C(F)(F)F)s2)c1] | 1-[(5-chloro-2-thienyl)methyl]-3-{5-[3-(methylsulfonyl)phenyl]-2-thienyl}-5-(trifluoromethyl)-1H-pyrazole |
| 181 | 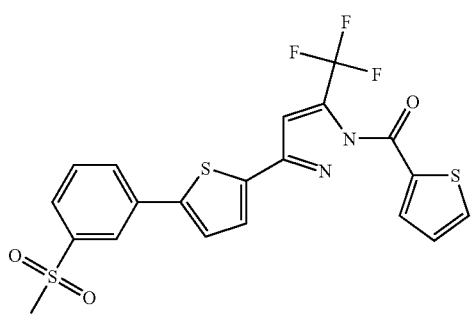 [SMILES: CS(=O)(=O)c1cccc(-c2ccc(C(=N)/C=C(\NC(=O)c3cccs3)C(F)(F)F)s2)c1] | 3-{5-[3-(methylsulfonyl)phenyl]-2-thienyl}-1-(2-thienylcarbonyl)-5-(trifluoromethyl)-1H-pyrazole |

TABLE 1-continued
| 182 | 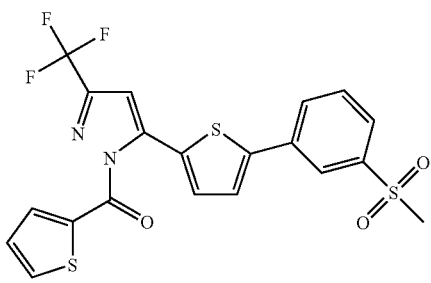 [SMILES: CS(=O)(=O)c1cccc(-c2ccc(/C(=C/C(=N)C(F)(F)F)NC(=O)c3cccs3)s2)c1] | 5-{5-[3-(methylsulfonyl)phenyl]-2-thienyl}-1-(2-thienylcarbonyl)-3-(trifluoromethyl)-1H-pyrazole |
| 183 | 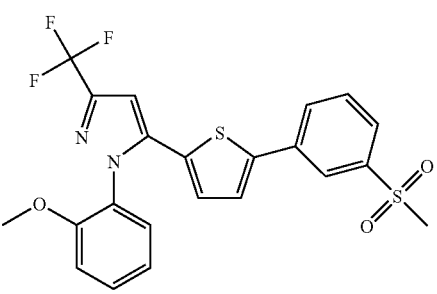 [SMILES: COc1ccccc1N/C(=C\C(=N)C(F)(F)F)c1ccc(-c2cccc(S(C)(=O)=O)c2)s1] | 1-[2-(methyloxy)phenyl]-5-{5-[3-(methylsulfonyl)phenyl]-2-thienyl}-3-(trifluoromethyl)-1H-pyrazole |
| 184 | 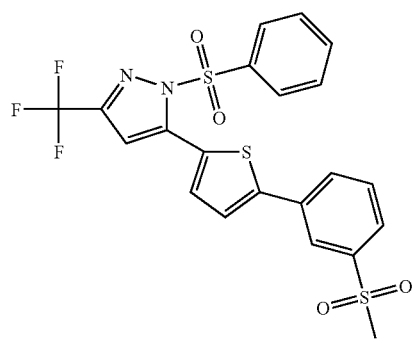 [SMILES: CS(=O)(=O)c1cccc(-c2ccc(-c3cc(C(F)(F)F)nn3S(=O)(=O)c3ccccc3)s2)c1] | 5-{5-[3-(methylsulfonyl)phenyl]-2-thienyl}-1-(phenylsulfonyl)-3-(trifluoromethyl)-1H-pyrazole |
| 185 | 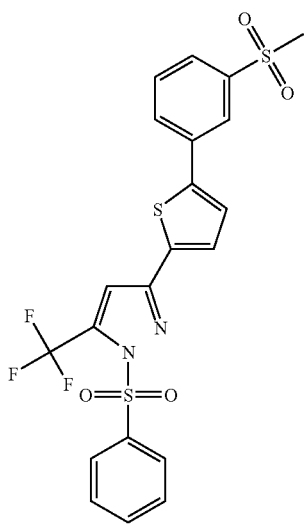 [SMILES: CS(=O)(=O)c1cccc(-c2ccc(C(=N)/C=C(\NS(=O)(=O)c3ccccc3)C(F)(F)F)s2)c1] | 3-{5-[3-(methylsulfonyl)phenyl]-2-thienyl}-1-(phenylsulfonyl)-5-(trifluoromethyl)-1H-pyrazole |

TABLE 1-continued

| 186 | 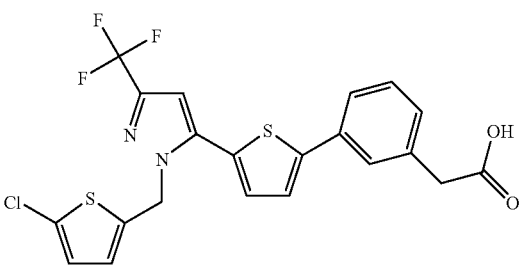 [SMILES: N=C(/C=C(\NCc1ccc(Cl)s1)c1ccc(-c2cccc(CC(=O)O)c2)s1)C(F)(F)F] | (3-{5-[1-[(5-chloro-2-thienyl)methyl]-3-(trifluoromethyl)-1H-pyrazol-5-yl]-2-thienyl}phenyl)acetic acid |
| 187 | 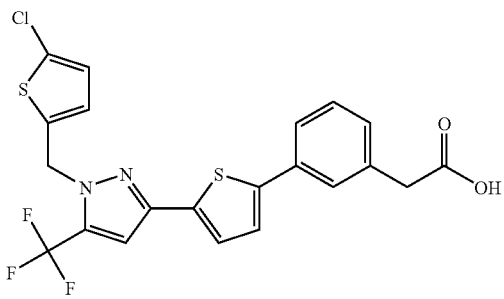 [SMILES: O=C(O)Cc1cccc(-c2ccc(-c3cc(C(F)(F)F)n(Cc4ccc(Cl)s4)n3)s2)c1] | (3-{5-[1-[(5-chloro-2-thienyl)methyl]-5-(trifluoromethyl)-1H-pyrazol-3-yl]-2-thienyl}phenyl)acetic acid |
| 188 | 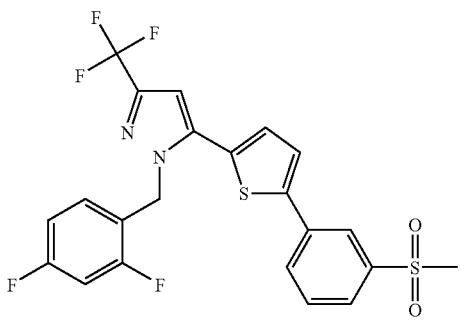 [SMILES: CS(=O)(=O)c1cccc(-c2ccc(/C(=C/C(=N)C(F)(F)F)NCc3ccc(F)cc3F)s2)c1] | 1-[(2,4-difluorophenyl)methyl]-5-{5-[3-(methylsulfonyl)phenyl]-2-thienyl}-3-(trifluoromethyl)-1H-pyrazole |
| 189 | 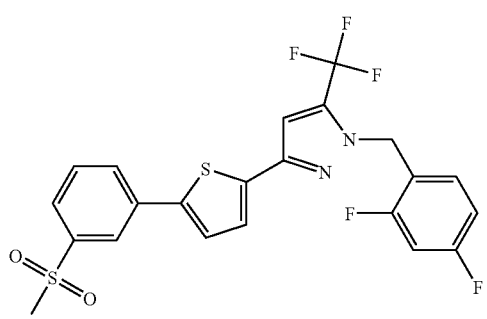 [SMILES: CS(=O)(=O)c1cccc(-c2ccc(C(=N)/C=C(\NCc3ccc(F)cc3F)C(F)(F)F)s2)c1] | 1-[(2,4-difluorophenyl)methyl]-3-{5-[3-(methylsulfonyl)phenyl]-2-thienyl}-5-(trifluoromethyl)-1H-pyrazole |
| 190 | 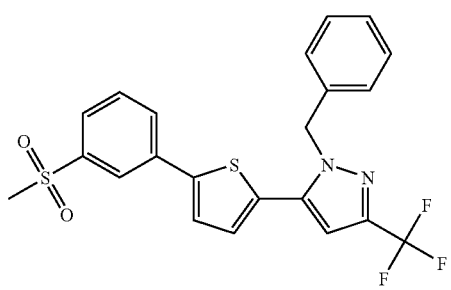 [SMILES: CS(=O)(=O)c1cccc(-c2ccc(-c3cc(C(F)(F)F)nn3Cc3ccccc3)s2)c1] | 5-{5-[3-(methylsulfonyl)phenyl]-2-thienyl}-1-(phenylmethyl)-3-(trifluoromethyl)-1H-pyrazole |

TABLE 1-continued

| | | |
|---|---|---|
| 191 | 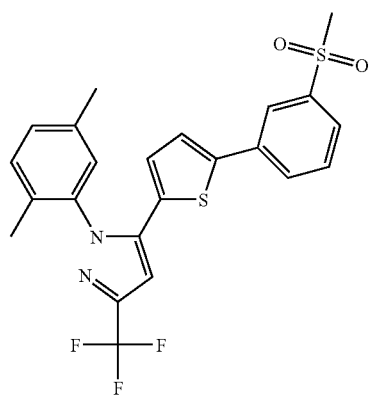 [SMILES: Cc1ccc(C)c(N/C(=C\C(=N)C(F)(F)F)c2ccc(-c3cccc(S(C)(=O)=O)c3)s2)c1] | 1-(2,5-dimethylphenyl)-5-{5-[3-(methylsulfonyl)phenyl]-2-thienyl}-3-(trifluoromethyl)-1H-pyrazole |
| 192 | 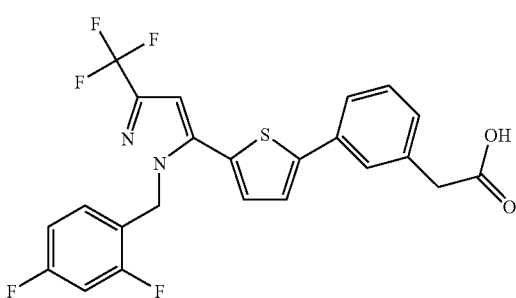 [SMILES: N=C(/C=C(\NCc1ccc(F)cc1F)c1ccc(-c2cccc(CC(=O)O)c2)s1)C(F)(F)F] | (3-{5-[1-[(2,4-difluorophenyl)methyl]-3-(trifluoromethyl)-1H-pyrazol-5-yl]-2-thienyl}phenyl)acetic acid |
| 193 | 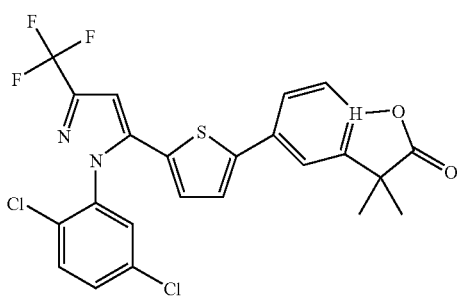 | 2-(3-{5-[1-(2,5-dichlorophenyl)-3-(trifluoromethyl)-1H-pyrazol-5-yl]-2-thienyl}phenyl)-2-methylpropanoic acid |
| 194 | 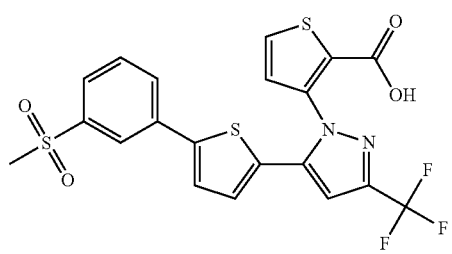 [SMILES: CS(=O)(=O)c1cccc(-c2ccc(-c3cc(C(F)(F)F)nn3-c3ccsc3C(=O)O)s2)c1] | 3-[5-{5-[3-(methylsulfonyl)phenyl]-2-thienyl}-3-(trifluoromethyl)-1H-pyrazol-1-yl]thiophene-2-carboxylic acid |
| 195 | 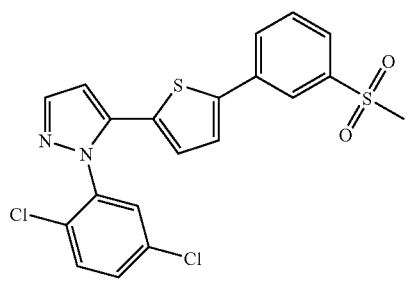 [SMILES: CS(=O)(=O)c1cccc(-c2ccc(-c3ccnn3-c3cc(Cl)ccc3Cl)s2)c1] | 1-(2,5-dichlorophenyl)-5-{5-[3-(methylsulfonyl)phenyl]-2-thienyl}-1H-pyrazole |

| | | |
|---|---|---|
| 196 | 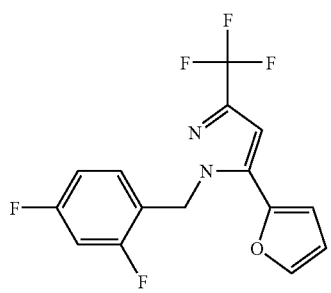 [SMILES: N=C(/C=C(\NCc1ccc(F)cc1F)c1ccco1)C(F)(F)F] | 1-[(2,4-difluorophenyl)methyl]-5-furan-2-yl-3-(trifluoromethyl)-1H-pyrazole |
| 197 | 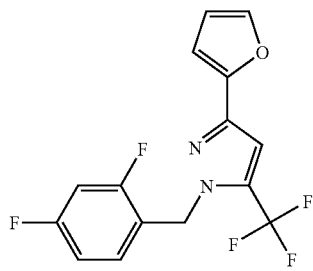 [SMILES: N=C(/C=C(\NCc1ccc(F)cc1F)C(F)(F)F)c1ccco1] | 1-[(2,4-difluorophenyl)methyl]-3-furan-2-yl-5-(trifluoromethyl)-1H-pyrazole |
| 198 | 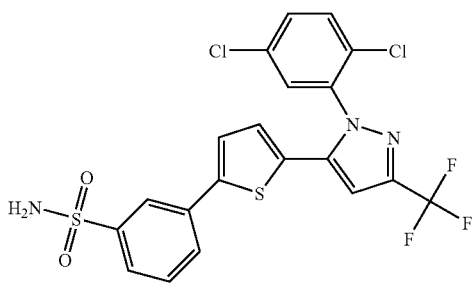 [SMILES: NS(=O)(=O)c1cccc(-c2ccc(-c3cc(C(F)(F)F)nn3-c3cc(Cl)ccc3Cl)s2)c1] | 3-{5-[1-(2,5-dichlorophenyl)-3-(trifluoromethyl)-1H-pyrazol-5-yl]-2-thienyl}benzenesulfonamide |
| 199 | 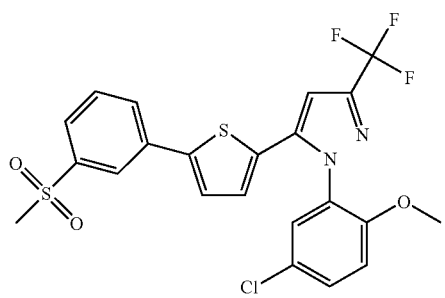 | 1-[5-chloro-2-(methyloxy)phenyl]-5-{5-[3-(methylsulfonyl)phenyl]-2-thienyl}-3-(trifluoromethyl)-1H-pyrazole |
| 200 | 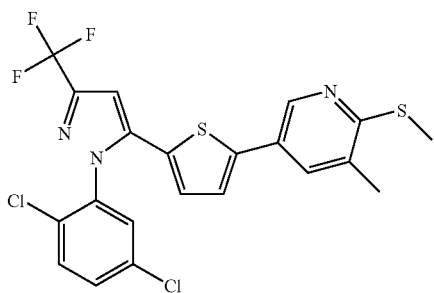 [SMILES: CSc1ncc(-c2ccc(/C(=C/C(=N)C(F)(F)F)Nc3cc(Cl)ccc3Cl)s2)cc1C] | 5-{5-[1-(2,5-dichlorophenyl)-3-(trifluoromethyl)-1H-pyrazol-5-yl]-2-thienyl}-3-methyl-2-(methylthio)pyridine |

TABLE 1-continued

| | | |
|---|---|---|
| 201 | 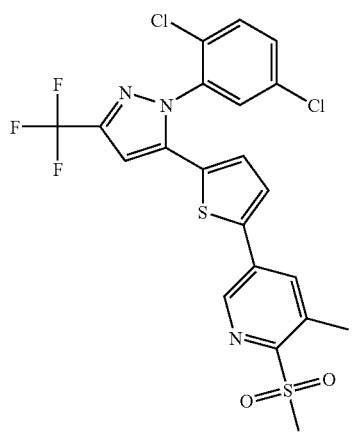 [SMILES: Cc1cc(-c2ccc(-c3cc(C(F)(F)F)nn3-c3cc(Cl)ccc3Cl)s2)cnc1S(C)(=O)=O] | 5-{5-[1-(2,5-dichlorophenyl)-3-(trifluoromethyl)-1H-pyrazol-5-yl]-2-thienyl}-3-methyl-2-(methylsulfonyl)pyridine |
| 202 | 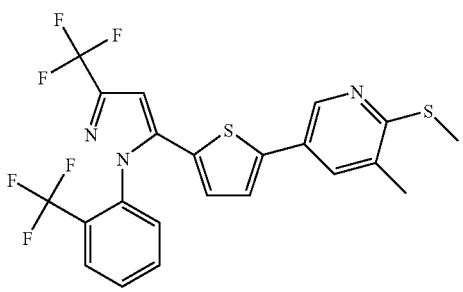 [SMILES: CSc1ncc(-c2ccc(/C(=C/C(=N)C(F)(F)F)Nc3ccccc3C(F)(F)F)s2)cc1C] | 3-methyl-2-(methylthio)-5-(5-{3-(trifluoromethyl)-1-[2-(trifluoromethyl)phenyl]-1H-pyrazol-5-yl}-2-thienyl)pyridine |
| 203 | 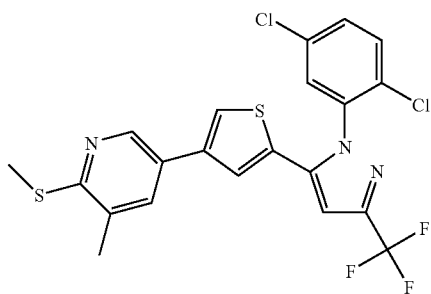 [SMILES: CSc1ncc(-c2csc(/C(=C/C(=N)C(F)(F)F)Nc3cc(Cl)ccc3Cl)c2)cc1C] | 5-{5-[1-(2,5-dichlorophenyl)-3-(trifluoromethyl)-1H-pyrazol-5-yl]-3-thienyl}-3-methyl-2-(methylthio)pyridine |
| 204 | 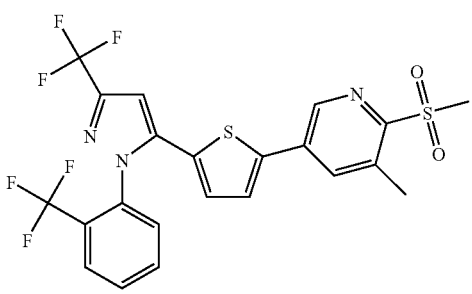 [SMILES: Cc1cc(-c2ccc(/C(=C/C(=N)C(F)(F)F)Nc3ccccc3C(F)(F)F)s2)cnc1S(C)(=O)=O] | 3-methyl-2-(methylsulfonyl)-5-(5-{3-(trifluoromethyl)-1-[2-(trifluoromethyl)phenyl]-1H-pyrazol-5-yl}-2-thienyl)pyridine |

TABLE 1-continued
| | | |
|---|---|---|
| 205 | 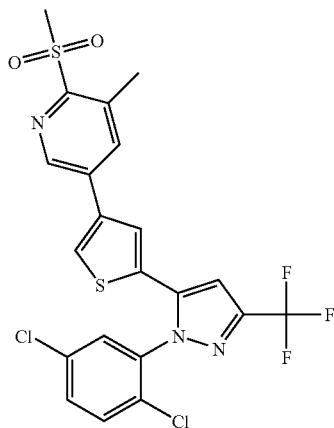 [SMILES: Cc1cc(-c2csc(-c3cc(C(F)(F)F)nn3-c3cc(Cl)ccc3Cl)c2)cnc1S(C)(=O)=O] | 5-{5-[1-(2,5-dichlorophenyl)-3-(trifluoromethyl)-1H-pyrazol-5-yl]-3-thienyl}-3-methyl-2-(methylsulfonyl)pyridine |
| 206 | 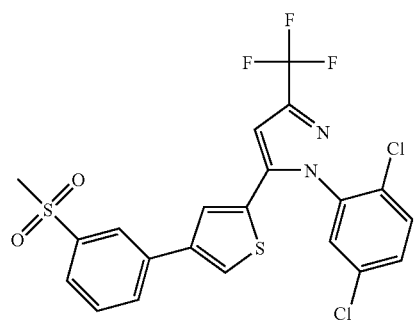 [SMILES: CS(=O)(=O)c1cccc(-c2csc(/C(=C/C(=N)C(F)(F)F)Nc3cc(Cl)ccc3Cl)c2)c1] | 1-(2,5-dichlorophenyl)-5-{4-[3-(methylsulfonyl)phenyl]-2-thienyl}-3-(trifluoromethyl)-1H-pyrazole |
| 207 | 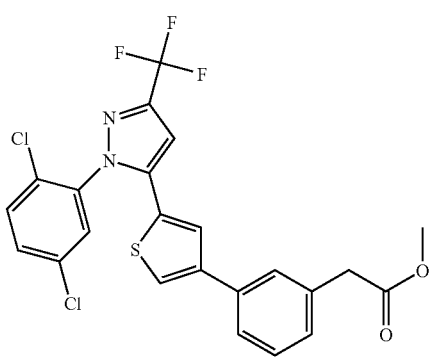 [SMILES: COC(=O)Cc1cccc(-c2csc(-c3cc(C(F)(F)F)nn3-c3cc(Cl)ccc3Cl)c2)c1] | methyl (3-{5-[1-(2,5-dichlorophenyl)-3-(trifluoromethyl)-1H-pyrazol-5-yl]-3-thienyl}phenyl)acetate |
| 208 | 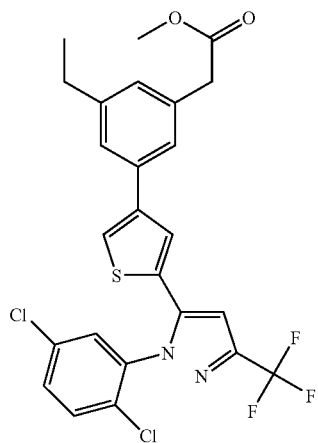 [SMILES: CCc1cc(CC(=O)OC)cc(-c2csc(/C(=C/C(=N)C(F)(F)F)Nc3cc(Cl)ccc3Cl)c2)c1] | methyl (3-{5-[1-(2,5-dichlorophenyl)-3-(trifluoromethyl)-1H-pyrazol-5-yl]-3-thienyl}-5-ethylphenyl)acetate |

| | | |
|---|---|---|
| 209 | 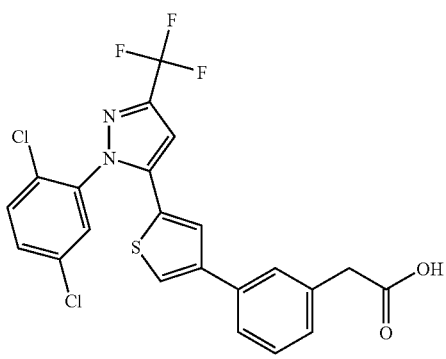 [SMILES: O=C(O)Cc1cccc(-c2csc(-c3cc(C(F)(F)F)nn3-c3cc(Cl)ccc3Cl)c2)c1] | (3-{5-[1-(2,5-dichlorophenyl)-3-(trifluoromethyl)-1H-pyrazol-5-yl]-3-thienyl}phenyl)acetic acid |
| 210 | 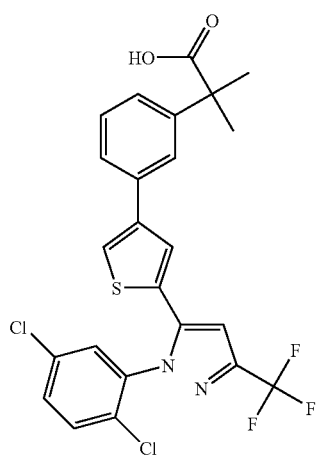 [SMILES: CC(C)(C(=O)O)c1cccc(-c2csc(/C(=C/C(=N)C(F)(F)F)Nc3cc(Cl)ccc3Cl)c2)c1] | 2-(3-{5-[1-(2,5-dichlorophenyl)-3-(trifluoromethyl)-1H-pyrazol-5-yl]-3-thienyl}phenyl)-2-methylpropanoic acid |
| 215 | 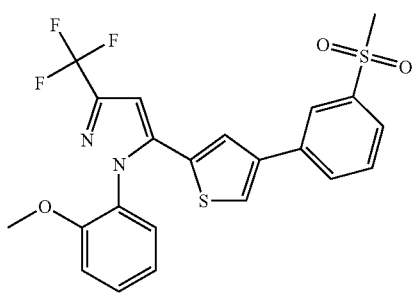 [SMILES: COc1ccccc1N/C(=C\C(=N)C(F)(F)F)c1cc(-c2cccc(S(C)(=O)=O)c2)cs1] | 1-[2-(methyloxy)phenyl]-5-{4-[3-(methylsulfonyl)phenyl]-2-thienyl}-3-(trifluoromethyl)-1H-pyrazole |
| 216 | 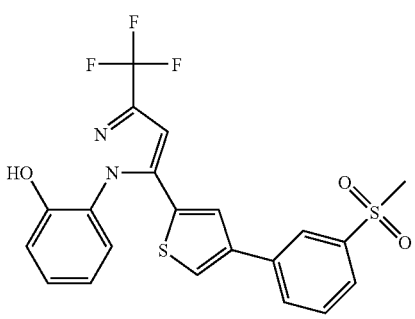 [SMILES: CS(=O)(=O)c1cccc(-c2csc(/C(=C/C(=N)C(F)(F)F)Nc3ccccc3O)c2)c1] | 2-[5-{4-[3-(methylsulfonyl)phenyl]-2-thienyl}-3-(trifluoromethyl)-1H-pyrazol-1-yl]phenol |

| | | |
|---|---|---|
| 218 | 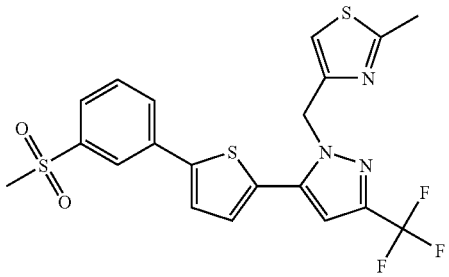 [SMILES: Cc1nc(Cn2nc(C(F)(F)F)cc2-c2ccc(-c3cccc(S(C)(=O)=O)c3)s2)cs1] | 2-methyl-4-{[5-{5-[3-(methylsulfonyl)phenyl]-2-thienyl}-3-(trifluoromethyl)-1H-pyrazol-1-yl]methyl}-1,3-thiazole |
| 219 | 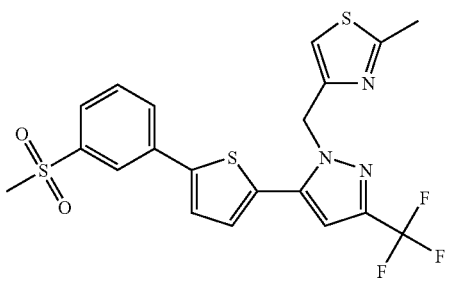 [SMILES: Cc1nc(Cn2nc(C(F)(F)F)cc2-c2ccc(-c3cccc(S(C)(=O)=O)c3)s2)cs1] | 2-methyl-4-{[5-{5-[3-(methylsulfonyl)phenyl]-2-thienyl}-3-(trifluoromethyl)-1H-pyrazol-1-yl]methyl}-1,3-thiazole |
| 221 | 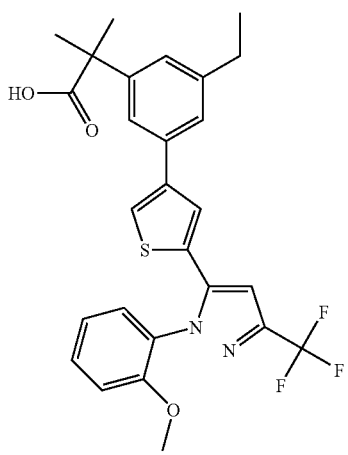 [SMILES: CCc1cc(-c2csc(/C(=C/C(=N)C(F)(F)F)Nc3ccccc3OC)c2)cc(C(C)(C)C(=O)O)c1] | 2-(3-ethyl-5-{5-[1-[2-(methyloxy)phenyl]-3-(trifluoromethyl)-1H-pyrazol-5-yl]-3-thienyl}phenyl)-2-methylpropanoic acid |
| 222 | 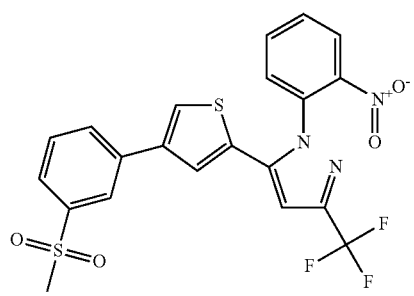 | 5-{4-[3-(methylsulfonyl)phenyl]-2-thienyl}-1-(2-nitrophenyl)-3-(trifluoromethyl)-1H-pyrazole |
| 223 | 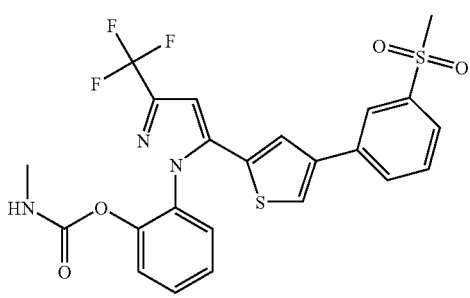 [SMILES: CNC(=O)Oc1ccccc1N/C(=C\C(=N)C(F)(F)F)c1cc(-c2cccc(S(C)(=O)=O)c2)cs1] | 2-[5-{4-[3-(methylsulfonyl)phenyl]-2-thienyl}-3-(trifluoromethyl)-1H-pyrazol-1-yl]phenyl methylcarbamate |

TABLE 1-continued

| 224 | 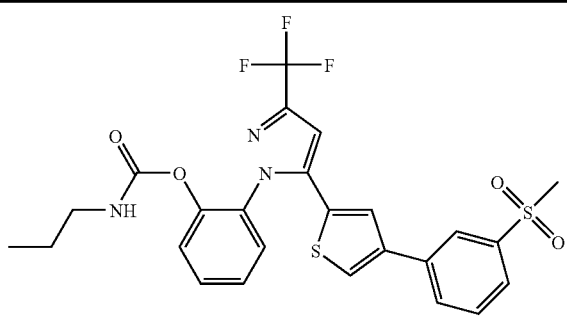 | 2-[5-{4-[3-(methylsulfonyl)phenyl]-2-thienyl}-3-(trifluoromethyl)-1H-pyrazol-1-yl]phenyl propylcarbamte |
| --- | --- | --- |
| 225 | 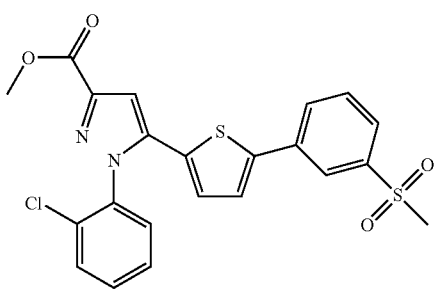 [SMILES: COC(=O)C(=N)/C=C(\Nc1ccccc1Cl)c1ccc(-c2cccc(S(C)(=O)=O)c2)s1] | methyl 1-(2-chlorophenyl)-5-{5-[3-(methylsulfonyl)phenyl]-2-thienyl}-1H-pyrazole-3-carboxylate |
| 226 | 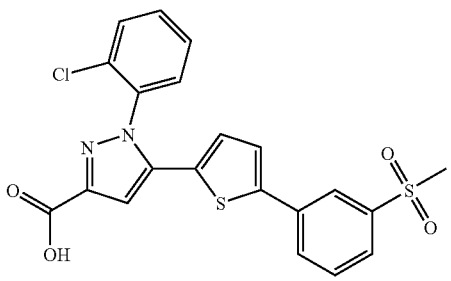 [SMILES: CS(=O)(=O)c1cccc(-c2ccc(-c3cc(C(=O)O)nn3-c3ccccc3Cl)s2)c1] | 1-(2-chlorophenyl)-5-{5-[3-(methylsulfonyl)phenyl]-2-thienyl}-1H-pyrazole-3-carboxylic acid |
| 227 | 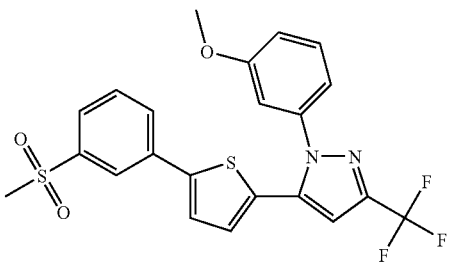 [SMILES: COc1cccc(-n2nc(C(F)(F)F)cc2-c2ccc(-c3cccc(S(C)(=O)=O)c3)s2)c1] | 1-[3-(methyloxy)phenyl]-5-{5-[3-(methylsulfonyl)phenyl]-2-thienyl}-3-(trifluoromethyl)-1H-pyrazole |
| 228 | 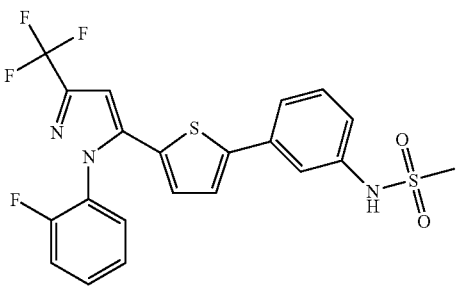 [SMILES: CS(=O)(=O)Nc1cccc(-c2ccc(/C(=C/C(=N)C(F)(F)F)Nc3ccccc3F)s2)c1] | N-(3-{5-[1-(2-fluorophenyl)-3-(trifluoromethyl)-1H-pyrazol-5-yl]-2-thienyl}phenyl)methanesulfonamide |

TABLE 1-continued

| | | |
|---|---|---|
| 229 | 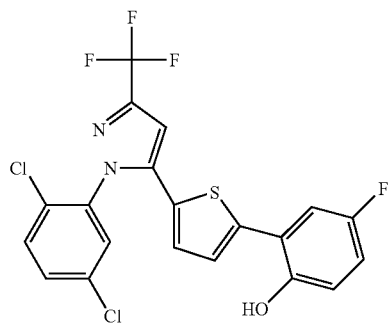 [SMILES: N=C(/C=C(\Nc1cc(Cl)ccc1Cl)c1ccc(-c2cc(F)ccc2O)s1)C(F)(F)F] | 2-{5-[1-(2,5-dichlorophenyl)-3-(trifluoromethyl)-1H-pyrazol-5-yl]-2-thienyl}-4-fluorophenyl |
| 230 | 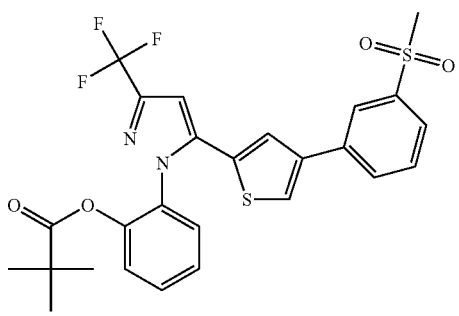 [SMILES: CC(C)(C)C(=O)Oc1ccccc1N/C(=C\C(=N)C(F)(F)F)c1cc(-c2cccc(S(C)(=O)=O)c2)cs1] | 2-[5-{4-[3-(methylsulfonyl)phenyl]-2-thienyl}-3-(trifluoromethyl)-1H-pyrazol-1-yl]phenyl 2,2-dimethylpropanoate |
| 231 | 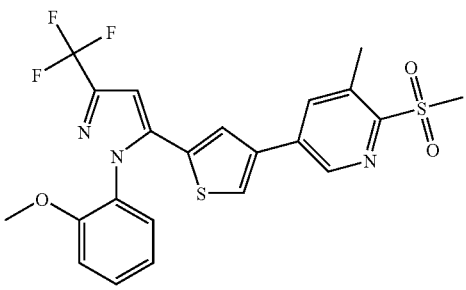 | 3-methyl-5-{5-[1-[2-(methyloxy)phenyl]-3-(trifluoromethyl)-1H-pyrazol-5-yl]-3-thienyl}-2-(methylsulfonyl)pyridine |
| 232 | 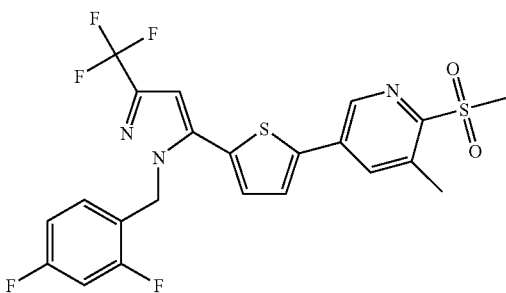 [SMILES: Cc1cc(-c2ccc(/C(=C/C(=N)C(F)(F)F)NCc3ccc(F)cc3F)s2)cnc1S(C)(=O)=O] | 5-{5-[1-[(2,4-difluorophenyl)methyl]-3-(trifluoromethyl)-1H-pyrazol-5-yl]-2-thienyl}-3-methyl-2-(methylsulfonyl)pyridine |
| 233 | 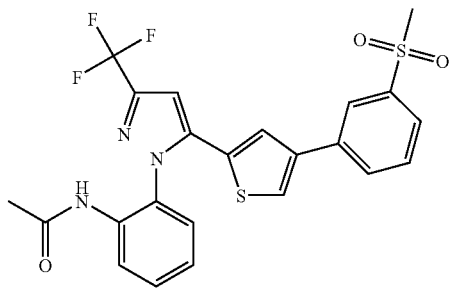 [SMILES: CC(=O)Nc1ccccc1N/C(=C\C(=N)C(F)(F)F)c1cc(-c2cccc(S(C)(=O)=O)c2)cs1] | N-{2-[5-{4-[3-(methylsulfonyl)phenyl]-2-thienyl}-3-(trifluoromethyl)-1H-pyrazol-1-yl]phenyl}acetamide |

| | | |
|---|---|---|
| 234 | 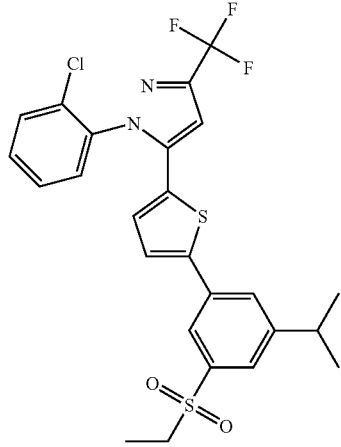 [SMILES: CCS(=O)(=O)c1cc(-c2ccc(/C(=C/C(=N)C(F)(F)F)Nc3ccccc3Cl)s2)cc(C(C)C)c1] | 1-(2-chlorophenyl)-5-{5-[3-(ethylsulfonyl)-5-(1-methylethyl)phenyl]-2-thienyl}-3-(trifluoromethyl)-1H-pyrazole |
| 235 | 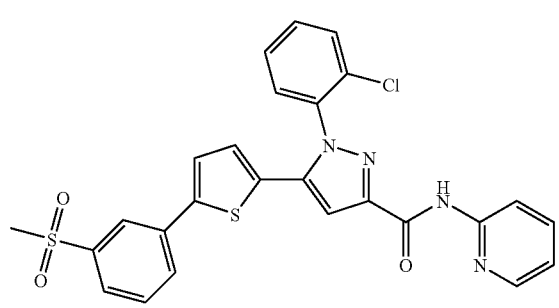 [SMILES: CS(=O)(=O)c1cccc(-c2ccc(-c3cc(C(=O)Nc4ccccn4)nn3-c3ccccc3Cl)s2)c1] | 1-(2-chlorophenyl)-5-{5-[3-(methylsulfonyl)phenyl]-2-thienyl}-N-pyridin-2-yl-1H-pyrazole-3-carboxamide |
| 236 | 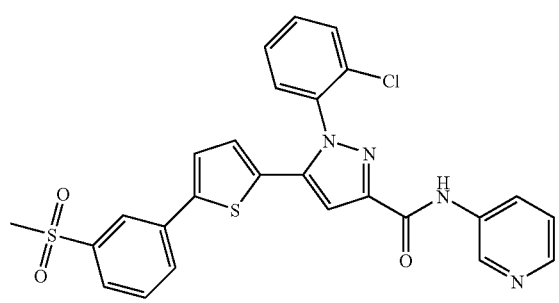 [SMILES: CS(=O)(=O)c1cccc(-c2ccc(-c3cc(C(=O)Nc4cccnc4)nn3-c3ccccc3Cl)s2)c1] | 1-(2-chlorophenyl)-5-{5-[3-(methylsulfonyl)phenyl]-2-thienyl}-N-pyridine-3-yl-1H-pyrazole-3-carboxamide |
| 237 | 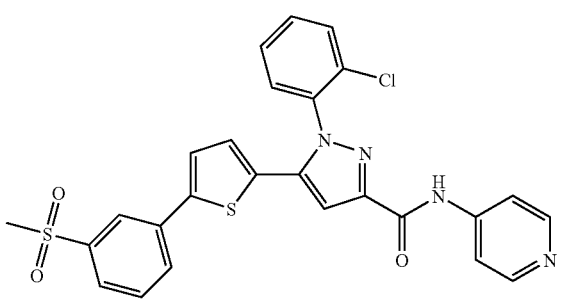 [SMILES: CS(=O)(=O)c1cccc(-c2ccc(-c3cc(C(=O)Nc4ccncc4)nn3-c3ccccc3Cl)s2)c1] | 1-(2-chlorophenyl)-5-{5-[3-(methylsulfonyl)phenyl]-2-thienyl}-N-pyridin-4-yl-1H-pyrazole-3-carboxamide |
| 238 | 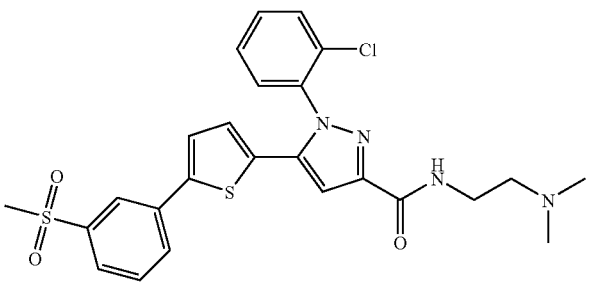 | 1-(2-chlorophenyl)-N-[2-(dimethylamino)ethyl]-5-{5-[3-(methylsulfonyl)phenyl]-2-thienyl}-1H-pyrazole-3-carboxamide |

TABLE 1-continued

| 239 | 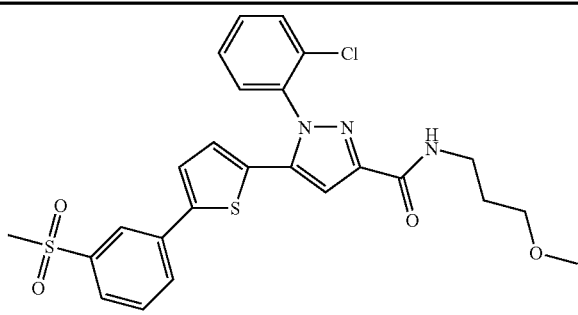 | 1-(2-chlorophenyl)-N-[3-(methyloxy)propyl]-5-{5-[3-(methylsulfonyl)phenyl]-2-thienyl}-1H-pyrazole-3-carboxamide |
| --- | --- | --- |
| 240 | 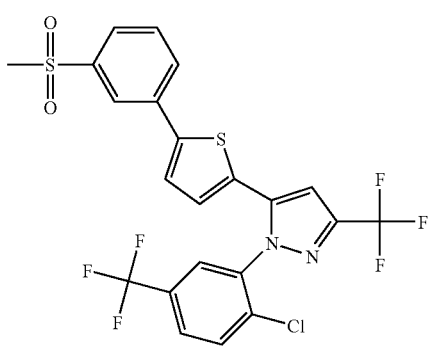 [SMILES: CS(=O)(=O)c1cccc(-c2ccc(-c3cc(C(F)(F)F)nn3-c3cc(C(F)(F)F)ccc3Cl)s2)c1] | 1-[2-chloro-5-(trifluoromethyl)phenyl]-5-{5-[3-(methylsulfonyl)phenyl]-2-thienyl}-3-(trifluoromethyl)-1H-pyrazole |
| 241 | 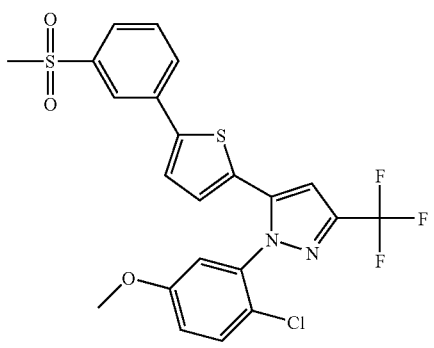 [SMILES: COc1ccc(Cl)c(-n2nc(C(F)(F)F)cc2-c2ccc(-c3cccc(S(C)(=O)=O)c3)s2)c1] | 1-[2-chloro-5-(methoxy)phenyl]-5-{5-[3-(methylsulfonyl)phenyl]-2-thienyl}-3-(trifluoromethyl)-1H-pyrazole |
| 242 | 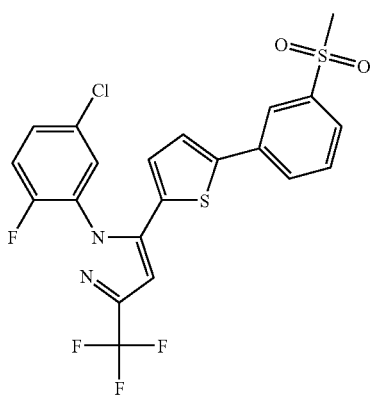 | 1-(5-chloro-2-fluorophenyl)-5-{5-[3-(methylsulfonyl)phenyl]-2-thienyl}-3-(trifluoromethyl)-1H-pyrazole |

| | | |
|---|---|---|
| 243 | 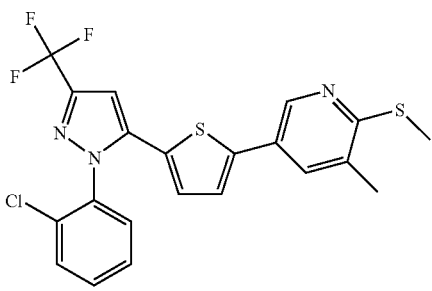 [SMILES: CSc1ncc(-c2ccc(-c3cc(C(F)(F)F)nn3-c3ccccc3Cl)s2)cc1C] | 5-{5-[1-(2-chlorophenyl)-3-(trifluoromethyl)-1H-pyrazol-5-yl]-2-thienyl}-3-methyl-2-(methylthio)pyridine |
| 244 | 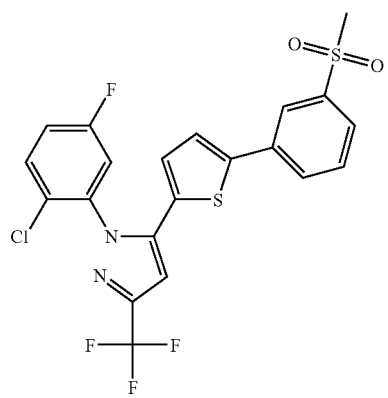 [SMILES: CS(=O)(=O)c1cccc(-c2ccc(/C(=C/C(=N)C(F)(F)F)Nc3cc(F)ccc3Cl)s2)c1] | 1-(2-chloro-5-fluorophenyl)-5-{5-[3-(methylsulfonyl)phenyl]-2-thienyl}-3-(trifluoromethyl)-1H-pyrazole |
| 245 | 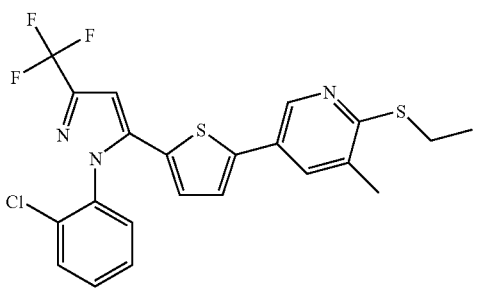 [SMILES: CCSc1ncc(-c2ccc(/C(=C/C(=N)C(F)(F)F)Nc3ccccc3Cl)s2)cc1C] | 5-{5-[1-(2-chlorophenyl)-3-(trifluoromethyl)-1H-pyrazol-5-yl]-2-thienyl}-2-(ethylthio)-3-methylpyridine |
| 246 | 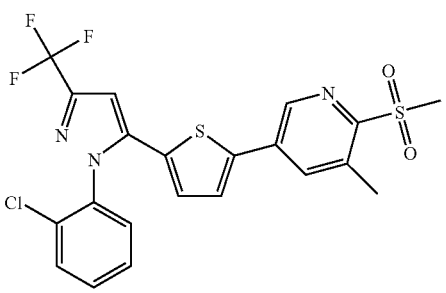 [SMILES: Cc1cc(-c2ccc(/C(=C/C(=N)C(F)(F)F)Nc3ccccc3Cl)s2)cnc1S(C)(=O)=O] | 5-{5-[1-(2-chlorophenyl)-3-(trifluoromethyl)-1H-pyrazol-5-yl]-2-thienyl}-3-methyl-2-(methylsulfonyl)pyridine |
| 247 | 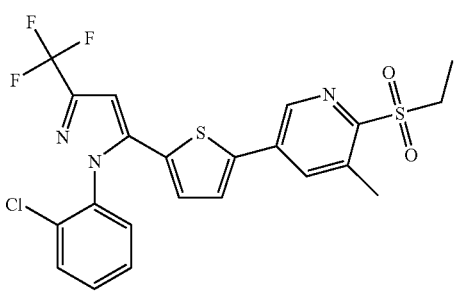 [SMILES: CCS(=O)(=O)c1ncc(-c2ccc(/C(=C/C(=N)C(F)(F)F)Nc3ccccc3Cl)s2)cc1C] | 5-{5-[1-(2-chlorophenyl)-3-(trifluoromethyl)-1H-pyrazol-5-yl]-2-thienyl}-2-(ethylsulfonyl)-3-methylpyridine |

TABLE 1-continued

| 248 | 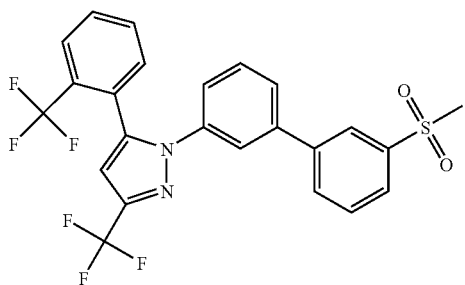 [SMILES: CS(=O)(=O)c1cccc(-c2cccc(-n3nc(C(F)(F)F)cc3-c3ccccc3C(F)(F)F)c2)c1] | 1-[3'-(methylsulfonyl)phenyl-3-yl]-3-(trifluoromethyl)-5-[2-(trifluoromethyl)phenyl]-1H-pyrazole |
| 249 | 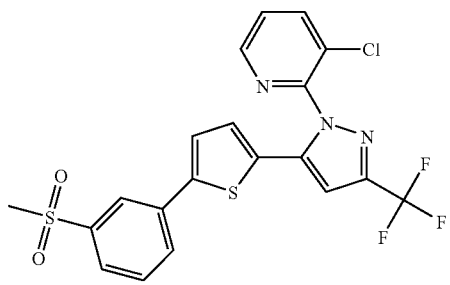 [SMILES: CS(=O)(=O)c1cccc(-c2ccc(-c3cc(C(F)(F)F)nn3-c3ncccc3Cl)s2)c1] | 3-chloro-2-[5-{5-[3-(methylsulfonyl)phenyl]-2-thienyl}-3-(trifluoromethyl)-1H-pyrazol-1-yl]pyridine |
| 251 | 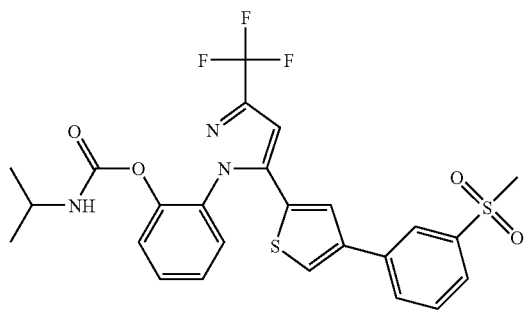 [SMILES: CC(C)NC(=O)Oc1ccccc1N/C(=C\C(=N)C(F)(F)F)c1cc(-c2cccc(S(C)(=O)=O)c2)cs1] | 2-[5-{4-[3-(methylsulfonyl)phenyl]-2-thienyl}-3-(trifluoromethyl)-1H-pyrazol-1-yl]phenyl (1-methylethyl)carbamate |
| 252 | 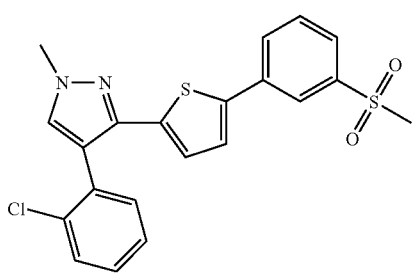 [SMILES: Cn1cc(-c2ccccc2Cl)c(-c2ccc(-c3cccc(S(C)(=O)=O)c3)s2)n1] | 4-(2-chlorophenyl)-1-methyl-{5-[3-(methylsulfonyl)phenyl]-2-thienyl}-1H-pyrazole |
| 253 | 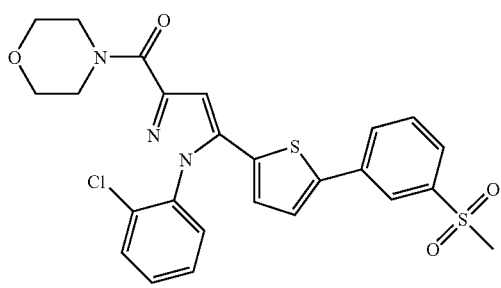 [SMILES: CS(=O)(=O)c1cccc(-c2ccc(/C(=C/C(=N)C(=O)N3CCOCC3)Nc3ccccc3Cl)s2)c1] | 4-[(1-(2-chlorophenyl)-5-{5-[3-(methylsulfonyl)phenyl]-2-thienyl}-1H-pyrazol-3-yl)carbonyl]morpholine |

TABLE 1-continued
| 254 | 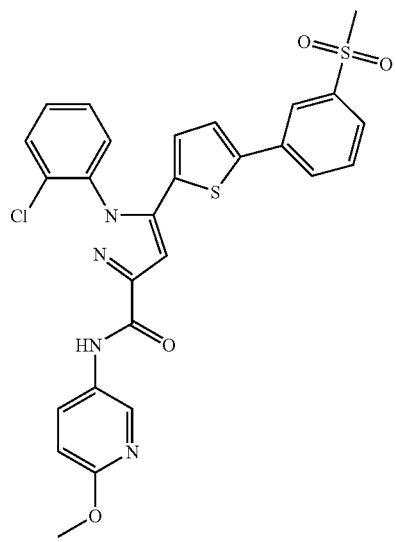 [SMILES: COc1ccc(NC(=O)C(=N)/C=C(\Nc2ccccc2Cl)c2ccc(-c3cccc(S(C)(=O)=O)c3)s2)cn1] | 1-(2-chlorophenyl)-N-[6-(methyloxy)pyridin-3-yl]-5-{5-[3-(methylsulfonyl)phenyl]-2-thienyl}-1H-pyrazole-3-carboxamide |
| 255 | 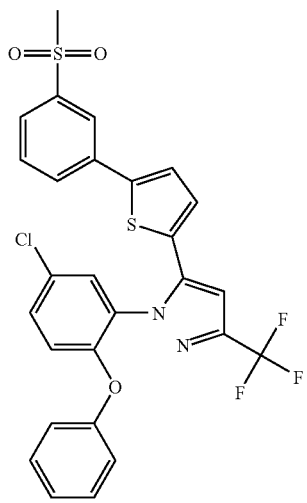 [SMILES: CS(=O)(=O)c1cccc(-c2ccc(/C(=C/C(=N)C(F)(F)F)Nc3cc(Cl)ccc3Oc3ccccc3)s2)c1] | 1-[5-chloro-2-(phenyloxy)phenyl]-5-{5-[3-(methylsulfonyl)phenyl]-2-thienyl}-3-(trifluoromethyl)-1H-pyrazole |
| 256 | 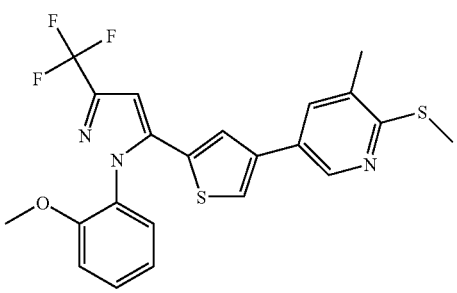 | 3-methyl-5-{5-[1-[2-(methyloxy)phenyl]-3-(trifluoromethyl)-1H-pyrazol-5-yl]-3-thienyl}-2-(methylthio)pyridine |
| 257 | 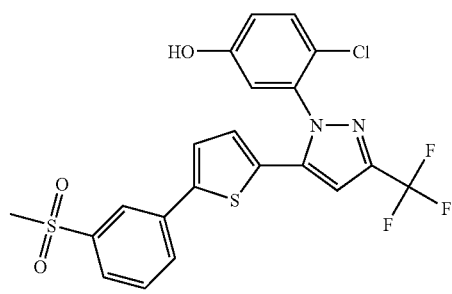 [SMILES: CS(=O)(=O)c1cccc(-c2ccc(-c3cc(C(F)(F)F)nn3-c3cc(O)ccc3Cl)s2)c1] | 4-chloro-3-[5-{5-[3-(methylsulfonyl)phenyl]-2-thienyl}-3-(trifluoromethyl)-1H-pyrazol-1-yl]phenol |

| | | |
|---|---|---|
| 258 | 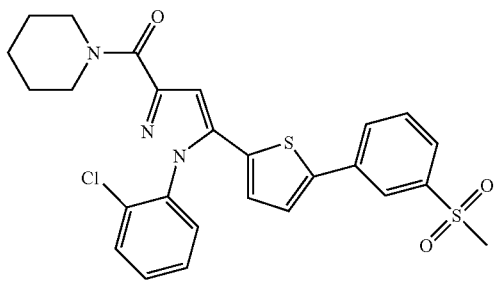 [SMILES: CS(=O)(=O)c1cccc(-c2ccc(/C(=C/C(=N)C(=O)N3CCCCC3)Nc3ccccc3Cl)s2)c1] | 1-[(1-(2-chlorophenyl)-5-{5-[3-(methylsulfonyl)phenyl]-2-thienyl}-1H-pyrazol-3-yl)carbonyl]piperidine |
| 261 | 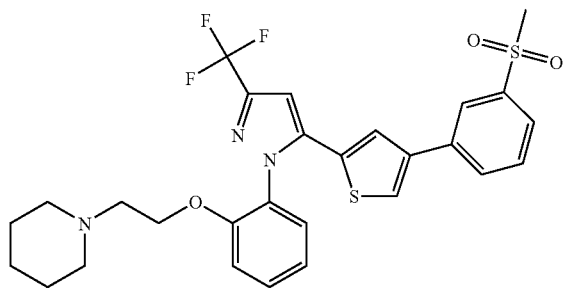 [SMILES: CS(=O)(=O)c1cccc(-c2csc(/C(=C/C(=N)C(F)(F)F)Nc3ccccc3OCCN3CCCCC3)c2)c1] | 1-[2-({2-[5-{4-[3-(methylsulfonyl)phenyl]-2-thienyl}-3-(trifluoromethyl)-1H-pyrazol-1-yl]phenyl}oxy)ethyl]piperidine |
| 262 | 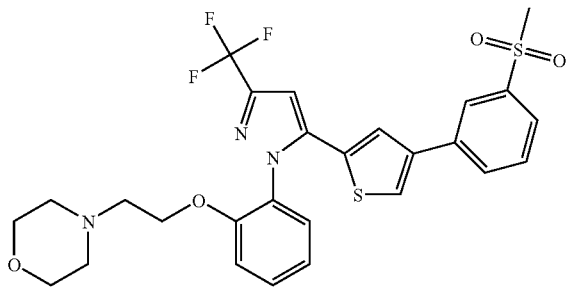 [SMILES: CS(=O)(=O)c1cccc(-c2csc(/C(=C/C(=N)C(F)(F)F)Nc3ccccc3OCCN3CCOCC3)c2)c1] | 4-[2-({2-[5-{4-[3-(methylsulfonyl)phenyl]-2-thienyl}-3-(trifluoromethyl)-1H-pyrazol-1-yl]phenyl}oxy)ethyl]morpholine |
| 263 | 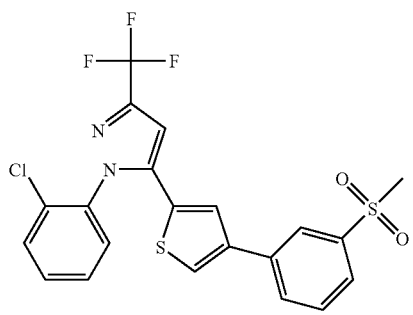 [SMILES: CS(=O)(=O)c1cccc(-c2csc(/C(=C/C(=N)C(F)(F)F)Nc3ccccc3Cl)c2)c1] | 1-(2-chlorophenyl)-5-{4-[3-(methylsulfonyl)phenyl]-2-thienyl}-3-(trifluoromethyl)-1H-pyrazole |
| 265 | 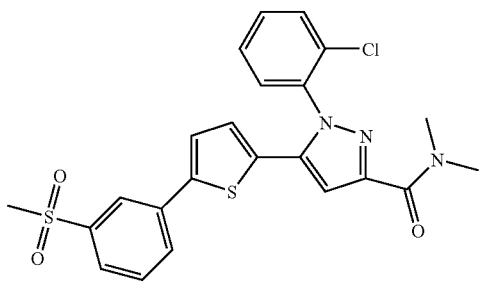 | 1-(2-chlorophenyl)-N,N-dimethyl-5-{5-[3-(methylsulfonyl)phenyl]-2-thienyl}-1H-pyrazole-3-carboxamide |

TABLE 1-continued

266 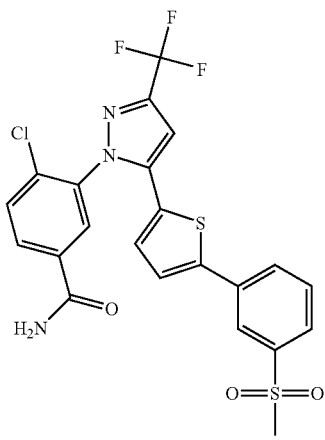 [SMILES: CS(=O)(=O)c1cccc(-c2ccc(-c3cc(C(F)(F)F)nn3-c3cc(C(N)=O)ccc3Cl)s2)c1] 4-chloro-3-[5-{5-[3-(methylsulfonyl)phenyl]-2-thienyl}-3-(trifluoromethyl)-1H-pyrazol-1-yl]benzamide 272 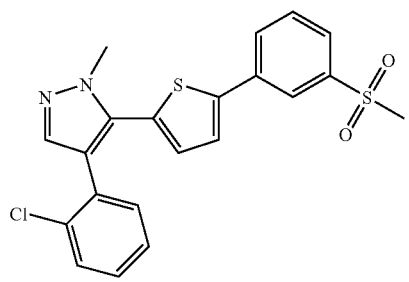 [SMILES: Cn1ncc(-c2ccccc2Cl)c1-c1ccc(-c2cccc(S(C)(=O)=O)c2)s1] 4-(2-chlorophenyl)-1-methyl-5-{5-[3-(methylsulfonyl)phenyl]-2-thienyl}-1H-pyrazole 273 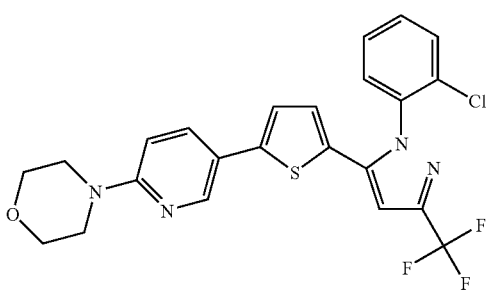 [SMILES: N=C(/C=C(\Nc1ccccc1Cl)c1ccc(-c2ccc(N3CCOCC3)nc2)s1)C(F)(F)F] 4-(5-{5-[1-(2-chlorophenyl)-3-(trifluoromethyl)-1H-pyrazol-5-yl]-2-thienyl}pyridin-2-yl)morpholine 274 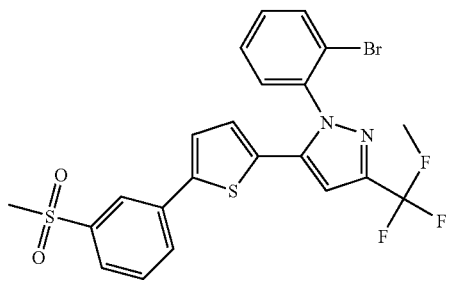 1-(2-bromophenyl)-5-{5-[3-(methylsulfonyl)phenyl]-2-thienyl}-3-(trifluoromethyl)-1H-pyrazole 275 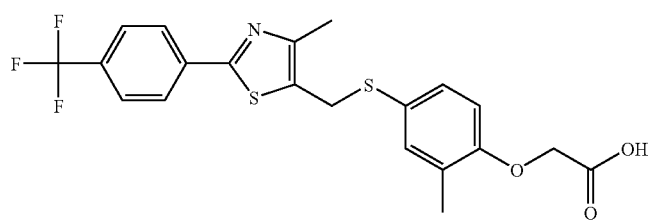 [SMILES: Cc1cc(SCc2sc(-c3ccc(C(F)(F)F)cc3)nc2C)ccc1OCC(=O)O] ({2-methyl-4-[({4-methyl-2-[4-(trifluoromethyl)phenyl]-1,3-thiazol-5-yl}methyl)thio]phenyl}oxy)acetic acid TABLE 1-continued

| 276 | 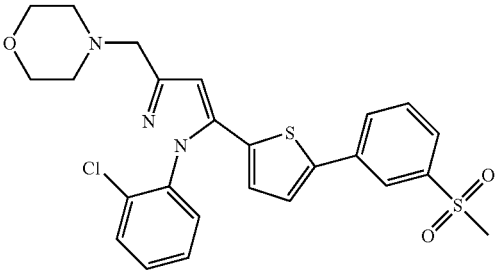 [SMILES: CS(=O)(=O)c1cccc(-c2ccc(/C(=C/C(=N)CN3CCOCC3)Nc3ccccc3Cl)s2)c1] | 4-[(1-(2-chlorophenyl)-5-{5-[3-(methylsulfonyl)phenyl]-2-thienyl}-1H-pyrazol-3-yl)methyl]morpholine |
| 277 | 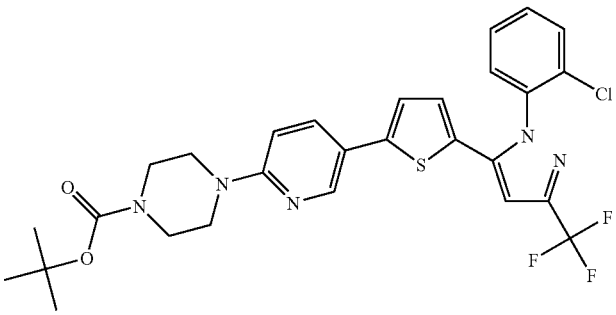 [SMILES: CC(C)(C)OC(=O)N1CCN(c2ccc(-c3ccc(/C(=C/C(=N)C(F)(F)F)Nc4ccccc4Cl)s3)cn2)CC1] | 1,1-dimethylethyl-4-(5-{5-[1-(2-chlorophenyl)-3-(trifluoromethyl)-1H-pyrazol-5-yl]-2-thienyl}pyridin-2-yl)piperazine-1-carboxylate |
| 279 | 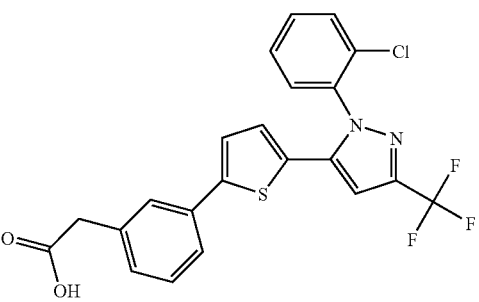 [SMILES: O=C(O)Cc1cccc(-c2ccc(-c3cc(C(F)(F)F)nn3-c3ccccc3Cl)s2)c1] | (3-{5-[1-(2-chlorophenyl)-3-(trifluoromethyl)-1H-pyrazol-5-yl]-2-thienyl}phenyl)acetic acid |
| 280 | 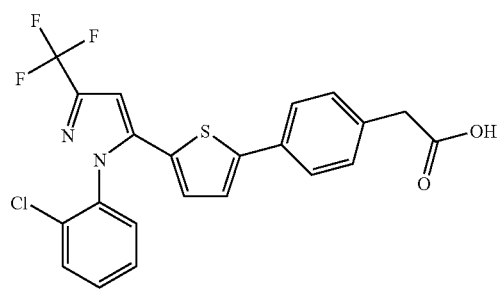 [SMILES: N=C(/C=C(\Nc1ccccc1Cl)c1ccc(-c2ccc(CC(=O)O)cc2)s1)C(F)(F)F] | (4-{5-[1-(2-chlorophenyl)-3-(trifluoromethyl)-1H-pyrazol-5-yl]-2-thienyl}phenyl)acetic acid |
| 281 | 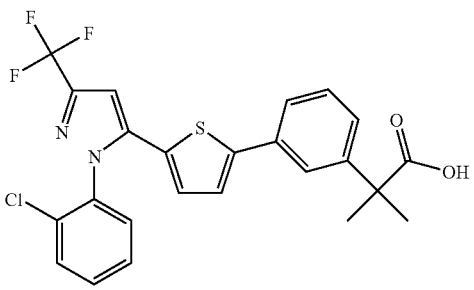 [SMILES: CC(C)(C(=O)O)c1cccc(-c2ccc(/C(=C/C(=N)C(F)(F)F)Nc3ccccc3Cl)s2)c1] | 2-(3-{5-[1-(2-chlorophenyl)-3-(trifluoromethyl)-1H-pyrazol-5-yl]-2-thienyl}phenyl)-2-methylpropanoic acid |

TABLE 1-continued

| | | |
|---|---|---|
| 282 | 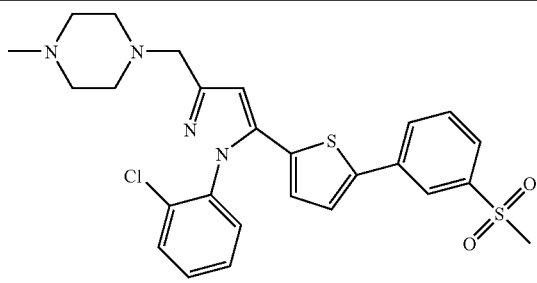 | 1-[(1-(2-chlorophenyl)-5-{5-[3-(methylsulfonyl)phenyl]-2-thienyl}-1H-pyrazol-3-yl)methyl]-4-methylpiperazine |
| 285 | 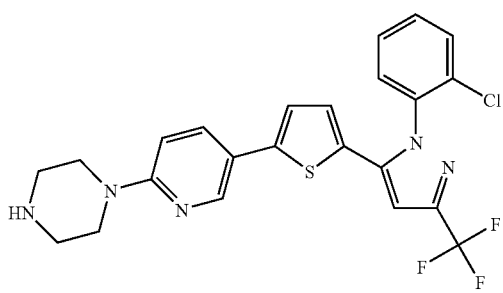 [SMILES: N=C(/C=C(\Nc1ccccc1Cl)c1ccc(-c2ccc(N3CCNCC3)nc2)s1)C(F)(F)F] | 1-(5-{5-[1-(2-chlorophenyl)-3-(trifluoromethyl)-1H-pyrazol-5-yl]-2-thienyl}pyridin-2-yl)piperazine |
| 286 | 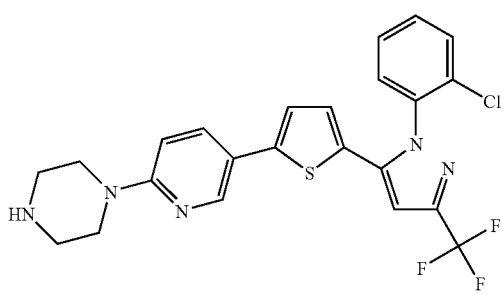 [SMILES: N=C(/C=C(\Nc1ccccc1Cl)c1ccc(-c2ccc(N3CCNCC3)nc2)s1)C(F)(F)F] | 1-(5-{5-[1-(2-chlorophenyl)-3-(trifluoromethyl)-1H-pyrazol-5-yl]-2-thienyl}pyridin-2-yl)piperazine |
| 287 | 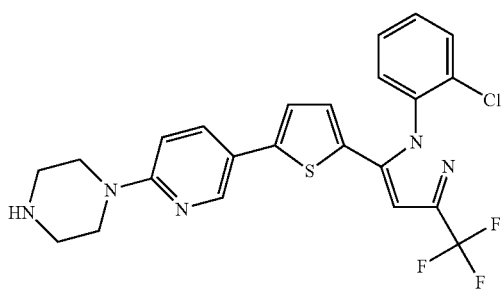 [SMILES: N=C(/C=C(\Nc1ccccc1Cl)c1ccc(-c2ccc(N3CCNCC3)nc2)s1)C(F)(F)F] | 1-(5-{5-[1-(2-chlorophenyl)-2-(trifluoromethyl)-1H-pyrazol-5-yl]-2-thienyl}pyridin-2-yl)piperazine |
| 288 | 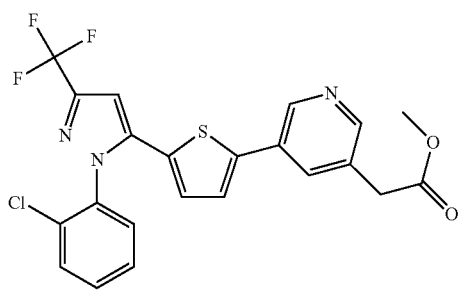 [SMILES: COC(=O)Cc1cncc(-c2ccc(/C(=C/C(=N)C(F)(F)F)Nc3ccccc3Cl)s2)c1] | methyl (5-{5-[1-(2-chlorophenyl)-3-(trifluoromethyl)-1H-pyrazol-5-yl]-2-thienyl}pyridin-3-yl)acetate |

| | | |
|---|---|---|
| 289 | 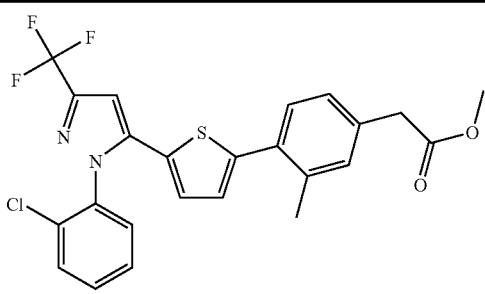 | methyl (4-{5-[1-(2-chlorophenyl)-3-(trifluoromethyl)-1H-pyrazol-5-yl]-2-thienyl}-3-methylphenyl)acetate |
| 290 | 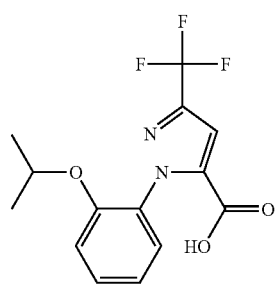 [SMILES: CC(C)Oc1ccccc1N/C(=C\C(=N)C(F)(F)F)C(=O)O] | 1-{2-[(1-methylethyl)oxy]phenyl}-3-(trifluoromethyl)-1H-pyrazole-5-carboxylic acid |
| 291 | 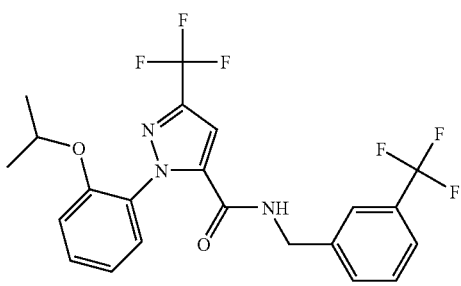 [SMILES: CC(C)Oc1ccccc1-n1nc(C(F)(F)F)cc1C(=O)NCc1cccc(C(F)(F)F)c1] | 1-{2-[(1-methylethyl)oxy]phenyl}-3-(trifluoromethyl)-N-{[3-(trifluoromethyl)phenyl]methyl}-1H-pyrazole-5-carboxamide |
| 292 | 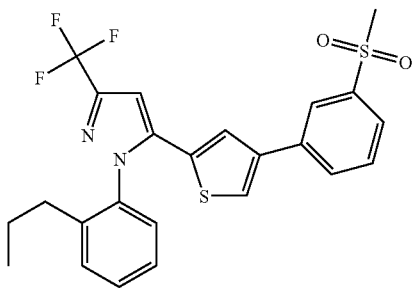 | 5-{4-[3-(methylsulfonyl)phenyl]-2-thienyl}-1-(2-propylphenyl)-3-(trifluoromethyl)-1H-pyrazole |
| 293 | 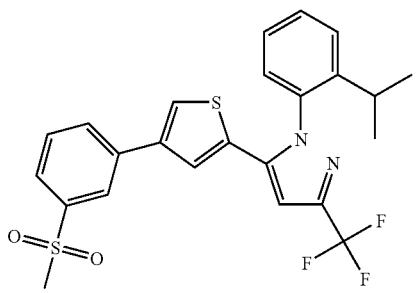 [SMILES: CC(C)c1ccccc1N/C(=C\C(=N)C(F)(F)F)c1cc(-c2cccc(S(C)(=O)=O)c2)cs1] | 1-[2-(1-methylethyl)phenyl]-5-{4-[3-(methylsulfonyl)phenyl]-2-thienyl}-3-(trifluoromethyl)-1H-pyrazole |

TABLE 1-continued

| | | |
|---|---|---|
| 294 | 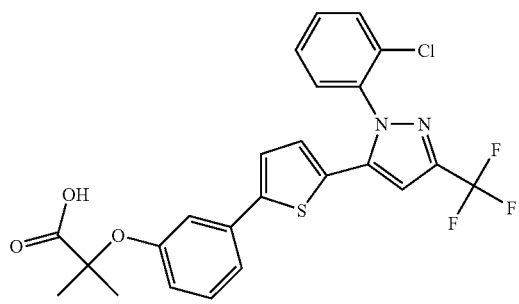 [SMILES: CC(C)(Oc1cccc(-c2ccc(-c3cc(C(F)(F)F)nn3-c3ccccc3Cl)s2)c1)C(=O)O] | 2-[(3-{5-[1-(2-chlorophenyl)-3-(trifluoromethyl)-1H-pyrazol-5-yl]-2-thienyl}phenyl)oxy]-2-methylpropanoic acid |
| 295 | 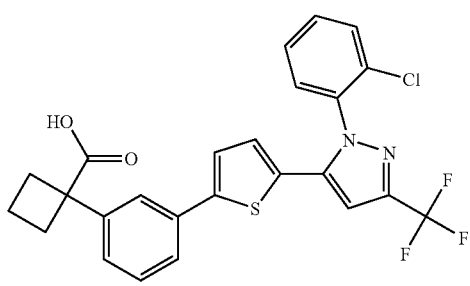 [SMILES: O=C(O)C1(c2cccc(-c3ccc(-c4cc(C(F)(F)F)nn4-c4ccccc4Cl)s3)c2)CCC1] | 1-(3-{5-[1-(2-chlorophenyl)-3-(trifluoromethyl)-1H-pyrazol-5-yl]-2-thienyl}phenyl)cyclobutanecarboxylic acid |
| 296 | 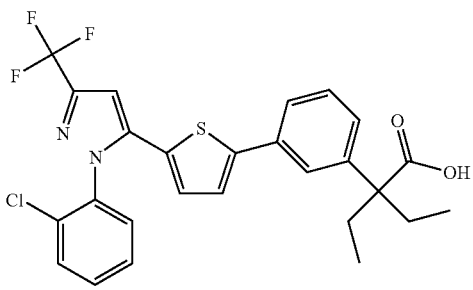 [SMILES: CCC(CC)(C(=O)O)c1cccc(-c2ccc(/C(=C/C(=N)C(F)(F)F)Nc3ccccc3Cl)s2)c1] | 2-(3-{5-[1-(2-chlorophenyl)-3-(trifluoromethyl)-1H-pyrazol-5-yl]-2-thienyl}phenyl)-2-ethylbutanoic acid |
| 297 | 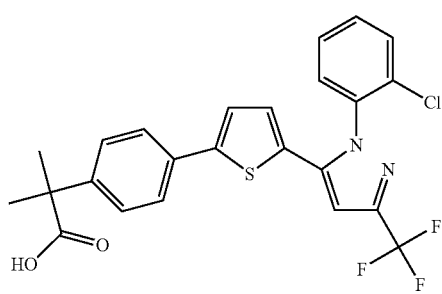 [SMILES: CC(C)(C(=O)O)c1ccc(-c2ccc(/C(=C/C(=N)C(F)(F)F)Nc3ccccc3Cl)s2)cc1] | 2-(4-{5-[1-(2-chlorophenyl)-3-(trifluoromethyl)-1H-pyrazol-5-yl]-2-thienyl}phenyl)-2-methylpropanoic acid |
| 298 | 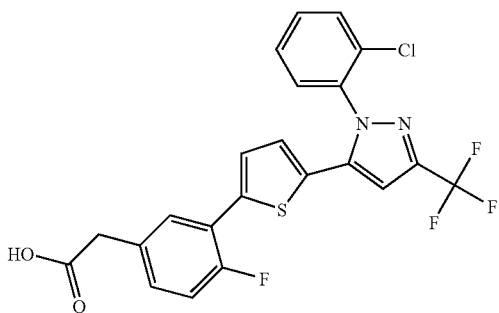 [SMILES: O=C(O)Cc1ccc(F)c(-c2ccc(-c3cc(C(F)(F)F)nn3-c3ccccc3Cl)s2)c1] | (3-{5-[1-(2-chlorophenyl)-3-(trifluoromethyl)-1H-pyrazol-5-yl]-2-thienyl}-4-fluorophenyl)acetic acid |

TABLE 1-continued

| | | |
|---|---|---|
| 300 | | methyl (3-{5-[1-(2-chlorophenyl)-3-(trifluoromethyl)-1H-pyrazol-5-yl]-2-thienyl}-4-fluorophenyl)acetate |
| 301 | | (4-{5-[1-(2-chlorophenyl)-3-(trifluoromethyl)-1H-pyrazol-5-yl]-2-thienyl}-3-methylphenyl)acetic acid |
| 302 | | 1-[3-(ethyloxy)phenyl]-5-{5-[3-(methylsulfonyl)phenyl]-2-thienyl}-3-(trifluoromethyl)-1H-pyrazole |
| 303 | | 4-{5-[1-(2-chlorophenyl)-3-(trifluoromethyl)-1H-pyrazol-5-yl]-2-thienyl}benzenesulfonamide |
| 304 | | 3-{5-[1-(2-chlorophenyl)-3-(trifluoromethyl)-1H-pyrazol-5-yl]-2-thienyl}benzenesulfonamide |

TABLE 1-continued
| 305 | 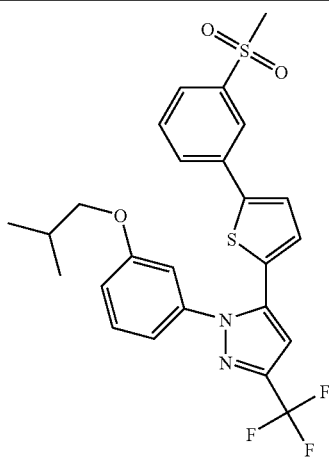 | 1-{3-[(2-methylpropyl)oxy]phenyl}-5-{5-[3-(methylsulfonyl)phenyl]-2-thienyl}-3-(trifluoromethyl)-1H-pyrazaole |
| 306 | 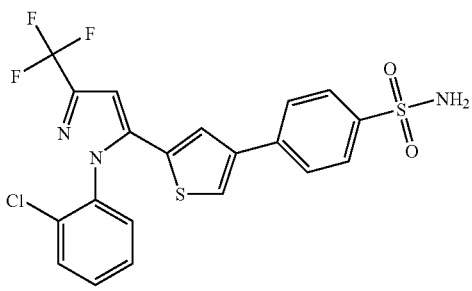 [SMILES: N=C(/C=C(\Nc1ccccc1Cl)c1cc(-c2ccc(S(N)(=O)=O)cc2)cs1)C(F)(F)F] | 4-{5-[1-(2-chlorophenyl)-3-(trifluoromethyl)-1H-pyrazol-5-yl]-3-thienyl}benzenesulfonamide |
| 307 | 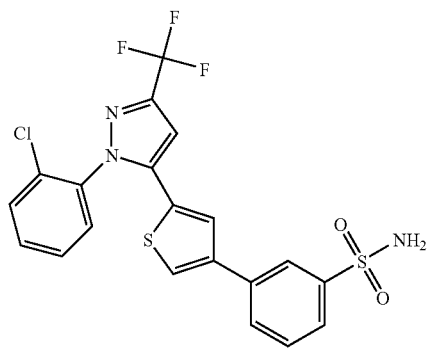 [SMILES: NS(=O)(=O)c1cccc(-c2csc(-c3cc(C(F)(F)F)nn3-c3ccccc3Cl)c2)c1] | 3-{5-[1-(2-chlorophenyl)-3-(trifluoromethyl)-1H-pyrazol-5-yl]-3-thienyl}benzenesulfonamide |
| 308 | 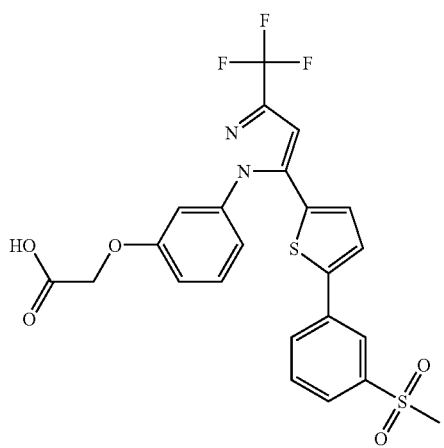 [SMILES: CS(=O)(=O)c1cccc(-c2ccc(/C(=C/C(=N)C(F)(F)F)Nc3cccc(OCC(=O)O)c3)s2)c1] | ({3-[5-{5-[3-(methylsulfonyl)phenyl]-2-thienyl}-3-(trifluoromethyl)-1H-pyrazol-1-yl]phenyl}oxy)acetic acid |

| | | |
|---|---|---|
| 309 | 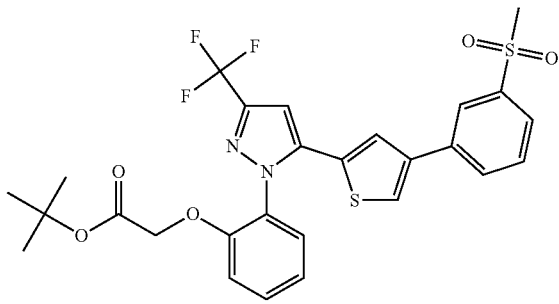 [SMILES: CC(C)(C)OC(=O)COc1ccccc1-n1nc(C(F)(F)F)cc1-c1cc(-c2cccc(S(C)(=O)=O)c2)cs1] | 1,1-dimethylethyl ({2-[5-{4-[3-(methylsulfonyl)phenyl]-2-thienyl}-3-(trifluoromethyl)-1H-pyrazol-1-yl]phenyl}oxy)acetate |
| 310 | 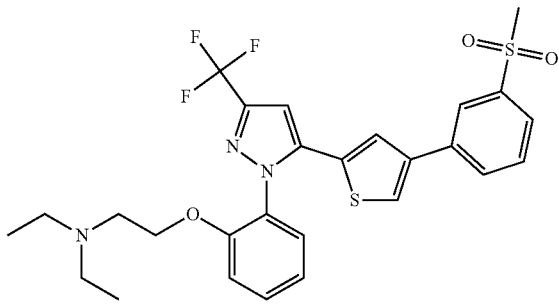 [SMILES: CCN(CC)CCOc1ccccc1-n1nc(C(F)(F)F)cc1-c1cc(-c2cccc(S(C)(=O)=O)c2)cs1] | N,N-diethyl-2-({2-[5-{4-[3-(methylsulfonyl)phenyl]-2-thienyl}-3-(trifluoromethyl)-1H-pyrazol-1-yl]phenyl}oxy)ethanamine |
| 311 | 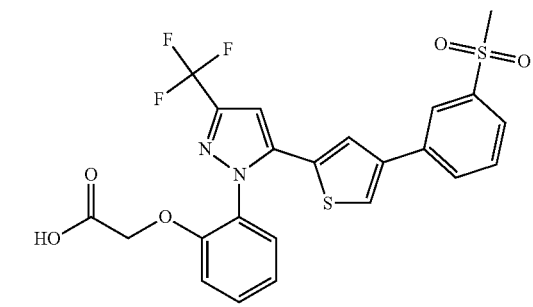 [SMILES: CS(=O)(=O)c1cccc(-c2csc(-c3cc(C(F)(F)F)nn3-c3ccccc3OCC(=O)O)c2)c1] | ({2-[5-{4-[3-(methylsulfonyl)phenyl]-2-thienyl}-3-(trifluoromethyl)-1H-pyrazol-1-yl]phenyl}oxy)acetic acid |
| 312 | 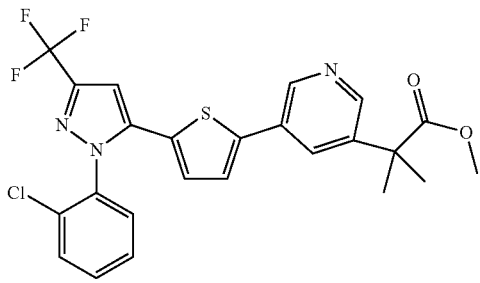 [SMILES: COC(=O)C(C)(C)c1cncc(-c2ccc(-c3cc(C(F)(F)F)nn3-c3ccccc3Cl)s2)c1] | methyl 2-(5-{5-[1-(2-chlorophenyl)-3-(trifluoromethyl)-1H-pyrazol-5-yl]-2-thienyl}pyridin-3-yl)-2-methylpropanoate |
| 313 | 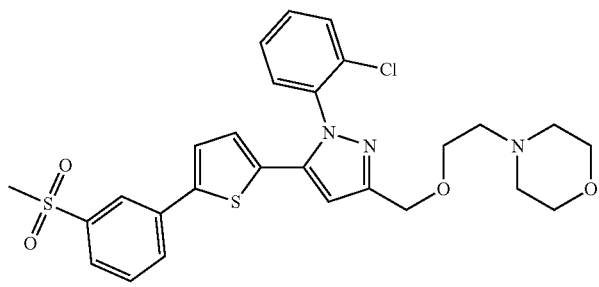 [SMILES: CS(=O)(=O)c1cccc(-c2ccc(-c3cc(COCCN4CCOCC4)nn3-c3ccccc3Cl)s2)c1] | 4-(2-{[(1-(2-chlorophenyl)-5-{5-[3-(methylsulfonyl)phenyl]-2-thienyl}-1H-pyrazol-3-yl)methyl]oxy}ethyl)morpholine |

TABLE 1-continued

| 314 | 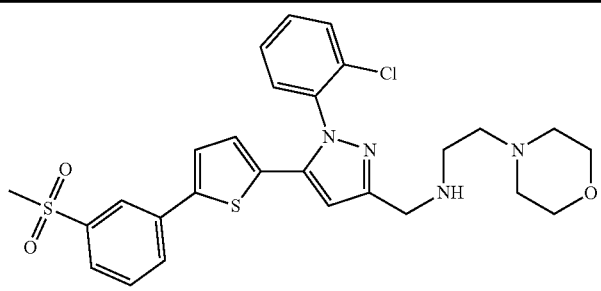 | N-[(1-(2-chlorophenyl)-5-{5-[3-(methylsulfonyl)phenyl]-2-thienyl}-1H-pyrazol-3-yl)methyl]-2-morpholin-4-ylethanamine |
| --- | --- | --- |
| 315 | 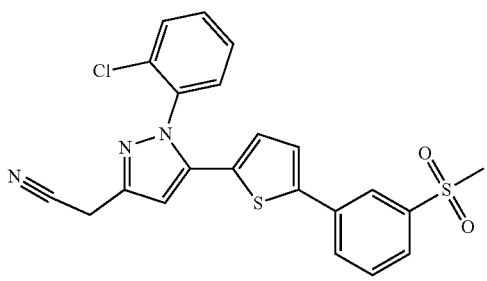 [SMILES: CS(=O)(=O)c1cccc(-c2ccc(-c3cc(CC#N)nn3-c3ccccc3Cl)s2)c1] | (1-(2-chlorophenyl)-5-{5-[3-(methylsulfonyl)phenyl]-2-thienyl}-1H-pyrazol-3-yl)acetonitrile |
| 316 | 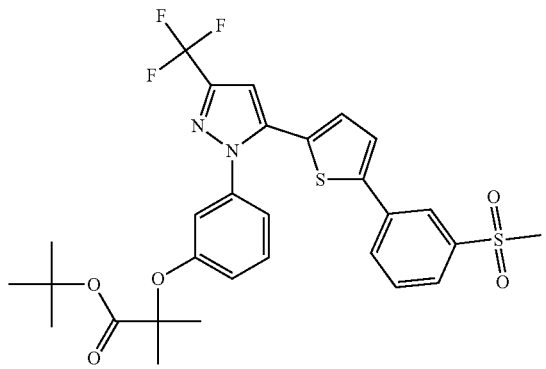 [SMILES: CC(C)(C)OC(=O)C(C)(C)Oc1cccc(-n2nc(C(F)(F)F)cc2-c2ccc(-c3cccc(S(C)(=O)=O)c3)s2)c1] | 1,1-dimethylethyl 2-methyl-2-({3-[5-{5-[3-(methylsulfonyl)phenyl]-2-thienyl}-3-(trifluoromethyl)-1H-pyrazol-1-yl]phenyl}oxy)propanoate |
| 317 | 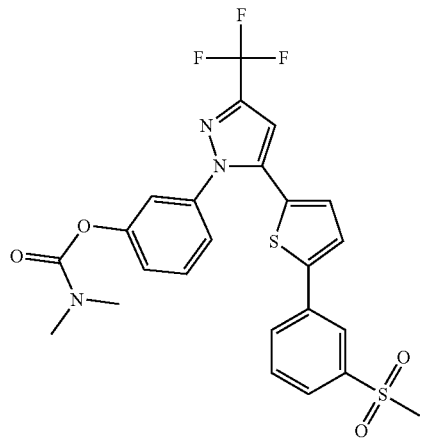 [SMILES: CN(C)C(=O)Oc1cccc(-n2nc(C(F)(F)F)cc2-c2ccc(-c3cccc(S(C)(=O)=O)c3)s2)c1] | 3-[5-{5-[3-(methylsulfonyl)phenyl]-2-thienyl}-3-(trifluoromethyl)-1H-pyrazol-1-yl]phenyl dimethylcarbamate |

| | | |
|---|---|---|
| 318 | 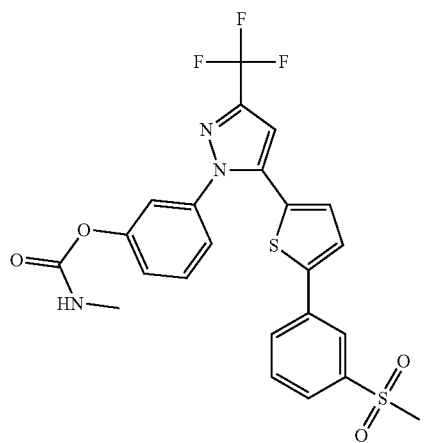 [SMILES: CNC(=O)Oc1cccc(-n2nc(C(F)(F)F)cc2-c2ccc(-c3cccc(S(C)(=O)=O)c3)s2)c1] | 3-[5-{5-[3-(methylsulfonyl)phenyl]-2-thienyl}-3-(trifluoromethyl)-1H-pyrazol-1-yl]phenyl methylcarbamate |
| 320 | 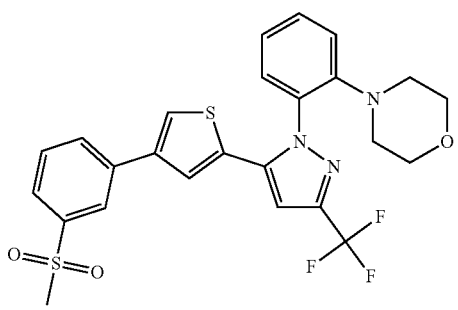 [SMILES: CS(=O)(=O)c1cccc(-c2csc(-c3cc(C(F)(F)F)nn3-c3ccccc3N3CCOCC3)c2)c1] | 4-{2-[5-{4-[3-(methylsulfonyl)phenyl]-2-thienyl}-3-(trifluoromethyl)-1H-pyrazol-1-yl]phenyl}morpholine |
| 321 | 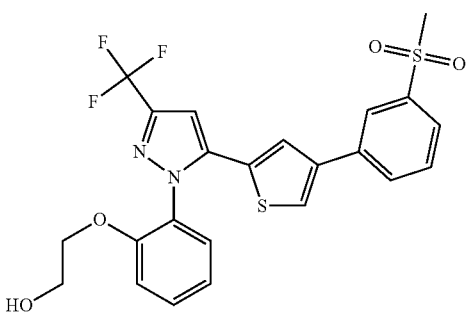 [SMILES: CS(=O)(=O)c1cccc(-c2csc(-c3cc(C(F)(F)F)nn3-c3ccccc3OCCO)c2)c1] | 2-({2-[5-{4-[3-(methylsulfonyl)phenyl]-2-thienyl}-3-(trifluoromethyl)-1H-pyrazol-1-yl]phenyl}oxy)ethanol |
| 323 | 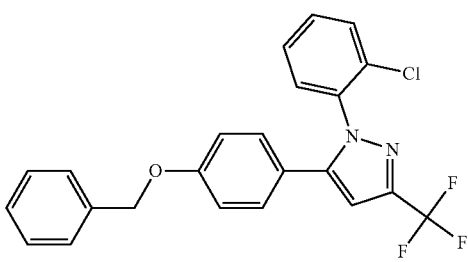 [SMILES: FC(F)(F)c1cc(-c2ccc(OCc3ccccc3)cc2)n(-c2ccccc2Cl)n1] | 1-(2-chlorophenyl)-5-{4-[(phenylmethyl)oxy]phenyl}-3-(trifluoromethyl)-1H-pyrazole |
| 327 | 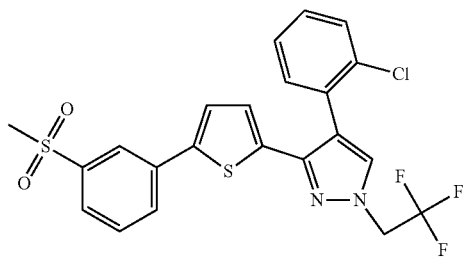 [SMILES: CS(=O)(=O)c1cccc(-c2ccc(-c3nn(CC(F)(F)F)cc3-c3ccccc3Cl)s2)c1] | 4-(2-chlorophenyl)-3-{5-[3-(methylsulfonyl)phenyl]-2-thienyl}-1-(2,2,2-trifluoroethyl)-1H-pyrazole |

| | | |
|---|---|---|
| 328 | 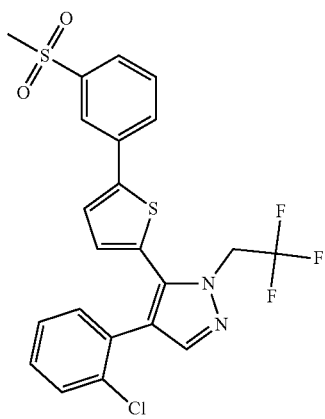 [SMILES: CS(=O)(=O)c1cccc(-c2ccc(-c3c(-c4ccccc4Cl)cnn3CC(F)(F)F)s2)c1] | 4-(2-chlorophenyl)-5-{5-[3-(methylsulfonyl)phenyl]-2-thienyl}-1-(2,2,2-trifluoroethyl)-1H-pyrazole |
| 329 | 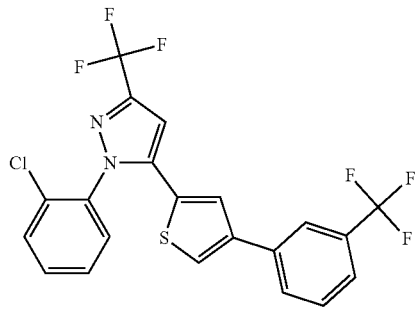 [SMILES: FC(F)(F)c1cccc(-c2csc(-c3cc(C(F)(F)F)nn3-c3ccccc3Cl)c2)c1] | 1-(2-chlorophenyl)-3-(trifluoromethyl)-5-{4-[3-(trifluoromethyl)phenyl]-2-thienyl}-1H-pyrazole |
| 330 | 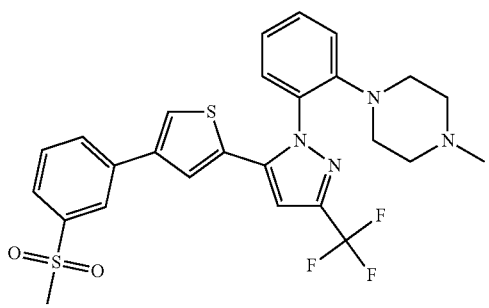 [SMILES: CN1CCN(c2ccccc2-n2nc(C(F)(F)F)cc2-c2cc(-c3cccc(S(C)(=O)=O)c3)cs2)CC1] | 1-methyl-4-{2-[5-{4-[3-(methylsulfonyl)phenyl]-2-thienyl}-3-(trifluoromethyl)-1H-pyrazol-1-yl]phenyl}piperazine |
| 331 | 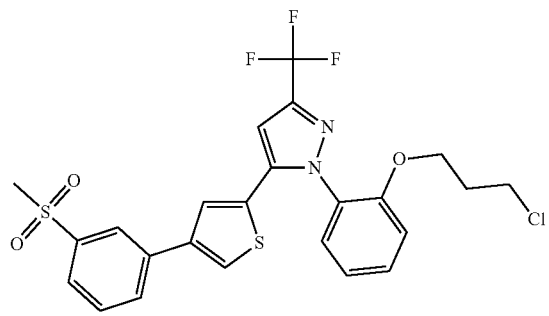 [SMILES: CS(=O)(=O)c1cccc(-c2csc(-c3cc(C(F)(F)F)nn3-c3ccccc3OCCCCl)c2)c1] | 1-{2-[(3-chloropropyl)oxy]phenyl}-5-{4-[3-(methylsulfonyl)phenyl]-2-thienyl}-3-(trifluoromethyl)-1H-pyrazole |

| | | |
|---|---|---|
| 332 | 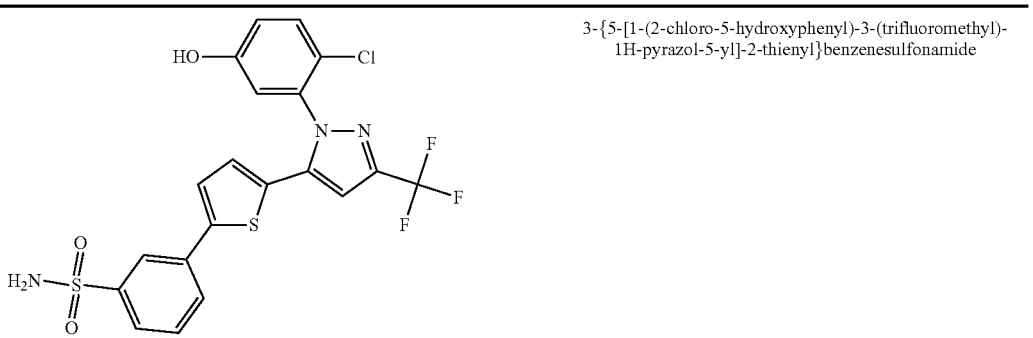 | 3-{5-[1-(2-chloro-5-hydroxyphenyl)-3-(trifluoromethyl)-1H-pyrazol-5-yl]-2-thienyl}benzenesulfonamide |
| 333 | 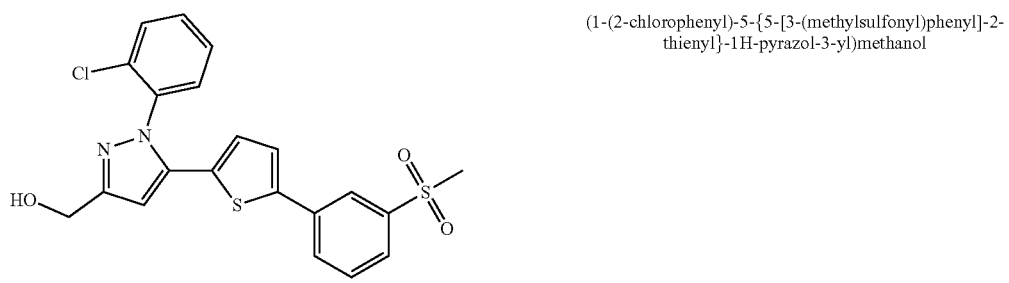 | (1-(2-chlorophenyl)-5-{5-[3-(methylsulfonyl)phenyl]-2-thienyl}-1H-pyrazol-3-yl)methanol |
| 334 | 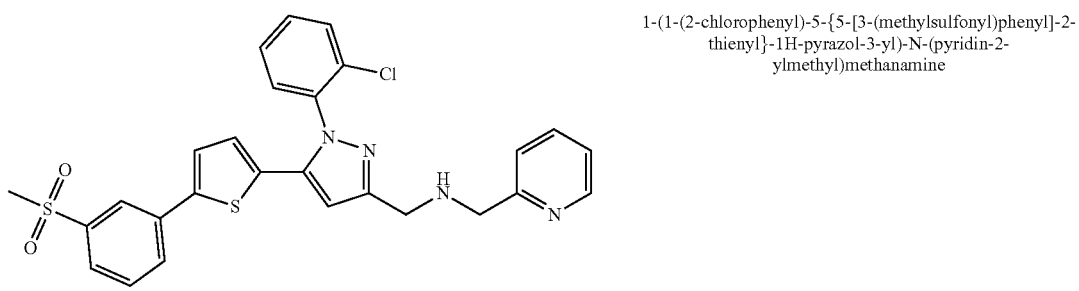 | 1-(1-(2-chlorophenyl)-5-{5-[3-(methylsulfonyl)phenyl]-2-thienyl}-1H-pyrazol-3-yl)-N-(pyridin-2-ylmethyl)methanamine |
| 335 | 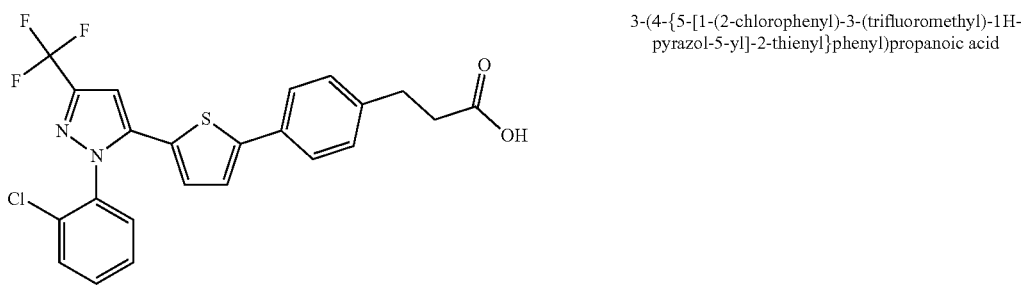 | 3-(4-{5-[1-(2-chlorophenyl)-3-(trifluoromethyl)-1H-pyrazol-5-yl]-2-thienyl}phenyl)propanoic acid |
| 336 | 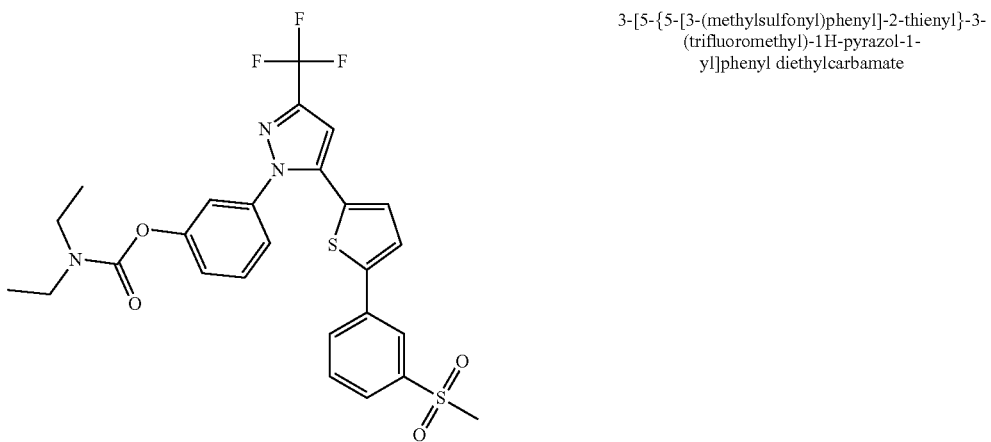 | 3-[5-{5-[3-(methylsulfonyl)phenyl]-2-thienyl}-3-(trifluoromethyl)-1H-pyrazol-1-yl]phenyl diethylcarbamate |

TABLE 1-continued
| 337 | 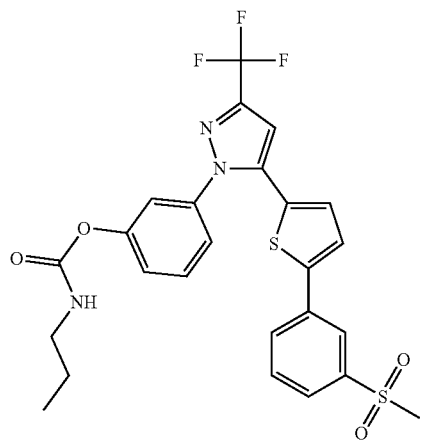 [SMILES: CCCNC(=O)Oc1cccc(-n2nc(C(F)(F)F)cc2-c2ccc(-c3cccc(S(C)(=O)=O)c3)s2)c1] | 3-[5-{5-[3-(methylsulfonyl)phenyl]-2-thienyl}-3-(trifluoromethyl)-1H-pyrazol-1-yl]phenyl propylcarbamate |
| 338 | 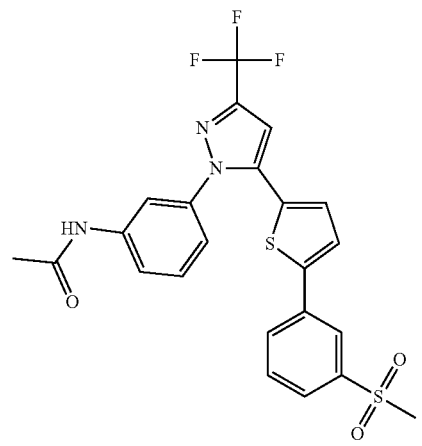 [SMILES: CC(=O)Nc1cccc(-n2nc(C(F)(F)F)cc2-c2ccc(-c3cccc(S(C)(=O)=O)c3)s2)c1] | N-{3-[5-{5-[3-(methylsulfonyl)phenyl]-2-thienyl}-3-(trifluoromethyl)-1H-pyrazol-1-yl]phenyl}acetamide |
| 340 | 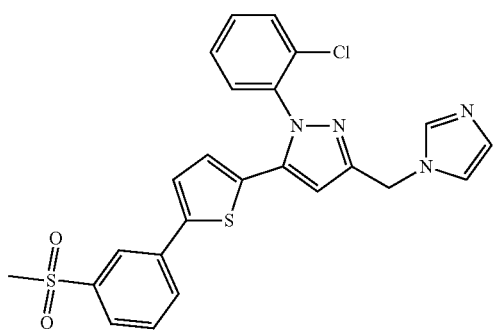 [SMILES: CS(=O)(=O)c1cccc(-c2ccc(-c3cc(Cn4ccnc4)nn3-c3ccccc3Cl)s2)c1] | 1-(2-chlorophenyl)-3-(1H-imidazol-1-ylmethyl)-5-{5-[3-(methylsulfonyl)phenyl]-2-thienyl}-1H-pyrazole |
| 341 | 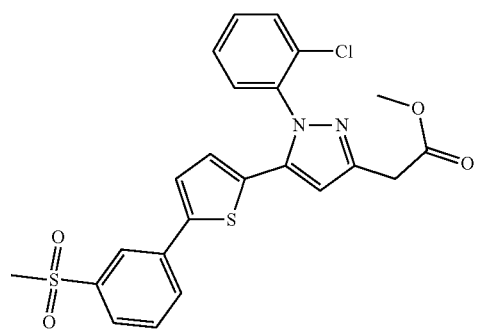 [SMILES: COC(=O)Cc1cc(-c2ccc(-c3cccc(S(C)(=O)=O)c3)s2)n(-c2ccccc2Cl)n1] | methyl (1-(2-chlorophenyl)-5-{5-[3-(methylsulfonyl)phenyl]-2-thienyl}-1H-pyrazol-3-yl)acetate |

TABLE 1-continued

| | | |
|---|---|---|
| 342 | 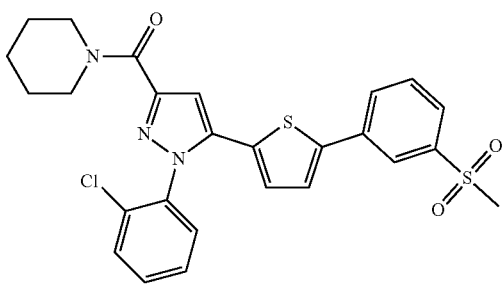 [SMILES: CS(=O)(=O)c1cccc(-c2ccc(-c3cc(C(=O)N4CCCCC4)nn3-c3ccccc3Cl)s2)c1] | 1-[(1-(2-chlorophenyl)-5-{5-[3-(methylsulfonyl)phenyl]-2-thienyl}-1H-pyrazol-3-yl)carbonyl]piperidine |
| 343 | 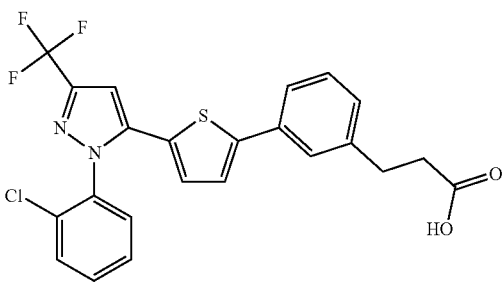 [SMILES: O=C(O)CCc1cccc(-c2ccc(-c3cc(C(F)(F)F)nn3-c3ccccc3Cl)s2)c1] | 3-(3-{5-[1-(2-chlorophenyl)-3-(trifluoromethyl)-1H-pyrazol-5-yl]-2-thienyl}phenyl)propanoic acid |
| 344 | 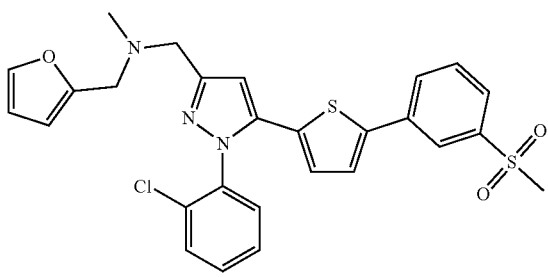 [SMILES: CN(Cc1cc(-c2ccc(-c3cccc(S(C)(=O)=O)c3)s2)n(-c2ccccc2Cl)n1)Cc1ccco1] | 1-(1-(2-chlorophenyl)-5-{5-[3-(methylsulfonyl)phenyl]-2-thienyl}-1H-pyrazol-3-yl)-N-(furan-2-ylmethyl)-N-methylmethanamine |
| 345 | 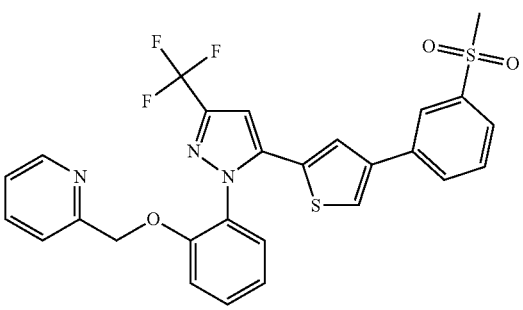 [SMILES: CS(=O)(=O)c1cccc(-c2csc(-c3cc(C(F)(F)F)nn3-c3ccccc3OCc3ccccn3)c2)c1] | 2-[({2-[5-{4-[3-(methylsulfonyl)phenyl]-2-thienyl}-3-(trifluoromethyl)-1H-pyrazol-1-yl]phenyl}oxy)methyl]pyridine |
| 346 | 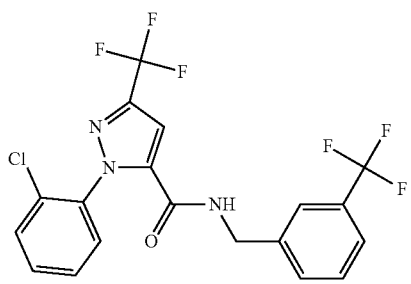 [SMILES: O=C(NCc1cccc(C(F)(F)F)c1)c1cc(C(F)(F)F)nn1-c1ccccc1Cl] | 1-(2-chlorophenyl)-3-(trifluoromethyl)-N-{[3-(trifluoromethyl)phenyl]methyl}-1H-pyrazole-5-carboxamide |

TABLE 1-continued

| | | |
|---|---|---|
| 347 | 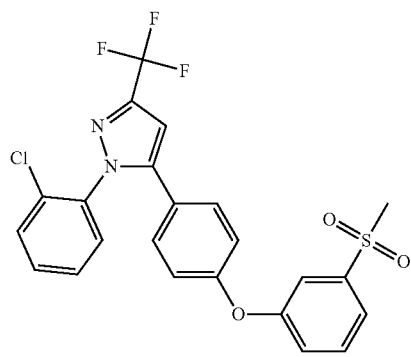 [SMILES: CS(=O)(=O)c1cccc(Oc2ccc(-c3cc(C(F)(F)F)nn3-c3ccccc3Cl)cc2)c1] | 1-(2-chlorophenyl)-5-(4-{[3-(methylsulfonyl)phenyl]oxy}phenyl)-3-(trifluoromethyl)-1H-pyrazole |
| 348 | 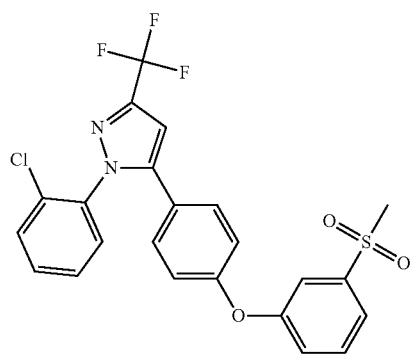 [SMILES: CS(=O)(=O)c1cccc(Oc2ccc(-c3cc(C(F)(F)F)nn3-c3ccccc3Cl)cc2)c1] | 1-(2-chlorophenyl)-5-(4-{[3-(methylsulfonyl)phenyl]oxy}phenyl)-3-(trifluoromethyl)-1H-pyrazole |
| 350 | 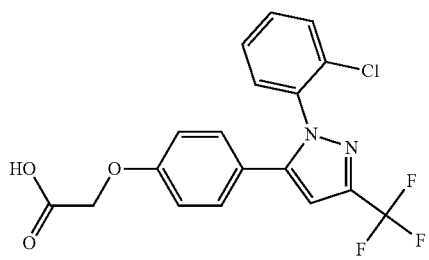 [SMILES: O=C(O)COc1ccc(-c2cc(C(F)(F)F)nn2-c2ccccc2Cl)cc1] | ({4-[1-(2-chlorophenyl)-3-(trifluoromethyl)-1H-pyrazol-5-yl]phenyl}oxy)acetic acid |
| 351 | 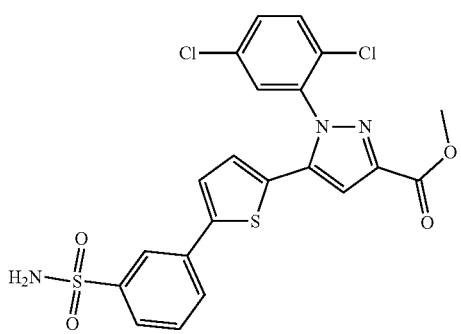 [SMILES: COC(=O)c1cc(-c2ccc(-c3cccc(S(N)(=O)=O)c3)s2)n(-c2cc(Cl)ccc2Cl)n1] | methyl 5-{5-[3-(aminosulfonyl)phenyl]-2-thienyl}-1-(2,5-dichlorophenyl)-1H-pyrazole-3-carboxylate |
| 352 | 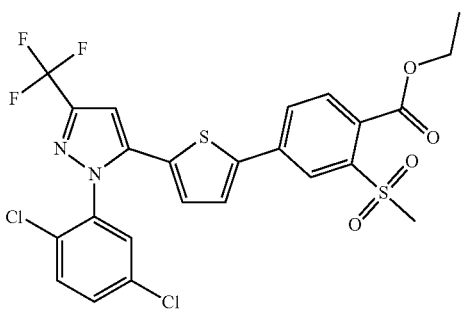 [SMILES: CCOC(=O)c1ccc(-c2ccc(-c3cc(C(F)(F)F)nn3-c3cc(Cl)ccc3Cl)s2)cc1S(C)(=O)=O] | ethyl 4-{5-[1-(2,5-dichlorophenyl)-3-(trifluoromethyl)-1H-pyrazol-5-yl]-2-thienyl}-2-(methylsulfonyl)benzoate |

TABLE 1-continued

| | | |
|---|---|---|
| 353 | 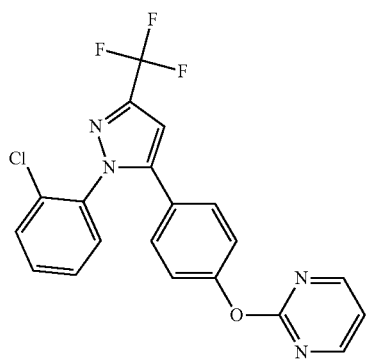 [SMILES: FC(F)(F)c1cc(-c2ccc(Oc3ncccn3)cc2)n(-c2ccccc2Cl)n1] | 2-({4-[1-(2-chlorophenyl)-3-(trifluoromethyl)-1H-pyrazol-5-yl]phenyl}oxy)pyrimidine |
| 354 | 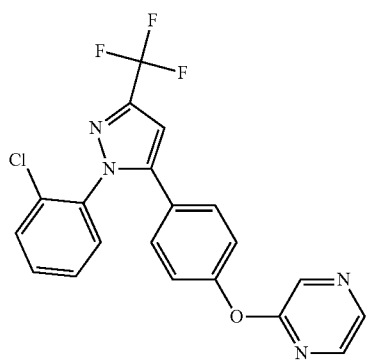 [SMILES: FC(F)(F)c1cc(-c2ccc(Oc3cnccn3)cc2)n(-c2ccccc2Cl)n1] | 2-({4-[1-(2-chlorophenyl)-3-(trifluoromethyl)-1H-pyrazol-5-yl]phenyl}oxy)pyrazine |
| 355 | 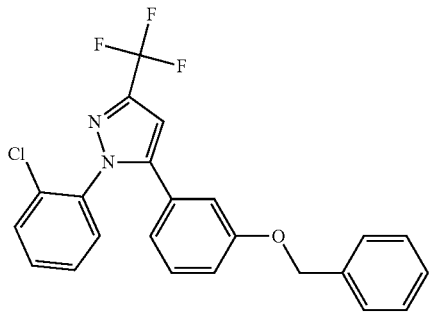 [SMILES: FC(F)(F)c1cc(-c2cccc(OCc3ccccc3)c2)n(-c2ccccc2Cl)n1] | 1-(2-chlorophenyl)-5-{3-[(phenylmethyl)oxy]phenyl}-3-(trifluoromethyl)-1H-pyrazole |
| 356 | 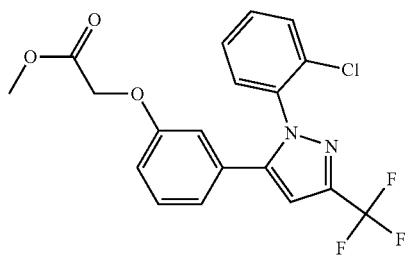 [SMILES: COC(=O)COc1cccc(-c2cc(C(F)(F)F)nn2-c2ccccc2Cl)c1] | methyl ({3-[1-(2-chlorophenyl)-3-(trifluoromethyl)-1H-pyrazol-5-yl]phenyl}oxy)acetate |
| 357 | 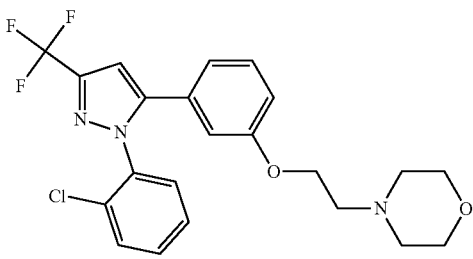 [SMILES: FC(F)(F)c1cc(-c2cccc(OCCN3CCOCC3)c2)n(-c2ccccc2Cl)n1] | 4-[2-({3-[1-(2-chlorophenyl)-3-(trifluoromethyl)-1H-pyrazol-5-yl]phenyl}oxy)ethyl]morpholine |

TABLE 1-continued

| | | |
|---|---|---|
| 358 | 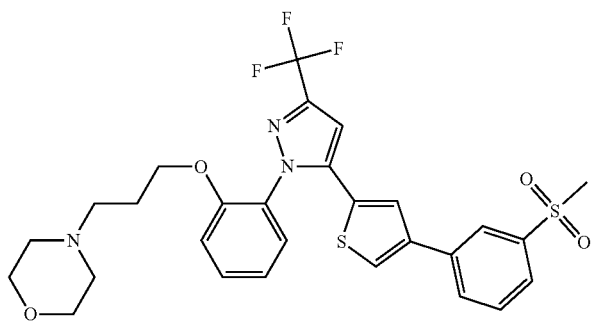 [SMILES: CS(=O)(=O)c1cccc(-c2csc(-c3cc(C(F)(F)F)nn3-c3ccccc3OCCCN3CCOCC3)c2)c1] | 4-[3-({2-[5-{4-[3-(methylsulfonyl)phenyl]-2-thienyl}-3-(trifluoromethyl)-1H-pyrazol-1-yl]phenyl}oxy)propyl]morpholine |
| 359 | 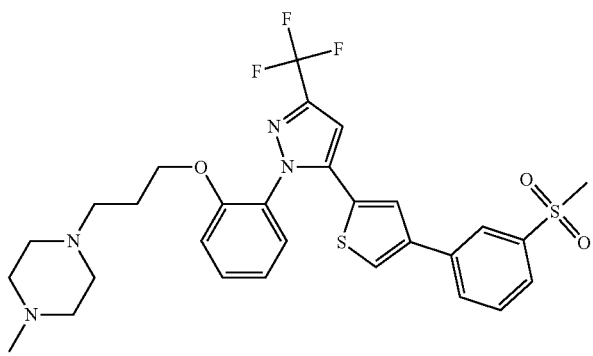 [SMILES: CN1CCN(CCCOc2ccccc2-n2nc(C(F)(F)F)cc2-c2cc(-c3cccc(S(C)(=O)=O)c3)cs2)CC1] | 1-methyl-4-[3-({2-[5-{4-[3-(methylsulfonyl)phenyl]-2-thienyl}-3-(trifluoromethyl)-1H-pyrazol-1-yl]phenyl}oxy)propyl]piperazine |
| 360 | 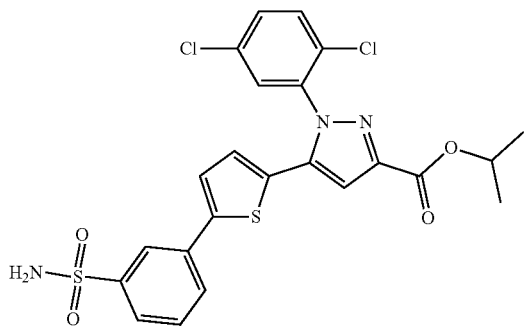 [SMILES: CC(C)OC(=O)c1cc(-c2ccc(-c3cccc(S(N)(=O)=O)c3)s2)n(-c2cc(Cl)ccc2Cl)n1] | 1-methylethyl 5-{5-[3-(aminosulfonyl)phenyl]-2-thienyl}-1-(2,5-dichlorophenyl)-1H-pyrazol-3-carboxylate |
| 361 | 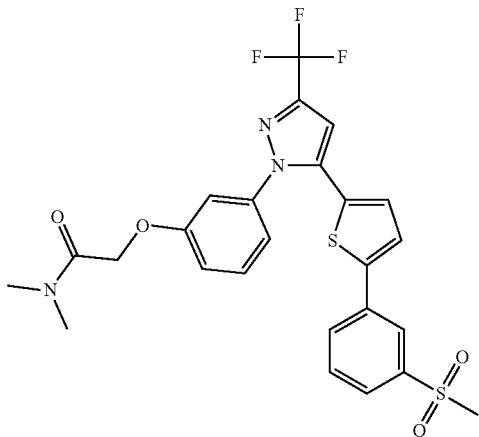 | N,N-dimethyl-2-({3-[5-{5-[3-(methylsulfonyl)phenyl]-2-thienyl}-3-(trifluoromethyl)-1H-pyrazol-1-yl]phenyl}oxy)acetamide |

| | | |
|---|---|---|
| 362 | 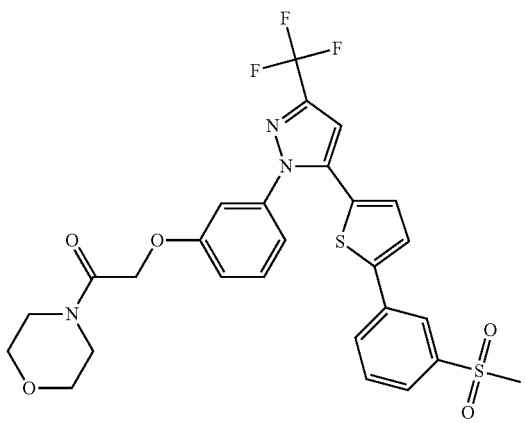 [SMILES: CS(=O)(=O)c1cccc(-c2ccc(-c3cc(C(F)(F)F)nn3-c3cccc(OCC(=O)N4CCOCC4)c3)s2)c1] | 4-[({3-[5-{5-[3-(methylsulfonyl)phenyl]-2-thienyl}-3-(trifluoromethyl)-1H-pyrazol-1-yl]phenyl}oxy)acetyl]morpholine |
| 363 | 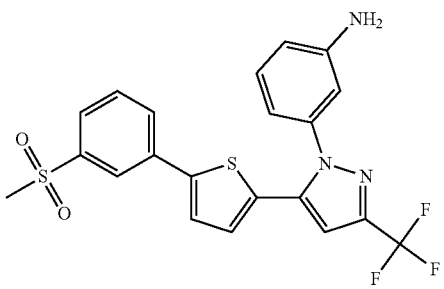 [SMILES: CS(=O)(=O)c1cccc(-c2ccc(-c3cc(C(F)(F)F)nn3-c3cccc(N)c3)s2)c1] | 3-[5-{5-[3-(methylsulfonyl)phenyl]-2-thienyl}-3-(trifluoromethyl)-1H-pyrazol-1-yl]aniline |
| 364 | 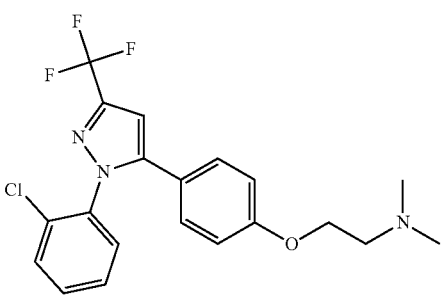 [SMILES: CN(C)CCOc1ccc(-c2cc(C(F)(F)F)nn2-c2ccccc2Cl)cc1] | 2-({4-[1-(2-chlorophenyl)-3-(trifluoromethyl)-1H-pyrazol-5-yl]phenyl}oxy)-N,N-dimethylethanamine |
| 365 | 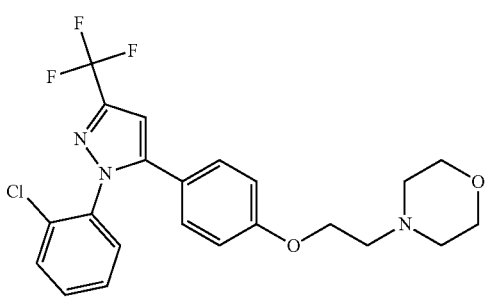 [SMILES: FC(F)(F)c1cc(-c2ccc(OCCN3CCOCC3)cc2)n(-c2ccccc2Cl)n1] | 4-[2-({4-[1-(2-chlorophenyl)-3-(trifluoromethyl)-1H-pyrazol-5-yl]phenyl}oxy)ethyl]morpholine |
| 366 | 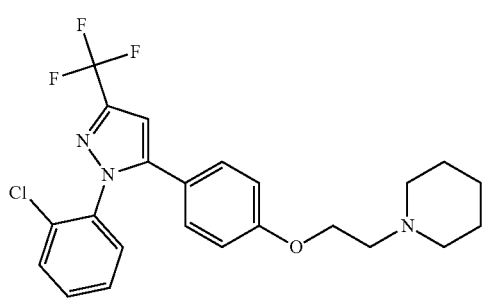 [SMILES: FC(F)(F)c1cc(-c2ccc(OCCN3CCCCC3)cc2)n(-c2ccccc2Cl)n1] | 1-[2-({4-[1-(2-chlorophenyl)-3-(trifluoromethyl)-1H-pyrazol-5-yl]phenyl}oxy)ethyl]piperidine |

TABLE 1-continued

| | | |
|---|---|---|
| 367 | 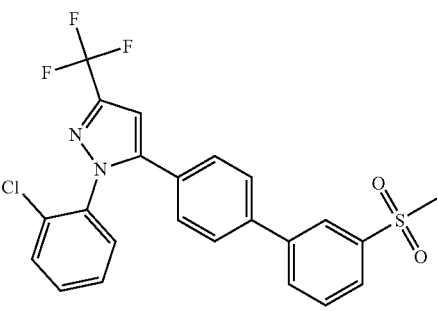 [SMILES: CS(=O)(=O)c1cccc(-c2ccc(-c3cc(C(F)(F)F)nn3-c3ccccc3Cl)cc2)c1] | 1-(2-chlorophenyl)-5-[3'-(methylsulfonyl)biphenyl-4-yl]-3-(trifluoromethyl)-1H-pyrazole |
| 368 | 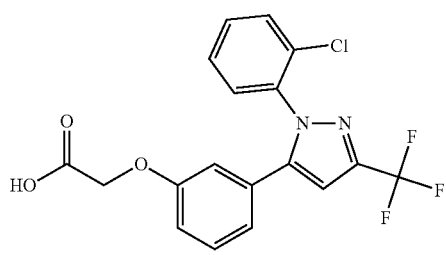 [SMILES: O=C(O)COc1cccc(-c2cc(C(F)(F)F)nn2-c2ccccc2Cl)c1] | ({3-[1-(2-chlorophenyl)-3-(trifluoromethyl)-1H-pyrazol-5-yl]phenyl}oxy)acetic acid |
| 369 | 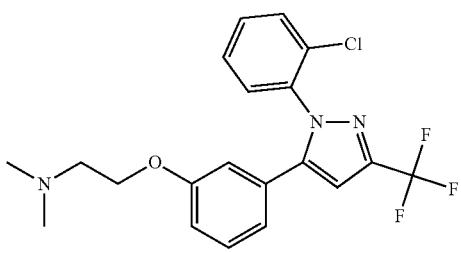 [SMILES: CN(C)CCOc1cccc(-c2cc(C(F)(F)F)nn2-c2ccccc2Cl)c1] | 2-({3-[1-(2-chlorophenyl)-3-(trifluoromethyl)-1H-pyrazol-5-yl]phenyl}oxy)-N,N-dimethylethanamine |
| 370 | 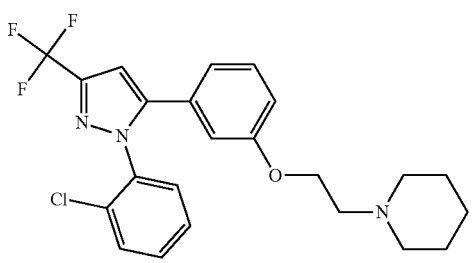 [SMILES: FC(F)(F)c1cc(-c2cccc(OCCN3CCCCC3)c2)n(-c2ccccc2Cl)n1] | 1-[2-({3-[1-(2-chlorophenyl)-3-(trifluoromethyl)-1H-pyrazol-5-yl]phenyl}oxy)ethyl]piperidine |
| 371 | 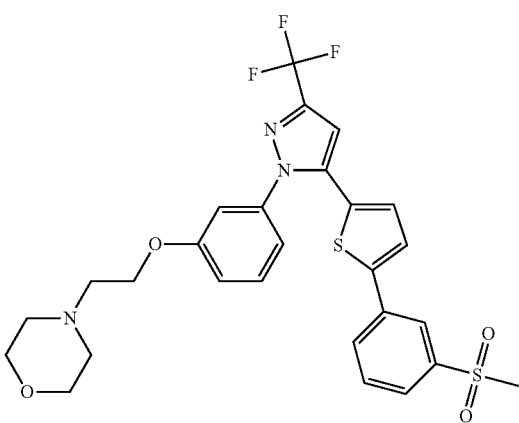 [SMILES: CS(=O)(=O)c1cccc(-c2ccc(-c3cc(C(F)(F)F)nn3-c3cccc(OCCN4CCOCC4)c3)s2)c1] | 4-[2-({3-[5-{5-[3-(methylsulfonyl)phenyl]-2-thienyl}-3-(trifluoromethyl)-1H-pyrazol-1-yl]phenyl}oxy)ethyl]morpholine |

TABLE 1-continued
| 372 | 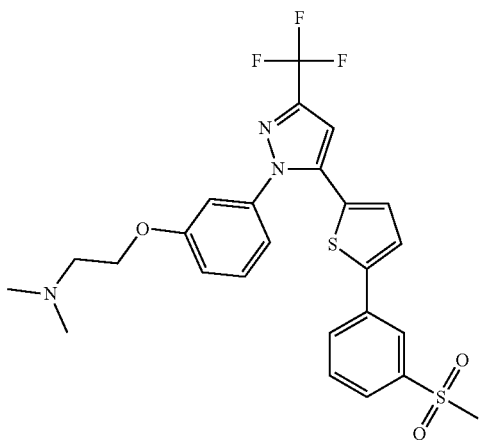 | N,N-dimethyl-2-({3-[5-{5-[3-(methylsulfonyl)phenyl]-2-thienyl}-3-(trifluoromethyl)-1H-pyrazol-1-yl]phenyl}oxy)ethanamine |
| --- | --- | --- |
| 373 | 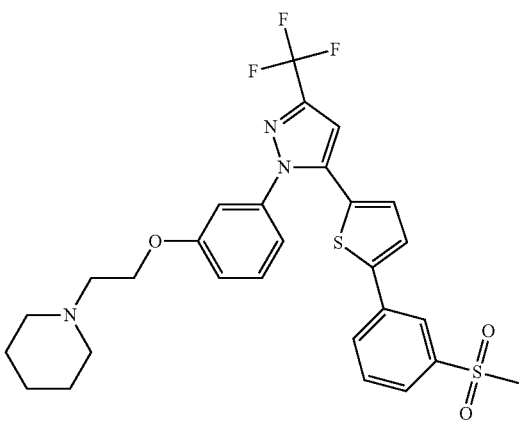 [SMILES: CS(=O)(=O)c1cccc(-c2ccc(-c3cc(C(F)(F)F)nn3-c3cccc(OCCN4CCCCC4)c3)s2)c1] | 1-[2-({3-[5-{5-[3-(methylsulfonyl)phenyl]-2-thienyl}-3-(trifluoromethyl)-1H-pyrazol-1-yl]phenyl}oxy)ethyl]piperidine |
| 374 | 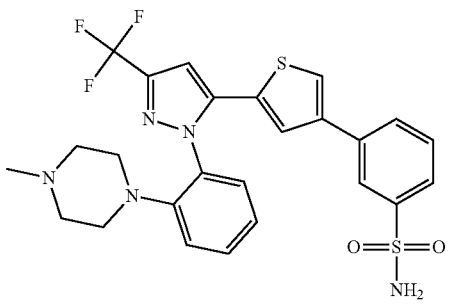 [SMILES: CN1CCN(c2ccccc2-n2nc(C(F)(F)F)cc2-c2cc(-c3cccc(S(N)(=O)=O)c3)cs2)CC1] | 3-{5-[1-[2-(4-methylpiperidin-1-yl)phenyl]-3-(trifluoromethyl)-1H-pyrazol-5-yl]-3-thienyl}benzenesulfonamide |
| 375 | 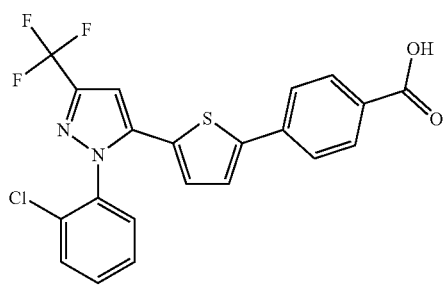 [SMILES: O=C(O)c1ccc(-c2ccc(-c3cc(C(F)(F)F)nn3-c3ccccc3Cl)s2)cc1] | 4-{5-[1-(2-chlorophenyl)-3-(trifluoromethyl)-1H-pyrazol-5-yl]-2-thienyl}benzoic acid |

TABLE 1-continued

| | | |
|---|---|---|
| 376 | | 3-{5-[1-(2-chlorophenyl)-3-(trifluoromethyl)-1H-pyrazol-5-yl]-2-thienyl}benzoic acid |
| 377 | | (2E)-3-(4-{5-[1-(2-chlorophenyl)-3-(trifluoromethyl)-1H-pyrazol-5-yl]-2-thienyl}phenyl)prop-2-enoic acid |
| 378 | | 1-(2-chlorophenyl)-5-[3'-(methylsulfonyl)biphenyl-3-yl]-3-(trifluoromethyl)-1H-pyrazole |
| 379 | | phenylmethyl 4-[(1-(2-chlorophenyl)-5-{5-[3-(methylsulfonyl)phenyl]-2-thienyl}-1H-pyrazol-3-yl)methyl]-3-oxopiperazine-1-carboxylate |
| 380 | | (1-(2-chlorophenyl)-5-{5-[3-(methylsulfonyl)phenyl]-2-thienyl}-1H-pyrazol-3-yl)methyl morpholin-4-ylacetate |

TABLE 1-continued

| | | |
|---|---|---|
| 381 | 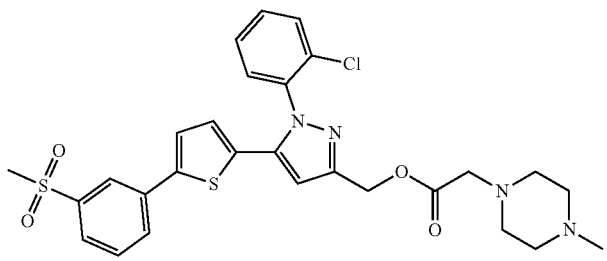 | (1-(2-chlorophenyl)-5-{5-[3-(methylsulfonyl)phenyl]-2-thienyl}-1H-pyrazol-3-yl)methyl (4-methylpiperazin-1-yl)acetate |
| 382 | 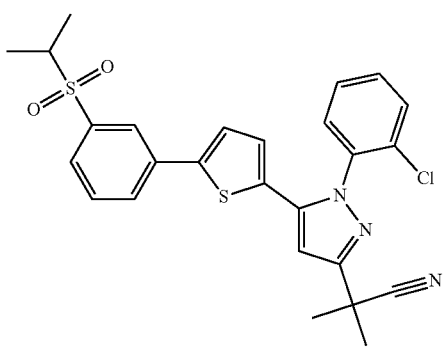 [SMILES: CC(C)S(=O)(=O)c1cccc(-c2ccc(-c3cc(C(C)(C)C#N)nn3-c3ccccc3Cl)s2)c1] | 2-[1-(2-chlorophenyl)-5-(5-{3-[(1-methylethyl)sulfonyl]phenyl}-2-thienyl)-1H-pyrazol-3-yl]-2-methylpropanenitrile |
| 383 | 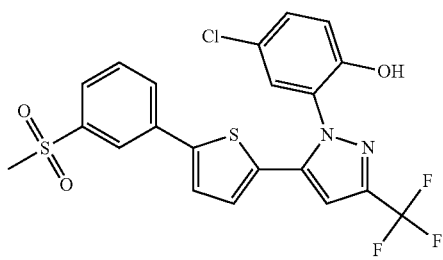 [SMILES: CS(=O)(=O)c1cccc(-c2ccc(-c3cc(C(F)(F)F)nn3-c3cc(Cl)ccc3O)s2)c1] | 4-chloro-2-[5-{5-[3-(methylsulfonyl)phenyl]-2-thienyl}-3-(trifluoromethyl)-1H-pyrazol-1-yl]phenol |
| 384 | 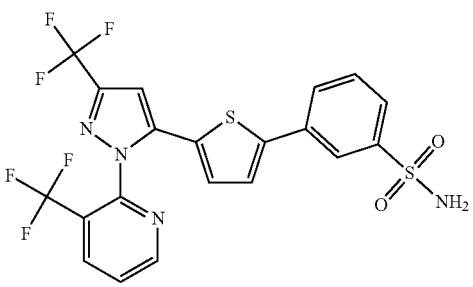 [SMILES: NS(=O)(=O)c1cccc(-c2ccc(-c3cc(C(F)(F)F)nn3-c3ncccc3C(F)(F)F)s2)c1] | 3-(5-{3-(trifluoromethyl)-1-[3-(trifluoromethyl)pyridin-2-yl]-1H-pyrazol-5-yl}-2-thienyl)benzenesulfonamide |
| 385 | 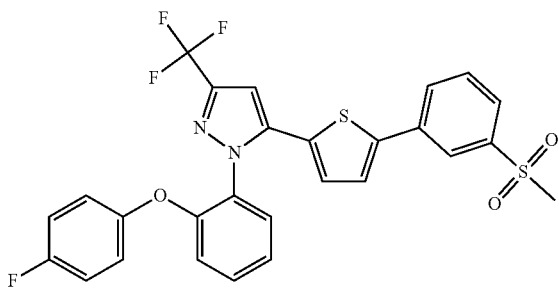 [SMILES: CS(=O)(=O)c1cccc(-c2ccc(-c3cc(C(F)(F)F)nn3-c3ccccc3Oc3ccc(F)cc3)s2)c1] | 1-{5-chloro-2-[(4-fluorophenyl)oxy]phenyl}-5-{5-[3-(methylsulfonyl)phenyl]-2-thienyl}-3-(trifluoromethyl)-1H-pyrazole |

| | | |
|---|---|---|
| 386 | 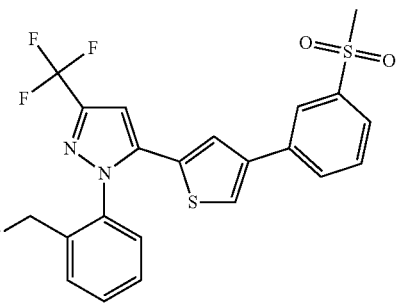 | 1-methyl-4-({2-[5-{4-[3-(methylsulfonyl)phenyl]-2-thienyl}-3-(trifluoromethyl)-1H-pyrazol-1-yl]phenyl}methyl)piperazine |
| 387 | 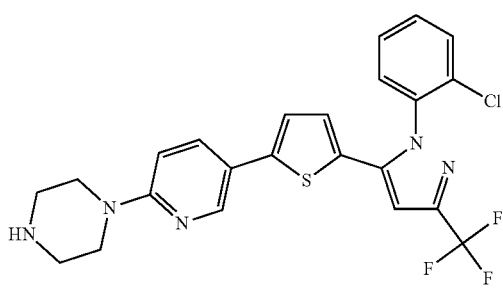 [SMILES: N=C(/C=C(\Nc1ccccc1Cl)c1ccc(-c2ccc(N3CCNCC3)nc2)s1)C(F)(F)F] | 1-(5-{5-[1-(2-chlorophenyl)-3-(trifluoromethyl)-1H-pyrazol-5-yl]-2-thienyl}pyridin-2-yl)piperazine |
| 388 | 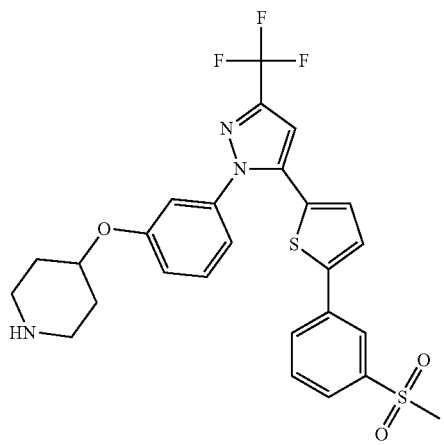 [SMILES: CS(=O)(=O)c1cccc(-c2ccc(-c3cc(C(F)(F)F)nn3-c3cccc(OC4CCNCC4)c3)s2)c1] | 4-({3-[5-{5-[3-(methylsulfonyl)phenyl]-2-thienyl}-3-(trifluoromethyl)-1H-pyrazol-1-yl]phenyl}oxy)piperidine |
| 389 | 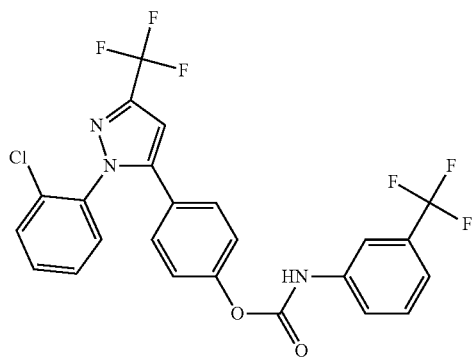 [SMILES: O=C(Nc1cccc(C(F)(F)F)c1)Oc1ccc(-c2cc(C(F)(F)F)nn2-c2ccccc2Cl)cc1] | 4-[1-(2-chlorophenyl)-3-(trifluoromethyl)-1H-pyrazol-5-yl]phenyl [3-(trifluoromethyl)phenyl]carbamate |

TABLE 1-continued

| | | |
|---|---|---|
| 390 | | 2-(5-{5-[1-(2-chlorophenyl)-3-(trifluoromethyl)-1H-pyrazol-5-yl]-2-thienyl}pyridin-3-yl)-2-methylpropanoic acid |
| 391 | | (5-{5-[1-(2-chlorophenyl)-3-(trifluoromethyl)-1H-pyrazol-5-yl]-2-thienyl}pyridin-3-yl)acetic acid |
| 394 | | 5-{5-[3-(methylsulfonyl)phenyl]-2-thienyl}-1-[3-(phenyloxy)phenyl]-3-(trifluoromethyl)-1H-pyrazole |
| 395 | | 1-[3'-(methylsulfonyl)biphenyl-4-yl]-3-(trifluoromethyl)-5-[2-(trifluoromethyl)phenyl]-1H-pyrazole |
| 396 | | 4'-{3-(trifluoromethyl)-5-[2-(trifluoromethyl)phenyl]-1H-pyrazol-1-yl}biphenyl-3-sulfonamide |

TABLE 1-continued

| 397 | 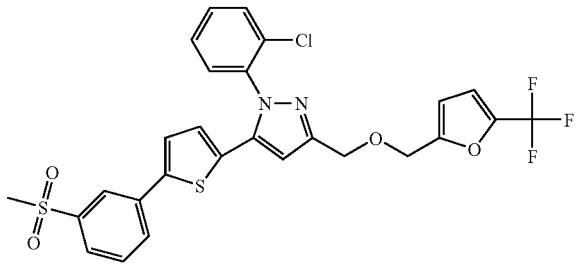 [SMILES: CS(=O)(=O)c1cccc(-c2ccc(-c3cc(COCc4ccc(C(F)(F)F)o4)nn3-c3ccccc3Cl)s2)c1] | 1-(2-chlorophenyl)-5-{5-[3-(methylsulfonyl)phenyl]-2-thienyl}-3-[({[5-(trifluoromethyl)furan-2-yl]methyl}oxy)methyl]-1H-pyrazole |
| --- | --- | --- |
| 398 | 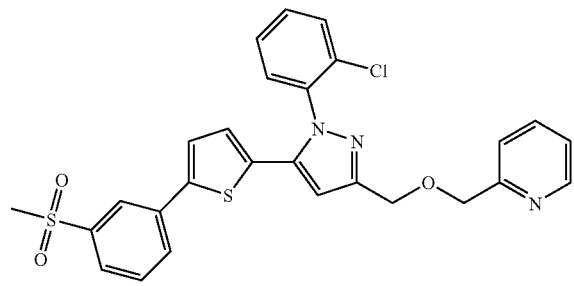 [SMILES: CS(=O)(=O)c1cccc(-c2ccc(-c3cc(COCc4ccccn4)nn3-c3ccccc3Cl)s2)c1] | 2-({[[1-(2-chlorophenyl)-3-{5-[3-(methylsulfonyl)phenyl]-2-thienyl}-1H-pyrazol-3-yl]methyl]oxy}methyl)pyridine |
| 399 | 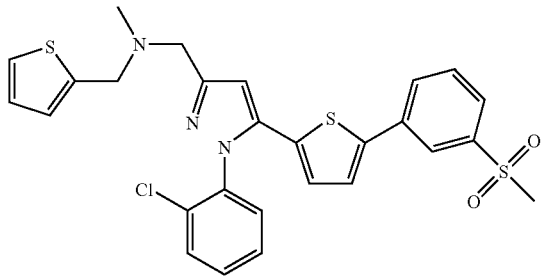 [SMILES: CN(CC(=N)/C=C(\Nc1ccccc1Cl)c1ccc(-c2cccc(S(C)(=O)=O)c2)s1)Cc1cccs1] | 1-(1-(2-chlorophenyl)-5-{5-[3-(methylsulfonyl)phenyl]-2-thienyl}-1H-pyrazol-3-yl)-N-methyl-N-(2-thienylmethyl)methanamine |
| 400 | 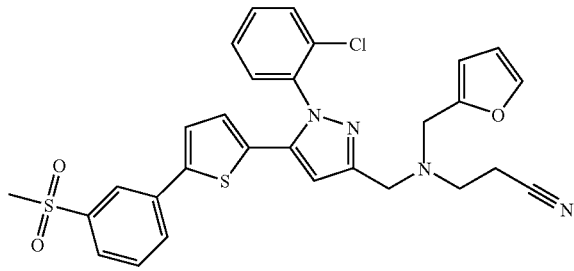 | 3-[[(1-(2-chlorophenyl)-5-{5-[3-(methylsulfonyl)phenyl]-2-thienyl}-1H-pyrazol-3-yl)methyl](furan-2-ylmethyl)amino]propanenitrile |
| 401 | 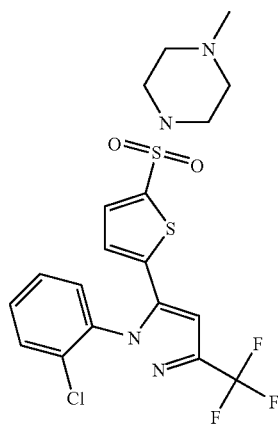 | 1-({5-[1-(2-chlorophenyl)-3-(trifluoromethyl)-1H-pyrazol-5-yl]-2-thienyl}sulfonyl)-4-methylpiperazine |

TABLE 1-continued

| | | |
|---|---|---|
| 402 | 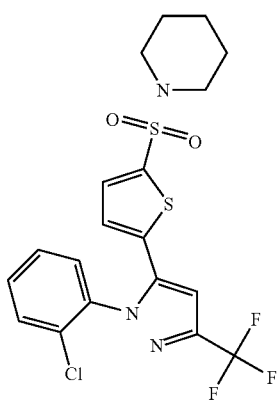 | 1-({5-[1-(2-chlorophenyl)-3-(trifluoromethyl)-1H-pyrazol-5-yl]-2-thienyl}sulfonyl)piperidine |
| 403 | 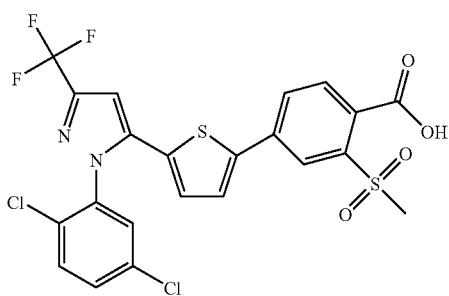 [SMILES: CS(=O)(=O)c1cc(-c2ccc(/C(=C/C(=N)C(F)(F)F)Nc3cc(Cl)ccc3Cl)s2)ccc1C(=O)O] | 4-{5-[1-(2,5-dichlorophenyl)-3-(trifluoromethyl)-1H-pyrazol-5-yl]-2-thienyl}-2-(methylsulfonyl)benzoic acid |
| 404 | 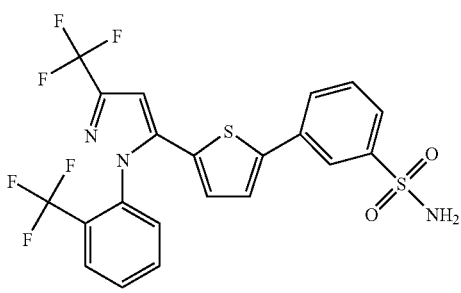 [SMILES: N=C(/C=C(\Nc1ccccc1C(F)(F)F)c1ccc(-c2cccc(S(N)(=O)=O)c2)s1)C(F)(F)F] | 3-(5-{3-(trifluoromethyl)-1-[2-(trifluoromethyl)phenyl]-1H-pyrazol-5-yl}-2-thienyl)benzenesulfonamide |
| 405 | 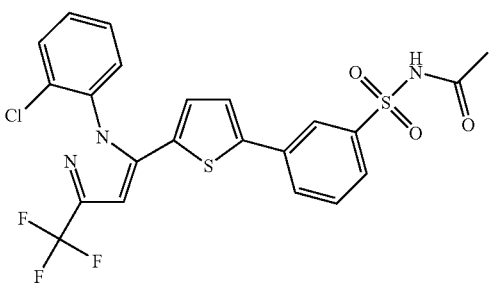 [SMILES: CC(=O)NS(=O)(=O)c1cccc(-c2ccc(/C(=C/C(=N)C(F)(F)F)Nc3ccccc3Cl)s2)c1] | N-[(3-{5-[1-(2-chlorophenyl)-3-(trifluoromethyl)-1H-pyrazol-5-yl]-2-thienyl}phenyl)sulfonyl]acetamide |
| 406 | 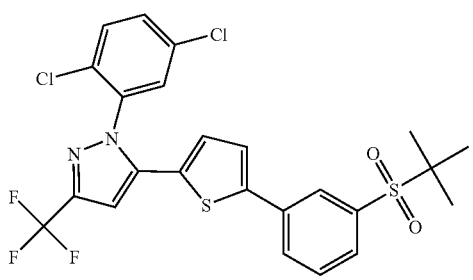 [SMILES: CC(C)(C)S(=O)(=O)c1cccc(-c2ccc(-c3cc(C(F)(F)F)nn3-c3cc(Cl)ccc3Cl)s2)c1] | 1-(2,5-dichlorophenyl)-5-(5-{3-[(1,1-dimethylethyl)sulfonyl]phenyl}-2-thienyl)-3-(trifluoromethyl)-1H-pyrazole |

TABLE 1-continued

| | | |
|---|---|---|
| 407 | 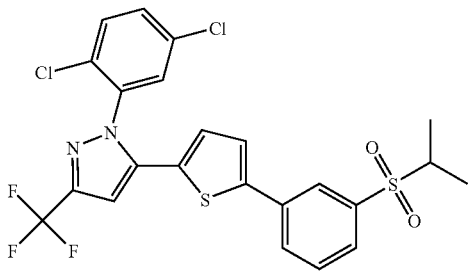 [SMILES: CC(C)S(=O)(=O)c1cccc(-c2ccc(-c3cc(C(F)(F)F)nn3-c3cc(Cl)ccc3Cl)s2)c1] | 1-(2,5-dichlorophenyl)-5-(5-{3-[(1-methylethyl)sulfonyl]phenyl}-2-thienyl)-3-(trifluoromethyl)-1H-pyrazole |
| 408 | 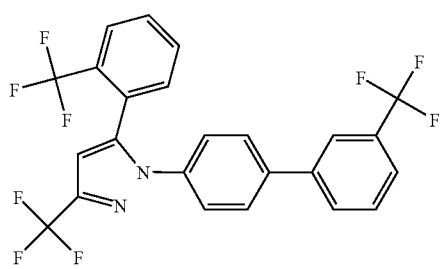 [SMILES: N=C(/C=C(\Nc1ccc(-c2cccc(C(F)(F)F)c2)cc1)c1ccccc1C(F)(F)F)C(F)(F)F] | 3-(trifluoromethyl)-1-[3'-(trifluoromethyl)biphenyl-4-yl]-5-[2-(trifluoromethyl)phenyl]-1H-pyrazole |
| 409 | 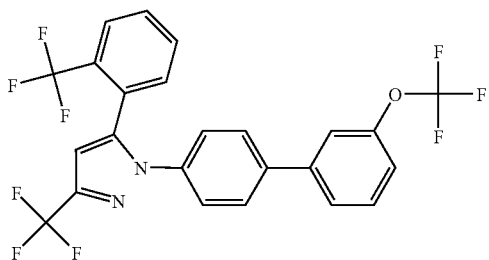 [SMILES: N=C(/C=C(\Nc1ccc(-c2cccc(OC(F)(F)F)c2)cc1)c1ccccc1C(F)(F)F)C(F)(F)F] | 3-(trifluoromethyl)-1-{3'-[(trifluoromethyl)oxy]biphenyl-4-yl}-5-[2-(trifluoromethyl)phenyl]-1H-pyrazole |
| 410 | 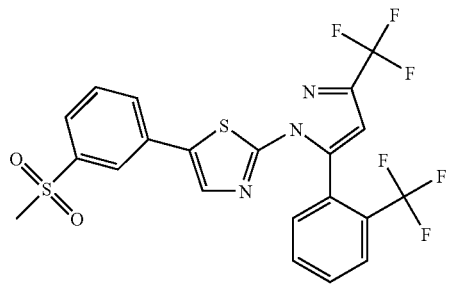 [SMILES: CS(=O)(=O)c1cccc(-c2cnc(N/C(=C\C(=N)C(F)(F)F)c3ccccc3C(F)(F)F)s2)c1] | 5-[3-(methylsulfonyl)phenyl]-2-{3-(trifluoromethyl)-5-[2-(trifluoromethyl)phenyl]-1H-pyrazol-1-yl}-1,3-thiazole |
| 411 | 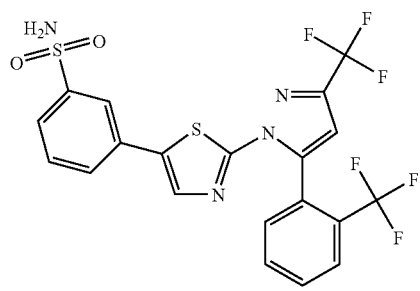 | 3-(2-{3-(trifluoromethyl)-5-[2-(trifluoromethyl)phenyl]-1H-pyrazol-1-yl}-1,3-thiazol-5-yl)benzenesulfonamide |

TABLE 1-continued

| | | |
|---|---|---|
| 412 | 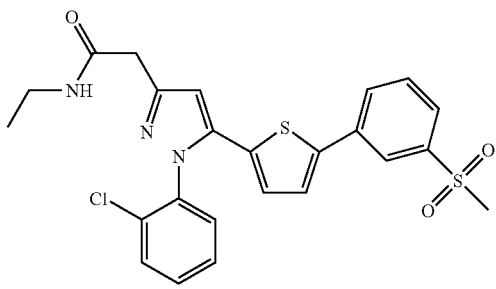 [SMILES: CCNC(=O)CC(=N)/C=C(\Nc1ccccc1Cl)c1ccc(-c2cccc(S(C)(=O)=O)c2)s1] | 2-(1-(2-chlorophenyl)-5-{5-[3-(methylsulfonyl)phenyl]-2-thienyl}-1H-pyrazol-3-yl)-N-ethylacetamide |
| 413 | 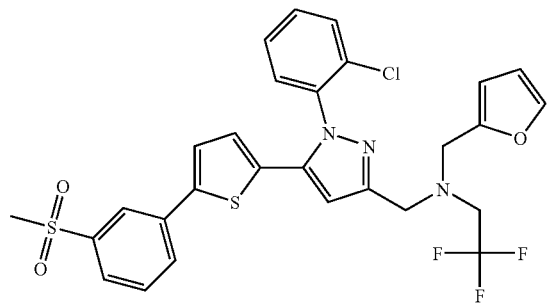 [SMILES: CS(=O)(=O)c1cccc(-c2ccc(-c3cc(CN(Cc4ccco4)CC(F)(F)F)nn3-c3ccccc3Cl)s2)c1] | N-[(1-(2-chlorophenyl)-5-{5-[3-(methylsulfonyl)phenyl]-2-thienyl}-1H-pyrazol-3-yl)methyl]-2,2,2-trifluoro-N-(furan-2-ylmethyl)ethanamine |
| 414 | 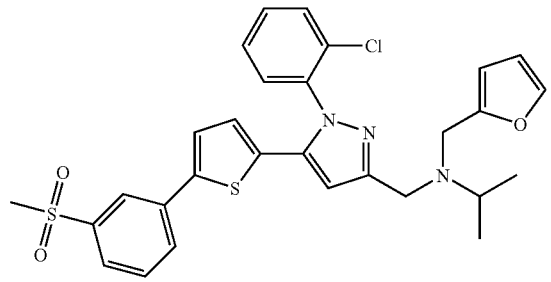 [SMILES: CC(C)N(Cc1cc(-c2ccc(-c3cccc(S(C)(=O)=O)c3)s2)n(-c2ccccc2Cl)n1)Cc1ccco1] | N-[(1-(2-chlorophenyl)-5-{5-[3-(methylsulfonyl)phenyl]-2-thienyl}-1H-pyrazol-3-yl)methyl]-N-(furan-2-ylmethyl)propan-2-amine |
| 415 | 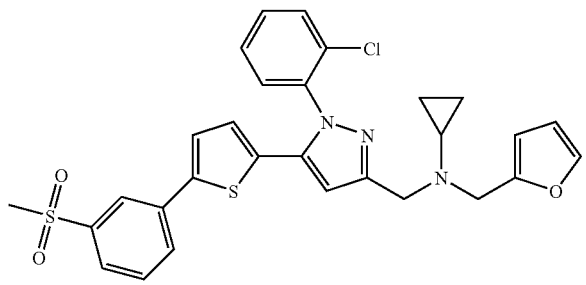 [SMILES: CS(=O)(=O)c1cccc(-c2ccc(-c3cc(CN(Cc4ccco4)C4CC4)nn3-c3ccccc3Cl)s2)c1] | N-[(1-(2-chlorophenyl)-5-{5-[3-(methylsulfonyl)phenyl]-2-thienyl}-1H-pyrazol-3-yl)methyl]-N-(furan-2-ylmethyl)cyclopropanamine |
| 416 | 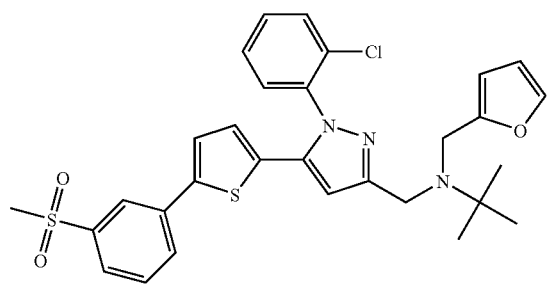 [SMILES: CC(C)(C)N(Cc1cc(-c2ccc(-c3cccc(S(C)(=O)=O)c3)s2)n(-c2ccccc2Cl)n1)Cc1ccco1] | N-[(1-(2-chlorophenyl)-5-{5-[3-(methylsulfonyl)phenyl]-2-thienyl}-1H-pyrazol-3-yl)methyl]-N-(furan-2-ylmethyl)-2-methylpropan-2-amine |

| | | |
|---|---|---|
| 417 | 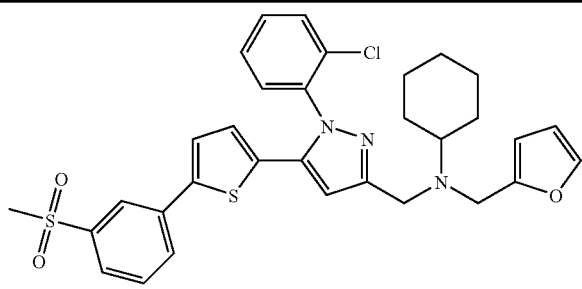 | N-[(1-(2-chlorophenyl)-5-{5-[3-(methylsulfonyl)phenyl]-2-thienyl}-1H-pyrazol-3-yl)methyl]-N-(furan-2-ylmethyl)cyclohexanamine |
| 418 | 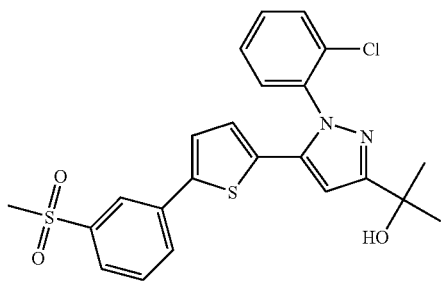 [SMILES: CC(C)(O)c1cc(-c2ccc(-c3cccc(S(C)(=O)=O)c3)s2)n(-c2ccccc2Cl)n1] | 2-(1-(2-chlorophenyl)-5-{5-[3-(methylsulfonyl)phenyl]-2-thienyl}-1H-pyrazol-3-yl)propan-2-ol |
| 419 | 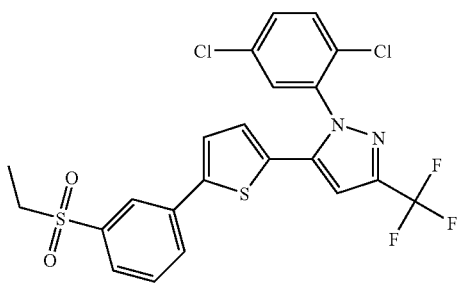 [SMILES: CCS(=O)(=O)c1cccc(-c2ccc(-c3cc(C(F)(F)F)nn3-c3cc(Cl)ccc3Cl)s2)c1] | 1-(2,5-dichlorophenyl)-5-{5-[3-(ethylsulfonyl)phenyl]-2-thienyl}-3-(trifluoromethyl)-1H-pyrazole |
| 420 | 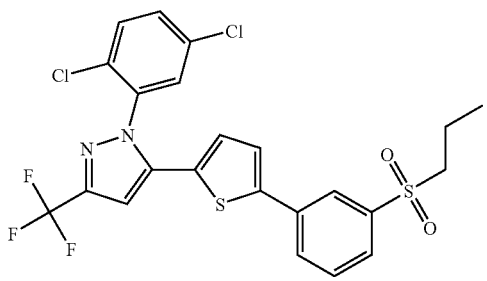 [SMILES: CCCS(=O)(=O)c1cccc(-c2ccc(-c3cc(C(F)(F)F)nn3-c3cc(Cl)ccc3Cl)s2)c1] | 1-(2,5-dichlorophenyl)-5-{5-[3-(propylsulfonyl)phenyl]-2-thienyl}-3-(trifluoromethyl)-1H-pyrazole |
| 421 | 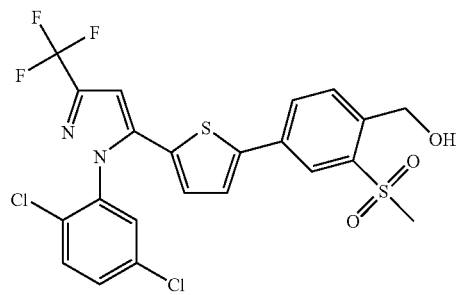 [SMILES: CS(=O)(=O)c1cc(-c2ccc(/C(=C/C(=N)C(F)(F)F)Nc3cc(Cl)ccc3Cl)s2)ccc1CO] | [4-{5-[1-(2,5-dichlorophenyl)-3-(trifluoromethyl)-1H-pyrazol-5-yl]-2-thienyl}-2-(methylsulfonyl)phenyl]methanol |

TABLE 1-continued

| 423 | 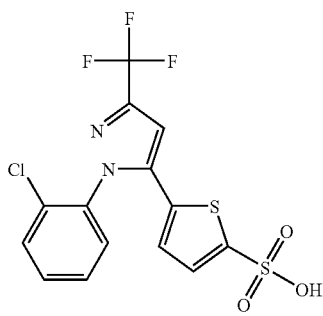 [SMILES: N=C(/C=C(\Nc1ccccc1Cl)c1ccc(S(=O)(=O)O)s1)C(F)(F)F] | 5-[1-(2-chlorophenyl)-3-(trifluoromethyl)-1H-pyrazol-5-yl]thiophene-2-sulfonic acid |
| 424 | 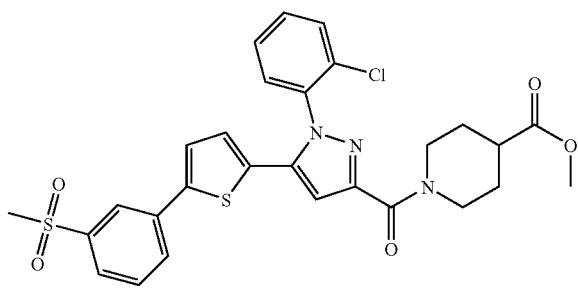 | methyl 1-[(1-(2-chlorophenyl)-5-{5-[3-(methylsulfonyl)phenyl]-2-thienyl}-1H-pyrazol-3-yl)carbonyl]piperidine-4-carboxylate |
| 425 | 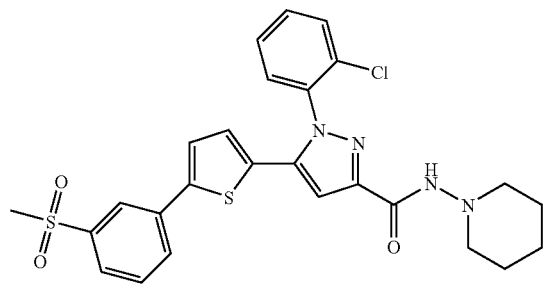 [SMILES: CS(=O)(=O)c1cccc(-c2ccc(-c3cc(C(=O)NN4CCCCC4)nn3-c3ccccc3Cl)s2)c1] | 1-(2-chlorophenyl)-5-{5-[3-(methylsulfonyl)phenyl]-2-thienyl}-N-piperidin-1-yl-1H-pyrazole-3-carboxamide |
| 426 | 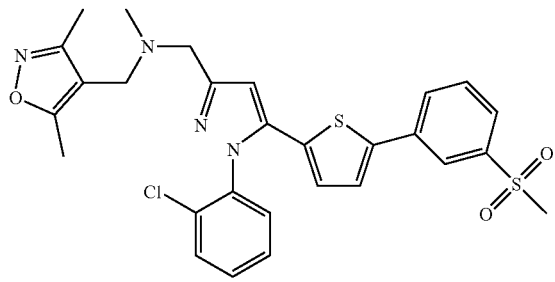 [SMILES: Cc1noc(C)c1CN(C)CC(=N)/C=C(\Nc1ccccc1Cl)c1ccc(-c2cccc(S(C)(=O)=O)c2)s1] | 1-[1-(2-chlorophenyl)-5-{5-[3-(methylsulfonyl)phenyl]-2-thienyl}-1H-pyrazol-3-yl]-N-[(3,5-dimethylisoxazol-4-yl)methyl]-N-methylmethanamine |
| 427 | 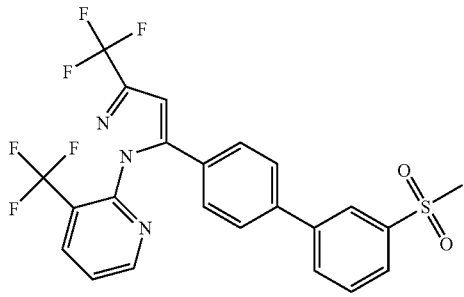 [SMILES: CS(=O)(=O)c1cccc(-c2ccc(/C(=C/C(=N)C(F)(F)F)Nc3ncccc3C(F)(F)F)cc2)c1] | 2-[5-[3'-(methylsulfonyl)biphenyl-4-yl]-3-(trifluoromethyl)-1H-pyrazol-1-yl]-3-(trifluoromethyl)pyridine |

TABLE 1-continued

| | | |
|---|---|---|
| 428 | 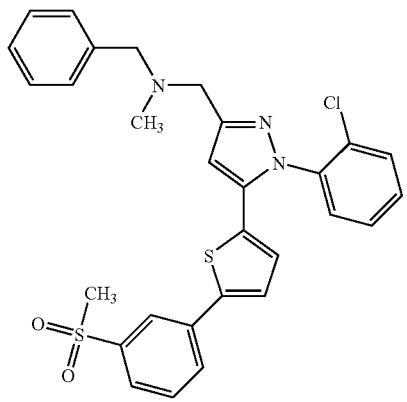 [SMILES: CN(Cc1ccccc1)Cc1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]-N-methyl-N-(phenylmethyl)methanamine |
| 429 | 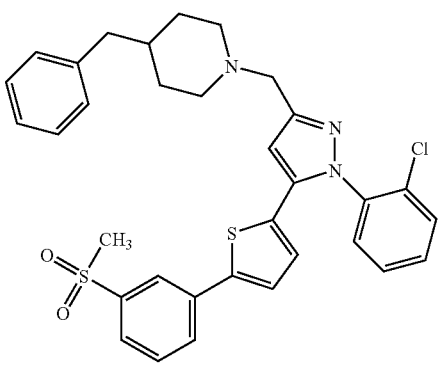 [SMILES: CS(=O)(=O)c1cccc(-c2ccc(-c3cc(CN4CCC(Cc5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-4-(phenylmethyl)piperidine |
| 430 | 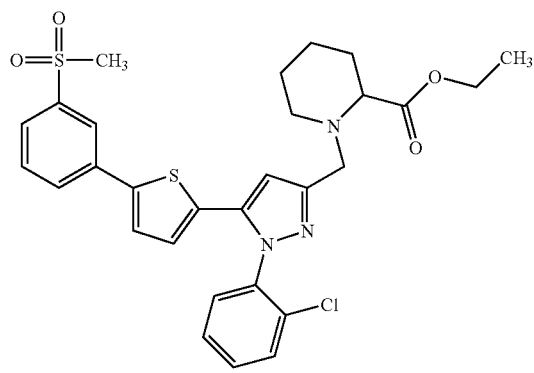 [SMILES: CCOC(=O)C1CCCCN1Cc1cc(-c2ccc(-c3cccc(S(C)(=O)=O)c3)s2)n(-c2ccccc2Cl)n1] | ethyl 1-{[1-(2-chlorophenyl)-5-{5-[3-(methylsulfonyl)phenyl]-2-thienyl}-1H-pyrazol-3-yl]methyl}piperidine-2-carboxylate |
| 431 | 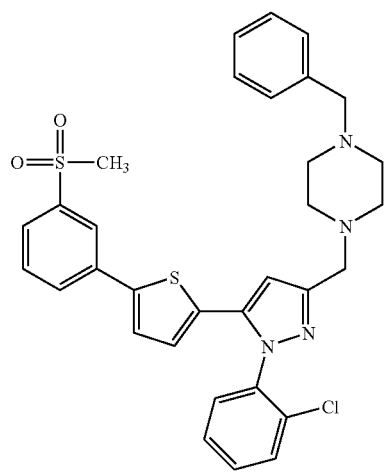 [SMILES: CS(=O)(=O)c1cccc(-c2ccc(-c3cc(CN4CCN(Cc5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-2-yl]methyl}-4-(phenylmethyl)piperazine |

| | | |
|---|---|---|
| 432 | 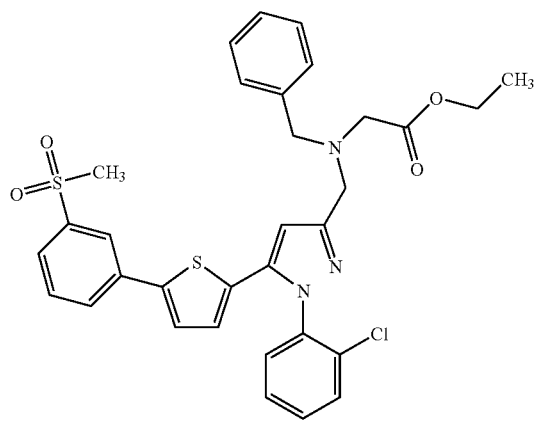 [SMILES: CCOC(=O)CN(CC(=N)/C=C(\Nc1ccccc1Cl)c1ccc(-c2cccc(S(C)(=O)=O)c2)s1)Cc1ccccc1] | ethyl N-{[1-(2-chlorophenyl)-5-{5-[3-(methylsulfonyl)phenyl]-2-thienyl}-1H-pyrazol-3-yl]methyl}-N-(phenylmethyl)glycinate |
| 433 | 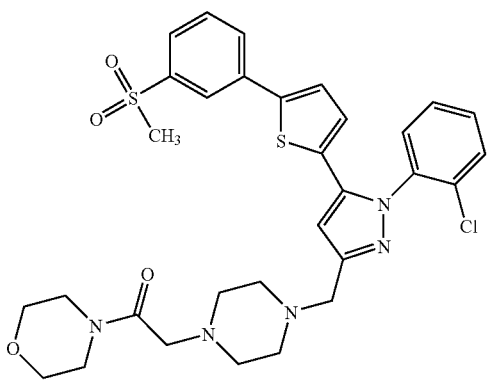 [SMILES: CS(=O)(=O)c1cccc(-c2ccc(-c3cc(CN4CCN(CC(=O)N5CCOCC5)CC4)nn3-c3ccccc3Cl)s2)c1] | 4-[(4-{[1-(2-chlorophenyl)-5-{5-[3-(methylsulfonyl)phenyl]-2-thienyl}-1H-pyrazol-3-yl]methyl}piperazin-1-yl)acetyl]morpholine |
| 434 | 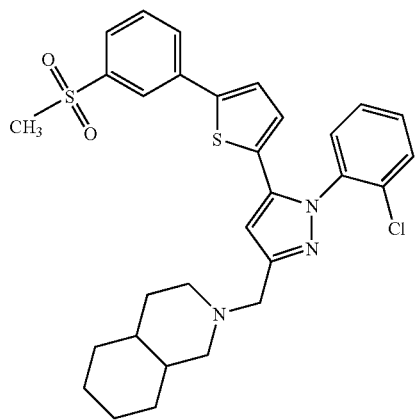 [SMILES: CS(=O)(=O)c1cccc(-c2ccc(-c3cc(CN4CCC5CCCCC5C4)nn3-c3ccccc3Cl)s2)c1] | 2-{[1-(2-chlorophenyl)-5-{5-[3-(methylsulfonyl)phenyl]-2-thienyl}-1H-pyrazol-3-yl]methyl}decahydroisoquinoline |

TABLE 1-continued

| 435 | 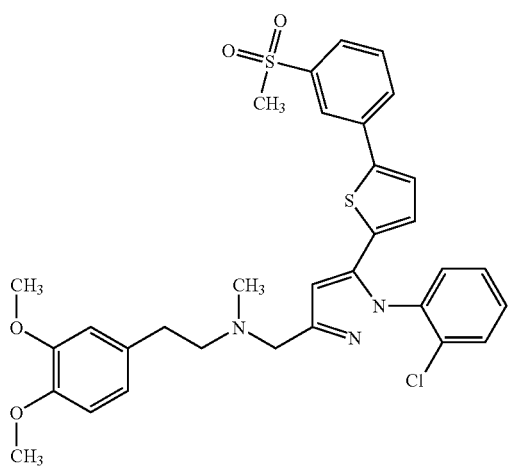 [SMILES: COc1ccc(CCN(C)CC(=N)/C=C(\Nc2ccccc2Cl)c2ccc(-c3cccc(S(C)(=O)=O)c3)s2)cc1OC] | 2-[3,4-bis(methyloxy)phenyl]-N-{[1-(2-chlorophenyl)-5-{5-[3-(methylsulfonyl)phenyl]-2-thienyl}-1H-pyrazol-3-yl]methyl}-N-methylmethanamine |
| --- | --- | --- |
| 436 | 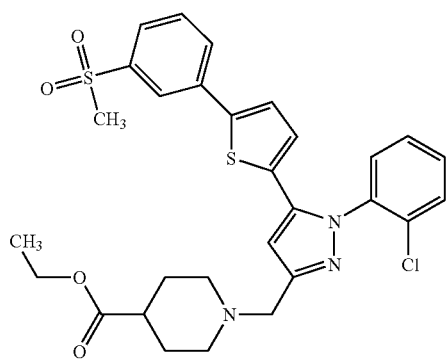 [SMILES: CCOC(=O)C1CCN(Cc2cc(-c3ccc(-c4cccc(S(C)(=O)=O)c4)s3)n(-c3ccccc3Cl)n2)CC1] | ethyl 1-{[1-(2-chlorophenyl)-5-{5-[3-(methylsulfonyl)phenyl]-2-thienyl}-1H-pyrazol-3-yl]methyl}piperidine-4-carboxylate |
| 437 | 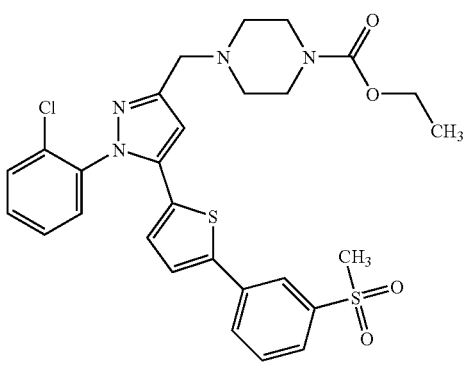 [SMILES: CCOC(=O)N1CCN(Cc2cc(-c3ccc(-c4cccc(S(C)(=O)=O)c4)s3)n(-c3ccccc3Cl)n2)CC1] | ethyl 4-{[1-(2-chlorophenyl)-5-{5-[3-(methylsulfonyl)phenyl]-2-thienyl}-1H-pyrazol-3-yl]methyl}piperazine-1-carboxylate |
| 438 | 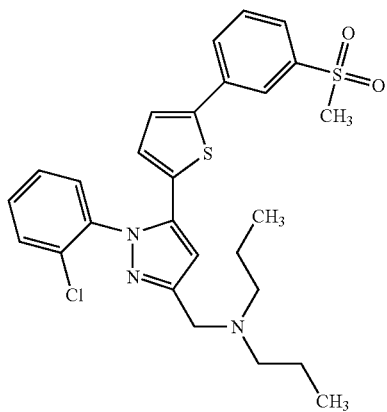 [SMILES: CCCN(CCC)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-propylpropan-1-amine |

| | | |
|---|---|---|
| 439 | 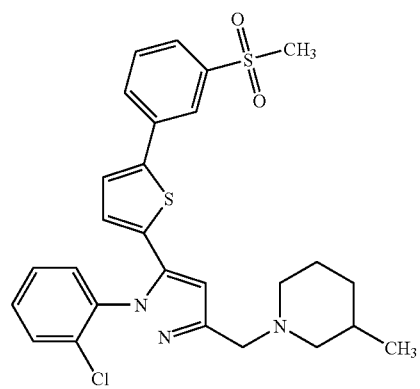 [SMILES: CC1CCCN(CC(=N)/C=C(\Nc2ccccc2Cl)c2ccc(-c3cccc(S(C)(=O)=O)c3)s2)C1] | 1-{[1-(2-chlorophenyl)-5-{5-[3-(methylsulfonyl)phenyl]-2-thienyl}-1H-pyrazol-3-yl]methyl}-3-methylpiperidine |
| 440 | 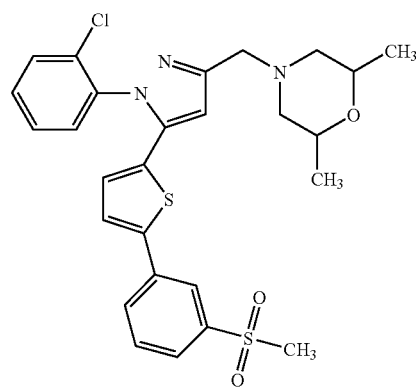 [SMILES: CC1CN(CC(=N)/C=C(\Nc2ccccc2Cl)c2ccc(-c3cccc(S(C)(=O)=O)c3)s2)CC(C)O1] | 4-{[1-(2-chlorophenyl)-5-{5-[3-(methylsulfonyl)phenyl]-2-thienyl}-1H-pyrazol-3-yl]methyl}-2,6-dimethylmorpholine |
| 441 | 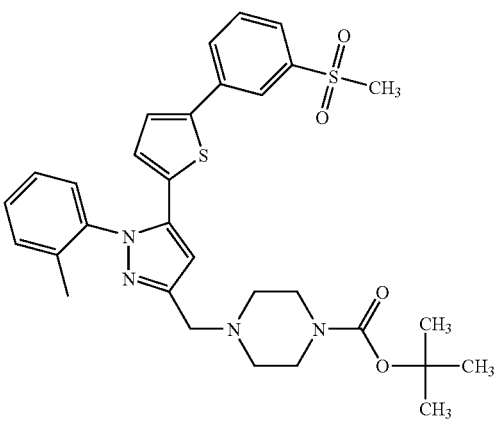 [SMILES: Cc1ccccc1-n1nc(CN2CCN(C(=O)OC(C)(C)C)CC2)cc1-c1ccc(-c2cccc(S(C)(=O)=O)c2)s1] | 1,1-dimethylethyl 4-{[1-(2-cholorophenyl)-5-{5-[3-(methylsulfonyl)phenyl]-2-thienyl}-1H-pyrazole-3-yl]methyl}piperazine-1-carboxylate |
| 442 | 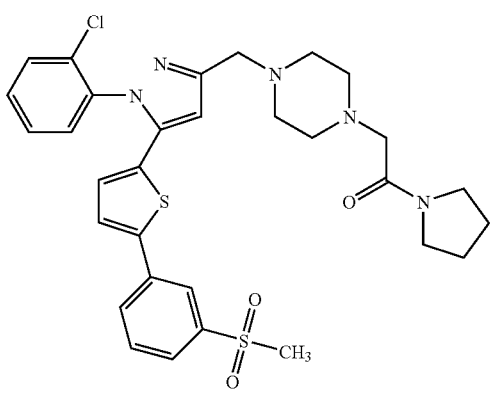 [SMILES: CS(=O)(=O)c1cccc(-c2ccc(/C(=C/C(=N)CN3CCN(CC(=O)N4CCCC4)CC3)Nc3ccccc3Cl)s2)c1] | 1-{[1-(2-chlorophenyl)-5-{5-[3-(methylsulfonyl)phenyl]-2-thienyl}-1H-pyrazol-3-yl]methyl}-4-(2-oxo-2-pyrrolidin-1-ylethyl)piperazine |

TABLE 1-continued

| | | |
|---|---|---|
| 443 | 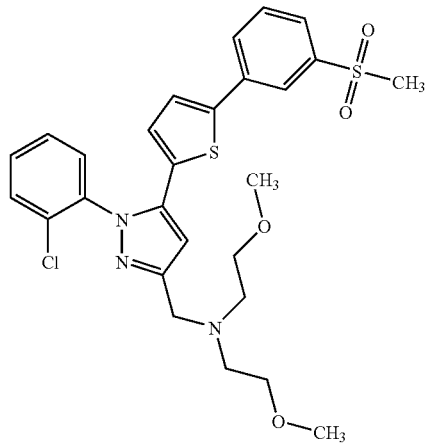 [SMILES: COCCN(CCOC)Cc1cc(-c2ccc(-c3cccc(S(C)(=O)=O)c3)s2)n(-c2ccccc2Cl)n1] | N-{1-(2-chlorophenyl)-5-{5-[3-(methylsulfonyl)phenyl]-2-thienyl}-1H-pyrazol-3-yl]methyl}-2-(methyloxy)-N-[2-(methyloxy)ethyl]ethanamine |
| 444 | 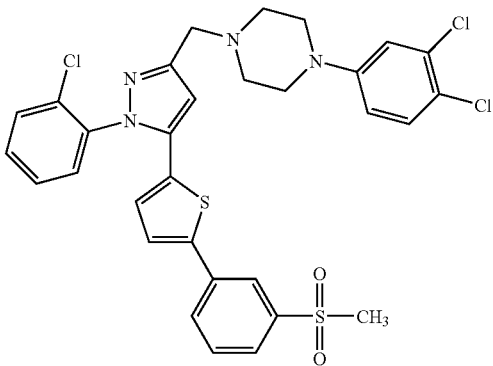 [SMILES: CS(=O)(=O)c1cccc(-c2ccc(-c3cc(CN4CCN(c5ccc(Cl)c(Cl)c5)CC4)nn3-c3ccccc3Cl)s2)c1] | 1-{[1-(2-chlorophenyl)-5-{5-[2-(methylsulfonyl)phenyl]-2-thienyl}-1H-pyrazol-3-yl]methyl}-4-(3,4-dichlorophenyl)piperazine |
| 445 | 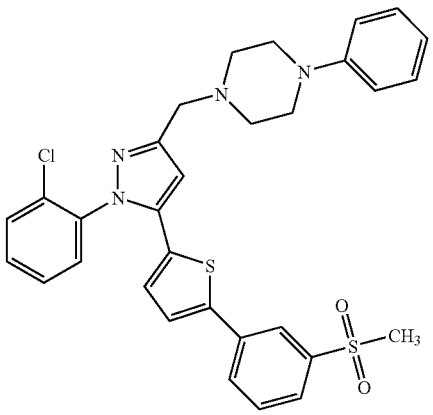 [SMILES: CS(=O)(=O)c1cccc(-c2ccc(-c3cc(CN4CCN(c5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-4-phenylpiperazine |
| 446 | 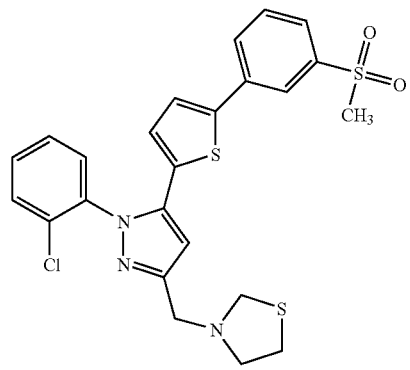 [SMILES: CS(=O)(=O)c1cccc(-c2ccc(-c3cc(CN4CCSC4)nn3-c3ccccc3Cl)s2)c1] | 3-{[1-(2-chlorophenyl)-5-{5-[3-(methylsulfonyl)phenyl]-2-thienyl}-1H-pyrazol-3-yl]methyl}-1,3-thiazolidine |

TABLE 1-continued
447 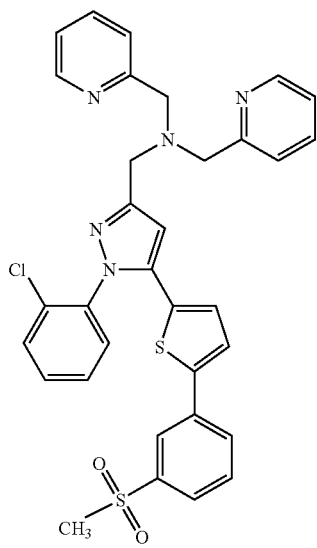 [SMILES: CS(=O)(=O)c1cccc(-c2ccc(-c3cc(CN(Cc4ccccn4)Cc4ccccn4)nn3-c3ccccc3Cl)s2)c1]
1-[1-(2-chlorophenyl)-5-{5-[3-(methylsulfonyl)phenyl]-2-thienyl]-1H-pyrazol-3-yl]-N,N-bis(pyridin-2-ylmethyl)methanamine
448 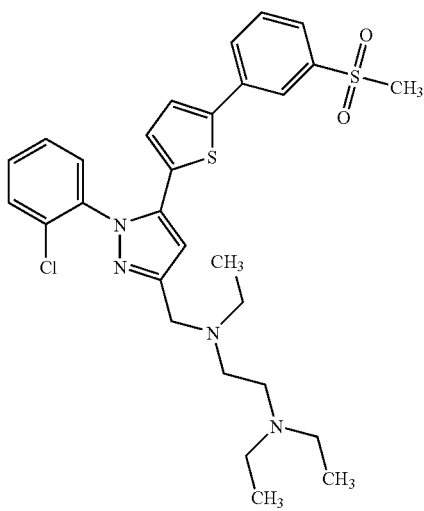 [SMILES: CCN(CC)CCN(CC)Cc1cc(-c2ccc(-c3cccc(S(C)(=O)=O)c3)s2)n(-c2ccccc2Cl)n1]
N-{[1-(2-chlorophenyl)-5-{5-[3-(methylsulfonyl)phenyl]-2-thienyl}-1H-pyrazol-3-yl]methyl}-N,N',N'-triethylethane-1,2-diamine
449 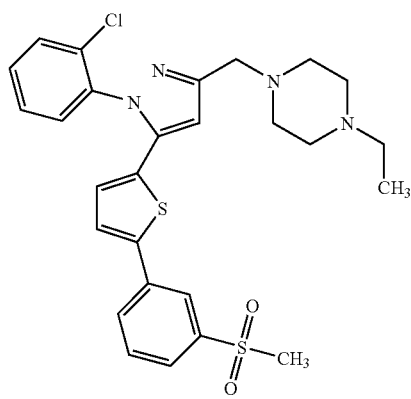 [SMILES: CCN1CCN(CC(=N)/C=C(\Nc2ccccc2Cl)c2ccc(-c3cccc(S(C)(=O)=O)c3)s2)CC1]
1-{[1-(2-chlorophenyl)-5-{5-[3-(mehtylsulfonyl)phenyl]-2-thienyl}-1H-pyrazol-3-yl]methyl}-4-ethylpiperazine TABLE 1-continued

| # | Structure | Name |
|---|---|---|
| 450 | 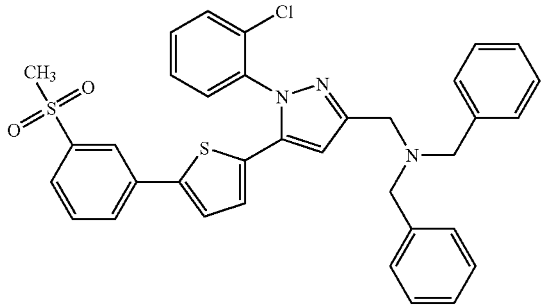 [SMILES: CS(=O)(=O)c1cccc(-c2ccc(-c3cc(CN(Cc4ccccc4)Cc4ccccc4)nn3-c3ccccc3Cl)s2)c1] | 1-[1-(2-chlorophenyl)-5-{5-[3-(methylsulfonyl)phenyl]-2-thienyl}-1H-pyrazol-3-yl]-N,N-bis(phenylmethyl)methanamine |
| 451 | 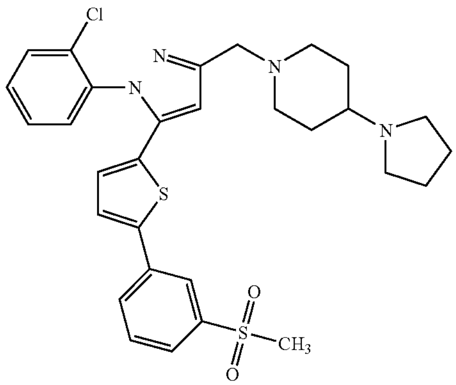 [SMILES: CS(=O)(=O)c1cccc(-c2ccc(/C(=C/C(=N)CN3CCC(N4CCCC4)CC3)Nc3ccccc3Cl)s2)c1] | 1-{[1-(2-chlorophenyl)-5-{5-[3-(methylsulfonyl)phenyl]-2-thienyl}-1H-pyrazol-3-yl]methyl}-4-pyrrolidin-1-ylpiperidine |
| 452 | 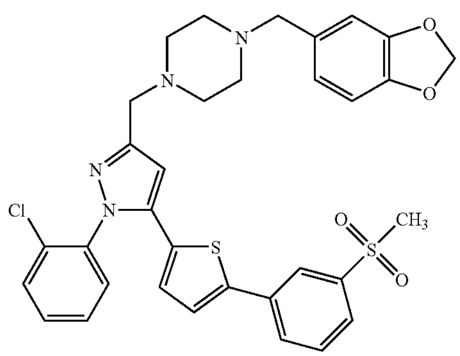 [SMILES: CS(=O)(=O)c1cccc(-c2ccc(-c3cc(CN4CCN(Cc5ccc6c(c5)OCO6)CC4)nn3-c3ccccc3Cl)s2)c1] | 1-(1,3-benzodioxol-5-ylmethyl)-4-{[1-(2-chlorophenyl)-5-{5-[3-(methylsulfonyl)phenyl]-2-thienyl}-1H-pyrazol-3-yl]methyl}piperazine |
| 453 | 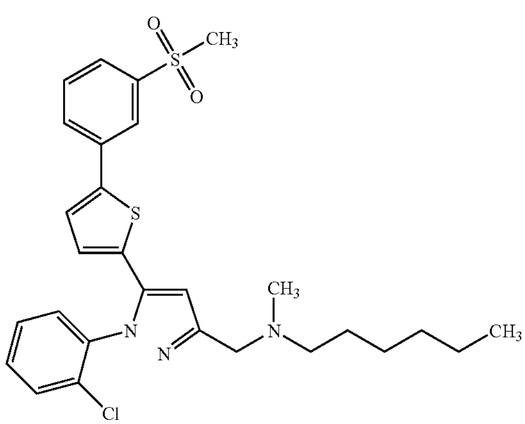 [SMILES: CCCCCCN(C)CC(=N)/C=C(\Nc1ccccc1Cl)c1ccc(-c2cccc(S(C)(=O)=O)c2)s1] | N-{[1-(2-chlorophenyl)-5-{5-[3-(methylsulfonyl)phenyl]-2-thienyl}-1H-pyrazol-3-yl]methyl}-N-methylhexan-1-amine |

| | | |
|---|---|---|
| 454 | 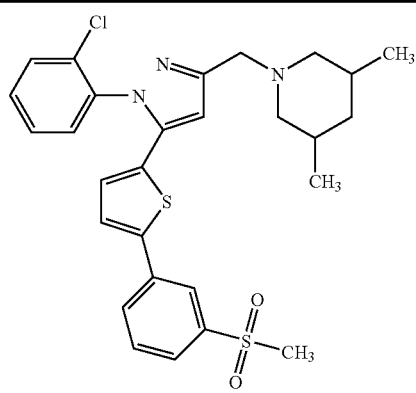 | 1-{[1-(2-chlorophenyl)-5-{6-[3-(methylsulfonyl)phenyl]-2-thienyl}-1H-pyrazol-3-yl]methyl}-3,5-dimethylpiperidine |
| 455 | 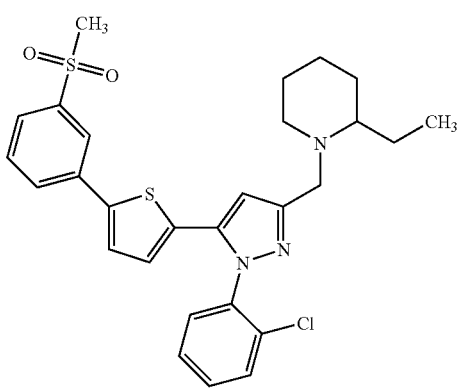 [SMILES: CCC1CCCCN1Cc1cc(-c2ccc(-c3cccc(S(C)(=O)=O)c3)s2)n(-c2ccccc2Cl)n1] | 1-{[1-(2-chlorophenyl)-5-{5-[3-(methylsulfonyl)phenyl]-2-thienyl}-1H-pyrazol-3-yl]methyl}-2-ethylpiperidine |
| 456 | 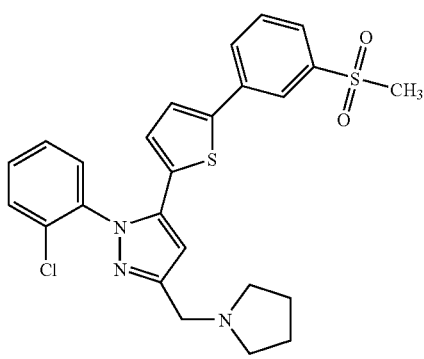 [SMILES: CS(=O)(=O)c1cccc(-c2ccc(-c3cc(CN4CCCC4)nn3-c3ccccc3Cl)s2)c1] | 1-(2-chlorophenyl)-5-{5-[3-(methylsulfonyl)phenyl]-2-thienyl}-3-(pyrrolidin-1-ylmethyl)-1H-pyrazole |
| 457 | 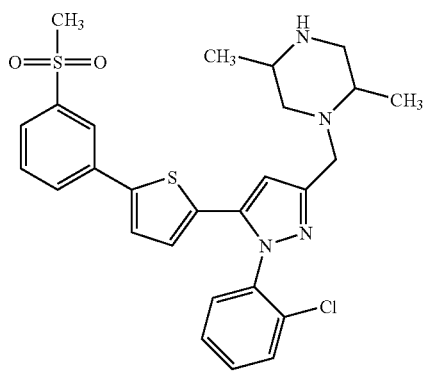 [SMILES: CC1CN(Cc2cc(-c3ccc(-c4cccc(S(C)(=O)=O)c4)s3)n(-c3ccccc3Cl)n2)C(C)CN1] | 1-{[1-(2-chlorophenyl)-5-{5-[3-(methylsulfonyl)phenyl]-2-thienyl}-1H-pyrazol-3-yl]methyl}-2,5-dimethylpiperazine |

TABLE 1-continued

| 458 | 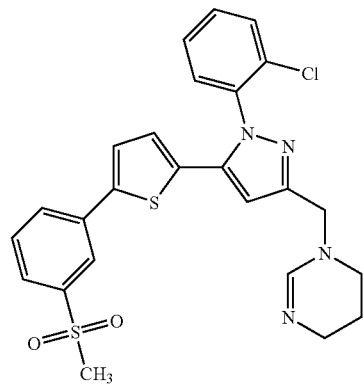 [SMILES: CS(=O)(=O)c1cccc(-c2ccc(-c3cc(CN4C=NCCC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-1,4,5,6-tetrahydropyrimidine |
| --- | --- | --- |
| 459 | 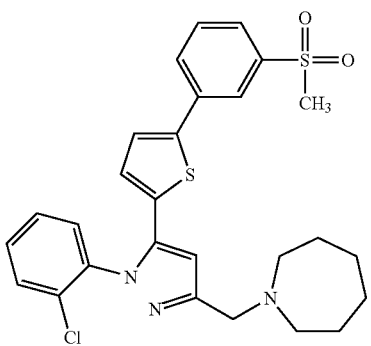 [SMILES: CS(=O)(=O)c1cccc(-c2ccc(/C(=C/C(=N)CN3CCCCCC3)Nc3ccccc3Cl)s2)c1] | 1-{[1-(2-chlorophenyl)-5-{5-[3-(methylsulfonyl)phenyl]-2-thienyl}-1H-pyrazol-3-yl]methyl}azepane |
| 460 | 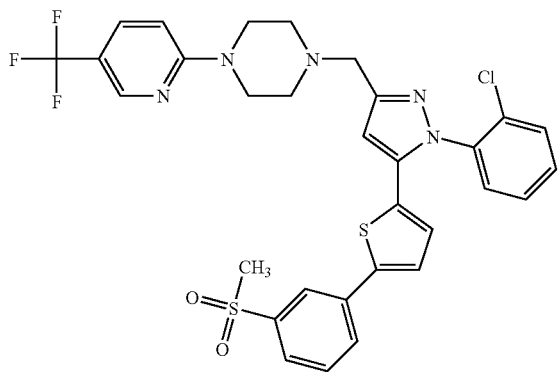 [SMILES: CS(=O)(=O)c1cccc(-c2ccc(-c3cc(CN4CCN(c5ccc(C(F)(F)F)cn5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-4-[5-(trifluoromethyl)pyridin-2-yl]piperazine |
| 461 | 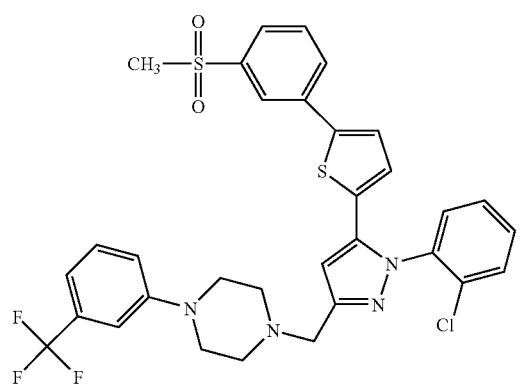 [SMILES: CS(=O)(=O)c1cccc(-c2ccc(-c3cc(CN4CCN(c5cccc(C(F)(F)F)c5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-4-{3-(trifluoromethyl)phenyl]piperazine |

TABLE 1-continued
462 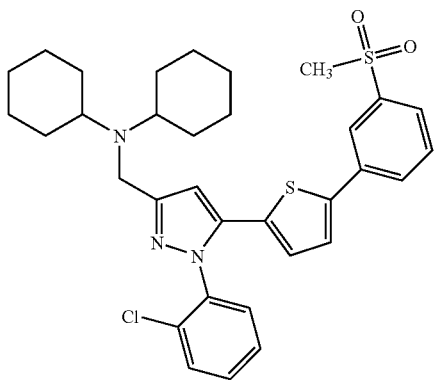 [SMILES: CS(=O)(=O)c1cccc(-c2ccc(-c3cc(CN(C4CCCCC4)C4CCCCC4)nn3-c3ccccc3Cl)s2)c1]
N-{[1-(2-chlorophenyl)-5-{5-[3-(methylsulfonyl)phenyl]-2-thienyl}-1H-pyrazol-3-yl]methyl}-N-cyclohexylcyclohexanamine
463 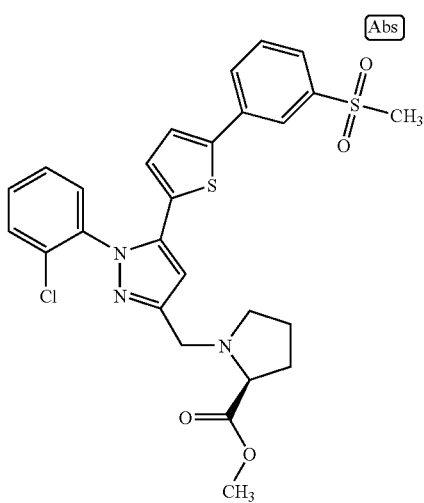 [SMILES: COC(=O)[C@@H]1CCCN1Cc1cc(-c2ccc(-c3cccc(S(C)(=O)=O)c3)s2)n(-c2ccccc2Cl)n1]
methyl 1-{[1-(2-chlorophenyl)-5-{5-[3-(methylsulfonyl)phenyl]-2-thienyl}-1H-pyrazol-3-yl]methyl}-L-prolinate
464 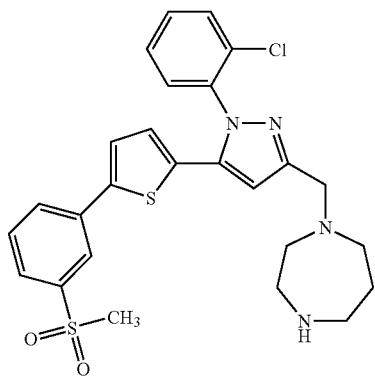 [SMILES: CS(=O)(=O)c1cccc(-c2ccc(-c3cc(CN4CCCNCC4)nn3-c3ccccc3Cl)s2)c1]
1-{[1-(2-chlorophenyl)-5-{5-[3-(methylsulfonyl)phenyl]-2-thienyl}-1H-pyrazol-3-yl]methyl}-1,4-diazepane TABLE 1-continued

| 465 | 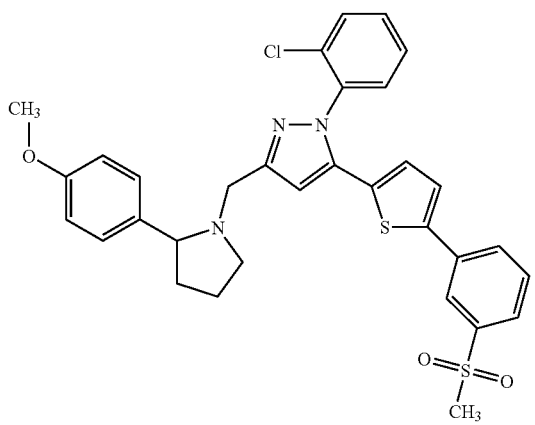 [SMILES: COc1ccc(C2CCCN2Cc2cc(-c3ccc(-c4cccc(S(C)(=O)=O)c4)s3)n(-c3ccccc3Cl)n2)cc1] | 1-(2-chlorophenyl)-3-({2-[4-(ethyloxy)phenyl]pyrrolidin-1-yl}methyl)-5-{5-[3-(methylsulfonyl)phenyl]-2-thienyl}-1H-pyrazole |
| --- | --- | --- |
| 466 | 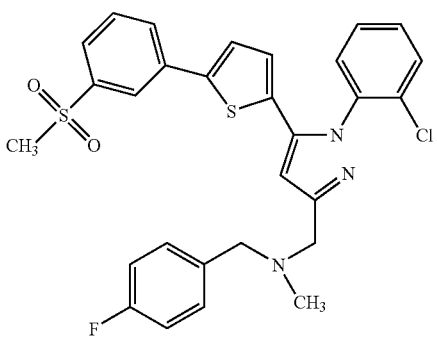 [SMILES: CN(CC(=N)/C=C(\Nc1ccccc1Cl)c1ccc(-c2cccc(S(C)(=O)=O)c2)s1)Cc1ccc(F)cc1] | 1-[1-(2-chlorophenyl)-5-{5-[3-(methylsulfonyl)phenyl]-2-thienyl}-1H-pyrazol-3-yl]-N-{(4-fluorophenyl)methyl]-N-methylmethanamine |
| 467 | 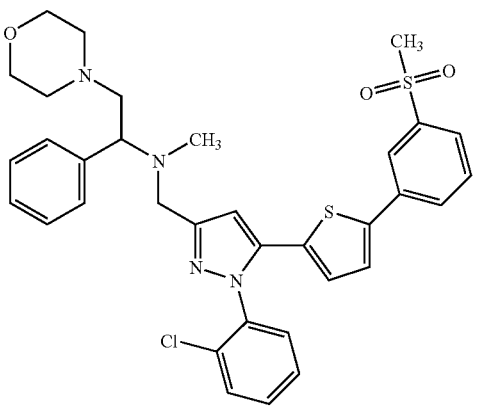 [SMILES: CN(Cc1cc(-c2ccc(-c3cccc(S(C)(=O)=O)c3)s2)n(-c2ccccc2Cl)n1)C(CN1CCOCC1)c1ccccc1] | N-{[1-(2-chlorophenyl)-5-{5-[3-(methylsulfonyl)phenyl]-2-thienyl}-1H-pyrazol-3-yl]methyl}-N-methyl-2-morpholin-4-yl-1-phenylethanamine |
| 468 | 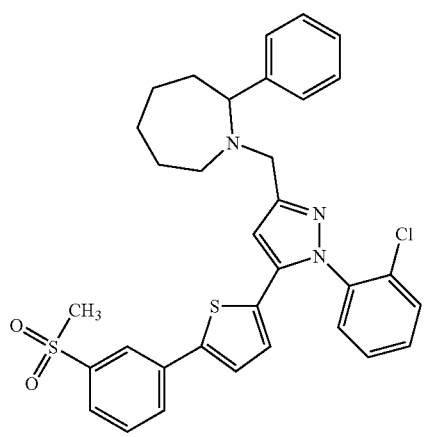 [SMILES: CS(=O)(=O)c1cccc(-c2ccc(-c3cc(CN4CCCCCC4c4ccccc4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-2-phenylazepan |

| | | |
|---|---|---|
| 469 | 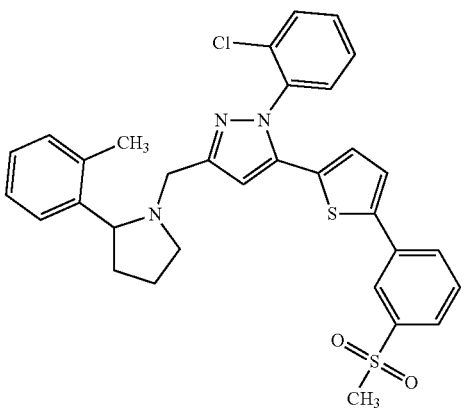 [SMILES: Cc1ccccc1C1CCCN1Cc1cc(-c2ccc(-c3cccc(S(C)(=O)=O)c3)s2)n(-c2ccccc2Cl)n1] | 1-(2-chlorophenyl)-3-{[2-(2-methylphenyl)pyrrolidin-1-yl]methyl}-5-{5-[3-(methylsulfonyl)phenyl]-2-thienyl}-1H-pyrazole |
| 470 | 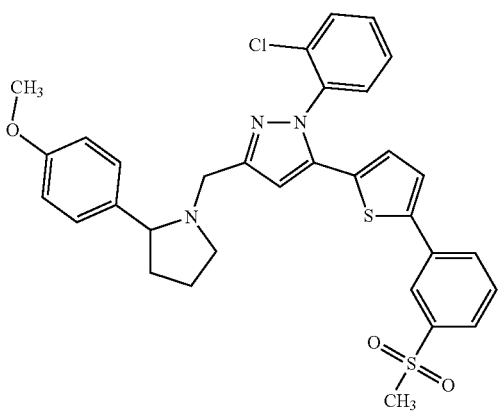 [SMILES: COc1ccc(C2CCCN2Cc2cc(-c3ccc(-c4cccc(S(C)(=O)=O)c4)s3)n(-c3ccccc3Cl)n2)cc1] | 1-(2-chlorophenyl)-3-({2-[4-(methyloxy)phenyl]pyrrolidin-1-yl}methyl)-5-{5-[3-(methylsulfonyl)phenyl]-2-thienyl}-1H-pyrazole |
| 471 | 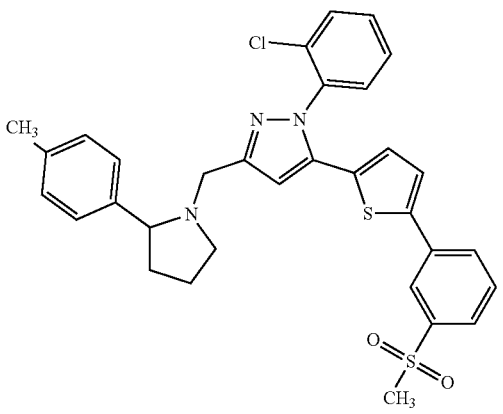 [SMILES: Cc1ccc(C2CCCN2Cc2cc(-c3ccc(-c4cccc(S(C)(=O)=O)c4)s3)n(-c3ccccc3Cl)n2)cc1] | 1-(2-chlorophenyl)-3-{[2-(4-methylphenyl)pyrrolidin-1-yl]methyl}-5-{5-[3-(methylsulfonyl)phenyl]-2-thienyl}-1H-pyrazole |
| 472 | 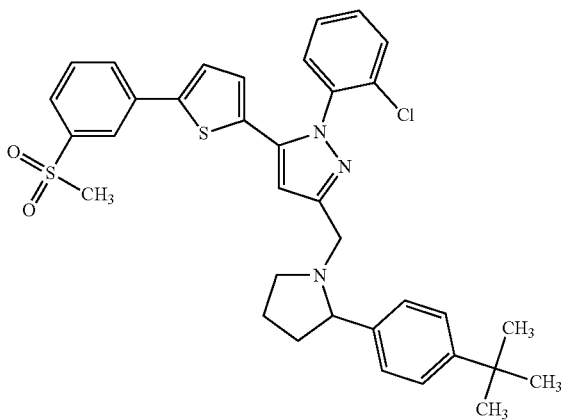 [SMILES: CC(C)(C)c1ccc(C2CCCN2Cc2cc(-c3ccc(-c4cccc(S(C)(=O)=O)c4)s3)n(-c3ccccc3Cl)n2)cc1] | 1-(2-chlorophenyl)-3-({2-[4-(1,1-dimethylethyl)phenyl]pyrrolidin-1-yl}methyl)-5-{5-[3-(methylsulfonyl)phenyl]-2-thienyl}-1H-pyrazole |

| | | |
|---|---|---|
| 473 | 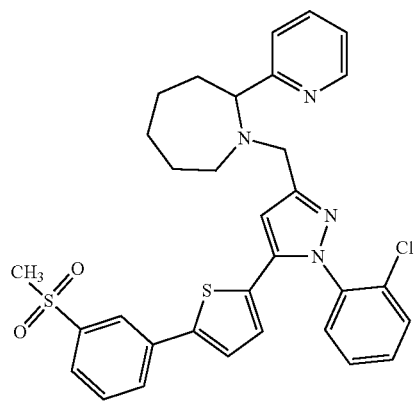 [SMILES: CS(=O)(=O)c1cccc(-c2ccc(-c3cc(CN4CCCCCC4c4ccccn4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-2-pyridin-2-ylazepane |
| 474 | 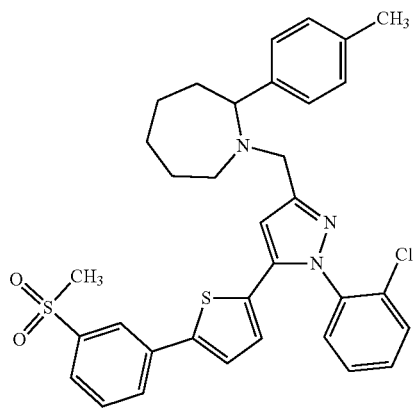 [SMILES: Cc1ccc(C2CCCCCN2Cc2cc(-c3ccc(-c4cccc(S(C)(=O)=O)c4)s3)n(-c3ccccc3Cl)n2)cc1] | 1-{[1-(2-chlorophenyl)-5-{5-[3-(methylsulfonyl)phenyl]-2-thienyl}-1H-pyrazol-3-yl]methyl}-2-(4-methylphenyl)azepane |
| 475 | 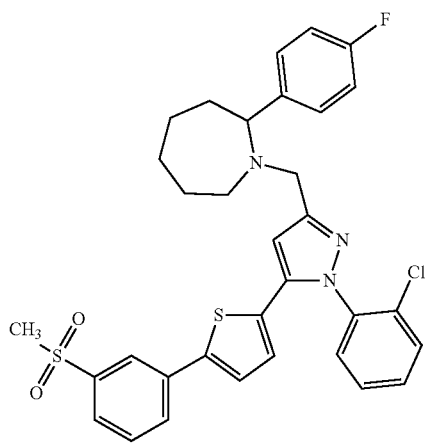 [SMILES: CS(=O)(=O)c1cccc(-c2ccc(-c3cc(CN4CCCCCC4c4ccc(F)cc4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-2-(4-fluorophenyl)azepane |

TABLE 1-continued
| | | |
|---|---|---|
| 476 | 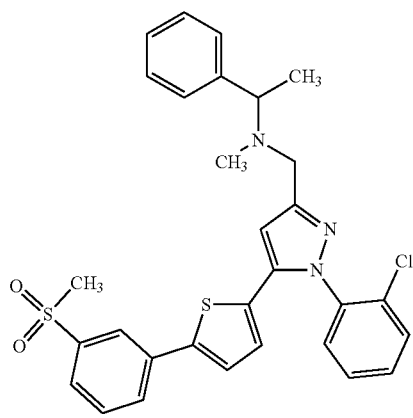 [SMILES: CC(c1ccccc1)N(C)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-methyl-1-phenylethanamine |
| 477 | 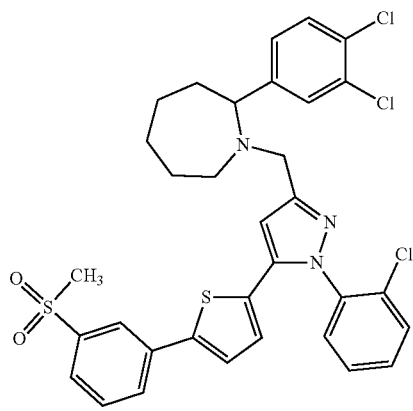 [SMILES: CS(=O)(=O)c1cccc(-c2ccc(-c3cc(CN4CCCCCC4c4ccc(Cl)c(Cl)c4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-2-(3,4-dichlorophenyl)azepane |
| 478 | 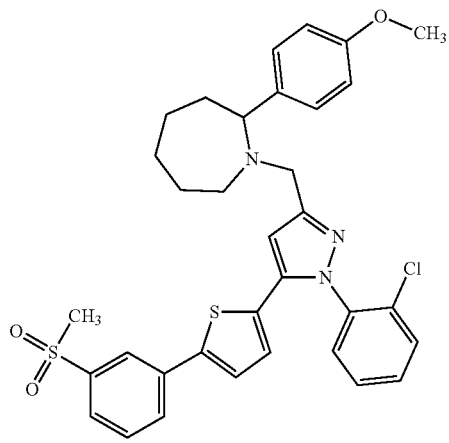 [SMILES: COc1ccc(C2CCCCCN2Cc2cc(-c3ccc(-c4cccc(S(C)(=O)=O)c4)s3)n(-c3ccccc3Cl)n2)cc1] | 1-{[1-(2-chlorophenyl)-5-{5-[3-(methylsulfonyl)phenyl]-2-thienyl}-1H-pyrazol-3-yl]methyl}-2-[4-(methyloxy)phenyl]azepane |

| | | |
|---|---|---|
| 479 | 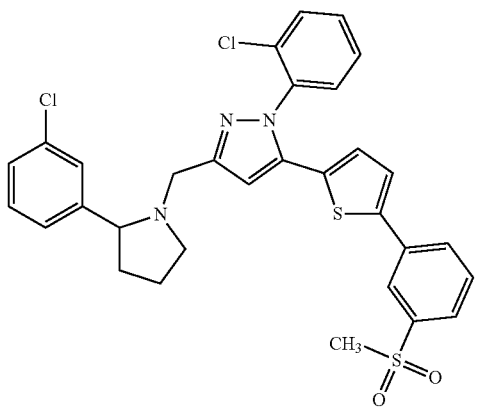 [SMILES: CS(=O)(=O)c1cccc(-c2ccc(-c3cc(CN4CCCC4c4cccc(Cl)c4)nn3-c3ccccc3Cl)s2)c1] | 1-(2-chlorophenyl)-3-{[2-(3-chlorophenyl)pyrrolidin-1-yl]methyl}-5-{5-[3-(methylsulfonyl)phenyl]-2-thienyl}-1H-pyrazole |
| 480 | 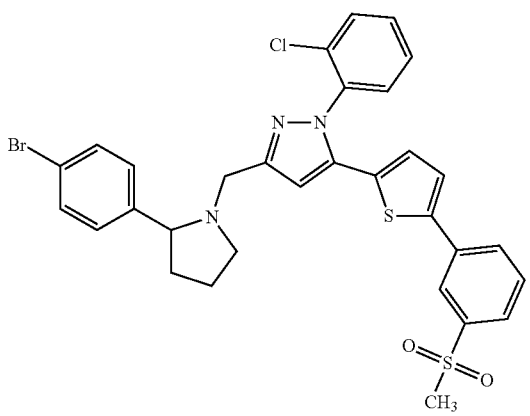 [SMILES: CS(=O)(=O)c1cccc(-c2ccc(-c3cc(CN4CCCC4c4ccc(Br)cc4)nn3-c3ccccc3Cl)s2)c1] | 3-{[2-(4-bromophenyl)pyrrolidin-1-yl]methyl}-1-(2-chlorophenyl)-5-{5-[3-(methylsulfonyl)phenyl]-2-thienyl}-1H-pyrazole |
| 481 | 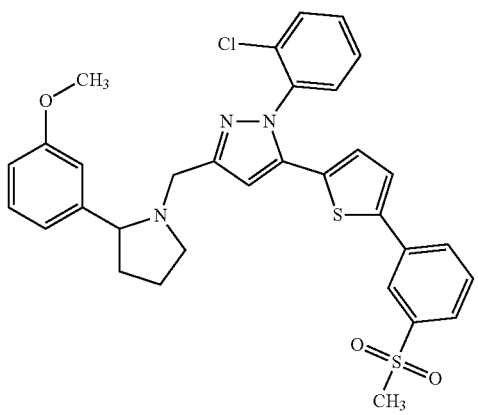 [SMILES: COc1cccc(C2CCCN2Cc2cc(-c3ccc(-c4cccc(S(C)(=O)=O)c4)s3)n(-c3ccccc3Cl)n2)c1] | 1-(2-chlorophenyl)-3-({2-[3-(methyloxy)phenyl]pyrrolidin-1-yl}methyl)-5-{5-[3-(methylsulfonyl)phenyl]-2-thienyl}-1H-pyrazole |
| 482 | 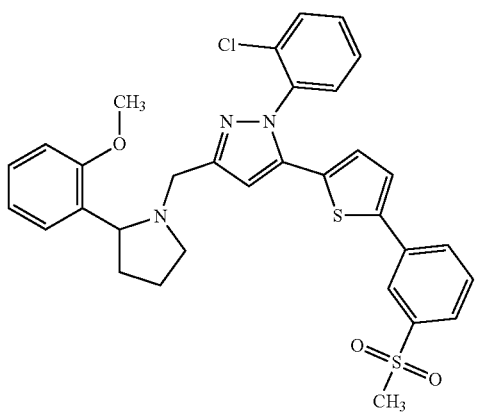 [SMILES: COc1ccccc1C1CCCN1Cc1cc(-c2ccc(-c3cccc(S(C)(=O)=O)c3)s2)n(-c2ccccc2Cl)n1] | 1-(2-chlorophenyl)-3-({2-[2-(methyloxy)phenyl]pyrrolidin-1-yl}methyl)-5-{5-[3-(methylsulfonyl)phenyl]-2-thienyl}-1H-pyrazole |

| | | |
|---|---|---|
| 483 | 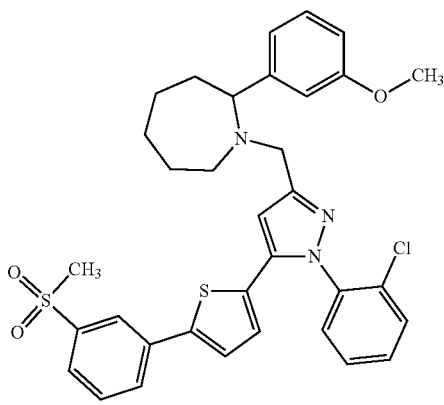 [SMILES: COc1cccc(C2CCCCCN2Cc2cc(-c3ccc(-c4cccc(S(C)(=O)=O)c4)s3)n(-c3ccccc3Cl)n2)c1] | 1-{[1-(2-chlorophenyl)-5-{5-[3-(methylsulfonyl)phenyl]-2-thienyl}-1H-pyrazol-3-yl]methyl}-2-[3-(methyloxy)phenyl]azepane |
| 484 | 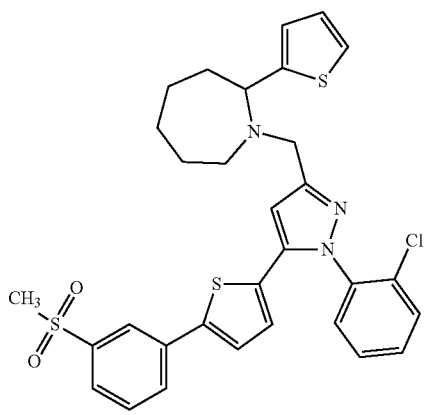 [SMILES: CS(=O)(=O)c1cccc(-c2ccc(-c3cc(CN4CCCCCC4c4cccs4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-2-(2-thienyl)azepane |
| 485 | 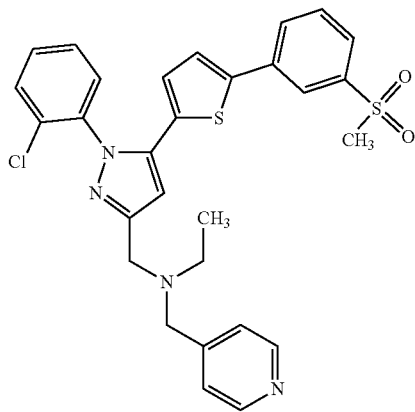 [SMILES: CCN(Cc1ccncc1)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-(pyridin-4-ylmethyl)ethanamine |
| 486 | 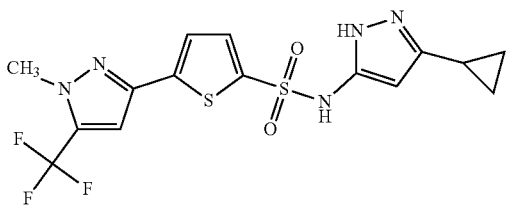 [SMILES: Cn1nc(-c2ccc(S(=O)(=O)Nc3cc(C4CC4)n[nH]3)s2)cc1C(F)(F)F] | N-(3-cyclopropyl-1H-pyrazol-5-yl)-5-[1-methyl-5-(trifluoromethyl)-1H-pyrazol-3-yl]thiophene-2-sulfonamide |

TABLE 1-continued

| | | |
|---|---|---|
| 487 | 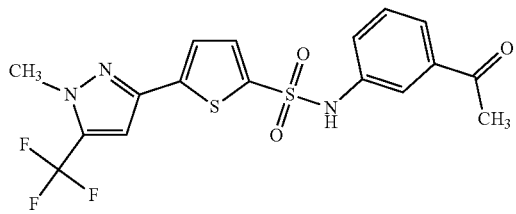 [SMILES: CC(=O)c1cccc(NS(=O)(=O)c2ccc(-c3cc(C(F)(F)F)n(C)n3)s2)c1] | N-(3-acetylphenyl)-5-[1-methyl-5-(trifluoromethyl)-1H-pyrazol-3-yl]thiophene-2-sulfonamide |
| 488 | 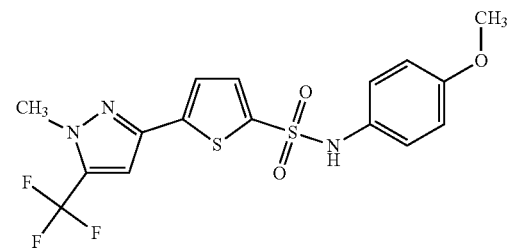 | N-[4-(methyloxy)phenyl]-5-[1-methyl-5-(trifluoromethyl)-1H-pyrazol-3-yl]thiophene-2-sulfonamide |
| 489 | 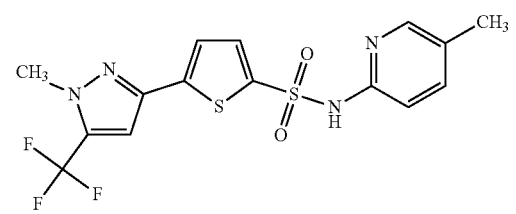 | N-(5-methylpyridin-2-yl)-5-[1-methyl-5-(trifluoromethyl)-1H-pyrazol-3-yl]thiophene-2-sulfonamide |
| 490 | 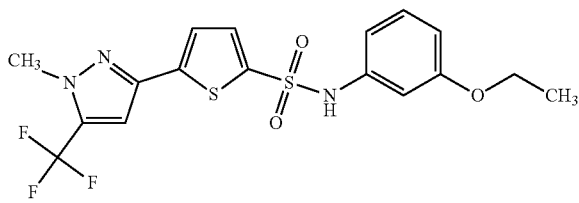 [SMILES: CCOc1cccc(NS(=O)(=O)c2ccc(-c3cc(C(F)(F)F)n(C)n3)s2)c1] | N-[3-(ethyloxy)phenyl]-5-[1-methyl-5-(trifluoromethyl)-1H-pyrazol-3-yl]thiophene-2-sulfonamide |
| 491 | 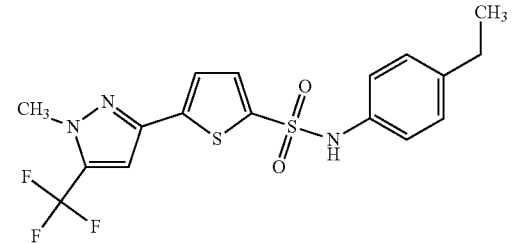 [SMILES: CCc1ccc(NS(=O)(=O)c2ccc(-c3cc(C(F)(F)F)n(C)n3)s2)cc1] | N-(4-ethylphenyl)-5-[1-methyl-5-(trifluoromethyl)-1H-pyrazol-3-yl]thiophene-2-sulfonamide |
| 492 | 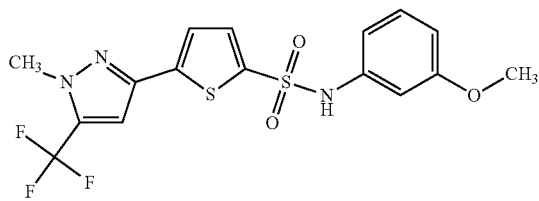 | N-[3-(methyloxy)phenyl]-5-[4-methyl-5-(trifluoromethyl)-1H-pyrazol-3-yl]thiophene-2-sulfonamide |
| 493 | 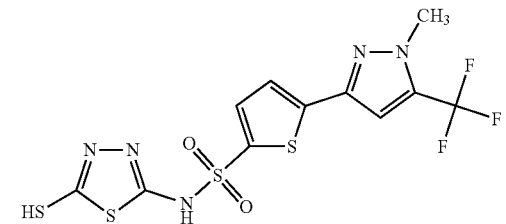 [SMILES: Cn1nc(-c2ccc(S(=O)(=O)Nc3nnc(S)s3)s2)cc1C(F)(F)F] | N-(5-mercapto-1,3,4-thiadiazol-2-yl)-5-[1-methyl-5-(trifluoromethyl)-1H-pyrazol-3-yl]thiophene-2-sulfonamide |

TABLE 1-continued

| | | |
|---|---|---|
| 494 | 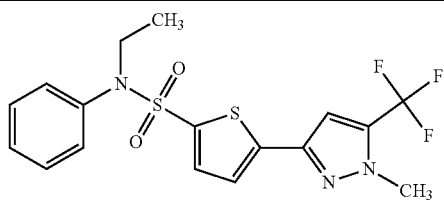 | N-ethyl-5-[1-methyl-5-(trifluoromethyl)-1H-pyrazol-3-yl]-N-phenylthiophene-2-sulfonamide |
| 495 | 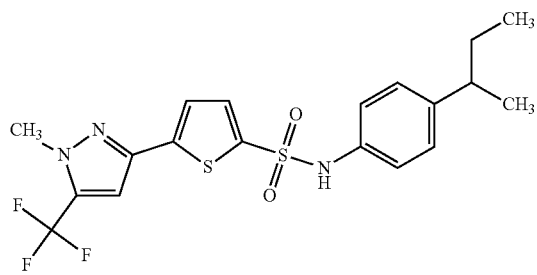 [SMILES: CCC(C)c1ccc(NS(=O)(=O)c2ccc(-c3cc(C(F)(F)F)n(C)n3)s2)cc1] | N-[4-(1-methylpropyl)phenyl]-5-[1-methyl-5-(trifluoromethyl)-1H-pyrazol-3-yl]thiophene-2-sulfonamide |
| 496 | 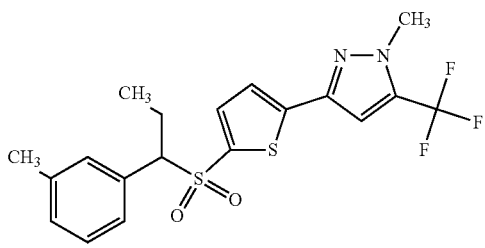 [SMILES: CCC(c1cccc(C)c1)S(=O)(=O)c1ccc(-c2cc(C(F)(F)F)n(C)n2)s1] | N-ethyl-N-(3-methylphenyl)-5-[1-methyl-5-(trifluoromethyl)-1H-pyrazol-3-yl]thiophene-2-sulfonamide |
| 497 | 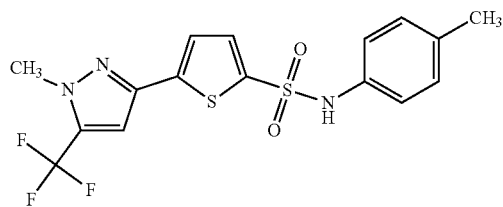 | N-(4-methylphenyl)-5-[1-methyl-5-(trifluoromethyl)-1H-pyrazol-3-yl]-thiophene-2-sulfonamide |
| 498 | 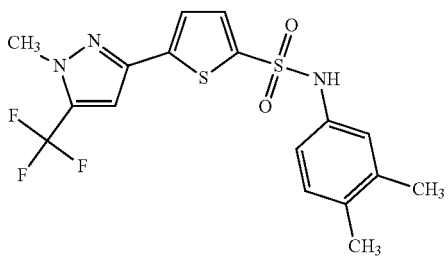 [SMILES: Cc1ccc(NS(=O)(=O)c2ccc(-c3cc(C(F)(F)F)n(C)n3)s2)cc1C] | N-(3,4-dimethylphenyl)-5-[1-methyl-5-(trifluoromethyl)-1H-pyrazol-5-yl]thiophene-2-sulfonamide |
| 499 | 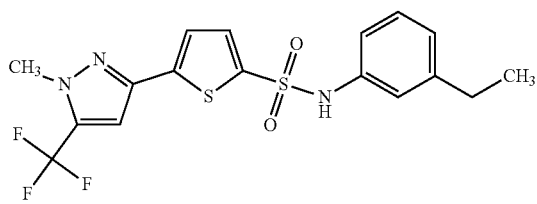 [SMILES: CCc1cccc(NS(=O)(=O)c2ccc(-c3cc(C(F)(F)F)n(C)n3)s2)c1] | N-(3-ethylphenyl)-5-[1-methyl-5-(trifluoromethyl)-1H-pyrazol-3-yl]thiophene-2-sulfonamide |
| 500 | 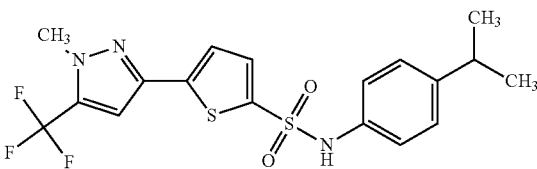 [SMILES: CC(C)c1ccc(NS(=O)(=O)c2ccc(-c3cc(C(F)(F)F)n(C)n3)s2)cc1] | N-[4-(1-methylethyl)phenyl]-5-[1-methyl-5-(trifluoromethyl)-1H-pyrazol-3-yl]thiophene-2-sulfonamide |

TABLE 1-continued

| | | |
|---|---|---|
| 501 | 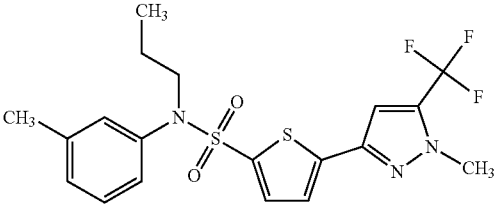 [SMILES: CCCN(c1cccc(C)c1)S(=O)(=O)c1ccc(-c2cc(C(F)(F)F)n(C)n2)s1] | N-(3-merthylphenyl)-5-[1-methyl-5-(trifluoromethyl)-1H-pyrazol-3-yl]-N-propylthiophene-2-sulfonamide |
| 502 | 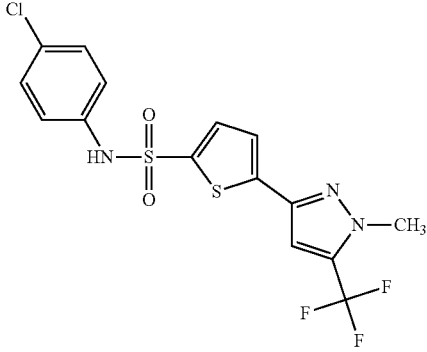 [SMILES: Cn1nc(-c2ccc(S(=O)(=O)Nc3ccc(Cl)cc3)s2)cc1C(F)(F)F] | N-(4-chlorophenyl)-5-[1-methyl-5-(trifluoromethyl)-1H-pyrazol-3-yl]thiophene-2-sulfonamide |
| 503 | 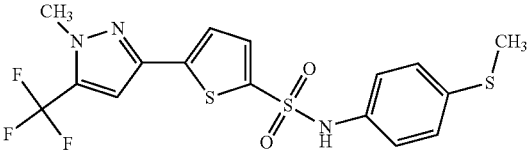 [SMILES: CSc1ccc(NS(=O)(=O)c2ccc(-c3cc(C(F)(F)F)n(C)n3)s2)cc1] | N-[4-(methylthio)phenyl]-5-[1-methyl-5-(trifluoromethyl)-1H-pyrazol-3-yl]thiophene-2-sulfonamide |
| 504 | 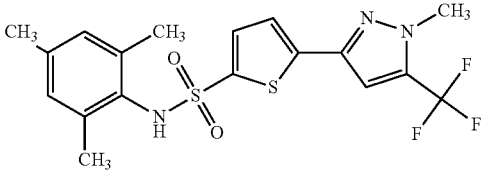 [SMILES: Cc1cc(C)c(NS(=O)(=O)c2ccc(-c3cc(C(F)(F)F)n(C)n3)s2)c(C)c1] | 5-[1-methyl-5-(trifluoromethyl)-1H-pyrazol-3-yl]-N-(2,4,6-trimethylphenyl)thiophene-2-sulfonamide |
| 505 | 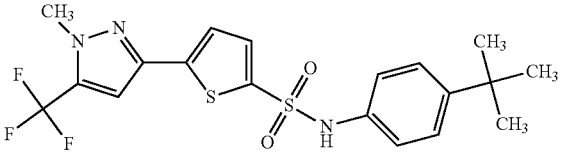 [SMILES: Cn1nc(-c2ccc(S(=O)(=O)Nc3ccc(C(C)(C)C)cc3)s2)cc1C(F)(F)F] | N-[4-(1,1-dimethylethyl)phenyl]-5-[1-methyl-5-(trifluoromethyl)-1H-pyrazol-3-yl]thiophene-2-sulfonamide |
| 506 | 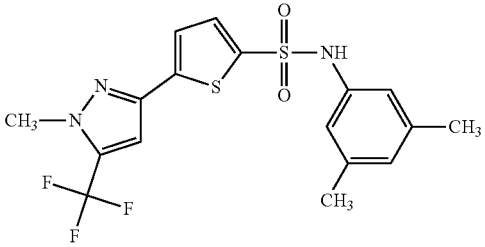 | N-(3,5-dimethylphenyl)-5-[1-methyl-5-(trifluoromethyl)-1H-pyrazol-3-yl]thiophene-2-sulfonamide |
| 507 | 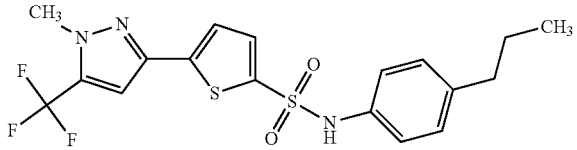 [SMILES: CCCc1ccc(NS(=O)(=O)c2ccc(-c3cc(C(F)(F)F)n(C)n3)s2)cc1] | 5-[1-methyl-5-(trifluoromethyl)-1H-pyrazol-3-yl]-N-(4-propylphenyl)thiophene-2-sulfonamide |

TABLE 1-continued

| 508 | 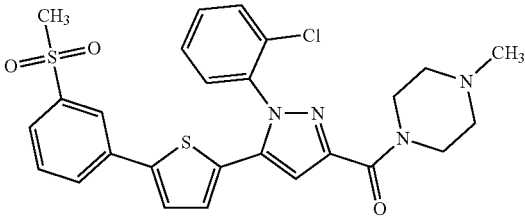 [SMILES: CN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazole-3-yl]carbonyl}-4-methylpiperazine |
| --- | --- | --- |
| 544 | 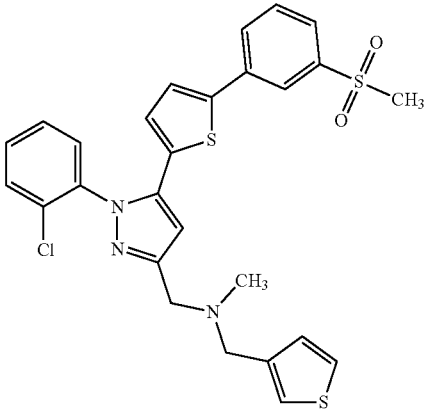 [SMILES: CN(Cc1ccsc1)Cc1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]-N-methyl-N-(3-thienylmethyl)methanamine |
| 545 | 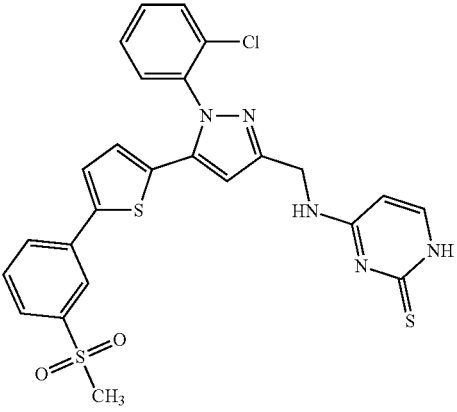 [SMILES: CS(=O)(=O)c1cccc(-c2ccc(-c3cc(CNc4cc[nH]c(=S)n4)nn3-c3ccccc3Cl)s2)c1] | 4-({[1-(2-chlorophenyl)-5-{5-[3-(methylsulfonyl)phenyl]-2-thienyl}-1H-pyrazol-3-yl]methyl}amino)pyrimidine-2(1H)-thione |
| 546 | 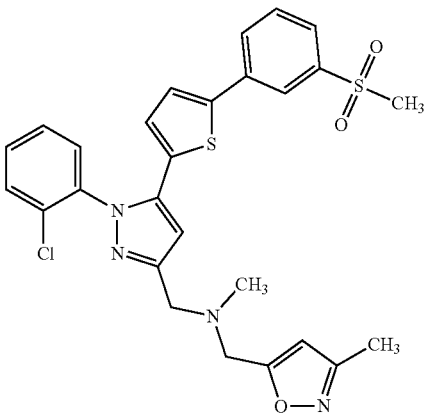 [SMILES: Cc1cc(CN(C)Cc2cc(-c3ccc(-c4cccc(S(C)(=O)=O)c4)s3)n(-c3ccccc3Cl)n2)on1] | 1-[1-(2-chlorophenyl)-5-{5-[3-(methylsulfonyl)phenyl]-2-thienyl}-1H-pyrazol-3-yl]-N-methyl-N-[(3-methylisoxazol-5-yl)methyl]methanamine |

TABLE 1-continued

| | | |
|---|---|---|
| 547 | 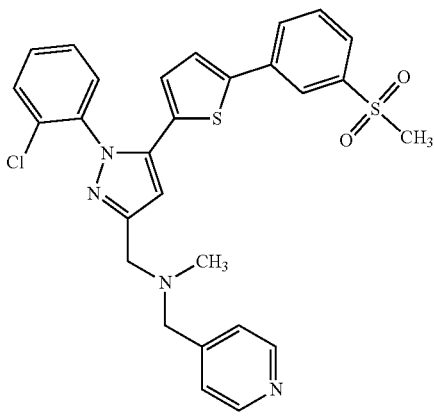 [SMILES: CN(Cc1ccncc1)Cc1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]-N-methyl-N-(pyridin-4-ylmethyl)methanamine |
| 548 | 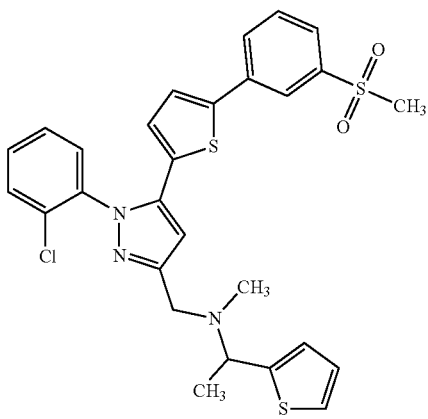 [SMILES: CC(c1cccs1)N(C)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-methyl-1-(2-thienyl)ethanamine |
| 549 | 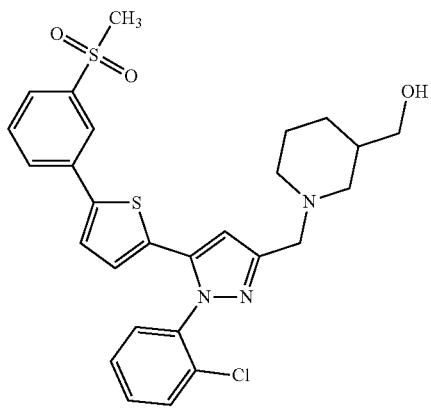 [SMILES: CS(=O)(=O)c1cccc(-c2ccc(-c3cc(CN4CCCC(CO)C4)nn3-c3ccccc3Cl)s2)c1] | (1-{[1-(2-chlorophenyl)-5-{5-[3-(methylsulfonyl)phenyl]-2-thienyl}-1H-pyrazol-3-yl]methyl}piperidin-3-yl)methanol |
| 550 | 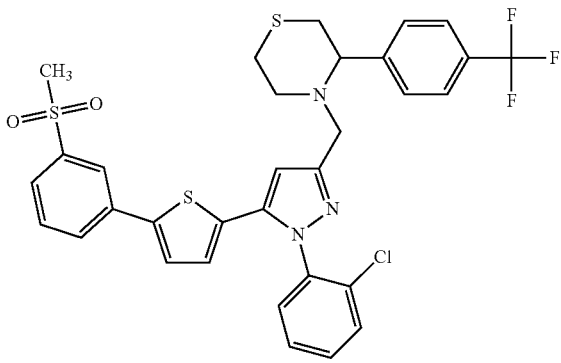 [SMILES: CS(=O)(=O)c1cccc(-c2ccc(-c3cc(CN4CCSCC4c4ccc(C(F)(F)F)cc4)nn3-c3ccccc3Cl)s2)c1] | 4-{[1-(2-chlorophenyl)-5-{5-[3-(methylsulfonyl)phenyl]-2-thienyl}-1H-pyrazol-3-yl]methyl}-3-[4-(trifluoromethyl)phenyl]thiomorpholine |

TABLE 1-continued

| | | |
|---|---|---|
| 551 | 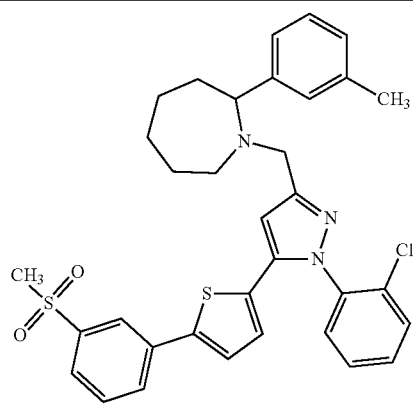 | 1-{[1-(2-chlorophenyl)-5-{5-[3-(methylsulfonyl)phenyl]-2-thienyl}-1H-pyrazol-3-yl]methyl}-2-(3-methylphenyl)azepane |
| 552 | 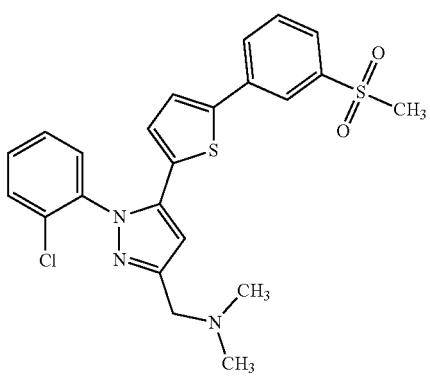 [SMILES: CN(C)Cc1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]-N,N-dimethylmethanamine |
| 553 | 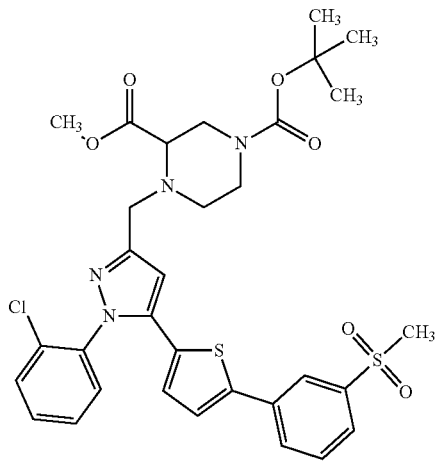 [SMILES: COC(=O)C1CN(C(=O)OC(C)(C)C)CCN1Cc1cc(-c2ccc(-c3cccc(S(C)(=O)=O)c3)s2)n(-c2ccccc2Cl)n1] | 1-(1,1-dimethylethyl)-3-methyl-4-{[1-(2-chlorophenyl)-5-{5-[3-(methylsulfonyl)phenyl]-2-thienyl}-1H-pyrazole-3-yl]methyl}piperazine-1,3-dicarboxylate |
| 554 | 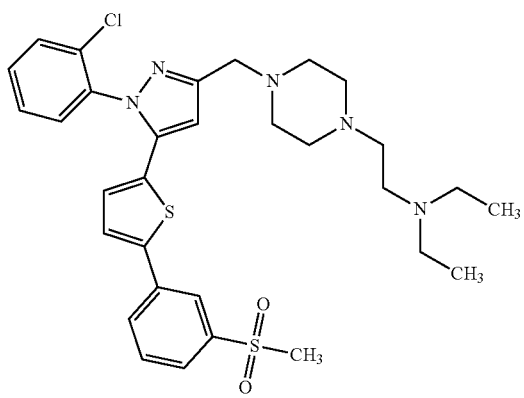 [SMILES: CCN(CC)CCN1CCN(Cc2cc(-c3ccc(-c4cccc(S(C)(=O)=O)c4)s3)n(-c3ccccc3Cl)n2)CC1] | 2-(4-{[1-(2-chlorophenyl)-5-{5-[3-(methylsulfonyl)phenyl]-2-thienyl}-1H-pyrazol-3-yl]methyl}piperazin-1-yl)-N,N-diethylethanamine |

| | | |
|---|---|---|
| 555 | 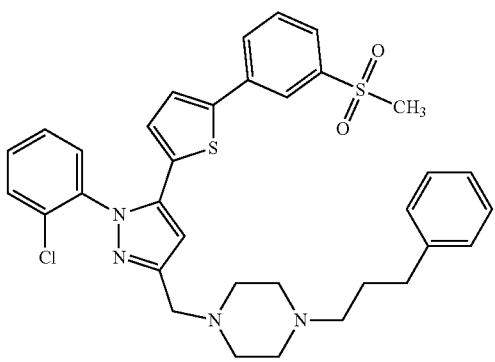 [SMILES: CS(=O)(=O)c1cccc(-c2ccc(-c3cc(CN4CCN(CCCc5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-4-(3-phenylpropyl)piperazine |
| 556 | 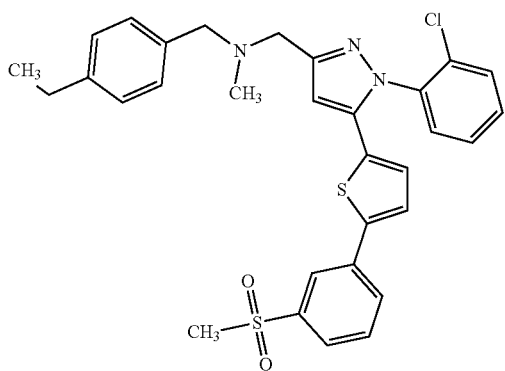 [SMILES: CCc1ccc(CN(C)Cc2cc(-c3ccc(-c4cccc(S(C)(=O)=O)c4)s3)n(-c3ccccc3Cl)n2)cc1] | 1-[1-(2-chlorophenyl)-5-{5-[3-(methylsufonyl)phenyl]-2-thienyl}-1H-pyrazol-3-yl]-N-[(4-ethylphenyl)methyl]-N-methylmethanamine |
| 557 | 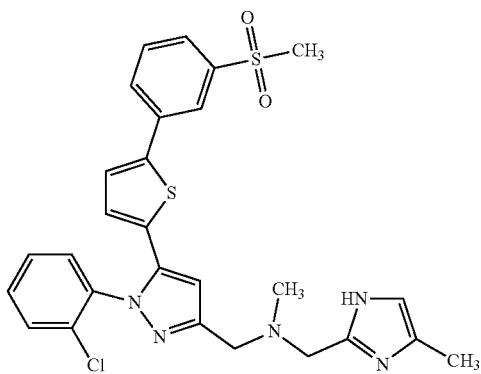 [SMILES: Cc1c[nH]c(CN(C)Cc2cc(-c3ccc(-c4cccc(S(C)(=O)=O)c4)s3)n(-c3ccccc3Cl)n2)n1] | 1-[1-(2-chlorophenyl)-5-{5-[3-(methylsulfonyl)phenyl]-2-thienyl}-1H-pyrazol-3-yl]-N-methyl-N-[(4-methyl-1H-imidazol-2-yl)methyl]methanamine |
| 558 | 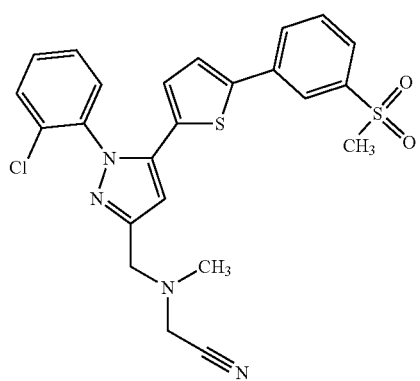 [SMILES: CN(CC#N)Cc1cc(-c2ccc(-c3cccc(S(C)(=O)=O)c3)s2)n(-c2ccccc2Cl)n1] | [{[1-(2-chlorophenyl)-5-{5-[3-(methylsulfonyl)phenyl]-2-thienyl}-1H-pyrazol-3-yl]methyl}(methyl)amino]acetonitrile |

| | | |
|---|---|---|
| 559 | 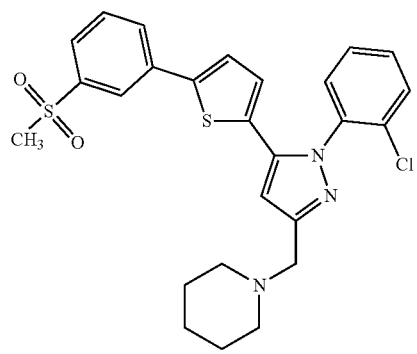 [SMILES: CS(=O)(=O)c1cccc(-c2ccc(-c3cc(CN4CCCCC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}piperidine |
| 560 | 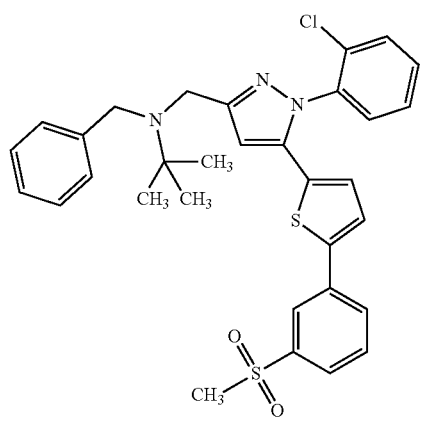 [SMILES: CC(C)(C)N(Cc1ccccc1)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-2-methyl-N-(phenylmethyl)propan-2-amine |
| 561 | 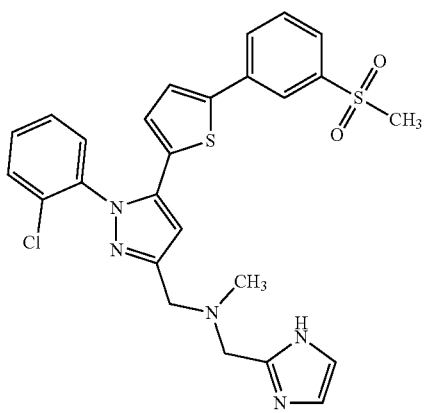 [SMILES: CN(Cc1cc(-c2ccc(-c3cccc(S(C)(=O)=O)c3)s2)n(-c2ccccc2Cl)n1)Cc1ncc[nH]1] | 1-[1-(2-chlorophenyl)-5-{5-[3-(methylsulfonyl)phenyl]-2-thienyl}-1H-pyrazol-2-yl]-N-(1H-imidazol-2-ylethyl)-N-methylmethanamine |
| 562 | 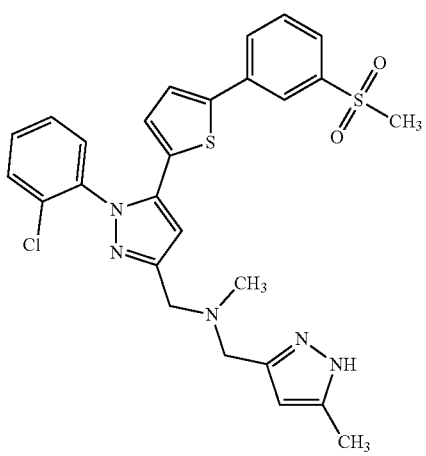 [SMILES: Cc1cc(CN(C)Cc2cc(-c3ccc(-c4cccc(S(C)(=O)=O)c4)s3)n(-c3ccccc3Cl)n2)n[nH]1] | 1-[1-(2-chlorophenyl)-5-{5-[3-(methylsulfonyl)phenyl]-2-thienyl}-1H-pyrazol-3-yl]-N-methyl-N-[(5-methyl-1H-pyrazol-3-yl)methyl]methanamine |

| | | |
|---|---|---|
| 563 | 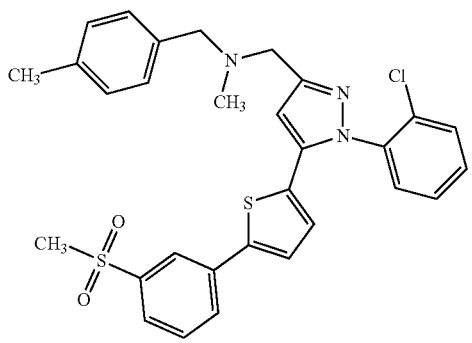 [SMILES: Cc1ccc(CN(C)Cc2cc(-c3ccc(-c4cccc(S(C)(=O)=O)c4)s3)n(-c3ccccc3Cl)n2)cc1] | 1-[1-(2-chlorophenyl)-5-{5-[3-(methylsulfonyl)phenyl]-2-thienyl}-1H-pyrazol-3-yl]-N-methyl-N-[(4-methylphenyl)methyl]methanamine |
| 564 | 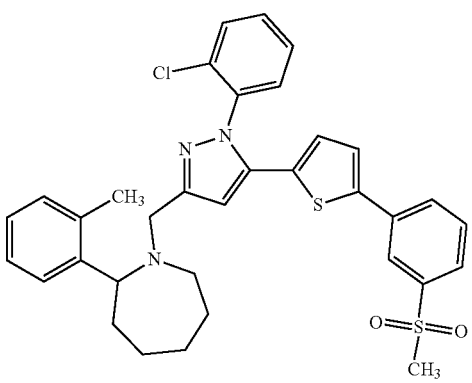 [SMILES: Cc1ccccc1C1CCCCCN1Cc1cc(-c2ccc(-c3cccc(S(C)(=O)=O)c3)s2)n(-c2ccccc2Cl)n1] | 1-{[1-(2-chlorophenyl)-5-{5-[6-(methylsulfonyl)phenyl]-2-thienyl}-1H-pyrazol-3-yl]methyl}-2-(2-methylphenyl)azepane |
| 565 | 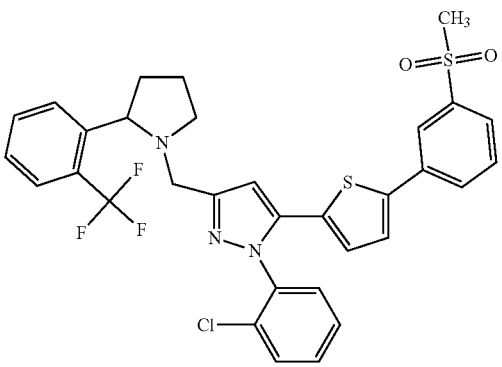 [SMILES: CS(=O)(=O)c1cccc(-c2ccc(-c3cc(CN4CCCC4c4ccccc4C(F)(F)F)nn3-c3ccccc3Cl)s2)c1] | 1-(2-chlorophenyl)-5-{5-[3-(methylsulfonyl)phenyl]-2-thienyl}-3-({2-(trifluoromethyl)phenyl]pyrrolidin-1-yl}methyl)-1H-pyrazole |
| 566 | 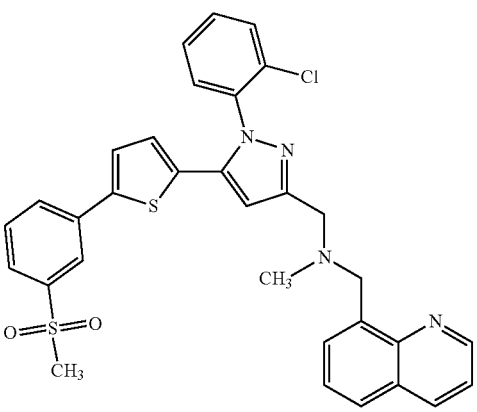 [SMILES: CN(Cc1cc(-c2ccc(-c3cccc(S(C)(=O)=O)c3)s2)n(-c2ccccc2Cl)n1)Cc1cccc2cccnc12] | 1-[1-(2-chlorophenyl)-5-{5-[3-(methylsulfonyl)phenyl]-2-thienyl}-1H-pyrazol-3-yl]-N-methyl-N-(quinolin-8-ylmethyl)methanamine |

TABLE 1-continued

| 567 | 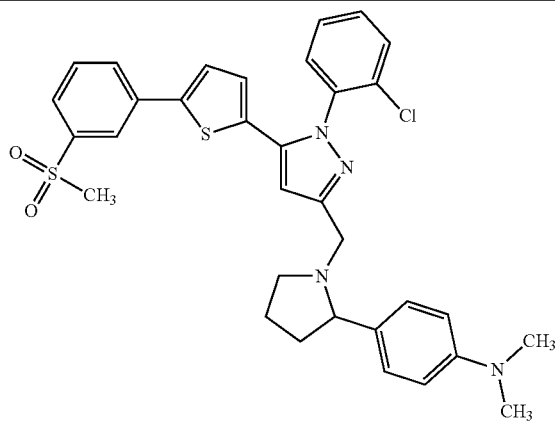 | 4-(1-{[1-(2-chlorophenyl)-5-{5-[3-(methylsulfonyl)phenyl]-2-thienyl}-1H-pyrazol-3-yl]methyl}pyrrolidin-2-yl)-N,N-dimethylaniline |
| 568 | 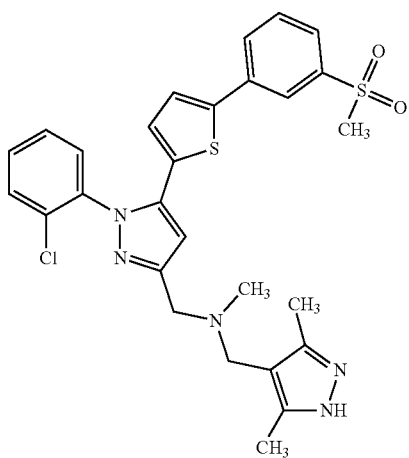 [SMILES: Cc1n[nH]c(C)c1CN(C)Cc1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]-N-[(3,5-dimethyl-1H-pyrazol-4-yl)methyl]-N-methylmethanamine |
| 569 | 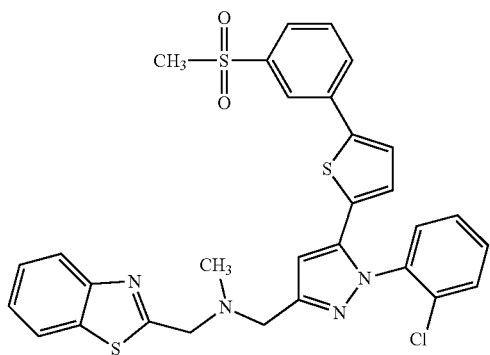 [SMILES: CN(Cc1cc(-c2ccc(-c3cccc(S(C)(=O)=O)c3)s2)n(-c2ccccc2Cl)n1)Cc1nc2ccccc2s1] | 1-(1,3-benzothiazol-2-yl)-N-{[1-(2-chlorophenyl)-5-{5-[3-(methylsulfonyl)phenyl]-2-thienyl}-1H-pyrazol-3-yl]methyl}-N-methylmethanamine |
| 570 | 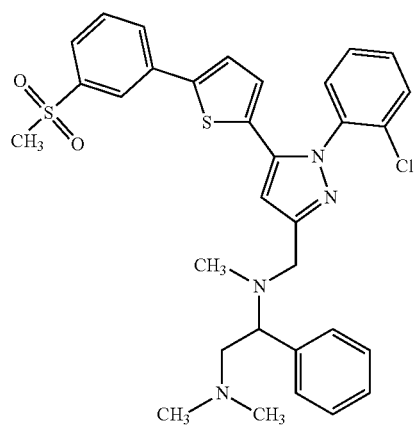 [SMILES: CN(C)CC(c1ccccc1)N(C)Cc1cc(-c2ccc(-c3cccc(S(C)(=O)=O)c3)s2)n(-c2ccccc2Cl)n1] | N~1~-{[1-(2-chlorophenyl)-5-{5-[3-(methylsulfonyl)phenyl]-2-thienyl}-1H-pyrazol-3-yl]methyl}-N~1~,N~2~-trimethyl-1-phenylethane-1,2-diamine |

| | | |
|---|---|---|
| 571 | 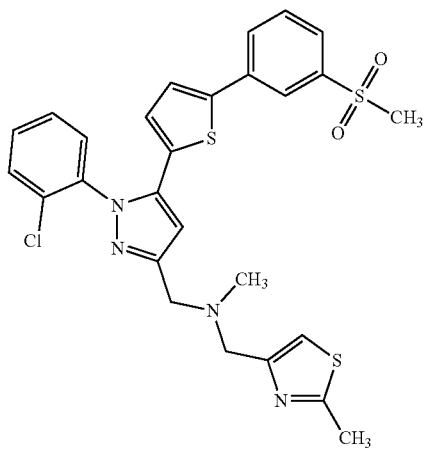 [SMILES: Cc1nc(CN(C)Cc2cc(-c3ccc(-c4cccc(S(C)(=O)=O)c4)s3)n(-c3ccccc3Cl)n2)cs1] | 1-[1-(2-chlorophenyl)-5-{5-[3-(trimethylsulfonyl)phenyl]-2-thienyl}-1H-pyrazol-3-yl]-N-methyl-N-[(2-methyl-1,3-thiazol-4-yl)methyl]methanamine |
| 572 | 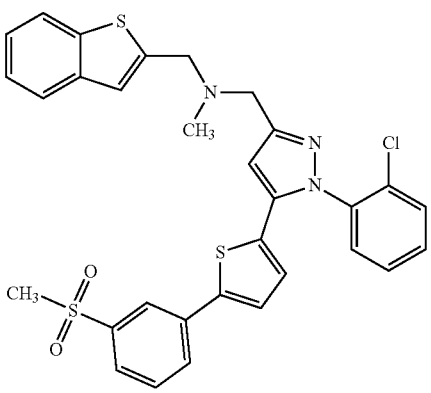 [SMILES: CN(Cc1cc(-c2ccc(-c3cccc(S(C)(=O)=O)c3)s2)n(-c2ccccc2Cl)n1)Cc1cc2ccccc2s1] | 1-(1-benzothien-2-yl)-N-{[1-(2-chlorophenyl)-5-{5-[3-(methylsulfonyl)phenyl]-2-thienyl}-1H-pyrazol-3-yl]methyl}-N-methylmethanamine |
| 573 | 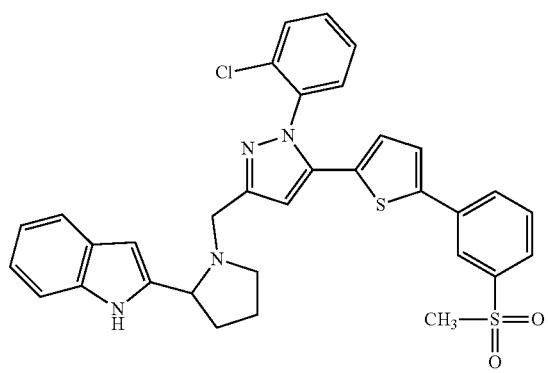 [SMILES: CS(=O)(=O)c1cccc(-c2ccc(-c3cc(CN4CCCC4c4cc5ccccc5[nH]4)nn3-c3ccccc3Cl)s2)c1] | 2-(1-{[1-(2-chlorophenyl)-5-{5-[3-(methylsulfonyl)phenyl]-2-thienyl}-1H-pyrazol-3-yl]methyl}pyrrolidin-2-yl)-1H-indole |
| 574 | 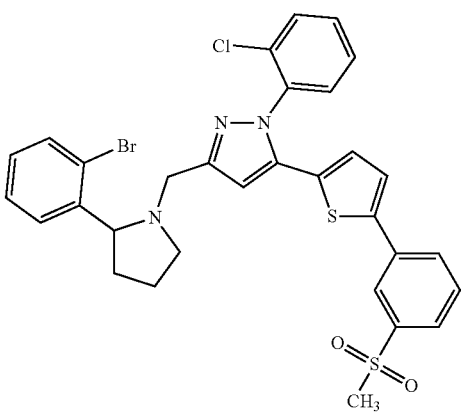 [SMILES: CS(=O)(=O)c1cccc(-c2ccc(-c3cc(CN4CCCC4c4ccccc4Br)nn3-c3ccccc3Cl)s2)c1] | 3-{[2-(2-bromophenyl)pyrrolidin-1-yl]methyl}-1-(2-chlorophenyl)-5-{5-[3-(methylsulfonyl)phenyl]-2-thienyl}-1H-pyrazole |

| | | |
|---|---|---|
| 575 | 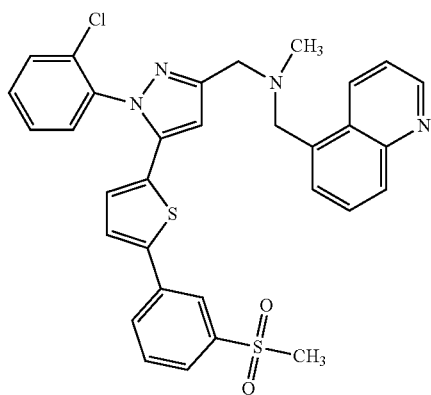 [SMILES: CN(Cc1cc(-c2ccc(-c3cccc(S(C)(=O)=O)c3)s2)n(-c2ccccc2Cl)n1)Cc1cccc2ncccc12] | 1-[1-(2-chlorophenyl)-5-{5-[3-(methylsulfonyl)phenyl]-2-thienyl}-1H-pyrazol-3-yl]-N-methyl-N-(quinolin-5-ylmethyl)methanamine |
| 576 | 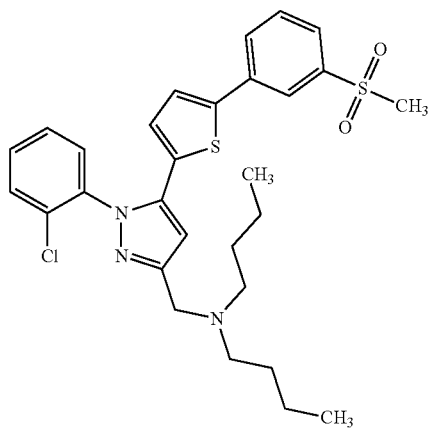 [SMILES: CCCCN(CCCC)Cc1cc(-c2ccc(-c3cccc(S(C)(=O)=O)c3)s2)n(-c2ccccc2Cl)n1] | N-butyl-N-{[1-(2-chlorophenyl)-5-{5-[3-(methylsulfonyl)phenyl]-2-thienyl}-1H-pyrazol-3-yl]methyl}butan-1-amine |
| 577 | 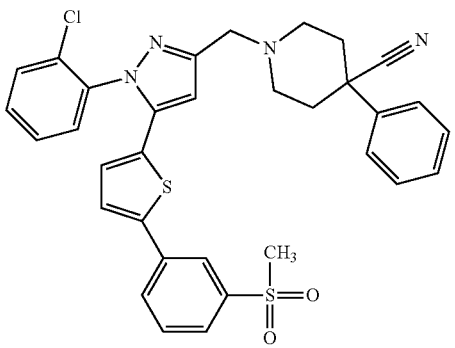 [SMILES: CS(=O)(=O)c1cccc(-c2ccc(-c3cc(CN4CCC(C#N)(c5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}-4-phenylpiperidine-4-carbonitrile |
| 578 | 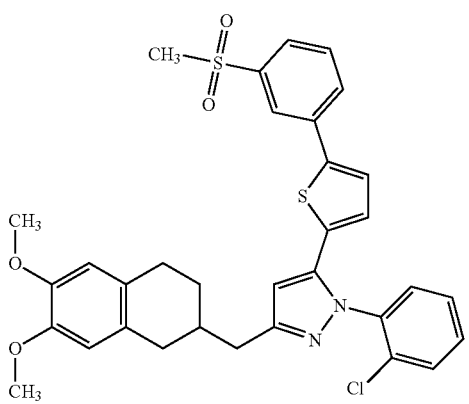 [SMILES: COc1cc2c(cc1OC)CC(Cc1cc(-c3ccc(-c4cccc(S(C)(=O)=O)c4)s3)n(-c3ccccc3Cl)n1)CC2] | 2-{[1-(2-chlorophenyl)-5-{5-[3-(methylsulfonyl)phenyl]-2-thienyl}-1H-pyrazol-3-yl]methyl}-6,7-bis(methyloxy)-1,2,3,4-tetrahydroisoquinoline |

TABLE 1-continued
| 579 | 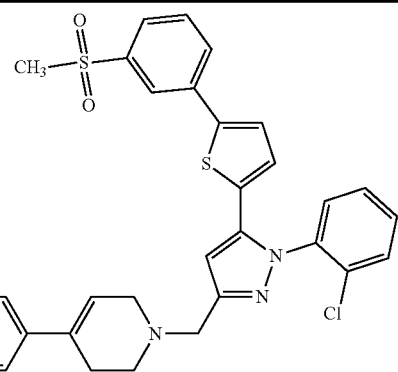 | 4-(4-chlorophenyl)-1-{[1-(2-chlorophenyl)-5-{5-[3-(methylsulfonyl)phenyl]-2-thienyl}-1H-pyrazol-3-yl]methyl}-1,2,3,6-tetrahydropyridine |
| --- | --- | --- |
| 580 | 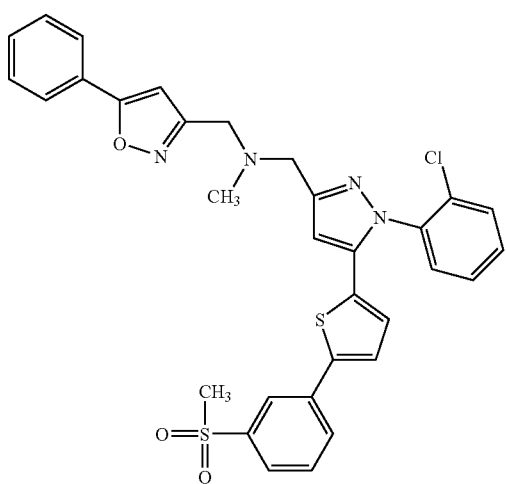 [SMILES: CN(Cc1cc(-c2ccccc2)on1)Cc1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]-N-methyl-N-[(5-phenylisoxazol-3-yl)methyl]methanamine |
| 581 | 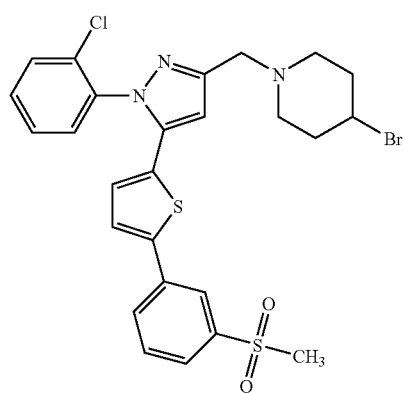 [SMILES: CS(=O)(=O)c1cccc(-c2ccc(-c3cc(CN4CCC(Br)CC4)nn3-c3ccccc3Cl)s2)c1] | 4-bromo-1-{[1-(2-chlorophenyl)-5-{5-[3-(methylsulfonyl)phenyl]-2-thienyl}-1H-pyrazol-3-yl]methyl}piperidine |

TABLE 1-continued

| | | |
|---|---|---|
| 582 | 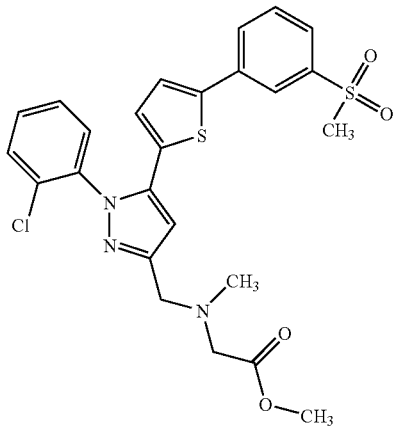 [SMILES: COC(=O)CN(C)Cc1cc(-c2ccc(-c3cccc(S(C)(=O)=O)c3)s2)n(-c2ccccc2Cl)n1] | methyl N-{[1-(2-chlorophenyl)-5-{5-[3-(methylsulfonyl)phenyl]-2-thienyl}-1H-pyrazol-3-yl]methyl}-N-methylglycinate |
| 583 | 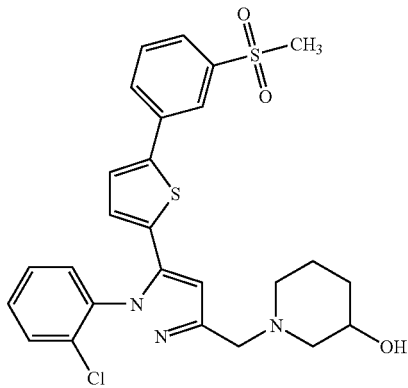 [SMILES: CS(=O)(=O)c1cccc(-c2ccc(/C(=C/C(=N)CN3CCCC(O)C3)Nc3ccccc3Cl)s2)c1] | 1-{[1-(2-chlorophenyl)-5-{5-[3-(methylsulfonyl)phenyl]-2-thienyl}-1H-pyrazol-3-yl]methyl}piperidin-3-ol |
| 584 | 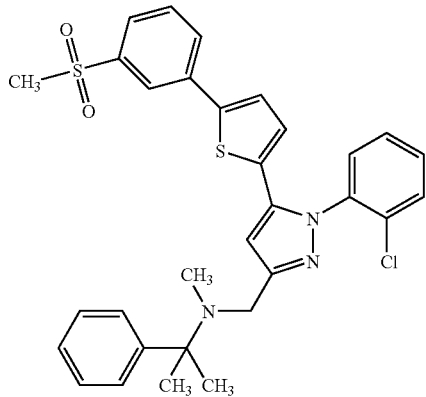 [SMILES: CN(Cc1cc(-c2ccc(-c3cccc(S(C)(=O)=O)c3)s2)n(-c2ccccc2Cl)n1)C(C)(C)c1ccccc1] | N-{[1-(2-chlorophenyl)-5-{5-[3-(methylsulfonyl)phenyl]-2-thienyl}-1H-pyrazol-2-yl]methyl}-N-methyl-2-phenylpropan-2-amine |
| 585 | 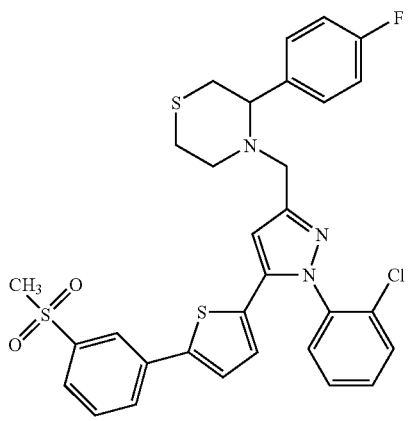 [SMILES: CS(=O)(=O)c1cccc(-c2ccc(-c3cc(CN4CCSCC4c4ccc(F)cc4)nn3-c3ccccc3Cl)s2)c1] | 4-{[1-(2-chlorophenyl)-5-{5-[3-(methylsulfonyl)phenyl]-2-thienyl}-1H-pyrazol-3-yl]methyl}-3-(4-fluorophenyl)thiomorpholine |

TABLE 1-continued

| 586 | 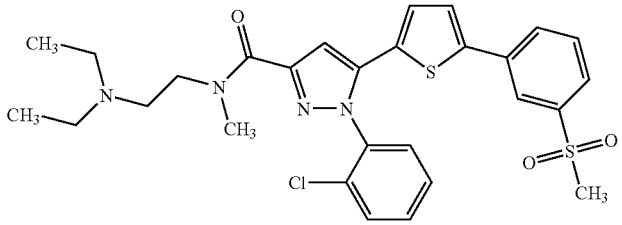 [SMILES: CCN(CC)CCN(C)C(=O)c1cc(-c2ccc(-c3cccc(S(C)(=O)=O)c3)s2)n(-c2ccccc2Cl)n1] | 1-(2-chlorophenyl)-N-[2-(dimethylamino)ethyl]-N-methyl-5-{5-[3-(methylsulfonyl)phenyl]-2-thienyl}-1H-pyrazole-3-carboxamide |
| --- | --- | --- |
| 587 | 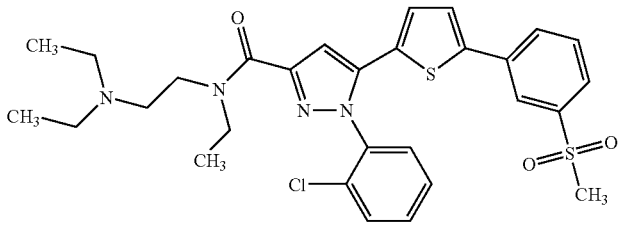 [SMILES: CCN(CC)CCN(CC)C(=O)c1cc(-c2ccc(-c3cccc(S(C)(=O)=O)c3)s2)n(-c2ccccc2Cl)n1] | 1-(2-chlorophenyl)-N-[2-(diethylamino)ethyl]-N-ethyl-5-{5-[3-(methylsulfonyl)phenyl]-2-thienyl}-1H-pyrazole-3-carboxamide |
| 588 | 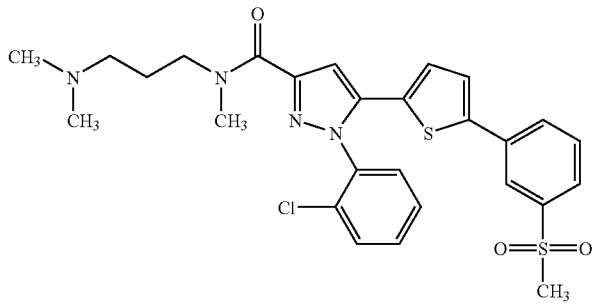 [SMILES: CN(C)CCCN(C)C(=O)c1cc(-c2ccc(-c3cccc(S(C)(=O)=O)c3)s2)n(-c2ccccc2Cl)n1] | 1-(2-chlorophenyl)-N-[3-(dimethylamino)propyl]-N-methyl-5-{5-[3-(methylsulfonyl)phenyl]-2-thienyl}-1H-pyrazole-3-carboxamide |
| 589 | 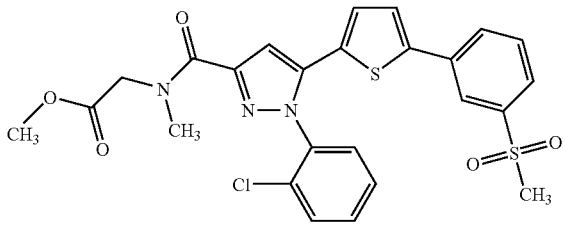 [SMILES: COC(=O)CN(C)C(=O)c1cc(-c2ccc(-c3cccc(S(C)(=O)=O)c3)s2)n(-c2ccccc2Cl)n1] | methyl N-{[1-(2-chlorophenyl)-5-{5-[3-(methylsulfonyl)phenyl]-2-thienyl}-1H-pyrazol-3-yl]carbonyl}-N-methylglycinate |
| 590 | 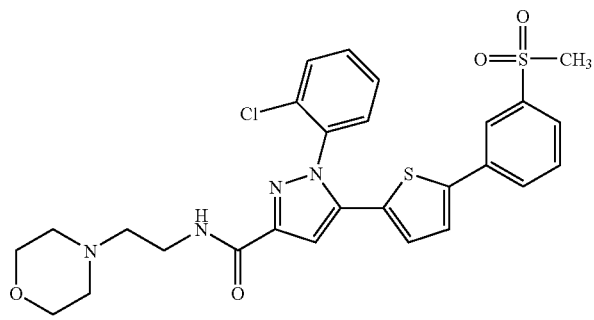 [SMILES: CS(=O)(=O)c1cccc(-c2ccc(-c3cc(C(=O)NCCN4CCOCC4)nn3-c3ccccc3Cl)s2)c1] | 1-(2-chlorophenyl)-5-{5-[3-(methylsulfonyl)phenyl]-2-thienyl}-N-(2-morpholin-4-ylmethyl)-1H-pyrazole-3-carboxamide |

TABLE 1-continued

| | | |
|---|---|---|
| 591 | | 1-{[1-(2-chlorophenyl)-5-{5-[3-(methylsulfonyl)phenyl]-2-thienyl}-1H-pyrazol-3-yl]carbonyl}-N,N-dimethylpiperidin-4-amine |
| 592 | | 1-(1-(2-chlorophenyl)-5-(5-(3-(methylsulfonyl)phenyl)thiophen-2-yl)-1H-pyrazole-3-carbonyl)piperidine-4-carboxylic acid |
| 594 | | 4-[(1-{[1-(2-chlorophenyl)-5-{5-[3-(methylsulfonyl)phenyl]-2-thienyl}-1H-pyrazol-3-yl]carbonyl}piperidin-3-yl)carbonyl]morpholine |
| 595 | | 1-(2-chlorophenyl)-5-{5-[3-(methylsulfonyl)phenyl]-2-thienyl}-N-(4-pyrrolidin-1-ylbutyl)-1H-pyrazole-3-carboxamide |

| | | |
|---|---|---|
| 596 | 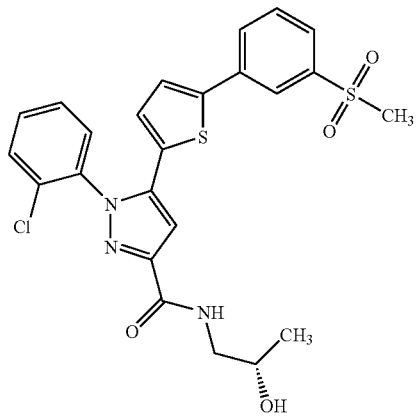 [SMILES: C[C@H](O)CNC(=O)c1cc(-c2ccc(-c3cccc(S(C)(=O)=O)c3)s2)n(-c2ccccc2Cl)n1] | 1-(2-chlorophenyl)-N-[(2S)-2-hydroxypropyl]-5-{5-[3-(methylsulfonyl)phenyl]-2-thienyl}-1H-pyrazole-3-carboxamide |
| 597 | 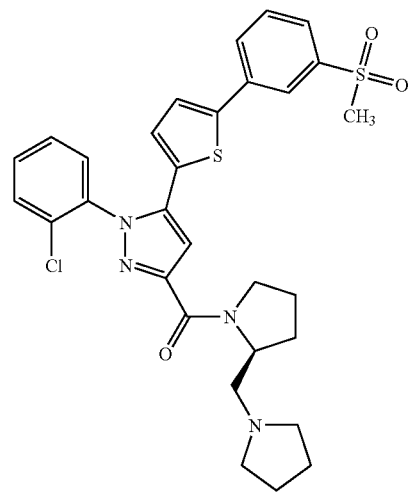 [SMILES: CS(=O)(=O)c1cccc(-c2ccc(-c3cc(C(=O)N4CCC[C@H]4CN4CCCC4)nn3-c3ccccc3Cl)s2)c1] | 1-(2-chlorophenyl)-5-{5-[3-(methylsulfonyl)phenyl]-2-thienyl}-3-{[(2S)-2-(pyrrolidin-1-ylmethyl)pyrrolidin-1-yl]carbonyl}-1H-pyrazole |
| 598 | 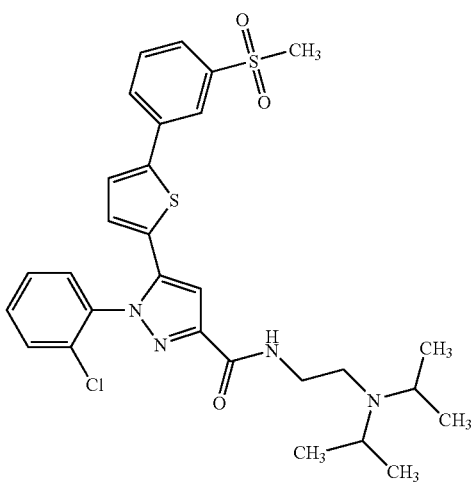 [SMILES: CC(C)N(CCNC(=O)c1cc(-c2ccc(-c3cccc(S(C)(=O)=O)c3)s2)n(-c2ccccc2Cl)n1)C(C)C] | N-{2-[bis(1-methylethyl)amino]ethyl}-1-(2-chlorophenyl)-5-{5-[3-(methylsulfonyl)phenyl]-2-thienyl}-1H-pyrazole-3-carboxamide |

| | | |
|---|---|---|
| 599 | 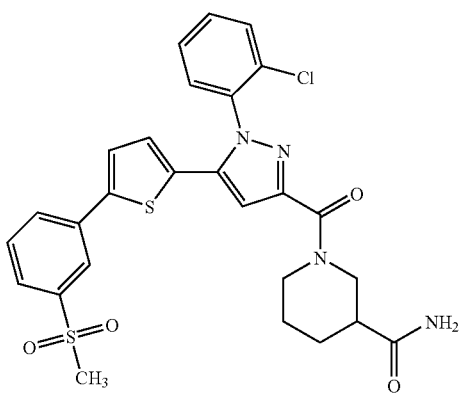 [SMILES: CS(=O)(=O)c1cccc(-c2ccc(-c3cc(C(=O)N4CCCC(C(N)=O)C4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}piperidine-3-carboxamide |
| 600 | 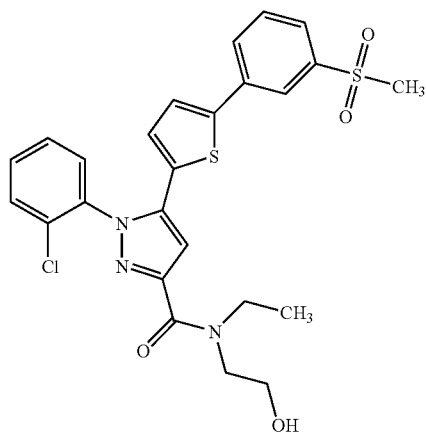 [SMILES: CCN(CCO)C(=O)c1cc(-c2ccc(-c3cccc(S(C)(=O)=O)c3)s2)n(-c2ccccc2Cl)n1] | 1-(2-chlorophenyl)-N-ethyl-N-(2-hydroxyethyl)-5-{5-[3-(methylsulfonyl)phenyl]-2-thienyl}-1H-pyrazole-3-carboxamide |
| 601 | 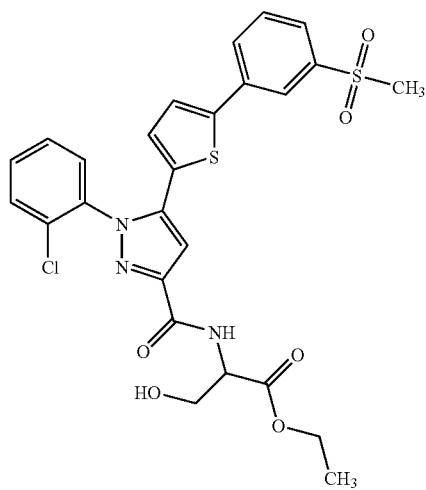 [SMILES: CCOC(=O)C(CO)NC(=O)c1cc(-c2ccc(-c3cccc(S(C)(=O)=O)c3)s2)n(-c2ccccc2Cl)n1] | ethyl N-{[1-(2-chlorophenyl)-5-{5-[3-(methylsulfonyl)phenyl]-2-thienyl}-1H-pyrazol-3-yl]carbonyl}serinate |

| | | |
|---|---|---|
| 602 | 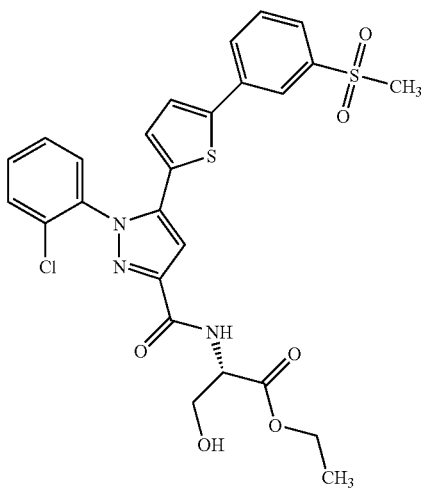 | ethyl N-{[1-(2-chlorophenyl)-5-{5-[3-(methylsulfonyl)phenyl]-2-thienyl}-1H-pyrazol-3-yl]carbonyl}-L-serinate |
| 603 | 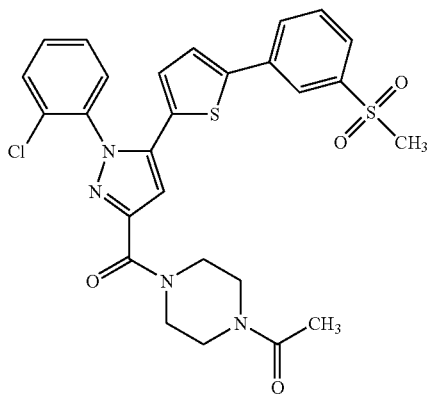 [SMILES: CC(=O)N1CCN(C(=O)c2cc(-c3ccc(-c4cccc(S(C)(=O)=O)c4)s3)n(-c3ccccc3Cl)n2)CC1] | 1-acetyl-4-{[1-(2-chlorophenyl)-5-{5-[3-(methylsulfonyl)phenyl]-2-thienyl}-1H-pyrazol-3-yl]carbonyl}piperazine |
| 604 | 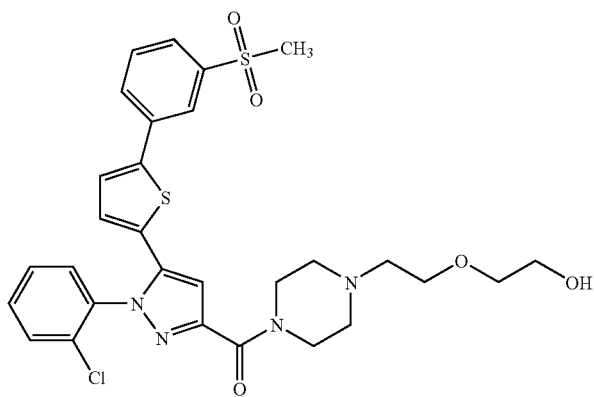 [SMILES: CS(=O)(=O)c1cccc(-c2ccc(-c3cc(C(=O)N4CCN(CCOCCO)CC4)nn3-c3ccccc3Cl)s2)c1] | 2-{[2-(4-{[1-(2-chlorophenyl)-5-{5-[3-(methylsulfonyl)phenyl]-2-thienyl}-1H-pyrazol-3-yl]carbonyl}piperazin-1-yl)ethyl]oxy}ethanol |

| | | |
|---|---|---|
| 605 | 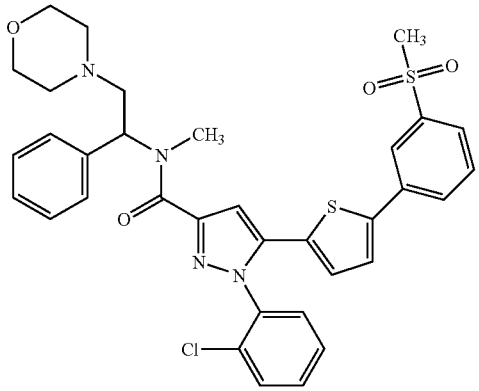 [SMILES: CN(C(=O)c1cc(-c2ccc(-c3cccc(S(C)(=O)=O)c3)s2)n(-c2ccccc2Cl)n1)C(CN1CCOCC1)c1ccccc1] | 1-(2-chlorophenyl)-N-methyl-5-{5-[3-(methylsulfonyl)phenyl]-2-thienyl}-N-(2-morpholin-4-yl-1-phenylethyl)-1H-pyrazole-3-carboxamide |
| 606 | 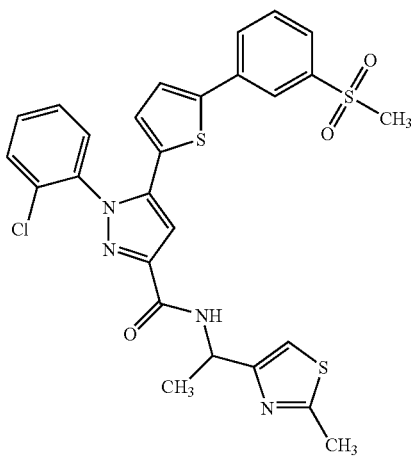 [SMILES: Cc1nc(C(C)NC(=O)c2cc(-c3ccc(-c4cccc(S(C)(=O)=O)c4)s3)n(-c3ccccc3Cl)n2)cs1] | 1-(2-chlorophenyl)-5-{5-[3-(methylsulfonyl)phenyl]-2-thienyl}-N-[1-(2-methyl-1,3-thiazol-4-yl)ethyl]-1H-pyrazole-3-carboxamide |
| 607 | 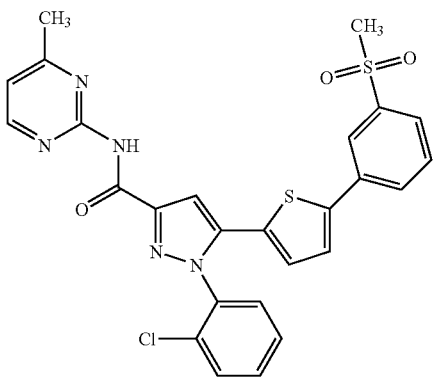 [SMILES: Cc1ccnc(NC(=O)c2cc(-c3ccc(-c4cccc(S(C)(=O)=O)c4)s3)n(-c3ccccc3Cl)n2)n1] | 1-(2-chlorophenyl)-N-(4-methylpyrimidin-2-yl)-5-{5-[3-(methylsulfonyl)phenyl]-2-thienyl}-1H-pyrazole-3-carboxamide |

| | | |
|---|---|---|
| 608 | 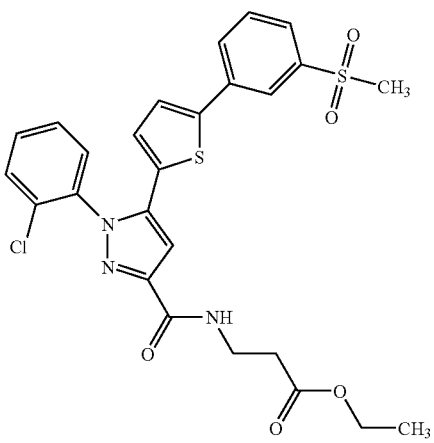 [SMILES: CCOC(=O)CCNC(=O)c1cc(-c2ccc(-c3cccc(S(C)(=O)=O)c3)s2)n(-c2ccccc2Cl)n1] | ethyl N-{[1-(2-chlorophenyl)-5-{5-[3-(methylsulfonyl)phenyl]-2-thienyl}-1H-pyrazol-3-yl]carbonyl}-beta-alaninate |
| 609 | 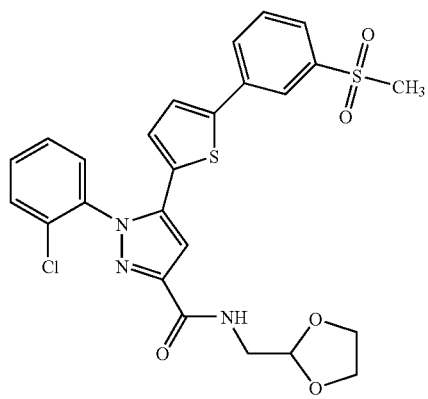 [SMILES: CS(=O)(=O)c1cccc(-c2ccc(-c3cc(C(=O)NCC4OCCO4)nn3-c3ccccc3Cl)s2)c1] | 1-(2-chlorophenyl)-N-(1,3-dioxolan-2-ylmethyl)-5-{5-[3-(methylsulfonyl)phenyl]-2-thienyl}-1H-pyrazole-3-carboxamide |
| 610 | 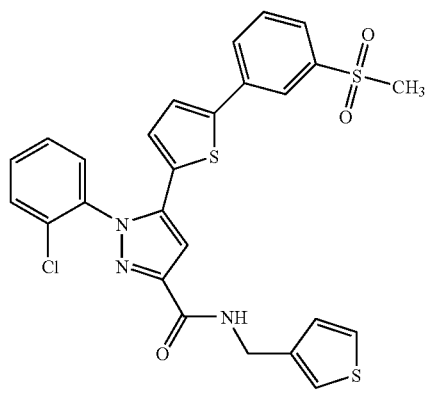 [SMILES: CS(=O)(=O)c1cccc(-c2ccc(-c3cc(C(=O)NCc4ccsc4)nn3-c3ccccc3Cl)s2)c1] | 1-(2-chlorophenyl)-5-{5-[3-(methylsulfonyl)phenyl]-2-thienyl}-N-(3-thienylmethyl)-1H-pyrazole-3-carboxamide |

| 611 | 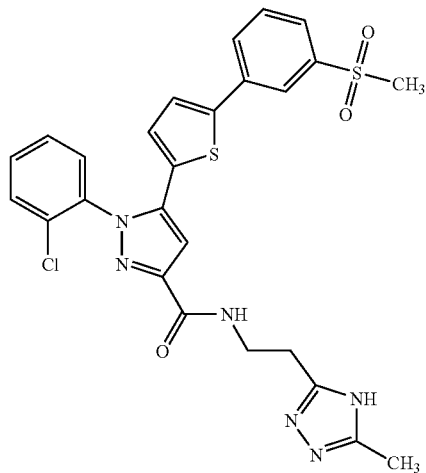 [SMILES: Cc1nnc(CCNC(=O)c2cc(-c3ccc(-c4cccc(S(C)(=O)=O)c4)s3)n(-c3ccccc3Cl)n2)[nH]1] | 1-(2-chlorophenyl)-5-{5-[3-(methylsulfonyl)phenyl]-2-thienyl}-N-[2-(5-methyl-4H-1,2,4-triazol-3-yl)ethyl]-1H-pyrazole-3-carboxamide |
|---|---|---|
| 612 | 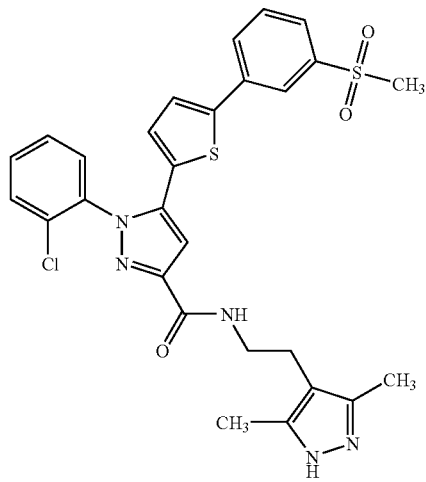 [SMILES: Cc1n[nH]c(C)c1CCNC(=O)c1cc(-c2ccc(-c3cccc(S(C)(=O)=O)c3)s2)n(-c2ccccc2Cl)n1] | 1-(2-chlorophenyl)-N-[2-(3,5-dimethyl-1H-pyrazol-4-yl)ethyl]-5-{5-[3-(methylsulfonyl)phenyl]-2-thienyl}-1H-pyrazole-3-carboxamide |
| 613 | 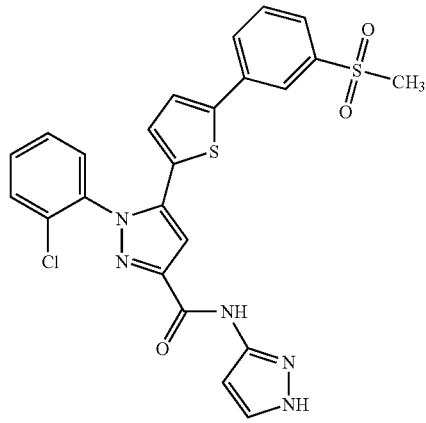 [SMILES: CS(=O)(=O)c1cccc(-c2ccc(-c3cc(C(=O)Nc4cc[nH]n4)nn3-c3ccccc3Cl)s2)c1] | 1-(2-chlorophenyl)-5-{5-[3-(methylsulfonyl)phenyl]-2-thienyl}-N-1H-pyrazol-3-yl-1H-pyrazole-3-carboxamide |

TABLE 1-continued
614 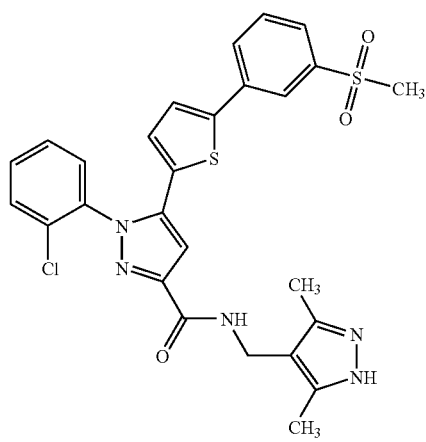 [SMILES: Cc1n[nH]c(C)c1CNC(=O)c1cc(-c2ccc(-c3cccc(S(C)(=O)=O)c3)s2)n(-c2ccccc2Cl)n1] 1-(2-chlorophenyl)-N-[(3,5-dimethyl-1H-pyrazol-4-yl)methyl]-5-{5-[3-(methylsulfonyl)phenyl]-2-thienyl}-1H-pyrazole-3-carboxamide
615 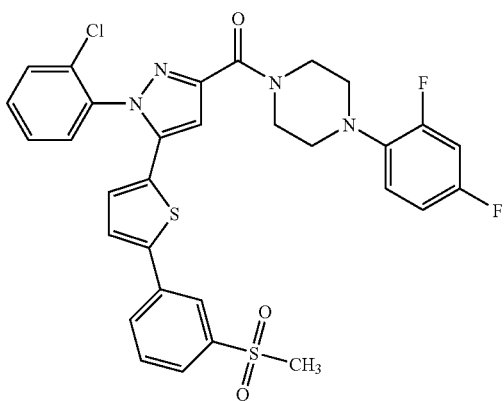 [SMILES: CS(=O)(=O)c1cccc(-c2ccc(-c3cc(C(=O)N4CCN(c5ccc(F)cc5F)CC4)nn3-c3ccccc3Cl)s2)c1] 1-{[1-(2-chlorophenyl)-5-{5-[3-(methylsulfonyl)phenyl]-2-thienyl}-1H-pyrazol-3-yl]carbonyl}-4-(2,4-difluorophenyl)piperazine
616 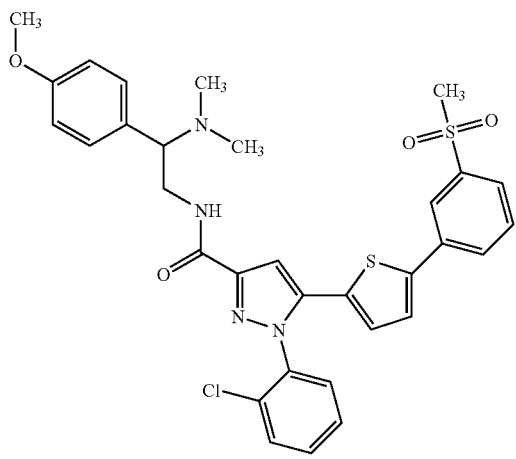 [SMILES: COc1ccc(C(CNC(=O)c2cc(-c3ccc(-c4cccc(S(C)(=O)=O)c4)s3)n(-c3ccccc3Cl)n2)N(C)C)cc1] 1-(2-chlorophenyl)-N-{2-(dimethylamino)-2-[4-(methyloxy)phenyl]ethyl}-5-{5-[3-(methylsulfonyl)phenyl]-2-thienyl}-1H-pyrazole-3-carboxamide

| | | |
|---|---|---|
| 617 | 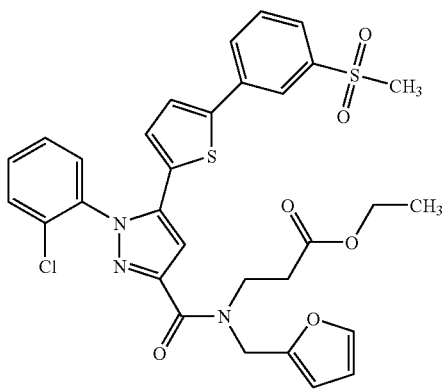 [SMILES: CCOC(=O)CCN(Cc1ccco1)C(=O)c1cc(-c2ccc(-c3cccc(S(C)(=O)=O)c3)s2)n(-c2ccccc2Cl)n1] | ethyl N-{[1-(2-chlorophenyl)-5-{5-[3-(methylsulfonyl)phenyl]-2-thienyl}-1H-pyrazol-3-yl]carbonyl}-N-(furan-2-ylmethyl)-beta-alaninate |
| 618 | 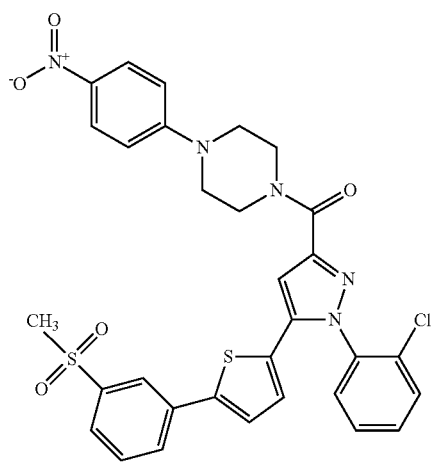 | 1-{[1-(2-chlorophenyl)-5-{5-[3-(methylsulfonyl)phenyl]-2-thienyl}-1H-pyrazol-3-yl]carbonyl}-4-(4-nitrophenyl)piperazine |
| 619 | 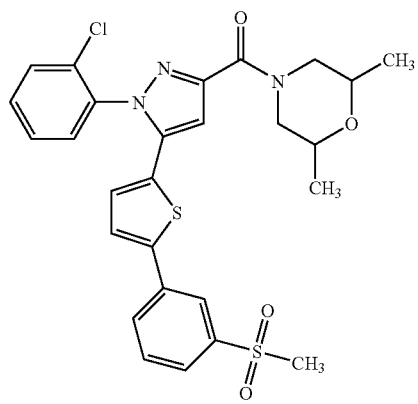 [SMILES: CC1CN(C(=O)c2cc(-c3ccc(-c4cccc(S(C)(=O)=O)c4)s3)n(-c3ccccc3Cl)n2)CC(C)O1] | 4-{[1-(2-chlorophenyl)-5-{5-[3-(methylsulfonyl)phenyl]-2-thienyl}-1H-pyrazol-3-yl]carbonyl}-2,6-dimethylmorpholine |
| 620 | 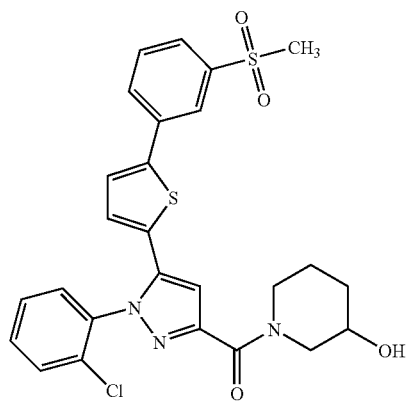 [SMILES: CS(=O)(=O)c1cccc(-c2ccc(-c3cc(C(=O)N4CCCC(O)C4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}piperidin-3-ol |

| | | |
|---|---|---|
| 621 | 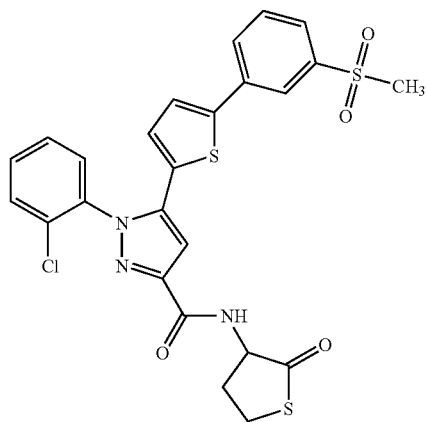 [SMILES: CS(=O)(=O)c1cccc(-c2ccc(-c3cc(C(=O)NC4CCSC4=O)nn3-c3ccccc3Cl)s2)c1] | 1-(2-chlorophenyl)-5-{5-[3-(methylsulfonyl)phenyl]-2-thienyl}-N-(2-oxotetrahydro-3-thienyl)-1H-pyrazole-3-carboxamide |
| 622 | 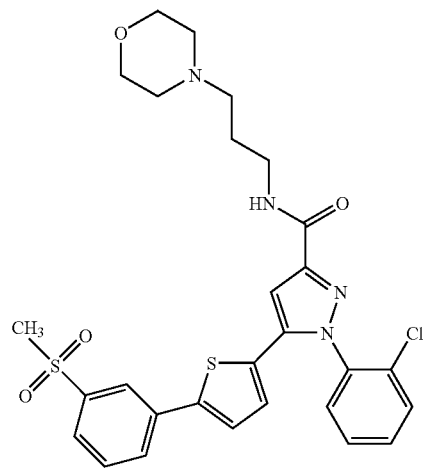 [SMILES: CS(=O)(=O)c1cccc(-c2ccc(-c3cc(C(=O)NCCCN4CCOCC4)nn3-c3ccccc3Cl)s2)c1] | 1-(2-chlorophenyl)-5-{5-[3-(methylsulfonyl)phenyl]-2-thienyl}-N-(3-morpholin-4-ylpropyl)-1H-pyrazole-3-carboxamide |
| 623 | 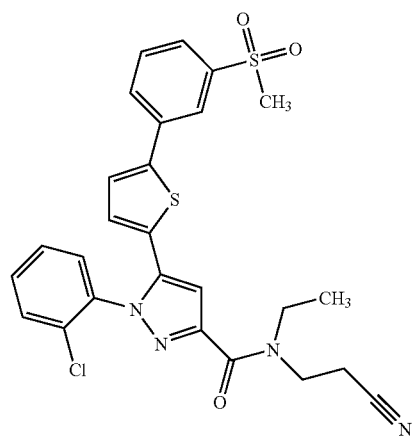 [SMILES: CCN(CCC#N)C(=O)c1cc(-c2ccc(-c3cccc(S(C)(=O)=O)c3)s2)n(-c2ccccc2Cl)n1] | 1-(2-chlorophenyl)-N-(2-cyanophenyl)-N-ethyl-5-{5-[3-(methylsulfonyl)phenyl]-2-thienyl}-1H-pyrazole-3-carboxamide |

| | | |
|---|---|---|
| 624 | 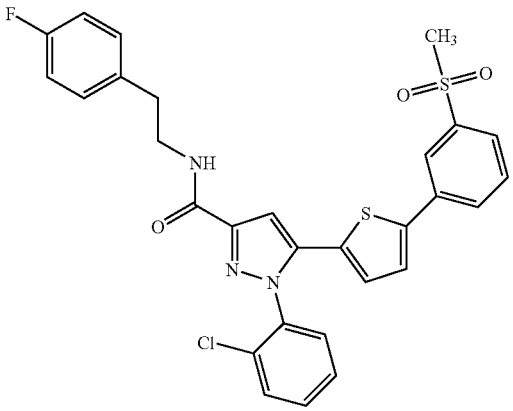 [SMILES: CS(=O)(=O)c1cccc(-c2ccc(-c3cc(C(=O)NCCc4ccc(F)cc4)nn3-c3ccccc3Cl)s2)c1] | 1-(2-chlorophenyl)-N-[2-(4-fluoropjhenyl)ethyl]-5-{5-[3-(methylsulfonyl)phenyl]-2-thienyl}-1H-pyrazole-3-carboxamide |
| 625 | 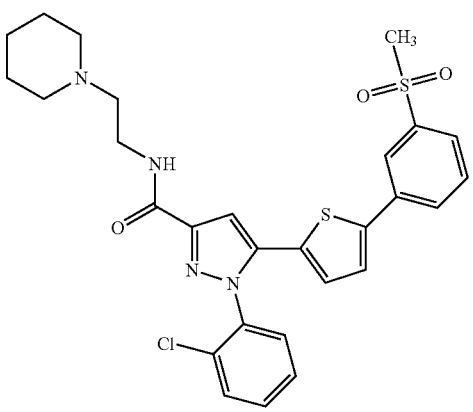 [SMILES: CS(=O)(=O)c1cccc(-c2ccc(-c3cc(C(=O)NCCN4CCCCC4)nn3-c3ccccc3Cl)s2)c1] | 1-(2-chlorophenyl)-5-{5-[3-(methylsulfonyl)phenyl]-2-thienyl}-N-(2-piperidin-1-ylethyl)-1H-pyrazole-3-carboxamide |
| 626 | 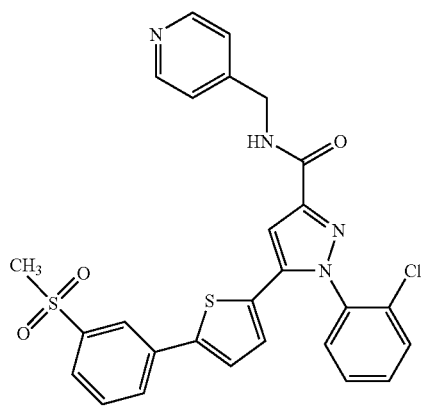 [SMILES: CS(=O)(=O)c1cccc(-c2ccc(-c3cc(C(=O)NCc4ccncc4)nn3-c3ccccc3Cl)s2)c1] | 1-(2-chlorophenyl)-5-{5-[3-(methylsulfonyl)phenyl]-2-thienyl}-N-(pyridin-4-ylmethyl)-1H-pyrazole-3-carboxamide |

| | | |
|---|---|---|
| 627 | 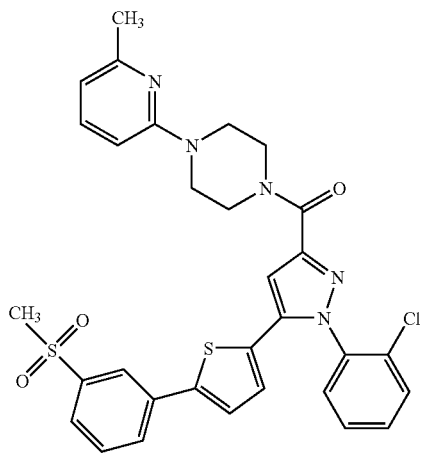 [SMILES: Cc1cccc(N2CCN(C(=O)c3cc(-c4ccc(-c5cccc(S(C)(=O)=O)c5)s4)n(-c4ccccc4Cl)n3)CC2)n1] | 1-{[1-(2-chlorophenyl)-5-{5-[3-(methylsulfonyl)phenyl]-2-thienyl}-1H-pyrazol-3-yl]carbonyl}-4-(6-methylpyridin-2-yl)piperazine |
| 628 | 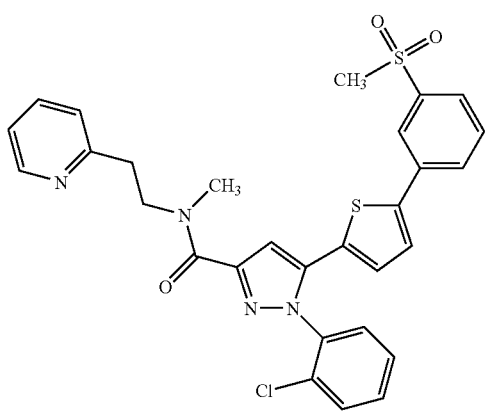 [SMILES: CN(CCc1ccccn1)C(=O)c1cc(-c2ccc(-c3cccc(S(C)(=O)=O)c3)s2)n(-c2ccccc2Cl)n1] | 1-(2-chlorophenyl)-N-methyl-5-{5-[3-(methylsulfonyl)phenyl]-2-thienyl}-N-(2-pyridin-2-ylethyl)-1H-pyrazole-3-carboxamide |
| 629 | 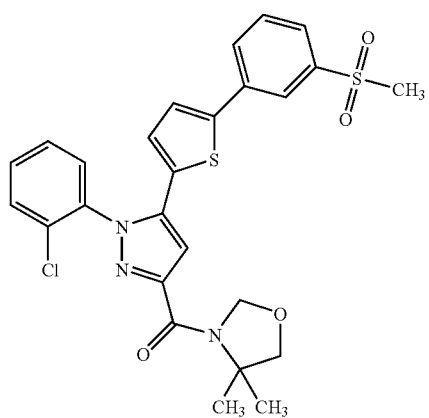 [SMILES: CC1(C)COCN1C(=O)c1cc(-c2ccc(-c3cccc(S(C)(=O)=O)c3)s2)n(-c2ccccc2Cl)n1] | 3-{[1-(2-chlorophenyl)-5-{5-[3-(methylsulfonyl)phenyl]-2-thienyl}-1H-pyrazol-3-yl]carbonyl}-4,4-dimethyl-1,3-oxazolidine |

| | | |
|---|---|---|
| 630 | 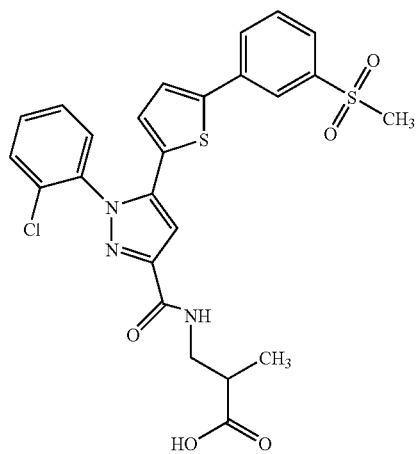 [SMILES: CC(CNC(=O)c1cc(-c2ccc(-c3cccc(S(C)(=O)=O)c3)s2)n(-c2ccccc2Cl)n1)C(=O)O] | 3-({[1-(2-chlorophenyl)-5-{5-[3-(methylsulfonyl)phenyl]-2-thienyl}-1H-pyrazol-3-yl]carbonyl}amino)-2-methylpropanoic acid |
| 631 | 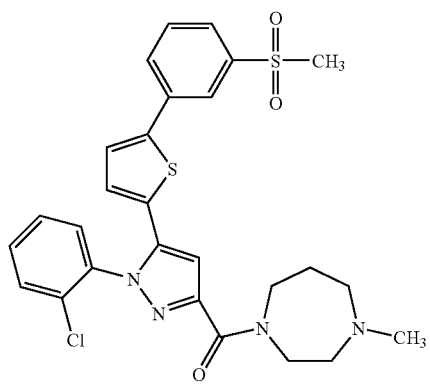 [SMILES: CN1CCCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-methyl-1,4-diazepane |
| 632 | 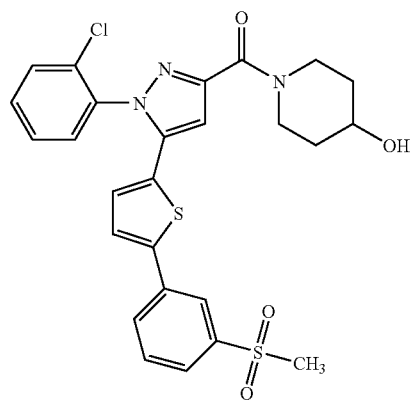 [SMILES: CS(=O)(=O)c1cccc(-c2ccc(-c3cc(C(=O)N4CCC(O)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}piperidin-4-ol |
| 633 | 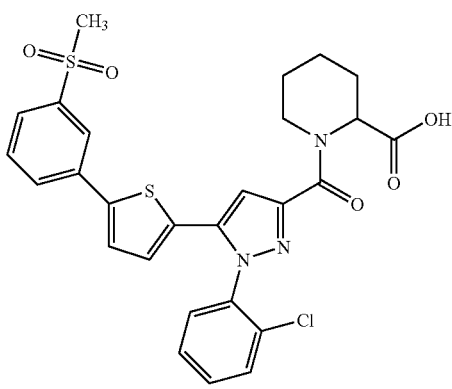 [SMILES: CS(=O)(=O)c1cccc(-c2ccc(-c3cc(C(=O)N4CCCCC4C(=O)O)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}piperidine-2-carboxylic acid |

TABLE 1-continued

| | | |
|---|---|---|
| 634 | 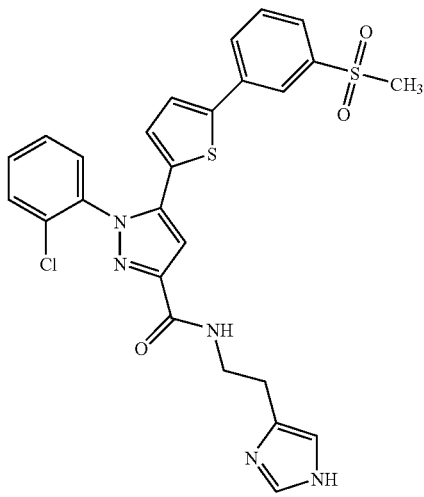 [SMILES: CS(=O)(=O)c1cccc(-c2ccc(-c3cc(C(=O)NCCc4c[nH]cn4)nn3-c3ccccc3Cl)s2)c1] | 1-(2-chlorophenyl)-N-[2-(1H-imidazol-4-yl)ethyl]-5-{5-[3-(methylsulfonyl)phenyl]-2-thienyl}-1H-pyrazole-3-carboxamide |
| 635 | 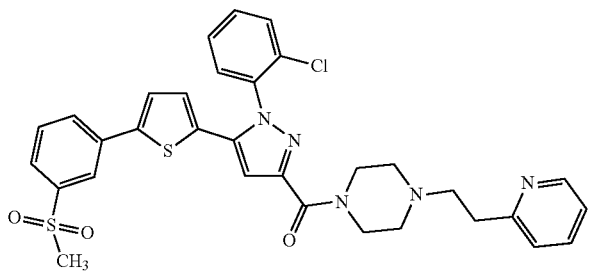 [SMILES: CS(=O)(=O)c1cccc(-c2ccc(-c3cc(C(=O)N4CCN(CCc5ccccn5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(2-pyridin-2-ylethyl)piperazine |
| 636 | 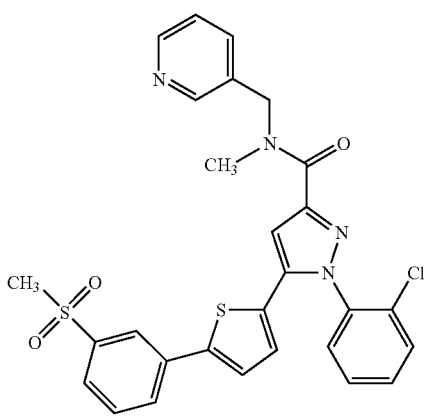 [SMILES: CN(Cc1cccnc1)C(=O)c1cc(-c2ccc(-c3cccc(S(C)(=O)=O)c3)s2)n(-c2ccccc2Cl)n1] | 1-(2-chlorophenyl)-N-methyl-5-{5-[3-(methylsulfonyl)phenyl]-2-thienyl}-N-(pyridin-3-ylmethyl)-1H-pyrazole-3-carboxamide |
| 637 | 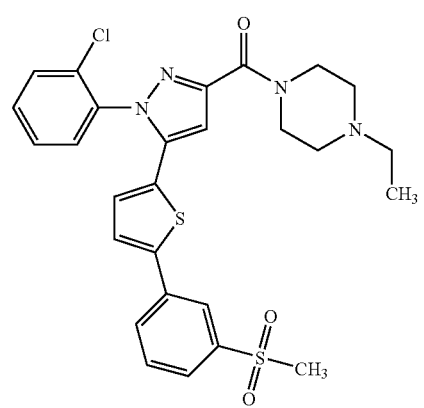 [SMILES: CCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-ethylpiperazine |

| | | |
|---|---|---|
| 638 | 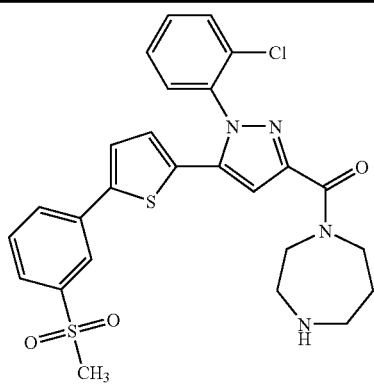 | 1-{[1-(2-chlorophenyl)-5-{5-[3-(methylsulfonyl)phenyl]-2-thienyl}-1H-pyrazol-3-yl]carbonyl}-1,4-diazepane |
| 639 | 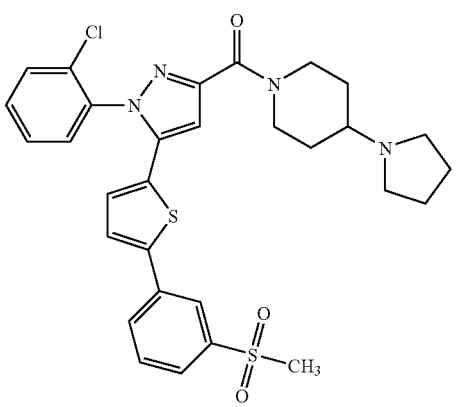 [SMILES: CS(=O)(=O)c1cccc(-c2ccc(-c3cc(C(=O)N4CCC(N5CCCC5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-pyrrolidin-1-ylpiperidine |
| 640 | 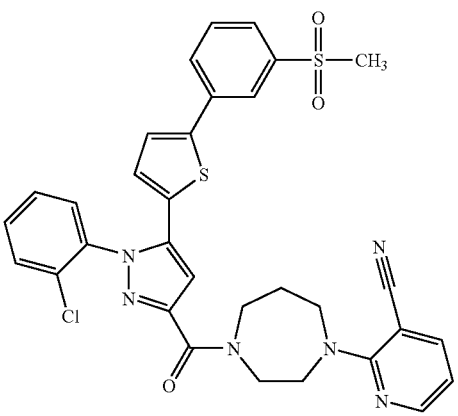 [SMILES: CS(=O)(=O)c1cccc(-c2ccc(-c3cc(C(=O)N4CCCN(c5ncccc5C#N)CC4)nn3-c3ccccc3Cl)s2)c1] | 2-(4-{[1-(2-chlorophenyl)-5-{5-[3-(methylsulfonyl)phenyl]-2-thienyl}-1H-pyrazol-3-yl]carbonyl}-1,4-diazepan-1-yl)pyridine-3-carbonitrile |
| 641 | 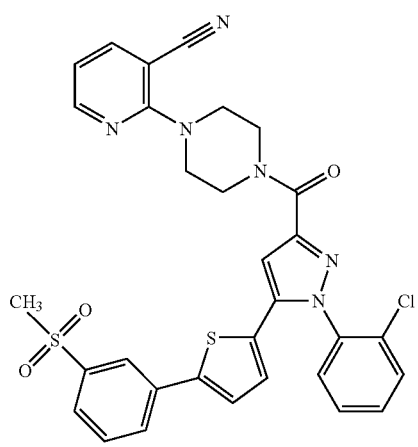 [SMILES: CS(=O)(=O)c1cccc(-c2ccc(-c3cc(C(=O)N4CCN(c5ncccc5C#N)CC4)nn3-c3ccccc3Cl)s2)c1] | 2-(4-{[1-(2-chlorophenyl)-5-{5-[3-(methylsulfonyl)phenyl]-2-thienyl}-1H-pyrazol-3-yl]carbonyl}piperazin-1-yl)pyridine-3-carboxamide |

TABLE 1-continued
| | | |
|---|---|---|
| 642 | 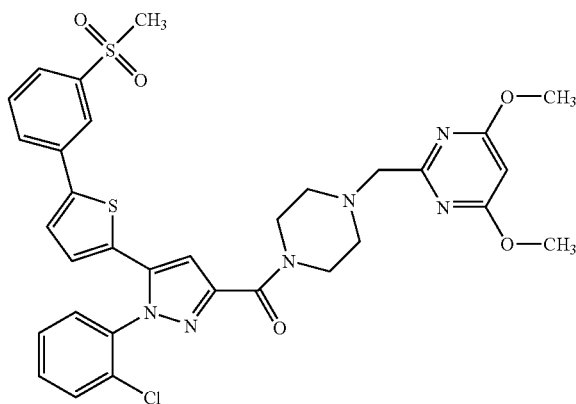 [SMILES: COc1cc(OC)nc(CN2CCN(C(=O)c3cc(-c4ccc(-c5cccc(S(C)(=O)=O)c5)s4)n(-c4ccccc4Cl)n3)CC2)n1] | 2-[(4-{[1-(2-chlorophenyl)-5-{5-[3-(methylsulfonyl)phenyl]-2-thienyl}-1H-pyrazol-3-yl]carbonyl}piperazin-1-yl)methyl]-4,6-bis(methyloxy)pyrimidine |
| 643 | 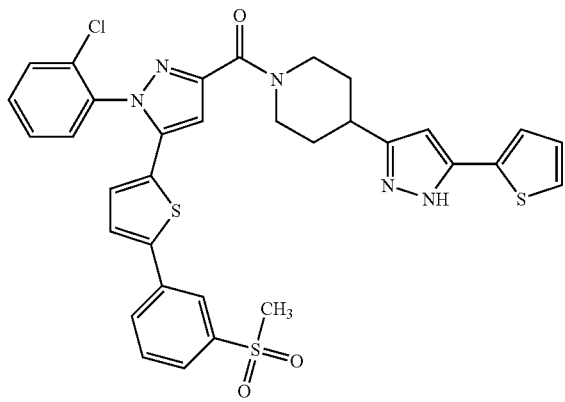 [SMILES: CS(=O)(=O)c1cccc(-c2ccc(-c3cc(C(=O)N4CCC(c5cc(-c6cccs6)[nH]n5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-[5-(2-thienyl)-1H-pyrazol-3-yl]piperidine |
| 644 | 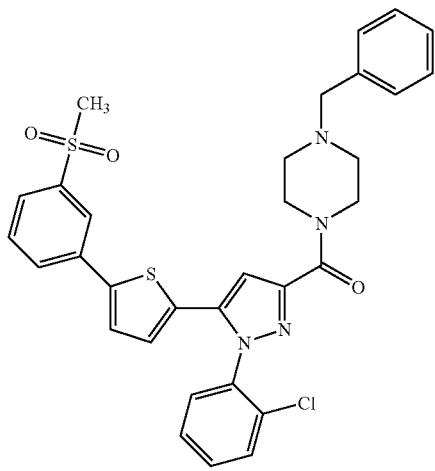 [SMILES: CS(=O)(=O)c1cccc(-c2ccc(-c3cc(C(=O)N4CCN(Cc5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(phenylmethyl)piperazine |

TABLE 1-continued
| 645 | 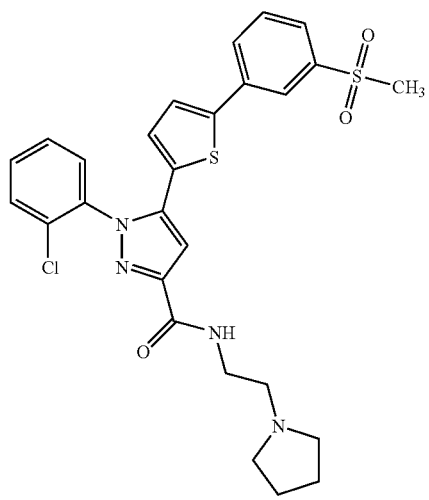 [SMILES: CS(=O)(=O)c1cccc(-c2ccc(-c3cc(C(=O)NCCN4CCCC4)nn3-c3ccccc3Cl)s2)c1] | 1-(2-chlorophenyl)-5-{5-[3-(methylsulfonyl)phenyl]-2-thienyl}-N-(2-pyrrolidin-1-ylethyl)-1H-pyrazole-3-carboxamide |
| 646 | 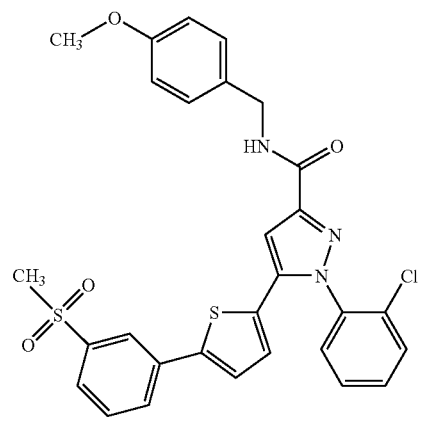 [SMILES: COc1ccc(CNC(=O)c2cc(-c3ccc(-c4cccc(S(C)(=O)=O)c4)s3)n(-c3ccccc3Cl)n2)cc1] | 1-(2-chlorophenyl)-N-{[4-(methyloxy)phenyl]methyl}-5-{5-[3-(methylsulfonyl)phenyl]-2-thienyl}-1H-pyrazole-3-carboxamide |
| 647 | 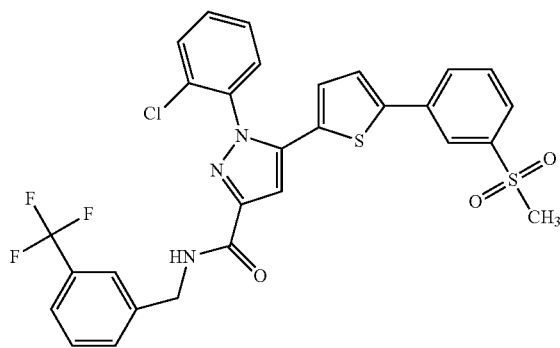 [SMILES: CS(=O)(=O)c1cccc(-c2ccc(-c3cc(C(=O)NCc4cccc(C(F)(F)F)c4)nn3-c3ccccc3Cl)s2)c1] | 1-(2-chlorophenyl)-5-{5-[3-(methylsulfonyl)phenyl]-2-thienyl}-N-{[3-(trifluoromethyl)phenyl]methyl}-1H-pyrazole-3-carboxamide |

TABLE 1-continued
648
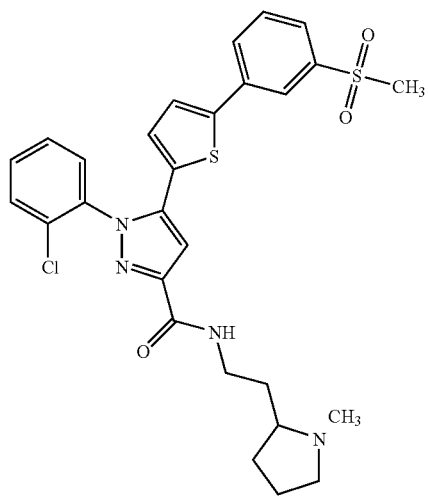
1-(2-chlorophenyl)-N-[2-(1-methylpyrrolidin-2-yl)ethyl]-5-{5-[3-(methylsulfonyl)phenyl-2-thienyl}-1H-pyrazole-3-carboxamide
649
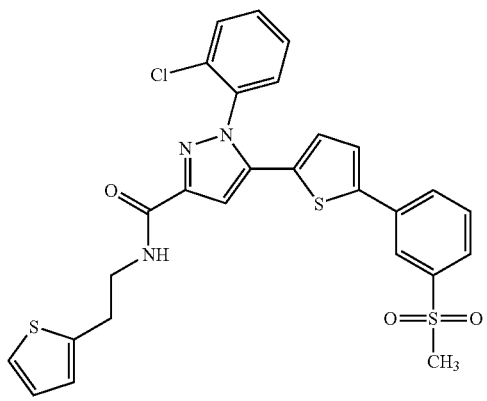 [SMILES: CS(=O)(=O)c1cccc(-c2ccc(-c3cc(C(=O)NCCc4cccs4)nn3-c3ccccc3Cl)s2)c1]
1-(2-chlorophenyl)-5-{5-[3-(methylsulfonyl)phenyl]-2-thienyl}-N-[2-(2-thienyl)ethyl]-1H-pyrazole-3-carboxamide
650
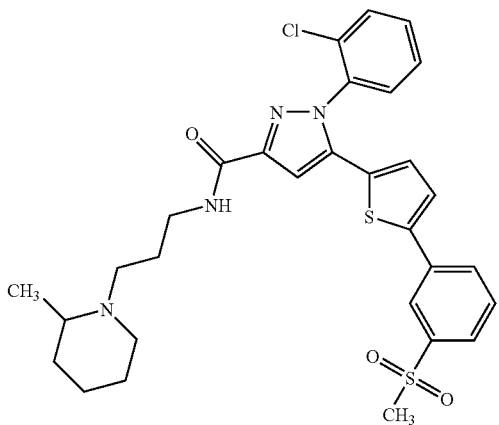 [SMILES: CC1CCCCN1CCCNC(=O)c1cc(-c2ccc(-c3cccc(S(C)(=O)=O)c3)s2)n(-c2ccccc2Cl)n1]
1-(2-chlorophenyl)-N-[3-(2-methylpiperidin-1-yl)propyl]-5-{5-[3-(methylsulfonyl)phenyl]-2-thienyl}-1H-pyrazole-3-carboxamide TABLE 1-continued

| | | |
|---|---|---|
| 651 | 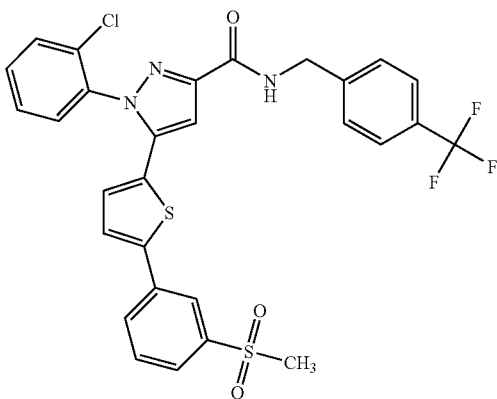 [SMILES: CS(=O)(=O)c1cccc(-c2ccc(-c3cc(C(=O)NCc4ccc(C(F)(F)F)cc4)nn3-c3ccccc3Cl)s2)c1] | 1-(2-chlorophenyl)-5-{5-[3-(methylsulfonyl)phenyl]-2-thienyl}-N-{[4-(trifluoromethyl)phenyl]methyl}-1H-pyrazole-3-carboxamide |
| 652 | 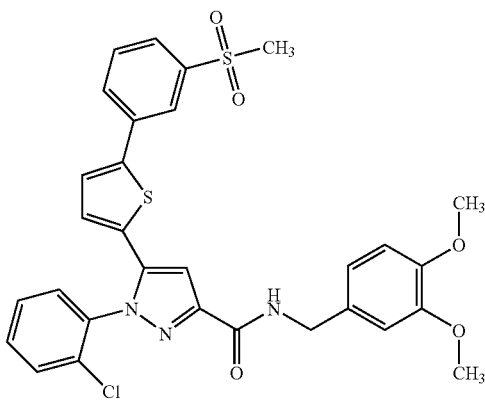 [SMILES: COc1ccc(CNC(=O)c2cc(-c3ccc(-c4cccc(S(C)(=O)=O)c4)s3)n(-c3ccccc3Cl)n2)cc1OC] | N-{[3,4-bis(methyloxy)phenyl]methyl}-1-(2-chlorophenyl)-5-{5-[3-(methylsulfonyl)phenyl]-2-thienyl}-1H-pyrazole-3-carboxamide |
| 653 | 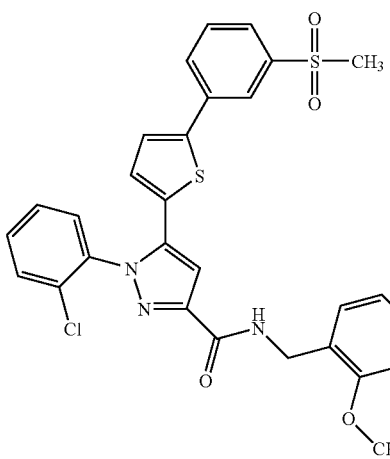 | 1-(2-chlorophenyl)-N-{[2-(methyloxy)phenyl]methyl}-5-{5-[3-(methylsulfonyl)phenyl]-2-thienyl}-1H-pyrazole-3-carboxamide |
| 654 | 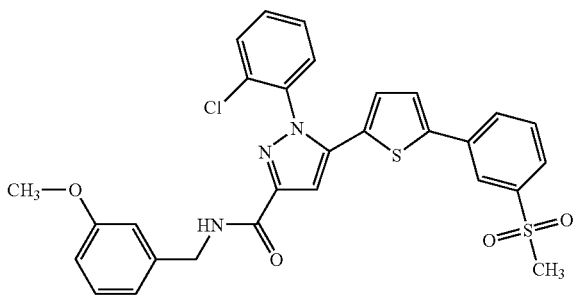 [SMILES: COc1cccc(CNC(=O)c2cc(-c3ccc(-c4cccc(S(C)(=O)=O)c4)s3)n(-c3ccccc3Cl)n2)c1] | 1-(2-chlorophenyl)-N-{[3-(methyloxy)phenyl]methyl}-5-{5-[3-(methylsulfonyl)phenyl]-2-thienyl}-1H-pyrazole-3-carboxamide |

TABLE 1-continued

| | | |
|---|---|---|
| 655 | 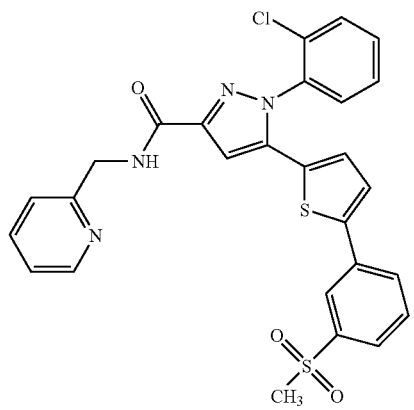 [SMILES: CS(=O)(=O)c1cccc(-c2ccc(-c3cc(C(=O)NCc4ccccn4)nn3-c3ccccc3Cl)s2)c1] | 1-(2-chlorophenyl)-5-{5-[3-(methylsulfonyl)phenyl]-2-thienyl}-N-(pyridin-2-ylmethyl)-1H-pyrazole-3-carboxamide |
| 656 | 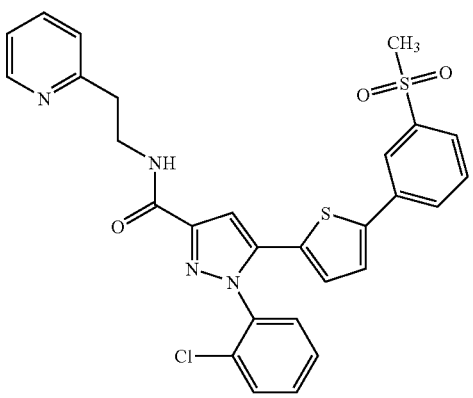 [SMILES: CS(=O)(=O)c1cccc(-c2ccc(-c3cc(C(=O)NCCc4ccccn4)nn3-c3ccccc3Cl)s2)c1] | 1-(2-chlorophenyl)-5-{5-[3-(methylsulfonyl)phenyl]-2-thienyl}-N-(2-pyridin-2-ylethyl)-1H-pyrazole-3-carboxamide |
| 657 | 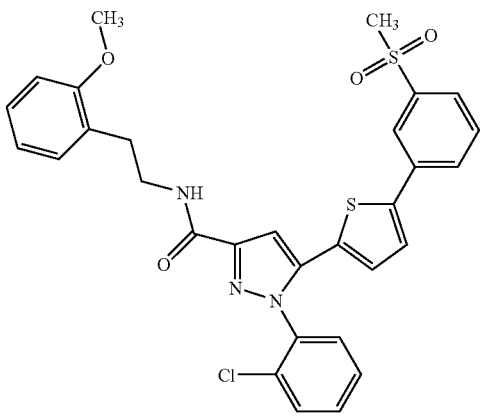 [SMILES: COc1ccccc1CCNC(=O)c1cc(-c2ccc(-c3cccc(S(C)(=O)=O)c3)s2)n(-c2ccccc2Cl)n1] | 1-(2-chlorophenyl)-N-{2-[2-(methyloxy)phenyl]ethyl}-5-{5-[3-(methylsulfonyl)phenyl]-2-thienyl-1H-pyrazole-3-carboxamide |
| 658 | 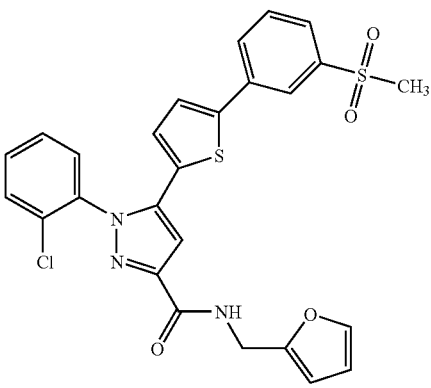 [SMILES: CS(=O)(=O)c1cccc(-c2ccc(-c3cc(C(=O)NCc4ccco4)nn3-c3ccccc3Cl)s2)c1] | 1-(2-chlorophenyl)-N-(furan-2-ylmethyl)-5-{5-[3-(methylsulfonyl)phenyl]-2-thienyl}-1H-pyrazole-3-carboxamide |

| | | |
|---|---|---|
| 659 | 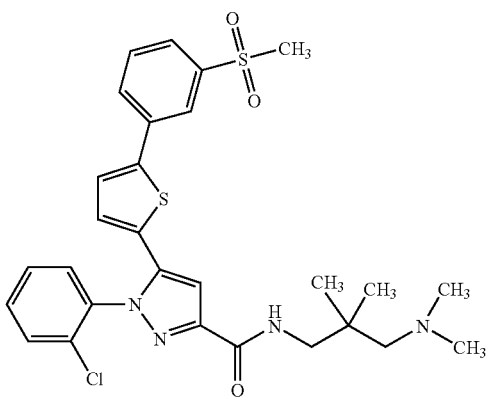 [SMILES: CN(C)CC(C)(C)CNC(=O)c1cc(-c2ccc(-c3cccc(S(C)(=O)=O)c3)s2)n(-c2ccccc2Cl)n1] | 1-(2-chlorophenyl)-N-[3-(dimethylamino)-2,2-dimethylpropyl]-5-{5-[3-(methylsulfonyl)phenyl]-2-thienyl}-1H-pyrazole-3-carboxamide |
| 660 | 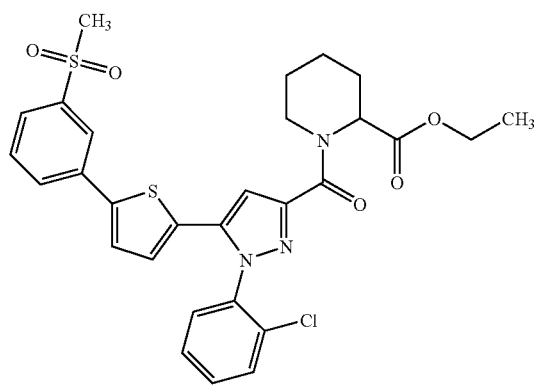 [SMILES: CCOC(=O)C1CCCCN1C(=O)c1cc(-c2ccc(-c3cccc(S(C)(=O)=O)c3)s2)n(-c2ccccc2Cl)n1] | ethyl 1-{[1-(2-chlorophenyl)-5-{5-[3-(methylsulfonyl)phenyl]-2-thienyl}-1H-pyrazol-3-yl]carbonyl}piperidine-2-carboxylate |
| 661 | 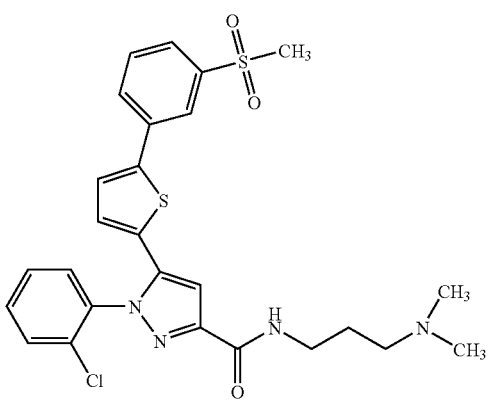 [SMILES: CN(C)CCCNC(=O)c1cc(-c2ccc(-c3cccc(S(C)(=O)=O)c3)s2)n(-c2ccccc2Cl)n1] | 1-(2-chlorophenyl)-N-[3-(dimethylamino)propyl]-5-{5-[3-(methylsulfonyl)phenyl]-2-thienyl}-1H-pyrazole-3-carboxamide |
| 662 | 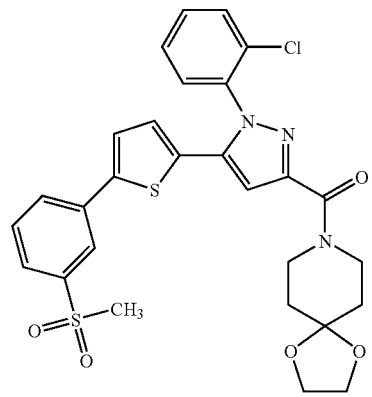 [SMILES: CS(=O)(=O)c1cccc(-c2ccc(-c3cc(C(=O)N4CCC5(CC4)OCCO5)nn3-c3ccccc3Cl)s2)c1] | 8-{[1-(2-chlorophenyl)-5-{5-[3-(methylsulfonyl)phenyl]-2-thienyl}-1H-pyrazol-3-yl]carbonyl}-1,4-dioxa-8-azaspiro[4.5]decane |

TABLE 1-continued

| | | |
|---|---|---|
| 663 | 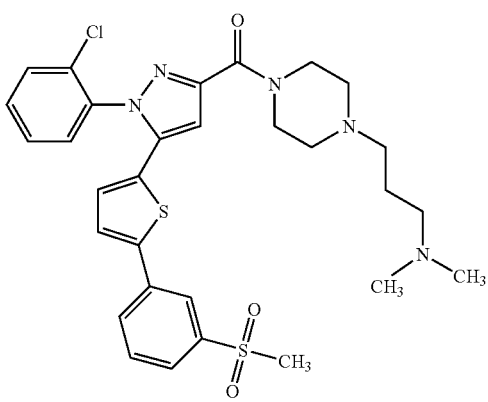 [SMILES: CN(C)CCCN1CCN(C(=O)c2cc(-c3ccc(-c4cccc(S(C)(=O)=O)c4)s3)n(-c3ccccc3Cl)n2)CC1] | 3-(4-{[1-(2-chlorophenyl)-5-{5-[3-(methylsulfonyl)phenyl]-2-thienyl)-1H-pyrazol-3-yl]carbonyl}piperazin-1-yl)-N,N-dimethylpropan-1-amine |
| 664 | 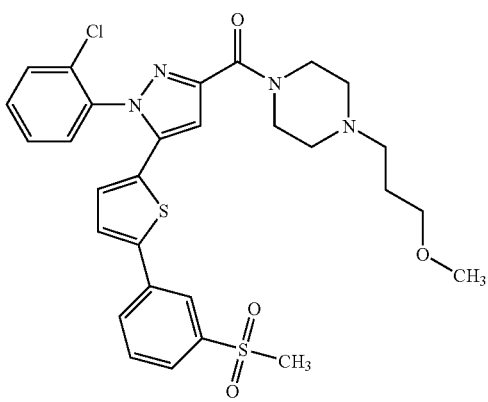 [SMILES: COCCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-[3-(methyloxy)propyl]piperazine |
| 665 | 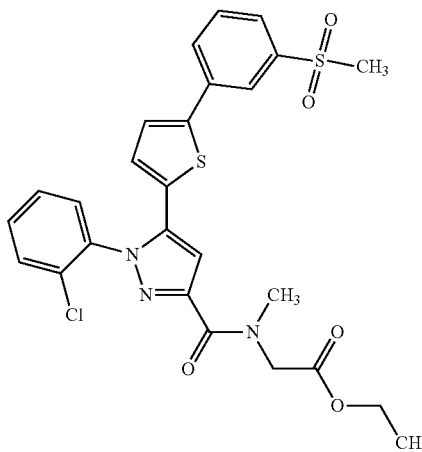 | ethyl N-{[1-(2-chlorophenyl)-5-{5-[3-(methylsulfonyl)phenyl]-2-thienyl-1H-pyrazol-3-yl]carbonyl}-N-methylglycinate |
| 666 | 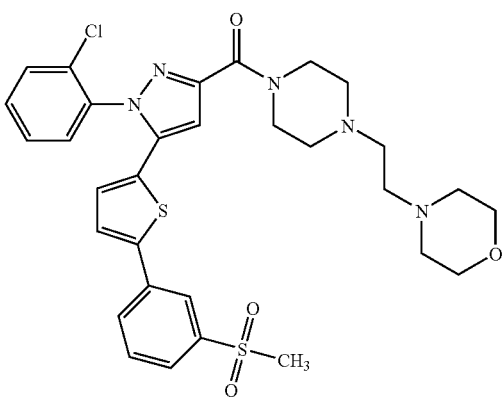 [SMILES: CS(=O)(=O)c1cccc(-c2ccc(-c3cc(C(=O)N4CCN(CCN5CCOCC5)CC4)nn3-c3ccccc3Cl)s2)c1] | 4-[2-(4-{[1-(2-chlorophenyl)-5-{5-[3-(methylsulfonyl)phenyl]-2-thienyl}-1H-pyrazol-3-yl]carbonyl}piperazin-1-yl)ethyl]morpholine |

| | | |
|---|---|---|
| 667 | 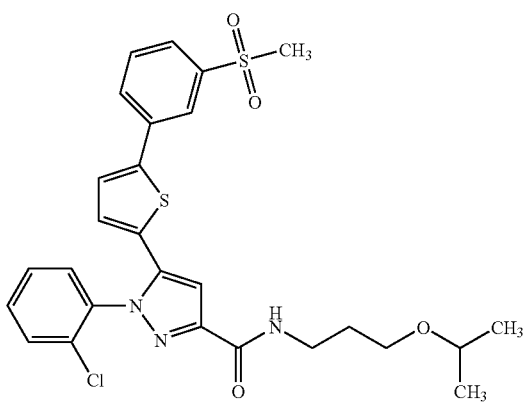 [SMILES: CC(C)OCCCNC(=O)c1cc(-c2ccc(-c3cccc(S(C)(=O)=O)c3)s2)n(-c2ccccc2Cl)n1] | 1-(2-chlorophenyl)-N-{3-[(1-methylethyl)oxy]propyl}-5-{5-[3-(methylsulfonyl)phenyl]-2-thienyl}-1H-pyrazole-3-carboxamide |
| 668 | 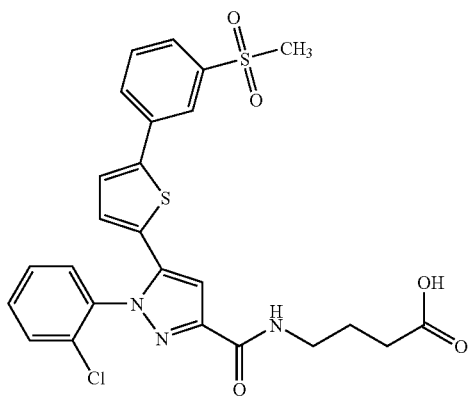 [SMILES: CS(=O)(=O)c1cccc(-c2ccc(-c3cc(C(=O)NCCCC(=O)O)nn3-c3ccccc3Cl)s2)c1] | 4-({[1-(2-chlorophenyl)-5-{5-[3-(methylsulfonyl)phenyl]-2-thienyl}-1H-pyrazol-3-yl]carbonyl}amino)butanoic acid |
| 669 | 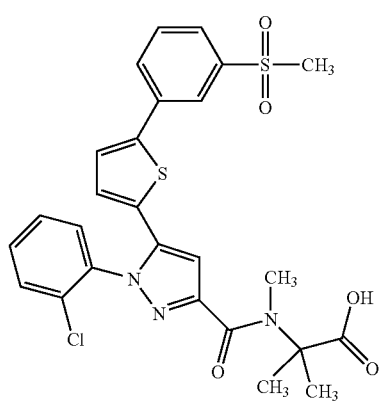 [SMILES: CN(C(=O)c1cc(-c2ccc(-c3cccc(S(C)(=O)=O)c3)s2)n(-c2ccccc2Cl)n1)C(C)(C)C(=O)O] | N-{[1-(2-chlorophenyl)-5-{5-[3-(methylsulfonyl)phenyl]-2-thienyl}-1H-pyrazol-3-yl]carbonyl}-N,2-dimethylalanine |

TABLE 1-continued

| 670 | 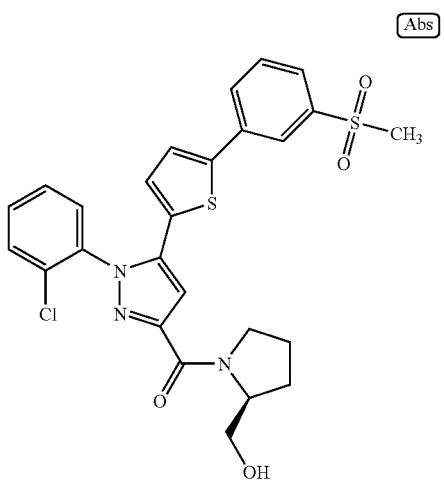 [SMILES: CS(=O)(=O)c1cccc(-c2ccc(-c3cc(C(=O)N4CCC[C@H]4CO)nn3-c3ccccc3Cl)s2)c1] | [(2S)-1-{[1-(2-chlorophenyl)-5-{5-[3-(methylsulfonyl)phenyl]-2-thienyl}-1H-pyrazol-3-yl]carbonyl}pyrrolidin-2-yl]methanol |
| 671 | 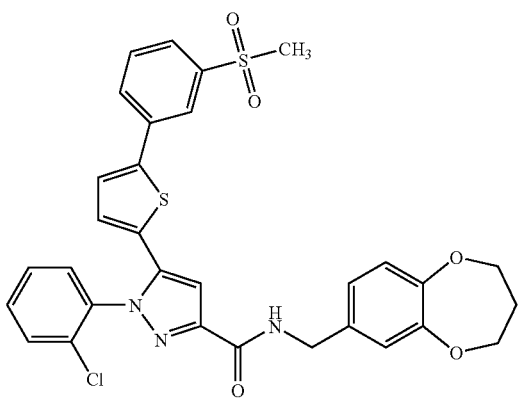 [SMILES: CS(=O)(=O)c1cccc(-c2ccc(-c3cc(C(=O)NCc4ccc5c(c4)OCCCO5)nn3-c3ccccc3Cl)s2)c1] | 1-(2-chlorophenyl)-N-(3,4-dihydro-2H-1,5-benzodioxepin-7-ylmethyl)-5-{5-[3-(methylsulfonyl)phenyl]-2-thienyl}-1H-pyrazole-3-carboxamide |
| 672 | 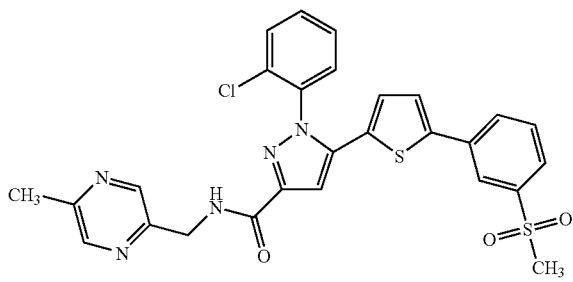 [SMILES: Cc1cnc(CNC(=O)c2cc(-c3ccc(-c4cccc(S(C)(=O)=O)c4)s3)n(-c3ccccc3Cl)n2)cn1] | 1-(2-chlorophenyl)-N-[(5-methylpyrazin-2-yl)methyl]-5-{5-[3-(methylsulfonyl)phenyl]-2-thienyl}-1H-pyrazole-3-carboxamide |
| 673 | 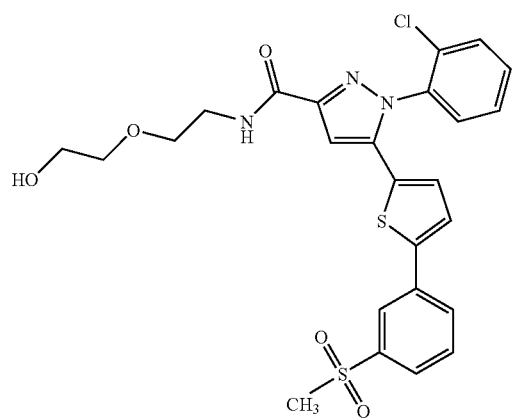 [SMILES: CS(=O)(=O)c1cccc(-c2ccc(-c3cc(C(=O)NCCOCCO)nn3-c3ccccc3Cl)s2)c1] | 1-(2-chlorophenyl)-N-{2-[(2-hydroxyethyl)oxy]methyl}-5-{5-[3-(methylsulfonyl)phenyl]-2-thienyl}-1H-pyrazole-3-carboxamide |

| | | |
|---|---|---|
| 674 | 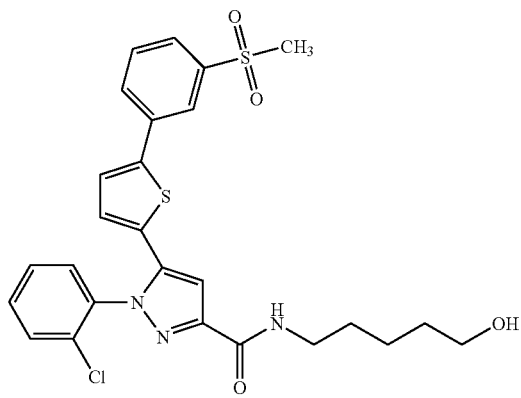 [SMILES: CS(=O)(=O)c1cccc(-c2ccc(-c3cc(C(=O)NCCCCCO)nn3-c3ccccc3Cl)s2)c1] | 1-(2-chlorophenyl)-N-(5-hydroxypentyl)-5-{5-[3-(methylsulfonyl)phenyl]-2-thienyl}-1H-pyrazole-3-carboxamide |
| 675 | 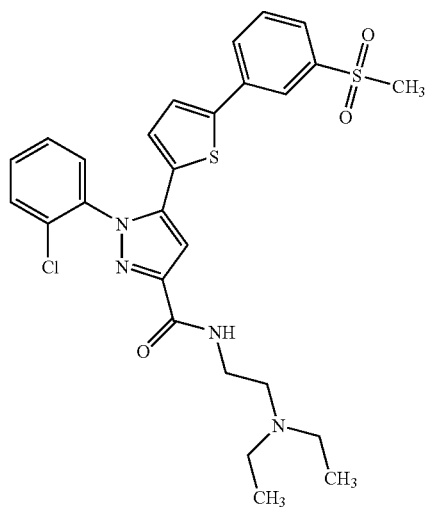 [SMILES: CCN(CC)CCNC(=O)c1cc(-c2ccc(-c3cccc(S(C)(=O)=O)c3)s2)n(-c2ccccc2Cl)n1] | 1-(2-chlorophenyl)-N-[2-(diethylamino)ethyl]-5-{5-[3-(methylsulfonyl)phenyl]-2-thienyl}-1H-pyrazole-3-carboxamide |
| 676 | 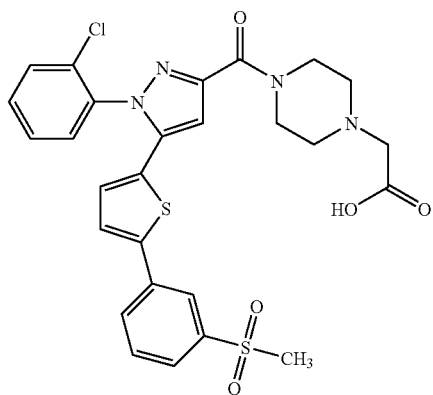 [SMILES: CS(=O)(=O)c1cccc(-c2ccc(-c3cc(C(=O)N4CCN(CC(=O)O)CC4)nn3-c3ccccc3Cl)s2)c1] | (4-{[1(2-chlorophenyl)-5-{5-[3-(methylsulfonyl)phenyl]-2-thienyl}-1H-pyrazol-3-yl]carbonyl}piperazin-1-yl)acetic acid |

| | | |
|---|---|---|
| 677 | 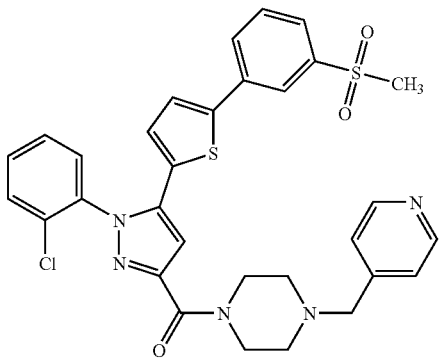 [SMILES: CS(=O)(=O)c1cccc(-c2ccc(-c3cc(C(=O)N4CCN(Cc5ccncc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(pyridin-4-ylmethyl)piperazine |
| 678 | 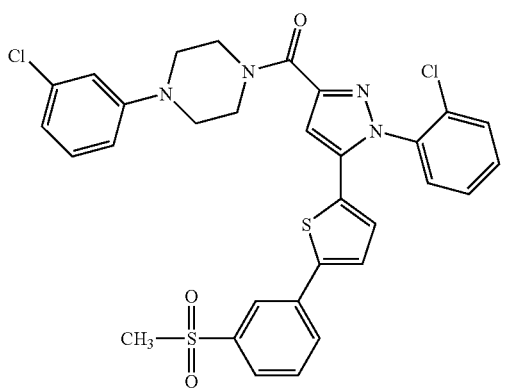 [SMILES: CS(=O)(=O)c1cccc(-c2ccc(-c3cc(C(=O)N4CCN(c5cccc(Cl)c5)CC4)nn3-c3ccccc3Cl)s2)c1] | 1-(3-chlorophenyl)-4-{[1-(2-chlorophenyl)-5-{5-[3-(methylsulfonyl)phenyl]-2-thienyl}-1H-pyrazol-3-yl]carbonyl}piperazine |
| 679 | 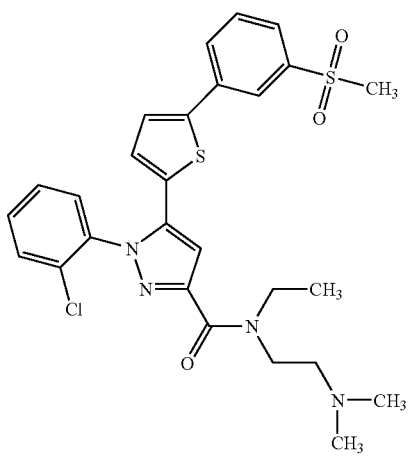 [SMILES: CCN(CCN(C)C)C(=O)c1cc(-c2ccc(-c3cccc(S(C)(=O)=O)c3)s2)n(-c2ccccc2Cl)n1] | 1-(2-chlorophenyl)-N-[2-(dimethylamino)ethyl]-N-ethyl-5-{5-[3-(methylsulfonyl)phenyl-2-thienyl}-1H-pyrazole-3-carboxamide |
| 680 | 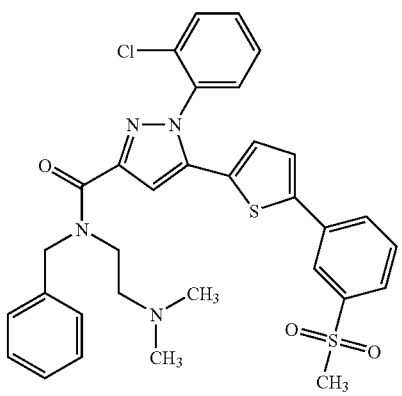 [SMILES: CN(C)CCN(Cc1ccccc1)C(=O)c1cc(-c2ccc(-c3cccc(S(C)(=O)=O)c3)s2)n(-c2ccccc2Cl)n1] | 1-(2-chlorophenyl)-N-[2-(dimethylamino)ethyl]-5-{5-[3-(methylsulfonyl)phenyl]-2-thienyl}-N-(phenylmethyl)-1H-pyrazole-3-carboxamide |

| 681 | 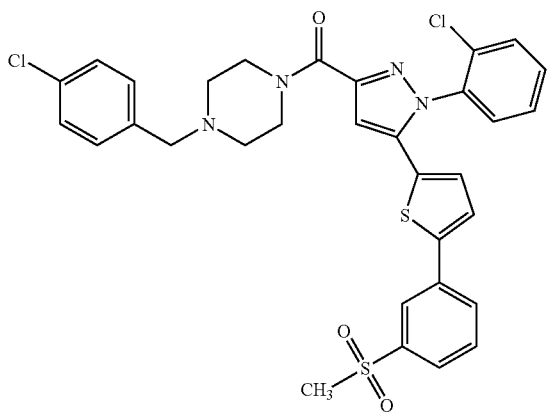 [SMILES: CS(=O)(=O)c1cccc(-c2ccc(-c3cc(C(=O)N4CCN(Cc5ccc(Cl)cc5)CC4)nn3-c3ccccc3Cl)s2)c1] | 1-[(4-chlorophenyl)methyl]-4-{[1-(2-chlorophenyl)-5-{5-[3-(methylsulfonyl)phenyl]-2-thienyl}-1H-pyrazol-3-yl]carbonyl}piperazine |
| --- | --- | --- |
| 682 | 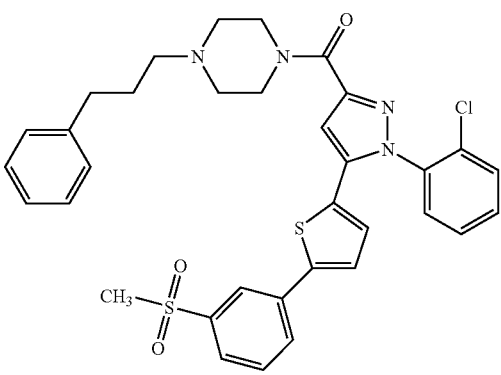 [SMILES: CS(=O)(=O)c1cccc(-c2ccc(-c3cc(C(=O)N4CCN(CCCc5ccccc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(3-phenylpropyl)piperazine |
| 683 | 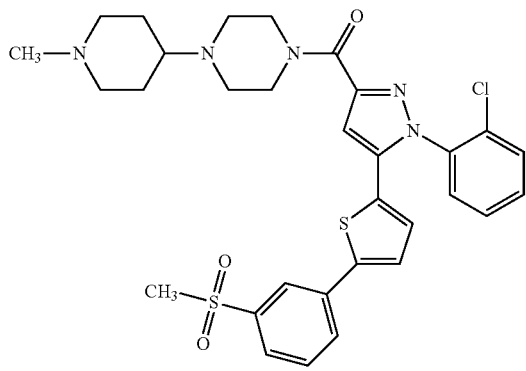 [SMILES: CN1CCC(N2CCN(C(=O)c3cc(-c4ccc(-c5cccc(S(C)(=O)=O)c5)s4)n(-c4ccccc4Cl)n3)CC2)CC1] | 1-{[1-(2-chlorophenyl)-5-{5-[3-(methylsulfonyl)phenyl]-2-thienyl}-1H-pyrazol-3-yl]carbonyl}-4-(1-methylpiperidin-4-yl)piperazine |
| 684 | 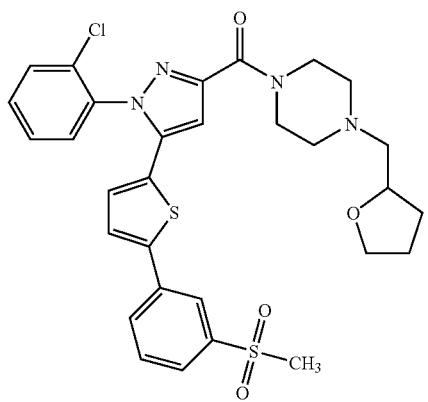 [SMILES: CS(=O)(=O)c1cccc(-c2ccc(-c3cc(C(=O)N4CCN(CC5CCCO5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(tetrahydrofuran-2-ylmethyl)piperazine |

TABLE 1-continued

| | | |
|---|---|---|
| 685 | 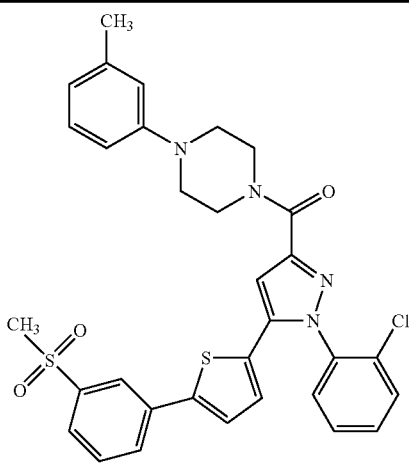 | 1-{[1-(2-chlorophenyl)-5-{5-[3-(methylsulfonyl)phenyl]-2-thienyl}-1H-pyrazol-3-yl]carbonyl}-4-(3-methylphenyl)piperazine |
| 686 | 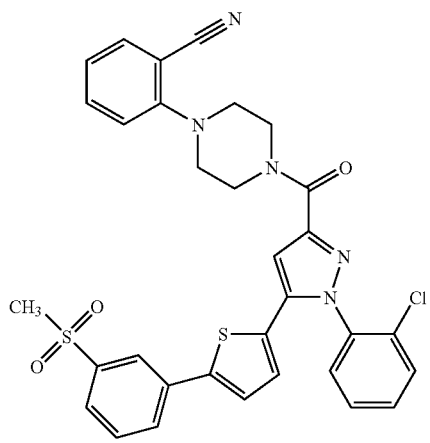 [SMILES: CS(=O)(=O)c1cccc(-c2ccc(-c3cc(C(=O)N4CCN(c5ccccc5C#N)CC4)nn3-c3ccccc3Cl)s2)c1] | 2-(4-{[1-(2-chlorophenyl)-5-{5-[3-(methylsulfonyl)phenyl]-2-thienyl-1H-pyrazol-3-yl]carbonyl}piperazin-1-yl)benzonitrile |
| 687 | 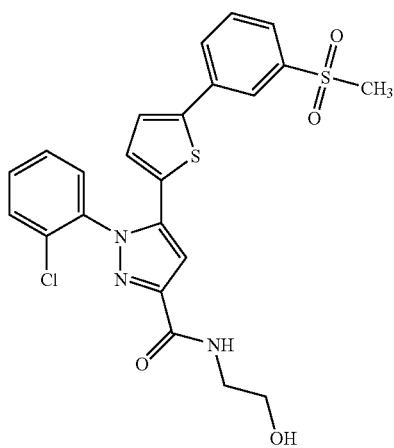 [SMILES: CS(=O)(=O)c1cccc(-c2ccc(-c3cc(C(=O)NCCO)nn3-c3ccccc3Cl)s2)c1] | 1-(2-chlorophenyl)-N-(2-hydroxyethyl)-5-{5-[3-(methylsulfonyl)phenyl]-2-thienyl}-1H-pyrazole-3-carboxamide |
| 688 | 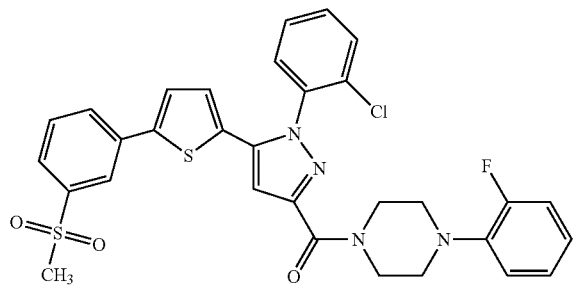 [SMILES: CS(=O)(=O)c1cccc(-c2ccc(-c3cc(C(=O)N4CCN(c5ccccc5F)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(2-fluorophenyl)piperazine |

TABLE 1-continued

| 689 | 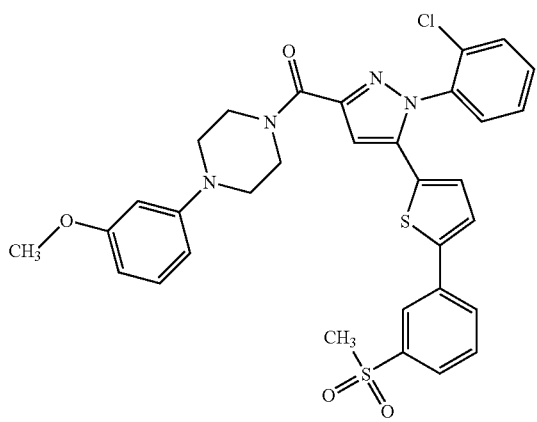 [SMILES: COc1cccc(N2CCN(C(=O)c3cc(-c4ccc(-c5cccc(S(C)(=O)=O)c5)s4)n(-c4ccccc4Cl)n3)CC2)c1] | 1-{[1-(2-chlorophenyl)-5-{5-[3-(methylsulfonyl)phenyl]-2-thienyl}-1H-pyrazol-3-yl]carbonyl}-4-[3-(methyloxy)phenyl]piperazine |
| --- | --- | --- |
| 690 | 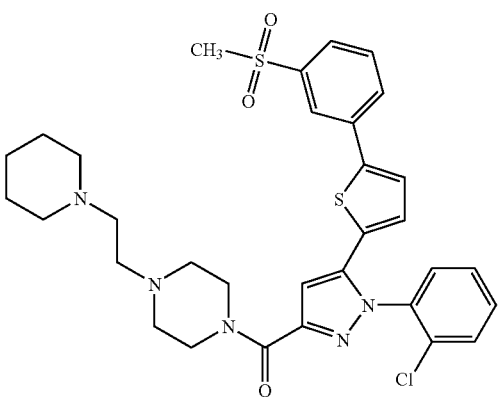 [SMILES: CS(=O)(=O)c1cccc(-c2ccc(-c3cc(C(=O)N4CCN(CCN5CCCCC5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(2-piperidin-1-ylethyl)piperazine |
| 691 | 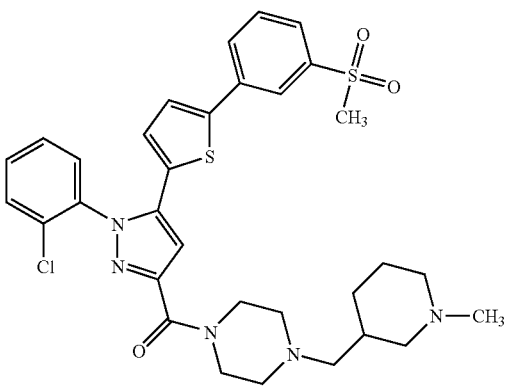 [SMILES: CN1CCCC(CN2CCN(C(=O)c3cc(-c4ccc(-c5cccc(S(C)(=O)=O)c5)s4)n(-c4ccccc4Cl)n3)CC2)C1] | 1-{[1-(2-chlorophenyl)-5-{5-[3-(methylsulfonyl)phenyl]-2-thienyl}-1H-pyrazol-3-yl]carbonyl}-4-[(1-methylpiperidin-3-yl)methyl]piperazine |
| 692 | 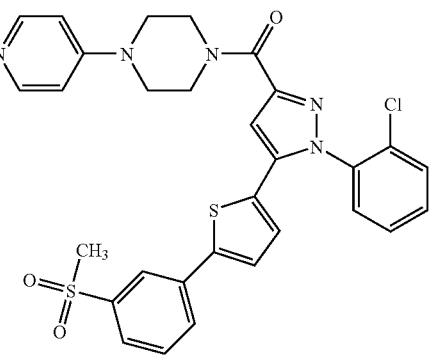 | 1-{[1-(2-chlorophenyl)-5-{5-[3-(methylsulfonyl)phenyl]-2-thienyl}-1H-pyrazol-3-yl]carbonyl}-4-pyridin-4-ylpiperazine |

TABLE 1-continued

| 693 |  | 1-(2-chlorophenyl)-N-(1,3-dioxolan-2-ylmethyl)-N-methyl-5-{5-[3-(methylsulfonyl)phenyl]-2-thienyl}-1H-pyrazole-3-carboxamide |
| 694 | 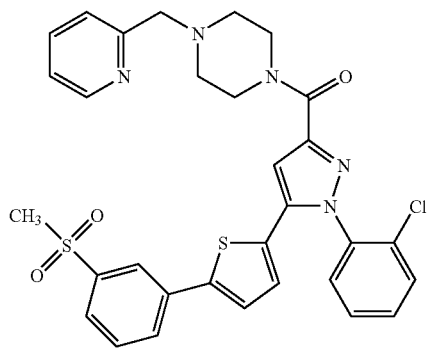 [SMILES: CS(=O)(=O)c1cccc(-c2ccc(-c3cc(C(=O)N4CCN(Cc5ccccn5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(pyridin-2-ylmethyl)piperazine |
| 695 | 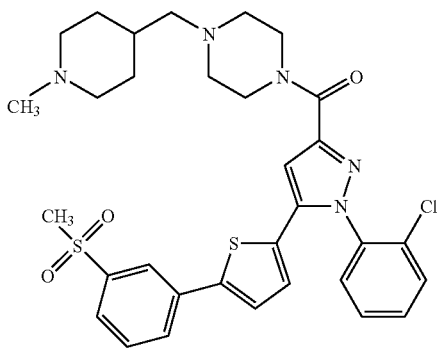 [SMILES: CN1CCC(CN2CCN(C(=O)c3cc(-c4ccc(-c5cccc(S(C)(=O)=O)c5)s4)n(-c4ccccc4Cl)n3)CC2)CC1] | 1-{[1-(2-chlorophenyl)-5-{5-[3-(methylsulfonyl)phenyl]-2-thienyl}-1H-pyrazol-3-yl]carbonyl}-4-[(1-methylpiperidin-4-yl)methyl]piperazine |
| 696 | 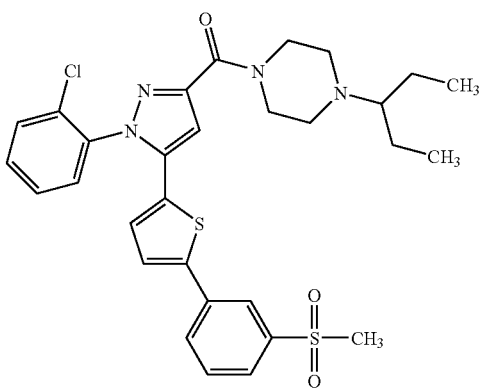 [SMILES: CCC(CC)N1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-(1-ethylpropyl)piperazine |

TABLE 1-continued

| 697 | 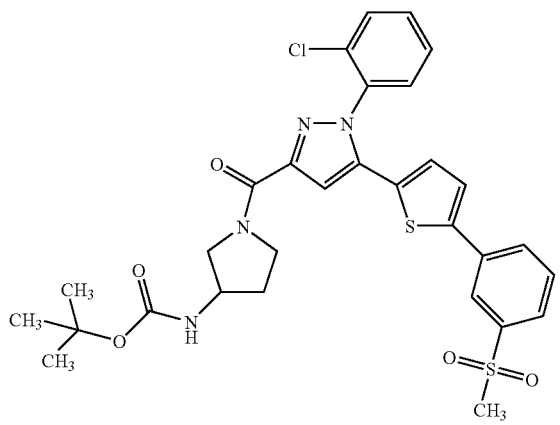 [SMILES: CC(C)(C)OC(=O)NC1CCN(C(=O)c2cc(-c3ccc(-c4cccc(S(C)(=O)=O)c4)s3)n(-c3ccccc3Cl)n2)C1] | 1,1-dimethylethyl (1-{[1-(2-chlorophenyl)-5-{5-[3-(methylsulfonyl)phenyl]-2-thienyl}-1H-pyrazol-3-yl]carbonyl}pyrrolidin-3-yl)carbamate |
| --- | --- | --- |
| 698 | 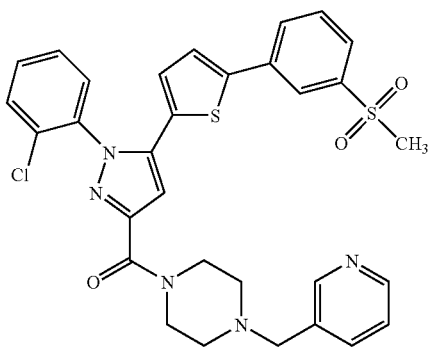 [SMILES: CS(=O)(=O)c1cccc(-c2ccc(-c3cc(C(=O)N4CCN(Cc5cccnc5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(pyridin-3-ylmethyl)piperazine |
| 699 | 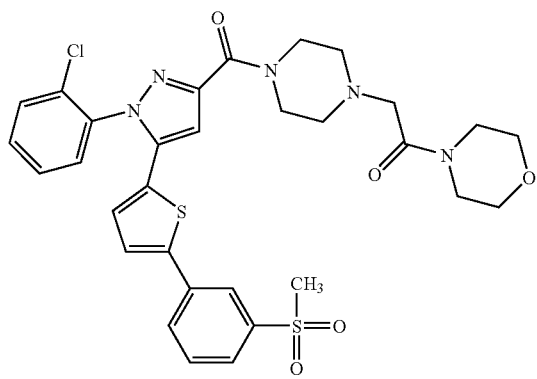 [SMILES: CS(=O)(=O)c1cccc(-c2ccc(-c3cc(C(=O)N4CCN(CC(=O)N5CCOCC5)CC4)nn3-c3ccccc3Cl)s2)c1] | 4-[(4-{[1-(2-chlorophenyl)-5-{5-[3-(methylsulfonyl)phenyl]-2-thienyl}-1H-pyrazol-3-yl]carbonyl}piperazin-1-yl)acetyl]morpholine |
| 700 | 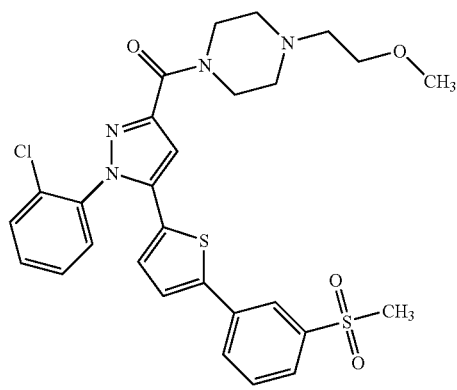 [SMILES: COCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-[2-(methyloxy)ethyl]piperazine |

TABLE 1-continued

| | | |
|---|---|---|
| 701 | 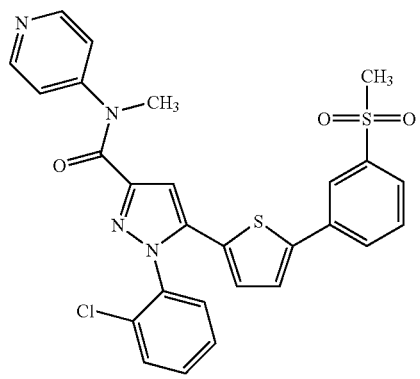 [SMILES: CN(C(=O)c1cc(-c2ccc(-c3cccc(S(C)(=O)=O)c3)s2)n(-c2ccccc2Cl)n1)c1ccncc1] | 1-(2-chlorophenyl)-N-methyl-5-{5-[3-(methylsulfonyl)phenyl]-2-thienyl}-N-pyridin-4-yl-1H-pyrazole-3-carboxamide |
| 702 | 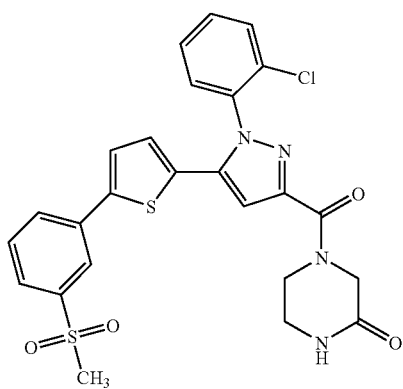 [SMILES: CS(=O)(=O)c1cccc(-c2ccc(-c3cc(C(=O)N4CCNC(=O)C4)nn3-c3ccccc3Cl)s2)c1] | 4-{[1-(2-chlorophenyl)-5-{5-[3-(methylsulfonyl)phenyl]-2-thienyl}-1H-pyrazol-3-yl]carbonyl}piperazin-2-one |
| 703 | 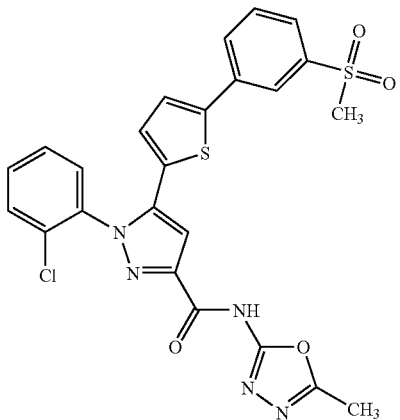 [SMILES: Cc1nnc(NC(=O)c2cc(-c3ccc(-c4cccc(S(C)(=O)=O)c4)s3)n(-c3ccccc3Cl)n2)o1] | 1-(2-chlorophenyl)-N-(5-methyl-1,3,4-oxadiazol-2-yl)-5-{5-[3-(methylsulfonyl)phenyl]-2-thienyl}-1H-pyrazole-3-carboxamide |
| 704 | 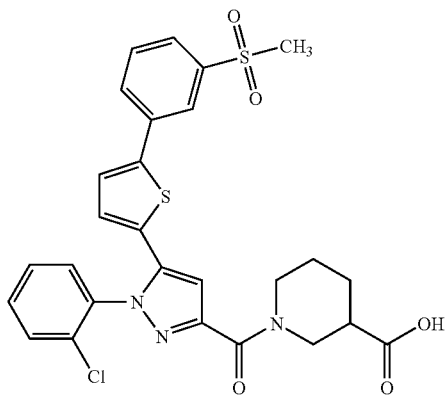 [SMILES: CS(=O)(=O)c1cccc(-c2ccc(-c3cc(C(=O)N4CCCC(C(=O)O)C4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}piperidine-3-carboxylic acid |

| | | |
|---|---|---|
| 705 | 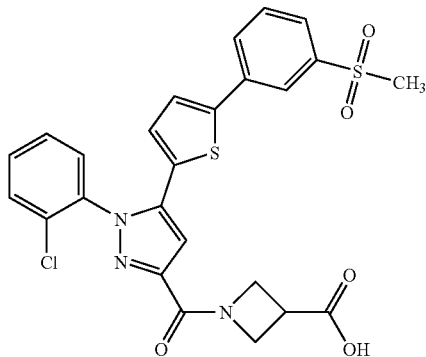 [SMILES: CS(=O)(=O)c1cccc(-c2ccc(-c3cc(C(=O)N4CC(C(=O)O)C4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}aztidine-3-carboxylic acid |
| 706 | 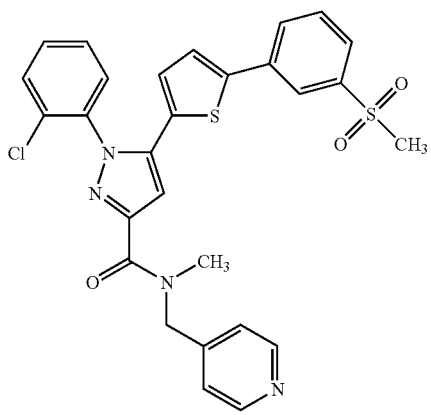 [SMILES: CN(Cc1ccncc1)C(=O)c1cc(-c2ccc(-c3cccc(S(C)(=O)=O)c3)s2)n(-c2ccccc2Cl)n1] | 1-(2-chlorophenyl)-N-methyl-5-{5-[3-(methylsulfonyl)phenyl]-2-thienyl}-N-(pyridin-4-ylmethyl)-1H-pyrazole-1-carboxamide |
| 707 | 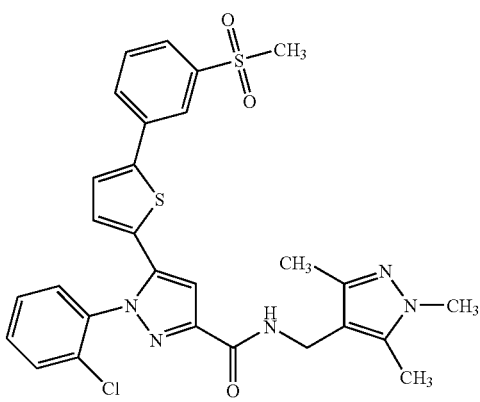 [SMILES: Cc1nn(C)c(C)c1CNC(=O)c1cc(-c2ccc(-c3cccc(S(C)(=O)=O)c3)s2)n(-c2ccccc2Cl)n1] | 1-(2-chlorophenyl)-5-{5-[3-(methylsulfonyl)phenyl]-2-thienyl}-N-[(1,3,5-trimethyl-1H-pyrazol-4-yl)methyl]-1H-pyrazole-3-carboxamide |
| 708 | 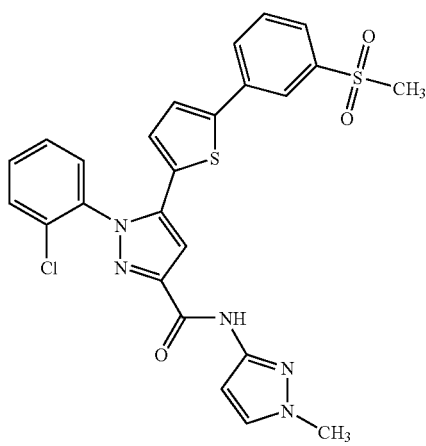 [SMILES: Cn1ccc(NC(=O)c2cc(-c3ccc(-c4cccc(S(C)(=O)=O)c4)s3)n(-c3ccccc3Cl)n2)n1] | 1-(2-chlorophenyl)-N-(1-methyl-1H-pyrazol-3-yl)-5-{5-[3-(methylsulfonyl)phenyl]-2-thienyl}-1H-pyrazole-3-carboxamide |

| # | | Name |
|---|---|---|
| 709 | 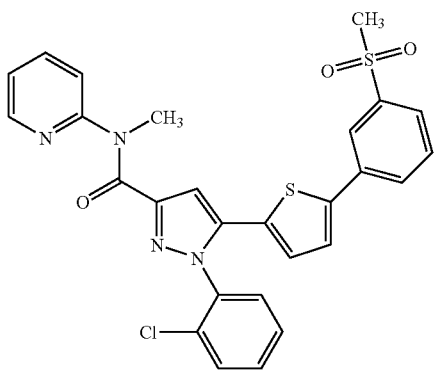 [SMILES: CN(C(=O)c1cc(-c2ccc(-c3cccc(S(C)(=O)=O)c3)s2)n(-c2ccccc2Cl)n1)c1ccccn1] | 1-(2-chlorophenyl)-N-methyl-5-{5-[3-(methylsulfonyl)phenyl]-2-thienyl}-N-pyridin-2-yl-1H-pyrazole-3-carboxamide |
| 710 | 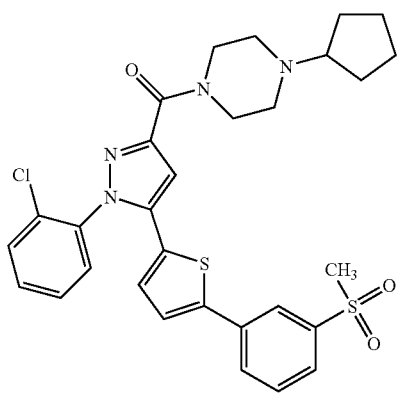 [SMILES: CS(=O)(=O)c1cccc(-c2ccc(-c3cc(C(=O)N4CCN(C5CCCC5)CC4)nn3-c3ccccc3Cl)s2)c1] | 1-{[1-(2-chlorophenyl)-5-{5-[3-(methylsulfonyl)phenyl]-2-thienyl}-1H-pyrazole-3-yl]carbonyl}-4-[4-(methyloxy)butyl]piperazine |
| 711 | 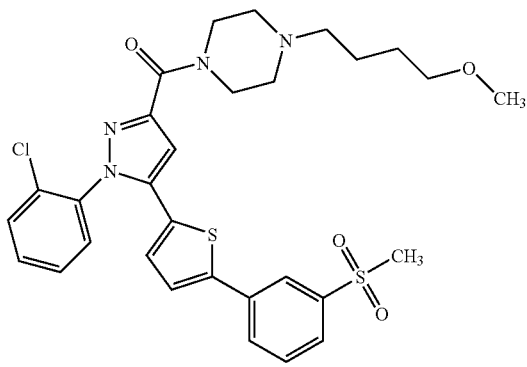 [SMILES: COCCCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-[4-(methyloxy)butyl]piperazine |
| 712 | 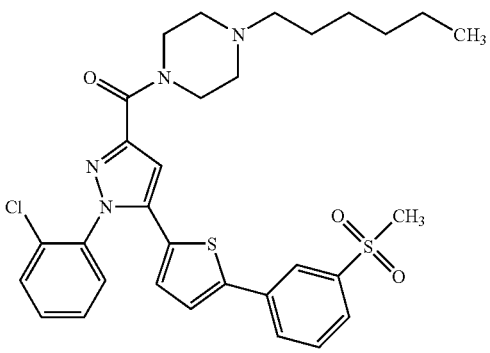 [SMILES: CCCCCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-hexylpiperazine |

TABLE 1-continued
| 713 | 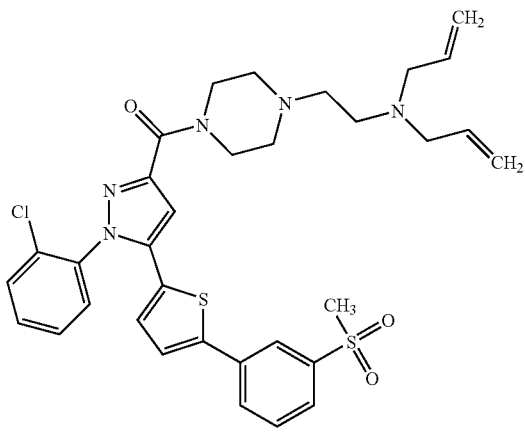 [SMILES: C=CCN(CC=C)CCN1CCN(C(=O)c2cc(-c3ccc(-c4cccc(S(C)(=O)=O)c4)s3)n(-c3ccccc3Cl)n2)CC1] | N-[2-(4-{[1-(2-chlorophenyl)-5-{5-[3-(methylsulfonyl)phenyl]-2-thienyl}-1H-pyrazol-3-yl]carbonyl}piperazin-1-yl)ethyl]-N-prop-2-en-1-ylprop-2-en-1-amine |
| 714 | 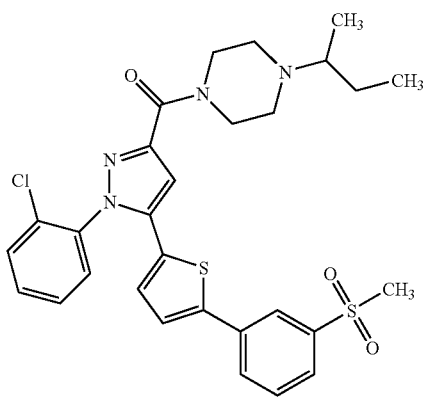 [SMILES: CCC(C)N1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-(1-methylpropyl)piperazine |
| 715 | 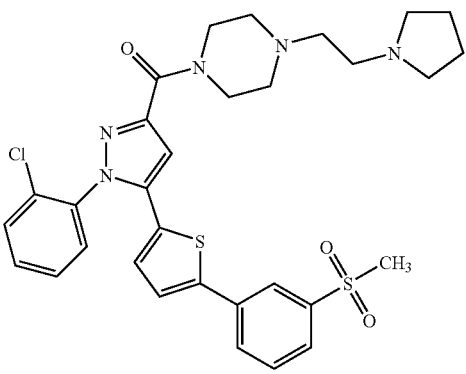 [SMILES: CS(=O)(=O)c1cccc(-c2ccc(-c3cc(C(=O)N4CCN(CCN5CCCC5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(2-pyrrolidin-1-ylethyl)piperazine |

| | | |
|---|---|---|
| 716 | 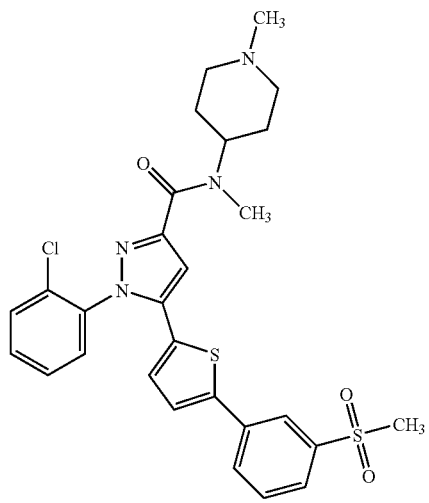 [SMILES: CN1CCC(N(C)C(=O)c2cc(-c3ccc(-c4cccc(S(C)(=O)=O)c4)s3)n(-c3ccccc3Cl)n2)CC1] | 1-(2-chlorophenyl)-N-methyl-N-(1-methylpiperidin-4-yl)-5-{5-[3-(methylsulfonyl)phenyl]-2-thienyl}-1H-pyrazole-3-carboxamide |
| 717 | 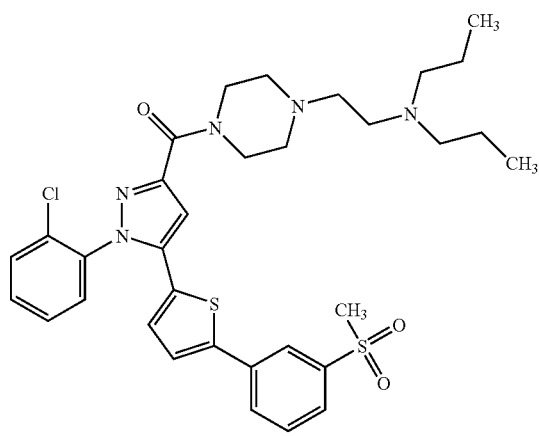 [SMILES: CCCN(CCC)CCN1CCN(C(=O)c2cc(-c3ccc(-c4cccc(S(C)(=O)=O)c4)s3)n(-c3ccccc3Cl)n2)CC1] | N-[2-(4-{[1-(2-chlorophenyl)-5-{5-[3-(methylsulfonyl)phenyl]-2-thienyl}-1H-pyrazol-3-yl]carbonyl}piperidin-1-yl)ethyl]-N-propylpropan-1-amine |
| 718 | 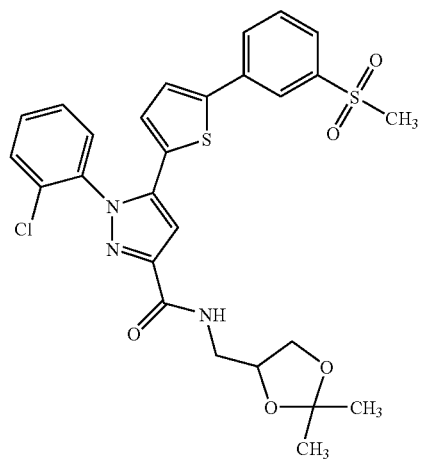 [SMILES: CC1(C)OCC(CNC(=O)c2cc(-c3ccc(-c4cccc(S(C)(=O)=O)c4)s3)n(-c3ccccc3Cl)n2)O1] | 1-(2-chlorophenyl)-N-[(2,2-dimethyl-1,3-dioxolan-4-yl)methyl]-5-{5-[3-(methylsulfonyl)phenyl]-2-thienyl}-1H-pyrazole-3-carboxamide |

TABLE 1-continued

| 719 | 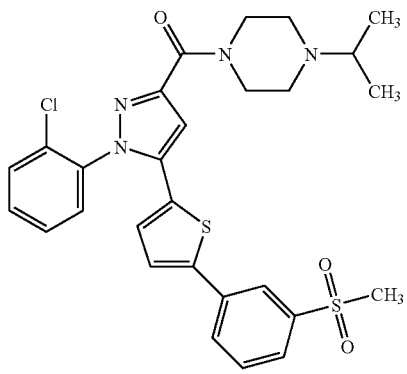 [SMILES: CC(C)N1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-(1-methylethyl)piperazine |
| 720 | 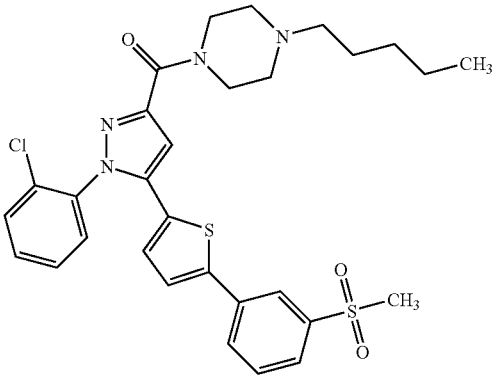 [SMILES: CCCCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-pentylpiperazine |
| 721 | 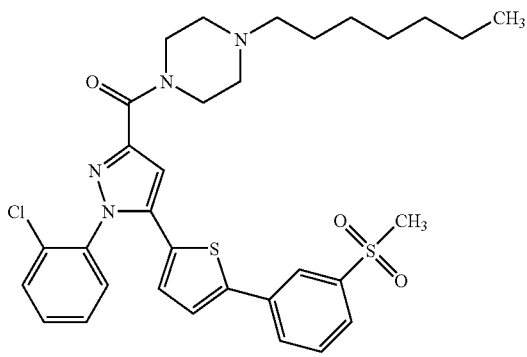 [SMILES: CCCCCCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-heptylpiperazine |
| 722 | 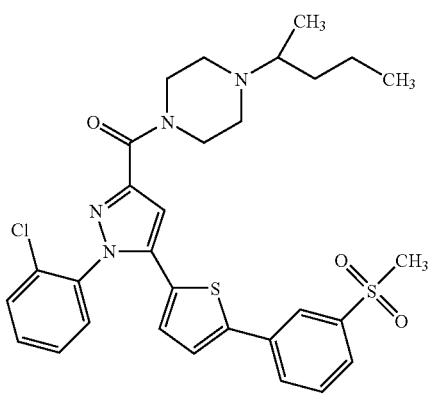 [SMILES: CCCC(C)N1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-(1-methylbutyl)piperazine |

TABLE 1-continued

| | | |
|---|---|---|
| 723 | 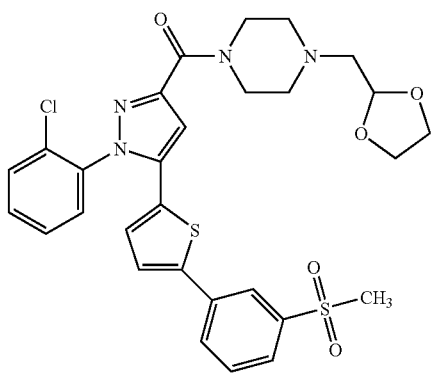 [SMILES: CS(=O)(=O)c1cccc(-c2ccc(-c3cc(C(=O)N4CCN(CC5OCCO5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-(1,3-dioxolan-2-ylmethyl)piperazine |
| 724 | 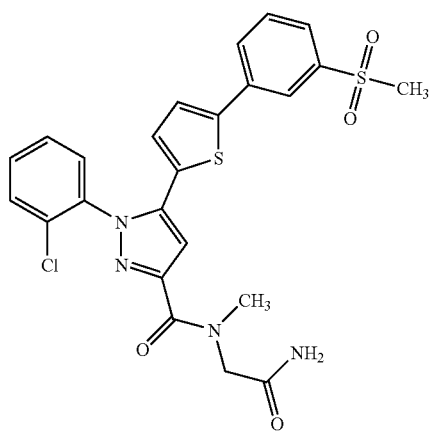 [SMILES: CN(CC(N)=O)C(=O)c1cc(-c2ccc(-c3cccc(S(C)(=O)=O)c3)s2)n(-c2ccccc2Cl)n1] | N-(2-amino-2-oxoethyl)-1-(2-chlorophenyl)-N-methyl-5-{5-[3-(methylsulfonyl)phenyl]-2-thienyl}-1H-pyrazole-3-carboxamide |
| 725 | 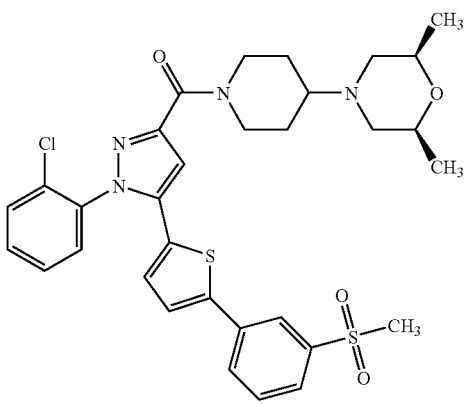 [SMILES: C[C@@H]1CN(C2CCN(C(=O)c3cc(-c4ccc(-c5cccc(S(C)(=O)=O)c5)s4)n(-c4ccccc4Cl)n3)CC2)C[C@H](C)O1] | (2R,6S)-4-(1-{[1-(2-chlorophenyl)-5-(5-{3-(methylsulfonyl)phenyl]-2-thienyl}-1H-pyrazol-3-yl]carbonyl}piperidin-4-yl)-2,6-dimethylmorpholine |
| 726 | 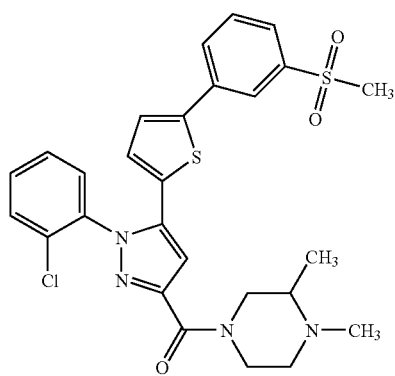 [SMILES: CC1CN(C(=O)c2cc(-c3ccc(-c4cccc(S(C)(=O)=O)c4)s3)n(-c3ccccc3Cl)n2)CCN1C] | 4-{[1-(2-chlorophenyl)-5-{5-[3-(methylsulfonyl)phenyl]-2-thienyl}-1H-pyrazol-3-yl]carbonyl}-1,2-dimethylpiperazine |

TABLE 1-continued

| 727 | 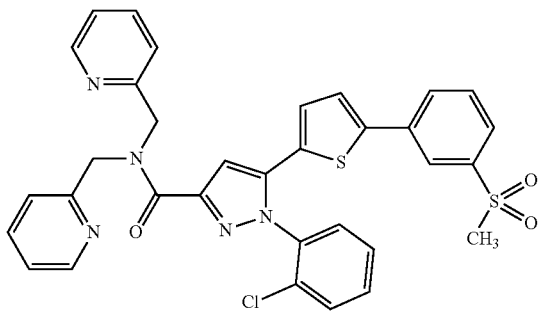 [SMILES: CS(=O)(=O)c1cccc(-c2ccc(-c3cc(C(=O)N(Cc4ccccn4)Cc4ccccn4)nn3-c3ccccc3Cl)s2)c1] | 1-(2-chlorophenyl)-5-{5-[3-(methylsulfonyl)phenyl]-2-thienyl}-N,N-bis(pyridin-2-ylmethyl)-1H-pyrazole-3-carboxamide |
| 728 | 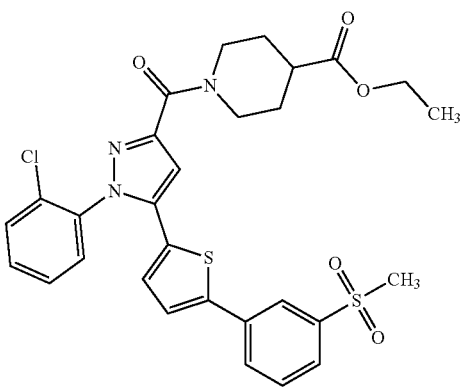 [SMILES: CCOC(=O)C1CCN(C(=O)c2cc(-c3ccc(-c4cccc(S(C)(=O)=O)c4)s3)n(-c3ccccc3Cl)n2)CC1] | ethyl 1-{[1-(2-chlorophenyl)-5-{5-[3-(methylsulfonyl)phenyl]-2-thienyl}-1H-pyrazol-3-yl]carbonyl}piperidin-4-carboxylate |
| 729 | 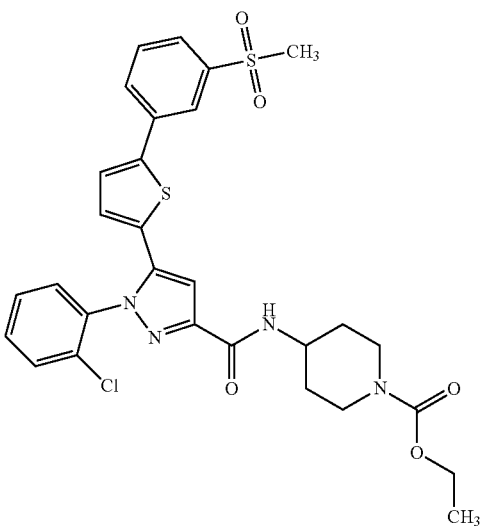 [SMILES: CCOC(=O)N1CCC(NC(=O)c2cc(-c3ccc(-c4cccc(S(C)(=O)=O)c4)s3)n(-c3ccccc3Cl)n2)CC1] | ethyl 4-({[1-(2-chlorophenyl)-5-{5-[3-(methylsulfonyl)phenyl]-2-thienyl}-1H-pyrazol-3-yl]carbonyl}amino)piperidin-1-carboxylate |
| 730 | 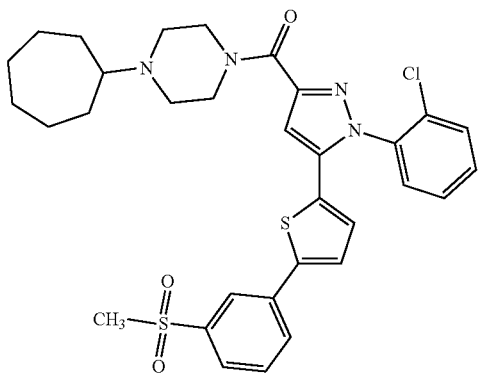 [SMILES: CS(=O)(=O)c1cccc(-c2ccc(-c3cc(C(=O)N4CCN(C5CCCCCC5)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]carbonyl}-4-cycloheptylpiperazine |

TABLE 1-continued
| 731 | 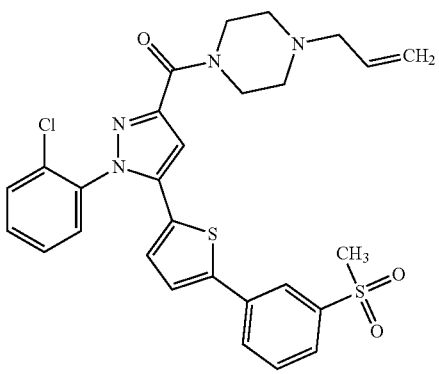 [SMILES: C=CCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-prop-2-en-1-ylpiperazine |
| --- | --- | --- |
| 732 | 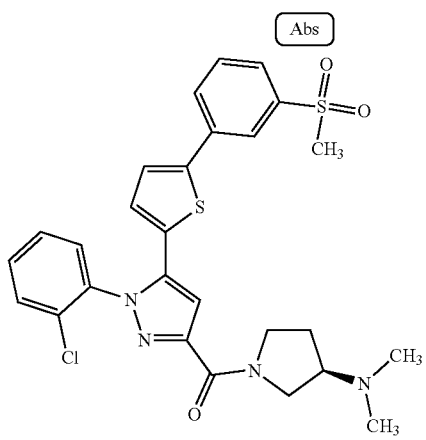 [SMILES: CN(C)[C@@H]1CCN(C(=O)c2cc(-c3ccc(-c4cccc(S(C)(=O)=O)c4)s3)n(-c3ccccc3Cl)n2)C1] | (3R)-1-{[1-(2-chlorophenyl)-5-{5-[3-(methylsulfonyl)phenyl]-2-thienyl}-1H-pyrazol-3-yl]carbonyl}-N,N-dimethylpyrrolidin-3-amine |
| 733 | 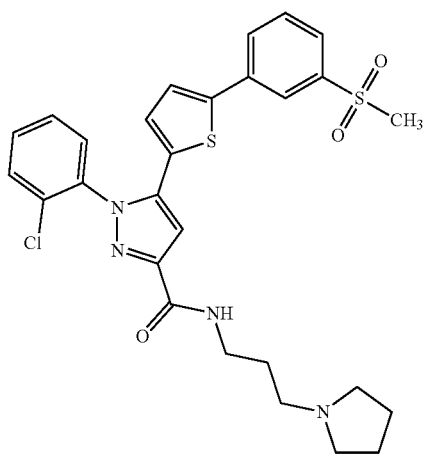 [SMILES: CS(=O)(=O)c1cccc(-c2ccc(-c3cc(C(=O)NCCCN4CCCC4)nn3-c3ccccc3Cl)s2)c1] | 1-(2-chlorophenyl)-5-{5-[3-(methylsulfonyl)phenyl]-2-thienyl}-N-(3-pyrrolidin-1-ylpropyl)-1H-pyrazol-3-carboxamide |

TABLE 1-continued
| | | |
|---|---|---|
| 734 | 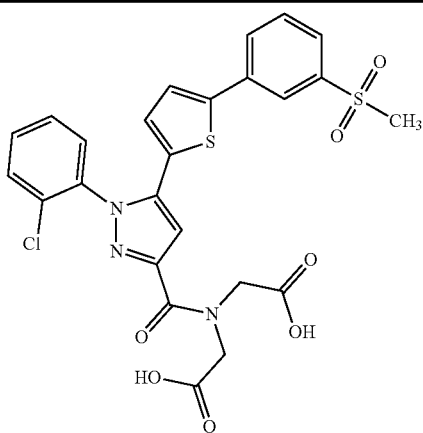 | 2,2'-({[1-(2-chlorophenyl)-5-{5-[3-(methylsulfonyl)phenyl]-2-thienyl}-1H-pyrazol-3-yl]carbonyl}imino)diacetic acid |
| 735 | 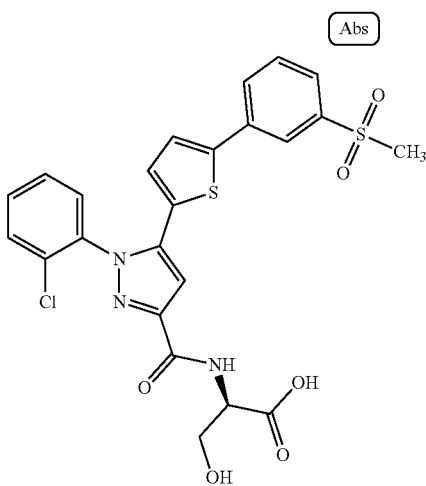 [SMILES: CS(=O)(=O)c1cccc(-c2ccc(-c3cc(C(=O)N[C@H](CO)C(=O)O)nn3-c3ccccc3Cl)s2)c1] | N-{[1-(2-chlorophenyl)-5-{5-[3-(methylsulfonyl)phenyl]-2-thienyl}-1H-pyrazol-3-yl]carbonyl}-D-serine |
| 736 | 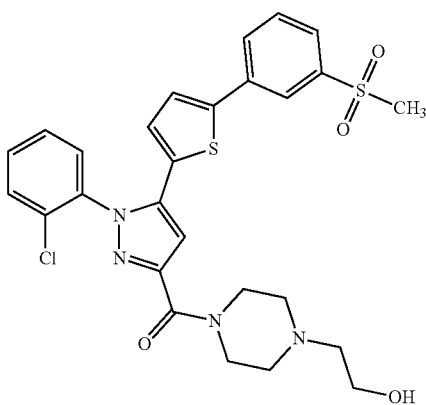 [SMILES: CS(=O)(=O)c1cccc(-c2ccc(-c3cc(C(=O)N4CCN(CCO)CC4)nn3-c3ccccc3Cl)s2)c1] | 2-(4-{[1-(2-chlorophenyl)-5-{5-[3-(methylsulfonyl)phenyl]-2-thienyl}-1H-pyrazol-3-yl]carbonyl}piperazin-1-yl)ethanol |

TABLE 1-continued
| 737 | 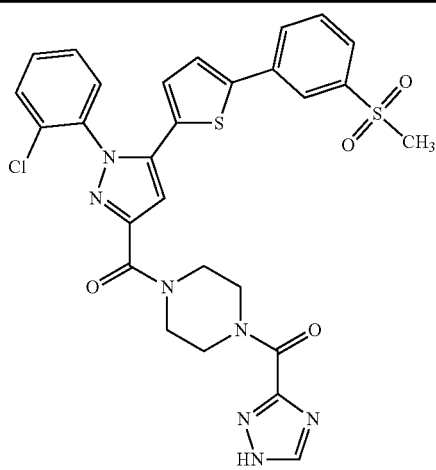 | 1-{[1-(2-chlorophenyl)-5-{5-[3-(methylsulfonyl)phenyl]-2-thienyl}-1H-pyrazol-3-yl]carbonyl}-4-(1H-1,2,4-triazol-3-ylcarbonyl)piperazine |
| --- | --- | --- |
| 738 | 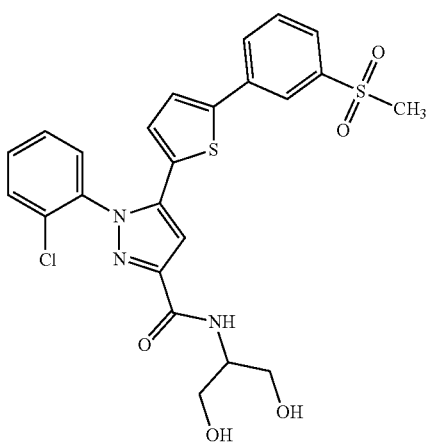 [SMILES: CS(=O)(=O)c1cccc(-c2ccc(-c3cc(C(=O)NC(CO)CO)nn3-c3ccccc3Cl)s2)c1] | 1-(2-chlorophenyl)-N-[2-hydroxy-1-(hydroxymethyl)ethyl]-5-{5-[3-(methylsulfonyl)phenyl]-2-thienyl}-1H-pyrazole-3-carboxamide |
| 739 | 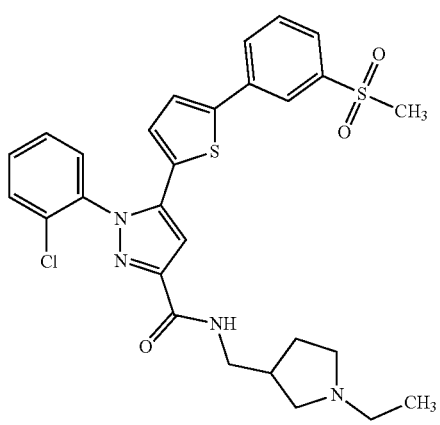 [SMILES: CCN1CCC(CNC(=O)c2cc(-c3ccc(-c4cccc(S(C)(=O)=O)c4)s3)n(-c3ccccc3Cl)n2)C1] | 1-(2-chlorophenyl)-N-[(1-ethylpyrrolidin-3-yl)methyl]-5-{5-[3-(methylsulfonyl)phenyl]-2-thienyl}-1H-pyrazole-3-carboxamide |

| | | |
|---|---|---|
| 740 | 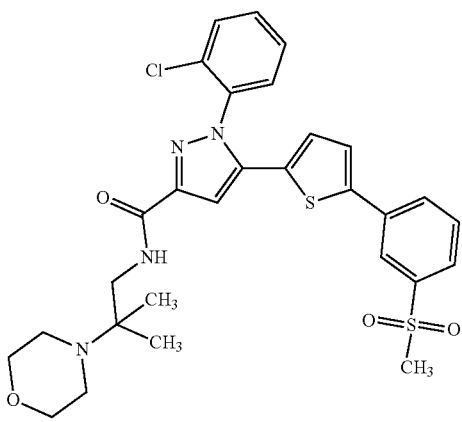 [SMILES: CC(C)(CNC(=O)c1cc(-c2ccc(-c3cccc(S(C)(=O)=O)c3)s2)n(-c2ccccc2Cl)n1)N1CCOCC1] | 1-(2-chlorophenyl)-N-(2-methyl-2-morpholin-4-yl)propyl)-5-{5-[3-(methylsulfonyl)phenyl]-2-thienyl}-1H-pyrazole-3-carboxamide |
| 741 | 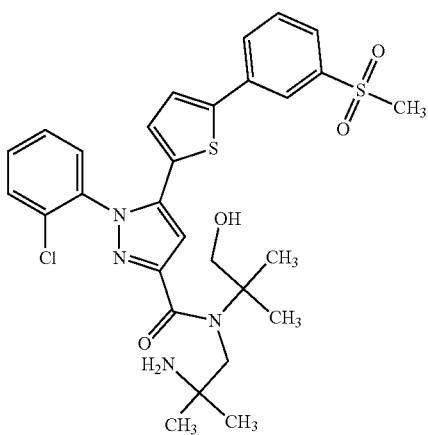 [SMILES: CC(C)(N)CN(C(=O)c1cc(-c2ccc(-c3cccc(S(C)(=O)=O)c3)s2)n(-c2ccccc2Cl)n1)C(C)(C)CO] | N-(2-amino-2-methylpropyl)-1-(2-chlorophenyl)-N-(2-hydroxy-1,1-dimethylethyl)-5-{5-[3-(methylsulfonyl)phenyl]-2-thienyl}-1H-pyrazole-3-carboxamide |
| 742 | 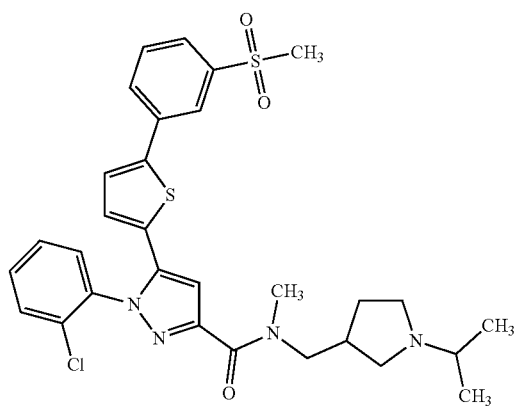 [SMILES: CC(C)N1CCC(CN(C)C(=O)c2cc(-c3ccc(-c4cccc(S(C)(=O)=O)c4)s3)n(-c3ccccc3Cl)n2)C1] | 1-(2-chlorophenyl)-N-methyl-N-{[1-(1-methylethyl)pyrrolidin-3-yl]methyl}-5-{5-[3-(methylsulfonyl)phenyl]-2-thienyl}-1H-pyrazole-3-carboxamide |

TABLE 1-continued
| 743 | 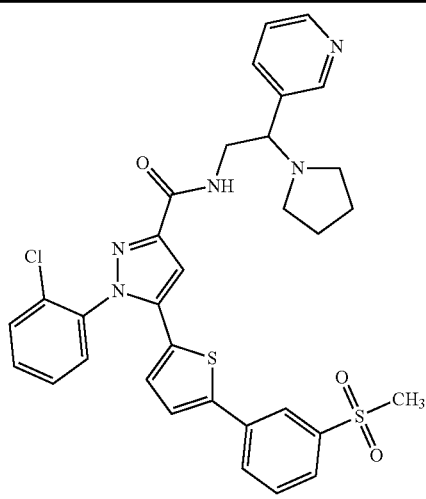 | 1-(2-chlorophenyl)-5-{5-[3-(methylsulfonyl)phenyl]-2-thienyl}-N-(2-pyridin-3-yl-2-pyrrolidin-1-ylethyl)-1H-pyrazole-3-carboxamide |
| 744 | 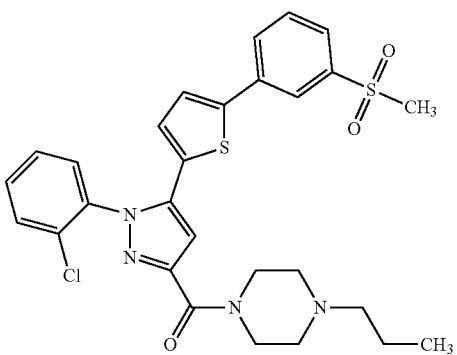 [SMILES: CCCN1CCN(C(=O)c2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]carbonyl}-4-propylpiperazine |
| 745 | 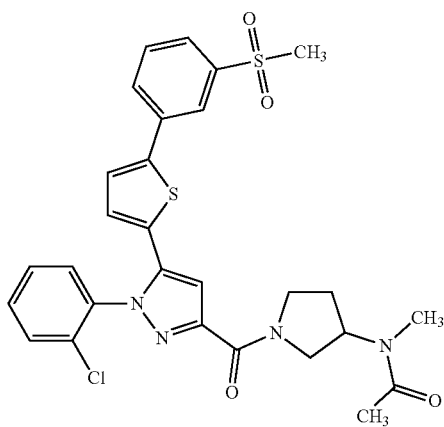 [SMILES: CC(=O)N(C)C1CCN(C(=O)c2cc(-c3ccc(-c4cccc(S(C)(=O)=O)c4)s3)n(-c3ccccc3Cl)n2)C1] | N-(1-{[1-(2-chlorophenyl)-5-{5-[3-(methylsulfonyl)phenyl]-2-thienyl}-1H-pyrazol-3-yl]carbonyl}pyrrolidin-3-yl)-N-methylacetamide |

TABLE 1-continued

| 746 | 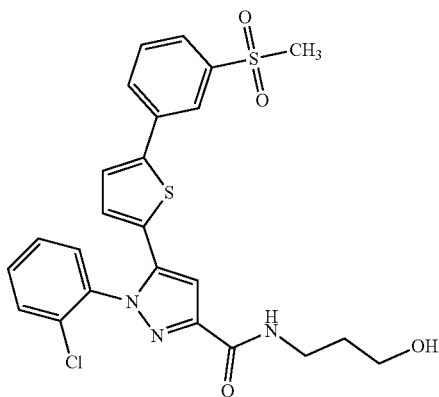 [SMILES: CS(=O)(=O)c1cccc(-c2ccc(-c3cc(C(=O)NCCCO)nn3-c3ccccc3Cl)s2)c1] | 1-(2-chlorophenyl)-N-(3-hydroxypropyl)-5-{5-[3-(methylsulfonyl)phenyl]-2-thienyl}-1H-pyrazole-3-carboxamide |
| --- | --- | --- |
| 747 | 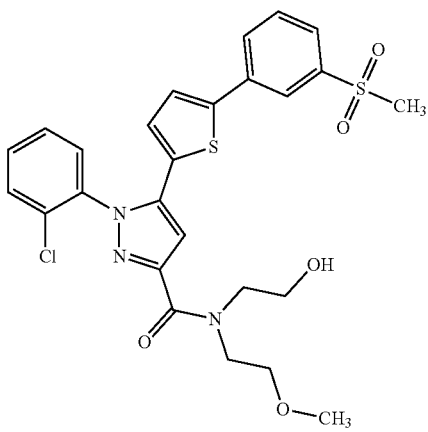 [SMILES: COCCN(CCO)C(=O)c1cc(-c2ccc(-c3cccc(S(C)(=O)=O)c3)s2)n(-c2ccccc2Cl)n1] | 1-(2-chlorophenyl)-N-(2-hydroxyethyl)-N-[2-(methyloxy)ethyl]-5-{5-[3-(methylsulfonyl)phenyl]-2-thienyl}-1H-pyrazole-3-carboxamide |
| 748 | 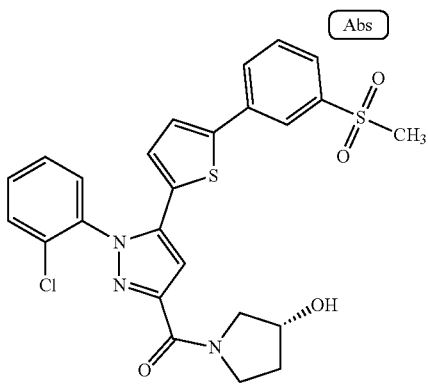 [SMILES: CS(=O)(=O)c1cccc(-c2ccc(-c3cc(C(=O)N4CC[C@@H](O)C4)nn3-c3ccccc3Cl)s2)c1] | (3R)-1-{[1-(2-chlorophenyl)-5-{5-[3-(methylsulfonyl)phenyl]-2-thienyl}-1H-pyrazol-3-yl]carbonyl}pyrrolidin-3-ol |
| 749 | 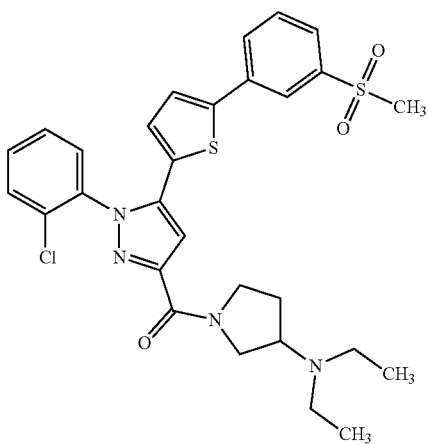 [SMILES: CCN(CC)C1CCN(C(=O)c2cc(-c3ccc(-c4cccc(S(C)(=O)=O)c4)s3)n(-c3ccccc3Cl)n2)C1] | 1-{[1-(2-chlorophenyl)-5-{5-[3-(methylsulfonyl)phenyl]-2-thienyl}-1H-pyrazol-3-yl]carbonyl}-N,N-diethylpyrrolidin-3-amine |

| | | |
|---|---|---|
| 750 | 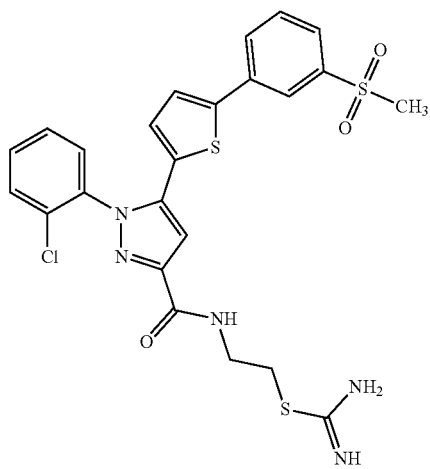 [SMILES: CS(=O)(=O)c1cccc(-c2ccc(-c3cc(C(=O)NCCSC(=N)N)nn3-c3ccccc3Cl)s2)c1] | 2-({[1-(2-chlorophenyl)-5-{5-[3-(methylsulfonyl)phenyl]-2-thienyl}-1H-pyrazol-3-yl]carbonyl}amino)ethyl imidothiocarbamate |
| 751 | 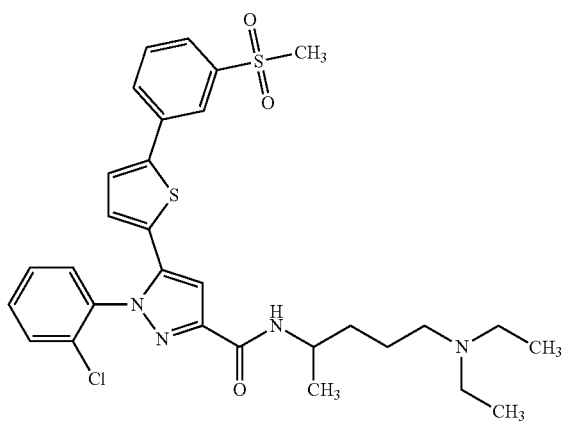 [SMILES: CCN(CC)CCCC(C)NC(=O)c1cc(-c2ccc(-c3cccc(S(C)(=O)=O)c3)s2)n(-c2ccccc2Cl)n1] | 1-(2-chlorophenyl)-N-[4-(diethylamino)-1-methylbutyl]-5-{5-[3-(methylsulfonyl)phenyl]-2-thienyl}-1H-pyrazole-3-carboxamide |
| 752 | 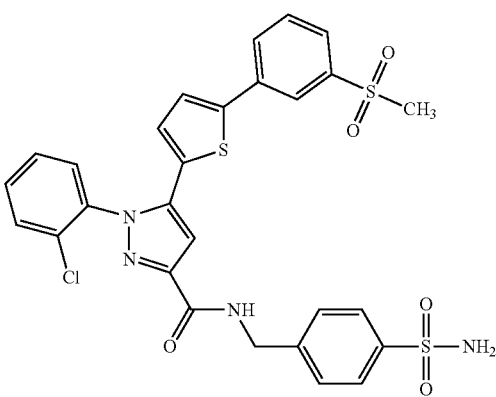 [SMILES: CS(=O)(=O)c1cccc(-c2ccc(-c3cc(C(=O)NCc4ccc(S(N)(=O)=O)cc4)nn3-c3ccccc3Cl)s2)c1] | N-{[4-(aminosulfonyl)phenyl]methyl}-1-(2-chlorophenyl)-5-{5-[3-(methylsulfonyl)phenyl]-2-thienyl}-1H-pyrazole-3-carboxamide |

TABLE 1-continued

| | | |
|---|---|---|
| 753 | 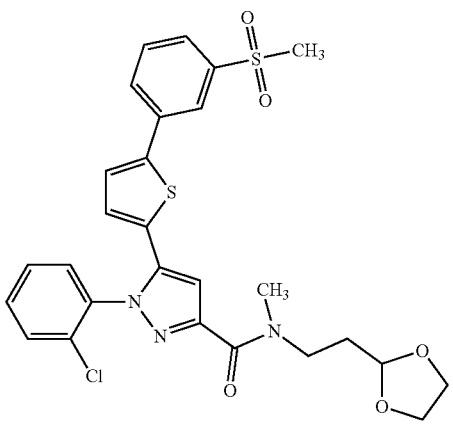 [SMILES: CN(CCC1OCCO1)C(=O)c1cc(-c2ccc(-c3cccc(S(C)(=O)=O)c3)s2)n(-c2ccccc2Cl)n1] | 1-(2-chlorophenyl)-N-[2-(1,3-dioxolan-2-yl)ethyl]-N-methyl-5-{5-[3-(methylsulfonyl)phenyl]-2-thienyl}-N-pyrazole-3-carboxamide |
| 754 | 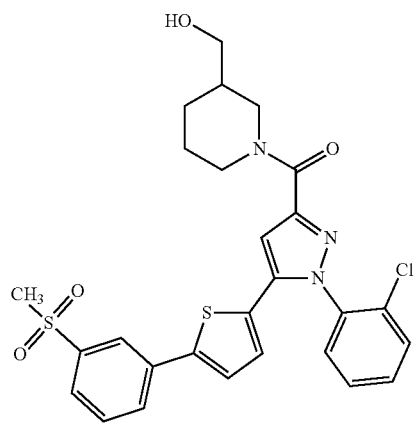 [SMILES: CS(=O)(=O)c1cccc(-c2ccc(-c3cc(C(=O)N4CCCC(CO)C4)nn3-c3ccccc3Cl)s2)c1] | (1-{[2-(2-chlorophenyl)-5-{5-[3-(methylsulfonyl)phenyl]-2-thienyl}-1H-pyrazol-3-yl]carbonyl}piperidin-3-yl)methanol |
| 755 | 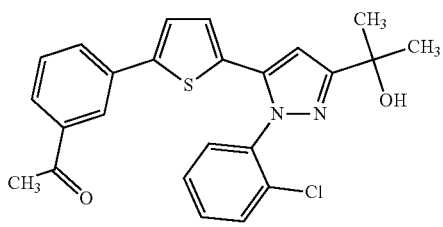 [SMILES: CC(=O)c1cccc(-c2ccc(-c3cc(C(C)(C)O)nn3-c3ccccc3Cl)s2)c1] | 1-(3-{5-[1-(2-chlorophenyl)-3-(1-hydroxy-1-methylethyl)-1H-pyrazol-5-yl]-2-thienyl}phenyl)ethanone |
| 804 | 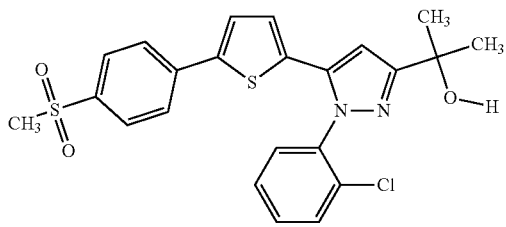 [SMILES: CC(C)(O)c1cc(-c2ccc(-c3ccc(S(C)(=O)=O)cc3)s2)n(-c2ccccc2Cl)n1] | 2-[1-(2-chlorophenyl)-5-{5-[4-(methylsulfonyl)phenyl]-2-thienyl}-1H-pyrazol-3-yl]propan-2-ol |
| 805 | 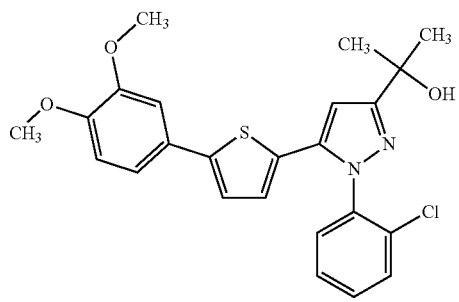 [SMILES: COc1ccc(-c2ccc(-c3cc(C(C)(C)O)nn3-c3ccccc3Cl)s2)cc1OC] | 2-[5-{5-[3,4-bis(methyloxy)phenyl]-2-thienyl}-1-(2-chlorophenyl)-1H-pyrazol-3-yl]propan-2-ol |

TABLE 1-continued

| 806 | 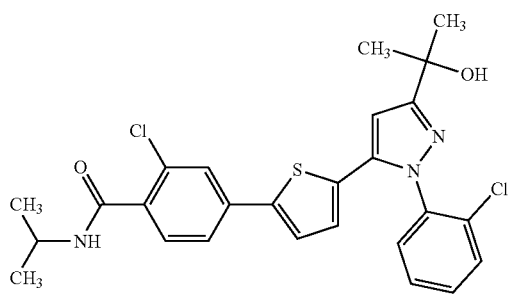 [SMILES: CC(C)NC(=O)c1ccc(-c2ccc(-c3cc(C(C)(C)O)nn3-c3ccccc3Cl)s2)cc1Cl] | 2-chloro-4-{5-[1-(2-chlorophenyl)-3-(1-hydroxy-1-methylethyl)-1H-pyrazol-5-yl]-2-thienyl}-N-(1-methylethyl)benzamide |
| 807 | 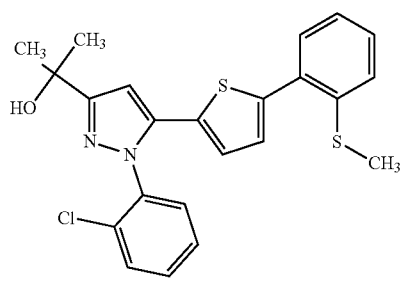 [SMILES: CSc1ccccc1-c1ccc(-c2cc(C(C)(C)O)nn2-c2ccccc2Cl)s1] | 2-[1-(2-chlorophenyl)-5-{5-[2-(methylthio)phenyl]-2-thienyl}-1H-pyrazol-3-yl]propan-2-ol |
| 808 | 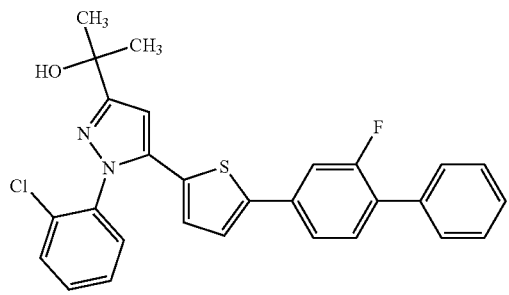 [SMILES: CC(C)(O)c1cc(-c2ccc(-c3ccc(-c4ccccc4)c(F)c3)s2)n(-c2ccccc2Cl)n1] | 2-{1-(2-chlorophenyl)-5-[5-(2-fluorobiphenyl-4-yl)-2-thienyl]-1H-pyrazol-3-yl}propan-2-ol |
| 809 | 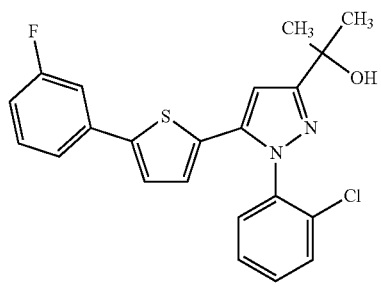 [SMILES: CC(C)(O)c1cc(-c2ccc(-c3cccc(F)c3)s2)n(-c2ccccc2Cl)n1] | 2-{1-(2-chlorophenyl)-5-[5-(3-fluorophenyl)-2-thienyl]-1H-pyrazol-3-yl}propan-2-ol |
| 810 | 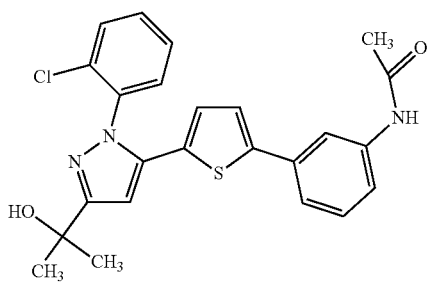 [SMILES: CC(=O)Nc1cccc(-c2ccc(-c3cc(C(C)(C)O)nn3-c3ccccc3Cl)s2)c1] | N-(3-{5-[1-(2-chlorophenyl)-3-(1-hydroxy-1-methylethyl)-1H-pyrazol-5-yl]-2-thienyl}phenyl)acetamide |

TABLE 1-continued

| | | |
|---|---|---|
| 811 | 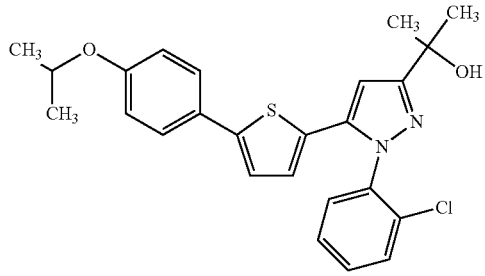 [SMILES: CC(C)Oc1ccc(-c2ccc(-c3cc(C(C)(C)O)nn3-c3ccccc3Cl)s2)cc1] | 2-[1-(2-chlorophenyl)-5-(5-{4-[(1-methylethyl)oxy]phenyl}-2-thienyl)-1H-pyrazol-3-yl]propan-2-ol |
| 812 | 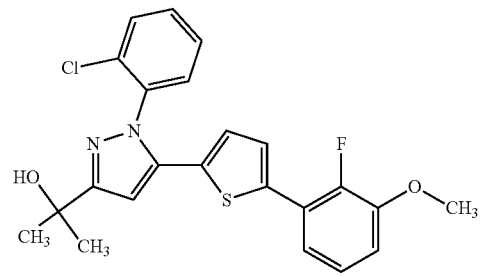 [SMILES: COc1cccc(-c2ccc(-c3cc(C(C)(C)O)nn3-c3ccccc3Cl)s2)c1F] | 2-[1-(2-chlorophenyl)-5-{5-[2-fluoro-3-(methyloxy)phenyl]-2-thienyl}-1H-pyrazol-3-yl]propan-2-ol |
| 813 | 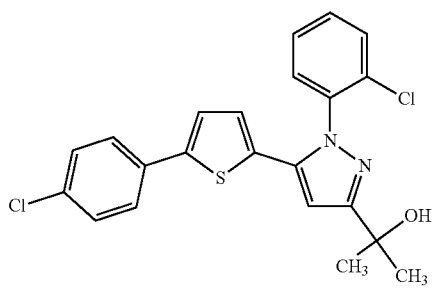 [SMILES: CC(C)(O)c1cc(-c2ccc(-c3ccc(Cl)cc3)s2)n(-c2ccccc2Cl)n1] | 2-{1-(2-chlorophenyl)-5-[5-(4-chlorophenyl)-2-thienyl]-1H-pyrazol-3-yl}propan-2-ol |
| 814 | 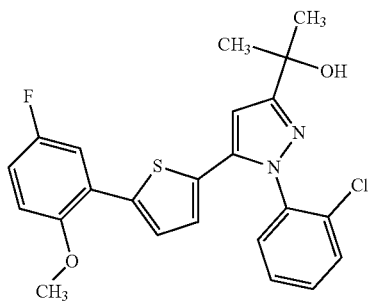 [SMILES: COc1ccc(F)cc1-c1ccc(-c2cc(C(C)(C)O)nn2-c2ccccc2Cl)s1] | 2-[1-(2-chlorophenyl)-5-{5-[5-fluoro-2-(methyloxy)phenyl]-2-thienyl}-1H-pyrazol-3-yl]propan-2-ol |
| 815 | 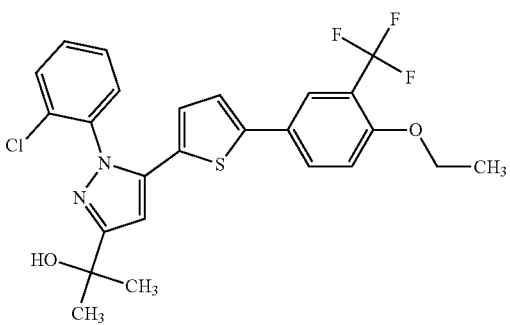 [SMILES: CCOc1ccc(-c2ccc(-c3cc(C(C)(C)O)nn3-c3ccccc3Cl)s2)cc1C(F)(F)F] | 2-[1-(2-chlorophenyl)-5-{5-[4-(ethyloxy)-3-(trifluoromethyl)phenyl]-2-thienyl}-1H-pyrazol-3-yl]propan-2-ol |

TABLE 1-continued

| 816 | 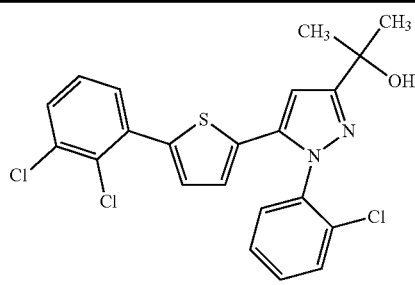 | 2-{1-(2-chlorophenyl)-5-[5-(2,3-dichlorophenyl)-2-thienyl]-1H-pyrazol-3-yl}propan-2-ol |
| 817 | 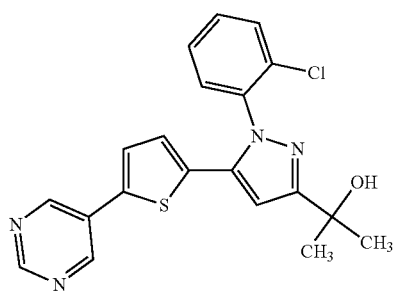 [SMILES: CC(C)(O)c1cc(-c2ccc(-c3cncnc3)s2)n(-c2ccccc2Cl)n1] | 2-[1-(2-chlorophenyl)-5-(5-pyrimidin-5-yl-2-thienyl)-1H-pyrazol-3-yl]propan-2-ol |
| 818 | 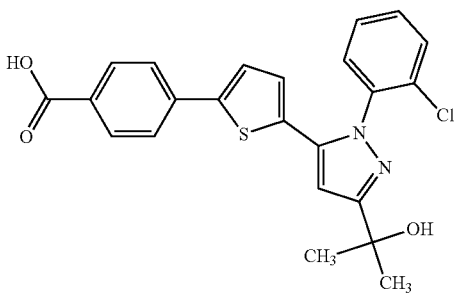 [SMILES: CC(C)(O)c1cc(-c2ccc(-c3ccc(C(=O)O)cc3)s2)n(-c2ccccc2Cl)n1] | 4-{5-[1-(2-chlorophenyl)-3-(1-hydroxy-1-methylethyl)-1H-pyrazol-5-yl]-2-thienyl}benzoic acid |
| 819 | 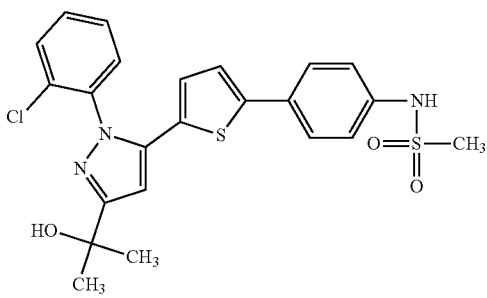 [SMILES: CC(C)(O)c1cc(-c2ccc(-c3ccc(NS(C)(=O)=O)cc3)s2)n(-c2ccccc2Cl)n1] | N-(4-{5-[1-(2-chlorophenyl)-3-(1-hydroxy-1-methylethyl)-1H-pyrazol-5-yl]-2-thienyl}phenyl)methanesulfonamide |
| 820 | 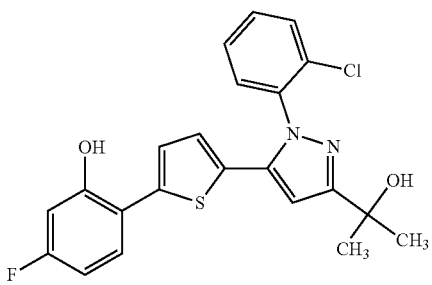 [SMILES: CC(C)(O)c1cc(-c2ccc(-c3ccc(F)cc3O)s2)n(-c2ccccc2Cl)n1] | 2-{5-[1-(2-chlorophenyl)-3-(1-hydroxy-1-methylethyl)-1H-pyrazol-5-yl]-2-thienyl}-5-fluorophenol |

| | | |
|---|---|---|
| 821 | 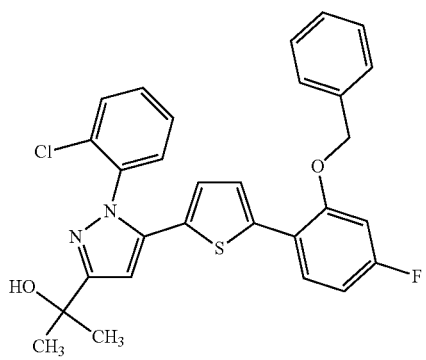 [SMILES: CC(C)(O)c1cc(-c2ccc(-c3ccc(F)cc3OCc3ccccc3)s2)n(-c2ccccc2Cl)n1] | 2-[1-(2-chlorophenyl)-5-(5-{4-fluoro-2-[(phenylmethyl)oxy]phenyl}-2-thienyl)-1H-pyrazol-3-yl]propan-2-ol |
| 822 | 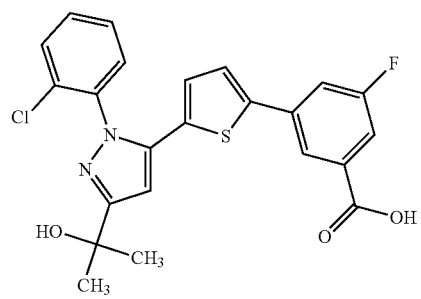 [SMILES: CC(C)(O)c1cc(-c2ccc(-c3cc(F)cc(C(=O)O)c3)s2)n(-c2ccccc2Cl)n1] | 3-{5-[1-(2-chlorophenyl)-3-(1-hydroxy-1-methylethyl)-1H-pyrazol-5-yl]-2-thienyl}-5-fluorobenzoic acid |
| 823 | 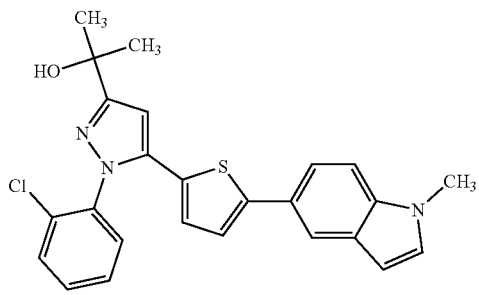 [SMILES: Cn1ccc2cc(-c3ccc(-c4cc(C(C)(C)O)nn4-c4ccccc4Cl)s3)ccc21] | 2-{1-(2-chlorophenyl)-5-[5-(1-methyl-1H-indol-5-yl)-2-thienyl]-1H-pyrazol-3-yl}propan-2-ol |
| 824 | 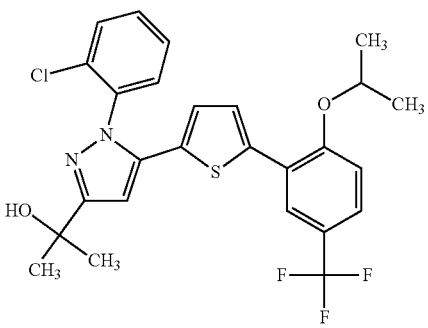 [SMILES: CC(C)Oc1ccc(C(F)(F)F)cc1-c1ccc(-c2cc(C(C)(C)O)nn2-c2ccccc2Cl)s1] | 2-[1-(2-chlorophenyl)-5-(5-{2-[(1-methylethyl)oxy]-5-(trifluoromethyl)phenyl}-2-thienyl)-1H-pyrazol-3-yl]propan-2-ol |
| 825 | 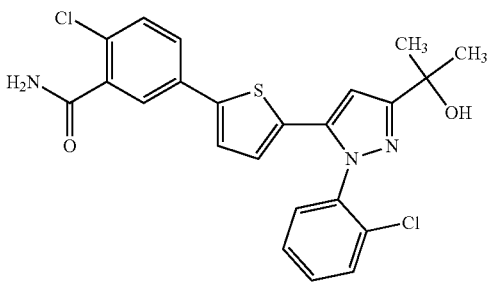 [SMILES: CC(C)(O)c1cc(-c2ccc(-c3ccc(Cl)c(C(N)=O)c3)s2)n(-c2ccccc2Cl)n1] | 2-chloro-5-{5-[1-(2-chlorophenyl)-3-(1-hydroxy-1-methylethyl)-1H-pyrazol-5-yl]-2-thienyl}benzamide |

TABLE 1-continued

| | | |
|---|---|---|
| 826 | 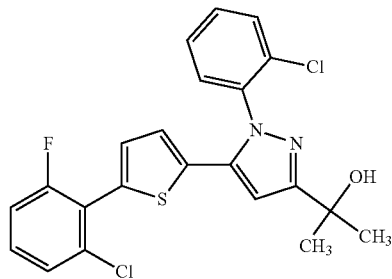 [SMILES: CC(C)(O)c1cc(-c2ccc(-c3c(F)cccc3Cl)s2)n(-c2ccccc2Cl)n1] | 2-{5-[5-(2-chloro-6-fluorophenyl)-2-thienyl]-1-(2-chlorophenyl)-1H-pyrazol-3-yl}propan-2-ol |
| 827 | 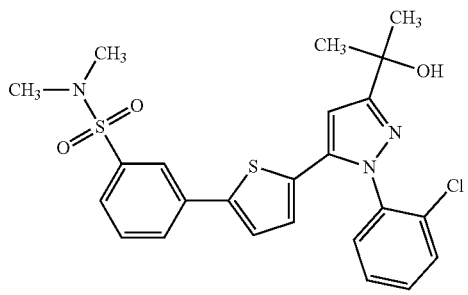 [SMILES: CN(C)S(=O)(=O)c1cccc(-c2ccc(-c3cc(C(C)(C)O)nn3-c3ccccc3Cl)s2)c1] | 3-{5-[1-(2-chlorophenyl)-3-(1-hydroxy-1-methylethyl)-1H-pyrazol-5-yl]-2-thienyl}-N,N-dimethylbenzenesulfonamide |
| 828 | 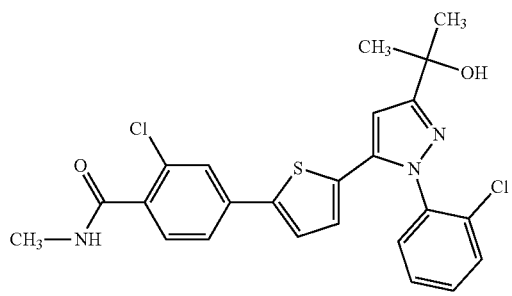 [SMILES: CNC(=O)c1ccc(-c2ccc(-c3cc(C(C)(C)O)nn3-c3ccccc3Cl)s2)cc1Cl] | 2-chloro-4-{5-[1-(2-chlorophenyl)-3-(1-hydroxy-1-methylethyl)-1H-pyrazol-5-yl]-2-thienyl}-N-methylbenzamide |
| 829 | 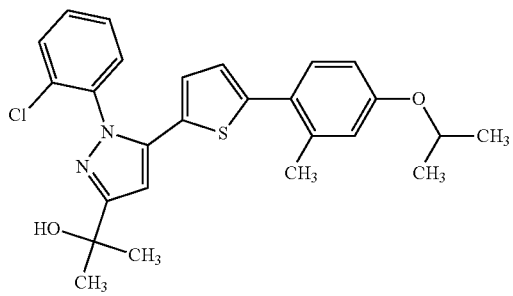 [SMILES: Cc1cc(OC(C)C)ccc1-c1ccc(-c2cc(C(C)(C)O)nn2-c2ccccc2Cl)s1] | 2-[1-(2-chlorophenyl)-5-(5-{2-methyl-4-[(1-methylethyl)oxy]phenyl}-2-thienyl)-1H-pyrazol-3-yl]propan-2-ol |
| 830 | 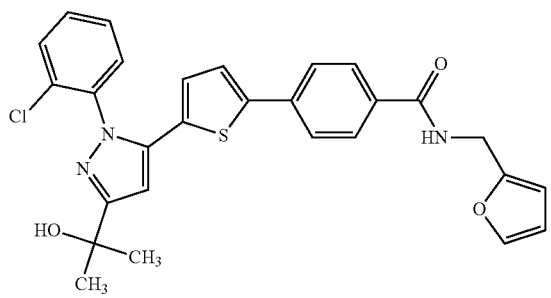 [SMILES: CC(C)(O)c1cc(-c2ccc(-c3ccc(C(=O)NCc4ccco4)cc3)s2)n(-c2ccccc2Cl)n1] | 4-{5-[1-(2-chlorophenyl)-3-(1-hydroxy-1-methylethyl)-1H-pyrazol-5-yl]-2-thienyl}-N-furan-2-ylmethyl)benzamide |

TABLE 1-continued

| 831 | 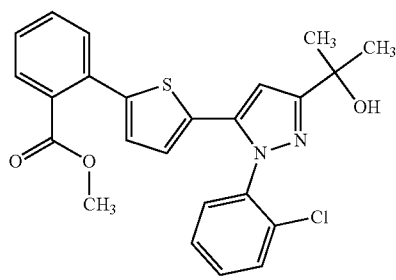 [SMILES: COC(=O)c1ccccc1-c1ccc(-c2cc(C(C)(C)O)nn2-c2ccccc2Cl)s1] | methyl 2-{5-[1-(2-chlorophenyl)-3-(1-hydroxy-1-methylethyl)-1H-pyrazol-5-yl]-2-thienyl}benzoate |
| 832 | 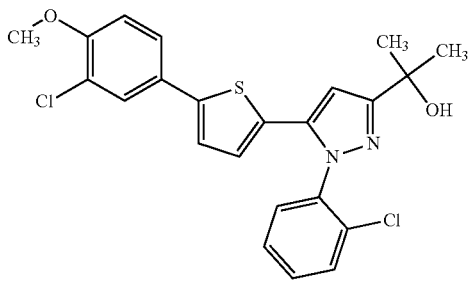 [SMILES: COc1ccc(-c2ccc(-c3cc(C(C)(C)O)nn3-c3ccccc3Cl)s2)cc1Cl] | 2-[5-{5-[3-chloro-4-(methyloxy)phenyl]-2-thienyl}-1-(2-chlorophenyl)-1H-pyrazol-3-yl]propan-2-ol |
| 833 | 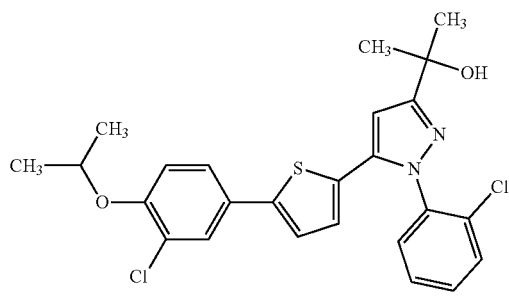 [SMILES: CC(C)Oc1ccc(-c2ccc(-c3cc(C(C)(C)O)nn3-c3ccccc3Cl)s2)cc1Cl] | 2-[5-(5-{3-chloro-4-[(1-methylethyl)oxy]phenyl}-2-thienyl)-1-(2-chlorophenyl)-1H-pyrazol-3-yl]propan-2-ol |
| 834 | 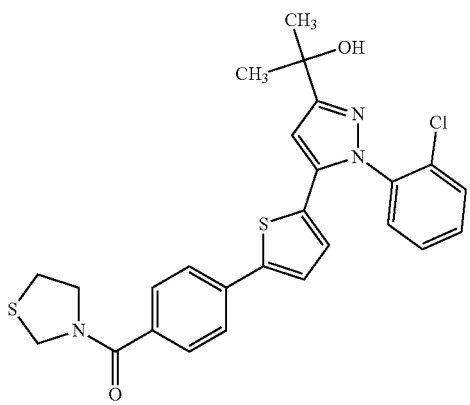 [SMILES: CC(C)(O)c1cc(-c2ccc(-c3ccc(C(=O)N4CCSC4)cc3)s2)n(-c2ccccc2Cl)n1] | 2-[1-(2-chlorophenyl)-5-{5-[4-(1,3-thiazolidin-3-ylcarbonyl)phenyl]-2-thienyl}-1H-pyrazol-3-yl]propan-2-ol |
| 835 | 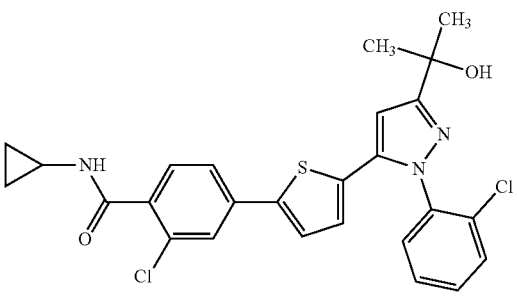 [SMILES: CC(C)(O)c1cc(-c2ccc(-c3ccc(C(=O)NC4CC4)c(Cl)c3)s2)n(-c2ccccc2Cl)n1] | 2-chloro-4-{5-[1-(2-chlorophenyl)-3-(1-hydroxy-1-methylethyl)-1H-pyrazol-5-yl]-2-thienyl}-N-cyclopropylbenzamide |

TABLE 1-continued

| 836 | 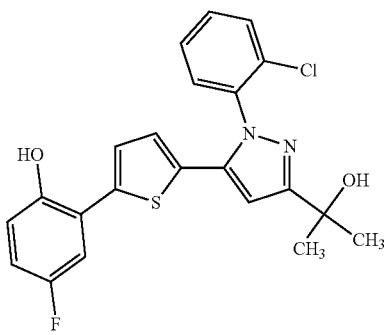 [SMILES: CC(C)(O)c1cc(-c2ccc(-c3cc(F)ccc3O)s2)n(-c2ccccc2Cl)n1] | 2-{5-[1-(2-chlorophenyl)-3-(1-hydroxy-1-methylethyl)-1H-pyrazol-5-yl]-2-thienyl}-4-fluorophenol |
| 837 | 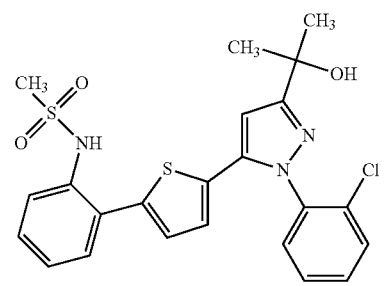 [SMILES: CC(C)(O)c1cc(-c2ccc(-c3ccccc3NS(C)(=O)=O)s2)n(-c2ccccc2Cl)n1] | N-(2-{5-[1-(2-chlorophenyl)-3-(1-hydroxy-1-methylethyl)-1H-pyrazol-5-yl]-2-thienyl}phenyl)methanesulfonamide |
| 838 | 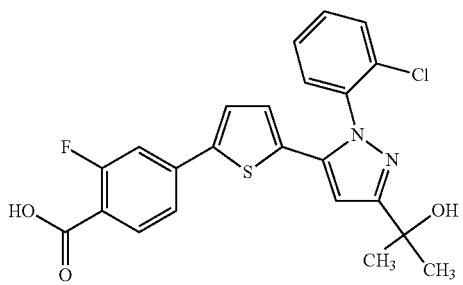 [SMILES: CC(C)(O)c1cc(-c2ccc(-c3ccc(C(=O)O)c(F)c3)s2)n(-c2ccccc2Cl)n1] | 4-{5-[1-(2-chlorophenyl)-3-(1-hydroxy-1-methylethyl)-1H-pyrazol-5-yl]-2-thienyl}-2-fluorobenzoic acid |
| 839 | 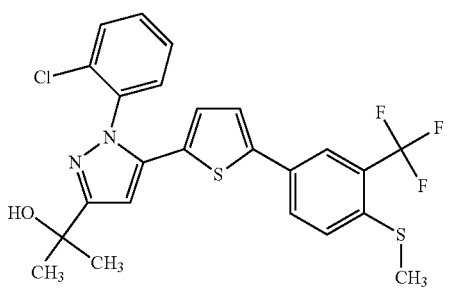 | 2-{1-(2-chlorophenyl)-5-{5-[4-(methylthio)-3-(trifluoromethyl)phenyl]-2-thienyl}-1H-pyrazol-3-yl]propan-2-ol |
| 840 | 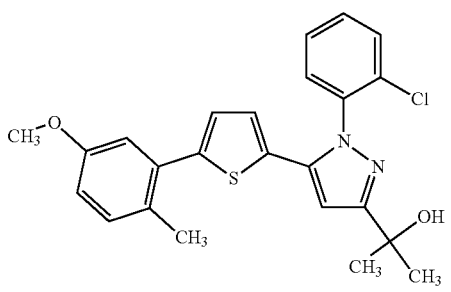 | 2-[1-(2-chlorophenyl)-5-{5-[2-methyl-5-(methyloxy)phenyl]-2-thienyl}-1H-pyrazol-3-yl]propan-2-ol |

TABLE 1-continued
841 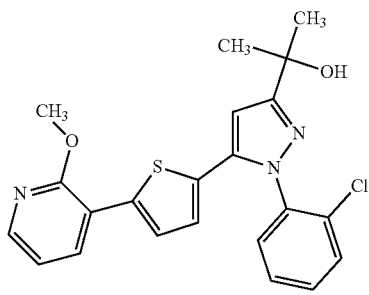 [SMILES: COc1ncccc1-c1ccc(-c2cc(C(C)(C)O)nn2-c2ccccc2Cl)s1] 2-[1-(2-chlorophenyl)-5-{5-[2-(methyloxy)pyridin-3-yl]-2-thienyl}-1H-pyrazol-3-yl]propan-2-ol
842 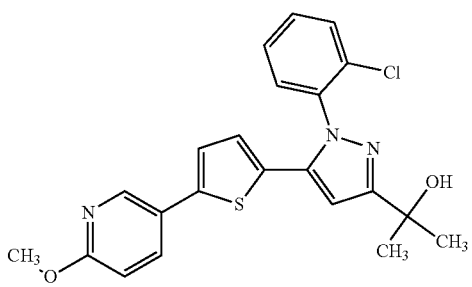 [SMILES: COc1ccc(-c2ccc(-c3cc(C(C)(C)O)nn3-c3ccccc3Cl)s2)cn1] 2-[1-(2-chlorophenyl)-5-{5-[6-(methyloxy)pyridin-3-yl]-2-thienyl}-1H-pyrazol-3-yl]propan-2-ol
843 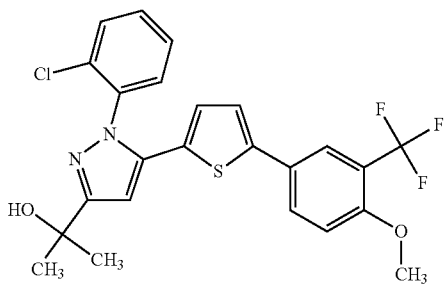 [SMILES: COc1ccc(-c2ccc(-c3cc(C(C)(C)O)nn3-c3ccccc3Cl)s2)cc1C(F)(F)F] 2-[1-(2-chlorophenyl)-5-{5-[4-(methyloxy)-3-(trifluoromethyl)phenyl]-2-thienyl}-1H-pyrazol-3-yl]propan-2-ol
844 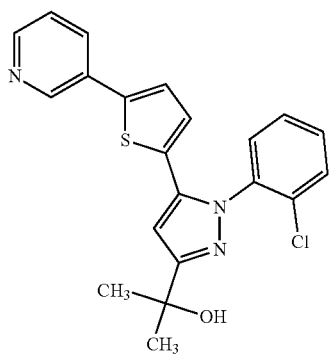 [SMILES: CC(C)(O)c1cc(-c2ccc(-c3cccnc3)s2)n(-c2ccccc2Cl)n1] 2-[1-(2-chlorophenyl)-5-(5-pyridin-3-yl-2-thienyl)-1H-pyrazol-3-yl]propan-2-ol
845 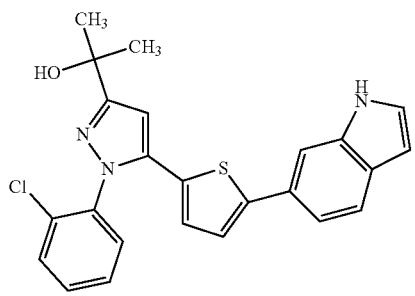 [SMILES: CC(C)(O)c1cc(-c2ccc(-c3ccc4cc[nH]c4c3)s2)n(-c2ccccc2Cl)n1] 2-{1-(2-chlorophenyl)-5-[5-(1H-indol-6-yl)-2-thienyl]-1H-pyrazol-3-yl}propan-2-ol TABLE 1-continued

| 846 | 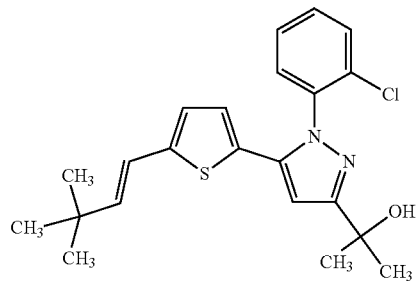 [SMILES: CC(C)(C)/C=C/c1ccc(-c2cc(C(C)(C)O)nn2-c2ccccc2Cl)s1] | 2-[1-(2-chlorophenyl)-5-{5-[(1E)-3,3-dimethylbut-1-en-1-yl]-2-thienyl}-1H-pyrazol-3-yl]propan-2-ol |
| 847 | 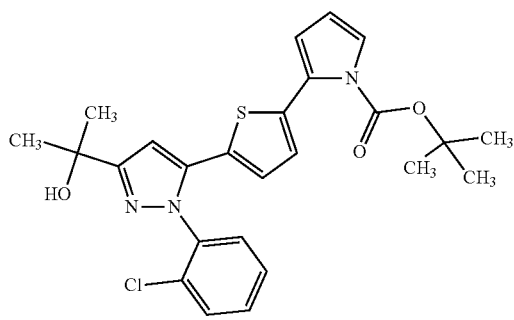 [SMILES: CC(C)(C)OC(=O)n1cccc1-c1ccc(-c2cc(C(C)(C)O)nn2-c2ccccc2Cl)s1] | 1,1-dimethylethyl 2-{5-[1-(2-chlorophenyl)-3-(1-hydroxy-1-methylethyl)-1H-pyrazol-5-yl]-2-thienyl}-1H-pyrrole-1-carboxylate |
| 848 | 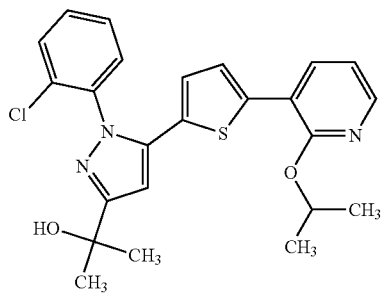 [SMILES: CC(C)Oc1ncccc1-c1ccc(-c2cc(C(C)(C)O)nn2-c2ccccc2Cl)s1] | 2-[1-(2-chlorophenyl)-5-(5-{2-[(1-methylethyl)oxy]pyridin-3-yl}-2-thienyl-1H-pyrazol-3-yl]propan-2-ol |
| 849 | 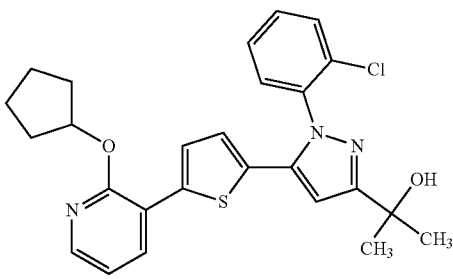 [SMILES: CC(C)(O)c1cc(-c2ccc(-c3cccnc3OC3CCCC3)s2)n(-c2ccccc2Cl)n1] | 2-[1-(2-chlorophenyl)-5-{5-[2-(cyclopentyloxy)pyridin-3-yl]-2-thienyl}-1H-pyrazol-3-yl]propan-2-ol |
| 850 | 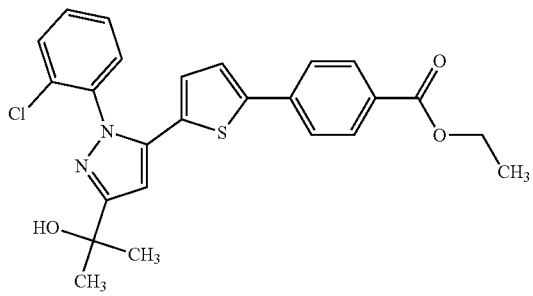 [SMILES: CCOC(=O)c1ccc(-c2ccc(-c3cc(C(C)(C)O)nn3-c3ccccc3Cl)s2)cc1] | ethyl 4-{5-[1-(2-chlorophenyl)-3-(1-hydroxy-1-methylethyl)-1H-pyrazol-5-yl]-2-thienyl}benzoate |

TABLE 1-continued

| | | |
|---|---|---|
| 851 | 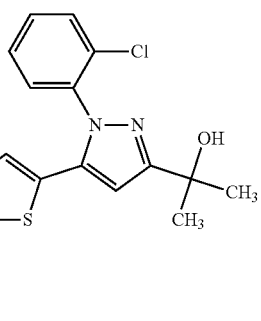 | 2-{1-(2-chlorophenyl)-5-[5-(5-methylfuran-2-yl)-2-thienyl]-1H-pyrazol-3-yl}propan-2-ol |
| 852 | 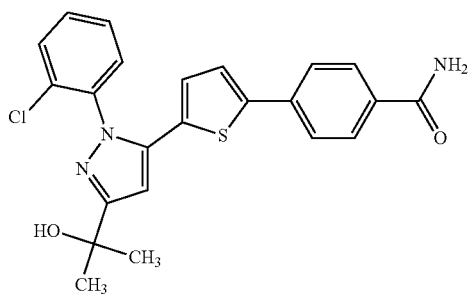 [SMILES: CC(C)(O)c1cc(-c2ccc(-c3ccc(C(N)=O)cc3)s2)n(-c2ccccc2Cl)n1] | 4-{5-[1-(2-chlorophenyl)-3-(1-hydroxy-1-methylethyl)-1H-pyrazol-5-yl]-2-thienyl}benzamide |
| 853 | 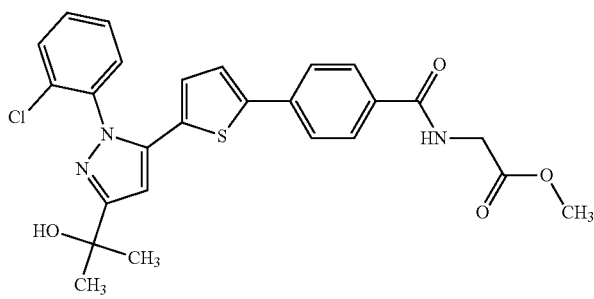 [SMILES: COC(=O)CNC(=O)c1ccc(-c2ccc(-c3cc(C(C)(C)O)nn3-c3ccccc3Cl)s2)cc1] | methyl N-[(4-{5-[1-(2-chlorophenyl)-3-(1-hydroxy-1-methylethyl)-1H-pyrazol-5-yl]-2-thienyl}phenyl)carbonyl]glycinate |
| 854 | 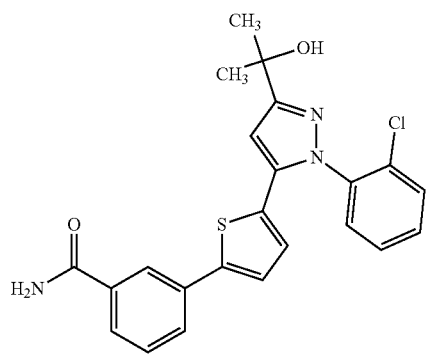 [SMILES: CC(C)(O)c1cc(-c2ccc(-c3cccc(C(N)=O)c3)s2)n(-c2ccccc2Cl)n1] | 3-{5-[1-(2-chlorophenyl)-3-(1-hydroxy-1-methylethyl)-1H-pyrazol-5-yl]-2-thienyl}benzamide |
| 855 | 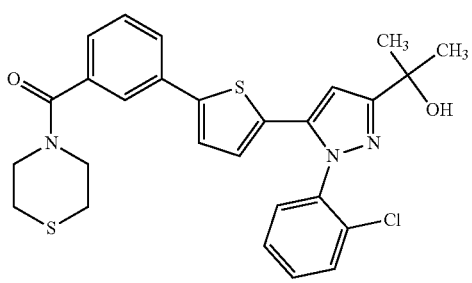 [SMILES: CC(C)(O)c1cc(-c2ccc(-c3cccc(C(=O)N4CCSCC4)c3)s2)n(-c2ccccc2Cl)n1] | 2-[1-(2-chlorophenyl)-5-{5-[3-(thiomorpholin-4-ylcarbonyl)phenyl]-2-thienyl}-1H-pyrazol-3-yl]propan-2-ol |

TABLE 1-continued

| | | |
|---|---|---|
| 856 | 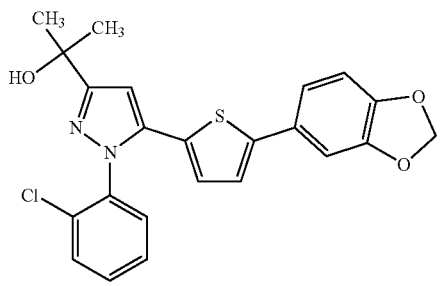 [SMILES: CC(C)(O)c1cc(-c2ccc(-c3ccc4c(c3)OCO4)s2)n(-c2ccccc2Cl)n1] | 2-{5-[5-(1,3-benzodioxol-5-yl)-2-thienyl]-1-(2-chlorophenyl)-1H-pyrazol-3-yl}propan-2-ol |
| 857 | 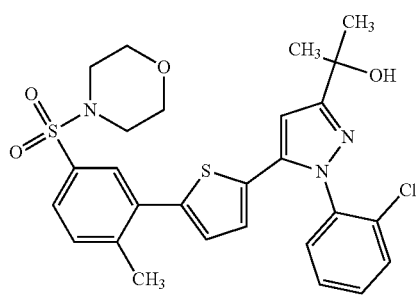 [SMILES: Cc1ccc(S(=O)(=O)N2CCOCC2)cc1-c1ccc(-c2cc(C(C)(C)O)nn2-c2ccccc2Cl)s1] | 2-[1-(2-chlorophenyl)-5-{5-[2-methyl-5-(morpholin-4-ylsulfonyl)phenyl]-2-thienyl}-1H-pyrazol-3-yl]propan-2-ol |
| 858 | 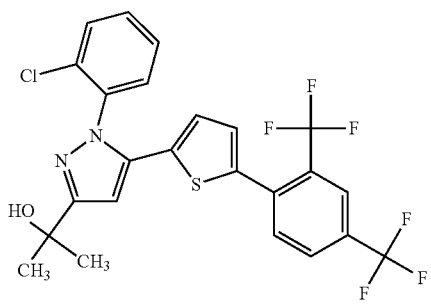 [SMILES: CC(C)(O)c1cc(-c2ccc(-c3ccc(C(F)(F)F)cc3C(F)(F)F)s2)n(-c2ccccc2Cl)n1] | 2-[5-{5-[2,4-bis(trifluoromethyl)phenyl]-2-thienyl}-1-(2-chlorophenyl)-1H-pyrazol-5-yl]propan-2-ol |
| 859 | 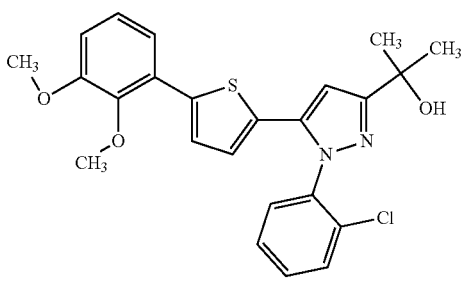 [SMILES: COc1cccc(-c2ccc(-c3cc(C(C)(C)O)nn3-c3ccccc3Cl)s2)c1OC] | 2-[5-{5-[2,3-bis(methyloxy)phenyl]-2-thienyl}-1-(2-chlorophenyl)-1H-pyrazol-3-yl]propan-2-ol |
| 860 | 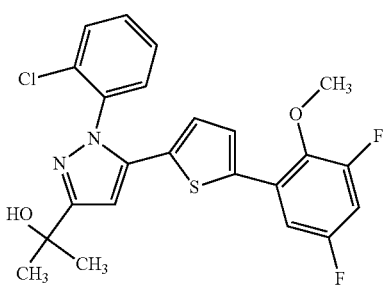 [SMILES: COc1c(F)cc(F)cc1-c1ccc(-c2cc(C(C)(C)O)nn2-c2ccccc2Cl)s1] | 2-[1-(2-chlorophenyl)-5-{5-[3,5-difluoro-2-(methyloxy)phenyl]-2-thienyl}-1H-pyrazol-3-yl]propan-2-ol |

TABLE 1-continued
| 861 | 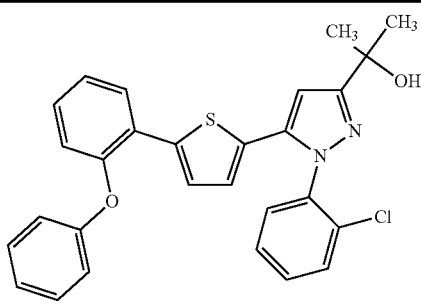 | 2-[1-(2-chlorophenyl)-5-{5-[2-(phenyloxy)phenyl]-2-thienyl}-1H-pyrazol-3-yl]propan-2-ol |
| 862 | 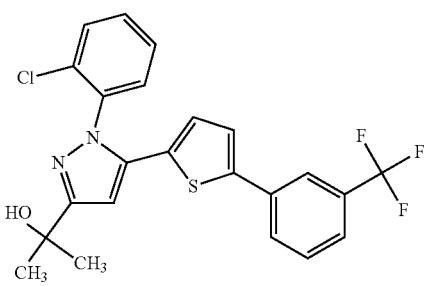 [SMILES: CC(C)(O)c1cc(-c2ccc(-c3cccc(C(F)(F)F)c3)s2)n(-c2ccccc2Cl)n1] | 2-[1-(2-chlorophenyl)-5-{5-[3-(trifluoromethyl)phenyl]-2-thienyl}-1H-pyrazol-3-yl]propan-2-ol |
| 863 | 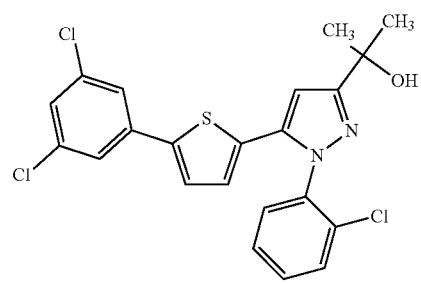 [SMILES: CC(C)(O)c1cc(-c2ccc(-c3cc(Cl)cc(Cl)c3)s2)n(-c2ccccc2Cl)n1] | 2-{1-(2-chlorophenyl)-5-[5-(3,5-dichlorophenyl)-2-thienyl]-1H-pyrazol-3-yl}propan-2-ol |
| 864 | 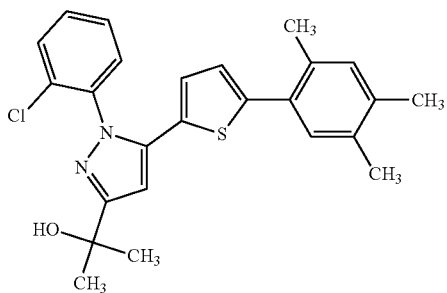 [SMILES: Cc1cc(C)c(-c2ccc(-c3cc(C(C)(C)O)nn3-c3ccccc3Cl)s2)cc1C] | 2-{1-(2-chlorophenyl)-5-[5-(2,4,5-trimethylphenyl)-2-thienyl]-1H-pyrazol-3-yl}propan-2-ol |
| 865 | 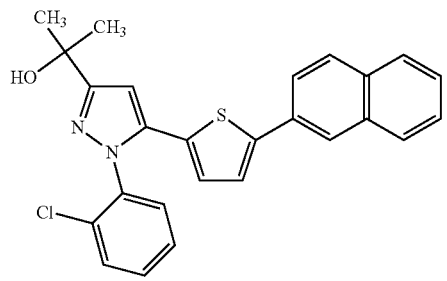 [SMILES: CC(C)(O)c1cc(-c2ccc(-c3ccc4ccccc4c3)s2)n(-c2ccccc2Cl)n1] | 2-[1-(2-chlorophenyl)-5-{5-naphthalen-2-yl-2-thienyl)-1H-pyrazol-3-yl]propan-2-ol |

TABLE 1-continued
| 866 | 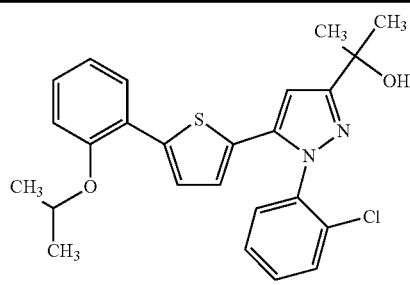 | 2-[1-(2-chlorophenyl)-5-(5-{2-[(1-methylethyl)oxy]phenyl}-2-thienyl)-1H-pyrazol-3-yl]propan-2-ol |
|---|---|---|
| 867 | 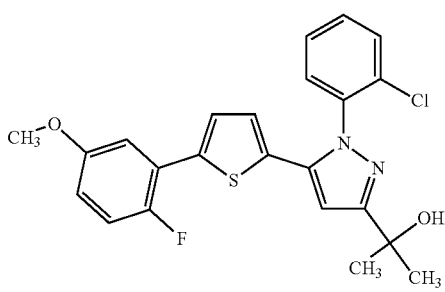 [SMILES: COc1ccc(F)c(-c2ccc(-c3cc(C(C)(C)O)nn3-c3ccccc3Cl)s2)c1] | 2-[1-(2-chlorophenyl)-5-{5-[2-fluoro-5-(methyloxy)phenyl]-2-thienyl}-1H-pyrazol-3-yl]propan-2-ol |
| 868 | 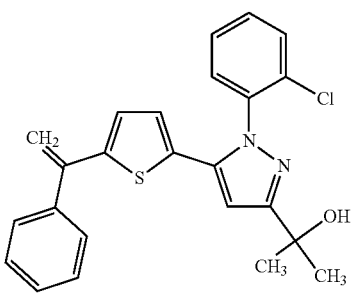 [SMILES: C=C(c1ccccc1)c1ccc(-c2cc(C(C)(C)O)nn2-c2ccccc2Cl)s1] | 2-{1-(2-chlorophenyl)-5-[5-(1-phenylethyl)-2-thienyl]-1H-pyrazol-3-yl}propan-2-ol |
| 869 | 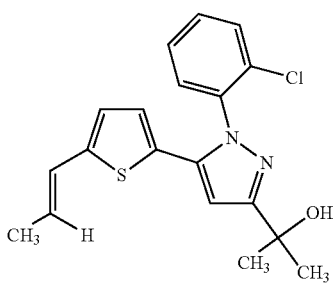 [SMILES: C/C=C/c1ccc(-c2cc(C(C)(C)O)nn2-c2ccccc2Cl)s1] | 2-[1-(2-chlorophenyl)-5-{5-[(1E)-prop-1-en-1-yl]-2-thienyl}-1H-pyrazol-3-yl]propan-2-ol |
| 870 | 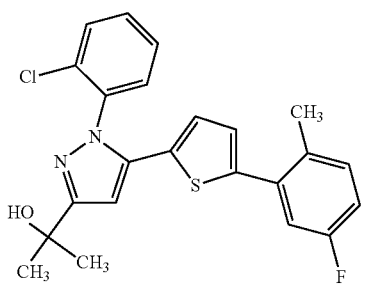 [SMILES: Cc1ccc(F)cc1-c1ccc(-c2cc(C(C)(C)O)nn2-c2ccccc2Cl)s1] | 2-{1-(2-chlorophenyl)-5-[5-(5-fluoro-2-methylphenyl)-2-thienyl]-1H-pyrazol-3-yl}propan-2-ol |

| | | |
|---|---|---|
| 871 | 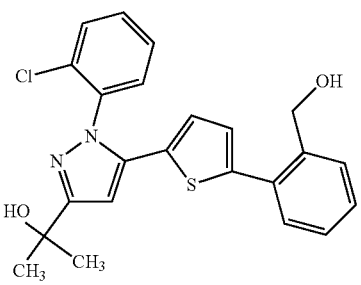 [SMILES: CC(C)(O)c1cc(-c2ccc(-c3ccccc3CO)s2)n(-c2ccccc2Cl)n1] | 2-[1-(2-chlorophenyl)-5-{5-[2-(hydroxymethyl)phenyl]-2-thienyl}-1H-pyrazol-3-yl]propan-2-ol |
| 872 | 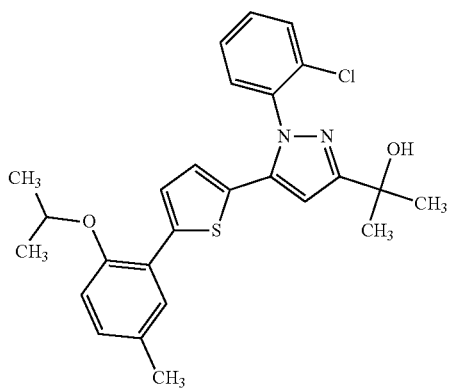 [SMILES: Cc1ccc(OC(C)C)c(-c2ccc(-c3cc(C(C)(C)O)nn3-c3ccccc3Cl)s2)c1] | 2-[1-(2-chlorophenyl)-5-(5-{5-methyl-2-[(1-methylethyl)oxy]phenyl}-2-thienyl)-1H-pyrazol-3-yl]propan-2-ol |
| 873 | 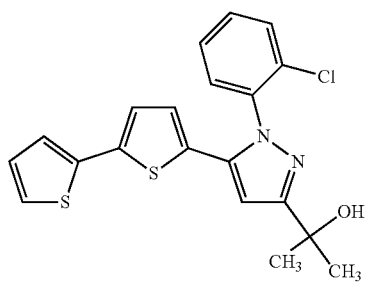 [SMILES: CC(C)(O)c1cc(-c2ccc(-c3cccs3)s2)n(-c2ccccc2Cl)n1] | 2-[5-(2,2'-bithien-5-yl)-1-(2-chlorophenyl)-1H-pyrazol-3-yl]propan-2-ol |
| 874 | 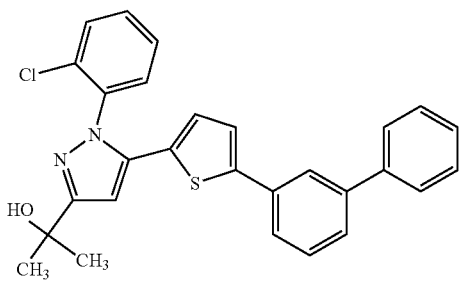 [SMILES: CC(C)(O)c1cc(-c2ccc(-c3cccc(-c4ccccc4)c3)s2)n(-c2ccccc2Cl)n1] | 2-[5-(5-biphenyl-3-yl-2-thienyl)-1-(2-chlorophenyl)-1H-pyrazol-3-yl]propan-2-ol |
| 875 | 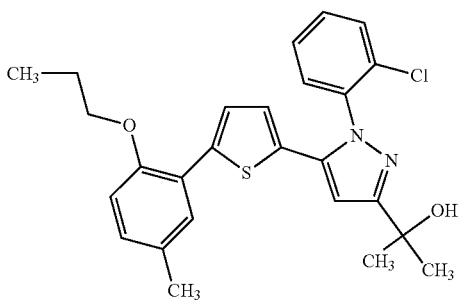 [SMILES: CCCOc1ccc(C)cc1-c1ccc(-c2cc(C(C)(C)O)nn2-c2ccccc2Cl)s1] | 2-[1-(2-chlorophenyl)-5-{5-[5-methyl-2-(propyloxy)phenyl]-2-thienyl}-1H-pyrazol-3-yl]propan-2-ol |

| | | |
|---|---|---|
| 876 | | 2-{1-(2-chlorophenyl)-5-[5-(4-propylphenyl)-2-thienyl]-1H-pyrazol-3-yl}propan-2-ol |
| 877 | | 2-[1-(2-chlorophenyl)-5-(5-{4-[(trifluoromethyl)oxy]phenyl}-2-thienyl)-1H-pyrazol-3-yl]propan-2-ol |
| 878 | | 4-{5-[1-(2-chlorophenyl)-3-(1-hydroxy-1-methylethyl)-1H-pyrazol-5-yl]-2-thienyl}-N-(2-methylpropyl)benzamide |
| 879 | | 2-[1-(2-chlorophenyl)-5-{5-[3-(ethyloxy)phenyl]-2-thienyl}-1H-pyrazol-3-yl]propan-2-ol |
| 880 | | 2-{1-(2-chlorophenyl)-5-[5-(4-ethylphenyl)-2-thienyl]-1H-pyrazol-3-yl}propan-2-ol |

TABLE 1-continued
| | | |
|---|---|---|
| 881 | 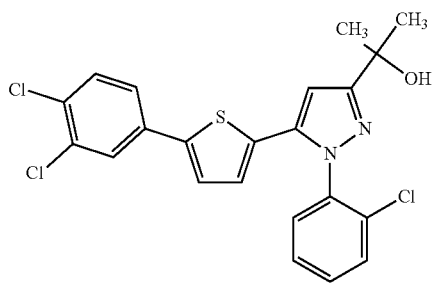 [SMILES: CC(C)(O)c1cc(-c2ccc(-c3ccc(Cl)c(Cl)c3)s2)n(-c2ccccc2Cl)n1] | 2-{1-(2-chlorophenyl)-5-[5-(3,4-dichlorophenyl)-2-thienyl]-1H-pyrazol-3-yl}propan-2-ol |
| 882 | 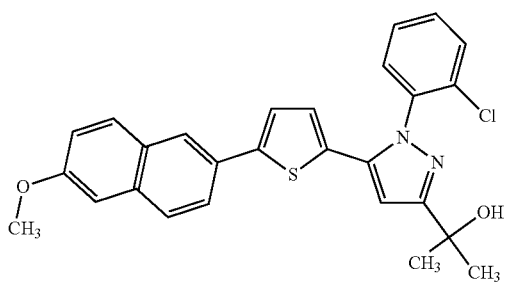 [SMILES: COc1ccc2cc(-c3ccc(-c4cc(C(C)(C)O)nn4-c4ccccc4Cl)s3)ccc2c1] | 2-[1-(2-chlorophenyl)-5-{5-[6-(methyloxy)naphthalen-2-yl]-2-thienyl}-1H-pyrazol-3-yl]propan-2-ol |
| 883 | 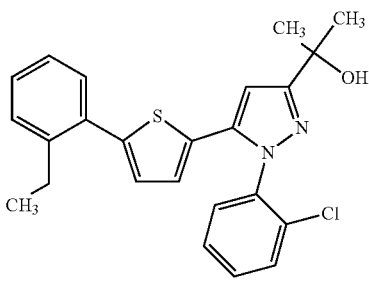 [SMILES: CCc1ccccc1-c1ccc(-c2cc(C(C)(C)O)nn2-c2ccccc2Cl)s1] | 2-{1-(2-chlorophenyl)-5-[5-(2-ethylphenyl)-2-thienyl]-1H-pyrazol-3-yl}propan-2-ol |
| 884 | 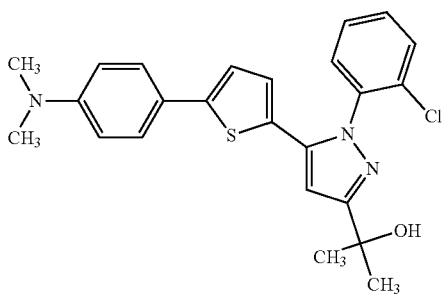 [SMILES: CN(C)c1ccc(-c2ccc(-c3cc(C(C)(C)O)nn3-c3ccccc3Cl)s2)cc1] | 2-[1-(2-chlorophenyl)-5-{5-[4-(dimethylamino)phenyl]-2-thienyl}-1H-pyrazol-3-yl]propan-2-ol |
| 885 | 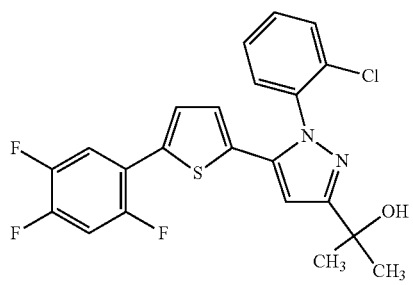 [SMILES: CC(C)(O)c1cc(-c2ccc(-c3cc(F)c(F)cc3F)s2)n(-c2ccccc2Cl)n1] | 2-{1-(2-chlorophenyl)-5-[5-(2,4,5-trifluorophenyl)-2-thienyl]-1H-pyrazol-3-yl}propan-2-ol |

| | | |
|---|---|---|
| 886 | 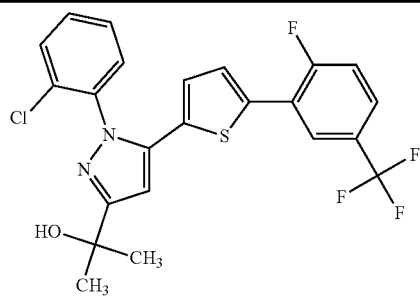 | 2-[1-(2-chlorophenyl)-5-{5-[2-fluoro-5-(trifluoromethyl)phenyl]-2-thienyl}-1H-pyrazol-3-yl]propan-2-ol |
| 887 | 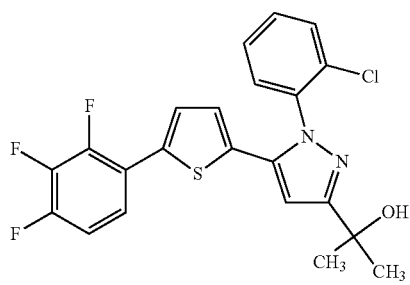 [SMILES: CC(C)(O)c1cc(-c2ccc(-c3ccc(F)c(F)c3F)s2)n(-c2ccccc2Cl)n1] | 2-{1-(2-chlorophenyl)-5-[5-(2,3,4-trifluorophenyl)-2-thienyl]-1H-pyrazol-3-yl}propan-2-ol |
| 888 | 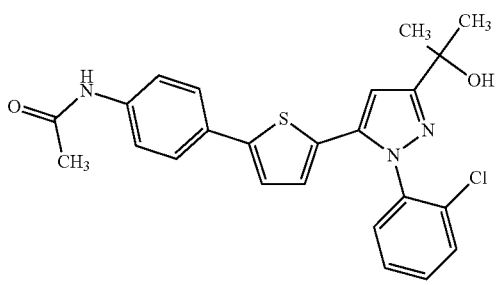 [SMILES: CC(=O)Nc1ccc(-c2ccc(-c3cc(C(C)(C)O)nn3-c3ccccc3Cl)s2)cc1] | N-(4-{5-[1-(2-chlorophenyl)-3-(1-hydroxy-1-methylethyl)-1H-pyrazol-5-yl]-2-thienyl}phenyl)acetamide |
| 889 | 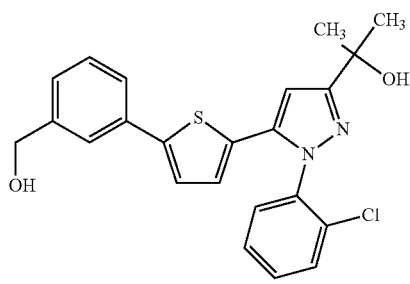 [SMILES: CC(C)(O)c1cc(-c2ccc(-c3cccc(CO)c3)s2)n(-c2ccccc2Cl)n1] | 2-[1-(2-chlorophenyl)-5-{5-[3-(hydroxymethyl)phenyl]-2-thienyl}-1H-pyrazol-3-yl]propan-2-ol |
| 890 | 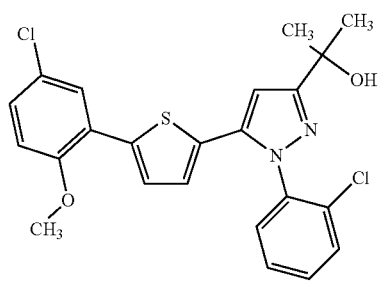 [SMILES: COc1ccc(Cl)cc1-c1ccc(-c2cc(C(C)(C)O)nn2-c2ccccc2Cl)s1] | 2-[5-{5-[5-chloro-2-(methyoxy)phenyl]-2-thienyl}-1-(2-chlorophenyl)-1H-pyrazol-3-yl]propan-2-ol |

TABLE 1-continued
| | | |
|---|---|---|
| 891 | 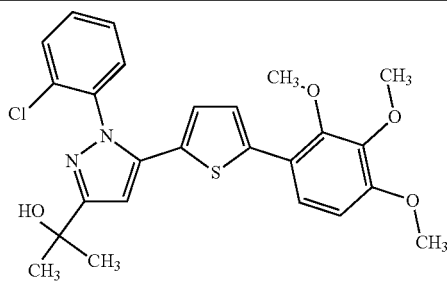 | 2-[1-(2-chlorophenyl)-5-{5-[2,3,4-tris(methyloxy)phenyl]-2-thienyl}-1H-pyrazol-3-yl]propan-2-ol |
| 892 | 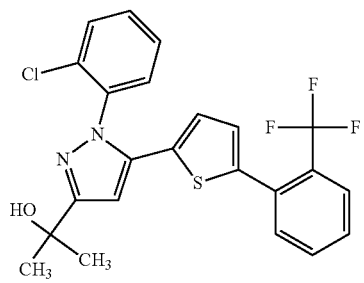 [SMILES: CC(C)(O)c1cc(-c2ccc(-c3ccccc3C(F)(F)F)s2)n(-c2ccccc2Cl)n1] | 2-[1-(2-chlorophenyl)-5-{5-[2-(trifluoromethyl)phenyl]-2-thienyl}-1H-pyrazol-3-yl]propan-2-ol |
| 893 | 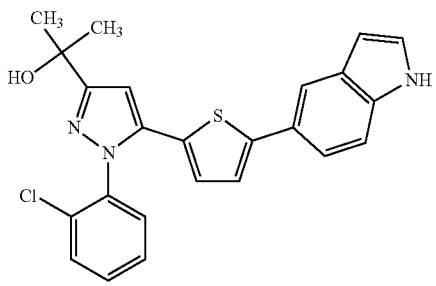 [SMILES: CC(C)(O)c1cc(-c2ccc(-c3ccc4[nH]ccc4c3)s2)n(-c2ccccc2Cl)n1] | 2-{1-(2-chlorophenyl)-5-[5-(1H-indol-5-yl)-2-thienyl]-1H-pyrazol-3-yl}propan-2-ol |
| 894 | 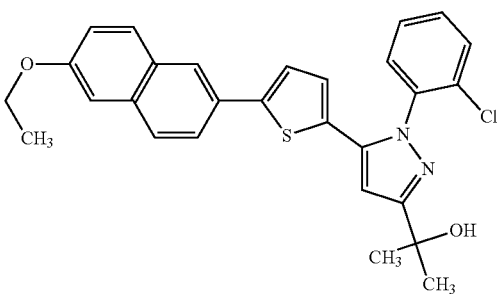 [SMILES: CCOc1ccc2cc(-c3ccc(-c4cc(C(C)(C)O)nn4-c4ccccc4Cl)s3)ccc2c1] | 2-[1-(2-chlorophenyl)-5-{5-[6-(ethyloxy)naphthalen-2-yl]-2-thienyl}-1H-pyrazol-3-yl]propan-2-ol |
| 895 | 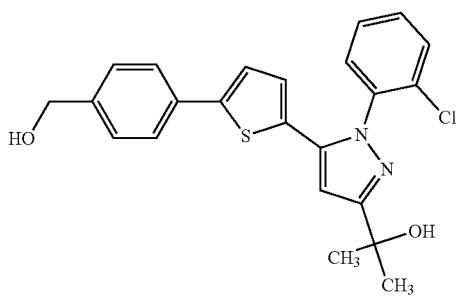 [SMILES: CC(C)(O)c1cc(-c2ccc(-c3ccc(CO)cc3)s2)n(-c2ccccc2Cl)n1] | 2-[1-(2-chlorophenyl)-5-{5-[4-(hydroxymethyl)phenyl]-2-thienyl}-1H-pyrazol-3-yl]propan-2-ol |

TABLE 1-continued
| 896 | 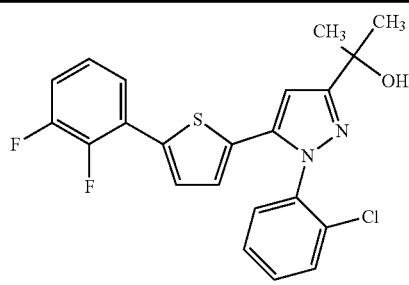 | 2-{1-(2-chlorophenyl)-5-[5-(2,3-difluorophenyl)-2-thienyl]-1H-pyrazol-3-yl}propan-2-ol |
| 897 | 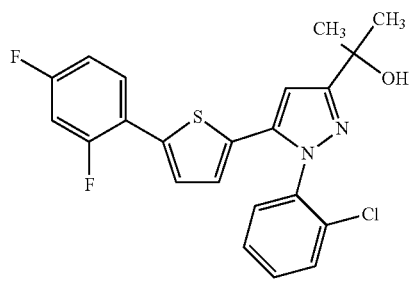 [SMILES: CC(C)(O)c1cc(-c2ccc(-c3ccc(F)cc3F)s2)n(-c2ccccc2Cl)n1] | 2-{1-(2-chlorophenyl)-5-[5-(2,4-difluorophenyl)-2-thienyl]-1H-pyrazol-3-yl}propan-2-ol |
| 898 | 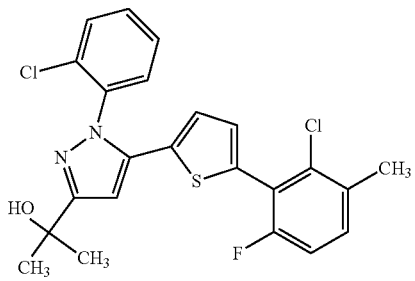 [SMILES: Cc1ccc(F)c(-c2ccc(-c3cc(C(C)(C)O)nn3-c3ccccc3Cl)s2)c1Cl] | 2-{5-[5-(2-chloro-6-fluoro-3-methylphenyl)-2-thienyl]-1-(2-chlorophenyl)-1H-pyrazol-3-yl}propan-2-ol |
| 899 | 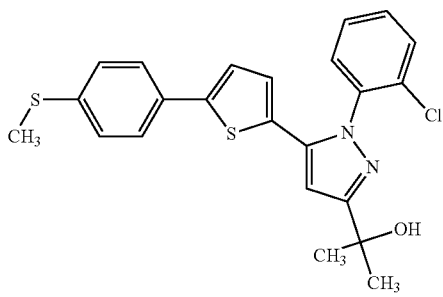 [SMILES: CSc1ccc(-c2ccc(-c3cc(C(C)(C)O)nn3-c3ccccc3Cl)s2)cc1] | 2-[1-(2-chlorophenyl)-5-{5-[4-(methylthio)phenyl]-2-thienyl}-1H-pyrazol-3-yl]propan-2-ol |
| 900 | 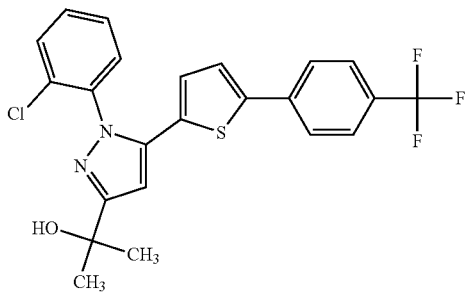 [SMILES: CC(C)(O)c1cc(-c2ccc(-c3ccc(C(F)(F)F)cc3)s2)n(-c2ccccc2Cl)n1] | 2-[1-(2-chlorophenyl)-5-{5-[4-(trifluoromethyl)phenyl]-2-thienyl}-1H-pyrazol-3-yl]propan-2-ol |

TABLE 1-continued
| | | |
|---|---|---|
| 901 | 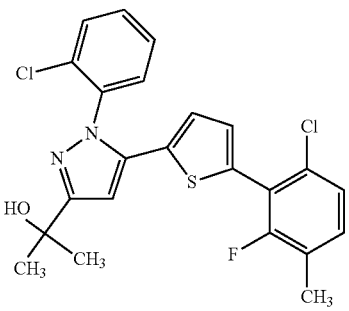 [SMILES: Cc1ccc(Cl)c(-c2ccc(-c3cc(C(C)(C)O)nn3-c3ccccc3Cl)s2)c1F] | 2-{5-[5-(6-chloro-2-fluoro-3-methylphenyl)-2-thienyl]-1-(2-chlorophenyl)-1H-pyrazol-3-yl}propan-2-ol |
| 902 | 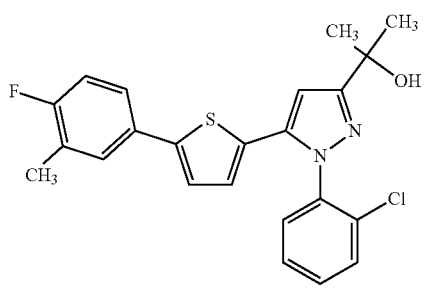 [SMILES: Cc1cc(-c2ccc(-c3cc(C(C)(C)O)nn3-c3ccccc3Cl)s2)ccc1F] | 2-{1-(2-chlorophenyl)-5-[5-(4-fluoro-3-methylphenyl)-2-thienyl]-1H-pyrazol-3-yl}propan-2-ol |
| 903 | 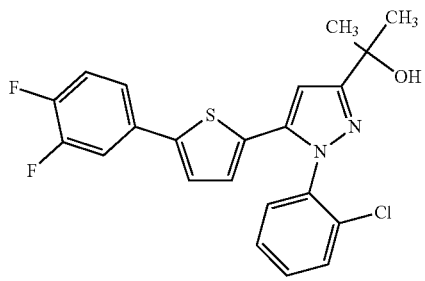 [SMILES: CC(C)(O)c1cc(-c2ccc(-c3ccc(F)c(F)c3)s2)n(-c2ccccc2Cl)n1] | 2-{1-(2-chlorophenyl)-5-[5-(3,4-difluorophenyl)-2-thienyl]-1H-pyrazol-3-yl}propan-2-ol |
| 904 | 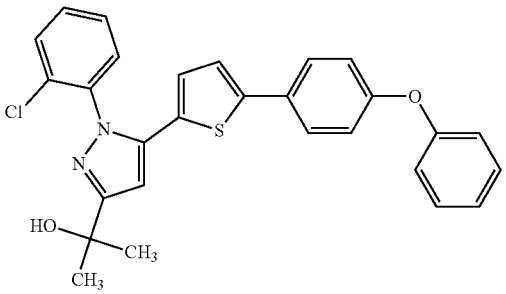 [SMILES: CC(C)(O)c1cc(-c2ccc(-c3ccc(Oc4ccccc4)cc3)s2)n(-c2ccccc2Cl)n1] | 2-[1-(2-chlorophenyl)-5-{5-[4-(phenyloxy)phenyl]-2-thienyl}-1H-pyrazol-3-yl]propan-2-ol |
| 905 | 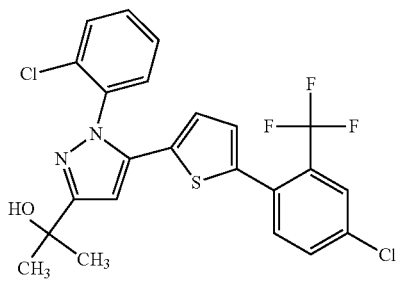 [SMILES: CC(C)(O)c1cc(-c2ccc(-c3ccc(Cl)cc3C(F)(F)F)s2)n(-c2ccccc2Cl)n1] | 2-[1-(2-chlorophenyl)-5-{5-[4-chloro-2-(trifluoromethyl)phenyl]-2-thienyl}-1H-pyrazol-3-yl]propan-2-ol |

TABLE 1-continued
| | | |
|---|---|---|
| 906 | 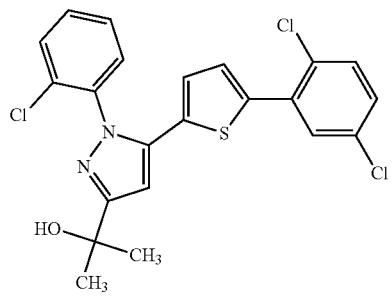 [SMILES: CC(C)(O)c1cc(-c2ccc(-c3cc(Cl)ccc3Cl)s2)n(-c2ccccc2Cl)n1] | 2-{1-(2-chlorophenyl)-5-[5-(2,5-dichlorophenyl)-2-thienyl]-1H-pyrazol-3-yl}propan-2-ol |
| 907 | 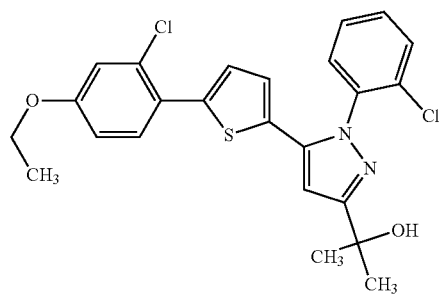 [SMILES: CCOc1ccc(-c2ccc(-c3cc(C(C)(C)O)nn3-c3ccccc3Cl)s2)c(Cl)c1] | 2-[5-{5-[2-chloro-4-(ethyloxy)phenyl]-2-thienyl}-1-(2-chlorophenyl)-1H-pyrazol-3-yl]propan-2-ol |
| 908 | 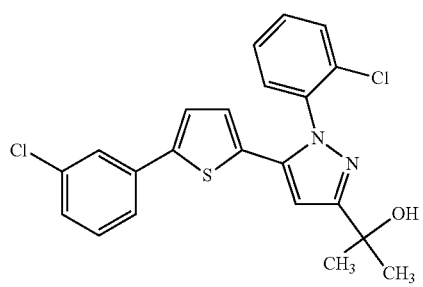 [SMILES: CC(C)(O)c1cc(-c2ccc(-c3cccc(Cl)c3)s2)n(-c2ccccc2Cl)n1] | 2-{1-(2-chlorophenyl)-5-[5-(3-chlorophenyl)-2-thienyl]-1H-pyrazol-3-yl}propan-2-ol |
| 909 | 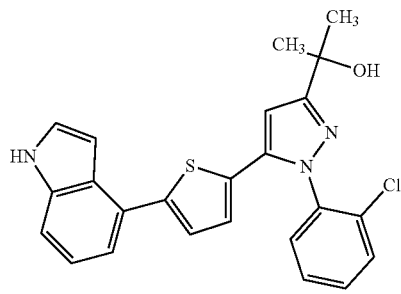 [SMILES: CC(C)(O)c1cc(-c2ccc(-c3cccc4[nH]ccc34)s2)n(-c2ccccc2Cl)n1] | 2-{1-(2-chlorophenyl)-5-[5-(1H-indol-4-yl)-2-thienyl]-1H-pyrazol-3-yl}propan-2-ol |
| 910 | 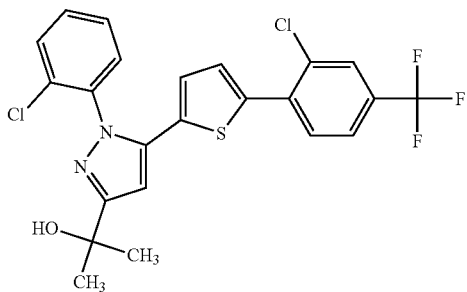 [SMILES: CC(C)(O)c1cc(-c2ccc(-c3ccc(C(F)(F)F)cc3Cl)s2)n(-c2ccccc2Cl)n1] | 2-[1-(2-chlorophenyl)-5-{5-[2-chloro-4-(trifluoromethyl)phenyl]-2-thienyl}-1H-pyrazol-3-yl]propan-2-ol |

TABLE 1-continued

| | | |
|---|---|---|
| 911 | 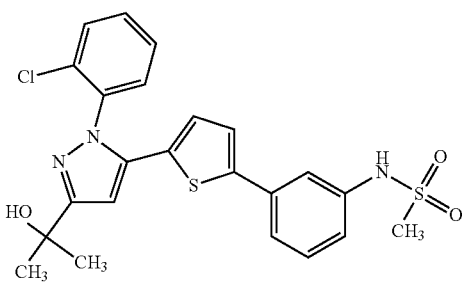 [SMILES: CC(C)(O)c1cc(-c2ccc(-c3cccc(NS(C)(=O)=O)c3)s2)n(-c2ccccc2Cl)n1] | N-(3-{5-[1-(2-chlorophenyl)-3-(1-hydroxy-1-methylethyl)-1H-pyrazol-5-yl]-2-thienyl}phenyl)methanesulfonamide |
| 912 | 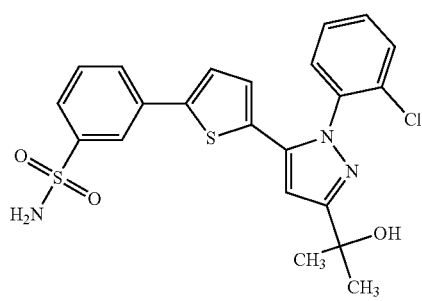 [SMILES: CC(C)(O)c1cc(-c2ccc(-c3cccc(S(N)(=O)=O)c3)s2)n(-c2ccccc2Cl)n1] | 3-{5-[1-(2-chlorophenyl)-3-(1-hydroxy-1-methylethyl)-1H-pyrazol-5-yl]-2-thienyl}benzenesulfonamide |
| 913 | 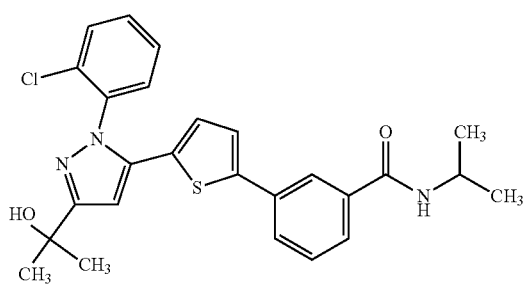 [SMILES: CC(C)NC(=O)c1cccc(-c2ccc(-c3cc(C(C)(C)O)nn3-c3ccccc3Cl)s2)c1] | 3-{5-[1-(2-chlorophenyl)-3-(1-hydroxy-1-methylethyl)-1H-pyrazol-5-yl]-2-thienyl}-N-(1-methylethyl)benzamide |
| 914 | 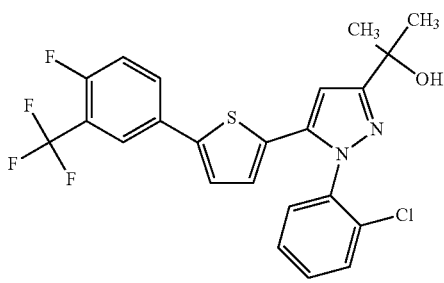 [SMILES: CC(C)(O)c1cc(-c2ccc(-c3ccc(F)c(C(F)(F)F)c3)s2)n(-c2ccccc2Cl)n1] | 2-[1-(2-chlorophenyl)-5-{5-[4-fluoro-3-(trifluoromethyl)phenyl]-2-thienyl}-1H-pyrazol-3-yl]propan-2-ol |
| 915 | 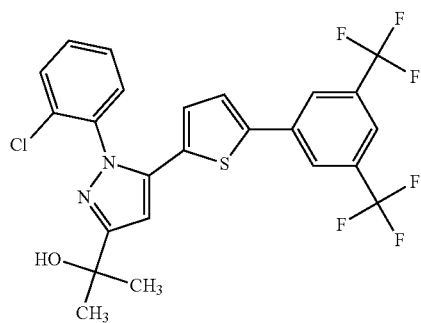 [SMILES: CC(C)(O)c1cc(-c2ccc(-c3cc(C(F)(F)F)cc(C(F)(F)F)c3)s2)n(-c2ccccc2Cl)n1] | 2-[5-{5-(3,5-bis(trifluoromethyl)phenyl]-2-thienyl}-1-(2-chlorophenyl)-1H-pyrazol-3-yl]propan-2-ol |

| | | |
|---|---|---|
| 916 | 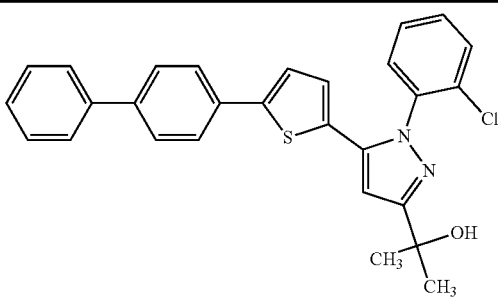 | 2-[5-(5-biphenyl-4-yl-2-thienyl)-1-(2-chlorophenyl)-1H-pyrazol-3-yl]propan-2-ol |
| 917 | 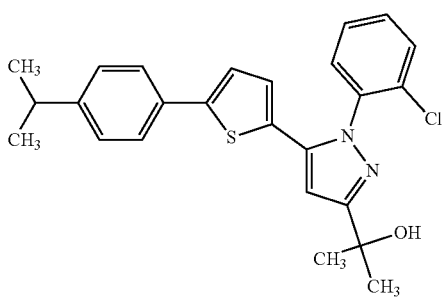 [SMILES: CC(C)c1ccc(-c2ccc(-c3cc(C(C)(C)O)nn3-c3ccccc3Cl)s2)cc1] | 2-[1-(2-chlorophenyl)-5-{5-[4-(1-methylethyl)phenyl]-2-thienyl}-1H-pyrazol-3-yl]propan-2-ol |
| 918 | 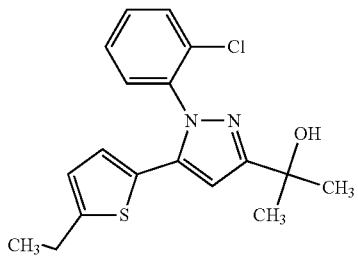 [SMILES: CCc1ccc(-c2cc(C(C)(C)O)nn2-c2ccccc2Cl)s1] | 2-[1-(2-chlorophenyl)-5-(5-ethyl-2-thienyl)-1H-pyrazol-3-yl]propan-2-ol |
| 919 | 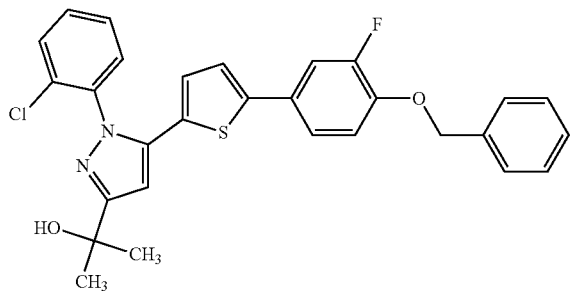 [SMILES: CC(C)(O)c1cc(-c2ccc(-c3ccc(OCc4ccccc4)c(F)c3)s2)n(-c2ccccc2Cl)n1] | 2-[1-(2-chlorophenyl)-5-(5-{3-fluoro-4-[(phenylmethyl)oxy]phenyl}-2-thienyl)-1H-pyrazol-3-yl]propan-2-ol |
| 920 | 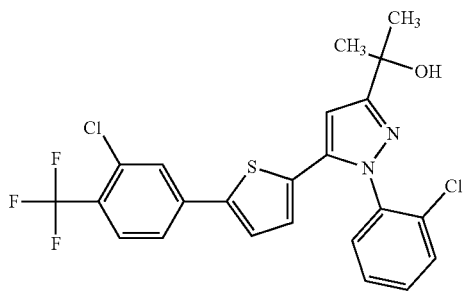 [SMILES: CC(C)(O)c1cc(-c2ccc(-c3ccc(C(F)(F)F)c(Cl)c3)s2)n(-c2ccccc2Cl)n1] | 2-[1-(2-chlorophenyl)-5-{5-[3-chloro-4-(trifluoromethyl)phenyl]-2-thienyl}-1H-pyrazol-3-yl]propan-2-ol |

TABLE 1-continued
| | | |
|---|---|---|
| 921 | 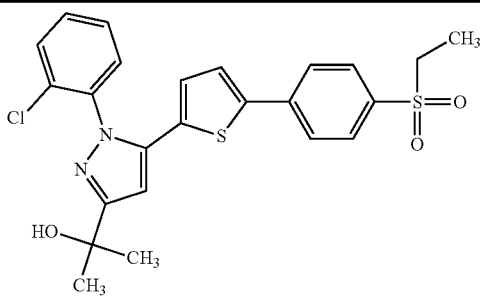 | 2-[1-(2-chlorophenyl)-5-{5-[4-(ethylsulfonyl)phenyl]-2-thienyl}-1H-pyrazol-3-yl]propan-2-ol |
| 922 | 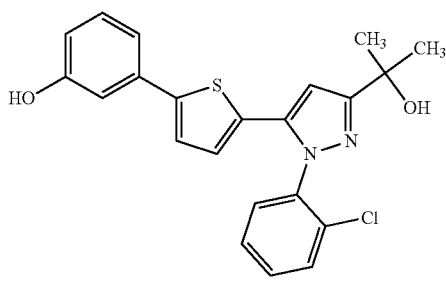 [SMILES: CC(C)(O)c1cc(-c2ccc(-c3cccc(O)c3)s2)n(-c2ccccc2Cl)n1] | 3-{5-[1-(2-chlorophenyl)-3-(1-hydroxy-1-methylethyl)-1H-pyrazol-5-yl]-2-thienyl}phenol |
| 923 | 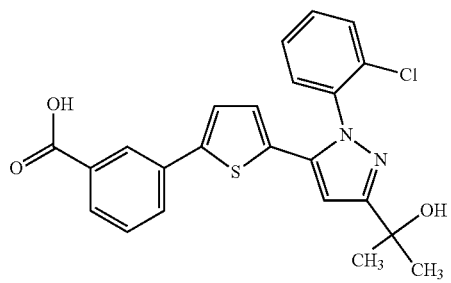 [SMILES: CC(C)(O)c1cc(-c2ccc(-c3cccc(C(=O)O)c3)s2)n(-c2ccccc2Cl)n1] | 3-{5-[1-(2-chlorophenyl)-3-(1-hydroxy-1-methylethyl)-1H-pyrazol-5-yl]-2-thienyl}benzoic acid |
| 924 | 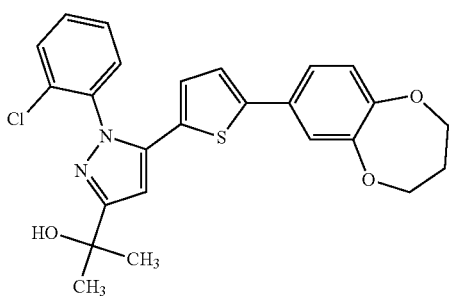 [SMILES: CC(C)(O)c1cc(-c2ccc(-c3ccc4c(c3)OCCCO4)s2)n(-c2ccccc2Cl)n1] | 2-{1-(2-chlorophenyl)-5-[5-(3,4-dihydro-2H-1,5-benzodioxepin-7-yl)-2-thienyl]-1H-pyrazol-3-yl}propan-2-ol |
| 925 | 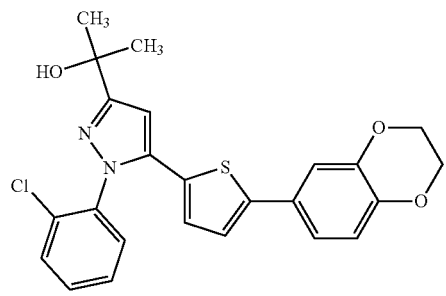 [SMILES: CC(C)(O)c1cc(-c2ccc(-c3ccc4c(c3)OCCO4)s2)n(-c2ccccc2Cl)n1] | 2-{1-(2-chlorophenyl)-5-[5-(2,3-dihydro-1,4-benzodioxin-6-yl)-2-thienyl]-1H-pyrazol-3-yl}propan-2-ol |

TABLE 1-continued
| 926 | 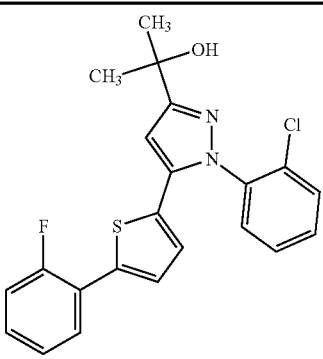 | 2-{1-(2-chlorophenyl)-5-[5-(2-fluorophenyl)-2-thienyl]-1H-pyrazol-3-yl}propan-2-ol |
| 927 | 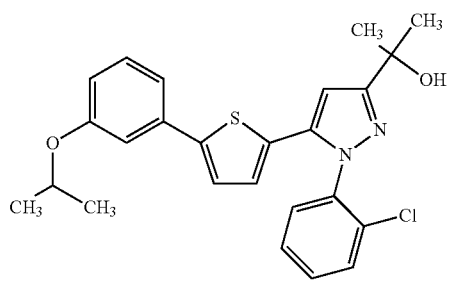 [SMILES: CC(C)Oc1cccc(-c2ccc(-c3cc(C(C)(C)O)nn3-c3ccccc3Cl)s2)c1] | 2-[1-(2-chlorophenyl)-5-(5-{3-[(1-methylethyl)oxy]phenyl}-2-thienyl)-1H-pyrazol-3-yl]propan-2-ol |
| 928 | 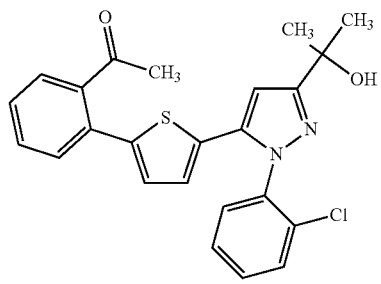 [SMILES: CC(=O)c1ccccc1-c1ccc(-c2cc(C(C)(C)O)nn2-c2ccccc2Cl)s1] | 1-(2-{5-[1-(2-chlorophenyl)-3-(1-hydroxy-1-methylethyl)-1H-pyrazol-5-yl]-2-thienyl}phenyl)ethanone |
| 929 | 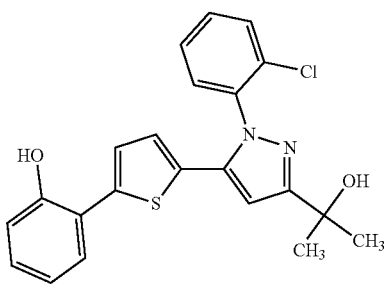 [SMILES: CC(C)(O)c1cc(-c2ccc(-c3ccccc3O)s2)n(-c2ccccc2Cl)n1] | 2-{5-[1-(2-chlorophenyl)-3-(1-hydroxy-1-methylethyl)-1H-pyrazol-5-yl]-2-thienyl}phenol |
| 930 | 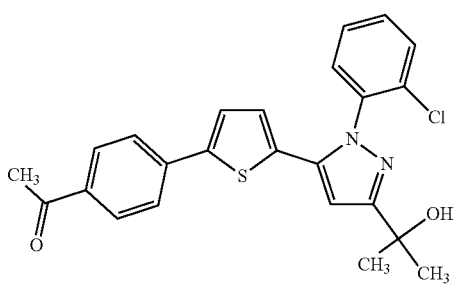 [SMILES: CC(=O)c1ccc(-c2ccc(-c3cc(C(C)(C)O)nn3-c3ccccc3Cl)s2)cc1] | 1-(4-{5-[1-(2-chlorophenyl)-3-(1-hydroxy-1-methylethyl)-1H-pyrazol-5-yl]-2-thienyl}phenyl)ethanone |

TABLE 1-continued

| | | |
|---|---|---|
| 931 | 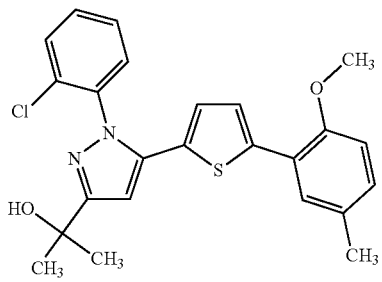 [SMILES: COc1ccc(C)cc1-c1ccc(-c2cc(C(C)(C)O)nn2-c2ccccc2Cl)s1] | 2-[1-(2-chlorophenyl)-5-{5-[5-methyl-2-(methyloxy)phenyl]-2-thienyl}-1H-pyrazol-3-yl]propan-2-ol |
| 932 | 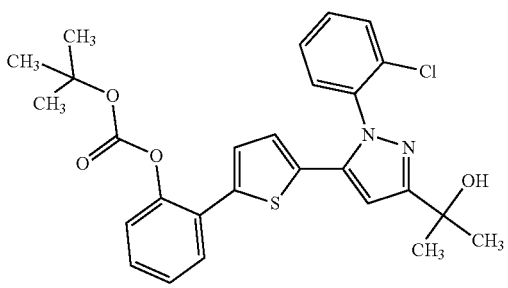 [SMILES: CC(C)(C)OC(=O)Oc1ccccc1-c1ccc(-c2cc(C(C)(C)O)nn2-c2ccccc2Cl)s1] | 2-{5-[1-(2-chlorophenyl)-3-(1-hydroxy-1-methylethyl)-1H-pyrazol-5-yl]-2-thienyl}phenyl 1,1-dimethylethyl carbonate |
| 933 | 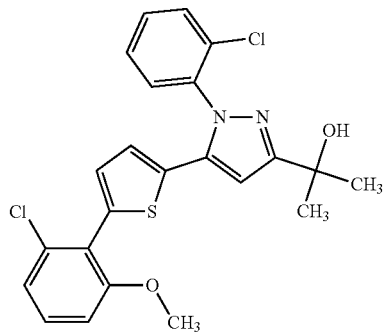 [SMILES: COc1cccc(Cl)c1-c1ccc(-c2cc(C(C)(C)O)nn2-c2ccccc2Cl)s1] | 2-[5-{5-[2-chloro-6-(methyloxy)phenyl]-2-thienyl}-1-(2-chlorophenyl)-1H-pyrazol-3-yl]propan-2-ol |
| 934 | 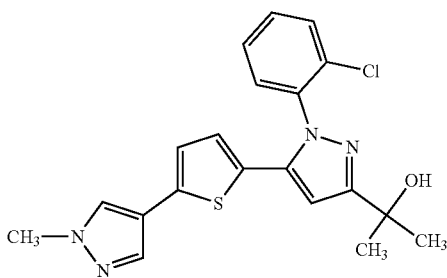 [SMILES: Cn1cc(-c2ccc(-c3cc(C(C)(C)O)nn3-c3ccccc3Cl)s2)cn1] | 2-{1-(2-chlorophenyl)-5-[5-(1-methyl-1H-pyrazol-4-yl)-2-thienyl]-1H-pyrazol-3-yl}propan-2-ol |
| 935 | 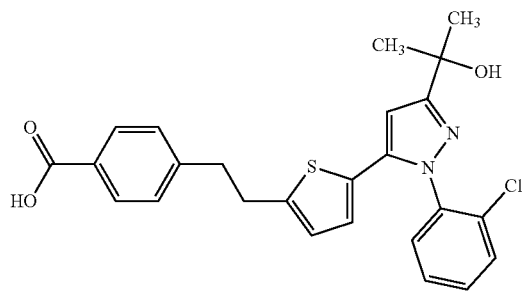 [SMILES: CC(C)(O)c1cc(-c2ccc(CCc3ccc(C(=O)O)cc3)s2)n(-c2ccccc2Cl)n1] | 4-(2-{5-[1-(2-chlorophenyl)-3-(1-hydroxy-1-methylethyl)-1H-pyrazol-5-yl]-2-thienyl}ethyl)benzoic acid |

| | | |
|---|---|---|
| 936 | 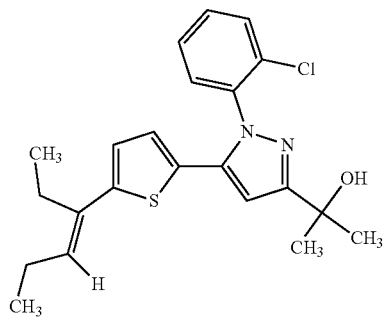 [SMILES: CC/C=C(\CC)c1ccc(-c2cc(C(C)(C)O)nn2-c2ccccc2Cl)s1] | 2-[1-(2-chlorophenyl)-5-{5-[(1E)-1-ethylbut-1-en-1-yl]-2-thienyl}-1H-pyrazol-3-yl]propan-2-ol |
| 937 | 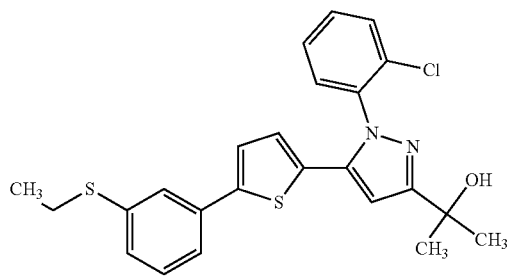 [SMILES: CCSc1cccc(-c2ccc(-c3cc(C(C)(C)O)nn3-c3ccccc3Cl)s2)c1] | 2-[1-(2-chlorophenyl)-5-{5-[3-(ethylthio)phenyl]-2-thienyl}-1H-pyrazol-3-yl]propan-2-ol |
| 938 | 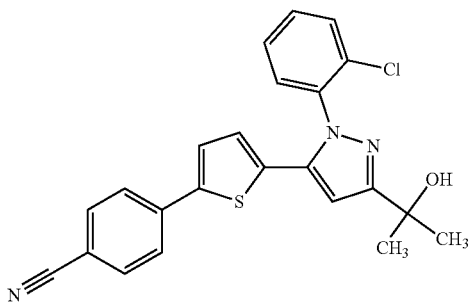 [SMILES: CC(C)(O)c1cc(-c2ccc(-c3ccc(C#N)cc3)s2)n(-c2ccccc2Cl)n1] | 4-{5-[1-(2-chlorophenyl)-3-(1-hydroxy-1-methylethyl)-1H-pyrazol-5-yl]-2-thienyl}benzonitrile |
| 939 | 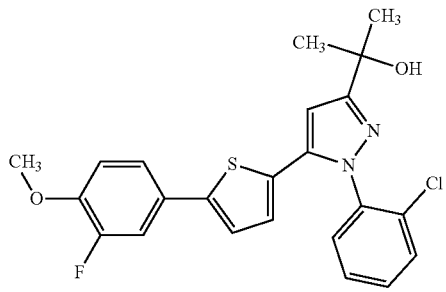 [SMILES: COc1ccc(-c2ccc(-c3cc(C(C)(C)O)nn3-c3ccccc3Cl)s2)cc1F] | 2-[1-(2-chlorophenyl)-5-{5-[3-fluoro-4-(methyloxy)phenyl]-2-thienyl}-1H-pyrazol-3-yl]propan-2-ol |
| 940 | 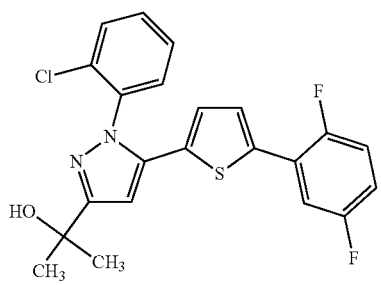 [SMILES: CC(C)(O)c1cc(-c2ccc(-c3cc(F)ccc3F)s2)n(-c2ccccc2Cl)n1] | 2-{1-(2-chlorophenyl)-5-[5-(2,5-difluorophenyl)-2-thienyl]-1H-pyrazol-3-yl}propan-2-ol |

TABLE 1-continued

| | | |
|---|---|---|
| 941 | [structure] | 2-[1-(2-chlorophenyl)-5-(5-{(E)-2-[4-(trifluoromethyl)phenyl]ethenyl}-2-thienyl)-1H-pyrazol-3-yl]propan-2-ol |
| 942 | [structure] | 2-[1-(2-chlorophenyl)-5-{5-[2-(ethyloxy)phenyl]-2-thienyl}-1H-pyrazol-3-yl]propan-2-ol |
| 943 | [structure] | 2-{5-[5-(1-benzothien-3-yl)-2-thienyl]-1-(2-chlorophenyl)-1H-pyrazol-3-yl}propan-2-ol |
| 944 | [structure] | ethyl 2-{5-[1-(2-chlorophenyl)-3-(1-hydroxy-1-methylethyl)-1H-pyrazol-5-yl]-2-thienyl}benzoate |
| 945 | [structure] | 2-[1-(2-chlorophenyl)-5-{5-[(E)-2-(4-fluorophenyl)ethenyl]-2-thienyl}-1H-pyrazol-3-yl]propan-2-ol |

| | | |
|---|---|---|
| 946 | 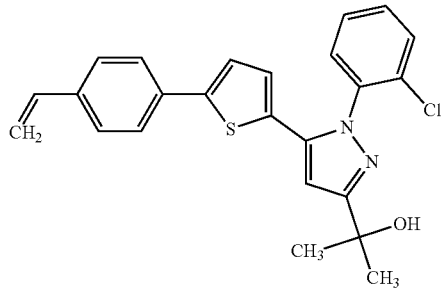 [SMILES: C=Cc1ccc(-c2ccc(-c3cc(C(C)(C)O)nn3-c3ccccc3Cl)s2)cc1] | 2-{1-(2-chlorophenyl)-5-[5-(4-ethenylphenyl)-2-thienyl]-1H-pyrazol-3-yl)propan-2-ol |
| 947 | 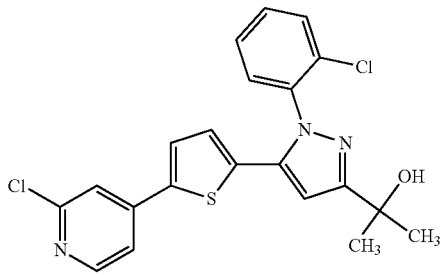 [SMILES: CC(C)(O)c1cc(-c2ccc(-c3ccnc(Cl)c3)s2)n(-c2ccccc2Cl)n1] | 2-{1-(2-chlorophenyl)-5-[5-(2-chloropyridin-4-yl)-2-thienyl]-1H-pyrazol-3-yl}propan-2-ol |
| 948 | 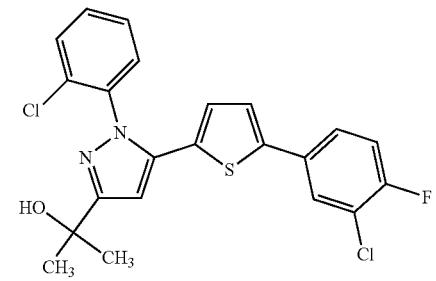 [SMILES: CC(C)(O)c1cc(-c2ccc(-c3ccc(F)c(Cl)c3)s2)n(-c2ccccc2Cl)n1] | 2-{5-[5-(3-chloro-4-fluorophenyl)-2-thienyl]-1-(2-chlorophenyl)-1H-pyrazol-3-yl}propan-2-ol |
| 949 | 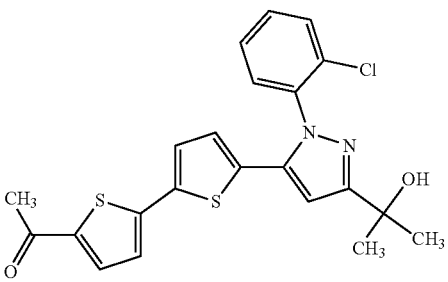 [SMILES: CC(=O)c1ccc(-c2ccc(-c3cc(C(C)(C)O)nn3-c3ccccc3Cl)s2)s1] | 1-{5'-[1-(2-chlorophenyl)-3-(1-hydroxy-1-methylethyl)-1H-pyrazol-5-yl]-2,2'-bithien-5-yl}ethanone |
| 950 | 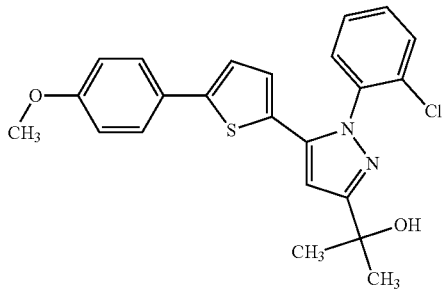 [SMILES: COc1ccc(-c2ccc(-c3cc(C(C)(C)O)nn3-c3ccccc3Cl)s2)cc1] | 2-[1-(2-chlorophenyl)-5-{5-[4-(methyloxy)phenyl]-2-thienyl}-1H-pyrazol-3-yl]propan-2-ol |

TABLE 1-continued
| | | |
|---|---|---|
| 951 | 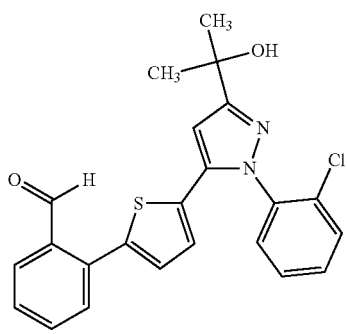 [SMILES: CC(C)(O)c1cc(-c2ccc(-c3ccccc3C=O)s2)n(-c2ccccc2Cl)n1] | 2-{5-[1-(2-chlorophenyl)-3-(1-hydroxy-1-methylethyl)-1H-pyrazol-5-yl]-2-thienyl}benzaldehyde |
| 952 | 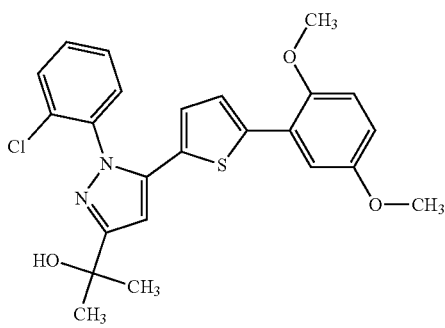 [SMILES: COc1ccc(OC)c(-c2ccc(-c3cc(C(C)(C)O)nn3-c3ccccc3Cl)s2)c1] | 2-[5-{5-[2,5-bis(methyloxy)phenyl]-2-thienyl}-1-(2-chlorophenyl)-1H-pyrazol-3-yl]propan-2-ol |
| 953 | 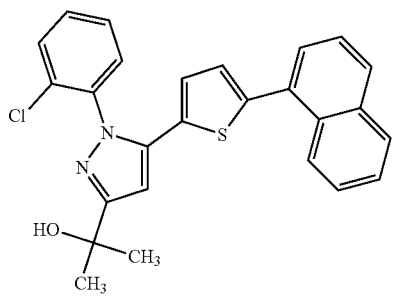 [SMILES: CC(C)(O)c1cc(-c2ccc(-c3cccc4ccccc34)s2)n(-c2ccccc2Cl)n1] | 2-[1-(2-chlorophenyl)-5-(5-naphthalen-1-yl-2-thienyl)-1H-pyrazol-3-yl]propan-2-ol |
| 954 | 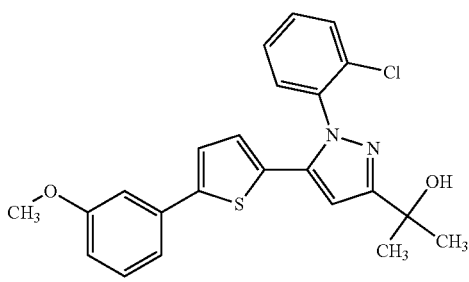 [SMILES: COc1cccc(-c2ccc(-c3cc(C(C)(C)O)nn3-c3ccccc3Cl)s2)c1] | 2-[1-(2-chlorophenyl)-5-{5-[3-(methyloxy)phenyl]-2-thienyl}-1H-pyrazol-3-yl]propan-2-ol |
| 955 | 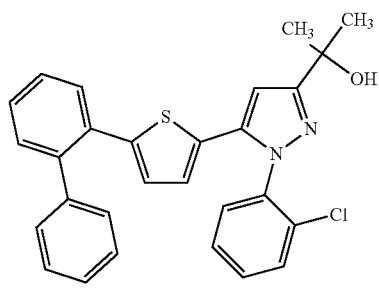 [SMILES: CC(C)(O)c1cc(-c2ccc(-c3ccccc3-c3ccccc3)s2)n(-c2ccccc2Cl)n1] | 2-[5-(5-biphenyl-2-yl-2-thienyl)-1-(2-chlorophenyl)-1H-pyrazol-3-yl]propan-2-ol |

TABLE 1-continued
| 956 | 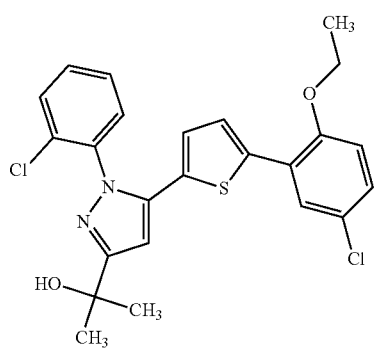 [SMILES: CCOc1ccc(Cl)cc1-c1ccc(-c2cc(C(C)(C)O)nn2-c2ccccc2Cl)s1] | 2-[5-{5-[5-chloro-2-(ethyloxy)phenyl]-2-thienyl}-1-(2-chlorophenyl)-1H-pyrazol-3-yl]propan-2-ol |
| --- | --- | --- |
| 957 | 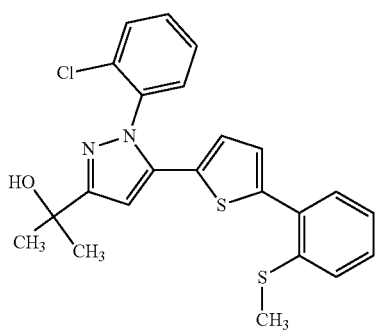 [SMILES: CSc1ccccc1-c1ccc(-c2cc(C(C)(C)O)nn2-c2ccccc2Cl)s1] | 2-[1-(2-chlorophenyl)-5-{5-[2-(ethylthio)phenyl]-2-thienyl}-1H-pyrazol-3-yl]propan-2-ol |
| 958 | 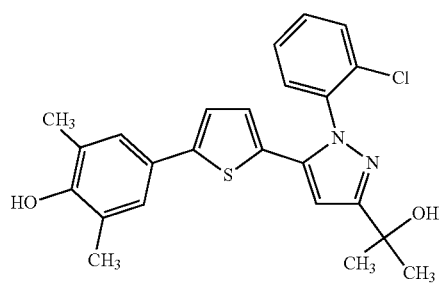 [SMILES: Cc1cc(-c2ccc(-c3cc(C(C)(C)O)nn3-c3ccccc3Cl)s2)cc(C)c1O] | 4-{5-[1-(2-chlorophenyl)-3-(1-hydroxy-1-methylethyl)-1H-pyrazol-5-yl]-2-thienyl}-2,6-dimethylphenol |
| 959 | 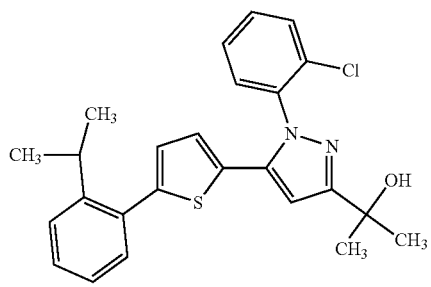 [SMILES: CC(C)c1ccccc1-c1ccc(-c2cc(C(C)(C)O)nn2-c2ccccc2Cl)s1] | 2-[1-(2-chlorophenyl)-5-{5-[2-(1-methylethyl)phenyl]-2-thienyl}-1H-pyrazol-3-yl]propan-2-ol |
| 960 | 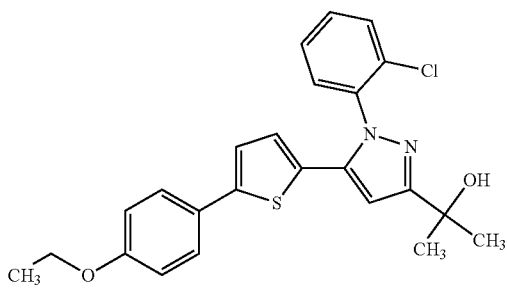 [SMILES: CCOc1ccc(-c2ccc(-c3cc(C(C)(C)O)nn3-c3ccccc3Cl)s2)cc1] | 2-[1-(2-chlorophenyl)-5-{5-[4-(ethyloxy)phenyl]-2-thienyl}-1H-pyrazol-3-yl]propan-2-ol |

TABLE 1-continued

| 961 | 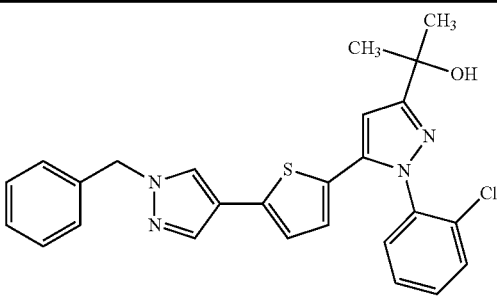 | 2-[1-(2-chlorophenyl)-5-{5-[1-(phenylmethyl)-1H-pyrazol-4-yl]-2-thienyl}-1H-pyrazol-3-yl]propan-2-ol |
| --- | --- | --- |
| 962 | 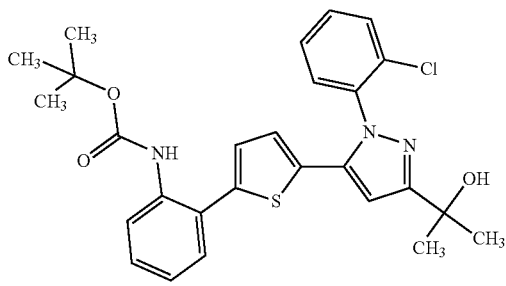 [SMILES: CC(C)(C)OC(=O)Nc1ccccc1-c1ccc(-c2cc(C(C)(C)O)nn2-c2ccccc2Cl)s1] | 1,1-dimethylethyl (2-{5-[1-(2-chlorophenyl)-3-(1-hydroxy-1-methylethyl)-1H-pyrazol-5-yl]-2-thienyl}phenyl)carbamate |
| 963 | 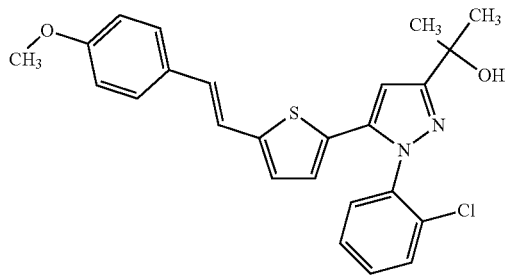 [SMILES: COc1ccc(/C=C/c2ccc(-c3cc(C(C)(C)O)nn3-c3ccccc3Cl)s2)cc1] | 2-[1-(2-chlorophenyl)-5-(5-{(E)-2-[4-(methyloxy)phenyl]ethenyl}-2-thienyl)-1H-pyrazol-3-yl]propan-2-ol |
| 964 | 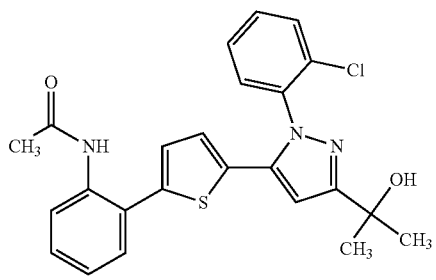 [SMILES: CC(=O)Nc1ccccc1-c1ccc(-c2cc(C(C)(C)O)nn2-c2ccccc2Cl)s1] | N-(2-{5-[1-(2-chlorophenyl)-3-(1-hydroxy-1-methylethyl)-1H-pyrazol-5-yl]-2-thienyl}phenyl)acetamide |
| 965 | 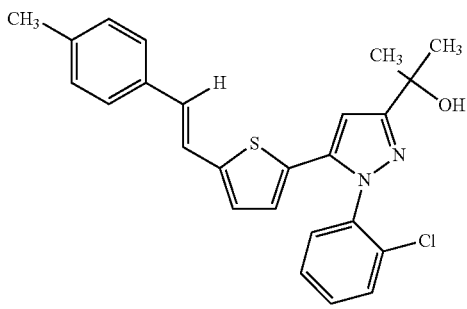 [SMILES: Cc1ccc(/C=C/c2ccc(-c3cc(C(C)(C)O)nn3-c3ccccc3Cl)s2)cc1] | 2-[1-(2-chlorophenyl)-5-{5-[(E)-2-(4-methylphenyl)ethenyl]-2-thienyl}-1H-pyrazol-3-yl]propan-2-ol |

TABLE 1-continued

| | | |
|---|---|---|
| 966 | 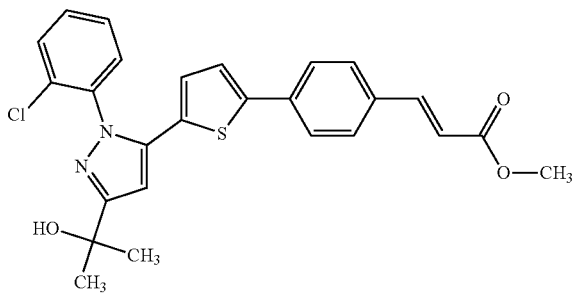 [SMILES: COC(=O)/C=C/c1ccc(-c2ccc(-c3cc(C(C)(C)O)nn3-c3ccccc3Cl)s2)cc1] | methyl (2E)-3-(4-{5-[1-(2-chlorophenyl)-3-(1-hydroxy-1-methylethyl)-1H-pyrazol-5-yl]-2-thienyl}phenyl)prop-2-enoate |
| 967 | 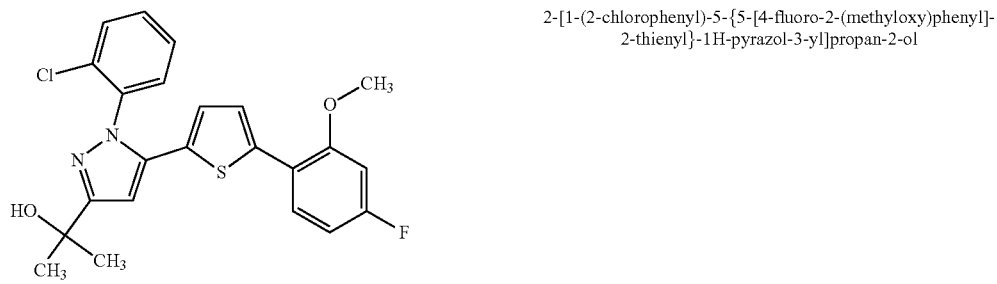 | 2-[1-(2-chlorophenyl)-5-{5-[4-fluoro-2-(methyloxy)phenyl]-2-thienyl}-1H-pyrazol-3-yl]propan-2-ol |
| 968 | 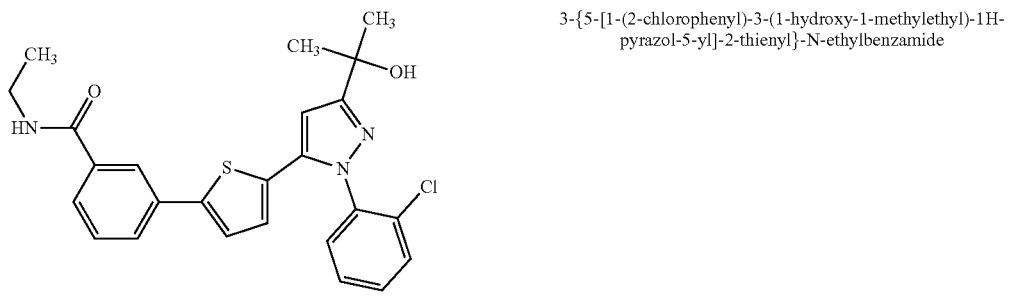 | 3-{5-[1-(2-chlorophenyl)-3-(1-hydroxy-1-methylethyl)-1H-pyrazol-5-yl]-2-thienyl}-N-ethylbenzamide |
| 969 | 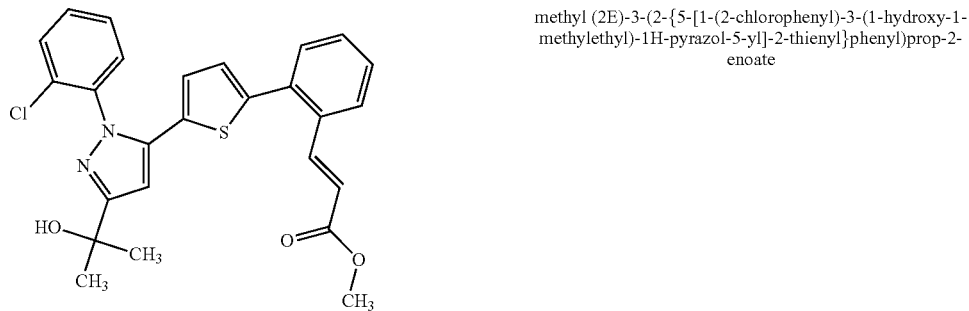 | methyl (2E)-3-(2-{5-[1-(2-chlorophenyl)-3-(1-hydroxy-1-methylethyl)-1H-pyrazol-5-yl]-2-thienyl}phenyl)prop-2-enoate |
| 970 | 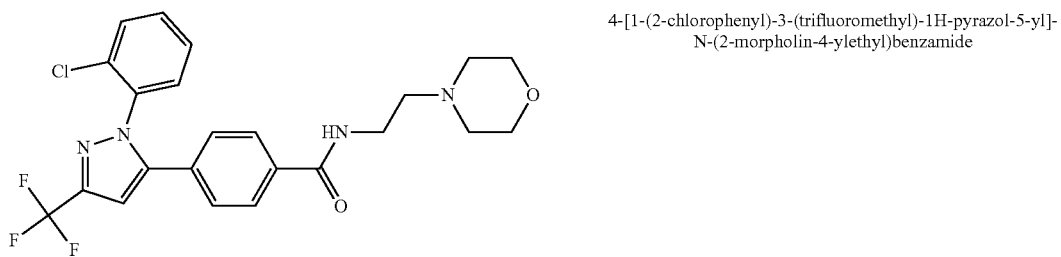 | 4-[1-(2-chlorophenyl)-3-(trifluoromethyl)-1H-pyrazol-5-yl]-N-(2-morpholin-4-ylethyl)benzamide |

TABLE 1-continued

| 971 | 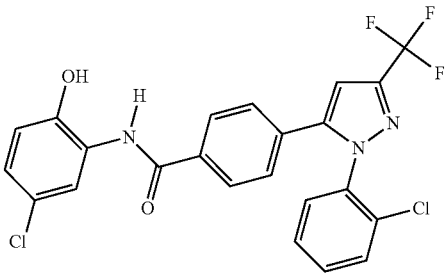 [SMILES: O=C(Nc1cc(Cl)ccc1O)c1ccc(-c2cc(C(F)(F)F)nn2-c2ccccc2Cl)cc1] | N-(5-chloro-2-hydroxyphenyl)-4-[1-(2-chlorophenyl)-3-(trifluoromethyl)-1H-pyrazol-5-yl]benzamide |
| 972 | 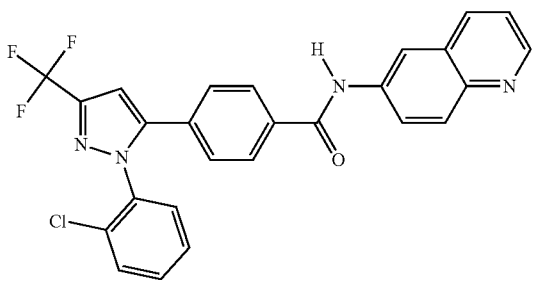 [SMILES: O=C(Nc1ccc2ncccc2c1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-quinolin-6-ylbenzamide |
| 973 | 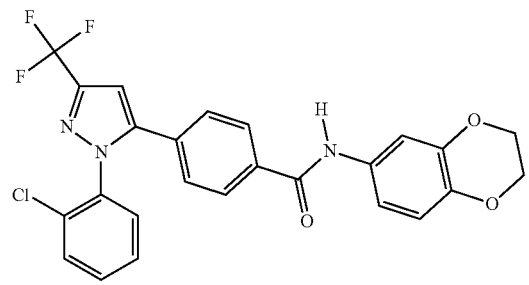 [SMILES: O=C(Nc1ccc2c(c1)OCCO2)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,3-dihydro-1,4-benzodioxin-6-yl)benzamide |
| 974 | 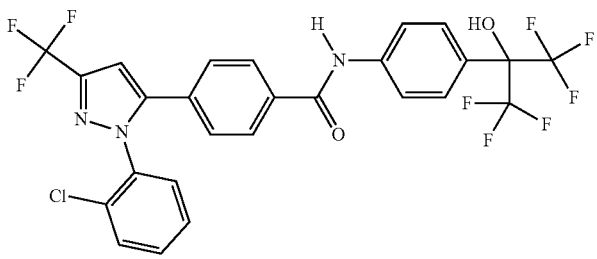 [SMILES: O=C(Nc1ccc(C(O)(C(F)(F)F)C(F)(F)F)cc1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{4-[2,2,2-trifluoro-1-hydroxy-1-(trifluoromethyl)ethyl]phenyl}benzamide |
| 975 | 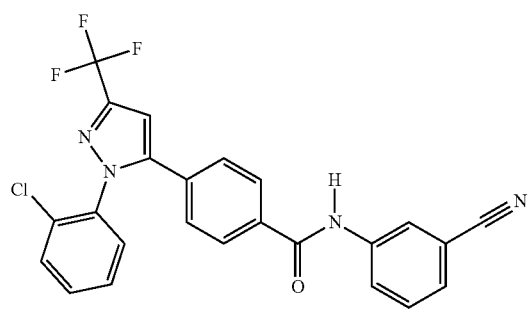 [SMILES: N#Cc1cccc(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-(3-cyanophenyl)benzamide |

| | | |
|---|---|---|
| 976 | 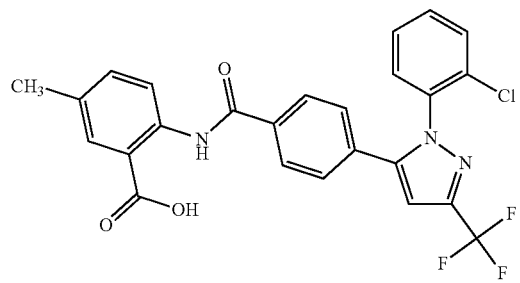 [SMILES: Cc1ccc(NC(=O)c2ccc(-c3cc(C(F)(F)F)nn3-c3ccccc3Cl)cc2)c(C(=O)O)c1] | 2-[({4-[1-(2-chlorophenyl)-3-(trifluoromethyl)-1H-pyrazol-5-yl]phenyl}carbonyl)amino]-5-methylbenzoic acid |
| 977 | 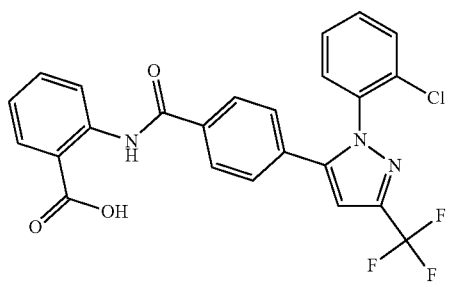 [SMILES: O=C(Nc1ccccc1C(=O)O)c1ccc(-c2cc(C(F)(F)F)nn2-c2ccccc2Cl)cc1] | 2-[({4-[1-(2-chlorophenyl)-3-(trifluoromethyl)-1H-pyrazol-5-yl]phenyl}carbonyl)amino]benzoic acid |
| 978 | 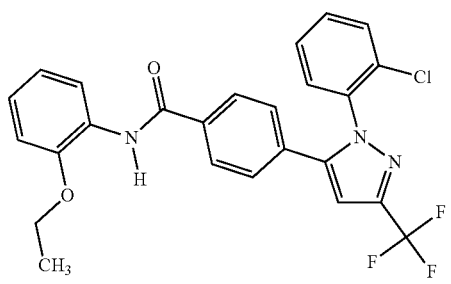 [SMILES: CCOc1ccccc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(ethyloxy)phenyl]benzamide |
| 979 | 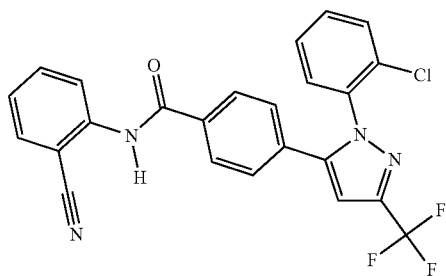 [SMILES: N#Cc1ccccc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2-cyanophenyl)benzamide |
| 980 | 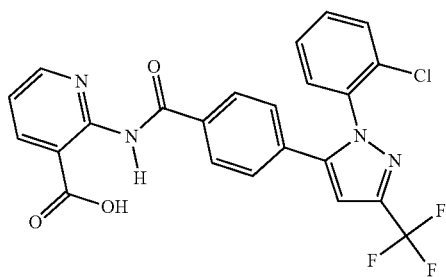 [SMILES: O=C(Nc1ncccc1C(=O)O)c1ccc(-c2cc(C(F)(F)F)nn2-c2ccccc2Cl)cc1] | 2-[({4-[1-(2-chlorophenyl)-3-(trifluoromethyl)-1H-pyrazol-5-yl]phenyl}carbonyl)amino]pyridine-3-carboxylic acid |

TABLE 1-continued

| | | |
|---|---|---|
| 981 | 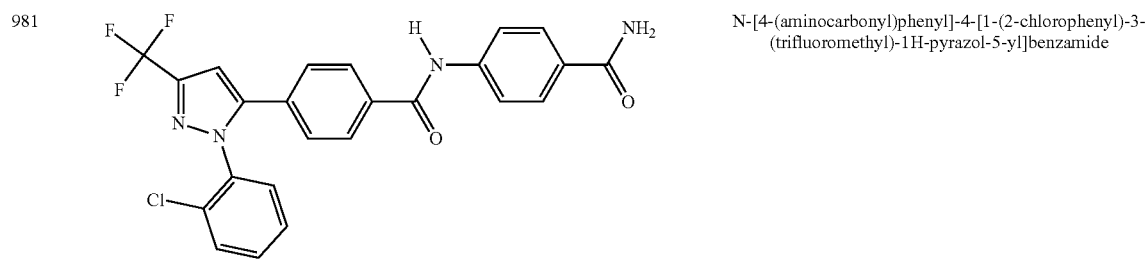 | N-[4-(aminocarbonyl)phenyl]-4-[1-(2-chlorophenyl)-3-(trifluoromethyl)-1H-pyrazol-5-yl]benzamide |
| 982 | 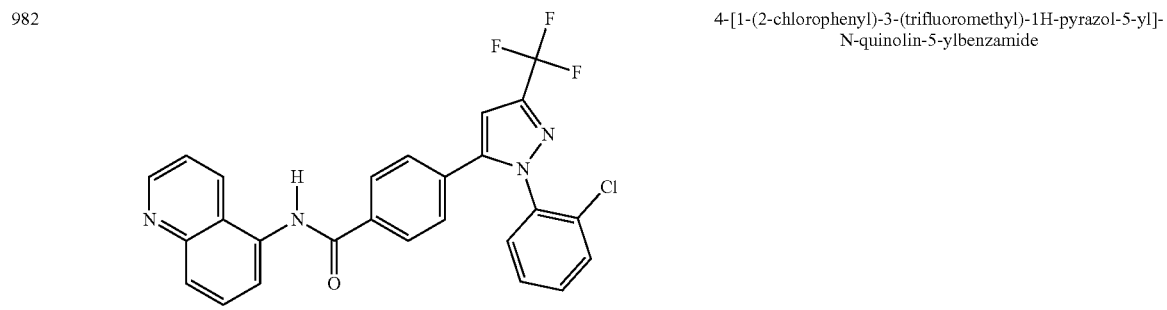 | 4-[1-(2-chlorophenyl)-3-(trifluoromethyl)-1H-pyrazol-5-yl]-N-quinolin-5-ylbenzamide |
| 983 | 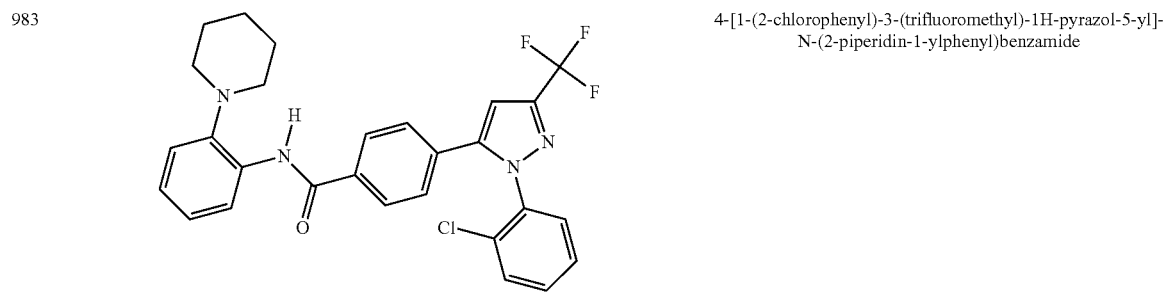 | 4-[1-(2-chlorophenyl)-3-(trifluoromethyl)-1H-pyrazol-5-yl]-N-(2-piperidin-1-ylphenyl)benzamide |
| 984 | 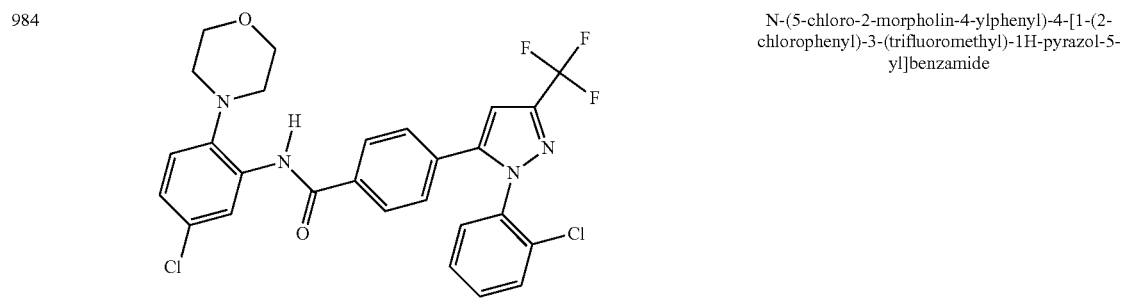 | N-(5-chloro-2-morpholin-4-ylphenyl)-4-[1-(2-chlorophenyl)-3-(trifluoromethyl)-1H-pyrazol-5-yl]benzamide |
| 985 | 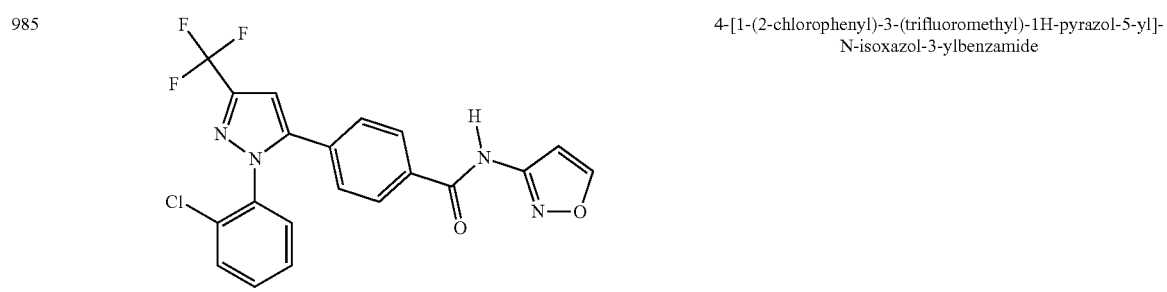 | 4-[1-(2-chlorophenyl)-3-(trifluoromethyl)-1H-pyrazol-5-yl]-N-isoxazol-3-ylbenzamide |

TABLE 1-continued

| 986 | 4-[1-(2-chlorophenyl)-3-(trifluoromethyl)-1H-pyrazol-5-yl]-N-[5-(1,1-dimethylethyl)-1,3,4-thiadiazol-2-yl]benzamide |
| 987 | 2-[({4-[1-(2-chlorophenyl)-3-(trifluoromethyl)-1H-pyrazol-5-yl]phenyl}carbonyl)amino]-4-methylbenzoic acid |
| 988 | 4-[1-(2-chlorophenyl)-3-(trifluoromethyl)-1H-pyrazol-5-yl]-N-1H-indazol-5-ylbenzamide |
| 989 | 4-[1-(2-chlorophenyl)-3-(trifluoromethyl)-1H-pyrazol-5-yl]-N-{4-[(1-methylethyl)oxy]phenyl}benzamide |
| 990 | 4-[1-(2-chlorophenyl)-3-(trifluoromethyl)-1H-pyrazol-5-yl]-N-(4-methyl-1,3-thiazol-2-yl)benzamide |

TABLE 1-continued

| | | |
|---|---|---|
| 991 | | N-(2-chloro-3-hydroxy-4-methylphenyl)-4-[1-(2-chlorophenyl)-3-(trifluoromethyl)-1H-pyrazol-5-yl]benzamide |
| 992 | | {4-[({4-[1-(2-chlorophenyl)-3-(trifluoromethyl)-1H-pyrazol-5-yl]phenyl}carbonyl)amino]phenyl}acetic acid |
| 993 | | 4-[1-(2-chlorophenyl)-3-(trifluoromethyl)-1H-pyrazol-5-yl]-N-(furan-2-ylmethyl)-N-methylbenzamide |
| 994 | | 4-({4-[1-(2-chlorophenyl)-3-(trifluoromethyl)-1H-pyrazol-5-yl]phenyl}carbonyl)-2,6-dimethylmorpholine |
| 995 | | 1-({4-[1-(2-chlorophenyl)-3-(trifluoromethyl)-1H-pyrazol-5-yl]phenyl}carbonyl)-4-(ethylsulfonyl)piperazine |

TABLE 1-continued

| 996 | 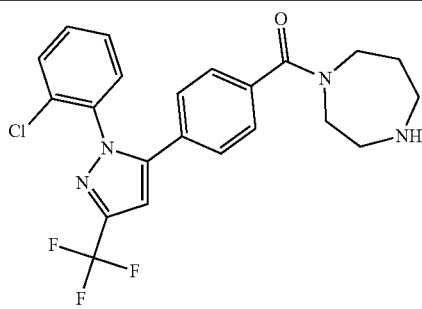 | 1-({4-[1-(2-chlorophenyl)-3-(trifluoromethyl)-1H-pyrazol-5-yl]phenyl}carbonyl)-1,4-diazepane |
| 997 | 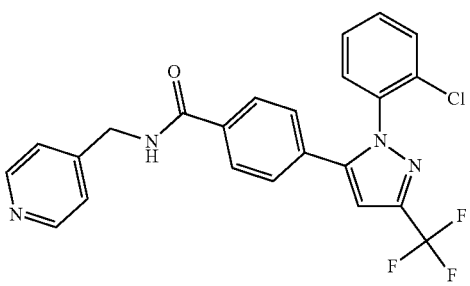 [SMILES: O=C(NCc1ccncc1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-methyl-N-(pyridin-4-ylmethyl)benzamide |
| 998 | 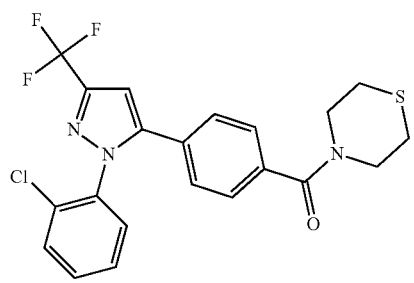 [SMILES: O=C(c1ccc(-c2cc(C(F)(F)F)nn2-c2ccccc2Cl)cc1)N1CCSCC1] | 4-({4-[1-(2-chlorophenyl)-3-(trifluoromethyl)-1H-pyrazol-5-yl]phenyl}carbonyl)thiomorpholine |
| 999 | 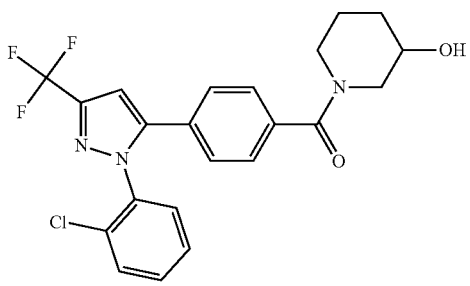 [SMILES: O=C(c1ccc(-c2cc(C(F)(F)F)nn2-c2ccccc2Cl)cc1)N1CCCC(O)C1] | 1-({4-[1-(2-chlorophenyl)-3-(trifluoromethyl)-1H-pyrazol-5-yl]phenyl}carbonyl)piperidin-3-ol |
| 1000 | 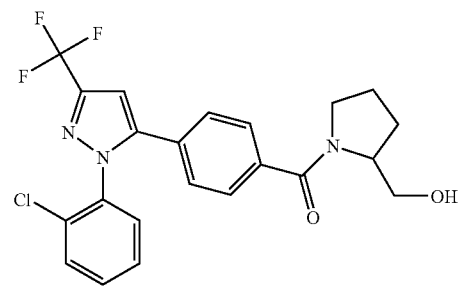 [SMILES: O=C(c1ccc(-c2cc(C(F)(F)F)nn2-c2ccccc2Cl)cc1)N1CCCC1CO] | [1-({4-[1-(2-chlorophenyl)-3-(trifluoromethyl)-1H-pyrazol-5-yl]phenyl}carbonyl)pyrrolidin-2-yl]methanol |

TABLE 1-continued

| | | |
|---|---|---|
| 1001 | 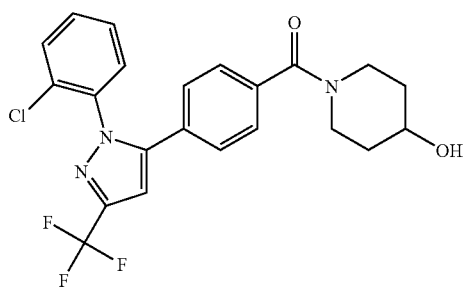 [SMILES: O=C(c1ccc(-c2cc(C(F)(F)F)nn2-c2ccccc2Cl)cc1)N1CCC(O)CC1] | 1-({4-[1-(2-chlorophenyl)-3-(trifluoromethyl)-1H-pyrazol-5-yl]phenyl}carbonyl)piperidin-4-ol |
| 1002 | 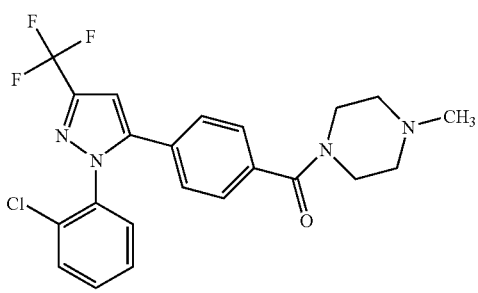 [SMILES: CN1CCN(C(=O)c2ccc(-c3cc(C(F)(F)F)nn3-c3ccccc3Cl)cc2)CC1] | 1-({4-[1-(2-chlorophenyl)-3-(trifluoromethyl)-1H-pyrazol-5-yl]phenyl}carbonyl)-4-methyl-1,4-diazepane |
| 1003 | 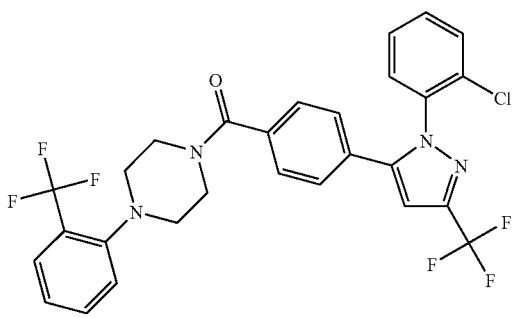 [SMILES: O=C(c1ccc(-c2cc(C(F)(F)F)nn2-c2ccccc2Cl)cc1)N1CCN(c2ccccc2C(F)(F)F)CC1] | 1-({4-[1-(2-chlorophenyl)-3-(trifluoromethyl)-1H-pyrazol-5-yl]phenyl}carbonyl)-4-[2-(trifluoromethyl)phenyl]piperazine |
| 1004 | 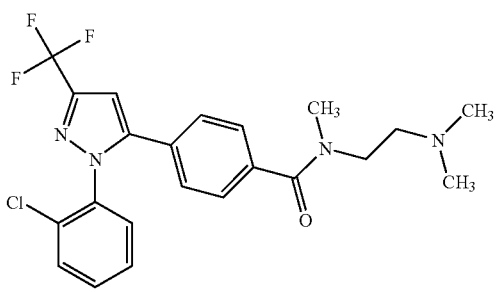 [SMILES: CN(C)CCN(C)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(dimethylamino)ethyl]-N-methylbenzamide |
| 1005 | 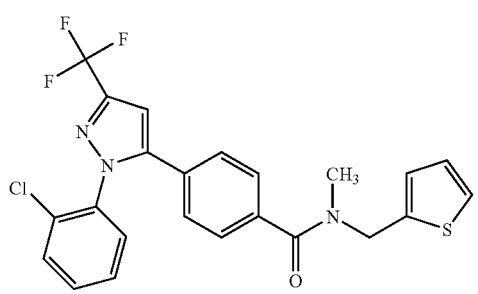 [SMILES: CN(Cc1cccs1)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-methyl-N-(2-thienylmethyl)benzamide |

TABLE 1-continued

| | | |
|---|---|---|
| 1006 | | 4-[1-(2-chlorophenyl)-3-(trifluoromethyl)-1H-pyrazol-5-yl]-N-(4-piperidin-1-ylphenyl)benzamide |
| 1007 | | 1-({4-[1-(2-chlorophenyl)-3-(trifluoromethyl)-1H-pyrazol-5-yl]phenyl}carbonyl)piperidin-4-carboxylic acid |
| 1008 | | 4-({4-[1-(2-chlorophenyl)-3-(trifluoromethyl)-1H-pyrazol-5-yl]phenyl}carbonyl)morpholine |
| 1009 | | 4-[1-(2-chlorophenyl)-3-(trifluoromethyl)-1H-pyrazol-5-yl]-N-1,3,4-thiadiazol-2-ylbenzamide |
| 1010 | | 4-[1-(2-chlorophenyl)-3-(trifluoromethyl)-1H-pyrazol-5-yl]-N-(4-hydroxy-3-methylphenyl)benzamide |

TABLE 1-continued

| 1011 | 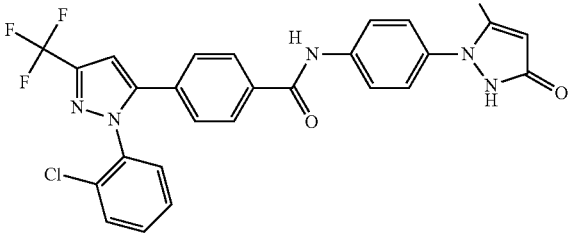 | 4-[1-(2-chlorophenyl)-3-(trifluoromethyl)-1H-pyrazol-5-yl]-N-[4-(5-methyl-3-oxo-2,3-dihydro-1H-pyrazol-1-yl)phenyl]benzamide |
| 1012 | 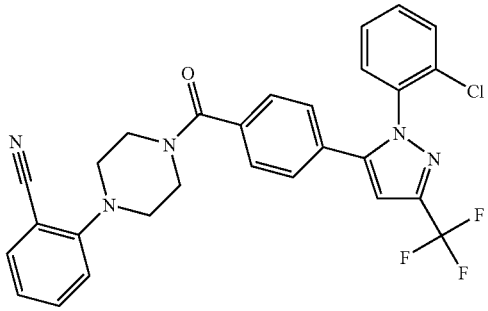 [SMILES: N#Cc1ccccc1N1CCN(C(=O)c2ccc(-c3cc(C(F)(F)F)nn3-c3ccccc3Cl)cc2)CC1] | 2-[4-({4-[1-(2-chlorophenyl)-3-(trifluoromethyl)-1H-pyrazol-5-yl]phenyl}carbonyl)piperazin-1-yl]benzonitrile |
| 1013 | 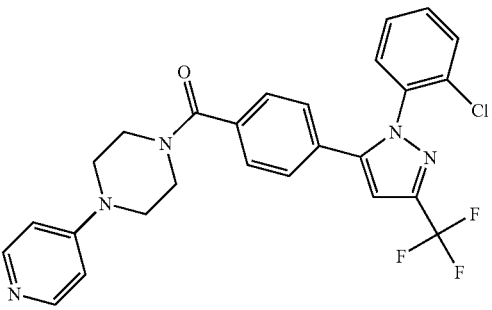 [SMILES: O=C(c1ccc(-c2cc(C(F)(F)F)nn2-c2ccccc2Cl)cc1)N1CCN(c2ccncc2)CC1] | 1-({4-[1-(2-chlorophenyl)-3-(trifluoromethyl)-1H-pyrazol-5-yl]phenyl}carbonyl)-4-pyridin-4-ylpiperazine |
| 1014 | 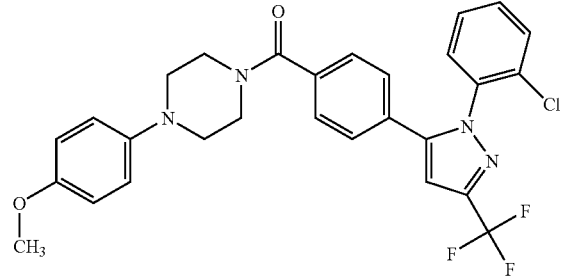 [SMILES: COc1ccc(N2CCN(C(=O)c3ccc(-c4cc(C(F)(F)F)nn4-c4ccccc4Cl)cc3)CC2)cc1] | 1-({4-[1-(2-chlorophenyl)-3-(trifluoromethyl)-1H-pyrazol-5-yl]phenyl}carbonyl)-4-[4-(methyloxy)phenyl]piperazine |
| 1015 | 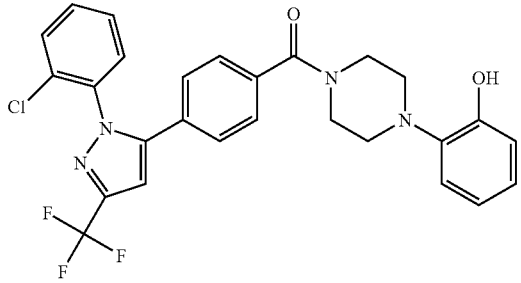 [SMILES: O=C(c1ccc(-c2cc(C(F)(F)F)nn2-c2ccccc2Cl)cc1)N1CCN(c2ccccc2O)CC1] | 2-[4-({4-[1-(2-chlorophenyl)-3-(trifluoromethyl)-1H-pyrazol-5-yl]phenyl}carbonyl)piperazin-1-yl]phenol |

TABLE 1-continued

| | | |
|---|---|---|
| 1016 | 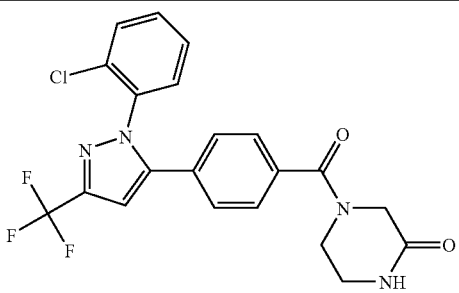 | 4-({4-[1-(2-chlorophenyl)-3-(trifluoromethyl)-1H-pyrazol-3-yl]phenyl}carbonyl)piperazin-2-one |
| 1017 | 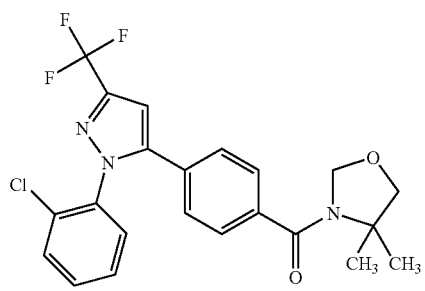 [SMILES: CC1(C)COCN1C(=O)c1ccc(-c2cc(C(F)(F)F)nn2-c2ccccc2Cl)cc1] | 3-({4-[1-(2-chlorophenyl)-3-(trifluoromethyl)-1H-pyrazol-5-yl]phenyl}carbonyl)-4,4-dimethyl-1,3-oxazolidine |
| 1018 | 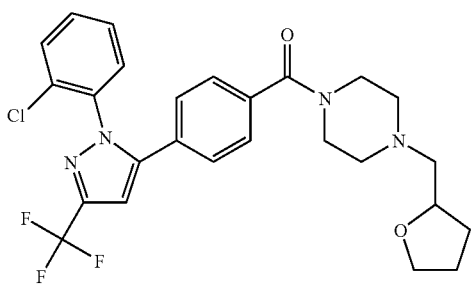 [SMILES: O=C(c1ccc(-c2cc(C(F)(F)F)nn2-c2ccccc2Cl)cc1)N1CCN(CC2CCCO2)CC1] | 1-({4-[1-(2-chlorophenyl)-3-(trifluoromethyl)-1H-pyrazol-5-yl]phenyl}carbonyl)-4-(tetrahydrofuran-2-ylmethyl)piperazine |
| 1019 | 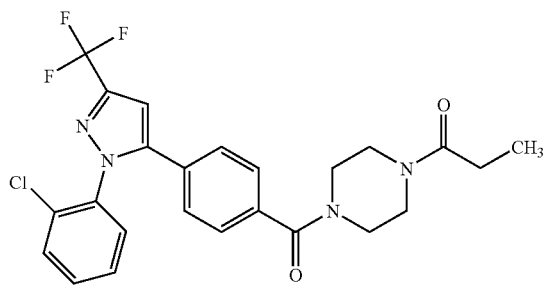 [SMILES: CCC(=O)N1CCN(C(=O)c2ccc(-c3cc(C(F)(F)F)nn3-c3ccccc3Cl)cc2)CC1] | 1-({4-[1-(2-chlorophenyl)-3-(trifluoromethyl)-1H-pyrazol-5-yl]phenyl}carbonyl)-4-propanoylpiperazine |
| 1020 | 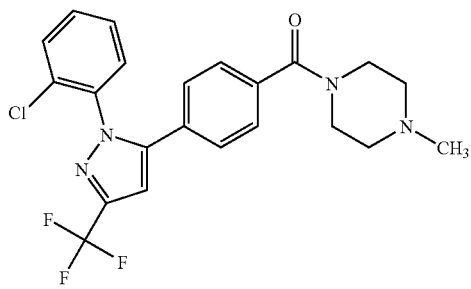 [SMILES: CN1CCN(C(=O)c2ccc(-c3cc(C(F)(F)F)nn3-c3ccccc3Cl)cc2)CC1] | 1-({4-[1-(2-chlorophenyl)-3-(trifluoromethyl)-1H-pyrazol-5-yl]phenyl}carbonyl)-4-methylpiperazine |

TABLE 1-continued

| | |
|---|---|
| 1021 | 1,1-dimethylethyl [1-({4-[1-(2-chlorophenyl)-3-(trifluoromethyl)-1H-pyrazol-5-yl]phenyl}carbonyl)pyrrolidin-3-yl]carbamate |
| 1022 | 1-({4-[1-(2-chlorophenyl)-3-(trifluoromethyl)-1H-pyrazol-5-yl]phenyl}carbonyl)azetidine-3-carboxylic acid |
| 1023 | 4-[4-({4-[1-(2-chlorophenyl)-3-(trifluoromethyl)-1H-pyrazol-5-yl]phenyl}carbonyl)piperazin-1-yl]phenol |
| 1024 | 4-[1-(2-chlorophenyl)-3-(trifluoromethyl)-1H-pyrazol-5-yl]-N-[2-(methyloxy)ethyl]-N-(1-methylpiperidin-4-yl)benzamide |
| 1025 | 4-[1-(2-chlorophenyl)-3-(trifluoromethyl)-1H-pyrazol-5-yl]-N-methyl-N-(1-methylpyrrolidin-3-yl)benzamide |

TABLE 1-continued

| | | |
|---|---|---|
| 1026 | 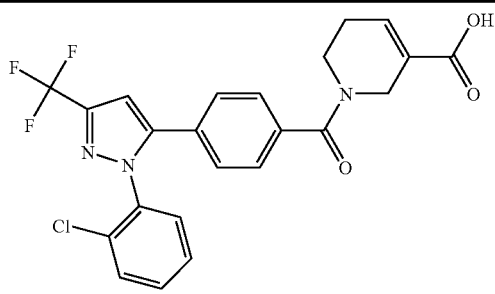 | 1-({4-[1-(2-chlorophenyl)-3-(trifluoromethyl)-1H-pyrazol-5-yl]phenyl}carbonyl)-1,2,5,6-tetrahydropyridine-3-carboxylic acid |
| 1027 | 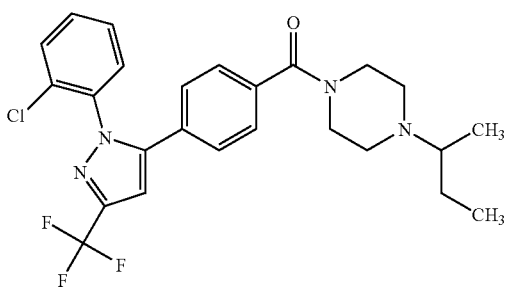 [SMILES: CCC(C)N1CCN(C(=O)c2ccc(-c3cc(C(F)(F)F)nn3-c3ccccc3Cl)cc2)CC1] | 1-({4-[1-(2-chlorophenyl)-3-(trifluoromethyl)-1H-pyrazol-5-yl]phenyl}carbonyl)-4-(1-methylpropyl)piperazine |
| 1028 | 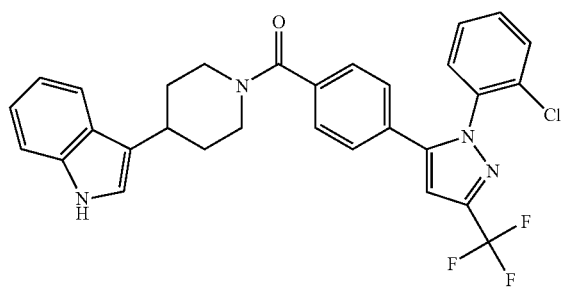 [SMILES: O=C(c1ccc(-c2cc(C(F)(F)F)nn2-c2ccccc2Cl)cc1)N1CCC(c2c[nH]c3ccccc23)CC1] | 3-[1-({4-[1-(2-chlorophenyl)-3-(trifluoromethyl)-1H-pyrazol-5-yl]phenyl}carbonyl)piperidin-4-yl]-1H-indole |
| 1029 | 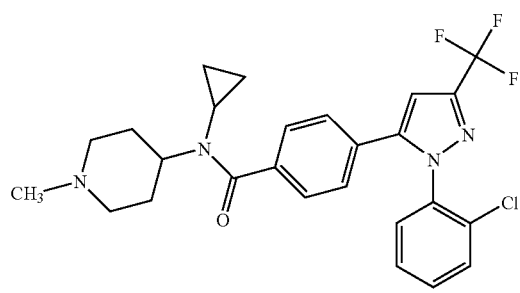 [SMILES: CN1CCC(N(C(=O)c2ccc(-c3cc(C(F)(F)F)nn3-c3ccccc3Cl)cc2)C2CC2)CC1] | 4-[1-(2-chlorophenyl)-3-(trifluoromethyl)-1H-pyrazol-5-yl]-N-cyclopropyl-N-(1-methylpiperidin-4-yl)benzamide |
| 1030 | 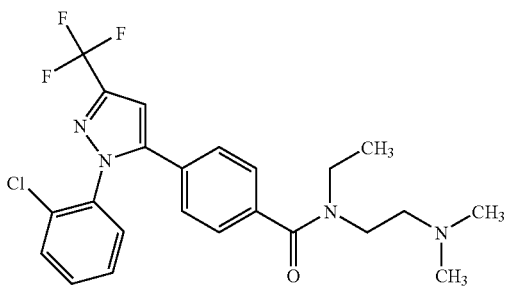 [SMILES: CCN(CCN(C)C)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(dimethylamino)ethyl]-N-ethylbenzamide |

TABLE 1-continued

| 1031 | 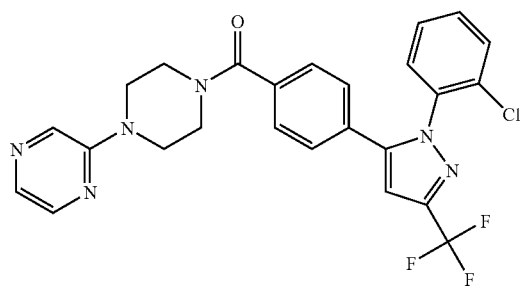 [SMILES: O=C(c1ccc(-c2cc(C(F)(F)F)nn2-c2ccccc2Cl)cc1)N1CCN(c2cnccn2)CC1] | 2-[4-({4-[1-(2-chlorophenyl)-3-(trifluoromethyl)-1H-pyrazol-5-yl]phenyl}carbonyl)piperazin-1-yl]pyrazine |
| 1032 | 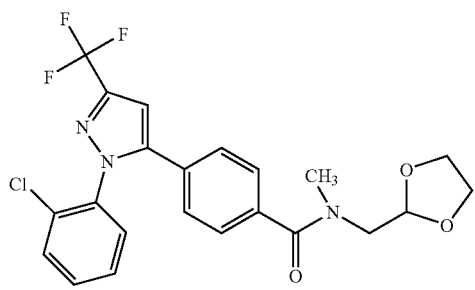 [SMILES: CN(CC1OCCO1)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(1,3-dioxolan-2-ylmethyl)-N-methylbenzamide |
| 1033 | 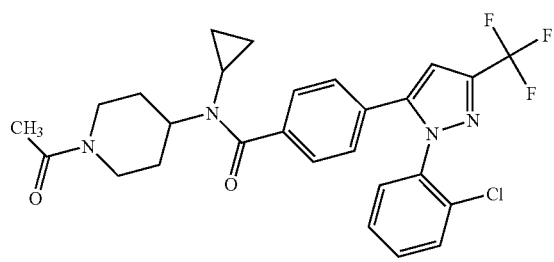 [SMILES: CC(=O)N1CCC(N(C(=O)c2ccc(-c3cc(C(F)(F)F)nn3-c3ccccc3Cl)cc2)C2CC2)CC1] | N-(1-acetylpiperidin-4-yl)-4-[1-(2-chlorophenyl)-3-(trifluoromethyl)-1H-pyrazol-5-yl]-N-cyclopropylbenzamide |
| 1034 | 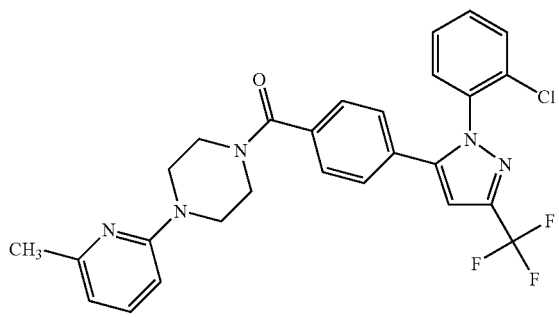 [SMILES: Cc1cccc(N2CCN(C(=O)c3ccc(-c4cc(C(F)(F)F)nn4-c4ccccc4Cl)cc3)CC2)n1] | 1-({4-[1-(2-chlorophenyl)-3-(trifluoromethyl)-1H-pyrazol-5-yl]phenyl}carbonyl)-4-(6-methylpyridin-2-yl)piperazine |
| 1035 | 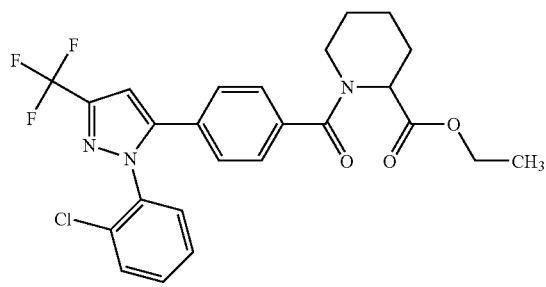 [SMILES: CCOC(=O)C1CCCCN1C(=O)c1ccc(-c2cc(C(F)(F)F)nn2-c2ccccc2Cl)cc1] | ethyl 1-({4-[1-(2-chlorophenyl)-3-(trifluoromethyl)-1H-pyrazol-5-yl]phenyl}carbonyl)piperidin-2-carboxylate |

TABLE 1-continued

| 1036 | 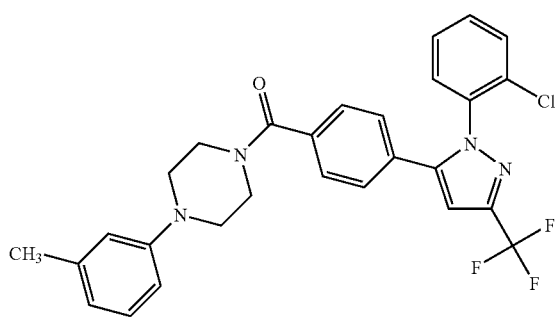 | 1-({4-[1-(2-chlorophenyl)-3-(trifluoromethyl)-1H-pyrazol-5-yl]phenyl}carbonyl)-4-(3-methylphenyl)piperazine |
| 1037 | 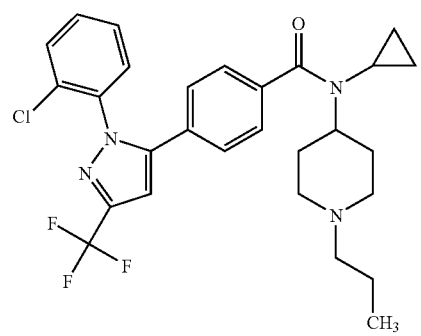 [SMILES: CCCN1CCC(N(C(=O)c2ccc(-c3cc(C(F)(F)F)nn3-c3ccccc3Cl)cc2)C2CC2)CC1] | 4-[1-(2-chlorophenyl)-3-(trifluoromethyl)-1H-pyrazol-5-yl]-N-cyclopropyl-N-(1-propylpiperidin-4-yl)benzamide |
| 1038 | 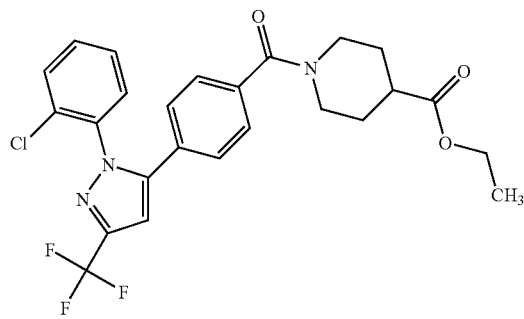 [SMILES: CCOC(=O)C1CCN(C(=O)c2ccc(-c3cc(C(F)(F)F)nn3-c3ccccc3Cl)cc2)CC1] | ethyl 1-({4-[1-(2-chlorophenyl)-3-(trifluoromethyl)-1H-pyrazol-5-yl]phenyl}carbonyl)piperidin-4-carboxylate |
| 1039 | 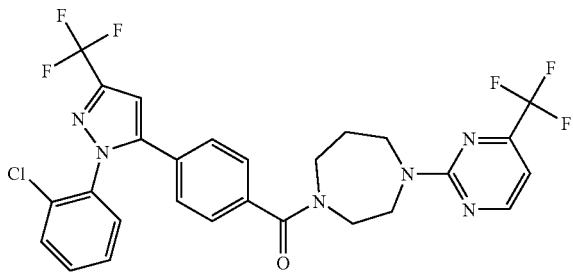 [SMILES: O=C(c1ccc(-c2cc(C(F)(F)F)nn2-c2ccccc2Cl)cc1)N1CCCN(c2nccc(C(F)(F)F)n2)CC1] | 1-({4-[1-(2-chlorophenyl)-3-(trifluoromethyl)-1H-pyrazol-5-yl]phenyl}carbonyl)-4-[4-(trifluoromethyl)pyrimidin-2-yl]-1,4-diazepane |
| 1040 | 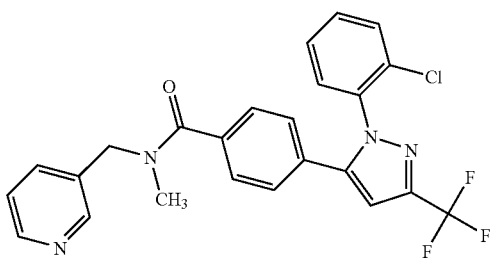 [SMILES: CN(Cc1cccnc1)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-methyl-N-(pyridin-3-ylmethyl)benzamide |

TABLE 1-continued

| | | |
|---|---|---|
| 1041 | | N-butyl-4-[1-(2-chlorophenyl)-3-(trifluoromethyl)-1H-pyrazol-5-yl]-N-(2-thienylmethyl)benzamide |
| 1042 | | 1-({4-[1-(2-chlorophenyl)-3-(trifluoromethyl)-1H-pyrazol-5-yl]phenyl}carbonyl)-4-ethylpiperazine |
| 1043 | | 1-({4-[1-(2-chlorophenyl)-3-(trifluoromethyl)-1H-pyrazol-5-yl]phenyl}carbonyl)-4-[3-(methyloxy)phenyl]piperazine |
| 1044 | | 4-[1-(2-chlorophenyl)-3-(trifluoromethyl)-1H-pyrazol-5-yl]-N-methyl-N-(1-methylpiperidin-4-yl)benzamide |
| 1045 | | N-(2-amino-2-oxoethyl)-4-[1-(2-chlorophenyl)-3-(trifluoromethyl)-1H-pyrazol-5-yl]-N-methylbenzamide |

TABLE 1-continued

| 1046 | 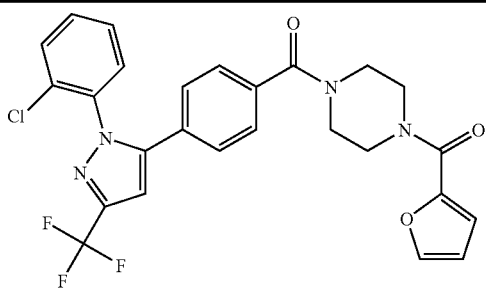 | 1-({4-[1-(2-chlorophenyl)-3-(trifluoromethyl)-1H-pyrazol-5-yl]phenyl}carbonyl)-4-(furan-2-ylcarbonyl)piperazine |
| 1047 | 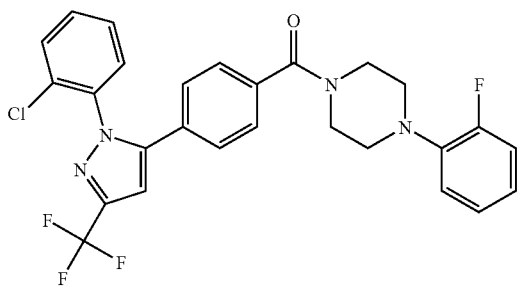 [SMILES: O=C(c1ccc(-c2cc(C(F)(F)F)nn2-c2ccccc2Cl)cc1)N1CCN(c2ccccc2F)CC1] | 1-({4-[1-(2-chlorophenyl)-3-(trifluoromethyl)-1H-pyrazol-5-yl]phenyl}carbonyl)-4-(2-fluorophenyl)piperazine |
| 1048 | 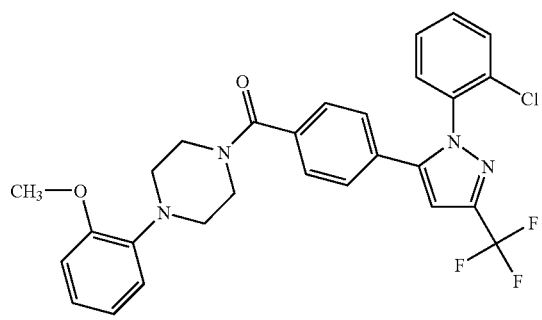 [SMILES: COc1ccccc1N1CCN(C(=O)c2ccc(-c3cc(C(F)(F)F)nn3-c3ccccc3Cl)cc2)CC1] | 1-({4-[1-(2-chlorophenyl)-3-(trifluoromethyl)-1H-pyrazol-5-yl]phenyl}carbonyl)-4-[2-(methyloxy)phenyl]piperazine |
| 1049 | 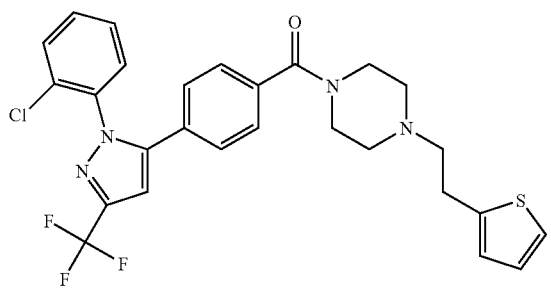 [SMILES: O=C(c1ccc(-c2cc(C(F)(F)F)nn2-c2ccccc2Cl)cc1)N1CCN(CCc2cccs2)CC1] | 1-({4-[1-(2-chlorophenyl)-3-(trifluoromethyl)-1H-pyrazol-5-yl]phenyl}carbonyl)-4-[2-(2-thienyl)ethyl]piperazine |
| 1050 | 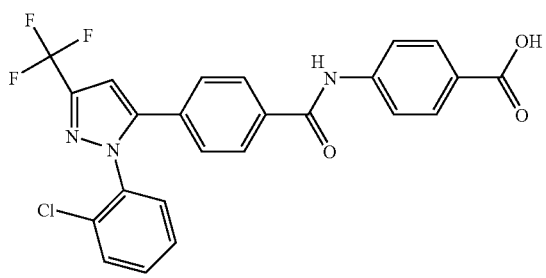 | 4-[({4-[1-(2-chlorophenyl)-3-(trifluoromethyl)-1H-pyrazol-5-yl]phenyl}carbonyl)amino]benzoic acid |

| | | |
|---|---|---|
| 1051 | 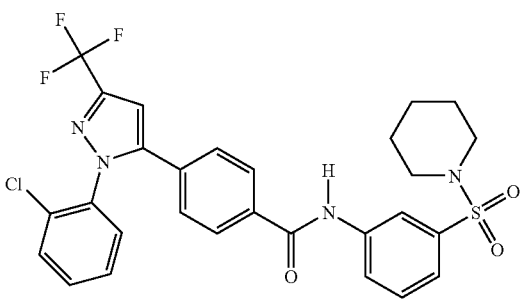 | 4-[1-(2-chlorophenyl)-3-(trifluoromethyl)-1H-pyrazol-5-yl]-N-[3-(piperidin-1-ylsulfonyl)phenyl]benzamide |
| 1052 | 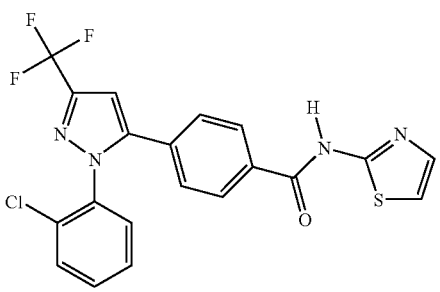 [SMILES: O=C(Nc1nccs1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-1,3-thiazol-2-ylbenzamide |
| 1053 | 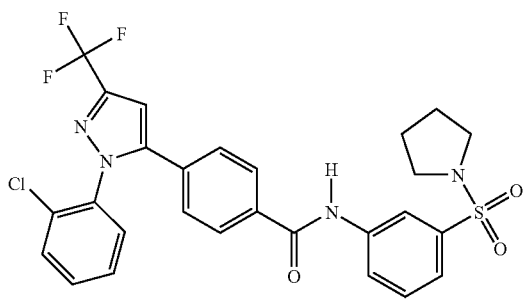 [SMILES: O=C(Nc1cccc(S(=O)(=O)N2CCCC2)c1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[3-(pyrrolidin-1-ylsulfonyl)phenyl]benzamide |
| 1054 | 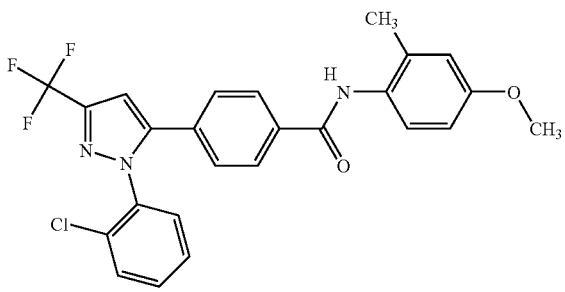 | 4-[1-(2-chlorophenyl)-3-(trifluoromethyl)-1H-pyrazol-5-yl]-N-[2-methyl-4-(methyloxy)phenyl]benzamide |
| 1055 | 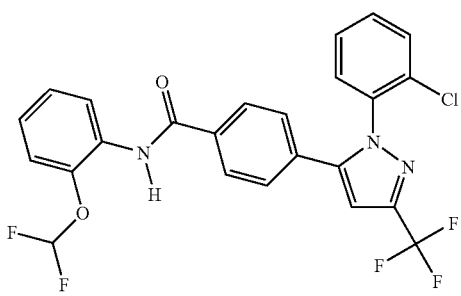 [SMILES: O=C(Nc1ccccc1OC(F)F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{2-[(difluoromethyl)oxy]phenyl}benzamide |

TABLE 1-continued

| | | |
|---|---|---|
| 1056 | | 4-[1-(2-chlorophenyl)-3-(trifluoromethyl)-1H-pyrazol-5-yl]-N-{4-[(difluoromethyl)oxy]phenyl}benzamide |
| 1057 | | 4-[1-(2-chlorophenyl)-3-(trifluoromethyl)-1H-pyrazol-5-yl]-N-(3-fluorophenyl)benzamide |
| 1058 | | 4-[1-(2-chlorophenyl)-3-(trifluoromethyl)-1H-pyrazol-5-yl]-N-[3-(morpholin-4-ylsulfonyl)phenyl]benzamide |
| 1059 | | 4-[1-(2-chlorophenyl)-3-(trifluoromethyl)-1H-pyrazol-5-yl]-N-[4-(trifluoromethyl)phenyl]benzamide |
| 1060 | | N-(3-chlorophenyl)-4-[1-(2-chlorophenyl)-3-(trifluoromethyl)-1H-pyrazol-5-yl]benzamide |

TABLE 1-continued

| | | |
|---|---|---|
| 1061 | | 4-[1-(2-chlorophenyl)-3-(trifluoromethyl)-1H-pyrazol-5-yl]-N-[6-(methylsulfonyl)pyridin-3-yl]benzamide |
| 1062 | | 4-[1-(2-chlorophenyl)-3-(trifluoromethyl)-1H-pyrazol-5-yl]-N-[2-(trifluoromethyl)phenyl]benzamide |
| 1063 | | 4-[1-(2-chlorophenyl)-3-(trifluoromethyl)-1H-pyrazol-5-yl]-N-[2-(methyloxy)phenyl]benzamide |
| 1064 | | 4-[1-(2-chlorophenyl)-3-(trifluoromethyl)-1H-pyrazol-5-yl]-N-[2-fluoro-5-(trifluoromethyl)phenyl]benzamide |
| 1065 | | N-(2-chlorophenyl)-4-[1-(2-chlorophenyl)-3-(trifluoromethyl)-1H-pyrazol-5-yl]benzamide |

TABLE 1-continued

| | | |
|---|---|---|
| 1066 | | 4-[1-(2-chlorophenyl)-3-(trifluoromethyl)-1H-pyrazol-5-yl]-N-[3-(methyloxy)phenyl]benzamide |
| 1067 | | 4-[1-(2-chlorophenyl)-3-(trifluoromethyl)-1H-pyrazol-5-yl]-N-[3-(trifluoromethyl)phenyl]benzamide |
| 1068 | | 4-[1-(2-chlorophenyl)-3-(trifluoromethyl)-1H-pyrazol-5-yl]-N-{2-[(trifluoromethyl)oxy]phenyl}benzamide |
| 1069 | | 4-[1-(2-chlorophenyl)-3-(trifluoromethyl)-1H-pyrazol-5-yl]-N-[4-(pyridin-4-ylcarbonyl)phenyl]benzamide |
| 1070 | | N-[3,5-bis(methyloxy)phenyl]-4-[1-(2-chlorophenyl)-3-(trifluoromethyl)-1H-pyrazol-5-yl]benzamide |

TABLE 1-continued

| | | |
|---|---|---|
| 1071 | | 4-[1-(2-chlorophenyl)-3-(trifluoromethyl)-1H-pyrazol-5-yl]-N-pyridin-3-ylbenzamide |
| 1072 | | N-(2-chloro-5-hydroxymethyl)-4-[1-(2-chlorophenyl)-3-(trifluoromethyl)-1H-pyrazol-5-yl]benzamide |
| 1073 | | 4-[1-(2-chlorophenyl)-3-(trifluoromethyl)-1H-pyrazol-5-yl]-N-pyridin-4-ylbenzamide |
| 1074 | | N-1,3-benzodioxol-5-yl-4-[1-(2-chlorophenyl)-3-(trifluoromethyl)-1H-pyrazol-5-yl]benzamide |
| 1075 | | 3-[({4-[1-(2-chlorophenyl)-3-(trifluoromethyl)-1H-pyrazol-5-yl]phenyl}carbonyl)amino]benzoic acid |

TABLE 1-continued

| | | |
|---|---|---|
| 1076 | 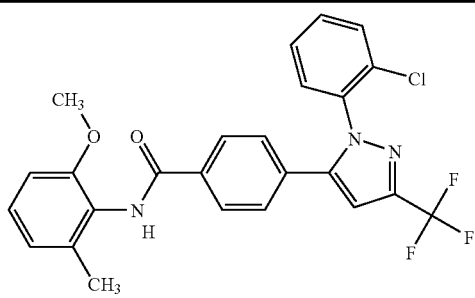 | 4-[1-(2-chlorophenyl)-3-(trifluoromethyl)-1H-pyrazol-5-yl]-N-[2-methyl-5-(methyloxy)phenyl]benzamide |
| 1077 | 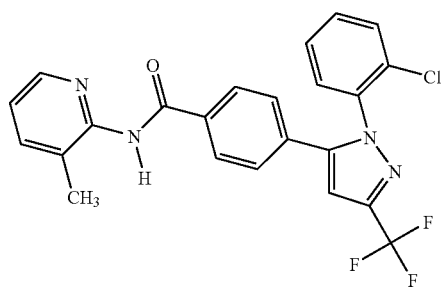 [SMILES: Cc1cccnc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-methylpyridin-2-yl)benzamide |
| 1078 | 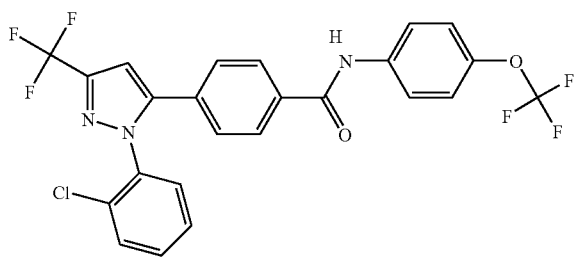 | 4-[1-(2-chlorophenyl)-3-(trifluoromethyl)-1H-pyrazol-5-yl]-N-{4-[(trifluoromethyl)oxy]phenyl}benzamide |
| 1079 | 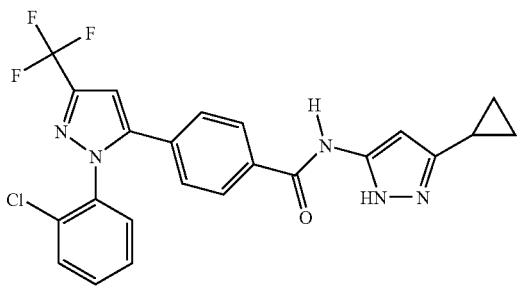 [SMILES: O=C(Nc1cc(C2CC2)n[nH]1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-cyclopropyl-1H-pyrazol-5-yl)benzamide |
| 1080 | 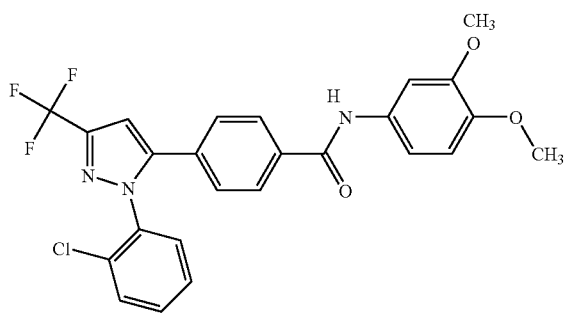 | N-[3,4-bis(methyloxy)phenyl]-4-[1-(2-chlorophenyl)-3-(trifluoromethyl)-1H-pyrazol-5-yl]benzamide |

TABLE 1-continued

| 1081 | 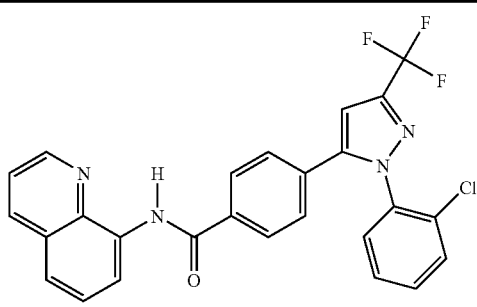 | 4-[1-(2-chlorophenyl)-3-(trifluoromethyl)-1H-pyrazol-5-yl]-N-quinolin-8-ylbenzamide |
| 1082 | 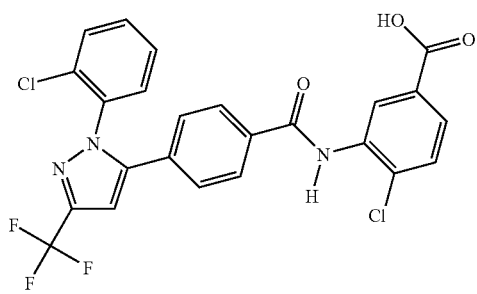 [SMILES: O=C(O)c1ccc(Cl)c(NC(=O)c2ccc(-c3cc(C(F)(F)F)nn3-c3ccccc3Cl)cc2)c1] | 4-chloro-3-[({4-[1-(2-chlorophenyl)-3-(trifluoromethyl)-1H-pyrazol-5-yl]phenyl}carbonyl)amino]benzoic acid |
| 1083 | 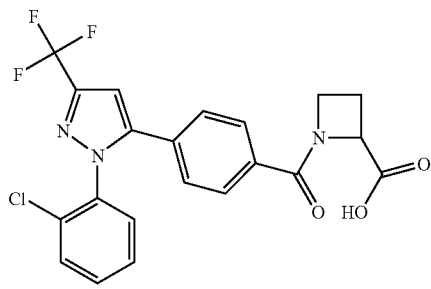 [SMILES: O=C(O)C1CCN1C(=O)c1ccc(-c2cc(C(F)(F)F)nn2-c2ccccc2Cl)cc1] | 1-({4-[1-(2-chlorophenyl)-3-(trifluoromethyl)-1H-pyrazol-5-yl]phenyl}carbonyl)azetidin-2-carboxylic acid |
| 1084 | 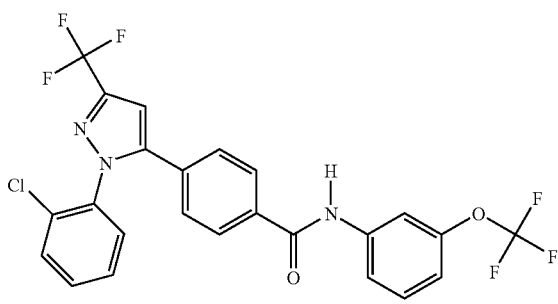 [SMILES: O=C(Nc1cccc(OC(F)(F)F)c1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{3-[(trifluoromethyl)oxy]phenyl}benzamide |
| 1085 | 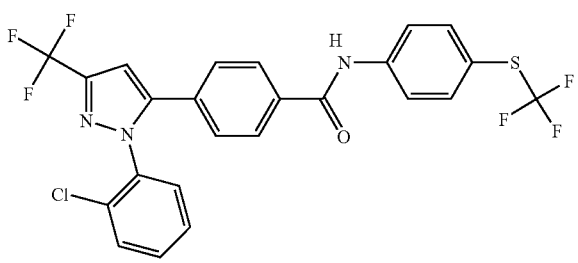 | 4-[1-(2-chlorophenyl)-3-(trifluoromethyl)-1H-pyrazol-5-yl]-N-{4-[(trifluoromethyl)thio]phenyl}benzamide |

TABLE 1-continued

1086 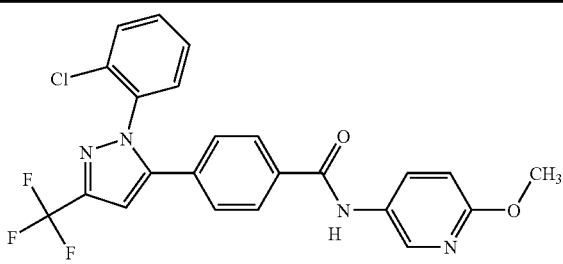 4-[1-(2-chlorophenyl)-3-(trifluoromethyl)-1H-pyrazol-5-yl]-
N-[6-(methyloxy)pyridin-3-yl]benzamide 1087 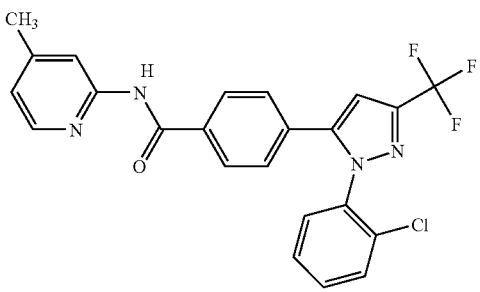 4-[1-(2-chlorophenyl)-3-(trifluoromethyl)-1H-pyrazol-5-yl]-
N-(4-methylpyridin-2-yl)benzamide 1088 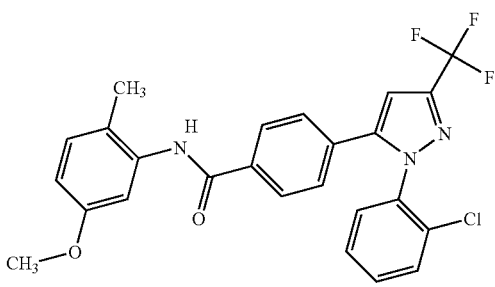 4-[1-(2-chlorophenyl)-3-(trifluoromethyl)-1H-pyrazol-5-yl]-
N-[2-methyl-5-(methyloxy)phenyl]benzamide 1089 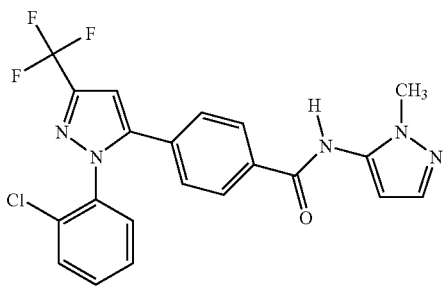 [SMILES: Cn1nccc1NC(=O)c1ccc(-c2cc(C(F)(F)F)nn2-c2ccccc2Cl)cc1] 4-[1-(2-chlorophenyl)-3-(trifluoromethyl)-1H-pyrazol-5-yl]-
N-(1-methyl-1H-pyrazol-5-yl)benzamide 1090 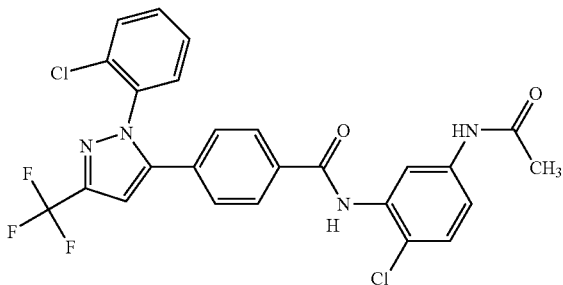 N-[5-(acetylamino)-2-chlorophenyl]-4-[1-(2-chlorophenyl)-
3-(trifluoromethyl)-1H-pyrazol-5-yl]benzamide TABLE 1-continued

| | | |
|---|---|---|
| 1091 | | 4-[1-(2-chlorophenyl)-3-(trifluoromethyl)-1H-pyrazol-5-yl]-N-[5-(trifluoromethyl)-1,3,4-thiadiazol-2-yl]benzamide |
| 1092 | | 4-[1-(2-chlorophenyl)-3-(trifluoromethyl)-1H-pyrazol-5-yl]-N-[4-chloro-2-(trifluoromethyl)phenyl]benzamide |
| 1093 | | 4-[1-(2-chlorophenyl)-3-(trifluoromethyl)-1H-pyrazol-5-yl]-N-(5-methylpyridin-2-yl)benzamide |
| 1094 | | 4-[1-(2-chlorophenyl)-3-(trifluoromethyl)-1H-pyrazol-5-yl]-N-[2-(methyloxy)-5-(trifluoromethyl)phenyl]benzamide |
| 1095 | | 4-[1-(2-chlorophenyl)-3-(trifluoromethyl)-1H-pyrazol-5-yl]-N-(6-methylpyridin-2-yl)benzamide |

TABLE 1-continued

| | | |
|---|---|---|
| 1096 | 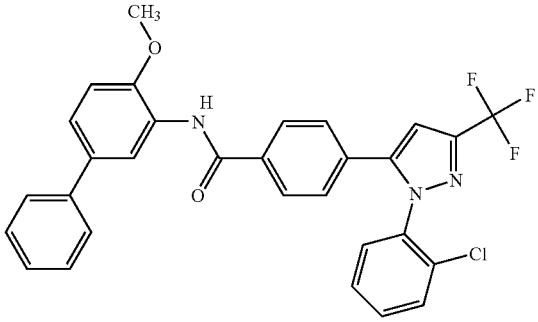 | 4-[1-(2-chlorophenyl)-3-(trifluoromethyl)-1H-pyrazol-5-yl]-N-[4-(methyloxy)biphenyl-3-yl]benzamide |
| 1097 | 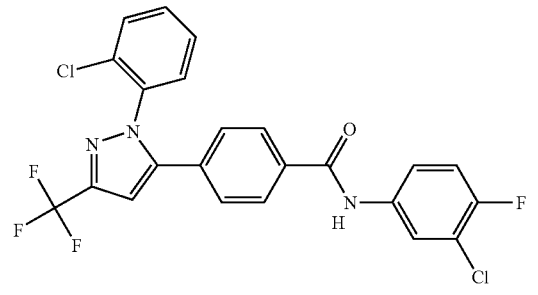 | N-(3-chloro-4-fluorophenyl)-4-[1-(2-chlorophenyl)-3-(trifluoromethyl)-1H-pyrazol-5-yl]benzamide |
| 1098 | 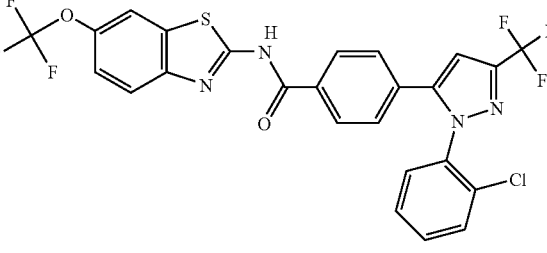 | 4-[1-(2-chlorophenyl)-3-(trifluoromethyl)-1H-pyrazol-5-yl]-N-{6-[(trifluoromethyl)oxy]-1,3-benzothiazol-2-yl}benzamide |
| 1099 | 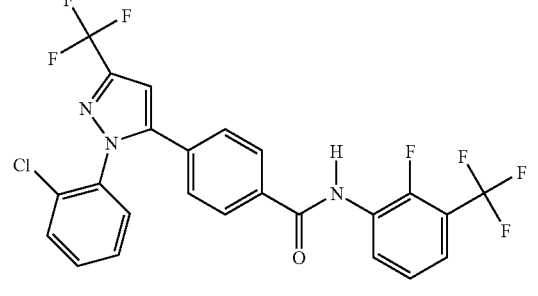 | 4-[1-(2-chlorophenyl)-3-(trifluoromethyl)-1H-pyrazol-5-yl]-N-[2-fluoro-3-(trifluoromethyl)phenyl]benzamide |
| 1100 | 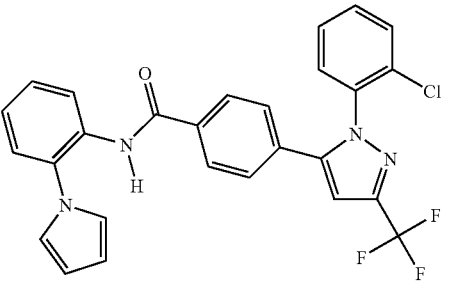 [SMILES: O=C(Nc1ccccc1-n1cccc1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(1H-pyrrol-1-yl)phenyl]benzamide |

TABLE 1-continued

| | | |
|---|---|---|
| 1101 | 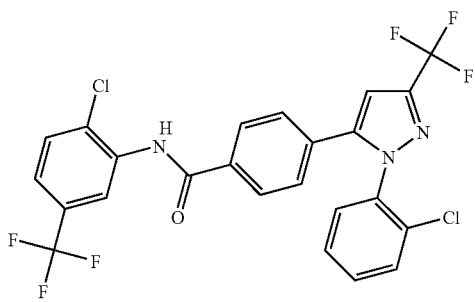 | 4-[1-(2-chlorophenyl)-3-(trifluoromethyl)-1H-pyrazol-5-yl]-N-[2-chloro-5-(trifluoromethyl)phenyl]benzamide |
| 1102 | 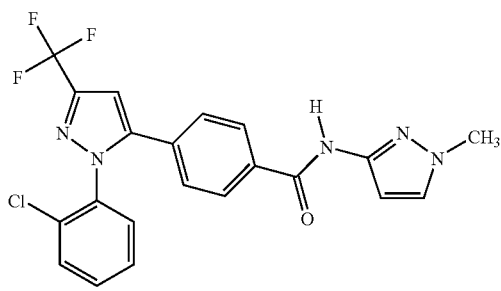 [SMILES: Cn1ccc(NC(=O)c2ccc(-c3cc(C(F)(F)F)nn3-c3ccccc3Cl)cc2)n1] | 4-[1-(2-chlorophenyl)-3-(trifluoromethyl)-1H-pyrazol-5-yl]-N-(1-methyl-1H-pyrazol-3-yl)benzamide |
| 1103 | 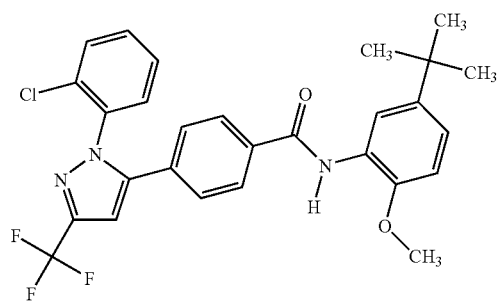 [SMILES: COc1ccc(C(C)(C)C)cc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[5-(1,1-dimethylethyl)-2-(methyloxy)phenyl]benzamide |
| 1104 | 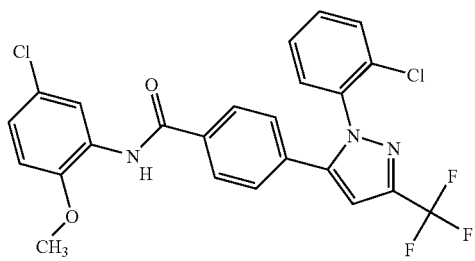 | N-[5-chloro-2-(methyloxy)phenyl]-4-[1-(2-chlorophenyl)-3-(trifluoromethyl)-1H-pyrazol-5-yl]benzamide |
| 1105 | 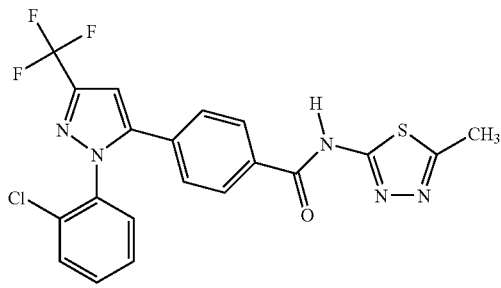 [SMILES: Cc1nnc(NC(=O)c2ccc(-c3cc(C(F)(F)F)nn3-c3ccccc3Cl)cc2)s1] | 4-[1-(2-chlorophenyl)-3-(trifluoromethyl)-1H-pyrazol-5-yl]-N-(5-methyl-1,3,4-thiadiazol-2-yl)benzamide |

TABLE 1-continued

| 1106 | 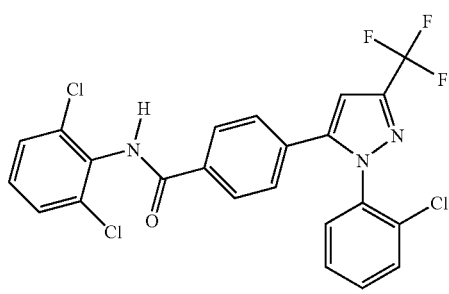 [SMILES: O=C(Nc1c(Cl)cccc1Cl)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,6-dichlorophenyl)benzamide |
| --- | --- | --- |
| 1107 | 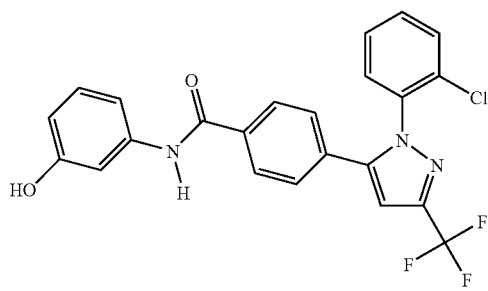 [SMILES: O=C(Nc1cccc(O)c1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-hydroxyphenyl)benzamide |
| 1108 | 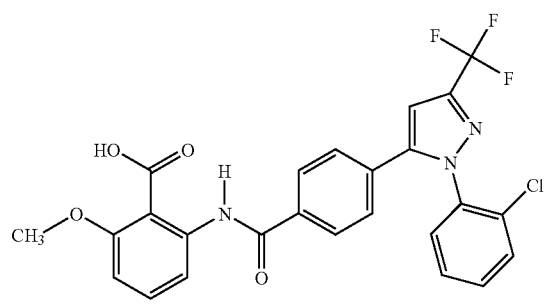 [SMILES: COc1cccc(NC(=O)c2ccc(-c3cc(C(F)(F)F)nn3-c3ccccc3Cl)cc2)c1C(=O)O] | 2-[({4-[1-(2-chlorophenyl)-3-(trifluoromethyl)-1H-pyrazol-5-yl]phenyl}carbonyl)amino]-6-(methyloxy)benzoic acid |
| 1109 | 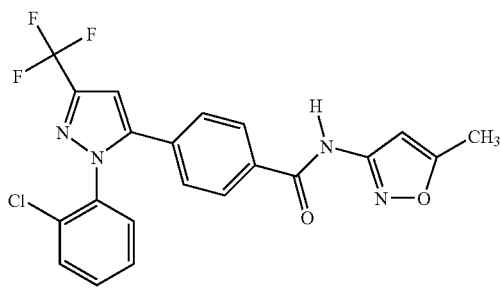 [SMILES: Cc1cc(NC(=O)c2ccc(-c3cc(C(F)(F)F)nn3-c3ccccc3Cl)cc2)no1] | 4-[1-(2-chlorophenyl)-3-(trifluoromethyl)-1H-pyrazol-5-yl]-N-(5-methylisoxazol-3-yl)benzamide |
| 1110 | 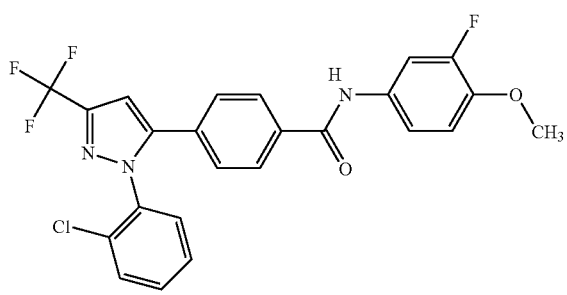 | 4-[1-(2-chlorophenyl)-3-(trifluoromethyl)-1H-pyrazol-5-yl]-N-[3-fluoro-4-(methyloxy)phenyl]benzamide |

TABLE 1-continued

| # | Structure | Name |
|---|---|---|
| 1111 | 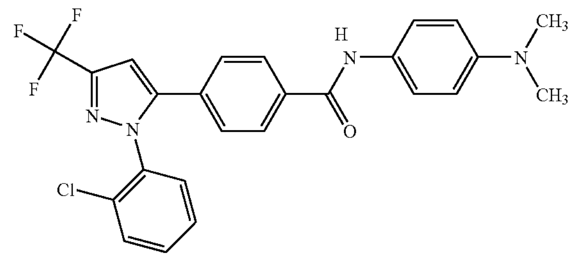 | 4-[1-(2-chlorophenyl)-3-(trifluoromethyl)-1H-pyrazol-5-yl]-N-[4-(dimethylamino)phenyl]benzamide |
| 1112 | 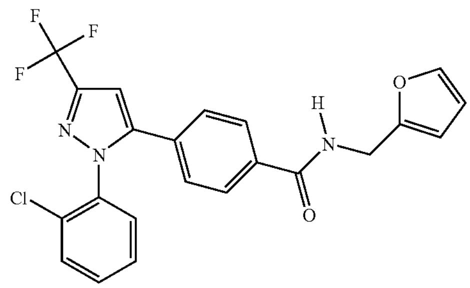 [SMILES: O=C(NCc1ccco1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(furan-2-ylmethyl)benzamide |
| 1113 | 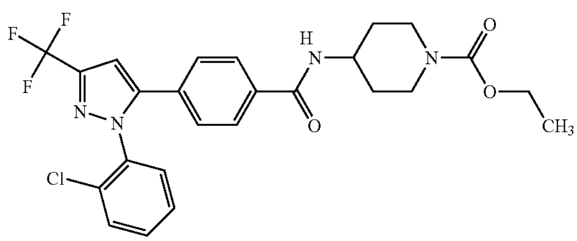 | ethyl 4-[({4-[1-(2-chlorophenyl)-3-(trifluoromethyl)-1H-pyrazol-5-yl]phenyl}carbonyl)amino]piperidine-1-carboxylate |
| 1114 | 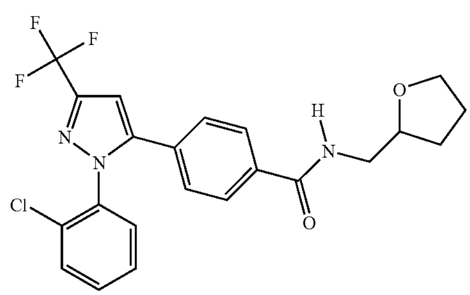 [SMILES: O=C(NCC1CCCO1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(tetrahydrofuran-2-ylmethyl)benzamide |
| 1115 | 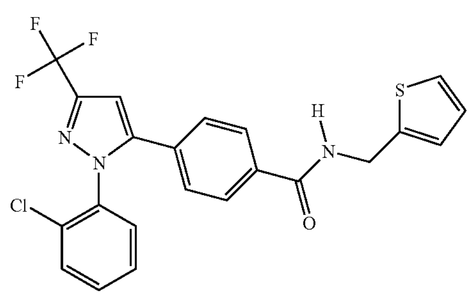 | 4-[1-(2-chlorophenyl)-3-(trifluoromethyl)-1H-pyrazol-5-yl]-N-(2-thienylmethyl)benzamide |

TABLE 1-continued

| | | |
|---|---|---|
| 1116 | 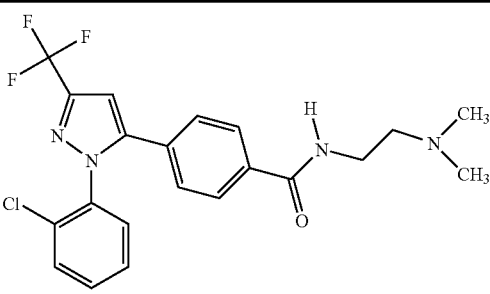 | 4-[1-(2-chlorophenyl)-3-(trifluoromethyl)-1H-pyrazol-5-yl]-N-[2-(dimethylamino)ethyl]benzamide |
| 1117 | 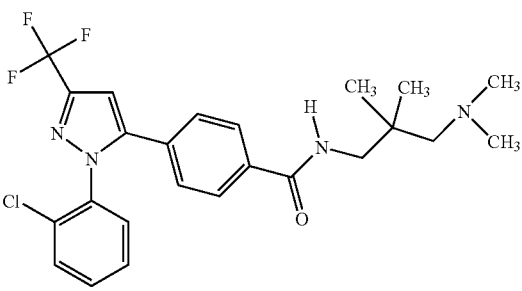 [SMILES: CN(C)CC(C)(C)CNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[3-(dimethylamino)-2,2-dimethylpropyl]benzamide |
| 1118 | 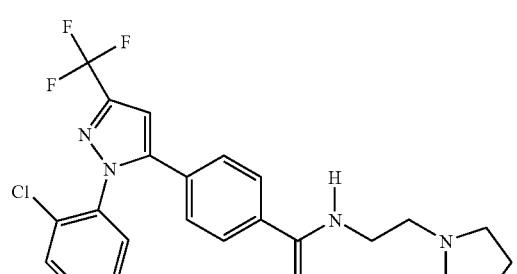 | 4-[1-(2-chlorophenyl)-3-(trifluoromethyl)-1H-pyrazol-5-yl]-N-(2-pyrrolidin-1-ylethyl)benzamide |
| 1119 | 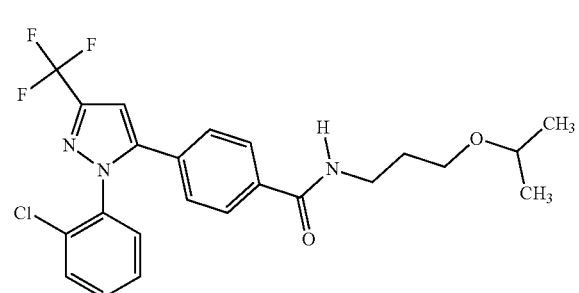 | 4-[1-(2-chlorophenyl)-3-(trifluoromethyl)-1H-pyrazol-5-yl]-N-{3-[(1-methylethyl)oxy]propyl}benzamide |
| 1120 | 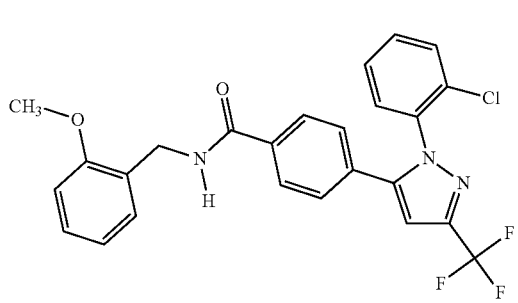 [SMILES: COc1ccccc1CNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{[2-(methyloxy)phenyl]methyl}benzamide |

| | | |
|---|---|---|
| 1121 | 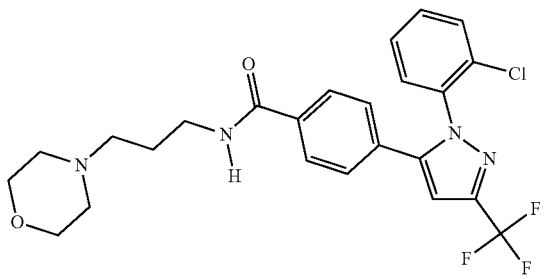 [SMILES: O=C(NCCCN1CCOCC1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-morpholin-4-ylpropyl)benzamide |
| 1122 | 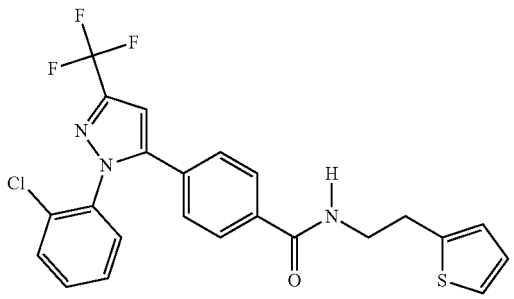 [SMILES: O=C(NCCc1cccs1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(2-thienyl)ethyl]benzamide |
| 1123 | 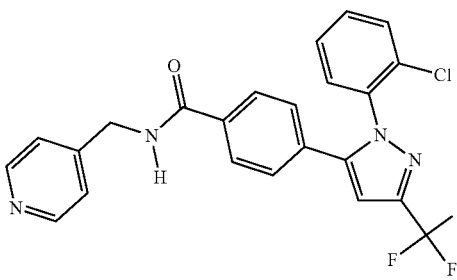 | 4-[1-(2-chlorophenyl)-3-(trifluoromethyl)-1H-pyrazol-5-yl]-N-(pyridin-4-ylmethyl)benzamide |
| 1124 | 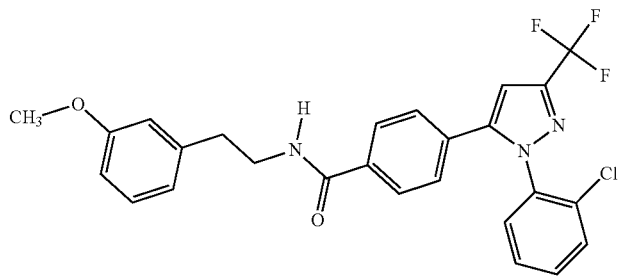 [SMILES: COc1cccc(CCNC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-{2-[3-(methyloxy)phenyl]ethyl}benzamide |
| 1125 | 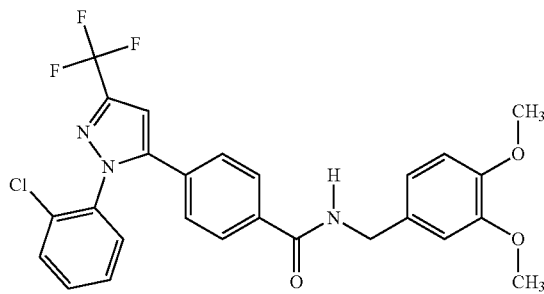 [SMILES: COc1ccc(CNC(=O)c2ccc(-c3cc(C(F)(F)F)nn3-c3ccccc3Cl)cc2)cc1OC] | N-{[3,4-bis(methyloxy)phenyl]methyl}-4-[1-(2-chlorophenyl)-3-(trifluoromethyl)-1H-pyrazol-5-yl]benzamide |

TABLE 1-continued
| | | |
|---|---|---|
| 1126 | 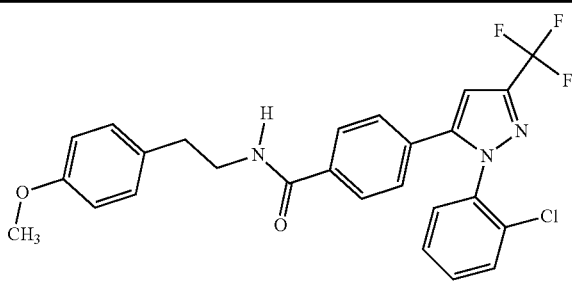 | 4-[1-(2-chlorophenyl)-3-(trifluoromethyl)-1H-pyrazol-5-yl]-N-{2-[4-(methyloxy)phenyl]ethyl}benzamide |
| 1127 | 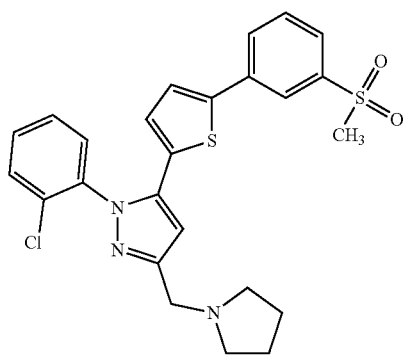 [SMILES: CS(=O)(=O)c1cccc(-c2ccc(-c3cc(CN4CCCC4)nn3-c3ccccc3Cl)s2)c1] | 1-(2-chlorophenyl)-5-{5-[3-(methylsulfonyl)phenyl]-2-thienyl}-3-(pyrrolidin-1-ylmethyl)-1H-pyrazole |
| 1128 | 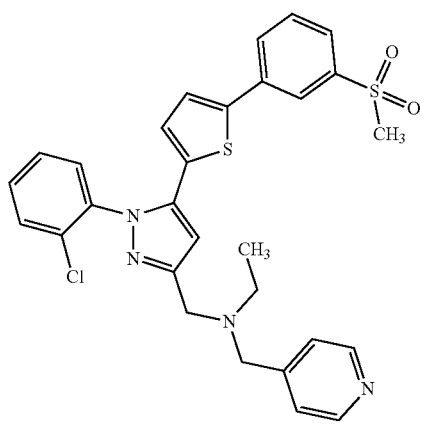 [SMILES: CCN(Cc1ccncc1)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-(pyridin-4-ylmethyl)ethanamine |
| 1129 | 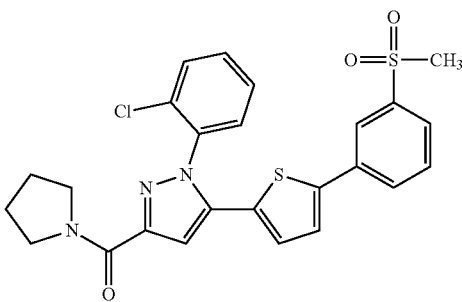 [SMILES: CS(=O)(=O)c1cccc(-c2ccc(-c3cc(C(=O)N4CCCC4)nn3-c3ccccc3Cl)s2)c1] | 1-(2-chlorophenyl)-5-{5-[3-(methylsulfonyl)phenyl]-2-thienyl}-3-(pyrrolidin-1-ylcarbonyl)-1H-pyrazole |

TABLE 1-continued

| | | |
|---|---|---|
| 1130 | 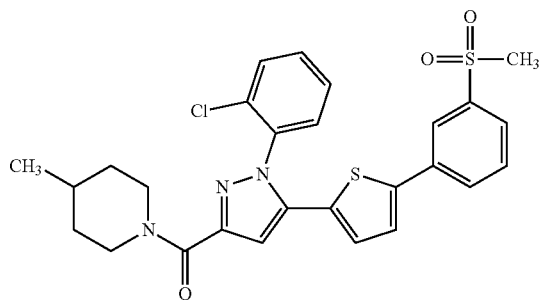 | 1-{[1-(2-chlorophenyl)-5-{5-[3-(methylsulfonyl)phenyl]-2-thienyl}-1H-pyrazol-3-yl]carbonyl}-4-methylpiperazine |
| 1131 | 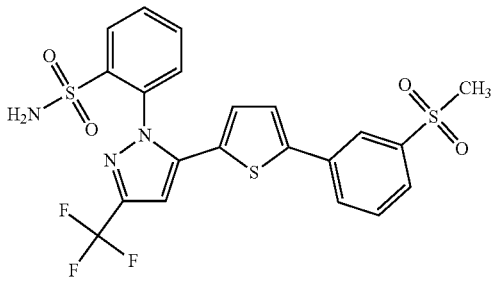 [SMILES: CS(=O)(=O)c1cccc(-c2ccc(-c3cc(C(F)(F)F)nn3-c3ccccc3S(N)(=O)=O)s2)c1] | 2-[5-{5-[3-(methylsulfonyl)phenyl]-2-thienyl}-3-(trifluoromethyl)-1H-pyrazol-1-yl]benzenesulfonamide |
| 1133 | 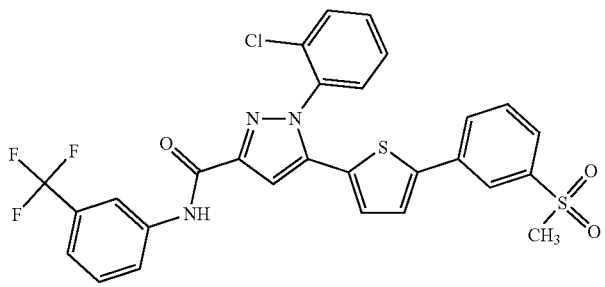 [SMILES: CS(=O)(=O)c1cccc(-c2ccc(-c3cc(C(=O)Nc4cccc(C(F)(F)F)c4)nn3-c3ccccc3Cl)s2)c1] | 1-(2-chlorophenyl)-5-{5-[3-(methylsulfonyl)phenyl]-2-thienyl}-N-[3-(trifluoromethyl)phenyl]-1H-pyrazole-3-carboxamide |
| 1134 | 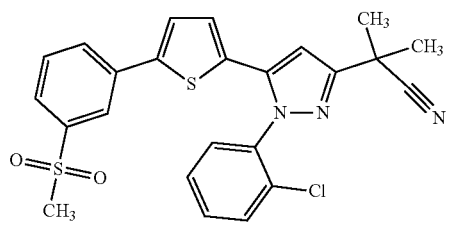 [SMILES: CC(C)(C#N)c1cc(-c2ccc(-c3cccc(S(C)(=O)=O)c3)s2)n(-c2ccccc2Cl)n1] | 2-[1-(2-chlorophenyl)-5-{5-[3-(methylsulfonyl)phenyl]-2-thienyl}-1H-pyrazol-3-yl]-2-methylpropanenitrile |
| 1135 | 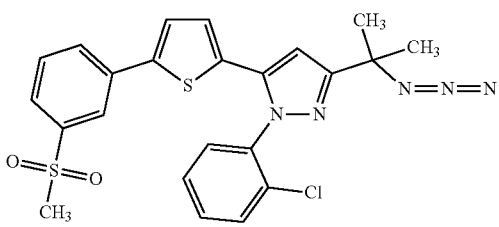 | 1-(2-chlorophenyl)-5-{5-[3-(methylsulfonyl)phenyl]-2-thienyl}-3-[1-methyl-1-(2lambda~5~-triaz-1-en-2-yn-1-yl)ethyl]-1H-pyrazole |
| 1136 | 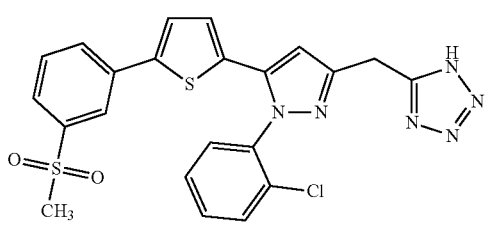 [SMILES: CS(=O)(=O)c1cccc(-c2ccc(-c3cc(Cc4nnn[nH]4)nn3-c3ccccc3Cl)s2)c1] | 5-{[1-(2-chlorophenyl)-5-{5-[3-(methylsulfonyl)phenyl]-2-thienyl}-1H-pyrazol-3-yl]methyl}-1H-tetrazole |

TABLE 1-continued

| 1137 | 4'-[1-(2-chlorophenyl)-3-(trifluoromethyl)-1H-pyrazol-5-yl]biphenyl-3-sulfonamide |
| 1138 | methyl 4-[1-(2-chlorophenyl)-3-(trifluoromethyl)-1H-pyrazol-5-yl]-3'-(methylsulfonyl)biphenyl-2-carboxylate |
| 1139 | 4-[1-(2-chlorophenyl)-3-(trifluoromethyl)-1H-pyrazol-5-yl]-3'-(methylsulfonyl)biphenyl-2-carboxylic acid |
| 1140 | 1-(2-chlorophenyl)-N-[2-(diethylamino)ethyl]-N-methyl-5-{5-[3-(methylsulfonyl)phenyl]-2-thienyl}-1H-pyrazole-5-carboxamide |
| 1142 | 4-({4-[1-(2-chlorophenyl)-3-(trifluoromethyl)-1H-pyrazol-5-yl]-3'-(methylsulfonyl)biphenyl-2-yl}carbonyl)morpholine |

TABLE 1-continued

| | | |
|---|---|---|
| 1143 | 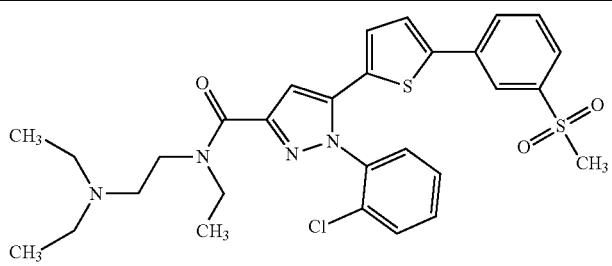 | 1-(2-chlorophenyl)-N-[2-(diethylamino)ethyl]-N-ethyl-5-{5-[3-(methylsulfonyl)phenyl]-2-thienyl}-1H-pyrazole-3-carboxamide |
| 1144 | 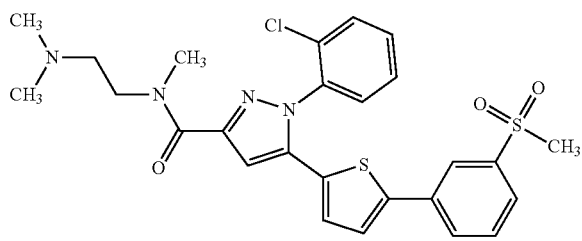 | 1-(2-chlorophenyl)-N-[2-(dimethylamino)ethyl]-N-methyl-5-{5-[3-(methylsulfonyl)phenyl]-2-thienyl}-1H-pyrazole-3-carboxamide |
| 1145 | 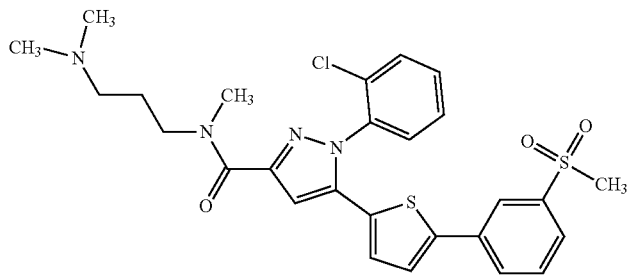 | 1-(2-chlorophenyl)-N-[3-(dimethylamino)propyl]-N-methyl-5-{5-[3-(methylsulfonyl)phenyl]-2-thienyl}-1H-pyrazole-3-carboxamide |
| 1146 | 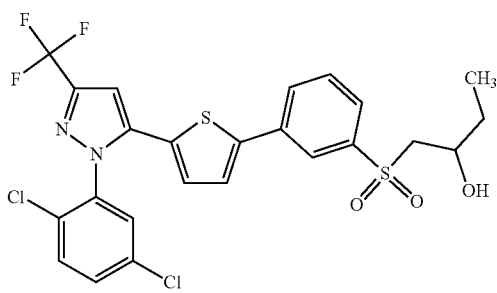 [SMILES: CCC(O)CS(=O)(=O)c1cccc(-c2ccc(-c3cc(C(F)(F)F)nn3-c3cc(Cl)ccc3Cl)s2)c1] | 1-[(3-{5-[1-(2,5-dichlorophenyl)-3-(trifluoromethyl)-1H-pyrazol-5-yl]-2-thienyl}phenyl)sulfonyl]butan-2-ol |
| 1147 | 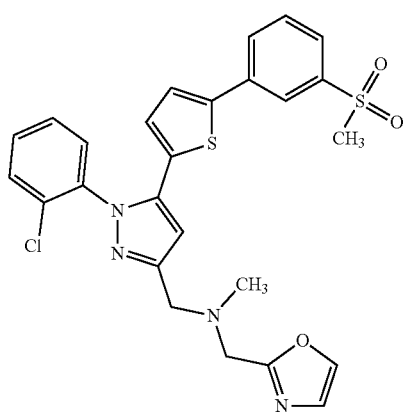 [SMILES: CN(Cc1cc(-c2ccc(-c3cccc(S(C)(=O)=O)c3)s2)n(-c2ccccc2Cl)n1)Cc1ncco1] | 1-[1-(2-chlorophenyl)-5-{5-[3-(methylsulfonyl)phenyl]-2-thienyl}-1H-pyrazol-3-yl]-N-methyl-N-(1,3-oxazol-2-ylmethyl)methanamine |

TABLE 1-continued

| | | |
|---|---|---|
| 1148 | 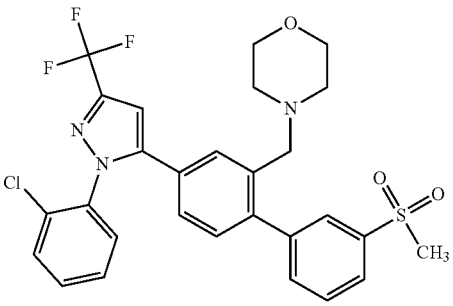 [SMILES: CS(=O)(=O)c1cccc(-c2ccc(-c3cc(C(F)(F)F)nn3-c3ccccc3Cl)cc2CN2CCOCC2)c1] | 4-({4-[1-(2-chlorophenyl)-3-(trifluoromethyl)-1H-pyrazol-5-yl]-3'-(methylsulfonyl)biphenyl-2-yl}methyl)morpholine |
| 1149 | 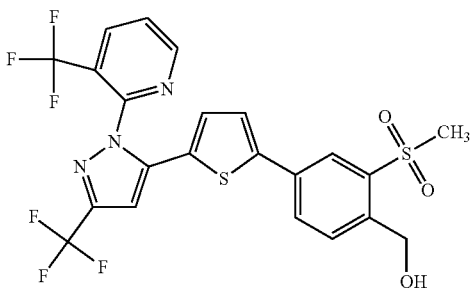 [SMILES: CS(=O)(=O)c1cc(-c2ccc(-c3cc(C(F)(F)F)nn3-c3ncccc3C(F)(F)F)s2)ccc1CO] | [2-(methylsulfonyl)-4-(5-{3-(trifluoromethyl)-1-[3-(trifluoromethyl)pyridin-2-yl]-1H-pyrazol-5-yl}-2-thienyl)phenyl]methanol |
| 1150 | 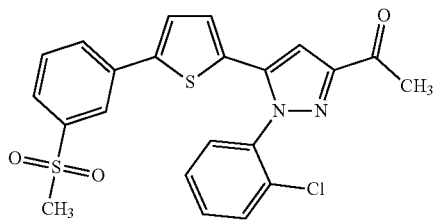 [SMILES: CC(=O)c1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]ethanone |
| 1151 | 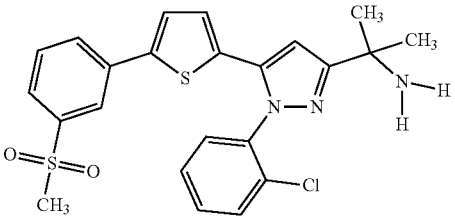 [SMILES: CC(C)(N)c1cc(-c2ccc(-c3cccc(S(C)(=O)=O)c3)s2)n(-c2ccccc2Cl)n1] | 2-[1-(2-chlorophenyl)-5-{5-[3-(methylsulfonyl)phenyl]-2-thienyl}-1H-pyrazol-3-yl]propan-2-amine |
| 1152 | 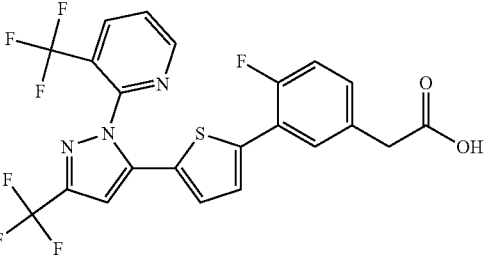 | [4-fluoro-3-(5-{3-(trifluoromethyl)-1-[3-(trifluoromethyl)pyridin-2-yl]-1H-pyrazol-5-yl}-2-thienyl)phenyl]acetic acid |
| 1153 | 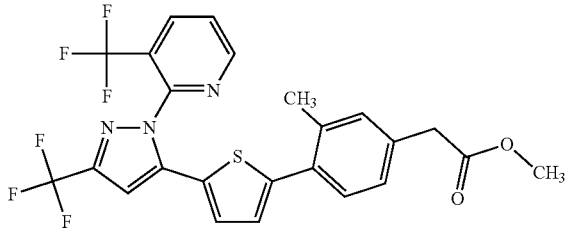 [SMILES: COC(=O)Cc1ccc(-c2ccc(-c3cc(C(F)(F)F)nn3-c3ncccc3C(F)(F)F)s2)c(C)c1] | methyl [3-methyl-4-(5-{3-(trifluoromethyl)-1-[3-(trifluoromethyl)pyridin-2-yl]-1H-pyrazol-5-yl}-2-thienyl)phenyl]acetate |

TABLE 1-continued

| | | |
|---|---|---|
| 1154 | | N-{[1-(2-chlorophenyl)-5-{5-[3-(methylsulfonyl)phenyl]-2-thienyl}-1H-pyrazol-3-yl]carbonyl}-N-methylglycine |
| 1155 | | [3-methyl-4-(5-{3-(trifluoromethyl)-1-[3-(trifluoromethyl)pyridin-2-yl]-1H-pyrazol-5-yl}-2-thienyl)phenyl]acetic acid |
| 1156 | | methyl 5-{5-[3-(methylsulfonyl)phenyl]-2-thienyl}-1-[2-(trifluoromethyl)phenyl]-1H-pyrazole-3-carboxylate |
| 1157 | | 1-[1-(2-chlorophenyl)-5-{5-[3-(methylsulfonyl)phenyl]-2-thienyl}-1H-pyrazol-3-yl]ethanol |
| 1158 | | 2-(5-{5-[3-(methylsulfonyl)phenyl]-2-thienyl}-1-[2-(trifluoromethyl)phenyl]-1H-pyrazol-3-yl)propan-2-ol |
| 1159 | | 4-{1-[1-(2-chlorophenyl)-5-{5-[3-(methylsulfonyl)phenyl]-2-thienyl}-1H-pyrazol-3-yl]-1-methylethyl}morpholine |

TABLE 1-continued

| | | |
|---|---|---|
| 1160 | | 1-(2-chlorophenyl)-3-(1-methyl-1-pyridin-1-ylethyl)-5-{5-[3-(methylsulfonyl)phenyl]-2-thienyl}-1H-pyrazole |
| 1161 | | 1-(2-chlorophenyl)-5-{5-[3-(methylsulfonyl)phenyl]-2-thienyl}-N-(2,2,2-trifluoroethyl)-1H-pyrazole-3-carboxamide |
| 1162 | | 1-(2-chlorophenyl)-N-methyl-N-(methyloxy)-5-{5-[3-(methylsulfonyl)phenyl]-2-thienyl}-1H-pyrazole-3-carboxamide |
| 1163 | | 1-(2-chlorophenyl)-N-(methyloxy)-5-{5-[3-(methylsulfonyl)phenyl]-2-thienyl}-1H-pyrazole-3-carboxamide |
| 1164 | | 2-[1-(2-chlorophenyl)-5-{5-[3-(methylsulfonyl)phenyl]-2-thienyl}-1H-pyrazol-3-yl]-1,1,1,3,3,3-hexafluoropropan-2-ol |
| 1165 | | 2-methyl-2-[3-(5-{3-(trifluoromethyl)-1-[3-(trifluoromethyl)pyridin-2-yl]-1H-pyrazol-5-yl}-2-thienyl)phenyl]propanoic acid |

TABLE 1-continued

| 1166 | 2-[3-(5-{1-[(5-chloro-2-thienyl)methyl]-3-(trifluoromethyl)-1H-pyrazol-5-yl}-2-thienyl)phenyl]-2-methylpropanoic acid |
| 1167 | 1-(2-chlorophenyl)-5-{3'-[(1-methylethyl)sulfonyl]biphenyl-4-yl}-3-(trifluoromethyl)-1H-pyrazole |
| 1168 | 5-{3'-[(1-methylethyl)sulfonyl]biphenyl-4-yl}-3-(trifluoromethyl)-1-[2-(trifluoromethyl)phenyl]-1H-pyrazole |
| 1169 | 2-[5-(5-{3-[(1-methylethyl)sulfonyl]phenyl}-2-thienyl)-3-(trifluoromethyl)-1H-pyrazol-1-yl]-3-(trifluoromethyl)pyridine |
| 1170 | methyl 5-(5-{3-[(1-methylethyl)sulfonyl]phenyl}-2-thienyl)-1-[3-(trifluoromethyl)pyridin-2-yl]-1H-pyrazole-3-carboxylate |

TABLE 1-continued

| 1171 | 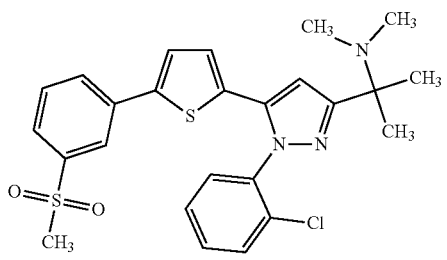 [SMILES: CN(C)C(C)(C)c1cc(-c2ccc(-c3cccc(S(C)(=O)=O)c3)s2)n(-c2ccccc2Cl)n1] | N-[(3-{5-(2,5-dichlorophenyl)-3-(trifluoromethyl)-1H-pyrazol-5-yl]-2-thienyl}phenyl)sulfonyl]-2,2-dimethylpropanamide |
| --- | --- | --- |
| 1172 | 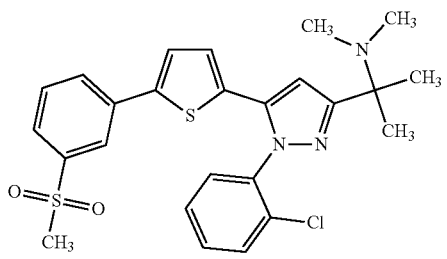 [SMILES: CN(C)C(C)(C)c1cc(-c2ccc(-c3cccc(S(C)(=O)=O)c3)s2)n(-c2ccccc2Cl)n1] | 2-[1-(2-chlorophenyl)-5-{5-[3-(methylsulfonyl)phenyl]-2-thienyl}-1H-pyrazol-3-yl]-N,N-dimethylpropan-2-amine |
| 1173 | 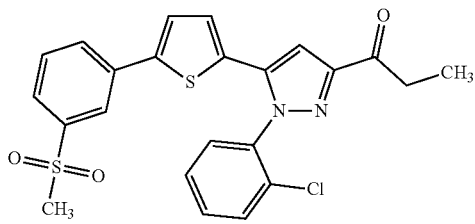 [SMILES: CCC(=O)c1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]propan-1-one |
| 1174 | 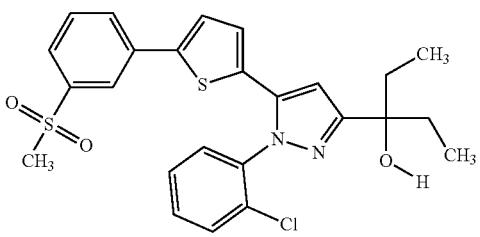 [SMILES: CCC(O)(CC)c1cc(-c2ccc(-c3cccc(S(C)(=O)=O)c3)s2)n(-c2ccccc2Cl)n1] | 3-[1-(2-chlorophenyl)-5-{5-[3-(methylsulfonyl)phenyl]-2-thienyl}-1H-pyrazol-3-yl]pentan-3-ol |
| 1175 | 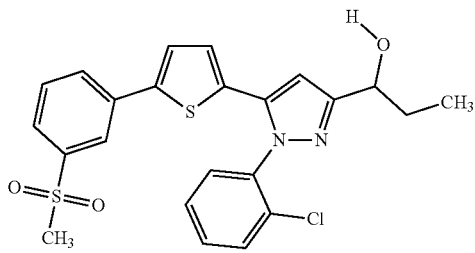 [SMILES: CCC(O)c1cc(-c2ccc(-c3cccc(S(C)(=O)=O)c3)s2)n(-c2ccccc2Cl)n1] | 1-[1-(2-chlorophenyl)-5-{5-[3-(methylsulfonyl)phenyl]-2-thienyl}-1H-pyrazol-3-yl]propan-1-ol |
| 1176 | 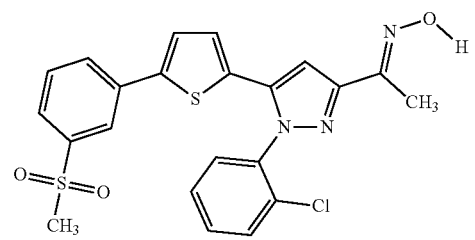 [SMILES: C/C(=N\O)c1cc(-c2ccc(-c3cccc(S(C)(=O)=O)c3)s2)n(-c2ccccc2Cl)n1] | (1E)-1-[1-(2-chlorophenyl)-5-{5-[3-(methylsulfonyl)phenyl]-2-thienyl}-1H-pyrazol-3-yl]ethanone oxime |

TABLE 1-continued

| 1177 | 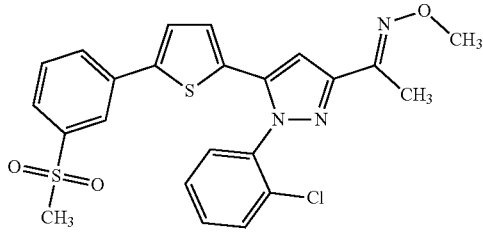 [SMILES: CO/N=C(\C)c1cc(-c2ccc(-c3cccc(S(C)(=O)=O)c3)s2)n(-c2ccccc2Cl)n1] | (1E)-1-[1-(2-chlorophenyl)-5-{5-[3-(methylsulfonyl)phenyl]-2-thienyl}-1H-pyrazol-3-yl]ethanone O-methyloxime |
| --- | --- | --- |
| 1178 | 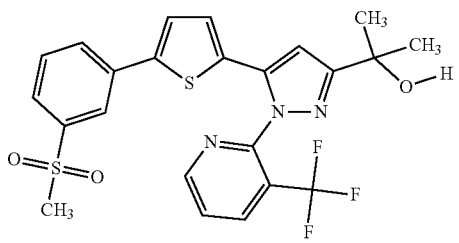 [SMILES: CC(C)(O)c1cc(-c2ccc(-c3cccc(S(C)(=O)=O)c3)s2)n(-c2ncccc2C(F)(F)F)n1] | 2-(5-{5-[3-(methylsulfonyl)phenyl]-2-thienyl}-1-[3-(trifluoromethyl)pyridin-2-yl]-1H-pyrazol-3-yl)propan-2-ol |
| 1179 | 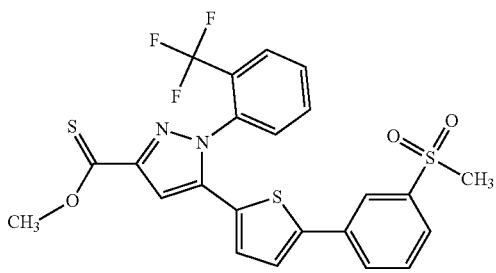 | O-methyl 5-{5-[3-(methylsulfonyl)phenyl]-2-thienyl}-1-[2-(trifluoromethyl)phenyl]-1H-pyrazol-3-carbothioate |
| 1180 | 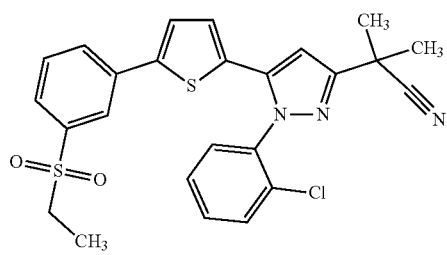 [SMILES: CCS(=O)(=O)c1cccc(-c2ccc(-c3cc(C(C)(C)C#N)nn3-c3ccccc3Cl)s2)c1] | 2-[1-(2-chlorophenyl)-5-{5-[3-(ethylsulfonyl)phenyl]-2-thienyl}-1H-pyrazol-3-yl]-2-methylpropanenitrile |
| 1181 | 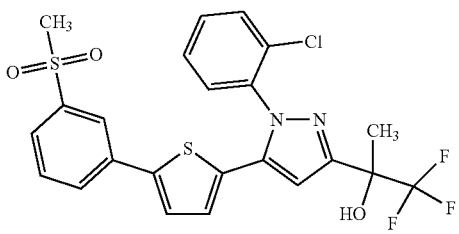 [SMILES: CC(O)(c1cc(-c2ccc(-c3cccc(S(C)(=O)=O)c3)s2)n(-c2ccccc2Cl)n1)C(F)(F)F] | 2-[1-(2-chlorophenyl)-5-{5-[3-(methylsulfonyl)phenyl]-2-thienyl}-1H-pyrazol-3-yl]-1,1,1-trifluoropropan-2-ol |
| 1182 | 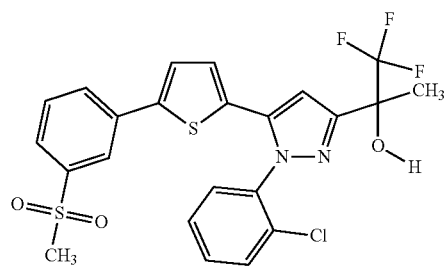 [SMILES: CC(O)(c1cc(-c2ccc(-c3cccc(S(C)(=O)=O)c3)s2)n(-c2ccccc2Cl)n1)C(F)(F)F] | 2-[1-(2-chlorophenyl)-5-{5-[3-(methylsulfonyl)phenyl]-2-thienyl}-1H-pyrazol-3-yl]-1,1,1-trifluoropropan-2-ol |

TABLE 1-continued

| 1183 | 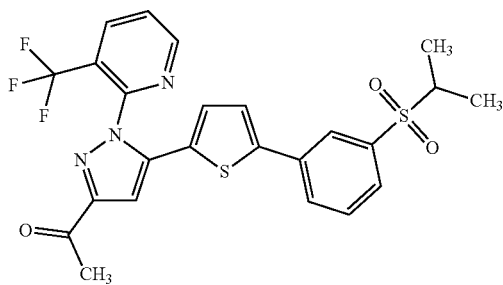 [SMILES: CC(=O)c1cc(-c2ccc(-c3cccc(S(=O)(=O)C(C)C)c3)s2)n(-c2ncccc2C(F)(F)F)n1] | 1-{5-(5-{3-[(1-methylethyl)sulfonyl]phenyl}-2-thienyl)-1-[3-(trifluoromethyl)pyridin-2-yl]-1H-pyrazol-3-yl}ethanone |
| 1184 | 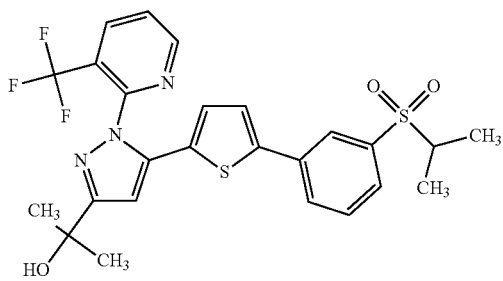 [SMILES: CC(C)S(=O)(=O)c1cccc(-c2ccc(-c3cc(C(C)(C)O)nn3-c3ncccc3C(F)(F)F)s2)c1] | 2-{5-(5-{3-[(1-methylethyl)sulfonyl]phenyl}-2-thienyl)-1-[3-(trifluoromethyl)pyridin-2-yl]-1H-pyrazol-3-yl}propan-2-ol |
| 1185 | 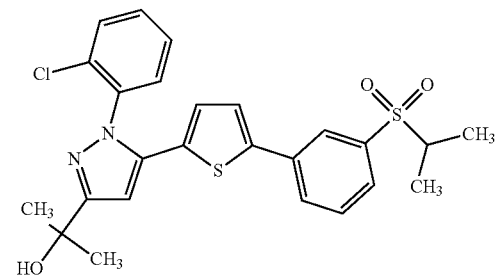 [SMILES: CC(C)S(=O)(=O)c1cccc(-c2ccc(-c3cc(C(C)(C)O)nn3-c3ccccc3Cl)s2)c1] | 2-[1-(2-chlorophenyl)-5-(5-{3-[(1-methylethyl)sulfonyl]phenyl}-2-thienyl)-1H-pyrazol-3-yl]propan-2-ol |
| 1186 | 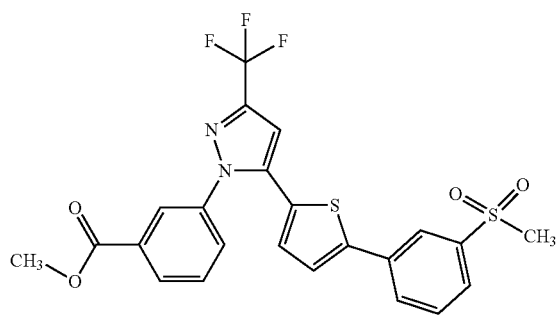 | methyl 3-[5-{5-[3-(methylsulfonyl)phenyl]-2-thienyl}-3-(trifluoromethyl)-1H-pyrazol-1-yl]benzoate |
| 1187 | 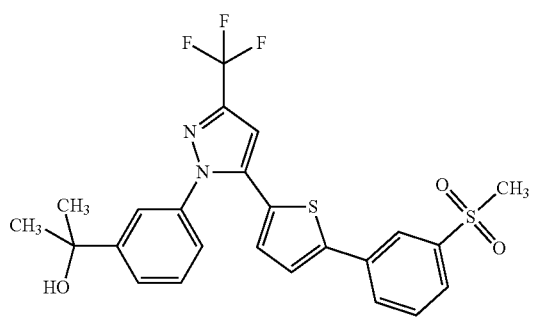 [SMILES: CC(C)(O)c1cccc(-n2nc(C(F)(F)F)cc2-c2ccc(-c3cccc(S(C)(=O)=O)c3)s2)c1] | 2-{3-[5-{5-[3-(methylsulfonyl)phenyl]-2-thienyl}-3-(trifluoromethyl)-1H-pyrazol-1-yl]phenyl}propan-2-ol |

TABLE 1-continued

| | | |
|---|---|---|
| 1188 | 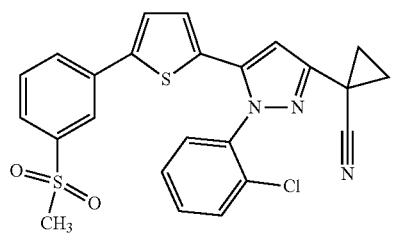 [SMILES: CS(=O)(=O)c1cccc(-c2ccc(-c3cc(C4(C#N)CC4)nn3-c3ccccc3Cl)s2)c1] | 1-[1-(2-chlorophenyl)-5-{5-[3-(methylsulfonyl)phenyl]-2-thienyl}-1H-pyrazol-3-yl]cyclopropanecarbonitrile |
| 1189 | 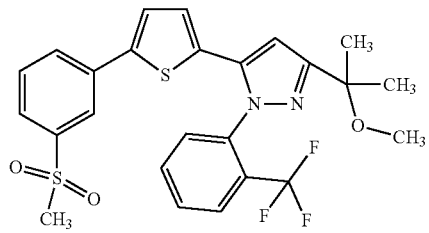 [SMILES: COC(C)(C)c1cc(-c2ccc(-c3cccc(S(C)(=O)=O)c3)s2)n(-c2ccccc2C(F)(F)F)n1] | 3-[1-methyl-1-(methyloxy)ethyl]-5-{5-[3-(methylsulfonyl)phenyl]-2-thienyl}-1-[2-(trifluoromethyl)phenyl]-1H-pyrazole |
| 1190 | 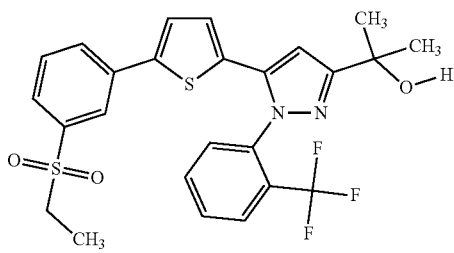 [SMILES: CCS(=O)(=O)c1cccc(-c2ccc(-c3cc(C(C)(C)O)nn3-c3ccccc3C(F)(F)F)s2)c1] | 5-{5-[3-(ethylsulfonyl)phenyl]-2-thienyl}-3-[1-methyl-1-(methyloxy)ethyl]-1-[2-(trifluoromethyl)phenyl]-1H-pyrazole |
| 1191 | 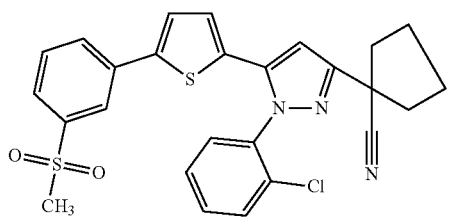 [SMILES: CS(=O)(=O)c1cccc(-c2ccc(-c3cc(C4(C#N)CCCC4)nn3-c3ccccc3Cl)s2)c1] | 1-[1-(2-chlorophenyl)-5-{5-[3-(methylsulfonyl)phenyl]-2-thienyl}-1H-pyrazol-3-yl]cyclopentanecarbonitrile |
| 1192 | 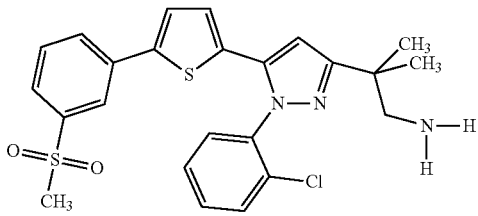 [SMILES: CC(C)(CN)c1cc(-c2ccc(-c3cccc(S(C)(=O)=O)c3)s2)n(-c2ccccc2Cl)n1] | 2-[1-(2-chlorophenyl)-5-{5-[3-(methylsulfonyl)phenyl]-2-thienyl}-1H-pyrazol-3-yl]-2-methylpropan-1-amine |
| 1193 | 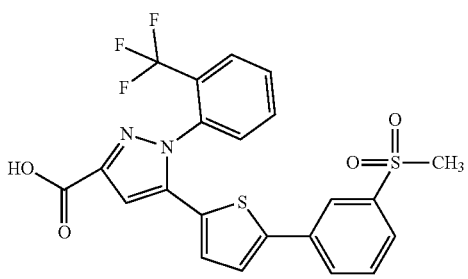 [SMILES: CS(=O)(=O)c1cccc(-c2ccc(-c3cc(C(=O)O)nn3-c3ccccc3C(F)(F)F)s2)c1] | 5-{5-[3-(methylsulfonyl)phenyl]-2-thienyl}-1-[2-(trifluoromethyl)phenyl]-1H-pyrazole-3-carboxylic acid |

TABLE 1-continued

| | | |
|---|---|---|
| 1194 | | 1-(2-chlorophenyl)-N-ethyl-5-{5-[3-(methylsulfonyl)phenyl]-2-thienyl}-1H-pyrazole-3-carbothioamide |
| 1195 | | 5-{5-[3-(methylsulfonyl)phenyl]-2-thienyl}-N-(2,2,2-trifluoroethyl)-1-[2-(trifluoromethyl)phenyl]-1H-pyrazole-3-carboxamide |
| 1196 | | N-(methylsulfonyl)-5-{5-[3-(methylsulfonyl)phenyl]-2-thienyl}-1-[2-(trifluoromethyl)phenyl]-1H-pyrazole-3-carboxamide |
| 1198 | | 3-(5-{1-[5-chloro-2-(phenyloxy)phenyl]-3-(trifluoromethyl)-1H-pyrazol-5-yl}-2-thienyl)benzenesulfonamide |
| 1201 | | 2-{5-[3'-(methylsulfonyl)biphenyl-4-yl]-1-[2-(trifluoromethyl)phenyl]-1H-pyrazol-3-yl}propan-2-ol |

TABLE 1-continued

| | | |
|---|---|---|
| 1202 | 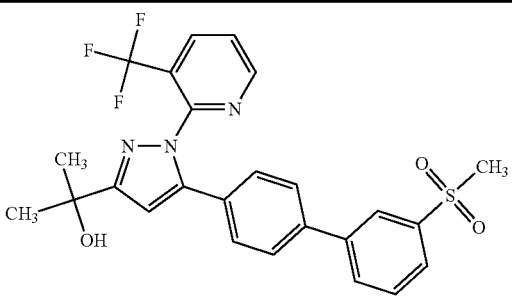 | 2-{5-[3'-(methylsulfonyl)phenyl-4-yl]-1-[3-(trifluoromethyl)pyridin-2-yl]-1H-pyrazol-3-yl}propan-2-ol |
| 1203 | 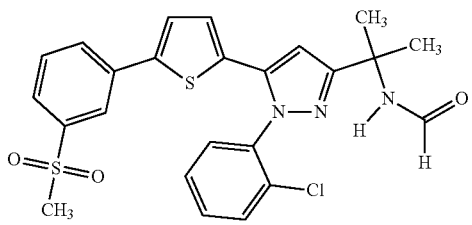 [SMILES: CC(C)(NC=O)c1cc(-c2ccc(-c3cccc(S(C)(=O)=O)c3)s2)n(-c2ccccc2Cl)n1] | N-{1-[1-(2-chlorophenyl)-5-{5-[3-(methylsulfonyl)phenyl]-2-thienyl}-1H-pyrazol-3-yl]-1-methylethyl}formamide |
| 1204 | 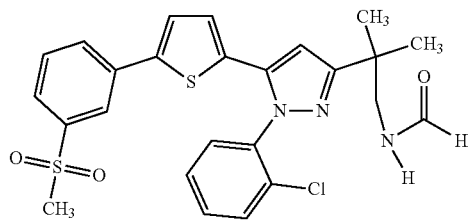 [SMILES: CC(C)(CNC=O)c1cc(-c2ccc(-c3cccc(S(C)(=O)=O)c3)s2)n(-c2ccccc2Cl)n1] | N-{2-[1-(2-chlorophenyl)-5-{5-[3-(methylsulfonyl)phenyl]-2-thienyl}-1H-pyrazol-3-yl]-2-methylpropyl}formamide |
| 1205 | 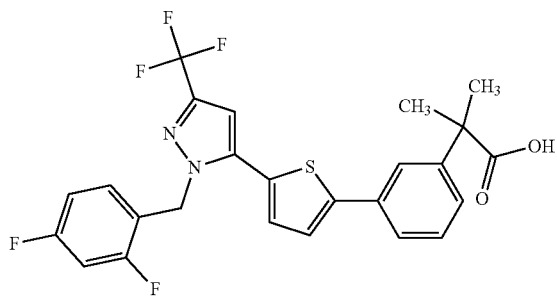 [SMILES: CC(C)(C(=O)O)c1cccc(-c2ccc(-c3cc(C(F)(F)F)nn3Cc3ccc(F)cc3F)s2)c1] | 2-[3-(5-{1-[(2,4-difluorophenyl)methyl]-3-(trifluoromethyl)-1H-pyrazol-5-yl}-2-thienyl)phenyl]-2-methylpropanoic acid |
| 1206 | 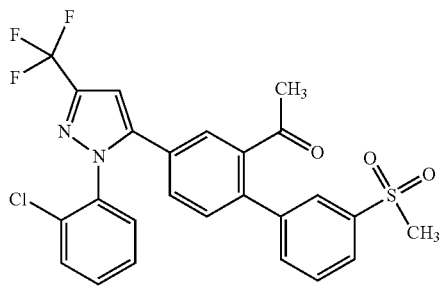 [SMILES: CC(=O)c1cc(-c2cc(C(F)(F)F)nn2-c2ccccc2Cl)ccc1-c1cccc(S(C)(=O)=O)c1] | 1-{4-[1-(2-chlorophenyl)-3-(trifluoromethyl)-1H-pyrazol-5-yl]-3'-(methylsulfonyl)biphenyl-2-yl}ethanone |
| 1207 | 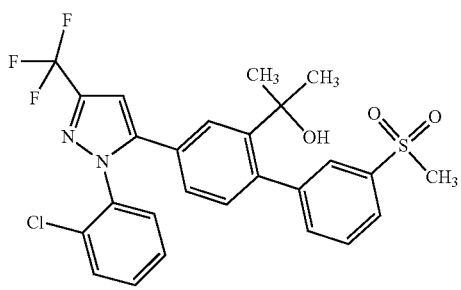 [SMILES: CC(C)(O)c1cc(-c2cc(C(F)(F)F)nn2-c2ccccc2Cl)ccc1-c1cccc(S(C)(=O)=O)c1] | 2-{4-[1-(2-chlorophenyl)-3-(trifluoromethyl)-1H-pyrazol-5-yl]-3'-(methylsulfonyl)biphenyl-2-yl}propan-2-ol |

| | | |
|---|---|---|
| 1208 | 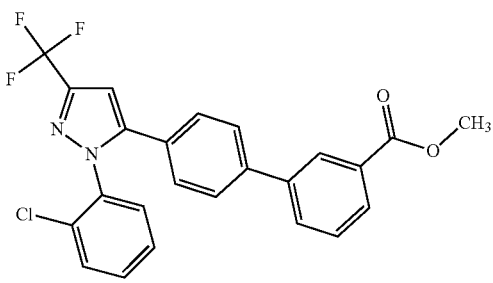 [SMILES: COC(=O)c1cccc(-c2ccc(-c3cc(C(F)(F)F)nn3-c3ccccc3Cl)cc2)c1] | methyl 4'-[1-(2-chlorophenyl)-3-(trifluoromethyl)-1H-pyrazol-5-yl]biphenyl-3-carboxylate |
| 1209 | 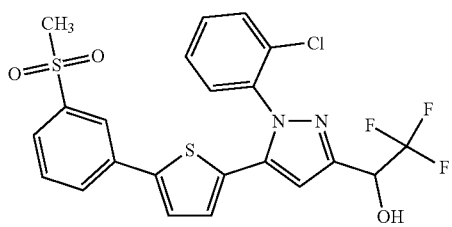 [SMILES: CS(=O)(=O)c1cccc(-c2ccc(-c3cc(C(O)C(F)(F)F)nn3-c3ccccc3Cl)s2)c1] | 1-[1-(2-chlorophenyl)-5-{5-[3-(methylsulfonyl)phenyl]-2-thienyl}-1H-pyrazol-3-yl]-2,2,2-trifluoroethanol |
| 1210 | 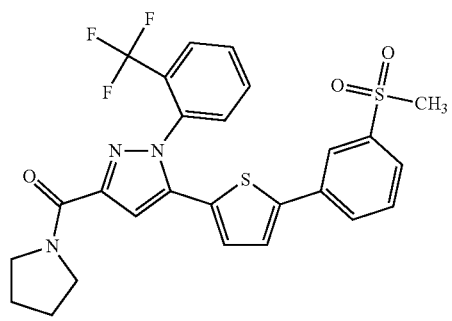 [SMILES: CS(=O)(=O)c1cccc(-c2ccc(-c3cc(C(=O)N4CCCC4)nn3-c3ccccc3C(F)(F)F)s2)c1] | 5-{5-[3-(methylsulfonyl)phenyl]-2-thienyl}-3-(pyrrolidin-1-ylcarbonyl)-1-[2-(trifluoromethyl)phenyl]-1H-pyrazole |
| 1211 | 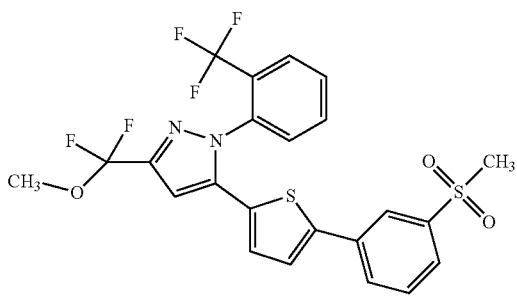 [SMILES: COC(F)(F)c1cc(-c2ccc(-c3cccc(S(C)(=O)=O)c3)s2)n(-c2ccccc2C(F)(F)F)n1] | 3-[difluoro(methyloxy)methyl]-5-{5-[3-(methylsulfonyl)phenyl]-2-thienyl}-1-[2-(trifluoromethyl)phenyl]-1H-pyrazole |
| 1212 | 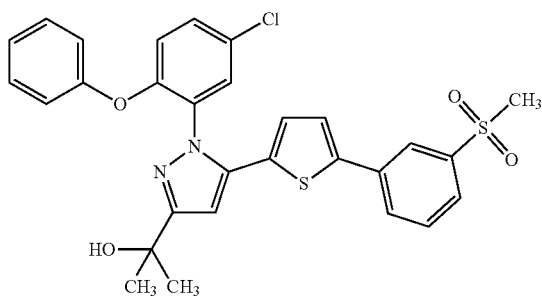 [SMILES: CC(C)(O)c1cc(-c2ccc(-c3cccc(S(C)(=O)=O)c3)s2)n(-c2cc(Cl)ccc2Oc2ccccc2)n1] | 2-(1-[5-chloro-2-(phenyloxy)phenyl]-5-{5-[3-(methylsulfonyl)phenyl]-2-thienyl}-1H-pyrazol-3-yl)propan-2-ol |

TABLE 1-continued

| | | |
|---|---|---|
| 1213 | | 1-(1-[5-chloro-2-(phenyloxy)phenyl]-5-{5-[3-(methylsulfonyl)phenyl]-2-thienyl}-1H-pyrazol-3-yl)ethanone |
| 1214 | | 3-{5-[1-(2,5-dichlorophenyl)-3-(1-hydroxy-1-methylethyl)-1H-pyrazol-5-yl]-2-thienyl}benzenesulfonamide |
| 1215 | | 5-{5-[3-(methylsulfonyl)phenyl]-2-thienyl}-1-[2-(phenyloxy)phenyl]-3-(trifluoromethyl)-1H-pyrazole |
| 1216 | | 3-{5-[3-acetyl-1-(2,5-dichlorophenyl)-1H-pyrazol-5-yl]-2-thienyl}benzenesulfonamide |
| 1217 | | 2-{5-(2-chlorophenyl)-1-[3'-(methylsulfonyl)biphenyl-4-yl]-1H-pyrazol-3-yl}propan-2-ol |

TABLE 1-continued

| | | |
|---|---|---|
| 1218 | 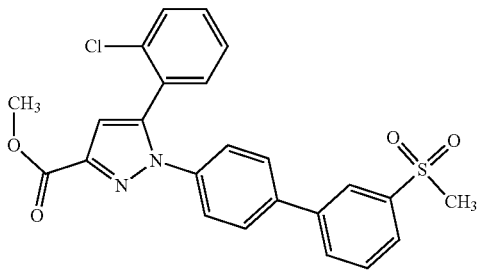 [SMILES: COC(=O)c1cc(-c2ccccc2Cl)n(-c2ccc(-c3cccc(S(C)(=O)=O)c3)cc2)n1] | methyl 5-(2-chlorophenyl)-1-[3'-(methylsulfonyl)biphenyl-4-yl]-1H-pyrazole-3-carboxylate |
| 1219 | 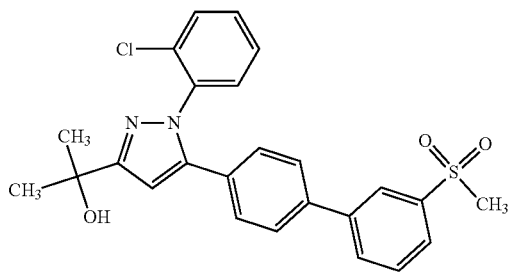 [SMILES: CC(C)(O)c1cc(-c2ccc(-c3cccc(S(C)(=O)=O)c3)cc2)n(-c2ccccc2Cl)n1] | 2-{1-(2-chlorophenyl)-5-[3'-(methylsulfonyl)biphenyl-4-yl]-1H-pyrazol-3-yl}propan-2-ol |
| 1220 | 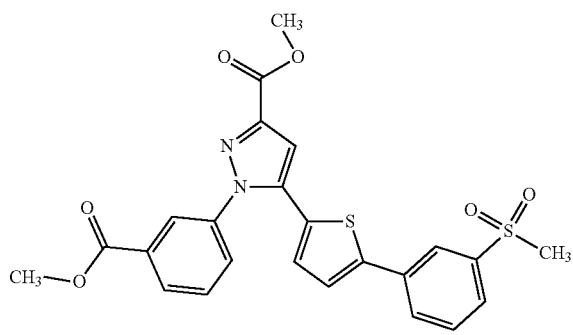 | methyl 1-{3-[(methyloxy)carbonyl]phenyl}-5-{5-[3-(methylsulfonyl)phenyl]-2-thienyl}-1H-pyrazole-3-carboxylate |
| 1221 | 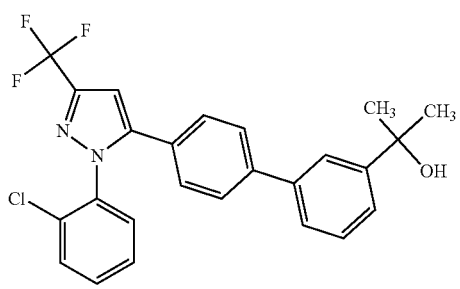 [SMILES: CC(C)(O)c1cccc(-c2ccc(-c3cc(C(F)(F)F)nn3-c3ccccc3Cl)cc2)c1] | 2-{4'-[1-(2-chlorophenyl)-3-(trifluoromethyl)-1H-pyrazol-5-yl]biphenyl-3-yl}propan-2-ol |
| 1222 | 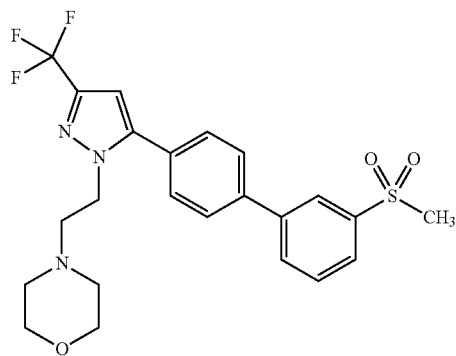 [SMILES: CS(=O)(=O)c1cccc(-c2ccc(-c3cc(C(F)(F)F)nn3CCN3CCOCC3)cc2)c1] | 4-(2-{5-[3'-(methylsulfonyl)phenyl-4-yl]-3-(trifluoromethyl)-1H-pyrazol-1-yl}ethyl)morpholine |

TABLE 1-continued

| | | |
|---|---|---|
| 1223 | 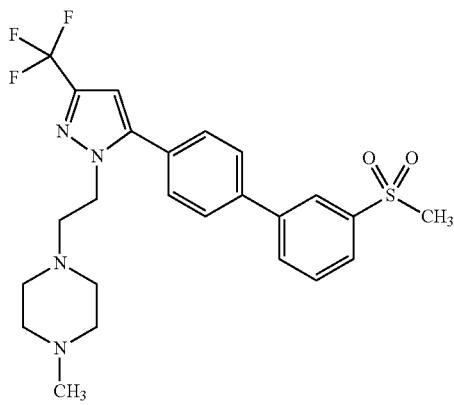 [SMILES: CN1CCN(CCn2nc(C(F)(F)F)cc2-c2ccc(-c3cccc(S(C)(=O)=O)c3)cc2)CC1] | 1-methyl-4-(2-{5-[3'-(methylsulfonyl)biphenyl-4-yl]-3-(trifluoromethyl)-1H-pyrazol-1-yl}ethyl)piperazine |
| 1224 | 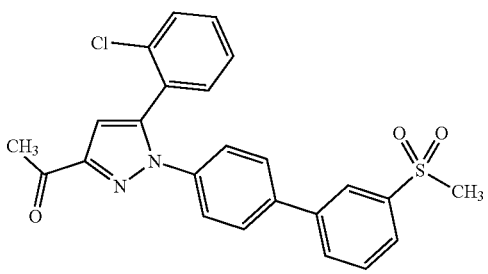 [SMILES: CC(=O)c1cc(-c2ccccc2Cl)n(-c2ccc(-c3cccc(S(C)(=O)=O)c3)cc2)n1] | 1-{5-(2-chlorophenyl)-1-[3'-(methylsulfonyl)biphenyl-4-yl]-1H-pyrazol-3-yl}ethanone |
| 1225 | 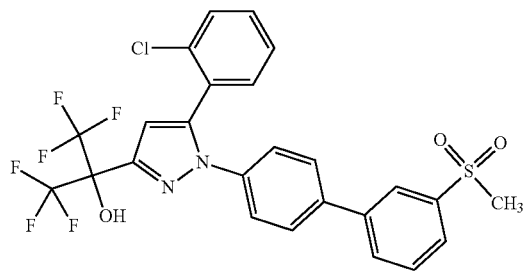 [SMILES: CS(=O)(=O)c1cccc(-c2ccc(-n3nc(C(O)(C(F)(F)F)C(F)(F)F)cc3-c3ccccc3Cl)cc2)c1] | 2-{5-(2-chlorophenyl)-1-[3'-(methylsulfonyl)biphenyl-4-yl]-1H-pyrazol-3-yl}-1,1,1,3,3,3-hexafluoropropan-2-ol |
| 1226 | 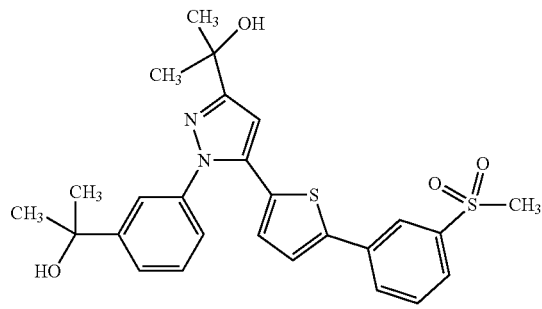 [SMILES: CC(C)(O)c1cccc(-n2nc(C(C)(C)O)cc2-c2ccc(-c3cccc(S(C)(=O)=O)c3)s2)c1] | 2-{3-[3-(1-hydroxy-1-methylethyl)-5-{5-[3-(methylsulfonyl)phenyl]-2-thienyl}-1H-pyrazol-1-yl]phenyl}propan-2-ol |
| 1227 | 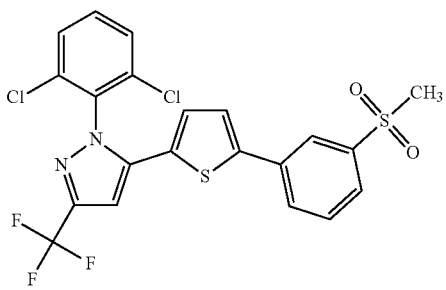 [SMILES: CS(=O)(=O)c1cccc(-c2ccc(-c3cc(C(F)(F)F)nn3-c3c(Cl)cccc3Cl)s2)c1] | 1-(2,6-dichlorophenyl)-5-{5-[3-(methylsulfonyl)phenyl]-2-thienyl}-3-(trifluoromethyl)-1H-pyrazole |

TABLE 1-continued

| 1228 |  | 1-[1-(2-chlorophenyl)-5-{5-[3-(methylsulfonyl)phenyl]-2-thienyl}-1H-pyrazol-3-yl]cyclopentanol |
| 1229 | 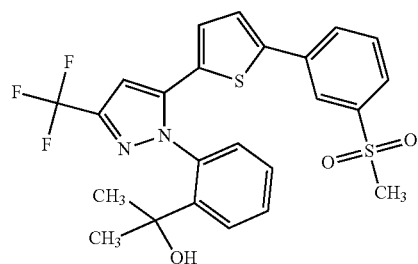 [SMILES: CC(C)(O)c1ccccc1-n1nc(C(F)(F)F)cc1-c1ccc(-c2cccc(S(C)(=O)=O)c2)s1] | 2-{2-[5-{5-[3-(methylsulfonyl)phenyl]-2-thienyl}-3-(trifluoromethyl)-1H-pyrazol-1-yl[phenyl}propan-2-ol |
| 1230 | 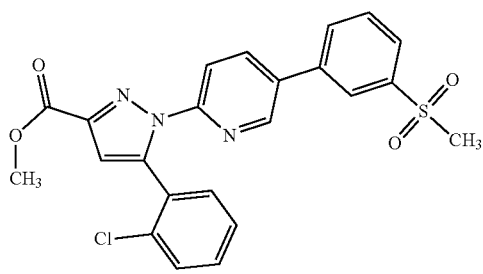 [SMILES: COC(=O)c1cc(-c2ccccc2Cl)n(-c2ccc(-c3cccc(S(C)(=O)=O)c3)cn2)n1] | methyl 5-(2-chlorophenyl)-1-{5-[3-(methylsulfonyl)phenyl]pyridin-2-yl}-1H-pyrazole-3-carboxylate |
| 1231 | 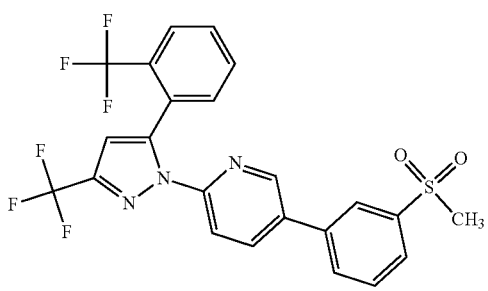 [SMILES: CS(=O)(=O)c1cccc(-c2ccc(-n3nc(C(F)(F)F)cc3-c3ccccc3C(F)(F)F)nc2)c1] | 5-[3-(methylsulfonyl)phenyl]-2-{3-(trifluoromethyl)-5-[2-(trifluoromethyl)phenyl]-1H-pyrazol-1-yl}pyridine |
| 1232 | 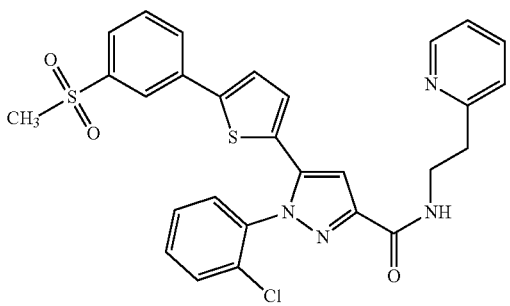 [SMILES: CS(=O)(=O)c1cccc(-c2ccc(-c3cc(C(=O)NCCc4ccccn4)nn3-c3ccccc3Cl)s2)c1] | 1-(2-chlorophenyl)-5-{5-[3-(methylsulfonyl)phenyl]-2-thienyl}-N-(2-pyridin-2-ylethyl)-1H-pyrazole-3-carboxamide |
| 1233 | 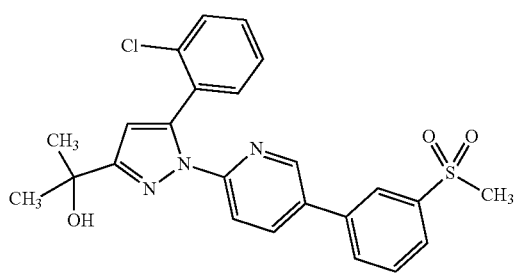 [SMILES: CC(C)(O)c1cc(-c2ccccc2Cl)n(-c2ccc(-c3cccc(S(C)(=O)=O)c3)cn2)n1] | 2-[5-(2-chlorophenyl)-1-{5-[3-(methylsulfonyl)phenyl]pyridin-2-yl}-1H-pyrazol-3-yl]propan-2-ol |

TABLE 1-continued

| | | |
|---|---|---|
| 1234 | 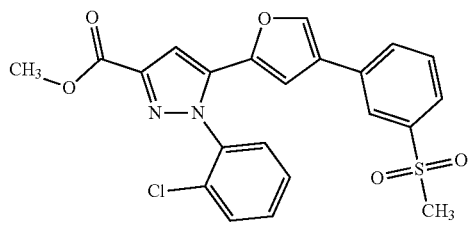 [SMILES: COC(=O)c1cc(-c2cc(-c3cccc(S(C)(=O)=O)c3)co2)n(-c2ccccc2Cl)n1] | methyl 1-(2-chlorophenyl)-5-{4-[3-(methylsulfonyl)phenyl]furan-2-yl}-1H-pyrazole-3-carboxylate |
| 1235 | 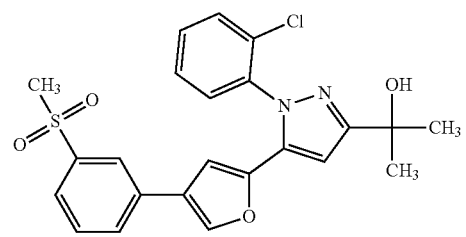 [SMILES: CC(C)(O)c1cc(-c2cc(-c3cccc(S(C)(=O)=O)c3)co2)n(-c2ccccc2Cl)n1] | 2-[1-(2-chlorophenyl)-5-{4-[3-(methylsulfonyl)phenyl]furan-2-yl}-1H-pyrazol-3-yl]propan-2-ol |
| 1236 | 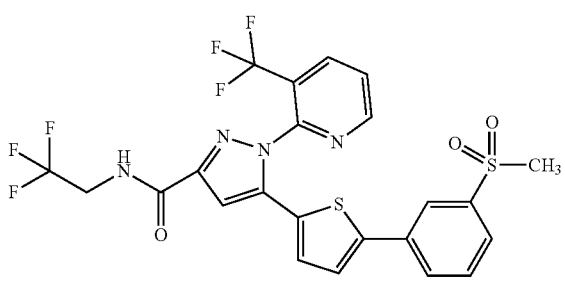 [SMILES: CS(=O)(=O)c1cccc(-c2ccc(-c3cc(C(=O)NCC(F)(F)F)nn3-c3ncccc3C(F)(F)F)s2)c1] | 5-{5-[3-(methylsulfonyl)phenyl]-2-thienyl}-N-(2,2,2-trifluoroethyl)-1-[3-(trifluoromethyl)pyridin-2-yl]-1H-pyrazole-3-carboxamide |
| 1237 | 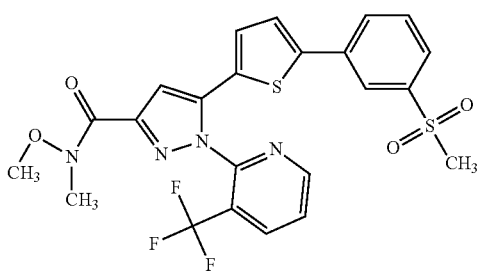 [SMILES: CON(C)C(=O)c1cc(-c2ccc(-c3cccc(S(C)(=O)=O)c3)s2)n(-c2ncccc2C(F)(F)F)n1] | N-methyl-N-(methyloxy)-5-{5-[3-(methylsulfonyl)phenyl]-2-thienyl}-1-[3-(trifluoromethyl)pyridin-2-yl]-1H-pyrazole-3-carboxamide |
| 1238 | 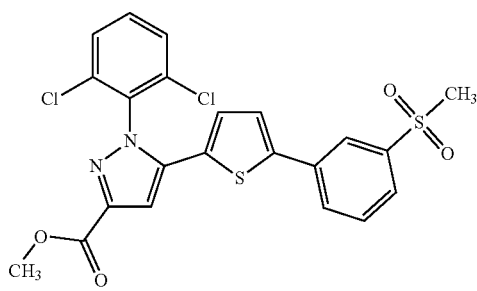 | methyl 1-(2,6-dichlorophenyl)-5-{5-[3-(methylsulfonyl)phenyl]-2-thienyl}-1H-pyrazole-3-carboxylate |
| 1239 | 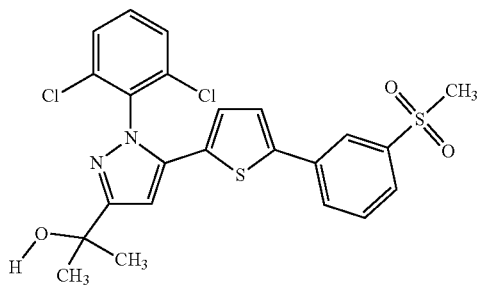 [SMILES: CC(C)(O)c1cc(-c2ccc(-c3cccc(S(C)(=O)=O)c3)s2)n(-c2c(Cl)cccc2Cl)n1] | 2-[1-(2,6-dichlorophenyl)-5-{5-[3-(methylsulfonyl)phenyl]-2-thienyl}-1H-pyrazol-3-yl]propan-2-ol |

TABLE 1-continued

| | | |
|---|---|---|
| 1240 | 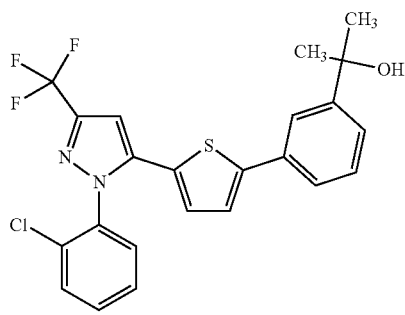 [SMILES: CC(C)(O)c1cccc(-c2ccc(-c3cc(C(F)(F)F)nn3-c3ccccc3Cl)s2)c1] | 2-(3-{5-[1-(2-chlorophenyl)-3-(trifluoromethyl)-1H-pyrazol-5-yl]-2-thienyl}phenyl)propan-2-ol |
| 1241 | 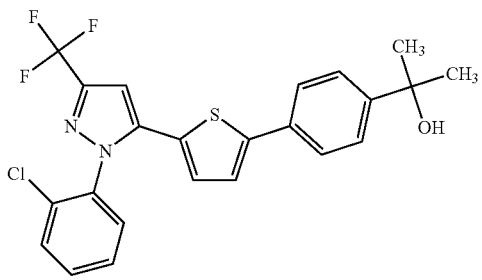 [SMILES: CC(C)(O)c1ccc(-c2ccc(-c3cc(C(F)(F)F)nn3-c3ccccc3Cl)s2)cc1] | 2-(4-{5-[1-(2-chlorophenyl)-3-(trifluoromethyl)-1H-pyrazol-5-yl]-2-thienyl}phenyl)propan-2-ol |
| 1242 | 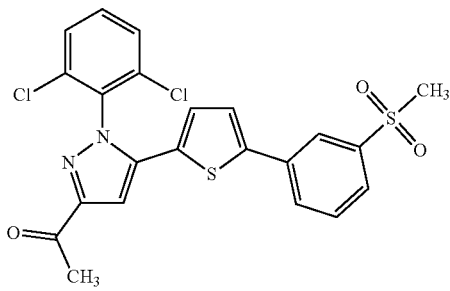 [SMILES: CC(=O)c1cc(-c2ccc(-c3cccc(S(C)(=O)=O)c3)s2)n(-c2c(Cl)cccc2Cl)n1] | 1-[1-(2,6-dichlorophenyl)-5-{5-[3-(methylsulfonyl)phenyl]-2-thienyl}-1H-pyrazol-3-yl]ethanone |
| 1243 | 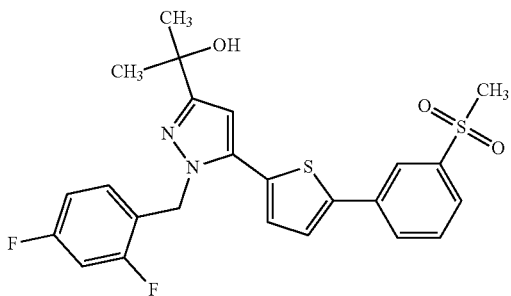 [SMILES: CC(C)(O)c1cc(-c2ccc(-c3cccc(S(C)(=O)=O)c3)s2)n(Cc2ccc(F)cc2F)n1] | 2-(1-[(2,4-difluorophenyl)methyl]-5-{5-[3-(methylsulfonyl)phenyl]-2-thienyl}-1H-pyrazol-3-yl)propan-2-ol |
| 1244 | 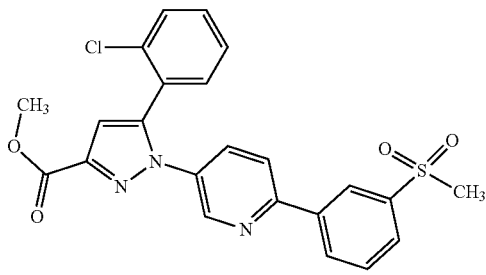 [SMILES: COC(=O)c1cc(-c2ccccc2Cl)n(-c2ccc(-c3cccc(S(C)(=O)=O)c3)nc2)n1] | methyl 5-(2-chlorophenyl)-1-{6-[3-(methylsulfonyl)phenyl]pyridin-3-yl}-1H-pyrazole-3-carboxylate |

TABLE 1-continued

| | | |
|---|---|---|
| 1245 | 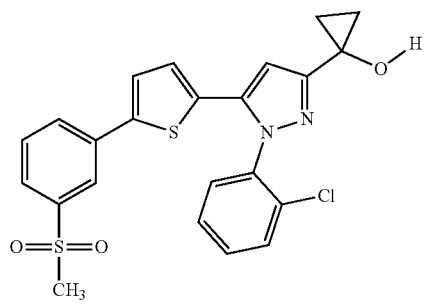 [SMILES: CS(=O)(=O)c1cccc(-c2ccc(-c3cc(C4(O)CC4)nn3-c3ccccc3Cl)s2)c1] | 1-[1-(2-chlorophenyl)-5-{5-[3-(methylsulfonyl)phenyl]-2-thienyl}-1H-pyrazol-3-yl]cyclopropanol |
| 1246 | 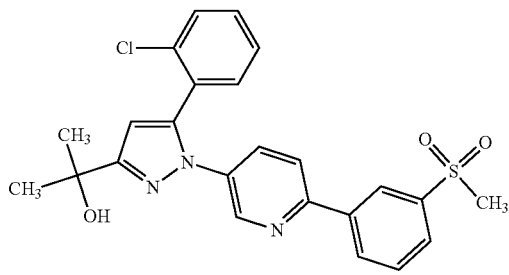 [SMILES: CC(C)(O)c1cc(-c2ccccc2Cl)n(-c2ccc(-c3cccc(S(C)(=O)=O)c3)nc2)n1] | 2-[5-(2-chlorophenyl)-1-(6-[3-(methylsulfonyl)phenyl]pyridin-3-yl}-1H-pyrazol-3-yl]propan-2-ol |
| 1247 | 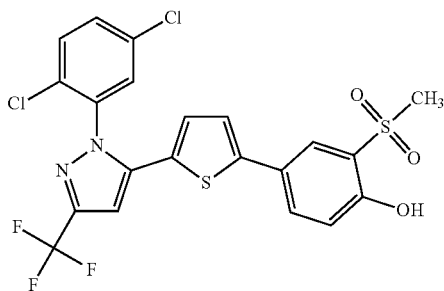 [SMILES: CS(=O)(=O)c1cc(-c2ccc(-c3cc(C(F)(F)F)nn3-c3cc(Cl)ccc3Cl)s2)ccc1O] | 4-{5-[1-(2,5-dichlorophenyl)-3-(trifluoromethyl)-1H-pyrazol-5-yl]-2-thienyl}-2-(methylsulfonyl)phenol |
| 1248 | 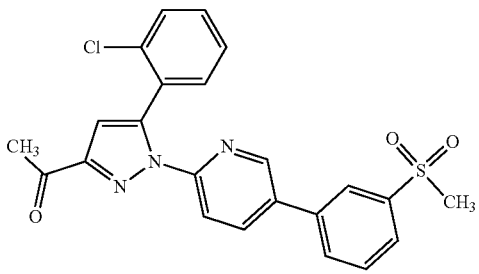 [SMILES: CC(=O)c1cc(-c2ccccc2Cl)n(-c2ccc(-c3cccc(S(C)(=O)=O)c3)cn2)n1] | 1-[5-(2-chlorophenyl)-1-(5-[3-(methylsulfonyl)phenyl]pyridin-2-yl}-1H-pyrazol-3-yl]ethanone |
| 1249 | 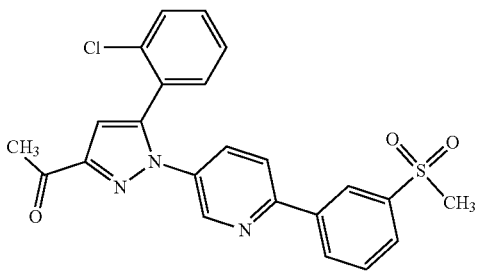 [SMILES: CC(=O)c1cc(-c2ccccc2Cl)n(-c2ccc(-c3cccc(S(C)(=O)=O)c3)nc2)n1] | 1-[5-(2-chlorophenyl)-1-{6-[3-(methylsulfonyl)phenyl]pyridin-3-yl}-1H-pyrazol-3-yl]ethanone |

TABLE 1-continued

| | | |
|---|---|---|
| 1250 | 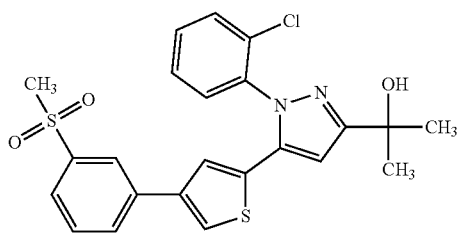 [SMILES: CC(C)(O)c1cc(-c2cc(-c3cccc(S(C)(=O)=O)c3)cs2)n(-c2ccccc2Cl)n1] | 2-[1-(2-chlorophenyl)-5-{4-[3-(methylsulfonyl)phenyl]-2-thienyl}-1H-pyrazol-3-yl]propan-2-ol |
| 1251 | 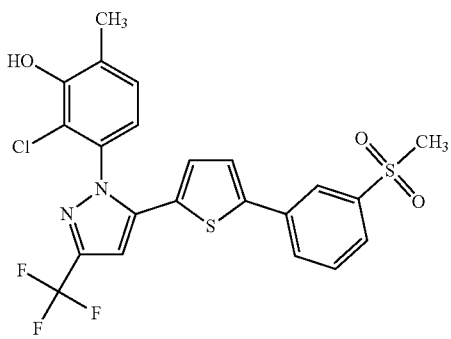 [SMILES: Cc1ccc(-n2nc(C(F)(F)F)cc2-c2ccc(-c3cccc(S(C)(=O)=O)c3)s2)c(Cl)c1O] | 2-chloro-6-methyl-3-[5-{5-[3-(methylsulfonyl)phenyl]-2-thienyl}-3-(trifluoromethyl)-1H-pyrazol-1-yl]phenol |
| 1252 | 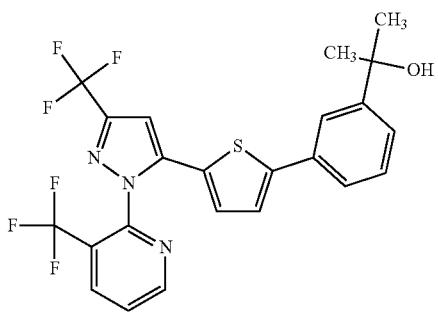 [SMILES: CC(C)(O)c1cccc(-c2ccc(-c3cc(C(F)(F)F)nn3-c3ncccc3C(F)(F)F)s2)c1] | 2-[3-(5-{3-(trifluoromethyl)-1-[3-(trifluoromethyl)pyridin-2-yl]-1H-pyrazol-5-yl}-2-thienyl)phenyl]propan-2-ol |
| 1253 | 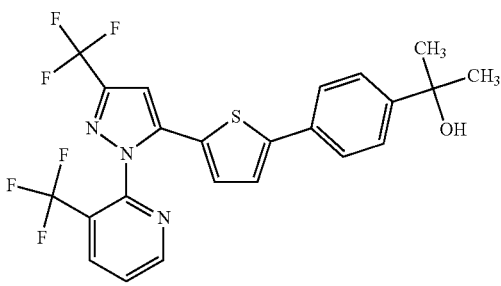 [SMILES: CC(C)(O)c1ccc(-c2ccc(-c3cc(C(F)(F)F)nn3-c3ncccc3C(F)(F)F)s2)cc1] | 2-[4-(5-{3-(trifluoromethyl)-1-[3-(trifluoromethyl)pyridin-2-yl]-1H-pyrazol-5-yl}-2-thienyl)phenyl]propan-2-ol |
| 1254 | 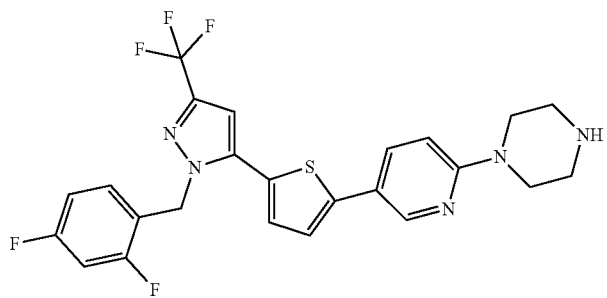 [SMILES: Fc1ccc(Cn2nc(C(F)(F)F)cc2-c2ccc(-c3ccc(N4CCNCC4)nc3)s2)c(F)c1] | 1-[5-(5-{1-[(2,4-difluorophenyl)methyl]-3-(trifluoromethyl)-1H-pyrazol-5-yl}-2-thienyl)pyridin-2-yl]pyridine |

TABLE 1-continued

| | | |
|---|---|---|
| 1255 | | 2-{[4-{5-[1-(2,5-dichlorophenyl)-3-(trifluoromethyl)-1H-pyrazol-5-yl]-2-thienyl}-2-(methylsulfonyl)phenyl]oxy}ethanol |
| 1256 | | 2-[1-(3-chlorophenyl)-5-{5-[3-(methylsulfonyl)phenyl]-2-thienyl}-1H-pyrazol-3-yl]propan-2-ol |
| 1257 | | 2-[1-(4-chlorophenyl)-5-{5-[3-(methylsulfonyl)phenyl]-2-thienyl}-1H-pyrazol-3-yl]propan-2-ol |
| 1258 | | 2-[1-(3-fluorophenyl)-5-{5-[3-(methylsulfonyl)phenyl]-2-thienyl}-1H-pyrazol-3-yl]propan-2-ol |
| 1259 | | 4-(2-{[4-{5-[1-(2,5-dichlorophenyl)-3-(trifluoromethyl)-1H-pyrazol-5-yl]-2-thienyl}-2-(methylsulfonyl)phenyl]oxy}ethyl)morpholine |

TABLE 1-continued

| | | |
|---|---|---|
| 1260 | 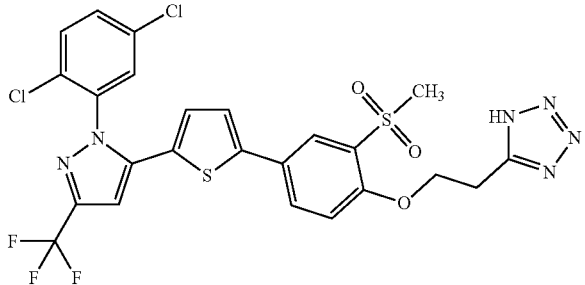 [SMILES: CS(=O)(=O)c1cc(-c2ccc(-c3cc(C(F)(F)F)nn3-c3cc(Cl)ccc3Cl)s2)ccc1OCCc1nnn[nH]1] | 5-(2-{[4-{5-[1-(2,5-dichlorophenyl)-3-(trifluoromethyl)-1H-pyrazol-5-yl]-2-thienyl}-2-(methylsulfonyl)phenyl]oxy}ethyl)-1H-tetrazole |
| 1261 | 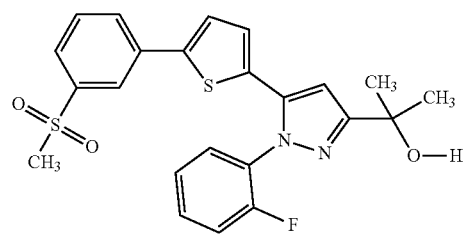 [SMILES: CC(C)(O)c1cc(-c2ccc(-c3cccc(S(C)(=O)=O)c3)s2)n(-c2ccccc2F)n1] | 2-[1-(2-fluorophenyl)-5-{5-[3-(methylsulfonyl)phenyl]-2-thienyl}-1H-pyrazol-3-yl]propan-2-ol |
| 1262 | 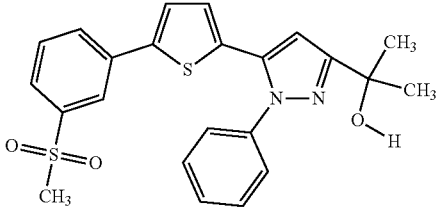 [SMILES: CC(C)(O)c1cc(-c2ccc(-c3cccc(S(C)(=O)=O)c3)s2)n(-c2ccccc2)n1] | 2-(5-{5-[3-(methylsulfonyl)phenyl]-2-thienyl}-1-phenyl-1H-pyrazol-3-yl)propan-2-ol |
| 1263 | 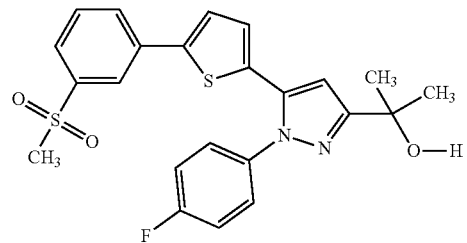 [SMILES: CC(C)(O)c1cc(-c2ccc(-c3cccc(S(C)(=O)=O)c3)s2)n(-c2ccc(F)cc2)n1] | 2-[1-(4-fluorophenyl)-5-{5-[3-(methylsulfonyl)phenyl]-2-thienyl}-1H-pyrazol-3-yl]propan-2-ol |
| 1264 | 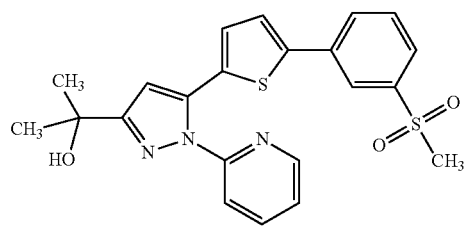 [SMILES: CC(C)(O)c1cc(-c2ccc(-c3cccc(S(C)(=O)=O)c3)s2)n(-c2ccccn2)n1] | 2-(5-{5-[3-(methylsulfonyl)phenyl]-2-thienyl}-1-pyridin-2-yl-1H-pyrazol-3-yl)propan-2-ol |
| 1265 | 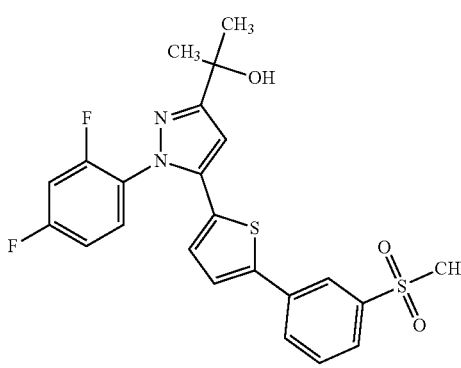 | 2-[1-(2,4-difluorophenyl)-5-{5-[3-(methylsulfonyl)phenyl]-2-thienyl}-1H-pyrazol-3-yl]propan-2-ol |

TABLE 1-continued

| | | |
|---|---|---|
| 1266 | 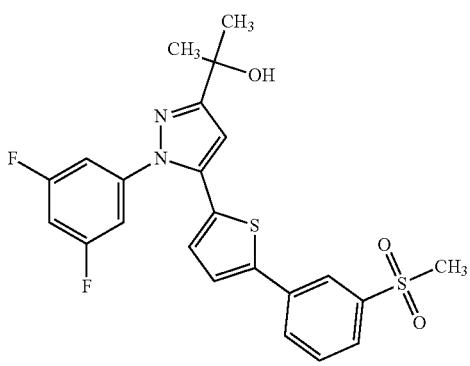 [SMILES: CC(C)(O)c1cc(-c2ccc(-c3cccc(S(C)(=O)=O)c3)s2)n(-c2cc(F)cc(F)c2)n1] | 2-[1-(3,5-dichlorophenyl)-5-{5-[3-(methylsulfonyl)phenyl]-2-thienyl}-1H-pyrazol-3-yl]propan-2-ol |
| 1267 | 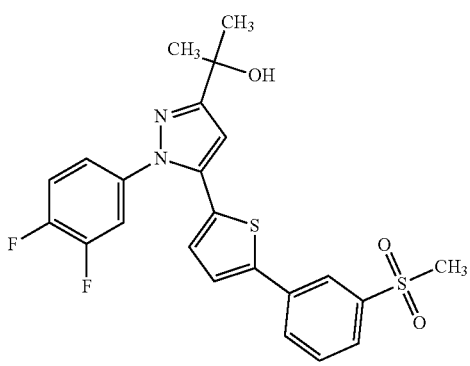 [SMILES: CC(C)(O)c1cc(-c2ccc(-c3cccc(S(C)(=O)=O)c3)s2)n(-c2ccc(F)c(F)c2)n1] | 2-[1-(3,4-difluorophenyl)-5-{5-[3-(methylsulfonyl)phenyl]-2-thienyl}-1H-pyrazol-3-yl]propan-2-ol |
| 1268 | 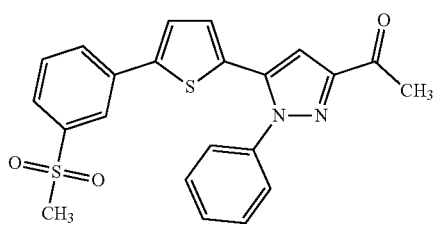 [SMILES: CC(=O)c1cc(-c2ccc(-c3cccc(S(C)(=O)=O)c3)s2)n(-c2ccccc2)n1] | 1-(5-{5-[3-(methylsulfonyl)phenyl]-2-thienyl}-1-phenyl-1H-pyrazol-3-yl)ethanone |
| 1269 | 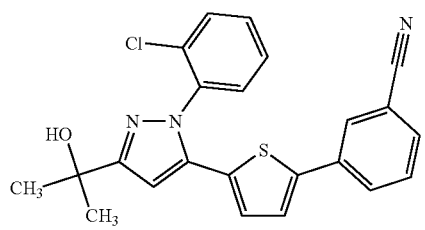 [SMILES: CC(C)(O)c1cc(-c2ccc(-c3cccc(C#N)c3)s2)n(-c2ccccc2Cl)n1] | 3-{5-[1-(2-chlorophenyl)-3-(1-hydroxy-1-methylethyl)-1H-pyrazol-5-yl]-2-thienyl}benzonitrile |
| 1270 | 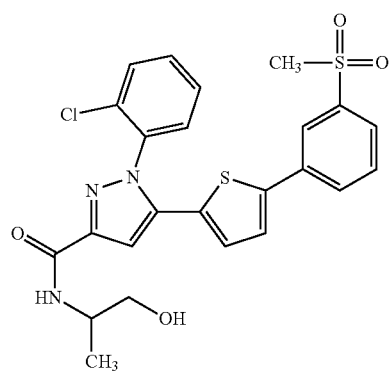 [SMILES: CC(CO)NC(=O)c1cc(-c2ccc(-c3cccc(S(C)(=O)=O)c3)s2)n(-c2ccccc2Cl)n1] | 1-(2-chlorophenyl)-N-(2-hydroxy-1-methylethyl)-5-{5-[3-(methylsulfonyl)phenyl]-2-thienyl}-1H-pyrazole-3-carboxamide |

| | | |
|---|---|---|
| 1271 | 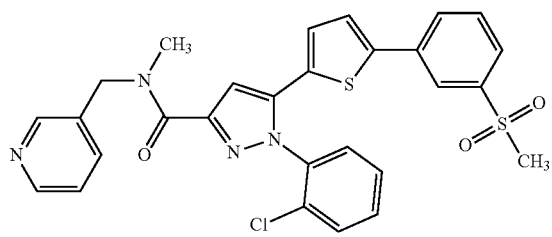 [SMILES: CN(Cc1cccnc1)C(=O)c1cc(-c2ccc(-c3cccc(S(C)(=O)=O)c3)s2)n(-c2ccccc2Cl)n1] | 1-(2-chlorophenyl)-N-methyl-5-{5-[3-(methylsulfonyl)phenyl]-2-thienyl}-N-(pyridin-3-ylmethyl)-1H-pyrazole-3-carboxamide |
| 1272 | 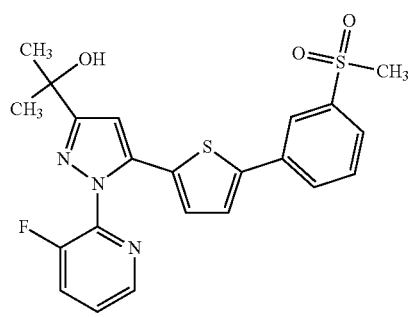 [SMILES: CC(C)(O)c1cc(-c2ccc(-c3cccc(S(C)(=O)=O)c3)s2)n(-c2ncccc2F)n1] | 2-[1-(3-fluoropyridin-2-yl)-5-{5-[3-(methylsulfonyl)phenyl]-2-thienyl}-1H-pyrazol-3-yl]propan-2-ol |
| 1273 | 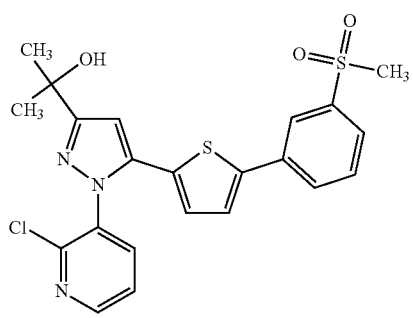 [SMILES: CC(C)(O)c1cc(-c2ccc(-c3cccc(S(C)(=O)=O)c3)s2)n(-c2cccnc2Cl)n1] | 2-[1-(2-chloropyridin-3-yl)-5-{5-[3-(methylsulfonyl)phenyl]-2-thienyl}-1H-pyrazol-3-yl]propan-2-ol |
| 1274 | 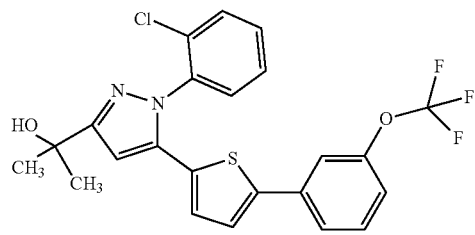 [SMILES: CC(C)(O)c1cc(-c2ccc(-c3cccc(OC(F)(F)F)c3)s2)n(-c2ccccc2Cl)n1] | 2-[1-(2-chlorophenyl)-5-(5-{3-[(trifluoromethyl)oxy]phenyl}-2-thienyl)-1H-pyrazol-3-yl]propan-2-ol |
| 1275 | 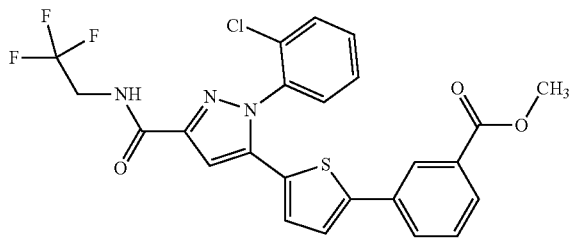 [SMILES: COC(=O)c1cccc(-c2ccc(-c3cc(C(=O)NCC(F)(F)F)nn3-c3ccccc3Cl)s2)c1] | methyl 3-{5-[1-(2-chlorophenyl)-3-{[(2,2,2-trifluoroethyl)amino]carbonyl}-1H-pyrazol-5-yl]-2-thienyl}benzoate |
| 1276 | 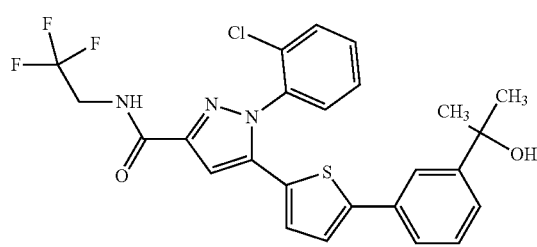 [SMILES: CC(C)(O)c1cccc(-c2ccc(-c3cc(C(=O)NCC(F)(F)F)nn3-c3ccccc3Cl)s2)c1] | 1-(2-chlorophenyl)-5-{5-[3-(1-hydroxy-1-methylethyl)phenyl]-2-thienyl}-N-(2,2,2-trifluoroethyl)-1H-pyrazole-3-carboxamide |

TABLE 1-continued

| # | Structure | Name |
|---|---|---|
| 1277 | 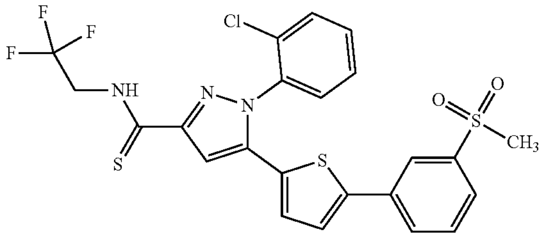 [SMILES: CS(=O)(=O)c1cccc(-c2ccc(-c3cc(C(=S)NCC(F)(F)F)nn3-c3ccccc3Cl)s2)c1] | 1-(2-chlorophenyl)-5-{5-[3-(methylsulfonyl)phenyl]-2-thienyl}-N-(2,2,2-trifluoromethyl)-1H-pyrazole-3-carbothioamide |
| 1278 | 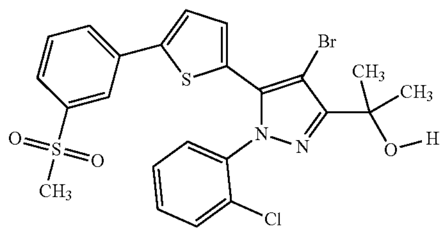 [SMILES: CC(C)(O)c1nn(-c2ccccc2Cl)c(-c2ccc(-c3cccc(S(C)(=O)=O)c3)s2)c1Br] | 2-[4-bromo-1-(2-chlorophenyl)-5-{5-[3-(methylsulfonyl)phenyl]-2-thienyl}-1H-pyrazol-3-yl]propan-2-ol |
| 1279 | 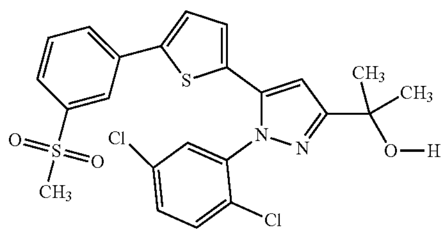 [SMILES: CC(C)(O)c1cc(-c2ccc(-c3cccc(S(C)(=O)=O)c3)s2)n(-c2cc(Cl)ccc2Cl)n1] | 2-[1-(2,5-dichlorophenyl)-5-{5-[3-(methylsulfonyl)phenyl]-2-thienyl}-1H-pyrazol-3-yl]propan-2-ol |
| 1280 | 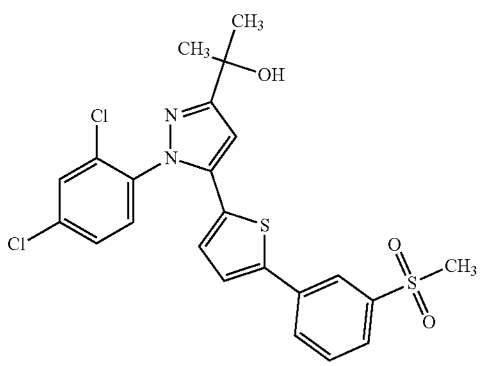 [SMILES: CC(C)(O)c1cc(-c2ccc(-c3cccc(S(C)(=O)=O)c3)s2)n(-c2ccc(Cl)cc2Cl)n1] | 2-[1-(2,4-dichlorophenyl)-5-{5-[3-(methylsulfonyl)phenyl]-2-thienyl}-1H-pyrazol-3-yl]propan-2-ol |
| 1281 | 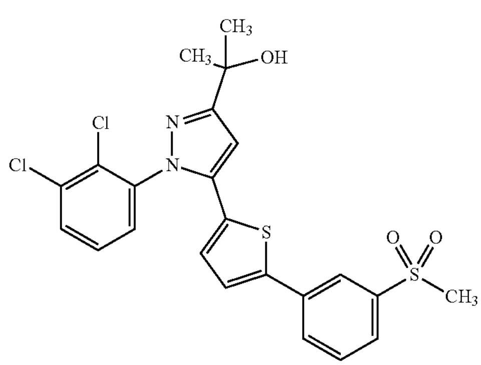 [SMILES: CC(C)(O)c1cc(-c2ccc(-c3cccc(S(C)(=O)=O)c3)s2)n(-c2cccc(Cl)c2Cl)n1] | 2-[1-(2,3-dichlorophenyl)-5-{5-[3-(methylsulfonyl)phenyl]-2-thienyl}-1H-pyrazol-3-yl]propan-2-ol |

| | | |
|---|---|---|
| 1282 | 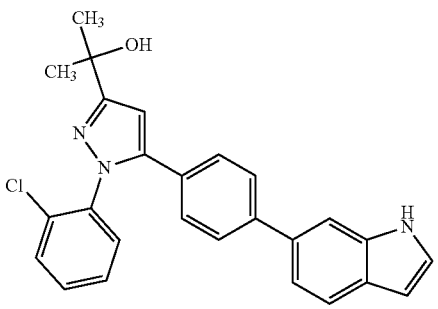 [SMILES: CC(C)(O)c1cc(-c2ccc(-c3ccc4cc[nH]c4c3)cc2)n(-c2ccccc2Cl)n1] | 2-{1-(2-chlorophenyl)-5-[4-(1H-indol-6-yl)phenyl]-1H-pyrazol-3-yl}propan-2-ol |
| 1283 | 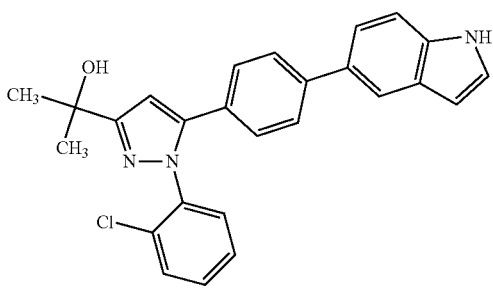 [SMILES: CC(C)(O)c1cc(-c2ccc(-c3ccc4[nH]ccc4c3)cc2)n(-c2ccccc2Cl)n1] | 2-{1-(2-chlorophenyl)-5-[4-(1H-indol-5-yl)phenyl]-1H-pyrazol-3-yl}propan-2-ol |
| 1284 | 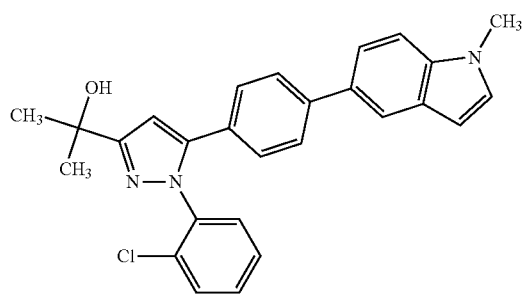 [SMILES: Cn1ccc2cc(-c3ccc(-c4cc(C(C)(C)O)nn4-c4ccccc4Cl)cc3)ccc21] | 2-{1-(2-chlorophenyl)-5-[4-(1-methyl-1H-indol-5-yl)phenyl]-1H-pyrazol-3-yl}propan-2-ol |
| 1285 | 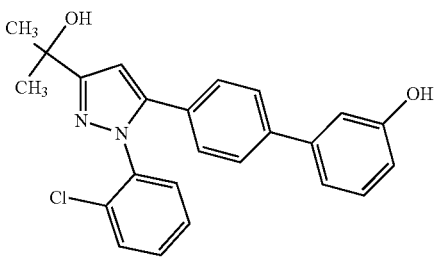 [SMILES: CC(C)(O)c1cc(-c2ccc(-c3cccc(O)c3)cc2)n(-c2ccccc2Cl)n1] | 4'-[1-(2-chlorophenyl)-3-(1-hydroxy-1-methylethyl)-1H-pyrazol-5-yl]biphenyl-3-ol |
| 1286 | 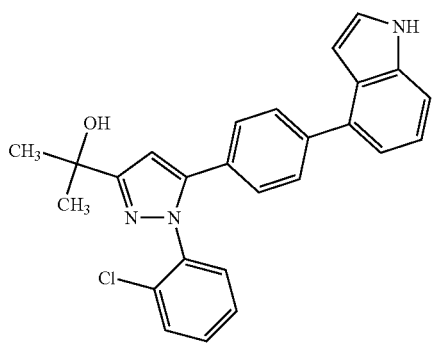 [SMILES: CC(C)(O)c1cc(-c2ccc(-c3cccc4[nH]ccc34)cc2)n(-c2ccccc2Cl)n1] | 2-{1-(2-chlorophenyl)-5-[4-(1H-indol-4-yl)phenyl]-1H-pyrazol-3-yl}propan-2-ol |

TABLE 1-continued

| | | |
|---|---|---|
| 1287 | 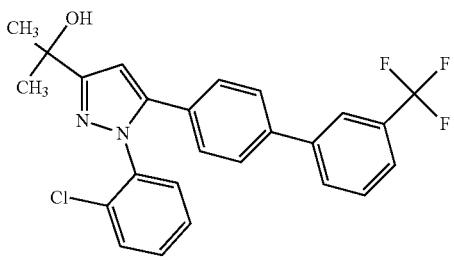 [SMILES: CC(C)(O)c1cc(-c2ccc(-c3cccc(C(F)(F)F)c3)cc2)n(-c2ccccc2Cl)n1] | 2-{1-(2-chlorophenyl)-5-[3'-(trifluoromethyl)biphenyl-4-yl]-1H-pyrazol-3-yl}propan-2-ol |
| 1288 | 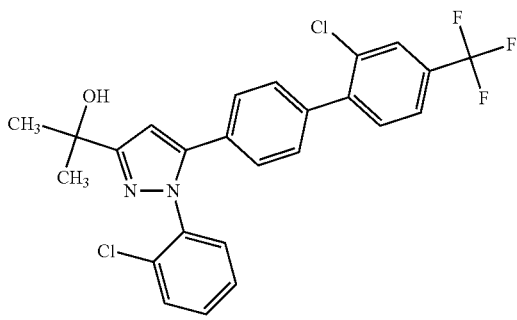 [SMILES: CC(C)(O)c1cc(-c2ccc(-c3ccc(C(F)(F)F)cc3Cl)cc2)n(-c2ccccc2Cl)n1] | 2-{1-(2-chlorophenyl)-5-[2'-chloro-4'-(trifluoromethyl)biphenyl-4-yl]-1H-pyrazol-3-yl}propan-2-ol |
| 1289 | 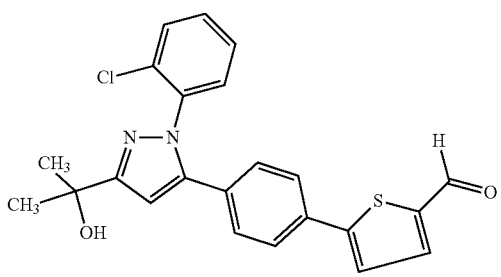 [SMILES: CC(C)(O)c1cc(-c2ccc(-c3ccc(C=O)s3)cc2)n(-c2ccccc2Cl)n1] | 5-{4-[1-(2-chlorophenyl)-3-(1-hydroxy-1-methylethyl)-1H-pyrazol-5-yl]phenyl}thiophene-2-carbaldehyde |
| 1290 | 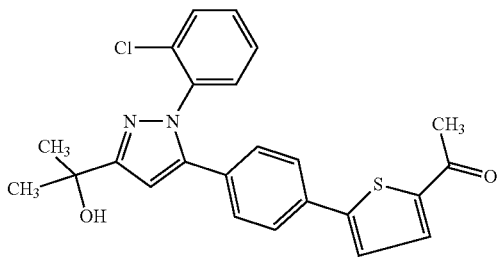 [SMILES: CC(=O)c1ccc(-c2ccc(-c3cc(C(C)(C)O)nn3-c3ccccc3Cl)cc2)s1] | 1-(5-{4-[1-(2-chlorophenyl)-3-(1-hydroxy-1-methylethyl)-1H-pyrazole-5-yl]phenyl}-2-thienyl)ethanone |
| 1291 | 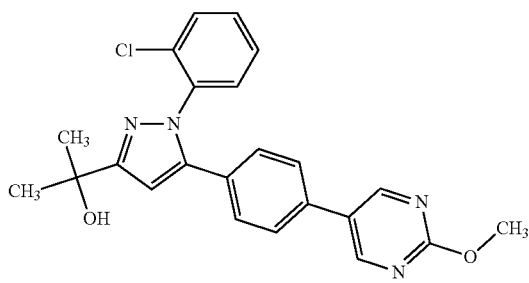 [SMILES: COc1ncc(-c2ccc(-c3cc(C(C)(C)O)nn3-c3ccccc3Cl)cc2)cn1] | 2-[1-(2-chlorophenyl)-5-{4-[2-(methyloxy)pyrimidin-5-yl]phenyl}-1H-pyrazol-3-yl]propan-2-ol |

TABLE 1-continued

| 1292 | 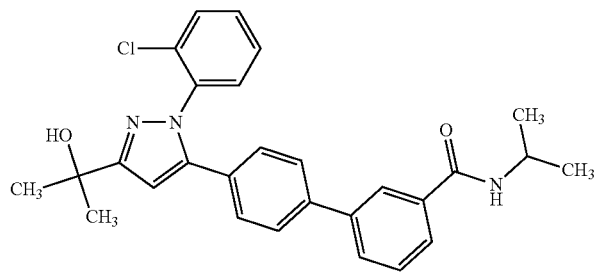 [SMILES: CC(C)NC(=O)c1cccc(-c2ccc(-c3cc(C(C)(C)O)nn3-c3ccccc3Cl)cc2)c1] | 4'-[1-(2-chlorophenyl)-3-(1-hydroxy-1-methylethyl)-1H-pyrazol-5-yl]-N-(1-methylethyl)biphenyl-3-carboxamide |
| 1293 | 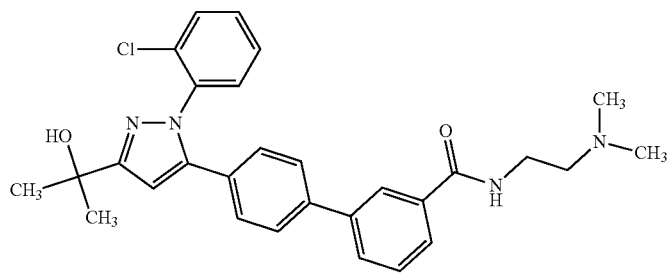 [SMILES: CN(C)CCNC(=O)c1cccc(-c2ccc(-c3cc(C(C)(C)O)nn3-c3ccccc3Cl)cc2)c1] | 4'-[1-(2-chlorophenyl)-3-(1-hydroxy-methylethyl)-1H-pyrazol-5-yl]-N-[2-(dimethylamino)ethyl]biphenyl-3-carboxamide |
| 1294 | 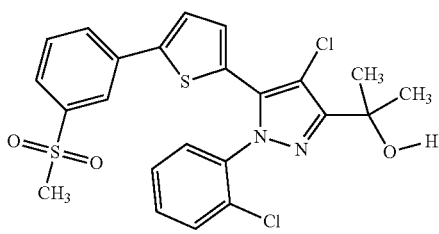 [SMILES: CC(C)(O)c1nn(-c2ccccc2Cl)c(-c2ccc(-c3cccc(S(C)(=O)=O)c3)s2)c1Cl] | 2-[4-chloro-1-(2-chlorophenyl)-5-{5-[3-(methylsulfonyl)phenyl]-2-thienyl}-1H-pyrazol-3-yl]propan-2-ol |
| 1295 | 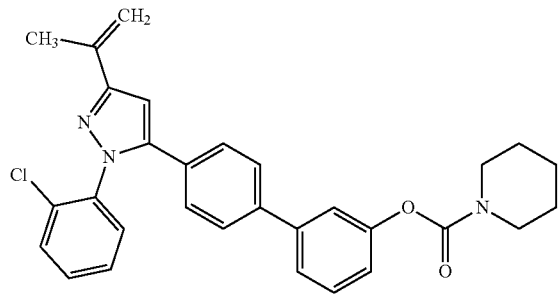 [SMILES: C=C(C)c1cc(-c2ccc(-c3cccc(OC(=O)N4CCCCC4)c3)cc2)n(-c2ccccc2Cl)n1] | 4'-[1-(2-chlorophenyl)-3-(1-methylethyl)-1H-pyrazol-5-yl]biphenyl-3-yl piperidin-1-carboxylate |
| 1296 | 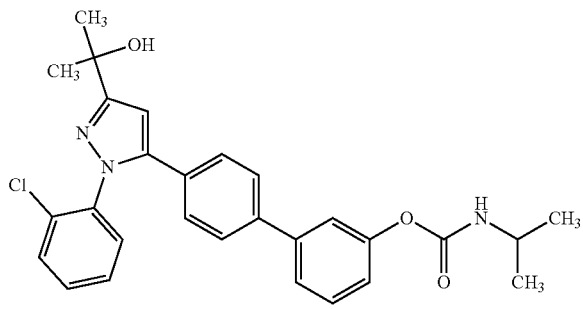 [SMILES: CC(C)NC(=O)Oc1cccc(-c2ccc(-c3cc(C(C)(C)O)nn3-c3ccccc3Cl)cc2)c1] | 4'-[1-(2-chlorophenyl)-3-(1-hydroxy-1-methylethyl)-1H-pyrazol-5-yl]biphenyl-3-yl (1-methylethyl)carbamate |

TABLE 1-continued

| | | |
|---|---|---|
| 1297 | 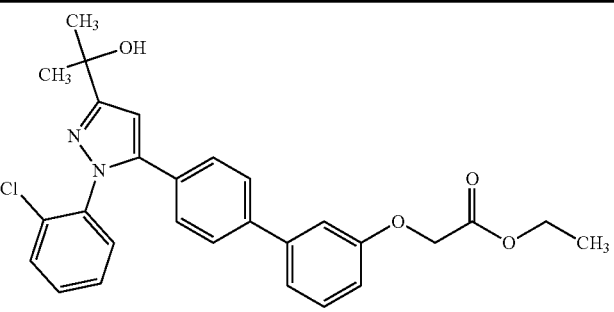 | ethyl ({4'-[1-(2-chlorophenyl)-3-(1-hydroxy-1-methylethyl)-1H-pyrazol-5-yl]biphenyl-3-yl}oxy)acetate |
| 1298 | 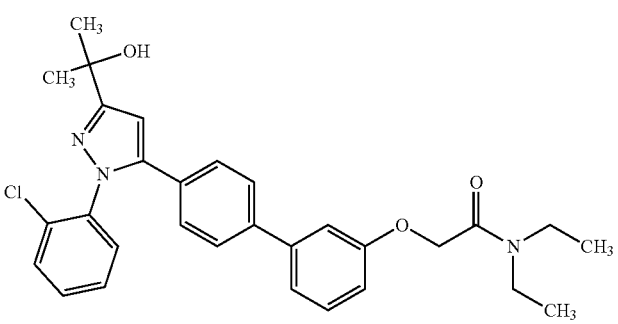 [SMILES: CCN(CC)C(=O)COc1cccc(-c2ccc(-c3cc(C(C)(C)O)nn3-c3ccccc3Cl)cc2)c1] | 2-({4'-[1-(2-chlorophenyl)-3-(1-hydroxy-1-methylethyl)-1H-pyrazol-5-yl]biphenyl-3-yl}oxy)-N,N-diethylacetamide |
| 1299 | 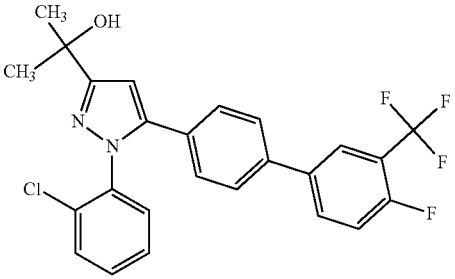 [SMILES: CC(C)(O)c1cc(-c2ccc(-c3ccc(F)c(C(F)(F)F)c3)cc2)n(-c2ccccc2Cl)n1] | 2-{1-(2-chlorophenyl)-5-[4'-fluoro-3'-(trifluoromethyl)biphenyl-4-yl]-1H-pyrazol-3-yl}propan-2-ol |
| 1300 | 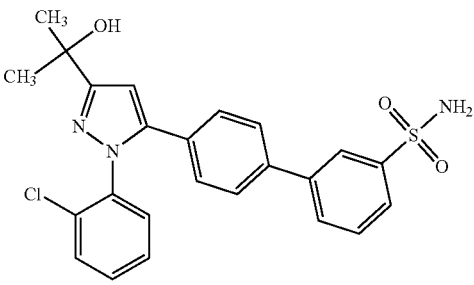 [SMILES: CC(C)(O)c1cc(-c2ccc(-c3cccc(S(N)(=O)=O)c3)cc2)n(-c2ccccc2Cl)n1] | 4'-[1-(2-chlorophenyl)-3-(1-hydroxy-1-methylethyl)-1H-pyrazol-5-yl]biphenyl-3-sulfonamide |
| 1301 | 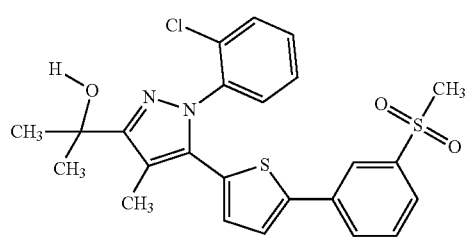 [SMILES: Cc1c(C(C)(C)O)nn(-c2ccccc2Cl)c1-c1ccc(-c2cccc(S(C)(=O)=O)c2)s1] | 2-[1-(2-chlorophenyl)-4-methyl-5-{5-[3-(methylsulfonyl)phenyl]-2-thienyl}-1H-pyrazol-3-yl]propan-2-ol |

| | | |
|---|---|---|
| 1302 | 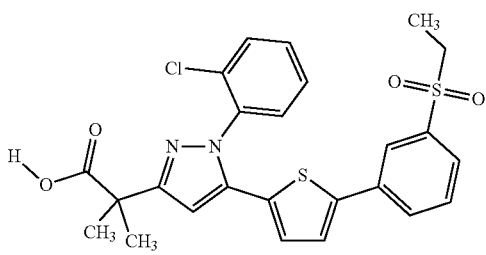 [SMILES: CCS(=O)(=O)c1cccc(-c2ccc(-c3cc(C(C)(C)C(=O)O)nn3-c3ccccc3Cl)s2)c1] | 2-[1-(2-chlorophenyl)-5-{5-[3-(ethylsulfonyl)phenyl]-2-thienyl}-1H-pyrazol-3-yl]-2-methylpropanoic acid |
| 1303 | 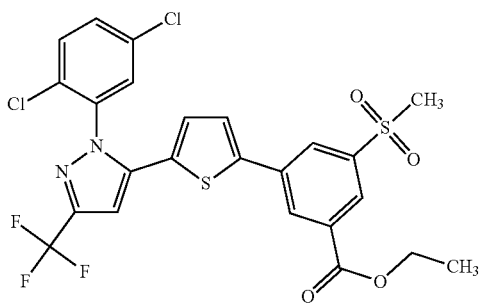 [SMILES: CCOC(=O)c1cc(-c2ccc(-c3cc(C(F)(F)F)nn3-c3cc(Cl)ccc3Cl)s2)cc(S(C)(=O)=O)c1] | ethyl 3-{5-[1-(2,4-dichlorophenyl)-3-(trifluoromethyl)-1H-pyrazol-5-yl]-2-thienyl}-5-(methylsulfonyl)benzoate |
| 1304 | 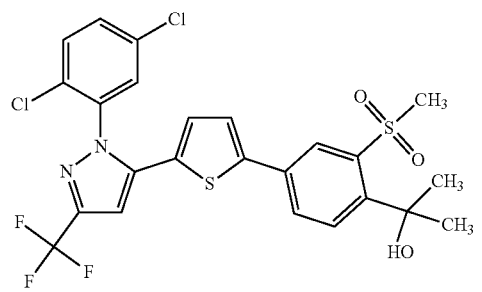 [SMILES: CC(C)(O)c1ccc(-c2ccc(-c3cc(C(F)(F)F)nn3-c3cc(Cl)ccc3Cl)s2)cc1S(C)(=O)=O] | 2-[4-{5-[1-(2,5-dichlorophenyl)-3-(trifluoromethyl)-1H-pyrazol-5-yl]-2-thienyl}-2-(methylsulfonyl)phenyl]propan-2-ol |
| 1305 | 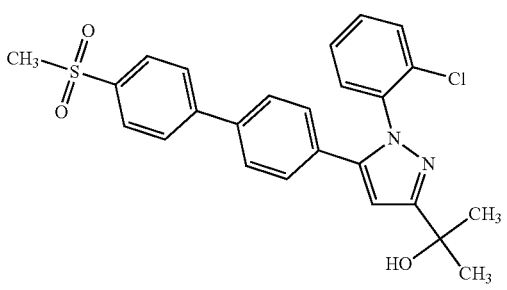 [SMILES: CC(C)(O)c1cc(-c2ccc(-c3ccc(S(C)(=O)=O)cc3)cc2)n(-c2ccccc2Cl)n1] | 2-{1-(2-chlorophenyl)-5-[4'-(methylsulfonyl)biphenyl-4-yl]-1H-pyrazol-3-yl}propan-2-ol |
| 1306 | 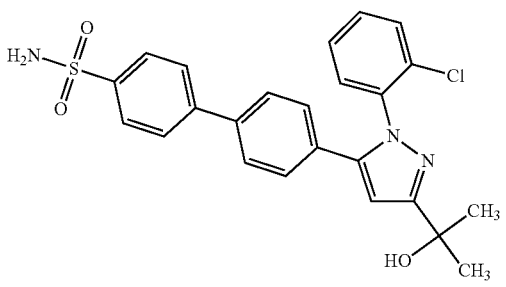 [SMILES: CC(C)(O)c1cc(-c2ccc(-c3ccc(S(N)(=O)=O)cc3)cc2)n(-c2ccccc2Cl)n1] | 4'-[1-(2-chlorophenyl)-3-(1-hydroxy-1-methylethyl)-1H-pyrazol-5-yl]biphenyl-4-sulfonamide |

TABLE 1-continued

| | | |
|---|---|---|
| 1307 | 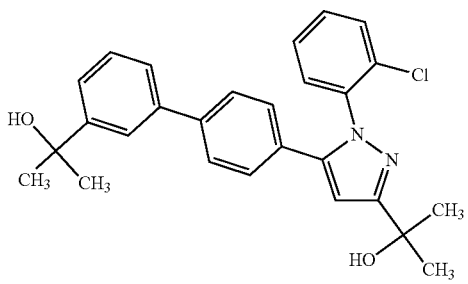 [SMILES: CC(C)(O)c1cccc(-c2ccc(-c3cc(C(C)(C)O)nn3-c3ccccc3Cl)cc2)c1] | 2-{1-(2-chlorophenyl)-5-[3'-(1-hydroxy-1-methylethyl)biphenyl-4-yl]-1H-pyrazol-3-yl}propan-2-ol |
| 1308 | 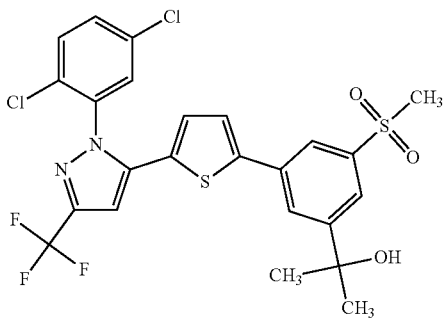 [SMILES: CC(C)(O)c1cc(-c2ccc(-c3cc(C(F)(F)F)nn3-c3cc(Cl)ccc3Cl)s2)cc(S(C)(=O)=O)c1] | 2-[3-{5-[1-(2,5-dichlorophenyl)-3-(trifluoromethyl)-1H-pyrazol-5-yl]-2-thienyl}-5-(methylsulfonyl)phenyl]propan-2-ol |
| 1309 | 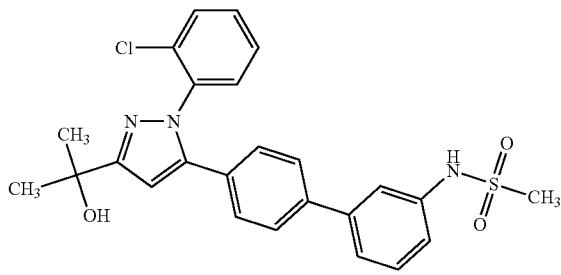 [SMILES: CC(C)(O)c1cc(-c2ccc(-c3cccc(NS(C)(=O)=O)c3)cc2)n(-c2ccccc2Cl)n1] | N-{4'-[1-(2-chlorophenyl)-3-(1-hydroxy-1-methylethyl)-1H-pyrazol-5-yl]biphenyl-3-yl}methanesulfonamide |
| 1310 | 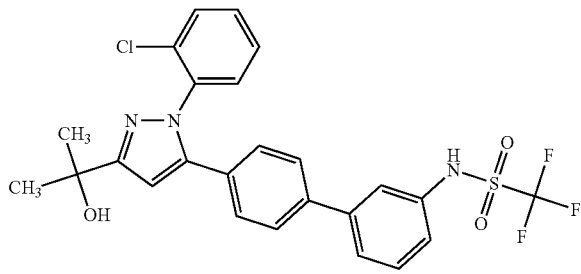 [SMILES: CC(C)(O)c1cc(-c2ccc(-c3cccc(NS(=O)(=O)C(F)(F)F)c3)cc2)n(-c2ccccc2Cl)n1] | N-{4'-[1-(2-chlorophenyl)-3-(1-hydroxy-1-methylethyl)-1H-pyrazol-5-yl]biphenyl-3-yl}-1,1,1-trifluoromethanesulfonamide |
| 1311 | 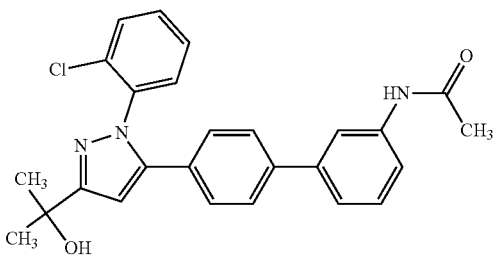 [SMILES: CC(=O)Nc1cccc(-c2ccc(-c3cc(C(C)(C)O)nn3-c3ccccc3Cl)cc2)c1] | N-{4'-[1-(2-chlorophenyl)-3-(1-hydroxy-1-methylethyl)-1H-pyrazol-5-yl]biphenyl-3-yl}acetamide |

TABLE 1-continued

| | | |
|---|---|---|
| 1312 | 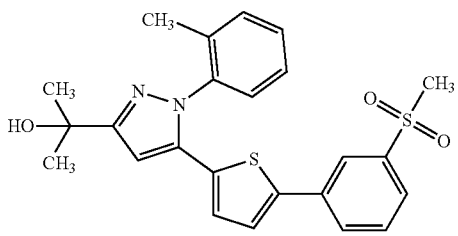 [SMILES: Cc1ccccc1-n1nc(C(C)(C)O)cc1-c1ccc(-c2cccc(S(C)(=O)=O)c2)s1] | 2-[1-(2-methylethyl)-5-{5-[3-(methylsulfonyl)phenyl]-2-thienyl}-1H-pyrazol-3-yl]propan-2-ol |
| 1313 | 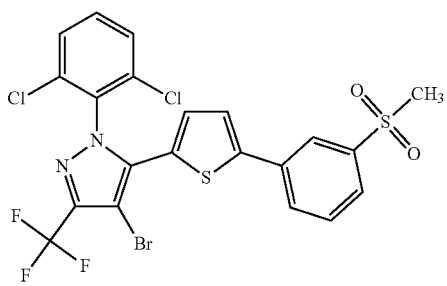 [SMILES: CS(=O)(=O)c1cccc(-c2ccc(-c3c(Br)c(C(F)(F)F)nn3-c3c(Cl)cccc3Cl)s2)c1] | 4-bromo-1-(2,6-dichlorophenyl)-5-{5-[3-(methylsulfonyl)phenyl]-2-thienyl}-3-(trifluoromethyl)-1H-pyrazole |
| 1314 | 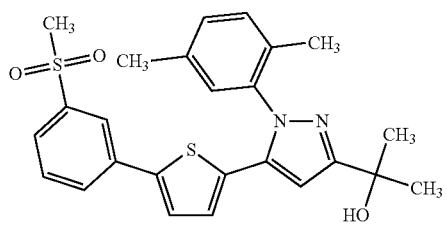 [SMILES: Cc1ccc(C)c(-n2nc(C(C)(C)O)cc2-c2ccc(-c3cccc(S(C)(=O)=O)c3)s2)c1] | 2-[1-(2,5-dimethylphenyl)-5-{5-[3-(methylsulfonyl)phenyl]-2-thienyl}-1H-pyrazol-3-yl]propan-2-ol |
| 1315 | 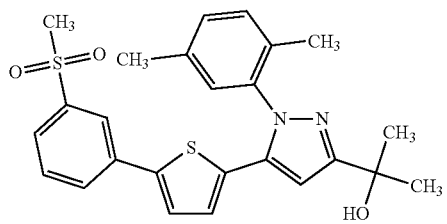 [SMILES: Cc1ccc(C)c(-n2nc(C(C)(C)O)cc2-c2ccc(-c3cccc(S(C)(=O)=O)c3)s2)c1] | 2-[1-(2,3-dimethylphenyl)-5-{5-[3-(methylsulfonyl)phenyl]-2-thienyl}-1H-pyrazol-3-yl]propan-2-ol |
| 1316 | 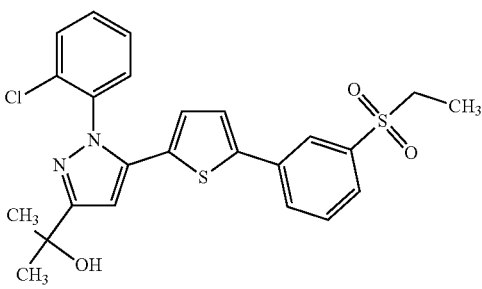 [SMILES: CCS(=O)(=O)c1cccc(-c2ccc(-c3cc(C(C)(C)O)nn3-c3ccccc3Cl)s2)c1] | 2-[1-(2-chlorophenyl)-5-{5-[3-(ethylsulfonyl)phenyl]-2-thienyl}-1H-pyrazol-3-yl]propan-2-ol |
| 1317 | 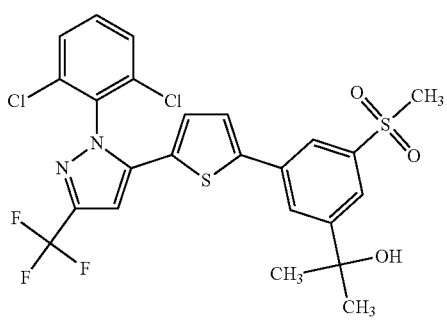 [SMILES: CC(C)(O)c1cc(-c2ccc(-c3cc(C(F)(F)F)nn3-c3c(Cl)cccc3Cl)s2)cc(S(C)(=O)=O)c1] | 2-[3-{5-[1-(2,6-dichlorophenyl)-3-(trifluoromethyl)-1H-pyrazol-5-yl]-2-thienyl}-5-(methylsulfonyl)phenyl]propan-2-ol |

TABLE 1-continued

| | | |
|---|---|---|
| 1318 | 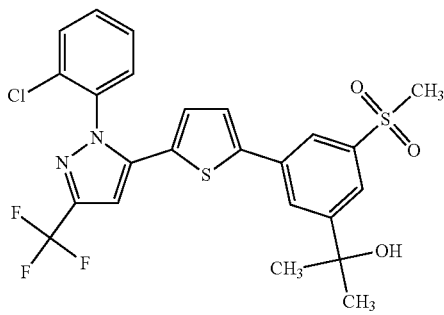 [SMILES: CC(C)(O)c1cc(-c2ccc(-c3cc(C(F)(F)F)nn3-c3ccccc3Cl)s2)cc(S(C)(=O)=O)c1] | 2-[3-{5-[1-(2-chlorophenyl)-3-(trifluoromethyl)-1H-pyrazol-5-yl]-2-thienyl}-5-(methylsulfonyl)phenyl]propan-2-ol |
| 1319 | 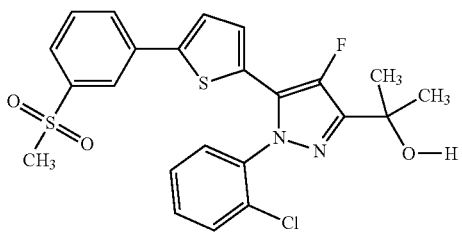 [SMILES: CC(C)(O)c1nn(-c2ccccc2Cl)c(-c2ccc(-c3cccc(S(C)(=O)=O)c3)s2)c1F] | 2-[1-(2-chlorophenyl)-4-fluoro-5-{5-[3-(methylsulfonyl)phenyl]-2-thienyl}-1H-pyrazol-3-yl]propan-2-ol |
| 1320 | 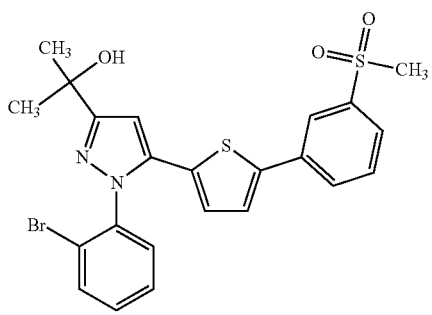 [SMILES: CC(C)(O)c1cc(-c2ccc(-c3cccc(S(C)(=O)=O)c3)s2)n(-c2ccccc2Br)n1] | 2-[1-(2-bromophenyl)-5-{5-[3-(methylsulfonyl)phenyl]-2-thienyl}-1H-pyrazol-3-yl]propan-2-ol |
| 1321 | 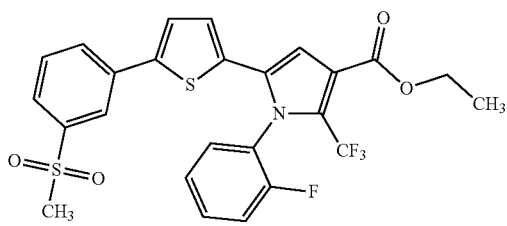 [SMILES: CCOC(=O)c1cc(-c2ccc(-c3cccc(S(C)(=O)=O)c3)s2)n(-c2ccccc2F)c1C(F)(F)F] | ethyl 1-(2-fluorophenyl)-2-methyl-5-{5-[3-(methylsulfonyl)phenyl]-2-thienyl}-1H-pyrrole-3-carboxylate |
| 1322 | 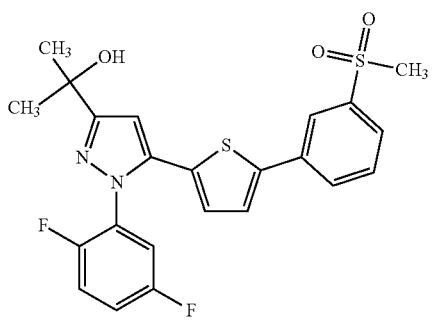 [SMILES: CC(C)(O)c1cc(-c2ccc(-c3cccc(S(C)(=O)=O)c3)s2)n(-c2cc(F)ccc2F)n1] | 2-[1-(2,5-difluorophenyl)-5-{5-[3-(methylsulfonyl)phenyl]-2-thienyl}-1H-pyrazol-3-yl]propan-2-ol |

| | | |
|---|---|---|
| 1323 | 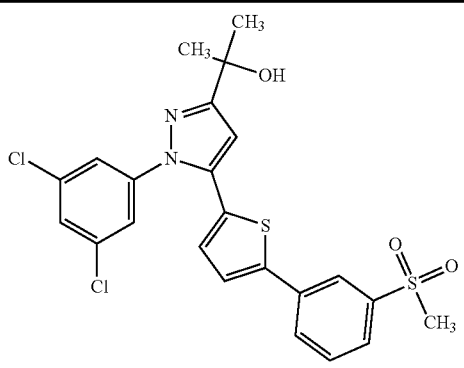 | 2-[1-(3,5-dichlorophenyl)-5-{5-[3-(methylsulfonyl)phenyl]-2-thienyl}-1H-pyrazol-3-yl]propan-2-ol |
| 1324 | 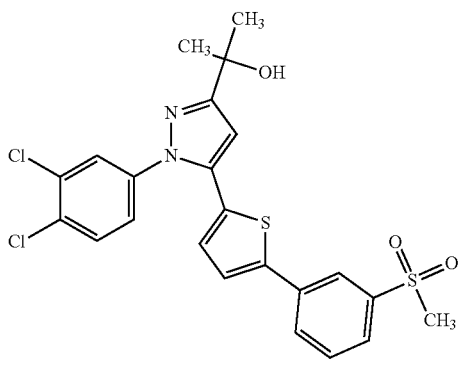 [SMILES: CC(C)(O)c1cc(-c2ccc(-c3cccc(S(C)(=O)=O)c3)s2)n(-c2ccc(Cl)c(Cl)c2)n1] | 2-[1-(3,4-dichlorophenyl)-5-{5-[3-(methylsulfonyl)phenyl]-2-thienyl}-1H-pyrazol-3-yl]propan-2-ol |
| 1325 | 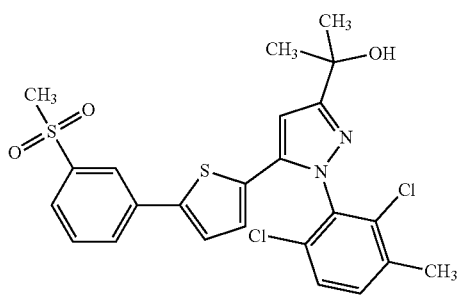 [SMILES: Cc1ccc(Cl)c(-n2nc(C(C)(C)O)cc2-c2ccc(-c3cccc(S(C)(=O)=O)c3)s2)c1Cl] | 2-[1-(2,6-dichloro-3-methylphenyl)-5-{5-[3-(methylsulfonyl)phenyl]-2-thienyl}-1H-pyrazol-3-yl]propan-2-ol |
| 1326 | 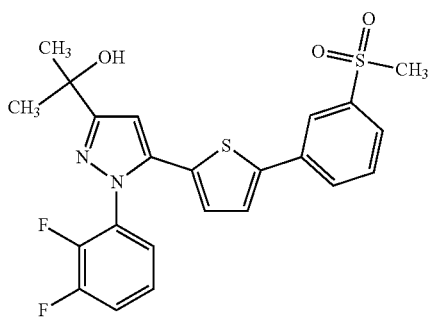 [SMILES: CC(C)(O)c1cc(-c2ccc(-c3cccc(S(C)(=O)=O)c3)s2)n(-c2cccc(F)c2F)n1] | 2-[1-(2,3-difluorophenyl)-5-{5-[3-(methylsulfonyl)phenyl]-2-thienyl}-1H-pyrazol-3-yl]propan-2-ol |
| 1327 | 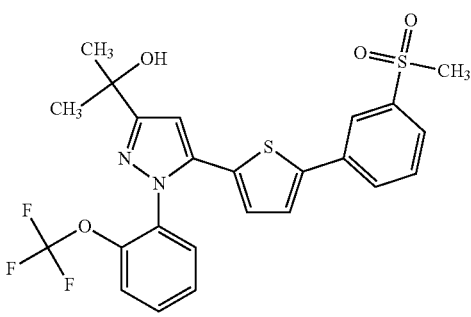 [SMILES: CC(C)(O)c1cc(-c2ccc(-c3cccc(S(C)(=O)=O)c3)s2)n(-c2ccccc2OC(F)(F)F)n1] | 2-(5-{5-[3-(methylsulfonyl)phenyl]-2-thienyl}-1-(2-[(trifluoromethyl)oxy]phenyl}-1H-pyrazol-3-yl)propan-2-ol |

TABLE 1-continued

| | | |
|---|---|---|
| 1328 | 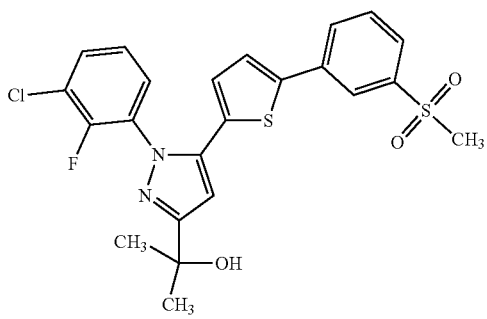 [SMILES: CC(C)(O)c1cc(-c2ccc(-c3cccc(S(C)(=O)=O)c3)s2)n(-c2cccc(Cl)c2F)n1] | 2-[1-(3-chloro-2-fluorophenyl)-5-{5-[3-(methylsulfonyl)phenyl]-2-thienyl}-1H-pyrazol-3-yl]propan-2-ol |
| 1329 | 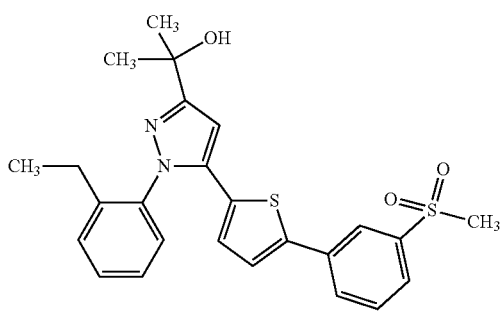 [SMILES: CCc1ccccc1-n1nc(C(C)(C)O)cc1-c1ccc(-c2cccc(S(C)(=O)=O)c2)s1] | 2-[1-(2-ethylphenyl)-5-{5-[3-(methylsulfonyl)phenyl]-2-thienyl}-1H-pyrazol-3-yl]propan-2-ol |
| 1330 | 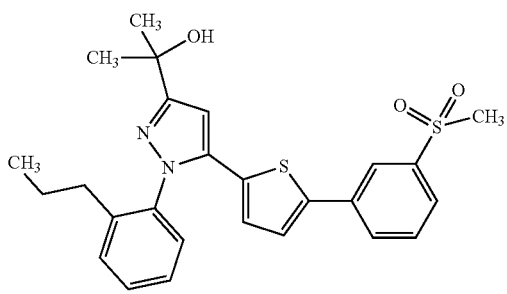 [SMILES: CCCc1ccccc1-n1nc(C(C)(C)O)cc1-c1ccc(-c2cccc(S(C)(=O)=O)c2)s1] | 2-[5-{5-[3-(methylsulfonyl)phenyl]-2-thienyl}-1-(2-propylphenyl)-1H-pyrazol-3-yl]propan-2-ol |
| 1331 | 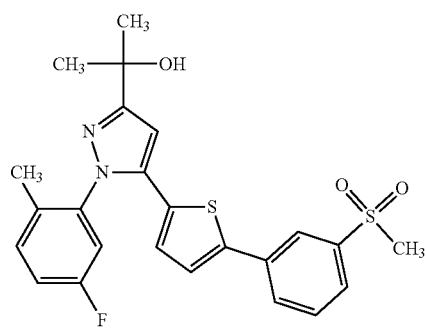 [SMILES: Cc1ccc(F)cc1-n1nc(C(C)(C)O)cc1-c1ccc(-c2cccc(S(C)(=O)=O)c2)s1] | 2-[1-(5-fluoro-2-methylphenyl)-5-{5-[3-(methylsulfonyl)phenyl]-2-thienyl}-1H-pyrazol-3-yl]propan-2-ol |
| 1332 | 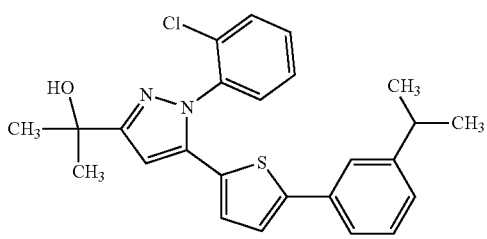 [SMILES: CC(C)c1cccc(-c2ccc(-c3cc(C(C)(C)O)nn3-c3ccccc3Cl)s2)c1] | 2-[1-(2-chlorophenyl)-5-{5-[3-(1-methylethyl)phenyl]-2-thienyl}-1H-pyrazol-3-yl]propan-2-ol |

TABLE 1-continued

| 1333 | 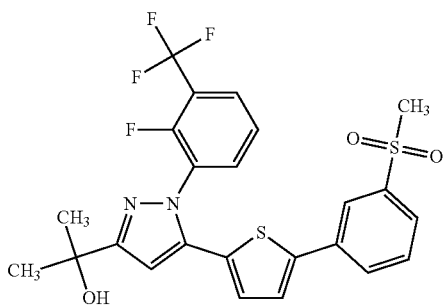 [SMILES: CC(C)(O)c1cc(-c2ccc(-c3cccc(S(C)(=O)=O)c3)s2)n(-c2cccc(C(F)(F)F)c2F)n1] | 2-(1-[2-fluoro-3-(trifluoromethyl)phenyl]-5-{5-[3-(methylsulfonyl)phenyl]-2-thienyl}-1H-pyrazol-3-yl)propan-2-ol |
| --- | --- | --- |
| 1334 | 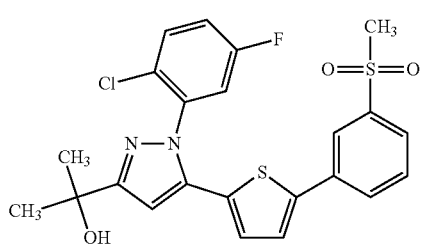 [SMILES: CC(C)(O)c1cc(-c2ccc(-c3cccc(S(C)(=O)=O)c3)s2)n(-c2cc(F)ccc2Cl)n1] | 2-[1-(2-chloro-5-fluorophenyl)-5-{5-[3-(methylsulfonyl)phenyl]-2-thienyl}-1H-pyrazol-3-yl]propan-2-ol |
| 1335 | 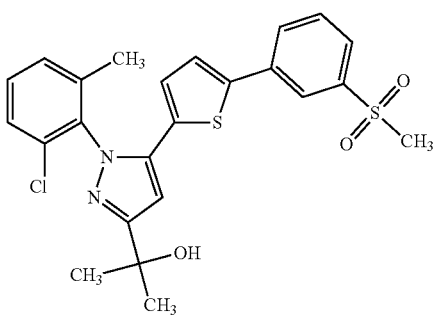 [SMILES: Cc1cccc(Cl)c1-n1nc(C(C)(C)O)cc1-c1ccc(-c2cccc(S(C)(=O)=O)c2)s1] | 2-[1-(2-chloro-6-methylphenyl)-5-{5-[3-(methylsulfonyl)phenyl]-2-thienyl}-1H-pyrazol-3-yl]propan-2-ol |
| 1336 | 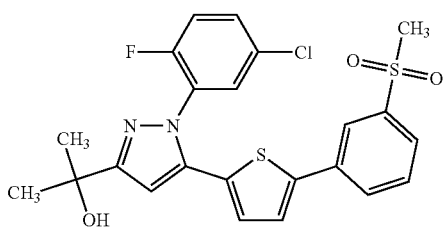 [SMILES: CC(C)(O)c1cc(-c2ccc(-c3cccc(S(C)(=O)=O)c3)s2)n(-c2cc(Cl)ccc2F)n1] | 2-[1-(5-chloro-2-fluorophenyl)-5-{5-[3-(methylsulfonyl)phenyl]-2-thienyl}-1H-pyrazol-3-yl]propan-2-ol |
| 1337 | 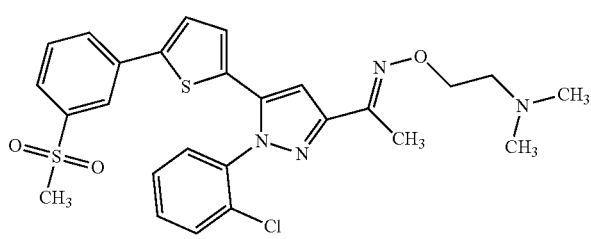 [SMILES: C/C(=N\OCCN(C)C)c1cc(-c2ccc(-c3cccc(S(C)(=O)=O)c3)s2)n(-c2ccccc2Cl)n1] | (1E)-1-[1-(2-chlorophenyl)-5-{5-[3-(methylsulfonyl)phenyl]-2-thienyl}-1H-pyrazol-3-yl]ethanone O-[2-(dimethylamino)ethyl]oxime |

TABLE 1-continued
| | | |
|---|---|---|
| 1338 | 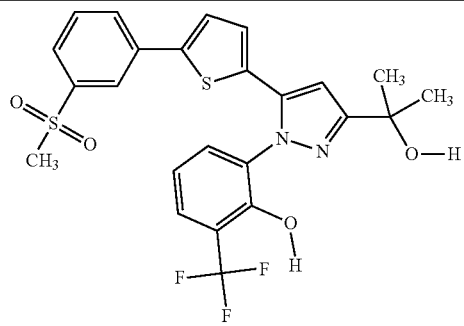 | 2-[3-(1-hydroxy-1-methylethyl)-5-{5-[3-(methylsulfonyl)phenyl]-2-thienyl}-1H-pyrazol-1-yl]-6-(trifluoromethyl)phenol |
| 1339 | 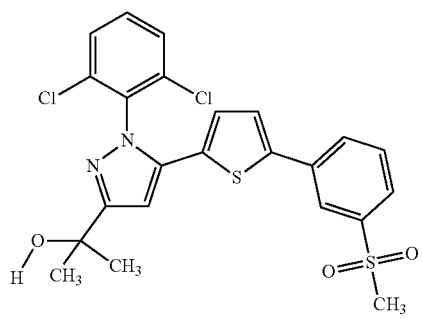 [SMILES: CC(C)(O)c1cc(-c2ccc(-c3cccc(S(C)(=O)=O)c3)s2)n(-c2c(Cl)cccc2Cl)n1] | 2-[4-bromo-1-(2,6-dichlorophenyl)-5-{5-[3-(methylsulfonyl)phenyl]-2-thienyl}-1H-pyrazol-3-yl]propan-2-ol |
| 1340 | 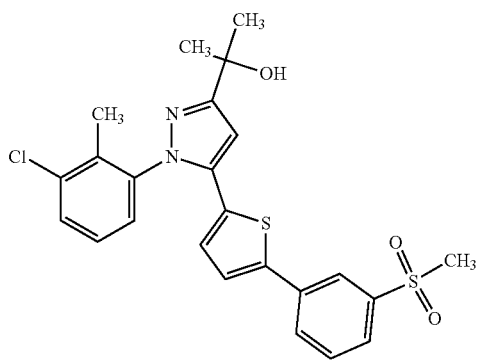 [SMILES: Cc1c(Cl)cccc1-n1nc(C(C)(C)O)cc1-c1ccc(-c2cccc(S(C)(=O)=O)c2)s1] | 2-[1-(3-chloro-2-methylphenyl)-5-{5-[3-(methylsulfonyl)phenyl]-2-thienyl}-1H-pyrazol-3-yl]propan-2-ol |
| 1341 | 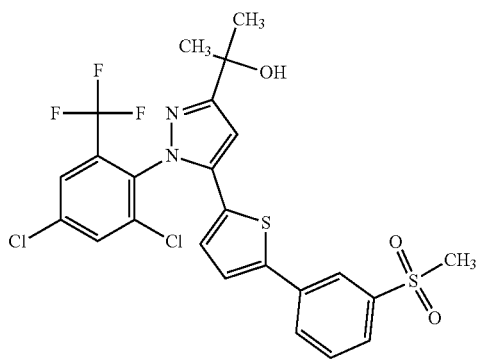 [SMILES: CC(C)(O)c1cc(-c2ccc(-c3cccc(S(C)(=O)=O)c3)s2)n(-c2c(Cl)cc(Cl)cc2C(F)(F)F)n1] | 2-(1-[2,4-dichloro-6-(trifluoromethyl)phenyl]-5-{5-[3-(methylsulfonyl)phenyl]-2-thienyl}-1H-pyrazol-3-yl)propan-2-ol |

| | | |
|---|---|---|
| 1342 | 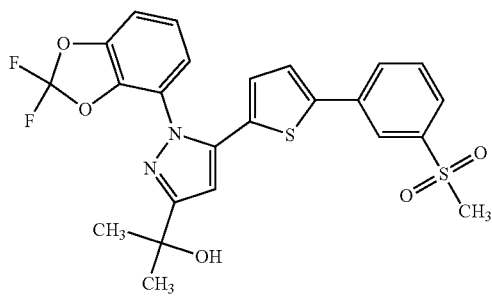 [SMILES: CC(C)(O)c1cc(-c2ccc(-c3cccc(S(C)(=O)=O)c3)s2)n(-c2cccc3c2OC(F)(F)O3)n1] | 2-[1-(2,2-difluoro-1,3-benzodioxol-4-yl)-5-{5-[3-(methylsulfonyl)phenyl]-2-thienyl}-1H-pyrazol-3-yl]propan-2-ol |
| 1343 | 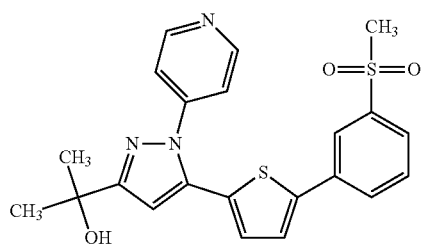 [SMILES: CC(C)(O)c1cc(-c2ccc(-c3cccc(S(C)(=O)=O)c3)s2)n(-c2ccncc2)n1] | 2-(5-{5-[3-(methylsulfonyl)phenyl]-2-thienyl}-1-pyridin-4-yl-1H-pyrazol-3-yl)propan-2-ol |
| 1344 | 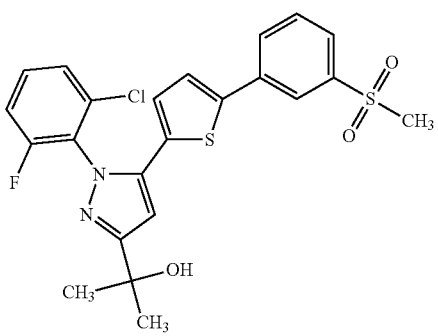 [SMILES: CC(C)(O)c1cc(-c2ccc(-c3cccc(S(C)(=O)=O)c3)s2)n(-c2c(F)cccc2Cl)n1] | 2-[1-(2-chloro-6-fluorophenyl)-5-{5-[3-(methylsulfonyl)phenyl]-2-thienyl}-1H-pyrazol-3-yl]propan-2-ol |
| 1345 | 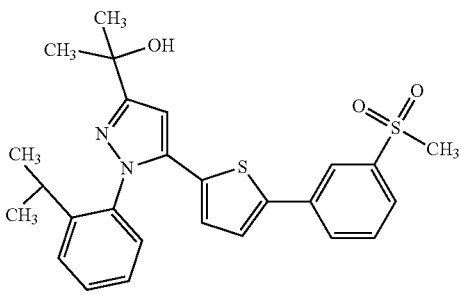 [SMILES: CC(C)c1ccccc1-n1nc(C(C)(C)O)cc1-c1ccc(-c2cccc(S(C)(=O)=O)c2)s1] | 2-(1-[2-(1-methylethyl)phenyl]-5-{5-[3-(methylsulfonyl)phenyl]-2-thienyl}-1H-pyrazol-3-yl)propan-2-ol |
| 1346 | 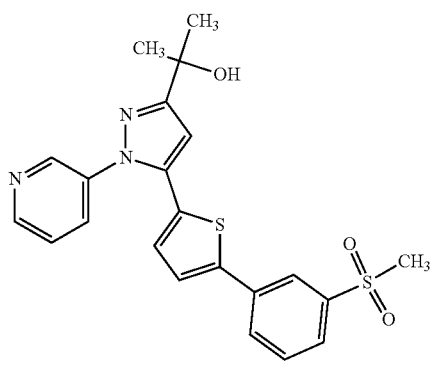 [SMILES: CC(C)(O)c1cc(-c2ccc(-c3cccc(S(C)(=O)=O)c3)s2)n(-c2cccnc2)n1] | 2-(5-{5-[3-(methylsulfonyl)phenyl]-2-thienyl}-1-pyridin-3-yl-1H-pyrazol-3-yl)propan-2-ol |

TABLE 1-continued

| 1347 | 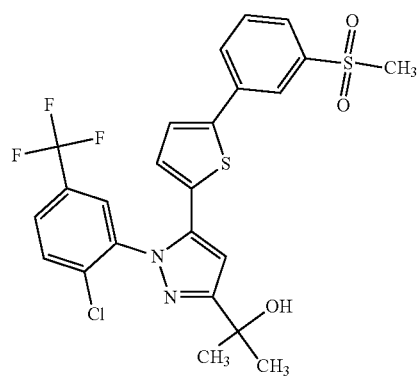 [SMILES: CC(C)(O)c1cc(-c2ccc(-c3cccc(S(C)(=O)=O)c3)s2)n(-c2cc(C(F)(F)F)ccc2Cl)n1] | 2-(1-[2-chloro-5-(trifluoromethyl)phenyl]-5-{5-[3-(methylsulfonyl)phenyl]-2-thienyl}-1H-pyrazol-3-yl)propan-2-ol |
| --- | --- | --- |
| 1348 | 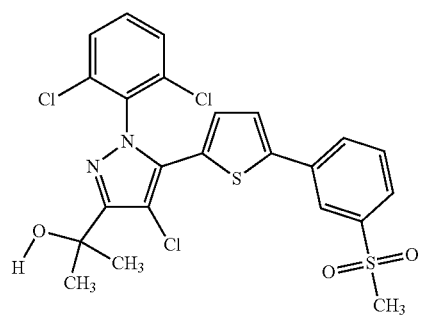 [SMILES: CC(C)(O)c1nn(-c2c(Cl)cccc2Cl)c(-c2ccc(-c3cccc(S(C)(=O)=O)c3)s2)c1Cl] | 2-[4-chloro-1-(2,6-dichlorophenyl)-5-{5-[3-(methylsulfonyl)phenyl]-2-thienyl}-1H-pyrazol-3-yl]propan-2-ol |
| 1349 | 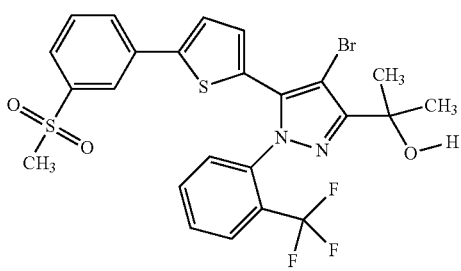 [SMILES: CC(C)(O)c1nn(-c2ccccc2C(F)(F)F)c(-c2ccc(-c3cccc(S(C)(=O)=O)c3)s2)c1Br] | 2-(4-bromo-5-{5-[3-(methylsulfonyl)phenyl]-2-thienyl}-1-[2-(trifluoromethyl)phenyl]-1H-pyrazol-3-yl)propan-2-ol |
| 1350 | 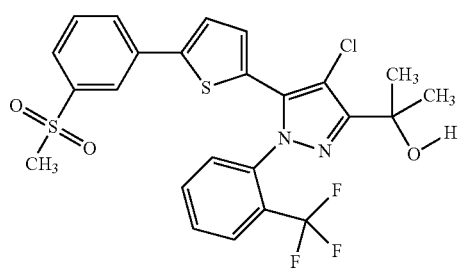 [SMILES: CC(C)(O)c1nn(-c2ccccc2C(F)(F)F)c(-c2ccc(-c3cccc(S(C)(=O)=O)c3)s2)c1Cl] | 2-(4-chloro-5-{5-[3-(methylsulfonyl)phenyl]-2-thienyl}-1-[2-(trifluoromethyl)phenyl]-1H-pyrazol-3-yl)propan-2-ol |
| 1351 | 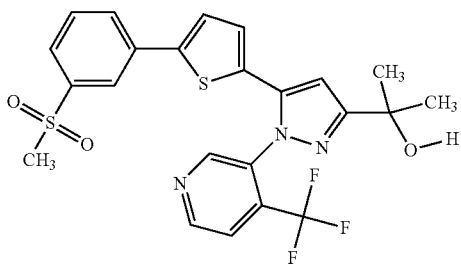 [SMILES: CC(C)(O)c1cc(-c2ccc(-c3cccc(S(C)(=O)=O)c3)s2)n(-c2cnccc2C(F)(F)F)n1] | 2-(5-{5-[3-(methylsulfonyl)phenyl]-2-thienyl}-1-[4-(trifluoromethyl)pyridin-3-yl]-1H-pyrazol-3-yl)propan-2-ol |

TABLE 1-continued

| 1352 | 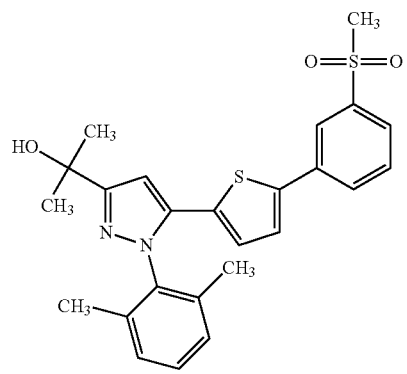 [SMILES: Cc1cccc(C)c1-n1nc(C(C)(C)O)cc1-c1ccc(-c2cccc(S(C)(=O)=O)c2)s1] | 2-[1-(2,6-dimethylphenyl)-5-{5-[3-(methylsulfonyl)phenyl]-2-thienyl}-1H-pyrazol-3-yl]propan-2-ol |
| --- | --- | --- |
| 1353 | 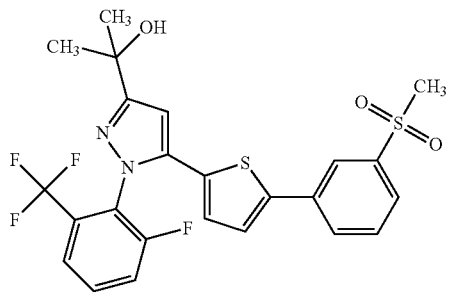 [SMILES: CC(C)(O)c1cc(-c2ccc(-c3cccc(S(C)(=O)=O)c3)s2)n(-c2c(F)cccc2C(F)(F)F)n1] | 2-(1-[2-fluoro-6-(trifluoromethyl)phenyl]-5-{5-[3-(methylsulfonyl)phenyl]-2-thienyl}-1H-pyrazol-3-yl)propan-2-ol |
| 1354 | 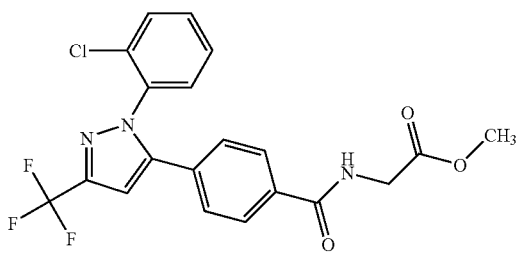 [SMILES: COC(=O)CNC(=O)c1ccc(-c2cc(C(F)(F)F)nn2-c2ccccc2Cl)cc1] | methyl N-({4-[1-(2-chlorophenyl)-3-(trifluoromethyl)-1H-pyrazol-5-yl]phenyl}carbonyl)glycinate |
| 1355 | 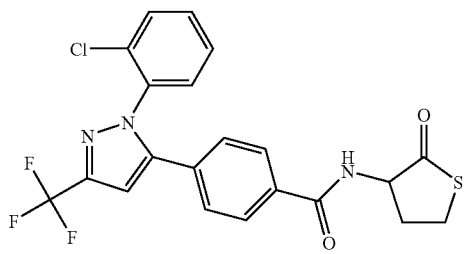 [SMILES: O=C(NC1CCSC1=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2-oxotetrahydro-3-thienyl)benzamide |
| 1356 | 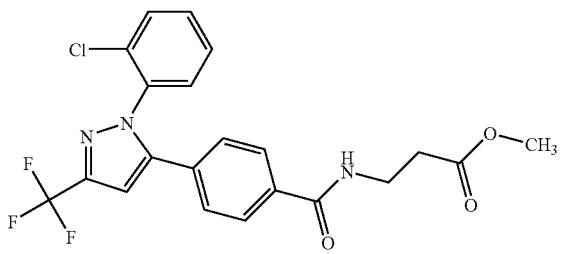 [SMILES: COC(=O)CCNC(=O)c1ccc(-c2cc(C(F)(F)F)nn2-c2ccccc2Cl)cc1] | methyl N-({4-[1-(2-chlorophenyl)-3-(trifluoromethyl)-1H-pyrazol-5-yl]phenyl}carbonyl)-beta-alaninate |

TABLE 1-continued

| | | |
|---|---|---|
| 1357 | 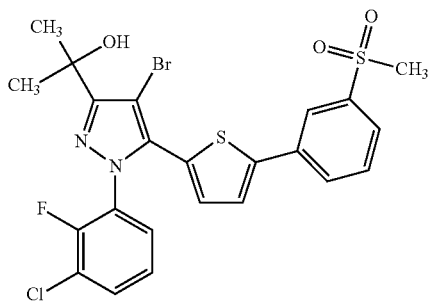 [SMILES: CC(C)(O)c1nn(-c2cccc(Cl)c2F)c(-c2ccc(-c3cccc(S(C)(=O)=O)c3)s2)c1Br] | 2-[4-bromo-1-(3-chloro-2-fluorophenyl)-5-{5-[3-(methylsulfonyl)phenyl]-2-thienyl}-1H-pyrazol-3-yl]propan-2-ol |
| 1358 | 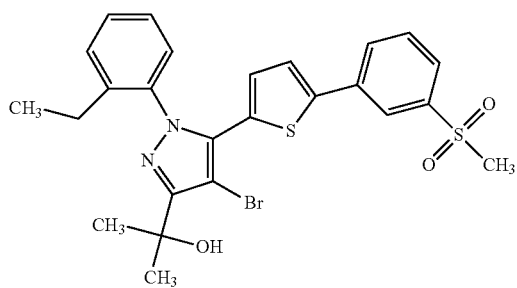 [SMILES: CCc1ccccc1-n1nc(C(C)(C)O)c(Br)c1-c1ccc(-c2cccc(S(C)(=O)=O)c2)s1] | 2-[4-bromo-1-(2-ethylphenyl)-5-{5-[3-(methylsulfonyl)phenyl]-2-thienyl}-1H-pyrazol-3-yl]propan-2-ol |
| 1359 | 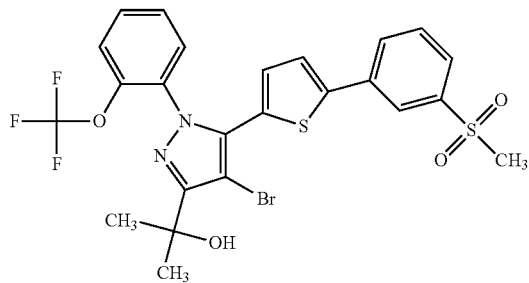 | 2-(4-bromo-5-{5-[3-(methylsulfonyl)phenyl]-2-thienyl}-1-{2-[(trifluoromethyl)oxy]phenyl}-1H-pyrazol-3-yl)propan-2-ol |
| 1360 | 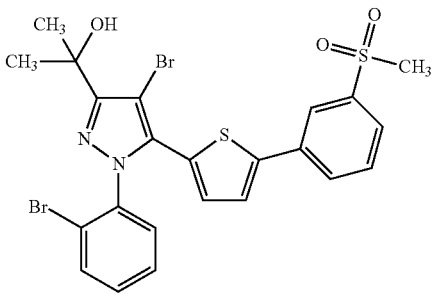 [SMILES: CC(C)(O)c1nn(-c2ccccc2Br)c(-c2ccc(-c3cccc(S(C)(=O)=O)c3)s2)c1Br] | 2-[4-bromo-1-(2-bromophenyl)-5-{5-[3-(methylsulfonyl)phenyl]-2-thienyl}-1H-pyrazol-3-yl]propan-2-ol |
| 1361 | 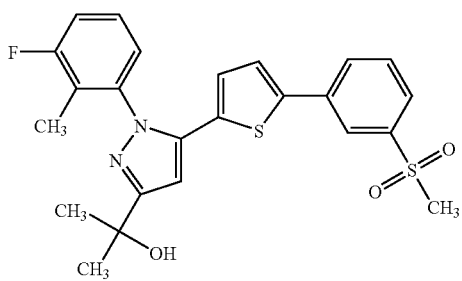 [SMILES: Cc1c(F)cccc1-n1nc(C(C)(C)O)cc1-c1ccc(-c2cccc(S(C)(=O)=O)c2)s1] | 2-[1-(3-fluoro-2-methylphenyl)-5-{5-[3-(methylsulfonyl)phenyl]-2-thienyl}-1H-pyrazol-3-yl]propan-2-ol |

| | | |
|---|---|---|
| 1362 | 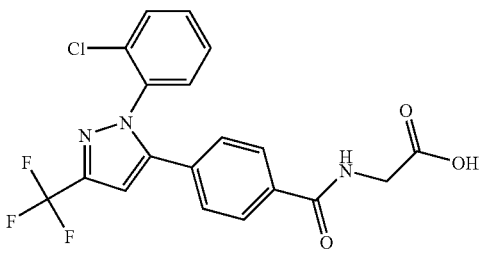 [SMILES: O=C(O)CNC(=O)c1ccc(-c2cc(C(F)(F)F)nn2-c2ccccc2Cl)cc1] | N-({4-[1-(2-chlorophenyl)-3-(trifluoromethyl)-1H-pyrazol-5-yl]phenyl}carbonyl)glycine |
| 1363 | 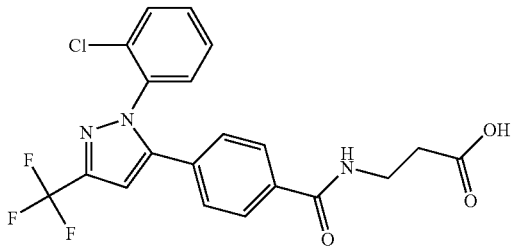 [SMILES: O=C(O)CCNC(=O)c1ccc(-c2cc(C(F)(F)F)nn2-c2ccccc2Cl)cc1] | N-({4-[1-(2-chlorophenyl)-3-(trifluoromethyl)-1H-pyrazol-5-yl]phenyl}carbonyl)-beta-alanine |
| 1364 | 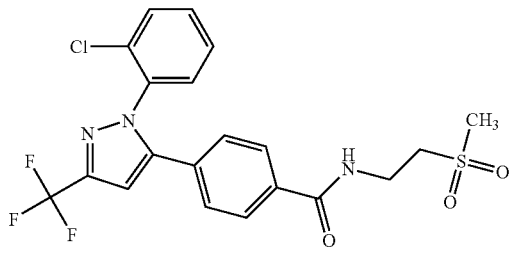 [SMILES: CS(=O)(=O)CCNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(methylsulfonyl)ethyl]benzamide |
| 1365 | 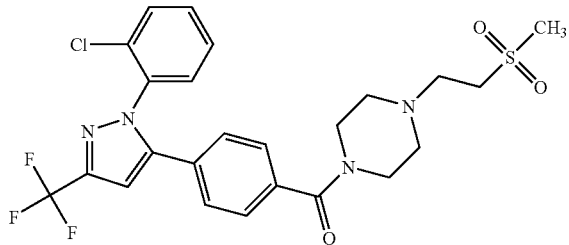 [SMILES: CS(=O)(=O)CCN1CCN(C(=O)c2ccc(-c3cc(C(F)(F)F)nn3-c3ccccc3Cl)cc2)CC1] | 1-({4-[1-(2-chlorophenyl)-3-(trifluoromethyl)-1H-pyrazol-5-yl]phenyl}carbonyl)-4-[2-(methylsulfonyl)ethyl]piperazine |
| 1366 | 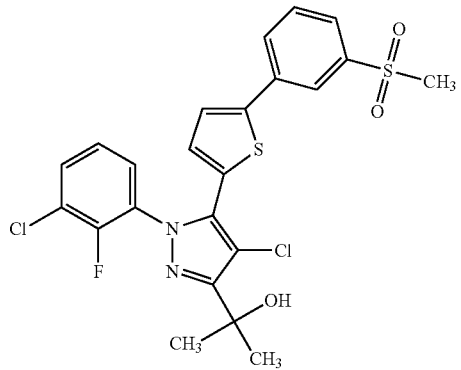 [SMILES: CC(C)(O)c1nn(-c2cccc(Cl)c2F)c(-c2ccc(-c3cccc(S(C)(=O)=O)c3)s2)c1Cl] | 2-[4-chloro-1-(3-chloro-2-fluorophenyl)-5-{5-[3-(methylsulfonyl)phenyl]-2-thienyl}-1H-pyrazol-3-yl]propan-2-ol |

TABLE 1-continued

| 1367 | 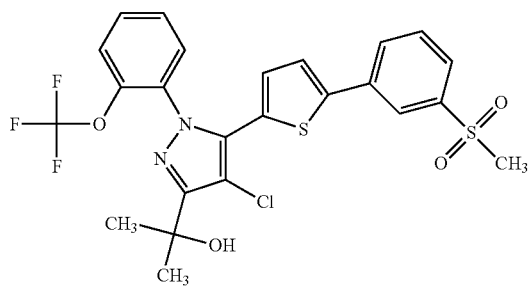 [SMILES: CC(C)(O)c1nn(-c2ccccc2OC(F)(F)F)c(-c2ccc(-c3cccc(S(C)(=O)=O)c3)s2)c1Cl] | 2-(4-chloro-5-{5-[3-(methylsulfonyl)phenyl]-2-thienyl}-1-{2-[(trifluoromethyl)oxy]phenyl}-1H-pyrazol-3-yl)propan-2-ol |
| --- | --- | --- |
| 1368 | 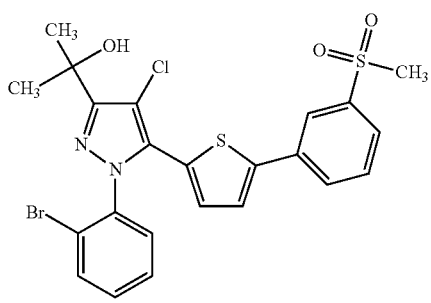 [SMILES: CC(C)(O)c1nn(-c2ccccc2Br)c(-c2ccc(-c3cccc(S(C)(=O)=O)c3)s2)c1Cl] | 2-[1-(2-bromophenyl)-4-chloro-5-{5-[3-(methylsulfonyl)phenyl]-2-thienyl}-1H-pyrazol-3-yl]propan-2-ol |
| 1369 | 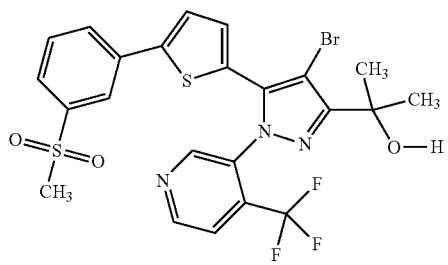 [SMILES: CC(C)(O)c1nn(-c2cnccc2C(F)(F)F)c(-c2ccc(-c3cccc(S(C)(=O)=O)c3)s2)c1Br] | 2-(4-bromo-5-{5-[3-(methylsulfonyl)phenyl]-2-thienyl}-1-[4-(trifluoromethyl)pyridin-3-yl]-1H-pyrazol-3-yl)propan-2-ol |
| 1370 | 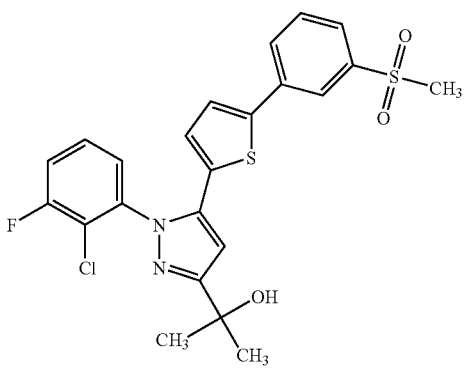 [SMILES: CC(C)(O)c1cc(-c2ccc(-c3cccc(S(C)(=O)=O)c3)s2)n(-c2cccc(F)c2Cl)n1] | 2-[1-(2-chloro-5-fluorophenyl)-5-{5-[3-(methylsulfonyl)phenyl]-2-thienyl}-1H-pyrazol-3-yl]propan-2-ol |
| 1371 | 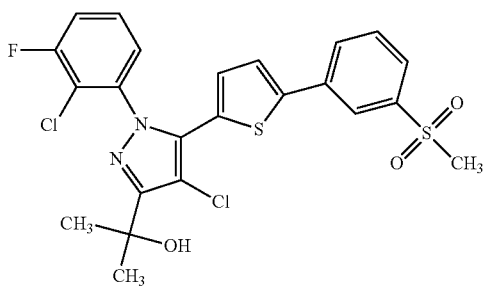 [SMILES: CC(C)(O)c1nn(-c2cccc(F)c2Cl)c(-c2ccc(-c3cccc(S(C)(=O)=O)c3)s2)c1Cl] | 2-[4-chloro-1-(2-chloro-3-fluorophenyl)-5-{5-[3-(methylsulfonyl)phenyl]-2-thienyl}-1H-pyrazol-3-yl]propan-2-ol |

| | | |
|---|---|---|
| 1372 | 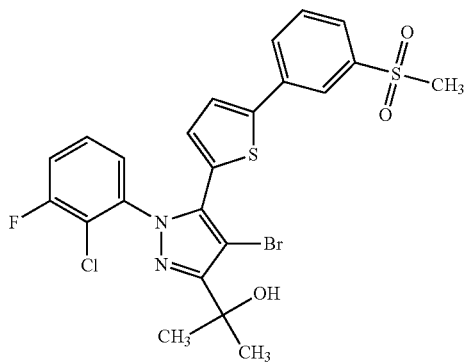 [SMILES: CC(C)(O)c1nn(-c2cccc(F)c2Cl)c(-c2ccc(-c3cccc(S(C)(=O)=O)c3)s2)c1Br] | 2-[4-bromo-1-(2-chloro-3-fluorophenyl)-5-{5-[3-(methylsulfonyl)phenyl]-2-thienyl}-1H-pyrazol-3-yl]propan-2-ol |
| 1373 | 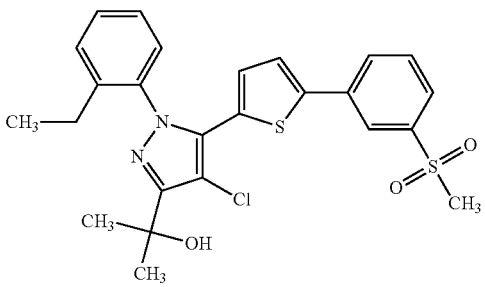 [SMILES: CCc1ccccc1-n1nc(C(C)(C)O)c(Cl)c1-c1ccc(-c2cccc(S(C)(=O)=O)c2)s1] | 2-[4-chloro-1-(2-ethylphenyl)-5-{5-[3-(methylsulfonyl)phenyl]-2-thienyl}-1H-pyrazol-3-yl]propan-2-ol |
| 1383 | 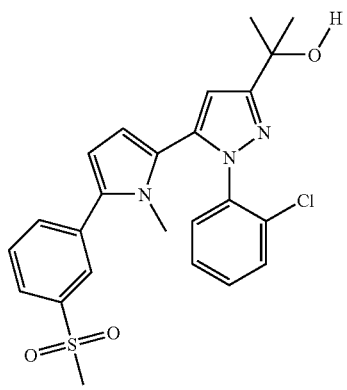 [SMILES: Cn1c(-c2cccc(S(C)(=O)=O)c2)ccc1-c1cc(C(C)(C)O)nn1-c1ccccc1Cl] | 2-(1-(2-chlorophenyl)-5-(1-methyl-5-(3-(methylsulfonyl)phenyl)-1H-pyrrol-2-yl)-1H-pyrazol-3-yl)propan-2-ol |
| 1384 | 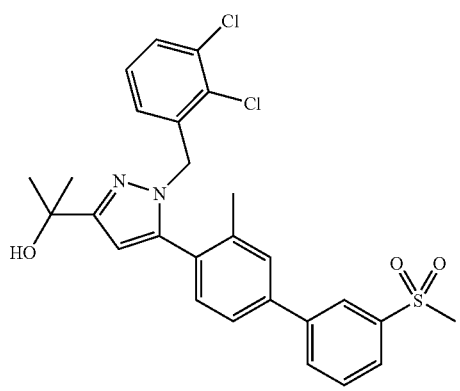 [SMILES: Cc1cc(-c2cccc(S(C)(=O)=O)c2)ccc1-c1cc(C(C)(C)O)nn1Cc1cccc(Cl)c1Cl] | 2-(1-(2,3-dichlorobenzyl)-5-(3-methyl-3'-(methylsulfonyl)biphenyl-4-yl)-1H-pyrazol-3-yl)propan-2-ol |

| | | |
|---|---|---|
| 1385 | 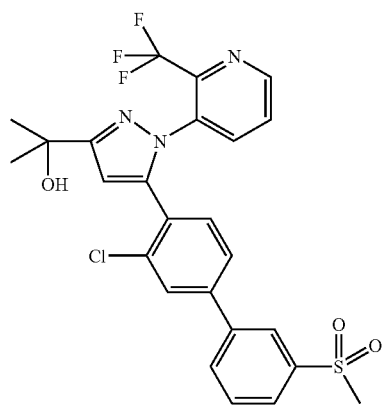 [SMILES: CC(C)(O)c1cc(-c2ccc(-c3cccc(S(C)(=O)=O)c3)cc2Cl)n(-c2cccnc2C(F)(F)F)n1] | 2-(5-(3-chloro-3'-(methylsulfonyl)biphenyl-4-yl)-1-(2-(trifluoromethyl)pyridin-3-yl)-1H-pyrazol-3-yl)propan-2-ol |
| 1386 | 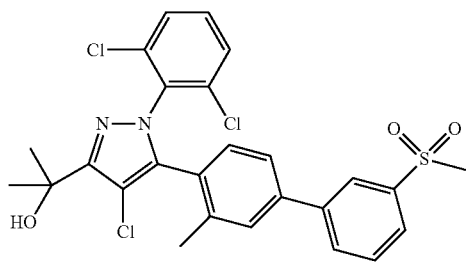 [SMILES: Cc1cc(-c2cccc(S(C)(=O)=O)c2)ccc1-c1c(Cl)c(C(C)(C)O)nn1-c1c(Cl)cccc1Cl] | 2-(4-chloro-1-(2,6-dichlorophenyl)-5-(3-methyl-3'-(methylsulfonyl)biphenyl-4-yl)-1H-pyrazol-3-yl)propan-2-ol |
| 1387 | 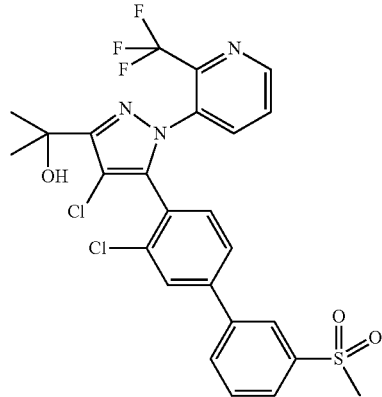 [SMILES: CC(C)(O)c1nn(-c2cccnc2C(F)(F)F)c(-c2ccc(-c3cccc(S(C)(=O)=O)c3)cc2Cl)c1Cl] | 2-(4-chloro-5-(3-chloro-3'-(methylsulfonyl)biphenyl-4-yl)-1-(2-(trifluoromethyl)pyridin-3-yl)-1H-pyrazol-3-yl)propan-2-ol |
| 1388 | 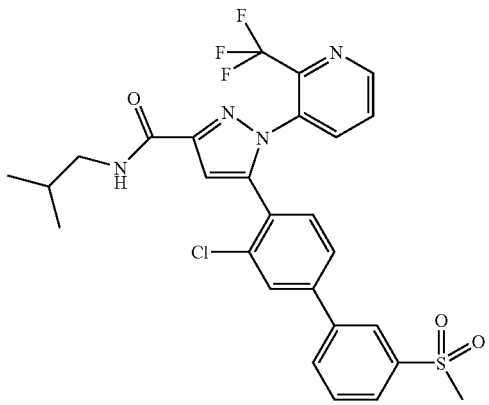 [SMILES: CC(C)CNC(=O)c1cc(-c2ccc(-c3cccc(S(C)(=O)=O)c3)cc2Cl)n(-c2cccnc2C(F)(F)F)n1] | 5-(3-chloro-3'-(methylsulfonyl)biphenyl-4-yl)-N-isobutyl-1-(2-(trifluoromethyl)pyridin-3-yl)-1H-pyrazole-3-carboxamide |

TABLE 1-continued

| 1389 | 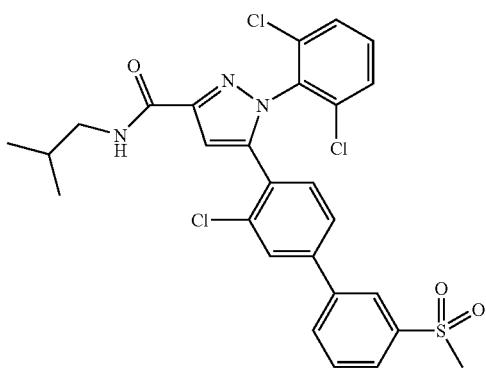 [SMILES: CC(C)CNC(=O)c1cc(-c2ccc(-c3cccc(S(C)(=O)=O)c3)cc2Cl)n(-c2c(Cl)cccc2Cl)n1] | 5-(3-chloro-3'-(methylsulfonyl)biphenyl-4-yl)-1-(2,6-dichlorophenyl)-N-isobutyl-1H-pyrazole-3-carboxamide |
| 1390 | 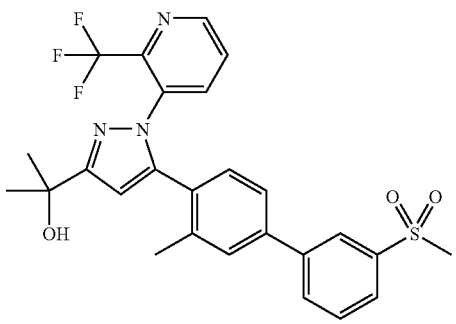 | 2-(5-(3-methyl-3'-(methylsulfonyl)biphenyl-4-yl)-1-(2-(trifluoromethyl)pyridin-3-yl)-1H-pyrazol-3-yl)propan-2-ol |
| 1391 | 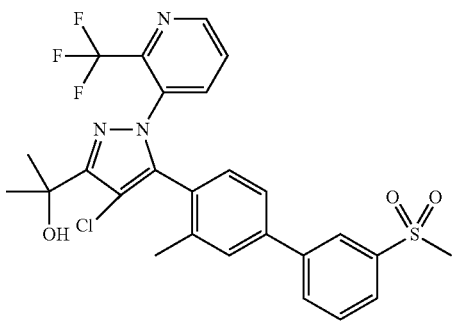 [SMILES: Cc1cc(-c2cccc(S(C)(=O)=O)c2)ccc1-c1c(Cl)c(C(C)(C)O)nn1-c1cccnc1C(F)(F)F] | 2-(4-chloro-5-(3-methyl-3'-(methylsulfonyl)biphenyl-4-yl)-1-(2-(trifluoromethyl)pyridin-3-yl)-1H-pyrazol-3-yl)propan-2-ol |
| 1392 | 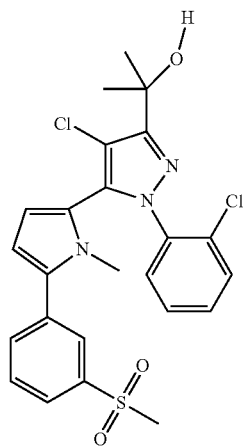 [SMILES: Cn1c(-c2cccc(S(C)(=O)=O)c2)ccc1-c1c(Cl)c(C(C)(C)O)nn1-c1ccccc1Cl] | 2-(4-chloro-1-(2-chlorophenyl)-5-(1-methyl-5-(3-(methylsulfonyl)phenyl)-1H-pyrrol-2-yl)-1H-pyrazol-3-yl)propan-2-ol |

TABLE 1-continued

| | | |
|---|---|---|
| 1393 | 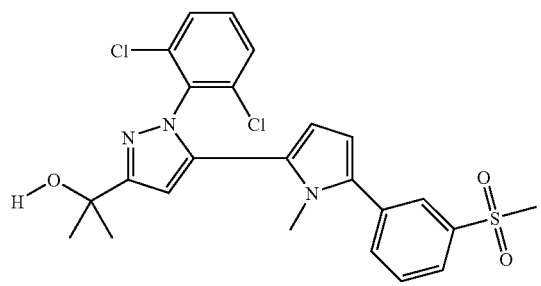 [SMILES: Cn1c(-c2cccc(S(C)(=O)=O)c2)ccc1-c1cc(C(C)(C)O)nn1-c1c(Cl)cccc1Cl] | 2-(1-(2,6-dichlorophenyl)-5-(1-methyl-5-(3-(methylsulfonyl)phenyl)-1H-pyrrol-2-yl)-1H-pyrazole-3-yl)propan-2-ol |
| 1394 | 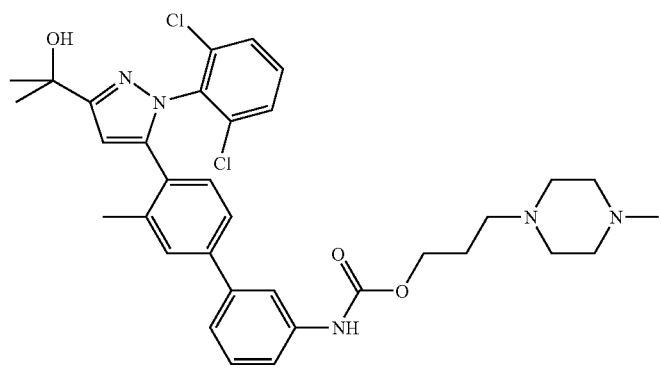 [SMILES: Cc1cc(-c2cccc(NC(=O)OCCCN3CCN(C)CC3)c2)ccc1-c1cc(C(C)(C)O)nn1-c1c(Cl)cccc1Cl] | 3-(4-methylpiperazin-1-yl)propyl 4'-(1-(2,6-dichlorophenyl)-3-(2-hydroxypropan-2-yl)-1H-pyrazol-5-yl)-3'-methylbiphenyl-3-ylcarbamate |
| 1395 | 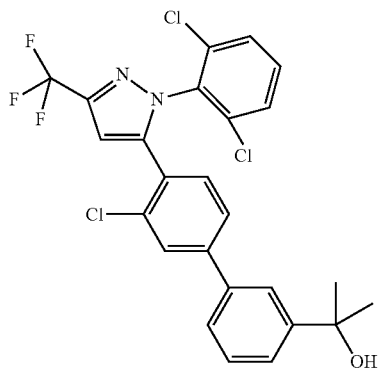 [SMILES: CC(C)(O)c1cccc(-c2ccc(-c3cc(C(F)(F)F)nn3-c3c(Cl)cccc3Cl)c(Cl)c2)c1] | 2-(3'-chloro-4'-(1-(2,6-dichlorophenyl)-3-(trifluoromethyl)-1H-pyrazol-5-yl)biphenyl-3-yl)propan-2-ol |
| 1396 | 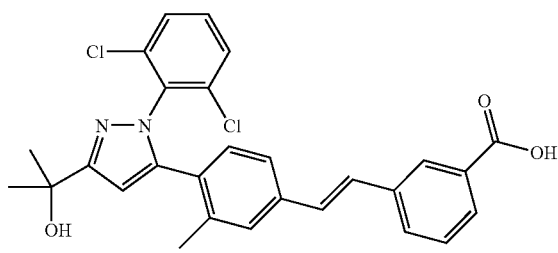 [SMILES: Cc1cc(/C=C/c2cccc(C(=O)O)c2)ccc1-c1cc(C(C)(C)O)nn1-c1c(Cl)cccc1Cl] | (E)-3-(4-(1-(2,6-dichlorophenyl)-3-(2-hydroxypropan-2-yl)-1H-pyrazol-5-yl)-3-methylstyryl)benzoic acid |
| 1397 | 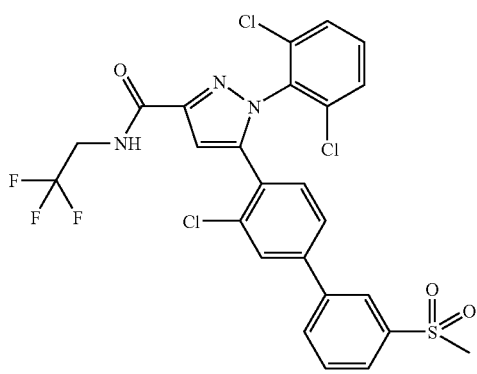 [SMILES: CS(=O)(=O)c1cccc(-c2ccc(-c3cc(C(=O)NCC(F)(F)F)nn3-c3c(Cl)cccc3Cl)c(Cl)c2)c1] | 5-(3-chloro-3'-(methylsulfonyl)biphenyl-4-yl)-1-(2,6-dichlorophenyl)-N-(2,2,2-trifluoroethyl)-1H-pyrazole-3-carboxamide |

TABLE 1-continued

| | | |
|---|---|---|
| 1398 | 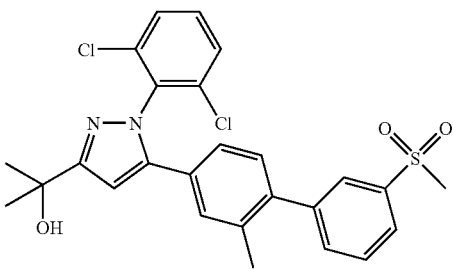 [SMILES: Cc1cc(-c2cc(C(C)(C)O)nn2-c2c(Cl)cccc2Cl)ccc1-c1cccc(S(C)(=O)=O)c1] | 2-(1-(2,6-dichlorophenyl)-5-(2-methyl-3'-(methylsulfonyl)biphenyl-4-yl)-1H-pyrazol-3-yl)propan-2-ol |
| 1399 | 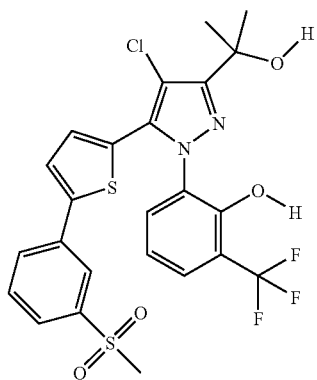 [SMILES: CC(C)(O)c1nn(-c2cccc(C(F)(F)F)c2O)c(-c2ccc(-c3cccc(S(C)(=O)=O)c3)s2)c1Cl] | 2-(4-chloro-3-(3-hydroxypropan-2-yl)-5-(5-(3-(methylsulfonyl)phenyl)thiophen-2-yl)-1H-pyrazol-1-yl)-6-(trifluoromethyl)phenol |
| 1400 | 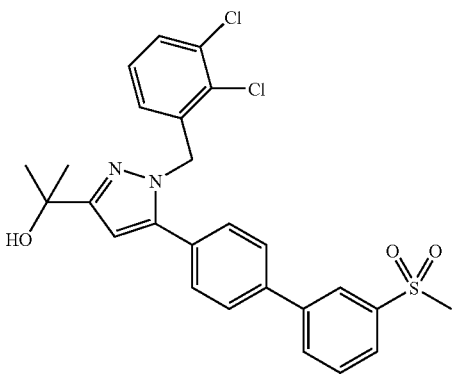 [SMILES: CC(C)(O)c1cc(-c2ccc(-c3cccc(S(C)(=O)=O)c3)cc2)n(Cc2cccc(Cl)c2Cl)n1] | 2-(1-(2,3-dichlorobenzyl)-5-(3'-(methylsulfonyl)biphenyl-4-yl)-1H-pyrazol-3-yl)propan-2-ol |
| 1401 | 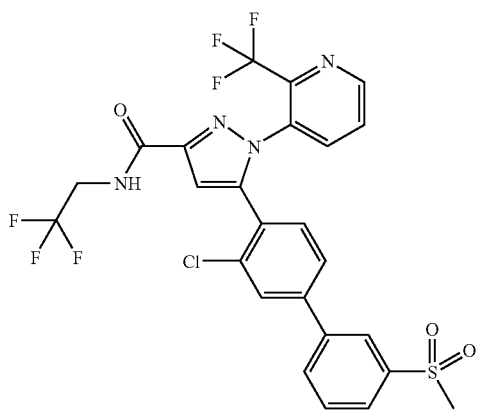 [SMILES: CS(=O)(=O)c1cccc(-c2ccc(-c3cc(C(=O)NCC(F)(F)F)nn3-c3cccnc3C(F)(F)F)c(Cl)c2)c1] | 5-(3-chloro-3'-(methylsulfonyl)biphenyl-4-yl)-N-(2,2,2-trifluoroethyl)-1-(2-(trifluoromethyl)pyridin-3-yl)-1H-pyrazole-3-carboxamide |

TABLE 1-continued

| | | |
|---|---|---|
| 1402 | 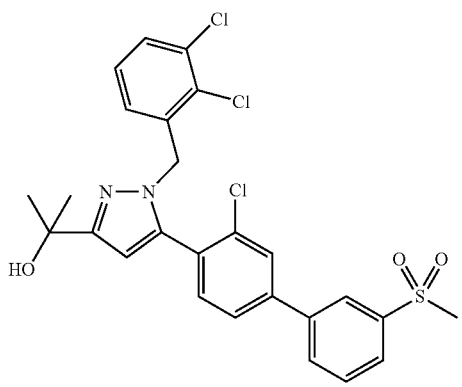 [SMILES: CC(C)(O)c1cc(-c2ccc(-c3cccc(S(C)(=O)=O)c3)cc2Cl)n(Cc2cccc(Cl)c2Cl)n1] | 2-(5-(3-chloro-3'-(methylsulfonyl)biphenyl-4-yl)-1-(2,3-dichlorobenzyl)-1H-pyrazol-3-yl)propan-2-ol |
| 1403 | 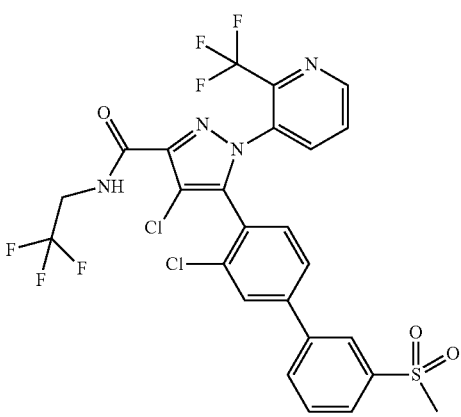 [SMILES: CS(=O)(=O)c1cccc(-c2ccc(-c3c(Cl)c(C(=O)NCC(F)(F)F)nn3-c3cccnc3C(F)(F)F)c(Cl)c2)c1] | 4-chloro-5-(3-chloro-3'-(methylsulfonyl)biphenyl-4-yl)-N-(2,2,2-trifluoromethyl)-1-(2-(trifluoromethyl)pyridin-3-yl)-1H-pyrazole-3-carboxamide |
| 1404 | 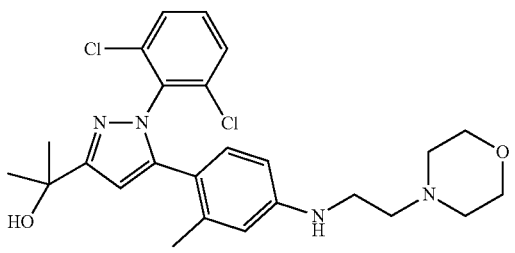 [SMILES: Cc1cc(NCCN2CCOCC2)ccc1-c1cc(C(C)(C)O)nn1-c1c(Cl)cccc1Cl] | 2-(1-(2,6-dichlorophenyl)-5-(2-methyl-4-(2-morpholinoethylamino)phenyl)-1H-pyrazol-3-yl)propan-2-ol |
| 1405 | 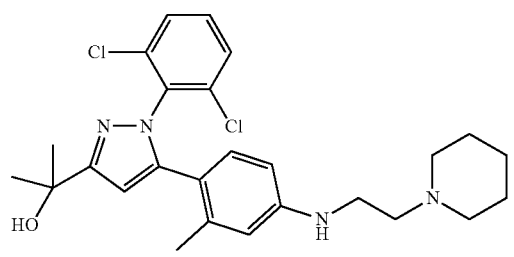 [SMILES: Cc1cc(NCCN2CCCCC2)ccc1-c1cc(C(C)(C)O)nn1-c1c(Cl)cccc1Cl] | 2-(1-(2,6-dichlorophenyl)-5-(2-methyl-4-(2-(piperidin-1-yl)ethylamino)phenyl)-1H-pyrazol-3-yl)propan-2-ol |
| 1406 | 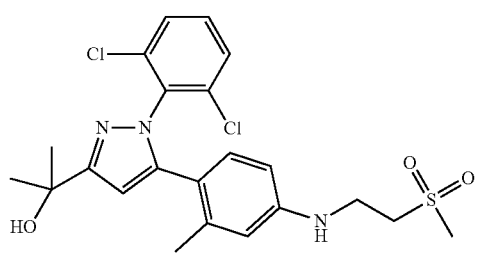 [SMILES: Cc1cc(NCCS(C)(=O)=O)ccc1-c1cc(C(C)(C)O)nn1-c1c(Cl)cccc1Cl] | 2-(1-(2,6-dichlorophenyl)-5-(2-methyl-4-(2-(methylsulfonyl)ethylamino)phenyl)-1H-pyrazol-3-yl)propan-2-ol |

| | | |
|---|---|---|
| 1407 | 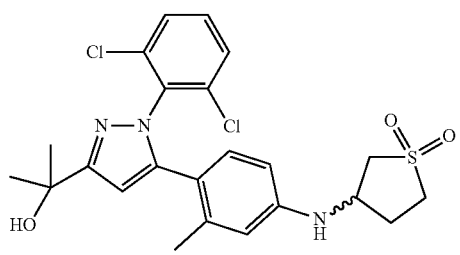 [SMILES: Cc1cc(NC2CCS(=O)(=O)C2)ccc1-c1cc(C(C)(C)O)nn1-c1c(Cl)cccc1Cl] | 2-[1-(2,6-dichlorophenyl)-5-{4-[(1,1-dioxidotetrahydro-3-thienyl)amino]-2-methylphenyl}-1H-pyrazol-3-yl]propan-2-ol |
| 1408 | 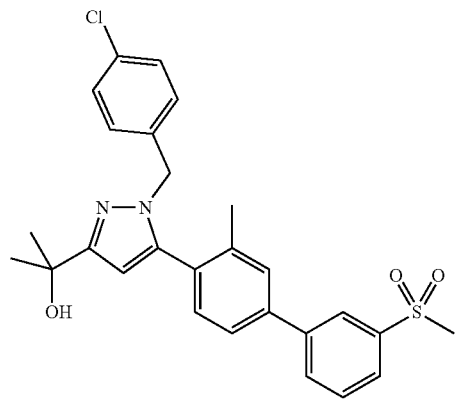 [SMILES: Cc1cc(-c2cccc(S(C)(=O)=O)c2)ccc1-c1cc(C(C)(C)O)nn1Cc1ccc(Cl)cc1] | 2-(1-(4-chlorobenzyl)-5-(3-methyl-3'-(methylsulfonyl)biphenyl-4-yl)-1H-pyrazol-3-yl)propan-2-ol |
| 1409 | 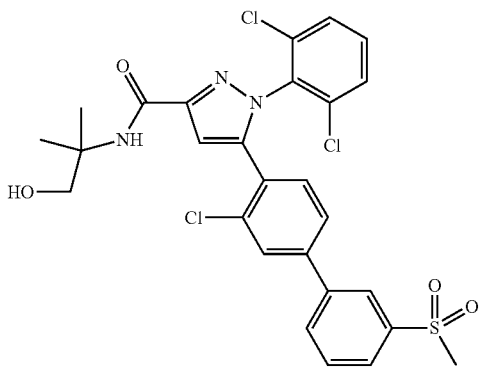 [SMILES: CC(C)(CO)NC(=O)c1cc(-c2ccc(-c3cccc(S(C)(=O)=O)c3)cc2Cl)n(-c2c(Cl)cccc2Cl)n1] | 5-(3-chloro-3'-(methylsulfonyl)biphenyl-4-yl)-1-(2,6-dichlorophenyl)-N-(1-hydroxy-2-methylpropan-2-yl)-1H-pyrazole-3-carboxamide |
| 1410 | 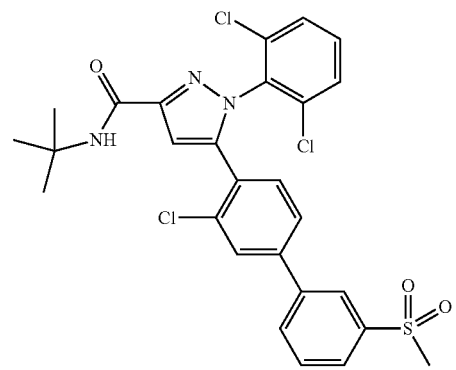 [SMILES: CC(C)(C)NC(=O)c1cc(-c2ccc(-c3cccc(S(C)(=O)=O)c3)cc2Cl)n(-c2c(Cl)cccc2Cl)n1] | N-tert-butyl-5-(3-chloro-3'-(methylsulfonyl)biphenyl-4-yl)-1-(2,6-dichlorophenyl)-1H-pyrazole-3-carboxamide |

| | | |
|---|---|---|
| 1411 | 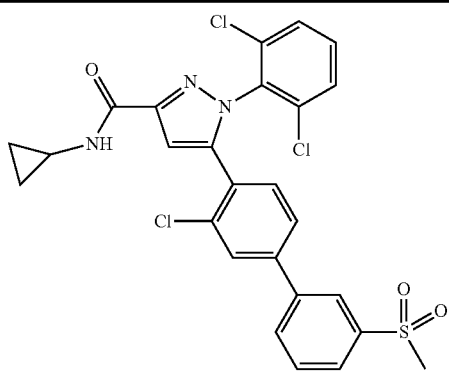 | 5-(3-chloro-3'-(methylsulfonyl)biphenyl-4-yl)-N-cyclopropyl-1-(2,6-dichlorophenyl)-1H-pyrazole-3-carboxamide |
| 1412 | 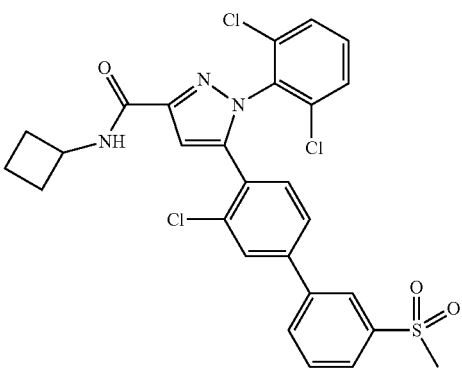 [SMILES: CS(=O)(=O)c1cccc(-c2ccc(-c3cc(C(=O)NC4CCC4)nn3-c3c(Cl)cccc3Cl)c(Cl)c2)c1] | 5-(3-chloro-3'-(methylsulfonyl)biphenyl-4-yl)-N-cyclobutyl-1-(2,6-dichlorophenyl)-1H-pyrazole-3-carboxamide |
| 1413 | 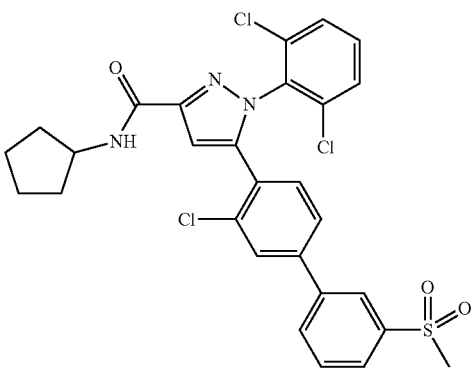 [SMILES: CS(=O)(=O)c1cccc(-c2ccc(-c3cc(C(=O)NC4CCCC4)nn3-c3c(Cl)cccc3Cl)c(Cl)c2)c1] | 5-(3-chloro-3'-(methylsulfonyl)biphenyl-4-yl)-N-cyclopentyl-1-(2,6-dichlorophenyl)-1H-pyrazole-3-carboxamide |
| 1414 | 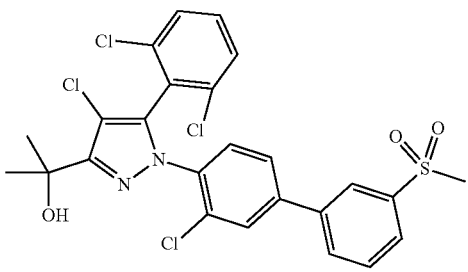 [SMILES: CC(C)(O)c1nn(-c2ccc(-c3cccc(S(C)(=O)=O)c3)cc2Cl)c(-c2c(Cl)cccc2Cl)c1Cl] | 2-(4-chloro-1-(3-chloro-3'-(methylsulfonyl)biphenyl-4-yl)-5-(2,6-dichlorophenyl)-1H-pyrazol-3-yl)propan-2-ol |
| 1415 | 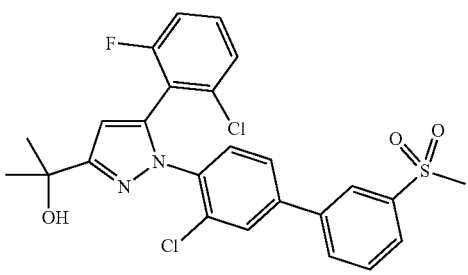 [SMILES: CC(C)(O)c1cc(-c2c(F)cccc2Cl)n(-c2ccc(-c3cccc(S(C)(=O)=O)c3)cc2Cl)n1] | 2-(4-chloro-1-(3-chloro-3'-(methylsulfonyl)biphenyl-4-yl)-5-(2-chloro-6-fluorophenyl)-1H-pyrazol-3-yl)propan-2-ol |

| | | |
|---|---|---|
| 1416 | 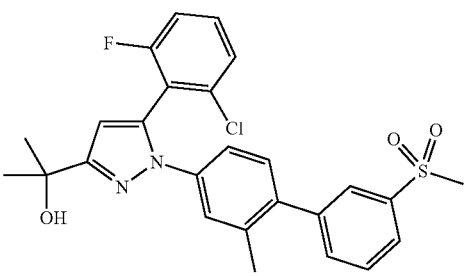 [SMILES: Cc1cc(-n2nc(C(C)(C)O)cc2-c2c(F)cccc2Cl)ccc1-c1cccc(S(C)(=O)=O)c1] | 2-(5-(2-chloro-6-fluorophenyl)-1-(2-methyl-3'-(methylsulfonyl)biphenyl-4-yl)-1H-pyrazol-3-yl)propan-2-ol |
| 1417 | 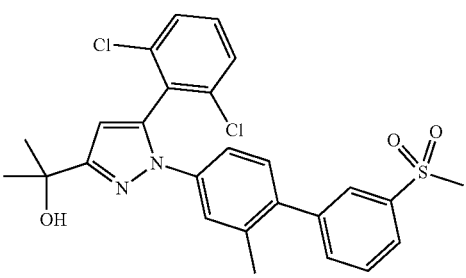 [SMILES: Cc1cc(-n2nc(C(C)(C)O)cc2-c2c(Cl)cccc2Cl)ccc1-c1cccc(S(C)(=O)=O)c1] | 2-(5-(2,6-dichlorophenyl)-1-(2-methyl-3'-(methylsulfonyl)biphenyl-4-yl)-1H-pyrazol-3-yl)propan-2-ol |
| 1418 | 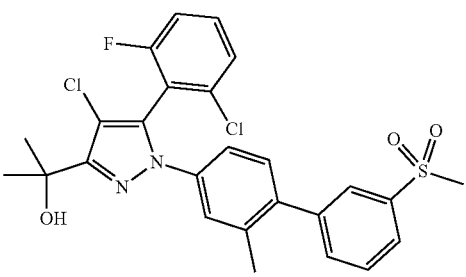 | 2-(4-chloro-5-(2-chloro-5-fluorophenyl)-1-(2-methyl-3'-(methylsulfonyl)biphenyl-4-yl)-1H-pyrazol-3-yl)propan-2-ol |
| 1419 | 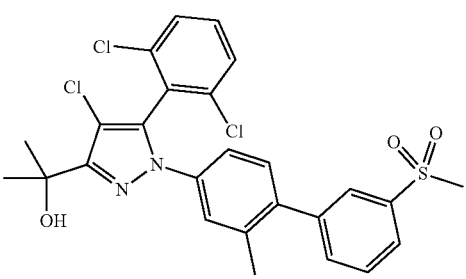 [SMILES: Cc1cc(-n2nc(C(C)(C)O)c(Cl)c2-c2c(Cl)cccc2Cl)ccc1-c1cccc(S(C)(=O)=O)c1] | 2-(4-chloro-5-(2,6-dichlorophenyl)-1-(2-methyl-3'-(methylsulfonyl)biphenyl-4-yl)-1H-pyrazol-3-yl)propan-2-ol |
| 1420 | 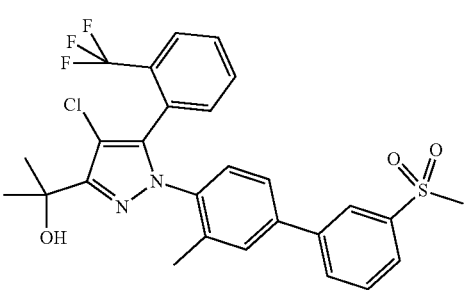 [SMILES: Cc1cc(-c2cccc(S(C)(=O)=O)c2)ccc1-n1nc(C(C)(C)O)c(Cl)c1-c1ccccc1C(F)(F)F] | 2-(4-chloro-1-(3-methyl-3'-(methylsulfonyl)biphenyl-4-yl)-5-(2-(trifluoromethyl)phenyl)-1H-pyrazol-3-yl)propan-2-ol |

TABLE 1-continued

| | | |
|---|---|---|
| 1421 | 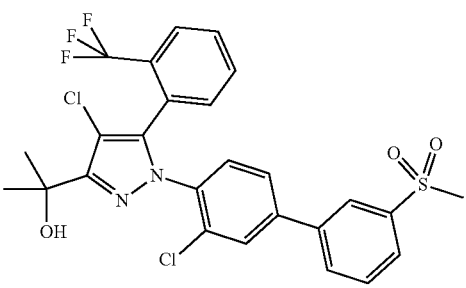 [SMILES: CC(C)(O)c1nn(-c2ccc(-c3cccc(S(C)(=O)=O)c3)cc2Cl)c(-c2ccccc2C(F)(F)F)c1Cl] | 2-(4-chloro-1-(3-chloro-3'-(methylsulfonyl)biphenyl-4-yl)-5-(2-(trifluoromethyl)phenyl)-1H-pyrazol-3-yl)propan-2-ol |
| 1422 | 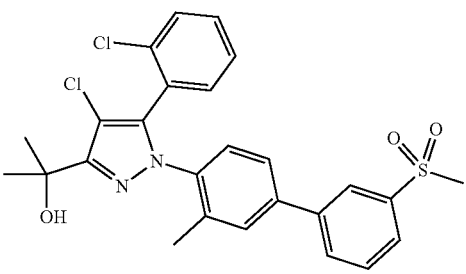 [SMILES: Cc1cc(-c2cccc(S(C)(=O)=O)c2)ccc1-n1nc(C(C)(C)O)c(Cl)c1-c1ccccc1Cl] | 2-(4-chloro-5-(2-chlorophenyol)-1-(3-methyl-3'-(methylsulfonyl)biphenyl-4-yl)-1H-pyrazol-3-yl)propan-2-ol |
| 1423 | 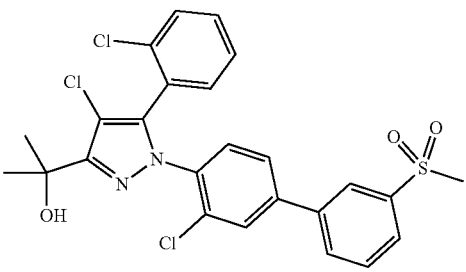 [SMILES: CC(C)(O)c1nn(-c2ccc(-c3cccc(S(C)(=O)=O)c3)cc2Cl)c(-c2ccccc2Cl)c1Cl] | 2-(4-chloro-1-(3-chloro-3'-(methylsulfonyl)biphenyl-4-yl)-5-(2-chlorophenyl)-1H-pyrazol-3-yl)propan-2-ol |
| 1424 | 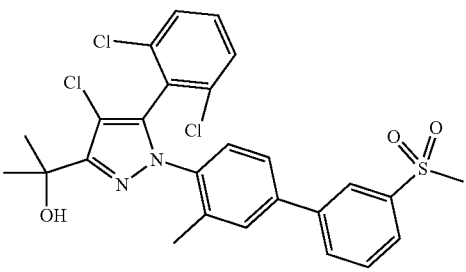 [SMILES: Cc1cc(-c2cccc(S(C)(=O)=O)c2)ccc1-n1nc(C(C)(C)O)c(Cl)c1-c1c(Cl)cccc1Cl] | 2-(4-chloro-5-(2,6-dichlorophenyl)-1-(3-methyl-3'-(methylsulfonyl)biphenyl-4-yl)-1H-pyrazol-3-yl)propan-2-ol |
| 1425 | 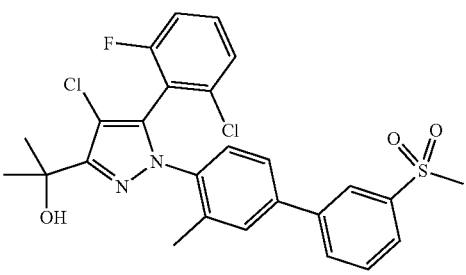 [SMILES: Cc1cc(-c2cccc(S(C)(=O)=O)c2)ccc1-n1nc(C(C)(C)O)c(Cl)c1-c1c(F)cccc1Cl] | 2-(4-chloro-5-(2-chloro-6-fluorophenyl)-1-(3-fluoro-3'-(methylsulfonyl)biphenyl-4-yl)-1H-pyrazol-3-yl)propan-2-ol |

| | | |
|---|---|---|
| 1426 | 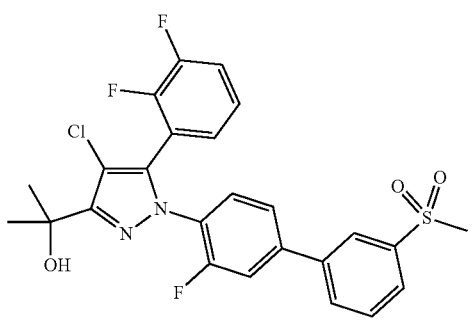 | 2-(4-chloro-5-(2,3-dichlorophenyl)-1-(3-fluoro-3'-(methylsulfonyl)biphenyl-4-yl)-1H-pyrazol-3-yl)propan-2-ol |
| 1427 | 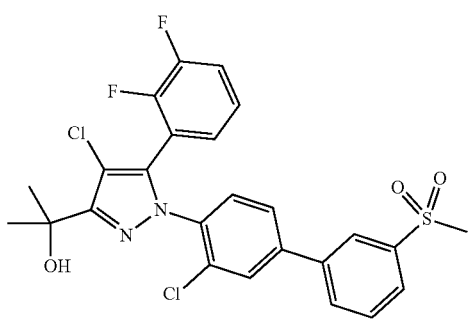 [SMILES: CC(C)(O)c1nn(-c2ccc(-c3cccc(S(C)(=O)=O)c3)cc2Cl)c(-c2cccc(F)c2F)c1Cl] | 2-(4-chloro-1-(3-chloro-3'-(methylsulfonyl)biphenyl-4-yl)-5-(2,3-difluorophenyl)-1H-pyrazol-3-yl)propan-2-ol |
| 1428 | 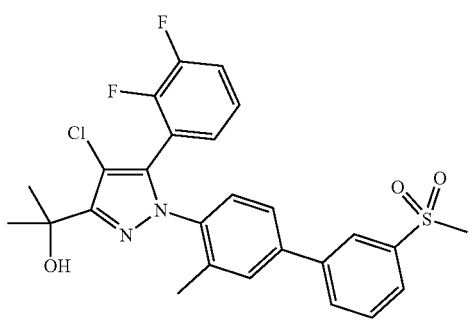 [SMILES: Cc1cc(-c2cccc(S(C)(=O)=O)c2)ccc1-n1nc(C(C)(C)O)c(Cl)c1-c1cccc(F)c1F] | 2-(4-chloro-5-(2,3-difluorophenyl)-1-(3-methyl-3'-(methylsulfonyl)biphenyl-4-yl)-1H-pyrazol-3-yl)propan-2-ol |
| 1429 | 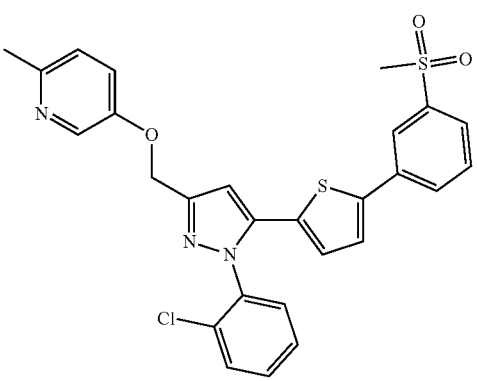 [SMILES: Cc1ccc(OCc2cc(-c3ccc(-c4cccc(S(C)(=O)=O)c4)s3)n(-c3ccccc3Cl)n2)cn1] | 5-({[1-(2-chlorophenyl)-5-{5-[3-(methylsulfonyl)phenyl]-2-thienyl}-1H-pyrazol-3-yl]methyl}oxy)-2-methylpyridine |

| | | |
|---|---|---|
| 1430 | 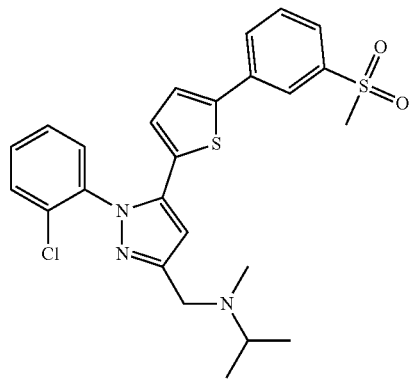 [SMILES: CC(C)N(C)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-methylpropan-2-amine |
| 1431 | 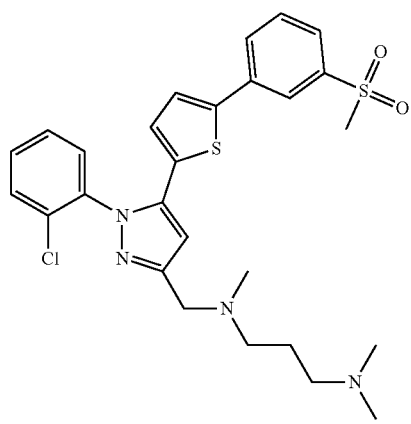 [SMILES: CN(C)CCCN(C)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N,N',N'-trimethylpropane-1,3-diamine |
| 1432 | 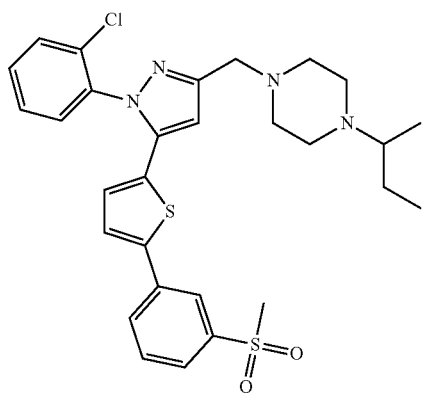 [SMILES: CCC(C)N1CCN(Cc2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]methyl}-4-(1-methylpropyl)piperazine |
| 1433 | Abs 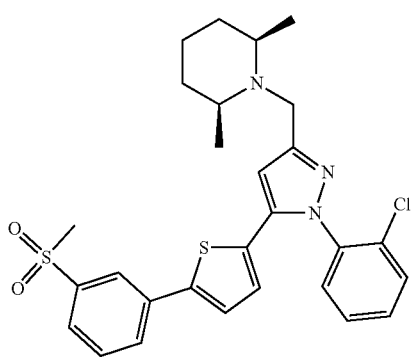 | (2R,6S)-1-{[1-(2-chlorophenyl)-5-{5-[3-(methylsulfonyl)phenyl]-2-thienyl}-1H-pyrazol-3-yl]methyl}-2,6-dimethylpiperidine |

| | | |
|---|---|---|
| 1434 | 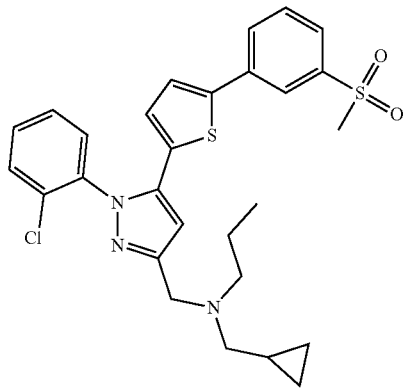 [SMILES: CCCN(Cc1cc(-c2ccc(-c3cccc(S(C)(=O)=O)c3)s2)n(-c2ccccc2Cl)n1)CC1CC1] | N-{[1-(2-chlorophenyl)-5-{5-[3-(methylsulfonyl)phenyl]-2-thienyl}-1H-pyrazol-3-yl]methyl}-N-(cyclopropylmethyl)propan-1-amine |
| 1435 | 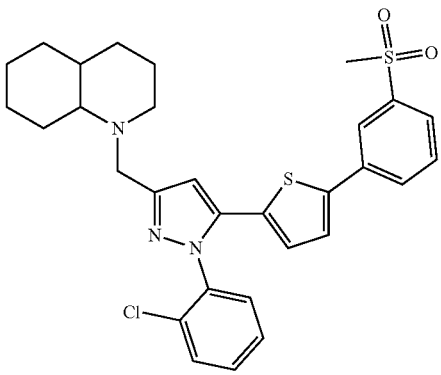 [SMILES: CS(=O)(=O)c1cccc(-c2ccc(-c3cc(CN4CCCC5CCCCC54)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}decahydroquinoline |
| 1436 | 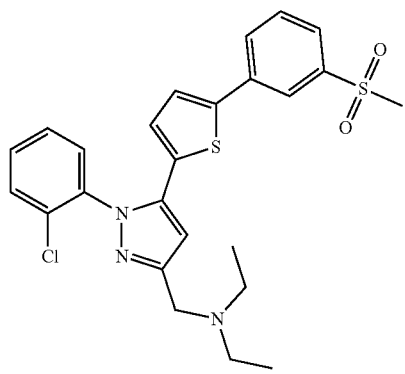 [SMILES: CCN(CC)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-ethylethanamine |
| 1437 | 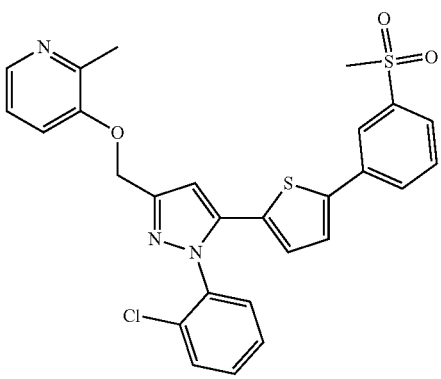 [SMILES: Cc1ncccc1OCc1cc(-c2ccc(-c3cccc(S(C)(=O)=O)c3)s2)n(-c2ccccc2Cl)n1] | 3-({[1-(2-chlorophenyl)-5-{5-[3-(methylsulfonyl)phenyl]-2-thienyl}-1H-pyrazol-3-yl]methyl}oxy)-2-methylpyridine |

| | | |
|---|---|---|
| 1438 | 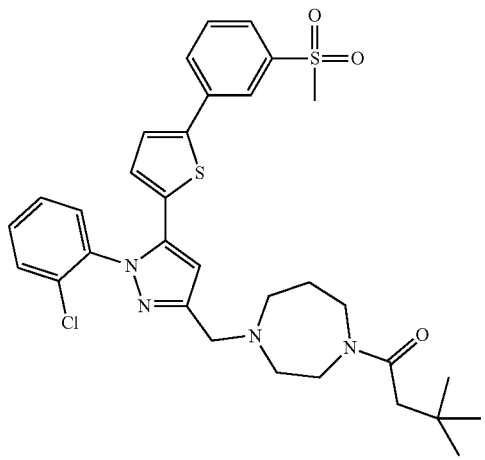 [SMILES: CC(C)(C)CC(=O)N1CCCN(Cc2cc(-c3ccc(-c4cccc(S(C)(=O)=O)c4)s3)n(-c3ccccc3Cl)n2)CC1] | 1,1-dimethylethyl 4-{[1-(2-chlorophenyl)-5-{5-[3-(methylsulfonyl)phenyl]-2-thienyl}-1H-pyrazol-3-yl]methyl}-1,4-diazepane-1-carboxylate |
| 1439 | 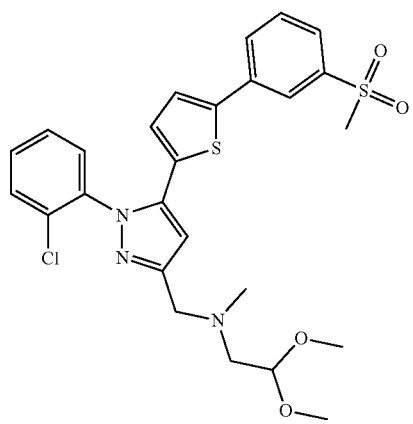 [SMILES: COC(CN(C)Cc1cc(-c2ccc(-c3cccc(S(C)(=O)=O)c3)s2)n(-c2ccccc2Cl)n1)OC] | N-{[1-(2-chlorophenyl)-5-{5-[3-(methylsulfonyl)phenyl]-2-thienyl}-1H-pyrazol-3-yl]methyl}-N-methyl-2,2-bis(methyloxy)ethanamine |
| 1440 | 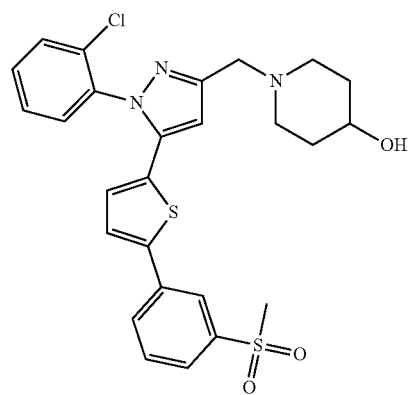 [SMILES: CS(=O)(=O)c1cccc(-c2ccc(-c3cc(CN4CCC(O)CC4)nn3-c3ccccc3Cl)s2)c1] | 1-{[1-(2-chlorophenyl)-5-{5-[3-(methylsulfonyl)phenyl]-2-thienyl}-1H-pyrazol-3-yl]methyl}piperidin-4-ol |

| | | | |
|---|---|---|---|
| 1441 | 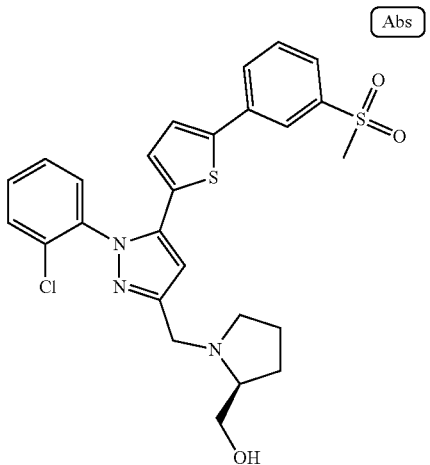 [SMILES: CS(=O)(=O)c1cccc(-c2ccc(-c3cc(CN4CCC[C@H]4CO)nn3-c3ccccc3Cl)s2)c1] | Abs | [(2S)-1-{[1-(2-chlorophenyl)-5-{5-[3-(methylsulfonyl)phenyl]-2-thienyl}-1H-pyrazol-3-yl]methyl}pyrrolidin-2-yl]methanol |
| 1442 | 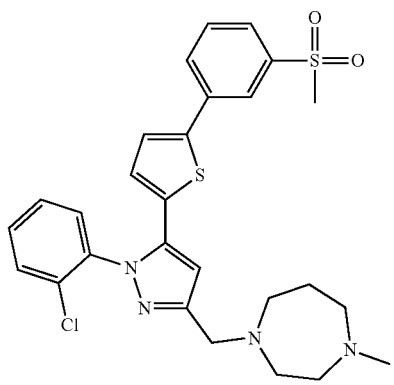 [SMILES: CN1CCCN(Cc2cc(-c3ccc(-c4cccc(S(C)(=O)=O)c4)s3)n(-c3ccccc3Cl)n2)CC1] | | 1-{[1-(2-chlorophenyl)-5-{5-[3-(methylsulfonyl)phenyl]-2-thienyl}-1H-pyrazol-3-yl]methyl}-4-methyl-1,4-diazepane |
| 1443 | 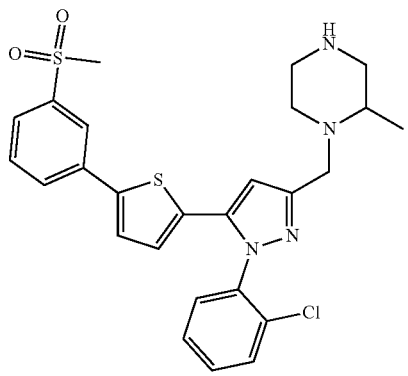 [SMILES: CC1CNCCN1Cc1cc(-c2ccc(-c3cccc(S(C)(=O)=O)c3)s2)n(-c2ccccc2Cl)n1] | | 1-{[1-(2-chlorophenyl)-5-{5-[3-(methylsulfonyl)phenyl]-2-thienyl}-1H-pyrazol-3-yl]methyl}-2-methylpiperazine |
| 1444 | 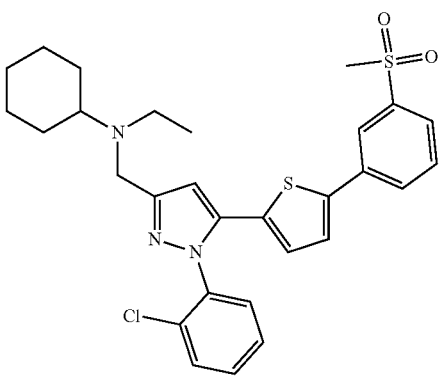 [SMILES: CCN(Cc1cc(-c2ccc(-c3cccc(S(C)(=O)=O)c3)s2)n(-c2ccccc2Cl)n1)C1CCCCC1] | | N-{[1-(2-chlorophenyl)-5-{5-[3-(methylsulfonyl)phenyl]-2-thienyl}-1H-pyrazol-3-yl]methyl}-N-ethylcyclohexanamine |

TABLE 1-continued

| | | |
|---|---|---|
| 1445 | 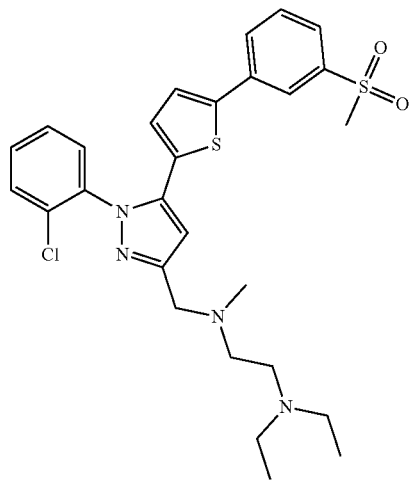 [SMILES: CCN(CC)CCN(C)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N',N'-diethyl-N-methylethane-1,2-diamine |
| 1446 | 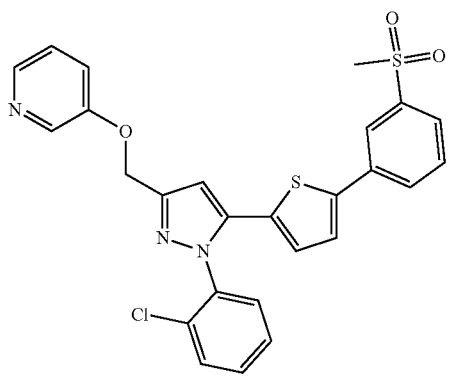 [SMILES: CS(=O)(=O)c1cccc(-c2ccc(-c3cc(COc4cccnc4)nn3-c3ccccc3Cl)s2)c1] | 3-({[1-(2-chlorophenyl)-5-{5-[3-(methylsulfonyl)phenyl]-2-thienyl}-1H-pyrazol-3-yl]methyl}oxy)pyridine |
| 1447 | 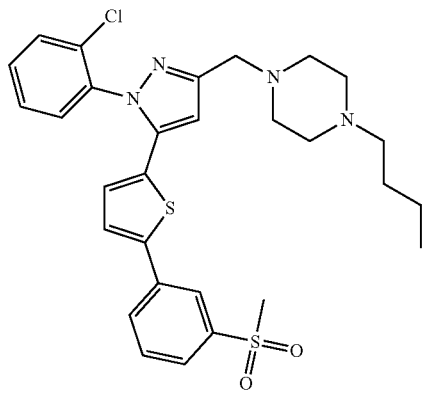 [SMILES: CCCCN1CCN(Cc2cc(-c3ccc(-c4cccc(S(C)(=O)=O)c4)s3)n(-c3ccccc3Cl)n2)CC1] | 1-butyl-4-{[1-(2-chlorophenyl)-5-{5-[3-(methylsulfonyl)phenyl]-2-thoenyl}-1H-pyrazol-3-yl]methyl}piperazine |
| 1448 | 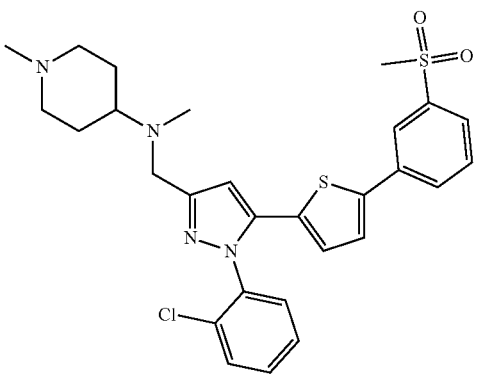 [SMILES: CN1CCC(N(C)Cc2cc(-c3ccc(-c4cccc(S(C)(=O)=O)c4)s3)n(-c3ccccc3Cl)n2)CC1] | N-{[1-(2-chlorophenyl)-5-{5-[3-(methylsulfonyl)phenyl]-2-thienyl}-1H-pyrazol-3-yl]methyl-N,1-dimethylpiperidin-4-amine |

| | | |
|---|---|---|
| 1449 | 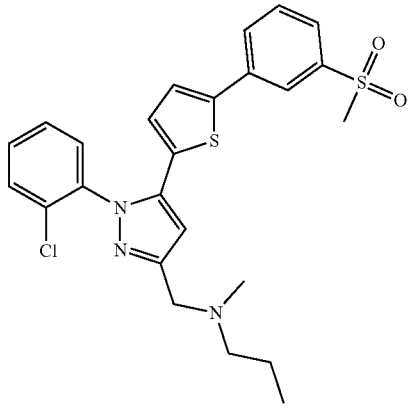 [SMILES: CCCN(C)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazole-3-yl]methyl}-N-methylpropan-1-amine |
| 1450 | 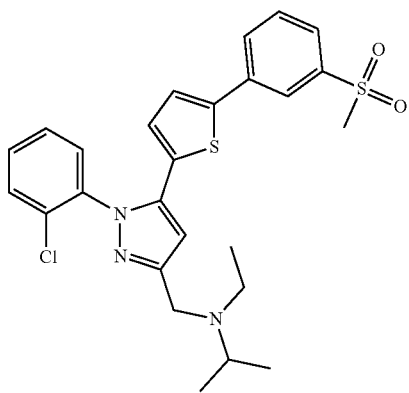 [SMILES: CCN(Cc1cc(-c2ccc(-c3cccc(S(C)(=O)=O)c3)s2)n(-c2ccccc2Cl)n1)C(C)C] | N-{[1-(2-chlorophenyl)-5-{5-[3-(methylsulfonyl)phenyl]-2-thienyl}-1H-pyrazol-3-yl]methyl}-N-ethylpropan-2-amine |
| 1451 | 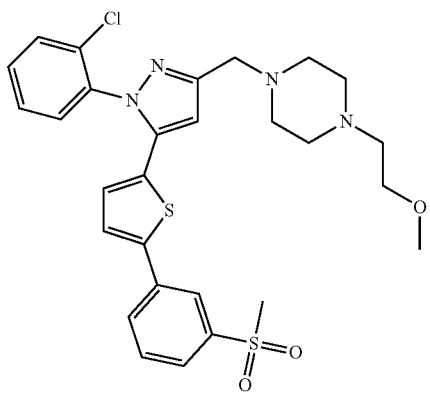 [SMILES: COCCN1CCN(Cc2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]methyl}-4-[2-(methyloxy)ethyl]piperazine |
| 1452 | 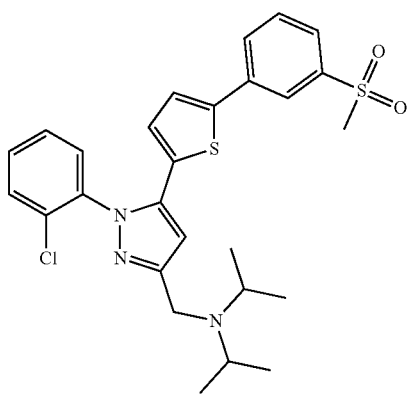 [SMILES: CC(C)N(Cc1cc(-c2ccc(-c3cccc(S(C)(=O)=O)c3)s2)n(-c2ccccc2Cl)n1)C(C)C] | N-{[1-(2-chlorophenyl)-5-{5-[3-(methylsulfonyl)phenyl]-2-thienyl}-1H-pyrazol-3-yl]methyl}-N-(1-methylethyl)propan-2-amine |

TABLE 1-continued

| | | |
|---|---|---|
| 1453 | 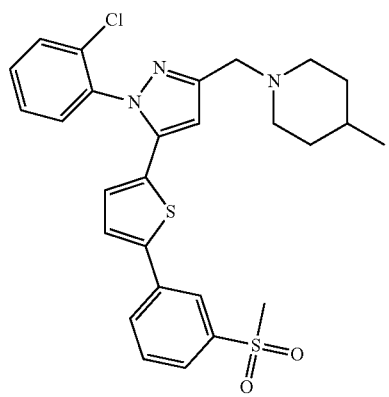 [SMILES: CC1CCN(Cc2cc(-c3ccc(-c4cccc(S(C)(=O)=O)c4)s3)n(-c3ccccc3Cl)n2)CC1] | 1-{[1-(2-chlorophenyl)-5-{5-[3-(methylsulfonyl)phenyl]-2-thienyl}-1H-pyrazol-3-yl]methyl}-4-methylpiperidine |
| 1455 | 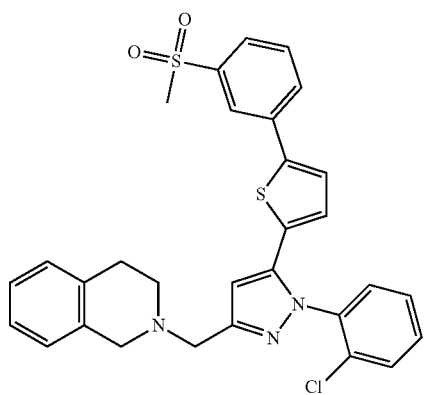 [SMILES: CS(=O)(=O)c1cccc(-c2ccc(-c3cc(CN4CCc5ccccc5C4)nn3-c3ccccc3Cl)s2)c1] | 2-{[1-(2-chlorophenyl)-5-{5-[3-(methylsulfonyl)phenyl]-2-thienyl}-1H-pyrazol-3-yl]methyl}-1,2,3,4-tetrahydroisoquinoline |
| 1456 | 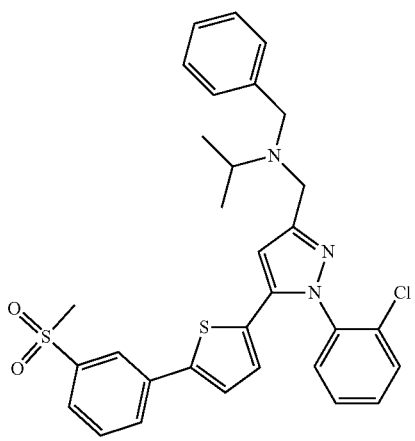 [SMILES: CC(C)N(Cc1ccccc1)Cc1cc(-c2ccc(-c3cccc(S(C)(=O)=O)c3)s2)n(-c2ccccc2Cl)n1] | N-{[1-(2-chlorophenyl)-5-{5-[3-(methylsulfonyl)phenyl]-2-thienyl}-1H-pyrazol-3-yl]methyl}-N-(phenylmethyl)propan-2-amine |
| 1457 | 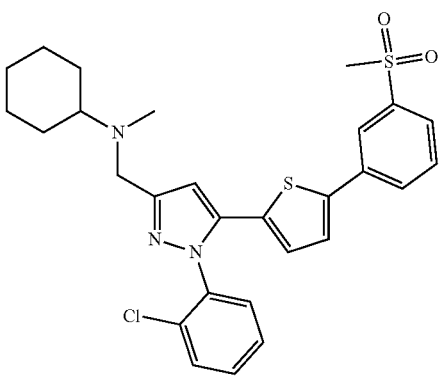 [SMILES: CN(Cc1cc(-c2ccc(-c3cccc(S(C)(=O)=O)c3)s2)n(-c2ccccc2Cl)n1)C1CCCCC1] | N-{[1-(2-chlorophenyl)-5-{5-[3-(methylsulfonyl)phenyl]-2-thienyl}-1H-pyrazol-3-yl]methyl}-N-methylcyclohexanamine |

TABLE 1-continued

| | | |
|---|---|---|
| 1458 | 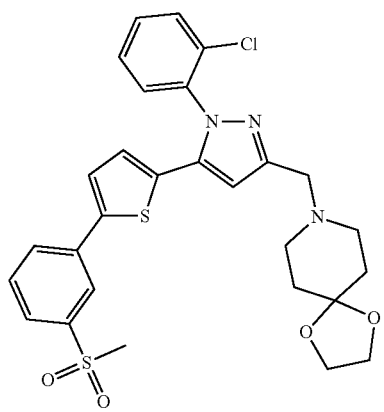 [SMILES: CS(=O)(=O)c1cccc(-c2ccc(-c3cc(CN4CCC5(CC4)OCCO5)nn3-c3ccccc3Cl)s2)c1] | 8-{[1-(2-chlorophenyl)-5-{5-[3-(mehtylsulfonyl)phenyl]-2-thienyl}-1H-pyrazol-3-yl]methyl}-1,4-dioxa-8-azaspiro[4.5]decane |
| 1459 | 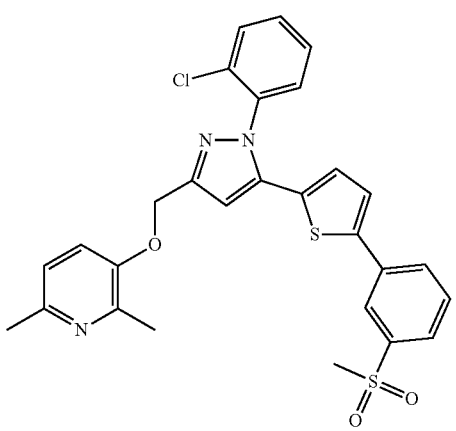 [SMILES: Cc1ccc(OCc2cc(-c3ccc(-c4cccc(S(C)(=O)=O)c4)s3)n(-c3ccccc3Cl)n2)c(C)n1] | 3-({[1-(2-chlorophenyl)-5-{5-[3-(mehtylsulfonyl)phenyl]-2-thienyl}-1H-pyrazol-3-yl]methyl}oxy)-2,6-dimethylpyridine |
| 1460 | 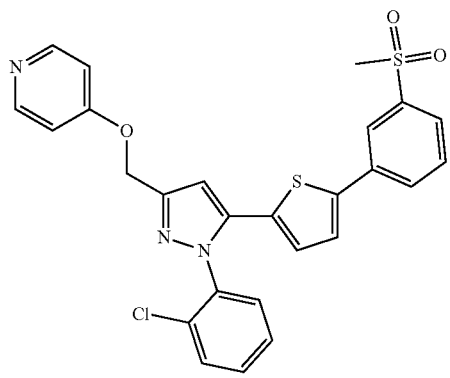 [SMILES: CS(=O)(=O)c1cccc(-c2ccc(-c3cc(COc4ccncc4)nn3-c3ccccc3Cl)s2)c1] | 4-({[1-(2-chlorophenyl)-5-{5-[3-(methylsulfonyl)phenyl]-2-thienyl}-1H-pyrazol-3-yl]methyl}oxy)pyridine |
| 1461 | 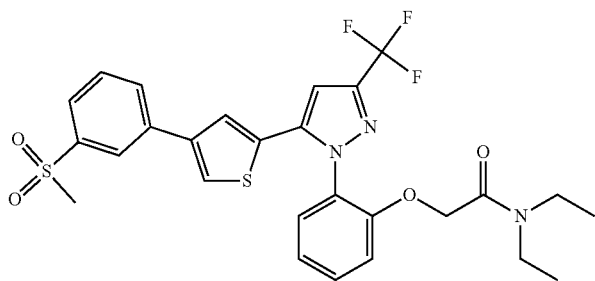 [SMILES: CCN(CC)C(=O)COc1ccccc1-n1nc(C(F)(F)F)cc1-c1cc(-c2cccc(S(C)(=O)=O)c2)cs1] | N,N-diethyl-2-({2-[5-{4-[3-(methylsulfonyl)phenyl]-2-thienyl}-3-(trifluoromethyl)-1H-pyrazol-1-yl]phenyl}oxy)acetamide |

| | | |
|---|---|---|
| 1462 | 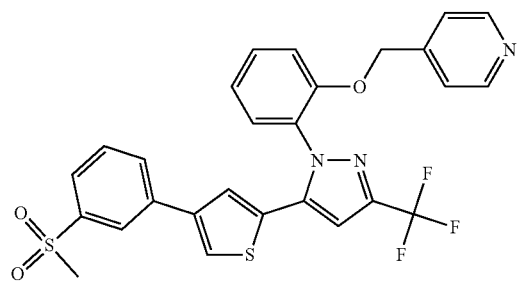 [SMILES: CS(=O)(=O)c1cccc(-c2csc(-c3cc(C(F)(F)F)nn3-c3ccccc3OCc3ccncc3)c2)c1] | 4-[({2-[5-{4-[3-(methylsulfonyl)phenyl]-2-thienyl}-3-(trifluoromethyl)-1H-pyrazol-1-yl]phenyl}oxy)methyl]pyridine |
| 1463 | 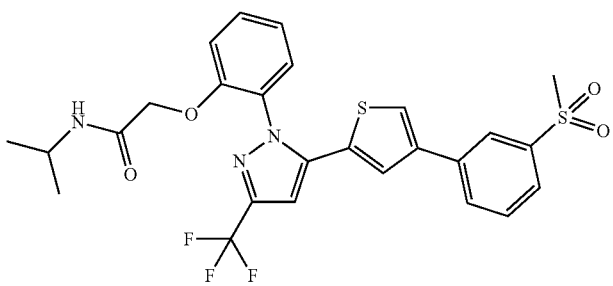 [SMILES: CC(C)NC(=O)COc1ccccc1-n1nc(C(F)(F)F)cc1-c1cc(-c2cccc(S(C)(=O)=O)c2)cs1] | N-(1-methylethyl)-2-({2-[5-{4-[3-(methylsulfonyl)phenyl]-2-thienyl}-3-(trifluoromethyl)-1H-pyrazol-1-yl]phenyl}oxy)acetamide |
| 1464 | 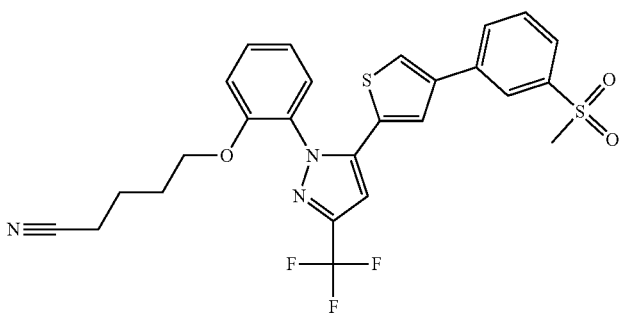 [SMILES: CS(=O)(=O)c1cccc(-c2csc(-c3cc(C(F)(F)F)nn3-c3ccccc3OCCCCC#N)c2)c1] | 5-({2-[5-{4-[3-(methylsulfonyl)phenyl]-2-thienyl}-3-(trifluoromethyl)-1H-pyrazol-1-yl]phenyl}oxy)pentanenitrile |
| 1465 | 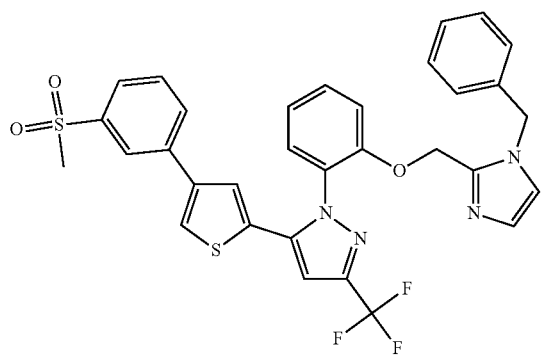 [SMILES: CS(=O)(=O)c1cccc(-c2csc(-c3cc(C(F)(F)F)nn3-c3ccccc3OCc3nccn3Cc3ccccc3)c2)c1] | 5-{4-[3-(methylsulfonyl)phenyl]-2-thienyl}-1-[2-({[1-(phenylmethyl)-1H-imidazol-2-yl]methyl}oxy)phenyl]-3-(trifluoromethyl)-1H-pyrazole |
| 1466 | 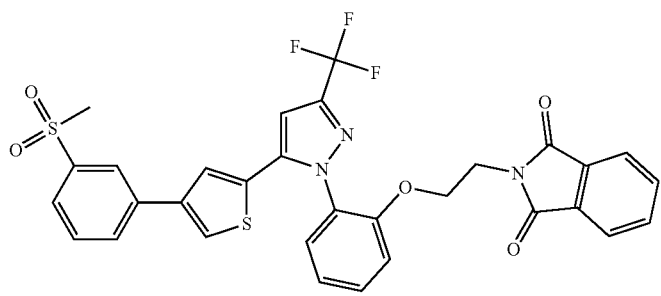 [SMILES: CS(=O)(=O)c1cccc(-c2csc(-c3cc(C(F)(F)F)nn3-c3ccccc3OCCN3C(=O)c4ccccc4C3=O)c2)c1] | 2-[2-({2-[5-{4-[3-(methylsulfonyl)phenyl]-2-thienyl}-3-(trifluoromethyl)-1H-pyrazol-1-yl]phenyl}oxy)ethyl]-1H-isoindole-1,3(2H)-dione |

| | | |
|---|---|---|
| 1467 | 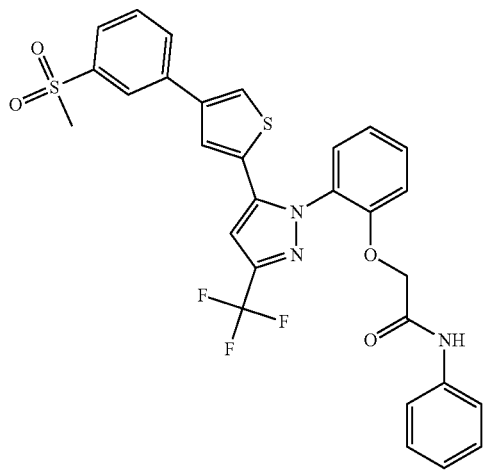 [SMILES: CS(=O)(=O)c1cccc(-c2csc(-c3cc(C(F)(F)F)nn3-c3ccccc3OCC(=O)Nc3ccccc3)c2)c1] | 2-({2-[5-{4-[3-(methylsulfonyl)phenyl]-2-thienyl}-3-(trifluoromethyl)-1H-pyrazol-1-yl]phenyl}oxy)-N-phenylacetamide |
| 1468 | 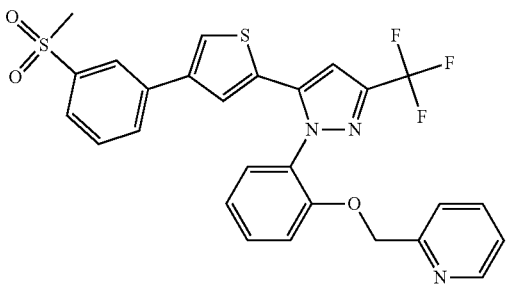 [SMILES: CS(=O)(=O)c1cccc(-c2csc(-c3cc(C(F)(F)F)nn3-c3ccccc3OCc3ccccn3)c2)c1] | 2-[({2-[5-{4-[3-(methylsulfonyl)phenyl]-2-thienyl}-3-(trifluoromethyl)-1H-pyrazol-1-yl]phenyl}oxy)methyl]pyridine |
| 1469 | 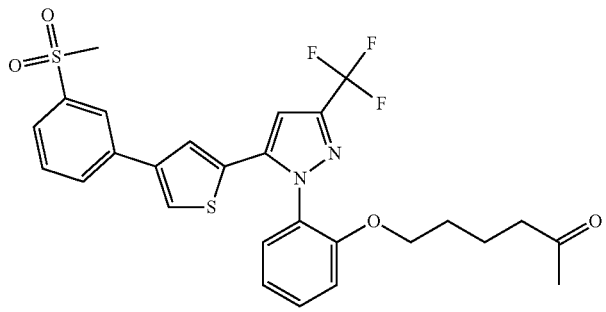 [SMILES: CC(=O)CCCCOc1ccccc1-n1nc(C(F)(F)F)cc1-c1cc(-c2cccc(S(C)(=O)=O)c2)cs1] | 6-({2-[5-{4-[3-(methylsulfonyl)phenyl]-2-thienyl}-3-(trifluoromethyl)-1H-pyrazol-1-yl]phenyl}oxy)hexan-2-one |
| 1470 | 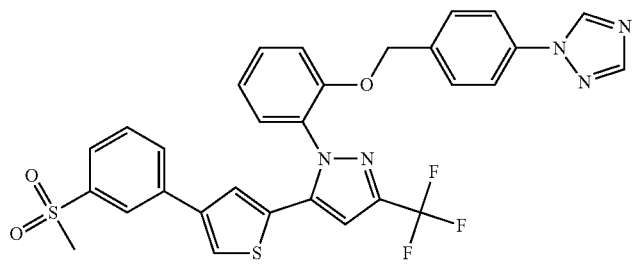 [SMILES: CS(=O)(=O)c1cccc(-c2csc(-c3cc(C(F)(F)F)nn3-c3ccccc3OCc3ccc(-n4cncn4)cc3)c2)c1] | 1-{4-[({2-[5-{4-[3-(methylsulfonyl)phenyl]-2-thienyl}-3-(trifluoromethyl)-1H-pyrazol-1-yl]phenyl}oxy)methyl]phenyl}-1H-1,2,4-triazole |

| | | |
|---|---|---|
| 1471 | 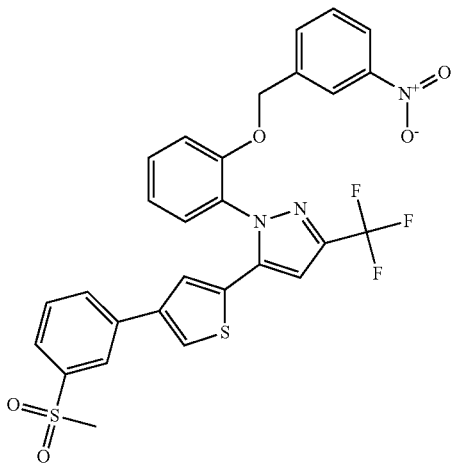 [SMILES: CS(=O)(=O)c1cccc(-c2csc(-c3cc(C(F)(F)F)nn3-c3ccccc3OCc3cccc([N+](=O)[O-])c3)c2)c1] | 5-{4-[3-(mehtylsulfonyl)phenyl]-2-thianyl}-1-(2-{[(3-nitrophenyl)methyl]oxy}phenyl)-3-(trifluoromethyl)-1H-pyrazole |
| 1472 | 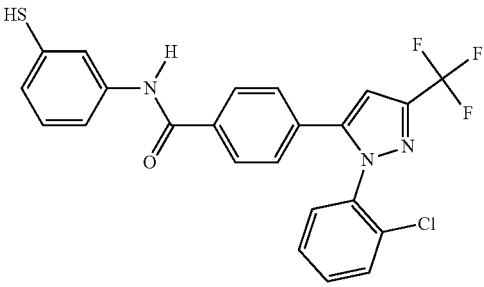 [SMILES: O=C(Nc1cccc(S)c1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-mercaptophenyl)benzamide |
| 1473 | 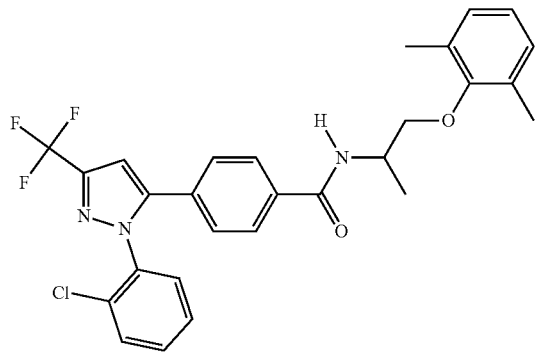 [SMILES: Cc1cccc(C)c1OCC(C)NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{2-[(2,6-dimethylphenyl)oxy]-1-methylethyl}benzamide |
| 1474 | 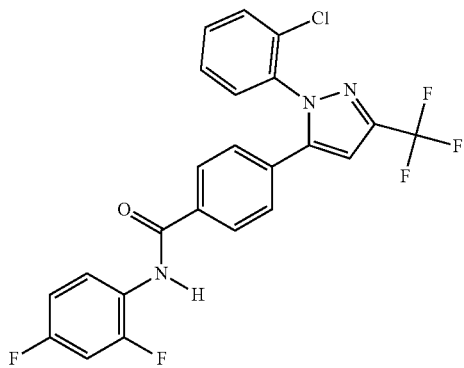 [SMILES: O=C(Nc1ccc(F)cc1F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,4-difluorophenyl)benzamide |

| | | |
|---|---|---|
| 1475 | 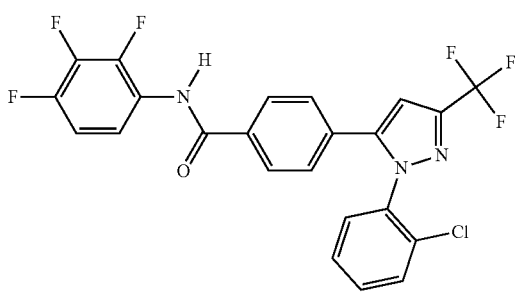 [SMILES: O=C(Nc1ccc(F)c(F)c1F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,3,4-trifluorophenyl)benzamide |
| 1477 | 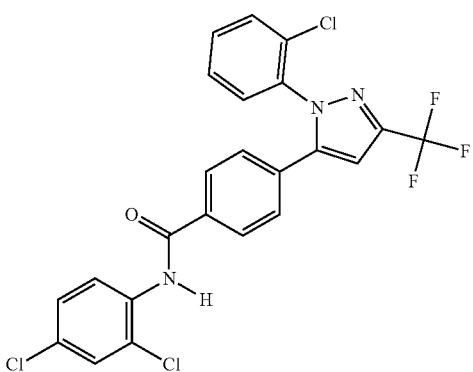 [SMILES: O=C(Nc1ccc(Cl)cc1Cl)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,4-dichlorophenyl)benzamide |
| 1478 | 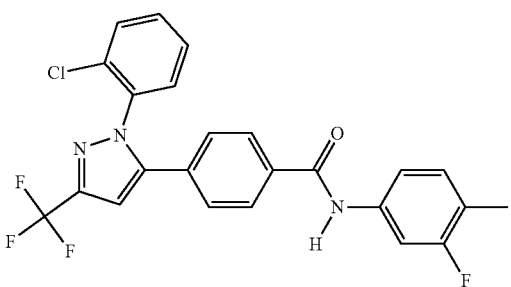 [SMILES: Cc1ccc(NC(=O)c2ccc(-c3cc(C(F)(F)F)nn3-c3ccccc3Cl)cc2)cc1F] | 4-[1-(2-chlorophenyl)-3-(trifluoromethyl)-1H-pyrazol-5-yl]-N-(2-fluoro-4-methylphenyl)benzamide |
| 1479 | 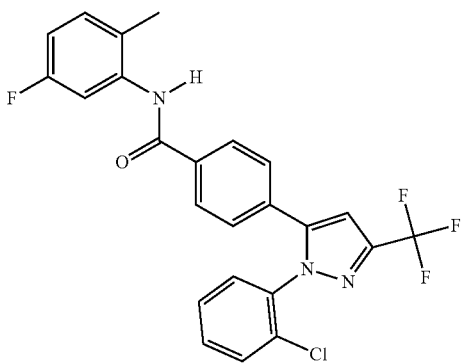 [SMILES: Cc1ccc(F)cc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(5-fluoro-2-methylphenyl)benzamide |

| | | |
|---|---|---|
| 1480 | 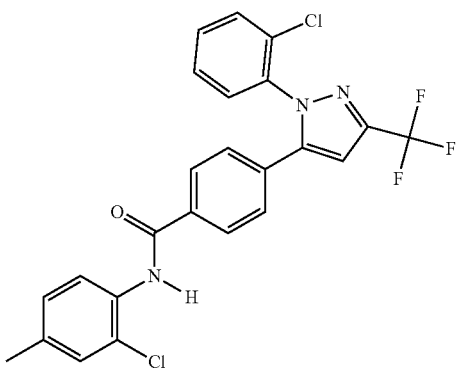 [SMILES: Cc1ccc(NC(=O)c2ccc(-c3cc(C(F)(F)F)nn3-c3ccccc3Cl)cc2)c(Cl)c1] | N-(2-chloro-4-methylphenyl)-4-[1-(2-chlorophenyl)-3-(trifluoromethyl)-1H-pyrazol-5-yl]benzamide |
| 1481 | 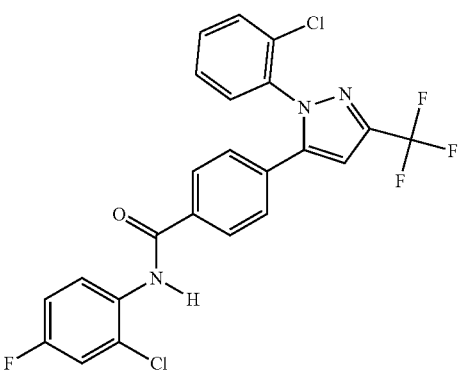 [SMILES: O=C(Nc1ccc(F)cc1Cl)c1ccc(-c2cc(C(F)(F)F)nn2-c2ccccc2Cl)cc1] | N-(2-chloro-4-fluorophenyl)-4-[1-(2-chlorophenyl)-3-(trifluoromethyl)-1H-pyrazol-5-yl]benzamide |
| 1482 | 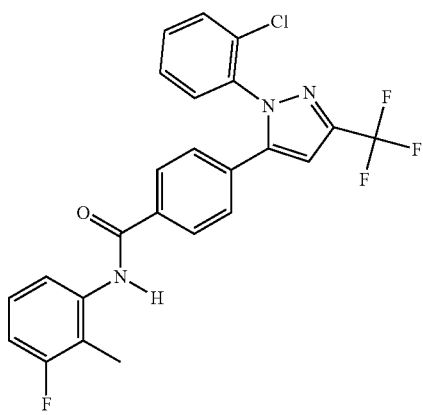 [SMILES: Cc1c(F)cccc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-fluoro-2-methylphenyl)benzamide |
| 1483 | 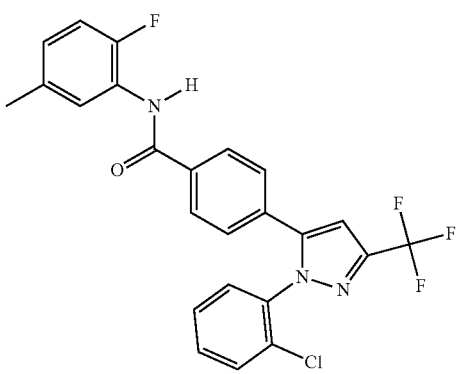 [SMILES: Cc1ccc(F)c(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-(2-fluoro-5-methylphenyl)benzamide |

TABLE 1-continued
1485 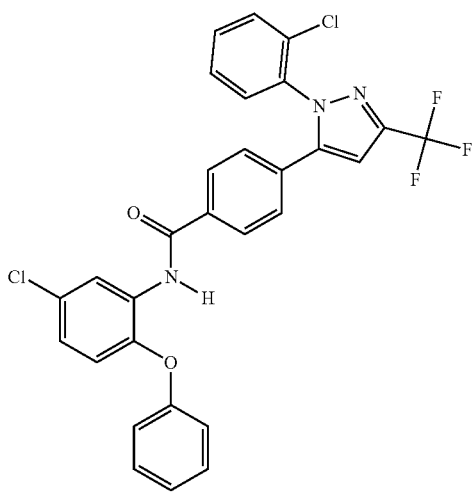 [SMILES: O=C(Nc1cc(Cl)ccc1Oc1ccccc1)c1ccc(-c2cc(C(F)(F)F)nn2-c2ccccc2Cl)cc1]
N-[5-chloro-2-(phenyloxy)phenyl]-4-[1-(2-chlorophenyl)-23-(trifluoromethyl)-1H-pyrazol-5-yl]benzamide
1486 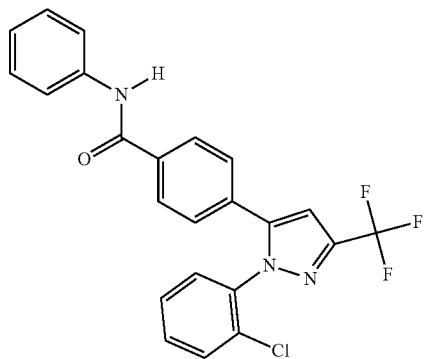 [SMILES: O=C(Nc1ccccc1)c1ccc(-c2cc(C(F)(F)F)nn2-c2ccccc2Cl)cc1]
4-[1-(2-chlorophenyl)-3-(trifluoromethyl)-1H-pyrazol-5-yl]-N-phenylbenzamide
1487 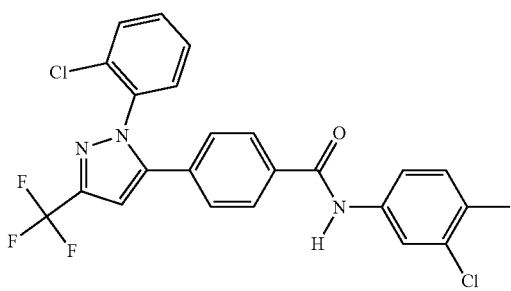
N-(3-chloro-4-methylphenyl)-4-[1-(2-chlorophenyl)-3-(trifluoromethyl)-1H-pyrazol-5-yl]benzamide
1488 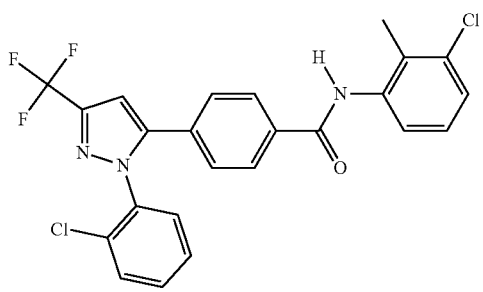 [SMILES: Cc1c(Cl)cccc1NC(=O)c1ccc(-c2cc(C(F)(F)F)nn2-c2ccccc2Cl)cc1]
N-(3-chloro-2-methylphenyl)-4-[1-(2-chlorophenyl)-3-(trifluoromethyl)-1H-pyrazol-5-yl]benzamide TABLE 1-continued

| 1489 | 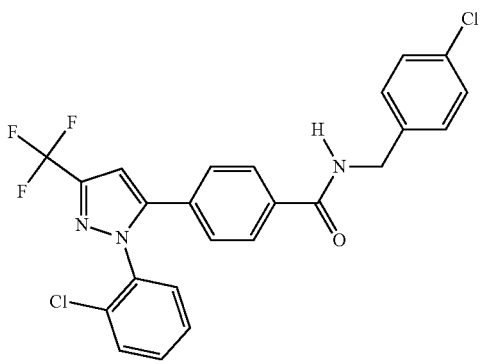 [SMILES: O=C(NCc1ccc(Cl)cc1)c1ccc(-c2cc(C(F)(F)F)nn2-c2ccccc2Cl)cc1] | N-[(4-chlorophenyl)methyl]-4-[1-(2-chlorophenyl)-3-(trifluoromethyl)-1H-pyrazol-5-yl]benzamide |
| 1490 | 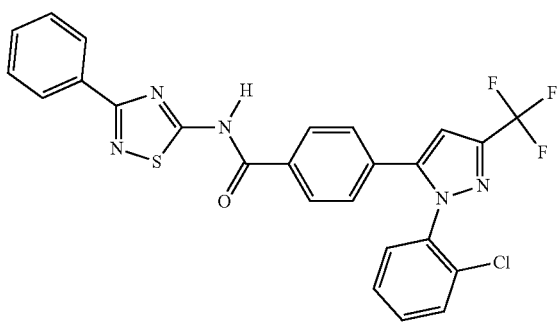 [SMILES: O=C(Nc1nc(-c2ccccc2)ns1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-phenyl-1,2,4-thiadiazol-5-yl)benzamide |
| 1491 | 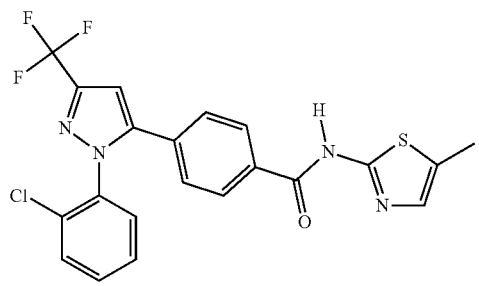 [SMILES: Cc1cnc(NC(=O)c2ccc(-c3cc(C(F)(F)F)nn3-c3ccccc3Cl)cc2)s1] | 4-[1-(2-chlorophenyl)-3-(trifluoromethyl)-1H-pyrazol-5-yl]-N-(5-methyl-1,3-thiazol-2-yl)benzamide |
| 1492 | 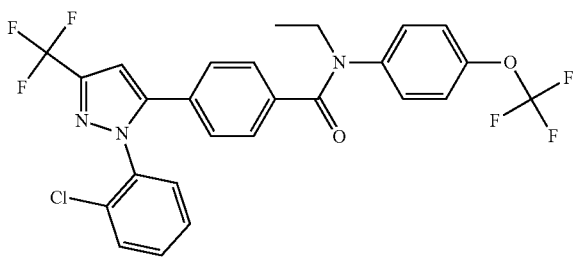 [SMILES: CCN(C(=O)c1ccc(-c2cc(C(F)(F)F)nn2-c2ccccc2Cl)cc1)c1ccc(OC(F)(F)F)cc1] | 4-[1-(2-chlorophenyl)-3-(trifluoromethyl)-1H-pyrazol-5-yl]-N-ethyl-N-{4-[(trifluoromethyl)oxy]phenyl}benzamide |
| 1493 | 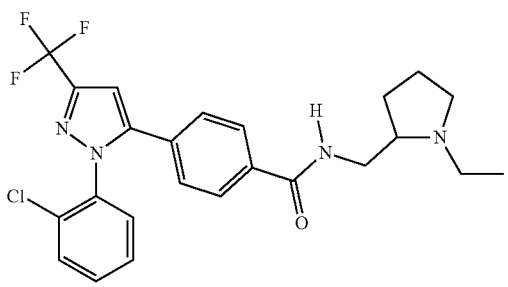 [SMILES: CCN1CCCC1CNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(1-ethylpyrrolidin-2-yl)methyl]benzamide |

TABLE 1-continued

| | | |
|---|---|---|
| 1494 | | 4-[1-(2-chlorophenyl)-3-(trifluoromethyl)-1H-pyrazol-5-yl]-N-(5-ethyl-1,3,4-thiadiazol-2-yl)benzamide |
| 1495 | | 4-[1-(2-chlorophenyl)-3-(trifluoromethyl)-1H-pyrazol-5-yl]-N-(2,6-difluorophenyl)benzamide |
| 1496 | | 4-[1-(2-chlorophenyl)-3-(trifluoromethyl)-1H-pyrazol-5-yl]-N-[3,4,5-tris(methyloxy)phenyl]benzamide |
| 1497 | | 4-[1-(2-chlorophenyl)-3-(trifluoromethyl)-1H-pyrazol-5-yl]-N-(2,4,5-trifluorophenyl)benzamide |
| 1498 | | 4-[1-(2-chlorophenyl)-3-(trifluoromethyl)-1H-pyrazol-5-yl]-N-(3-hydroxy-2-methylphenyl)benzamide |

TABLE 1-continued
| | | |
|---|---|---|
| 1499 | 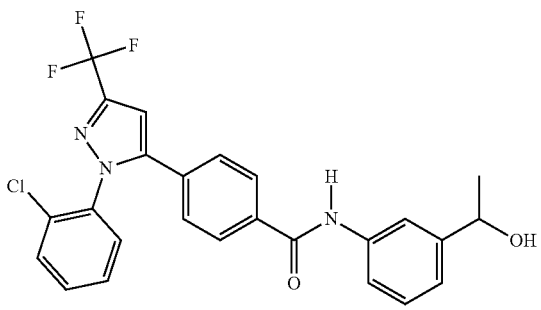 [SMILES: CC(O)c1cccc(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-[3-(1-hydroxyethyl)phenyl]benzamide |
| 1500 | 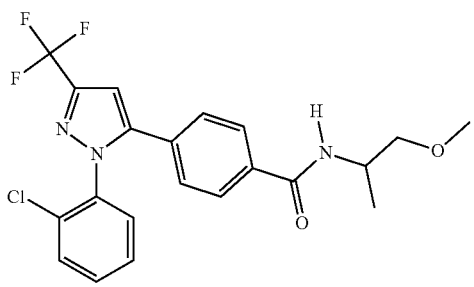 [SMILES: COCC(C)NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[1-methyl-2-(methyloxy)ethyl]benzamide |
| 1501 | 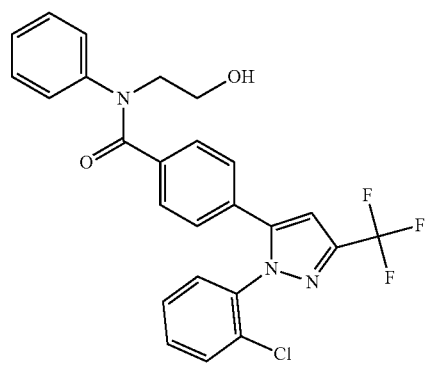 [SMILES: O=C(c1ccc(-c2cc(C(F)(F)F)nn2-c2ccccc2Cl)cc1)N(CCO)c1ccccc1] | 4-[1-(2-chlorophenyl)-3-(trifluoromethyl)-1H-pyrazol-5-yl]-N-(2-hydroxyethyl)-N-phenylbenzamide |
| 1502 | 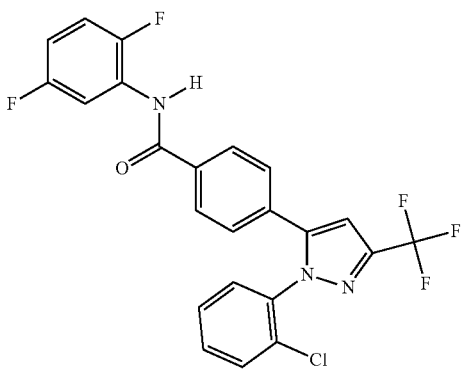 [SMILES: O=C(Nc1cc(F)ccc1F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,5-difluorophenyl)benzamide |

TABLE 1-continued

| | | |
|---|---|---|
| 1503 | | 4-[1-(2-chlorophenyl)-3-(trifluoromethyl)-1H-pyrazol-5-yl]-N-[(2,6-dichlorophenyl)methyl]benzamide |
| 1504 | | 4-[1-(2-chlorophenyl)-3-(trifluoromethyl)-1H-pyrazol-5-yl]-N-[2-(methylthio)phenyl]benzamide |
| 1506 | | 4-[1-(2-chlorophenyl)-3-(trifluoromethyl)-1H-pyrazol-5-yl]-N-{4-[(1,3-thiazol-2-ylamino)sulfonyl]phenyl}benzamide |
| 1507 | | 4-[1-(2-chlorophenyl)-3-(trifluoromethyl)-1H-pyrazol-5-yl]-N-methyl-N-pyridin-4-ylbenzamide |
| 1508 | | 4-[1-(2-chlorophenyl)-3-(trifluoromethyl)-1H-pyrazol-5-yl]-N-(2,3-difluorophenyl)benzamide |

TABLE 1-continued
| | | |
|---|---|---|
| 1509 | 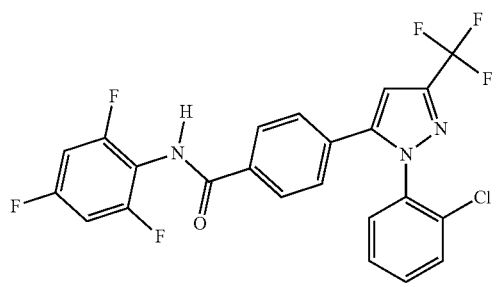 [SMILES: O=C(Nc1c(F)cc(F)cc1F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,4,6-trifluorophenyl)benzamide |
| 1510 | 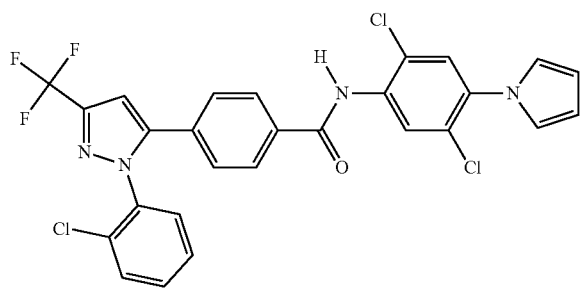 [SMILES: O=C(Nc1cc(Cl)c(-n2cccc2)cc1Cl)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2,5-dichloro-4-(1H-pyrrol-1-yl)phenyl]benzamide |
| 1511 | 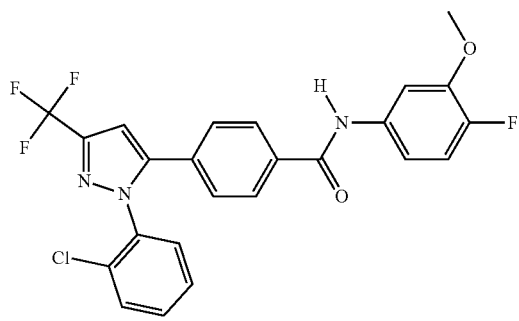 [SMILES: COc1cc(NC(=O)c2ccc(-c3cc(C(F)(F)F)nn3-c3ccccc3Cl)cc2)ccc1F] | 4-[1-(2-chlorophenyl)-3-(trifluoromethyl)-1H-pyrazol-5-yl]-N-[4-fluoro-3-(methyloxy)phenyl]benzamide |
| 1512 | 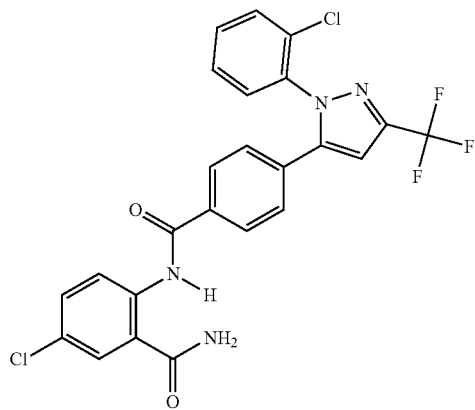 [SMILES: NC(=O)c1cc(Cl)ccc1NC(=O)c1ccc(-c2cc(C(F)(F)F)nn2-c2ccccc2Cl)cc1] | 5-chloro-2-[({4-[1-(2-chlorophenyl)-3-(trifluoromethyl)-1H-pyrazol-5-yl]phenyl}carbonyl)amino]benzamide |

TABLE 1-continued

| | | |
|---|---|---|
| 1513 | 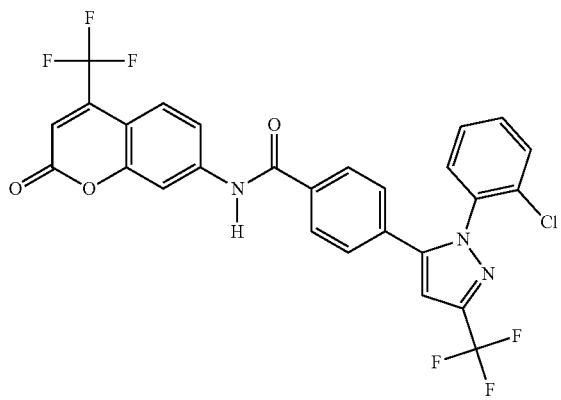 [SMILES: O=C(Nc1ccc2c(C(F)(F)F)cc(=O)oc2c1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-oxo-4-(trifluoromethyl)-2H-chromen-7-yl]benzamide |
| 1515 | 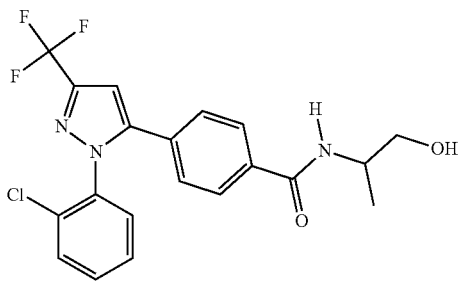 [SMILES: CC(CO)NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2-hydroxy-1-methylethyl)benzamide |
| 1516 | 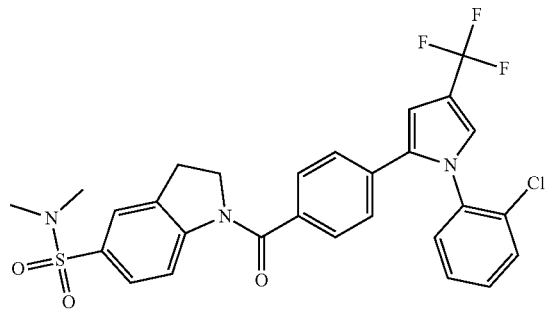 [SMILES: CN(C)S(=O)(=O)c1ccc2c(c1)CCN2C(=O)c1ccc(-c2cc(C(F)(F)F)cn2-c2ccccc2Cl)cc1] | 1-({4-[1-(2-chlorophenyl)-3-(trifluoromethyl)-1H-pyrazol-5-yl]phenyl}carbonyl)-N,N-dimethyl-2,3-dihydro-1H-indole-5-sulfonamide |
| 1517 | 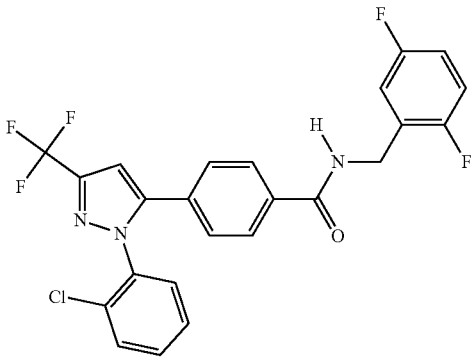 [SMILES: O=C(NCc1cc(F)ccc1F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(2,5-difluorophenyl)methyl]benzamide |

TABLE 1-continued

| 1518 | 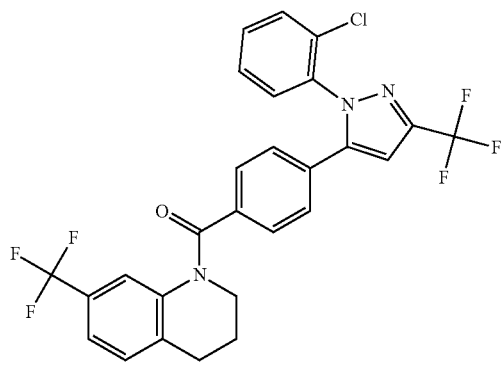 [SMILES: O=C(c1ccc(-c2cc(C(F)(F)F)nn2-c2ccccc2Cl)cc1)N1CCCc2ccc(C(F)(F)F)cc21] | 1-({4-[1-(2-chlorophenyl)-3-(trifluoromethyl)-1H-pyrazol-5-yl[phenyl}carbonyl)-7-(trifluoromethyl)-1,2,3,4-tetrahydroquinoline |
| 1519 | 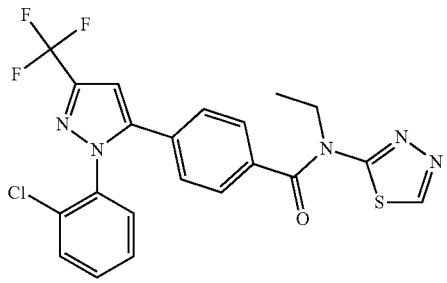 [SMILES: CCN(C(=O)c1ccc(-c2cc(C(F)(F)F)nn2-c2ccccc2Cl)cc1)c1nncs1] | 4-[1-(2-chlorophenyl)-3-(trifluoromethyl)-1H-pyrazol-5-yl]-N-ethyl-N-1,3,4-thiadiazol-2-ylbenzamide |
| 1520 | 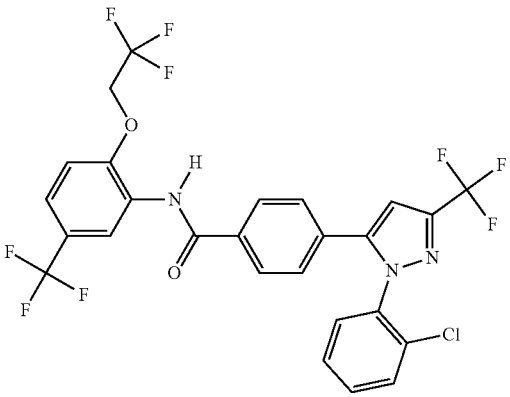 [SMILES: O=C(Nc1cc(C(F)(F)F)ccc1OCC(F)(F)F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{2-[(2,2,2-trifluoromethyl)oxy]-5-(trifluoromethyl)phenyl}benzamide |
| 1521 | 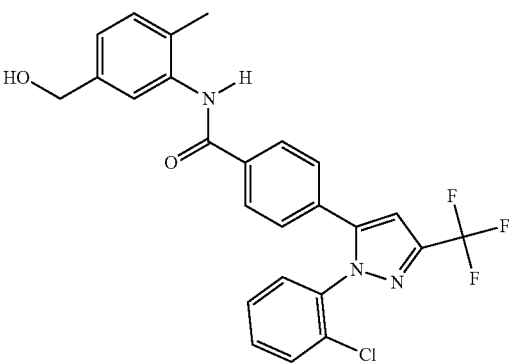 [SMILES: Cc1ccc(CO)cc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[5-(hydroxymethyl)-2-methylphenyl]benzamide |

TABLE 1-continued

| | | |
|---|---|---|
| 1522 | 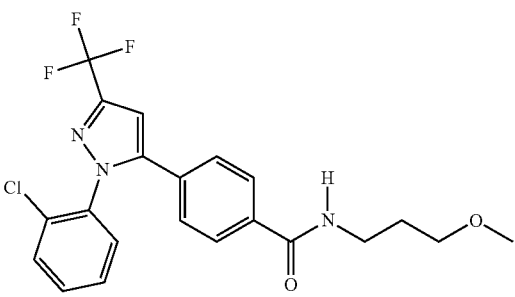 [SMILES: COCCCNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[3-(methyloxy)propyl]benzamide |
| 1523 | 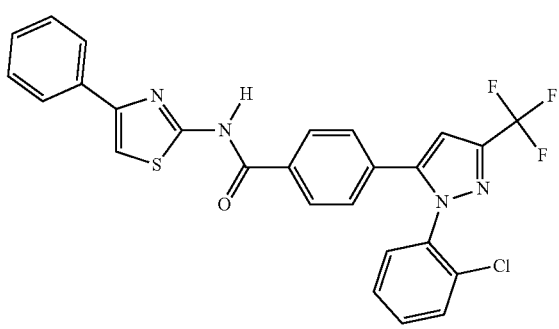 [SMILES: O=C(Nc1nc(-c2ccccc2)cs1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(4-phenyl-1,3-thiazol-2-yl)benzamide |
| 1524 | 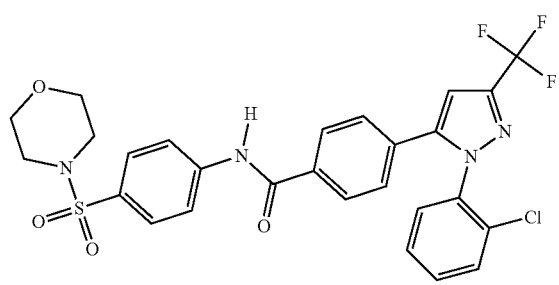 [SMILES: O=C(Nc1ccc(S(=O)(=O)N2CCOCC2)cc1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[4-(morpholin-4-ylsulfonyl)phenyl]benzamide |
| 1525 | 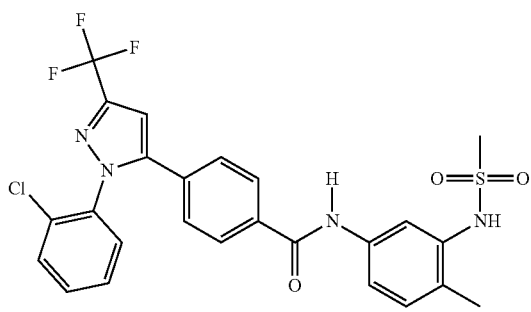 [SMILES: Cc1ccc(NC(=O)c2ccc(-c3cc(C(F)(F)F)nn3-c3ccccc3Cl)cc2)cc1NS(C)(=O)=O] | 4-[1-(2-chlorophenyl)-3-(trifluoromethyl)-1H-pyrazol-5-yl]-N-{4-methyl-3-[(methylsulfonyl)amino]phenyl}benzamide |
| 1526 | 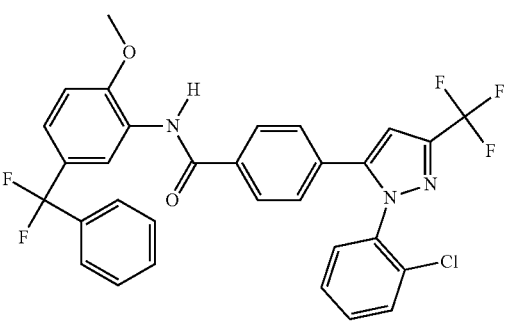 [SMILES: COc1ccc(C(F)(F)c2ccccc2)cc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(methyloxy)-5-(1-methyl-1-phenylethyl)phenyl]benzamide |

TABLE 1-continued
| | | |
|---|---|---|
| 1527 | 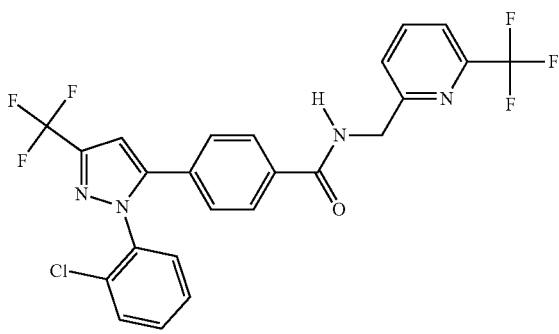 [SMILES: O=C(NCc1cccc(C(F)(F)F)n1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[6-(trifluoromethyl)pyridin-3-yl]benzamide |
| 1529 | 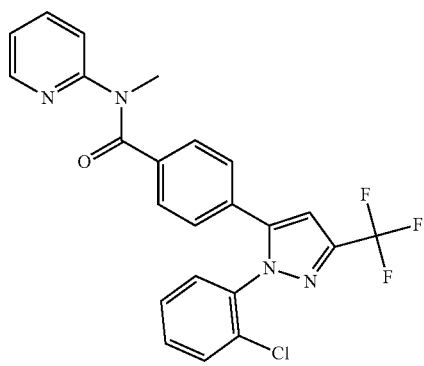 [SMILES: CN(C(=O)c1ccc(-c2cc(C(F)(F)F)nn2-c2ccccc2Cl)cc1)c1ccccn1] | 4-[1-(2-chlorophenyl)-3-(trifluoromethyl)-1H-pyrazol-5-yl]-N-methyl-N-pyridin-2-ylbenzamide |
| 1530 | 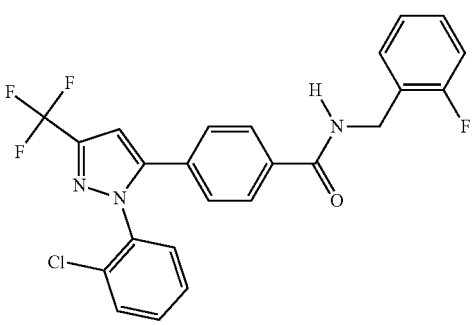 [SMILES: O=C(NCc1ccccc1F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(2-fluorophenyl)methyl]benzamide |
| 1531 | 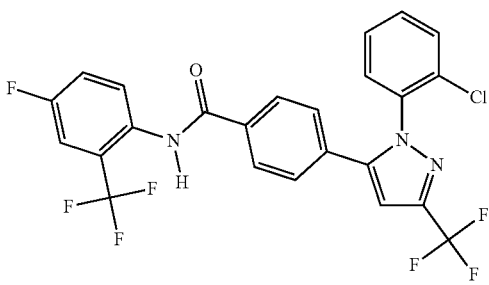 [SMILES: O=C(Nc1ccc(F)cc1C(F)(F)F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[4-fluoro-2-(trifluoromethyl)phenyl]benzamide |

| | | |
|---|---|---|
| 1532 | 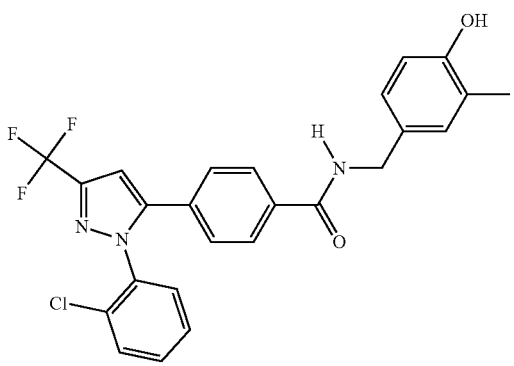 [SMILES: Cc1cc(CNC(=O)c2ccc(-c3cc(C(F)(F)F)nn3-c3ccccc3Cl)cc2)ccc1O] | 4-[1-(2-chlorophenyl)-3-(trifluoromethyl)-1H-pyrazol-5-yl]-N-(3-hydroxy-4-methylphenyl)benzamide |
| 1533 | 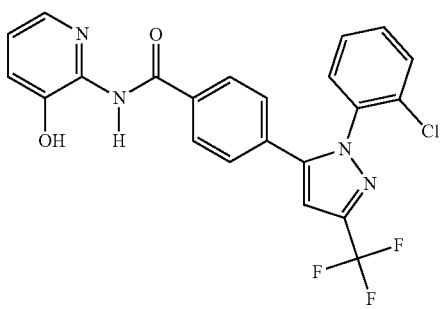 [SMILES: O=C(Nc1ncccc1O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(3-hydroxypyridin-2-yl)benzamide |
| 1534 | 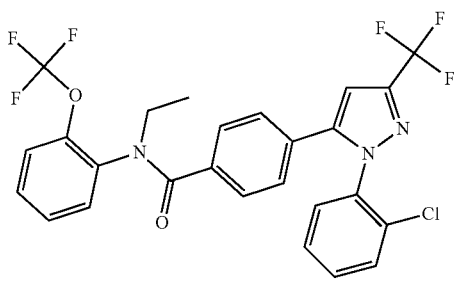 [SMILES: CCN(C(=O)c1ccc(-c2cc(C(F)(F)F)nn2-c2ccccc2Cl)cc1)c1ccccc1OC(F)(F)F] | 4-[1-(2-chlorophenyl)-3-(trifluoromethyl)-1H-pyrazol-5-yl]-N-ethyl-N-{2-[(trifluoromethyl)oxy]phenyl}benzamide |
| 1535 | 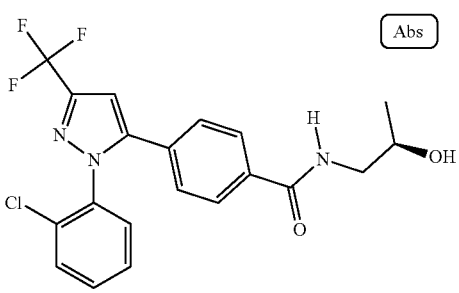 [SMILES: C[C@@H](O)CNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(2R)-2-hydroxypropyl]benzamide |
| 1536 | 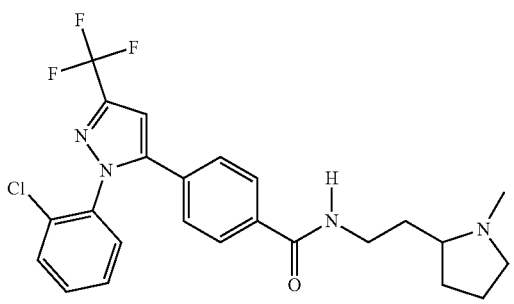 [SMILES: CN1CCCC1CCNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[2-(1-methylpyrrolidin-2-yl)ethyl]benzamide |

TABLE 1-continued

| | | |
|---|---|---|
| 1537 | 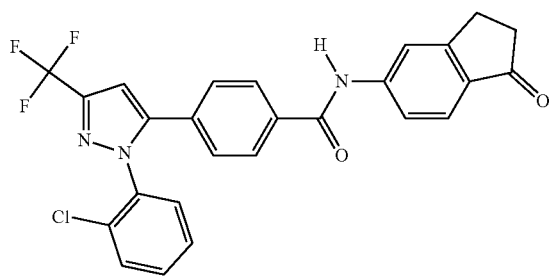 [SMILES: O=C(Nc1ccc2c(c1)CCC2=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(1-oxo-2,3-dihydro-1H-inden-5-yl)benzamide |
| 1538 | 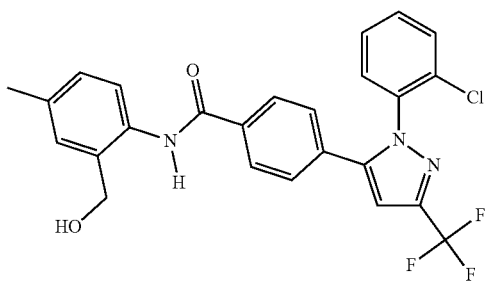 [SMILES: Cc1ccc(NC(=O)c2ccc(-c3cc(C(F)(F)F)nn3-c3ccccc3Cl)cc2)c(CO)c1] | 4-[1-(2-chlorophenyl)-3-(trifluoromethyl)-1H-pyrazol-5-yl]-N-[2-(hydroxymethyl)-4-methylphenyl]benzamide |
| 1539 | 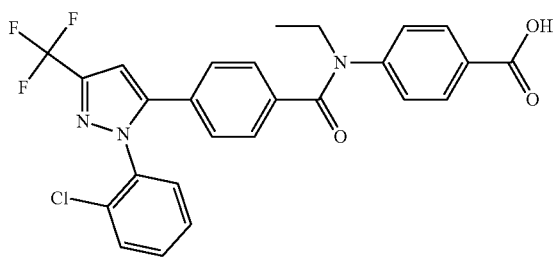 [SMILES: CCN(C(=O)c1ccc(-c2cc(C(F)(F)F)nn2-c2ccccc2Cl)cc1)c1ccc(C(=O)O)cc1] | 4-[({4-[1-(2-chlorophenyl)-3-(trifluoromethyl)-1H-pyrazol-5-yl]phenyl}carbonyl)(ethyl)amino]benzoic acid |
| 1540 | 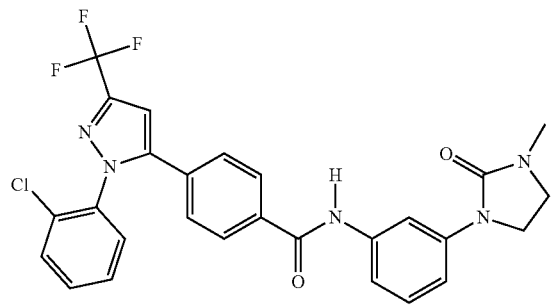 [SMILES: CN1CCN(c2cccc(NC(=O)c3ccc(-c4cc(C(F)(F)F)nn4-c4ccccc4Cl)cc3)c2)C1=O] | 4-[1-(2-chlorophenyl)-3-(trifluoromethyl)-1H-pyrazol-5-yl]-N-[3-(3-methyl-2-oxoimidazolidin-1-yl)phenyl]benzamide |
| 1541 | 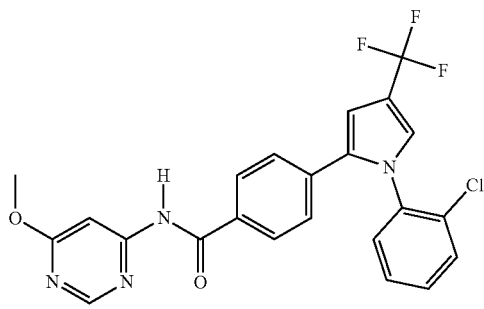 [SMILES: COc1cc(NC(=O)c2ccc(-c3cc(C(F)(F)F)cn3-c3ccccc3Cl)cc2)ncn1] | 4-[1-(2-chlorophenyl)-3-(trifluoromethyl)-1H-pyrazol-5-yl]-N-[6-(methyloxy)pyrimidin-4-yl]benzamide |

TABLE 1-continued

| | | |
|---|---|---|
| 1542 | 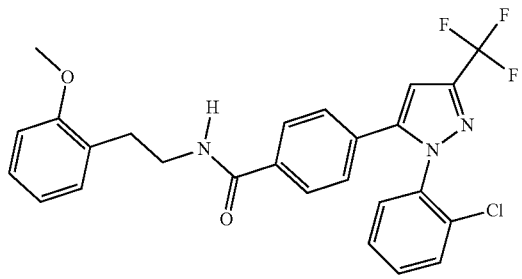 [SMILES: COc1ccccc1CCNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{2-[2-(methyloxy)phenyl]ethyl}benzamide |
| 1543 | 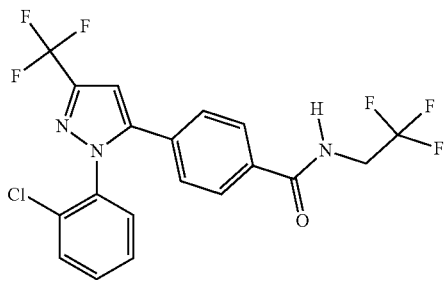 [SMILES: O=C(NCC(F)(F)F)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2,2,2-trifluoromethyl)benzamide |
| 1544 | 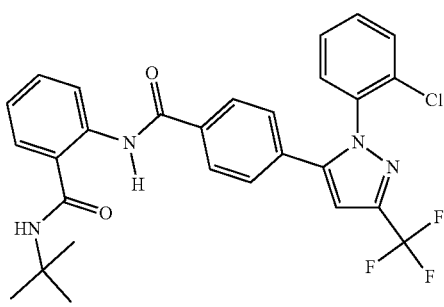 [SMILES: CC(C)(C)NC(=O)c1ccccc1NC(=O)c1ccc(-c2cc(C(F)(F)F)nn2-c2ccccc2Cl)cc1] | 3-[({4-[1-(2-chlorophenyl)-3-(trifluoromethyl)-1H-pyrazol-5-yl]phenyl}carbonyl)amino]-N-(1,1-dimethylethyl)benzamide |
| 1545 | 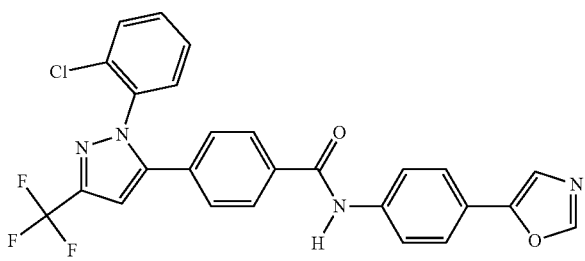 [SMILES: O=C(Nc1ccc(-c2cnco2)cc1)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[4-(1,3-oxazol-5-yl)phenyl]benzamide |
| 1546 | 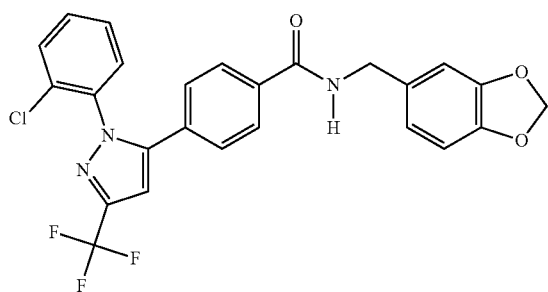 [SMILES: O=C(NCc1ccc2c(c1)OCO2)c1ccc(-c2cc(C(F)(F)F)nn2-c2ccccc2Cl)cc1] | N-(1,3-benzodioxol-5-ylmethyl)-4-[1-(2-chlorophenyl)-3-(trifluoromethyl)-1H-pyrazol-5-yl]benzamide |

TABLE 1-continued

| | | |
|---|---|---|
| 1547 | 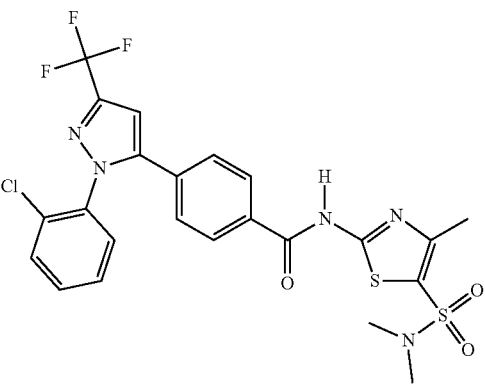 [SMILES: Cc1nc(NC(=O)c2ccc(-c3cc(C(F)(F)F)nn3-c3ccccc3Cl)cc2)sc1S(=O)(=O)N(C)C] | 4-[1-(2-chlorophenyl)-3-(trifluoromethyl)-1H-pyrazol-5-yl]-N-{5-[(dimethylamino)sulfonyl]-4-methyl-1,3-thiazol-2-yl}benzamide |
| 1548 | 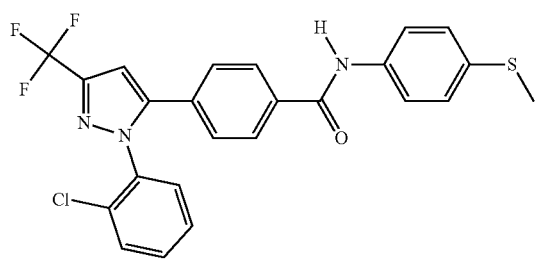 [SMILES: CSc1ccc(NC(=O)c2ccc(-c3cc(C(F)(F)F)nn3-c3ccccc3Cl)cc2)cc1] | 4-[1-(2-chlorophenyl)-3-(trifluoromethyl)-1H-pyrazol-5-yl]-N-[4-(methylthio)phenyl]benzamide |
| 1549 | 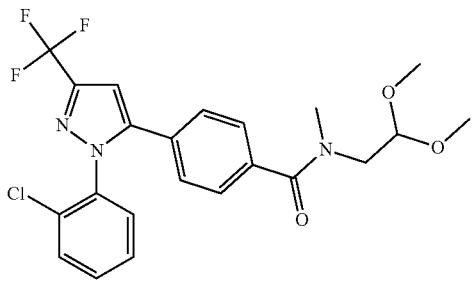 [SMILES: COC(CN(C)C(=O)c1ccc(-c2cc(C(F)(F)F)nn2-c2ccccc2Cl)cc1)OC] | N-[2,2-bis(methyloxy)ethyl]-4-[1-(2-chlorophenyl)-3-(trifluoromethyl)-1H-pyrazol-5-yl]-N-methylbenzamide |
| 1550 | 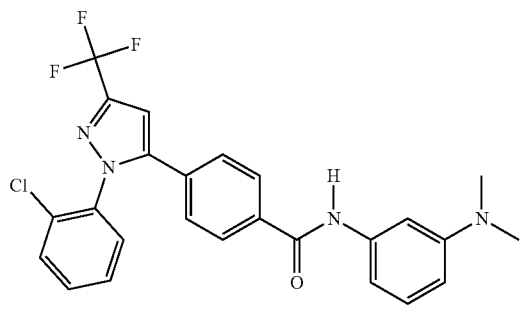 [SMILES: CN(C)c1cccc(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-[3-(dimethylamino)phenyl]benzamide |
| 1551 | 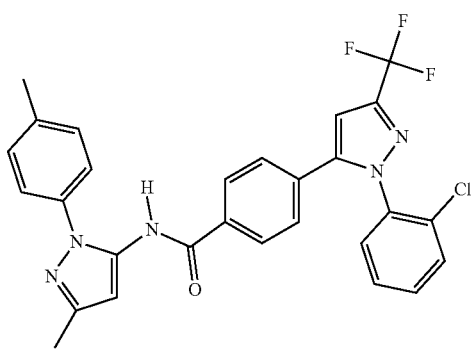 [SMILES: Cc1ccc(-n2nc(C)cc2NC(=O)c2ccc(-c3cc(C(F)(F)F)nn3-c3ccccc3Cl)cc2)cc1] | 4-[1-(2-chlorophenyl)-3-(trifluoromethyl)-1H-pyrazol-5-yl]-N-[3-methyl-1-(4-methylphenyl)-1H-pyrazol-5-yl]benzamide |

TABLE 1-continued

| | | |
|---|---|---|
| 1552 | 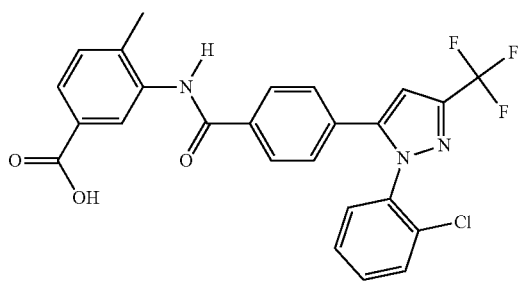 [SMILES: Cc1ccc(C(=O)O)cc1NC(=O)c1ccc(-c2cc(C(F)(F)F)nn2-c2ccccc2Cl)cc1] | 3-[({4-[1-(2-chlorophenyl)-3-(trifluoromethyl)-1H-pyrazol-5-yl]phenyl}carbonyl)amino]-4-methylbenzoic acid |
| 1553 | 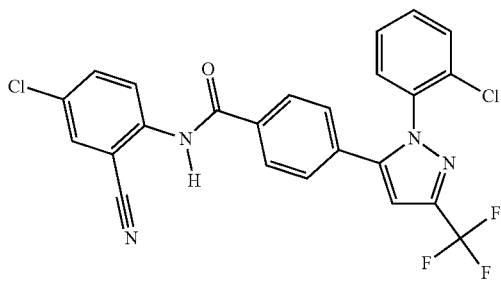 [SMILES: N#Cc1cc(Cl)ccc1NC(=O)c1ccc(-c2cc(C(F)(F)F)nn2-c2ccccc2Cl)cc1] | N-(4-chloro-2-cyanophenyl)-4-[1-(2-chlorophenyl)-3-(trifluoromethyl)-1H-pyrazol-5-yl]benzamide |
| 1554 | 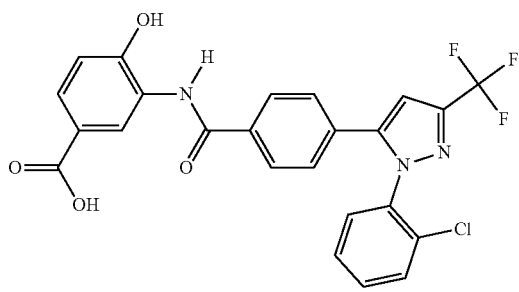 [SMILES: O=C(O)c1ccc(O)c(NC(=O)c2ccc(-c3cc(C(F)(F)F)nn3-c3ccccc3Cl)cc2)c1] | 3-[({4-[1-(2-chlorophenyl)-3-(trifluoromethyl)-1H-pyrazol-5-yl]phenyl}carbonyl)amino]-4-hydroxybenzoic acid |
| 1555 | 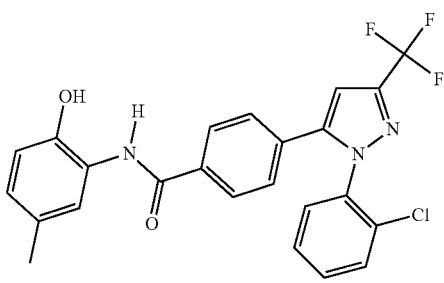 [SMILES: Cc1ccc(O)c(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-(2-hydroxy-5-methylphenyl)benzamide |
| 1556 | 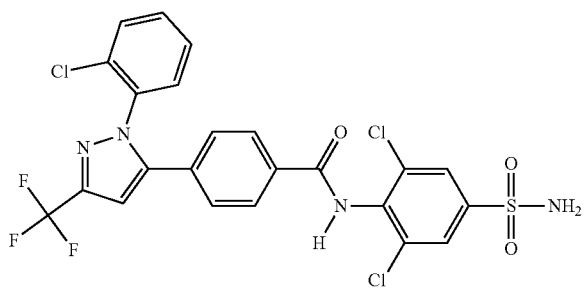 [SMILES: NS(=O)(=O)c1cc(Cl)c(NC(=O)c2ccc(-c3cc(C(F)(F)F)nn3-c3ccccc3Cl)cc2)c(Cl)c1] | N-[4-(aminomethyl)-2,6-dichlorophenyl]-4-[1-(2-chlorophenyl)-3-(trifluoromethyl)-1H-pyrazol-5-yl]benzamide |

TABLE 1-continued

| | | |
|---|---|---|
| 1557 | 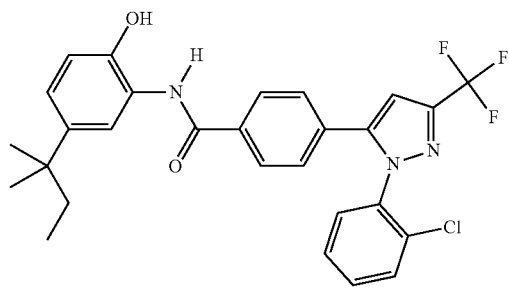 [SMILES: CCC(C)(C)c1ccc(O)c(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-[5-(1,1-dimethylpropyl)-2-hydroxyphenyl]benzamide |
| 1558 | 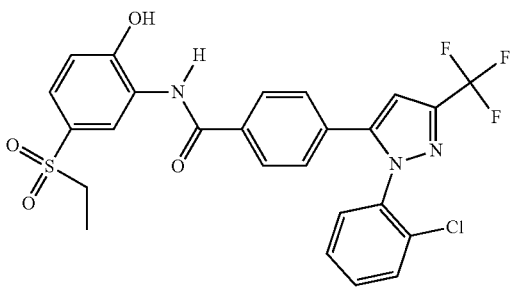 [SMILES: CCS(=O)(=O)c1ccc(O)c(NC(=O)c2ccc(-c3cc(C(F)(F)F)nn3-c3ccccc3Cl)cc2)c1] | 4-[1-(2-chlorophenyl)-3-(trifluoromethyl)-1H-pyrazol-5-yl]-N-[5-(ethylsulfonyl)-2-hydroxyphenyl]benzamide |
| 1559 | 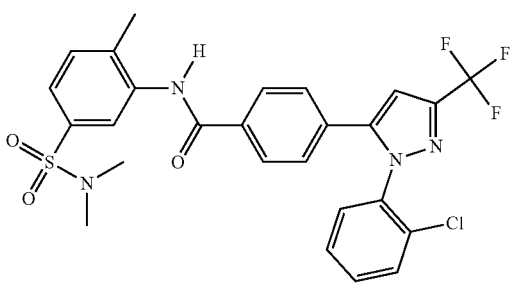 [SMILES: Cc1ccc(S(=O)(=O)N(C)C)cc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-{5-[(dimethylamino)sulfonyl]-2-methylphenyl}benzamide |
| 1560 | 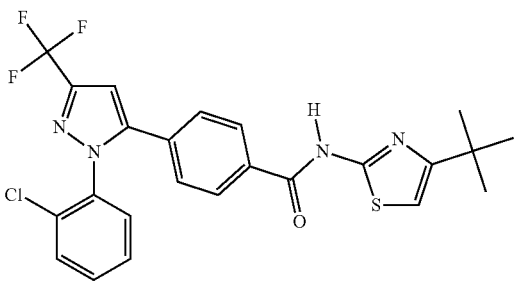 [SMILES: CC(C)(C)c1csc(NC(=O)c2ccc(-c3cc(C(F)(F)F)nn3-c3ccccc3Cl)cc2)n1] | 4-[1-(2-chlorophenyl)-3-(trifluoromethyl)-1H-pyrazol-5-yl]-N-[4-(1,1-dimethylethyl)-1,3-thiazol-2-yl]benzamide |
| 1561 | 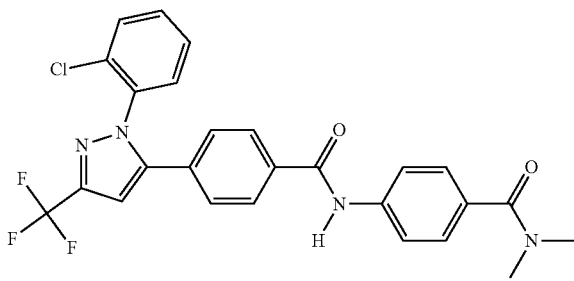 [SMILES: CN(C)C(=O)c1ccc(NC(=O)c2ccc(-c3cc(C(F)(F)F)nn3-c3ccccc3Cl)cc2)cc1] | 4-[({4-[1-(2-chlorophenyl)-3-(trifluoromethyl)-1H-pyrazol-5-yl]phenyl}carbonyl)amino]-N,N-dimethylbenzamide |

TABLE 1-continued
| | | |
|---|---|---|
| 1562 | 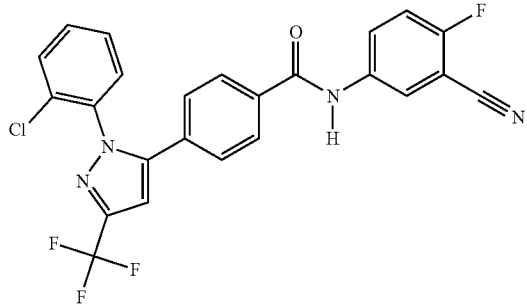 [SMILES: N#Cc1cc(NC(=O)c2ccc(-c3cc(C(F)(F)F)nn3-c3ccccc3Cl)cc2)ccc1F] | 4-[1-(2-chlorophenyl)-3-(trifluoromethyl)-1H-pyrazol-5-yl]-N-(3-cyano-4-fluorophenyl)benzamide |
| 1563 | 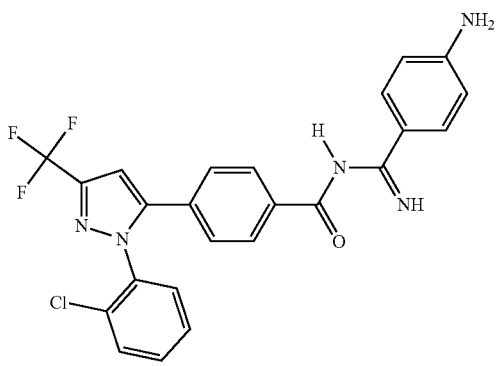 [SMILES: N=C(NC(=O)c1ccc(-c2cc(C(F)(F)F)nn2-c2ccccc2Cl)cc1)c1ccc(N)cc1] | N-[(4-aminophenyl)(imino)methyl]-4-[1-(2-chlorophenyl)-3-(trifluoromethyl)-1H-pyrazol-5-yl]benzamide |
| 1564 | 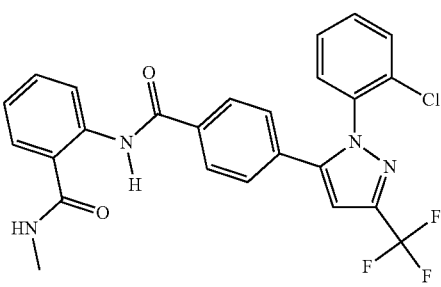 [SMILES: CNC(=O)c1ccccc1NC(=O)c1ccc(-c2cc(C(F)(F)F)nn2-c2ccccc2Cl)cc1] | 2-[({4-[1-(2-chlorophenyl)-3-(trifluoromethyl)-1H-pyrazol-5-yl]phenyl}carbonyl)amino]-N-methylbenzamide |
| 1565 | 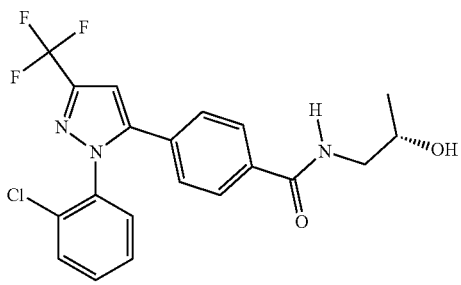 [SMILES: C[C@H](O)CNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(2S)-2-hydroxypropyl]benzamide |

TABLE 1-continued

| | | |
|---|---|---|
| 1566 | 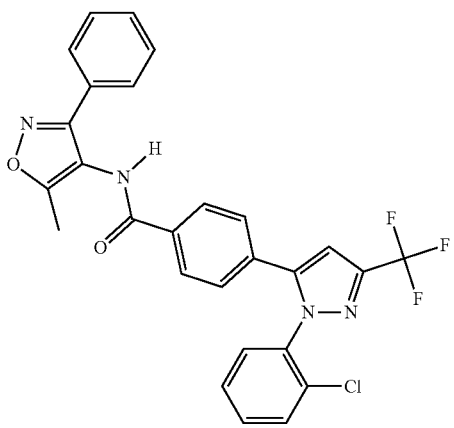 [SMILES: Cc1onc(-c2ccccc2)c1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(5-methyl-3-phenylisoxazol-4-yl)benzamide |
| 1567 | 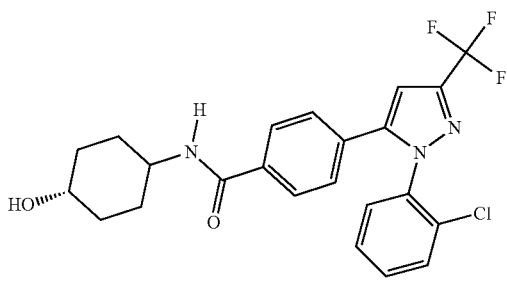 | 4-[1-(2-chlorophenyl)-3-(trifluoromethyl)-1H-pyrazol-5-yl]-N-(4-hydroxycyclohexyl)benzamide |
| 1568 | 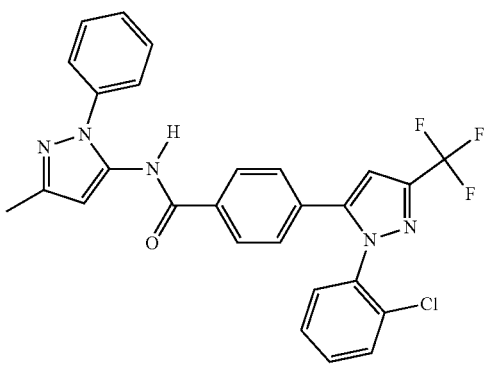 [SMILES: Cc1cc(NC(=O)c2ccc(-c3cc(C(F)(F)F)nn3-c3ccccc3Cl)cc2)n(-c2ccccc2)n1] | 4-[1-(2-chlorophenyl)-3-(trifluoromethyl)-1H-pyrazol-5-yl]-N-(3-methyl-1-phenyl-1H-pyrazol-5-yl)benzamide |
| 1569 | 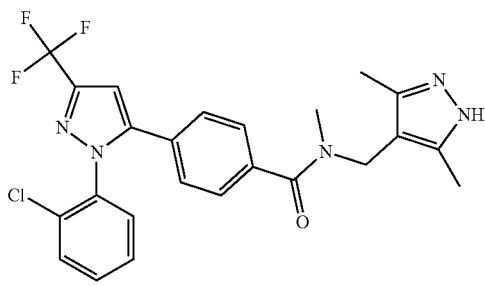 [SMILES: Cc1n[nH]c(C)c1CN(C)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(3,5-dimethyl-1H-pyrazol-4-yl)methyl]-N-methylbenzamide |
| 1570 | 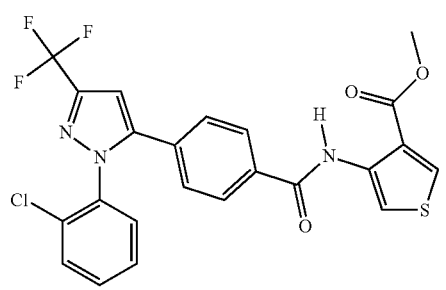 [SMILES: COC(=O)c1cscc1NC(=O)c1ccc(-c2cc(C(F)(F)F)nn2-c2ccccc2Cl)cc1] | methyl 4-[({4-[1-(2-chlorophenyl)-3-(trifluoromethyl)-1H-pyrazol-5-yl]phenyl}carbonyl)amino]thiophene-3-carboxylate |

TABLE 1-continued

1571 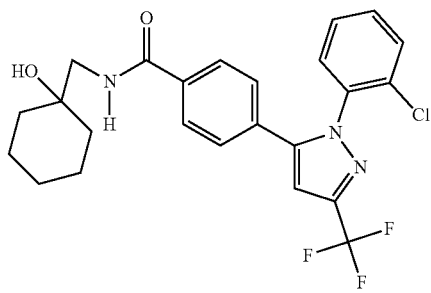 [SMILES: O=C(NCC1(O)CCCCC1)c1ccc(-c2cc(C(F)(F)F)nn2-c2ccccc2Cl)cc1] 4-[1-(2-chlorophenyl)-3-(trifluoromethyl)-1H-pyrazol-5-yl]-N-[(1-hydroxycyclohexyl)methyl]benzamide 1572 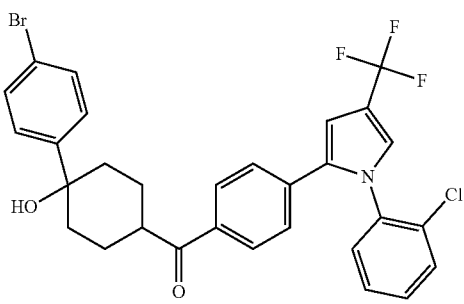 [SMILES: O=C(c1ccc(-c2cc(C(F)(F)F)cn2-c2ccccc2Cl)cc1)C1CCC(O)(c2ccc(Br)cc2)CC1] 4-(4-bromophenyl)-1-({4-[1-(2-chlorophenyl)-3-(trifluoromethyl)-1H-pyrazol-5-yl]phenyl}carbonyl)piperidin-4-ol 1573 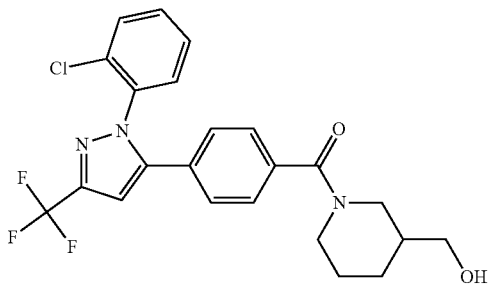 [SMILES: O=C(c1ccc(-c2cc(C(F)(F)F)nn2-c2ccccc2Cl)cc1)N1CCCC(CO)C1] [1-({4-[1-(2-chlorophenyl)-3-(trifluoromethyl)-1H-pyrazol-5-yl]phenyl}carbonyl)piperidin-3-yl]methanol 1574 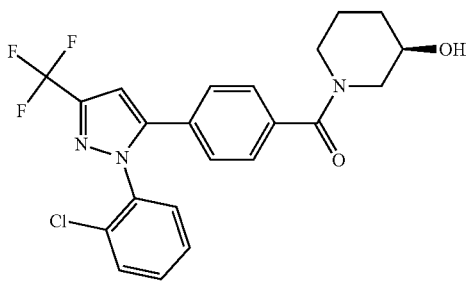 [SMILES: O=C(c1ccc(-c2cc(C(F)(F)F)nn2-c2ccccc2Cl)cc1)N1CCC[C@@H](O)C1] (3R)-1-({4-[1-(2-chlorophenyl)-3-(trifluoromethyl)-1H-pyrazol-5-yl]phenyl}carbonyl)piperidin-3-ol 1575 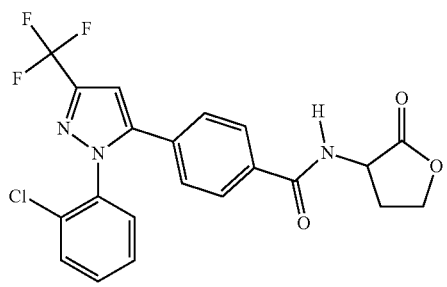 [SMILES: O=C(NC1CCOC1=O)c1ccc(-c2cc(C(F)(F)F)nn2-c2ccccc2Cl)cc1] 4-[1-(2-chlorophenyl)-3-(trifluoromethyl)-1H-pyrazol-5-yl]-N-(2-oxatetrahydrofuran-3-yl)benzamide

| | | |
|---|---|---|
| 1576 | 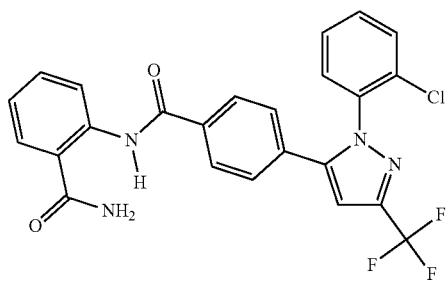 [SMILES: NC(=O)c1ccccc1NC(=O)c1ccc(-c2cc(C(F)(F)F)nn2-c2ccccc2Cl)cc1] | N-[2-(aminocarbonyl)phenyl]-4-[1-(2-chlorophenyl)-3-(trifluoromethyl)-1H-pyrazol-5-yl]benzamide |
| 1577 | 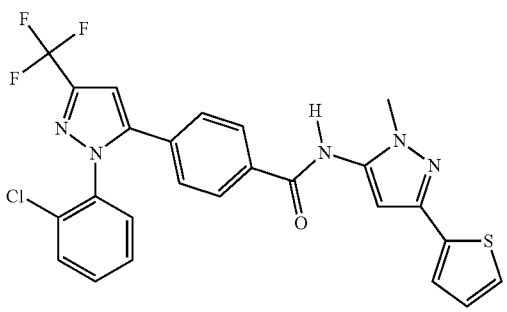 [SMILES: Cn1nc(-c2cccs2)cc1NC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[1-methyl-3-(2-thienyl)-1H-pyrazol-5-yl]benzamide |
| 1578 | 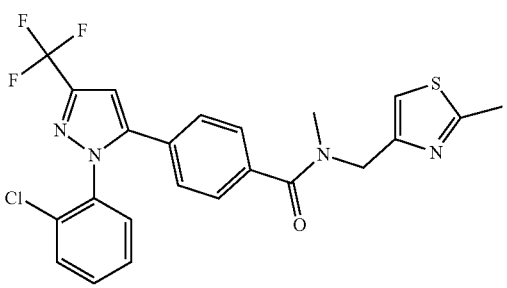 [SMILES: Cc1nc(CN(C)C(=O)c2ccc(-c3cc(C(F)(F)F)nn3-c3ccccc3Cl)cc2)cs1] | 4-[1-(2-chlorophenyl)-3-(trifluoromethyl)-1H-pyrazol-5-yl]-N-methyl-N-[(2-methyl-1,3-thiazol-4-yl)methyl]benzamide |
| 1579 | 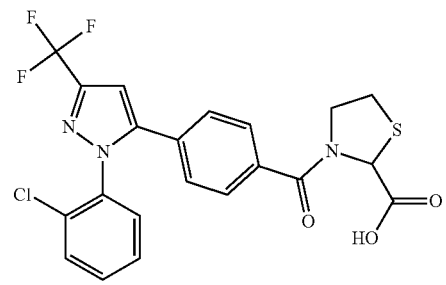 [SMILES: O=C(O)C1SCCN1C(=O)c1ccc(-c2cc(C(F)(F)F)nn2-c2ccccc2Cl)cc1] | 3-({4-[1-(2-chlorophenyl)-3-(trifluoromethyl)-1H-pyrazol-5-yl]phenyl}carbonyl)-1,3-thiazolidine-2-carboxylic acid |
| 1580 | 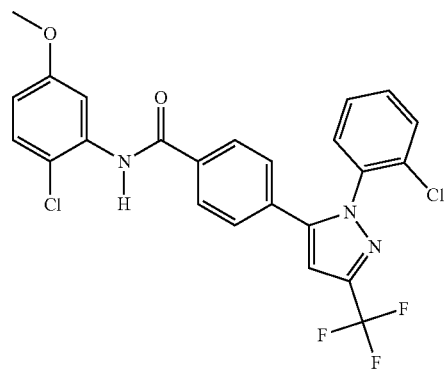 [SMILES: COc1ccc(Cl)c(NC(=O)c2ccc(-c3cc(C(F)(F)F)nn3-c3ccccc3Cl)cc2)c1] | N-[2-chloro-5-(methyloxy)phenyl]-4-[1-(2-chlorophenyl)-3-(trifluoromethyl)-1H-pyrazol-5-yl]benzamide |

TABLE 1-continued

| 1581 | 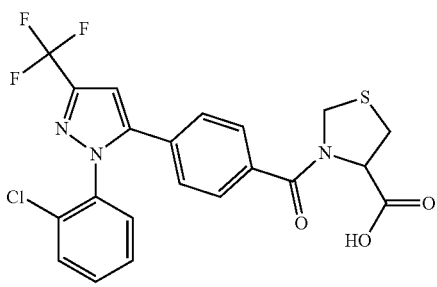 [SMILES: O=C(O)C1CSCN1C(=O)c1ccc(-c2cc(C(F)(F)F)nn2-c2ccccc2Cl)cc1] | 3-({4-[1-(2-chlorophenyl)-3-(trifluoromethyl)-1H-pyrazol-5-yl]phenyl}carbonyl)-1,3-thiazolidine-4-carboxylic acid |
| --- | --- | --- |
| 1582 | 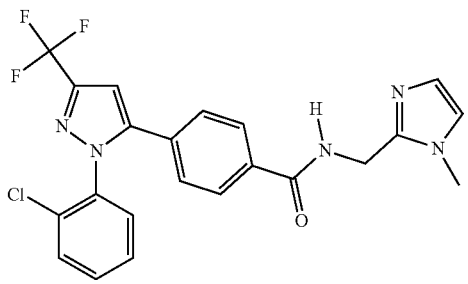 [SMILES: Cn1ccnc1CNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-[(1-methyl-1H-imidazol-2-yl)methyl]benzamide |
| 1583 | 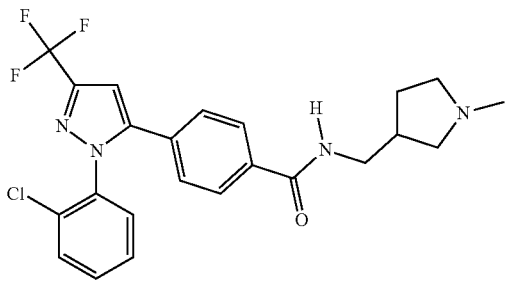 [SMILES: CN1CCC(CNC(=O)c2ccc(-c3cc(C(F)(F)F)nn3-c3ccccc3Cl)cc2)C1] | 4-[1-(2-chlorophenyl)-3-(trifluoromethyl)-1H-pyrazol-5-yl]-N-[(1-methylpyrrolidin-3-yl)methyl]benzamide |
| 1584 | 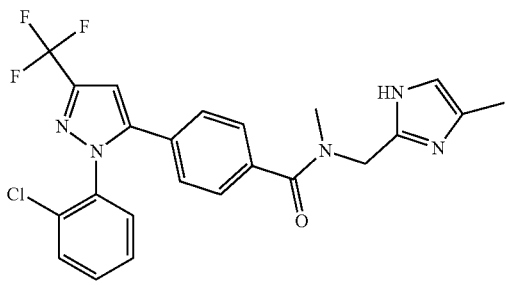 [SMILES: Cc1c[nH]c(CN(C)C(=O)c2ccc(-c3cc(C(F)(F)F)nn3-c3ccccc3Cl)cc2)n1] | 4-[1-(2-chlorophenyl)-3-(trifluoromethyl)-1H-pyrazol-5-yl]-N-methyl-N-[(4-methyl-1H-imidazol-2-yl)methyl]benzamide |
| 1585 | 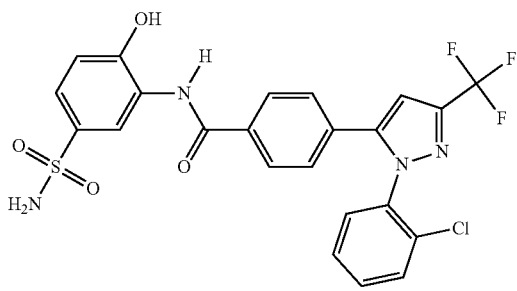 [SMILES: NS(=O)(=O)c1ccc(O)c(NC(=O)c2ccc(-c3cc(C(F)(F)F)nn3-c3ccccc3Cl)cc2)c1] | N-[5-(aminosulfonyl)-2-hydroxyphenyl]-4-[1-(2-chlorophenyl)-3-(trifluoromethyl)-1H-pyrazol-5-yl]benzamide |

| | | | |
|---|---|---|---|
| 1586 | 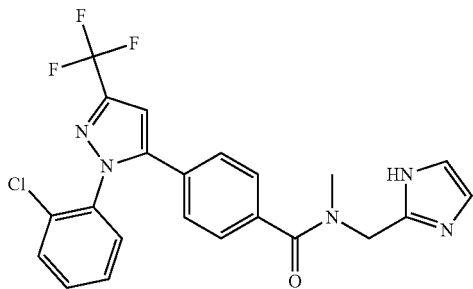 [SMILES: CN(Cc1ncc[nH]1)C(=O)c1ccc(-c2cc(C(F)(F)F)nn2-c2ccccc2Cl)cc1] | | 4-[1-(2-chlorophenyl)-3-(trifluoromethyl)-1H-pyrazol-5-yl]-N-(1H-imidazol-2-ylmethyl)-N-methylbenzamide |
| 1587 | 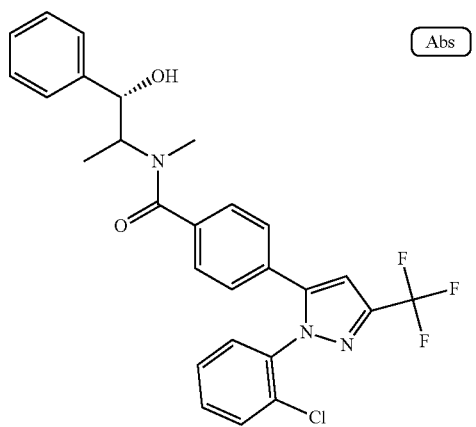 [SMILES: CC([C@@H](O)c1ccccc1)N(C)C(=O)c1ccc(-c2cc(C(F)(F)F)nn2-c2ccccc2Cl)cc1] | Abs | 4-[1-(2-chlorophenyl)-3-(trifluoromethyl)-1H-pyrazol-5-yl]-N-[(2S)-2-hydroxy-1-methyl-2-phenylethyl]-N-methylbenzamide |
| 1588 | 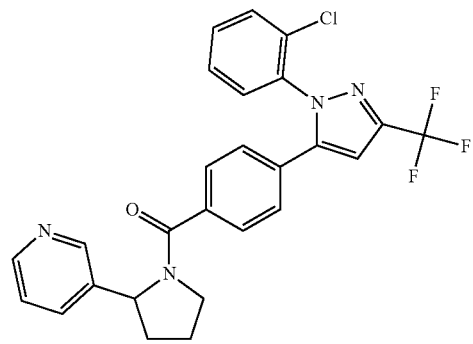 [SMILES: O=C(c1ccc(-c2cc(C(F)(F)F)nn2-c2ccccc2Cl)cc1)N1CCCC1c1cccnc1] | | 3-[1-({4-[1-(2-chlorophenyl)-3-(trifluoromethyl)-1H-pyrazol-5-yl]phenyl}carbonyl)pyrrolidin-2-yl]pyridine |
| 1589 | 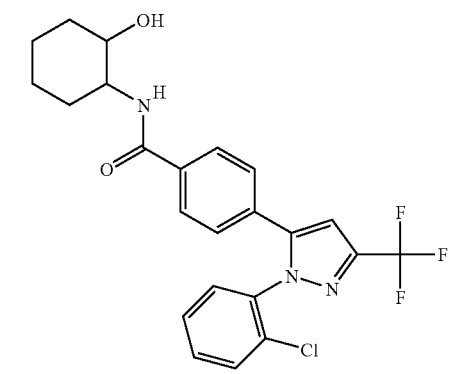 | | 4-[1-(2-chlorophenyl)-3-(trifluoromethyl)-1H-pyrazol-5-yl]-N-(2-hydroxycyclohexyl)benzamide |

TABLE 1-continued

| | | |
|---|---|---|
| 1590 | | 4-[1-(2-chlorophenyl)-3-(trifluoromethyl)-1H-pyrazol-5-yl]-N-{[4-(methylsulfonyl)phenyl]methyl}benzamide |
| 1591 | | 4-[1-(2-chlorophenyl)-3-(trifluoromethyl)-1H-pyrazol-5-yl]-N-[(2S)-2-hydroxycyclopentyl]benzamide |
| 1592 | | 1-(2-chlorophenyl)-3-(trifluoromethyl)-5-[4-({2-[2-(trifluoromethyl)phenyl]pyrrolidin-1-yl}carbony)phenyl]-1H-pyrazole |
| 1593 | | 1-({4-[1-(2-chlorophenyl)-3-(trifluoromethyl)-1H-pyrazol-5-yl]phenyl}carbonyl)-4-(phenylmethyl)piperidin-4-ol |
| 1594 | | 1-({4-[1-(2-chlorophenyl)-3-(trifluoromethyl)-1H-pyrazol-5-yl]phenyl}carbonyl)-4-phenylpiperidin-4-ol |

| | | |
|---|---|---|
| 1595 | 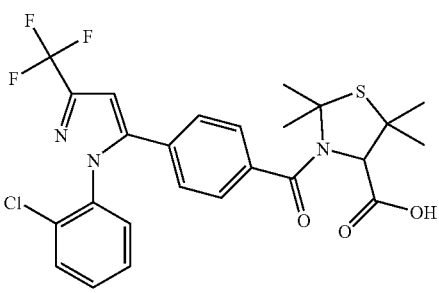 [SMILES: CC1(C)SC(C)(C)N(C(=O)c2ccc(/C(=C/C(=N)C(F)(F)F)Nc3ccccc3Cl)cc2)C1C(=O)O] | 3-({4-[1-(2-chlorophenyl)-3-(trifluoromethyl)-1H-pyrazol-5-yl]phenyl}carbonyl)-2,2,5,5-tetramethyl-1,3-thiazolidine-4-carboxylic acid |
| 1596 | 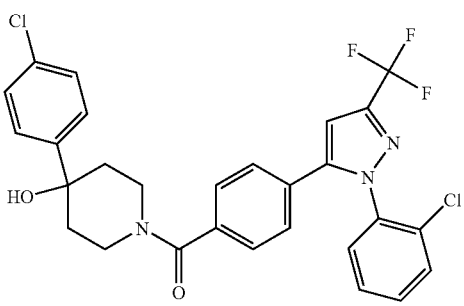 [SMILES: O=C(c1ccc(-c2cc(C(F)(F)F)nn2-c2ccccc2Cl)cc1)N1CCC(O)(c2ccc(Cl)cc2)CC1] | 4-(4-chlorophenyl)-1-({4-[1-(2-chlorophenyl)-3-(trifluoromethyl)-1H-pyrazol-5-yl]phenyl}carbonyl)piperidin-4-ol |
| 1597 | 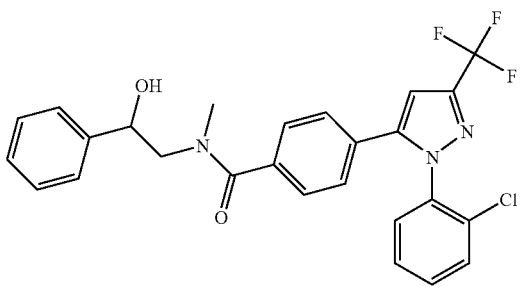 [SMILES: CN(CC(O)c1ccccc1)C(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2-hydroxy-2-phenylethyl)-N-methylbenzamide |
| 1598 | 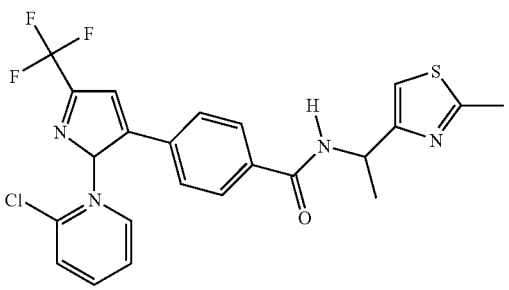 | 4-[1-(2-chlorophenyl)-3-(trifluoromethyl)-1H-pyrazol-5-yl]-N-[1-(2-methyl-1,3-thiazol-4-yl)ethyl]benzamide |
| 1599 | 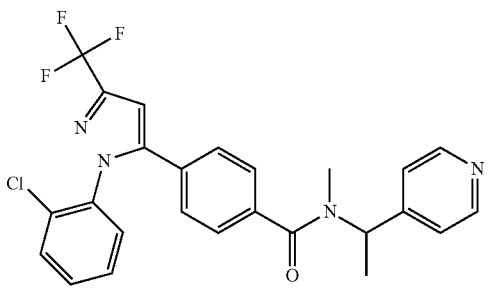 [SMILES: CC(c1ccncc1)N(C)C(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-methyl-N-(1-pyridin-4-ylethyl)benzamide |

TABLE 1-continued

| | | |
|---|---|---|
| 1600 | | 4-[1-(2-chlorophenyl)-3-(trifluoromethyl)-1H-pyrazol-5-yl]-N-[(6-methylpyridin-2-yl)methyl]benzamide |
| 1601 | | 4-[1-(2-chlorophenyl)-3-(trifluoromethyl)-1H-pyrazol-5-yl]-N-[(2S)-2-hydroxycyclohexyl]benzamide |
| 1602 | | 4-[1-(2-chlorophenyl)-3-(trifluoromethyl)-1H-pyrazol-5-yl]-N-[1-(hydroxymethyl)propyl]benzamide |
| 1603 | | 4-[1-(2-chlorophenyl)-3-(trifluoromethyl)-1H-pyrazol-5-yl]-N-methyl-N-(1-pyridin-3-ylethyl)benzamide |
| 1604 | | 4-[1-(2-chlorophenyl)-3-(trifluoromethyl)-1H-pyrazol-5-yl]-N-[5-methyl-2-(methyloxy)phenyl]benzamide |

TABLE 1-continued

| | | |
|---|---|---|
| 1605 | 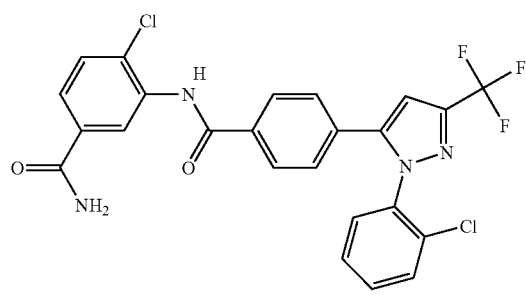 | 4-chloro-3-[({4-[1-(2-chlorophenyl)-3-(trifluoromethyl)-1H-pyrazol-5-yl]phenyl}carbonyl)amino]benzamide |
| 1606 | 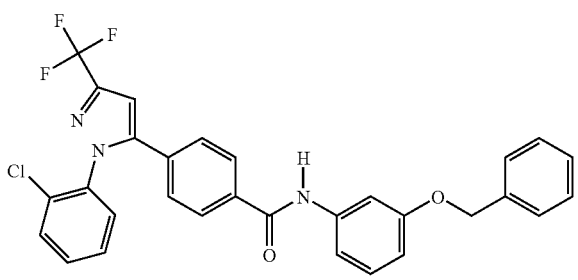 [SMILES: N=C(/C=C(\Nc1ccccc1Cl)c1ccc(C(=O)Nc2cccc(OCc3ccccc3)c2)cc1)C(F)(F)F] | 4-[1-(2-chlorophenyl)-3-(trifluoromethyl)-1H-pyrazol-5-yl]-N-{3-[(phenylmethyl)oxy]phenyl}benzamide |
| 1607 | 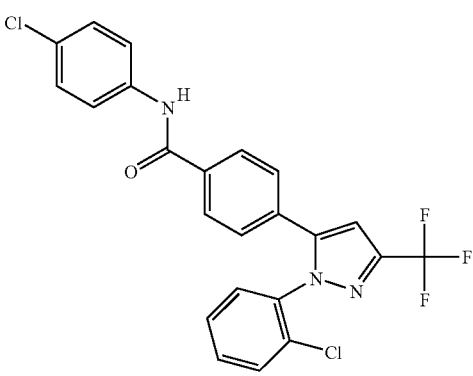 | N-(4-chlorophenyl)-4-[1-(2-chlorophenyl)-3-(trifluoromethyl)-1H-pyrazol-5-yl]benzamide |
| 1608 | 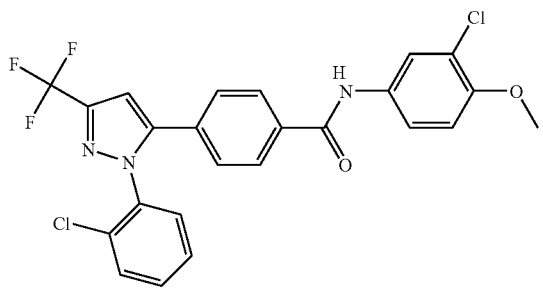 | N-[3-chloro-4-(methyloxy)phenyl]-4-[1-(2-chlorophenyl)-3-(trifluoromethyl)-1H-pyrazol-5-yl]benzamide |
| 1609 | 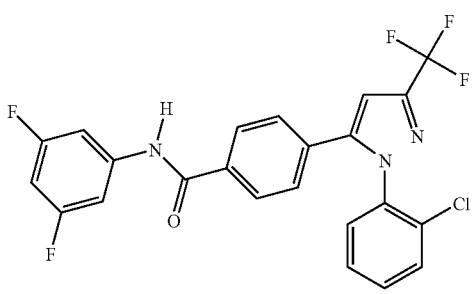 [SMILES: N=C(/C=C(\Nc1ccccc1Cl)c1ccc(C(=O)Nc2cc(F)cc(F)c2)cc1)C(F)(F)F] | 4-[1-(2-chlorophenyl)-3-(trifluoromethyl)-1H-pyrazol-5-yl]-N-(3,5-difluorophenyl)benzamide |

| | | |
|---|---|---|
| 1610 | 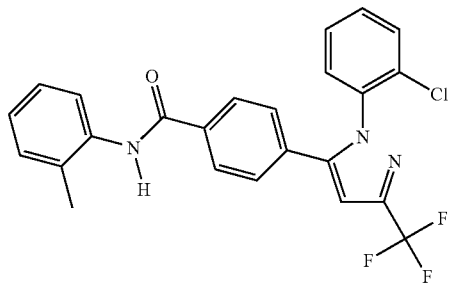 [SMILES: Cc1ccccc1NC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-(2-methylphenyl)benzamide |
| 1611 | 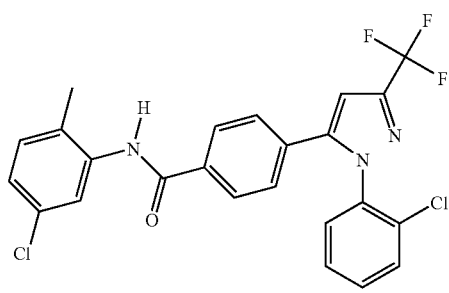 [SMILES: Cc1ccc(Cl)cc1NC(=O)c1ccc(/C(=C/C(=N)C(F)(F)F)Nc2ccccc2Cl)cc1] | N-(5-chloro-2-methylphenyl)-4-[1-(2-chlorophenyl)-3-(trifluoromethyl)-1H-pyrazol-5-yl]benzamide |
| 1612 | 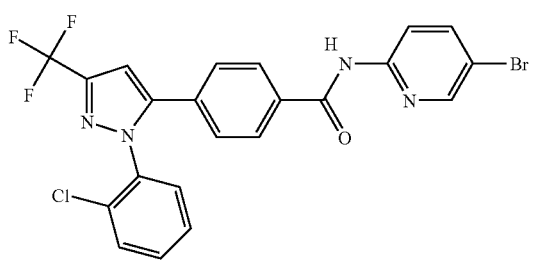 | N-(5-bromopyridin-2-yl)-4-[1-(2-chlorophenyl)-3-(trifluoromethyl)-1H-pyrazol-5-yl]benzamide |
| 1613 | 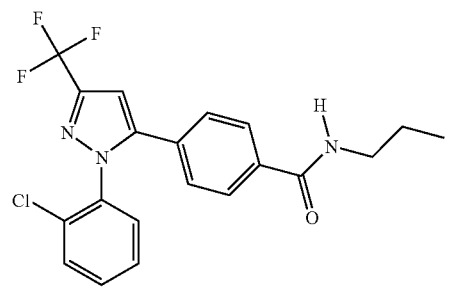 [SMILES: CCCNC(=O)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-propylbenzamide |
| 1614 | 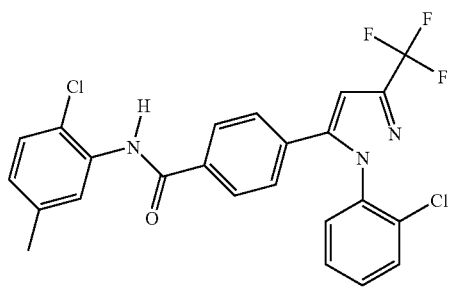 [SMILES: Cc1ccc(Cl)c(NC(=O)c2ccc(/C(=C/C(=N)C(F)(F)F)Nc3ccccc3Cl)cc2)c1] | N-(2-chloro-5-methylphenyl)-4-[1-(2-chlorophenyl)-3-(trifluoromethyl)-1H-pyrazol-5-yl]benzamide |

| | | |
|---|---|---|
| 1615 | 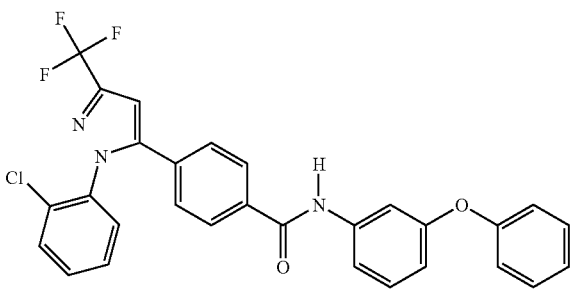 [SMILES: N=C(/C=C(\Nc1ccccc1Cl)c1ccc(C(=O)Nc2cccc(Oc3ccccc3)c2)cc1)C(F)(F)F] | 4-[1-(2-chlorophenyl)-3-(trifluoromethyl)-1H-pyrazol-5-yl]-N-[3-(phenyloxy)phenyl]benzamide |
| 1616 | 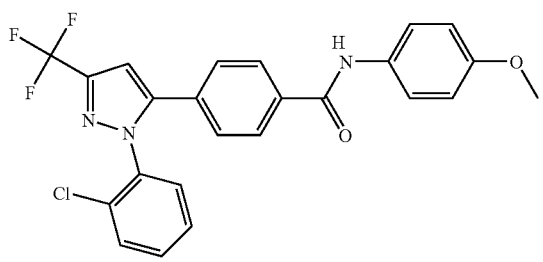 | 4-[1-(2-chlorophenyl)-3-(trifluoromethyl)-1H-pyrazol-5-yl]-N-[4-(methyloxy)phenyl]benzamide |
| 1617 | 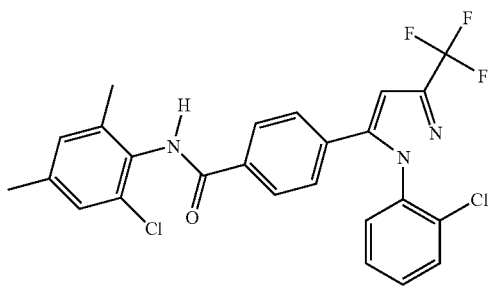 [SMILES: Cc1cc(C)c(NC(=O)c2ccc(/C(=C/C(=N)C(F)(F)F)Nc3ccccc3Cl)cc2)c(Cl)c1] | N-(2-chloro-4,6-dimethylphenyl)-4-[1-(2-chlorophenyl)-3-(trifluoromethyl)-1H-pyrazol-5-yl]benzamide |
| 1618 | 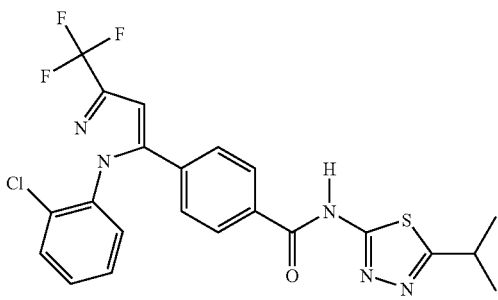 [SMILES: CC(C)c1nnc(NC(=O)c2ccc(/C(=C/C(=N)C(F)(F)F)Nc3ccccc3Cl)cc2)s1] | 4-[1-(2-chlorophenyl)-3-(trifluoromethyl)-1H-pyrazol-5-yl]-N-[5-(1-methylethyl)-1,3,4-thiadiazol-2-yl]benzamide |
| 1619 | 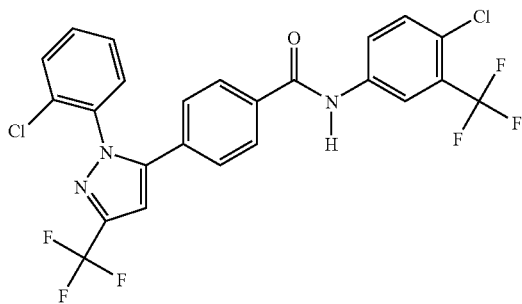 [SMILES: O=C(Nc1ccc(Cl)c(C(F)(F)F)c1)c1ccc(-c2cc(C(F)(F)F)nn2-c2ccccc2Cl)cc1] | N-(4-chloro-3-(trifluoromethyl)phenyl)-4-(1-(2-chlorophenyl)-3-(trifluoromethyl)-1H-pyrazol-5-yl)benzamide |

TABLE 1-continued

| 1620 | 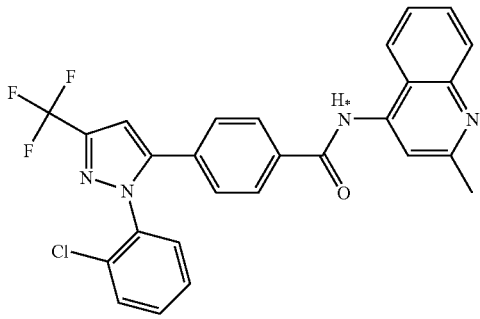 [SMILES: Cc1cc(NC(=O)c2ccc(-c3cc(C(F)(F)F)nn3-c3ccccc3Cl)cc2)c2ccccc2n1] | 4-(1-(2-chlorophenyl)-3-(trifluoromethyl)-1H-pyrazol-5-yl)-N-(2-methylquinolin-4-yl)benzamide |
| 1621 | 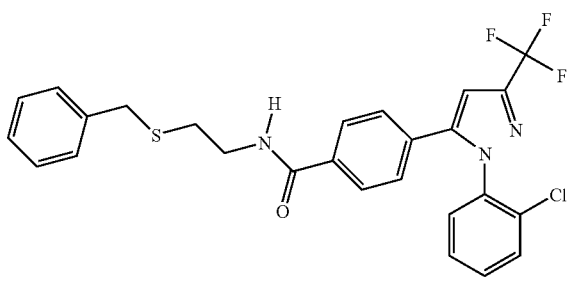 [SMILES: N=C(/C=C(\Nc1ccccc1Cl)c1ccc(C(=O)NCCSCc2ccccc2)cc1)C(F)(F)F] | N-(2-(benzylthio)ethyl)-4-(1-(2-chlorophenyl)-3-(trifluoromethyl)-1H-pyrazol-5-yl)benzamide |
| 1622 | 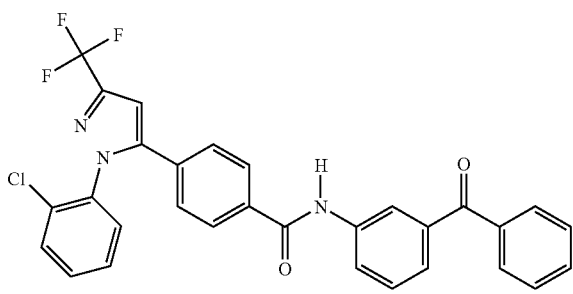 [SMILES: N=C(/C=C(\Nc1ccccc1Cl)c1ccc(C(=O)Nc2cccc(C(=O)c3ccccc3)c2)cc1)C(F)(F)F] | N-(3-benzoylphenyl)-4-(1-(2-chlorophenyl)-3-(trifluoromethyl)-1H-pyrazol-5-yl)benzamide |
| 1623 | 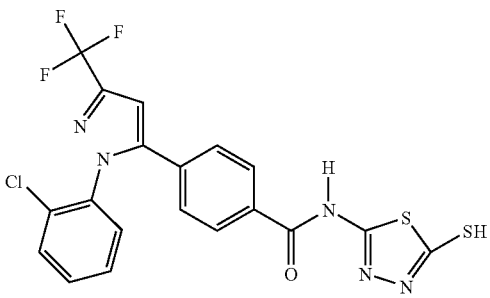 [SMILES: N=C(/C=C(\Nc1ccccc1Cl)c1ccc(C(=O)Nc2nnc(S)s2)cc1)C(F)(F)F] | 4-(1-(2-chlorophenyl)-3-(trifluoromethyl)-1H-pyrazol-5-yl)-N-(5-mercapto-1,3,4-thiadiazol-2-yl)benzamide |
| 1624 | 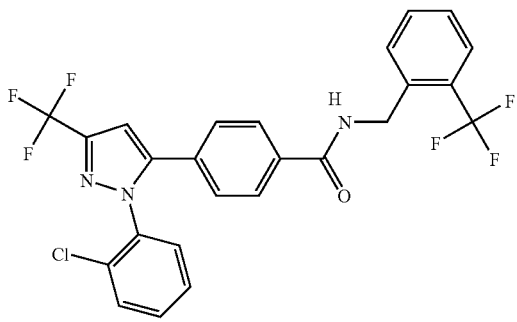 | 4-(1-(2-chlorophenyl)-3-(trifluoromethyl)-1H-pyrazol-5-yl)-N-(2-(trifluoromethyl)benzyl)benzamide |

TABLE 1-continued

| 1625 | 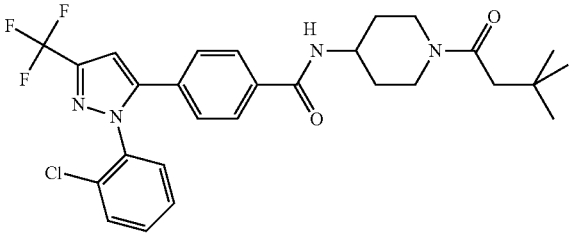 | tert-butyl 4-(4-(1-(2-chlorophenyl)-3-(trifluoromethyl)-1H-pyrazol-5-yl)benzamido)piperidin-1-carboxylate |
| --- | --- | --- |
| 1626 | 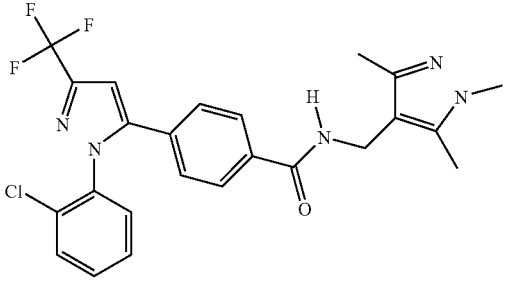 [SMILES: CN/C(C)=C(/CNC(=O)c1ccc(/C(=C/C(=N)C(F)(F)F)Nc2ccccc2Cl)cc1)C(C)=N] | 4-(1-(2-chlorophenyl)-3-(trifluoromethyl)-1H-pyrazol-5-yl)-N-((1,3,5-trimethyl-1H-pyrazol-4-yl)methyl)benzamide |
| 1627 | 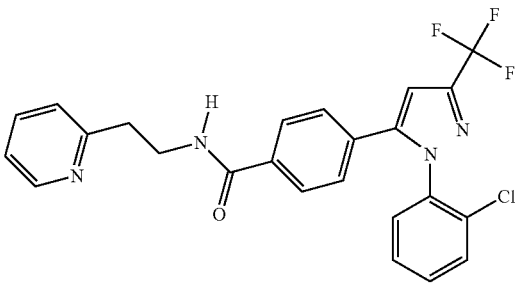 [SMILES: N=C(/C=C(\Nc1ccccc1Cl)c1ccc(C(=O)NCCc2ccccn2)cc1)C(F)(F)F] | 4-[1-(2-chlorophenyl)-3-(trifluoromthyl)-1H-pyrazol-5-yl]-N-(2-pyridin-2-ylethyl)benzamide |
| 1628 | 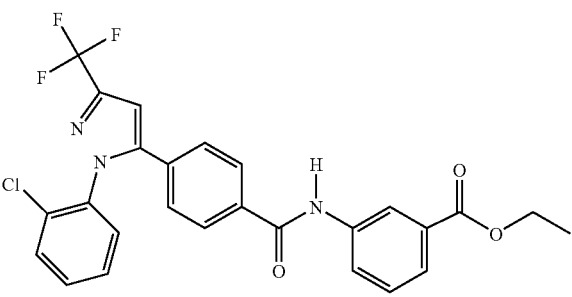 [SMILES: CCOC(=O)c1cccc(NC(=O)c2ccc(/C(=C/C(=N)C(F)(F)F)Nc3ccccc3Cl)cc2)c1] | ethyl 3-[({4-[1-(2-chlorophenyl)-3-(trifluoromethyl)-1H-pyrazol-5-yl]phenyl}carbonyl)amino]benzoate |
| 1629 | 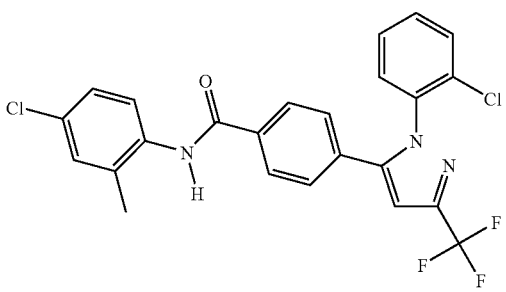 [SMILES: Cc1cc(Cl)ccc1NC(=O)c1ccc(/C(=C/C(=N)C(F)(F)F)Nc2ccccc2Cl)cc1] | N-(4-chloro-2-methylphenyl)-4-[1-(2-chlorophenyl)-3-(trifluoromethyl)-1H-pyrazol-5-yl]benzamide |

TABLE 1-continued

| 1630 | 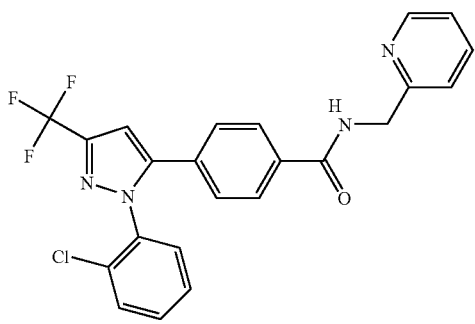 | 4-[1-(2-chlorophenyl)-3-(trifluoromethyl)-1H-pyrazol-5-yl]-N-(pyridin-2-ylmethyl)benzamide |
| --- | --- | --- |
| 1631 | 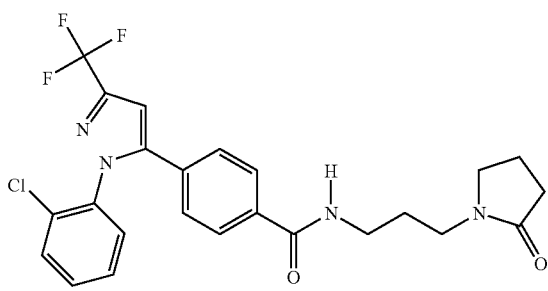 [SMILES: N=C(/C=C(\Nc1ccccc1Cl)c1ccc(C(=O)NCCCN2CCCC2=O)cc1)C(F)(F)F] | 4-[1-(2-chlorophenyl)-3-(trifluoromethyl)-1H-pyrazol-5-yl]-N-[3-(2-oxopyrrolidin-1-yl)propyl]benzamide |
| 1632 | 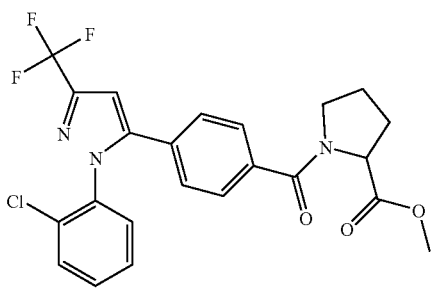 [SMILES: COC(=O)C1CCCN1C(=O)c1ccc(/C(=C/C(=N)C(F)(F)F)Nc2ccccc2Cl)cc1] | methyl 1-({4-[1-(2-chlorophenyl)-3-(trifluoromethyl)-1H-pyrazol-5-yl]phenyl}carbonyl)prolinate |
| 1633 | 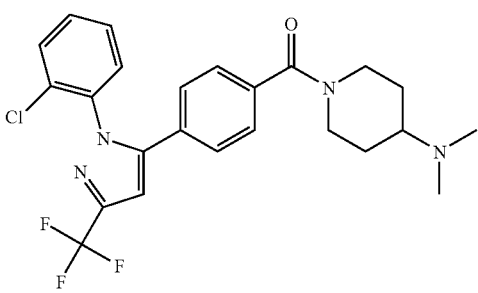 [SMILES: CN(C)C1CCN(C(=O)c2ccc(/C(=C/C(=N)C(F)(F)F)Nc3ccccc3Cl)cc2)CC1] | 1-({4-[1-(2-chlorophenyl)-3-(trifluoromethyl)-1H-pyrazol-5-yl]phenyl}carbonyl)-N,N-dimethylpiperidin-4-amine |
| 1634 | 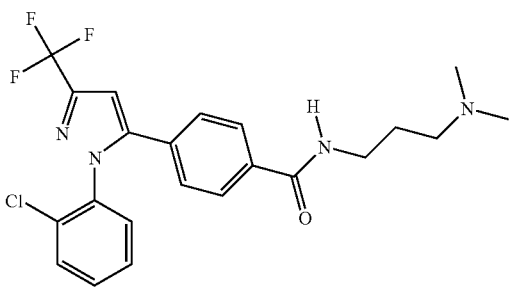 [SMILES: CN(C)CCCNC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-[3-(dimethylamino)propyl]benzamide |

TABLE 1-continued

| 1635 | | 4-[1-(2-chlorophenyl)-3-(trifluoromethyl)-1H-pyrazol-5-yl]-N-[1-(phenylmethyl)piperidin-4-yl]benzamide |
| --- | --- | --- |
| 1636 | | 4-[1-(2-chlorophenyl)-3-(trifluoromethyl)-1H-pyrazol-5-yl]-N-(2-piperidin-1-ylethyl)benzamide |
| 1638 | | N-[2,4-bis(methyloxy)phenyl]-4-[1-(2-chlorophenyl)-3-(trifluoromethyl)-1H-pyrazol-5-yl]benzamide |
| 1639 | | N-(4-chloro-2-fluorophenyl)-4-[1-(2-chlorophenyl)-3-(trifluoromethyl)-1H-pyrazol-5-yl]benzamide |
| 1640 | | N-{-2,4-bis(methyloxy)phenyl]methyl}-4-[1-(2-chlorophenyl)-3-(trifluoromethyl)-1H-pyrazol-5-yl]benzamide |

TABLE 1-continued

| | | |
|---|---|---|
| 1642 | 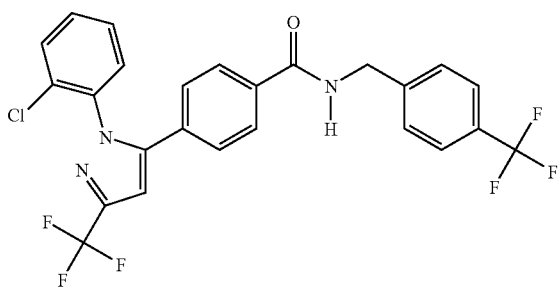 [SMILES: N=C(/C=C(\Nc1ccccc1Cl)c1ccc(C(=O)NCc2ccc(C(F)(F)F)cc2)cc1)C(F)(F)F] | 4-[1-(2-chlorophenyl)-3-(trifluoromethyl)-1H-pyrazol-5-yl]-N-{[4-(trifluoromethyl)phenyl]methyl}benzamide |
| 1643 | 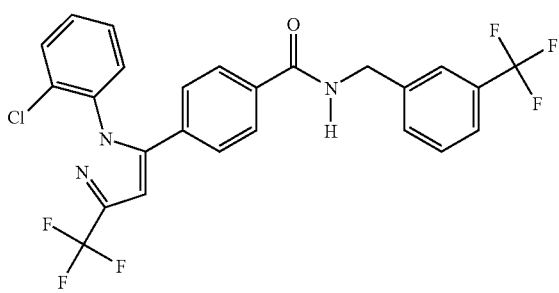 [SMILES: N=C(/C=C(\Nc1ccccc1Cl)c1ccc(C(=O)NCc2cccc(C(F)(F)F)c2)cc1)C(F)(F)F] | 4-[1-(2-chlorophenyl)-3-(trifluoromethyl)-1H-pyrazol-5-yl]-N-{[3-(trifluoromethyl)phenyl]methyl}benzamide |
| 1644 | 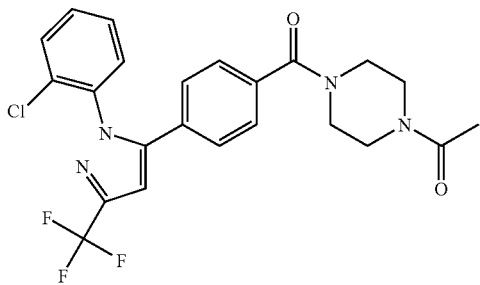 [SMILES: CC(=O)N1CCN(C(=O)c2ccc(/C(=C/C(=N)C(F)(F)F)Nc3ccccc3Cl)cc2)CC1] | 1-acetyl-4-({4-[1-(2-chlorophenyl)-3-(trifluoromethyl)-1H-pyrazol-5-yl]phenyl}carbonyl)piperazine |
| 1645 | 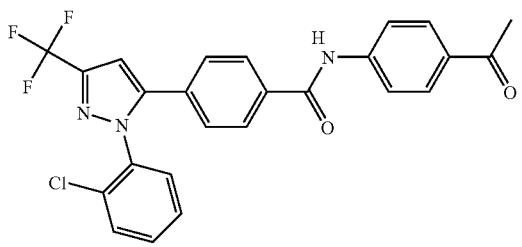 | N-(4-acetylphenyl)-4-[1-(2-chlorophenyl)-3-(trifluoromethyl)-1H-pyrazol-5-yl]benzamide |
| 1646 | 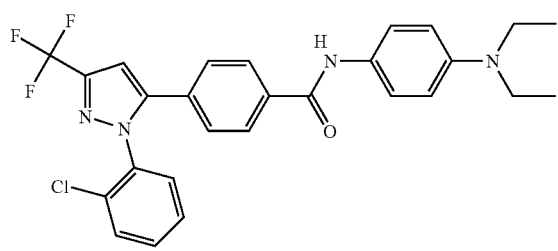 | 4-[1-(2-chlorophenyl)-3-(trifluoromethyl)-1H-pyrazol-5-yl]-N-[4-(diethylamino)phenyl]benzamide |

| | | |
|---|---|---|
| 1647 | 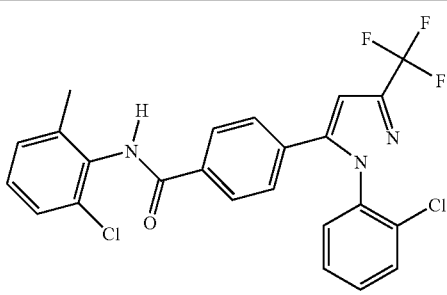 [SMILES: Cc1cccc(Cl)c1NC(=O)c1ccc(/C(=C/C(=N)C(F)(F)F)Nc2ccccc2Cl)cc1] | N-(2-chloro-6-methylphenyl)-4-[1-(2-chlorophenyl)-3-(trifluoromethyl)-1H-pyrazol-5-yl]benzamide |
| 1648 | 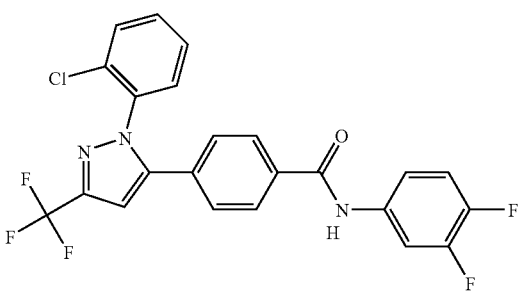 | 4-[1-(2-chlorophenyl)-3-(trifluoromethyl)-1H-pyrazol-5-yl]-N-(3,4-difluorophenyl)benzamide |
| 1649 | 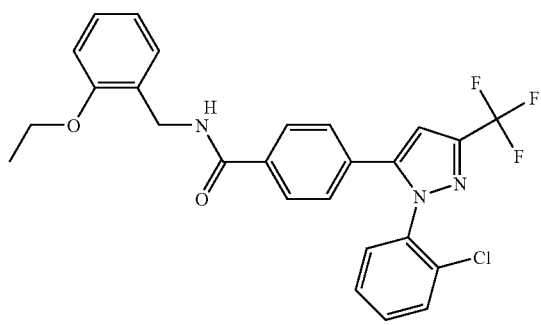 | 4-[1-(2-chlorophenyl)-3-(trifluoromethyl)-1H-pyrazol-5-yl]-N-{[2-(ethyloxy)phenyl]methyl}benzamide |
| 1650 | 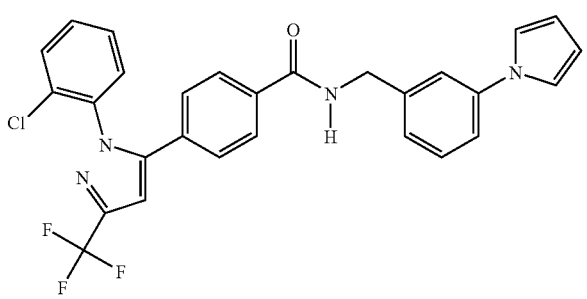 [SMILES: N=C(/C=C(\Nc1ccccc1Cl)c1ccc(C(=O)NCc2cccc(-n3cccc3)c2)cc1)C(F)(F)F] | 4-[1-(2-chlorophenyl)-3-(trifluoromethyl)-1H-pyrazol-5-yl]-N-{[3-(1H-pyrrol-1-yl)phenyl]methyl}benzamide |
| 1651 | 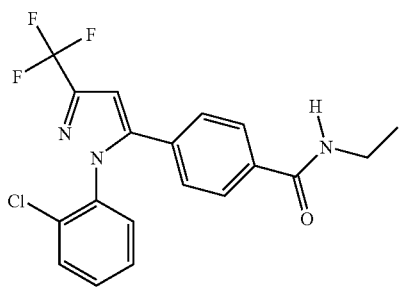 [SMILES: CCNC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-ethylbenzamide |

TABLE 1-continued

| | | |
|---|---|---|
| 1652 | 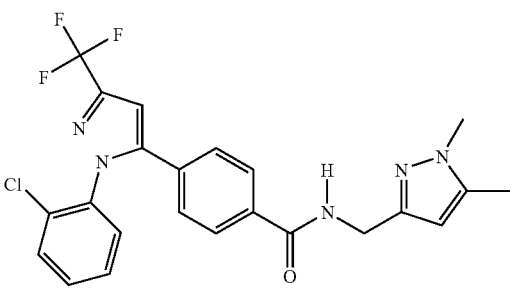 [SMILES: Cc1cc(CNC(=O)c2ccc(/C(=C/C(=N)C(F)(F)F)Nc3ccccc3Cl)cc2)nn1C] | 4-[1-(2-chlorophenyl)-3-(trifluoromethyl)-1H-pyrazol-5-yl]-N-[(1,5-dimethyl-1H-pyrazol-3-yl)methyl]benzamide |
| 1653 | 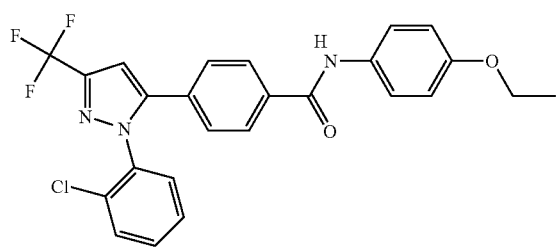 | 4-[1-(2-chlorophenyl)-3-(trifluoromethyl)-1H-pyrazol-5-yl]-N-[4-(ethyloxy)phenyl]benzamide |
| 1654 | 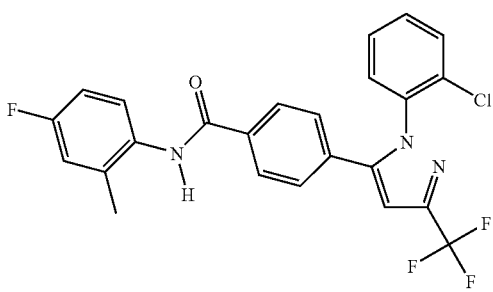 [SMILES: Cc1cc(F)ccc1NC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-(4-fluoro-2-methylphenyl)benzamide |
| 1655 | 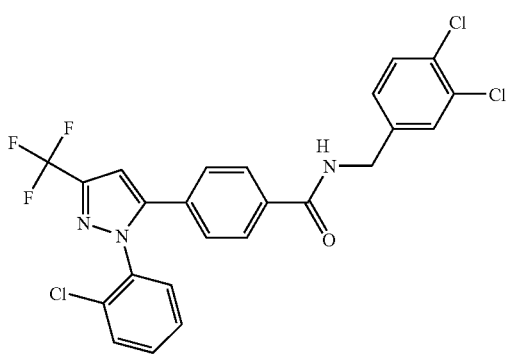 | 4-[1-(2-chlorophenyl)-3-(trifluoromethyl)-1H-pyrazol-5-yl]-N-[(3,4-dichlorophenyl)methyl]benzamide |
| 1656 | 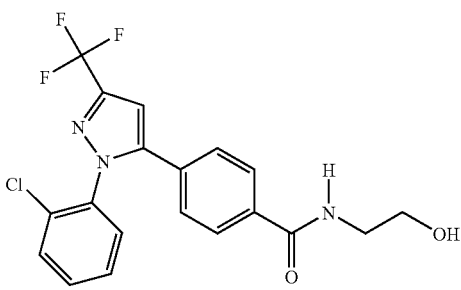 [SMILES: O=C(NCCO)c1ccc(-c2cc(C(F)(F)F)nn2-c2ccccc2Cl)cc1] | 4-[1-(2-chlorophenyl)-3-(trifluoromethyl)-1H-pyrazol-5-yl]-N-(2-hydroxyethyl)benzamide |

TABLE 1-continued

| | | |
|---|---|---|
| 1657 | | 4-[1-(2-chlorophenyl)-3-(trifluoromethyl)-1H-pyrazol-5-yl]-N-[(5-methylisoxazol-3-yl)methyl]benzamide |
| 1658 | | 4-[1-(2-chlorophenyl)-3-(trifluoromethyl)-1H-pyrazol-5-yl]-N,N-dimethylbenzamide |
| 1659 | | 4-[1-(2-chlorophenyl)-3-(trifluoromethyl)-1H-pyrazol-5-yl]-N-[3-(2-methylpiperidin-1-yl)propyl]benzamide |
| 1660 | | 4-[1-(2-chlorophenyl)-3-(trifluoromethyl)-1H-pyrazol-5-yl]-N-[2-(methyloxy)ethyl]benzamide |
| 1662 | | N-[4-chloro-5-methyl-2-(methyloxy)phenyl]-4-[1-(2-chlorophenyl)-3-(trifluoromethyl)-1H-pyrazol-5-yl]benzamide |

TABLE 1-continued

| 1663 | 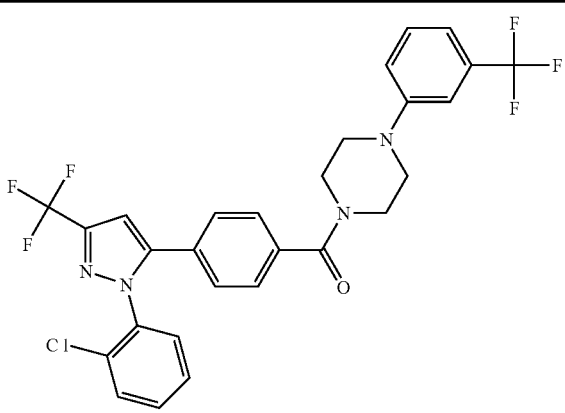 | 1-({4-[1-(2-chlorophenyl)-3-(trifluoromethyl)-1H-pyrazol-5-yl]phenyl}carbonyl)-4-[3-(trifluoromethyl)phenyl]piperazine |
| 1664 | 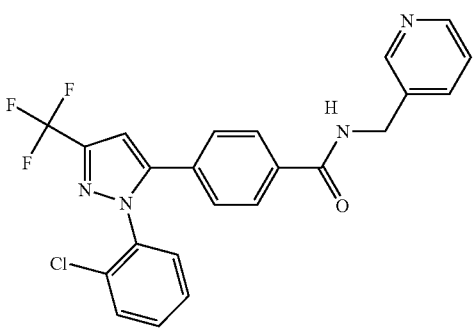 | 4-[1-(2-chlorophenyl)-3-(trifluoromethyl)-1H-pyrazol-5-yl]-N-(pyridin-3-ylmethyl)benzamide |
| 1665 | 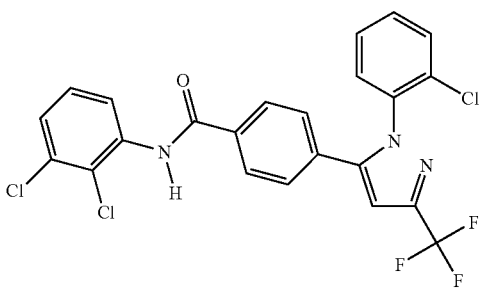 [SMILES: N=C(/C=C(\Nc1ccccc1Cl)c1ccc(C(=O)Nc2cccc(Cl)c2Cl)cc1)C(F)(F)F] | 4-[1-(2-chlorophenyl)-3-(trifluoromethyl)-1H-pyrazol-5-yl]-N-(2,3-dichlorophenyl)benzamide |
| 1666 | 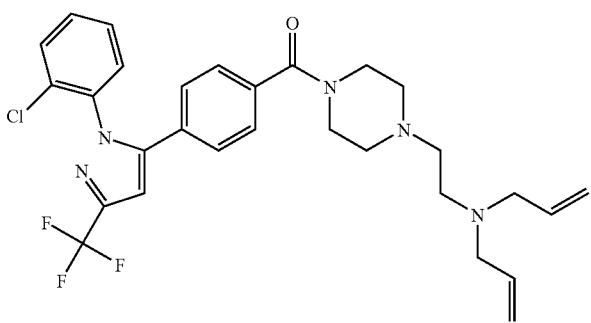 [SMILES: C=CCN(CC=C)CCN1CCN(C(=O)c2ccc(/C(=C/C(=N)C(F)(F)F)Nc3ccccc3Cl)cc2)CC1] | N-{2-[4-({4-[1-(2-chlorophenyl)-3-(trifluoromethyl)-1H-pyrazol-5-yl]phenyl}carbonyl)piperazin-1-yl]ethyl}-N-prop-2-en-1-ylprop-2-en-1-amine |

TABLE 1-continued

| 1667 | 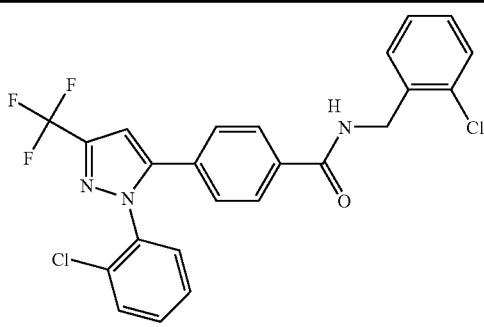 | N-[(2-chlorophenyl)methyl]-4-[1-(2-chlorophenyl)-3-(trifluoromethyl)-1H-pyrazol-5-yl]benzamide |
| 1668 | 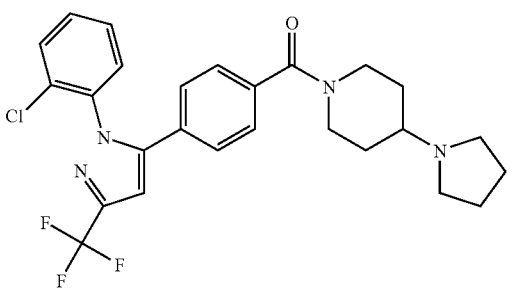 [SMILES: N=C(/C=C(\Nc1ccccc1Cl)c1ccc(C(=O)N2CCC(N3CCCC3)CC2)cc1)C(F)(F)F] | 1-({4-[1-(2-chlorophenyl)-3-(trifluoromethyl)-1H-pyrazol-5-yl]phenyl}carbonyl)-4-pyrrolidin-1-ylpiperidine |
| 1669 | 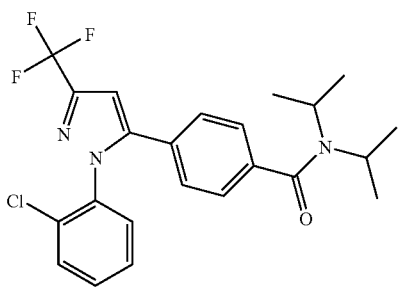 [SMILES: CC(C)N(C(=O)c1ccc(/C(=C/C(=N)C(F)(F)F)Nc2ccccc2Cl)cc1)C(C)C] | 4-[1-(2-chlorophenyl)-3-(trifluoromethyl)-1H-pyrazol-5-yl]-N,N-bis(methylethyl)benzamide |
| 1670 | 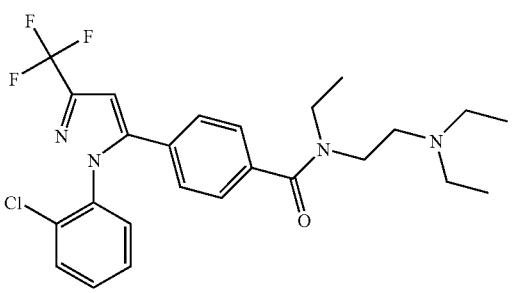 [SMILES: CCN(CC)CCN(CC)C(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-[2-(diethylamino)ethyl]-N-ethylbenzamide |
| 1671 | 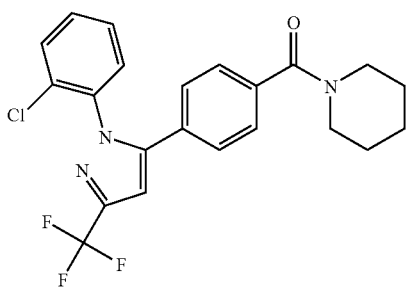 [SMILES: N=C(/C=C(\Nc1ccccc1Cl)c1ccc(C(=O)N2CCCCC2)cc1)C(F)(F)F] | 1-({4-[1-(2-chlorophenyl)-3-(trifluoromethyl)-1H-pyrazol-5-yl]phenyl}carbonyl)piperidine |

TABLE 1-continued

| | | |
|---|---|---|
| 1672 | 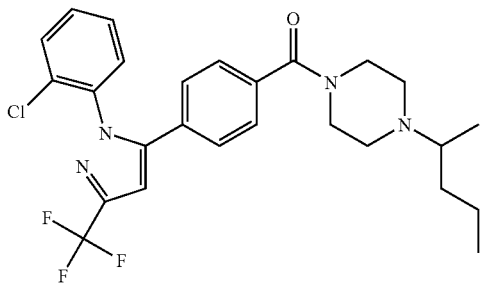 [SMILES: CCCC(C)N1CCN(C(=O)c2ccc(/C(=C/C(=N)C(F)(F)F)Nc3ccccc3Cl)cc2)CC1] | 1-({4-[1-(2-chlorophenyl)-3-(trifluoromethyl)-1H-pyrazol-5-yl]phenyl}carbonyl)-4-(1-methylbutyl)piperazine |
| 1673 | 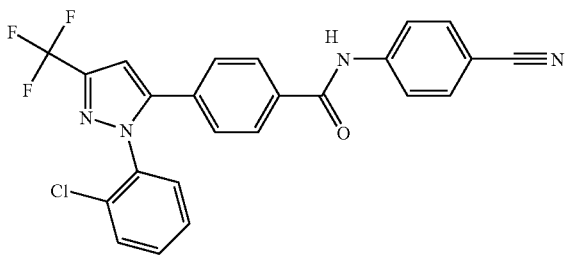 | 4-[1-(2-chlorophenyl)-3-(trifluoromethyl)-1H-pyrazol-5-yl]-N-(4-cyanophenyl)benzamide |
| 1674 | 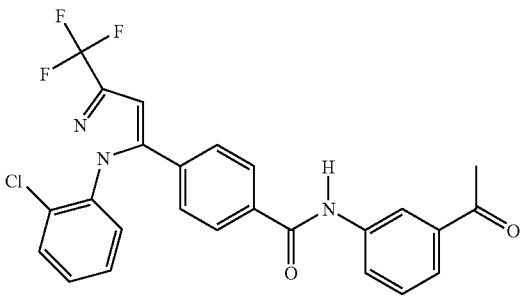 [SMILES: CC(=O)c1cccc(NC(=O)c2ccc(/C(=C/C(=N)C(F)(F)F)Nc3ccccc3Cl)cc2)c1] | N-(3-acetylphenyl)-4-[1-(2-chlorophenyl)-3-(trifluoromethyl)-1H-pyrazol-5-yl]benzamide |
| 1675 | 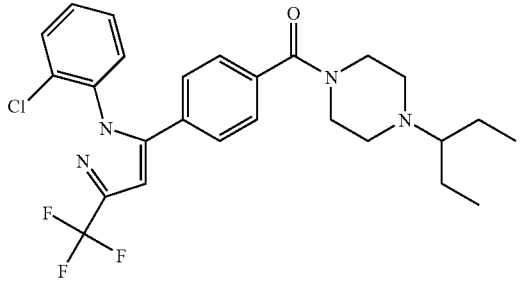 [SMILES: CCC(CC)N1CCN(C(=O)c2ccc(/C(=C/C(=N)C(F)(F)F)Nc3ccccc3Cl)cc2)CC1] | 1-({4-[1-(2-chlorophenyl)-3-(trifluoromethyl)-1H-pyrazol-5-yl]phenyl}carbonyl)-4-(1-ethylpropyl)piperazine |
| 1676 | 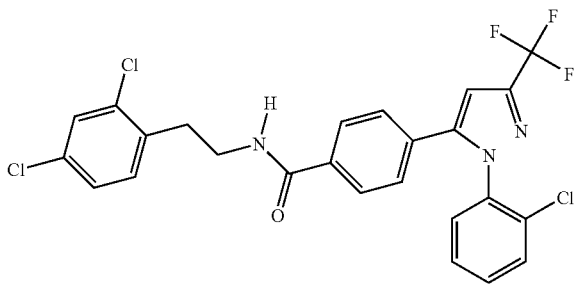 [SMILES: N=C(/C=C(\Nc1ccccc1Cl)c1ccc(C(=O)NCCc2ccc(Cl)cc2Cl)cc1)C(F)(F)F] | 4-[1-(2-chlorophenyl)-3-(trifluoromethyl)-1H-pyrazol-5-yl]-N-[2-(2,4-dichlorophenyl)ethyl]benzamide |

| | | |
|---|---|---|
| 1677 | 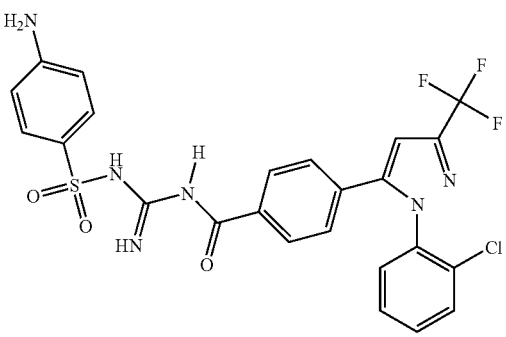 [SMILES: N=C(NC(=O)c1ccc(/C(=C/C(=N)C(F)(F)F)Nc2ccccc2Cl)cc1)NS(=O)(=O)c1ccc(N)cc1] | N-[{[(4-aminophenyl)sulfonyl]amino}(imino)methyl]-4-[1-(2-chlorophenyl)-3-(trifluoromethyl)-1H-pyrazol-5-yl]benzamide |
| 1678 | 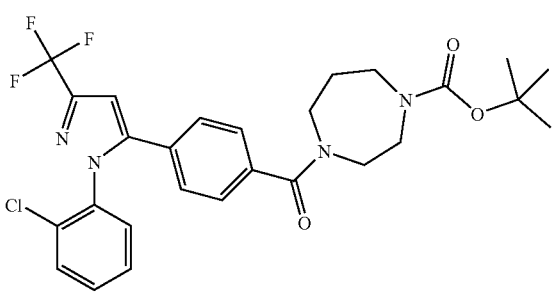 [SMILES: CC(C)(C)OC(=O)N1CCCN(C(=O)c2ccc(/C(=C/C(=N)C(F)(F)F)Nc3ccccc3Cl)cc2)CC1] | 1,1-dimethylethyl 4-({4-[1-(2-chlorophenyl)-3-(trifluoromethyl)-1H-pyrazol-5-yl]phenyl}carbonyl)-1,4-diazepane-1-carboxylate |
| 1679 | 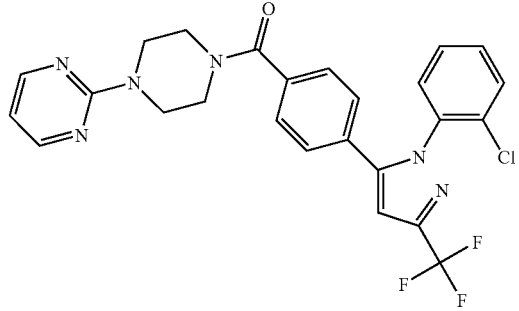 [SMILES: N=C(/C=C(\Nc1ccccc1Cl)c1ccc(C(=O)N2CCN(c3ncccn3)CC2)cc1)C(F)(F)F] | 2-[4-({4-[1-(2-chlorophenyl)-3-(trifluoromethyl)-1H-pyrazol-5-yl]phenyl}carbonyl)piperazin-1-yl]pyrimidine |
| 1680 | 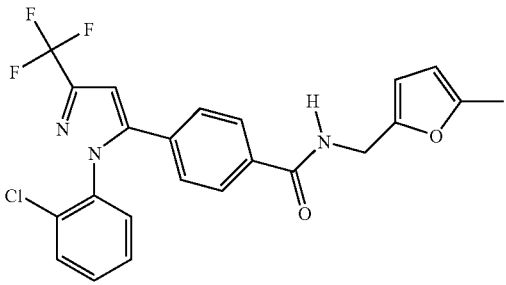 [SMILES: Cc1ccc(CNC(=O)c2ccc(/C(=C/C(=N)C(F)(F)F)Nc3ccccc3Cl)cc2)o1] | 4-[1-(2-chlorophenyl)-3-(trifluoromethyl)-1H-pyrazol-5-yl]-N-[(5-methylfuran-2-yl)methyl]benzamide |
| 1681 | 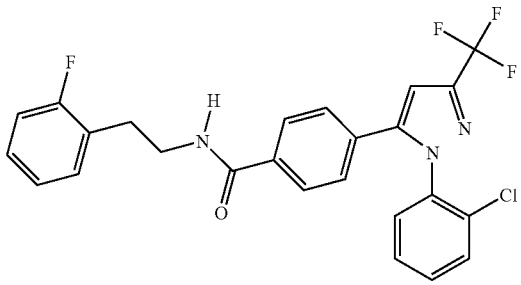 [SMILES: N=C(/C=C(\Nc1ccccc1Cl)c1ccc(C(=O)NCCc2ccccc2F)cc1)C(F)(F)F] | 4-[1-(2-chlorophenyl)-3-(trifluoromethyl)-1H-pyrazol-5-yl]-N-[2-(2-fluorophenyl)ethyl]benzamide |

TABLE 1-continued

| | | |
|---|---|---|
| 1682 | 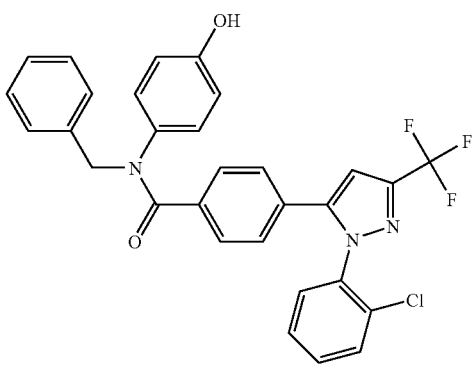 [SMILES: O=C(c1ccc(-c2cc(C(F)(F)F)nn2-c2ccccc2Cl)cc1)N(Cc1ccccc1)c1ccc(O)cc1] | 4-[1-(2-chlorophenyl)-3-(trifluoromethyl)-1H-pyrazol-5-yl]-N-(4-hydroxyphenyl)-N-(phenylmethyl)benzamide |
| 1683 | 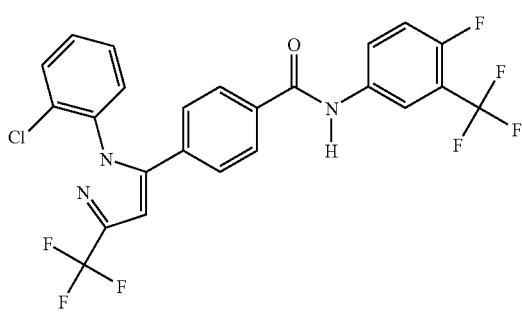 [SMILES: N=C(/C=C(\Nc1ccccc1Cl)c1ccc(C(=O)Nc2ccc(F)c(C(F)(F)F)c2)cc1)C(F)(F)F] | 4-[1-(2-chlorophenyl)-3-(trifluoromethyl)-1H-pyrazol-5-yl]-N-[4-fluoro-3-(trifluoromethyl)phenyl]benzamide |
| 1684 | 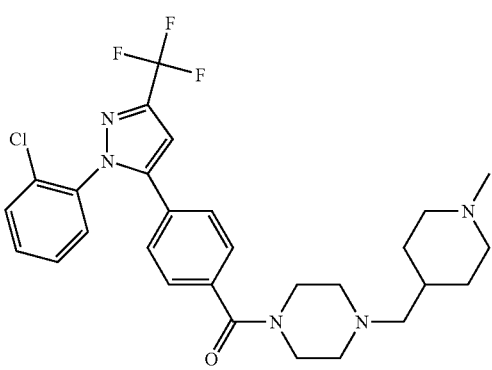 [SMILES: CN1CCC(CN2CCN(C(=O)c3ccc(-c4cc(C(F)(F)F)nn4-c4ccccc4Cl)cc3)CC2)CC1] | 1-({4-[1-(2-chlorophenyl)-3-(trifluoromethyl)-1H-pyrazol-5-yl]phenyl}carbonyl)-4-[(1-methylpiperidin-4-yl)methyl]piperazine |
| 1685 | 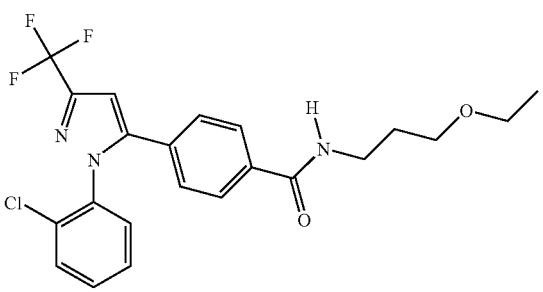 [SMILES: CCOCCCNC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-[3-(ethyloxy)propyl]benzamide |
| 1686 | 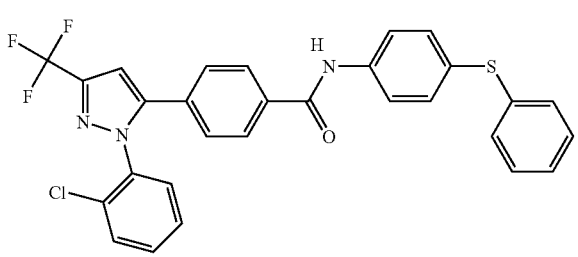 | 4-[1-(2-chlorophenyl)-3-(trifluoromethyl)-1H-pyrazol-5-yl]-N-[4-(phenylthio)phenyl]benzamide |

TABLE 1-continued

| 1687 | 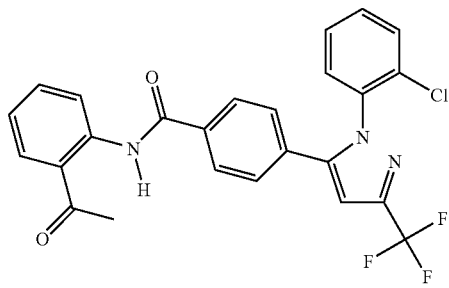 [SMILES: CC(=O)c1ccccc1NC(=O)c1ccc(/C(=C/C(=N)C(F)(F)F)Nc2ccccc2Cl)cc1] | N-(2-acetylphenyl)-4-[1-(2-chlorophenyl)-3-(trifluoromethyl)-1H-pyrazol-5-yl]benzamide |
| 1688 | 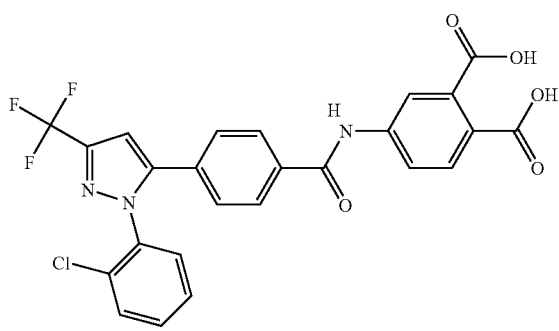 | 4-[({4-[1-(2-chlorophenyl)-3-(trifluoromethyl)-1H-pyrazol-5-yl]phenyl}carbonyl)amino]benzene-1,2-dicarboxylic acid |
| 1689 | 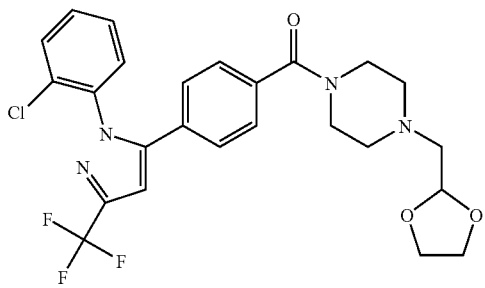 [SMILES: N=C(/C=C(\Nc1ccccc1Cl)c1ccc(C(=O)N2CCN(CC3OCCO3)CC2)cc1)C(F)(F)F] | 1-({4-[1-(2-chlorophenyl)-3-(trifluoromethyl)-1H-pyrazol-5-yl]phenyl}carbonyl)-4-(1,3-dioxolan-2-ylmethyl)piperazine |
| 1690 | 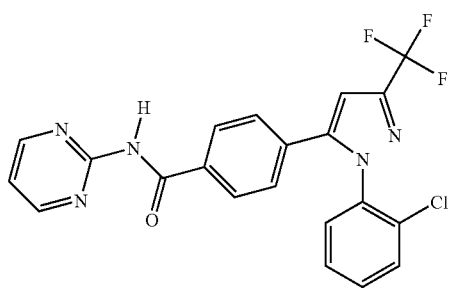 [SMILES: N=C(/C=C(\Nc1ccccc1Cl)c1ccc(C(=O)Nc2ncccn2)cc1)C(F)(F)F] | 4-[1-(2-chlorophenyl)-3-(trifluoromethyl)-1H-pyrazaol-5-yl]-N-pyrimidin-2-ylbenzamide |
| 1691 | 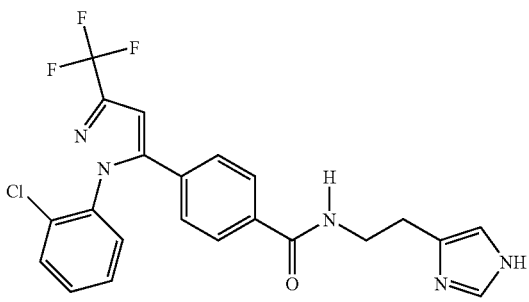 [SMILES: N=C(/C=C(\Nc1ccccc1Cl)c1ccc(C(=O)NCCc2c[nH]cn2)cc1)C(F)(F)F] | 4-[1-(2-chlorophenyl)-3-(trifluoromethyl)-1H-pyrazol-5-yl]-N-[2-(1H-imidazol-4-yl)ethyl]benzamide |

TABLE 1-continued

| 1692 | 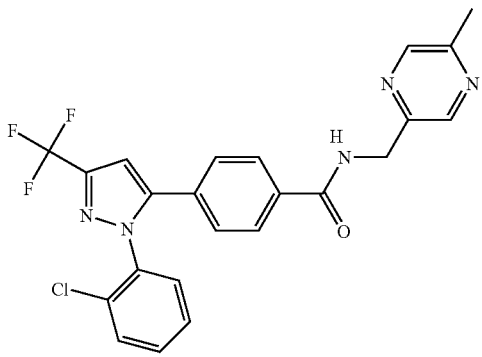 | 4-[1-(2-chlorophenyl)-3-(trifluoromethyl)-1H-pyrazol-5-yl]-N-[(5-methylpyrazin-2-yl)methyl]benzamide |
| 1693 | 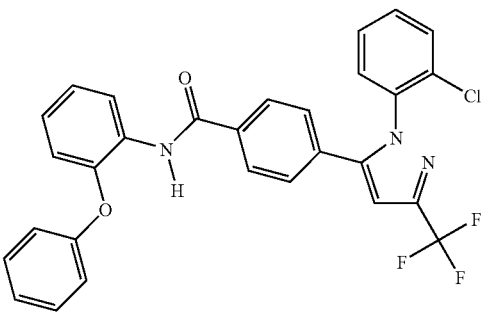 [SMILES: N=C(/C=C(\Nc1ccccc1Cl)c1ccc(C(=O)Nc2ccccc2Oc2ccccc2)cc1)C(F)(F)F] | 4-[1-(2-chlorophenyl)-3-(trifluoromethyl)-1H-pyrazol-5-yl]-N-[2-(phenyloxy)phenyl]benzamide |
| 1694 | 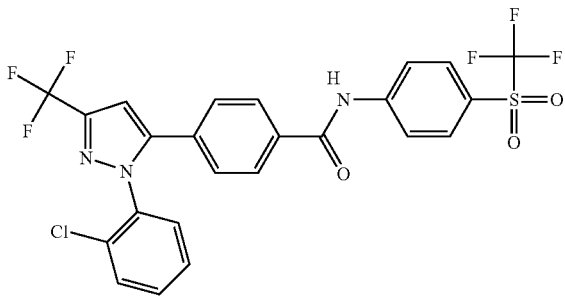 | 4-[1-(2-chlorophenyl)-3-(trifluoromethyl)-1H-pyrazol-5-yl]-N-{4-[(trifluoromethyl)sulfonyl]phenyl}benzamide |
| 1695 | 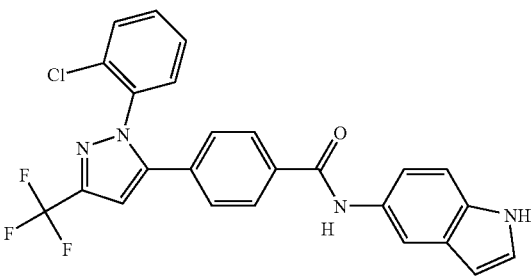 | 4-[1-(2-chlorophenyl)-3-(trifluoromethyl)-1H-pyrazol-5-yl]-N-1H-indol-5-ylbenzamide |
| 1696 | 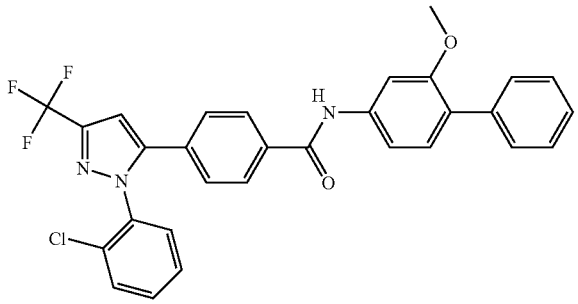 | 4-[1-(2-chlorophenyl)-3-(trifluoromethyl)-1H-pyrazole-5-yl]-N-[2-(methyloxy)biphenyl-4-yl]benzamide |

TABLE 1-continued

| | | |
|---|---|---|
| 1698 | | 4-[1-(2-chlorophenyl)-3-(trifluoromethyl)-1H-pyrazol-5-yl]-N-[4-(phenyloxy)phenyl]benzamide |
| 1699 | | N-[3-(acetylamino)phenyl]-4-[1-(2-chlorophenyl)-3-(trifluoromethyl)-1H-pyrazol-5-yl]benzamide |
| 1700 | | 4-[1-(2-chlorophenyl)-3-(trifluoromethyl)-1H-pyrazol-5-yl]-N-[(2,5-dimethylfuran-3-yl)methyl]benzamide |
| 1701 | | N-[2-(aminosulfonyl)phenyl]-4-[1-(2-chlorophenyl)-3-(trifluoromethyl)-1H-pyrazol-5-yl]benzamide |
| 1702 | | 4-[1-(2-chlorophenyl)-3-(trifluoromethyl)-1H-pyrazol-5-yl]-N-isoquinolin-1-ylbenzamide |

TABLE 1-continued

| | | |
|---|---|---|
| 1703 | | [4-({4-[1-(2-chlorophenyl)-3-(trifluoromethyl)-1H-pyrazol-5-yl]phenyl}carbonyl)piperazin-1-yl]acetic acid |
| 1705 | | 4-[1-(2-chlorophenyl)-3-(trifluoromethyl)-1H-pyrazol-5-yl]-N-(2,3-dihydroxypropyl)benzamide |
| 1706 | | N-[3-(aminocarbonyl)phenyl]-4-[1-(2-chlorophenyl)-3-(trifluoromethyl)-1H-pyrazol-5-yl]benzamide |
| 1707 | | 4-[1-(2-chlorophenyl)-3-(trifluoromethyl)-1H-pyrazol-5-yl]-N-[5-(ethylthio)-1,3,4-thiadiazol-2-yl]benzamide |
| 1708 | | 4-[1-(2-chlorophenyl)-3-(trifluoromethyl)-1H-pyrazol-5-yl]-N-{2-[(2-hydroxyethyl)oxy]ethyl}benzamide |

| | | |
|---|---|---|
| 1709 | 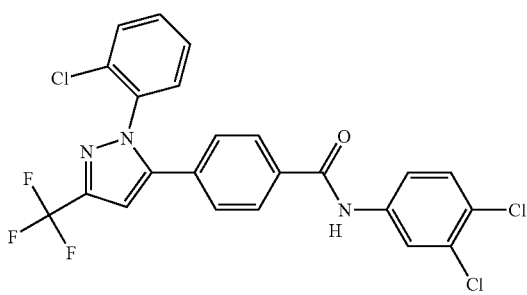 | 4-[1-(2-chlorophenyl)-3-(trifluoromethyl)-1H-pyrazol-5-yl]-N-(3,4-dichlorophenyl)benzamide |
| 1710 | 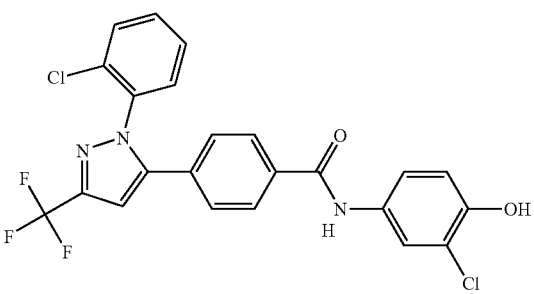 | N-(3-chloro-4-hydroxyphenyl)-4-[1-(2-chlorophenyl)-3-(trifluoromethyl)-1H-pyrazol-5-yl]benzamide |
| 1711 | 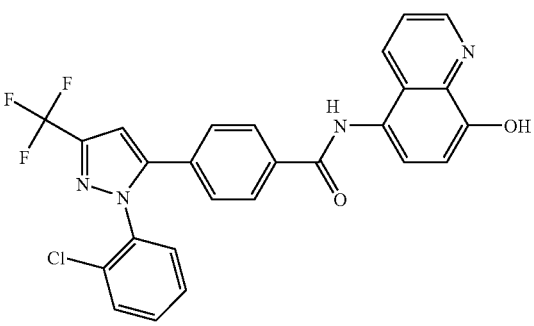 | 4-[1-(2-chlorophenyl)-3-(trifluoromethyl)-1H-pyrazol-5-yl]-N-(8-hydroxyquinolin-5-yl)benzamide |
| 1712 | 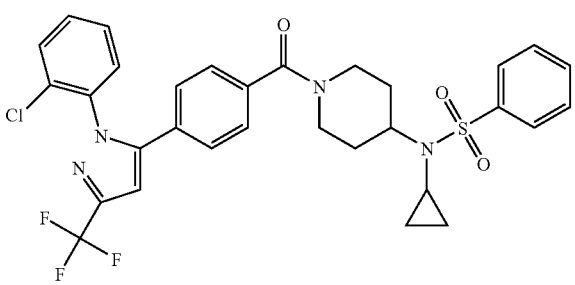 [SMILES: N=C(/C=C(\Nc1ccccc1Cl)c1ccc(C(=O)N2CCC(N(C3CC3)S(=O)(=O)c3ccccc3)CC2)cc1)C(F)(F)F] | N-[1-({4-[1-(2-chlorophenyl)-3-(trifluoromethyl)-1H-pyrazol-5-yl]phenyl}carbonyl)piperidin-4-yl]-N-cyclopropylbenzenesulfonamide |
| 1713 | 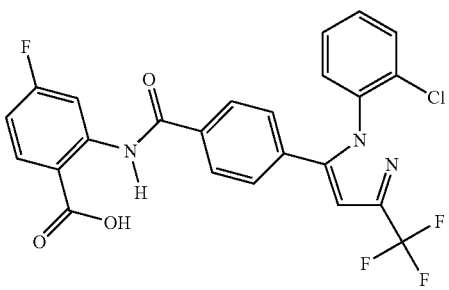 [SMILES: N=C(/C=C(\Nc1ccccc1Cl)c1ccc(C(=O)Nc2cc(F)ccc2C(=O)O)cc1)C(F)(F)F] | 2-[({4-[1-(2-chlorophenyl)-3-(trifluoromethyl)-1H-pyrazol-5-yl]phenyl}carbonyl)amino]-4-fluorobenzoic acid |

| | | |
|---|---|---|
| 1714 | 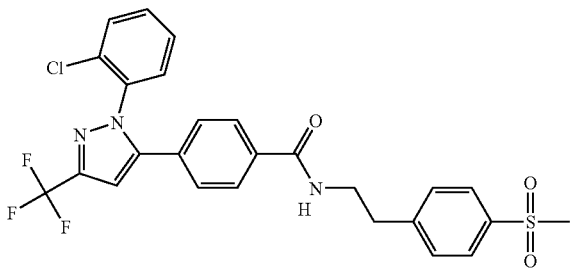 | 4-[1-(2-chlorophenyl)-3-(trifluoromethyl)-1H-pyrazol-5-yl]-N-{2-[4-(methylsulfonyl)phenyl]ethyl}benzamide |
| 1715 | 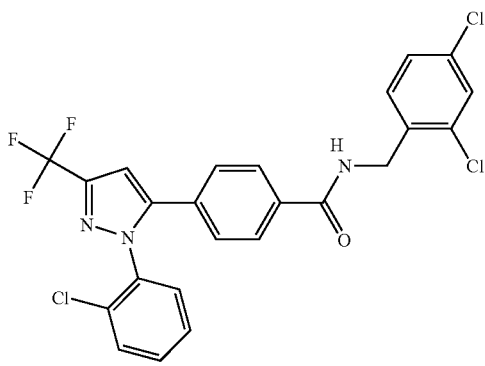 | 4-[1-(2-chlorophenyl)-3-(trifluoromethyl)-1H-pyrazol-5-yl]-N-[(2,4-dichlorophenyl)methyl]benzamide |
| 1716 | 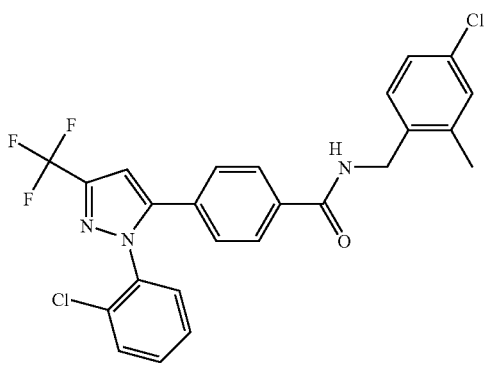 | N-(4-chloro-2-methylphenyl)methyl]-4-[1-(2-chlorophenyl)-3-(trifluoromethyl)-1H-pyrazol-5-yl]benzamide |
| 1717 | 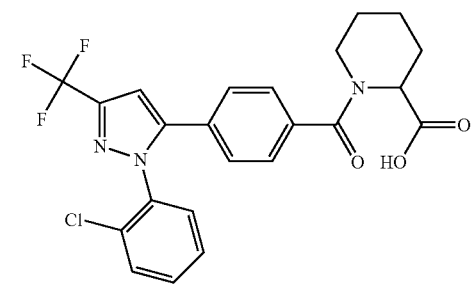 [SMILES: O=C(O)C1CCCCN1C(=O)c1ccc(-c2cc(C(F)(F)F)nn2-c2ccccc2Cl)cc1] | 1-({4-[1-(2-chlorophenyl)-3-(trifluoromethyl)-1H-pyrazol-5-yl]phenyl}carbonyl)piperidin-2-carboxylic acid |
| 1718 | 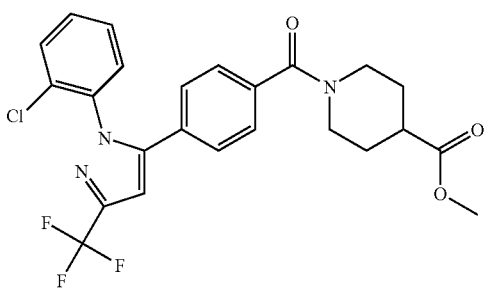 [SMILES: COC(=O)C1CCN(C(=O)c2ccc(/C(=C/C(=N)C(F)(F)F)Nc3ccccc3Cl)cc2)CC1] | methyl 1-({4-[1-(2-chlorophenyl)-3-(trifluoromethyl)-1H-pyrazol-5-yl]phenyl}carbonyl)piperidine-4-carboxylate |

TABLE 1-continued

| | | |
|---|---|---|
| 1719 | 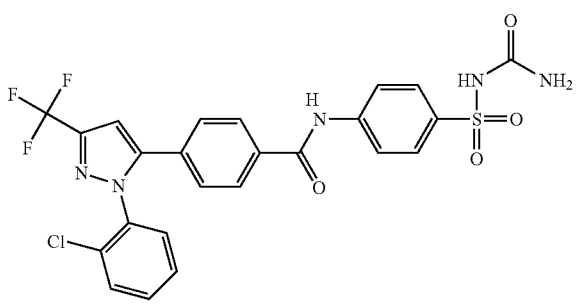 | N-(4-{[(aminocarbonyl)amino]sulfonyl}phenyl)-4-[1-(2-chlorophenyl)-3-(trifluoromethyl)-1H-pyrazol-5-yl]benzamide |
| 1720 | 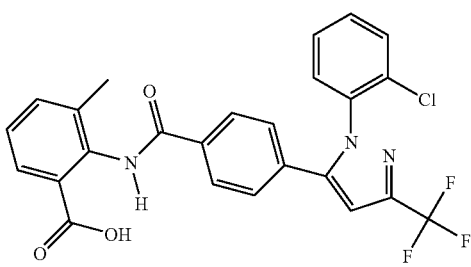 [SMILES: Cc1cccc(C(=O)O)c1NC(=O)c1ccc(/C(=C/C(=N)C(F)(F)F)Nc2ccccc2Cl)cc1] | 2-[({4-[1-(2-chlorophenyl)-3-(trifluoromethyl)-1H-pyrazol-5-yl]phenyl}carbonyl)amino]-3-methylbenzoic acid |
| 1721 | 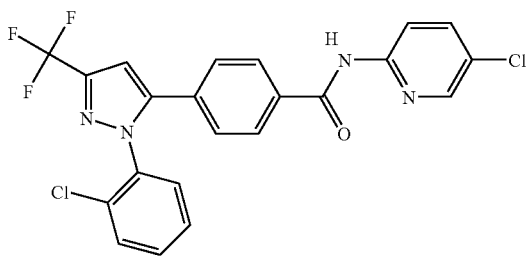 | 4-[1-(2-chlorophenyl)-3-(trifluoromethyl)-1H-pyrazol-5-yl]-N-(5-chloropyridin-2-yl)benzamide |
| 1722 | 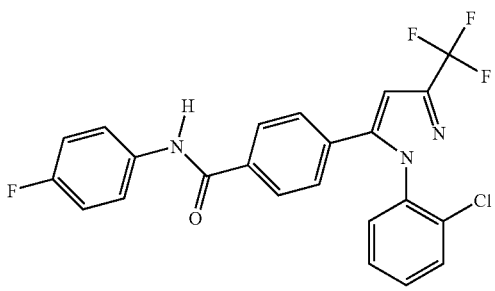 [SMILES: N=C(/C=C(\Nc1ccccc1Cl)c1ccc(C(=O)Nc2ccc(F)cc2)cc1)C(F)(F)F] | 4-[1-(2-chlorophenyl)-3-(trifluoromethyl)-1H-pyrazol-5-yl]-N-(4-fluorophenyl)benzamide |
| 1723 | 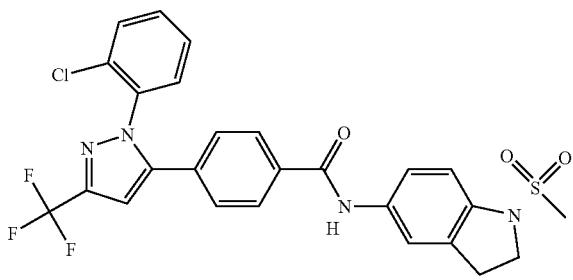 | 4-[1-(2-chlorophenyl)-3-(trifluoromethyl)-1H-pyrazol-5-yl]-N-[1-(methylsulfonyl)-2,3-dihydro-1H-indol-5-yl]benzamide |

| | | |
|---|---|---|
| 1724 | 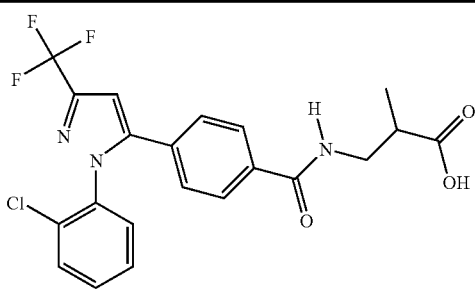 | 3-[({4-[1-(2-chlorophenyl)-3-(trifluoromethyl)-1H-pyrazol-5-yl]phenyl}carbonyl)amino]-2-methylpropanoic acid |
| 1725 | 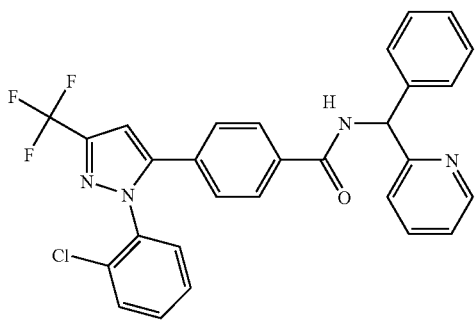 | 4-[1-(2-chlorophenyl)-3-(trifluoromethyl)-1H-pyrazol-5-yl]-N-[phenyl(pyridin-2-yl)methyl]benzamide |
| 1726 | 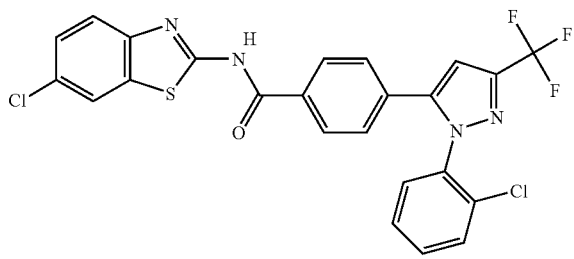 | N-(6-chloro-1,3-benzothiazol-2-yl)-4-[1-(2-chlorophenyl)-3-(trifluoromethyl)-1H-pyrazol-5-yl]benzamide |
| 1727 | 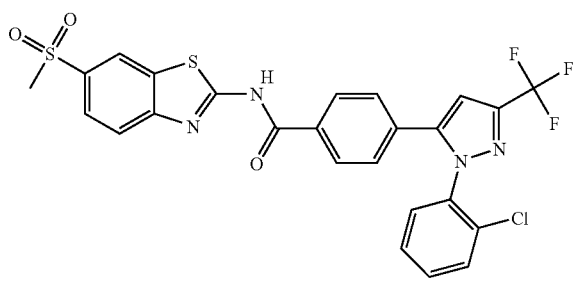 | 4-[1-(2-chlorophenyl)-3-(trifluoromethyl)-1H-pyrazol-5-yl]-N-[6-(methylsulfonyl)-1,3-benzothiazol-2-yl]benzamide |
| 1728 | 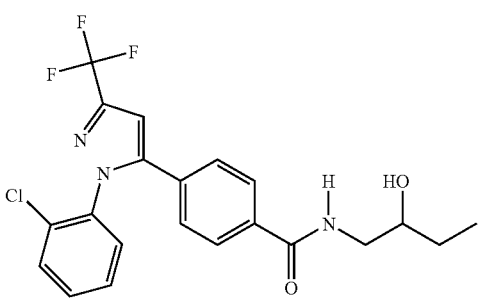 [SMILES: CCC(O)CNC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-(2-hydroxybutyl)benzamide |

TABLE 1-continued

| | | |
|---|---|---|
| 1729 | | N-[4-(acetylamino)phenyl]-4-[1-(2-chlorophenyl)-3-(trifluoromethyl)-1H-pyrazol-5-yl]benzamide |
| 1730 | | 4-[1-(2-chlorophenyl)-3-(trifluoromethyl)-1H-pyrazol-5-yl]-N-[4-(1H-imidazol-1-yl)phenyl]benzamide |
| 1731 | | 4-[1-(2-chlorophenyl)-3-(trifluoromethyl)-1H-pyrazol-5-yl]-N-(4-morpholin-4-ylphenyl)benzamide |
| 1732 | | 4-[1-(2-chlorophenyl)-3-(trifluoromethyl)-1H-pyrazol-5-yl]-N-[(1-methyl-1H-pyrrol-2-yl)methyl]benzamide |
| 1733 | | 4-[1-(2-chlorophenyl)-3-(trifluoromethyl)-1H-pyrazol-5-yl]-N-[5-(methylthio)-1,3,4-thiadiazol-2-yl]benzamide |

TABLE 1-continued

| | | |
|---|---|---|
| 1734 | 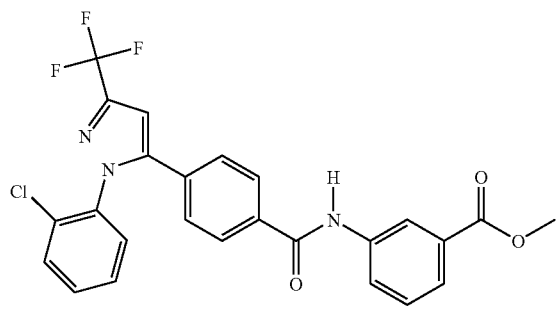 [SMILES: COC(=O)c1cccc(NC(=O)c2ccc(/C(=C/C(=N)C(F)(F)F)Nc3ccccc3Cl)cc2)c1] | methyl 3-[({4-[1-(2-chlorophenyl)-3-(trifluoromethyl)-1H-pyrazol-5-yl]phenyl}carbonyl)amino]benzoate |
| 1735 | 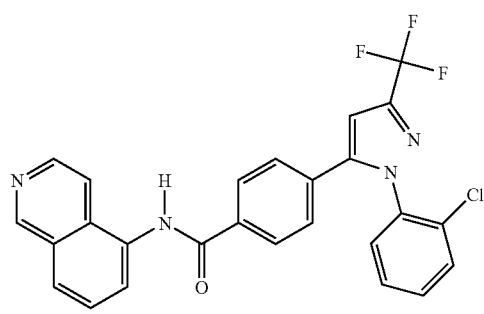 [SMILES: N=C(/C=C(\Nc1ccccc1Cl)c1ccc(C(=O)Nc2cccc3cnccc23)cc1)C(F)(F)F] | 4-[1-(2-chlorophenyl)-3-(trifluoromethyl)-1H-pyrazol-5-yl]-N-isoquinolin-5-ylbenzamide |
| 1736 | 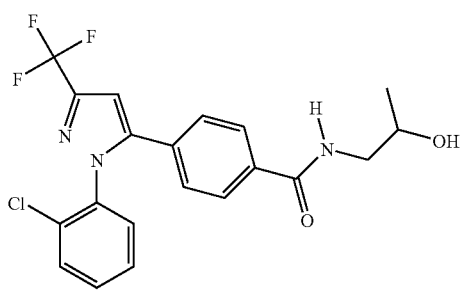 [SMILES: CC(O)CNC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-(2-hydroxypropyl)benzamide |
| 1737 | 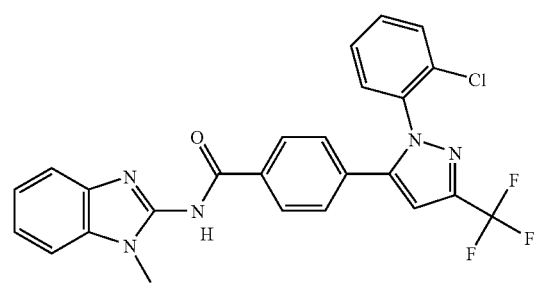 | 4-[1-(2-chlorophenyl)-3-(trifluoromethyl)-1H-pyrazol-5-yl]-N-(1-methyl-1H-benzimidazol-2-yl)benzamide |
| 1738 | 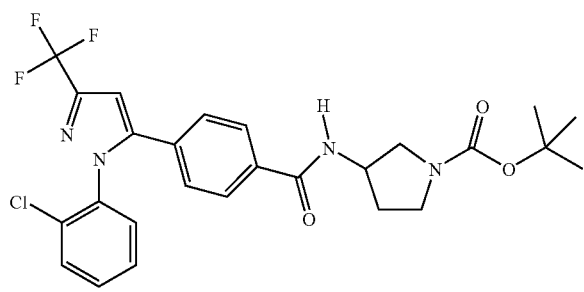 [SMILES: CC(C)(C)OC(=O)N1CCC(NC(=O)c2ccc(/C(=C/C(=N)C(F)(F)F)Nc3ccccc3Cl)cc2)C1] | 1,1-dimethylethyl 3-[{(4-[1-(2-chlorophenyl)-3-(trifluoromethyl)-1H-pyrazol-5-yl]phenyl}carbonyl)amino]pyrrolidine-1-carboxylate |

TABLE 1-continued

| | | |
|---|---|---|
| 1739 | 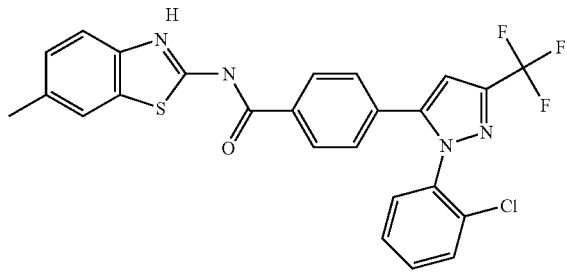 | 4-[1-(2-chlorophenyl)-3-(trifluoromethyl)-1H-pyrazol-5-yl]-N-(6-methyl-1,3-benzothiazol-2-yl)benzamide |
| 1740 | 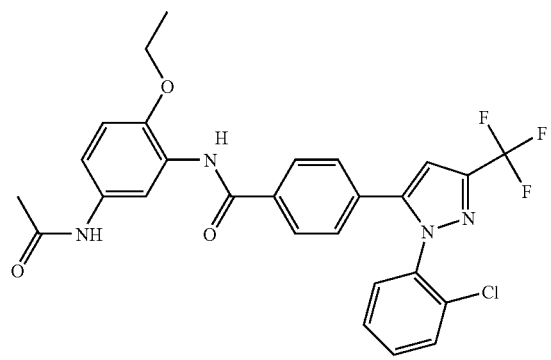 | N-[5-(acetylamino)-2-(ethyloxy)phenyl]-4-[1-(2-chlorophenyl)-3-(trifluoromethyl)-1H-pyrazol-5-yl]benzamide |
| 1741 | 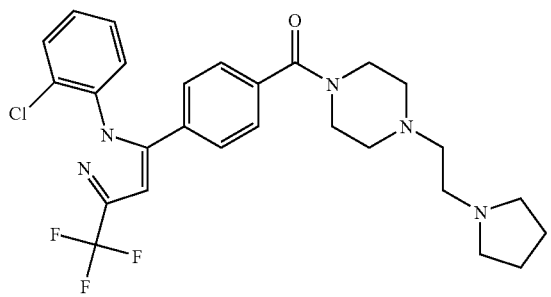 [SMILES: N=C(/C=C(\Nc1ccccc1Cl)c1ccc(C(=O)N2CCN(CCN3CCCC3)CC2)cc1)C(F)(F)F] | 1-({4-[1-(2-chlorophenyl)-3-(trifluoromethyl)-1H-pyrazol-5-yl]phenyl}carbonyl)-4-(2-pyrrolidin-1-ylethyl)piperazine |
| 1742 | 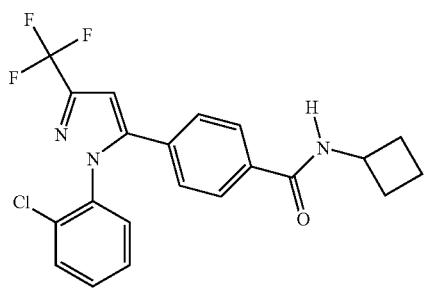 [SMILES: N=C(/C=C(\Nc1ccccc1Cl)c1ccc(C(=O)NC2CCC2)cc1)C(F)(F)F] | 4-[1-(2-chlorophenyl)-3-(trifluoromethyl)-1H-pyrazol-5-yl]-N-cyclobutylbenzamide |
| 1743 | 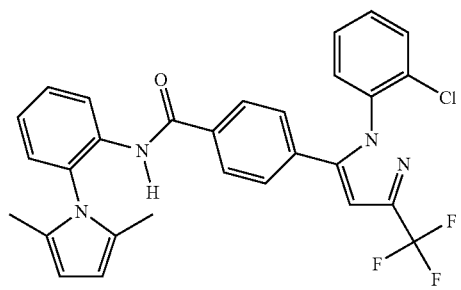 [SMILES: Cc1ccc(C)n1-c1ccccc1NC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-[2-(2,5-dimethyl-1H-pyrrol-1-yl)phenyl]benzamide |

TABLE 1-continued

| | | |
|---|---|---|
| 1744 | | 4-[1-(2-chlorophenyl)-3-(trifluoromethyl)-1H-pyrazol-5-yl]-N-[3-(diethylamino)propyl]benzamide |
| 1745 | | 2-({4-[1-(2-chlorophenyl)-3-(trifluoromethyl)-1H-pyrazol-5-yl]phenyl}carbonyl)-1,2,3,4-tetrahydroisoquinoline |
| 1746 | | 2-[4-({4-[1-(2-chlorophenyl)-3-(trifluoromethyl)-1H-pyrazol-5-yl]phenyl}carbonyl)piperazin-1-yl]propanoic acid |
| 1747 | | N-[3-bromo-5-(trifluoromethyl)phenyl]-4-[1-(2-chlorophenyl)-3-(trifluoromethyl)-1H-pyrazol-5-yl]benzamide |
| 1748 | | 4-[1-(2-chlorophenyl)-3-(trifluoromethyl)-1H-pyrazol-5-yl]-N-piperidin-4-yl-N-{3-[(trifluoromethyl)sulfonyl]phenyl}benzamide |

TABLE 1-continued

| 1749 | 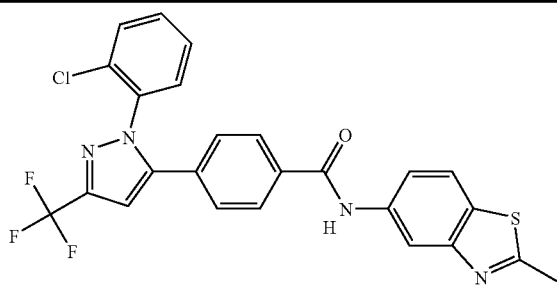 | 4-[1-(2-chlorophenyl)-3-(trifluoromethyl)-1H-pyrazol-5-yl]-N-(2-methyl-1,3-benzothiazol-5-yl)benzamide |
| 1750 | 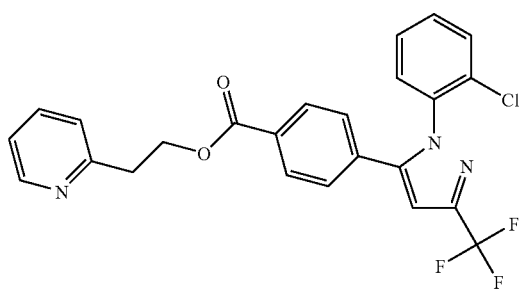 [SMILES: N=C(/C=C(\Nc1ccccc1Cl)c1ccc(C(=O)OCCc2ccccn2)cc1)C(F)(F)F] | 2-pyridin-2-ylethyl 4-[1-(2-chlorophenyl)-3-(trifluoromethyl)-1H-pyrazol-5-yl]benzoate |
| 1751 | 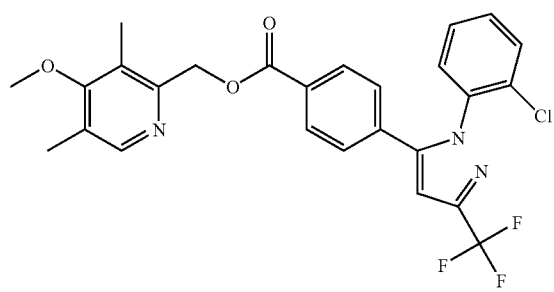 [SMILES: COc1c(C)cnc(COC(=O)c2ccc(/C(=C/C(=N)C(F)(F)F)Nc3ccccc3Cl)cc2)c1C] | [3,5-dimethyl-4-(methyloxy)pyridin-2-yl]methyl 4-[1-(2-chlorophenyl)-3-(trifluoromethyl)-1H-pyrazol-5-yl]benzoate |
| 1752 | 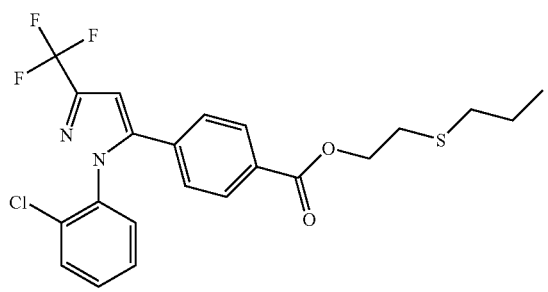 [SMILES: CCCSCCOC(=O)c1ccc(/C(=C/C(=N)C(F)(F)F)Nc2ccccc2Cl)cc1] | 2-(propylthio)ethyl 4-[1-(2-chlorophenyl)-3-(trifluoromethyl)-1H-pyrazol-5-yl]benzoate |
| 1753 | 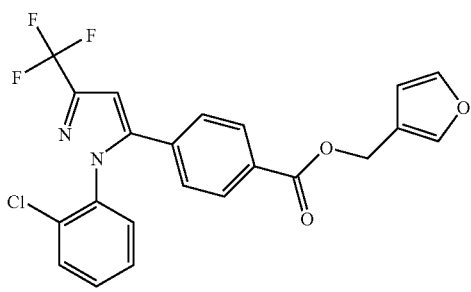 [SMILES: N=C(/C=C(\Nc1ccccc1Cl)c1ccc(C(=O)OCc2ccoc2)cc1)C(F)(F)F] | furan-3-ylmethyl 4-[1-(2-chlorophenyl)-3-(trifluoromethyl)-1H-pyrazol-5-yl]benzoate |

| | | |
|---|---|---|
| 1754 | 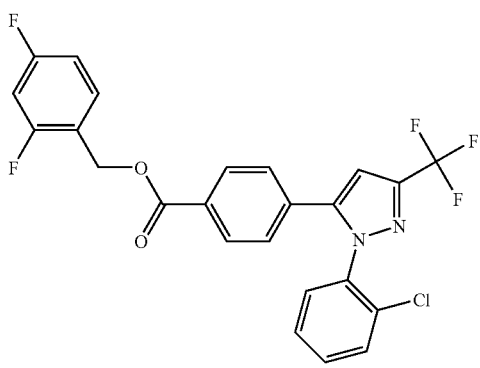 [SMILES: O=C(OCc1ccc(F)cc1F)c1ccc(-c2cc(C(F)(F)F)nn2-c2ccccc2Cl)cc1] | (2,4-difluorophenyl)methyl 4-[1-(2-chlorophenyl)-3-(trifluoromethyl)-1H-pyrazol-5-yl]benzoate |
| 1755 | 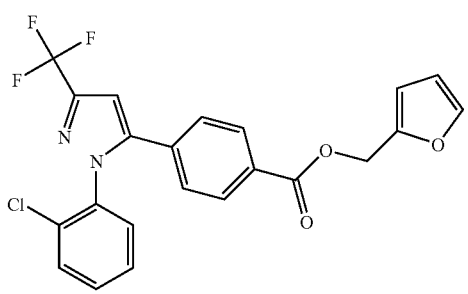 [SMILES: N=C(/C=C(\Nc1ccccc1Cl)c1ccc(C(=O)OCc2ccco2)cc1)C(F)(F)F] | furan-2-ylmethyl 4-[1-(2-chlorophenyl)-3-(trifluoromethyl)-1H-pyrazol-5-yl]benzoate |
| 1756 | 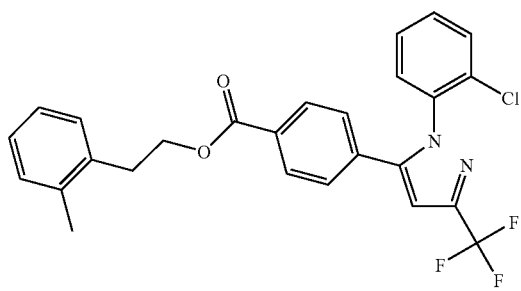 [SMILES: Cc1ccccc1CCOC(=O)c1ccc(/C(=C/C(=N)C(F)(F)F)Nc2ccccc2Cl)cc1] | 2-(2-methylphenyl)ethyl 4-[1-(2-chlorophenyl)-3-(trifluoromethyl)-1H-pyrazol-5-yl]benzoate |
| 1757 | 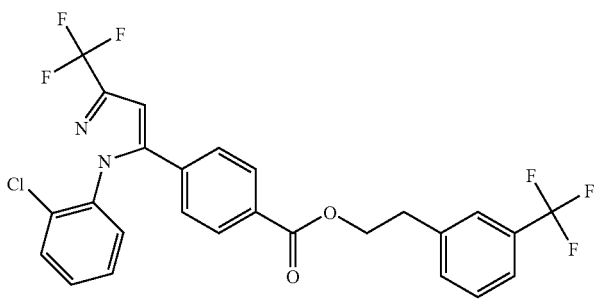 [SMILES: N=C(/C=C(\Nc1ccccc1Cl)c1ccc(C(=O)OCCc2cccc(C(F)(F)F)c2)cc1)C(F)(F)F] | 2-[3-(trifluoromethyl)phenyl]ethyl 4-[1-(2-chlorophenyl)-3-(trifluoromethyl)-1H-pyrazol-5-yl]benzoate |
| 1758 | 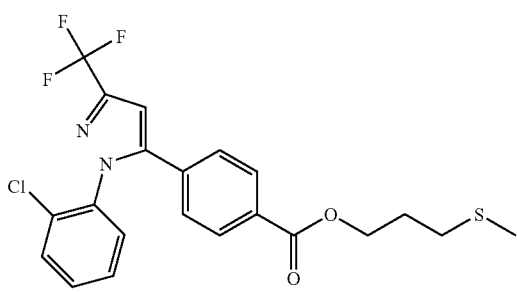 [SMILES: CSCCCOC(=O)c1ccc(/C(=C/C(=N)C(F)(F)F)Nc2ccccc2Cl)cc1] | 3-(methylthio)propyl 4-[1-(2-chlorophenyl)-3-(trifluoromethyl)-1H-pyrazol-5-yl]benzoate |

TABLE 1-continued

| | | |
|---|---|---|
| 1759 | 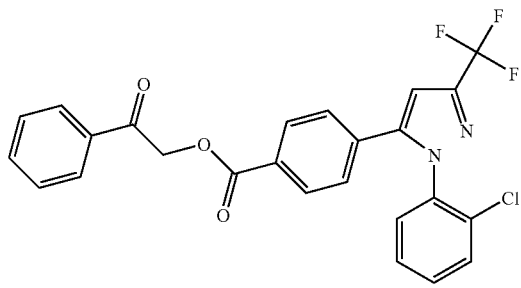 [SMILES: N=C(/C=C(\Nc1ccccc1Cl)c1ccc(C(=O)OCC(=O)c2ccccc2)cc1)C(F)(F)F] | 2-oxo-2-phenylethyl 4-[1-(2-chlorophenyl)-3-(trifluoromethyl)-1H-pyrazol-5-yl]benzoate |
| 1760 | 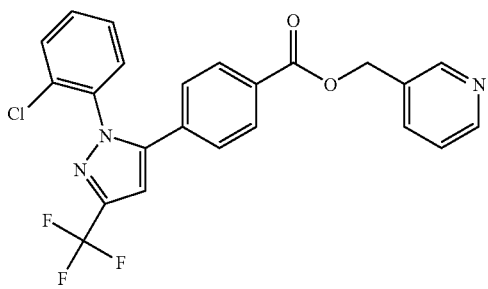 [SMILES: O=C(OCc1cccnc1)c1ccc(-c2cc(C(F)(F)F)nn2-c2ccccc2Cl)cc1] | pyridin-3-ylmethyl 4-[1-(2-chlorophenyl)-3-(trifluoromethyl)-1H-pyrazol-5-yl]benzoate |
| 1761 | 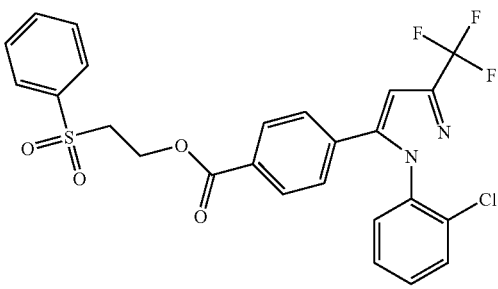 [SMILES: N=C(/C=C(\Nc1ccccc1Cl)c1ccc(C(=O)OCCS(=O)(=O)c2ccccc2)cc1)C(F)(F)F] | 2-(phenylsulfonyl)ethyl 4-[1-(2-chlorophenyl)-3-(trifluoromethyl)-1H-pyrazol-5-yl]benzoate |
| 1762 | 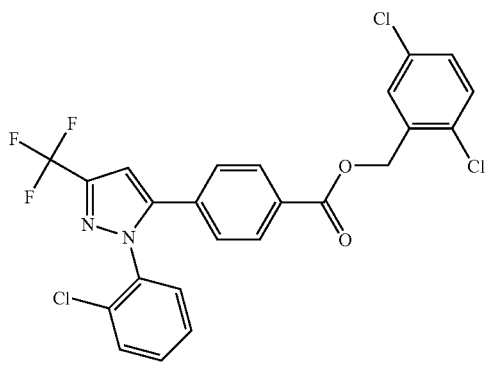 [SMILES: O=C(OCc1cc(Cl)ccc1Cl)c1ccc(-c2cc(C(F)(F)F)nn2-c2ccccc2Cl)cc1] | (2,5-dichlorophenyl)methyl 4-[1-(2-chlorophenyl)-3-(trifluoromethyl)-1H-pyrazol-5-yl]benzoate |
| 1763 | 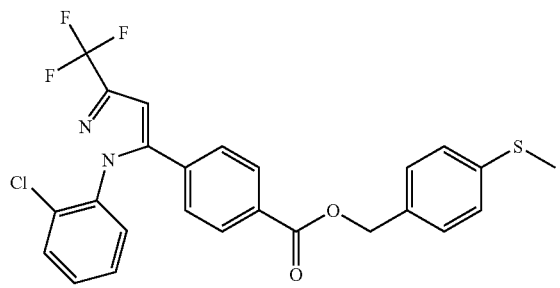 [SMILES: CSc1ccc(COC(=O)c2ccc(/C(=C/C(=N)C(F)(F)F)Nc3ccccc3Cl)cc2)cc1] | [4-(methylthio)phenyl]methyl 4-[1-(2-chlorophenyl)-3-(trifluoromethyl)-1H-pyrazol-5-yl]benzoate |

TABLE 1-continued

| 1764 | 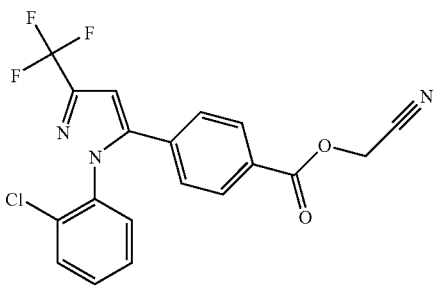 [SMILES: N#CCOC(=O)c1ccc(/C(=C/C(=N)C(F)(F)F)Nc2ccccc2Cl)cc1] | cyanomethyl 4-[1-(2-chlorophenyl)-3-(trifluoromethyl)-1H-pyrazol-5-yl]benzoate |
| 1765 | 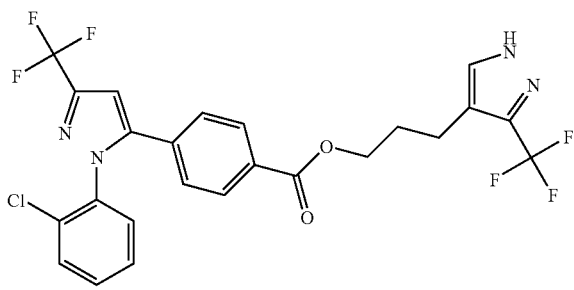 [SMILES: N=C(/C=C(\Nc1ccccc1Cl)c1ccc(C(=O)OCCC/C(=C/N)C(=N)C(F)(F)F)cc1)C(F)(F)F] | 3-[3-(trifluoromethyl)-1H-pyrazol-4-yl]propyl 4-[1-(2-chlorophenyl)-3-(trifluoromethyl)-1H-pyrazol-5-yl]benzoate |
| 1766 | 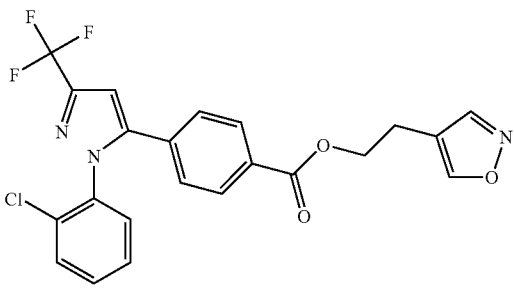 [SMILES: N=C(/C=C(\Nc1ccccc1Cl)c1ccc(C(=O)OCCc2cnoc2)cc1)C(F)(F)F] | 2-isoxazol-4-ylethyl 4-[1-(2-chlorophenyl)-3-(trifluoromethyl)-1H-pyrazol-5-yl]benzoate |
| 1767 | 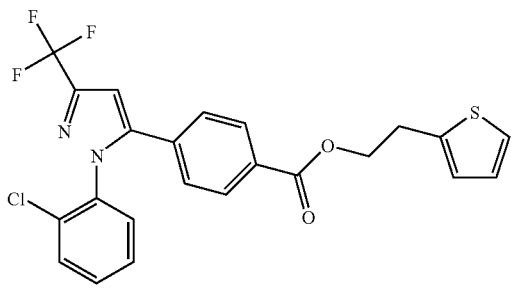 [SMILES: N=C(/C=C(\Nc1ccccc1Cl)c1ccc(C(=O)OCCc2cccs2)cc1)C(F)(F)F] | 2-(2-thienyl)ethyl 4-[1-(2-chlorophenyl)-3-(trifluoromethyl)-1H-pyrazol-5-yl]benzoate |
| 1768 | 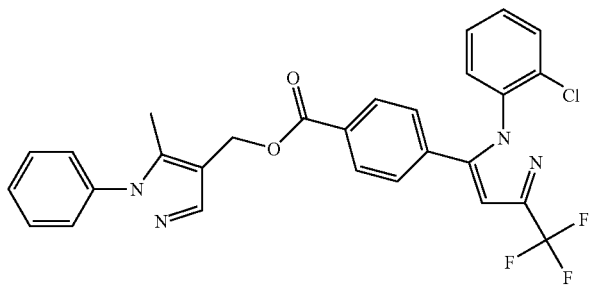 [SMILES: C/C(Nc1ccccc1)=C(/C=N)COC(=O)c1ccc(/C(=C/C(=N)C(F)(F)F)Nc2ccccc2Cl)cc1] | (5-methyl-1-phenyl-1H-pyrazol-4-yl)methyl 4-[1-(2-chlorophenyl)-3-(trifluoromethyl)-1H-pyrazol-5-yl]benzoate |

TABLE 1-continued

| | | |
|---|---|---|
| 1769 | | 2,2'-bithien-5-ylmethyl 4-[1-(2-chlorophenyl)-3-(trifluoromethyl)-1H-pyrazol-5-yl]benzoate |
| 1770 | | 3-pyridin-2-ylpropyl 4-[1-(2-chlorophenyl)-3-(trifluoromethyl)-1H-pyrazol-5-yl]benzoate |
| 1771 | | 2-(methylthio)ethyl 4-[1-(2-chlorophenyl)-3-(trifluoromethyl)-1H-pyrazol-5-yl]benzoate |
| 1772 | | pyridin-4-ylmethyl 4-[1-(2-chlorophenyl)-3-(trifluoromethyl)-1H-pyrazol-5-yl]benzoate |
| 1773 | | 1,3-benzothiazol-2-ylmethyl 4-[1-(2-chlorophenyl)-3-(trifluoromethyl)-1H-pyrazol-5-yl]benzoate |

TABLE 1-continued

| 1774 | 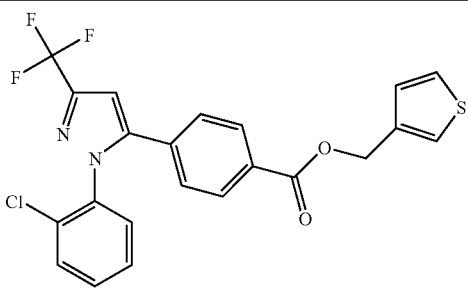 | 2-thienylmethyl 4-[1-(2-chlorophenyl)-3-(trifluoromethyl)-1H-pyrazol-5-yl]benzoate |
| 1775 | 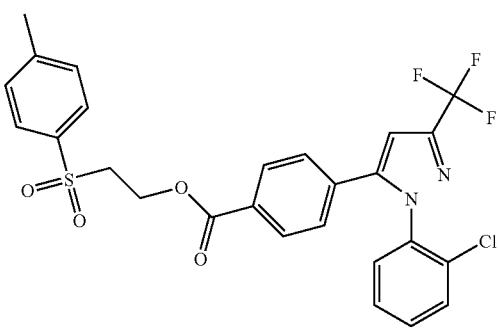 [SMILES: Cc1ccc(S(=O)(=O)CCOC(=O)c2ccc(/C(=C/C(=N)C(F)(F)F)Nc3ccccc3Cl)cc2)cc1] | 2-[(4-methylphenyl)sulfonyl]ethyl 4-[1-(2-chlorophenyl)-3-(trifluoromethyl)-1H-pyrazol-5-yl]benzoate |
| 1776 | 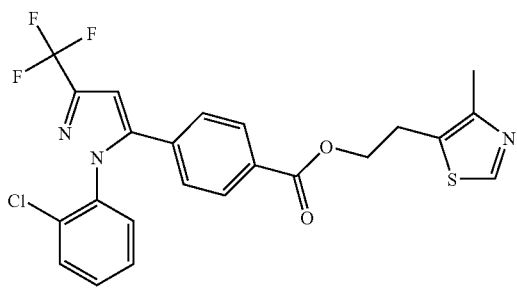 [SMILES: Cc1ncsc1CCOC(=O)c1ccc(/C(=C/C(=N)C(F)(F)F)Nc2ccccc2Cl)cc1] | 2-(4-methyl-1,3-thiazol-5-yl)ethyl 4-[1-(2-chlorophenyl)-3-(trifluoromethyl)-1H-pyrazol-5-yl]benzoate |
| 1777 | 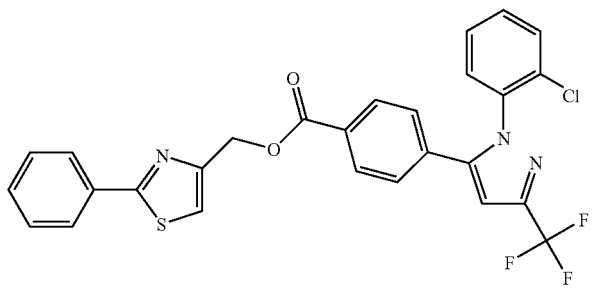 [SMILES: N=C(/C=C(\Nc1ccccc1Cl)c1ccc(C(=O)OCc2csc(-c3ccccc3)n2)cc1)C(F)(F)F] | (2-phenyl-1,3-thiazol-4-yl)methyl 4-[1-(2-chlorophenyl)-3-(trifluoromethyl)-1H-pyrazol-5-yl]benzoate |
| 1778 | 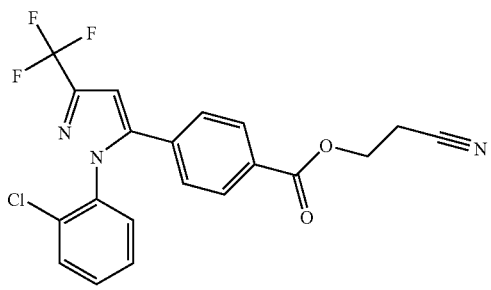 [SMILES: N#CCCOC(=O)c1ccc(/C(=C/C(=N)C(F)(F)F)Nc2ccccc2Cl)cc1] | 2-cyanoethyl 4-[1-(2-chlorophenyl)-3-(trifluoromethyl)-1H-pyrazol-5-yl]benzoate |

TABLE 1-continued

| 1779 | 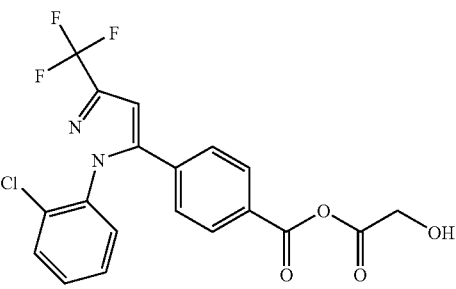 [SMILES: N=C(/C=C(\Nc1ccccc1Cl)c1ccc(C(=O)OC(=O)CO)cc1)C(F)(F)F] | 4-[1-(2-chlorophenyl)-3-(trifluoromethyl)-1H-pyrazol-5-yl]benzoic hydroxyacetic anhydride |
| 1780 | 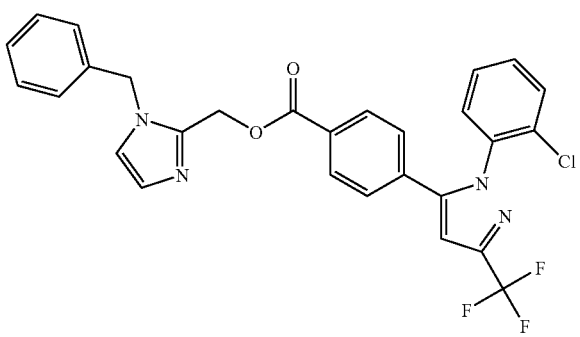 [SMILES: N=C(/C=C(\Nc1ccccc1Cl)c1ccc(C(=O)OCc2nccn2Cc2ccccc2)cc1)C(F)(F)F] | [1-(phenylmethyl)(-1H-imidazol-2-yl]methyl 4-[1-(2-chlorophenyl)-3-(trifluoromethyl)-1H-pyrazol-5-yl]benzoate |
| 1781 | 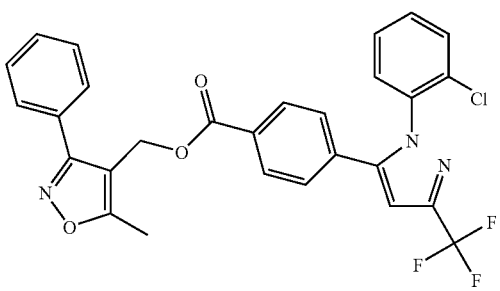 [SMILES: Cc1onc(-c2ccccc2)c1COC(=O)c1ccc(/C(=C/C(=N)C(F)(F)F)Nc2ccccc2Cl)cc1] | (5-methyl-3-phenylisoxazol-4-yl)methyl 4-[1-(2-chlorophenyl)-3-(trifluoromethyl)-1H-pyrazol-5-yl]benzoate |
| 1782 | 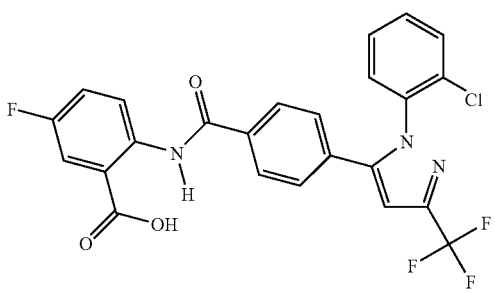 [SMILES: N=C(/C=C(\Nc1ccccc1Cl)c1ccc(C(=O)Nc2ccc(F)cc2C(=O)O)cc1)C(F)(F)F] | 2-[({4-[1-(2-chlorophenyl)-3-(trifluoromethyl)-1H-pyrazol-5-yl]phenyl}carbonyl)amino]-5-fluorobenzoic acid |
| 1783 | 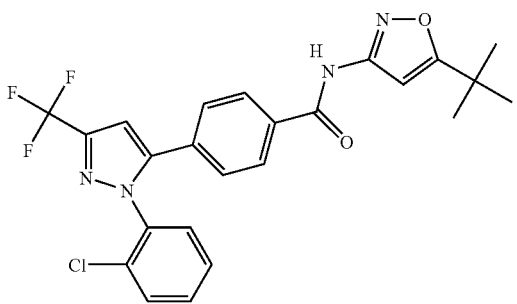 | 4-[1-(2-chlorophenyl)-3-(trifluoromethyl)-1H-pyrazol-5-yl]-N-[5-(1,1-dimethylethyl)isoxazol-3-yl]benzamide |

TABLE 1-continued

| | | |
|---|---|---|
| 1784 | 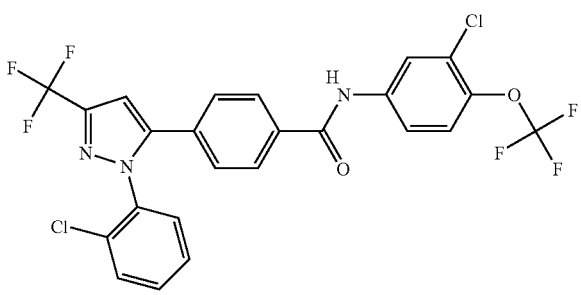 | 4-[1-(2-chlorophenyl)-3-(trifluoromethyl)-1H-pyrazol-5-yl]-N-{3-chloro-4-[(trifluoromethyl)oxy]phenyl}benzamide |
| 1785 | 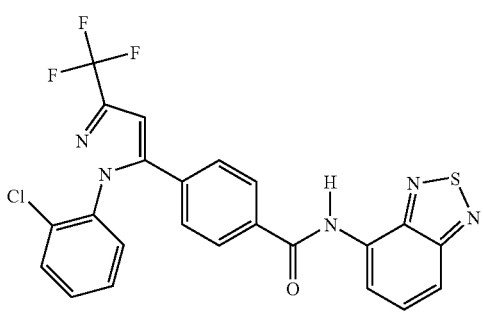 [SMILES: N=C(/C=C(\Nc1ccccc1Cl)c1ccc(C(=O)Nc2cccc3nsnc23)cc1)C(F)(F)F] | N-2,1,3-benzothiadiazol-4-yl-4-[1-(2-chlorophenyl)-3-(trifluoromethyl)-1H-pyrazol-5-yl]benzamide |
| 1786 | 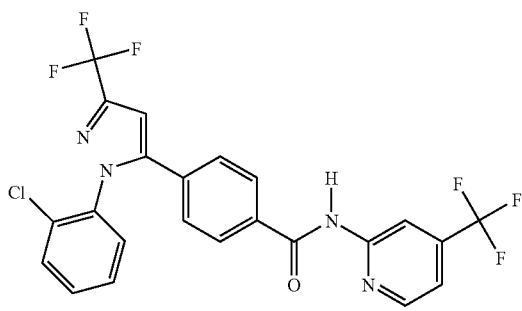 [SMILES: N=C(/C=C(\Nc1ccccc1Cl)c1ccc(C(=O)Nc2cc(C(F)(F)F)ccn2)cc1)C(F)(F)F] | 4-[1-(2-chlorophenyl)-3-(trifluoromethyl)-1H-pyrazol-5-yl]-N-[4-(trifluoromethyl)pyridin-2-yl]benzamide |
| 1787 | 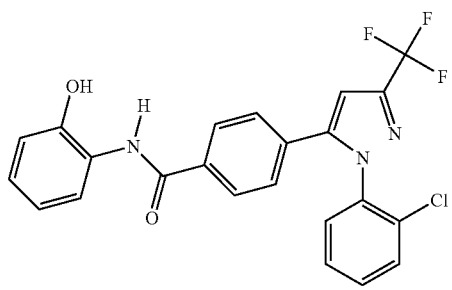 [SMILES: N=C(/C=C(\Nc1ccccc1Cl)c1ccc(C(=O)Nc2ccccc2O)cc1)C(F)(F)F] | 4-[1-(2-chlorophenyl)-3-(trifluoromethyl)-1H-pyrazol-5-yl]-N-(2-hydroxyphenyl)benzamide |
| 1788 | 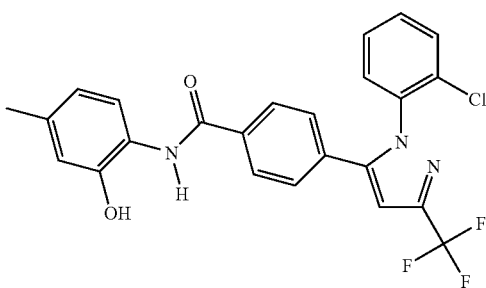 [SMILES: Cc1ccc(NC(=O)c2ccc(/C(=C/C(=N)C(F)(F)F)Nc3ccccc3Cl)cc2)c(O)c1] | 4-[1-(2-chlorophenyl)-3-(trifluoromethyl)-1H-pyrazol-5-yl]-N-(2-hydroxy-4-methylphenyl)benzamide |

TABLE 1-continued

| | | |
|---|---|---|
| 1789 | 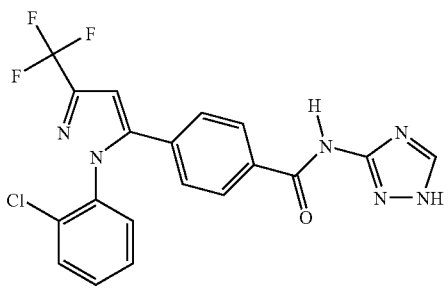 [SMILES: N=C(/C=C(\Nc1ccccc1Cl)c1ccc(C(=O)Nc2nc[nH]n2)cc1)C(F)(F)F] | 4-[1-(2-chlorophenyl)-3-(trifluoromethyl)-1H-pyrazol-5-yl]-N-1H-1,2,4-triazol-3-ylbenzamide |
| 1790 | 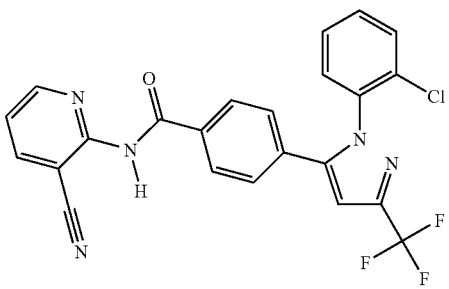 [SMILES: N#Cc1cccnc1NC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-(3-cyanopyridin-2-yl)benzamide |
| 1791 | 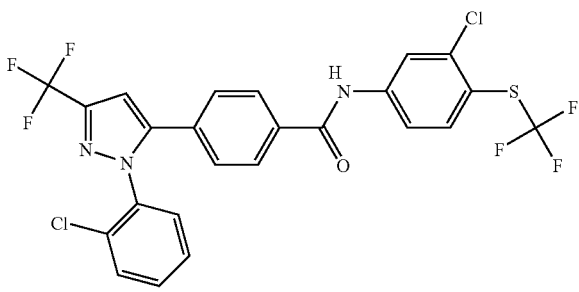 | 4-[1-(2-chlorophenyl)-3-(trifluoromethyl)-1H-pyrazol-5-yl]-N-{3-chloro-4-[(trifluoromethyl)thio]phenyl}benzamide |
| 1792 | 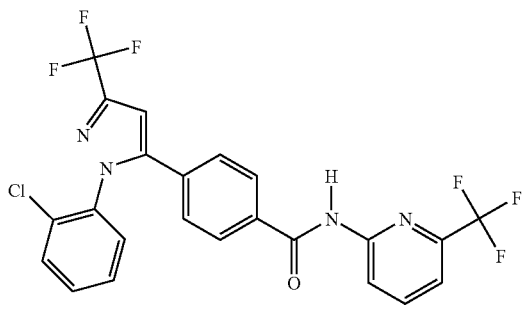 [SMILES: N=C(/C=C(\Nc1ccccc1Cl)c1ccc(C(=O)Nc2cccc(C(F)(F)F)n2)cc1)C(F)(F)F] | 4-[1-(2-chlorophenyl)-3-(trifluoromethyl)-1H-pyrazol-5-yl]-N-[6-(trifluoromethyl)pyridin-2-yl]benzamide |
| 1793 | 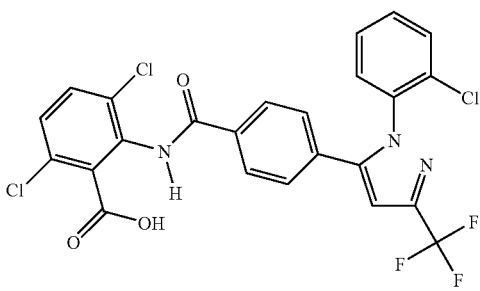 [SMILES: N=C(/C=C(\Nc1ccccc1Cl)c1ccc(C(=O)Nc2c(Cl)ccc(Cl)c2C(=O)O)cc1)C(F)(F)F] | 3,6-dichloro 2-[({4-[1-(2-chlorophenyl)-3-(trifluoromethyl)-1H-pyrazol-5-yl]phenyl}carbonyl)amino]benzoic acid |

| | | |
|---|---|---|
| 1794 | 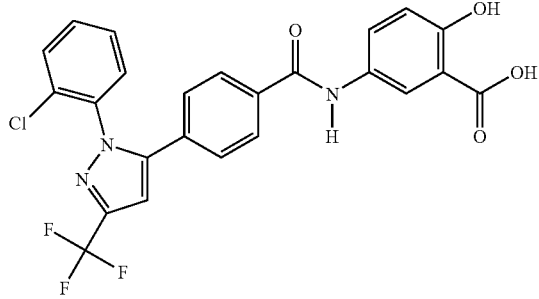 | 5-[({4-[1-(2-chlorophenyl)-3-(trifluoromethyl)-1H-pyrazol-5-yl]phenyl}carbonyl)amino]-2-hydroxybenzoic acid |
| 1795 | 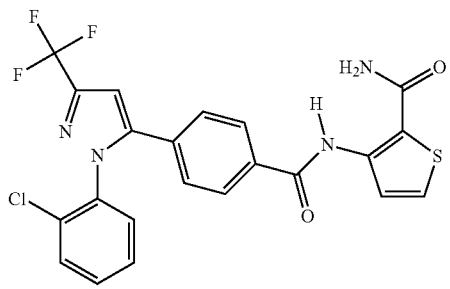 [SMILES: N=C(/C=C(\Nc1ccccc1Cl)c1ccc(C(=O)Nc2ccsc2C(N)=O)cc1)C(F)(F)F] | 3-[({4-[1-(2-chlorophenyl)-3-(trifluoromethyl)-1H-pyrazol-5-yl]phenyl}carbonyl)amino]thiophene-2-carboxamide |
| 1796 | 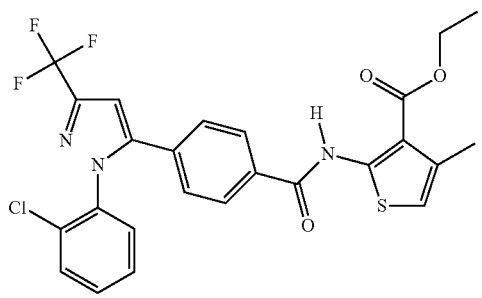 [SMILES: CCOC(=O)c1c(C)csc1NC(=O)c1ccc(/C(=C/C(=N)C(F)(F)F)Nc2ccccc2Cl)cc1] | ethyl 2-[({4-[1-(2-chlorophenyl)-3-(trifluoromethyl)-1H-pyrazol-5-yl]phenyl}carbonyl)amino]-4-methylthiophene-3-carboxylate |
| 1797 | 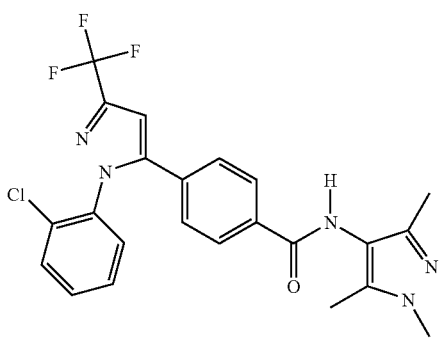 [SMILES: CN/C(C)=C(/NC(=O)c1ccc(/C(=C/C(=N)C(F)(F)F)Nc2ccccc2Cl)cc1)C(C)=N] | 4-[1-(2-chlorophenyl)-3-(trifluoromethyl)-1H-pyrazol-5-yl]-N-(1,3,5-trimethyl-1H-pyrazol-4-yl)benzamide |
| 1798 | 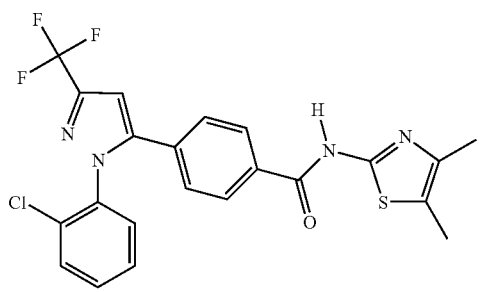 [SMILES: Cc1nc(NC(=O)c2ccc(/C(=C/C(=N)C(F)(F)F)Nc3ccccc3Cl)cc2)sc1C] | 4-[1-(2-chlorophenyl)-3-(trifluoromethyl)-1H-pyrazol-5-yl]-N-(4,5-dimethyl-1,3-thiazol-2-yl)benzamide |

TABLE 1-continued

1799 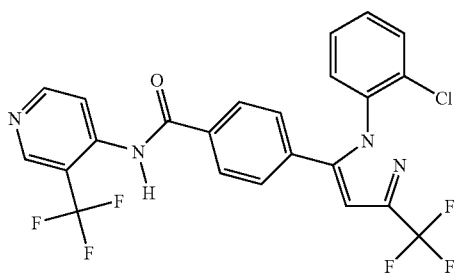 [SMILES: N=C(/C=C(\Nc1ccccc1Cl)c1ccc(C(=O)Nc2ccncc2C(F)(F)F)cc1)C(F)(F)F] 4-[1-(2-chlorophenyl)-3-(trifluoromethyl)-1H-pyrazol-5-yl]-N-[3-(trifluoromethyl)pyridin-4-yl]benzamide 1800 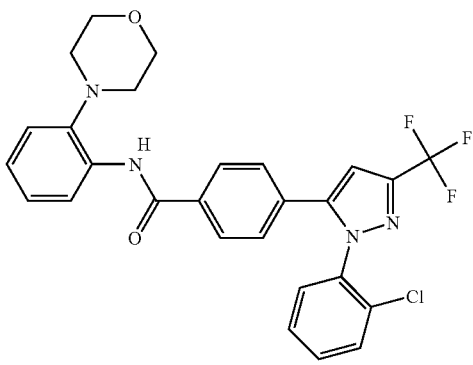 4-[1-(2-chlorophenyl)-3-(trifluoromethyl)-1H-pyrazol-5-yl]-N-(2-morpholin-4-ylphenyl)benzamide 1801 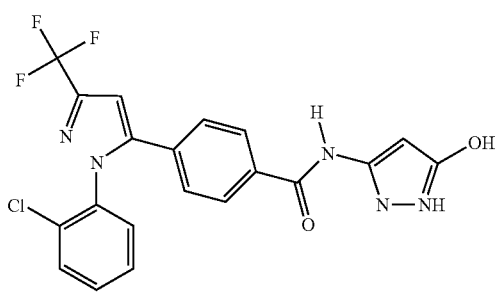 [SMILES: N=C(/C=C(\Nc1ccccc1Cl)c1ccc(C(=O)Nc2cc(O)n[nH]2)cc1)C(F)(F)F] 4-[1-(2-chlorophenyl)-3-(trifluoromethyl)-1H-pyrazol-5-yl]-N-(5-hydroxy-1H-pyrazol-3-yl)benzamide 1802 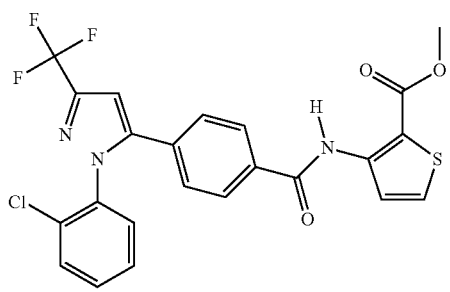 [SMILES: COC(=O)c1sccc1NC(=O)c1ccc(/C(=C/C(=N)C(F)(F)F)Nc2ccccc2Cl)cc1] methyl 3-[({4-[1-(2-chlorophenyl)-3-(trifluoromethyl)-1H-pyrazol-5-yl]phenyl}carbonyl)amino]thiophene-2-carboxylate 1803 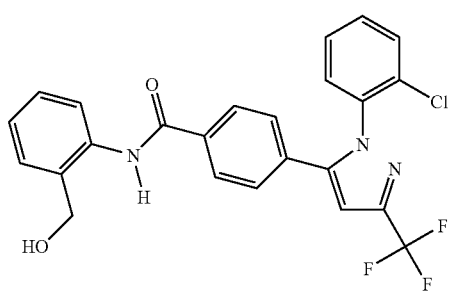 [SMILES: N=C(/C=C(\Nc1ccccc1Cl)c1ccc(C(=O)Nc2ccccc2CO)cc1)C(F)(F)F] 4-[1-(2-chlorophenyl)-3-(trifluoromethyl)-1H-pyrazol-5-yl]-N-[2-(hydroxymethyl)phenyl]benzamide TABLE 1-continued

| 1804 | 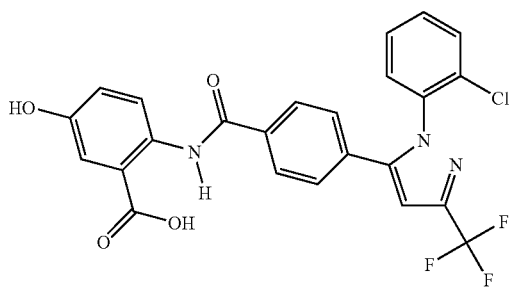 [SMILES: N=C(/C=C(\Nc1ccccc1Cl)c1ccc(C(=O)Nc2ccc(O)cc2C(=O)O)cc1)C(F)(F)F] | 2-[({4-[1-(2-chlorophenyl)-3-(trifluoromethyl)-1H-pyrazol-5-yl]phenyl}carbonyl)amino]-5-hydroxybenzoic acid |
| --- | --- | --- |
| 1805 | 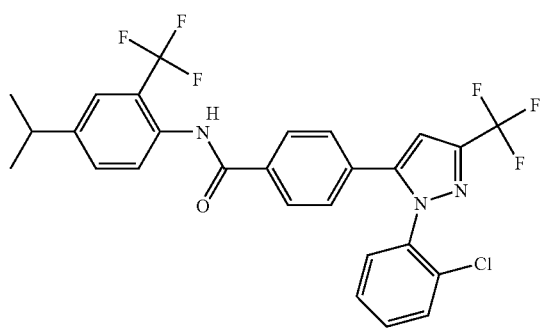 | 4-[1-(2-chlorophenyl)-3-(trifluoromethyl)-1H-pyrazol-5-yl]-N-[4-(1-methylethyl)-2-(trifluoromethyl)phenyl]benzamide |
| 1806 | 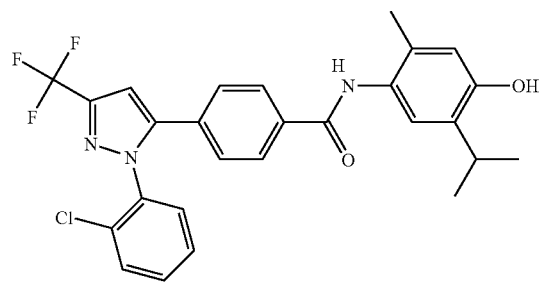 | 4-[1-(2-chlorophenyl)-3-(trifluoromethyl)-1H-pyrazol-5-yl]-N-[4-hydroxy-2-methyl-5-(1-methylethyl)phenyl]benzamide |
| 1807 | 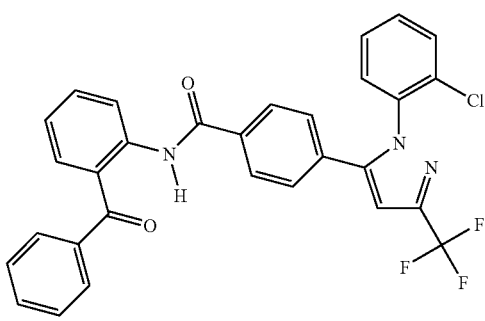 [SMILES: N=C(/C=C(\Nc1ccccc1Cl)c1ccc(C(=O)Nc2ccccc2C(=O)c2ccccc2)cc1)C(F)(F)F] | 4-[1-(2-chlorophenyl)-3-(trifluoromethyl)-1H-pyraozl-5-yl]-N-[2-(phenylcarbonyl)phenyl]benzamide |
| 1808 | 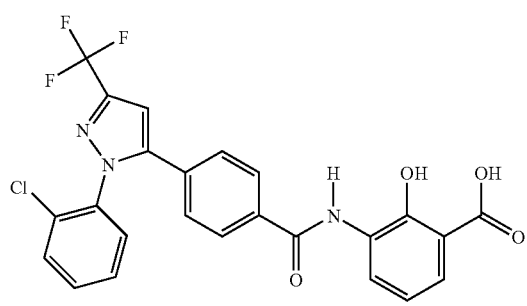 [SMILES: O=C(Nc1cccc(C(=O)O)c1O)c1ccc(-c2cc(C(F)(F)F)nn2-c2ccccc2Cl)cc1] | 3-[({4-[1-(2-chlorophenyl)-3-(trifluoromethyl)-1H-pyrazol-5-yl]phenyl}carbonyl)amino]-2-hydroxybenzoic acid |

TABLE 1-continued

| | | |
|---|---|---|
| 1809 | | 4-[({4-[1-(2-chlorophenyl)-3-(trifluoromethyl)-1H-pyrazol-5-yl]phenyl}carbonyl)amino]-3-methylbenzoic acid |
| 1810 | | 4-[1-(2-chlorophenyl)-3-(trifluoromethyl)-1H-pyrazol-5-yl]-N-(5-furan-2-yl-1H-pyrazol-3-yl)benzamide |
| 1811 | | 4-[1-(2-chlorophenyl)-3-(trifluoromethyl)-1H-pyrazol-5-yl]-N-[3-hydroxy-4-(methyloxy)phenyl]benzamide |
| 1812 | | 4-[1-(2-chlorophenyl)-3-(trifluoromethyl)-1H-pyrazol-5-yl]-N-1H-tetrazol-5-ylbenzamide |
| 1813 | | 4-[1-(2-chlorophenyl)-3-(trifluoromethyl)-1H-pyrazol-5-yl]-N-[5-(methylthio)-1H-1,2,4-triazol-3-yl]benzamide |

TABLE 1-continued

| | | |
|---|---|---|
| 1814 | 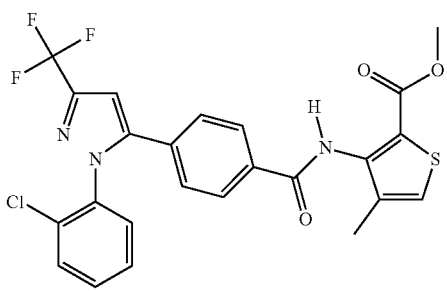 [SMILES: COC(=O)c1scc(C)c1NC(=O)c1ccc(/C(=C/C(=N)C(F)(F)F)Nc2ccccc2Cl)cc1] | methyl 3-[({4-[1-(2-chlorophenyl)-3-(trifluoromethyl)-1H-pyrazol-5-yl]phenyl}carbonyl)amino]-4-methylthiophene-2-carboxylate |
| 1815 | 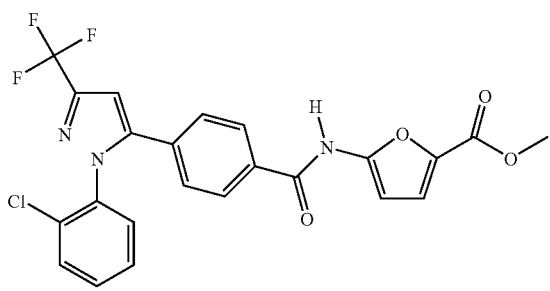 [SMILES: COC(=O)c1ccc(NC(=O)c2ccc(/C(=C/C(=N)C(F)(F)F)Nc3ccccc3Cl)cc2)o1] | methyl 5-[({4-[1-(2-chlorophenyl)-3-(trifluoromethyl)-1H-pyrazol-5-yl]phenyl}carbonyl)amino]furan-2-carboxylate |
| 1816 | 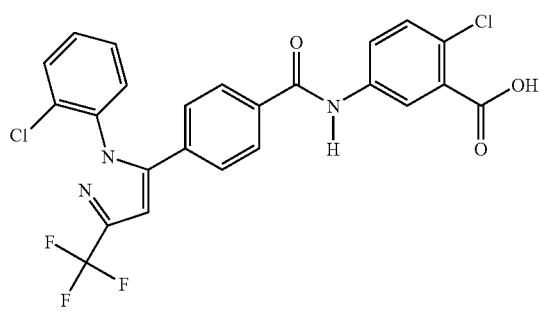 | 2-chloro-5-[({4-[1-(2-chlorophenyl)-3-(trifluoromethyl)-1H-pyrazol-5-yl]phenyl}carbonyl)amino]benzoic acid |
| 1817 | 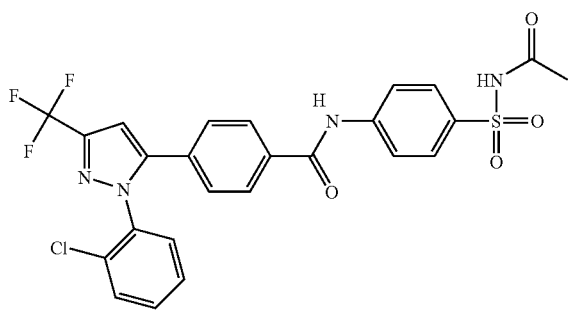 | N-{4-[(acetylamino)sulfonyl]phenyl}-4-[1-(2-chlorophenyl)-3-(trifluoromethyl)-1H-pyrazol-5-yl]benzamide |
| 1818 | 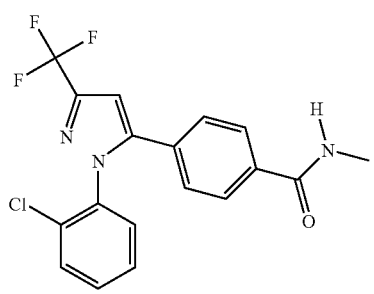 [SMILES: CNC(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-methylbenzamide |

TABLE 1-continued

| | | |
|---|---|---|
| 1819 |  | ethyl 4-[({4-[1-(2-chlorophenyl)-3-(trifluoromethyl)-1H-pyrazol-5-yl]phenyl}carbonyl)amino]benzoate |
| 1820 | 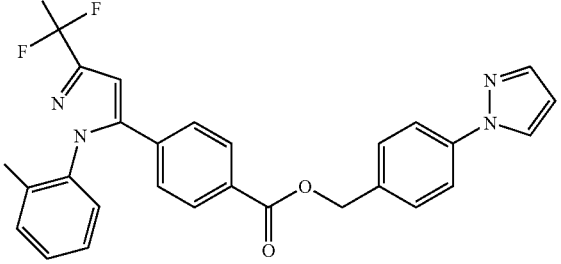 | [4-(1H-pyrazol-1-yl)phenyl]methyl 4-[1-(2-chlorophenyl)-3-(trifluoromethyl)-1H-pyrazol-5-yl]benzoate |
| 1821 | 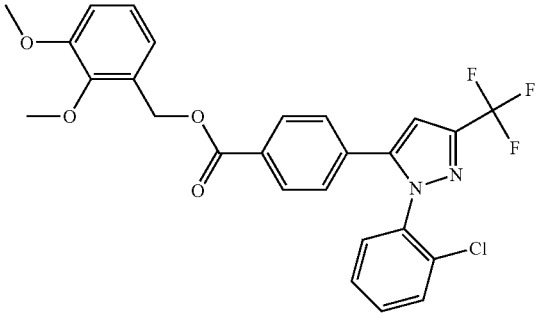 [SMILES: COc1cccc(COC(=O)c2ccc(-c3cc(C(F)(F)F)nn3-c3ccccc3Cl)cc2)c1OC] | [2,3-bis(methyloxy)phenyl]methyl 4-[1-(2-chlorophenyl)-3-(trifluoromethyl)-1H-pyrazol-5-yl]benzoate |
| 1822 | 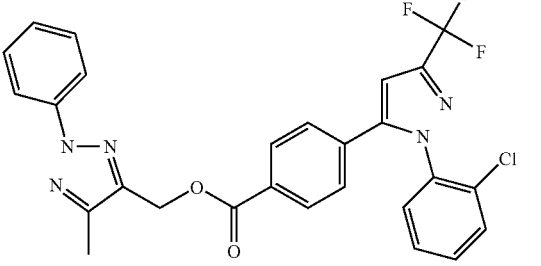 | (5-methyl-2-phenyl-2H-1,2,3-triazol-4-yl)methyl 4-[1-(2-chlorophenyl)-3-(trifluoromethyl)-1H-pyrazol-5-yl]benzoate |
| 1823 | 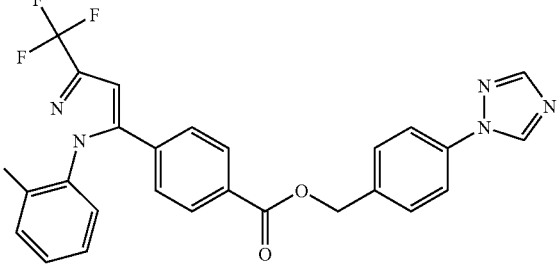 | [4-(1H-1,2,4-triazol-1-yl)phenyl]methyl 4-[1-(2-chlorophenyl)-3-(trifluoromethyl)-1H-pyrazol-5-yl]benzoate |

TABLE 1-continued

| | | |
|---|---|---|
| 1824 | | [6-(phenyloxy)pyridin-3-yl]methyl 4-[1-(2-chlorophenyl)-3-(trifluoromethyl)-1H-pyrazol-5-yl]benzoate |
| 1825 | | 2-{[4-(trifluoromethyl)pyridin-2-yl]oxy}ethyl 4-[1-(2-chlorophenyl)-3-(trifluoromethyl)-1H-pyrazol-5-yl]benzoate |
| 1826 | | 2-(3-methyl-5-oxo-4,5-dihydro-1H-pyrazol-4-yl)ethyl 4-[1-(2-chlorophenyl)-3-(trifluoromethyl)-1H-pyrazol-5-yl]benzoate |
| 1827 | | (2-butyl-5-chloro-1H-imidazol-4-yl)methyl 4-[1-(2-chlorophenyl)-3-(trifluoromethyl)-1H-pyrazol-5-yl]benzoate |
| 1828 | | (5-pyridin-2-yl-2-thienyl)methyl 4-[1-(2-chlorophenyl)-3-(trifluoromethyl)-1H-pyrazol-5-yl]benzoate |

TABLE 1-continued

| | | |
|---|---|---|
| 1829 | | (5-methyl-1H-imidazol-4-yl)methyl 4-[1-(2-chlorophenyl)-3-(trifluoromethyl)-1H-pyrazol-5-yl]benzoate |
| 1830 | | 3-pyridin-3-ylpropyl 4-[1-(2-chlorophenyl)-3-(trifluoromethyl)-1H-pyrazol-5-yl]benzoate |
| 1831 | | 2-[(2-methylpropyl)thio]ethyl 4-[1-(2-chlorophenyl)-3-(trifluoromethyl)-1H-pyrazol-5-yl]benzoate |
| 1832 | | [5-(2-methyl-1,3-thiazol-4-yl)-2-thienyl]methyl 4-[1-(2-chlorophenyl)-3-(trifluoromethyl)-1H-pyrazol-5-yl]benzoate |
| 1833 | | 2-(2-chlorophenyl)ethyl 4-[1-(2-chlorophenyl)-3-(trifluoromethyl)-1H-pyrazol-5-yl]benzoate |

TABLE 1-continued

| | | |
|---|---|---|
| 1834 | 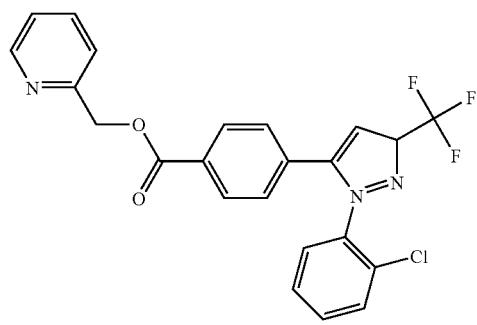 | pyridin-2-ylmethyl 4-[1-(2-chlorophenyl)-3-(trifluoromethyl)-1H-pyrazol-5-yl]benzoate |
| 1835 | 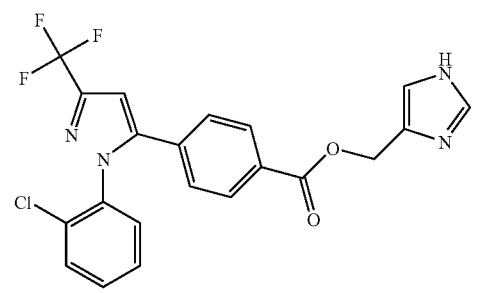 [SMILES: N=C(/C=C(\Nc1ccccc1Cl)c1ccc(C(=O)OCc2c[nH]cn2)cc1)C(F)(F)F] | 1H-imidazol-4-ylmethyl 4-[1-(2-chlorophenyl)-3-(trifluoromethyl)-1H-pyrazol-5-yl]benzoate |
| 1836 | 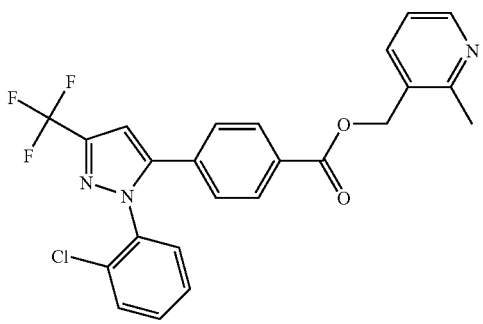 [SMILES: Cc1ncccc1COC(=O)c1ccc(-c2cc(C(F)(F)F)nn2-c2ccccc2Cl)cc1] | (2-methylpyridin-3-yl)methyl 4-[1-(2-chlorophenyl)-3-(trifluoromethyl)-1H-pyrazol-5-yl]benzoate |
| 1837 | 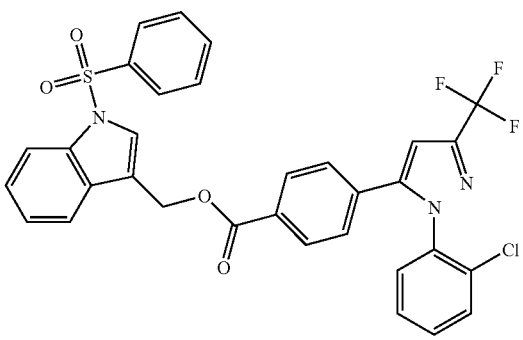 [SMILES: N=C(/C=C(\Nc1ccccc1Cl)c1ccc(C(=O)OCc2cn(S(=O)(=O)c3ccccc3)c3ccccc23)cc1)C(F)(F)F] | [1-(phenylsulfonyl)-1H-indol-3-yl]methyl 4-[1-(2-chlorophenyl)-3-(trifluoromethyl)-1H-pyrazol-5-yl]benzoate |
| 1838 | 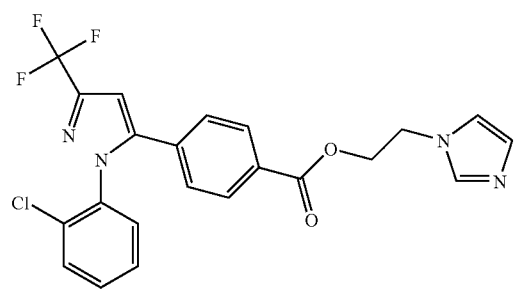 [SMILES: N=C(/C=C(\Nc1ccccc1Cl)c1ccc(C(=O)OCCn2ccnc2)cc1)C(F)(F)F] | 2-(1H-imidazol-1-yl)ethyl 4-[1-(2-chlorophenyl)-3-(trifluoromethyl)-1H-pyrazol-5-yl]benzoate |

TABLE 1-continued

| 1839 | 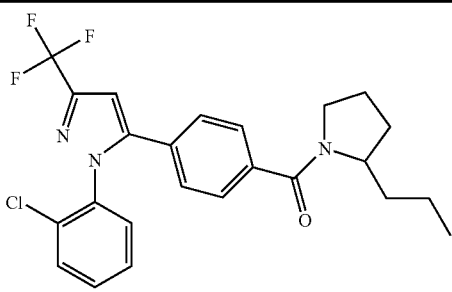 | 1-(2-chlorophenyl)-5-{4-[(2-propylpyrrolidin-1-yl)carbonyl]phenyl}-3-(trifluoromethyl)-1H-pyrazole |
| 1840 | 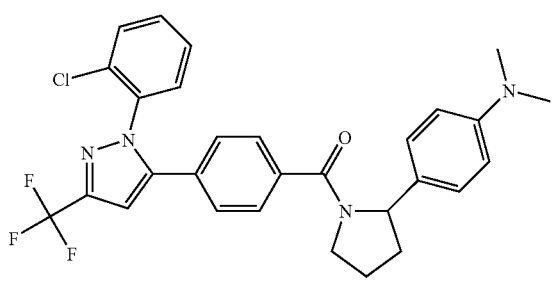 [SMILES: CN(C)c1ccc(C2CCCN2C(=O)c2ccc(-c3cc(C(F)(F)F)nn3-c3ccccc3Cl)cc2)cc1] | 4-[1-({4-[1-(2-chlorophenyl)-3-(trifluoromethyl)-1H-pyrazol-5-yl]phenyl}carbonyl)pyrrolidin-2-yl]-N,N-dimethylaniline |
| 1841 | 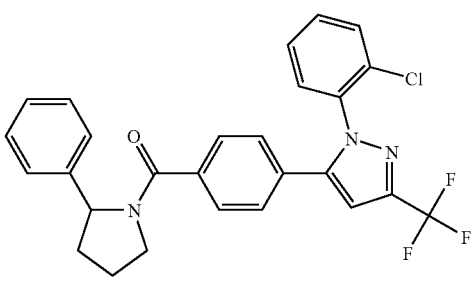 [SMILES: O=C(c1ccc(-c2cc(C(F)(F)F)nn2-c2ccccc2Cl)cc1)N1CCCC1c1ccccc1] | 1-(2-chlorophenyl)-5-{4-[(2-phenylpyrrolidin-1-yl)carbonyl]phenyl}-3-(trifluoromethyl)-1H-pyrazole |
| 1842 | 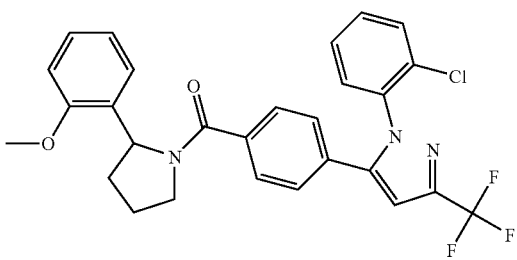 [SMILES: COc1ccccc1C1CCCN1C(=O)c1ccc(/C(=C/C(=N)C(F)(F)F)Nc2ccccc2Cl)cc1] | 1-(2-chlorophenyl)-5-[4-({3-[2-(methyloxy)phenyl]pyrrolidin-1-yl}carbonyl)phenyl]-3-(trifluoromethyl)-1H-pyrazole |
| 1843 | 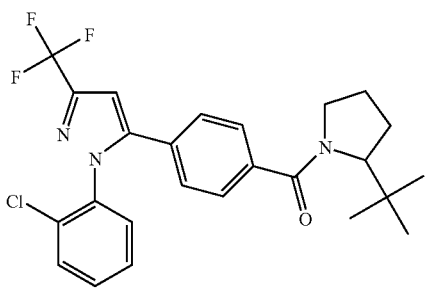 [SMILES: CC(C)(C)C1CCCN1C(=O)c1ccc(/C(=C/C(=N)C(F)(F)F)Nc2ccccc2Cl)cc1] | 1-(2-chlorophenyl)-5-(4-{[2-(1,1-dimethylethyl)pyrrolidin-1-yl]carbonyl}phenyl)-3-(trifluoromethyl)-1H-pyrazole |

TABLE 1-continued

| | | |
|---|---|---|
| 1844 | 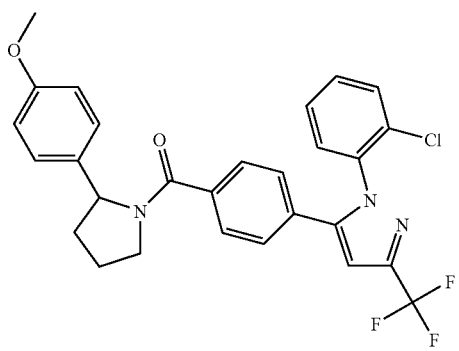 [SMILES: COc1ccc(C2CCCN2C(=O)c2ccc(/C(=C/C(=N)C(F)(F)F)Nc3ccccc3Cl)cc2)cc1] | 1-(2-chlorophenyl)-5-{4-({2-[4-(methyloxy)phenyl]pyrrolidin-1-yl}carbonyl)phenyl]-3-(trifluoromethyl)-1H-pyrazole |
| 1845 | 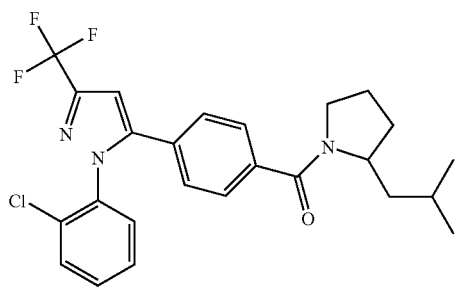 [SMILES: CC(C)CC1CCCN1C(=O)c1ccc(/C(=C/C(=N)C(F)(F)F)Nc2ccccc2Cl)cc1] | 1-(2-chlorophenyl)-5-(4-{[2-(2-methylpropyl)pyrrolidin-1-yl]carbony}phenyl)-3-(trifluoromethyl)-1H-pyrazole |
| 1846 | 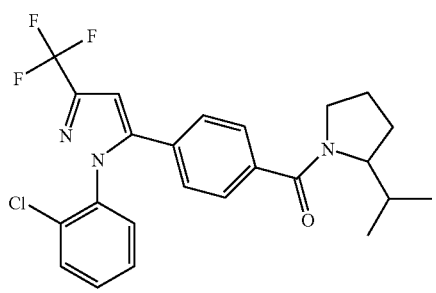 [SMILES: CC(C)C1CCCN1C(=O)c1ccc(/C(=C/C(=N)C(F)(F)F)Nc2ccccc2Cl)cc1] | 1-(2-chlorophenyl)-5-(4-{[2-(1-methylethyl)pyrrolidin-1-yl]carbonyl}phenyl)-3-(trifluoromethyl)-1H-pyrazole |
| 1847 | 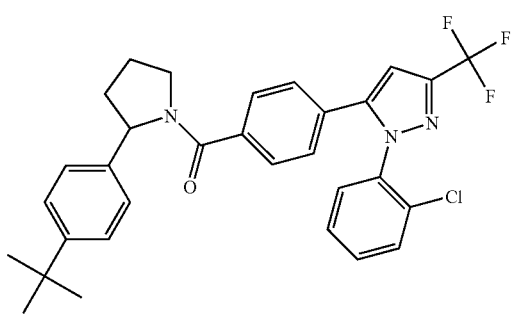 [SMILES: CC(C)(C)c1ccc(C2CCCN2C(=O)c2ccc(-c3cc(C(F)(F)F)nn3-c3ccccc3Cl)cc2)cc1] | 1-(2-chlorophenyl)-5-[4-({2-[4-(1,1-dimethylethyl)phenyl]pyrrolidin-1-yl}carbonyl)phenyl]-3-(trifluoromethyl)-1H-pyrazole |
| 1848 | 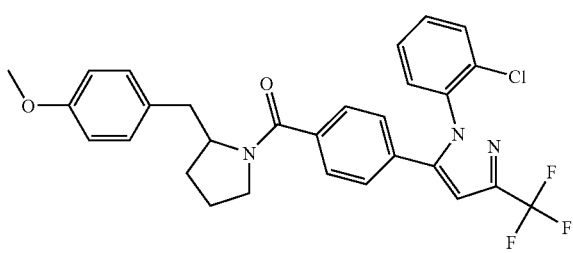 [SMILES: COc1ccc(CC2CCCN2C(=O)c2ccc(/C(=C/C(=N)C(F)(F)F)Nc3ccccc3Cl)cc2)cc1] | 1-(2-chlorophenyl)-5-{4-[(2-{[4-(methyloxy)phenyl]methyl}pyrrolidin-1-yl)carbonyl]phenyl}-3-(trifluoromethyl)-1H-pyrazole |

TABLE 1-continued

| 1850 | 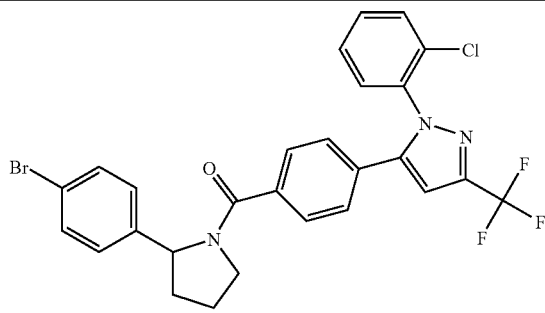 | 5-(4-{[2-(4-bromophenyl)pyrrolidin-1-yl]carbonyl}phenyl)-1-(2-chlorophenyl)-3-(trifluoromethyl)-1H-pyrazole |
| 1851 | 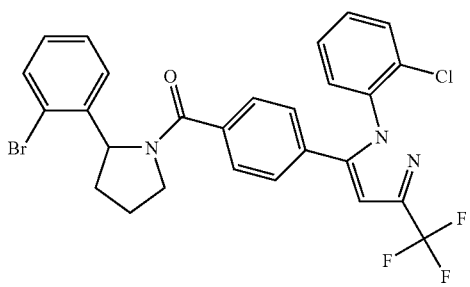 [SMILES: N=C(/C=C(\Nc1ccccc1Cl)c1ccc(C(=O)N2CCCC2c2ccccc2Br)cc1)C(F)(F)F] | 5-(4-{[2-(2-bromophenyl)pyrrolidin-1-yl]carbonyl}phenyl)-1-(2-chlorophenyl)-3-(trifluoromethyl)-1H-pyrazole |
| 1852 | 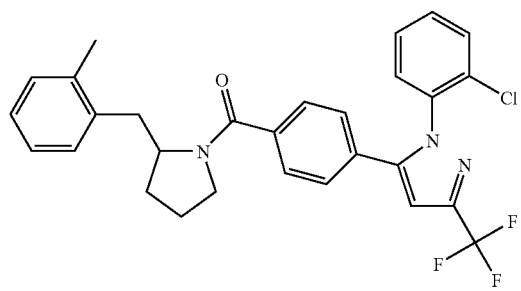 [SMILES: Cc1ccccc1CC1CCCN1C(=O)c1ccc(/C(=C/C(=N)C(F)(F)F)Nc2ccccc2Cl)cc1] | 1-(2-chlorophenyl)-5-[4-({2-[(2-methylphenyl)methyl]pyrrolidin-1-yl}carbonyl)phenyl]-3-(trifluoromethyl)-1H-pyrazole |
| 1853 | 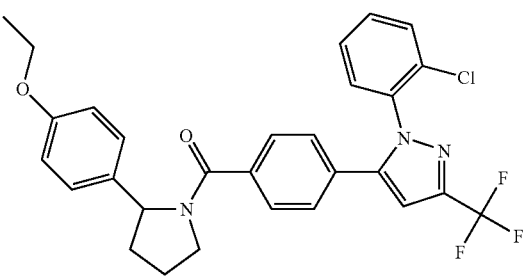 [SMILES: CCOc1ccc(C2CCCN2C(=O)c2ccc(-c3cc(C(F)(F)F)nn3-c3ccccc3Cl)cc2)cc1] | 1-(2-chlorophenyl)-5-[4-({2-[4-(ethyloxy)phenyl]pyrrolidin-1-yl}carbonyl)phenyl]-3-(trifluoromethyl)-1H-pyrazole |
| 1854 | 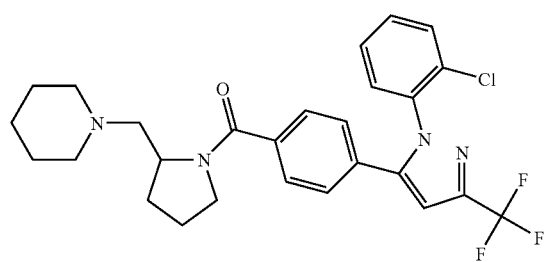 [SMILES: N=C(/C=C(\Nc1ccccc1Cl)c1ccc(C(=O)N2CCCC2CN2CCCCC2)cc1)C(F)(F)F] | 1-{[1-({4-[1-(2-chlorophenyl)-3-(trifluoromethyl)-1H-pyrazol-5-yl]phenyl}carbonyl)pyrrolidin-2-yl]methyl}piperidine |

TABLE 1-continued

| | | |
|---|---|---|
| 1855 | 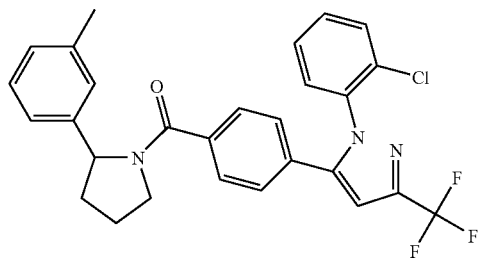 [SMILES: Cc1cccc(C2CCCN2C(=O)c2ccc(/C(=C/C(=N)C(F)(F)F)Nc3ccccc3Cl)cc2)c1] | 1-(2-chlorophenyl)-5-(4-{[2-(3-methylphenyl)pyrrolidin-1-yl]carbonyl}phenyl-3-(trifluoromethyl)-1H-pyrazole |
| 1856 | 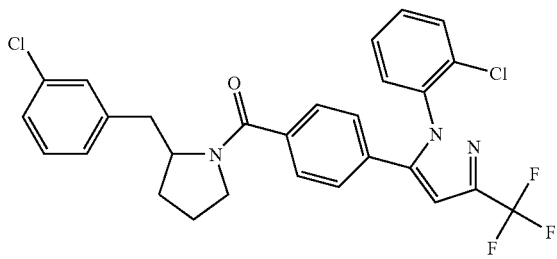 [SMILES: N=C(/C=C(\Nc1ccccc1Cl)c1ccc(C(=O)N2CCCC2Cc2cccc(Cl)c2)cc1)C(F)(F)F] | 1-(2-chlorophenyl)-5-[4-({2-[(3-chlorophenyl)methyl]pyrrolidin-1-yl}carbonyl)phenyl]-3-(trifluoromethyl)-1H-pyrazole |
| 1857 | 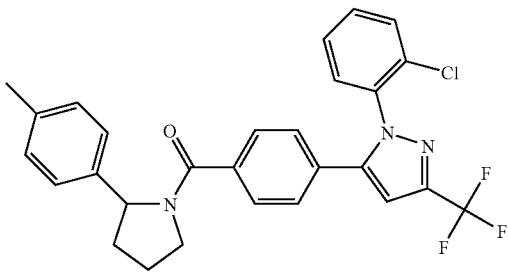 [SMILES: Cc1ccc(C2CCCN2C(=O)c2ccc(-c3cc(C(F)(F)F)nn3-c3ccccc3Cl)cc2)cc1] | 1-(2-chlorophenyl)-5-(4-{[2-(4-methylphenyl)pyrrolidin-1-yl]carbonyl}phenyl)-3-(trifluoromethyl)-1H-pyrazole |
| 1858 | 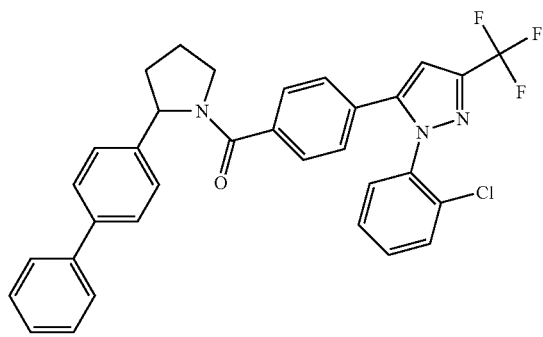 [SMILES: O=C(c1ccc(-c2cc(C(F)(F)F)nn2-c2ccccc2Cl)cc1)N1CCCC1c1ccc(-c2ccccc2)cc1] | 5-{4-[(2-biphenyl-4-ylpyrrolidin-1-yl)carbonyl]phenyl}-1-(2-chlorophenyl)-3-(trifluoromethyl)-1H-pyrazole |
| 1859 | 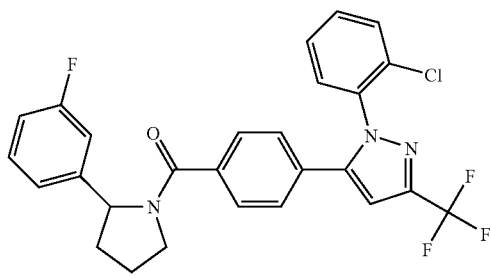 [SMILES: O=C(c1ccc(-c2cc(C(F)(F)F)nn2-c2ccccc2Cl)cc1)N1CCCC1c1cccc(F)c1] | 1-(2-chlorophenyl)-5-(4-{[2-(3-fluorophenyl)pyrrolidin-1-yl]carbonyl}phenyl)-3-(trifluoromethyl)-1H-pyrazole |

TABLE 1-continued

| | | |
|---|---|---|
| 1860 | 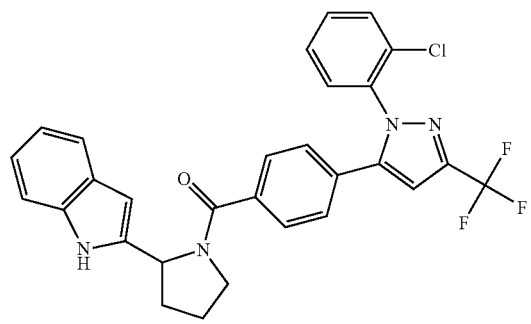 [SMILES: O=C(c1ccc(-c2cc(C(F)(F)F)nn2-c2ccccc2Cl)cc1)N1CCCC1c1cc2ccccc2[nH]1] | 2-[1-({4-[1-(2-chlorophenyl)-3-(trifluoromethyl)-1H-pyrazol-5-yl]phenyl}carbonyl)pyrrolidin-2-yl]-1H-indole |
| 1861 | 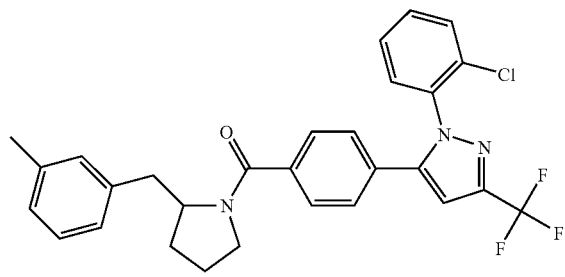 [SMILES: Cc1cccc(CC2CCCN2C(=O)c2ccc(-c3cc(C(F)(F)F)nn3-c3ccccc3Cl)cc2)c1] | 1-(2-chlorophenyl)-5-[4-({2-[(3-methylphenyl)methyl]pyrrolidin-1-yl}carbonyl)phenyl]-3-(trifluoromethyl)-1H-pyrazole |
| 1862 | 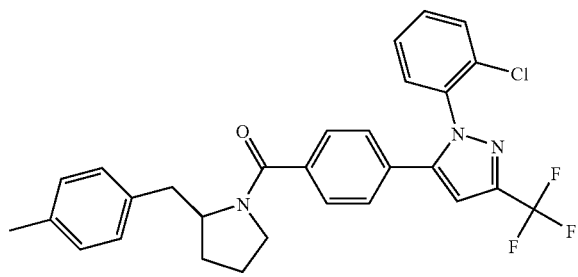 [SMILES: Cc1ccc(CC2CCCN2C(=O)c2ccc(-c3cc(C(F)(F)F)nn3-c3ccccc3Cl)cc2)cc1] | 1-(2-chlorophenyl)-5-[4-({2-[(4-methylphenyl)methyl]pyrrolidin-1-yl}carbonyl)phenyl]-3-(trifluoromethyl)-1H-pyrazole |
| 1863 | 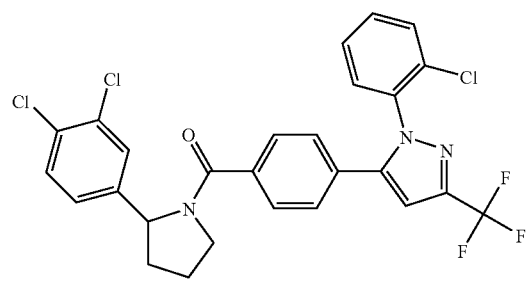 [SMILES: O=C(c1ccc(-c2cc(C(F)(F)F)nn2-c2ccccc2Cl)cc1)N1CCCC1c1ccc(Cl)c(Cl)c1] | 1-(2-chlorophenyl)-5-(4-{[2-(3,4-dichlorophenyl)pyrrolidin-1-yl]carbonyl}phenyl)-3-(trifluoromethyl)-1H-pyrazole |
| 1864 | 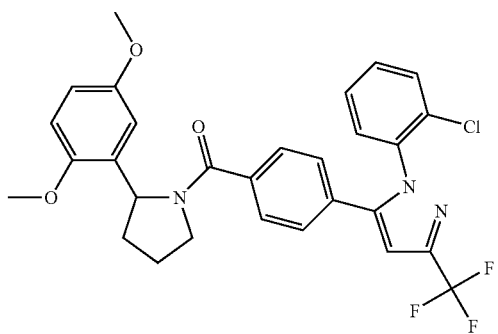 [SMILES: COc1ccc(OC)c(C2CCCN2C(=O)c2ccc(/C(=C/C(=N)C(F)(F)F)Nc3ccccc3Cl)cc2)c1] | 5-[4-({2-[2,5-bis(methyloxy)phenyl]pyrrolidin-1-yl}carbonyl)phenyl]-1-(2-chlorophenyl)-3-(trifluoromethyl)-1H-pyrazole |

TABLE 1-continued

| 1865 | 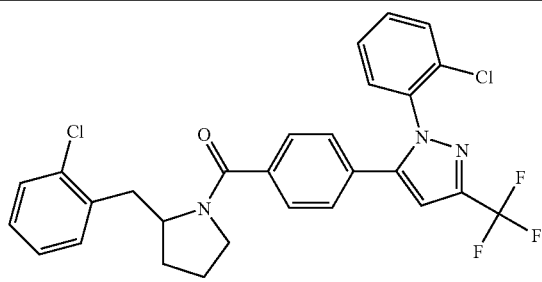 | 1-(2-chlorophenyl)-5-[4-({2-[(2-chlorophenyl)methyl]pyrrolidin-1-yl}carbonyl)phenyl]-3-(trifluoromethyl)-1H-pyrazole |
| 1866 | 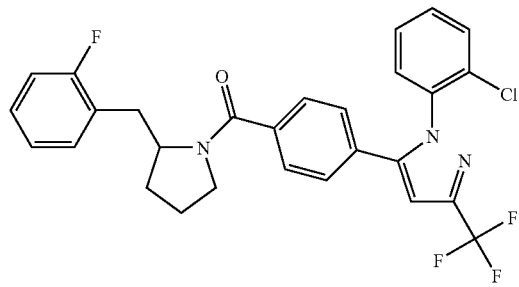 | 1-(2-chlorophenyl)-5-[4-({2-[(2-fluorophenyl)methyl]pyrrolidin-1-yl}carbonyl)phenyl]-3-(trifluoromethyl)-1H-pyrazole |
| 1867 | 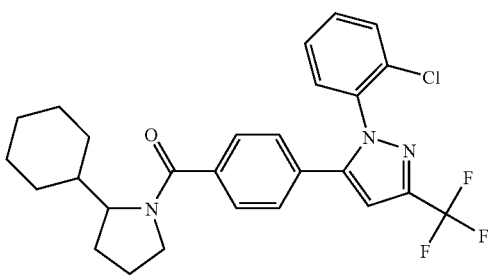 [SMILES: O=C(c1ccc(-c2cc(C(F)(F)F)nn2-c2ccccc2Cl)cc1)N1CCCC1C1CCCCC1] | 1-(2-chlorophenyl)-5-{4-[(2-cyclohexylpyrrolidin-1-yl)carbonyl]phenyl}-3-(trifluoromethyl)-1H-pyrazole |
| 1868 | 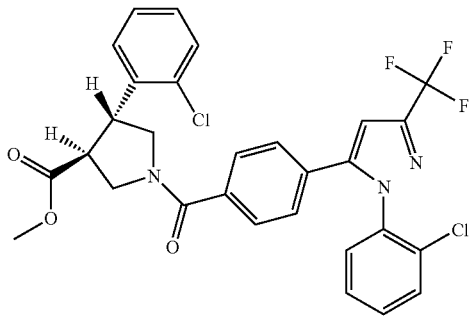 [SMILES: COC(=O)[C@@H]1CN(C(=O)c2ccc(/C(=C/C(=N)C(F)(F)F)Nc3ccccc3Cl)cc2)C[C@H]1c1ccccc1Cl] | methyl (3S,4R)-4-(2-chlorophenyl)-1-({4-[1-(2-chlorophenyl)-3-(trifluoromethyl)-1H-pyrazol-5-yl]phenyl}carbonyl)pyrrolidin-3-carboxylate |
| 1869 | 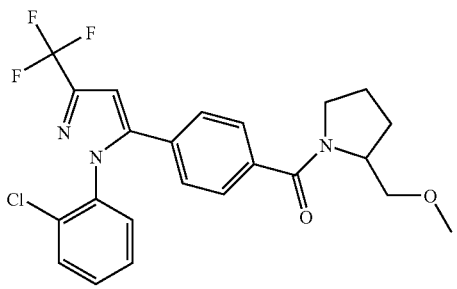 [SMILES: COCC1CCCN1C(=O)c1ccc(/C(=C/C(=N)C(F)(F)F)Nc2ccccc2Cl)cc1] | 1-(2-chlorophenyl)-5-[4-({2-[(methyloxy)methyl]pyrrolidin-1-yl}carbonyl)phenyl]-3-(trifluoromethyl)-1H-pyrazole |

TABLE 1-continued

| | | |
|---|---|---|
| 1870 | | 1-(2-chlorophenyl)-5-(4-{[2-(pyrrolidin-1-ylmethyl)pyrrolidin-1-yl]carbonyl}phenyl)-3-(trifluoromethyl)-1H-pyrazole |
| 1871 | | (3R)-1-({4-[1-(2-chlorophenyl)-3-(trifluoromethyl)-1H-pyrazol-5-yl]phenyl}carbonyl)pyrrolidin-3-ol |
| 1872 | | 1-({4-[1-(2-chlorophenyl)-3-(trifluoromethyl)-1H-pyrazol-5-yl]phenyl}carbonyl)prolinamide |
| 1873 | | (3R)-1-({4-[1-(2-chlorophenyl)-3-(trifluoromethyl)-1H-pyrazol-5-yl]phenyl}carbonyl)-N,N-dimethylpyrrolidin-3-amine |
| 1874 | | 1-(2-chlorophenyl)-5-{4-[(2-methylpyrrolidin-1-yl)carbonyl]phenyl}-3-(trifluoromethyl)-1H-pyrazole |

| | | |
|---|---|---|
| 1875 | | methyl (3S,4R)-1-({4-[1-(2-chlorophenyl)-3-(trifluoromethyl)-1H-pyrazol-5-yl]phenyl}carbonyl)-4-[4-(methyloxy)phenyl]pyrrolidin-3-carboxylate |
| 1876 | | methyl (3S,4R)-1-({4-[1-(2-chlorophenyl)-3-(trifluoromethyl)-1H-pyrazol-5-yl]phenyl}carbonyl)-4-[4-(trifluoromethyl)phenyl]pyrrolidin-3-carboxylate |
| 1877 | | 1-(2-chlorophenyl)-5-(4-{[2-(4-fluorophenyl)pyrrolidin-1-yl]carbonyl}phenyl)-3-(trifluoromethyl)-1H-pyrazole |
| 1878 | | 2-[1-({4-[1-(2-chlorophenyl)-3-(trifluoromethyl)-1H-pyrazol-5-yl]phenyl}carbonyl)pyrrolidin-2-yl]-6-methyl-1H-benzimidazole |
| 1879 | | phenylmethyl 1-({4-[1-(2-chlorophenyl)-3-(trifluoromethyl)-1H-pyrazol-5-yl]phenyl}carbonyl)prolinate |

TABLE 1-continued

| 1880 | N-[(3S)-1-({4-[1-(2-chlorophenyl)-3-(trifluoromethyl)-1H-pyrazol-5-yl]phenyl}carbonyl)pyrrolidin-3-yl]-2,2,2-trifluoroacetamide |
| 1881 | (4R)-2-({4-[1-(2-chlorophenyl)-3-(trifluoromethyl)-1H-pyrazol-5-yl]phenyl}carbonyl)-5-(phenylmethyl)-2,5-diazabicyclo[2.2.1]heptane |
| 1882 | 1-(2-{5-[1-(2-chlorophenyl)-3-(1-hydroxy-1-methylethyl)-1H-pyrazol-5-yl]-2-thienyl}phenyl)ethanone; |
| 1883 | 1-(2-ethylphenyl)-5-{4-[3-(methylsulfonyl)phenyl]-2-thienyl}-3-(trifluoromethyl)-1H-pyrazole |
| 1884 | 4-[1-(2-chlorophenyl)-3-(trifluoromethyl)-1H-pyrazol-5-yl]-N-(2,2,2-trifluoro-1-pyridin-3-ylethyl)benzamide |

| | | |
|---|---|---|
| 1885 | 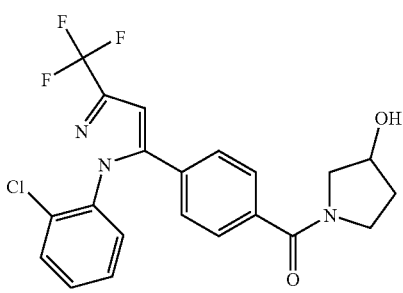 [SMILES: N=C(/C=C(\Nc1ccccc1Cl)c1ccc(C(=O)N2CCC(O)C2)cc1)C(F)(F)F] | 1-({4-[1-(2-chlorophenyl)-3-(trifluoromethyl)-1H-pyrazol-5-yl]phenyl}carbonyl)pyrrolidin-3-ol |
| 1886 | 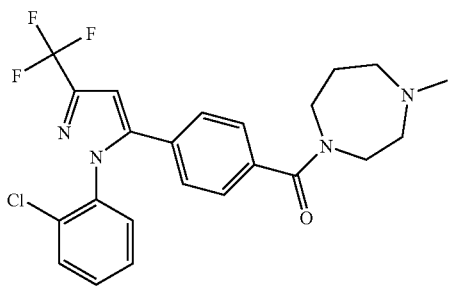 [SMILES: CN1CCCN(C(=O)c2ccc(/C(=C/C(=N)C(F)(F)F)Nc3ccccc3Cl)cc2)CC1] | 1-({4-[1-(2-chlorophenyl)-3-(trifluoromethyl)-1H-pyrazol-5-yl]phenyl}carbonyl)-4-methyl-1,4-diazepane |
| 1887 | 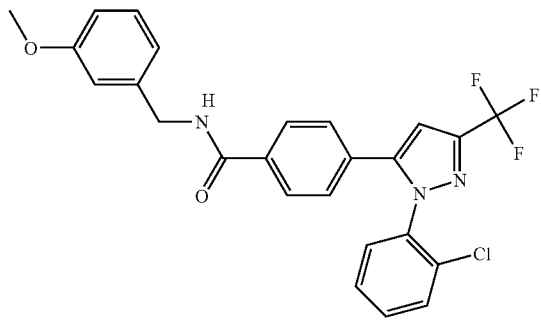 | 4-[1-(2-chlorophenyl)-3-(trifluoromethyl)-1H-pyrazol-5-yl]-N-{[3-(methyloxy)phenyl]methyl}benzamide |
| 1888 | 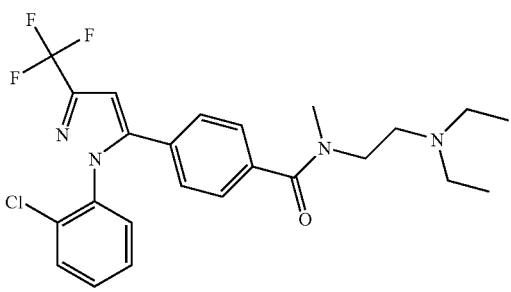 [SMILES: CCN(CC)CCN(C)C(=O)c1ccc(/C(=C/C(=N)C(F)(F)F)Nc2ccccc2Cl)cc1] | 4-[1-(2-chlorophenyl)-3-(trifluoromethyl)-1H-pyrazol-5-yl]-N-[2-(diethylamino)ethyl]-N-methylbenzamide |
| 1889 | 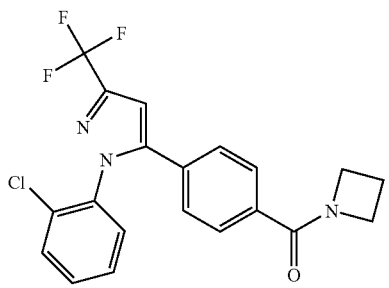 [SMILES: N=C(/C=C(\Nc1ccccc1Cl)c1ccc(C(=O)N2CCC2)cc1)C(F)(F)F] | 5-[4-(azetidin-1-ylcarbonyl)phenyl]-1-(2-chlorophenyl)-3-(trifluoromethyl)-1H-pyrazole |

TABLE 2
| 1374 | 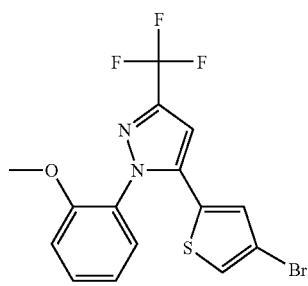 [SMILES: COc1ccccc1-n1nc(C(F)(F)F)cc1-c1cc(Br)cs1] | 5-(4-bromo-2-thienyl)-1-[2-(methyloxy)phenyl]-3-(trifluoromethyl)-1H-pyrazole; |
| 1375 | 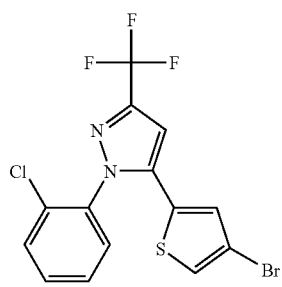 [SMILES: FC(F)(F)c1cc(-c2cc(Br)cs2)n(-c2ccccc2Cl)n1] | 5-(4-bromo-2-thienyl)-1-(2-chlorophenyl)-3-(trifluoromethyl)-1H-pyrazole; |
| 1376 | 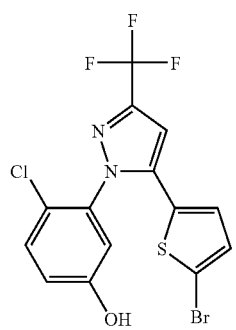 [SMILES: Oc1ccc(Cl)c(-n2nc(C(F)(F)F)cc2-c2ccc(Br)s2)c1] | 3-[5-(5-bromo-2-thienyl)-3-(trifluoromethyl)-1H-pyrazol-1-yl]-4-chlorophenol; |
| 1377 | 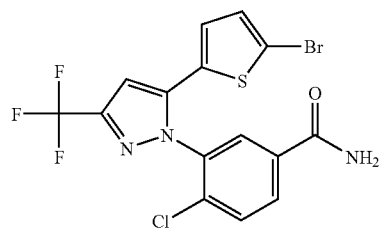 [SMILES: NC(=O)c1ccc(Cl)c(-n2nc(C(F)(F)F)cc2-c2ccc(Br)s2)c1] | 3-[5-(5-bromo-2-thienyl)-3-(trifluoromethyl)-1H-pyrazol-1-yl]-4-chlorobenzamide; |
| 1378 | 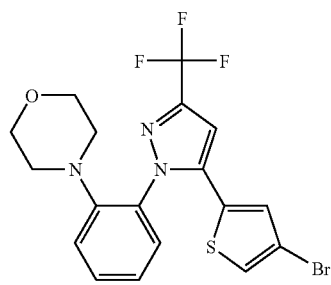 [SMILES: FC(F)(F)c1cc(-c2cc(Br)cs2)n(-c2ccccc2N2CCOCC2)n1] | 4-{2-[5-(4-bromo-2-thienyl)-3-(trifluoromethyl)-1H-pyrazol-1-yl]phenyl}morpholine; or |

TABLE 2-continued

| # | Structure | Name |
|---|---|---|
| 1379 | 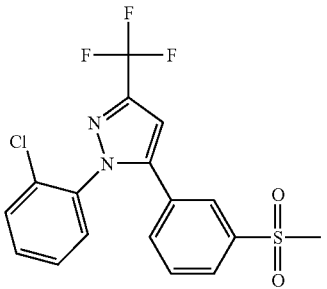 [SMILES: CS(=O)(=O)c1cccc(-c2cc(C(F)(F)F)nn2-c2ccccc2Cl)c1] | 1-(2-chlorophenyl)-5-[3-(methylsulfonyl)phenyl]-3-(trifluoromethyl)-1H-pyrazole. |
| 1380 | 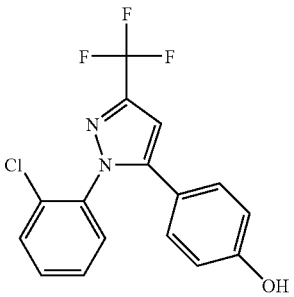 [SMILES: Oc1ccc(-c2cc(C(F)(F)F)nn2-c2ccccc2Cl)cc1] | 4-[1-(2-chlorophenyl)-3-(trifluoromethyl)-1H-pyrazol-5-yl]phenol |
| 1381 | 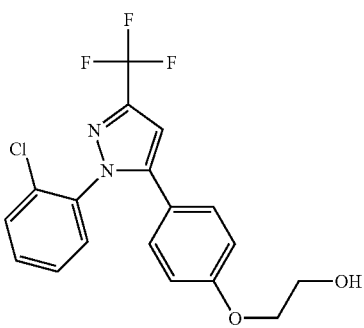 [SMILES: OCCOc1ccc(-c2cc(C(F)(F)F)nn2-c2ccccc2Cl)cc1] | 2-({4-[1-(2-chlorophenyl)-3-(trifluoromethyl)-1H-pyrazol-5-yl]phenyl}oxy)ethanol |
| 1382 | 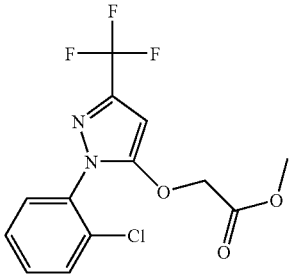 [SMILES: COC(=O)COc1cc(C(F)(F)F)nn1-c1ccccc1Cl] | methyl {[1-(2-chlorophenyl)-3-(trifluoromethyl)-1H-pyrazol-5-yl]oxy}acetate |

Example 107

FRET Coactivator Assay

The FRET coactivator assay measures the ability of LXR ligands to promote protein-protein interactions between the ligand binding domain (LBD) of LXR and transcriptional coactivator proteins. The assay involves the use a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction.

Required Materials:

Partially purified recombinant protein comprising glutathione-S-transferase fused in frame to the LXR-ligand binding domain (comprising amino acids 188-447 of human LXRα, or amino acids 198461 of human LXRβ)

Biotinylated peptide containing a SRC-1 LXXLL receptor interaction motif (B-SRC-1).

Anti-GST antibody conjugated to a Europium chelate (αGST-K) (From Wallac/PE Life Sciences Cat# AD0064).

Streptavidin linked allophycocyanin (SA-APC) (From Wallac/PE Life Sciences CAT# AD0059A).

1×FRET Buffer: (20 mM $KH_2PO_4/K_2HPO_4$ pH 7.3, 150 mM NaCl, 2.5 mM CHAPS, 2 mM EDTA, 1 mM DTT (add fresh)).

96 well or 384 well black multiwell plates (from LJL)

Stock Solutions:

0.5 M $KH_2PO_4/K_2HPO_4$: pH 7.3; 5 M NaCl; 80 mM (5%) CHAPS; 0.5 M EDTA pH 8.0; 1 M DTT (keep at −20° C.)

Preparation of Screening Reagents:

Prepare reaction mixture for the appropriate number of wells by combining the following reagents 5 nM/well GST-hLXRαLBD, 5 nM/well GST-hLXRβLBD, 5 nM/well Anti-GST antibody (Eu), 12 nM/well biotin-SRC-1 peptide, 12 nM/well APC-SA adjust the volume to 10 μL/well with 1x-FRET buffer.

Procedure:

Add 0.5 μL of a 1 mM stock compound (for approx. 10 μM final concentration) or solvent to each well in a 96 well or 384 well black plate (LJL). Add 10 μl reaction mixture (prepared above) to each well of the multiwell plate. Incubate covered or in the dark (the APC is light sensitive) at ambient temperature for 1-4 hours. After this time if reactions are not read they can be stored at 4° C. for several more hours without too much loss of signal.

Read the plate using an LJL Analyst, or similar instrument, using the following conditions: Channel 1: Excitation is 330 nm and emission is 615. This is for Eu chelate; Channel 2: Excitation is 330 nm and emission is 665. This is for APC; For channel 1: Flashes per well=100; Integration time=1000 μs; interval between flashes=1×10 ms; Delay after flash=200 μs; For channel 2: Flashes per well=100; Integration time=100 μs; interval between flashes=1×10 ms; Delay after flashes=65 μs.

Example 108

Scintillation Proximity Assay (SPA)

The SPA assay measures the radioactive signal generated by the binding of $^3$H-24,25-epoxycholesterol to LXRα or LXRβ. The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

Required Materials:

Label: $^3$H-24,25-epoxy-cholesterol (Amersham)

LXRα lysate: Baculovirus expressed LXRα/RXR heterodimer with RXR having a 6-HIS tag produced as a crude lysate LXRβ lysate: Baculovirus expressed LXRβ/RXR heterodimer with RXR having a 6-HIS tag produced as a crude lysate SPA beads: Ysi copper His-tag SPA beads (Amersham)

Plates: Non-binding surface 96-well plate (Corning)

Protein lysate dilution buffer: (20 mM Tris-HCl pH 7.9, 500 mM NaCl, 5 mM Imidazole). 2×SPA Buffer: (40 mM $K_2HPO_4/KH_2PO_4$ pH7.3, 100 mM NaCl, 0.05% Tween 20, 20% Glycerol, 4 mM EDTA) 2×SPA Buffer w/o EDTA: (40 mM $K_2HPO_4/KH_2PO_4$ pH7.3, 100 mM NaCl, 0.05% Tween 20, 20% Glycerol)

Stock Solutions 0.5 M $K_2HPO_4/KH_2PO_4$ pH 7.3; 0.5 M EDTA pH 8.0; 5 M NaCl; 10% Tween-20; Glycerol Preparation of Protein Lysates Baculovirus expression plasmids for human RXRα (accession No NM_002957), LXRα (accession No U22662), LXRβ (accession No U07132) were made by cloning the appropriate full-length cDNAs into the pBacPakhis1 vector (Clontech, CA) following standard procedures. Insertion of the cDNAs into the pBAcPakhis1 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately 1.25×10$^6$/ml at 27° C., in a total volume of 500 mL per 1 L sized spinner flasks, cultured under standard conditions. To prepare LXRα lysate, insect cells were co-transfected with the LXRα expression cassette at an M.O.I of 0.5 to 0.8 and with the RXR expression cassette at a M.O.I. of approximately 1.6. To prepare LXRβ lysate, insect cells were co-transfected with the LXRβ expression cassette at an M.O.I of approximately 1.6 and with the RXR expression cassette at a M.O.I. of approximately 1.6. In both cases cells were incubated for 48 hours at 27° C. with constant shaking prior to harvesting.

After incubation, cells were harvested by centrifugation and pelleted. Cell pellets were resuspended in two volumes of ice-cold freshly prepared extraction buffer (20 mM Tris pH 8.0, 10 mM Imidazole, 400 mM NaCl, containing one EDTA free protease inhibitor tablet (Roche Catalog No: 1836170) per 10 ml of extraction buffer). Cells were homogenized slowly on ice using a Douncer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) and adjusted for protein concentration and expression level prior to use in screening assays.

Preparation of Screening Reagents

[$^3$H] 24,25 Epoxycholesterol (EC) solution: For a single 384-well plate (or 400 wells), 21 μL of [$^3$H] EC (specific activity 76.5 Ci/mmol, concentration 3.2 mCi/mL) was added to 4.4 mL of 2×SPA buffer to provide for a final concentration of 200 nM. For each additional 384-well plate, an additional 19.1 μL of [$^3$H] EC was added to 4.0 mL of additional 2×SPA buffer. The final concentration of [$^3$H] EC in the well was 50 nM. LXRα lysate (prepared as above) was diluted with protein lysate dilution buffer. 1400 μL of diluted LXRα lysate was prepared per 384-well plate, (or 200 wells) and 1120 μL of diluted LXRα lysate was prepared for each additional 384-well plate. LXRβ lysate (prepared as above) was diluted with protein lysate dilution buffer. 1400 μL of diluted LXRβ lysate was prepared per 384-well plate, (or 200 wells) and 1120 μL of diluted LXRβ lysate was prepared for each additional 384-well plate. SPA bead solution: For a 384-well plate (or 400 wells), 3.75 mL of 2×SPA buffer w/o EDTA, 225 mL of H₂O, and 1.5 mL of Ysi His-tag SPA beads (vortex well before taking) were mixed together. For each additional 384-well plate, an additional 3.5 mL of 2×SPA buffer w/o EDTA, 2.1 mL of H₂O, and 1.4 mL of Ysi His-tag SPA beads were mixed together.

Procedure:

Appropriate dilutions of each compound were prepared and pipetted into the appropriate wells of a multiwell plate. 9.1 µL of [$^3$H] EC was added to each well of column 2-23 of the multiwell plate. 5 µl of diluted LXRα lysate was added to each well of column 2-23 on odd rows of the multiwell plate. 5 µl, of diluted LXRβ lysate was added to each well of column 2-23 on even rows of the multiwell plate. 17.5 µL of SPA bead solution was added to each well of column 2-23 of the multiwell plate.

The plates were covered with clear sealer and placed in an incubator at ambient temperature for 1 hour. After incubation plates were analyzed using a luminescent plate reader (MicroBeta, Wallac) using the program nABASE 3H_384DPM. The setting for n ABASE 3H_384DPM was: Counting Mode: DPM; Sample Type: SPA; ParaLux Mode: low background; Count time: 30 sec.

Assays for LXRα and LXRβ were performed in the identical manner. The determined Ki represents the average of at least two independent dose response experiments. The binding affinity for each compound may be determined by nonlinear regression analysis using the one site competition formula to determine the IC$_{50}$ where:

$$Y = \text{Bottom}^+ \frac{(\text{Top} - \text{Bottom})}{(1 + 10^{X - \log IC50})}$$

The Ki is than calculated using the Cheng and Prusoff equation where:

$$Ki = IC_{50}/(1^+[\text{Concentration of Ligand}]/\text{Kd of Ligand})$$

For this assay, typically the Concentration of Ligand=50 nM and the Kd of EC for the receptor is 200 nM as determined by saturation binding.

The compounds of the invention demonstrated the ability to bind to LXRα and/or LXRβ when tested in this assay.

Example 109

Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay; expression plasmids for LXR and RXR are introduced via transient transfection into mammalian cells along with a luciferase reporter plasmid that contains one copy of a DNA sequence that is bound by LXR-RXR heterodimers (LXRE; Willy, P. ad. 1995). Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials

CV-1 African Green Monkey Kidney Cells Co-transfection expression plasmids, comprising full-length LXRα (pCMX-h LXRα, LXRβ (pCMX-hLXRβ), or RXRα (pCMX-RXR), reporter plasmid (LXREx1-Tk-Luciferase), and control (pCMX-Galactosidase expression vector) (Willey et al. Genes & Development 91033-1045 (1995)).

Transfection reagent such as FuGENE6 (Roche).
1× Cell lysis buffer (1% Triton X 100 (IT Baker X200-07), 10% Glycerol (JT Baker M778-07), 5 mM Ditriotreitol (Quantum Bioprobe DTT03; add fresh before lysing), 1 mM EGTA (Ethylene Glycol-bis(B-Amino ethyl ether)-N, N,N',N'-Tetracetic Acid) (Sigma E-4378), 25 mM Tricine (ICN 807420) pH 7.8)
1× Luciferase assay buffer (pH at 7.8) (0.73 mM ATP, 22.3 mM Tricine, 0.11 mM EDTA, 33.3 mM DTT)
1× Luciferrin/CoA (11 mM Luciferin, 3.05 mM Coenzyme A, 10 mM HEPES)

Preparation of Screening Reagents

CV-1 cells were prepared 24 hours prior to the experiment by plating them into T-175 flasks or 500 cm² dishes in order to achieve 70-80% confluency on the day of the transfection. The number of cells to be transfected was determined by the number of plates to be screened. each 384 well plate requires 1.92×106 cells or 5000 cells per well. DNA Transfection Reagent was prepared by mixing the required plasmid DNAs with a cationic lipid transfection reagent FuGENE6 (Roche) by following the instructions provided with the reagents. Optimal DNA amounts were determined empirically per cell line and size of vessel to be transfected. 10-12 mL of media was added to the DNA Transfection Reagent and this mixture was added to the cells after aspirating media from the T175 cm² flask. Cells were then incubated at least 5 hours at 37° C. to prepare screening cells.

Luciferase assay reagent was prepared by combining before use (per 10 mL): 10 mL 1× Luciferase assay buffer, 0.54 mL of 1× Luciferrin/CoA; 0.54 mL of 0.2 M Magnesium sulfate Procedure Assay plates were prepared by dispensing 5 µL of compound per well of a 384 well plate to achieve final compound concentration of 10 µM and no more than 1% DMSO. Media was removed from the screening cells, the cells trypsinized, harvested cells by centrifugation, counted, and plated at a density of approximately 5000 cells per well in the 384 well assay plate prepared above in a volume of about 45 µL. Assay plates containing both compounds and screening cells (50 µL in total volume) were incubated for 20 hours at 37° C.

After incubation with compounds, media was removed from the cells and lysis buffer (30 µL/well) added. After 30 minutes at ambient temperature, luciferase assay buffer (30 µL/well) was added and the assay plates read on a luminometer (PE Biosystems Northstar reader with on-board injectors, or equivalent). Plates were read immediately after addition of luciferase assay buffer.

The LXR/LXRE co-transfection assay can be used to establish the EC$_{50}$/IC$_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethylpropionamide)) or a low control (DMSO/vehicle). The dose response curves are generated from an 8 point curve with concentrations differing by ½ LOG units. each point represents the average of 4 wells of data from a 384 well plate.

The data from this assay is fitted to the following equation, from the EC$_{50}$ value may be solved:

$$Y = \text{Bottom}^+(\text{Top} - \text{Bottom})/(1 + 10^{(\log EC50 - X)*HillSlope})$$

The EC$_{50}$/IC$_{50}$ is therefore defined as the concentration at which an agonist or antagonist elicits a response that is half way between the Top (maximum) and Bottom (baseline) values. The EC$_{50}$/IC$_{50}$ values represented are the averages of at least 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethyl-propionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example, 100% inhibition would indicate that the activity of a specific concentration of LXR agonist has been reduced to baseline levels, defined as the activity of the assay in the presence of DMSO only.

Compounds of the invention, when tested in this assay, demonstrated the ability to modulate the activity of LXRα and/or LXRβ. Preferably, the active compounds modulate the activity of LXR with a EC50 or IC50 of about 10 μM or less. More preferably, the EC50 or IC50 of the preferred active compounds is about 1 μM or less.

Example 110

In Vivo Studies

In order to evaluate direct regulation of key target genes by the compounds of the invention, animals are administered a single oral dose of the test compound and tissues collected at various time points after dose. Male $C_5$7BL/6 mice (n=8) are dosed by oral gavage with vehicle or compound. At various time points after the dose, animals are bled via the retro orbital sinus for plasma collection. Animals are then euthanized and tissues, such as liver and intestinal mucosa are collected and snap frozen for further analysis. Plasma is analyzed for a lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα-/- or LXRβ-/-) and C57BL/6 wild-type controls are used in this same protocol.

Plasma Lipid Evaluation:

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day −1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα-/- or LXRβ-/-) and $C_5$7BL/6 wild-type controls are used in this same protocol.

Example 111

Measured $EC_{50}$ or $IC_{50}$ for LXR for Compounds of the Invention

Compounds of the invention, when tested as described in Example 109, demonstrated the ability to modulate the activity of $LXR_\alpha$ and/or $LXR_\beta$. LXR activities for various compounds of the invention are presented in the following table; those compounds with $EC_{50}$ or $IC_{50}$ values <10 μM for at least one of $LXR_\alpha$ and $LXR_\beta$ are considered to be active. In the following Table, $IC_{50}$ or $EC_{50}$ data is represented as follows: A=<1 μM, B=1-10 μm, and C=>10 μM.

| No. | $EC_{50}$ |
|---|---|
| 2 | B |
| 3 | A |
| 4 | A |
| 5 | A |
| 6 | A |
| 7 | A |
| 8 | A |
| 11 | C |
| 15 | B |
| 16 | B |
| 17 | C |
| 18 | B |
| 19 | B |
| 20 | B |
| 21 | A |
| 22 | A |
| 23 | A |
| 24 | A |
| 25 | A |
| 26 | A |
| 27 | A |
| 29 | C |
| 34 | A |
| 35 | A |
| 38 | B |
| 39 | A |
| 40 | A |
| 41 | A |
| 42 | A |
| 45 | B |
| 47 | A |
| 48 | C |
| 49 | A |
| 51 | B |
| 52 | A |
| 53 | B |
| 54 | B |
| 55 | A |
| 56 | A |
| 57 | A |
| 58 | A |
| 59 | A |
| 60 | A |
| 62 | A |
| 63 | A |
| 64 | A |
| 65 | A |
| 66 | A |
| 67 | B |
| 68 | A |
| 69 | A |
| 70 | A |
| 71 | A |
| 72 | A |
| 73 | A |
| 74 | A |
| 75 | B |
| 76 | A |
| 77 | B |
| 78 | A |
| 79 | C |
| 80 | C |
| 81 | B |
| 82 | B |
| 85 | A |
| 86 | B |
| 87 | B |
| 88 | B |
| 89 | C |

1073
-continued

| No. | EC$_{50}$ |
|---|---|
| 90 | B |
| 91 | B |
| 92 | A |
| 93 | A |
| 94 | A |
| 95 | A |
| 96 | A |
| 97 | A |
| 98 | A |
| 99 | B |
| 100 | A |
| 101 | A |
| 102 | A |
| 103 | B |
| 104 | C |
| 105 | A |
| 106 | B |
| 107 | A |
| 108 | B |
| 109 | B |
| 110 | A |
| 111 | A |
| 112 | B |
| 113 | A |
| 114 | A |
| 115 | A |
| 116 | A |
| 117 | B |
| 118 | A |
| 119 | B |
| 120 | A |
| 121 | B |
| 122 | A |
| 123 | A |
| 124 | A |
| 125 | A |
| 126 | A |
| 127 | A |
| 128 | B |
| 130 | A |
| 131 | A |
| 132 | B |
| 133 | A |
| 134 | A |
| 135 | A |
| 136 | A |
| 137 | A |
| 138 | A |
| 139 | A |
| 140 | A |
| 142 | A |
| 143 | A |
| 144 | A |
| 145 | A |
| 146 | A |
| 147 | A |
| 148 | A |
| 149 | A |
| 150 | B |
| 456 | B |
| 485 | A |
| 508 | B |
| 527 | B |
| 544 | B |
| 545 | B |
| 547 | A |
| 558 | B |
| 568 | B |
| 586 | B |
| 587 | A |
| 588 | A |
| 589 | A |
| 590 | B |
| 591 | B |
| 592 | B |
| 593 | B |
| 710 | B |
| 716 | A |

1074
-continued

| No. | EC$_{50}$ |
|---|---|
| 724 | B |
| 733 | A |
| 739 | B |
| 755 | B |
| 804 | B |
| 859 | B |
| 970 | B |
| 1000 | B |
| 1029 | B |
| 1127 | B |
| 1128 | A |
| 1129 | A |
| 1130 | A |
| 1131 | A |
| 1133 | B |
| 1134 | A |
| 1135 | A |
| 1136 | B |
| 1137 | A |
| 1138 | B |
| 1139 | B |
| 1140 | B |
| 1142 | B |
| 1143 | A |
| 1144 | B |
| 1145 | A |
| 1146 | A |
| 1147 | A |
| 1148 | B |
| 1149 | A |
| 1150 | A |
| 1151 | B |
| 1152 | B |
| 1153 | B |
| 1154 | B |
| 1155 | B |
| 1156 | B |
| 1157 | A |
| 1158 | A |
| 1159 | A |
| 1160 | A |
| 1161 | A |
| 1162 | A |
| 1163 | B |
| 1164 | A |
| 1165 | B |
| 1166 | A |
| 1167 | A |
| 1168 | A |
| 1169 | A |
| 1170 | A |
| 1171 | B |
| 1172 | A |
| 1173 | A |
| 1174 | A |
| 1175 | A |
| 1176 | A |
| 1177 | A |
| 1178 | A |
| 1179 | B |
| 1180 | A |
| 1181 | A |
| 1182 | A |
| 1183 | A |
| 1184 | B |
| 1185 | A |
| 1186 | A |
| 1187 | A |
| 1188 | A |
| 1189 | A |
| 1190 | A |
| 1191 | A |
| 1192 | A |
| 1193 | B |
| 1194 | A |
| 1195 | A |
| 1196 | B |
| 1197 | A |

-continued

| No. | EC$_{50}$ |
|---|---|
| 1198 | A |
| 1199 | B |
| 1200 | B |
| 1201 | A |
| 1202 | A |
| 1203 | B |
| 1204 | B |
| 1205 | A |
| 1206 | A |
| 1207 | B |
| 1208 | B |
| 1209 | A |
| 1210 | A |
| 1211 | A |
| 1212 | A |
| 1213 | A |
| 1214 | B |
| 1215 | A |
| 1216 | A |
| 1217 | B |
| 1218 | A |
| 1219 | A |
| 1220 | A |
| 1221 | A |
| 1222 | A |
| 1223 | B |
| 1224 | A |
| 1225 | A |
| 1226 | B |
| 1227 | A |
| 1228 | A |
| 1229 | A |
| 1230 | B |
| 1231 | A |
| 1232 | B |
| 1233 | B |
| 1234 | A |
| 1235 | B |
| 1236 | B |
| 1237 | B |
| 1238 | A |
| 1239 | A |
| 1240 | A |
| 1241 | B |
| 1242 | A |
| 1243 | A |
| 1244 | B |
| 1245 | A |
| 1246 | B |
| 1247 | B |
| 1248 | B |
| 1249 | B |
| 1250 | B |
| 1251 | B |
| 1252 | B |
| 1253 | B |
| 1254 | A |
| 1255 | B |
| 1256 | B |
| 1257 | B |
| 1258 | B |
| 1259 | B |
| 1260 | B |
| 1261 | A |
| 1262 | A |
| 1263 | B |
| 1264 | B |
| 1265 | A |
| 1266 | B |
| 1267 | B |
| 1268 | A |
| 1269 | B |
| 1270 | B |
| 1271 | B |
| 1272 | B |
| 1273 | A |
| 1274 | B |
| 1275 | B |

-continued

| No. | EC$_{50}$ |
|---|---|
| 1276 | B |
| 1277 | A |
| 1278 | A |
| 1279 | B |
| 1280 | B |
| 1281 | A |
| 1282 | B |
| 1283 | B |
| 1284 | B |
| 1285 | B |
| 1286 | B |
| 1287 | B |
| 1288 | B |
| 1289 | B |
| 1290 | B |
| 1291 | B |
| 1292 | B |
| 1293 | B |
| 1294 | A |
| 1295 | B |
| 1296 | B |
| 1297 | B |
| 1298 | B |
| 1299 | B |
| 1300 | B |
| 1301 | A |
| 1302 | B |
| 1303 | B |
| 1304 | A |
| 1305 | B |
| 1306 | B |
| 1307 | A |
| 1308 | A |
| 1309 | B |
| 1310 | B |
| 1311 | B |
| 1312 | A |
| 1313 | A |
| 1314 | A |
| 1315 | A |
| 1316 | B |
| 1317 | A |
| 1318 | A |
| 1319 | A |
| 1320 | A |
| 1321 | A |
| 1322 | B |
| 1323 | B |
| 1324 | B |
| 1325 | A |
| 1326 | A |
| 1327 | A |
| 1328 | A |
| 1329 | A |
| 1330 | A |
| 1331 | A |
| 1332 | B |
| 1333 | B |
| 1334 | A |
| 1335 | A |
| 1336 | A |
| 1337 | A |
| 1338 | B |
| 1139 | A |
| 1340 | A |
| 1341 | B |
| 1342 | A |
| 1343 | B |
| 1344 | A |
| 1345 | A |
| 1346 | A |
| 1347 | B |
| 1348 | A |
| 1349 | A |
| 1350 | A |
| 1351 | B |
| 1352 | A |
| 1353 | A |

-continued

| No. | EC$_{50}$ |
|---|---|
| 1354 | B |
| 1355 | B |
| 1356 | B |
| 1357 | A |
| 1358 | A |
| 1359 | A |
| 1360 | A |
| 1361 | A |
| 1362 | B |
| 1363 | B |
| 1364 | B |
| 1365 | B |
| 1366 | A |
| 1367 | A |
| 1368 | A |
| 1369 | A |
| 1370 | A |
| 1371 | A |
| 1372 | A |
| 1373 | A |
| 1383 | A |
| 1384 | A |
| 1385 | A |
| 1386 | A |
| 1387 | A |
| 1388 | A |
| 1389 | A |
| 1390 | A |
| 1391 | A |
| 1393 | B |
| 1395 | A |
| 1397 | A |
| 1398 | B |
| 1399 | C |
| 1400 | A |
| 1401 | A |
| 1402 | A |
| 1403 | A |
| 1405 | C |
| 1414 | A |
| 1415 | A |
| 1417 | B |
| 1418 | B |
| 1419 | B |
| 1420 | A |
| 1421 | A |
| 1422 | A |
| 1423 | A |
| 1424 | A |
| 1425 | A |
| 1426 | A |
| 1427 | A |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

All of the U.S. patents, U.S. patent application publications, U.S. patent applications, foreign patents, foreign patent applications and non-patent publications referred to in this specification and/or listed in the Sheet, are incorporated herein by reference, in their entirety.

From the foregoing it will be appreciated that although specific embodiments of the invention have been described herein for purposes of illustration, various modifications may be made without deviating from the spirit and scope of the invention. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments. Accordingly, the invention is not limited except as by the appended claims.

We claim:

1. A compound according to one of the following formulas,

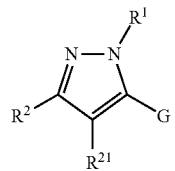

Ia

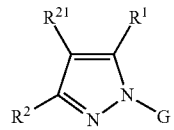

Id or a pharmaceutically acceptable salt thereof, wherein, (A) $R^1$ is -$L^1$-$R^5$, wherein
$L^1$ is a bond, $L^5$, or $L^6$, wherein $L^5$ is —[C($R^{15}$)$_2$]$_2$—, wherein
each $R^{15}$ is independently hydrogen, halogen, ($C_1$-$C_6$)alkyl, ($C_3$-$C_6$)cycloalkyl, or ($C_1$-$C_6$)haloalkyl;
$L^6$ is $C_3$-$C_8$ cycloalkyl, cyclo$C_{3-8}$haloalkyl, or heterocyclyl, wherein the cycloalkyl, cyclo$C_{3-8}$haloalkyl, or heterocyclyl are optionally substituted with one or more radicals of $R^{14}$;
$R^5$ is aryl, or heteroaryl, wherein $R^5$ is optionally substituted with one or more $R^{5a}$, wherein
each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C', or -A'-B'—C' wherein
A' is —O—;
B' is —[C($R^{15}$)$_2$]$_m$— or —$C_3$-$C_8$ cycloalkyl-;
C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl,
$R^2$ is -$L^3$-$R^7$, wherein
$L^3$ is a bond; and
$R^7$ is hydrogen, halogen, —Z, or —Y—Z, wherein
Y is —[C($R^{15'}$)$_2$]$_m$— or $C_2$-$C_6$alkenyl,
wherein each $R^{15'}$ is independently H, halogen, or ($C_1$-$C_6$)alkyl; and
Z is —H, halogen, —O$R^{11}$, —C(=O)$R^{11}$, —C(=O)O$R^{11}$, —C(=O)N($R^{11}$)$_2$, —C(=N—OH)$R^{11}$, or —C(=S)N($R^{11}$)$_2$;
$R^{21}$ is hydrogen, halogen, nitro, cyano, $C_1$-$C_6$alkyl, or $C_1$-$C_6$haloalkyl;
provided that $R^2$ and $R^{21}$ are not simultaneously —H;
each $R^{10}$ is independently —$R^{11}$, —C(=O)$R^{11}$, —CO$_2$$R^{11}$, or —SO$_2$$R^{11}$;

each $R^{11}$ is independently -hydrogen, $C_2$-$C_6$ alkenyl, $C_2$-$C_6$ alkynyl, ($C_3$-$C_8$ cycloalkenyl)-$C_1$-$C_6$ alkyl-, ($C_3$-$C_8$ cycloalkyl)-$C_2$-$C_6$ alkenyl-, —N($R^{12}$)$_2$, —$C_1$-$C_6$ alkyl, —$C_1$-$C_6$ haloalkyl, —$C_3$-$C_8$ cycloalkyl, —($C_1$-$C_6$)alkyl-($C_3$-$C_8$)cycloalkyl, aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl, wherein any of $R^{11}$ is optionally substituted with one or more radicals of $R^{12}$;

each $R^{12}$ is independently hydrogen, halogen, $C_1$-$C_6$haloalkyl, $C_1$-$C_6$ alkyl, $C_1$-$C_6$ alkoxy, ($C_0$-$C_6$ alkyl)C=O(O$R^{13}$); $C_0$-$C_6$ alkylO$R^{13}$, $C_0$-$C_6$ alkylCO$R^{13}$, $C_0$-$C_6$ alkylSO$_2R^{13}$, $C_0$-$C_6$ alkylCN, $C_0$-$C_6$ alkylCON($R^{13}$)$_2$, $C_0$-$C_6$ alkylCON$R^{13}$O$R^{13}$, $C_0$-$C_6$ alkylSO$_2$N($R^{13}$)$_2$, $C_0$-$C_6$ alkylS$R^{13}$, $C_0$-$C_6$ haloalkylO$R^{13}$, aryloxy, aralkyloxy, aryloxyalkyl, $C_0$-$C_6$alkoxyaryl, aryl $C_0$-$C_6$ alkylcarboxy, $C_0$-$C_6$ alkylN$R^{13}$SO$_2R^{13}$, —$C_0$-$C_6$ alkylN($R^{13}$)$_2$, or O$C_0$-$C_6$ alkylCOO$R^{13}$;

each $R^{13}$ is independently hydrogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;

each $R^{14}$ is independently $C_1$-$C_6$ alkyl, $C_1$-$C_6$ alkoxy, halogen, $C_1$-$C_6$ haloalkyl, $C_0$-$C_6$ alkylCON($R^{11}$)$_2$, $C_0$-$C_6$ alkylCON$R^{11}$O$R^{11}$, $C_0$-$C_6$ alkylO$R^{11}$, or $C_0$-$C_6$ alkylCOO$R^{11}$;

G is a group of the formula,

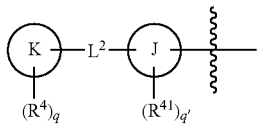

wherein
J is thienyl;
K is phenyl;
each $R^4$ is independently halogen, nitro, $C_2$-$C_6$ alkenyl, $C_3$-$C_8$ cycloalkyl, —$C_1$-$C_6$ alkyl-heterocyclyl, —$C_1$-$C_6$ alkyl-heteroaryl, —$C_1$-$C_6$ alkyl-aryl, -heterocyclyl-aryl, -heterocyclyl-heteroaryl, $CR^{11}$=$CR^{11}$COO$R^{11}$, aryloxy, —S-aryl, aralkyloxy, aryloxyalkyl, $C_1$-$C_6$ alkoxyaryl, aryl $C_0$-$C_6$ alkylcarboxy, $C_0$-$C_6$ alkoxyheteroaryl, $C_0$-$C_6$ alkoxyheterocyclyl, aryl, heteroaryl, heterocyclyl, -M, -E-M, or -D-E-M, wherein
D is —O—;
E is —[C($R^{15}$)$_2$]$_m$— or $C_3$-$C_8$ cycloalkyl;
M is $C_1$-$C_6$alkyl, $C_1$-$C_6$haloalkyl, —CO$R^{11}$, —COO$R^{11}$, —OC(=O)$R^{11}$, —CON($R^{11}$)$_2$, —C≡N, —O$R^{11}$, —OCON($R^{11}$)$_2$, —OCO$_2$—$R^{11}$, —N$_3$, —N$R^{11}$CO$R^{11}$, —N$R^{11}$SO$_2R^{11}$, —N($R^{11}$)$_2$, —N$R^{11}$COO$R^{11}$, —SO$R^{11}$, —SO$_2R^{11}$, —SO$_2$N$R^{11}$CO$R^{11}$, —SO$_2$N($R^{11}$)$_2$, or —S$R^{11}$, wherein at least one $R^4$ is -M or -E-M, wherein
E is —[C($R^{15}$)$_2$]$_m$—;
M is —COO$R^{11}$, —O$R^{11}$, —SO$_2R^{11}$, or —SO$_2$N($R^{11}$)$_2$;

wherein each $R^4$ is optionally substituted with one or more $R^{4a}$, wherein each $R^{4a}$ is independently halogen, aryloxy, aralkyloxy, aryloxyalkyl, —$C_1$-$C_6$ alkyl-aryl, $C_1$-$C_6$ alkoxyaryl, aryl $C_0$-$C_6$ alkylcarboxy, -M', -E'-M', or -D'-E'-M'

D' is —O—;
E' is —[C($R^{15}$)$_2$]$_m$— or $C_3$-$C_8$ cycloalkyl;
M' is —$C_1$-$C_6$alkyl, —$C_1$-$C_6$haloalkyl, CO$R^{11}$, —CON($R^{11}$)$_2$, —N($R^{11}$)COO$R^{11}$, —N($R^{11}$)$_2$, COO$R^{11}$, C≡N, O$R^{11}$, —N$R^{11}$CO$R^{11}$, N$R^{11}$SO$_2R^{11}$, SO$_2R^{11}$, SO$_2$N($R^{11}$)$_2$, or S$R^{11}$;

each $R^{41}$ is independently halogen, nitro, $C_1$-$C_6$ alkyl-heterocyclyl, —$C_1$-$C_6$ alkyl-heteroaryl, —$C_1$-$C_6$ alkyl-aryl, -M", -E"-M", or -D"-E"-M", wherein
D" is —O—;
E" is —[C($R^{15}$)$_2$]$_m$— or $C_3$-$C_8$ cycloalkyl;
M" is —$C_1$-$C_6$alkyl, —$C_1$-$C_6$haloalkyl, —CO$R^{11}$, —COO$R^{11}$, —CON($R^{11}$)$_2$, —C≡N, —O$R^{11}$, —OCON($R^{11}$)$_2$, —OCO$_2$—$R^{11}$, —N$_3$, —N$R^{11}$CO$R^{11}$, —N$R^{11}$SO$_2R^{11}$, —N($R^{11}$)$_2$, —N$R^{11}$COO$R^{11}$, —SO$R^{11}$, —SO$_2R^{11}$, —SO$_2$N$R^{11}$CO$R^{11}$, —SO$_2$N($R^{11}$)$_2$, or —S$R^{11}$, wherein each $R^{41}$ is optionally substituted with one or more $R^{4a}$;

$L^2$ is a bond, or $L^2$ is a $C_{2-6}$ alidiyl chain, wherein alidiyl chain is optionally interrupted by —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$N$R^{11}$—, —C($R^{11}$)$_2$N$R^{11}$—, —C≡C—, —O—, —S—, —N($R^{10}$)CO—, —N($R^{10}$)CO$_2$—, —CON($R^{10}$)—, —CON($R^{11}$)—, —CON($R^{11}$)O—, —CO—, —CO$_2$—, —OC(=O)—, —OC(=O)N($R^{10}$)—, —SO$_2$—, —N($R^{10}$)SO$_2$—, —SO$_2$N($R^{10}$)—; aryl, $C_3$-$C_8$ cycloalkyl, heteroaryl, or heterocyclyl wherein the aryl, cycloalkyl, heteroaryl, or heterocyclyl is optionally substituted with one or more $R^9$, wherein each $R^9$ is independently halogen, $C_1$-$C_6$ haloalkyl, $C_1$-$C_6$ alkyl, $C_1$-$C_6$ alkyloxy, $C_0$-$C_6$ alkyl or $C_1$-$C_6$ alkylCOO$R^{11}$;

each m is independently 0, 1, 2, 3, 4, 5 or 6;
q is 1, 2, 3, 4 or 5; and
q' is 0, 1, 2, 3, or 4, (B) provided that,
  (i) if the compound is defined by formula Ia, then $R^1$ is not 4-(NH$_2$SO$_2$)phenyl, 4-(CH$_3$SO$_2$)phenyl, or 4-(CH$_2$FSO$_2$)phenyl;
  (ii) if the compound is defined by formula Id, then
    (a) if $L^1$ is a bond, then $R^1$ is not thienyl or 5-methylthienyl; and
    (b) $R^1$ is not 4-Me-phenyl.

2. The compound according to claim 1, of the formula

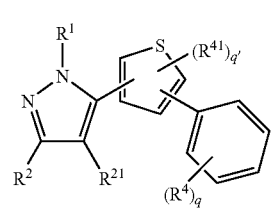

or a pharmaceutically acceptable salt thereof.

3. The compound according to claim 2, of the formula,

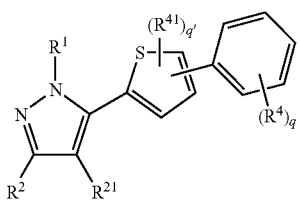

or a pharmaceutically acceptable salt thereof.

4. The compound according to claim 3, of the formula,

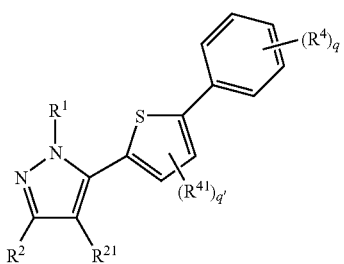

or a pharmaceutically acceptable salt thereof.

5. The compound according to claim 4, wherein $L^1$ is a bond; and $R^5$ is phenyl optionally substituted with one or more $R^{5a}$.

6. The compound according to claim 5, wherein each $R^{5a}$ is independently halogen, nitro, heterocyclyloxy, aryloxy, —C', —B'—C' or -A'-B'—C' wherein
A' is —O—;
B' is —[C(R$^{15}$)$_2$]$_m$—; and
C' is —H, halogen, —SO$_2$R$^{11}$, —OR$^{11}$, —SR$^{11}$, —COR$^{11}$, —SO$_2$N(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, —N(R$^{11}$)$_2$, aryl, heteroaryl, or heterocyclyl.

7. The compound according to claim 6, wherein each $R^{5a}$ is independently halogen, nitro, heterocyclyloxy, phenoxy, —C', —B'—C', or -A'-B'—C' wherein
A' is —O—;
B' is —[C(R$^{15}$)$_2$]$_m$—;
C' is —H, halogen, —OR$^{18}$, —COR$^{18}$, —C≡N, —C(O)OR$^{18}$, —OC(=O)R$^{18}$, —CON(R$^{18}$)$_2$, —OCON(R$^{18}$)$_2$, —NR$^{18}$COR$^{18}$, —NR$^{18}$CON(R$^{18}$)$_2$, —NR$^{18}$COOR$^{18}$, —N(R$^{18}$)$_2$, or heterocyclyl;
wherein each $R^{18}$ is independently —H, —C$_1$-C$_6$ alkyl, —C$_1$-C$_6$ haloalkyl, —C$_3$-C$_8$ cycloalkyl, aryl, heteroaryl, or heterocyclyl.

8. The compound according to claim 5, wherein each $R^{41}$ is independently halogen, —C$_1$-C$_6$alkyl, —C$_1$-C$_6$haloalkyl, —COR$^{16}$, —COOR$^{16}$, —CON(R$^{16}$)$_2$, —C≡N, —OR$^{16}$, or —N(R$^{16}$)$_2$,
wherein each $R^{16}$ is independently hydrogen, —C$_1$-C$_6$ alkyl, or —C$_1$-C$_6$ haloalkyl.

9. The compound according to claim 8, wherein each $R^{41}$ is independently halogen, —C$_1$-C$_6$alkyl, or —C$_1$-C$_6$haloalkyl.

10. The compound according to claim 5, wherein each $R^4$ is independently halogen, nitro, CR$^{11'}$=CR$^{11'}$COOR$^{11'}$, -M, or -E-M, wherein
E is —[C(R$^{15}$)$_2$]$_m$— or C$_3$-C$_8$ cycloalkyl;
M is C$_1$-C$_6$alkyl, C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —NR$^{11}$COR$^{11}$, —NR$^{11}$SO$_2$R$^{11}$, —N(R$^{11}$)$_2$, —NR$^{11}$COOR$^{11}$, —SO$_2$R$^{11}$, —SO$_2$NR$^{11}$COR$^{11}$, —SO$_2$N(R$^{11}$)$_2$, or —SR$^{11}$—,
wherein at least one $R^4$ is -M or -E-M, wherein
E is —[C(R$^{15}$)$_2$]$_m$—;
M is —COOR$^{11}$, —OR$^{11}$, —SO$_2$R$^{11}$, or —SO$_2$N(R$^{11}$)$_2$.

11. The compound according to claim 10, wherein each $R^4$ is independently halogen, CR$^{11'}$=CR$^{11'}$COOR$^{11'}$, -M, or -E-M, wherein
E is —[C(R$^{15}$)$_2$]$_m$— or C$_3$-C$_8$ cycloalkyl;
M is C$_1$-C$_6$alkyl, C$_1$-C$_6$haloalkyl, —COR$^{11'}$, —COOR$^{11'}$, —CON(R$^{11'}$)$_2$, —C≡N, —OR$^{11'}$, —NR$^{11'}$SO$_2$R$^{11'}$, —N(R$^{11'}$)$_2$, —SO$_2$R$^{11'}$, —SO$_2$NR$^{11'}$COR$^{11'}$, or —SO$_2$N(R$^{11'}$)$_2$,
wherein at least one $R^4$ is -M or -E-M, wherein
E is —[C(R$^{15}$)$_2$]$_m$—;
M is —COOR$^{11'}$, —OR$^{11'}$, —SO$_2$R$^{11'}$, or —SO$_2$N(R$^{11'}$)$_2$,
wherein each $R^{11'}$ is independently -hydrogen, —C$_1$-C$_6$ alkyl, or —C$_1$-C$_6$ haloalkyl,
wherein any of $R^{11'}$ is optionally substituted with one or more radicals of $R^{12'}$;
each $R^{12'}$ is independently halogen, C$_1$-C$_6$haloalkyl, C$_1$-C$_6$ alkyl, C$_1$-C$_6$ alkoxy, C=O(OR$^{13}$), COR$^{13}$, SO$_2$R$^{13}$, CON(R$^{13}$)$_2$, SO$_2$N(R$^{13}$)$_2$, or —N(R$^{13}$)$_2$.

12. The compound according to claim 11, wherein $R^2$ is -L$^3$-R$^7$, wherein
L$^3$ is a bond; and
$R^7$ is hydrogen, halogen, —C$_1$-C$_3$alkyl, —C$_1$-C$_3$haloalkyl, or —(C(R$^{15}$)$_2$)—Z, wherein
Z is –OR$^{11''}$ wherein R$^{11''}$ is —H or C$_1$-C$_6$alkyl.

13. The compound according to claim 7, wherein each $R^{41}$ is independently halogen, —C$_1$-C$_6$alkyl, or —C$_1$-C$_6$haloalkyl.

14. The compound according to claim 9, wherein each $R^4$ is independently halogen, CR$^{11'}$=CR$^{11'}$COOR$^{11'}$, -M, or -E-M, wherein
E is —[C(R$^{15}$)$_2$]$_m$— or C$_3$-C$_8$ cycloalkyl;
M is C$_1$-C$_6$alkyl, C$_1$-C$_6$haloalkyl, —COR$^{11'}$, —COOR$^{11'}$, —CON(R$^{11'}$)$_2$, —C≡N, —OR$^{11'}$, —NR$^{11'}$SO$_2$R$^{11'}$, —N(R$^{11'}$)$_2$, —SO$_2$R$^{11'}$, —SO$_2$NR$^{11'}$COR$^{11'}$, or —SO$_2$N(R$^{11'}$)$_2$,
wherein at least one $R^4$ is -M or -E-M, wherein
E is —[C(R$^{15}$)$_2$]$_m$—;
M is —COOR$^{11'}$, —OR$^{11'}$, —SO$_2$R$^{11'}$, or —SO$_2$N(R$^{11'}$)$_2$,
wherein each $R^{11'}$ is independently -hydrogen, —C$_1$-C$_6$ alkyl, or —C$_1$-C$_6$ haloalkyl,
wherein each $R^{11'}$ is optionally substituted with one or more radicals of $R^{12'}$;
each $R^{12'}$ is independently halogen, C$_1$-C$_6$ haloalkyl, C$_1$-C$_6$ alkyl, C$_1$-C$_6$ alkoxy, C=O (OR$^{13}$), COR$^{13}$, SO$_2$R$^{13}$, CON(R$^{13}$)$_2$, or —N(R$^{13}$)$_2$.

15. The compound according to claim 11, wherein each $R^{5a}$ is independently halogen, nitro, heterocyclyloxy, phenoxy, —C', —B'—C', or -A'-B'—C' wherein
A' is —O—;
B' is —[C(R$^{15}$)$_2$]$_m$—;
C' is —H, halogen, —OR$^{18}$, —COR$^{18}$, —C≡N, —C(O)OR$^{18}$, —OC(=O)R$^{18}$, —CON(R$^{18}$)$_2$, —OCON(R$^{18}$)$_2$, —NR$^{18}$COR$^{18}$, —NR$^{18}$CON(R$^{18}$)$_2$, —NR$^{18}$COOR$^{18}$, —N(R$^{18}$)$_2$, or heterocyclyl;
wherein each $R^{18}$ is independently —H, —C$_1$-C$_6$ alkyl, —C$_1$-C$_6$ haloalkyl, —C$_3$-C$_8$ cycloalkyl, aryl, heteroaryl, or heterocyclyl.

16. The compound according to claim 12, wherein each $R^4$ is independently halogen, $CR^{11'}$=$CR^{11'}COOR^{11'}$, -M, or -E-M, wherein
  E is —[C(R$^{15}$)$_2$]$_m$— or C$_3$-C$_8$ cycloalkyl;
  M is C$_1$-C$_6$alkyl, C$_1$-C$_6$haloalkyl, —COR$^{11'}$, —COOR$^{11'}$, —CON(R$^{11'}$)$_2$, —C≡N, —OR$^{11'}$, —NR$^{11'}$SO$_2$R$^{11'}$, —N(R$^{11'}$)$_2$, —SO$_2$R$^{11'}$, —SO$_2$NR$^{11'}$COR$^{11'}$, or —SO$_2$N(R$^{11'}$)$_2$,
wherein at least one $R^4$ is -M or -E-M, wherein
  E is —[C(R$^{15}$)$_2$]$_m$—;
  M is —COOR$^{11'}$, —OR$^{11'}$, —SO$_2$R$^{11'}$, or —SO$_2$N(R$^{11'}$)$_2$,
    wherein each R$^{11'}$ is independently -hydrogen, —C$_1$-C$_6$ alkyl, or —C$_1$-C$_6$ haloalkyl,
    wherein any of R$^{11'}$ is optionally substituted with one or more radicals of R$^{12'}$;
    each R$^{12'}$ is independently halogen, C$_1$-C$_6$haloalkyl, C$_1$-C$_6$ alkyl, C$_1$-C$_6$ alkoxy, C=O(OR$^{13}$), COR$^{13}$, SO$_2$R$^{13}$, CON(R$^{13}$)$_2$, SO$_2$N(R$^{13}$)$_2$, or —N(R$^{13}$)$_2$.

17. The compound according to claim 11, wherein each $R^{5a}$ is independently halogen, nitro, heterocyclyloxy, phenoxy, —C', —B'—C', or -A'-B'—C' wherein
  A' is —O—;
  B' is —[C(R$^{15}$)$_2$]$_m$—;
  C' is —H, halogen, —OR$^{18}$, —COR$^{18}$, —C≡N, —C(O)OR$^{18}$, —OC(=O)R$^{18}$, —CON(R$^{18}$)$_2$, —OCON(R$^{18}$)$_2$, —NR$^{18}$COR$^{18}$, —NR$^{18}$CON(R$^{18}$)$_2$, —NR$^{18}$COOR$^{18}$, —N(R$^{18}$)$_2$, or heterocyclyl;
    wherein each R$^{18}$ is independently —H, —C$_1$-C$_6$ alkyl, —C$_1$-C$_6$ haloalkyl, —C$_3$-C$_8$ cycloalkyl, aryl, heteroaryl, or heterocyclyl.

18. The compound according to claim 15, wherein each $R^{41}$ is independently hydrogen, halogen, —C$_1$-C$_6$alkyl, or —C$_1$-C$_6$haloalkyl.

19. A compound according to formula:

or a pharmaceutically acceptable salt thereof, wherein
(A) $R^1$ is -L$^1$-R$^5$, wherein
  L$^1$ is -L$^5$- or -L$^6$-, wherein
  each L$^5$ is —C(R$^{15}$)$_2$—,
    wherein
      each R$^{15}$ is independently hydrogen, halogen, (C$_1$-C$_6$)alkyl, or (C$_1$-C$_6$)halo alkyl; and
  L$^6$ is C$_3$-C$_8$ cycloalkyl, cycloC$_{3-8}$haloalkyl, or heterocyclyl, wherein the cycloalkyl, cycloC$_{3-8}$haloalkyl, or heterocyclyl are optionally substituted with one or more radicals of R$^{14}$;
  $R^5$ is aryl or heteroaryl optionally substituted with one or more R$^{5a}$, wherein
    each R$^{5a}$ is independently halogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, nitro, heterocyclyloxy, aryl, aryloxy, arylalkyl, aryloxyaryl, aryl C$_1$-C$_6$ alkoxy, —C', —B'—C', or -A'-B'—C' wherein
      A' is —O—;
      B' is —[C(R$^{15}$)$_2$]$_m$— or —C$_3$-C$_8$ cycloalkyl-;
      C' is —H, halogen, —SO$_2$R$^{11}$, —OR$^{11}$, —SR$^{11}$, —N$_3$, —COR$^{11}$, —SON(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, —N(R$^{11}$)$_2$, aryl, heteroaryl, or heterocyclyl;
$R^2$ is -L$^3$-R$^7$, wherein
  L$^3$ is a bond; and
  $R^7$ is hydrogen, halogen, —Z, or —Y—Z, wherein
    Y is —[C(R$^{15'}$)$_2$]$_m$— or C$_2$-C$_6$alkenyl,
      wherein each R$^{15'}$ is independently H, halogen, or (C$_1$-C$_6$)alkyl; and
    Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$;
$R^{21}$ is hydrogen, halogen, nitro, cyano, C$_1$-C$_6$alkyl, or C$_1$-C$_6$haloalkyl;
  provided that R$^2$ and R$^{21}$ are not simultaneously —H;
each $R^4$ is independently halogen, nitro, C$_2$-C$_6$ alkenyl, C$_3$-C$_8$ cycloalkyl, —C$_1$-C$_6$ alkyl-heterocyclyl, —C$_1$-C$_6$ alkyl-heteroaryl, —C$_1$-C$_6$ alkyl-aryl, -heterocyclyl-aryl, -heterocyclyl-heteroaryl, CR$^{11}$=CR$^{11}$COOR$^{11}$, aryloxy, —S-aryl, aralkyloxy, aryloxyalkyl, C$_1$-C$_6$ alkoxyaryl, aryl C$_0$-C$_6$ alkylcarboxy, C$_0$-C$_6$ alkoxyheteroaryl, C$_0$-C$_6$ alkoxyheterocyclyl, aryl, heteroaryl, heterocyclyl, -M, -E-M, or -D-E-M, wherein
  D is —O—;
  E is —[C(R$^{15}$)$_2$]$_m$— or C$_3$-C$_8$ cycloalkyl;
  M is C$_1$-C$_6$alkyl, C$_1$-C$_6$haloalkyl, —COR$^{11}$, —COOR$^{11}$, —OC(=O)R$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$,
wherein each $R^4$ is optionally substituted with one or more R$^{4a}$,
  wherein each R$^{4a}$ is independently halogen, aryloxy, aralkyloxy, aryloxyalkyl, —C$_1$-C$_6$ alkyl-aryl, C$_1$-C$_6$ alkoxyaryl, aryl C$_0$-C$_6$ alkylcarboxy, -M', -E'-M', or -D'-E'-M'
    D' is —O—;
    E' is —[C(R$^{15}$)$_2$]$_m$— or C$_3$-C$_8$ cycloalkyl;
    M' is —C$_1$-C$_6$alkyl, —C$_1$-C$_6$haloalkyl, COR$^{11}$, —CON(R$^{11}$)$_2$, —N(R$^{11}$)COOR$^{11}$, —N(R$^{11}$)$_2$, COOR$^{11}$, C≡N, OR$^{11}$, —NR$^{11}$COR$^{11}$, NR$^{11}$SO$_2$R$^{11}$, SO$_2$R$^{11}$, SON(R$^{11}$)$_2$, or SR$^{11}$;
each $R^{41}$ is independently halogen, nitro, C$_1$-C$_6$ alkyl-heterocyclyl, —C$_1$-C$_6$ alkyl-heteroaryl, —C$_1$-C$_6$ alkyl-aryl, -M'', -E''-M'', or -D''-E''-M'', wherein
  D'' is —O—;
  E'' is —[C(R$^{15}$)$_2$]$_m$— or C$_3$-C$_8$ cycloalkyl;
  M'' is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$,
wherein each $R^{41}$ is optionally substituted with one or more R$^{4a}$;
each R$^{11}$ is independently -hydrogen, C$_2$-C$_6$ alkenyl, C$_2$-C$_6$ alkynyl, (C$_3$-C$_8$ cycloalkenyl)-C$_1$-C$_6$ alkyl-, (C$_3$-C$_8$ cycloalkyl)-C$_2$-C$_6$ alkenyl-, —N(R$^{12}$)$_2$, —C$_1$-C$_6$ alkyl, —C$_1$-C$_6$ haloalkyl, —C$_3$-C$_8$ cycloalkyl, —(C$_1$-C$_6$)alkyl-(C$_3$-C$_8$)cycloalkyl, aryl, —(C$_1$-C$_6$)alkyl-aryl, heteroaryl, —($C_1$-$C_6$)alkyl-heteroaryl, heterocyclyl, or —($C_1$-$C_6$)alkyl-heterocyclyl,
  wherein any of $R^{11}$ is optionally substituted with one or more radicals of $R^{12}$;
    each $R^{12}$ is independently hydrogen, halogen, $C_1$-$C_6$haloalkyl, $C_1$-$C_6$ alkyl, $C_1$-$C_6$ alkoxy, ($C_0$-$C_6$ alkyl)C=O(O$R^{13}$); $C_0$-$C_6$ alkylO$R^{13}$, $C_0$-$C_6$ alkylCO$R^{13}$, $C_0$-$C_6$ alkylSO$_2$$R^{13}$, $C_0$-$C_6$ alkylCN, $C_0$-$C_6$ alkylCON($R^{13}$)$_2$, $C_0$-$C_6$ alkylCON$R^{13}$O$R^{13}$, $C_0$-$C_6$ alkylSO$_2$N($R^{13}$)$_2$, $C_0$-$C_6$ alkylS$R^{13}$, $C_0$-$C_6$ haloalkylO$R^{13}$, aryloxy, aralkyloxy, aryloxyalkyl, $C_0$-$C_6$alkoxyaryl, aryl $C_0$-$C_6$ alkylcarboxy, $C_0$-$C_6$ alkylN$R^{13}$SO$_2$$R^{13}$, —$C_0$-$C_6$ alkylN($R^{13}$)$_2$, or O$C_0$-$C_6$ alkylCOO$R^{13}$;
    each $R^{13}$ is independently hydrogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;
    each $R^{14}$ is independently $C_1$-$C_6$ alkyl, $C_1$-$C_6$ alkoxy, halogen, $C_1$-$C_6$ haloalkyl, $C_0$-$C_6$ alkylCON($R^{11}$)$_2$, $C_0$-$C_6$ alkylCON$R^{11}$O$R^{11}$, $C_0$-$C_6$ alkylO$R^{11}$, or $C_0$-$C_6$ alkylCOO$R^{11}$;
    wherein the aryl, cycloalkyl, heteroaryl, or heterocyclyl is optionally substituted with one or more $R^9$, wherein each $R^9$ is independently halogen, $C_1$-$C_6$ haloalkyl, $C_1$-$C_6$ alkyl, $C_1$-$C_6$ alkyloxy, $C_0$-$C_6$ alkyl or $C_1$-$C_6$ alkylCOO$R^{11}$;
  each m is independently 0, 1, 2, 3, 4, 5 or 6;
  q is 0, 1, 2, 3, 4 or 5; and
  q' is 0, 1, 2, 3, or 4,
    (B) provided that $R^1$ is not 4-(NH$_2$SO$_2$)phenyl, 4-(CH$_3$SO$_2$)phenyl, or 4-(CH$_2$FSO$_2$)phenyl.

20. The compound according to claim 19, wherein $R^5$ is phenyl, thienyl, furyl, pyrrolyl, thiazolyl, oxazolyl, isothiazolyl, isoxazolyl, pyridyl, pyrimidinyl, or pyrazinyl optionally substituted with one or more $R^{5a}$.

21. The compound according to claim 20, wherein each $R^{5a}$ is independently -halogen, —$C_1$-$C_6$alkyl, —$C_1$-$C_6$haloalkyl, —O$R^{11}$, —CO$R^{11}$, —C≡N, —C(O)O$R^{11}$, —CON($R^{11}$)$_2$, or —N($R^{11}$)$_2$.

22. The compound according to claim 20, wherein each $R^{41}$ is independently halogen, —$C_1$-$C_6$alkyl, or —$C_1$-$C_6$haloalkyl.

23. The compound according to claim 20, wherein each $R^4$ is independently halogen —$C_1$-$C_6$alkyl, —$C_1$-$C_6$haloalkyl, —CO$R^{11'}$, —COO$R^{11'}$, —CON($R^{11'}$)$_2$, —C≡N, —O$R^{11'}$, —N($R^{11'}$)$_2$, —SO$_2$$R^{11'}$, or —SO$_2$N($R^{11'}$)$_2$, wherein each $R^{11'}$ is independently -hydrogen, —$C_1$-$C_6$ alkyl, or —$C_1$-$C_6$ haloalkyl.

24. The compound according to formula:

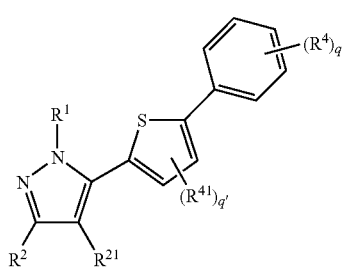

or a pharmaceutically acceptable salt thereof, wherein
(A) $R^1$ is -$L^1$-$R^5$, wherein $L^1$ is a bond; and
$R^5$ is heteroaryl optionally substituted with one or more $R^{5a}$,
  wherein
    each $R^{5a}$ is independently halogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, nitro, heterocyclyloxy, aryl, aryloxy, arylalkyl, aryloxyaryl, aryl $C_1$-$C_6$ alkoxy, —C', —B'—C', or -A'-B'—C'
    wherein
      A' is —O—;
      B' is —[C($R^{15}$)$_2$]$_m$— or —$C_3$-$C_8$ cycloalkyl-;
      C' is —H, halogen, —SO$_2$$R^{11}$, —O$R^{11}$, —S$R^{11}$, —N$_3$, —CO$R^{11}$, —SO$_2$N($R^{11}$)$_2$, —SO$_2$N$R^{11}$CO$R^{11}$, —C≡N, —C(O)O$R^{11}$, —OC(=O)$R^{11}$, —CON($R^{11}$)$_2$, —CON($R^{11}$)O$R^{11}$, —OCON($R^{11}$)$_2$, —N$R^{11}$CO$R^{11}$, —N$R^{11}$CON($R^{11}$)$_2$, —N$R^{11}$COO$R^{11}$, —N($R^{11}$)$_2$, aryl, heteroaryl, or heterocyclyl;
$R^2$ is -$L^3$-$R^7$, wherein
  $L^3$ is a bond; and
  $R^7$ is hydrogen, halogen, —Z, or —Y—Z, wherein
    Y is —[C($R^{15'}$)$_2$]$_m$— or $C_2$-$C_6$alkenyl,
      wherein each $R^{15'}$ is independently H, halogen, or ($C_1$-$C_6$)alkyl; and
    Z is —H, halogen, —O$R^{11}$, —C(=O)$R^{11}$, —C(=O)O$R^{11}$, —C(=O)N($R^{11}$)$_2$, —C(=N—OH)$R^{11}$, or —C(=S)N($R^{11}$)$_2$;
$R^{21}$ is hydrogen, halogen, nitro, cyano, $C_1$-$C_6$alkyl, or $C_1$-$C_6$haloalkyl;
provided that $R^2$ and $R^{21}$ are not simultaneously —H;
each $R^4$ is independently halogen, nitro, $C_2$-$C_6$ alkenyl, $C_3$-$C_8$ cycloalkyl, —$C_1$-$C_6$ alkyl-heterocyclyl, —$C_1$-$C_6$ alkyl-heteroaryl, —$C_1$-$C_6$ alkyl-aryl, -heterocyclyl-aryl, -heterocyclyl-heteroaryl, C$R^{11}$=C$R^{11}$COO$R^{11}$, aryloxy, —S-aryl, aralkyloxy, aryloxyalkyl, $C_1$-$C_6$ alkoxyaryl, aryl $C_0$-$C_6$ alkylcarboxy, $C_0$-$C_6$ alkoxyheteroaryl, $C_0$-$C_6$ alkoxyheterocyclyl, aryl, heteroaryl, heterocyclyl, -M, -E-M, or -D-E-M, wherein
  D is —O—;
  E is —[C($R^{15}$)$_2$]$_m$— or $C_3$-$C_8$ cycloalkyl;
  M is $C_1$-$C_6$alkyl, $C_1$-$C_6$haloalkyl, —CO$R^{11}$, —COO$R^{11}$, —OC(=O)$R^{11}$, —CON($R^{11}$)$_2$, —C≡N, —O$R^{11}$, —OCON($R^{11}$)$_2$, —OCO$_2$—$R^{11}$, —N$_3$, —N$R^{11}$CO$R^{11}$, —N$R^{11}$SO$_2$$R^{11}$, —N($R^{11}$)$_2$, —N$R^{11}$COO$R^{11}$, —SO$R^{11}$, —SO$_2$$R^{11}$, —SO$_2$N$R^{11}$CO$R^{11}$, —SO$_2$N($R^{11}$)$_2$, or —S$R^{11}$,
wherein each $R^4$ is optionally substituted with one or more $R^{4a}$,
  wherein each $R^{4a}$ is independently halogen, aryloxy, aralkyloxy, aryloxyalkyl, —$C_1$-$C_6$ alkyl-aryl, $C_1$-$C_6$ alkoxyaryl, aryl $C_0$-$C_6$ alkylcarboxy, -M', -E'-M', or -D'-E'-M'
    D' is —O—;
    E' is —[C($R^{15}$)$_2$]$_m$— or $C_3$-$C_8$ cycloalkyl;
    M' is —$C_1$-$C_6$alkyl, —$C_1$-$C_6$haloalkyl, CO$R^{11}$, —CON($R^{11}$)$_2$, —N($R^{11}$)COO$R^{11}$, —N($R^{11}$)$_2$, COO$R^{11}$, C≡N, O$R^{11}$, —N$R^{11}$CO$R^{11}$, N$R^{11}$SO$_2$$R^{11}$, SO$_2$$R^{11}$, SO$_2$N($R^{11}$)$_2$, or S$R^{11}$;
each $R^{41}$ is independently halogen, nitro, $C_1$-$C_6$ alkyl-heterocyclyl, —$C_1$-$C_6$ alkyl-heteroaryl, —$C_1$-$C_6$ alkyl-aryl, -M", -E"-M", or -D"-E"-M", wherein
  D" is —O—;
  E" is —[C($R^{15}$)$_2$]$_m$— or $C_3$-$C_8$ cycloalkyl;
  M" is —$C_1$-$C_6$alkyl, —$C_1$-$C_6$haloalkyl, —CO$R^{11}$, —COO$R^{11}$, —CON($R^{11}$)$_2$, —C≡N, —O$R^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$, wherein each R$^{41}$ is optionally substituted with one or more R$^{4a}$;

each R$^{11}$ is independently -hydrogen, C$_2$-C$_6$ alkenyl, C$_2$-C$_6$ alkynyl, (C$_3$-C$_8$ cycloalkenyl)-C$_1$-C$_6$ alkyl-, (C$_3$-C$_8$ cycloalkyl)-C$_2$-C$_6$ alkenyl-, —N(R$^{12}$)$_2$, —C$_1$-C$_6$ alkyl, —C$_1$-C$_6$ haloalkyl, —C$_3$-C$_8$ cycloalkyl, —(C$_1$-C$_6$)alkyl-(C$_3$-C$_8$)cycloalkyl, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl, wherein any of R$^{11}$ is optionally substituted with one or more radicals of R$^{12}$;

each R$^{12}$ is independently hydrogen, halogen, C$_1$-C$_6$haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCN, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_0$-C$_6$alkoxyaryl, aryl C$_0$-C$_6$ alkylcarboxy, C$_0$-C$_6$ alkylNR$^{13}$SO$_2$R$^{13}$, —C$_0$-C$_6$ alkylN(R$^{13}$)$_2$, or OC$_0$-C$_6$ alkylCOOR$^{13}$;

each R$^{13}$ is independently hydrogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

wherein the aryl, cycloalkyl, heteroaryl, or heterocyclyl is optionally substituted with one or more R$^9$, wherein each R$^9$ is independently halogen, C$_1$-C$_6$ haloalkyl, C$_1$-C$_6$ alkyl, C$_1$-C$_6$ alkyloxy, C$_0$-C$_6$ alkyl or C$_1$-C$_6$ alkylCOOR$^{11}$;

each m is independently 0, 1, 2, 3, 4, 5 or 6;

q is 0, 1, 2, 3, 4 or 5; and q' is 0, 1, 2, 3, or 4, (B) provided that R$^1$ is not 4-(NH$_2$SO$_2$)phenyl, 4-(CH$_3$SO$_2$)phenyl, or 4-(CH$_2$FSO$_2$)phenyl.

25. The compound according to claim 24, wherein R$^5$ is thienyl, furyl, pyrrolyl, thiazolyl, oxazolyl, isothiazolyl, isoxazolyl, pyridyl, pyrimidinyl, or pyrazinyl optionally substituted with one or more R$^{5a}$.

26. The compound according to claim 25, wherein R$^5$ is thienyl, furyl, pyrrolyl, thiazoyl, oxazoyl, isothiazoyl, or isoxazoyl optionally substituted with one or more R$^{5a}$.

27. The compound according to claim 26, wherein each R$^{5a}$ is independently -halogen, —C$_1$-C$_6$alkyl, —C$_1$-C$_6$haloalkyl, —OR$^{11}$, —COR$^{11}$, —C≡N, —C(O)OR$^{11}$, —CON(R$^{11}$)$_2$, or —N(R$^{11}$)$_2$.

28. The compound according to claim 26, wherein each R$^4$ is independently halogen —C$_1$-C$_6$alkyl, —C$_1$-C$_6$haloalkyl, —COR$^{11'}$, —COOR$^{11'}$, —CON(R$^{11'}$)$_2$, —C≡N, —OR$^{11'}$, —N(R$^{11'}$)$_2$, —SO$_2$(R$^{11'}$)$_2$, or —SO$_2$N(R$^{11'}$)$_2$, wherein each R$^{11'}$ is independently -hydrogen, —C$_1$-C$_6$ alkyl, or —C$_1$-C$_6$ haloalkyl.

29. The compound according to claim 26, wherein each R$^{41}$ is independently halogen, —C$_1$-C$_6$alkyl, or —C$_1$-C$_6$haloalkyl.

30. The compound according to claim 25, wherein R$^5$ is pyridyl, pyrimidinyl, or pyrazinyl optionally substituted with one or more R$^{5a}$.

31. The compound according to claim 30, wherein each R$^{5a}$ is -halogen, —C$_1$-C$_6$alkyl, —C$_1$-C$_6$haloalkyl, —OR$^{11}$, —COR$^{11}$, —C≡N, —C(O)OR$^{11}$, —CON(R$^{11}$)$_2$, or —N(R$^{11}$)$_2$.

32. The compound according to claim 30, wherein each R$^4$ is independently halogen —C$_1$-C$_6$alkyl, —C$_1$-C$_6$haloalkyl, —COR$^{11'}$, —COOR$^{11'}$, —CON(R$^{11'}$)$_2$, —C≡N, —OR$^{11'}$, —N(R$^{11'}$)$_2$, —SO$_2$R$^{11'}$, or —SO$_2$N(R$^{11'}$)$_2$, wherein each R$^{11'}$ is independently -hydrogen, —C$_1$-C$_6$ alkyl, or —C$_1$-C$_6$ haloalkyl.

33. The compound according to claim 30, wherein each R$^{41}$ is independently halogen, —C$_1$-C$_6$alkyl, or —C$_1$-C$_6$haloalkyl.

34. A compound according to one of the following formulas:

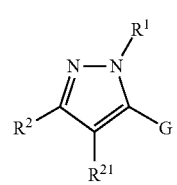

Ia

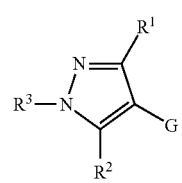

Ib

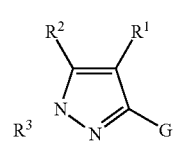

Ic

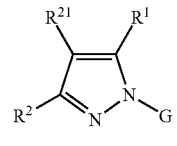

Id or a pharmaceutically acceptable salt thereof, wherein (A) R$^1$ is -L$^1$-R$^5$, wherein L$^1$ is a bond, L$^5$, or L$^6$, wherein L$^5$ is —[C(R$^{15}$)$_2$]$_m$—, wherein each R$^{15}$ is independently hydrogen, halogen, (C$_1$-C$_6$)alkyl, (C$_3$-C$_6$)cycloalkyl, or (C$_1$-C$_6$)haloalkyl;

L$^6$ is C$_3$-C$_8$ cycloalkyl, cycloC$_{3-8}$haloalkyl, or heterocyclyl, wherein the cycloalkyl, cycloC$_{3-8}$haloalkyl, or heterocyclyl are optionally substituted with one or more radicals of R$^{14}$;

R$^5$ is aryl, heterocyclyl, or heteroaryl, wherein R$^5$ is optionally substituted with one or more R$^{5a}$, wherein each R$^{5a}$ is independently halogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$alkenyl-, nitro, heterocyclyloxy, aryl, aryloxy, arylalkyl, aryloxyaryl, aryl C$_1$-C$_6$ alkoxy, —C', —B'—C', or -A'-B'—C' wherein A' is —O—;

B' is —[C(R$^{15}$)$_2$]$_m$— or —C$_3$-C$_8$ cycloalkyl-;

C' is —H, halogen, —SO$_2$R$^{11}$, —OR$^{11}$, —SR$^{11}$, —N$_3$, —COR$^{11}$, —SO$_2$N(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$,　　　—NR$^{11}$COOR$^{11}$,
—N(R$^{11}$)$_2$, aryl, heteroaryl, or heterocyclyl, R$^2$ is -L$^3$-R$^7$, wherein L$^3$ is a bond; and R$^7$ is hydrogen, halogen, —Z, or —Y—Z, wherein Y is —[C(R$^{15'}$)$_2$]$_m$— or C$_2$-C$_6$alkenyl,
　　　wherein each R$^{15'}$ is independently H, halogen, or (C$_1$-C$_6$)alkyl; and Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$;

R$^{21}$ is hydrogen, halogen, nitro, cyano, C$_1$-C$_6$alkyl, or C$_1$-C$_6$haloalkyl;

provided that R$^2$ and R$^{21}$ are not simultaneously —H;

R$^3$ is -L-R$^6$, wherein

L is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$— wherein n is 0-6; each w is independently 0-5; and each X$^3$ is independently a bond, —C(R$^{11}$)$_2$—, —C(R$^{11}$)$_2$C(R$^{11}$)$_2$—, —C(R$^{11}$)=C(R$^{11}$)—, —C≡C—, —CO—, —CS—, —CONR$^{10}$—, —C(=N)(R$^{11}$)—, —C(=N—OR$^{11}$)—, —C[=N—N(R$^{11}$)$_2$], —CO$_2$—, —SO$_2$—, or —SO$_2$N(R$^{10}$)—; and Y$^3$ is —O—, —S—, —NR$^7$—, —N(R$^{10}$)CO—, —N(R$^{10}$)CO$_2$—, —OCO—, —OC(=O)N(R$^{10}$)—, —NR$^{10}$CONR$^{10}$—, —N(R$^{10}$)SO$_2$—, or —NR$^{10}$CSNR$^{10}$—;

or L is a C$_{2-6}$ alidiyl chain, wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$); and R$^6$ is C$_1$-C$_6$ alkyl, C$_1$-C$_6$ haloalkyl, aryl, C$_3$-C$_8$ cycloalkyl, heteroaryl, heterocyclyl, —CN, —C(=O)R$^{11}$, —C(=O)OR$^{11}$, —C(=O)N(R$^{11}$)$_2$, —N(R$^{11}$)$_2$, —SO$_2$R$^{11}$, —S(=O)$_2$N(R$^{11}$)$_2$, —C(=O)N(R$^{11}$)N(R$^{11}$)$_2$, or —C(=O)N(R$^{11}$)(OR$^{11}$), wherein the aryl, heteroaryl, cycloalkyl, or heterocyclyl is optionally substituted with one or more R$^{6a}$, wherein each R$^{6a}$ is independently —Z", —Y"—Z", or —X"—Y"—Z", wherein X" is —O—;

Y" is —[C(R$^{15}$)$_2$]$_m$—, —C$_2$-C$_6$ alkenyl, C$_3$-C$_8$ cycloalkyl, heterocyclyl, aryl, or heteroaryl, wherein the aryl, heteroaryl, cycloalkyl, or heterocyclyl is optionally substituted with at least one group which is each independently Z";

Z" is —H, —CN, halogen, —OR$^{11}$, —C(=O)R$^{11}$, —C(=O)OR$^{11}$, —C(=O)N(R$^{11}$)$_2$, —N(R$^{11}$)$_2$, —N$_3$, —SO$_2$R$^{11}$, —S(=O)$_2$N(R$^{11}$)$_2$, —C(=O)N(R$^{11}$)N(R$^{11}$)$_2$, —N(R$^{11}$)C(O)N(R$^{11}$)$_2$, —OC(=O)—OR$^{11}$, —C(=O)N(R$^{11}$)(OR$^{11}$), —OC(=O)—R$^{11}$, —OC(=O)—N(R$^{11}$)$_2$, or —N(R$^{11}$)COOR$^{11}$;

each R$^{10}$ is independently —R$^{11}$, —C(=O)R$^{11}$, —CO$_2$R$^{11}$, or —SO$_2$R$^{11}$;

each R$^{11}$ is independently -hydrogen, C$_2$-C$_6$ alkenyl, C$_2$-C$_6$ alkynyl, (C$_3$-C$_8$ cycloalkenyl)-C$_1$-C$_6$ alkyl-, (C$_3$-C$_8$ cycloalkyl)-C$_2$-C$_6$ alkenyl-, —N(R$^{12}$)$_2$, —C$_1$-C$_6$ alkyl, —C$_1$-C$_6$ haloalkyl, —C$_3$-C$_8$ cycloalkyl, —(C$_1$-C$_6$)alkyl-(C$_3$-C$_8$)cycloalkyl, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl, wherein any of R$^{11}$ is optionally substituted with one or more radicals of R$^{12}$;

each R$^{12}$ is independently hydrogen, halogen, C$_1$-C$_6$haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCN, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_0$-C$_6$alkoxyaryl, aryl C$_0$-C$_6$ alkylcarboxy, C$_0$-C$_6$ alkylNR$^{13}$SO$_2$R$^{13}$, —C$_0$-C$_6$ alkyN(R$^{13}$)$_2$, or OC$_0$-C$_6$ alkylCOOR$^{13}$;

each R$^{13}$ is independently hydrogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$ alkylCONR$^{11}$OR$^{11}$, C$_0$-C$_6$ alkylOR$^{11}$, or C$_0$-C$_6$ alkylCOOR$^{11}$;

G is a group of the formula:

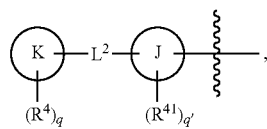

wherein J is thienyl, K is heteroaryl; and L$^2$ is a bond;

each R$^4$ is independently halogen, nitro, C$_2$-C$_6$ alkenyl, C$_3$-C$_8$ cycloalkyl, —C$_1$-C$_6$ alkyl-heterocyclyl, —C$_1$-C$_6$ alkyl-heteroaryl, —C$_1$-C$_6$ alkyl-aryl, -heterocyclyl-aryl, -heterocyclyl-heteroaryl, CR$^{11}$=CR$^{11}$COOR$^{11}$, aryloxy, —S-aryl, aralkyloxy, aryloxyalkyl, C$_1$-C$_6$ alkoxyaryl, aryl C$_0$-C$_6$ alkylcarboxy, C$_0$-C$_6$ alkoxyheteroaryl, C$_0$-C$_6$ alkoxyheterocyclyl, aryl, heteroaryl, heterocyclyl, -M, -E-M, or -D-E-M, wherein D is —O—;

E is —[C(R$^{15}$)$_2$]$_m$— or C$_3$-C$_8$ cycloalkyl;

M is C$_1$-C$_6$alkyl, C$_1$-C$_6$haloalkyl, —COR$^{11}$, —COOR$^{11}$, —OC(=O)R$^{11}$, —CON(R$^{11}$)$_2$, —C≡N, —OR$^{11}$, —OCON(R$^{11}$)$_2$, —OCO$_2$R$^{11}$, N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$, COR$^{11}$, —SO$_2$N(R$^{11}$)$_2$, or —SR$^{11}$, wherein each R$^4$ is optionally substituted with one or more R$^{4a}$, wherein each R$^{4a}$ is independently halogen, aryloxy, aralkyloxy, aryloxyalkyl, —C$_1$-C$_6$ alkyl-aryl, C$_1$-C$_6$ alkoxyaryl, aryl C$_0$-C$_6$ alkylcarboxy, -M', -E'-M', or -D'-E'-M'

D' is —O—;

E' is —[C(R$^{15}$)$_2$]$_m$— or C$_3$-C$_8$ cycloalkyl;

M' is —C$_1$-C$_6$alkyl, —C$_1$-C$_6$haloalkyl, COR$^{11}$, —CON(R$^{11}$)$_2$, —N(R$^{11}$)COOR$^{11}$, —N(R$^{11}$)$_2$, COOR$^{11}$, C≡N, OR$^{11}$, —NR$^{11}$COR$^{11}$, NR$^{11}$SO$_2$R$^{11}$, SO$_2$R$^{11}$, SO$_2$N(R$^{11}$)$_2$, or SR$^{11}$;

each R$^{41}$ is independently halogen, nitro, C$_1$-C$_6$ alkyl-heterocyclyl, —C$_1$-C$_6$ alkyl-heteroaryl, —C$_1$-C$_6$ alkyl-aryl, -M", -E"-M", or -D"-E"-M", wherein D" is —O—;

E" is —[C(R$^{15}$)$_2$]$_m$— or C$_3$-C$_8$ cycloalkyl;
M" is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$, wherein each R$^{41}$ is optionally substituted with one or more R$^{4a}$;

wherein the aryl, cycloalkyl, heteroaryl, or heterocyclyl is optionally substituted with one or more R$^9$, wherein each R$^9$ is independently halogen, C$_1$-C$_6$ haloalkyl, C$_1$-C$_6$ alkyl, C$_1$-C$_6$ alkyloxy, C$_0$-C$_6$ alkyl or C$_1$-C$_6$ alkylCOOR$^{11}$;

each m is independently 0, 1, 2, 3, 4, 5 or 6;
q is 0, 1, 2, 3, 4 or 5; and
q' is 0, 1, 2, 3, or 4, (B) provided that,
(i) if the compound is defined by formula Ia, then R$^1$ is not 4-(NH$_2$SO$_2$)phenyl, 4-(CH$_3$SO$_2$)phenyl, or 4-(CH$_2$FSO$_2$)phenyl;
(ii) if the compound is defined by formula Ib, then
(a) R$^2$ is not 4-(NH$_2$SO$_2$)phenyl, 4-(CH$_3$SO$_2$)phenyl, or 4-(CH$_2$FSO$_2$)phenyl; and
(b) R$^1$ is not 4-hydroxyphenyl;
(iii) if the compound is defined by formula Ic, then R$^2$ is not 4-(NH$_2$SO$_2$)phenyl, 4-(CH$_3$SO$_2$)phenyl, or 4-(CH$_2$FSO$_2$)phenyl;
(iv) if the compound is defined by formula Id, then
(a) if L$^1$ is a bond, then R$^1$ is not thienyl or 5-methylthienyl; and
(b) R$^1$ is not 4-Me-phenyl.

35. The compound according to claim 34, wherein K is thienyl, furyl, pyrrolyl, thiazolyl, oxazolyl, isothiazolyl, isoxazolyl, pyridyl, pyrimidinyl, or pyrazinyl.

36. The compound according to claim 35, wherein K is pyridyl.

37. The compound according to claim 36, wherein
L$^1$ is a bond; and
R$^5$ is phenyl optionally substituted with one or more R$^{5s}$.

38. A compound according to one of the following formulas:

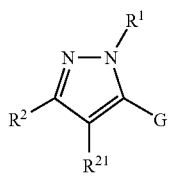

Ia

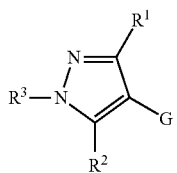

Ib

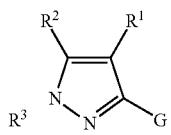

Ic

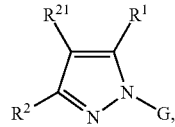

Id or a pharmaceutically acceptable salt thereof, wherein
(A) R$^1$ is -L$^1$-R$^5$, wherein
L$^1$ is a bond, L$^5$, or L$^6$, wherein L$^5$ is —[C(R$^{15}$)$_2$]$_m$—, wherein
each R$^{15}$ is independently hydrogen, halogen, (C$_1$-C$_6$)alkyl, (C$_3$-C$_6$)cycloalkyl, or (C$_1$-C$_6$)haloalkyl;
L$^6$ is C$_3$-C$_8$ cycloalkyl, cycloC$_{3-8}$haloalkyl, or heterocyclyl, wherein the cycloalkyl, cycloC$_{3-8}$haloalkyl, or heterocyclyl are optionally substituted with one or more radicals of R$^{14}$;

R$^5$ is aryl, heterocyclyl, or heteroaryl, wherein R$^5$ is optionally substituted with one or more R$^{5a}$, wherein
each R$^{5a}$ is independently halogen, C$_1$-C$_6$ alkyl, C$_2$-C$_6$ alkenyl, alkenyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, nitro, heterocyclyloxy, aryl, aryloxy, arylalkyl, aryloxyaryl, aryl C$_1$-C$_6$ alkoxy, —C', —B'—C', or -A'-B'—C' wherein
A' is —O—;
B' is —[C(R$^{15}$)$_2$]$_m$— or —C$_3$-C$_8$ cycloalkyl-;
C' is —H, halogen, —SO$_2$R$^{11}$, —OR$^{11}$, —SR$^{11}$, —N$_3$, —COR$^{11}$, —SO$_2$N(R$^{11}$)$_2$, —SO$_2$NR$^{11}$COR$^{11}$, —C≡N, —C(O)OR$^{11}$, —OC(=O)R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, —N(R$^{11}$)$_2$, aryl, heteroaryl, or heterocyclyl, R$^2$ is -L$^3$-R$^7$, wherein
L$^3$ is a bond; and
R$^7$ is hydrogen, halogen, —Z, or —Y—Z, wherein
Y is —[C(R$^{15'}$)$_2$]$_m$— or C$_2$-C$_6$alkenyl,
wherein each R$^{15'}$ is independently H, halogen, or (C$_1$-C$_6$)alkyl; and
Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$;

R$^{21}$ is hydrogen, halogen, nitro, cyano, C$_1$-C$_6$alkyl, or C$_1$-C$_6$haloalkyl;
provided that R$^2$ and R$^{21}$ are not simultaneously —H;
R$^3$ is -L-R$^6$, wherein
L is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$— wherein
n is 0-6; each w is independently 0-5; and
each X$^3$ is independently a bond, —C(R$^{11}$)$_2$—, —C(R$^{11}$)$_2$C(R$^{11}$)$_2$—, —C(R$^{11}$)=C(R$^{11}$)—, —C≡C—, —CO—, —CS—, —CONR$^{10}$—, —C(=N)(R$^{11}$)—, —C(=N—OR$^{11}$)—, —C[=N—N(R$^{11}$)$_2$], —CO$_2$—, —SO$_2$—, or —SO$_2$N(R$^{10}$)—; and
Y$^3$ is —O—, —S—, —NR$^7$—, —N(R$^{10}$)CO—, —N(R$^{10}$)CO$_2$—, —OCO—, —OC(=O)N(R$^{10}$)—, —NR$^{10}$CONR$^{10}$—, —N(R$^{10}$)SO$_2$—, or —NR$^{10}$CSNR$^{10}$—;

or L is a C$_{2-6}$ alidiyl chain, wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$); and R$^6$ is C$_1$-C$_6$ alkyl, C$_1$-C$_6$ haloalkyl, aryl, C$_3$-C$_8$ cycloalkyl, heteroaryl, heterocyclyl, —CN, —C(=O)R$^{11}$, —C(=O)OR$^{11}$, —C(=O)N(R$^{11}$)$_2$, —N(R$^{11}$)$_2$, —SO$_2$R$^{11}$, —S(=O)$_2$N(R$^{11}$)$_2$, —C(=O)N(R$^{11}$)N(R$^{11}$)$_2$, or —C(=O)N(R$^{11}$)(OR$^{11}$), wherein
the aryl, heteroaryl, cycloalkyl, or heterocyclyl is optionally substituted with one or more R$^{6a}$, wherein
each R$^{6a}$ is independently —Z'', —Y''—Z'', or —X''—Y''—Z'', wherein
X'' is —O—;
Y'' is —[C(R$^{15}$)$_2$]$_m$—, —C$_2$-C$_6$ alkenyl, C$_3$-C$_8$ cycloalkyl, heterocyclyl, aryl, or heteroaryl, wherein
the aryl, heteroaryl, cycloalkyl, or heterocyclyl is optionally substituted with at least one group which is each independently Z'';
Z'' is —H, —CN, halogen, —OR$^{11}$, —C(=O)R$^{11}$, —C(=O)OR$^{11}$, —C(=O)N(R$^{11}$)$_2$, —N(R$^{11}$)$_2$, —N$_3$, —SO$_2$R$^{11}$, —S(=O)$_2$N(R$^{11}$)$_2$, —C(=O)N(R$^{11}$)N(R$^{11}$)$_2$, —N(R$^{11}$)C(O)N(R$^{11}$)$_2$, —OC(=O)—OR$^{11}$, —C(=O)N(R$^{11}$)(OR$^{11}$), —OC(=O)—R$^{11}$, —OC(=O)—N(R$^{11}$)$_2$, or —N(R$^{11}$)COOR$^{11}$;

each R$^{10}$ is independently —R$^{11}$, —C(=O)R$^{11}$, —CO$_2$R$^{11}$, or —SO$_2$R$^{11}$;
each R$^{11}$ is independently -hydrogen, C$_2$-C$_6$ alkenyl, C$_2$-C$_6$ alkynyl, (C$_3$-C$_8$ cycloalkenyl)-C$_1$-C$_6$ alkyl-, (C$_3$-C$_8$ cycloalkyl)-C$_2$-C$_6$ alkenyl-, —N(R$^{12}$)$_2$, —C$_1$-C$_6$ alkyl, —C$_1$-C$_6$ haloalkyl, —C$_3$-C$_8$ cycloalkyl, —(C$_1$-C$_6$)alkyl-(C$_3$-C$_8$)cycloalkyl, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl,
wherein any of R$^{11}$ is optionally substituted with one or more radicals of R$^{12}$;
each R$^{12}$ is independently hydrogen, halogen, C$_1$-C$_6$haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCN, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_0$-C$_6$alkoxyaryl, aryl C$_0$-C$_6$ alkylcarboxy, C$_0$-C$_6$ alkylNR$^{13}$SO$_2$R$^{13}$, —C$_0$-C$_6$ alkyN(R$^{13}$)$_2$, or OC$_0$-C$_6$ alkylCOOR$^{13}$;

each R$^{13}$ is independently hydrogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;
each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$ alkylCONR$^{11}$OR$^{11}$, C$_0$-C$_6$ alkylOR$^{11}$, or C$_0$-C$_6$ alkyl-COOR$^{11}$;
G is a group of the formula:

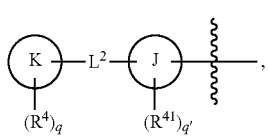

wherein J is thienyl; K is absent; and L$^2$ is —SO$_2$— or —CO—;

each R$^4$ is independently heterocyclyl, —OR$^{11}$, or —N(R$^{11}$)$_2$,
wherein the heterocyclyl is optionally substituted with one or more -E'-M', wherein
E' is —[C(R$^{15}$)$_2$]$_m$— or C$_3$-C$_8$ cycloalkyl;
M' is COR$^{11}$, COOR$^{11}$, C≡N, OR$^{11}$, —NR$^{11}$COR$^{11}$, NR$^{11}$SO$_2$R$^{11}$, SO$_2$R$^{11}$, SO$_2$N(R$^{11}$)$_2$, or SR$^{11}$,
each R$^{41}$ is independently halogen, nitro, C$_1$-C$_6$ alkyl-heterocyclyl, —C$_1$-C$_6$ alkyl-heteroaryl, —C$_1$-C$_6$ alkyl-aryl, -M'', -E''-M'', or -D''-E''-M'', wherein
D'' is —O—;
E'' is —[C(R$^{15}$)$_2$]$_m$— or C$_3$-C$_8$ cycloalkyl;
M'' is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCO$_2$—R$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$,
wherein each R$^{41}$ is optionally substituted with one or more R$^{4a}$;
wherein the aryl, cycloalkyl, heteroaryl, or heterocyclyl is optionally substituted with one or more R$^9$, wherein
each R$^9$ is independently halogen, C$_1$-C$_6$ haloalkyl, C$_1$-C$_6$ alkyl, C$_1$-C$_6$ alkyloxy, C$_0$-C$_6$ alkyl or C$_1$-C$_6$ alkylCOOR$^{11}$;
each m is independently 0, 1, 2, 3, 4, 5 or 6;
q is 1; and
q' is 0, 1, 2, 3, or 4,
(B) provided that,
(i) R$^4$ is bonded directly to L$^2$;
(ii) if L$^2$ is SO$_2$, then R$^5$ is substituted with at least one R$^{5a}$;
(iii) if the compound is defined by formula Ia, then R$^1$ is not 4-(NH$_2$SO$_2$)phenyl, 4-(CH$_3$SO$_2$)phenyl, or 4-(CH$_2$FSO$_2$)phenyl;
(iv) if the compound is defined by formula Ib, then
(a) R$^2$ and R$^3$ are not 4-(NH$_2$SO$_2$)-phenyl, 4-(CH$_3$SO$_2$)-phenyl, or 4-(CH$_2$FSO$_2$)phenyl; and
(b) R$^1$ is not 4-hydroxyphenyl;
(v) if the compound is defined by formula Ic, then R$^2$ and R$^3$ are not 4-(NH$_2$SO$_2$)phenyl, 4-(CH$_3$SO$_2$)-phenyl, or 4-(CH$_2$FSO$_2$)phenyl;
(vi) if the compound is defined by formula Id, then
(a) if L$^1$ is a bond, then R$^1$ is not thienyl or 5-methylthienyl; and
(b) R$^1$ is not 4-Me-phenyl.

39. A pharmaceutical composition comprising a compound of claim 1, or a pharmaceutically acceptable salt thereof in a pharmaceutically acceptable carrier.

40. A compound selected from the group consisting of
2-(4-chloro-5-(5-(3-(methylsulfonyl)phenyl)thiophen-2-yl)-1-(4-(trifluoromethyl)pyridin-3-yl)-1H-pyrazol-3-yl)propan-2-ol;
2-(4-chloro-1-(3-fluoro-2-methylphenyl)-5-(5-(3-(methylsulfonyl)phenyl)thiophen-2-yl)-1H-pyrazol-3-yl)propan-2-ol;
2-(4-bromo-1-(3-fluoro-2-methylphenyl)-5-(5-(3-(methylsulfonyl)phenyl)thiophen-2-yl)-1H-pyrazol-3-yl)propan-2-ol;
2-(4-chloro-1-(2,3-difluorophenyl)-5-(5-(3-(methylsulfonyl)phenyl)thiophen-2-yl)-1H-pyrazol-3-yl)propan-2-ol;
2-(1-(2-(difluoromethoxy)phenyl)-5-(5-(3-(methylsulfonyl)phenyl)thiophen-2-yl)-1H-pyrazol-3-yl)propan-2-ol;

2-(1-(3-fluoro-2-(trifluoromethyl)phenyl)-5-(5-(3-(methylsulfonyl)phenyl)thiophen-2-yl)-1H-pyrazol-3-yl)propan-2-ol;
2-(4-chloro-1-(2,6-dimethylphenyl)-5-(5-(3-(methylsulfonyl)phenyl)thiophen-2-yl)-1H-pyrazol-3-yl)propan-2-ol;
2-(4-chloro-1-(2-fluorophenyl)-5-(5-(3-(methylsulfonyl)phenyl)thiophen-2-yl)-1H-pyrazol-3-yl)propan-2-ol;
2-(4-chloro-1-(2,6-difluorophenyl)-5-(5-(3-(methylsulfonyl)phenyl)thiophen-2-yl)-1H-pyrazol-3-yl)propan-2-ol;
2-(4-chloro-1-(2-chloro-6-fluorophenyl)-5-(5-(3-(methylsulfonyl)phenyl)thiophen-2-yl)-1H-pyrazol-3-yl)propan-2-ol;
2-(4-chloro-1-(2-chloro-6-methylphenyl)-5-(5-(3-(methylsulfonyl)phenyl)thiophen-2-yl)-1H-pyrazol-3-yl)propan-2-ol;
2-(4-chloro-1-(2,4-difluorophenyl)-5-(5-(3-(methylsulfonyl)phenyl)thiophen-2-yl)-1H-pyrazol-3-yl)propan-2-ol;
2-(1-(2-chlorophenyl)-5-(4-methyl-5-(3-(methylsulfonyl)phenyl)thiophen-2-yl)-1H-pyrazol-3-yl)propan-2-ol;
2-(5-(4-bromo-5-(3-(methylsulfonyl)phenyl)thiophen-2-yl)-1-(2-chlorophenyl)-1H-pyrazol-3-yl)propan-2-ol;
2-(5-(4-bromo-3-methyl-5-(3-(methylsulfonyl)phenyl)thiophen-2-yl)-1-(2-chlorophenyl)-1H-pyrazol-3-yl)propan-2-ol;
2-(1-(2-chlorophenyl)-5-(3-methyl-5-(3-(methylsulfonyl)phenyl)thiophen-2-yl)-1H-pyrazol-3-yl)propan-2-ol;
2-(1-(2-chlorophenyl)-5-(3-methyl-4-(3-(methylsulfonyl)phenyl)thiophen-2-yl)-1H-pyrazol-3-yl)propan-2-ol;
2-(1-(4-methylpyridin-3-yl)-5-(5-(3-(methylsulfonyl)phenyl)thiophen-2-yl)-1H-pyrazol-3-yl)propan-2-ol;
2-(1-(2,6-dimethylpyridin-3-yl)-5-(5-(3-(methylsulfonyl)phenyl)thiophen-2-yl)-1H-pyrazol-3-yl)propan-2-ol;
2-(1-(3-fluoro-2-(trifluoromethyl)phenyl)-5-(3-methyl-5-(3-(methylsulfonyl)phenyl)thiophen-2-yl)-1H-pyrazol-3-yl)propan-2-ol;
2-(5-(3-bromo-5-(3-(methylsulfonyl)phenyl)thiophen-2-yl)-1-(3-fluoro-2-methylphenyl)-1H-pyrazol-3-yl)propan-2-ol;
2-(5-(3-bromo-5-(3-(methylsulfonyl)phenyl)thiophen-2-yl)-1-(2-chloro-3-fluorophenyl)-1H-pyrazol-3-yl)propan-2-ol;
2-(5-(3-bromo-5-(3-(methylsulfonyl)phenyl)thiophen-2-yl)-1-(2-chlorophenyl)-1H-pyrazol-3-yl)propan-2-ol;
2-(5-(3-chloro-5-(3-(methylsulfonyl)phenyl)thiophen-2-yl)-1-(2-chlorophenyl)-1H-pyrazol-3-yl)propan-2-ol;
2-(1-(2-chloro-3-fluorophenyl)-5-(3-chloro-5-(3-(methylsulfonyl)phenyl)thiophen-2-yl)-1H-pyrazol-3-yl)propan-2-ol;
2-(5-(3-chloro-5-(3-(methylsulfonyl)phenyl)thiophen-2-yl)-1-(3-fluoro-2-(trifluoromethyl)phenyl)-1H-pyrazol-3-yl)propan-2-ol;
2-(1-(2-chloro-3-fluorophenyl)-5-(3-methyl-5-(3-(methylsulfonyl)phenyl)thiophen-2-yl)-1H-pyrazol-3-yl)propan-2-ol;
2-(5-(3-bromo-5-(3-(methylsulfonyl)phenyl)thiophen-2-yl)-1-(3-fluoro-2-(trifluoromethyl)phenyl)-1H-pyrazol-3-yl)propan-2-ol;
3-(5-(1-(2-chlorophenyl)-3-(2-hydroxypropan-2-yl)-1H-pyrazol-5-yl)thiophen-2-yl)-N-(2-(dimethylamino)ethyl)benzenesulfonamide;
2-(1-(6-methyl-4-(trifluoromethyl)-1,6-dihydropyridin-3-yl)-5-(5-(3-(methylsulfonyl)phenyl)thiophen-2-yl)-1H-pyrazol-3-yl)propan-2-ol;
2-(1-(3-fluoro-2-methylphenyl)-5-(3-methyl-5-(3-(methylsulfonyl)phenyl)thiophen-2-yl)-1H-pyrazol-3-yl)propan-2-ol;
2-(4-chloro-5-(5-(3-(methylsulfonyl)phenyl)thiophen-2-yl)-1-(3-(trifluoromethyl)pyridin-2-yl)-1H-pyrazol-3-yl)propan-2-ol;
2-(4-bromo-5-(5-(3-(methylsulfonyl)phenyl)thiophen-2-yl)-1-(3-(trifluoromethyl)pyridin-2-yl)-1H-pyrazol-3-yl)propan-2-ol;
2-(5-(5-(3-(methylsulfonyl)phenyl)thiophen-2-yl)-1-(2-(trifluoromethyl)pyridin-3-yl)-1H-pyrazol-3-yl)propan-2-ol;
2-(4-chloro-5-(5-(3-(methylsulfonyl)phenyl)thiophen-2-yl)-1-(2-(trifluoromethyl)pyridin-3-yl)-1H-pyrazol-3-yl)propan-2-ol;
2-(4-bromo-5-(5-(3-(methylsulfonyl)phenyl)thiophen-2-yl)-1-(2-(trifluoromethyl)pyridin-3-yl)-1H-pyrazol-3-yl)propan-2-ol;
5-(5-(3-(methylsulfonyl)phenyl)thiophen-2-yl)-3-(prop-1-en-2-yl)-1-(2-(trifluoromethyl)phenyl)-1H-pyrazole;
2-(1-(5-fluoropyridin-3-yl)-5-(5-(3-(methylsulfonyl)phenyl)thiophen-2-yl)-1H-pyrazol-3-yl)propan-2-ol;
2-(5-(5-(3-(methylsulfonyl)phenyl)thiophen-2-yl)-3-(prop-1-en-2-yl)-1H-pyrazol-1-yl)-3-(trifluoromethyl)pyridine;
2-(1-(2-chlorophenyl)-5-(3-ethyl-5-(3-(methylsulfonyl)phenyl)thiophen-2-yl)-1H-pyrazol-3-yl)propan-2-ol;
2-(1-(2-chloro-3-fluorophenyl)-5-(3-ethyl-5-(3-(methylsulfonyl)phenyl)thiophen-2-yl)-1H-pyrazol-3-yl)propan-2-ol;
3-(5-(5-(3-(methylsulfonyl)phenyl)thiophen-2-yl)-3-(prop-1-en-2-yl)-1H-pyrazol-1-yl)-4-(trifluoromethyl)pyridine;
2-(5-(3-methyl-5-(3-(methylsulfonyl)phenyl)thiophen-2-yl)-1-(4-(trifluoromethyl)pyridin-3-yl)-1H-pyrazol-3-yl)propan-2-ol;
2-(5-(3-methyl-5-(3-(methylsulfonyl)phenyl)thiophen-2-yl)-1-(4-(trifluoromethyl)pyridin-3-yl)-1H-pyrazol-3-yl)propan-2-ol;
2-(4-chloro-5-(3-methyl-5-(3-(methylsulfonyl)phenyl)thiophen-2-yl)-1-(4-(trifluoromethyl)pyridin-3-yl)-1H-pyrazol-3-yl)propan-2-ol;
2-(4-chloro-1-(5-fluoropyridin-3-yl)-5-(5-(3-(methylsulfonyl)phenyl)thiophen-2-yl)-1H-pyrazol-3-yl)propan-2-ol;
2-(4-bromo-1-(5-fluoropyridin-3-yl)-5-(5-(3-(methylsulfonyl)phenyl)thiophen-2-yl)-1H-pyrazol-3-yl)propan-2-ol;
2-(5-(3-methyl-5-(3-(methylsulfonyl)phenyl)thiophen-2-yl)-1-(2-(trifluoromethyl)pyridin-3-yl)-1H-pyrazol-3-yl)propan-2-ol;
2-(4-chloro-5-(3-methyl-5-(3-(methylsulfonyl)phenyl)thiophen-2-yl)-1-(2-(trifluoromethyl)pyridin-3-yl)-1H-pyrazol-3-yl)propan-2-ol;
1-(2-(1H-imidazol-1-yl)ethyl)-5-(5-(3-(methylsulfonyl)phenyl)thiophen-2-yl)-3-(trifluoromethyl)-1H-pyrazole;
2-(5-(5-(3-(methylsulfonyl)phenyl)thiophen-2-yl)-1-(3-(trifluoromethyl)pyridin-4-yl)-1H-pyrazol-3-yl)propan-2-ol;
1-methyl-4-(2-(5-(5-(3-(methylsulfonyl)phenyl)thiophen-2-yl)-3-(trifluoromethyl)-1H-pyrazol-1-yl)ethyl)piperazine;
1-(2-(5-(5-(3-(methylsulfonyl)phenyl)thiophen-2-yl)-3-(trifluoromethyl)-1H-pyrazol-1-yl)ethyl)pyrrolidin-3-ol;

2-(4-chloro-5-(5-(3-(methylsulfonyl)phenyl)thiophen-2-yl)-1-(3-(trifluoromethyl)pyridin-4-yl)-1H-pyrazol-3-yl)propan-2-ol;
2-(1-(3-fluoropyridin-4-yl)-5-(5-(3-(methylsulfonyl)phenyl)thiophen-2-yl)-1H-pyrazol-3-yl)propan-2-ol;
2-(4-chloro-1-(3-fluoropyridin-4-yl)-5-(5-(3-(methylsulfonyl)phenyl)thiophen-2-yl)-1H-pyrazol-3-yl)propan-2-ol;
2-(1-(3-chloropyridin-4-yl)-5-(5-(3-(methylsulfonyl)phenyl)thiophen-2-yl)-1H-pyrazol-3-yl)propan-2-ol;
1-(2-chlorophenyl)-5-(5-(3-(methylsulfonyl)phenyl)thiophen-2-yl)-3-(prop-1-en-2-yl)-1H-pyrazole;
2-(4-chloro-1-(3-chloropyridin-4-yl)-5-(5-(3-(methylsulfonyl)phenyl)thiophen-2-yl)-1H-pyrazol-3-yl)propan-2-ol;
2-(1-(3,5-dichloropyridin-4-yl)-5-(5-(3-(methylsulfonyl)phenyl)thiophen-2-yl)-1H-pyrazol-3-yl)propan-2-ol;
2-(4-chloro-1-(3,5-dichloropyridin-4-yl)-5-(5-(3-(methylsulfonyl)phenyl)thiophen-2-yl)-1H-pyrazol-3-yl)propan-2-ol;
1-(2-chlorophenyl)-3-(2-methoxypropan-2-yl)-5-(5-(3-(methylsulfonyl)phenyl)thiophen-2-yl)-1H-pyrazole;
2-(1-(2,6-dichlorophenyl)-5-(3-methyl-5-(3-(methylsulfonyl)phenyl)thiophen-2-yl)-1H-pyrazol-3-yl)propan-2-ol;
1-{2-[(2,2-dimethylpropyl)oxy]phenyl}-5-{4-[3-(methylsulfonyl)phenyl]-2-thienyl}-3-(trifluoromethyl)-1H-pyrazole;
1-(2-chlorophenyl)-5-{5-[3-(methylsulfonyl)phenyl]-2-thienyl}-3-(trifluoromethyl)-1H-pyrazole;
1-(2,5-dichlorophenyl)-5-{5-[3-(methylsulfonyl)phenyl]-2-thienyl}-3-(trifluoromethyl)-1H-pyrazole;
1-{2-[(2-methylpropyl)oxy]phenyl}-5-{4-[3-(methylsulfonyl)phenyl]-2-thienyl}-3-(trifluoromethyl)-1H-pyrazole;
1-[2-(ethyloxy)phenyl]-5-{4-[3-(methylsulfonyl)phenyl]-2-thienyl}-3-(trifluoromethyl)-1H-pyrazole;
1-{2-[(1-methylethyl)oxy]phenyl}-5-{4-[3-(methylsulfonyl)phenyl]-2-thienyl}-3-(trifluoromethyl)-1H-pyrazole;
2-[5-{4-[3-(methylsulfonyl)phenyl]-2-thienyl}-3-(trifluoromethyl)-1H-pyrazol-1-yl]phenyl 2-methylpropanoate;
2-[5-{5-[3-(methylsulfonyl)phenyl]-2-thienyl}-3-(trifluoromethyl)-1H-pyrazol-1-yl]-3-(trifluoromethyl)pyridine;
2-[5-{4-[3-(methylsulfonyl)phenyl]-2-thienyl}-3-(trifluoromethyl)-1H-pyrazol-1-yl]phenyl dimethylcarbamate;
5-{5-[3-(methylsulfonyl)phenyl]-2-thienyl}-3-(trifluoromethyl)-1-[2-(trifluoromethyl)phenyl]-1H-pyrazole;
2-(ethylsulfonyl)-3-methyl-5-(5-{3-(trifluoromethyl)-1-[2-(trifluoromethyl)phenyl]-1H-pyrazol-5-yl}-2-thienyl)pyridine;
2-(ethylthio)-3-methyl-5-(5-{3-(trifluoromethyl)-1-[2-(trifluoromethyl)phenyl]-1H-pyrazol-5-yl}-2-thienyl)pyridine;
1-(2-methylphenyl)-5-{5-[3-(methylsulfonyl)phenyl]-2-thienyl}-3-(trifluoromethyl)-1H-pyrazole;
1-(2-fluorophenyl)-5-{5-[3-(methylsulfonyl)phenyl]-2-thienyl}-3-(trifluoromethyl)-1H-pyrazole;
2-{[5-{5-[3-(methylsulfonyl)phenyl]-2-thienyl}-3-(trifluoromethyl)-1H-pyrazol-1-yl]methyl}pyridine;
2-methyl-4-{[5-{5-[3-(methylsulfonyl)phenyl]-2-thienyl}-3-(trifluoromethyl)-1H-pyrazol-1-yl]methyl}-1,3-thiazole;
4-{2-[5-{5-[3-(methylsulfonyl)phenyl]-2-thienyl}-3-(trifluoromethyl)-1H-pyrazol-1-yl]ethyl}morpholine;
5-methyl-3-{[5-{5-[3-(methylsulfonyl)phenyl]-2-thienyl}-3-(trifluoromethyl)-1H-pyrazol-1-yl]methyl}isoxazole;
2-[5-{5-[3-(methylsulfonyl)phenyl]-2-thienyl}-3-(trifluoromethyl)-1H-pyrazol-1-yl]benzoic acid;
1-(2,4-dichlorophenyl)-5-{5-[3-(methylsulfonyl)phenyl]-2-thienyl}-3-(trifluoromethyl)-1H-pyrazole;
1-(2,3-dichlorophenyl)-5-{5-[3-(methylsulfonyl)phenyl]-2-thienyl}-3-(trifluoromethyl)-1H-pyrazole;
5-{[5-{5-[3-(methylsulfonyl)phenyl]-2-thienyl}-3-(trifluoromethyl)-1H-pyrazol-1-yl]methyl}furan-2-carboxylic acid;
4-{[5-{5-[3-(methylsulfonyl)phenyl]-2-thienyl}-3-(trifluoromethyl)-1H-pyrazol-1-yl]methyl}benzoic acid;
1-(2,5-difluorophenyl)-5-{5-[3-(methylsulfonyl)phenyl]-2-thienyl}-3-(trifluoromethyl)-1H-pyrazole;
1-[(5-chloro-2-thienyl)methyl]-5-{5-[3-(methylsulfonyl)phenyl]-2-thienyl}-3-(trifluoromethyl)-1H-pyrazole;
1-[2-(methyloxy)phenyl]-5-{5-[3-(methylsulfonyl)phenyl]-2-thienyl}-3-(trifluoromethyl)-1H-pyrazole;
(3-{5-[1-[(5-chloro-2-thienyl)methyl]-3-(trifluoromethyl)-1H-pyrazol-5-yl]-2-thienyl}phenyl)acetic acid;
1-[(2,4-difluorophenyl)methyl]-5-{5-[3-(methylsulfonyl)phenyl]-2-thienyl}-3-(trifluoromethyl)-1H-pyrazole;
5-{5-[3-(methylsulfonyl)phenyl]-2-thienyl}-1-(phenylmethyl)-3-(trifluoromethyl)-1H-pyrazole;
1-(2,5-dimethylphenyl)-5-{5-[3-(methylsulfonyl)phenyl]-2-thienyl}-3-(trifluoromethyl)-1H-pyrazole;
(3-{5-[1-[(2,4-difluorophenyl)methyl]-3-(trifluoromethyl)-1H-pyrazol-5-yl]-2-thienyl}phenyl)acetic acid;
2-(3-{5-[1-(2,5-dichlorophenyl)-3-(trifluoromethyl)-1H-pyrazol-5-yl]-2-thienyl}phenyl)-2-methylpropanoic acid;
3-[5-{5-[3-(methylsulfonyl)phenyl]-2-thienyl}-3-(trifluoromethyl)-1H-pyrazol-1-yl]thiophene-2-carboxylic acid;
3-{5-[1-(2,5-dichlorophenyl)-3-(trifluoromethyl)-1H-pyrazol-5-yl]-2-thienyl}benzenesulfonamide;
1-[5-chloro-2-(methyloxy)phenyl]-5-{5-[3-(methylsulfonyl)phenyl]-2-thienyl}-3-(trifluoromethyl)-1H-pyrazole;
5-{5-[1-(2,5-dichlorophenyl)-3-(trifluoromethyl)-1H-pyrazol-5-yl]-2-thienyl}-3-methyl-2-(methylthio)pyridine;
5-{5-[1-(2,5-dichlorophenyl)-3-(trifluoromethyl)-1H-pyrazol-5-yl]-2-thienyl}-3-methyl-2-(methylsulfonyl)pyridine;
3-methyl-2-(methylthio)-5-(5-{3-(trifluoromethyl)-1-[2-(trifluoromethyl)phenyl]-1H-pyrazol-5-yl}-2-thienyl)pyridine;
5-{5-[1-(2,5-dichlorophenyl)-3-(trifluoromethyl)-1H-pyrazol-5-yl]-3-thienyl}-3-methyl-2-(methylthio)pyridine;
3-methyl-2-(methylsulfonyl)-5-(5-{3-(trifluoromethyl)-1-[2-(trifluoromethyl)phenyl]-1H-pyrazol-5-yl}-2-thienyl)pyridine;
5-{5-[1-(2,5-dichlorophenyl)-3-(trifluoromethyl)-1H-pyrazol-5-yl]-3-thienyl}-3-methyl-2-(methylsulfonyl)pyridine;
1-(2,5-dichlorophenyl)-5-{4-[3-(methylsulfonyl)phenyl]-2-thienyl}-3-(trifluoromethyl)-1H-pyrazole;
methyl (3-{5-[1-(2,5-dichlorophenyl)-3-(trifluoromethyl)-1H-pyrazol-5-yl]-3-thienyl}phenyl)acetate;
methyl (3-{5-[1-(2,5-dichlorophenyl)-3-(trifluoromethyl)-1H-pyrazol-5-yl]-3-thienyl}-5-ethylphenyl)acetate;

(3-{5-[1-(2,5-dichlorophenyl)-3-(trifluoromethyl)-1H-pyrazol-5-yl]-3-thienyl}phenyl)acetic acid;
2-(3-{5-[1-(2,5-dichlorophenyl)-3-(trifluoromethyl)-1H-pyrazol-5-yl]-3-thienyl}phenyl)-2-methylpropanoic acid;
1-[2-(methyloxy)phenyl]-5-{4-[3-(methylsulfonyl)phenyl]-2-thienyl}-3-(trifluoromethyl)-1H-pyrazole;
2-[5-{4-[3-(methylsulfonyl)phenyl]-2-thienyl}-3-(trifluoromethyl)-1H-pyrazol-1-yl]phenol;
2-methyl-4-{[5-{5-[3-(methylsulfonyl)phenyl]-2-thienyl}-3-(trifluoromethyl)-1H-pyrazol-1-yl]methyl}-1,3-thiazole;
2-methyl-4-{[5-{5-[3-(methylsulfonyl)phenyl]-2-thienyl}-3-(trifluoromethyl)-1H-pyrazol-1-yl]methyl}-1,3-thiazole;
2-(3-ethyl-5-{5-[1-[2-(methyloxy)phenyl]-3-(trifluoromethyl)-1H-pyrazol-5-yl]-3-thienyl}phenyl)-2-methylpropanoic acid;
5-{4-[3-(methylsulfonyl)phenyl]-2-thienyl}-1-(2-nitrophenyl)-3-(trifluoromethyl)-1H-pyrazole;
2-[5-{4-[3-(methylsulfonyl)phenyl]-2-thienyl}-3-(trifluoromethyl)-1H-pyrazol-1-yl]phenyl methylcarbamate;
2-[5-{4-[3-(methylsulfonyl)phenyl]-2-thienyl}-3-(trifluoromethyl)-1H-pyrazol-1-yl]phenyl propylcarbamate;
methyl 1-(2-chlorophenyl)-5-{5-[3-(methylsulfonyl)phenyl]-2-thienyl}-1H-pyrazole-3-carboxylate;
1-(2-chlorophenyl)-5-{5-[3-(methylsulfonyl)phenyl]-2-thienyl}-1H-pyrazole-3-carboxylic acid;
1-[3-(methyloxy)phenyl]-5-{5-[3-(methylsulfonyl)phenyl]-2-thienyl}-3-(trifluoromethyl)-1H-pyrazole;
N-(3-{5-[1-(2-fluorophenyl)-3-(trifluoromethyl)-1H-pyrazol-5-yl]-2-thienyl}phenyl)methanesulfonamide;
2-{5-[1-(2,5-dichlorophenyl)-3-(trifluoromethyl)-1H-pyrazol-5-yl]-2-thienyl}-4-fluorophenol;
2-[5-{4-[3-(methylsulfonyl)phenyl]-2-thienyl}-3-(trifluoromethyl)-1H-pyrazol-1-yl]phenyl 2,2-dimethylpropanoate;
3-methyl-5-{5-[1-[2-(methyloxy)phenyl]-3-(trifluoromethyl)-1H-pyrazol-5-yl]-3-thienyl}-2-(methylsulfonyl)pyridine;
5-{5-[1-[(2,4-difluorophenyl)methyl]-3-(trifluoromethyl)-1H-pyrazol-5-yl]-2-thienyl}-3-methyl-2-(methylsulfonyl)pyridine;
N-{2-[5-{4-[3-(methylsulfonyl)phenyl]-2-thienyl}-3-(trifluoromethyl)-1H-pyrazol-1-yl]phenyl}acetamide;
1-(2-chlorophenyl)-5-{5-[3-(ethylsulfonyl)-5-(1-methylethyl)phenyl]-2-thienyl}-3-(trifluoromethyl)-1H-pyrazole;
1-(2-chlorophenyl)-5-{5-[3-(methylsulfonyl)phenyl]-2-thienyl}-N-pyridin-2-yl-1H-pyrazole-3-carboxamide;
1-(2-chlorophenyl)-5-{5-[3-(methylsulfonyl)phenyl]-2-thienyl}-N-pyridin-3-yl-1H-pyrazole-3-carboxamide;
1-(2-chlorophenyl)-5-{5-[3-(methylsulfonyl)phenyl]-2-thienyl}-N-pyridin-4-yl-1H-pyrazole-3-carboxamide;
1-(2-chlorophenyl)-N-[2-(dimethylamino)ethyl]-5-{5-[3-(methylsulfonyl)phenyl]-2-thienyl}-1H-pyrazole-3-carboxamide;
1-(2-chlorophenyl)-N-[3-(methyloxy)propyl]-5-{5-[3-(methylsulfonyl)phenyl]-2-thienyl}-1H-pyrazole-3-carboxamide;
1-[2-chloro-5-(trifluoromethyl)phenyl]-5-{5-[3-(methylsulfonyl)phenyl]-2-thienyl}-3-(trifluoromethyl)-1H-pyrazole;
1-[2-chloro-5-(methyloxy)phenyl]-5-{5-[3-(methylsulfonyl)phenyl]-2-thienyl}-3-(trifluoromethyl)-1H-pyrazole;
1-(5-chloro-2-fluorophenyl)-5-{5-[3-(methylsulfonyl)phenyl]-2-thienyl}-3-(trifluoromethyl)-1H-pyrazole;
5-{5-[1-(2-chlorophenyl)-3-(trifluoromethyl)-1H-pyrazol-5-yl]-2-thienyl}-3-methyl-2-(methylthio)pyridine;
1-(2-chloro-5-fluorophenyl)-5-{5-[3-(methylsulfonyl)phenyl]-2-thienyl}-3-(trifluoromethyl)-1H-pyrazole;
5-{5-[1-(2-chlorophenyl)-3-(trifluoromethyl)-1H-pyrazol-5-yl]-2-thienyl}-2-(ethylthio)-3-methylpyridine;
5-{5-[1-(2-chlorophenyl)-3-(trifluoromethyl)-1H-pyrazol-5-yl]-2-thienyl}-3-methyl-2-(methylsulfonyl)pyridine;
5-{5-[1-(2-chlorophenyl)-3-(trifluoromethyl)-1H-pyrazol-5-yl]-2-thienyl}-2-(ethylsulfonyl)-3-methylpyridine;
3-chloro-2-[5-{5-[3-(methylsulfonyl)phenyl]-2-thienyl}-3-(trifluoromethyl)-1H-pyrazol-1-yl]pyridine;
2-[5-{4-[3-(methylsulfonyl)phenyl]-2-thienyl}-3-(trifluoromethyl)-1H-pyrazol-1-yl]phenyl (1-methylethyl)carbamate;
4-(2-chlorophenyl)-1-methyl-3-{5-[3-(methylsulfonyl)phenyl]-2-thienyl}-1H-pyrazole;
4-[(1-(2-chlorophenyl)-5-{5-[3-(methylsulfonyl)phenyl]-2-thienyl}-1H-pyrazol-3-yl)carbonyl]morpholine;
1-(2-chlorophenyl)-N-[6-(methyloxy)pyridin-3-yl]-5-{5-[3-(methylsulfonyl)phenyl]-2-thienyl}-1H-pyrazole-3-carboxamide;
1-[5-chloro-2-(phenyloxy)phenyl]-5-{5-[3-(methylsulfonyl)phenyl]-2-thienyl}-3-(trifluoromethyl)-1H-pyrazole;
3-methyl-5-{5-[1-[2-(methyloxy)phenyl]-3-(trifluoromethyl)-1H-pyrazol-5-yl]-3-thienyl}-2-(methylthio)pyridine;
4-chloro-3-[5-{5-[3-(methylsulfonyl)phenyl]-2-thienyl}-3-(trifluoromethyl)-1H-pyrazol-1-yl]phenol;
1-[(1-(2-chlorophenyl)-5-{5-[3-(methylsulfonyl)phenyl]-2-thienyl}-1H-pyrazol-3-yl)carbonyl]piperidine;
1-[2-({2-[5-{4-[3-(methylsulfonyl)phenyl]-2-thienyl}-3-(trifluoromethyl)-1H-pyrazol-1-yl]phenyl}oxy)ethyl]piperidine;
4-[2-({2-[5-{4-[3-(methylsulfonyl)phenyl]-2-thienyl}-3-(trifluoromethyl)-1H-pyrazol-1-yl]phenyl}oxy)ethyl]morpholine;
1-(2-chlorophenyl)-5-{4-[3-(methylsulfonyl)phenyl]-2-thienyl}-3-(trifluoromethyl)-1H-pyrazole;
1-(2-chlorophenyl)-N,N-dimethyl-5-{5-[3-(methylsulfonyl)phenyl]-2-thienyl}-1H-pyrazole-3-carboxamide;
4-chloro-3-[5-{5-[3-(methylsulfonyl)phenyl]-2-thienyl}-3-(trifluoromethyl)-1H-pyrazol-1-yl]benzamide;
4-(2-chlorophenyl)-1-methyl-5-{5-[3-(methylsulfonyl)phenyl]-2-thienyl}-1H-pyrazole;
4-(5-{5-[1-(2-chlorophenyl)-3-(trifluoromethyl)-1H-pyrazol-5-yl]-2-thienyl}pyridin-2-yl)morpholine;
1-(2-bromophenyl)-5-{5-[3-(methylsulfonyl)phenyl]-2-thienyl}-3-(trifluoromethyl)-1H-pyrazole;
1,1-dimethylethyl 4-(5-{5-[1-(2-chlorophenyl)-3-(trifluoromethyl)-1H-pyrazol-5-yl]-2-thienyl}pyridin-2-yl)piperazine-1-carboxylate;
(3-{5-[1-(2-chlorophenyl)-3-(trifluoromethyl)-1H-pyrazol-5-yl]-2-thienyl}phenyl)acetic acid;
(4-{5-[1-(2-chlorophenyl)-3-(trifluoromethyl)-1H-pyrazol-5-yl]-2-thienyl}phenyl)acetic acid;
2-(3-{5-[1-(2-chlorophenyl)-3-(trifluoromethyl)-1H-pyrazol-5-yl]-2-thienyl}phenyl)-2-methylpropanoic acid;
1-(5-{5-[1-(2-chlorophenyl)-3-(trifluoromethyl)-1H-pyrazol-5-yl]-2-thienyl}pyridin-2-yl)piperazine;

1-(5-{5-[1-(2-chlorophenyl)-3-(trifluoromethyl)-1H-pyrazol-5-yl]-2-thienyl}pyridin-2-yl)piperazine;
1-(5-{5-[1-(2-chlorophenyl)-3-(trifluoromethyl)-1H-pyrazol-5-yl]-2-thienyl}pyridin-2-yl)piperazine;
methyl (5-{5-[1-(2-chlorophenyl)-3-(trifluoromethyl)-1H-pyrazol-5-yl]-2-thienyl}pyridin-3-yl)acetate;
methyl (4-{5-[1-(2-chlorophenyl)-3-(trifluoromethyl)-1H-pyrazol-5-yl]-2-thienyl}-3-methylphenyl)acetate;
5-{4-[3-(methylsulfonyl)phenyl]-2-thienyl}-1-(2-propylphenyl)-3-(trifluoromethyl)-1H-pyrazole;
1-[2-(1-methylethyl)phenyl]-5-{4-[3-(methylsulfonyl)phenyl]-2-thienyl}-3-(trifluoromethyl)-1H-pyrazole;
2-[(3-{5-[1-(2-chlorophenyl)-3-(trifluoromethyl)-1H-pyrazol-5-yl]-2-thienyl}phenyl)oxy]-2-methylpropanoic acid;
1-(3-{5-[1-(2-chlorophenyl)-3-(trifluoromethyl)-1H-pyrazol-5-yl]-2-thienyl}phenyl)cyclobutanecarboxylic acid;
2-(3-{5-[1-(2-chlorophenyl)-3-(trifluoromethyl)-1H-pyrazol-5-yl]-2-thienyl}phenyl)-2-ethylbutanoic acid;
2-(4-{5-[1-(2-chlorophenyl)-3-(trifluoromethyl)-1H-pyrazol-5-yl]-2-thienyl}phenyl)-2-methylpropanoic acid;
(3-{5-[1-(2-chlorophenyl)-3-(trifluoromethyl)-1H-pyrazol-5-yl]-2-thienyl}-4-fluorophenyl)acetic acid;
methyl (3-{5-[1-(2-chlorophenyl)-3-(trifluoromethyl)-1H-pyrazol-5-yl]-2-thienyl}-4-fluorophenyl)acetate;
(4-{5-[1-(2-chlorophenyl)-3-(trifluoromethyl)-1H-pyrazol-5-yl]-2-thienyl}-3-methylphenyl)acetic acid;
1-[3-(ethyloxy)phenyl]-5-{5-[3-(methylsulfonyl)phenyl]-2-thienyl}-3-(trifluoromethyl)-1H-pyrazole;
4-{5-[1-(2-chlorophenyl)-3-(trifluoromethyl)-1H-pyrazol-5-yl]-2-thienyl}benzenesulfonamide;
3-{5-[1-(2-chlorophenyl)-3-(trifluoromethyl)-1H-pyrazol-5-yl]-2-thienyl}benzenesulfonamide;
1-{3-[(2-methylpropyl)oxy]phenyl}-5-{5-[3-(methylsulfonyl)phenyl]-2-thienyl}-3-(trifluoromethyl)-1H-pyrazole;
4-{5-[1-(2-chlorophenyl)-3-(trifluoromethyl)-1H-pyrazol-5-yl]-3-thienyl}benzenesulfonamide;
3-{5-[1-(2-chlorophenyl)-3-(trifluoromethyl)-1H-pyrazol-5-yl]-3-thienyl}benzenesulfonamide;
({3-[5-{5-[3-(methylsulfonyl)phenyl]-2-thienyl}-3-(trifluoromethyl)-1H-pyrazol-1-yl]phenyl}oxy)acetic acid;
1,1-dimethylethyl ({2-[5-{4-[3-(methylsulfonyl)phenyl]-2-thienyl}-3-(trifluoromethyl)-1H-pyrazol-1-yl]phenyl}oxy)acetate;
N,N-diethyl-2-({2-[5-{4-[3-(methylsulfonyl)phenyl]-2-thienyl}-3-(trifluoromethyl)-1H-pyrazol-1-yl]phenyl}oxy)ethanamine;
({2-[5-{4-[3-(methylsulfonyl)phenyl]-2-thienyl}-3-(trifluoromethyl)-1H-pyrazol-1-yl]phenyl}oxy)acetic acid;
methyl 2-(5-{5-[1-(2-chlorophenyl)-3-(trifluoromethyl)-1H-pyrazol-5-yl]-2-thienyl}pyridin-3-yl)-2-methylpropanoate;
4-(2-{[(1-(2-chlorophenyl)-5-{5-[3-(methylsulfonyl)phenyl]-2-thienyl}-1H-pyrazol-3-yl)methyl]oxy}ethyl)morpholine;
1,1-dimethylethyl 2-methyl-2-({3-[5-{5-[3-(methylsulfonyl)phenyl]-2-thienyl}-3-(trifluoromethyl)-1H-pyrazol-1-yl]phenyl}oxy)propanoate;
3-[5-{5-[3-(methylsulfonyl)phenyl]-2-thienyl}-3-(trifluoromethyl)-1H-pyrazol-1-yl]phenyl dimethylcarbamate;
3-[5-{5-[3-(methylsulfonyl)phenyl]-2-thienyl}-3-(trifluoromethyl)-1H-pyrazol-1-yl]phenyl methylcarbamate;
4-{2-[5-{4-[3-(methylsulfonyl)phenyl]-2-thienyl}-3-(trifluoromethyl)-1H-pyrazol-1-yl]phenyl}morpholine;
2-({2-[5-{4-[3-(methylsulfonyl)phenyl]-2-thienyl}-3-(trifluoromethyl)-1H-pyrazol-1-yl]phenyl}oxy)ethanol;
4-(2-chlorophenyl)-3-{5-[3-(methylsulfonyl)phenyl]-2-thienyl}-1-(2,2,2-trifluoroethyl)-1H-pyrazole;
1-(2-chlorophenyl)-3-(trifluoromethyl)-5-{4-[3-(trifluoromethyl)phenyl]-2-thienyl}-1H-pyrazole;
1-methyl-4-{2-[5-{4-[3-(methylsulfonyl)phenyl]-2-thienyl}-3-(trifluoromethyl)-1H-pyrazol-1-yl]phenyl}piperazine;
1-{2-[(3-chloropropyl)oxy]phenyl}-5-{4-[3-(methylsulfonyl)phenyl]-2-thienyl}-3-(trifluoromethyl)-1H-pyrazole;
3-{5-[1-(2-chloro-5-hydroxyphenyl)-3-(trifluoromethyl)-1H-pyrazol-5-yl]-2-thienyl}benzenesulfonamide;
(1-(2-chlorophenyl)-5-{5-[3-(methylsulfonyl)phenyl]-2-thienyl}-1H-pyrazol-3-yl)methanol;
3-(4-{5-[1-(2-chlorophenyl)-3-(trifluoromethyl)-1H-pyrazol-5-yl]-2-thienyl}phenyl)propanoic acid;
3-[5-{5-[3-(methylsulfonyl)phenyl]-2-thienyl}-3-(trifluoromethyl)-1H-pyrazol-1-yl]phenyl diethylcarbamate;
3-[5-{5-[3-(methylsulfonyl)phenyl]-2-thienyl}-3-(trifluoromethyl)-1H-pyrazol-1-yl]phenyl propylcarbamate;
N-{3-[5-{5-[3-(methylsulfonyl)phenyl]-2-thienyl}-3-(trifluoromethyl)-1H-pyrazol-1-yl]phenyl}acetamide;
methyl (1-(2-chlorophenyl)-5-{5-[3-(methylsulfonyl)phenyl]-2-thienyl}-1H-pyrazol-3-yl)acetate;
1-[(1-(2-chlorophenyl)-5-{5-[3-(methylsulfonyl)phenyl]-2-thienyl}-1H-pyrazol-3-yl)carbonyl]piperidine;
3-(3-{5-[1-(2-chlorophenyl)-3-(trifluoromethyl)-1H-pyrazol-5-yl]-2-thienyl}phenyl)propanoic acid;
2-[({2-[5-{4-[3-(methylsulfonyl)phenyl]-2-thienyl}-3-(trifluoromethyl)-1H-pyrazol-1-yl]phenyl}oxy)methyl]pyridine;
methyl 5-{5-[3-(aminosulfonyl)phenyl]-2-thienyl}-1-(2,5-dichlorophenyl)-1H-pyrazole-3-carboxylate;
ethyl 4-{5-[1-(2,5-dichlorophenyl)-3-(trifluoromethyl)-1H-pyrazol-5-yl]-2-thienyl}-2-(methylsulfonyl)benzoate;
4-[3-({2-[5-{4-[3-(methylsulfonyl)phenyl]-2-thienyl}-3-(trifluoromethyl)-1H-pyrazol-1-yl]phenyl}oxy)propyl]morpholine;
1-methyl-4-[3-({2-[5-{4-[3-(methylsulfonyl)phenyl]-2-thienyl}-3-(trifluoromethyl)-1H-pyrazol-1-yl]phenyl}oxy)propyl]piperazine;
1-methylethyl 5-{5-[3-(aminosulfonyl)phenyl]-2-thienyl}-1-(2,5-dichlorophenyl)-1H-pyrazole-3-carboxylate;
N,N-dimethyl-2-({3-[5-{5-[3-(methylsulfonyl)phenyl]-2-thienyl}-3-(trifluoromethyl)-1H-pyrazol-1-yl]phenyl}oxy)acetamide;
4-[({3-[5-{5-[3-(methylsulfonyl)phenyl]-2-thienyl}-3-(trifluoromethyl)-1H-pyrazol-1-yl]phenyl}oxy)acetyl]morpholine;
3-[5-{5-[3-(methylsulfonyl)phenyl]-2-thienyl}-3-(trifluoromethyl)-1H-pyrazol-1-yl]aniline;
4-[2-({3-[5-{5-[3-(methylsulfonyl)phenyl]-2-thienyl}-3-(trifluoromethyl)-1H-pyrazol-1-yl]phenyl}oxy)ethyl]morpholine;
N,N-dimethyl-2-({3-[5-{5-[3-(methylsulfonyl)phenyl]-2-thienyl}-3-(trifluoromethyl)-1H-pyrazol-1-yl]phenyl}oxy)ethanamine;
1-[2-({3-[5-{5-[3-(methylsulfonyl)phenyl]-2-thienyl}-3-(trifluoromethyl)-1H-pyrazol-1-yl]phenyl}oxy)ethyl]piperidine;
4-{5-[1-(2-chlorophenyl)-3-(trifluoromethyl)-1H-pyrazol-5-yl]-2-thienyl}benzoic acid;

3-{5-[1-(2-chlorophenyl)-3-(trifluoromethyl)-1H-pyrazol-5-yl]-2-thienyl}benzoic acid;
(2E)-3-(4-{5-[1-(2-chlorophenyl)-3-(trifluoromethyl)-1H-pyrazol-5-yl]-2-thienyl}phenyl)prop-2-enoic acid;
4-chloro-2-[5-{5-[3-(methylsulfonyl)phenyl]-2-thienyl}-3-(trifluoromethyl)-1H-pyrazol-1-yl]phenol;
3-(5-{3-(trifluoromethyl)-1-[3-(trifluoromethyl)pyridin-2-yl]-1H-pyrazol-5-yl}-2-thienyl)benzenesulfonamide;
1-{5-chloro-2-[(4-fluorophenyl)oxy]phenyl}-5-{5-[3-(methylsulfonyl)phenyl]-2-thienyl}-3-(trifluoromethyl)-1H-pyrazole;
1-(5-{5-[1-(2-chlorophenyl)-3-(trifluoromethyl)-1H-pyrazol-5-yl]-2-thienyl}pyridin-2-yl)piperazine;
4-({3-[5-{5-[3-(methylsulfonyl)phenyl]-2-thienyl}-3-(trifluoromethyl)-1H-pyrazol-1-yl]phenyl}oxy)piperidine;
2-(5-{5-[1-(2-chlorophenyl)-3-(trifluoromethyl)-1H-pyrazol-5-yl]-2-thienyl}pyridin-3-yl)-2-methylpropanoic acid;
(5-{5-[1-(2-chlorophenyl)-3-(trifluoromethyl)-1H-pyrazol-5-yl]-2-thienyl}pyridin-3-yl)acetic acid;
5-{5-[3-(methylsulfonyl)phenyl]-2-thienyl}-1-[3-(phenyloxy)phenyl]-3-(trifluoromethyl)-1H-pyrazole;
1-(2-chlorophenyl)-5-{5-[3-(methylsulfonyl)phenyl]-2-thienyl}-3-[({[5-(trifluoromethyl)furan-2-yl]methyl}oxy)methyl]-1H-pyrazole;
2-({[(1-(2-chlorophenyl)-5-{5-[3-(methylsulfonyl)phenyl]-2-thienyl}-1H-pyrazol-3-yl)methyl]oxy}methyl)pyridine;
1-({5-[1-(2-chlorophenyl)-3-(trifluoromethyl)-1H-pyrazol-5-yl]-2-thienyl}sulfonyl)-4-methylpiperazine;
1-({5-[1-(2-chlorophenyl)-3-(trifluoromethyl)-1H-pyrazol-5-yl]-2-thienyl}sulfonyl)piperidine;
4-{5-[1-(2,5-dichlorophenyl)-3-(trifluoromethyl)-1H-pyrazol-5-yl]-2-thienyl}-2-(methylsulfonyl)benzoic acid;
3-(5-{3-(trifluoromethyl)-1-[2-(trifluoromethyl)phenyl]-1H-pyrazol-5-yl}-2-thienyl)benzenesulfonamide;
N-[(3-{5-[1-(2-chlorophenyl)-3-(trifluoromethyl)-1H-pyrazol-5-yl]-2-thienyl}phenyl)sulfonyl]acetamide;
1-(2,5-dichlorophenyl)-5-(5-{3-[(1,1-dimethylethyl)sulfonyl]phenyl}-2-thienyl)-3-(trifluoromethyl)-1H-pyrazole;
1-(2,5-dichlorophenyl)-5-(5-{3-[(1-methylethyl)sulfonyl]phenyl}-2-thienyl)-3-(trifluoromethyl)-1H-pyrazole;
2-(1-(2-chlorophenyl)-5-{5-[3-(methylsulfonyl)phenyl]-2-thienyl}-1H-pyrazol-3-yl)-N-ethylacetamide;
2-(1-(2-chlorophenyl)-5-{5-[3-(methylsulfonyl)phenyl]-2-thienyl}-1H-pyrazol-3-yl)propan-2-ol;
1-(2,5-dichlorophenyl)-5-{5-[3-(ethylsulfonyl)phenyl]-2-thienyl}-3-(trifluoromethyl)-1H-pyrazole;
1-(2,5-dichlorophenyl)-5-{5-[3-(propylsulfonyl)phenyl]-2-thienyl}-3-(trifluoromethyl)-1H-pyrazole;
[4-{5-[1-(2,5-dichlorophenyl)-3-(trifluoromethyl)-1H-pyrazol-5-yl]-2-thienyl}-2-(methylsulfonyl)phenyl]methanol;
5-[1-(2-chlorophenyl)-3-(trifluoromethyl)-1H-pyrazol-5-yl]thiophene-2-sulfonic acid;
methyl 1-[(1-(2-chlorophenyl)-5-{5-[3-(methylsulfonyl)phenyl]-2-thienyl}-1H-pyrazol-3-yl)carbonyl]piperidine-4-carboxylate;
1-(2-chlorophenyl)-5-{5-[3-(methylsulfonyl)phenyl]-2-thienyl}-N-piperidin-1-yl-1H-pyrazole-3-carboxamide;
1-{[1-(2-chlorophenyl)-5-{5-[3-(methylsulfonyl)phenyl]-2-thienyl}-1H-pyrazol-3-yl]carbonyl}-4-methylpiperazine;
1-(2-chlorophenyl)-N-[2-(diethylamino)ethyl]-N-methyl-5-{5-[3-(methylsulfonyl)phenyl]-2-thienyl}-1H-pyrazole-3-carboxamide;
1-(2-chlorophenyl)-N-[2-(diethylamino)ethyl]-N-ethyl-5-{5-[3-(methylsulfonyl)phenyl]-2-thienyl}-1H-pyrazole-3-carboxamide;
1-(2-chlorophenyl)-N-[3-(dimethylamino)propyl]-N-methyl-5-{5-[3-(methylsulfonyl)phenyl]-2-thienyl}-1H-pyrazole-3-carboxamide;
methyl N-{[1-(2-chlorophenyl)-5-{5-[3-(methylsulfonyl)phenyl]-2-thienyl}-1H-pyrazol-3-yl]carbonyl}-N-methylglycinate;
1-(2-chlorophenyl)-5-{5-[3-(methylsulfonyl)phenyl]-2-thienyl}-N-(2-morpholin-4-ylethyl)-1H-pyrazole-3-carboxamide;
1-{[1-(2-chlorophenyl)-5-{5-[3-(methylsulfonyl)phenyl]-2-thienyl}-1H-pyrazol-3-yl]carbonyl}-N,N-dimethylpiperidin-4-amine;
1-(1-(2-chlorophenyl)-5-(5-(3-(methylsulfonyl)phenyl)thiophen-2-yl)-1H-pyrazole-3-carbonyl)piperidine-4-carboxylic acid;
1-(2-chlorophenyl)-5-{5-[3-(methylsulfonyl)phenyl]-2-thienyl}-N-(4-pyrrolidin-1-ylbutyl)-1H-pyrazole-3-carboxamide;
1-(2-chlorophenyl)-N-[(2S)-2-hydroxypropyl]-5-{5-[3-(methylsulfonyl)phenyl]-2-thienyl}-1H-pyrazole-3-carboxamide;
N-{2-[bis(1-methylethyl)amino]ethyl}-1-(2-chlorophenyl)-5-{5-[3-(methylsulfonyl)phenyl]-2-thienyl}-1H-pyrazole-3-carboxamide;
1-{[1-(2-chlorophenyl)-5-{5-[3-(methylsulfonyl)phenyl]-2-thienyl}-1H-pyrazol-3-yl]carbonyl}piperidine-3-carboxamide;
1-(2-chlorophenyl)-N-ethyl-N-(2-hydroxyethyl)-5-{5-[3-(methylsulfonyl)phenyl]-2-thienyl}-1H-pyrazole-3-carboxamide;
ethyl N-{[1-(2-chlorophenyl)-5-{5-[3-(methylsulfonyl)phenyl]-2-thienyl}-1H-pyrazol-3-yl]carbonyl}serinate;
ethyl N-{[1-(2-chlorophenyl)-5-{5-[3-(methylsulfonyl)phenyl]-2-thienyl}-1H-pyrazol-3-yl]carbonyl}-L-serinate;
1-acetyl-4-{[1-(2-chlorophenyl)-5-{5-[3-(methylsulfonyl)phenyl]-2-thienyl}-1H-pyrazol-3-yl]carbonyl}piperazine;
1-(2-chlorophenyl)-5-{5-[3-(methylsulfonyl)phenyl]-2-thienyl}-N-[1-(2-methyl-1,3-thiazol-4-yl)ethyl]-1H-pyrazole-3-carboxamide;
1-(2-chlorophenyl)-N-(4-methylpyrimidin-2-yl)-5-{5-[3-(methylsulfonyl)phenyl]-2-thienyl}-1H-pyrazole-3-carboxamide;
ethyl N-{[1-(2-chlorophenyl)-5-{5-[3-(methylsulfonyl)phenyl]-2-thienyl}-1H-pyrazol-3-yl]carbonyl}-beta-alaninate;
1-(2-chlorophenyl)-N-(1,3-dioxolan-2-ylmethyl)-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-(3-thienylmethyl)-1H-pyrazole-3-carboxamide;
1-(2-chlorophenyl)-5-{5-[3-(methylsulfonyl)phenyl]-2-thienyl}-N-[2-(5-methyl-4H-1,2,4-triazol-3-yl)ethyl]-1H-pyrazole-3-carboxamide;
1-(2-chlorophenyl)-N-[2-(3,5-dimethyl-1H-pyrazol-4-yl)ethyl]-5-{5-[3-(methylsulfonyl)phenyl]-2-thienyl}-1H-pyrazole-3-carboxamide;

1-(2-chlorophenyl)-5-{5-[3-(methylsulfonyl)phenyl]-2-thienyl}-N-1H-pyrazol-3-yl-1H-pyrazole-3-carboxamide;
1-(2-chlorophenyl)-N-[(3,5-dimethyl-1H-pyrazol-4-yl)methyl]-5-{5-[3-(methylsulfonyl)phenyl]-2-thienyl}-1H-pyrazole-3-carboxamide;
1-(2-chlorophenyl)-N-{2-(dimethylamino)-2-[4-(methyloxy)phenyl]ethyl}-5-{5-[3-(methylsulfonyl)phenyl]-2-thienyl}-1H-pyrazole-3-carboxamide;
ethyl N-{[1-(2-chlorophenyl)-5-{5-[3-(methylsulfonyl)phenyl]-2-thienyl}-1H-pyrazol-3-yl]carbonyl}-N-(furan-2-ylmethyl)-beta-alaninate;
4-{[1-(2-chlorophenyl)-5-{5-[3-(methylsulfonyl)phenyl]-2-thienyl}-1H-pyrazol-3-yl]carbonyl}-2,6-dimethylmorpholine;
1-{[1-(2-chlorophenyl)-5-{5-[3-(methylsulfonyl)phenyl]-2-thienyl}-1H-pyrazol-3-yl]carbonyl}piperidin-3-ol;
1-(2-chlorophenyl)-5-{5-[3-(methylsulfonyl)phenyl]-2-thienyl}-N-(2-oxotetrahydro-3-thienyl)-1H-pyrazole-3-carboxamide;
1-(2-chlorophenyl)-5-{5-[3-(methylsulfonyl)phenyl]-2-thienyl}-N-(3-morpholin-4-ylpropyl)-1H-pyrazole-3-carboxamide;
1-(2-chlorophenyl)-N-(2-cyanoethyl)-N-ethyl-5-{5-[3-(methylsulfonyl)phenyl]-2-thienyl}-1H-pyrazole-3-carboxamide;
1-(2-chlorophenyl)-N-[2-(4-fluorophenyl)ethyl]-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-(2-piperidin-1-ylethyl)-1H-pyrazole-3-carboxamide;
1-(2-chlorophenyl)-5-{5-[3-(methylsulfonyl)phenyl]-2-thienyl}-N-(pyridin-4-ylmethyl)-1H-pyrazole-3-carboxamide;
1-(2-chlorophenyl)-N-methyl-5-{5-[3-(methylsulfonyl)phenyl]-2-thienyl}-N-(2-pyridin-2-ylethyl)-1H-pyrazole-3-carboxamide;
3-{[1-(2-chlorophenyl)-5-{5-[3-(methylsulfonyl)phenyl]-2-thienyl}-1H-pyrazol-3-yl]carbonyl}-4,4-dimethyl-1,3-oxazolidine;
3-({[1-(2-chlorophenyl)-5-{5-[3-(methylsulfonyl)phenyl]-2-thienyl}-1H-pyrazol-3-yl]carbonyl}amino)-2-methylpropanoic acid;
1-{[1-(2-chlorophenyl)-5-{5-[3-(methylsulfonyl)phenyl]-2-thienyl}-1H-pyrazol-3-yl]carbonyl}-4-methyl-1,4-diazepane;
1-{[1-(2-chlorophenyl)-5-{5-[3-(methylsulfonyl)phenyl]-2-thienyl}-1H-pyrazol-3-yl]carbonyl}piperidin-4-ol;
1-{[1-(2-chlorophenyl)-5-{5-[3-(methylsulfonyl)phenyl]-2-thienyl}-1H-pyrazol-3-yl]carbonyl}piperidine-2-carboxylic acid;
1-(2-chlorophenyl)-N-[2-(1H-imidazol-4-yl)ethyl]-5-{5-[3-(methylsulfonyl)phenyl]-2-thienyl}-1H-pyrazole-3-carboxamide;
1-(2-chlorophenyl)-N-methyl-5-{5-[3-(methylsulfonyl)phenyl]-2-thienyl}-N-(pyridin-3-ylmethyl)-1H-pyrazole-3-carboxamide;
1-{[1-(2-chlorophenyl)-5-{5-[3-(methylsulfonyl)phenyl]-2-thienyl}-1H-pyrazol-3-yl]carbonyl}-4-ethylpiperazine;
1-{[1-(2-chlorophenyl)-5-{5-[3-(methylsulfonyl)phenyl]-2-thienyl}-1H-pyrazol-3-yl]carbonyl}-1,4-diazepane;
1-(2-chlorophenyl)-5-{5-[3-(methylsulfonyl)phenyl]-2-thienyl}-N-(2-pyrrolidin-1-ylethyl)-1H-pyrazole-3-carboxamide;
1-(2-chlorophenyl)-N-{[4-(methyloxy)phenyl]methyl}-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-{[3-(trifluoromethyl)phenyl]methyl}-1H-pyrazole-3-carboxamide;
1-(2-chlorophenyl)-N-[2-(1-methylpyrrolidin-2-yl)ethyl]-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-[2-(2-thienyl)ethyl]-1H-pyrazole-3-carboxamide;
1-(2-chlorophenyl)-N-[3-(2-methylpiperidin-1-yl)propyl]-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-{[4-(trifluoromethyl)phenyl]methyl}-1H-pyrazole-3-carboxamide;
N-{[3,4-bis(methyloxy)phenyl]methyl}-1-(2-chlorophenyl)-5-{5-[3-(methylsulfonyl)phenyl]-2-thienyl}-1H-pyrazole-3-carboxamide;
1-(2-chlorophenyl)-N-{[2-(methyloxy)phenyl]methyl}-5-{5-[3-(methylsulfonyl)phenyl]-2-thienyl}-1H-pyrazole-3-carboxamide;
1-(2-chlorophenyl)-N-{[3-(methyloxy)phenyl]methyl}-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-(pyridin-2-ylmethyl)-1H-pyrazole-3-carboxamide;
1-(2-chlorophenyl)-5-{5-[3-(methylsulfonyl)phenyl]-2-thienyl}-N-(2-pyridin-2-ylethyl)-1H-pyrazole-3-carboxamide;
1-(2-chlorophenyl)-N-{2-[2-(methyloxy)phenyl]ethyl}-5-{5-[3-(methylsulfonyl)phenyl]-2-thienyl}-1H-pyrazole-3-carboxamide;
1-(2-chlorophenyl)-N-(furan-2-ylmethyl)-5-{5-[3-(methylsulfonyl)phenyl]-2-thienyl}-1H-pyrazole-3-carboxamide;
1-(2-chlorophenyl)-N-[3-(dimethylamino)-2,2-dimethylpropyl]-5-{5-[3-(methylsulfonyl)phenyl]-2-thienyl}-1H-pyrazole-3-carboxamide;
ethyl 1-{[1-(2-chlorophenyl)-5-{5-[3-(methylsulfonyl)phenyl]-2-thienyl}-1H-pyrazol-3-yl]carbonyl}piperidine-2-carboxylate;
1-(2-chlorophenyl)-N-[3-(dimethylamino)propyl]-5-{5-[3-(methylsulfonyl)phenyl]-2-thienyl}-1H-pyrazole-3-carboxamide;
8-{[1-(2-chlorophenyl)-5-{5-[3-(methylsulfonyl)phenyl]-2-thienyl}-1H-pyrazol-3-yl]carbonyl}-1,4-dioxa-8-azaspiro[4.5]decane;
3-(4-{[1-(2-chlorophenyl)-5-{5-[3-(methylsulfonyl)phenyl]-2-thienyl}-1H-pyrazol-3-yl]carbonyl}piperazin-1-yl)-N,N-dimethylpropan-1-amine;
1-{[1-(2-chlorophenyl)-5-{5-[3-(methylsulfonyl)phenyl]-2-thienyl}-1H-pyrazol-3-yl]carbonyl}-4-[3-(methyloxy)propyl]piperazine;
ethyl N-{[1-(2-chlorophenyl)-5-{5-[3-(methylsulfonyl)phenyl]-2-thienyl}-1H-pyrazol-3-yl]carbonyl}-N-methylglycinate;
1-(2-chlorophenyl)-N-{3-[(1-methylethyl)oxy]propyl}-5-{5-[3-(methylsulfonyl)phenyl]-2-thienyl}-1H-pyrazole-3-carboxamide;
4-({[1-(2-chlorophenyl)-5-{5-[3-(methylsulfonyl)phenyl]-2-thienyl}-1H-pyrazol-3-yl]carbonyl}amino)butanoic acid;

N-{[1-(2-chlorophenyl)-5-{5-[3-(methylsulfonyl)phenyl]-2-thienyl}-1H-pyrazol-3-yl]carbonyl}-N,2-dimethylalanine;

[(2S)-1-{[1-(2-chlorophenyl)-5-{5-[3-(methylsulfonyl)phenyl]-2-thienyl}-1H-pyrazol-3-yl]carbonyl}pyrrolidin-2-yl]methanol;

1-(2-chlorophenyl)-N-(3,4-dihydro-2H-1,5-benzodioxepin-7-ylmethyl)-5-{5-[3-(methylsulfonyl)phenyl]-2-thienyl}-1H-pyrazole-3-carboxamide;

1-(2-chlorophenyl)-N-[(5-methylpyrazin-2-yl)methyl]-5-{5-[3-(methylsulfonyl)phenyl]-2-thienyl}-1H-pyrazole-3-carboxamide;

1-(2-chlorophenyl)-N-(5-hydroxypentyl)-5-{5-[3-(methylsulfonyl)phenyl]-2-thienyl}-1H-pyrazole-3-carboxamide;

1-(2-chlorophenyl)-N-[2-(diethylamino)ethyl]-5-{5-[3-(methylsulfonyl)phenyl]-2-thienyl}-1H-pyrazole-3-carboxamide;

(4-{[1-(2-chlorophenyl)-5-{5-[3-(methylsulfonyl)phenyl]-2-thienyl}-1H-pyrazol-3-yl]carbonyl}piperazin-1-yl)acetic acid;

1-(2-chlorophenyl)-N-[2-(dimethylamino)ethyl]-N-ethyl-5-{5-[3-(methylsulfonyl)phenyl]-2-thienyl}-1H-pyrazole-3-carboxamide;

1-(2-chlorophenyl)-N-[2-(dimethylamino)ethyl]-5-{5-[3-(methylsulfonyl)phenyl]-2-thienyl}-N-(phenylmethyl)-1H-pyrazole-3-carboxamide;

1-(2-chlorophenyl)-N-(2-hydroxyethyl)-5-{5-[3-(methylsulfonyl)phenyl]-2-thienyl}-1H-pyrazole-3-carboxamide;

1-(2-chlorophenyl)-N-(1,3-dioxolan-2-ylmethyl)-N-methyl-5-{5-[3-(methylsulfonyl)phenyl]-2-thienyl}-1H-pyrazole-3-carboxamide;

1-{[1-(2-chlorophenyl)-5-{5-[3-(methylsulfonyl)phenyl]-2-thienyl}-1H-pyrazol-3-yl]carbonyl}-4-(1-ethylpropyl)piperazine;

1-{[1-(2-chlorophenyl)-5-{5-[3-(methylsulfonyl)phenyl]-2-thienyl}-1H-pyrazol-3-yl]carbonyl}-4-[2-(methyloxy)ethyl]piperazine;

1-(2-chlorophenyl)-N-methyl-5-{5-[3-(methylsulfonyl)phenyl]-2-thienyl}-N-pyridin-4-yl-1H-pyrazole-3-carboxamide;

4-{[1-(2-chlorophenyl)-5-{5-[3-(methylsulfonyl)phenyl]-2-thienyl}-1H-pyrazol-3-yl]carbonyl}piperazin-2-one;

1-(2-chlorophenyl)-N-(5-methyl-1,3,4-oxadiazol-2-yl)-5-{5-[3-(methylsulfonyl)phenyl]-2-thienyl}-1H-pyrazole-3-carboxamide;

1-{[1-(2-chlorophenyl)-5-{5-[3-(methylsulfonyl)phenyl]-2-thienyl}-1H-pyrazol-3-yl]carbonyl}piperidine-3-carboxylic acid;

1-{[1-(2-chlorophenyl)-5-{5-[3-(methylsulfonyl)phenyl]-2-thienyl}-1H-pyrazol-3-yl]carbonyl}azetidine-3-carboxylic acid;

1-(2-chlorophenyl)-N-methyl-5-{5-[3-(methylsulfonyl)phenyl]-2-thienyl}-N-(pyridin-4-ylmethyl)-1H-pyrazole-3-carboxamide;

1-(2-chlorophenyl)-5-{5-[3-(methylsulfonyl)phenyl]-2-thienyl}-N-[(1,3,5-trimethyl-1H-pyrazol-4-yl)methyl]-1H-pyrazole-3-carboxamide;

1-(2-chlorophenyl)-N-(1-methyl-1H-pyrazol-3-yl)-5-{5-[3-(methylsulfonyl)phenyl]-2-thienyl}-1H-pyrazole-3-carboxamide;

1-(2-chlorophenyl)-N-methyl-5-{5-[3-(methylsulfonyl)phenyl]-2-thienyl}-N-pyridin-2-yl-1H-pyrazole-3-carboxamide;

1-{[1-(2-chlorophenyl)-5-{5-[3-(methylsulfonyl)phenyl]-2-thienyl}-1H-pyrazol-3-yl]carbonyl}-4-[4-(methyloxy)butyl]piperazine;

1-{[1-(2-chlorophenyl)-5-{5-[3-(methylsulfonyl)phenyl]-2-thienyl}-1H-pyrazol-3-yl]carbonyl}-4-hexylpiperazine;

N-[2-(4-{[1-(2-chlorophenyl)-5-{5-[3-(methylsulfonyl)phenyl]-2-thienyl}-1H-pyrazol-3-yl]carbonyl}piperazin-1-yl)ethyl]-N-prop-2-en-1-ylprop-2-en-1-amine;

1-{[1-(2-chlorophenyl)-5-{5-[3-(methylsulfonyl)phenyl]-2-thienyl}-1H-pyrazol-3-yl]carbonyl}-4-(1-methylpropyl)piperazine;

1-(2-chlorophenyl)-N-methyl-N-(1-methylpiperidin-4-yl)-5-{5-[3-(methylsulfonyl)phenyl]-2-thienyl}-1H-pyrazole-3-carboxamide;

N-[2-(4-{[1-(2-chlorophenyl)-5-{5-[3-(methylsulfonyl)phenyl]-2-thienyl}-1H-pyrazol-3-yl]carbonyl}piperazin-1-yl)ethyl]-N-propylpropan-1-amine;

1-(2-chlorophenyl)-N-[(2,2-dimethyl-1,3-dioxolan-4-yl)methyl]-5-{5-[3-(methylsulfonyl)phenyl]-2-thienyl}-1H-pyrazole-3-carboxamide;

1-{[1-(2-chlorophenyl)-5-{5-[3-(methylsulfonyl)phenyl]-2-thienyl}-1H-pyrazol-3-yl]carbonyl}-4-(1-methylethyl)piperazine;

1-{[1-(2-chlorophenyl)-5-{5-[3-(methylsulfonyl)phenyl]-2-thienyl}-1H-pyrazol-3-yl]carbonyl}-4-pentylpiperazine;

1-{[1-(2-chlorophenyl)-5-{5-[3-(methylsulfonyl)phenyl]-2-thienyl}-1H-pyrazol-3-yl]carbonyl}-4-heptylpiperazine;

1-{[1-(2-chlorophenyl)-5-{5-[3-(methylsulfonyl)phenyl]-2-thienyl}-1H-pyrazol-3-yl]carbonyl}-4-(1-methylbutyl)piperazine;

N-(2-amino-2-oxoethyl)-1-(2-chlorophenyl)-N-methyl-5-{5-[3-(methylsulfonyl)phenyl]-2-thienyl}-1H-pyrazole-3-carboxamide;

4-{[1-(2-chlorophenyl)-5-{5-[3-(methylsulfonyl)phenyl]-2-thienyl}-1H-pyrazol-3-yl]carbonyl}-1,2-dimethylpiperazine;

1-(2-chlorophenyl)-5-{5-[3-(methylsulfonyl)phenyl]-2-thienyl}-N,N-bis(pyridin-2-ylmethyl)-1H-pyrazole-3-carboxamide;

ethyl 1-{[1-(2-chlorophenyl)-5-{5-[3-(methylsulfonyl)phenyl]-2-thienyl}-1H-pyrazol-3-yl]carbonyl}piperidine-4-carboxylate;

ethyl 4-({[1-(2-chlorophenyl)-5-{5-[3-(methylsulfonyl)phenyl]-2-thienyl}-1H-pyrazol-3-yl]carbonyl}amino)piperidine-1-carboxylate;

(3R)-1-{[1-(2-chlorophenyl)-5-{5-[3-(methylsulfonyl)phenyl]-2-thienyl}-1H-pyrazol-3-yl]carbonyl}-N,N-dimethylpyrrolidin-3-amine;

1-(2-chlorophenyl)-5-{5-[3-(methylsulfonyl)phenyl]-2-thienyl}-N-(3-pyrrolidin-1-ylpropyl)-1H-pyrazole-3-carboxamide;

2,2'-({[1-(2-chlorophenyl)-5-{5-[3-(methylsulfonyl)phenyl]-2-thienyl}-1H-pyrazol-3-yl]carbonyl}imino)diacetic acid;

N-{[1-(2-chlorophenyl)-5-{5-[3-(methylsulfonyl)phenyl]-2-thienyl}-1H-pyrazol-3-yl]carbonyl}-D-serine;

2-(4-{[1-(2-chlorophenyl)-5-{5-[3-(methylsulfonyl)phenyl]-2-thienyl}-1H-pyrazol-3-yl]carbonyl}piperazin-1-yl)ethanol;

1-(2-chlorophenyl)-N-[2-hydroxy-1-(hydroxymethyl)ethyl]-5-{5-[3-(methylsulfonyl)phenyl]-2-thienyl}-1H-pyrazole-3-carboxamide;

1-(2-chlorophenyl)-N-[(1-ethylpyrrolidin-3-yl)methyl]-5-{5-[3-(methylsulfonyl)phenyl]-2-thienyl}-1H-pyrazole-3-carboxamide;
1-(2-chlorophenyl)-N-(2-methyl-2-morpholin-4-ylpropyl)-5-{5-[3-(methylsulfonyl)phenyl]-2-thienyl}-1H-pyrazole-3-carboxamide;
N-(2-amino-2-methylpropyl)-1-(2-chlorophenyl)-N-(2-hydroxy-1,1-dimethylethyl)-5-{5-[3-(methylsulfonyl)phenyl]-2-thienyl}-1H-pyrazole-3-carboxamide;
1-(2-chlorophenyl)-N-methyl-N-{[1-(1-methylethyl)pyrrolidin-3-yl]methyl}-5-{5-[3-(methylsulfonyl)phenyl]-2-thienyl}-1H-pyrazole-3-carboxamide;
1-{[1-(2-chlorophenyl)-5-{5-[3-(methylsulfonyl)phenyl]-2-thienyl}-1H-pyrazol-3-yl]carbonyl}-4-propylpiperazine;
1-(2-chlorophenyl)-N-(3-hydroxypropyl)-5-{5-[3-(methylsulfonyl)phenyl]-2-thienyl}-1H-pyrazole-3-carboxamide;
1-(2-chlorophenyl)-N-(2-hydroxyethyl)-N-[2-(methyloxy)ethyl]-5-{5-[3-(methylsulfonyl)phenyl]-2-thienyl}-1H-pyrazole-3-carboxamide;
(3R)-1-{[1-(2-chlorophenyl)-5-{5-[3-(methylsulfonyl)phenyl]-2-thienyl}-1H-pyrazol-3-yl]carbonyl}pyrrolidin-3-ol;
1-{[1-(2-chlorophenyl)-5-{5-[3-(methylsulfonyl)phenyl]-2-thienyl}-1H-pyrazol-3-yl]carbonyl}-N,N-diethylpyrrolidin-3-amine;
1-(2-chlorophenyl)-N-[4-(diethylamino)-1-methylbutyl]-5-{5-[3-(methylsulfonyl)phenyl]-2-thienyl}-1H-pyrazole-3-carboxamide;
N-{[4-(aminosulfonyl)phenyl]methyl}-1-(2-chlorophenyl)-5-{5-[3-(methylsulfonyl)phenyl]-2-thienyl}-1H-pyrazole-3-carboxamide;
1-(2-chlorophenyl)-N-[2-(1,3-dioxolan-2-yl)ethyl]-N-methyl-5-{5-[3-(methylsulfonyl)phenyl]-2-thienyl}-1H-pyrazole-3-carboxamide;
(1-{[1-(2-chlorophenyl)-5-{5-[3-(methylsulfonyl)phenyl]-2-thienyl}-1H-pyrazol-3-yl]carbonyl}piperidin-3-yl)methanol;
1-(3-{5-[1-(2-chlorophenyl)-3-(1-hydroxy-1-methylethyl)-1H-pyrazol-5-yl]-2-thienyl}phenyl)ethanone;
2-[1-(2-chlorophenyl)-5-{5-[4-(methylsulfonyl)phenyl]-2-thienyl}-1H-pyrazol-3-yl]propan-2-ol;
2-[5-{5-[3,4-bis(methyloxy)phenyl]-2-thienyl}-1-(2-chlorophenyl)-1H-pyrazol-3-yl]propan-2-ol;
2-chloro-4-{5-[1-(2-chlorophenyl)-3-(1-hydroxy-1-methylethyl)-1H-pyrazol-5-yl]-2-thienyl}-N-(1-methylethyl)benzamide;
2-[1-(2-chlorophenyl)-5-{5-[2-(methylthio)phenyl]-2-thienyl}-1H-pyrazol-3-yl]propan-2-ol;
2-{1-(2-chlorophenyl)-5-[5-(2-fluorobiphenyl-4-yl)-2-thienyl]-1H-pyrazol-3-yl}propan-2-ol;
2-{1-(2-chlorophenyl)-5-[5-(3-fluorophenyl)-2-thienyl]-1H-pyrazol-3-yl}propan-2-ol;
N-(3-{5-[1-(2-chlorophenyl)-3-(1-hydroxy-1-methylethyl)-1H-pyrazol-5-yl]-2-thienyl}phenyl)acetamide;
2-[1-(2-chlorophenyl)-5-(5-{4-[(1-methylethyl)oxy]phenyl}-2-thienyl)-1H-pyrazol-3-yl]propan-2-ol;
2-[1-(2-chlorophenyl)-5-{5-[2-fluoro-3-(methyloxy)phenyl]-2-thienyl}-1H-pyrazol-3-yl]propan-2-ol;
2-{1-(2-chlorophenyl)-5-[5-(4-chlorophenyl)-2-thienyl]-1H-pyrazol-3-yl}propan-2-ol;
2-[1-(2-chlorophenyl)-5-{5-[5-fluoro-2-(methyloxy)phenyl]-2-thienyl}-1H-pyrazol-3-yl]propan-2-ol;
2-[1-(2-chlorophenyl)-5-{5-[4-(ethyloxy)-3-(trifluoromethyl)phenyl]-2-thienyl}-1H-pyrazol-3-yl]propan-2-ol;
2-{1-(2-chlorophenyl)-5-[5-(2,3-dichlorophenyl)-2-thienyl]-1H-pyrazol-3-yl}propan-2-ol;
2-[1-(2-chlorophenyl)-5-(5-pyrimidin-5-yl-2-thienyl)-1H-pyrazol-3-yl]propan-2-ol;
4-{5-[1-(2-chlorophenyl)-3-(1-hydroxy-1-methylethyl)-1H-pyrazol-5-yl]-2-thienyl}benzoic acid;
N-(4-{5-[1-(2-chlorophenyl)-3-(1-hydroxy-1-methylethyl)-1H-pyrazol-5-yl]-2-thienyl}phenyl)methanesulfonamide;
2-{5-[1-(2-chlorophenyl)-3-(1-hydroxy-1-methylethyl)-1H-pyrazol-5-yl]-2-thienyl}-5-fluorophenol;
2-[1-(2-chlorophenyl)-5-(5-{4-fluoro-2-[(phenylmethyl)oxy]phenyl}-2-thienyl)-1H-pyrazol-3-yl]propan-2-ol;
3-{5-[1-(2-chlorophenyl)-3-(1-hydroxy-1-methylethyl)-1H-pyrazol-5-yl]-2-thienyl}-5-fluorobenzoic acid;
2-{1-(2-chlorophenyl)-5-[5-(1-methyl-1H-indol-5-yl)-2-thienyl]-1H-pyrazol-3-yl}propan-2-ol;
2-[1-(2-chlorophenyl)-5-(5-{2-[(1-methylethyl)oxy]-5-(trifluoromethyl)phenyl}-2-thienyl)-1H-pyrazol-3-yl]propan-2-ol;
2-chloro-5-{5-[1-(2-chlorophenyl)-3-(1-hydroxy-1-methylethyl)-1H-pyrazol-5-yl]-2-thienyl}benzamide;
2-{5-[5-(2-chloro-6-fluorophenyl)-2-thienyl]-1-(2-chlorophenyl)-1H-pyrazol-3-yl}propan-2-ol;
3-{5-[1-(2-chlorophenyl)-3-(1-hydroxy-1-methylethyl)-1H-pyrazol-5-yl]-2-thienyl}-N,N-dimethylbenzenesulfonamide;
2-chloro-4-{5-[1-(2-chlorophenyl)-3-(1-hydroxy-1-methylethyl)-1H-pyrazol-5-yl]-2-thienyl}-N-methylbenzamide;
2-[1-(2-chlorophenyl)-5-(5-{2-methyl-4-[(1-methylethyl)oxy]phenyl}-2-thienyl)-1H-pyrazol-3-yl]propan-2-ol;
4-{5-[1-(2-chlorophenyl)-3-(1-hydroxy-1-methylethyl)-1H-pyrazol-5-yl]-2-thienyl}-N-(furan-2-ylmethyl)benzamide;
methyl 2-{5-[1-(2-chlorophenyl)-3-(1-hydroxy-1-methylethyl)-1H-pyrazol-5-yl]-2-thienyl}benzoate;
2-[5-{5-[3-chloro-4-(methyloxy)phenyl]-2-thienyl}-1-(2-chlorophenyl)-1H-pyrazol-3-yl]propan-2-ol;
2-[5-(5-{3-chloro-4-[(1-methylethyl)oxy]phenyl}-2-thienyl)-1-(2-chlorophenyl)-1H-pyrazol-3-yl]propan-2-ol;
2-[1-(2-chlorophenyl)-5-{5-[4-(1,3-thiazolidin-3-ylcarbonyl)phenyl]-2-thienyl}-1H-pyrazol-3-yl]propan-2-ol;
2-chloro-4-{5-[1-(2-chlorophenyl)-3-(1-hydroxy-1-methylethyl)-1H-pyrazol-5-yl]-2-thienyl}-N-cyclopropylbenzamide;
2-{5-[1-(2-chlorophenyl)-3-(1-hydroxy-1-methylethyl)-1H-pyrazol-5-yl]-2-thienyl}-4-fluorophenol;
N-(2-{5-[1-(2-chlorophenyl)-3-(1-hydroxy-1-methylethyl)-1H-pyrazol-5-yl]-2-thienyl}phenyl)methanesulfonamide;
4-{5-[1-(2-chlorophenyl)-3-(1-hydroxy-1-methylethyl)-1H-pyrazol-5-yl]-2-thienyl}-2-fluorobenzoic acid;
2-[1-(2-chlorophenyl)-5-{5-[4-(methylthio)-3-(trifluoromethyl)phenyl]-2-thienyl}-1H-pyrazol-3-yl]propan-2-ol;
2-[1-(2-chlorophenyl)-5-{5-[2-methyl-5-(methyloxy)phenyl]-2-thienyl}-1H-pyrazol-3-yl]propan-2-ol;
2-[1-(2-chlorophenyl)-5-{5-[2-(methyloxy)pyridin-3-yl]-2-thienyl}-1H-pyrazol-3-yl]propan-2-ol;
2-[1-(2-chlorophenyl)-5-{5-[6-(methyloxy)pyridin-3-yl]-2-thienyl}-1H-pyrazol-3-yl]propan-2-ol;
2-[1-(2-chlorophenyl)-5-{5-[4-(methyloxy)-3-(trifluoromethyl)phenyl]-2-thienyl}-1H-pyrazol-3-yl]propan-2-ol;

2-[1-(2-chlorophenyl)-5-(5-pyridin-3-yl-2-thienyl)-1H-pyrazol-3-yl]propan-2-ol;
2-{1-(2-chlorophenyl)-5-[5-(1H-indol-6-yl)-2-thienyl]-1H-pyrazol-3-yl}propan-2-ol;
2-[1-(2-chlorophenyl)-5-{5-[(1E)-3,3-dimethylbut-1-en-1-yl]-2-thienyl}-1H-pyrazol-3-yl]propan-2-ol;
1,1-dimethylethyl 2-{5-[1-(2-chlorophenyl)-3-(1-hydroxy-1-methylethyl)-1H-pyrazol-5-yl]-2-thienyl}-1H-pyrrole-1-carboxylate;
2-[1-(2-chlorophenyl)-5-(5-{2-[(1-methylethyl)oxy]pyridin-3-yl}-2-thienyl)-1H-pyrazol-3-yl]propan-2-ol;
2-[1-(2-chlorophenyl)-5-{5-[2-(cyclopentyloxy)pyridin-3-yl]-2-thienyl}-1H-pyrazol-3-yl]propan-2-ol;
ethyl 4-{5-[1-(2-chlorophenyl)-3-(1-hydroxy-1-methylethyl)-1H-pyrazol-5-yl]-2-thienyl}benzoate;
2-{1-(2-chlorophenyl)-5-[5-(5-methylfuran-2-yl)-2-thienyl]-1H-pyrazol-3-yl}propan-2-ol;
4-{5-[1-(2-chlorophenyl)-3-(1-hydroxy-1-methylethyl)-1H-pyrazol-5-yl]-2-thienyl}benzamide;
methyl N-[(4-{5-[1-(2-chlorophenyl)-3-(1-hydroxy-1-methylethyl)-1H-pyrazol-5-yl]-2-thienyl}phenyl)carbonyl]glycinate;
3-{5-[1-(2-chlorophenyl)-3-(1-hydroxy-1-methylethyl)-1H-pyrazol-5-yl]-2-thienyl}benzamide;
2-[1-(2-chlorophenyl)-5-{5-[3-(thiomorpholin-4-ylcarbonyl)phenyl]-2-thienyl}-1H-pyrazol-3-yl]propan-2-ol;
2-{5-[5-(1,3-benzodioxol-5-yl)-2-thienyl]-1-(2-chlorophenyl)-1H-pyrazol-3-yl}propan-2-ol;
2-[1-(2-chlorophenyl)-5-{5-[2-methyl-5-(morpholin-4-ylsulfonyl)phenyl]-2-thienyl}-1H-pyrazol-3-yl]propan-2-ol;
2-[5-{5-[2,4-bis(trifluoromethyl)phenyl]-2-thienyl}-1-(2-chlorophenyl)-1H-pyrazol-3-yl]propan-2-ol;
2-[5-{5-[2,3-bis(methyloxy)phenyl]-2-thienyl}-1-(2-chlorophenyl)-1H-pyrazol-3-yl]propan-2-ol;
2-[1-(2-chlorophenyl)-5-{5-[3,5-difluoro-2-(methyloxy)phenyl]-2-thienyl}-1H-pyrazol-3-yl]propan-2-ol;
2-[1-(2-chlorophenyl)-5-{5-[2-(phenyloxy)phenyl]-2-thienyl}-1H-pyrazol-3-yl]propan-2-ol;
2-[1-(2-chlorophenyl)-5-{5-[3-(trifluoromethyl)phenyl]-2-thienyl}-1H-pyrazol-3-yl]propan-2-ol;
2-{1-(2-chlorophenyl)-5-[5-(3,5-dichlorophenyl)-2-thienyl]-1H-pyrazol-3-yl}propan-2-ol;
2-{1-(2-chlorophenyl)-5-[5-(2,4,5-trimethylphenyl)-2-thienyl]-1H-pyrazol-3-yl}propan-2-ol;
2-[1-(2-chlorophenyl)-5-(5-naphthalen-2-yl-2-thienyl)-1H-pyrazol-3-yl]propan-2-ol;
2-[1-(2-chlorophenyl)-5-(5-{2-[(1-methylethyl)oxy]phenyl}-2-thienyl)-1H-pyrazol-3-yl]propan-2-ol;
2-[1-(2-chlorophenyl)-5-{5-[2-fluoro-5-(methyloxy)phenyl]-2-thienyl}-1H-pyrazol-3-yl]propan-2-ol;
2-[1-(2-chlorophenyl)-5-{5-[(1E)-prop-1-en-1-yl]-2-thienyl}-1H-pyrazol-3-yl]propan-2-ol;
2-{1-(2-chlorophenyl)-5-[5-(5-fluoro-2-methylphenyl)-2-thienyl]-1H-pyrazol-3-yl}propan-2-ol;
2-[1-(2-chlorophenyl)-5-{5-[2-(hydroxymethyl)phenyl]-2-thienyl}-1H-pyrazol-3-yl]propan-2-ol;
2-[1-(2-chlorophenyl)-5-(5-{5-methyl-2-[(1-methylethyl)oxy]phenyl}-2-thienyl)-1H-pyrazol-3-yl]propan-2-ol;
2-[5-(2,2'-bithien-5-yl)-1-(2-chlorophenyl)-1H-pyrazol-3-yl]propan-2-ol;
2-[5-(5-biphenyl-3-yl-2-thienyl)-1-(2-chlorophenyl)-1H-pyrazol-3-yl]propan-2-ol;
2-[1-(2-chlorophenyl)-5-{5-[5-methyl-2-(propyloxy)phenyl]-2-thienyl}-1H-pyrazol-3-yl]propan-2-ol;
2-{1-(2-chlorophenyl)-5-[5-(4-propylphenyl)-2-thienyl]-1H-pyrazol-3-yl}propan-2-ol;
2-[1-(2-chlorophenyl)-5-(5-{4-[(trifluoromethyl)oxy]phenyl}-2-thienyl)-1H-pyrazol-3-yl]propan-2-ol;
4-{5-[1-(2-chlorophenyl)-3-(1-hydroxy-1-methylethyl)-1H-pyrazol-5-yl]-2-thienyl}-N-(2-methylpropyl)benzamide;
2-[1-(2-chlorophenyl)-5-{5-[3-(ethyloxy)phenyl]-2-thienyl}-1H-pyrazol-3-yl]propan-2-ol;
2-{1-(2-chlorophenyl)-5-[5-(4-ethylphenyl)-2-thienyl]-1H-pyrazol-3-yl}propan-2-ol;
2-{1-(2-chlorophenyl)-5-[5-(3,4-dichlorophenyl)-2-thienyl]-1H-pyrazol-3-yl}propan-2-ol;
2-[1-(2-chlorophenyl)-5-{5-[6-(methyloxy)naphthalen-2-yl]-2-thienyl}-1H-pyrazol-3-yl]propan-2-ol;
2-{1-(2-chlorophenyl)-5-[5-(2-ethylphenyl)-2-thienyl]-1H-pyrazol-3-yl}propan-2-ol;
2-[1-(2-chlorophenyl)-5-{5-[4-(dimethylamino)phenyl]-2-thienyl}-1H-pyrazol-3-yl]propan-2-ol;
2-{1-(2-chlorophenyl)-5-[5-(2,4,5-trifluorophenyl)-2-thienyl]-1H-pyrazol-3-yl}propan-2-ol;
2-[1-(2-chlorophenyl)-5-{5-[2-fluoro-5-(trifluoromethyl)phenyl]-2-thienyl}-1H-pyrazol-3-yl]propan-2-ol;
2-{1-(2-chlorophenyl)-5-[5-(2,3,4-trifluorophenyl)-2-thienyl]-1H-pyrazol-3-yl}propan-2-ol;
N-(4-{5-[1-(2-chlorophenyl)-3-(1-hydroxy-1-methylethyl)-1H-pyrazol-5-yl]-2-thienyl}phenyl)acetamide;
2-[1-(2-chlorophenyl)-5-{5-[3-(hydroxymethyl)phenyl]-2-thienyl}-1H-pyrazol-3-yl]propan-2-ol;
2-[5-{5-[5-chloro-2-(methyloxy)phenyl]-2-thienyl}-1-(2-chlorophenyl)-1H-pyrazol-3-yl]propan-2-ol;
2-[1-(2-chlorophenyl)-5-{5-[2,3,4-tris(methyloxy)phenyl]-2-thienyl}-1H-pyrazol-3-yl]propan-2-ol;
2-[1-(2-chlorophenyl)-5-{5-[2-(trifluoromethyl)phenyl]-2-thienyl}-1H-pyrazol-3-yl]propan-2-ol;
2-{1-(2-chlorophenyl)-5-[5-(1H-indol-5-yl)-2-thienyl]-1H-pyrazol-3-yl}propan-2-ol;
2-[1-(2-chlorophenyl)-5-{5-[6-(ethyloxy)naphthalen-2-yl]-2-thienyl}-1H-pyrazol-3-yl]propan-2-ol;
2-[1-(2-chlorophenyl)-5-{5-[4-(hydroxymethyl)phenyl]-2-thienyl}-1H-pyrazol-3-yl]propan-2-ol;
2-{1-(2-chlorophenyl)-5-[5-(2,3-difluorophenyl)-2-thienyl]-1H-pyrazol-3-yl}propan-2-ol;
2-{1-(2-chlorophenyl)-5-[5-(2,4-difluorophenyl)-2-thienyl]-1H-pyrazol-3-yl}propan-2-ol;
2-{5-[5-(2-chloro-6-fluoro-3-methylphenyl)-2-thienyl]-1-(2-chlorophenyl)-1H-pyrazol-3-yl}propan-2-ol;
2-[1-(2-chlorophenyl)-5-{5-[4-(methylthio)phenyl]-2-thienyl}-1H-pyrazol-3-yl]propan-2-ol;
2-[1-(2-chlorophenyl)-5-{5-[4-(trifluoromethyl)phenyl]-2-thienyl}-1H-pyrazol-3-yl]propan-2-ol;
2-{5-[5-(6-chloro-2-fluoro-3-methylphenyl)-2-thienyl]-1-(2-chlorophenyl)-1H-pyrazol-3-yl}propan-2-ol;
2-{1-(2-chlorophenyl)-5-[5-(4-fluoro-3-methylphenyl)-2-thienyl]-1H-pyrazol-3-yl}propan-2-ol;
2-{1-(2-chlorophenyl)-5-[5-(3,4-difluorophenyl)-2-thienyl]-1H-pyrazol-3-yl}propan-2-ol
2-[1-(2-chlorophenyl)-5-{5-[4-(phenyloxy)phenyl]-2-thienyl}-1H-pyrazol-3-yl]propan-2-ol;
2-[1-(2-chlorophenyl)-5-{5-[4-chloro-2-(trifluoromethyl)phenyl]-2-thienyl}-1H-pyrazol-3-yl]propan-2-ol;
2-{1-(2-chlorophenyl)-5-[5-(2,5-dichlorophenyl)-2-thienyl]-1H-pyrazol-3-yl}propan-2-ol;
2-[5-{5-[2-chloro-4-(ethyloxy)phenyl]-2-thienyl}-1-(2-chlorophenyl)-1H-pyrazol-3-yl]propan-2-ol;
2-{1-(2-chlorophenyl)-5-[5-(3-chlorophenyl)-2-thienyl]-1H-pyrazol-3-yl}propan-2-ol;
2-{1-(2-chlorophenyl)-5-[5-(1H-indol-4-yl)-2-thienyl]-1H-pyrazol-3-yl}propan-2-ol;

2-[1-(2-chlorophenyl)-5-{5-[2-chloro-4-(trifluoromethyl)phenyl]-2-thienyl}-1H-pyrazol-3-yl]propan-2-ol;
N-(3-{5-[1-(2-chlorophenyl)-3-(1-hydroxy-1-methylethyl)-1H-pyrazol-5-yl]-2-thienyl}phenyl)methanesulfonamide;
3-{5-[1-(2-chlorophenyl)-3-(1-hydroxy-1-methylethyl)-1H-pyrazol-5-yl]-2-thienyl}benzenesulfonamide;
3-{5-[1-(2-chlorophenyl)-3-(1-hydroxy-1-methylethyl)-1H-pyrazol-5-yl]-2-thienyl}-N-(1-methylethyl)benzamide;
2-[1-(2-chlorophenyl)-5-{5-[4-fluoro-3-(trifluoromethyl)phenyl]-2-thienyl}-1H-pyrazol-3-yl]propan-2-ol;
2-[5-{5-[3,5-bis(trifluoromethyl)phenyl]-2-thienyl}-1-(2-chlorophenyl)-1H-pyrazol-3-yl]propan-2-ol;
2-[5-(5-biphenyl-4-yl-2-thienyl)-1-(2-chlorophenyl)-1H-pyrazol-3-yl]propan-2-ol;
2-[1-(2-chlorophenyl)-5-{5-[4-(1-methylethyl)phenyl]-2-thienyl}-1H-pyrazol-3-yl]propan-2-ol;
2-[1-(2-chlorophenyl)-5-(5-ethyl-2-thienyl)-1H-pyrazol-3-yl]propan-2-ol;
2-[1-(2-chlorophenyl)-5-(5-{3-fluoro-4-[(phenylmethyl)oxy]phenyl}-2-thienyl)-1H-pyrazol-3-yl]propan-2-ol;
2-[1-(2-chlorophenyl)-5-{5-[3-chloro-4-(trifluoromethyl)phenyl]-2-thienyl}-1H-pyrazol-3-yl]propan-2-ol;
2-[1-(2-chlorophenyl)-5-{5-[4-(ethylsulfonyl)phenyl]-2-thienyl}-1H-pyrazol-3-yl]propan-2-ol;
3-{5-[1-(2-chlorophenyl)-3-(1-hydroxy-1-methylethyl)-1H-pyrazol-5-yl]-2-thienyl}phenol;
3-{5-[1-(2-chlorophenyl)-3-(1-hydroxy-1-methylethyl)-1H-pyrazol-5-yl]-2-thienyl}benzoic acid;
2-{1-(2-chlorophenyl)-5-[5-(3,4-dihydro-2H-1,5-benzodioxepin-7-yl)-2-thienyl]-1H-pyrazol-3-yl}propan-2-ol;
2-{1-(2-chlorophenyl)-5-[5-(2,3-dihydro-1,4-benzodioxin-6-yl)-2-thienyl]-1H-pyrazol-3-yl}propan-2-ol;
2-{1-(2-chlorophenyl)-5-[5-(2-fluorophenyl)-2-thienyl]-1H-pyrazol-3-yl}propan-2-ol;
2-[1-(2-chlorophenyl)-5-(5-{3-[(1-methylethyl)oxy]phenyl}-2-thienyl)-1H-pyrazol-3-yl]propan-2-ol;
1-(2-{5-[1-(2-chlorophenyl)-3-(1-hydroxy-1-methylethyl)-1H-pyrazol-5-yl]-2-thienyl}phenyl)ethanone;
2-{5-[1-(2-chlorophenyl)-3-(1-hydroxy-1-methylethyl)-1H-pyrazol-5-yl]-2-thienyl}phenol;
1-(4-{5-[1-(2-chlorophenyl)-3-(1-hydroxy-1-methylethyl)-1H-pyrazol-5-yl]-2-thienyl}phenyl)ethanone;
2-[1-(2-chlorophenyl)-5-{5-[5-methyl-2-(methyloxy)phenyl]-2-thienyl}-1H-pyrazol-3-yl]propan-2-ol;
2-{5-[1-(2-chlorophenyl)-3-(1-hydroxy-1-methylethyl)-1H-pyrazol-5-yl]-2-thienyl}phenyl 1,1-dimethylethyl carbonate;
2-[5-{5-[2-chloro-6-(methyloxy)phenyl]-2-thienyl}-1-(2-chlorophenyl)-1H-pyrazol-3-yl]propan-2-ol;
2-{1-(2-chlorophenyl)-5-[5-(1-methyl-1H-pyrazol-4-yl)-2-thienyl]-1H-pyrazol-3-yl}propan-2-ol;
4-(2-{5-[1-(2-chlorophenyl)-3-(1-hydroxy-1-methylethyl)-1H-pyrazol-5-yl]-2-thienyl}ethyl)benzoic acid;
2-[1-(2-chlorophenyl)-5-{5-[(1E)-1-ethylbut-1-en-1-yl]-2-thienyl}-1H-pyrazol-3-yl]propan-2-ol;
2-[1-(2-chlorophenyl)-5-{5-[3-(ethylthio)phenyl]-2-thienyl}-1H-pyrazol-3-yl]propan-2-ol;
4-{5-[1-(2-chlorophenyl)-3-(1-hydroxy-1-methylethyl)-1H-pyrazol-5-yl]-2-thienyl}benzonitrile;
2-[1-(2-chlorophenyl)-5-{5-[3-fluoro-4-(methyloxy)phenyl]-2-thienyl}-1H-pyrazol-3-yl]propan-2-ol;
2-{1-(2-chlorophenyl)-5-[5-(2,5-difluorophenyl)-2-thienyl]-1H-pyrazol-3-yl}propan-2-ol;
2-[1-(2-chlorophenyl)-5-(5-{(E)-2-[4-(trifluoromethyl)phenyl]ethenyl}-2-thienyl)-1H-pyrazol-3-yl]propan-2-ol;
2-[1-(2-chlorophenyl)-5-{5-[2-(ethyloxy)phenyl]-2-thienyl}-1H-pyrazol-3-yl]propan-2-ol;
2-{5-[5-(1-benzothien-3-yl)-2-thienyl]-1-(2-chlorophenyl)-1H-pyrazol-3-yl}propan-2-ol;
ethyl 2-{5-[1-(2-chlorophenyl)-3-(1-hydroxy-1-methylethyl)-1H-pyrazol-5-yl]-2-thienyl}benzoate;
2-[1-(2-chlorophenyl)-5-{5-[(E)-2-(4-fluorophenyl)ethenyl]-2-thienyl}-1H-pyrazol-3-yl]propan-2-ol;
2-{1-(2-chlorophenyl)-5-[5-(4-ethenylphenyl)-2-thienyl]-1H-pyrazol-3-yl}propan-2-ol;
2-{1-(2-chlorophenyl)-5-[5-(2-chloropyridin-4-yl)-2-thienyl]-1H-pyrazol-3-yl}propan-2-ol;
2-{5-[5-(3-chloro-4-fluorophenyl)-2-thienyl]-1-(2-chlorophenyl)-1H-pyrazol-3-yl}propan-2-ol;
1-{5'-[1-(2-chlorophenyl)-3-(1-hydroxy-1-methylethyl)-1H-pyrazol-5-yl]-2,2'-bithien-5-yl}ethanone;
2-[1-(2-chlorophenyl)-5-{5-[4-(methyloxy)phenyl]-2-thienyl}-1H-pyrazol-3-yl]propan-2-ol;
2-{5-[1-(2-chlorophenyl)-3-(1-hydroxy-1-methylethyl)-1H-pyrazol-5-yl]-2-thienyl}benzaldehyde;
2-[5-{5-[2,5-bis(methyloxy)phenyl]-2-thienyl}-1-(2-chlorophenyl)-1H-pyrazol-3-yl]propan-2-ol;
2-[1-(2-chlorophenyl)-5-(5-naphthalen-1-yl-2-thienyl)-1H-pyrazol-3-yl]propan-2-ol;
2-[1-(2-chlorophenyl)-5-{5-[3-(methyloxy)phenyl]-2-thienyl}-1H-pyrazol-3-yl]propan-2-ol;
2-[5-(5-biphenyl-2-yl-2-thienyl)-1-(2-chlorophenyl)-1H-pyrazol-3-yl]propan-2-ol;
2-[5-{5-[5-chloro-2-(ethyloxy)phenyl]-2-thienyl}-1-(2-chlorophenyl)-1H-pyrazol-3-yl]propan-2-ol;
2-[1-(2-chlorophenyl)-5-{5-[2-(ethylthio)phenyl]-2-thienyl}-1H-pyrazol-3-yl]propan-2-ol;
4-{5-[1-(2-chlorophenyl)-3-(1-hydroxy-1-methylethyl)-1H-pyrazol-5-yl]-2-thienyl}-2,6-dimethylphenol;
2-[1-(2-chlorophenyl)-5-{5-[2-(1-methylethyl)phenyl]-2-thienyl}-1H-pyrazol-3-yl]propan-2-ol;
2-[1-(2-chlorophenyl)-5-{5-[4-(ethyloxy)phenyl]-2-thienyl}-1H-pyrazol-3-yl]propan-2-ol;
2-[1-(2-chlorophenyl)-5-{5-[1-(phenylmethyl)-1H-pyrazol-4-yl]-2-thienyl}-1H-pyrazol-3-yl]propan-2-ol;
1,1-dimethylethyl (2-{5-[1-(2-chlorophenyl)-3-(1-hydroxy-1-methylethyl)-1H-pyrazol-5-yl]-2-thienyl}phenyl)carbamate;
2-[1-(2-chlorophenyl)-5-(5-{(E)-2-[4-(methyloxy)phenyl]ethenyl}-2-thienyl)-1H-pyrazol-3-yl]propan-2-ol;
N-(2-{5-[1-(2-chlorophenyl)-3-(1-hydroxy-1-methylethyl)-1H-pyrazol-5-yl]-2-thienyl}phenyl)acetamide;
2-[1-(2-chlorophenyl)-5-{5-[(E)-2-(4-methylphenyl)ethenyl]-2-thienyl}-1H-pyrazol-3-yl]propan-2-ol;
methyl (2E)-3-(4-{5-[1-(2-chlorophenyl)-3-(1-hydroxy-1-methylethyl)-1H-pyrazol-5-yl]-2-thienyl}phenyl)prop-2-enoate;
2-[1-(2-chlorophenyl)-5-{5-[4-fluoro-2-(methyloxy)phenyl]-2-thienyl}-1H-pyrazol-3-yl]propan-2-ol;
3-{5-[1-(2-chlorophenyl)-3-(1-hydroxy-1-methylethyl)-1H-pyrazol-5-yl]-2-thienyl}-N-ethylbenzamide;
methyl (2E)-3-(2-{5-[1-(2-chlorophenyl)-3-(1-hydroxy-1-methylethyl)-1H-pyrazol-5-yl]-2-thienyl}phenyl)prop-2-enoate;
1-(2-chlorophenyl)-5-{5-[3-(methylsulfonyl)phenyl]-2-thienyl}-3-(pyrrolidin-1-ylcarbonyl)-1H-pyrazole;
1-{[1-(2-chlorophenyl)-5-{5-[3-(methylsulfonyl)phenyl]-2-thienyl}-1H-pyrazol-3-yl]carbonyl}-4-methylpiperidine;

2-[5-{5-[3-(methylsulfonyl)phenyl]-2-thienyl}-3-(trifluoromethyl)-1H-pyrazol-1-yl]benzenesulfonamide;
1-(2-chlorophenyl)-5-{5-[3-(methylsulfonyl)phenyl]-2-thienyl}-N-[3-(trifluoromethyl)phenyl]-1H-pyrazole-3-carboxamide;
1-(2-chlorophenyl)-N-[2-(diethylamino)ethyl]-N-methyl-5-{5-[3-(methylsulfonyl)phenyl]-2-thienyl}-1H-pyrazole-3-carboxamide;
1-(2-chlorophenyl)-N-[2-(diethylamino)ethyl]-N-ethyl-5-{5-[3-(methylsulfonyl)phenyl]-2-thienyl}-1H-pyrazole-3-carboxamide;
1-(2-chlorophenyl)-N-[2-(dimethylamino)ethyl]-N-methyl-5-{5-[3-(methylsulfonyl)phenyl]-2-thienyl}-1H-pyrazole-3-carboxamide;
1-(2-chlorophenyl)-N-[3-(dimethylamino)propyl]-N-methyl-5-{5-[3-(methylsulfonyl)phenyl]-2-thienyl}-1H-pyrazole-3-carboxamide;
1-[(3-{5-[1-(2,5-dichlorophenyl)-3-(trifluoromethyl)-1H-pyrazol-5-yl]-2-thienyl}phenyl)sulfonyl]butan-2-ol;
[2-(methylsulfonyl)-4-(5-{3-(trifluoromethyl)-1-[3-(trifluoromethyl)pyridin-2-yl]-1H-pyrazol-5-yl}-2-thienyl)phenyl]methanol;
1-[1-(2-chlorophenyl)-5-{5-[3-(methylsulfonyl)phenyl]-2-thienyl}-1H-pyrazol-3-yl]ethanone;
[4-fluoro-3-(5-{3-(trifluoromethyl)-1-[3-(trifluoromethyl)pyridin-2-yl]-1H-pyrazol-5-yl}-2-thienyl)phenyl]acetic acid;
methyl [3-methyl-4-(5-{3-(trifluoromethyl)-1-[3-(trifluoromethyl)pyridin-2-yl]-1H-pyrazol-5-yl}-2-thienyl)phenyl]acetate;
N-{[1-(2-chlorophenyl)-5-{5-[3-(methylsulfonyl)phenyl]-2-thienyl}-1H-pyrazol-3-yl]carbonyl}-N-methylglycine;
[3-methyl-4-(5-{3-(trifluoromethyl)-1-[3-(trifluoromethyl)pyridin-2-yl]-1H-pyrazol-5-yl}-2-thienyl)phenyl]acetic acid;
methyl 5-{5-[3-(methylsulfonyl)phenyl]-2-thienyl}-1-[2-(trifluoromethyl)phenyl]-1H-pyrazole-3-carboxylate;
1-[1-(2-chlorophenyl)-5-{5-[3-(methylsulfonyl)phenyl]-2-thienyl}-1H-pyrazol-3-yl]ethanol;
2-(5-{5-[3-(methylsulfonyl)phenyl]-2-thienyl}-1-[2-(trifluoromethyl)phenyl]-1H-pyrazol-3-yl)propan-2-ol;
1-(2-chlorophenyl)-5-{5-[3-(methylsulfonyl)phenyl]-2-thienyl}-N-(2,2,2-trifluoroethyl)-1H-pyrazole-3-carboxamide;
2-methyl-2-[3-(5-{3-(trifluoromethyl)-1-[3-(trifluoromethyl)pyridin-2-yl]-1H-pyrazol-5-yl}-2-thienyl)phenyl]propanoic acid;
2-[3-(5-{1-[(5-chloro-2-thienyl)methyl]-3-(trifluoromethyl)-1H-pyrazol-5-yl}-2-thienyl)phenyl]-2-methylpropanoic acid;
2-[5-(5-{3-[(1-methylethyl)sulfonyl]phenyl}-2-thienyl)-3-(trifluoromethyl)-1H-pyrazol-1-yl]-3-(trifluoromethyl)pyridine;
methyl 545-{3-[(1-methylethyl)sulfonyl]phenyl}-2-thienyl)-1-[3-(trifluoromethyl)pyridin-2-yl]-1H-pyrazole-3-carboxylate;
N-[(3-{5-[1-(2,5-dichlorophenyl)-3-(trifluoromethyl)-1H-pyrazol-5-yl]-2-thienyl}phenyl)sulfonyl]-2,2-dimethylpropanamide;
1-[1-(2-chlorophenyl)-5-{5-[3-(methylsulfonyl)phenyl]-2-thienyl}-1H-pyrazol-3-yl]propan-1-one;
3-[1-(2-chlorophenyl)-5-{5-[3-(methylsulfonyl)phenyl]-2-thienyl}-1H-pyrazol-3-yl]pentan-3-ol;
1-[1-(2-chlorophenyl)-5-{5-[3-(methylsulfonyl)phenyl]-2-thienyl}-1H-pyrazol-3-yl]propan-1-ol;
(1E)-1-[1-(2-chlorophenyl)-5-{5-[3-(methylsulfonyl)phenyl]-2-thienyl}-1H-pyrazol-3-yl]ethanone oxime;
2-(5-{5-[3-(methylsulfonyl)phenyl]-2-thienyl}-1-[3-(trifluoromethyl)pyridin-2-yl]-1H-pyrazol-3-yl)propan-2-ol;
1-{5-(5-{3-[(1-methylethyl)sulfonyl]phenyl}-2-thienyl)-1-[3-(trifluoromethyl)pyridin-2-yl]-1H-pyrazol-3-yl}ethanone;
2-{5-(5-{3-[(1-methylethyl)sulfonyl]phenyl}-2-thienyl)-1-[3-(trifluoromethyl)pyridin-2-yl]-1H-pyrazol-3-yl}propan-2-ol;
2-[1-(2-chlorophenyl)-5-(5-{3-[(1-methylethyl)sulfonyl]phenyl}-2-thienyl)-1H-pyrazol-3-yl]propan-2-ol;
methyl 3-[5-{5-[3-(methylsulfonyl)phenyl]-2-thienyl}-3-(trifluoromethyl)-1H-pyrazol-1-yl]benzoate;
2-{3-[5-{5-[3-(methylsulfonyl)phenyl]-2-thienyl}-3-(trifluoromethyl)-1H-pyrazol-1-yl]phenyl}propan-2-ol;
3-[1-methyl-1-(methyloxy)ethyl]-5-{5-[3-(methylsulfonyl)phenyl]-2-thienyl}-1-[2-(trifluoromethyl)phenyl]-1H-pyrazole;
5-{5-[3-(ethylsulfonyl)phenyl]-2-thienyl}-3-[1-methyl-1-(methyloxy)ethyl]-1-[2-(trifluoromethyl)phenyl]-1H-pyrazole;
5-{5-[3-(methylsulfonyl)phenyl]-2-thienyl}-1-[2-(trifluoromethyl)phenyl]-1H-pyrazole-3-carboxylic acid;
1-(2-chlorophenyl)-N-ethyl-5-{5-[3-(methylsulfonyl)phenyl]-2-thienyl}-1H-pyrazole-3-carbothioamide;
5-{5-[3-(methylsulfonyl)phenyl]-2-thienyl}-N-(2,2,2-trifluoroethyl)-1-[2-(trifluoromethyl)phenyl]-1H-pyrazole-3-carboxamide;
3-(5-{1-[5-chloro-2-(phenyloxy)phenyl]-3-(trifluoromethyl)-1H-pyrazol-5-yl}-2-thienyl)benzenesulfonamide;
2-[3-(5-{1-[(2,4-difluorophenyl)methyl]-3-(trifluoromethyl)-1H-pyrazol-5-yl}-2-thienyl)phenyl]-2-methylpropanoic acid;
5-{5-[3-(methylsulfonyl)phenyl]-2-thienyl}-3-(pyrrolidin-1-ylcarbonyl)-1-[2-(trifluoromethyl)phenyl]-1H-pyrazole;
3-[difluoro(methyloxy)methyl]-5-{5-[3-(methylsulfonyl)phenyl]-2-thienyl}-1-[2-(trifluoromethyl)phenyl]-1H-pyrazole;
2-(1-[5-chloro-2-(phenyloxy)phenyl]-5-{5-[3-(methylsulfonyl)phenyl]-2-thienyl}-1H-pyrazol-3-yl)propan-2-ol;
1-(1-[5-chloro-2-(phenyloxy)phenyl]-5-{5-[3-(methylsulfonyl)phenyl]-2-thienyl}-1H-pyrazol-3-yl)ethanone;
3-{5-[1-(2,5-dichlorophenyl)-3-(1-hydroxy-1-methylethyl)-1H-pyrazol-5-yl]-2-thienyl}benzenesulfonamide;
5-{5-[3-(methylsulfonyl)phenyl]-2-thienyl}-1-[2-(phenyloxy)phenyl]-3-(trifluoromethyl)-1H-pyrazole;
3-{5-[3-acetyl-1-(2,5-dichlorophenyl)-1H-pyrazol-5-yl]-2-thienyl}benzenesulfonamide;
methyl 1-{3-[(methyloxy)carbonyl]phenyl}-5-{5-[3-(methylsulfonyl)phenyl]-2-thienyl}-1H-pyrazole-3-carboxylate;
2-{3-[3-(1-hydroxy-1-methylethyl)-5-{5-[3-(methylsulfonyl)phenyl]-2-thienyl}-1H-pyrazol-1-yl]phenyl}propan-2-ol;
1-(2,6-dichlorophenyl)-5-{5-[3-(methylsulfonyl)phenyl]-2-thienyl}-3-(trifluoromethyl)-1H-pyrazole;
2-{2-[5-{5-[3-(methylsulfonyl)phenyl]-2-thienyl}-3-(trifluoromethyl)-1H-pyrazol-1-yl]phenyl}propan-2-ol;

1-(2-chlorophenyl)-5-{5-[3-(methylsulfonyl)phenyl]-2-thienyl}-N-(2-pyridin-2-ylethyl)-1H-pyrazole-3-carboxamide;
methyl 1-(2-chlorophenyl)-5-{4-[3-(methylsulfonyl)phenyl]furan-2-yl}-1H-pyrazole-3-carboxylate;
2-[1-(2-chlorophenyl)-5-{4-[3-(methylsulfonyl)phenyl]furan-2-yl}-1H-pyrazol-3-yl]propan-2-ol;
5-{5-[3-(methylsulfonyl)phenyl]-2-thienyl}-N-(2,2,2-trifluoroethyl)-1-[3-(trifluoromethyl)pyridin-2-yl]-1H-pyrazole-3-carboxamide;
methyl 1-(2,6-dichlorophenyl)-5-{5-[3-(methylsulfonyl)phenyl]-2-thienyl}-1H-pyrazole-3-carboxylate;
2-[1-(2,6-dichlorophenyl)-5-{5-[3-(methylsulfonyl)phenyl]-2-thienyl}-1H-pyrazol-3-yl]propan-2-ol;
2-(3-{5-[1-(2-chlorophenyl)-3-(trifluoromethyl)-1H-pyrazol-5-yl]-2-thienyl}phenyl)propan-2-ol;
2-(4-{5-[1-(2-chlorophenyl)-3-(trifluoromethyl)-1H-pyrazol-5-yl]-2-thienyl}phenyl)propan-2-ol;
1-[1-(2,6-dichlorophenyl)-5-{5-[3-(methylsulfonyl)phenyl]-2-thienyl}-1H-pyrazol-3-yl]ethanone;
2-(1-[(2,4-difluorophenyl)methyl]-5-{5-[3-(methylsulfonyl)phenyl]-2-thienyl}-1H-pyrazol-3-yl)propan-2-ol;
4-{5-[1-(2,5-dichlorophenyl)-3-(trifluoromethyl)-1H-pyrazol-5-yl]-2-thienyl}-2-(methylsulfonyl)phenol;
2-[1-(2-chlorophenyl)-5-{4-[3-(methylsulfonyl)phenyl]-2-thienyl}-1H-pyrazol-3-yl]propan-2-ol;
2-chloro-6-methyl-3-[5-{5-[3-(methylsulfonyl)phenyl]-2-thienyl}-3-(trifluoromethyl)-1H-pyrazol-1-yl]phenol;
2-[3-(5-{3-(trifluoromethyl)-1-[3-(trifluoromethyl)pyridin-2-yl]-1H-pyrazol-5-yl}-2-thienyl)phenyl]propan-2-ol;
2-[4-(5-{3-(trifluoromethyl)-1-[3-(trifluoromethyl)pyridin-2-yl]-1H-pyrazol-5-yl}-2-thienyl)phenyl]propan-2-ol;
1-[5-(5-{1-[(2,4-difluorophenyl)methyl]-3-(trifluoromethyl)-1H-pyrazol-5-yl}-2-thienyl)pyridin-2-yl]piperazine;
2-{[4-{5-[1-(2,5-dichlorophenyl)-3-(trifluoromethyl)-1H-pyrazol-5-yl]-2-thienyl}-2-(methylsulfonyl)phenyl]oxy}ethanol;
2-[1-(3-chlorophenyl)-5-{5-[3-(methylsulfonyl)phenyl]-2-thienyl}-1H-pyrazol-3-yl]propan-2-ol;
2-[1-(4-chlorophenyl)-5-{5-[3-(methylsulfonyl)phenyl]-2-thienyl}-1H-pyrazol-3-yl]propan-2-ol;
2-[1-(3-fluorophenyl)-5-{5-[3-(methylsulfonyl)phenyl]-2-thienyl}-1H-pyrazol-3-yl]propan-2-ol;
4-(2-{[4-{5-[1-(2,5-dichlorophenyl)-3-(trifluoromethyl)-1H-pyrazol-5-yl]-2-thienyl}-2-(methylsulfonyl)phenyl]oxy}ethyl)morpholine;
5-(2-{[4-{5-[1-(2,5-dichlorophenyl)-3-(trifluoromethyl)-1H-pyrazol-5-yl]-2-thienyl}-2-(methylsulfonyl)phenyl]oxy}ethyl)-1H-tetrazole;
2-[1-(2-fluorophenyl)-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-phenyl-1H-pyrazol-3-yl)propan-2-ol;
2-[1-(4-fluorophenyl)-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-pyridin-2-yl-1H-pyrazol-3-yl)propan-2-ol;
2-[1-(2,4-difluorophenyl)-5-{5-[3-(methylsulfonyl)phenyl]-2-thienyl}-1H-pyrazol-3-yl]propan-2-ol;
2-[1-(3,5-difluorophenyl)-5-{5-[3-(methylsulfonyl)phenyl]-2-thienyl}-1H-pyrazol-3-yl]propan-2-ol;
2-[1-(3,4-difluorophenyl)-5-{5-[3-(methylsulfonyl)phenyl]-2-thienyl}-1H-pyrazol-3-yl]propan-2-ol;
1-(5-{5-[3-(methylsulfonyl)phenyl]-2-thienyl}-1-phenyl-1H-pyrazol-3-yl)ethanone;
3-{5-[1-(2-chlorophenyl)-3-(1-hydroxy-1-methylethyl)-1H-pyrazol-5-yl]-2-thienyl}benzonitrile;
1-(2-chlorophenyl)-N-(2-hydroxy-1-methylethyl)-5-{5-[3-(methylsulfonyl)phenyl]-2-thienyl}-1H-pyrazole-3-carboxamide;
1-(2-chlorophenyl)-N-methyl-5-{5-[3-(methylsulfonyl)phenyl]-2-thienyl}-N-(pyridin-3-ylmethyl)-1H-pyrazole-3-carboxamide;
2-[1-(3-fluoropyridin-2-yl)-5-{5-[3-(methylsulfonyl)phenyl]-2-thienyl}-1H-pyrazol-3-yl]propan-2-ol;
2-[1-(2-chloropyridin-3-yl)-5-{5-[3-(methylsulfonyl)phenyl]-2-thienyl}-1H-pyrazol-3-yl]propan-2-ol;
2-[1-(2-chlorophenyl)-5-(5-{3-[(trifluoromethyl)oxy]phenyl}-2-thienyl)-1H-pyrazol-3-yl]propan-2-ol;
methyl 3-{5-[1-(2-chlorophenyl)-3-{[(2,2,2-trifluoroethyl)amino]carbonyl}-1H-pyrazol-5-yl]-2-thienyl}benzoate;
1-(2-chlorophenyl)-5-{5-[3-(1-hydroxy-1-methylethyl)phenyl]-2-thienyl}-N-(2,2,2-trifluoroethyl)-1H-pyrazole-3-carboxamide;
1-(2-chlorophenyl)-5-{5-[3-(methylsulfonyl)phenyl]-2-thienyl}-N-(2,2,2-trifluoroethyl)-1H-pyrazole-3-carbothioamide;
2-[4-bromo-1-(2-chlorophenyl)-5-{5-[3-(methylsulfonyl)phenyl]-2-thienyl}-1H-pyrazol-3-yl]propan-2-ol;
2-[1-(2,5-dichlorophenyl)-5-{5-[3-(methylsulfonyl)phenyl]-2-thienyl}-1H-pyrazol-3-yl]propan-2-ol;
2-[1-(2,4-dichlorophenyl)-5-{5-[3-(methylsulfonyl)phenyl]-2-thienyl}-1H-pyrazol-3-yl]propan-2-ol;
2-[1-(2,3-dichlorophenyl)-5-{5-[3-(methylsulfonyl)phenyl]-2-thienyl}-1H-pyrazol-3-yl]propan-2-ol;
2-[4-chloro-1-(2-chlorophenyl)-5-{5-[3-(methylsulfonyl)phenyl]-2-thienyl}-1H-pyrazol-3-yl]propan-2-ol;
2-[1-(2-chlorophenyl)-4-methyl-5-{5-[3-(methylsulfonyl)phenyl]-2-thienyl}-1H-pyrazol-3-yl]propan-2-ol;
2-[1-(2-chlorophenyl)-5-{5-[3-(ethylsulfonyl)phenyl]-2-thienyl}-1H-pyrazol-3-yl]-2-methylpropanoic acid;
ethyl 3-{5-[1-(2,5-dichlorophenyl)-3-(trifluoromethyl)-1H-pyrazol-5-yl]-2-thienyl}-5-(methylsulfonyl)benzoate;
2-[4-{5-[1-(2,5-dichlorophenyl)-3-(trifluoromethyl)-1H-pyrazol-5-yl]-2-thienyl}-2-(methylsulfonyl)phenyl]propan-2-ol;
2-[3-{5-[1-(2,5-dichlorophenyl)-3-(trifluoromethyl)-1H-pyrazol-5-yl]-2-thienyl}-5-(methylsulfonyl)phenyl]propan-2-ol;
2-[1-(2-methylphenyl)-5-{5-[3-(methylsulfonyl)phenyl]-2-thienyl}-1H-pyrazol-3-yl]propan-2-ol;
4-bromo-1-(2,6-dichlorophenyl)-5-{5-[3-(methylsulfonyl)phenyl]-2-thienyl}-3-(trifluoromethyl)-1H-pyrazole;
2-[1-(2,5-dimethylphenyl)-5-{5-[3-(methylsulfonyl)phenyl]-2-thienyl}-1H-pyrazol-3-yl]propan-2-ol;
2-[1-(2,3-dimethylphenyl)-5-{5-[3-(methylsulfonyl)phenyl]-2-thienyl}-1H-pyrazol-3-yl]propan-2-ol;
2-[1-(2-chlorophenyl)-5-{5-[3-(ethylsulfonyl)phenyl]-2-thienyl}-1H-pyrazol-3-yl]propan-2-ol;
2-[3-{5-[1-(2,6-dichlorophenyl)-3-(trifluoromethyl)-1H-pyrazol-5-yl]-2-thienyl}-5-(methylsulfonyl)phenyl]propan-2-ol;
2-[3-{5-[1-(2-chlorophenyl)-3-(trifluoromethyl)-1H-pyrazol-5-yl]-2-thienyl}-5-(methylsulfonyl)phenyl]propan-2-ol;
2-[1-(2-chlorophenyl)-4-fluoro-5-{5-[3-(methylsulfonyl)phenyl]-2-thienyl}-1H-pyrazol-3-yl]propan-2-ol;

2-[1-(2-bromophenyl)-5-{5-[3-(methylsulfonyl)phenyl]-2-thienyl}-1H-pyrazol-3-yl]propan-2-ol;
ethyl 1-(2-fluorophenyl)-2-methyl-5-{5-[3-(methylsulfonyl)phenyl]-2-thienyl}-1H-pyrrole-3-carboxylate;
2-[1-(2,5-difluorophenyl)-5-{5-[3-(methylsulfonyl)phenyl]-2-thienyl}-1H-pyrazol-3-yl]propan-2-ol;
2-[1-(3,5-dichlorophenyl)-5-{5-[3-(methylsulfonyl)phenyl]-2-thienyl}-1H-pyrazol-3-yl]propan-2-ol;
2-[1-(3,4-dichlorophenyl)-5-{5-[3-(methylsulfonyl)phenyl]-2-thienyl}-1H-pyrazol-3-yl]propan-2-ol;
2-[1-(2,6-dichloro-3-methylphenyl)-5-{5-[3-(methylsulfonyl)phenyl]-2-thienyl}-1H-pyrazol-3-yl]propan-2-ol;
2-[1-(2,3-difluorophenyl)-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-{2-[(trifluoromethyl)oxy]phenyl}-1H-pyrazol-3-yl)propan-2-ol;
2-[1-(3-chloro-2-fluorophenyl)-5-{5-[3-(methylsulfonyl)phenyl]-2-thienyl}-1H-pyrazol-3-yl]propan-2-ol;
2-[1-(2-ethylphenyl)-5-{5-[3-(methylsulfonyl)phenyl]-2-thienyl}-1H-pyrazol-3-yl]propan-2-ol;
2-[5-{5-[3-(methylsulfonyl)phenyl]-2-thienyl}-1-(2-propylphenyl)-1H-pyrazol-3-yl]propan-2-ol;
2-[1-(5-fluoro-2-methylphenyl)-5-{5-[3-(methylsulfonyl)phenyl]-2-thienyl}-1H-pyrazol-3-yl]propan-2-ol;
2-[1-(2-chlorophenyl)-5-{5-[3-(1-methylethyl)phenyl]-2-thienyl}-1H-pyrazol-3-yl]propan-2-ol;
2-(1-[2-fluoro-3-(trifluoromethyl)phenyl]-5-{5-[3-(methylsulfonyl)phenyl]-2-thienyl}-1H-pyrazol-3-yl)propan-2-ol;
2-[1-(2-chloro-5-fluorophenyl)-5-{5-[3-(methylsulfonyl)phenyl]-2-thienyl}-1H-pyrazol-3-yl]propan-2-ol;
2-[1-(2-chloro-6-methylphenyl)-5-{5-[3-(methylsulfonyl)phenyl]-2-thienyl}-1H-pyrazol-3-yl]propan-2-ol;
2-[1-(5-chloro-2-fluorophenyl)-5-{5-[3-(methylsulfonyl)phenyl]-2-thienyl}-1H-pyrazol-3-yl]propan-2-ol;
2-[3-(1-hydroxy-1-methylethyl)-5-{5-[3-(methylsulfonyl)phenyl]-2-thienyl}-1H-pyrazol-1-yl]-6-(trifluoromethyl)phenol;
2-[4-bromo-1-(2,6-dichlorophenyl)-5-{5-[3-(methylsulfonyl)phenyl]-2-thienyl}-1H-pyrazol-3-yl]propan-2-ol;
2-[1-(3-chloro-2-methylphenyl)-5-{5-[3-(methylsulfonyl)phenyl]-2-thienyl}-1H-pyrazol-3-yl]propan-2-ol;
2-(1-[2,4-dichloro-6-(trifluoromethyl)phenyl]-5-{5-[3-(methylsulfonyl)phenyl]-2-thienyl}-1H-pyrazol-3-yl)propan-2-ol;
2-[1-(2,2-difluoro-1,3-benzodioxol-4-yl)-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-pyridin-4-yl-1H-pyrazol-3-yl)propan-2-ol;
2-[1-(2-chloro-6-fluorophenyl)-5-{5-[3-(methylsulfonyl)phenyl]-2-thienyl}-1H-pyrazol-3-yl]propan-2-ol;
2-(1-[2-(1-methylethyl)phenyl]-5-{5-[3-(methylsulfonyl)phenyl]-2-thienyl}-1H-pyrazol-3-yl)propan-2-ol;
2-(5-{5-[3-(methylsulfonyl)phenyl]-2-thienyl}-1-pyridin-3-yl-1H-pyrazol-3-yl)propan-2-ol;
2-(1-[2-chloro-5-(trifluoromethyl)phenyl]-5-{5-[3-(methylsulfonyl)phenyl]-2-thienyl}-1H-pyrazol-3-yl)propan-2-ol;
2-[4-chloro-1-(2,6-dichlorophenyl)-5-{5-[3-(methylsulfonyl)phenyl]-2-thienyl}-1H-pyrazol-3-yl]propan-2-ol;
2-(4-bromo-5-{5-[3-(methylsulfonyl)phenyl]-2-thienyl}-1-[2-(trifluoromethyl)phenyl]-1H-pyrazol-3-yl)propan-2-ol;
2-(4-chloro-5-{5-[3-(methylsulfonyl)phenyl]-2-thienyl}-1-[2-(trifluoromethyl)phenyl]-1H-pyrazol-3-yl)propan-2-ol;
2-(5-{5-[3-(methylsulfonyl)phenyl]-2-thienyl}-1-[4-(trifluoromethyl)pyridin-3-yl]-1H-pyrazol-3-yl)propan-2-ol;
2-[1-(2,6-dimethylphenyl)-5-{5-[3-(methylsulfonyl)phenyl]-2-thienyl}-1H-pyrazol-3-yl]propan-2-ol;
2-(1-[2-fluoro-6-(trifluoromethyl)phenyl]-5-{5-[3-(methylsulfonyl)phenyl]-2-thienyl}-1H-pyrazol-3-yl)propan-2-ol;
2-[4-bromo-1-(3-chloro-2-fluorophenyl)-5-{5-[3-(methylsulfonyl)phenyl]-2-thienyl}-1H-pyrazol-3-yl]propan-2-ol;
2-[4-bromo-1-(2-ethylphenyl)-5-{5-[3-(methylsulfonyl)phenyl]-2-thienyl}-1H-pyrazol-3-yl]propan-2-ol;
2-(4-bromo-5-{5-[3-(methylsulfonyl)phenyl]-2-thienyl}-1-{2-[(trifluoromethyl)oxy]phenyl}-1H-pyrazol-3-yl)propan-2-ol;
2-[4-bromo-1-(2-bromophenyl)-5-{5-[3-(methylsulfonyl)phenyl]-2-thienyl}-1H-pyrazol-3-yl]propan-2-ol;
2-[1-(3-fluoro-2-methylphenyl)-5-{5-[3-(methylsulfonyl)phenyl]-2-thienyl}-1H-pyrazol-3-yl]propan-2-ol;
2-[4-chloro-1-(3-chloro-2-fluorophenyl)-5-{5-[3-(methylsulfonyl)phenyl]-2-thienyl}-1H-pyrazol-3-yl]propan-2-ol;
2-(4-chloro-5-{5-[3-(methylsulfonyl)phenyl]-2-thienyl}-1-{2-[(trifluoromethyl)oxy]phenyl}-1H-pyrazol-3-yl)propan-2-ol;
2-[1-(2-bromophenyl)-4-chloro-5-{5-[3-(methylsulfonyl)phenyl]-2-thienyl}-1H-pyrazol-3-yl]propan-2-ol;
2-(4-bromo-5-{5-[3-(methylsulfonyl)phenyl]-2-thienyl}-1-[4-(trifluoromethyl)pyridin-3-yl]-1H-pyrazol-3-yl)propan-2-ol;
2-[1-(2-chloro-3-fluorophenyl)-5-{5-[3-(methylsulfonyl)phenyl]-2-thienyl}-1H-pyrazol-3-yl]propan-2-ol;
2-[4-chloro-1-(2-chloro-3-fluorophenyl)-5-{5-[3-(methylsulfonyl)phenyl]-2-thienyl}-1H-pyrazol-3-yl]propan-2-ol;
2-[4-bromo-1-(2-chloro-3-fluorophenyl)-5-{5-[3-(methylsulfonyl)phenyl]-2-thienyl}-1H-pyrazol-3-yl]propan-2-ol;
2-[4-chloro-1-(2-ethylphenyl)-5-{5-[3-(methylsulfonyl)phenyl]-2-thienyl}-1H-pyrazol-3-yl]propan-2-ol;
2-(1-(2-chlorophenyl)-5-(1-methyl-5-(3-(methylsulfonyl)phenyl)-1H-pyrrol-2-yl)-1H-pyrazol-3-yl)propan-2-ol;
2-(4-chloro-1-(2-chlorophenyl)-5-(1-methyl-5-(3-(methylsulfonyl)phenyl)-1H-pyrrol-2-yl)-1H-pyrazol-3-yl)propan-2-ol;
2-(1-(2,6-dichlorophenyl)-5-(1-methyl-5-(3-(methylsulfonyl)phenyl)-1H-pyrrol-2-yl)-1H-pyrazol-3-yl)propan-2-ol;
2-(4-chloro-3-(2-hydroxypropan-2-yl)-5-(5-(3-(methylsulfonyl)phenyl)thiophen-2-yl)-1H-pyrazol-1-yl)-6-(trifluoromethyl)phenol;
5-({[1-(2-chlorophenyl)-5-{5-[3-(methylsulfonyl)phenyl]-2-thienyl}-1H-pyrazol-3-yl]methyl}oxy)-2-methylpyridine;
3-({[1-(2-chlorophenyl)-5-{5-[3-(methylsulfonyl)phenyl]-2-thienyl}-1H-pyrazol-3-yl]methyl}oxy)-2-methylpyridine;
3-({[1-(2-chlorophenyl)-5-{5-[3-(methylsulfonyl)phenyl]-2-thienyl}-1H-pyrazol-3-yl]methyl}oxy)pyridine;

3-({[1-(2-chlorophenyl)-5-{5-[3-(methylsulfonyl)phenyl]-2-thienyl}-1H-pyrazol-3-yl]methyl}oxy)-2,6-dimethylpyridine;
4-({[1-(2-chlorophenyl)-5-{5-[3-(methylsulfonyl)phenyl]-2-thienyl}-1H-pyrazol-3-yl]methyl}oxy)pyridine;
N,N-diethyl-2-({2-[5-{4-[3-(methylsulfonyl)phenyl]-2-thienyl}-3-(trifluoromethyl)-1H-pyrazol-1-yl]phenyl}oxy)acetamide;
4-[({2-[5-{4-[3-(methylsulfonyl)phenyl]-2-thienyl}-3-(trifluoromethyl)-1H-pyrazol-1-yl]phenyl}oxy)methyl]pyridine;
N-(1-methylethyl)-2-({2-[5-{4-[3-(methylsulfonyl)phenyl]-2-thienyl}-3-(trifluoromethyl)-1H-pyrazol-1-yl]phenyl}oxy)acetamide;
5-({2-[5-{4-[3-(methylsulfonyl)phenyl]-2-thienyl}-3-(trifluoromethyl)-1H-pyrazol-1-yl]phenyl}oxy)pentanenitrile;
2-[2-({2-[5-{4-[3-(methylsulfonyl)phenyl]-2-thienyl}-3-(trifluoromethyl)-1H-pyrazol-1-yl]phenyl}oxy)ethyl]-1H-isoindole-1,3(2H)-dione;
2-({2-[5-{4-[3-(methylsulfonyl)phenyl]-2-thienyl}-3-(trifluoromethyl)-1H-pyrazol-1-yl]phenyl}oxy)-N-phenylacetamide;
2-[({2-[5-{4-[3-(methylsulfonyl)phenyl]-2-thienyl}-3-(trifluoromethyl)-1H-pyrazol-1-yl]phenyl}oxy)methyl]pyridine;
6-({2-[5-{4-[3-(methylsulfonyl)phenyl]-2-thienyl}-3-(trifluoromethyl)-1H-pyrazol-1-yl]phenyl}oxy)hexan-2-one;
1-(2-{5-[1-(2-chlorophenyl)-3-(1-hydroxy-1-methylethyl)-1H-pyrazol-5-yl]-2-thienyl}phenyl)ethanone; and
1-(2-ethylphenyl)-5-{4-[3-(methylsulfonyl)phenyl]-2-thienyl}-3-(trifluoromethyl)-1H-pyrazole;
or a pharmaceutically acceptable salt thereof.

41. A compound selected from the group consisting of:
2-(4-chloro-5-(5-(3-(methylsulfonyl)phenyl)thiophen-2-yl)-1-(4-(trifluoromethyl)pyridin-3-yl)-1H-pyrazol-3-yl)propan-2-ol;
2-(4-chloro-1-(3-fluoro-2-methylphenyl)-5-(5-(3-(methylsulfonyl)phenyl)thiophen-2-yl)-1H-pyrazol-3-yl)propan-2-ol;
2-(4-bromo-1-(3-fluoro-2-methylphenyl)-5-(5-(3-(methylsulfonyl)phenyl)thiophen-2-yl)-1H-pyrazol-3-yl)propan-2-ol;
2-(4-chloro-1-(2,3-difluorophenyl)-5-(5-(3-(methylsulfonyl)phenyl)thiophen-2-yl)-1H-pyrazol-3-yl)propan-2-ol;
2-(1-(2-(difluoromethoxy)phenyl)-5-(5-(3-(methylsulfonyl)phenyl)thiophen-2-yl)-1H-pyrazol-3-yl)propan-2-ol;
2-(1-(3-fluoro-2-(trifluoromethyl)phenyl)-5-(5-(3-(methylsulfonyl)phenyl)thiophen-2-yl)-1H-pyrazol-3-yl)propan-2-ol;
2-(4-chloro-1-(2,6-dimethylphenyl)-5-(5-(3-(methylsulfonyl)phenyl)thiophen-2-yl)-1H-pyrazol-3-yl)propan-2-ol;
2-(4-chloro-1-(2-fluorophenyl)-5-(5-(3-(methylsulfonyl)phenyl)thiophen-2-yl)-1H-pyrazol-3-yl)propan-2-ol;
2-(4-chloro-1-(2,6-difluorophenyl)-5-(5-(3-(methylsulfonyl)phenyl)thiophen-2-yl)-1H-pyrazol-3-yl)propan-2-ol;
2-(4-chloro-1-(2-chloro-6-fluorophenyl)-5-(5-(3-(methylsulfonyl)phenyl)thiophen-2-yl)-1H-pyrazol-3-yl)propan-2-ol;
2-(4-chloro-1-(2-chloro-6-methylphenyl)-5-(5-(3-(methylsulfonyl)phenyl)thiophen-2-yl)-1H-pyrazol-3-yl)propan-2-ol;
2-(4-chloro-1-(2,4-difluorophenyl)-5-(5-(3-(methylsulfonyl)phenyl)thiophen-2-yl)-1H-pyrazol-3-yl)propan-2-ol;
2-(1-(2-chlorophenyl)-5-(3-methyl-5-(3-(methylsulfonyl)phenyl)thiophen-2-yl)-1H-pyrazol-3-yl)propan-2-ol;
2-(1-(2-chlorophenyl)-5-(3-methyl-4-(3-(methylsulfonyl)phenyl)thiophen-2-yl)-1H-pyrazol-3-yl)propan-2-ol;
2-(1-(3-fluoro-2-(trifluoromethyl)phenyl)-5-(3-methyl-5-(3-(methylsulfonyl)phenyl)thiophen-2-yl)-1H-pyrazol-3-yl)propan-2-ol;
2-(5-(3-bromo-5-(3-(methylsulfonyl)phenyl)thiophen-2-yl)-1-(3-fluoro-2-methylphenyl)-1H-pyrazol-3-yl)propan-2-ol;
2-(5-(3-bromo-5-(3-(methylsulfonyl)phenyl)thiophen-2-yl)-1-(2-chloro-3-fluorophenyl)-1H-pyrazol-3-yl)propan-2-ol;
2-(5-(3-bromo-5-(3-(methylsulfonyl)phenyl)thiophen-2-yl)-1-(2-chlorophenyl)-1H-pyrazol-3-yl)propan-2-ol;
2-(1-(2-chloro-3-fluorophenyl)-5-(3-methyl-5-(3-(methylsulfonyl)phenyl)thiophen-2-yl)-1H-pyrazol-3-yl)propan-2-ol;
2-(5-(3-bromo-5-(3-(methylsulfonyl)phenyl)thiophen-2-yl)-1-(3-fluoro-2-(trifluoromethyl)phenyl)-1H-pyrazol-3-yl)propan-2-ol;
2-(1-(3-fluoro-2-methylphenyl)-5-(3-methyl-5-(3-(methylsulfonyl)phenyl)thiophen-2-yl)-1H-pyrazol-3-yl)propan-2-ol;
2-(5-(5-(3-(methylsulfonyl)phenyl)thiophen-2-yl)-1-(2-(trifluoromethyl)pyridin-3-yl)-1H-pyrazol-3-yl)propan-2-ol;
2-(4-chloro-5-(5-(3-(methylsulfonyl)phenyl)thiophen-2-yl)-1-(2-(trifluoromethyl)pyridin-3-yl)-1H-pyrazol-3-yl)propan-2-ol;
2-(4-bromo-5-(5-(3-(methylsulfonyl)phenyl)thiophen-2-yl)-1-(2-(trifluoromethyl)pyridin-3-yl)-1H-pyrazol-3-yl)propan-2-ol;
5-(5-(3-(methylsulfonyl)phenyl)thiophen-2-yl)-3-(prop-1-en-2-yl)-1-(2-(trifluoromethyl)phenyl)-1H-pyrazole;
2-(5-(5-(3-(methylsulfonyl)phenyl)thiophen-2-yl)-3-(prop-1-en-2-yl)-1H-pyrazol-1-yl)-3-(trifluoromethyl)pyridine;
2-(1-(2-chlorophenyl)-5-(3-ethyl-5-(3-(methylsulfonyl)phenyl)thiophen-2-yl)-1H-pyrazol-3-yl)propan-2-ol;
2-(1-(2-chloro-3-fluorophenyl)-5-(3-ethyl-5-(3-(methylsulfonyl)phenyl)thiophen-2-yl)-1H-pyrazol-3-yl)propan-2-ol;
3-(5-(5-(3-(methylsulfonyl)phenyl)thiophen-2-yl)-3-(prop-1-en-2-yl)-1H-pyrazol-1-yl)-4-(trifluoromethyl)pyridine;
2-(5-(3-methyl-5-(3-(methylsulfonyl)phenyl)thiophen-2-yl)-1-(4-(trifluoromethyl)pyridin-3-yl)-1H-pyrazol-3-yl)propan-2-ol;
2-(5-(3-methyl-5-(3-(methylsulfonyl)phenyl)thiophen-2-yl)-1-(4-(trifluoromethyl)pyridin-3-yl)-1H-pyrazol-3-yl)propan-2-ol;
2-(4-chloro-5-(3-methyl-5-(3-(methylsulfonyl)phenyl)thiophen-2-yl)-1-(4-(trifluoromethyl)pyridin-3-yl)-1H-pyrazol-3-yl)propan-2-ol;
2-(4-bromo-1-(5-fluoropyridin-3-yl)-5-(5-(3-(methylsulfonyl)phenyl)thiophen-2-yl)-1H-pyrazol-3-yl)propan-2-ol;
2-(4-chloro-5-(3-methyl-5-(3-(methylsulfonyl)phenyl)thiophen-2-yl)-1-(2-(trifluoromethyl)pyridin-3-yl)-1H-pyrazol-3-yl)propan-2-ol;

2-(4-chloro-5-(5-(3-(methylsulfonyl)phenyl)thiophen-2-yl)-1-(3-(trifluoromethyl)pyridin-4-yl)-1H-pyrazol-3-yl)propan-2-ol;
2-(4-chloro-1-(3-fluoropyridin-4-yl)-5-(5-(3-(methylsulfonyl)phenyl)thiophen-2-yl)-1H-pyrazol-3-yl)propan-2-ol;
1-(2-chlorophenyl)-5-(5-(3-(methylsulfonyl)phenyl)thiophen-2-yl)-3-(prop-1-en-2-yl)-1H-pyrazole;
2-(4-chloro-1-(3-chloropyridin-4-yl)-5-(5-(3-(methylsulfonyl)phenyl)thiophen-2-yl)-1H-pyrazol-3-yl)propan-2-ol;
2-(1-(3,5-dichloropyridin-4-yl)-5-(5-(3-(methylsulfonyl)phenyl)thiophen-2-yl)-1H-pyrazol-3-yl)propan-2-ol;
2-(4-chloro-1-(3,5-dichloropyridin-4-yl)-5-(5-(3-(methylsulfonyl)phenyl)thiophen-2-yl)-1H-pyrazol-3-yl)propan-2-ol;
1-(2-chlorophenyl)-3-(2-methoxypropan-2-yl)-5-(5-(3-(methylsulfonyl)phenyl)thiophen-2-yl)-1H-pyrazole;
2-(1-(2,6-dichlorophenyl)-5-(3-methyl-5-(3-(methylsulfonyl)phenyl)thiophen-2-yl)-1H-pyrazol-3-yl)propan-2-ol;
1-(2-chlorophenyl)-N-[2-(diethylamino)ethyl]-N-ethyl-5-{5-[3-(methylsulfonyl)phenyl]-2-thienyl}-1H-pyrazole-3-carboxamide;
1-(2-chlorophenyl)-N-[3-(dimethylamino)propyl]-N-methyl-5-{5-[3-(methylsulfonyl)phenyl]-2-thienyl}-1H-pyrazole-3-carboxamide;
methyl N-{[1-(2-chlorophenyl)-5-{5-[3-(methylsulfonyl)phenyl]-2-thienyl}-1H-pyrazol-3-yl]carbonyl}-N-methylglycinate;
1-(2-chlorophenyl)-N-methyl-N-(1-methylpiperidin-4-yl)-5-{5-[3-(methylsulfonyl)phenyl]-2-thienyl}-1H-pyrazole-3-carboxamide;
1-(2-chlorophenyl)-5-{5-[3-(methylsulfonyl)phenyl]-2-thienyl}-N-(3-pyrrolidin-1-ylpropyl)-1H-pyrazole-3-carboxamide;
1-(2-chlorophenyl)-5-{5-[3-(methylsulfonyl)phenyl]-2-thienyl}-3-(pyrrolidin-1-ylcarbonyl)-1H-pyrazole;
1-{[1-(2-chlorophenyl)-5-{5-[3-(methylsulfonyl)phenyl]-2-thienyl}-1H-pyrazol-3-yl]carbonyl}-4-methylpiperidine;
2-[5-{5-[3-(methylsulfonyl)phenyl]-2-thienyl}-3-(trifluoromethyl)-1H-pyrazol-1-yl]benzenesulfonamide;
1-(2-chlorophenyl)-N-[2-(diethylamino)ethyl]-N-ethyl-5-{5-[3-(methylsulfonyl)phenyl]-2-thienyl}-1H-pyrazole-3-carboxamide;
1-(2-chlorophenyl)-N-[3-(dimethylamino)propyl]-N-methyl-5-{5-[3-(methylsulfonyl)phenyl]-2-thienyl}-1H-pyrazole-3-carboxamide;
1-[(3-{5-[1-(2,5-dichlorophenyl)-3-(trifluoromethyl)-1H-pyrazol-5-yl]-2-thienyl}phenyl)sulfonyl]butan-2-ol;
[2-(methylsulfonyl)-4-(5-{3-(trifluoromethyl)-1-[3-(trifluoromethyl)pyridin-2-yl]-1H-pyrazol-5-yl}-2-thienyl)phenyl]methanol;
1-[1-(2-chlorophenyl)-5-{5-[3-(methylsulfonyl)phenyl]-2-thienyl}-1H-pyrazol-3-yl]ethanone;
1-[1-(2-chlorophenyl)-5-{5-[3-(methylsulfonyl)phenyl]-2-thienyl}-1H-pyrazol-3-yl]ethanol;
2-(5-{5-[3-(methylsulfonyl)phenyl]-2-thienyl}-1-[2-(trifluoromethyl)phenyl]-1H-pyrazol-3-yl)propan-2-ol;
1-(2-chlorophenyl)-5-{5-[3-(methylsulfonyl)phenyl]-2-thienyl}-N-(2,2,2-trifluoroethyl)-1H-pyrazole-3-carboxamide;
2-[3-(5-{1-[(5-chloro-2-thienyl)methyl]-3-(trifluoromethyl)-1H-pyrazol-5-yl}-2-thienyl)phenyl]-2-methylpropanoic acid;
2-[5-(5-{3-[(1-methylethyl)sulfonyl]phenyl}-2-thienyl)-3-(trifluoromethyl)-1H-pyrazol-1-yl]-3-(trifluoromethyl)pyridine;
methyl 5-(5-{3-[(1-methylethyl)sulfonyl]phenyl}-2-thienyl)-1-[3-(trifluoromethyl)pyridin-2-yl]-1H-pyrazole-3-carboxylate;
1-[1-(2-chlorophenyl)-5-{5-[3-(methylsulfonyl)phenyl]-2-thienyl}-1H-pyrazol-3-yl]propan-1-one;
3-[1-(2-chlorophenyl)-5-{5-[3-(methylsulfonyl)phenyl]-2-thienyl}-1H-pyrazol-3-yl]pentan-3-ol;
1-[1-(2-chlorophenyl)-5-{5-[3-(methylsulfonyl)phenyl]-2-thienyl}-1H-pyrazol-3-yl]propan-1-ol;
(1E)-1-[1-(2-chlorophenyl)-5-{5-[3-(methylsulfonyl)phenyl]-2-thienyl}-1H-pyrazol-3-yl]ethanone oxime;
2-(5-{5-[3-(methylsulfonyl)phenyl]-2-thienyl}-1-[3-(trifluoromethyl)pyridin-2-yl]-1H-pyrazol-3-yl)propan-2-ol;
1-{5-(5-{3-[(1-methylethyl)sulfonyl]phenyl}-2-thienyl)-1-[3-(trifluoromethyl)pyridin-2-yl]-1H-pyrazol-3-yl}ethanone;
2-[1-(2-chlorophenyl)-5-(5-{3-[(1-methylethyl)sulfonyl]phenyl}-2-thienyl)-1H-pyrazol-3-yl]propan-2-ol;
methyl 3-[5-{5-[3-(methylsulfonyl)phenyl]-2-thienyl}-3-(trifluoromethyl)-1H-pyrazol-1-yl]benzoate;
2-{3-[5-{5-[3-(methylsulfonyl)phenyl]-2-thienyl}-3-(trifluoromethyl)-1H-pyrazol-1-yl]phenyl}propan-2-ol;
3-[1-methyl-1-(methyloxy)ethyl]-5-{5-[3-(methylsulfonyl)phenyl]-2-thienyl}-1-[2-(trifluoromethyl)phenyl]-1H-pyrazole;
5-{5-[3-(ethylsulfonyl)phenyl]-2-thienyl}-3-[1-methyl-1-(methyloxy)ethyl]-1-[2-(trifluoromethyl)phenyl]-1H-pyrazole;
1-(2-chlorophenyl)-N-ethyl-5-{5-[3-(methylsulfonyl)phenyl]-2-thienyl}-1H-pyrazole-3-carbothioamide;
5-{5-[3-(methylsulfonyl)phenyl]-2-thienyl}-N-(2,2,2-trifluoroethyl)-1-[2-(trifluoromethyl)phenyl]-1H-pyrazole-3-carboxamide;
3-(5-{1-[5-chloro-2-(phenyloxy)phenyl]-3-(trifluoromethyl)-1H-pyrazol-5-yl}-2-thienyl)benzenesulfonamide;
2-[3-(5-{1-[(2,4-difluorophenyl)methyl]-3-(trifluoromethyl)-1H-pyrazol-5-yl}-2-thienyl)phenyl]-2-methylpropanoic acid;
5-{5-[3-(methylsulfonyl)phenyl]-2-thienyl}-3-(pyrrolidin-1-ylcarbonyl)-1-[2-(trifluoromethyl)phenyl]-1H-pyrazole;
3-[difluoro(methyloxy)methyl]-5-{5-[3-(methylsulfonyl)phenyl]-2-thienyl}-1-[2-(trifluoromethyl)phenyl]-1H-pyrazole;
2-(1-[5-chloro-2-(phenyloxy)phenyl]-5-{5-[3-(methylsulfonyl)phenyl]-2-thienyl}-1H-pyrazol-3-yl)propan-2-ol;
1-(1-[5-chloro-2-(phenyloxy)phenyl]-5-{5-[3-(methylsulfonyl)phenyl]-2-thienyl}-1H-pyrazol-3-yl)ethanone;
5-{5-[3-(methylsulfonyl)phenyl]-2-thienyl}-1-[2-(phenyloxy)phenyl]-3-(trifluoromethyl)-1H-pyrazole;
3-{5-[3-acetyl-1-(2,5-dichlorophenyl)-1H-pyrazol-5-yl]-2-thienyl}benzenesulfonamide;
methyl 1-{3-[(methyloxy)carbonyl]phenyl}-5-{5-[3-(methylsulfonyl)phenyl]-2-thienyl}-1H-pyrazole-3-carboxylate;
1-(2,6-dichlorophenyl)-5-{5-[3-(methylsulfonyl)phenyl]-2-thienyl}-3-(trifluoromethyl)-1H-pyrazole;
2-{2-[5-{5-[3-(methylsulfonyl)phenyl]-2-thienyl}-3-(trifluoromethyl)-1H-pyrazol-1-yl]phenyl}propan-2-ol;

methyl 1-(2-chlorophenyl)-5-{4-[3-(methylsulfonyl)phenyl]furan-2-yl}-1H-pyrazole-3-carboxylate;
methyl 1-(2,6-dichlorophenyl)-5-{5-[3-(methylsulfonyl)phenyl]-2-thienyl}-1H-pyrazole-3-carboxylate;
2-[1-(2,6-dichlorophenyl)-5-{5-[3-(methylsulfonyl)phenyl]-2-thienyl}-1H-pyrazol-3-yl]propan-2-ol;
2-(3-{5-[1-(2-chlorophenyl)-3-(trifluoromethyl)-1H-pyrazol-5-yl]-2-thienyl}phenyl)propan-2-ol;
1-[1-(2,6-dichlorophenyl)-5-{5-[3-(methylsulfonyl)phenyl]-2-thienyl}-1H-pyrazol-3-yl]ethanone;
2-(1-[(2,4-difluorophenyl)methyl]-5-{5-[3-(methylsulfonyl)phenyl]-2-thienyl}-1H-pyrazol-3-yl)propan-2-ol;
1-[5-(5-{1-[(2,4-difluorophenyl)methyl]-3-(trifluoromethyl)-1H-pyrazol-5-yl}-2-thienyl)pyridin-2-yl]piperazine;
2-[1-(2-fluorophenyl)-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-phenyl-1H-pyrazol-3-yl)propan-2-ol;
2-[1-(2,4-difluorophenyl)-5-{5-[3-(methylsulfonyl)phenyl]-2-thienyl}-1H-pyrazol-3-yl]propan-2-ol;
1-(5-{5-[3-(methylsulfonyl)phenyl]-2-thienyl}-1-phenyl-1H-pyrazol-3-yl)ethanone;
2-[1-(2-chloropyridin-3-yl)-5-{5-[3-(methylsulfonyl)phenyl]-2-thienyl}-1H-pyrazol-3-yl]propan-2-ol;
1-(2-chlorophenyl)-5-{5-[3-(methylsulfonyl)phenyl]-2-thienyl}-N-(2,2,2-trifluoroethyl)-1H-pyrazole-3-carbothioamide;
2-[4-bromo-1-(2-chlorophenyl)-5-{5-[3-(methylsulfonyl)phenyl]-2-thienyl}-1H-pyrazol-3-yl]propan-2-ol;
2-[4-chloro-1-(2-chlorophenyl)-5-{5-[3-(methylsulfonyl)phenyl]-2-thienyl}-1H-pyrazol-3-yl]propan-2-ol;
2-[1-(2-chlorophenyl)-4-methyl-5-{5-[3-(methylsulfonyl)phenyl]-2-thienyl}-1H-pyrazol-3-yl]propan-2-ol;
2-[4-{5-[1-(2,5-dichlorophenyl)-3-(trifluoromethyl)-1H-pyrazol-5-yl]-2-thienyl}-2-(methylsulfonyl)phenyl]propan-2-ol;
2-[3-{5-[1-(2,5-dichlorophenyl)-3-(trifluoromethyl)-1H-pyrazol-5-yl]-2-thienyl}-5-(methylsulfonyl)phenyl]propan-2-ol;
2-[1-(2-methylphenyl)-5-{5-[3-(methylsulfonyl)phenyl]-2-thienyl}-1H-pyrazol-3-yl]propan-2-ol;
4-bromo-1-(2,6-dichlorophenyl)-5-{5-[3-(methylsulfonyl)phenyl]-2-thienyl}-3-(trifluoromethyl)-1H-pyrazole;
2-[1-(2,5-dimethylphenyl)-5-{5-[3-(methylsulfonyl)phenyl]-2-thienyl}-1H-pyrazol-3-yl]propan-2-ol;
2-[1-(2,3-dimethylphenyl)-5-{5-[3-(methylsulfonyl)phenyl]-2-thienyl}-1H-pyrazol-3-yl]propan-2-ol;
2-[3-{5-[1-(2,6-dichlorophenyl)-3-(trifluoromethyl)-1H-pyrazol-5-yl]-2-thienyl}-5-(methylsulfonyl)phenyl]propan-2-ol;
2-[3-{5-[1-(2-chlorophenyl)-3-(trifluoromethyl)-1H-pyrazol-5-yl]-2-thienyl}-5-(methylsulfonyl)phenyl]propan-2-ol;
2-[1-(2-chlorophenyl)-4-fluoro-5-{5-[3-(methylsulfonyl)phenyl]-2-thienyl}-1H-pyrazol-3-yl]propan-2-ol;
2-[1-(2-bromophenyl)-5-{5-[3-(methylsulfonyl)phenyl]-2-thienyl}-1H-pyrazol-3-yl]propan-2-ol;
ethyl 1-(2-fluorophenyl)-2-methyl-5-{5-[3-(methylsulfonyl)phenyl]-2-thienyl}-1H-pyrrole-3-carboxylate;
2-[1-(2,6-dichloro-3-methylphenyl)-5-{5-[3-(methylsulfonyl)phenyl]-2-thienyl}-1H-pyrazol-3-yl]propan-2-ol;
2-[1-(2,3-difluorophenyl)-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-{2-[(trifluoromethyl)oxy]phenyl}-1H-pyrazol-3-yl)propan-2-ol;
2-[1-(3-chloro-2-fluorophenyl)-5-{5-[3-(methylsulfonyl)phenyl]-2-thienyl}-1H-pyrazol-3-yl]propan-2-ol;
2-[1-(2-ethylphenyl)-5-{5-[3-(methylsulfonyl)phenyl]-2-thienyl}-1H-pyrazol-3-yl]propan-2-ol;
2-[5-{5-[3-(methylsulfonyl)phenyl]-2-thienyl}-1-(2-propylphenyl)-1H-pyrazol-3-yl]propan-2-ol;
2-[1-(5-fluoro-2-methylphenyl)-5-{5-[3-(methylsulfonyl)phenyl]-2-thienyl}-1H-pyrazol-3-yl]propan-2-ol;
2-[1-(2-chloro-5-fluorophenyl)-5-{5-[3-(methylsulfonyl)phenyl]-2-thienyl}-1H-pyrazol-3-yl]propan-2-ol;
2-[1-(2-chloro-6-methylphenyl)-5-{5-[3-(methylsulfonyl)phenyl]-2-thienyl}-1H-pyrazol-3-yl]propan-2-ol;
2-[1-(5-chloro-2-fluorophenyl)-5-{5-[3-(methylsulfonyl)phenyl]-2-thienyl}-1H-pyrazol-3-yl]propan-2-ol;
2-[4-bromo-1-(2,6-dichlorophenyl)-5-{5-[3-(methylsulfonyl)phenyl]-2-thienyl}-1H-pyrazol-3-yl]propan-2-ol;
2-[1-(3-chloro-2-methylphenyl)-5-{5-[3-(methylsulfonyl)phenyl]-2-thienyl}-1H-pyrazol-3-yl]propan-2-ol;
2-[1-(2,2-difluoro-1,3-benzodioxol-4-yl)-5-{5-[3-(methylsulfonyl)phenyl]-2-thienyl}-1H-pyrazol-3-yl]propan-2-ol;
2-[1-(2-chloro-6-fluorophenyl)-5-{5-[3-(methylsulfonyl)phenyl]-2-thienyl}-1H-pyrazol-3-yl]propan-2-ol;
2-(1-[2-(1-methylethyl)phenyl]-5-{5-[3-(methylsulfonyl)phenyl]-2-thienyl}-1H-pyrazol-3-yl]propan-2-ol;
2-(5-{5-[3-(methylsulfonyl)phenyl]-2-thienyl}-1-pyridin-3-yl-1H-pyrazol-3-yl)propan-2-ol;
2-[4-chloro-1-(2,6-dichlorophenyl)-5-{5-[3-(methylsulfonyl)phenyl]-2-thienyl}-1H-pyrazol-3-yl]propan-2-ol;
2-(4-bromo-5-{5-[3-(methylsulfonyl)phenyl]-2-thienyl}-1-[2-(trifluoromethyl)phenyl]-1H-pyrazol-3-yl)propan-2-ol;
2-(4-chloro-5-{5-[3-(methylsulfonyl)phenyl]-2-thienyl}-1-[2-(trifluoromethyl)phenyl]-1H-pyrazol-3-yl)propan-2-ol;
2-[1-(2,6-dimethylphenyl)-5-{5-[3-(methylsulfonyl)phenyl]-2-thienyl}-1H-pyrazol-3-yl]propan-2-ol;
2-(1-[2-fluoro-6-(trifluoromethyl)phenyl]-5-{5-[3-(methylsulfonyl)phenyl]-2-thienyl}-1H-pyrazol-3-yl)propan-2-ol;
2-[4-bromo-1-(3-chloro-2-fluorophenyl)-5-{5-[3-(methylsulfonyl)phenyl]-2-thienyl}-1H-pyrazol-3-yl]propan-2-ol;
2-[4-bromo-1-(2-ethylphenyl)-5-{5-[3-(methylsulfonyl)phenyl]-2-thienyl}-1H-pyrazol-3-yl]propan-2-ol;
2-(4-bromo-5-{5-[3-(methylsulfonyl)phenyl]-2-thienyl}-1-{2-[(trifluoromethyl)oxy]phenyl}-1H-pyrazol-3-yl)propan-2-ol;
2-[4-bromo-1-(2-bromophenyl)-5-{5-[3-(methylsulfonyl)phenyl]-2-thienyl}-1H-pyrazol-3-yl]propan-2-ol;
2-[1-(3-fluoro-2-methylphenyl)-5-{5-[3-(methylsulfonyl)phenyl]-2-thienyl}-1H-pyrazol-3-yl]propan-2-ol;
2-(4-chloro-5-{5-[3-(methylsulfonyl)phenyl]-2-thienyl}-1-{2-[(trifluoromethyl)oxy]phenyl}-1H-pyrazol-3-yl)propan-2-ol;
2-[1-(2-bromophenyl)-4-chloro-5-{5-[3-(methylsulfonyl)phenyl]-2-thienyl}-1H-pyrazol-3-yl]propan-2-ol;
2-(4-bromo-5-{5-[3-(methylsulfonyl)phenyl]-2-thienyl}-1-[4-(trifluoromethyl)pyridin-3-yl]-1H-pyrazol-3-yl)propan-2-ol;
2-[1-(2-chloro-3-fluorophenyl)-5-{5-[3-(methylsulfonyl)phenyl]-2-thienyl}-1H-pyrazol-3-yl]propan-2-ol;

2-[4-chloro-1-(2-chloro-3-fluorophenyl)-5-{5-[3-(methylsulfonyl)phenyl]-2-thienyl}-1H-pyrazol-3-yl]propan-2-ol;

2-[4-bromo-1-(2-chloro-3-fluorophenyl)-5-{5-[3-(methylsulfonyl)phenyl]-2-thienyl}-1H-pyrazol-3-yl]propan-2-ol;

2-[4-chloro-1-(2-ethylphenyl)-5-{5-[3-(methylsulfonyl)phenyl]-2-thienyl}-1H-pyrazol-3-yl]propan-2-ol; and 2-(1-(2-chlorophenyl)-5-(1-methyl-5-(3-(methylsulfonyl)phenyl)-1H-pyrrol-2-yl)-1H-pyrazol-3-yl)propan-2-ol;

or a pharmaceutically acceptable salt thereof.

\* \* \* \* \*

UNITED STATES PATENT AND TRADEMARK OFFICE
CERTIFICATE OF CORRECTION

PATENT NO. : 8,703,805 B2  Page 1 of 1
APPLICATION NO. : 11/993806
DATED : April 22, 2014
INVENTOR(S) : Brett B. Busch et al.

It is certified that error appears in the above-identified patent and that said Letters Patent is hereby corrected as shown below:

In the Claims:

Claim 19:

Column 1084, line 42, change "awl" to -- aryl --.

Column 1084, line 49, change "$SON(R^{11})_2$," to -- $SO_2N(R^{11})_2$, --.

Claim 34:

Column 1088, lines 30 to 34, change " 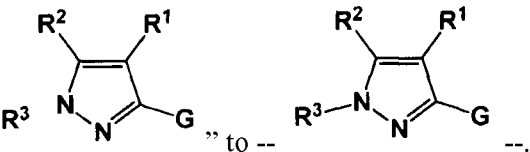 " to -- --.

Column 1090, line 50, change "—$SO_2NR^{11}$, $COR^{11}$," to -- —$SO_2NR^{11}COR^{11}$, --.

Claim 38:

Column 1091, lines 62 to 66, change " 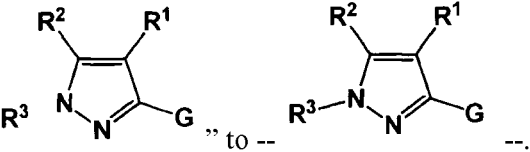 " to -- --.

Column 1092, line 23, change "$C_2$-$C_6$ alkenyl, alkenyl," to -- $C_2$-$C_6$ alkenyl, $C_2$-$C_6$ alkynyl, --.

Signed and Sealed this
Tenth Day of November, 2015

Michelle K. Lee
*Director of the United States Patent and Trademark Office*